United States Patent
Xu et al.

(10) Patent No.: US 11,746,100 B2
(45) Date of Patent: Sep. 5, 2023

(54) CYCLOALKYL PYRIMIDINES AS FERROPORTIN INHIBITORS

(71) Applicant: GLOBAL BLOOD THERAPEUTICS, INC., South San Francisco, CA (US)

(72) Inventors: Qing Xu, Foster City, CA (US); Carsten Alt, Fremont, CA (US); Zhe Li, San Diego, CA (US); Shahul Nilar, Foster City, CA (US); Peter Michael Rademacher, San Francisco, CA (US); Calvin Wesley Yee, Daly City, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/242,731

(22) Filed: Apr. 28, 2021

(65) Prior Publication Data
US 2022/0396562 A1    Dec. 15, 2022

Related U.S. Application Data

(60) Provisional application No. 63/127,774, filed on Dec. 18, 2020, provisional application No. 63/016,891, filed on Apr. 28, 2020.

(51) Int. Cl.
| | |
|---|---|
| C07D 401/14 | (2006.01) |
| C07D 401/04 | (2006.01) |
| C07D 403/04 | (2006.01) |
| C07D 403/14 | (2006.01) |
| C07D 405/14 | (2006.01) |
| C07D 413/04 | (2006.01) |
| C07D 413/14 | (2006.01) |
| C07D 417/04 | (2006.01) |
| C07D 417/14 | (2006.01) |
| C07D 471/04 | (2006.01) |
| C07D 471/08 | (2006.01) |
| C07D 491/056 | (2006.01) |
| C07D 498/08 | (2006.01) |

(52) U.S. Cl.
CPC ......... *C07D 401/14* (2013.01); *C07D 401/04* (2013.01); *C07D 403/04* (2013.01); *C07D 403/14* (2013.01); *C07D 405/14* (2013.01); *C07D 413/04* (2013.01); *C07D 413/14* (2013.01); *C07D 417/04* (2013.01); *C07D 417/14* (2013.01); *C07D 471/04* (2013.01); *C07D 471/08* (2013.01); *C07D 491/056* (2013.01); *C07D 498/08* (2013.01)

(58) Field of Classification Search
CPC .................................................. C07D 401/14
USPC .................................................. 514/210.18
See application file for complete search history.

(56) References Cited

U.S. PATENT DOCUMENTS 9,315,545 B2    4/2016    Merutka

FOREIGN PATENT DOCUMENTS

| CN | 104 011 066 | | 8/2014 | |
|---|---|---|---|---|
| EP | 0 407 899 | A2 | 1/1991 | |
| WO | WO 2005/014558 | A1 | 2/2005 | |
| WO | WO 2010/065815 | A2 | 6/2010 | |
| WO | WO 2011/026835 | A1 | 3/2011 | |
| WO | WO 2013/086143 | A1 | 6/2013 | |
| WO | WO 2014/145561 | A2 | 9/2014 | |
| WO | WO 2015/042515 | A1 | 3/2015 | |
| WO | WO 2015/157283 | A1 | 10/2015 | |
| WO | WO 2015/200916 | A2 | 12/2015 | |
| WO | WO 2016/109363 | A1 | 7/2016 | |
| WO | WO 2019/222238 | A2 | 11/2019 | |
| WO | WO-2019222238 | A2 | * 11/2019 | ......... A61K 31/4725 |
| WO | WO 2020/123850 | A1 | 6/2020 | |

OTHER PUBLICATIONS

Arezes et al., "Hepcidin-Induced Hypoferremia Is a Critical Host Defense Mechanism against the Siderophilic Bacterium Vibrio vlunificu," Cell Host & Microbe, 17:47-57, (2015).
Blanchette et al., "Modulation of hepcidin to treat iron deregulation: potential clinical applications," Expert Rev. Hematol., 9:169-186, (2016).
Carreau et al., "Ironing out the details of iron overload in myelofibrosis: Lessons from myelodysplastic syndromes," Blood Rev., 30:349-356, (2016).
Casu et al., "Minihepcidin peptides as disease modifiers in mice affected by β-thalassemia and polycythemia vera," Blood, 128:265-276, (2016).
Cui et al., "Serum iron metabolism and erythropoiesis in patients with myelodysplastic syndrome not receiving RBC transfusions," Leuk. Res., 38:545-550, (2014).
Ganz et al., "Irin Hematology: Hepcidin and Its Role in Regulating Systemic Iron Metabolism," Hematol., 507:29-35, (2006).
Hentze, M.W., "Balancing acts: molecular control of mammalian iron metabolism," Cell, 1(17):285-297, (2004).
Hunter et al., "The Solution Structure of Human Hepcidin, a Peptide Hormone with Antimicrobial Activity that is Involved in Iron Uptake and Hereditary Hemochromatosis," J. Biol. Chem., 277(40):37597-37603, (2002).
Jordan et al., "Hepcidin Revisited, Disulfide Connectivity, Dynamics, and Structure," J. Biol Chem., 284(36):24155-24167, (2009).
Krause et al., "LEAP-1, a novel highly disulfide-bonded human peptide, exhibits antimicrobial activity," FEBS Lett., 480:147-150, (2000).

(Continued)

*Primary Examiner* — Kahsay Habte

(57) ABSTRACT

The subject matter described herein is directed to ferroportin inhibitor compounds of Formula I or I' and pharmaceutical salts thereof, methods of preparing the compounds, pharmaceutical compositions comprising the compounds, and methods of administering the compounds for prophylaxis and/or treatment of diseases caused by a lack of hepcidin or iron metabolism disorders, particularly iron overload states, such as thalassemia, sickle cell disease and hemochromatosis, and also kidney injuries.

48 Claims, No Drawings

(56) References Cited

OTHER PUBLICATIONS

Nemeth et al., "The N-terminus of hepcidin is essential for its interaction with ferroportin: structure-function study," Blood, 107(1):328-333, (2006).
Origa et al., "Liver iron concentrations and urinary hepcidin in β-thalassemia," Haematologica, 92(05):583-588, (2007).
Park et al., "Hepcidin, a Urinary Antimicrobial Peptide Synthesized in the Liver," J. Biol. Chem., 276:7806-7810, (2001).
Powell et al., "Haemochromatosis," The Lancet, 388:706-716 (2016).
Preza et al., "Minihepcidins are rationally designed small peptides that mimic hepcidin activity in mice and may be useful for the treatment of iron overload," J. Clin Invest., 121(12):4888-4888, (2011).
Santini et al., "Hepcidin Levels and Their Determinants in Different Types of Myelodysplastic Syndromes," PLoS ONE, 6:e23109, (2011).
Sebastiani et al., "Pharmacological Targeting of the Hepcidin/Ferroportin Axis," Front. Pharmacol, 7(160):1-11, (2016).
Temraz et al., "Iron overload and chelation therapy in myelodysplastic syndromes," Crit. Rev. Oncol. Hematol., 91:64-73, (2014).
Walker et al., "Targeting Iron Homeostasis in Acute Kidney Injury," Semin Nephrol, 36(1):62-70, (2016).
Walter et al., "Iron Metabolism and Iron Chelation in Sickle Cell Disease," Acta Haematol., 122:174-183, (2009).
Zeng et al., "Hepatic Hepcidin Protects against Polymicrobial Sepsis in Mice by Regulating Host Iron Status," Anesthesiology, 122:374-386, (2015).
WIPO Appiication No. PCT/US2021/029574, PCT International Search Report and Written Opinion of the International Searching Authority dated Aug. 5, 2021.

\* cited by examiner

CYCLOALKYL PYRIMIDINES AS FERROPORTIN INHIBITORS

CROSS REFERENCE TO RELATED APPLICATIONS

This application claims the benefit of and priority to U.S. Provisional Application No. 63/016,891, filed on Apr. 28, 2020, and U.S. Provisional Application No. 63/127,774, filed on Dec. 18, 2020, the contents of each of which are hereby incorporated by reference in their entirety.

FIELD

The subject matter described herein is directed to ferroportin inhibitor compounds, methods of making the compounds, their pharmaceutical compositions, and their use in the prophylaxis and/or treatment of diseases caused by a lack of hepcidin or iron metabolism disorders, particularly iron overload states, such as thalassemia, sickle cell disease and hemochromatosis, and also kidney injuries.

BACKGROUND

In nearly all organisms, iron is an essential trace element. In humans, iron is a critical component for oxygen transport, oxygen uptake, cell functions such as mitochondrial electron transport, cognitive functions, and energy metabolism. Iron is present in enzymes, hemoglobin and myoglobin, as well as in depots in the form of ferritin and hemosiderin. With respect to hemoglobin, approximately half of all iron is present as heme iron, bound in the hemoglobin of the erythrocytes. The human body contains on average approximately 4 to 5 g iron. The iron requirement of a human adult is between 0.5 to 1.5 mg per day, whereas infants and women during pregnancy require 2 to 5 mg of iron per day.

In a healthy human adult, the normal daily loss of iron of about 1 mg is usually replaced via food intake. Iron balance is primarily regulated by recycling and iron recovery from hemoglobin of aging erythrocytes and the duodenal absorption of dietary iron in the form of divalent as well as trivalent iron ions.

Absorption is regulated by the organism depending on the iron requirement and the size of the iron depot. Usually, Fe(III) compounds are dissolved in the stomach at a sufficiently acidic pH value and thus made available for absorption. The absorption of the iron is carried out in the upper small intestine by mucosal cells. Trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or released into the blood by the transport protein ferroportin. The divalent iron transported into the blood by ferroportin is converted into trivalent iron by oxidases (ceruloplasmin, hephaestin). The trivalent iron is then transported to its destination in the organism by transferrin. ("Balancing acts: molecular control of mammalian iron metabolism," M. W. Hentze, Cell, 1:17, 2004, 285-297). Hepcidin plays a central role in this process because it is the essential regulating factor of iron absorption. The hepcidin-ferroportin system directly regulates iron metabolism.

Iron uptake and storage is regulated by hepcidin. Hepcidin Antimicrobial Peptide (HAMP; also known as LEAP-1; further referred to as Hepcidin) is a 25 amino acid peptide (Krause et al., FEBS Lett. 480, 147-150, 2000). Hepcidin has a hairpin structure with 8 cysteines that form 4 disulfide bridges (Jordan et al., J Biol Chem. 284, 24155-24167, 2009). The N-terminus appears to be important for the iron-regulatory function since deletion of the first 5 amino acids resulted in complete loss of bioactivity (Nemeth et al., Blood, 107, 328-333, 2006). Hepcidin is produced in the liver and functions as the master iron regulatory hormone controlling intestinal iron uptake, and also regulates iron storage in other organs (Ganz, Hematol. Am. Soc. Hematol. Educ. Program, 29-35, 507 2006; Hunter et al., J. Biol. Chem. 277, 37597-37603, 2002; Park et al., J. Biol. Chem. 276, 7806-7810, 2001). Hepcidin limits iron-uptake by binding to the iron transport molecule ferroportin and causing its degradation (Sebastiani et al., Front. Pharmacol. 7, 160, 2016).

The formation of hepcidin is regulated in direct correlation to the organism's iron level, i.e., if the organism is supplied with sufficient iron and oxygen, more hepcidin is formed; if iron and oxygen levels are low, or in case of increased erythropoiesis, less hepcidin is formed. In the small intestinal mucosal cells and in the macrophages hepcidin binds with the transport protein ferroportin, which conventionally transports the phagocytotically recycled iron from the interior of the cell into the blood.

Ferroportin is an iron transporter that plays a key role in regulating iron uptake and distribution in the body and thus in controlling iron levels in the blood. The transport protein ferroportin is a transmembrane protein consisting of 571 amino acids which is formed in the liver, spleen, kidneys, heart, intestine and placenta. In particular, ferroportin is localized in the basolateral membrane of intestinal epithelial cells. Ferroportin bound in this way thus acts to export the iron into the blood. In this case, it is most probable that ferroportin transports iron as $Fe^{2+}$. If hepcidin binds to ferroportin, ferroportin is transported into the interior of the cell, where its breakdown takes place so that the release of the phagocytotically recycled iron from the cells is then almost completely blocked. If the ferroportin is inactivated, for example by hepcidin, so that it is unable to export the iron which is stored in the mucosal cells, the stored iron is lost with the natural shedding of cells via the stools. The absorption of iron in the intestine is therefore reduced, when ferroportin is inactivated or inhibited, for example by hepcidin.

A decrease of hepcidin results in an increase of active ferroportin, thus allowing an enhanced release of stored iron and an enhanced iron uptake, e.g., from the food, resulting in an increase in serum iron levels, i.e., iron overload. Iron overload causes many diseases and undesired medical conditions. Iron overload can be treated by removal of the iron from the body. This treatment includes regularly scheduled phlebotomies (bloodletting). For patients unable to tolerate routine blood draws, there are chelating agents available for use. A disadvantage in the treatment of iron overload by chelation therapy is the removal of the chelated iron from the body when the iron overload has already occurred instead of preventing the occurrence of the disorder.

What is therefore needed and not effectively addressed by the art are compounds that act as ferroportin inhibitors that have desired efficacy and therapeutic potential. This problem as well as others stemming from iron imbalance are addressed by the subject matter described herein.

BRIEF SUMMARY

In certain embodiments, the subject matter described herein is directed to a compound of Formula I or Formula I' or a pharmaceutically acceptable salt thereof.

In certain embodiments, the subject matter described herein is directed to a pharmaceutical composition comprising a compound of Formula I or Formula I' or a pharmaceutically acceptable salt thereof.

In certain embodiments, the subject matter described herein is directed to methods of inhibiting iron transport mediated by ferroportin in a subject, comprising administering to the subject an effective amount of a compound of Formula I or Formula I', a pharmaceutically acceptable salt thereof, or a pharmaceutical composition comprising a compound of Formula I or Formula I'.

In certain embodiments, the subject matter described herein is directed to methods of preparing compounds of Formula I or Formula I'.

Other embodiments are also described.

DETAILED DESCRIPTION

Described herein are ferroportin inhibitor compounds of Formula I and Formula I', methods of making the compounds, pharmaceutical compositions comprising the compounds and their use in the prophylaxis and/or treatment of diseases caused by a lack of hepcidin or iron metabolism disorders, particularly iron overload states, such as thalassemia, sickle cell disease and hemochromatosis. Ferroportin is the iron transport protein responsible for the uptake of the released iron via the intestine and its transfer into the blood circulation, where ultimately the iron is delivered to the appropriate tissues and organs. Inactivation or inhibition of the ferroportin reduces or prevents the export of the iron, thereby reducing the absorption of iron in the intestine and ultimately the amount of iron in the body. These compounds, compositions and methods can be used for an effective therapy for the prophylaxis and treatment of iron metabolism disorders which are associated with increased iron levels. It is desirable to provide compounds, compositions and methods that exhibit few side effects, have very low toxicity and good bioavailability and compatibility.

Iron overload has been associated with a variety of diseases (Blanchette et al., Expert Rev. Hematol. 9, 169-186, 2016). Hereditary hemochromatosis is the most common inherited disease in Europe and is caused by lack of, or insensitivity to, hepcidin (Powell et al., The Lancet 388, 706-716, 2016). The clinical manifestation of hemochromatosis are hepatic cirrhosis, diabetes, and skin pigmentation (Powell et al., The Lancet 388, 706-716, 2016). While this disease can be managed by phlebotomy, this approach may be cumbersome and does not treat the cause of the disease.

Iron-loading anemias such as beta-thalassemia are also associated with reduced hepcidin levels (Origa et al., Haematologica 92, 583-588, 2007). Treatment of this disease with hepcidin mimetics may not only address the iron overload, but has also been shown to improve the ineffective erythropoiesis that occurs in this disease (Casu et al., Blood 128, 265-276, 2016). This may be of major benefit for thalassemia patients who may be less dependent on blood transfusions, which can contribute to the iron overload in these patients.

Myelofibrosis, myelodysplastic syndrome, and sickle cell disease are diseases that are also characterized by ineffective erythropoiesis and that may require frequent blood transfusions (Carreau et al., Blood Rev. 30, 349-356, 2016; Temraz et al., Crit. Rev. Oncol. Hematol. 91, 64-73, 2014; Walter et al., Acta Haematol. 122, 174-183, 2009). Reduced hepcidin levels have been described in some of these patients (Cui et al., Leuk. Res. 38, 545-550, 2014; Santini et al., PLoS ONE 6, e23109, 2011). Hepcidin mimetics may also be beneficial in these patients.

Polycythemia vera is a disease characterized by increased erythropoiesis. It has been shown in animal models that high doses of hepcidin mimetics can ameliorate this disease by diminishing erythropoiesis (Casu et al., Blood 128, 265-276, 2016).

Reduction of iron uptake and thereby serum iron levels may even be beneficial in diseases where iron load is normal, such as kidney diseases (Walker and Agarwal, Nephrol. 36, 62-70, 2016), infections with iron-dependent bacteria (Arezes et al., Cell Host Microbe 17, 47-57, 2015), and polymicrobial sepsis (Zeng et al., Anesthesiology, 122, 374-386, 2015).

Hepcidin itself is limited in its use as a drug because of its complex structure which requires a complicated manufacturing, and also its limited in vivo duration of action. Continuous efforts have been made to search for hepcidin mimetics and chemical compounds that could be used to increase hepcidin levels.

A common approach relates to small hepcidin-derived or hepcidin-like peptides, which can be produced affordably, and can be used to treat hepcidin-related diseases and disorders such as those described herein. Such so-called mini-hepcidins are rationally designed small peptides that mimic hepcidin activity and may be useful for the treatment of iron overload, and also iron overload related disease symptoms.

Such mini-hepcidin peptides are described for example in WO 2010/065815 A2 and WO 2013/086143 A1. WO 2015/157283 A1 and the corresponding U.S. Pat. No. 9,315,545 B2 describe hepcidin mimetic peptides and the use thereof in hepcidin-related disorders, such as iron overload, beta-thalassemia, hemochromatosis etc. and cover a development compound M012 of the company Merganser Biotech, having been under evaluation in a Phase 1 clinical program as a potentially transformative therapy for a number of hematological diseases including beta-thalassemia, low risk myelodysplasia and polycythemia vera.

WO 2014/145561 A2 and WO 2015/200916 A2 describe further small hepcidin peptide analogues and the use thereof in the treatment or prevention of a variety of hepcidin-related diseases, including iron overload diseases and iron-loading anemias, and further related disorders. Further, WO2015/042515 A1 relates to hepcidin and its peptide fragments, which are particularly intended for treating renal ischemia reperfusion injury or acute kidney injury. Further, mini-hepcidin analogs are described for example by Preza et al., J. Clin. Invest., 121 (12), 4880-4888, 2011 or in CN 104 011 066 and in WO 2016/109363 A1.

Ferroportin inhibitors as well as compounds that have hepcidin-like activity are needed that also possess additional beneficial properties such as improved solubility, stability, and/or potency. An advantage of the ferroportin inhibitor compounds of Formula I described herein is their preparation in sufficient yields by the synthetic routes disclosed herein.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literature, patents, and similar materials differs from or contradicts this application, including but not limited to defined terms, term usage, described techniques, or the like, this application controls.

I. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_u$-$C_v$" indicates that the following group has from u to v carbon atoms. For example, "$C_1$-$C_6$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±50%. In certain other embodiments, the term "about" includes the indicated amount±20%. In certain other embodiments, the term "about" includes the indicated amount±10%. In other embodiments, the term "about" includes the indicated amount±5%. In certain other embodiments, the term "about" includes the indicated amount±1%. In certain other embodiments, the term "about" includes the indicated amount±0.5% and in certain other embodiments, 0.1%. Such variations are appropriate to perform the disclosed methods or employ the disclosed compositions. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_1$-$C_{20}$ alkyl), 1 to 12 carbon atoms (i.e., $C_1$-$C_{12}$ alkyl), 1 to 8 carbon atoms (i.e., $C_1$-$C_8$ alkyl), 1 to 6 carbon atoms (i.e., $C_1$-$C_6$ alkyl), 1 to 4 carbon atoms (i.e., $C_1$-$C_4$ alkyl), or 1 to 3 carbon atoms (i.e., $C_1$-$C_3$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_2$-$C_6$ alkenyl) or 2 to 4 carbon atoms (i.e., $C_2$-$C_4$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_2$-$C_{20}$ alkynyl), 2 to 8 carbon atoms (i.e., $C_2$-$C_8$ alkynyl), 2 to 6 carbon atoms (i.e., $C_2$-$C_6$ alkynyl) or 2 to 4 carbon atoms (i.e., $C_2$-$C_4$ alkynyl). The term "alkynyl" also includes those groups having one triple bond and one double bond.

The term "alkylene" by itself or as part of another substituent means a divalent radical derived from an alkane, such as, methylene —CH$_2$—, ethylene —CH$_2$CH$_2$—, and the like. As an example, a "hydroxy-methylene" refers to HO—CH$_2$—*, where * is the attachment point to the molecule.

"Alkoxy" refers to the group "alkyl-O—" (e.g., $C_1$-$C_3$ alkoxy or $C_1$-$C_6$ alkoxy). Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkoxy-alkyl" refers to the group "-alkyl-alkoxy". The term "$C_1$-$C_3$ alkoxy-$C_1$-$C_3$ alkyl" refers to a one to three carbon alkyl chain where one hydrogen on any carbon is replaced by an alkoxy group having one to three carbons, in particular, one hydrogen on one carbon of the alkyl chain is replaced by an alkoxy group having one to three carbons. The term, "$C_1$-$C_6$ alkoxy-$C_1$-$C_3$ alkyl" refers to a one to three carbon alkyl chain where one hydrogen on any carbon is replaced by an alkoxy group having one to six carbons, in particular, one hydrogen on one carbon of the alkyl chain is replaced by an alkoxy group having one to six carbons. Non-limiting examples of alkoxy-alkyl are —CH$_2$OCH$_3$, —CH$_2$OC(CH$_3$)$_3$, and —C(CH$_3$)$_2$CH$_2$OCH$_3$.

"Alkylthio" refers to the group "alkyl-S—". "Alkylthio-alkyl" refers to the group -alkyl-S-alkyl, such as —C$_1$-C$_3$-alkyl-S—C$_1$-C$_3$ alkyl. A non-limiting example of alkylthio-alkyl is —CH$_2$CH$_2$SCH$_3$. "Alkylsulfinyl" refers to the group "alkyl-S(O)—". "Alkylsulfonyl" refers to the group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(NR$^y$)(NR$^z{}_2$), wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_6$-$C_{20}$ aryl), 6 to 12 carbon ring atoms (i.e., $C_6$-$C_{12}$ aryl), or 6 to 10 carbon ring atoms (i.e., $C_6$-$C_{10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclyl, the resulting ring system is heterocyclyl regardless of the point of attachment.

"Arylalkyl" or "Aralkyl" refers to the group "aryl-alkyl-", such as ($C_6$-$C_{10}$ aryl)-$C_1$-$C_3$ alkyl. As used herein, "($C_6$-$C_{10}$ aryl)-$C_1$-$C_3$ alkyl" refers to a one to three carbon alkyl chain where one of the hydrogen atoms on any carbon is replaced by an aryl group having six to ten carbon atoms, in particular, one hydrogen on one carbon of the alkyl chain is replaced by an aryl group having six to ten carbon atoms. A non-limiting example of arylalkyl is benzyl.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_3$-$C_{20}$ cycloalkyl), 3 to 12 ring carbon atoms (i.e., $C_3$-$C_{12}$ cycloalkyl), 3 to 10 ring carbon atoms (i.e., $C_3$-$C_{10}$ cycloalkyl), 3 to 8 ring carbon atoms (i.e., $C_3$-$C_8$ cycloalkyl), 3 to 7 ring carbon atoms (i.e., $C_3$-$C_7$ cycloalkyl), or 3 to 6 ring carbon atoms (i.e., $C_3$-$C_6$ cycloalkyl). Monocyclic groups include, for example, cyclopropyl, cyclobutyl, cyclopentyl, cyclohexyl, cycloheptyl and cyclooctyl. Polycyclic groups include, for example, bridged and/or fused rings, such as bicyclo[2.2.1]heptanyl, bicyclo[2.2.2]octanyl, bicyclo[1.1.1]pentan-1-yl, adamantyl, norbornyl, decalinyl, 7,7-dimethyl-bicyclo[2.2.1]heptanyl and the like. Further, the term cycloalkyl is intended to encompass any ring or ring system comprising a non-aromatic alkyl ring which may be fused to an aryl ring, regardless of the attachment to the remainder of the molecule. Further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-", such as ($C_3$-$C_6$ cycloalkyl)-$C_1$-$C_3$ alkyl. As used herein, "($C_3$-$C_6$ cycloalkyl)-$C_1$-$C_3$ alkyl" refers to a one to three carbon alkyl chain where one of the hydrogen atoms on any carbon is replaced by a cycloalkyl group having three to six carbon atoms, in particular, one hydrogen on one carbon of the chain is replaced by a cycloalkyl group having three to six carbon atoms.

"Cycloalkyl-alkoxy" refers to the group "-alkoxy-cycloalkyl" (e.g., $C_3$-$C_7$ cycloalkyl-$C_1$-$C_6$ alkoxy- or $C_3$-$C_7$ cycloalkyl-$C_1$-$C_3$ alkoxy-), such as —OCH$_2$-cyclopropyl. As used herein, "$C_3$-$C_7$ cycloalkyl-$C_1$-$C_6$ alkoxy" refers to an alkoxy group having a one to six carbon alkyl chain, wherein one of the hydrogen atoms on any carbon is replaced by a cycloalkyl group having three to seven carbon atoms, in particular, one hydrogen on one carbon of the chain is replaced by a cycloalkyl group having three to seven carbon atoms. As used herein, "$C_3$-$C_7$ cycloalkyl-$C_1$-$C_3$ alkoxy" refers to an alkoxy group having a one to three carbon alkyl chain, wherein one of the hydrogen atoms on any carbon is replaced by a cycloalkyl group having three to seven carbon atoms, in particular, one hydrogen on one carbon of the chain is replaced by a cycloalkyl group having three to seven carbon atoms.

"Guanidino" refers to —NR$^y$C(=NR$^z$)(NR$^y$R$^z$), wherein each R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Hydrazino" refers to —NHNH$_2$.

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro (fluorine), chloro (chlorine), bromo (bromine) or iodo (iodine).

"Haloalkyl" refers to an unbranched or branched alkyl group as defined above, wherein one or more (e.g., 1 to 6, or 1 to 3) hydrogen atoms are replaced by a halogen. For example, halo-$C_1$-$C_3$ alkyl refers to an alkyl group of 1 to 3 carbons wherein at least one hydrogen atom is replaced by a halogen. Where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6, or 1 to 3) hydrogen atoms are replaced by a halogen. Non-limiting examples of haloalkoxy are —$OCH_2CF_3$, —$OCF_2H$, and —$OCF_3$.

"Hydroxyalkyl" refers to an alkyl group as defined above, wherein one or more (e.g., 1 to 6, or 1 to 3) hydrogen atoms are replaced by a hydroxy group (e.g., hydroxy-$C_1$-$C_3$-alkyl, hydroxy-$C_1$-$C_6$-alkyl). The term "hydroxy-$C_1$-$C_3$ alkyl" refers to a one to three carbon alkyl chain where one or more hydrogens on any carbon is replaced by a hydroxy group, in particular, one hydrogen on one carbon of the chain is replaced by a hydroxy group. The term "hydroxy-$C_1$-$C_6$ alkyl" refers to a one to six carbon alkyl chain where one or more hydrogens on any carbon is replaced by a hydroxy group, in particular, one hydrogen on one carbon of the chain is replaced by a hydroxy group. Non-limiting examples of hydroxyalkyl include —$CH_2OH$, —$CH_2CH_2OH$, and —$C(CH_3)_2CH_2OH$.

"Hydroxyalkoxy" refers to the group "-alkoxy-hydroxy," (e.g., hydroxy-$C_1$-$C_3$ alkoxy, hydroxy-$C_1$-$C_6$ alkoxy). The term "hydroxy-$C_1$-$C_3$ alkoxy" refers to an alkoxy group containing a one to three carbon alkyl chain wherein one or more hydrogens on any carbon is replaced by a hydroxy group, in particular, one hydrogen on one carbon of the chain is replaced by a hydroxy group. The term "hydroxy-$C_1$-$C_6$ alkoxy" refers to an alkoxy group containing a one to six carbon alkyl chain wherein one or more hydrogens on any carbon is replaced by a hydroxy group, in particular, one hydrogen on one carbon of the chain is replaced by a hydroxy group. Non-limiting examples of hydroxyalkoxy include —$OCH_2CH_2OH$ and —$OCH_2C(CH_3)_2OH$.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. In certain embodiments, the heteroalkyl can have 1 to 3 carbon atoms (e.g., $C_1$-$C_3$ heteroalkyl) or 1 to 6 carbon atoms (e.g., $C_1$-$C_6$ heteroalkyl), and one or more (e.g., 1, 2, or 3) heteroatoms or heteroatomic groups. The term "heteroalkyl" includes unbranched or branched saturated chain having carbon and heteroatoms. By way of example, 1, 2 or 3 carbon atoms of the alkyl group in the "heteroalkyl" may be independently replaced with the same or different heteroatomic group. Heteroatomic groups include, but are not limited to, —$NR^y$—, —O—, —S—, —S(O)—, —$S(O)_2$—, and the like, wherein R is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.) and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where $R^y$ is hydrogen, alkyl, alkenyl, alkynyl, cycloalkyl, heterocyclyl, aryl, heteroalkyl, or heteroaryl; each of which may be optionally substituted, as defined herein). In certain embodiments, heteroalkyl can have 1 to 20 carbon atoms, 1 to 15 carbon atoms, 1 to 12 carbon atoms, 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_1$-$C_{20}$ heteroaryl), 3 to 12 ring carbon atoms (i.e., $C_3$-$C_{12}$ heteroaryl), or 3 to 8 carbon ring atoms (i.e., $C_3$-$C_8$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 9-10 membered ring systems (i.e., 9-10 membered heteroaryl), 5-10 membered ring systems (i.e., 5-10 membered heteroaryl), 5-7 membered ring systems (i.e., 5-7 membered heteroaryl), 5-6 membered ring systems (i.e., 5-6 membered heteroaryl), or 4-6 membered ring systems (i.e., 4-6 membered heteroaryl), each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring or ring system, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-", such as (5- to 10-membered monocyclic heteroaryl)-$C_1$-$C_3$ alkyl. As used, herein, "(5- to 10-membered monocyclic heteroaryl)-$C_1$-$C_3$ alkyl" refers to a one to three carbon alkyl chain where one or more hydrogens on any carbon is replaced by a monocyclic heteroaryl group having 5- to 10-members, in particular, one hydrogen on one carbon of the chain is replaced by a (5- to 10-membered monocyclic heteroaryl group.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro. Any non-aromatic ring containing at least one heteroatom is considered a heterocyclyl, regardless of the attachment (i.e., can be bound through a carbon atom or a heteroatom). Further, the term heterocyclyl is intended to encompass a ring or ring system comprising any non-aromatic ring containing at least one heteroatom, which ring may be fused to an aryl or heteroaryl ring, regardless of the attachment to the remainder of the molecule. The term heterocyclyl is also intended to encompass a ring system comprising a cycloalkyl ring which is fused to a heteroaryl ring, regardless of the attachment to the remainder of the molecule. Additionally, the term heterocyclyl is intended to encompass a ring system comprising a cycloalkyl ring which is fused to a heterocyclyl ring, regardless of the attachment to the remainder of the molecule. As used herein, heterocyclyl has 2 to 20 ring carbon atoms (i.e., $C_2$-$C_{20}$ heterocyclyl), 2 to 12 ring carbon atoms (i.e., $C_2$-$C_{12}$ heterocyclyl), 2 to 10 ring carbon atoms (i.e., $C_2$-$C_{10}$ heterocyclyl), 2 to 8 ring carbon atoms (i.e., $C_2$-$C_8$ heterocyclyl), 3 to 12 ring carbon atoms (i.e., $C_3$-$C_{12}$ heterocyclyl), 3 to 8 ring carbon atoms (i.e., $C_3$-$C_8$ heterocyclyl), or 3 to 6 ring carbon atoms (i.e., $C_3$-$C_6$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. When the heterocyclyl ring contains 4- to 6-ring atoms, it is also referred to herein as a 4- to 6-membered heterocyclyl. Also disclosed herein are 5- or 6-membered heterocyclyls, having 5 or 6 ring atoms, respectively, and 5- to 10-membered heterocyclyls, having 5 to 10 ring atoms. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. In certain embodiments, the term "heterocyclyl" can include "spiroheterocyclyl" when there are two positions for substitution on the same carbon atom. Examples of the spiroheterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

"Oxime" refers to the group —$CR^y$(=NOH) wherein $R^y$ is hydrogen, alkyl, alkenyl, alkynyl, cycloalkyl, heterocyclyl, aryl, heteroalkyl or heteroaryl; each of which may be optionally substituted, as defined herein.

"Oxo" refers to the group (=O).

"Sulfonyl" refers to the group —$S(O)_2R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —$S(O)R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, 1 to 4, or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5, 1 to 4, or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —$NHNH_2$, =$NNH_2$, imino, imido, hydroxy, oxo, oxime, nitro, sulfonyl, sulfinyl, alkylsulfonyl, alkylsulfinyl, thiocyanate, —$S(O)OH$, —$S(O)_2OH$, sulfonamido, thiol, thioxo, N-oxide or —$Si(R^y)_3$, wherein each $R^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5, 1 to 4, or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, —$OC(=O)NR^gR^h$, —$OR^g$, —$SR^g$, —$S(=O)R^g$, —$S(=O)_2R^g$, —$OS(=O)_{1-2}R^g$, —$S(=O)_{1-2}OR^g$, —$NR^gS(=O)_{1-2}NR^gR^h$, =$NSO_2R^g$, =$NOR^g$, —$S(=O)_{1-2}NR^gR^h$, —$SF_5$, —$SCF_3$ or —$OCF_3$. In certain embodiments, "substituted" also means any of the above groups in which one or more (e.g., 1 to 5, 1 to 4, or 1 to 3) hydrogen atoms are replaced with —$C(=O)R^g$, —$C(=O)OR^g$, —$C(=O)NR^gR^h$, —$CH_2SO_2R^g$, or —$CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5, 1 to 4, or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to four. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$ respectively. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^3H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term, "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) may be reduced in vivo to a —$CH_2OH$ moiety.

Use of the word "inhibitor," "inhibit" or "inhibition," herein refers to activity of a compound of Formula I or a pharmaceutically acceptable salt on ferroportin, unless specified otherwise. By "inhibit" herein is meant to decrease the activity of ferroportin, as compared to the activity of ferroportin in the absence of the compound. In some embodiments, the term "inhibit" means a decrease in ferroportin activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in ferroportin activity of about 5% to about 25%, about 25% to about 50%, about 50% to about 75%, or about 75% to 100%. In some embodiments, inhibit means a decrease in ferroportin activity of about 95% to 100%, e.g., a decrease in activity of 95%, 96%, 97%, 98%, 99%, or 100%. Such decreases can be measured using a variety of techniques that would be recognizable by one of skill in the art, including in vitro assays.

As used herein, the term "ferroportin inhibitor" and the like refers to a compound that reduces, inhibits, or otherwise diminishes one or more of the biological activities of ferroportin, for instance by inducing internalization of ferroportin. The activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of ferroportin compared to an appropriate control.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one of ordinary skill in the art.

When any variable or substituent occurs more than one time in any structure or formulae, its definition in each occurrence is independent of its definition at every other occurrence. Combinations of substituents and/or variables are permissible only if such combinations result in chemically stable compounds. It is understood that substituents and substitution patterns on the compounds described herein can be selected by one of ordinary skill in the art to provide compounds that are chemically stable and that can be readily synthesized by techniques known in the art as well as those methods set forth herein.

Additional definitions may also be provided below as appropriate.

II. Compounds

In certain embodiments, the subject matter described herein is directed to compounds of Formula I':

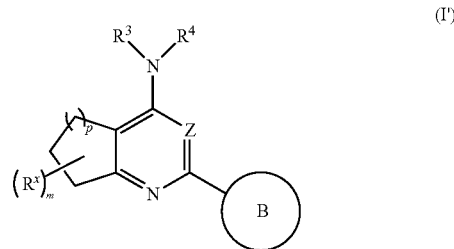

or a pharmaceutically acceptable salt thereof; wherein,
Z is N or CH;
Ring B is

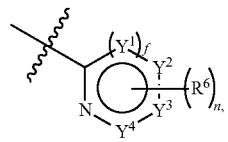

wherein ⸲ indicates the point of attachment to the remainder of the molecule;

$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_{10}$ alkoxy, hydroxy-$C_1$-$C_{10}$-alkyl, cyano, —$NR^GR^H$, halo-$C_1$-$C_3$ alkoxy, —O—($C_1$-$C_6$ alkyl)-$R^{bb}$, —O—$R^{bb}$, —($C_1$-$C_6$ alkyl)-$NR^{G1}R^{H1}$, —S—$C_1$-$C_3$ alkyl, —S—$C_1$-$C_3$ alkyl-$NR^{G1}R^{H1}$, halo-$C_1$-$C_3$ alkyl, —O—$R^{cc}$—O—$R^{dd}$, 5- to 7-membered monocyclic heteroaryl, and $C_3$-$C_6$ cycloalkyl; wherein, the alkyl moiety in hydroxy-$C_1$-$C_{10}$ alkoxy or —O—($C_1$-$C_6$ alkyl)-$R^{bb}$ is optionally substituted with cyano, hydroxy, hydroxy-$C_1$-$C_3$-alkyl, halogen, or $C_1$-$C_3$ alkoxy;

$R^{bb}$ is 4- to 7-membered monocyclic or bridged heterocyclyl, $C_3$-$C_7$ cycloalkyl, 5- or 6-membered monocyclic heteroaryl, —$SO_2$—$C_1$-$C_3$ alkyl, —S—$C_1$-$C_3$ alkyl, —C(O)$NR^{G1}R^{H1}$, or —$NR^GR^H$;

$R^{cc}$ is $C_1$-$C_3$ alkyl; and $R^{dd}$ is $C_1$-$C_3$ alkyl or a 6-membered heteroaryl;

wherein, said cycloalkyl, heterocyclyl, or heteroaryl of $R^6$, $R^{bb}$, or $R^{dd}$ is optionally substituted with one or two substituents, each independently selected from the group consisting of hydroxy, halogen, halo-$C_1$-$C_3$ alkyl, oxo, $C_1$-$C_3$ alkoxy, and $C_1$-$C_3$ alkyl;

$R^{G1}$ and $R^{H1}$ are each independently hydrogen or $C_1$-$C_3$ alkyl;

and, $R^G$ and $R^H$ are each independently hydrogen, —C(O) $R^{Ga}$, or optionally deuterated $C_1$-$C_3$ alkyl; wherein,
$R^{Ga}$ is $C_1$-$C_3$ alkyl or hydrogen;

or, two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- to 6-membered monocyclic heteroaryl fused with Ring B; wherein, said heterocyclyl, phenyl, cycloalkyl, or heteroaryl fused with ring B is optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl;

n is 0, 1, 2, or 3;

$Y^1$, $Y^2$, $Y^3$, and $Y^4$ are each independently selected from the group consisting of CH, N, NH, O, S, SH, S—$R^6$, N—$R^6$, and C—$R^6$, provided that 1 or 2 of $Y^1$, $Y^2$, $Y^3$, and $Y^4$ can be N, N—$R^6$, NH, O, SH or S—$R^6$;

f is 0 or 1;

p is 1 or 2;

$R^x$, in each instance, is halogen, $C_1$-$C_6$ alkyl, $C_1$-$C_3$ alkoxy, hydroxy, oxo, or cyano;

m is 0, 1, or 2;

$R^3$ is selected from the group consisting of hydrogen, optionally deuterated $C_1$-$C_3$ alkyl, hydroxy-$C_1$-$C_3$ alkyl, halo-$C_1$-$C_3$ alkyl, cyclopropyl, and phenyl;

$R^4$ is selected from the group consisting of:
i. (5- to 10-membered monocyclic or fused bicyclic heteroaryl)-$C_1$-$C_3$ alkyl, or (6- or 7-membered monocyclic heterocyclyl)-$C_1$-$C_3$ alkyl; wherein,
said heteroaryl or heterocyclyl is optionally substituted with one or two substituents, each independently selected from the group consisting of $C_6$-$C_{10}$ monocyclic or fused bicyclic aryl, $C_3$-$C_7$ cycloalkyl, 5- or 6-membered heteroaryl, —($C_1$-$C_3$ alkyl)-T, and 5- to 7-membered monocyclic heterocyclyl;
T is selected from the group consisting of $C_6$-$C_{10}$ monocyclic or fused bicyclic aryl, $C_3$-$C_7$ cycloalkyl, 5- or 6-membered heteroaryl, and 5- to 7-membered monocyclic heterocyclyl; and,
wherein T or said aryl, cycloalkyl, heteroaryl, or heterocyclyl substituent of $R^4$ is optionally substituted with one or two substituents, each individually selected from the group consisting of $C_1$-$C_3$ alkyl, halogen, and hydroxy; and
when p is 1, $C_1$-$C_3$ alkyl in the (5- to 10-membered monocyclic or fused bicyclic heteroaryl)-$C_1$-$C_3$ alkyl is linear;

and, ii.

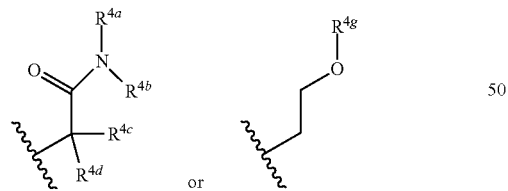

wherein,
$R^{4a}$ and $R^{4g}$ are each independently selected from the group consisting of hydrogen, $C_1$-$C_{10}$ alkyl, hydroxy-$C_1$-$C_6$ alkyl, halo-$C_1$-$C_3$ alkyl, $C_1$-$C_3$ alkoxy-$C_1$-$C_6$ alkyl, —$C_1$-$C_6$ alkyl-$NR^{J1}R^{J2}$, $C_3$-$C_7$ cycloalkyl, 4- to 10-membered monocyclic, fused bicyclic, bridged bicyclic, or spiro heterocyclyl, $C_6$-$C_{10}$ monocyclic or fused bicyclic aryl, 5- to 10-membered monocyclic or fused bicyclic heteroaryl, ($C_6$-$C_{10}$ monocyclic or fused bicyclic aryl)-$C_1$-$C_3$ alkyl, and (5- to 10-membered monocyclic or fused bicyclic heteroaryl)-$C_1$-$C_3$ alkyl;

$R^{J1}$ and $R^{J2}$ are independently hydrogen or $C_1$-$C_3$ alkyl;

wherein the cycloalkyl, heterocyclyl, aryl, heteroaryl, aryl-alkyl, or heteroaryl-alkyl of $R^{4a}$ or $R^{4g}$ is optionally substituted with one, two, or three substituents, each independently selected from the group consisting of halogen, $C_1$-$C_6$ alkyl, halo-$C_1$-$C_3$ alkyl, hydroxy, $C_1$-$C_3$ alkoxy, halo-$C_1$-$C_3$ alkoxy, oxo, $C_3$-$C_7$ cycloalkyl, and 5- to 10-membered monocyclic, fused bicyclic, or spiro heterocyclyl;

$R^{4b}$ is hydrogen or $C_1$-$C_6$ alkyl; or $R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy; or $R^{4b}$ and $R^{4c}$ taken together with the atom to which each is attached form a 5- to 7-membered monocyclic heterocyclyl optionally substituted with one, two, or three substituents, each independently selected from the group consisting of hydroxy, halogen, and $C_1$-$C_3$ alkyl; or $R^{4c}$ and $R^{4d}$ are each independently selected from the group consisting of hydrogen, $C_1$-$C_3$ alkoxy, hydroxy, $C_1$-$C_3$ alkyl-thio-$C_1$-$C_3$ alkyl, hydroxy-$C_1$-$C_6$ alkyl, $C_1$-$C_6$ alkoxy-$C_1$-$C_3$ alkyl, $C_3$-$C_7$ cycloalkyl, and $C_1$-$C_3$ alkyl; or $R^{4c}$ and $R^{4d}$ taken together with the atom to which each is attached form a $C_3$-$C_7$ cycloalkyl;

or, when p is 1, $R^3$ and $R^4$ taken together with the nitrogen atom to which each is attached can form a:
i. 7-membered fused bicyclic heterocyclyl, 7-membered bridged bicyclic heterocyclyl, or 7-membered monocyclic heterocyclyl containing one or two heteroatoms;
wherein when said 7-membered monocyclic heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and,
when said 7-membered monocyclic heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, halo-$C_1$-$C_3$ alkyl, and $C_6$-$C_{10}$ monocyclic or fused bicyclic aryl; and
wherein said aryl is optionally substituted with one or two substituents, each individually selected from the group consisting of $C_1$-$C_3$ alkoxy, hydroxy, halogen, and $C_1$-$C_3$ alkyl;
ii. 4- or 6-membered monocyclic heterocyclyl containing one heteroatom;
wherein said 4-membered monocyclic heterocyclyl is optionally substituted with one or two substituents, each independently selected from the group consisting of halogen, $C_1$-$C_3$ alkoxy, oxo, and —$(CH_2)_sC(=O)NR^kR^l$; wherein,
s is 0, 1, 2, or 3;
$R^k$ is hydrogen or $C_1$-$C_3$ alkyl; and
$R^l$ is selected from the group consisting of hydrogen, hydroxy, $C_1$-$C_3$ alkyl, $C_3$-$C_7$ cycloalkyl, and $C_6$-$C_{10}$ monocyclic or fused bicyclic aryl;

wherein said 6-membered monocyclic heterocyclyl is optionally substituted with one or two substituents, each independently selected from the group consisting of $C_1$-$C_3$ alkoxy, oxo, halogen, cyano, and —$NR^qR^w$; wherein, $R^q$ is hydrogen or $C_1$-$C_3$ alkyl; and $R^w$ is $C_6$-$C_{10}$ monocyclic or fused bicyclic aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy;

or, iii. 8-, 9-, 10- or 11-membered fused bicyclic heterocyclyl, or 12-membered bicyclic bridged and fused heterocyclyl, wherein said 8-, 9-, or 11-membered heterocyclyl contains one heteroatom and said 10- or 12-membered heterocyclyl contains one or two heteroatoms; and wherein said 10-, 11-, or 12-membered heterocyclyl is optionally substituted with one, two, or three substituents, each independently selected from the group consisting of halogen, $C_1$-$C_3$ alkyl, $C_1$-$C_3$ alkoxy, and hydroxy;

or, when p is 2, $R^3$ and $R^4$ taken together with the nitrogen atom to which each is attached can form a:

i. 6-membered monocyclic heterocyclyl containing one heteroatom, optionally substituted with one or two substituents, each independently selected from the group consisting of halogen, hydroxy-($C_1$-$C_6$ alkyl), hydroxy, oxo, and $C_1$-$C_3$ alkoxy; or ii. 4- or 7-membered monocyclic heterocyclyl containing one or two heteroatoms, or 7-, 8-, 9-, 10-, or 11-membered bridged bicyclic, fused bicyclic, or spiro heterocyclyl containing one, two, or three heteroatoms, optionally substituted with one or two substituents, each independently selected from the group consisting of halogen, oxo, cyano, $C_1$-$C_3$ alkyl, hydroxy, —$NR^GR^H$, and —$(CH_2)_sC(=O)NR^kR^l$;

provided that when the structure of Formula (I) is

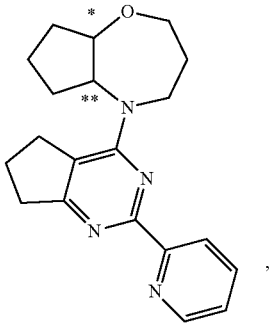

* is ⟋H and ** is ⟍H; or

* is ⟍H and ** is ⟋H;

and, wherein the compound of Formula (I) is not:
N-((1,4-dioxan-2-yl)methyl)-2-(pyridin-2-yl)-6,7-dihydro-5H-cyclopenta[d]pyrimidin-4-amine;

4-(piperidin-1-yl)-2-(pyridin-2-yl)-5,6,7,8-tetrahydroquinazoline;

4-(azepan-1-yl)-2-(6-propylpyridin-2-yl)-5,6,7,8-tetrahydroquinazoline;

1-propyl-4-(2-(pyridin-2-yl)-6,7-dihydro-5H-cyclopenta[d]pyrimidin-4-yl)-1,4-diazepan-2-one; or 2-(2-(pyridin-2-yl)-6,7-dihydro-5H-cyclopenta[d]pyrimidin-4-yl)-1,2-oxazepane; or a salt thereof.

In certain embodiments, the subject matter described herein is directed to compounds of Formula I':

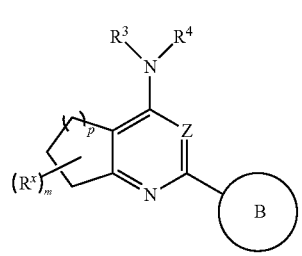

(I')

or a pharmaceutically acceptable salt thereof; wherein,

Z is N or CH;

Ring B is

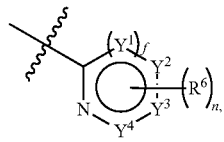

wherein ⁅ indicates the point of attachment to the remainder of the molecule;

$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$-alkyl, cyano, —$NR^GR^H$, halo-$C_1$-$C_3$ alkoxy, —O—$(CH_2)_u$—$R^{bb}$, halo-$C_1$-$C_3$ alkyl, —O—$R^{cc}$—O—$R^{dd}$, 5- to 7-membered monocyclic heteroaryl, and $C_3$-$C_6$ cycloalkyl; wherein, u is an integer from 0 to 6;

$R^{bb}$ is 4- to 7-membered monocyclic heterocyclyl, $C_3$-$C_7$ cycloalkyl, or —$NR^GR^H$;

$R^{cc}$ and $R^{dd}$ are each independently $C_1$-$C_3$ alkyl;

wherein, said cycloalkyl, heterocyclyl, or heteroaryl is optionally substituted with one or two substituents, each independently selected from the group consisting of hydroxy, $C_1$-$C_3$ alkoxy, and $C_1$-$C_3$ alkyl;

and, $R^G$ and $R^H$ are each independently hydrogen, —C(O)$R^{Ga}$, or $C_1$-$C_3$ alkyl; wherein, $R^{Ga}$ is $C_1$-$C_3$ alkyl or hydrogen;

or, two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- to 6-membered monocyclic heteroaryl fused with Ring B; wherein, said heterocyclyl, phenyl, cycloalkyl, or heteroaryl fused with ring B is optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl;

n is 0, 1, 2, or 3;

$Y^1$, $Y^2$, $Y^3$, and $Y^4$ are each independently selected from the group consisting of CH, N, NH, O, S, SH, S—$R^6$, N—$R^6$, and C—$R^6$, provided that 1 or 2 of $Y^1$, $Y^2$, $Y^3$, and $Y^4$ can be N, N—$R^6$, NH, O, SH or S—$R^6$;

f is 0 or 1;

p is 1 or 2;

$R^x$, in each instance, is halogen, $C_1$-$C_6$ alkyl, $C_1$-$C_3$ alkoxy, hydroxy, or cyano;

m is 0, 1, or 2;

$R^3$ is selected from the group consisting of hydrogen, $C_1$-$C_3$ alkyl, hydroxy-$C_1$-$C_3$ alkyl, cyclopropyl, and phenyl;

$R^4$ is selected from the group consisting of:
i. (5- to 10-membered monocyclic or fused bicyclic heteroaryl)-$C_1$-$C_3$ alkyl branched or linear, or (6- or 7-membered monocyclic heterocyclyl)-$C_1$-$C_3$ alkyl branched or linear; wherein,
said heteroaryl or heterocyclyl is optionally substituted with one or two substituents, each independently selected from the group consisting of $C_6$-$C_{10}$ monocyclic or fused bicyclic aryl, $C_3$-$C_7$ cycloalkyl, 5- or 6-membered heteroaryl, and 5- to 7-membered monocyclic heterocyclyl, and wherein said aryl, cycloalkyl, heteroaryl, or heterocyclyl is optionally substituted with one or two substituents, each individually selected from the group consisting of $C_1$-$C_3$ alkyl, halogen, and hydroxy; and,
when p is 1, $C_1$-$C_3$ alkyl in the (5- to 10-membered monocyclic or fused bicyclic heteroaryl)-$C_1$-$C_3$ alkyl is linear;
and,
ii.

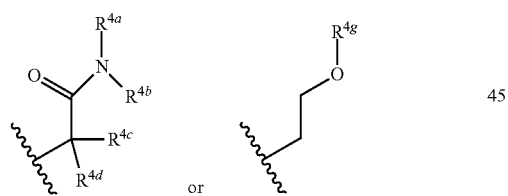

wherein,
$R^{4a}$ and $R^{4g}$ are each independently selected from the group consisting of hydrogen, $C_1$-$C_6$ alkyl, hydroxy-$C_1$-$C_6$ alkyl, $C_1$-$C_3$ alkoxy-$C_1$-$C_6$ alkyl, $C_3$-$C_7$ cycloalkyl, 5- to 10-membered monocyclic, fused bicyclic, bridged bicyclic, or spiro heterocyclyl, $C_6$-$C_{10}$ monocyclic or fused bicyclic aryl, 5- to 10-membered monocyclic or fused bicyclic heteroaryl, ($C_6$-$C_{10}$ monocyclic or fused bicyclic aryl)-$C_1$-$C_3$ alkyl, and (5- to 10-membered monocyclic or fused bicyclic heteroaryl)-$C_1$-$C_3$ alkyl;
wherein the cycloalkyl, heterocyclyl, aryl, heteroaryl, aryl-alkyl, or heteroaryl-alkyl of $R^{4a}$ or $R^{4g}$ is optionally substituted with one, two, or three substituents, each independently selected from the group consisting of halogen, $C_1$-$C_6$ alkyl, halo-$C_1$-$C_3$ alkyl, hydroxy, $C_1$-$C_3$ alkoxy, halo-$C_1$-$C_3$ alkoxy, oxo, $C_3$-$C_7$ cycloalkyl, and 5- to 10-membered monocyclic, fused bicyclic, or spiro heterocyclyl;
$R^{4b}$ is hydrogen or $C_1$-$C_6$ alkyl; or
$R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy; or
$R^{4b}$ and $R^{4c}$ taken together with the atom to which each is attached form a 5- to 7-membered monocyclic heterocyclyl optionally substituted with one, two, or three substituents, each independently selected from the group consisting of hydroxy, halogen, and $C_1$-$C_3$ alkyl; or
$R^{4c}$ and $R^{4d}$ are each independently selected from the group consisting of hydrogen, $C_1$-$C_3$ alkoxy, hydroxy, $C_1$-$C_3$ alkyl-thio-$C_1$-$C_3$ alkyl, hydroxy-$C_1$-$C_6$ alkyl, $C_1$-$C_6$ alkoxy-$C_1$-$C_3$ alkyl, $C_3$-$C_7$ cycloalkyl, and $C_1$-$C_3$ alkyl; or
$R^{4c}$ and $R^{4d}$ taken together with the atom to which each is attached form a $C_3$-$C_7$ cycloalkyl;

or, when p is 1,
$R^3$ and $R^4$ taken together with the nitrogen atom to which each is attached can form a:
i. 7-membered fused bicyclic heterocyclyl, 7-membered bridged bicyclic heterocyclyl, or 7-membered monocyclic heterocyclyl containing one or two heteroatoms;
wherein when said 7-membered monocyclic heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and,
when said 7-membered monocyclic heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, halo-$C_1$-$C_3$ alkyl, and $C_6$-$C_{10}$ monocyclic or fused bicyclic aryl; and
wherein said aryl is optionally substituted with one or two substituents, each individually selected from the group consisting of $C_1$-$C_3$ alkoxy, hydroxy, halogen, and $C_1$-$C_3$ alkyl;
ii. 4- or 6-membered monocyclic heterocyclyl containing one heteroatom;
wherein said 4-membered monocyclic heterocyclyl is optionally substituted with one or two substituents, each independently selected from the group consisting of halogen, $C_1$-$C_3$ alkoxy, oxo, and —$(CH_2)_s$C(=O)$NR^kR^l$; wherein,
s is 0, 1, 2, or 3;
$R^k$ is hydrogen or $C_1$-$C_3$ alkyl; and
$R^l$ is selected from the group consisting of hydrogen, hydroxy, $C_1$-$C_3$ alkyl, $C_3$-$C_7$ cycloalkyl, and $C_6$-$C_{10}$ monocyclic or fused bicyclic aryl;
wherein said 6-membered monocyclic heterocyclyl is optionally substituted with one or two substituents, each independently selected from the group consisting of $C_1$-$C_3$ alkoxy, oxo, halogen, cyano, and —$NR^qR^w$; wherein,
$R^q$ is hydrogen or $C_1$-$C_3$ alkyl; and
$R^w$ is $C_6$-$C_{10}$ monocyclic or fused bicyclic aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy;

or, iii. 8-, 9-, 10- or 11-membered fused bicyclic heterocyclyl, or 12-membered bicyclic bridged and fused heterocyclyl, wherein said 8-, 9-, or 11-membered heterocyclyl contains one heteroatom and said 10- or 12-membered heterocyclyl contains one or two heteroatoms; and wherein said 10-, 11-, or 12-membered heterocyclyl is optionally substituted with one, two, or three substituents, each independently selected from the group consisting of halogen, $C_1$-$C_3$ alkyl, $C_1$-$C_3$ alkoxy, and hydroxy;

or, when p is 2, $R^3$ and $R^4$ taken together with the nitrogen atom to which each is attached can form a:

i. 6-membered monocyclic heterocyclyl containing one heteroatom, optionally substituted with one or two substituents, each independently selected from the group consisting of halogen, hydroxy-($C_1$-$C_6$ alkyl), hydroxy, oxo, and $C_1$-$C_3$ alkoxy; or ii. 4- or 7-membered monocyclic heterocyclyl containing one or two heteroatoms, or 7-, 8-, 9-, 10-, or 11-membered bridged bicyclic, fused bicyclic, or spiro heterocyclyl containing one, two, or three heteroatoms, optionally substituted with one or two substituents, each independently selected from the group consisting of halogen, oxo, cyano, $C_1$-$C_3$ alkyl, hydroxy, —$NR^GR^H$, and —$(CH_2)_sC(=O)NR^kR^l$;

provided that when the structure of Formula (I) is

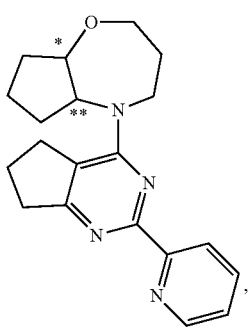 [SMILES: c1ccc(-c2nc3c(c(N4CCCOC5CCCC54)n2)CCC3)nc1]

* is ![wedge] and ** is ![hash] H; or
* is ![hash] and ** is ![hash] H;

and, wherein the compound of Formula (I) is not:

N-((1,4-dioxan-2-yl)methyl)-2-(pyridin-2-yl)-6,7-dihydro-5H-cyclopenta[d]pyrimidin-4-amine;

4-(piperidin-1-yl)-2-(pyridin-2-yl)-5,6,7,8-tetrahydroquinazoline;

4-(azepan-1-yl)-2-(6-propylpyridin-2-yl)-5,6,7,8-tetrahydroquinazoline;

1-propyl-4-(2-(pyridin-2-yl)-6,7-dihydro-5H-cyclopenta[d]pyrimidin-4-yl)-1,4-diazepan-2-one; or 2-(2-(pyridin-2-yl)-6,7-dihydro-5H-cyclopenta[d]pyrimidin-4-yl)-1,2-oxazepane; or a salt thereof.

In certain embodiments, the subject matter described herein is directed to compounds of Formula I:

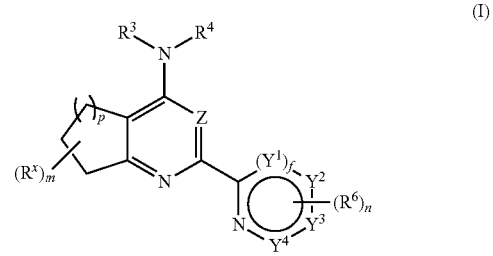

(I)

wherein,

Z is N or CH;

$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$-alkyl, cyano, $C_3$-$C_7$ cycloalkyl-$C_1$-$C_3$ alkoxy, $NR^GR^H$, halo-$C_1$-$C_3$ alkoxy, and $C_3$-$C_6$ cycloalkyl;

wherein $R^G$ and $R^H$ are each independently hydrogen or $C_1$-$C_3$ alkyl;

or, wherein two $R^6$ groups, taken together with the atom to which each is attached, form a 5- or 6-membered heterocyclyl, $C_3$-$C_7$ cycloalkyl, $C_6$-$C_{10}$ aryl, or 5- to 10-membered heteroaryl;

n is 0, 1, 2, or 3;

$Y^1$, $Y^2$, $Y^3$, and $Y^4$ are each independently selected from the group consisting of CH, N, NH, O, S, and C (when $R^6$ is attached thereto), provided that 1 or 2 of $Y^1$, $Y^2$, $Y^3$, and $Y^4$ can be N, NH, O, or S;

f is 0 or 1;

p is 1 or 2;

$R^x$, in each instance, is halogen, $C_1$-$C_6$ alkyl, $C_1$-$C_3$ alkoxy, hydroxy, or cyano;

m is 0, 1, or 2;

$R^3$ is selected from the group consisting of hydrogen, $C_1$-$C_3$ alkyl, hydroxy-$C_1$-$C_3$-alkyl, cyclopropyl, and phenyl;

$R^4$ is selected from the group consisting of:

i. (5- to 10-membered monocyclic or bicyclic fused heteroaryl)-$C_1$-$C_3$ alkyl branched or linear, or (6- or 7-membered monocyclic heterocyclyl)-$C_1$-$C_3$ alkyl branched or linear;

wherein, when p is 1, $C_1$-$C_3$ alkyl in (5- to 10-membered monocyclic or bicyclic fused heteroaryl)-$C_1$-$C_3$ alkyl is linear;

and, ii.

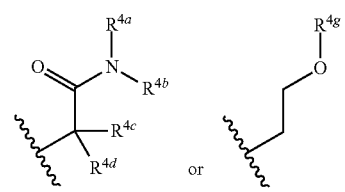

wherein, $R^{4a}$ and $R^{4g}$ are each independently selected from the group consisting of hydrogen, $C_1$-$C_6$ alkyl, hydroxy- $C_1$-$C_6$ alkyl, $C_1$-$C_3$ alkoxy-$C_1$-$C_6$ alkyl, $C_3$-$C_7$ cycloalkyl, 5- to 10-membered monocyclic, bicyclic fused, or spiro heterocyclyl, $C_6$-$C_{10}$ aryl, 5- to 10-membered monocyclic or bicyclic fused heteroaryl, ($C_6$-$C_{10}$ aryl)-$C_1$-$C_3$ alkyl, and (5- to 10-membered monocyclic heteroaryl)-$C_1$-$C_3$ alkyl;

wherein the cycloalkyl, heterocyclyl, aryl, heteroaryl, arylalkyl, or heteroaryl-alkyl of $R^{4a}$ or $R^{4g}$ is optionally substituted with one, two, or three substituents, each independently selected from the group consisting of halogen, $C_1$-$C_6$ alkyl, haloalkyl, hydroxy, $C_1$-$C_3$ alkoxy, oxo, $C_3$-$C_7$ cycloalkyl, and 5- to 10-membered monocyclic, bicyclic fused, or spiro heterocyclyl;

$R^{4b}$ is hydrogen or $C_1$-$C_6$ alkyl;

or, $R^{4a}$ and $R^{4b}$ taken together with the atom to which each is attached form a 5- to 7-membered heterocyclyl;

or, $R^{4b}$ and $R^{4c}$ taken together with the atom to which each is attached form a 5- to 7-membered heterocyclyl optionally substituted with one, two, or three substituents, each independently selected from the group consisting of hydroxy, halo, and $C_1$-$C_3$ alkyl;

$R^{4c}$ and $R^{4d}$ are each independently selected from the group consisting of hydrogen, $C_1$-$C_3$ alkoxy, hydroxy, $C_1$-$C_3$ alkyl-thio-$C_1$-$C_3$ alkyl, hydroxy-$C_1$-$C_6$ alkyl, $C_1$-$C_6$ alkoxy-$C_1$-$C_3$ alkyl, $C_3$-$C_7$ cycloalkyl, and $C_1$-$C_3$ alkyl;

or, $R^{4c}$ and $R^{4d}$ taken together with the atom to which each is attached form a $C_3$-$C_7$ cycloalkyl;

or, when p is 1, $R^3$ and $R^4$ taken together with the nitrogen atom to which each is attached can form a:

i. 7-membered bicyclic fused heterocyclyl, 7-membered bridged heterocyclyl, or 7-membered monocyclic heterocyclyl containing one or two heteroatoms;

wherein when said 7-membered monocyclic heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and when said 7-membered monocyclic heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, haloalkyl, and $C_6$-$C_{10}$ aryl; and wherein said aryl is optionally substituted with one or two substituents, each individually selected from the group consisting of $C_1$-$C_3$ alkoxy, hydroxy, halogen, and $C_1$-$C_3$ alkyl;

ii. 4- or 6-membered monocyclic heterocyclyl containing one heteroatom;

wherein said 4-membered monocyclic heterocyclyl is optionally substituted with one or two substituents, each independently selected from the group consisting of halogen, $C_1$-$C_3$ alkoxy, oxo, and —$(CH_2)_sC(=O)NR^kR^l$;

wherein s is 0, 1, 2, or 3;

$R^k$ is hydrogen or $C_1$-$C_3$ alkyl; and $R^l$ is selected from the group consisting of hydrogen, hydroxy, $C_1$-$C_3$ alkyl, $C_3$-$C_7$ cycloalkyl, and $C_6$-$C_{10}$ aryl;

wherein said 6-membered monocyclic heterocyclyl is optionally substituted with one or two substituents, each independently selected from the group consisting of $C_1$-$C_3$ alkoxy, oxo, halogen, cyano, and $NR^qR^w$;

wherein $R^q$ is hydrogen or $C_1$-$C_3$ alkyl and $R^w$ is $C_6$-$C_{10}$ aryl or $C_3$-$C_7$ cycloalkyl, and wherein said aryl or cycloalkyl is optionally substituted with one or two substituents, each independently selected from the group consisting of halogen, $C_1$-$C_3$ alkyl, hydroxy, and $C_1$-$C_3$ alkoxy;

iii. 8-, 9-, 10- or 11-membered bicyclic fused heterocyclyl, or 12-membered bicyclic bridged, fused heterocyclyl, wherein said 8-, 9-, or 11-membered heterocyclyl contains one heteroatom and said 10- or 12-membered heterocyclyl contains one or two heteroatoms; and wherein said 10-, 11-, or 12-membered heterocyclyl is optionally substituted with one, two, or three substituents, each independently selected from the group consisting of halogen, $C_1$-$C_3$ alkyl, $C_1$-$C_3$ alkoxy, and hydroxy;

or, when p is 2, $R^3$ and $R^4$ taken together with the nitrogen atom to which each is attached can form a:

i. 6-membered monocyclic heterocyclyl containing one heteroatom, optionally with one or two substituents, each independently selected from the group consisting of halogen, hydroxy-($C_1$-$C_6$ alkyl), hydroxy, oxo, and $C_1$-$C_3$ alkoxy; or ii. 4- or 7-membered monocyclic heterocyclyl containing one or two heteroatoms, or 7-, 8-, 9, 10-, or 11-membered bicyclic bridged, fused, or spiro heterocyclyl containing one, two, or three heteroatoms, optionally substituted with one or two substituents, each independently selected from the group consisting of halogen, oxo, cyano, $C_1$-$C_3$ alkyl, hydroxy, $NR^GR^H$, and —$(CH_2)_sC(=O)NR^kR^l$;

provided that when the structure of Formula (I) is

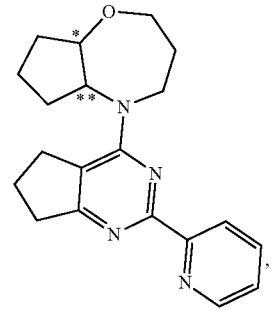 [SMILES: c1ccc(-c2nc3c(c(N4CCCOC5CCCC54)n2)CCC3)nc1]

* is ▲ and ** is ⟋H; or * is ⟋ and ** is ⟋H;

or a pharmaceutically acceptable salt thereof; and wherein the compound of Formula (I) is not:

N-((1,4-dioxan-2-yl)methyl)-2-(pyridin-2-yl)-6,7-dihydro-5H-cyclopenta[d]pyrimidin-4-amine;

4-(piperidin-1-yl)-2-(pyridin-2-yl)-5,6,7,8-tetrahydroquinazoline;

4-(azepan-1-yl)-2-(6-propylpyridin-2-yl)-5,6,7,8-tetrahydroquinazoline;

1-propyl-4-(2-(pyridin-2-yl)-6,7-dihydro-5H-cyclopenta[d]pyrimidin-4-yl)-1,4-diazepan-2-one; or 2-(2-(pyridin-2-yl)-6,7-dihydro-5H-cyclopenta[d]pyrimidin-4-yl)-1,2-oxazepane; or a salt thereof.

Useful compounds of Formula I' or I include those where p is 1.

Useful compounds of Formula I' or I include those where Z is N.

The integer n will decrease by one each time a compound of Formula I' or I contains a variable C—R$^6$, N—R$^6$, or S—R$^6$, and the total number of n (the total number of C—R$^6$, N—R$^6$, or S—R$^6$ cannot exceed 3).

Useful compounds of Formula I' or I include those where Y$^1$, Y$^2$, Y$^3$, and Y$^4$ are each CH or C—R$^6$. In certain embodiments, useful compounds of Formula I' or I include those where Y$^1$ is CH Y$^2$ is C—R$_6$, and Y$^3$, and Y$^4$ are each CH. Useful compounds of Formula I' or I include those where Y$^3$ is N and Y$^1$, Y$^2$, and Y$^4$ are each CH or C—R$^6$. Useful compounds of Formula I' or I include those where Y$^2$ is N and Y$^1$, Y$^3$, Y$^4$ are each CH or C—R$^6$. Useful compounds of Formula I' or I include those where Y$^1$ is N and Y$^2$, Y$^3$, and Y$^4$ are each CH or C—R$^6$. Useful compounds of Formula I' or I include those where Y$^1$ is CH, Y$^2$ is C—R$^6$, Y$^3$ is CH, and Y$^4$ is CH.

Useful compounds of Formula I' or I include those where R$^6$, in each instance, is selected from the group consisting of halogen, hydroxy, C$_1$-C$_3$ alkoxy, C$_1$-C$_3$ alkyl, C$_1$-C$_3$ alkoxy-C$_1$-C$_3$ alkyl, hydroxy-C$_1$-C$_6$ alkoxy, hydroxy-C$_1$-C$_3$-alkyl, —O—(CH$_2$)$_u$—R$^{bb}$, halo-C$_1$-C$_3$ alkoxy, —O—R$^{cc}$—O—R$^{dd}$, halo- C$_1$—C$_3$ alkyl, hydroxy-C$_1$-C$_{10}$-alkyl, —O—(C$_1$-C$_6$ alkyl)-R$^{bb}$, —O—R$^{bb}$, —S—C$_1$-C$_3$ alkyl, —S—C$_1$-C$_3$ alkyl-NR$^{G1}$R$^{H1}$ and —NR$^G$R$^H$; wherein, the alkyl moiety in hydroxy-C$_1$-C$_{10}$ alkoxy or —O—(C$_1$-C$_6$ alkyl)-R$^{bb}$ is optionally substituted with cyano, hydroxy, hydroxy-C$_1$-C$_3$-alkyl, halogen, or C$_1$-C$_3$ alkoxy; R$^{bb}$ is —NR$^G$R$^H$; u is an integer from 1 to 3; R$^G$ and R$^H$ are each independently hydrogen or C$_1$-C$_3$ alkyl; and R$^{cc}$ and R$^{dd}$ are each independently C$_1$-C$_3$ alkyl. Useful compounds of Formula I' or I include those where R$^6$, in each instance, is selected from the group consisting of methoxy, ethoxy, methyl, fluoro, chloro, ethyl, —N(CH$_3$)$_2$, hydroxy, —OCH$_2$CH$_2$OH, —CH$_2$OH, —CH$_2$OCH$_3$, —OCH$_2$CH$_2$NH$_2$, —OCH$_2$CH$_2$N(CH$_3$)$_2$, —OCH$_2$C(CH$_3$)$_2$O H, —OCH$_2$CF$_3$, —OCHF$_2$, —OCF$_3$, —OCH$_2$CH$_2$OCH$_3$, —OCH$_2$CH$_2$F, —OC(CH$_3$)$_2$CH$_2$OH, —OCH$_2$CH(CH$_3$)O H, —OCH$_2$CH$_2$NHC(O)CH$_3$, —OC(CH$_3$)$_2$CH$_2$N(CH$_3$)$_2$, —OCH(CH$_3$)CH$_2$OH, —OCH$_2$CH(CH(CH$_3$)$_2$)OH, —OCH$_2$CH(CH$_2$CH$_3$)OH, —OCH$_2$C(CH$_2$CH$_3$)$_2$OH, —OCH$_2$CH$_2$N(CH$_2$CH$_3$)$_2$, —OCH(CH$_3$)CH$_2$N(CH$_3$)$_2$, —OCH$_2$C(O)N(CH$_3$)$_2$, —OCH$_2$C(CH$_3$)$_2$N(CH$_3$)$_2$, —OCH$_2$CH(CH$_2$OH)OH, —OCH$_2$CH$_2$NH(CH$_3$), —OCH$_2$CH(CF$_3$)OH, —OCH$_2$C(CH$_3$)(CH$_2$CH$_3$)OH, —OCH$_2$CH(CH$_2$OCH$_3$)OH, —OCH$_2$CH(CH$_2$F)OH, —(CH$_2$)$_3$N(CH$_3$)$_2$, —(CH$_2$)$_3$N(CH$_3$)H, —O(CH$_2$)$_2$S(O)$_2$CH$_3$, —O(CH$_2$)$_2$SCH$_3$, —(CH$_2$)$_2$C(CH$_3$)$_2$OH, and —CH$_2$CH$_2$OH. Further, useful compounds of Formula I' or I include those where R$^6$, in each instance, is methoxy, —OCH$_2$CH$_2$N(CH$_3$)$_2$, —OCH$_2$CH$_2$OH, or —OCH$_2$C(CH$_3$)$_2$OH. Useful compounds of Formula I' or I include those where R$^6$, in each instance, is selected from the group consisting of —O—(CH$_2$)$_u$—R$^{bb}$, and C$_3$-C$_6$ cycloalkyl; wherein, u is an integer from 0 to 3; R$^{bb}$ is 4- to 7-membered monocyclic heterocyclyl or C$_3$-C$_7$ cycloalkyl; and wherein said cycloalkyl or heterocyclyl is optionally substituted with one or two substituents, each independently selected from the group consisting of hydroxy, C$_1$-C$_3$ alkoxy, and C$_1$-C$_3$ alkyl. Useful compounds of Formula I' or I include those where R$^6$, in each instance, is selected from the group consisting of cyclopropyl and —O—(CH$_2$)$_u$—R$^{bb}$; wherein, u is 0, 1, or 2; and R$^{bb}$ is selected from the group consisting of cyclopropyl, cyclobutyl, tetrahydrofuranyl, oxetanyl, and pyrrolidinyl, each optionally substituted with hydroxy or methyl. Useful compounds of Formula I' or I include those where R$^6$, in each instance, is selected from the group consisting of

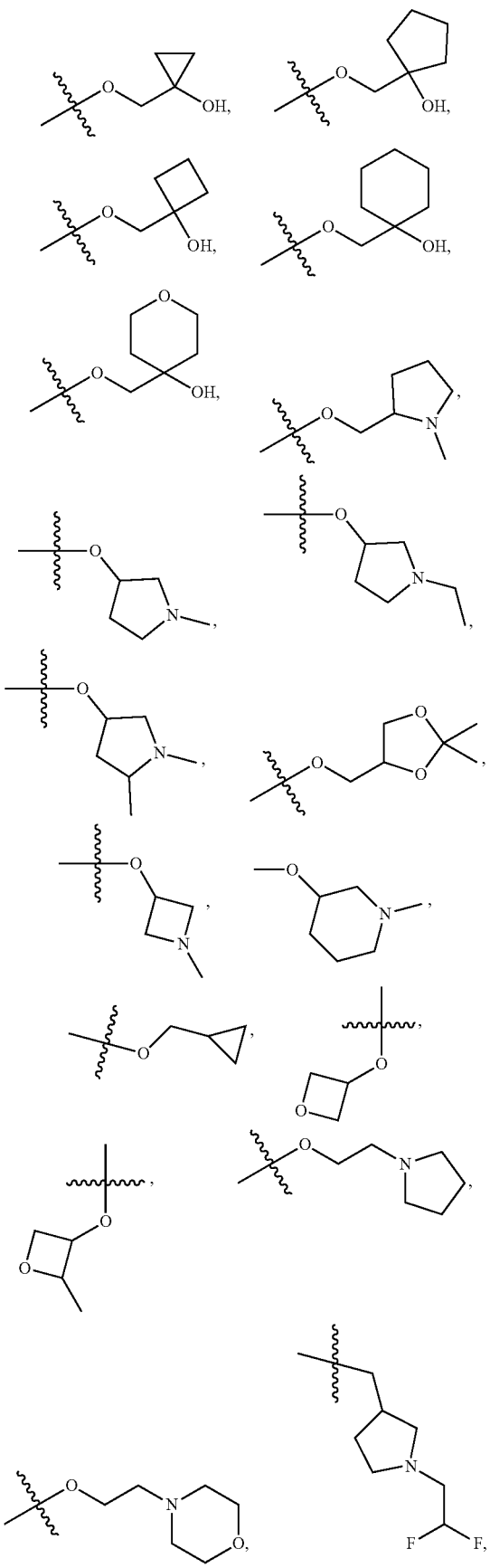

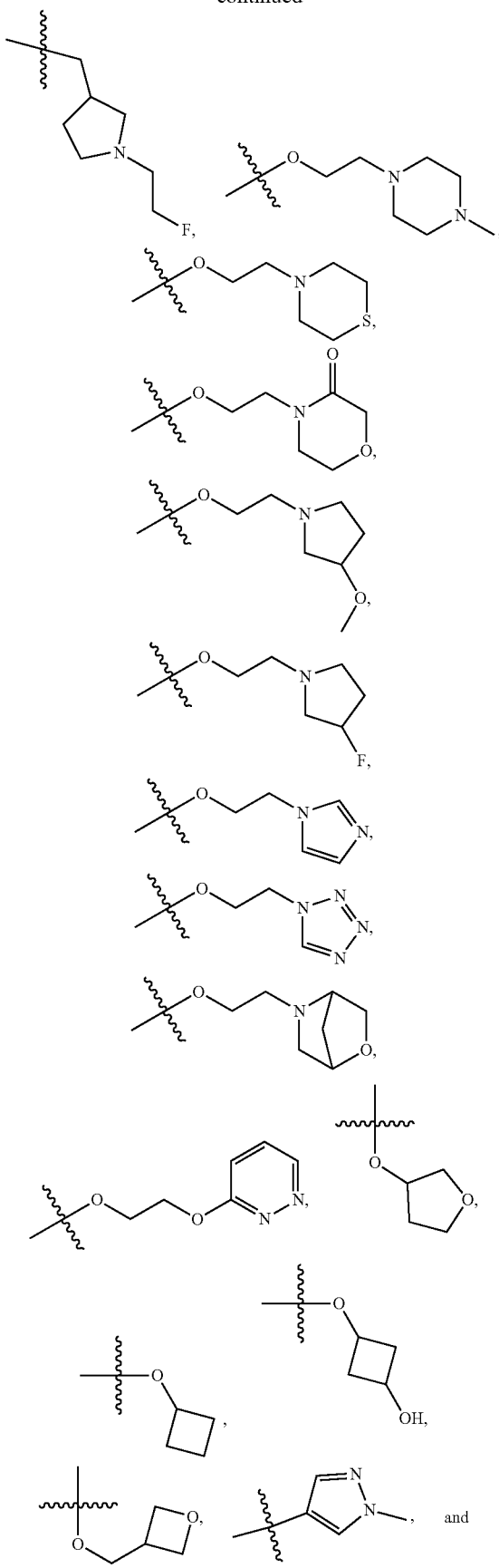

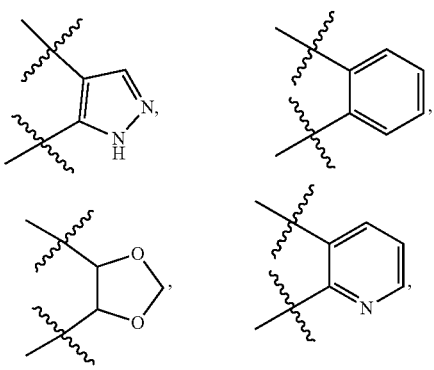

where ⌇ indicates the point of attachment to Ring B. Useful compounds of Formula I' or I include those where $R^6$ is Useful compounds of Formula I' or I include those where two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- or 6-membered monocyclic heteroaryl fused with Ring B, each optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl. Useful compounds of Formula I' or I include those where two $R^6$ groups, taken together with the atom to which each is attached, form a pyrazolyl, dioxanyl, pyridinyl, pyrimidinyl, thiazolyl, furanyl, dioxolanyl, or phenyl ring fused with Ring B, wherein said ring is optionally substituted with one substituent selected from the group consisting of hydroxy, methoxy, tetrahydropyranyl, —CH$_2$OH, and methyl. Useful compounds of Formula I' or I include those where two vicinal $R^6$ groups, taken together with the atom to which each is attached, form a ring selected from the group consisting of

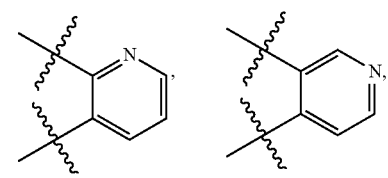

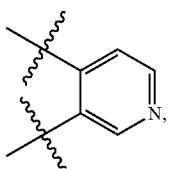

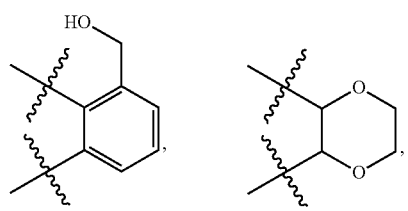

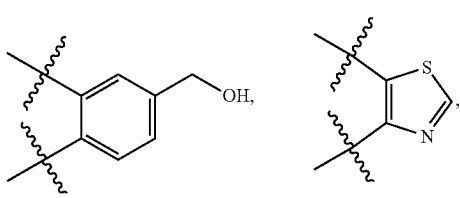

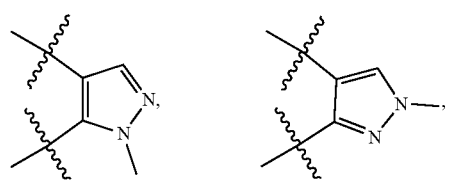

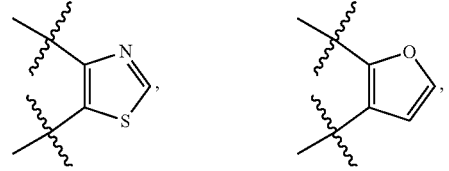

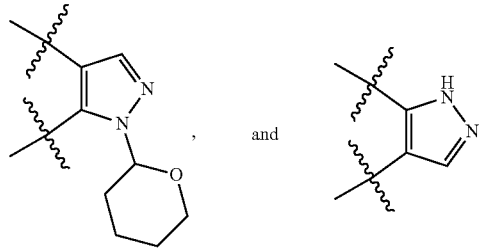

fused with ring B, wherein the pair of ⸺ represent the attachment of the ring with Ring B. Useful compounds of Formula I' or I include those where two vicinal $R^6$ groups, taken together with the atom to which each is attached, form a form a ring selected from the group consisting of

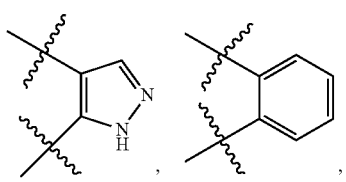

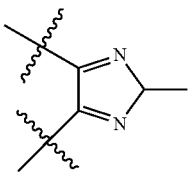

fused with Ring B. Useful compounds of Formula I' or Formula I include those where two vicinal $R^6$ groups taken together with the atom to which each is attached form a ring fused with Ring B, where the bicyclic ring formed by Ring B and the two vicinal $R^6$ groups is selected from the group consisting of

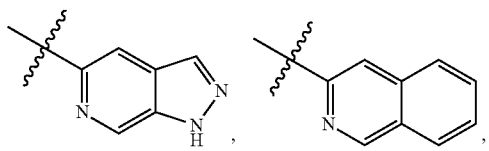

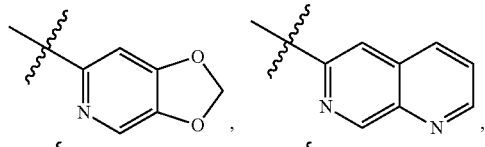

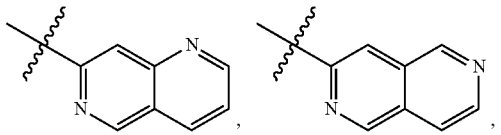

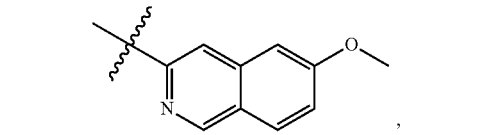

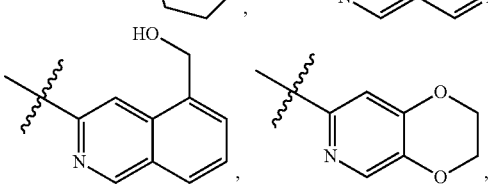

-continued

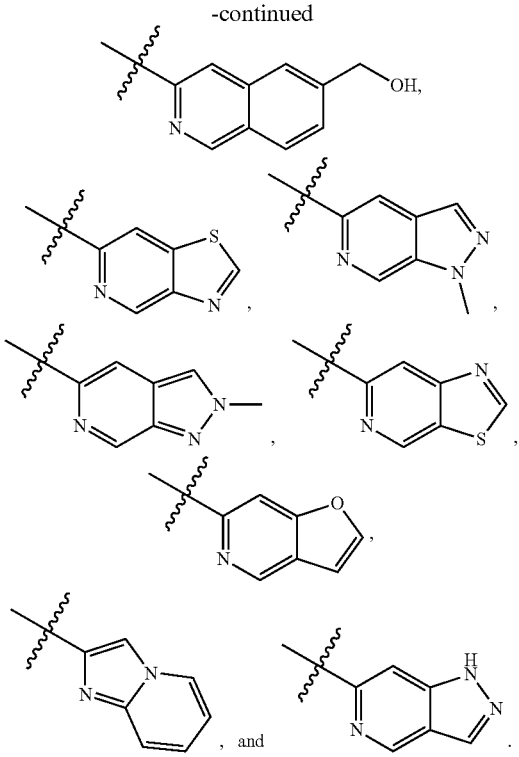

Useful compounds of Formula I' or Formula I include those where f is 1. Useful compounds of Formula I' or Formula I include those where f is 0, and Ring B is

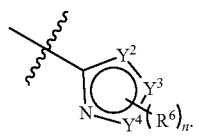

Useful compounds of Formula I' or Formula I include those where Ring B is

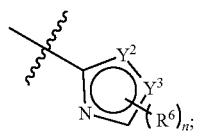

wherein, n is 0 or 1; and $Y^2$ and $Y^3$ are each independently selected from the group consisting of CH, N, NH, $NR^6$, S, O, and $CR^6$, provided that only one of $Y^2$ and $Y^3$ can be N, NH, $NR^6$, S, or O. Useful compounds of Formula I' or Formula I include those where Ring B is selected from the group consisting of

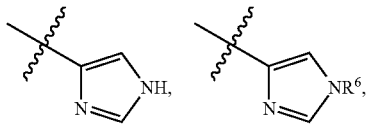

-continued

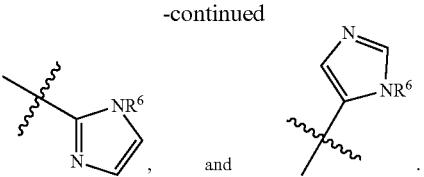

Useful compounds of Formula I' or Formula I include those where $R^6$, in each instance, is selected from the group consisting of $C_1$-$C_3$ alkyl and hydroxy-$C_1$-$C_3$ alkyl. Useful compounds of Formula I' or Formula I include those where $R^6$, in each instance, is selected from the group consisting of methyl, ethyl, n-propyl, —$CH_2CH_2OH$, and —$CH_2CH_2CH_2OH$.

Useful compounds of Formula I' or Formula I include those where n is 1. Useful compounds of Formula I' or Formula I include those where n is 0. Useful compounds of Formula I' or Formula I include those where n is 2, wherein one $R^6$ is selected from the group consisting of methyl and methoxy and the other $R^6$ is selected from the group consisting of methyl, methoxy, halogen, and —$OCH_2CH_2OH$.

Useful compounds of Formula I' or Formula I include those where $R^3$ is selected from the group consisting of hydrogen, methyl, ethyl, phenyl, and —$CH_2CH_2OH$. Useful compounds of Formula I' or Formula I include those where $R^3$ is selected from the group consisting of hydrogen, methyl, —$CD_3$, ethyl, phenyl, —$CH_2CF_3$, and —$CH_2CH_2OH$. Useful compounds of Formula I' or Formula I include those where $R^3$ is methyl.

Useful compounds of Formula I' or Formula I include those where $R^4$ is a (5- to 10-membered monocyclic or fused bicyclic heteroaryl)-methyl, wherein said heteroaryl is optionally substituted with one or two substituents, each independently selected from the group consisting of phenyl, $C_3$-$C_7$ cycloalkyl, and 5- to 7-membered monocyclic heterocyclyl, and wherein said phenyl, cycloalkyl, or heterocyclyl is optionally substituted with one or two substituents, each individually selected from the group consisting of $C_1$-$C_3$ alkyl, halogen, and hydroxy. Useful compounds of Formula I' or Formula I include those where $R^4$ is a (6-membered heteroaryl)-methyl, wherein at least one of the ring atoms ortho to the attachment point in said 6-membered heteroaryl is a nitrogen. Useful compounds of Formula I' or Formula I include those where $R^4$ is selected from the group consisting of pyridinyl-methyl, pyrimidinyl-methyl, benzoxazole-methyl, oxazolyl-methyl, and triazolyl-methyl, each optionally substituted with phenyl or benzyl, and wherein said phenyl is optionally substituted with one substituent selected from the group consisting of fluoro, methyl, and chloro. Useful compounds of Formula I' or Formula I include those where $R^4$ is selected from the group consisting of

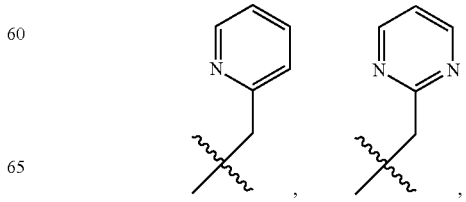

-continued

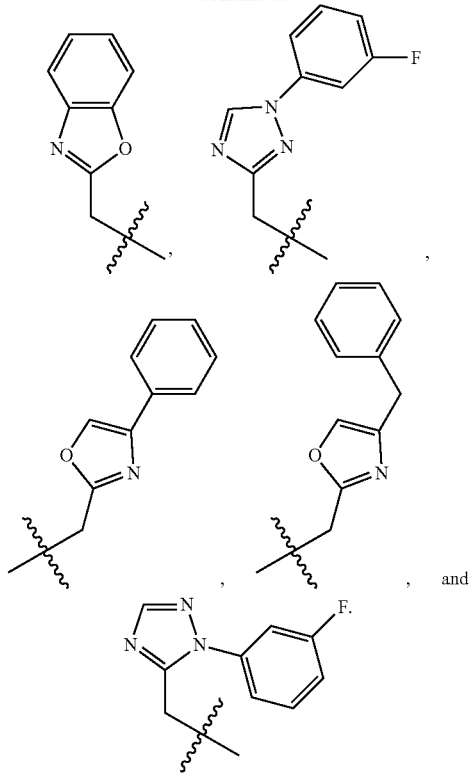

,

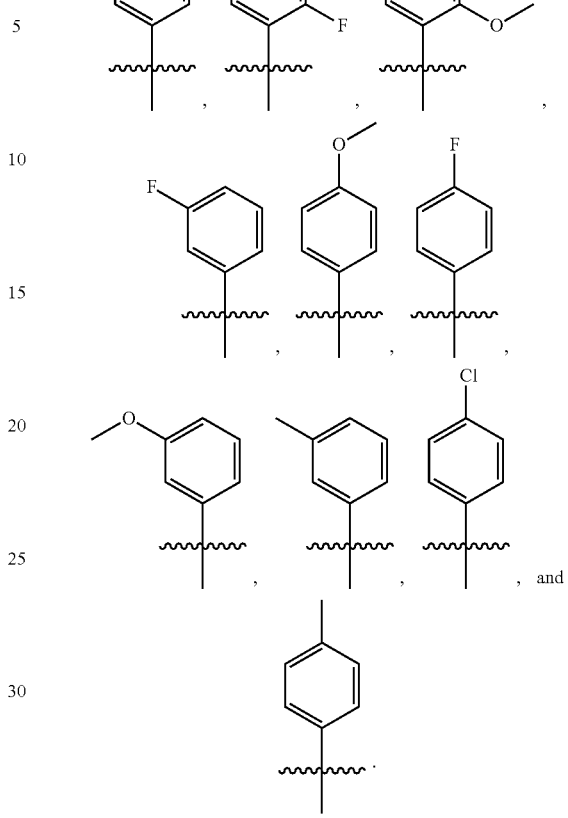

Useful compounds of Formula I' or Formula I include those where R⁴ is

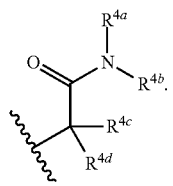

Useful compounds of Formula I' or Formula I include those where $R^{40}$ is selected from the group consisting of hydrogen, methyl, isopropyl, —CH₂OH, —CH₂OC(CH₃)₃, and —CH₂CH₂SCH₃; and $R^{4d}$ is selected from the group consisting of hydrogen and methyl; or, $R^{4c}$ and $R^{4d}$ taken together with the atom to which each is attached form a cyclopropyl ring. Useful compounds of Formula I' or Formula I include those where $R^{4c}$ and $R^{4d}$ are each hydrogen. Useful compounds of Formula I' or Formula I include those where $R^{4b}$ is hydrogen. Useful compounds of Formula I' or Formula I include those where $R^{4a}$ is $C_1$-$C_6$ alkyl. Useful compounds of Formula I' or Formula I include those where $R^{4a}$ tert-butyl or isopropyl. Useful compounds of Formula I' or Formula I include those where $R^{4a}$ is phenyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic or fused bicyclic heterocyclyl. Useful compounds of Formula I' or Formula I include those where $R^{4a}$ is phenyl optionally substituted with one substituent selected from the group consisting of fluoro, chloro, methyl, and methoxy. Useful compounds of Formula I' or Formula I include those where $R^{4a}$ is selected from the group consisting of Useful compounds of Formula I' or Formula I include those where $R^{4a}$ is 5- to 10-membered monocyclic or fused bicyclic heteroaryl optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic, fused bicyclic, or spiro heterocyclyl. Useful compounds of Formula I' or Formula I include those where $R^{4a}$ is pyridinyl, pyrimidinyl, pyrazolyl, isothiazolyl, pyridizinyl, or quinolinyl, optionally substituted with one substituent selected from the group consisting of fluoro, chloro, methoxy, azepanyl, cyclopropyl, —CF₃, —OCF₃, or methyl. Useful compounds of Formula I' or Formula I include those where $R^a$ is selected from the group consisting of

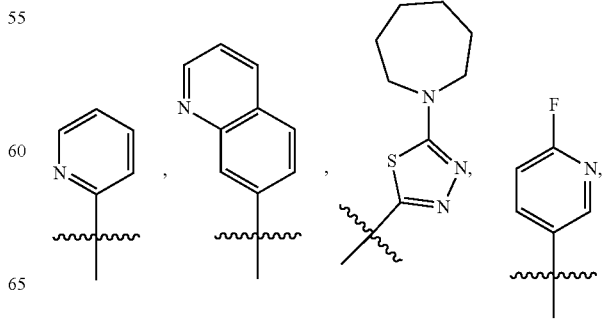

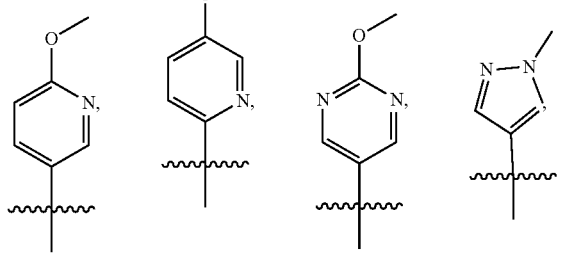

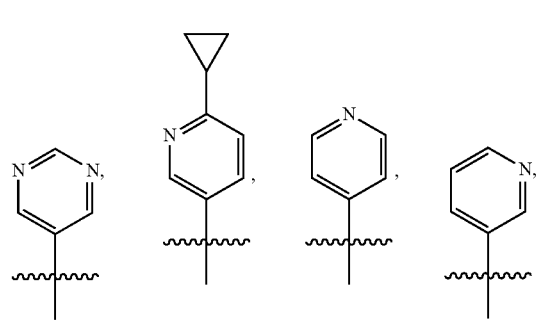

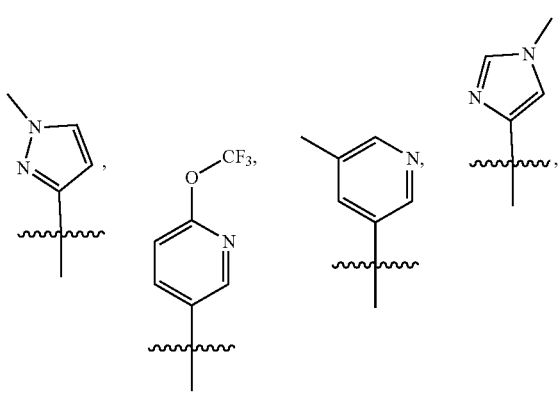

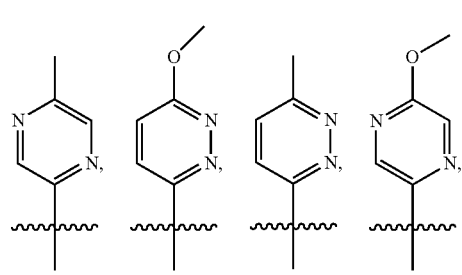

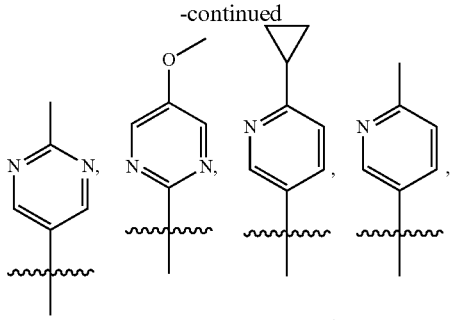

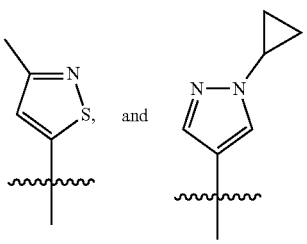

Useful compounds of Formula I' or Formula I include those where $R^{4a}$ is $C_3$-$C_7$ cycloalkyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic or fused bicyclic heterocyclyl. Useful compounds of Formula I' or Formula I include those where $R^{4a}$ is selected from the group consisting of cyclopropyl, cyclobutyl, cyclopentyl, cyclohexyl, and bicyclo[1.1.1]pentan-1-yl, optionally substituted with one or two substituents, each independently selected from the group consisting of methyl, —$CF_3$, fluoro, or hydroxy. Useful compounds of Formula I' or Formula I include those where $R^{4a}$ is selected from the group consisting of

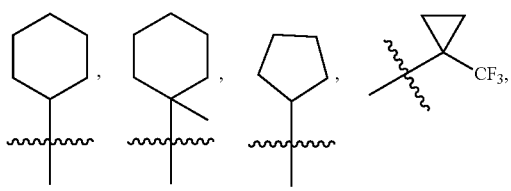

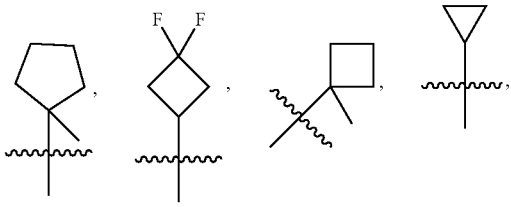

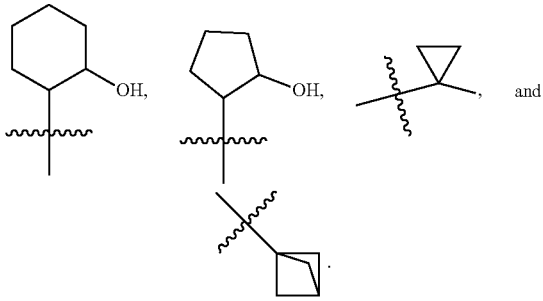

Useful compounds of Formula I' or Formula I include those where $R^{4a}$ is a 4- to 10-membered monocyclic or fused bicyclic heterocyclyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, oxo, $C_3$-$C_7$ cycloalkyl, and 5- to 10-membered monocyclic or fused bicyclic heterocyclyl. Useful compounds of Formula I' or Formula I include those where $R^{4a}$ is selected from the group consisting of tetrahydrofuranyl, pyrrolidinyl, benzo[d][1,3]dioxolyl, oxetanyl, and tetrahydropyranyl, optionally substituted with one or two substituents, each independently selected from the group consisting of methyl, methoxy, and oxo. Useful compounds of Formula I' or Formula I include those where $R^{4a}$ is selected from the group consisting of

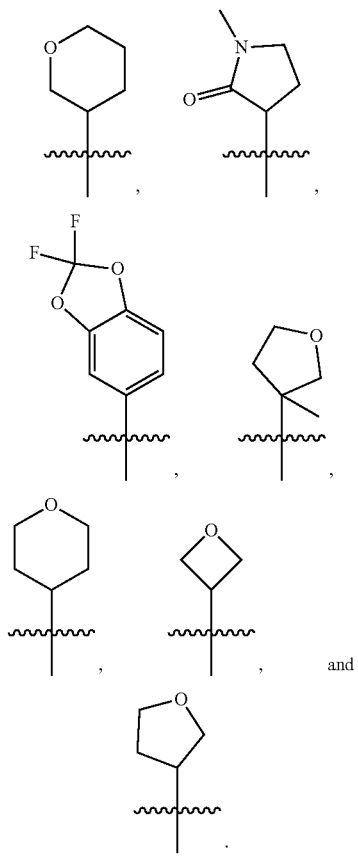

Useful compounds of Formula I' or Formula I include those where $R^{4a}$ is (C$_6$-C$_{10}$ monocyclic or fused bicyclic aryl)-$C_1$-$C_3$ alkyl or (5- to 10-membered monocyclic or fused bicyclic heteroaryl)-$C_1$-$C_3$ alkyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic, fused bicyclic heterocyclyl. Useful compounds of Formula I' or Formula I include those where $R^{4a}$ is selected from the group consisting of benzyl, 2-(1-cyclobutyl-5-methyl-1H-imidazol-2-yl)ethyl, and pyridinylmethyl. Useful compounds of Formula I' or Formula I include those where $R^{4a}$ is selected from the group consisting of

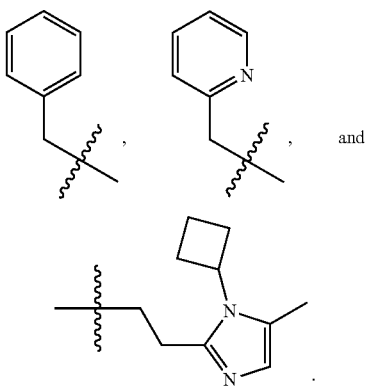

Useful compounds of Formula I' or Formula I include those where $R^{4a}$ is selected from the group consisting of —C(CH$_3$)$_2$CH$_2$OH, —CH$_2$CH$_2$OH, and —C(CH$_3$)$_2$CH$_2$OCH$_3$. Useful compounds of Formula I' or Formula I include those where $R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy. Useful compounds of Formula I' or Formula I include those where $R^{4a}$ and $R^{4b}$ taken together with the atom to which each is attached form a piperidinyl, morpholinyl, pyrrolidinyl, azepanyl, indolinyl, azabicyclo[3.1.1]heptanyl, or piperazinyl, optionally substituted with one or two substituents, each independently selected from the group consisting of methyl, fluoro, hydroxy, and methoxy. Useful compounds of Formula I' or Formula I include those where $R^{4a}$ and $R^{4b}$ taken together with the atom to which each is attached form a

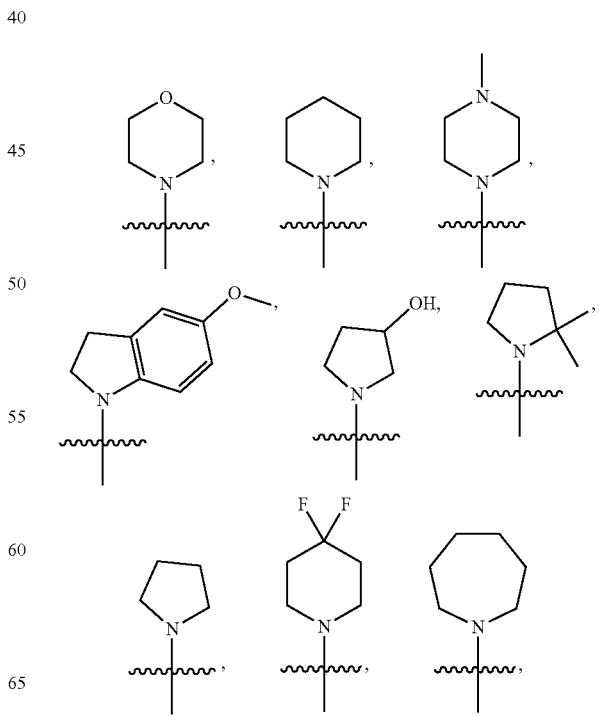

-continued

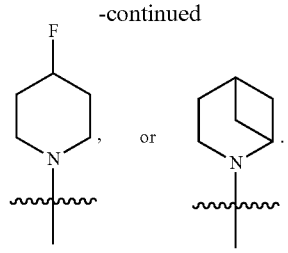

Useful compounds of Formula I' or Formula I include those where $R^{4b}$ and $R^{4c}$ taken together with the atom to which each is attached form a 5- to 7-membered monocyclic heterocyclyl, optionally substituted with one or two substituents, each independently selected from $C_1$-$C_3$ alkyl. Useful compounds of Formula I' or Formula I include those where $R^{4b}$ and $R^{4c}$ taken together with the atom to which each is attached form a piperidin-2-one or a pyrrolidine-2-one, optionally substituted one or two times with methyl.

Useful compounds of Formula I' or Formula I include those where $R^4$ is

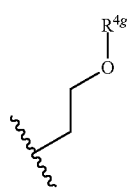

wherein $R^{4g}$ is selected from the group consisting of $C_6$-$C_{10}$ monocyclic or fused bicyclic aryl and $C_1$-$C_3$ alkyl. Useful compounds of Formula I' or Formula I include those where $R^{4g}$ is selected from the group consisting of phenyl and methyl.

Useful compounds of Formula I' or Formula I include those where $R^3$ and $R^4$ taken together with the nitrogen atom to which each is attached form a 7-membered monocyclic or bridged bicyclic heterocyclyl containing one or two heteroatoms; wherein when said 7-membered heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and when said 7-membered heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, halo-$C_1$-$C_3$ alkyl, and $C_6$-$C_{10}$ monocyclic or fused bicyclic aryl; and wherein said aryl is optionally substituted with one or two substituents, each individually selected from the group consisting of $C_1$-$C_3$ alkoxy, hydroxy, halogen, and $C_1$-$C_3$ alkyl. Useful compounds of Formula I' or Formula I include those where $R^3$ and $R^4$ taken together with the nitrogen atom to which each is attached form a 7-membered heterocyclyl containing one heteroatom, wherein said heterocyclyl is optionally substituted once with methyl or oxo; or, a 7-membered monocyclic or bridged bicyclic heterocyclyl containing two heteroatoms, wherein said heteroatoms are N or O, and said heterocyclyl is optionally substituted with one or two substituents, each independently selected from the group consisting of phenyl, methyl, and oxo, and wherein said phenyl is optionally substituted with methoxy. Useful compounds of Formula I' or Formula I include those where $R^3$ and $R^4$ taken together with the nitrogen atom to which each is attached form a

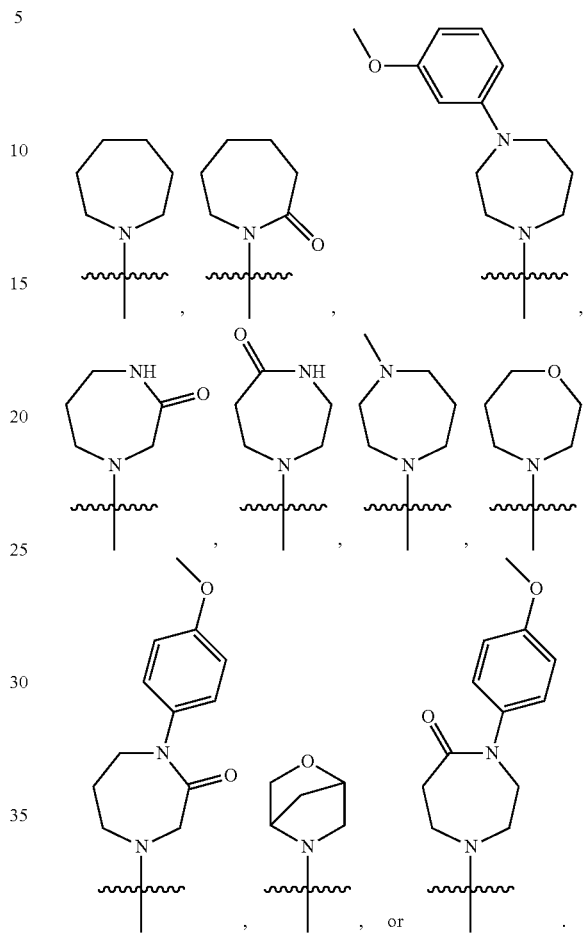

Useful compounds of Formula I' or Formula I include those where $R^3$ and $R^4$ taken together with the nitrogen atom to which each is attached form a 10- or 11-membered fused bicyclic heterocyclyl containing one heteroatom, or a 12-membered bicyclic fused and bridged heterocyclyl, each optionally substituted with one, two, or three substituents, each independently selected from the group consisting of $C_1$-$C_3$ alkyl, $C_1$-$C_3$ alkoxy, hydroxy, and halogen. Useful compounds of Formula I' or Formula I include those where $R^3$ and $R^4$ taken together with the nitrogen atom to which each is attached form a

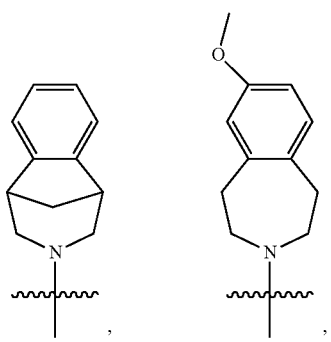

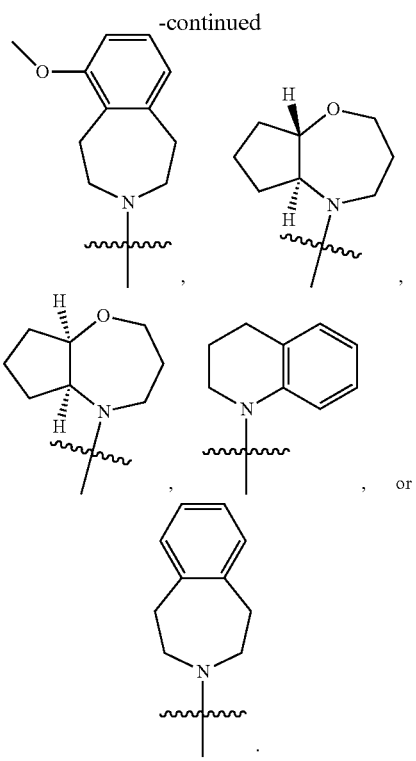

, , or

Useful compounds of Formula I' or Formula I include those where R³ and R⁴ taken together with the nitrogen atom to which each is attached form a 4- or 6-membered monocyclic heterocyclyl containing one heteroatom; wherein, said 4-membered monocyclic heterocyclyl is optionally substituted with —(CH₂)$_s$C(═O)NR$^k$R$^l$; wherein, s is 0, 1, or 2; R$^k$ is hydrogen or C₁-C₃ alkyl; and R$^l$ is selected from the group consisting of hydrogen, methyl, phenyl, cyclopentyl, and cyclohexyl; and, said 6-membered monocyclic heterocyclyl is optionally substituted with one or two substituents, each independently selected from the group consisting of C₁-C₃ alkoxy, oxo, halogen, cyano, and —NR$^q$R$^w$; wherein, R$^q$ is hydrogen or C₁-C₃ alkyl; R$^w$ is C₆-C₁₀ monocyclic or fused bicyclic aryl or C₃-C₇ cycloalkyl, wherein said aryl or cycloalkyl is optionally substituted with one or two substituents, each independently selected from the group consisting of halogen, C₁-C₃ alkyl, hydroxy, and C₁-C₃ alkoxy.

Useful compounds of Formula I' or Formula I include those where R³ and R⁴ taken together with the nitrogen atom to which each is attached form a

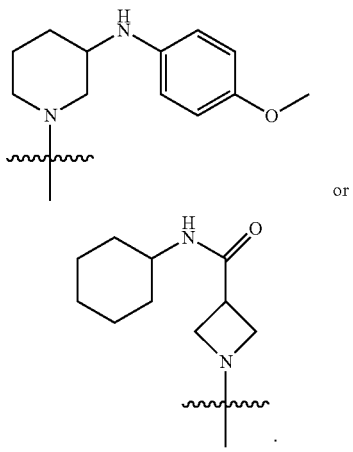

or

Useful compounds of Formula I' or Formula I include those where R$^x$, in each instance, is methyl. Useful compounds of Formula or Formula I include those where m is 0. Useful compounds of Formula I' or Formula I include those where m is 2.

The subject matter described herein includes the following compounds in Table 1, or pharmaceutically acceptable salts thereof:

TABLE 1

Where the mass for a compound is not provided in Table 1, the mass can be found for the compound in the synthetic examples.

| Compound No. | Structure | IUPAC Name | Mass Found (M + 1) |
|---|---|---|---|
| 1 | 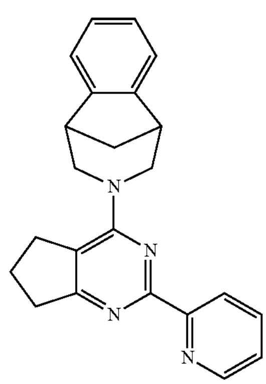 [SMILES: c1ccc(-c2nc3c(c(N4CC5CC(C4)c4ccccc45)n2)CCC3)nc1] | 10-[2-(pyridin-2-yl)-5H,6H,7H-cyclopenta[d]pyrimidin-4-yl]-10-azatricyclo[6.3.1.0^{2,7}]dodeca-2,4,6-triene | 355 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 2 | 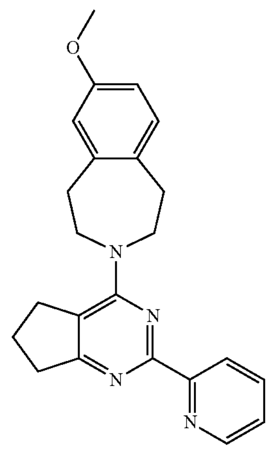 [SMILES: COc1ccc2c(c1)CCN(c1nc(-c3ccccn3)nc3c1CCC3)CC2] | 7-methoxy-3-[2-(pyridin-2-yl)-5H,6H,7H-cyclopenta[d]pyrimidin-4-yl]-2,3,4,5-tetrahydro-1H-3-benzazepine | 373.1 |
| 3 | 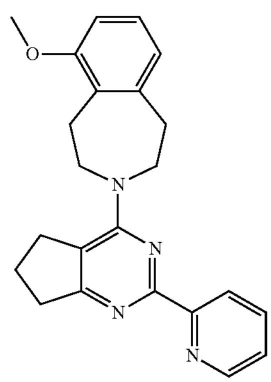 [SMILES: COc1cccc2c1CCN(c1nc(-c3ccccn3)nc3c1CCC3)CC2] | 6-methoxy-3-[2-(pyridin-2-yl)-5H,6H,7H-cyclopenta[d]pyrimidin-4-yl]-2,3,4,5-tetrahydro-1H-3-benzazepine | 373 |
| 4 | 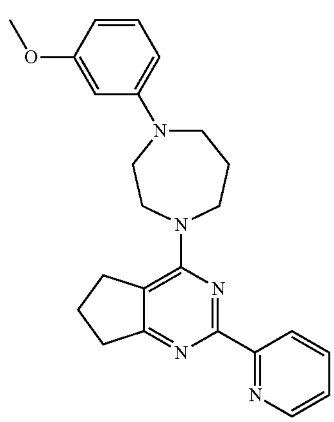 [SMILES: COc1cccc(N2CCCN(c3nc(-c4ccccn4)nc4c3CCC4)CC2)c1] | 1-(3-methoxyphenyl)-4-[2-(pyridin-2-yl)-5H,6H,7H-cyclopenta[d]pyrimidin-4-yl]-1,4-diazepane | 402.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 5 | 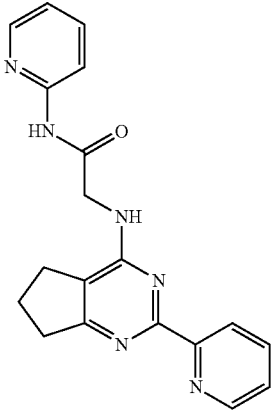 [SMILES: O=C(CNc1nc(-c2ccccn2)nc2c1CCC2)Nc1ccccn1] | N-(pyridin-2-yl)-2-{[2-(pyridin-2-yl)-5H,6H,7H-cyclopenta[d]pyrimidin-4-yl]amino}acetamide | 347.1 |
| 6 | 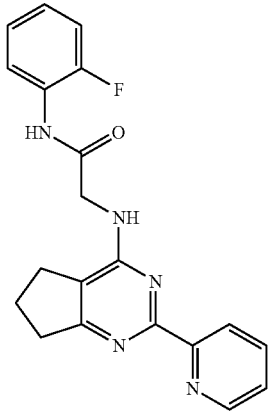 [SMILES: O=C(CNc1nc(-c2ccccn2)nc2c1CCC2)Nc1ccccc1F] | N-(2-fluroophenyl)-2-{[2-(pyridin-2-yl)-5H,6H,7H-cyclopenta[d]pyrimidin-4-yl]amino}acetamide | 364.1 |
| 7 | 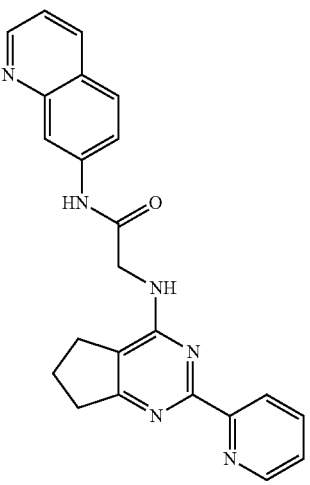 [SMILES: O=C(CNc1nc(-c2ccccn2)nc2c1CCC2)Nc1ccc2cccnc2c1] | 2-{[2-(pyridin-2-yl)-5H,6H,7H-cyclopenta[d]pyrimidin-4-yl]amino}-N-(quinolin-7-yl)acetamide | 397.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 8 | 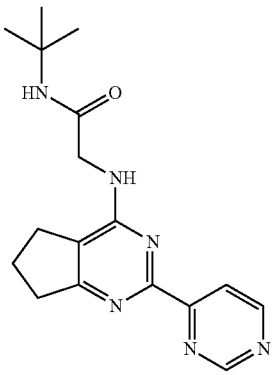 [SMILES: CC(C)(C)NC(=O)CNc1nc(-c2ccncn2)nc2c1CCC2] | N-tert-butyl-2-{[2-(pyrimidin-4-yl)-5H,6H,7H-cyclopenta[d]pyrimidin-4-yl]amino}acetamide | 327.2 |
| 9 | 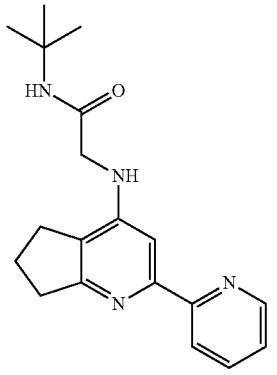 [SMILES: CC(C)(C)NC(=O)CNc1cc(-c2ccccn2)nc2c1CCC2] | N-tert-butyl-2-{[2-(pyridin-2-yl)-5H,6H,7H-cyclopenta[b]pyridin-4-yl]amino}acetamide | 325.1 |
| 10 | 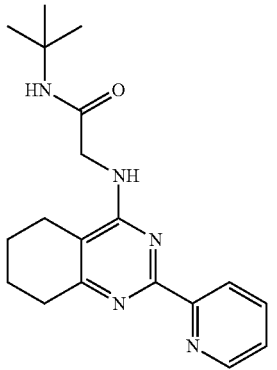 [SMILES: CC(C)(C)NC(=O)CNc1nc(-c2ccccn2)nc2c1CCCC2] | N-tert-butyl-2-{[2-(pyridin-2-yl)-5,6,7,8-tetrahydroquinazolin-4-yl]amino}acetamide | 340.1 |
| 11 | 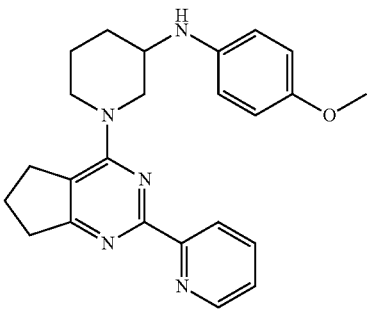 [SMILES: COc1ccc(NC2CCCN(c3nc(-c4ccccn4)nc4c3CCC4)C2)cc1] | N-(4-methoxyphenyl)-1-[2-(pyridin-2-yl)-5H,6H,7H-cyclopenta[d]pyrimidin-4-yl]piperidin-3-amine | 402.4 |

TABLE 1-continued

Where the mass for a compound is not provided in Table 1, the mass can be found for the compound in the synthetic examples.

| Compound No. | Structure | IUPAC Name | Mass Found (M + 1) |
| --- | --- | --- | --- |
| 12 | 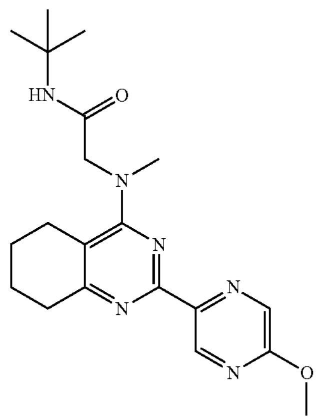 [SMILES: COc1cnc(-c2nc3c(c(N(C)CC(=O)NC(C)(C)C)n2)CCCC3)cn1] | N-tert-butyl-2-{[2-(5-methoxypyrazin-2-yl)-5H,6H,7H-cyclopenta[d]pyrimidin-4-yl](methyl)amino}acetamide | 371.2 |
| 13 | 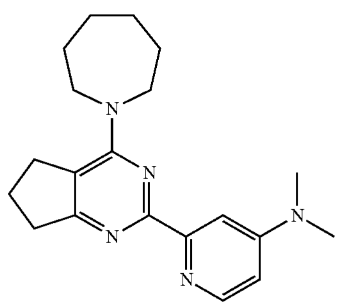 [SMILES: CN(C)c1ccnc(-c2nc3c(c(N4CCCCCC4)n2)CCC3)c1] | 2-[4-(azepan-1-yl)-5H,6H,7H-cyclopenta[d]pyrimidin-2-yl]-N,N-dimethylpyridin-4-amine | 338.1 |
| 14 | 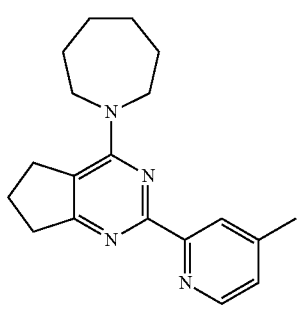 [SMILES: Cc1ccnc(-c2nc3c(c(N4CCCCCC4)n2)CCC3)c1] | 1-[2-(4-methylpyridin-2-yl)-5H,6H,7H-cyclopenta[d]pyrimidin-4-yl]azepane | 309.2 |
| 15 | 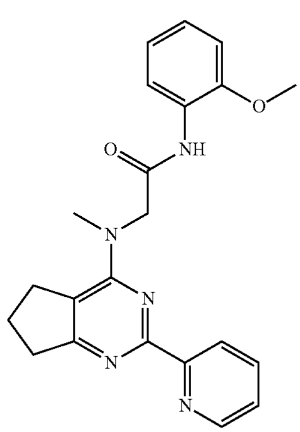 [SMILES: COc1ccccc1NC(=O)CN(C)c1nc(-c2ccccn2)nc2c1CCC2] | N-(2-methoxyphenyl)-2-{methyl[2-(pyridin-2-yl)-5H,6H,7H-cyclopenta[d]pyrimidin-4-yl]amino}acetamide | 390.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 16 | 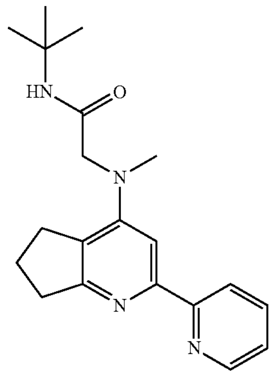 [SMILES: CN(CC(=O)NC(C)(C)C)c1cc(-c2ccccn2)nc2c1CCC2] | N-tert-butyl-2-{methyl[2-(pyridin-2-yl)-5H,6H,7H-cyclopenta[b]pyridin-4-yl]amino}acetamide | 339.2 |
| 17 | 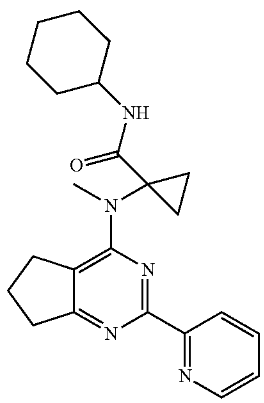 [SMILES: CN(c1nc(-c2ccccn2)nc2c1CCC2)C1(C(=O)NC2CCCCC2)CC1] | N-cyclohexyl-1-{methyl[2-(pyridin-2-yl)-5H,6H,7H-cyclopenta[d]pyrimidin-4-yl]amino}cyclopropane-1-carboxamide | 392.2 |
| 18 | 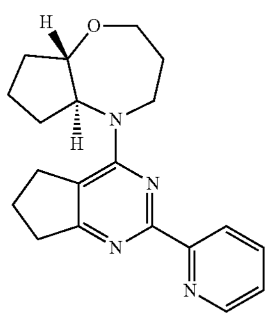 [SMILES: c1ccc(-c2nc3c(c(N4CCCO[C@H]5CCC[C@@H]54)n2)CCC3)nc1] | 2-{4-[(5aS,8aS)-octahydro-2H-cyclopenta[b][1,4]oxazepin-5-yl]-5H,6H,7H-cyclopenta[d]pyrimidin-2-yl}pyridine | |
| 19 | 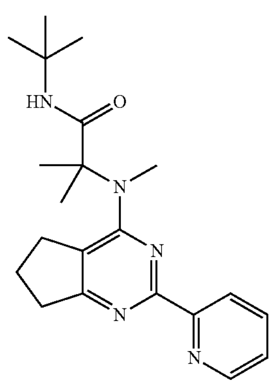 [SMILES: CN(c1nc(-c2ccccn2)nc2c1CCC2)C(C)(C)C(=O)NC(C)(C)C] | N-tert-butyl-2-methyl-2-{methyl[2-(pyridin-2-yl)-5H,6H,7H-cyclopenta[d]pyrimidin-4-yl]amino}propanamide | 368.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 20 | 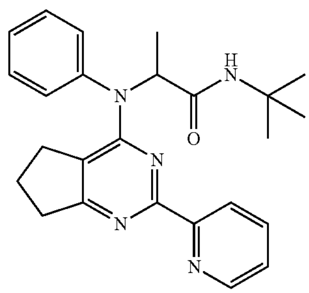 [SMILES: CC(C(=O)NC(C)(C)C)N(c1ccccc1)c1nc(-c2ccccn2)nc2c1CCC2] | N-tert-butyl-2-{phenyl[2-(pyridin-2-yl)-5H,6H,7H-cyclopenta[d]pyrimidin-4-yl]amino}propanamide | 415.8 |
| 21 | 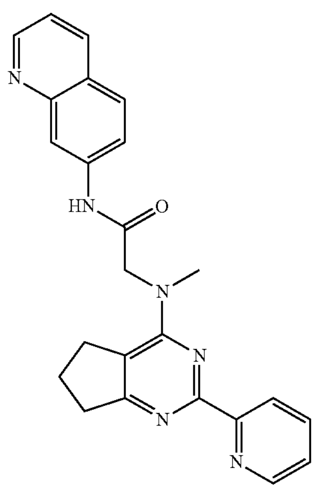 [SMILES: CN(CC(=O)Nc1ccc2cccnc2c1)c1nc(-c2ccccn2)nc2c1CCC2] | 2-{methyl[2-(pyridin-2-yl)-5H,6H,7H-cyclopenta[d]pyrimidin-4-yl]amino}-N-(quinolin-7-yl)acetamide | 411.2 |
| 22 | 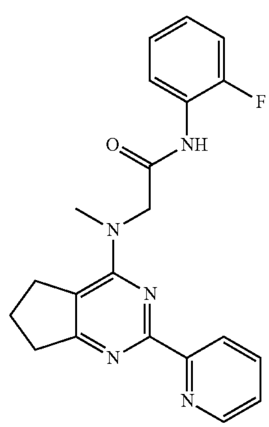 [SMILES: CN(CC(=O)Nc1ccccc1F)c1nc(-c2ccccn2)nc2c1CCC2] | N-(2-fluorophenyl)-2-{methyl[2-(pyridin-2-yl)-5H,6H,7H-cyclopenta[d]pyrimidin-4-yl]amino}acetamide | 378.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 23 | 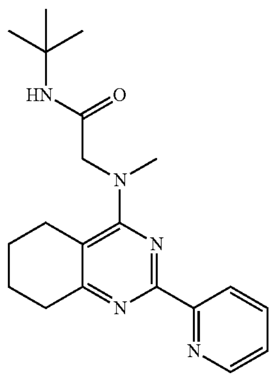 [SMILES: CN(CC(=O)NC(C)(C)C)c1nc(-c2ccccn2)nc2c1CCCC2] | N-tert-butyl-2-{methyl[2-(pyridin-2-yl)-5,6,7,8-tetrahydroquinazolin-4-yl]amino}acetamide | 354.2 |
| 24 | 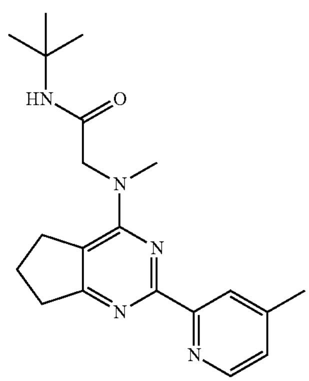 [SMILES: Cc1ccnc(-c2nc3c(c(N(C)CC(=O)NC(C)(C)C)n2)CCC3)c1] | N-tert-butyl-2-{methyl[2-(4-methylpyridin-2-yl)-5H,6H,7H-cyclopenta[d]pyrimidin-4-yl]amino}acetamide | 354.2 |
| 25 | 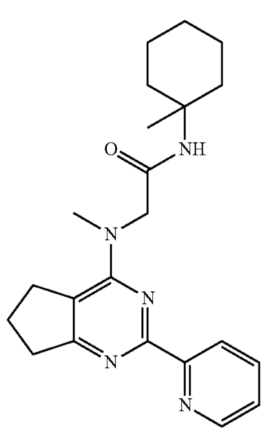 [SMILES: CN(CC(=O)NC1(C)CCCCC1)c1nc(-c2ccccn2)nc2c1CCC2] | 2-{methyl[2-(pyridin-2-yl)-5H,6H,7H-cyclopenta[d]pyrimidin-4-yl]amino}-N-(1-methylcyclohexyl)acetamide | 380.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 26 | 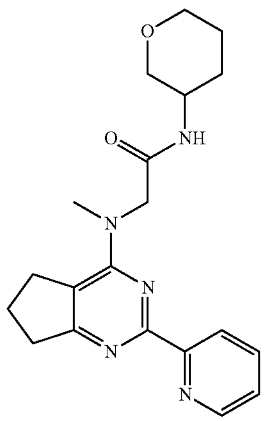 [SMILES: CN(CC(=O)NC1CCCOC1)c1nc(-c2ccccn2)nc2c1CCC2] | 2-{methyl[2-(pyridin-2-yl)-5H,6H,7H-cyclopenta[d]pyrimidin-4-yl]amino}-N-(oxan-3-yl)acetamide | 368.2 |
| 27 | 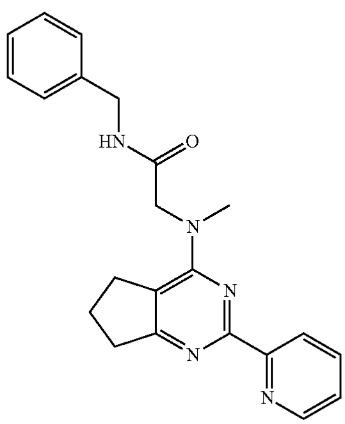 [SMILES: CN(CC(=O)NCc1ccccc1)c1nc(-c2ccccn2)nc2c1CCC2] | N-benzyl-2-{methyl[2-(pyridin-2-yl)-5H,6H,7H-cyclopenta[d]pyrimidin-4-yl]amino}acetamide | 374.2 |
| 28 | 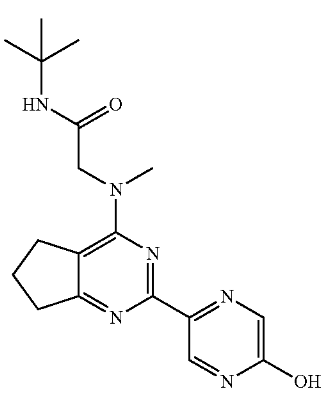 [SMILES: CN(CC(=O)NC(C)(C)C)c1nc(-c2cnc(O)cn2)nc2c1CCC2] | N-tert-butyl-2-{[2-(5-hydroxypyrazin-2-yl)-5H,6H,7H-cyclopenta[d]pyrimidin-4-yl](methyl)amino}acetamide | 357.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 29 | 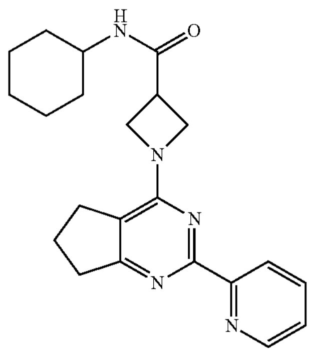 [SMILES: O=C(NC1CCCCC1)C1CN(c2nc(-c3ccccn3)nc3c2CCC3)C1] | N-cyclohexyl-1-[2-(pyridin-2-yl)-5H,6H,7H-cyclopenta[d]pyrimidin-4-yl]azetidine-3-carboxamide | 378.3 |
| 30 | 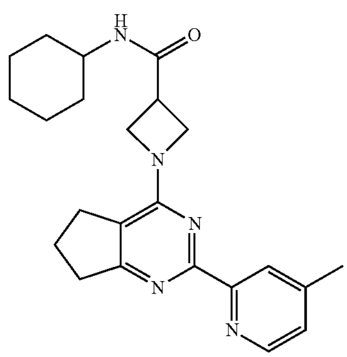 [SMILES: Cc1ccnc(-c2nc3c(c(N4CC(C(=O)NC5CCCCC5)C4)n2)CCC3)c1] | N-cyclohexyl-1-[2-(4-methylpyridin-2-yl)-5H,6H,7H-cyclopenta[d]pyrimidin-4-yl]azetidine-3-carboxamide | 392.4 |
| 31 | 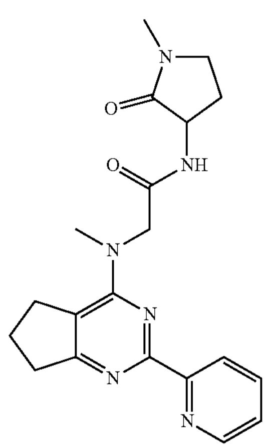 [SMILES: CN1CCC(NC(=O)CN(C)c2nc(-c3ccccn3)nc3c2CCC3)C1=O] | N-(1-methyl-2-oxopyrrolidin-3-yl)-2-{methyl[2-(pyridin-2-yl)-5H,6H,7H-cyclopenta[d]pyrimidin-4-yl]amino}acetamide | 381.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 32 | 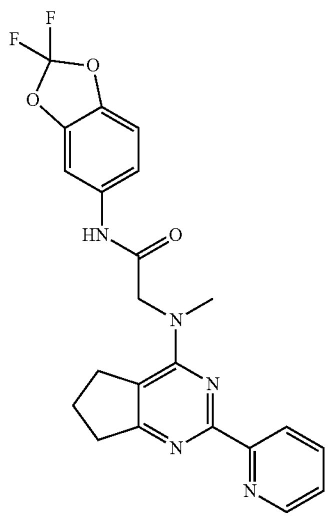 [SMILES: CN(CC(=O)Nc1ccc2c(c1)OC(F)(F)O2)c1nc(-c2ccccn2)nc2c1CCC2] | N-(2,2-difluoro-2H-1,3-benzodioxol-5-yl)-2-{methyl[2-(pyridin-2-yl)-5H,6H,7H-cyclopenta[d]pyrimidin-4-yl]amino}acetamide | 440.3 |
| 33 | 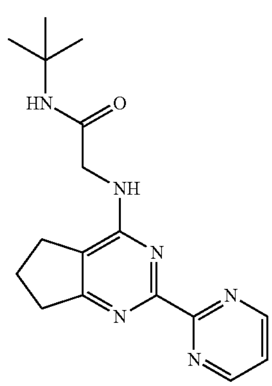 [SMILES: CC(C)(C)NC(=O)CNc1nc(-c2ncccn2)nc2c1CCC2] | N-tert-butyl-2-{[2-(pyrimidin-2-yl)-5H,6H,7H-cyclopenta[d]pyrimidin-4-yl]amino}acetamide | 327.2 |
| 34 | 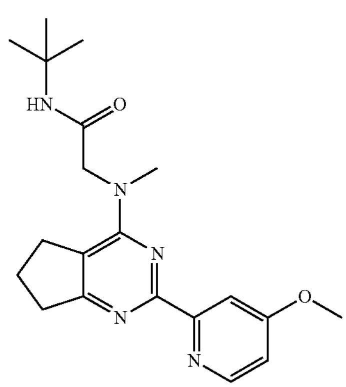 [SMILES: COc1ccnc(-c2nc3c(c(N(C)CC(=O)NC(C)(C)C)n2)CCC3)c1] | N-tert-butyl-2-{[2-(4-methoxypyridin-2-yl)-5H,6H,7H-cyclopenta[d]pyrimidin-4-yl](methyl)amino}acetamide | 370.2 |

TABLE 1-continued

Where the mass for a compound is not provided in Table 1, the mass can be found for the compound in the synthetic examples.

| Compound No. | Structure | IUPAC Name | Mass Found (M + 1) |
| --- | --- | --- | --- |
| 35 | 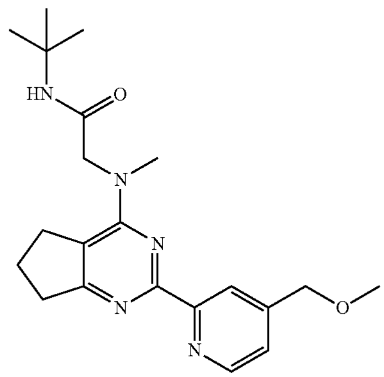 [SMILES: COCc1ccnc(-c2nc3c(c(N(C)CC(=O)NC(C)(C)C)n2)CCC3)c1] | N-tert-butyl-2-({2-[4-(methoxymethyl)pyridin-2-yl]-5H,6H,7H-cyclopenta[d]pyrimidin-4-yl}(methyl)amino)acetamide | 384.2 |
| 36 | 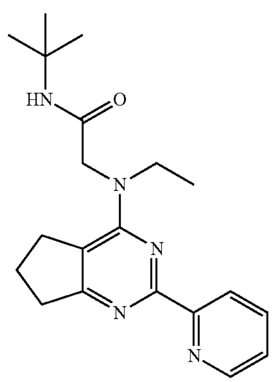 [SMILES: CCN(CC(=O)NC(C)(C)C)c1nc(-c2ccccn2)nc2c1CCC2] | N-tert-butyl-2-{ethyl[2-(pyridin-2-yl)-5H,6H,7H-cyclopenta[d]pyrimidin-4-yl]amino}acetamide | 354.2 |
| 37 | 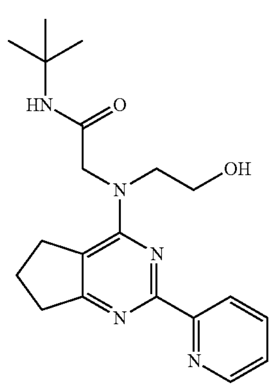 [SMILES: CC(C)(C)NC(=O)CN(CCO)c1nc(-c2ccccn2)nc2c1CCC2] | N-tert-butyl-2-[(2-hydroxyethyl)[2-(pyridin-2-yl)-5H,6H,7H-cyclopenta[d]pyrimidin-4-yl]amino]acetamide | 370.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 38 | 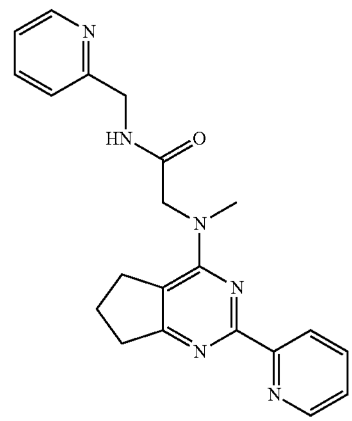 [SMILES: CN(CC(=O)NCc1ccccn1)c1nc(-c2ccccn2)nc2c1CCC2] | 2-{methyl[2-(pyridin-2-yl)-5H,6H,7H-cyclopenta[d]pyrimidin-4-yl]amino}-N-[(pyridin-2-yl)methyl]acetamide | 375.2 |
| 39 | 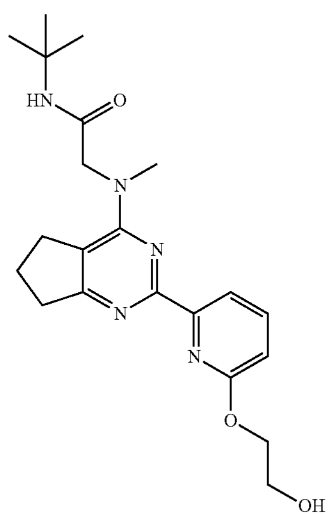 [SMILES: CN(CC(=O)NC(C)(C)C)c1nc(-c2cccc(OCCO)n2)nc2c1CCC2] | N-tert-butyl-2-({2-[6-(2-hydroxyethoxy)pyridin-2-yl]-5H,6H,7H-cyclopenta[d]pyrimidin-4-yl}(methyl)amino)acetamide | 400.2 |
| 40 | 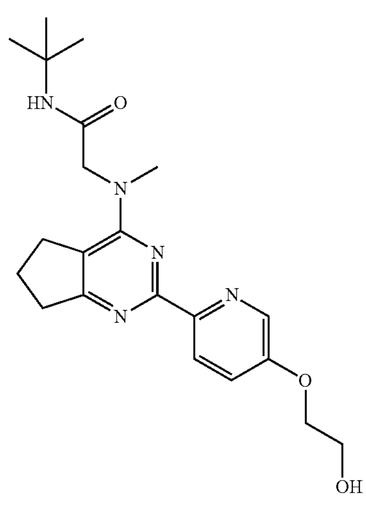 [SMILES: CN(CC(=O)NC(C)(C)C)c1nc(-c2ccc(OCCO)cn2)nc2c1CCC2] | N-tert-butyl-2-({2-[5-(2-hydroxyethoxy)pyridin-2-yl]-5H,6H,7H-cyclopenta[d]pyrimidin-4-yl}(methyl)amino)acetamide | 400.3 |

TABLE 1-continued

Where the mass for a compound is not provided in Table 1, the mass can be found for the compound in the synthetic examples.

| Compound No. | Structure | IUPAC Name | Mass Found (M + 1) |
| --- | --- | --- | --- |
| 41 | 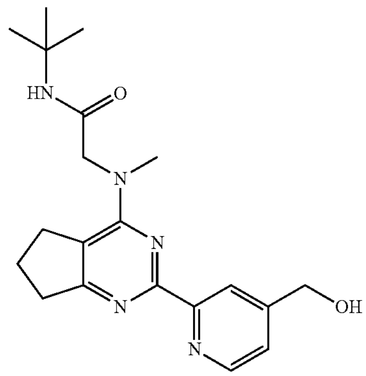 [SMILES: CN(CC(=O)NC(C)(C)C)c1nc(-c2cc(CO)ccn2)nc2c1CCC2] | N-tert-butyl-2-({2-[4-(hydroxymethyl)pyridin-2-yl]-5H,6H,7H-cyclopenta[d]pyrimidin-4-yl}(methyl)amino)acetamide | 370.2 |
| 42 | 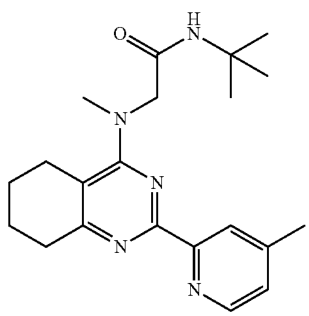 [SMILES: Cc1ccnc(-c2nc3c(c(N(C)CC(=O)NC(C)(C)C)n2)CCCC3)c1] | N-tert-butyl-2-{methyl[2-(4-methylpyridin-2-yl)-5,6,7,8-tetrahydroquinazolin-4-yl]amino}acetamide | 368.2 |
| 43 | 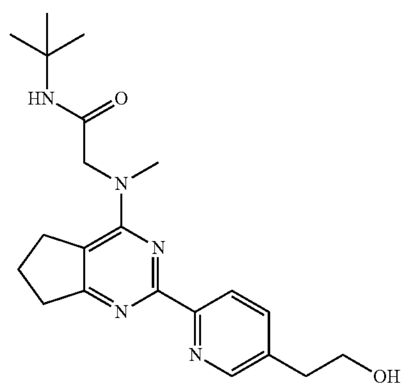 [SMILES: CN(CC(=O)NC(C)(C)C)c1nc(-c2ccc(CCO)cn2)nc2c1CCC2] | N-tert-butyl-2-({2-[5-(2-hydroxyethyl)pyridin-2-yl]-5H,6H,7H-cyclopenta[d]pyrimidin-4-yl}(methyl)amino)acetamide | 384.2 |
| 44 | 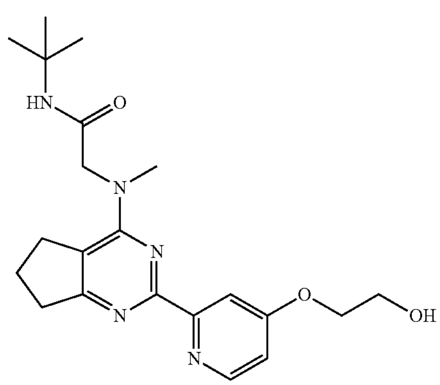 [SMILES: CN(CC(=O)NC(C)(C)C)c1nc(-c2cc(OCCO)ccn2)nc2c1CCC2] | N-tert-butyl-2-({2-[4-(2-hydroxyethoxy)pyridin-2-yl]-5H,6H,7H-cyclopenta[d]pyrimidin-4-yl}(methyl)amino)acetamide | 400.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 45 | 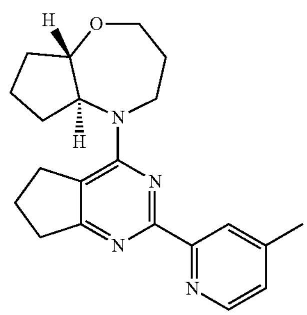 [SMILES: Cc1ccnc(-c2nc3c(c(N4CCCO[C@H]5CCC[C@@H]54)n2)CCC3)c1] | 2-{4-[(5aS,8aS)-octahydro-2H-cyclopenta[b][1,4]oxazepin-5-yl]-5H,6H,7H-cyclopenta[d]pyrimidin-2-yl}-4-methylpyridine | |
| 46 | 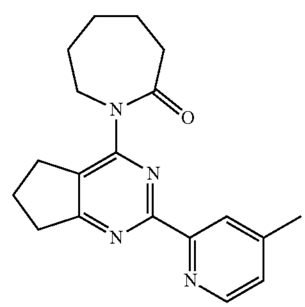 [SMILES: Cc1ccnc(-c2nc3c(c(N4CCCCCC4=O)n2)CCC3)c1] | 1-[2-(pyridin-2-yl)-5H,6H,7H-cyclopenta[d]pyrimidin-4-yl]azepan-2-one | |
| 47 | 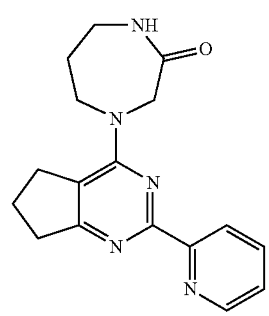 [SMILES: O=C1CN(c2nc(-c3ccccn3)nc3c2CCC3)CCCN1] | 4-[2-(pyridin-2-yl)-5H,6H,7H-cyclopenta[d]pyrimidin-4-yl]-1,4-diazepan-2-one | 310 |
| 48 | 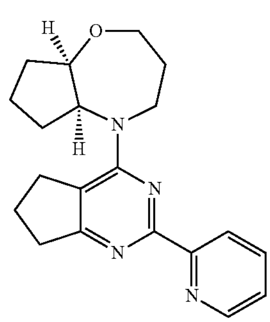 [SMILES: c1ccc(-c2nc3c(c(N4CCCO[C@@H]5CCC[C@@H]54)n2)CCC3)nc1] | 2-{4-[(5aS,8aR)-octahydro-2H-cyclopenta[b][1,4]oxazepin-5-yl]-5H,6H,7H-cyclopenta[d]pyrimidin-2-yl}pyridine | |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 49 | 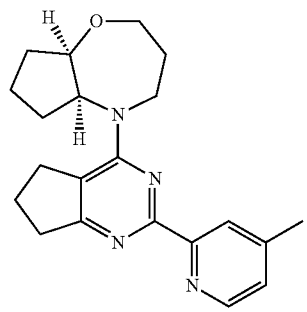 [SMILES: Cc1ccnc(-c2nc3c(c(N4CCCO[C@@H]5CCC[C@@H]54)n2)CCC3)c1] | 2-{4-[(5aS,8aR)-octahydro-2H-cyclopenta[b][1,4]oxazepin-5-yl]-5H,6H,7H-cyclopenta[d]pyrimidin-2-yl}-4-methylpyridine | |
| 50 | 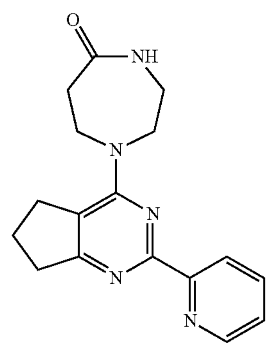 [SMILES: O=C1CCN(c2nc(-c3ccccn3)nc3c2CCC3)CCN1] | 1-[2-(pyridin-2-yl)-5H,6H,7H-cyclopenta[d]pyrimidin-4-yl]-1,4-diazepan-5-one | 309.9 |
| 51 | 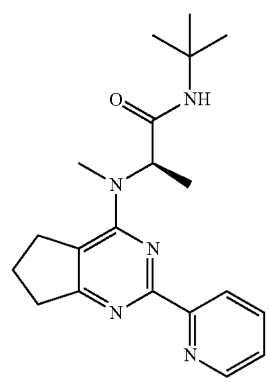 [SMILES: C[C@H](C(=O)NC(C)(C)C)N(C)c1nc(-c2ccccn2)nc2c1CCC2] | (2R)-N-tert-butyl-2-{methyl[2-(pyridin-2-yl)-5H,6H,7H-cyclopenta[d]pyrimidin-4-yl]amino}propanamide | 354.4 |
| 52 | 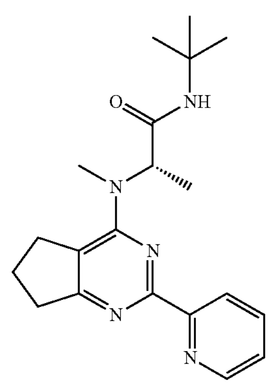 [SMILES: C[C@@H](C(=O)NC(C)(C)C)N(C)c1nc(-c2ccccn2)nc2c1CCC2] | (2S)-N-tert-butyl-2-{methyl[2-(pyridin-2-yl)-5H,6H,7H-cyclopenta[d]pyrimidin-4-yl]amino}propanamide | 354.4 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 53 | 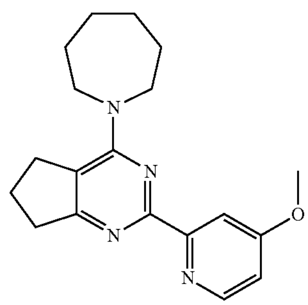 [SMILES: COc1ccnc(-c2nc3c(c(N4CCCCCC4)n2)CCC3)c1] | 1-[2-(4-methoxypyridin-2-yl)-5H,6H,7H-cyclopenta[d]pyrimidin-4-yl]azepane | 325.1 |
| 54 | 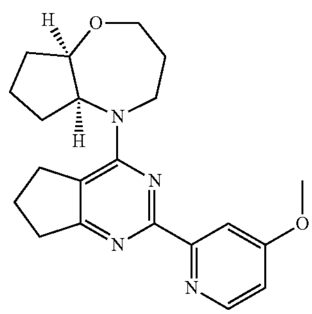 [SMILES: COc1ccnc(-c2nc3c(c(N4CCCO[C@@H]5CCC[C@@H]54)n2)CCC3)c1] | 2-{4-[(5aS,8aR)-octahydro-2H-cyclopenta[b][1,4]oxazepin-5-yl]-5H,6H,7H-cyclopenta[d]pyrimidin-2-yl}-4-methoxypyridine | |
| 55 | 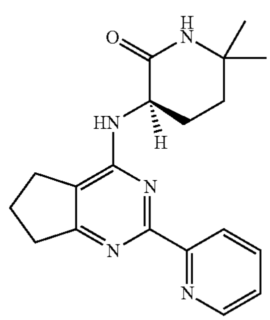 [SMILES: CC1(C)CC[C@@H](Nc2nc(-c3ccccn3)nc3c2CCC3)C(=O)N1] | (3R)-6,6-dimethyl-3-{[2-(pyridin-2-yl)-5H,6H,7H-cyclopenta[d]pyrimidin-4-yl]amino}piperidin-2-one | 338.2 |
| 56 | 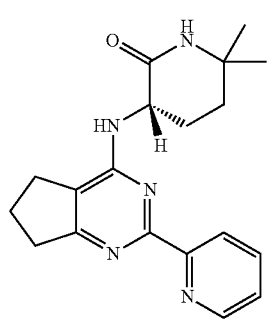 [SMILES: CC1(C)CC[C@H](Nc2nc(-c3ccccn3)nc3c2CCC3)C(=O)N1] | (3S)-6,6-dimethyl-3-{[2-(pyridin-2-yl)-5H,6H,7H-cyclopenta[d]pyrimdiin-4-yl]amino}piperidin-2-one | 338.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 57 | 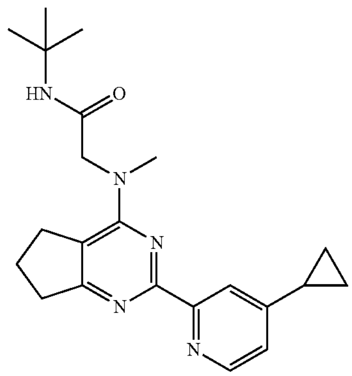 [SMILES: CN(CC(=O)NC(C)(C)C)c1nc(-c2cc(C3CC3)ccn2)nc2c1CCC2] | N-tert-butyl-2-{[2-(4-cyclopropylpyridin-2-yl)-5H,6H,7H-cyclopenta[d]pyrimidin-4-yl](methyl)amino}acetamide | 380.2 |
| 58 | 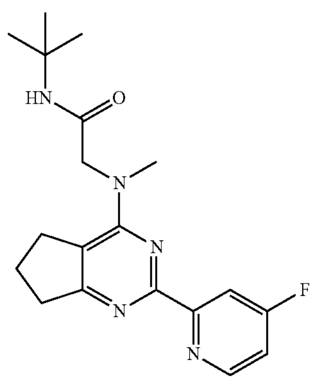 [SMILES: CN(CC(=O)NC(C)(C)C)c1nc(-c2cc(F)ccn2)nc2c1CCC2] | N-tert-butyl-2-{[2-(4-fluoropyridin-2-yl)-5H,6H,7H-cyclopenta[d]pyrimidin-4-yl](methyl)amino}acetamide | 358.1 |
| 59 | 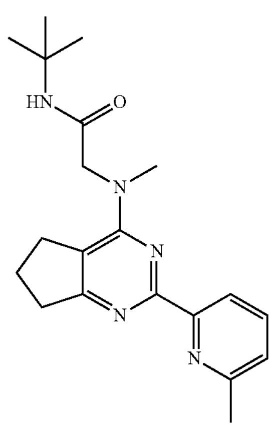 [SMILES: Cc1cccc(-c2nc3c(c(N(C)CC(=O)NC(C)(C)C)n2)CCC3)n1] | N-tert-butyl-2-{methyl[2-(6-methylpyridin-2-yl)-5H,6H,7H-cyclopenta[d]pyrimidin-4-yl]amino}acetamide | 354.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 60 | 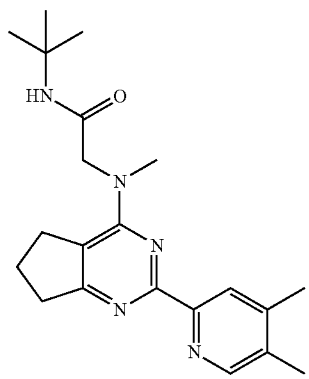 [SMILES: Cc1cnc(-c2nc3c(c(N(C)CC(=O)NC(C)(C)C)n2)CCC3)cc1C] | N-tert-butyl-2-{[2-(4,5-dimethylpyridin-2-yl)-5H,6H,7H-cyclopenta[d]pyrimidin-4-yl](methyl)amino}acetamide | 368.2 |
| 61 | 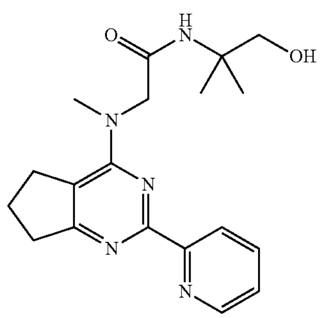 [SMILES: CN(CC(=O)NC(C)(C)CO)c1nc(-c2ccccn2)nc2c1CCC2] | N-(1-hydroxy-2-methylpropan-2-yl)-2-{methyl[2-(pyridin-2-yl)-5H,6H,7H-cyclopenta[d]pyrimidin-4-yl]amino}acetamide | 356.2 |
| 62 | 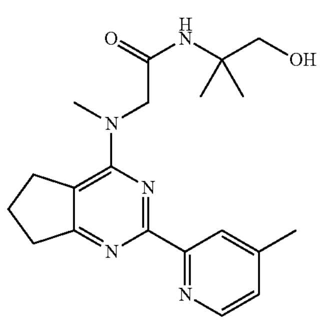 [SMILES: Cc1ccnc(-c2nc3c(c(N(C)CC(=O)NC(C)(C)CO)n2)CCC3)c1] | N-(1-hydroxy-2-methylpropan-2-yl)-2-{methyl[2-(4-methylpyridin-2-yl)-5H,6H,7H-cyclopenta[d]pyrimidin-4-yl]amino}acetamide | 370.1 |
| 63 | 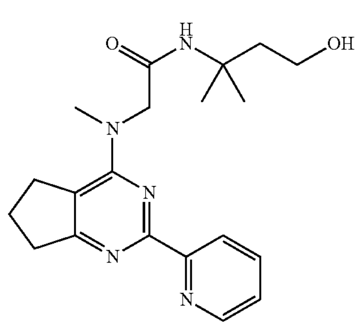 [SMILES: CN(CC(=O)NC(C)(C)CCO)c1nc(-c2ccccn2)nc2c1CCC2] | N-(4-hydroxy-2-methylbutan-2-yl)-2-{methyl[2-(pyridin-2-yl)-5H,6H,7H-cyclopenta[d]pyrimidin-4-yl]amino}acetamide | 370.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 64 | 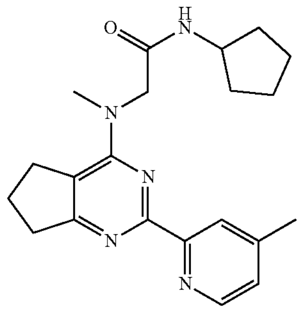 [SMILES: Cc1ccnc(-c2nc3c(c(N(C)CC(=O)NC4CCCC4)n2)CCC3)c1] | N-cyclopentyl-2-{methyl[2-(4-methylpyridin-2-yl)-5H,6H,7H-cyclopenta[d]pyrimidin-4-yl]amino}acetamide | 366.2 |
| 65 | 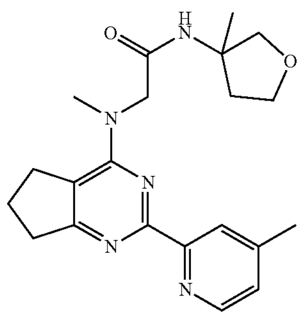 [SMILES: Cc1ccnc(-c2nc3c(c(N(C)CC(=O)NC4(C)CCOC4)n2)CCC3)c1] | 2-{methyl[2-(4-methylpyridin-2-yl)-5H,6H,7H-cyclopenta[d]pyrimidin-4-yl]amino}-N-(3-methyloxolan-3-yl)acetamide | 382.3 |
| 66 | 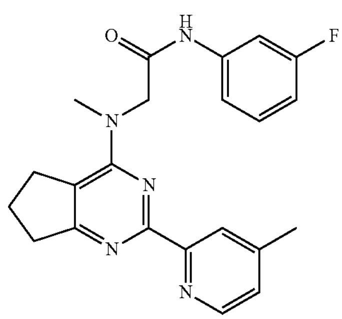 [SMILES: Cc1ccnc(-c2nc3c(c(N(C)CC(=O)Nc4cccc(F)c4)n2)CCC3)c1] | N-(3-fluorophenyl)-2-{methyl[2-(4-methylpyridin-2-yl)-5H,6H,7H-cyclopenta[d]pyrimidin-4-yl]amino}acetamide | 392.1 |
| 67 | 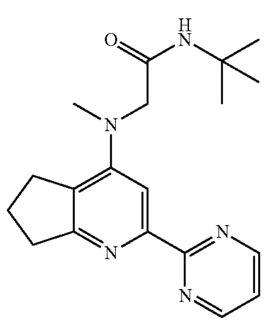 [SMILES: CN(CC(=O)NC(C)(C)C)c1cc(-c2ncccn2)nc2c1CCC2] | N-tert-butyl-2-{methyl[2-(pyrimidin-2-yl)-5H,6H,7H-cyclopenta[b]pyridin-4-yl]amino}acetamide | 340.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 68 | 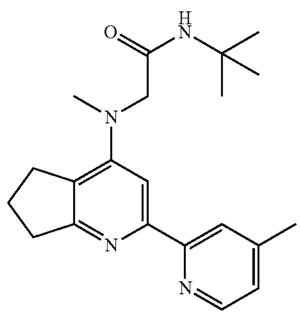 [SMILES: Cc1ccnc(-c2cc(N(C)CC(=O)NC(C)(C)C)c3c(n2)CCC3)c1] | N-tert-butyl-2-{methyl[2-(4-methylpyridin-2-yl)-5H,6H,7H-cyclopenta[b]pyridin-4-yl]amino}acetamide | 353.2 |
| 69 | 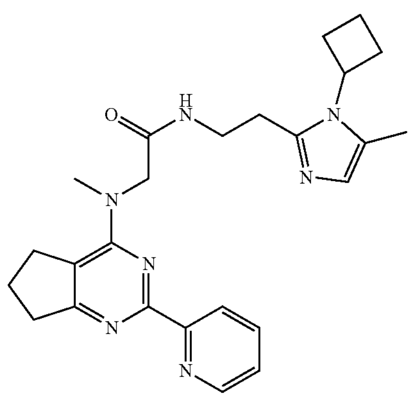 [SMILES: Cc1cnc(CCNC(=O)CN(C)c2nc(-c3ccccn3)nc3c2CCC3)n1C1CCC1] | N-[2-(1-cyclobutyl-5-methyl-1H-imidazol-2-yl)ethyl]-2-{methyl[2-(pyridin-2-yl)-5H,6H,7H-cyclopenta[d]pyrimidin-4-yl]amino}acetamide | 446.2 |
| 70 | 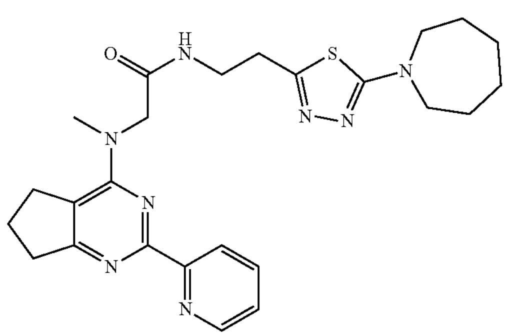 [SMILES: CN(CC(=O)NCCc1nnc(N2CCCCCC2)s1)c1nc(-c2ccccn2)nc2c1CCC2] | N-[5-(azepan-1-yl)-1,3,4-thiadiazol-2-yl]-2-{methyl[2-(pyridin-2-yl)-5H,6H,7H-cyclopenta[d]pyrimidin-4-yl]amino}acetamide | 465.3 |
| 71 | 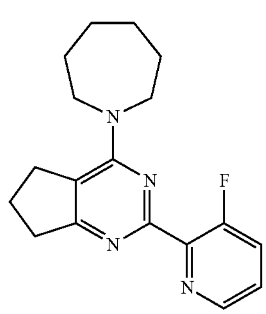 [SMILES: Fc1cccnc1-c1nc2c(c(N3CCCCCC3)n1)CCC2] | 1-[2-(3-fluoropyridin-2-yl)-5H,6H,7H-cyclopenta[d]pyrimidin-4-yl]azepane | 312.4 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 72 | 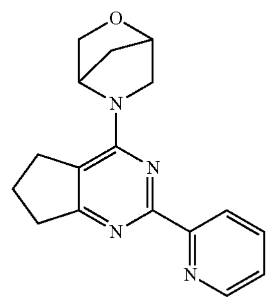 [SMILES: c1ccc(-c2nc3c(c(N4CC5CC4CO5)n2)CCC3)nc1] | 5-[2-(pyridin-2-yl)-5H,6H,7H-cyclopenta[d]pyrimidin-4-yl]-2-oxa-5-azabicyclo[2.2.1]heptane | 295 |
| 73 | 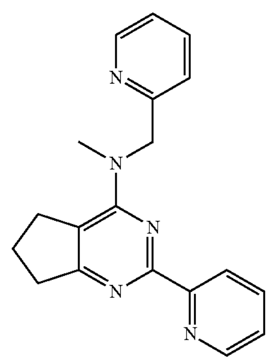 [SMILES: CN(Cc1ccccn1)c1nc(-c2ccccn2)nc2c1CCC2] | N-methyl-2-(pyridin-2-yl)-N-[(pyridin-2-yl)methyl]-5H,6H,7H-cyclopenta[d]pyrimidin-4-amine | 317.9 |
| 74 | 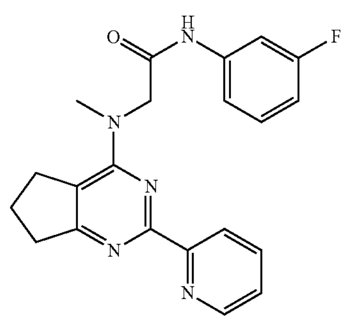 [SMILES: CN(CC(=O)Nc1cccc(F)c1)c1nc(-c2ccccn2)nc2c1CCC2] | N-(3-fluorophenyl)-2-{methyl[2-(pyridin-2-yl)-5H,6H,7H-cyclopenta[d]pyrimidin-4-yl]amino}acetamide | 379 |
| 75 | 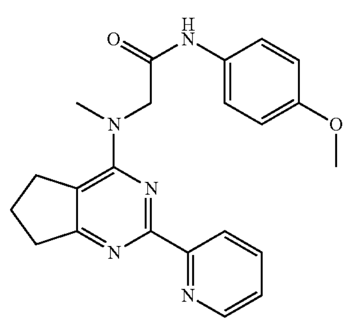 [SMILES: COc1ccc(NC(=O)CN(C)c2nc(-c3ccccn3)nc3c2CCC3)cc1] | N-(4-methoxyphenyl)-2-{methyl[2-(pyridin-2-yl)-5H,6H,7H-cyclopenta[d]pyrimidin-4-yl]amino}acetamide | 390.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 76 | 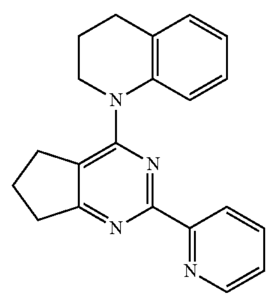 [SMILES: c1ccc(-c2nc3c(c(N4CCCc5ccccc54)n2)CCC3)nc1] | 1-[2-(pyridin-2-yl)-5H,6H,7H-cyclopenta[d]pyrimidin-4-yl]-1,2,3,4-tetrahydroquinoline | 329.1 |
| 77 | 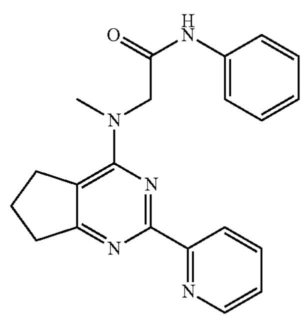 [SMILES: CN(CC(=O)Nc1ccccc1)c1nc(-c2ccccn2)nc2c1CCC2] | 2-{methyl[2-(pyridin-2-yl)-5H,6H,7H-cyclopenta[d]pyrimidin-4-yl]amino}-N-phenylacetamide | 360 |
| 78 | 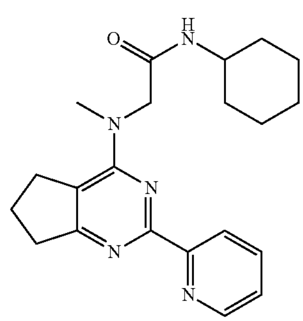 [SMILES: CN(CC(=O)NC1CCCCC1)c1nc(-c2ccccn2)nc2c1CCC2] | N-cyclohexyl-2-{methyl[2-(pyridin-2-yl)-5H,6H,7H-cyclopenta[d]pyrimidin-4-yl]amino}acetamide | 366 |
| 79 | 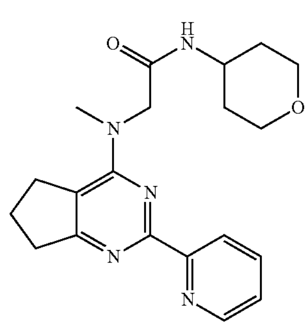 [SMILES: CN(CC(=O)NC1CCOCC1)c1nc(-c2ccccn2)nc2c1CCC2] | 2-{methyl[2-(pyridin-2-yl)-5H,6H,7H-cyclopenta[d]pyrimidin-4-yl]amino}-N-(oxan-4-yl)acetamide | 368.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 80 | 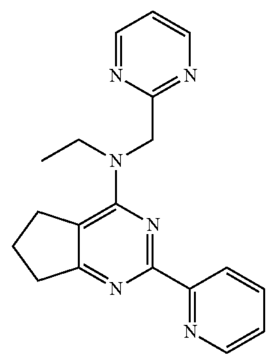 [SMILES: CCN(Cc1ncccn1)c1nc(-c2ccccn2)nc2c1CCC2] | N-ethyl-2-(pyridin-2-yl)-N-[(pyrimidin-2-yl)methyl]-5H,6H,7H-cyclopenta[d]pyrimidin-4-amine | 333 |
| 81 | 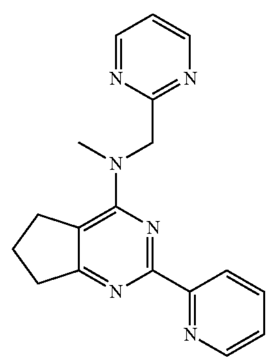 [SMILES: CN(Cc1ncccn1)c1nc(-c2ccccn2)nc2c1CCC2] | N-methyl-2-(pyridin-2-yl)-N-[(pyrimidin-2-yl)methyl]-5H,6H,7H-cyclopenta[d]pyrimidin-4-amine | 319.1 |
| 82 | 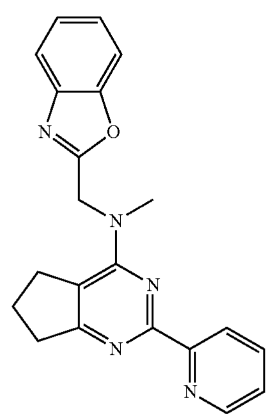 | N-[(1,3-benzoxazol-2-yl)methyl]-N-methyl-2-(pyridin-2-yl)-5H,6H,7H-cyclopenta[d]pyrimidin-4-amine | 358 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 83 | 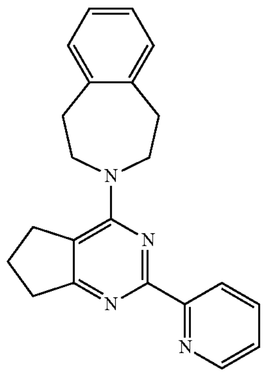 [SMILES: c1ccc(-c2nc3c(c(N4CCc5ccccc5CC4)n2)CCC3)nc1] | 3-[2-(pyridin-2-yl)-5H,6H,7H-cyclopenta[d]pyrimidin-4-yl]-2,3,4,5-tetrahydro-1H-3-benzazepine | 343 |
| 84 | 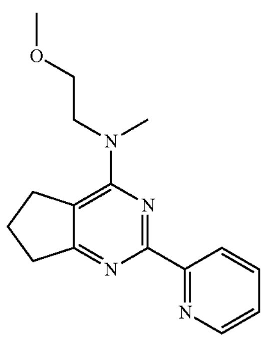 [SMILES: COCCN(C)c1nc(-c2ccccn2)nc2c1CCC2] | N-(2-methoxyethyl)-N-methyl-2-(pyridin-2-yl)-5H,6H,7H-cyclopenta[d]pyrimidin-4-amine | 285 |
| 85 | 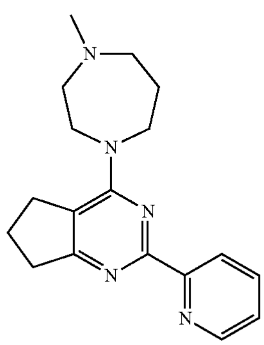 [SMILES: CN1CCCN(c2nc(-c3ccccn3)nc3c2CCC3)CC1] | 1-methyl-4-[2-(pyridin-2-yl)-5H,6H,7H-cyclopenta[d]pyrimidin-4-yl]-1,4-diazepane | 310.1 |
| 86 | 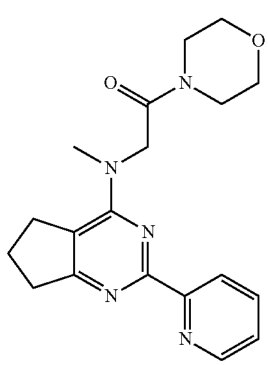 [SMILES: CN(CC(=O)N1CCOCC1)c1nc(-c2ccccn2)nc2c1CCC2] | 2-{methyl[2-(pyridin-2-yl)-5H,6H,7H-cyclopenta[d]pyrimidin-4-yl]amino}-1-(morpholin-4-yl)ethan-1-one | 354 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 87 | 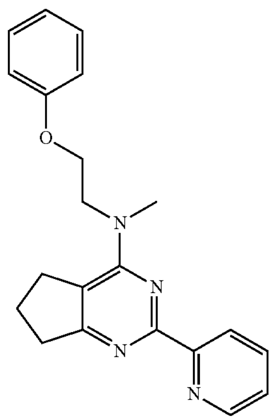 [SMILES: CN(CCOc1ccccc1)c1nc(-c2ccccn2)nc2c1CCC2] | N-methyl-N-(2-phenoxyethyl)-2-(pyridin-2-yl)-5H,6H,7H-cyclopenta[d]pyrimidin-4-amine | 347 |
| 88 | 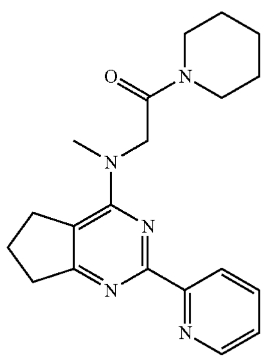 [SMILES: CN(CC(=O)N1CCCCC1)c1nc(-c2ccccn2)nc2c1CCC2] | 2-{methyl[2-(pyridin-2-yl)-5H,6H,7H-cyclopenta[d]pyrimidin-4-yl]amino}-1-(piperidin-1-yl)ethan-1-one | 352.1 |
| 89 | 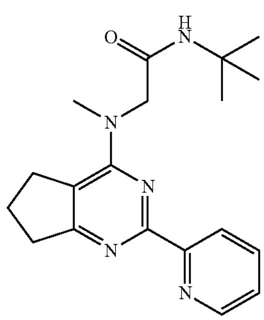 [SMILES: CN(CC(=O)NC(C)(C)C)c1nc(-c2ccccn2)nc2c1CCC2] | N-tert-butyl-2-{methyl[2-(pyridin-2-yl)-5H,6H,7H-cyclopenta[d]pyrimidin-4-yl]amino}acetamide | 340 |
| 90 | 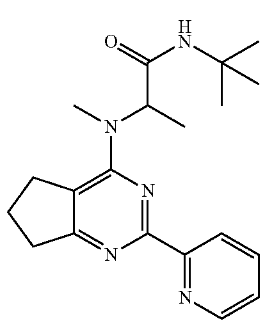 | N-tert-butyl-2-{methyl[2-(pyridin-2-yl)-5H,6H,7H-cyclopenta[d]pyrimidin-4-yl]amino}propanamide | 354.4 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 91 | 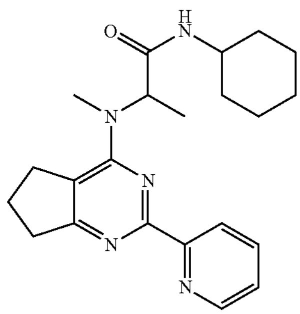 [SMILES: CC(C(=O)NC1CCCCC1)N(C)c1nc(-c2ccccn2)nc2c1CCC2] | N-cyclohexyl-2-{methyl[2-(pyridin-2-yl)-5H,6H,7H-cyclopenta[d]pyrimidin-4-yl]amino}propanamide | 380 |
| 92 | 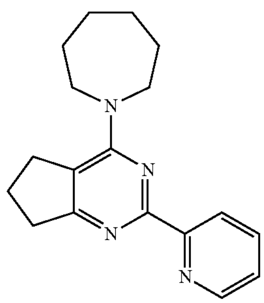 [SMILES: c1ccc(-c2nc3c(c(N4CCCCCC4)n2)CCC3)nc1] | 1-[2-(pyridin-2-yl)-5H,6H,7H-cyclopenta[d]pyrimidin-4-yl]azepane | 295.2 |
| 93 | 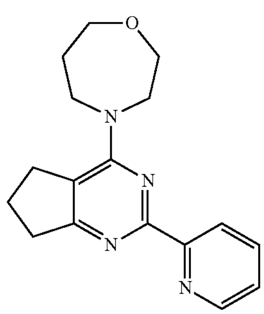 [SMILES: c1ccc(-c2nc3c(c(N4CCCOCC4)n2)CCC3)nc1] | 4-[2-(pyridin-2-yl)-5H,6H,7H-cyclopenta[d]pyrimidin-4-yl]-1,4-oxazepane | 297.2 |
| 94 | 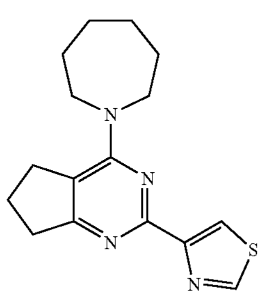 [SMILES: c1nc(-c2nc3c(c(N4CCCCCC4)n2)CCC3)cs1] | 1-[2-(1,3-thiazol-4-yl)-5H,6H,7H-cyclopenta[d]pyrimidin-4-yl]azepane | 301.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 95 | 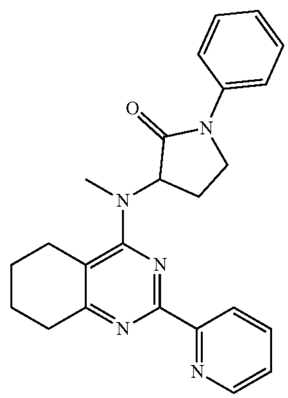 [SMILES: CN(c1nc(-c2ccccn2)nc2c1CCCC2)C1CCN(c2ccccc2)C1=O] | 3-{methyl[2-(pyridin-2-yl)-5H,6H,7H-cyclopenta[d]pyrimidin-4-yl]amino}-1-phenylpyrrolidin-2-one | 386.3 |
| 96 | 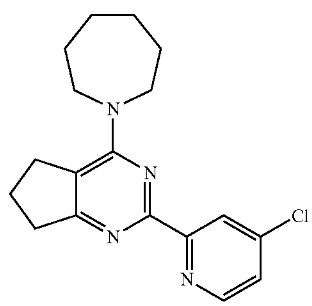 [SMILES: Clc1ccnc(-c2nc3c(c(N4CCCCCC4)n2)CCC3)c1] | 1-[2-(4-chloropyridin-2-yl)-5H,6H,7H-cyclopenta[d]pyrimidin-4-yl]azepane | 329.3 |
| 97 | 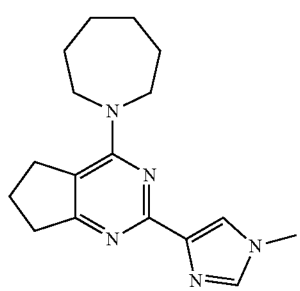 [SMILES: Cn1cnc(-c2nc3c(c(N4CCCCCC4)n2)CCC3)c1] | 1-[2-(1-methyl-1H-imidazol-4-yl)-5H,6H,7H-cyclopenta[d]pyrimidin-4-yl]azepane | 298.2 |
| 98 | 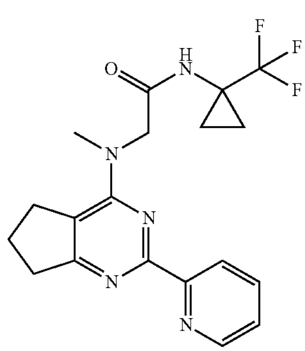 [SMILES: CN(CC(=O)NC1(C(F)(F)F)CC1)c1nc(-c2ccccn2)nc2c1CCC2] | 2-{methyl[2-(pyridin-2-yl)-5H,6H,7H-cyclopenta[d]pyrimidin-4-yl]amino}-N-[1-(trifluoromethyl)cyclopropyl]acetamide | 392 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 99 | 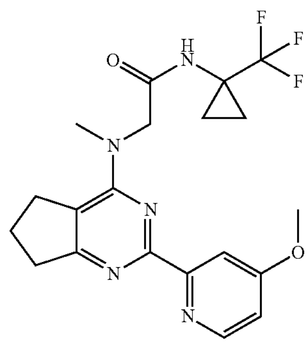 [SMILES: COc1ccnc(-c2nc3c(c(N(C)CC(=O)NC4(C(F)(F)F)CC4)n2)CCC3)c1] | 2-{[2-(4-methoxypyridin-2-yl)-5H,6H,7H-cyclopenta[d]pyrimidin-4-yl](methyl)amino}-N-[1-(trifluoromethyl)cyclopropyl]acetamide | 421.7 |
| 100 | 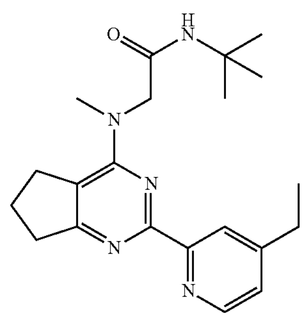 [SMILES: CCc1ccnc(-c2nc3c(c(N(C)CC(=O)NC(C)(C)C)n2)CCC3)c1] | N-tert-butyl-2-{[2-(4-ethylpyridin-2-yl)-5H,6H,7H-cyclopenta[d]pyrimidin-4-yl](methyl)amino}acetamide | 368.2 |
| 101 | 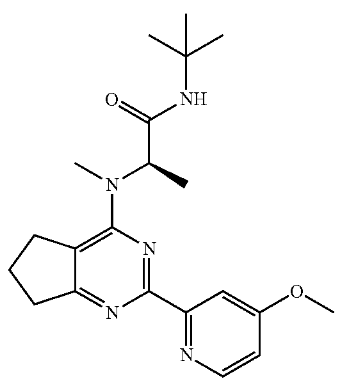 [SMILES: COc1ccnc(-c2nc3c(c(N(C)[C@H](C)C(=O)NC(C)(C)C)n2)CCC3)c1] | (2R)-N-tert-butyl-2-{[2-(4-methoxypyridin-2-yl)-5H,6H,7H-cyclopenta[d]pyrimidin-4-yl](methyl)amino}propanamide | 384.4 |
| 102 | 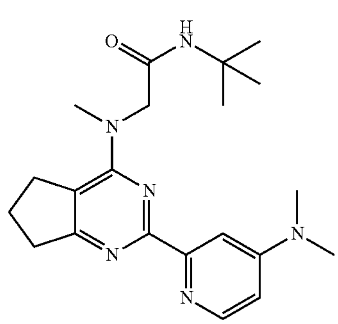 [SMILES: CN(C)c1ccnc(-c2nc3c(c(N(C)CC(=O)NC(C)(C)C)n2)CCC3)c1] | N-tert-butyl-2-({2-[4-(dimethylamino)pyridin-2-yl]-5H,6H,7H-cyclopenta[d]pyrimidin-4-yl}(methyl)amino)acetamide | 383.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 103 | 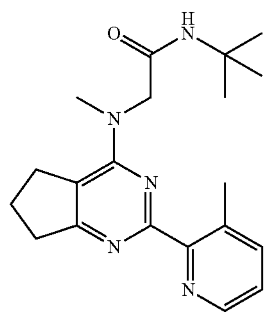 [SMILES: Cc1cccnc1-c1nc2c(c(N(C)CC(=O)NC(C)(C)C)n1)CCC2] | N-tert-butyl-2-{methyl[2-(3-methylpyridin-2-yl)-5H,6H,7H-cyclopenta[d]pyrimidin-4-yl]amino}acetamide | 354.2 |
| 104 | 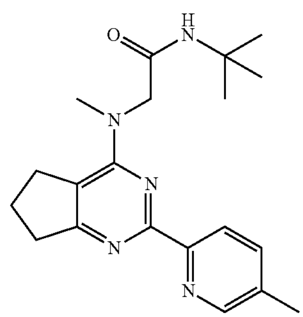 [SMILES: Cc1ccc(-c2nc3c(c(N(C)CC(=O)NC(C)(C)C)n2)CCC3)nc1] | N-tert-butyl-2-{methyl[2-(5-methylpyridin-2-yl)-5H,6H,7H-cyclopenta[d]pyrimidin-4-yl]amino}acetamide | 354.1 |
| 105 | 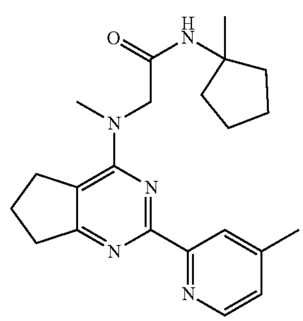 [SMILES: Cc1ccnc(-c2nc3c(c(N(C)CC(=O)NC4(C)CCCC4)n2)CCC3)c1] | 2-{methyl[2-(4-methylpyridin-2-yl)-5H,6H,7H-cyclopenta[d]pyrimidin-4-yl]amino}-N-(1-methylcyclopentyl)acetamide | 380.2 |
| 106 | 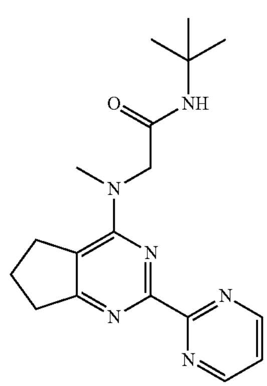 [SMILES: CN(CC(=O)NC(C)(C)C)c1nc(-c2ncccn2)nc2c1CCC2] | N-tert-butyl-2-{methyl[2-(pyrimidin-2-yl)-5H,6H,7H-cyclopenta[d]pyrimidin-4-yl]amino}acetamide | 341.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 107 | 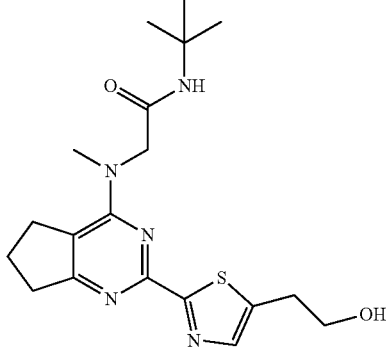 [SMILES: CN(CC(=O)NC(C)(C)C)c1nc(-c2ncc(CCO)s2)nc2c1CCC2] | N-tert-butyl-2-({2-[5-(2-hydroxyethyl)-1,3-thiazol-2-yl]-5H,6H,7H-cyclopenta[d]pyrimidin-4-yl}(methyl)amino)acetamide | 390.2 |
| 108 | 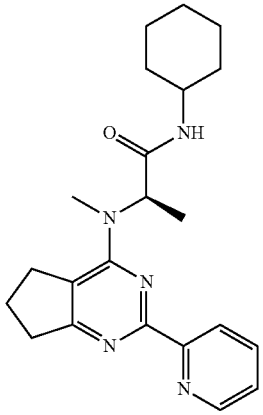 [SMILES: C[C@H](C(=O)NC1CCCCC1)N(C)c1nc(-c2ccccn2)nc2c1CCC2] | (2R)-N-cyclohexyl-2-{ethyl[2-(pyridin-2-yl)-5H,6H,7H-cyclopenta[d]pyrimidin-4-yl]amino}propanamide | 380.4 |
| 109 | 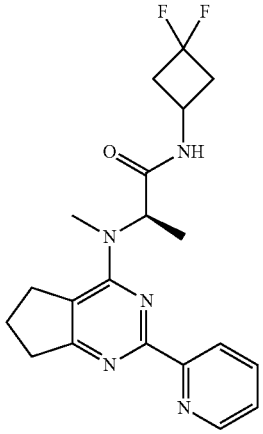 [SMILES: C[C@H](C(=O)NC1CC(F)(F)C1)N(C)c1nc(-c2ccccn2)nc2c1CCC2] | (2R)-N-(3,3-difluorocyclobutyl)-2-{methyl[2-(pyridin-2-yl)-5H,6H,7H-cyclopenta[d]pyrimidin-4-yl]amino}propanamide | 388.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 110 | 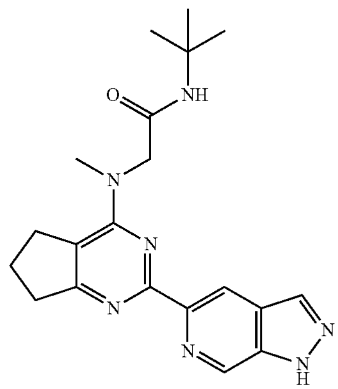 [SMILES: CN(CC(=O)NC(C)(C)C)c1nc(-c2cc3cn[nH]c3cn2)nc2c1CCC2] | N-tert-butyl-2-[methyl(2-{1H-pyrazolo[3,4-c]pyridin-5-yl}-5H,6H,7H-cyclopenta[d]pyrimidin-4-yl)amino]acetamide | 380.2 |
| 111 | 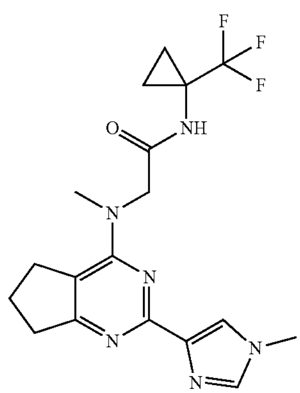 [SMILES: CN(CC(=O)NC1(C(F)(F)F)CC1)c1nc(-c2cn(C)cn2)nc2c1CCC2] | 2-{methyl[2-(1-methyl-1H-imidazol-4-yl)-5H,6H,7H-cyclopenta[d]pyrimidin-4-yl]amino}-N-[1-(trifluoromethyl)cyclopropyl]acetamide | 395.2 |
| 112 | 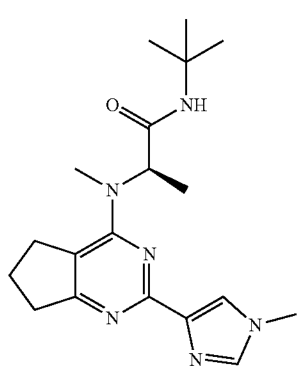 [SMILES: C[C@H](C(=O)NC(C)(C)C)N(C)c1nc(-c2cn(C)cn2)nc2c1CCC2] | (2R)-N-tert-butyl-2-{methyl[2-(1-methyl-1H-imidazol-4-yl)-5H,6H,7H-cyclopenta[d]pyrimidin-4-yl]amino}propanamide | 357.4 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 113 | 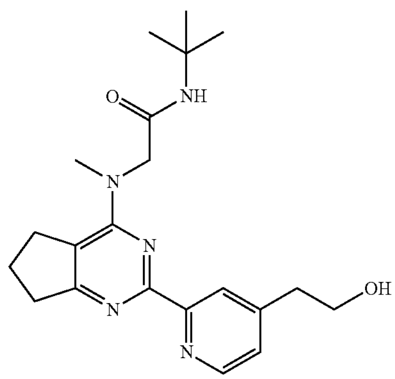 [SMILES: CN(CC(=O)NC(C)(C)C)c1nc(-c2cc(CCO)ccn2)nc2c1CCC2] | N-tert-butyl-2-({2-[4-(2-hydroxyethyl)pyridin-2-yl]-5H,6H,7H-cyclopenta[d]pyrimidin-4-yl}(methyl)amino)acetamide | 384.2 |
| 114 | 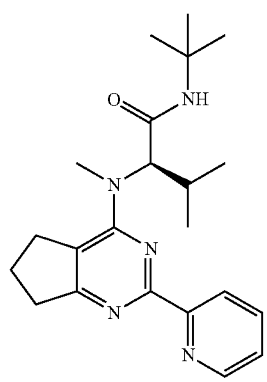 [SMILES: CC(C)[C@H](C(=O)NC(C)(C)C)N(C)c1nc(-c2ccccn2)nc2c1CCC2] | (2R)-N-tert-butyl-3-methyl-2-{methyl[2-(pyridin-2-yl)-5H,6H,7H-cyclopenta[d]pyrimidin-4-yl]amino}butanamide | 382 |
| 115 | 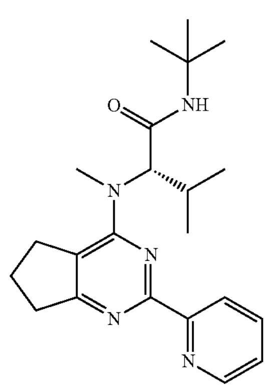 [SMILES: CC(C)[C@@H](C(=O)NC(C)(C)C)N(C)c1nc(-c2ccccn2)nc2c1CCC2] | (2S)-N-tert-butyl-3-methyl-2-{methyl[2-(pyridin-2-yl)-5H,6H,7H-cyclopenta[d]pyrimidin-4-yl]amino}butanamide | 382 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 116 | 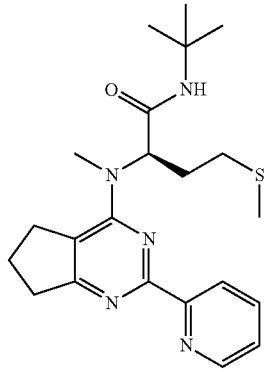 [SMILES: CSCC[C@H](C(=O)NC(C)(C)C)N(C)c1nc(-c2ccccn2)nc2c1CCC2] | (2R)-N-tert-butyl-2-{methyl[2-(pyridin-2-yl)-5H,6H,7H-cyclopenta[d]pyrimidin-4-yl]amino}-4-(methylsulfanyl)butanamide | 414 |
| 117 | 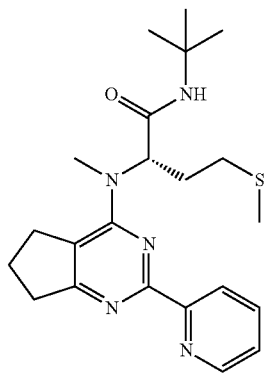 [SMILES: CSCC[C@@H](C(=O)NC(C)(C)C)N(C)c1nc(-c2ccccn2)nc2c1CCC2] | (2S)-N-tert-butyl-2-{methyl[2-(pyridin-2-yl)-5H,6H,7H-cyclopenta[d]pyrimidin-4-yl]amino}-4-(methylsulfanyl)butanamide | 414.1 |
| 118 | 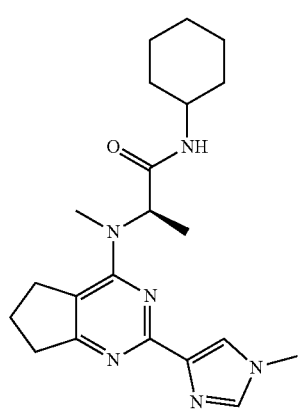 [SMILES: C[C@H](C(=O)NC1CCCCC1)N(C)c1nc(-c2cn(C)cn2)nc2c1CCC2] | (2R)-N-cyclohexyl-2-{methyl[2-(1-methyl-1H-imidazol-4-yl)-5H,6H,7H-cyclopenta[d]pyrimidin-4-yl]amino}propanamide | 383.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 119 | 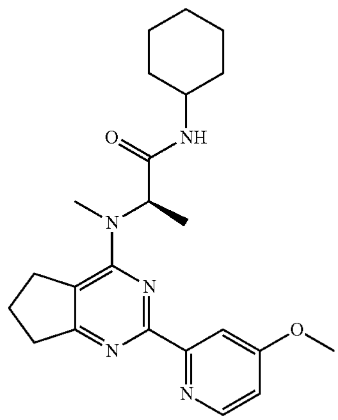 [SMILES: COc1ccnc(-c2nc3c(c(N(C)[C@H](C)C(=O)NC4CCCCC4)n2)CCC3)c1] | (2R)-N-cyclohexyl-2-{[2-(4-methoxypyridin-2-yl)-5H,6H,7H-cyclopenta[d]pyrimidin-4-yl](methyl)amino}propanamide | 410.1 |
| 120 | 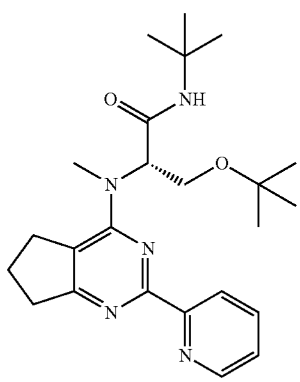 [SMILES: CN(c1nc(-c2ccccn2)nc2c1CCC2)[C@@H](COC(C)(C)C)C(=O)NC(C)(C)C] | (2S)-3-(tert-butoxy)-N-tert-butyl-2-{methyl[2-(pyridin-2-yl)-5H,6H,7H-cyclopenta[d]pyrimidin-4-yl]amino}propanamide | 426.1 |
| 121 | 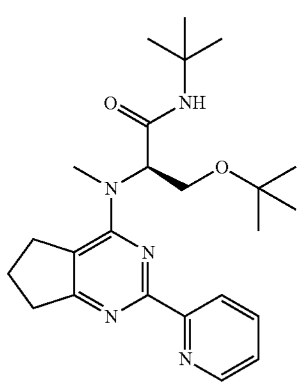 [SMILES: CN(c1nc(-c2ccccn2)nc2c1CCC2)[C@H](COC(C)(C)C)C(=O)NC(C)(C)C] | (2R)-3-(tert-btuoxy)-N-tert-butyl-2-{methyl[2-(pyridin-2-yl)-5H,6H,7H-cyclopenta[d]pyrimidin-4-yl]amino}propanamide | 426.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 122 | 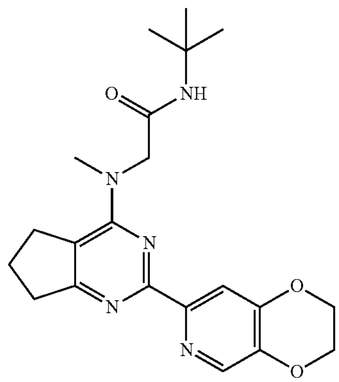 [SMILES: CN(CC(=O)NC(C)(C)C)c1nc(-c2cc3c(cn2)OCCO3)nc2c1CCC2] | N-tert-butyl-2-[(2-{2H,3H-[1,4]dioxino[2,3-c]pyridin-7-yl}-5H,6H,7H-cyclopenta[d]pyrimidin-4-yl)(methyl)amino]acetamide | 398.2 |
| 123 | 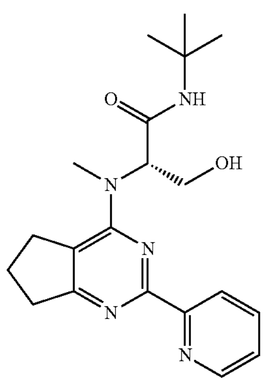 [SMILES: CN(c1nc(-c2ccccn2)nc2c1CCC2)[C@@H](CO)C(=O)NC(C)(C)C] | (2S)-N-tert-butyl-3-hydroxy-2-{methyl[2-(pyridin-2-yl)-5H,6H,7H-cyclopenta[d]pyrimidin-4-yl]amino}propanamide | 369.9 |
| 124 | 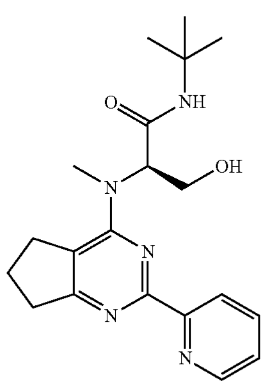 [SMILES: CN(c1nc(-c2ccccn2)nc2c1CCC2)[C@H](CO)C(=O)NC(C)(C)C] | (2R)-N-tert-butyl-3-hydroxy-2-{methyl[2-(pyridin-2-yl)-5H,6H,7H-cyclopenta[d]pyrimidin-4-yl]amino}propanamide | 370 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 125 | 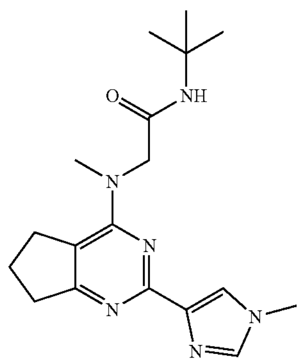 [SMILES: CN(CC(=O)NC(C)(C)C)c1nc(-c2cn(C)cn2)nc2c1CCC2] | N-tert-butyl-2-{methyl[2-(1-methyl-1H-imidazol-4-yl)-5H,6H,7H-cyclopenta[d]pyrimidin-4-yl]amino}acetamide | 343.2 |
| 126 | 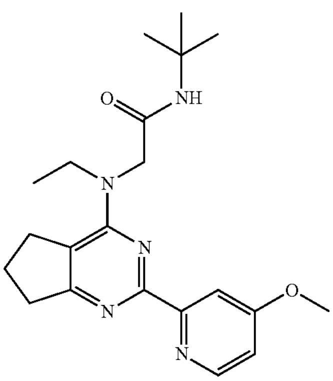 [SMILES: CCN(CC(=O)NC(C)(C)C)c1nc(-c2cc(OC)ccn2)nc2c1CCC2] | N-tert-butyl-2-{ethyl[2-(4-methoxypyridin-2-yl)-5H,6H,7H-cyclopenta[d]pyrimidin-4-yl]amino}acetamide | 384.1 |
| 127 | 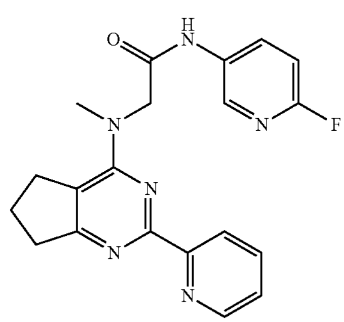 [SMILES: CN(CC(=O)Nc1ccc(F)nc1)c1nc(-c2ccccn2)nc2c1CCC2] | N-(6-fluoropyridin-3-yl)-2-{methyl[2-(pyridin-2-yl)-5H,6H,7H-cyclopenta[d]pyrimidin-4-yl]amino}acetamide | 379.1 |
| 128 | 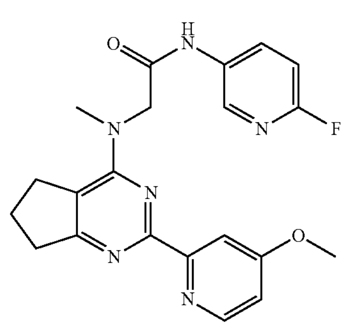 [SMILES: COc1ccnc(-c2nc3c(c(N(C)CC(=O)Nc4ccc(F)nc4)n2)CCC3)c1] | N-(6-fluoropyridin-3-yl)-2-{[2-(4-methoxypyridin-2-yl)-5H,6H,7H-cyclopenta[d]pyrimidin-4-yl](methyl)amino}acetamide | 409.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 129 | 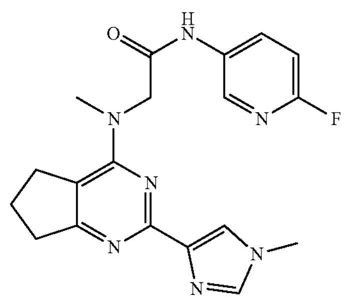 [SMILES: CN(CC(=O)Nc1ccc(F)nc1)c1nc(-c2cn(C)cn2)nc2c1CCC2] | N-(6-fluoropyridin-3-yl)-2-{methyl[2-(1-methyl-1H-imidazol-4-yl)-5H,6H,7H-cyclopenta[d]pyrimidin-4-yl]amino}acetamide | 382.2 |
| 130 | 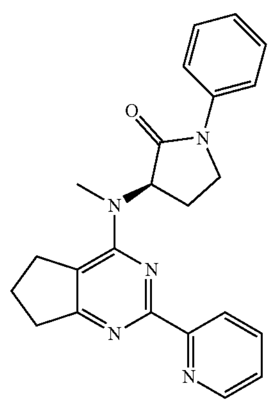 [SMILES: CN(c1nc(-c2ccccn2)nc2c1CCC2)[C@@H]1CCN(c2ccccc2)C1=O] | (3R)-3-{methyl[2-(pyridin-2-yl)-5H,6H,7H-cyclopenta[d]pyrimidin-4-yl]amino}-1-phenylpyrrolidin-2-one | 386 |
| 131 | 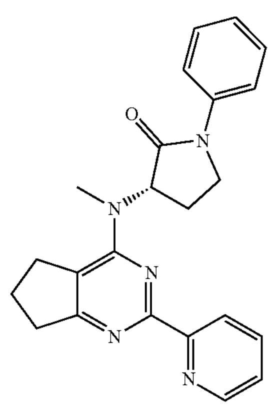 [SMILES: CN(c1nc(-c2ccccn2)nc2c1CCC2)[C@H]1CCN(c2ccccc2)C1=O] | (3S)-3-{methyl[2-(pyridin-2-yl)-5H,6H,7H-cyclopenta[d]pyrimidin-4-yl]amino}-1-phenylpyrrolidin-2-one | 386 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 132 | 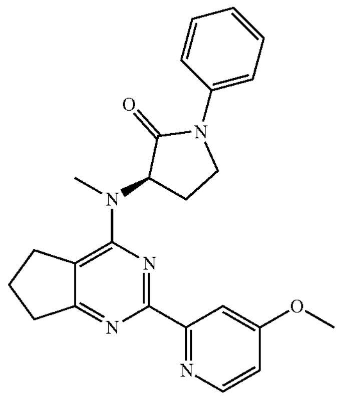 [SMILES: COc1ccnc(-c2nc3c(c(N(C)[C@@H]4CCN(c5ccccc5)C4=O)n2)CCC3)c1] | (3R)-3-{[2-(4-methoxypyridin-2-yl)-5H,6H,7H-cyclopenta[d]pyrimidin-4-yl](methyl)amino}-1-phenylpyrrolidin-2-one | 415.9 |
| 133 | 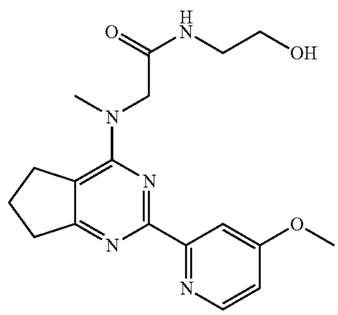 [SMILES: COc1ccnc(-c2nc3c(c(N(C)CC(=O)NCCO)n2)CCC3)c1] | N-(2-hydroxyethyl)-2-{[2-(4-methoxypyridin-2-yl)-5H,6H,7H-cyclopenta[d]pyrimidin-4-yl](methyl)amino}acetamide | 358.2 |
| 134 | 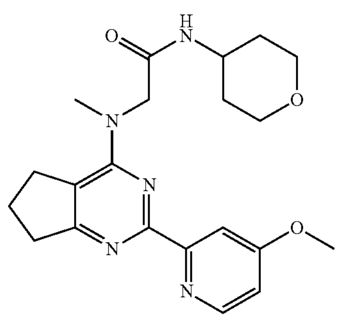 [SMILES: COc1ccnc(-c2nc3c(c(N(C)CC(=O)NC4CCOCC4)n2)CCC3)c1] | 2-{[2-(4-methoxypyridin-2-yl)-5H,6H,7H-cyclopenta[d]pyrimidin-4-yl](methyl)amino}-N-(oxan-4-yl)acetamide | 398.2 |
| 135 | 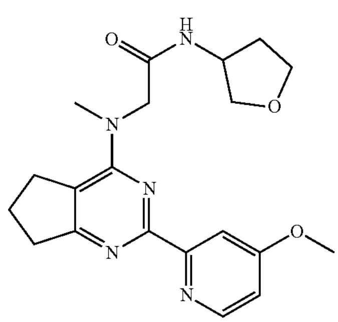 [SMILES: COc1ccnc(-c2nc3c(c(N(C)CC(=O)NC4CCOC4)n2)CCC3)c1] | 2-{[2-(4-methoxypyridin-2-yl)-5H,6H,7H-cyclopenta[d]pyrimidin-4-yl](methyl)amino}-N-(oxolan-3-yl)acetamide | 384.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 136 | 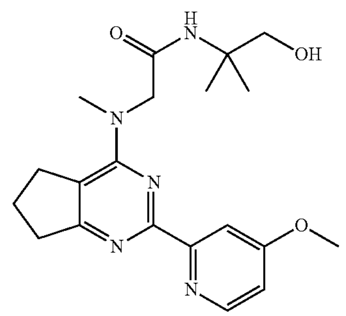 [SMILES: COc1ccnc(-c2nc3c(c(N(C)CC(=O)NC(C)(C)CO)n2)CCC3)c1] | N-(1-hydroxy-2-methylpropan-2-yl)-2-{[2-(4-methoxypyridin-2-yl)-5H,6H,7H-cyclopenta[d]pyrimidin-4-yl](methyl)amino}acetamide | 386.2 |
| 137 | 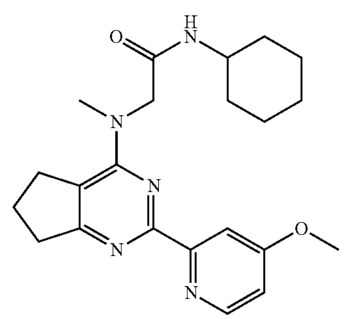 [SMILES: COc1ccnc(-c2nc3c(c(N(C)CC(=O)NC4CCCCC4)n2)CCC3)c1] | N-cyclohexyl-2-{[2-(4-methoxypyridin-2-yl)-5H,6H,7H-cyclopenta[d]pyrimidin-4-yl](methyl)amino}acetamide | 396.2 |
| 138 | 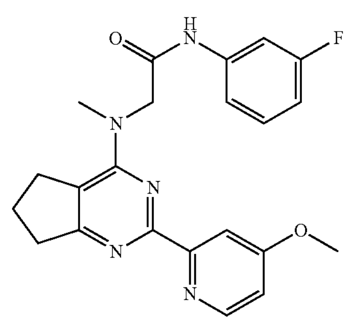 [SMILES: COc1ccnc(-c2nc3c(c(N(C)CC(=O)Nc4cccc(F)c4)n2)CCC3)c1] | N-(3-fluorophenyl)-2-{[2-(4-methoxypyridin-2-yl)-5H,6H,7H-cyclopenta[d]pyrimidin-4-yl](methyl)amino}acetamide | 408.2 |
| 139 | 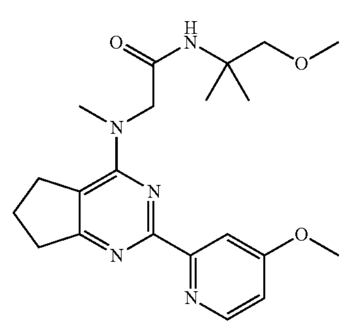 [SMILES: COCC(C)(C)NC(=O)CN(C)c1nc(-c2cc(OC)ccn2)nc2c1CCC2] | N-(1-methoxy-2-methylpropan-2-yl)-2-{[2-(4-methoxypyridin-2-yl)-5H,6H,7H-cyclopenta[d]pyrimidin-4-yl](methyl)amino}acetamide | 400.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 140 | 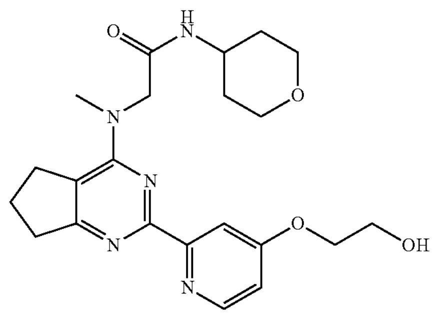 [SMILES: CN(CC(=O)NC1CCOCC1)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-N-(oxan-4-yl)acetamide | 428.2 |
| 141 | 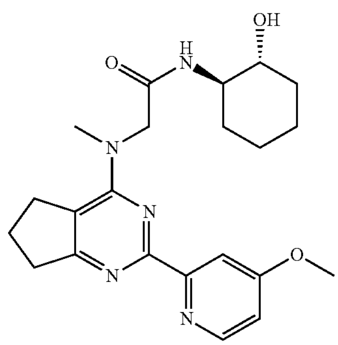 [SMILES: COc1ccnc(-c2nc3c(c(N(C)CC(=O)N[C@@H]4CCCC[C@H]4O)n2)CCC3)c1] | N-[(1R,2R)-2-hydroxycyclohexyl]-2-{[2-(4-methoxypyridin-2-yl)-5H,6H,7H-cyclopenta[d]pyrimidin-4-yl](methyl)amino}acetamide | 412.3 |
| 142 | 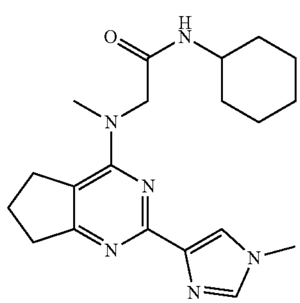 [SMILES: CN(CC(=O)NC1CCCCC1)c1nc(-c2cn(C)cn2)nc2c1CCC2] | N-cyclohexyl-2-{methyl[2-(1-methyl-1H-imidazol-4-yl)-5H,6H,7H-cyclopenta[d]pyrimidin-4-yl]amino}acetamide | 369.2 |
| 143 | 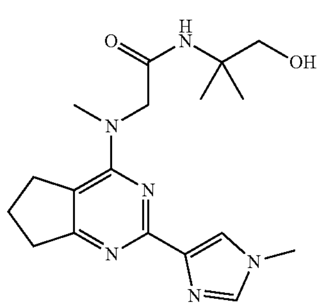 [SMILES: CN(CC(=O)NC(C)(C)CO)c1nc(-c2cn(C)cn2)nc2c1CCC2] | N-(1-hydroxy-2-methylpropan-2-yl)-2-{ethyl[2-(1-methyl-1H-imidazol-4-yl)-5H,6H,7H-cyclopenta[d]pyrimidin-4-yl]amino}acetamide | 359.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 144 | 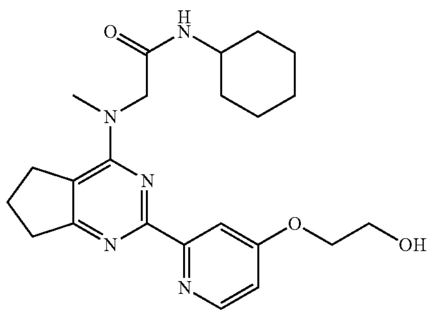 [SMILES: CN(CC(=O)NC1CCCCC1)c1nc(-c2cc(OCCO)ccn2)nc2c1CCC2] | N-cyclohexyl-2-({2-[4-(2-hydroxyethoxy)pyridin-2-yl]-5H,6H,7H-cyclopenta[d]pyrimidin-4-yl}(methyl)amino)acetamide | 426.2 |
| 145 | 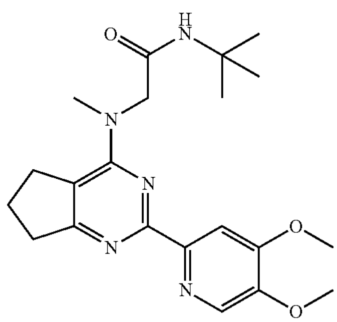 [SMILES: COc1cnc(-c2nc3c(c(N(C)CC(=O)NC(C)(C)C)n2)CCC3)cc1OC] | N-tert-butyl-2-{[2-(4,5-dimethoxypyridin-2-yl)-5H,6H,7H-cyclopenta[d]pyrimidin-4-yl](methyl)amino}acetamide | 400.2 |
| 146 | 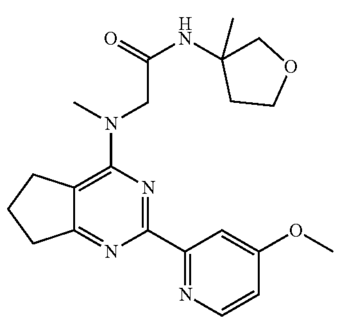 [SMILES: COc1ccnc(-c2nc3c(c(N(C)CC(=O)NC4(C)CCOC4)n2)CCC3)c1] | 2-{[2-(4-methoxypyridin-2-yl)-5H,6H,7H-cyclopenta[d]pyrimidin-4-yl](methyl)amino}-N-(3-methyloxolan-3-yl)acetamide | 398 |
| 147 | 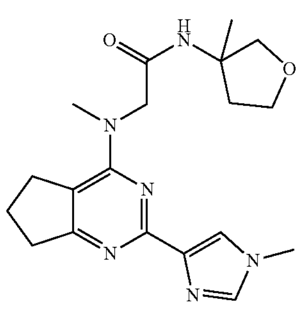 [SMILES: CN(CC(=O)NC1(C)CCOC1)c1nc(-c2cn(C)cn2)nc2c1CCC2] | 2-{methyl[2-(1-methyl-1H-imidazol-4-yl)-5H,6H,7H-cyclopenta[d]pyrimidin-4-yl]amino}-N-(3-methyloxolan-3-yl)acetamide | 371 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 148 | 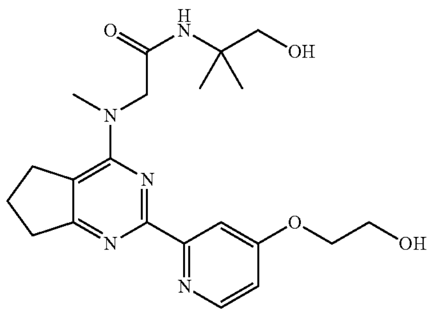 [SMILES: CN(CC(=O)NC(C)(C)CO)c1nc(-c2cc(OCCO)ccn2)nc2c1CCC2] | N-(1-hydroxy-2-methylpropan-2-yl)-2-({2-[4-(2-hydroxyethoxy)pyridin-2-yl]-5H,6H,7H-cyclopenta[d]pyrimidin-4-yl}(methyl)amino)acetamide | 416.2 |
| 149 | 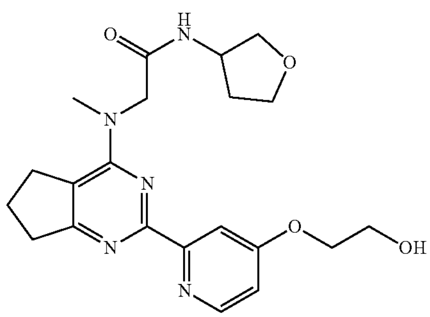 [SMILES: CN(CC(=O)NC1CCOC1)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-N-(oxolan-3-yl)acetamide | 414.2 |
| 150 | 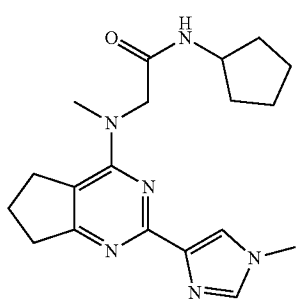 [SMILES: CN(CC(=O)NC1CCCC1)c1nc(-c2cn(C)cn2)nc2c1CCC2] | N-cyclopentyl-2-{methyl[2-(1-methyl-1H-imidazol-4-yl)-5H,6H,7H-cyclopenta[d]pyrimidin-4-yl]amino}acetamide | 355.2 |
| 151 | 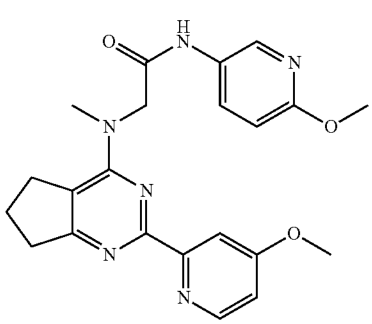 [SMILES: COc1ccnc(-c2nc3c(c(N(C)CC(=O)Nc4ccc(OC)nc4)n2)CCC3)c1] | 2-{[2-(4-methoxypyridin-2-yl)-5H,6H,7H-cyclopenta[d]pyrimidin-4-yl](methyl)amino}-N-(6-methoxypyridin-3-yl)acetamide | 421.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 152 | 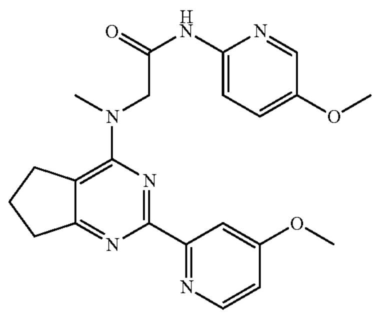 [SMILES: COc1ccc(NC(=O)CN(C)c2nc(-c3cc(OC)ccn3)nc3c2CCC3)nc1] | N-(5-methoxypyridin-2-yl)-2-{[2-(4-methoxypyridin-2-yl)-5H,6H,7H-cyclopenta[d]pyrimidin-4-yl](methyl)amino}acetamide | 421.2 |
| 153 | 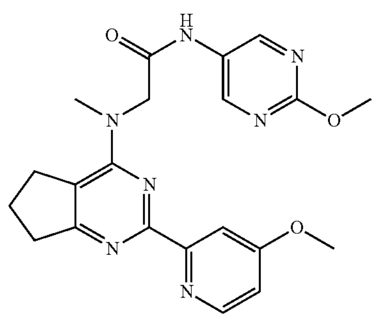 [SMILES: COc1ccnc(-c2nc3c(c(N(C)CC(=O)Nc4cnc(OC)nc4)n2)CCC3)c1] | 2-{[2-(4-methoxypyridin-2-yl)-5H,6H,7H-cyclopenta[d]pyrimidin-4-yl](methyl)amino}-N-(2-methoxypyrimidin-5-yl)acetamide | 422.2 |
| 154 | 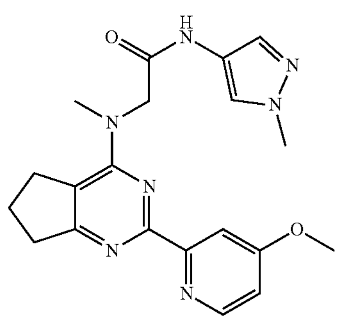 [SMILES: COc1ccnc(-c2nc3c(c(N(C)CC(=O)Nc4cnn(C)c4)n2)CCC3)c1] | 2-{[2-(4-methoxypyridin-2-yl)-5H,6H,7H-cyclopenta[d]pyrimidin-4-yl](methyl)amino}-N-(1-methyl-1H-pyrazol-4-yl)acetamide | 394.2 |
| 155 | 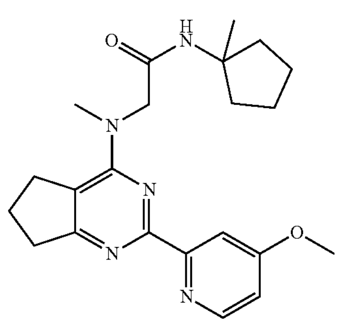 [SMILES: COc1ccnc(-c2nc3c(c(N(C)CC(=O)NC4(C)CCCC4)n2)CCC3)c1] | 2-{[2-(4-methoxypyridin-2-yl)-5H,6H,7H-cyclopenta[d]pyrimdiin-4-yl](methyl)amino}-N-(1-methylcyclopentyl)acetamide | 396.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 156 | 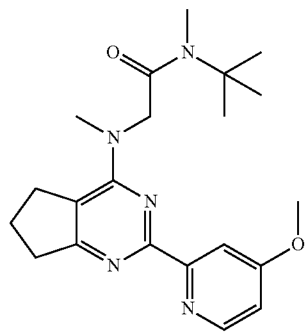 [SMILES: COc1ccnc(-c2nc3c(c(N(C)CC(=O)N(C)C(C)(C)C)n2)CCC3)c1] | N-tert-butyl-2-{[2-(4-methoxypyridin-2-yl)-5H,6H,7H-cyclopenta[d]pyrimidin-4-yl](methyl)amino}-N-methylacetamide | 384.2 |
| 157 | 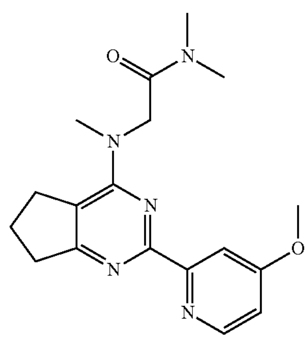 [SMILES: COc1ccnc(-c2nc3c(c(N(C)CC(=O)N(C)C)n2)CCC3)c1] | 2-{[2-(4-methoxypyridin-2-yl)-5H,6H,7H-cyclopenta[d]pyrimidin-4-yl](methyl)amino}-N,N-dimethylacetamide | 342.2 |
| 158 | 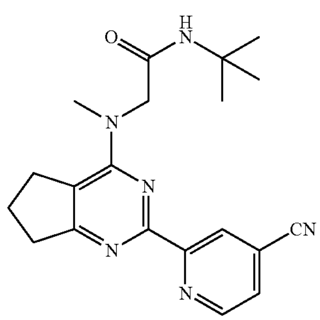 [SMILES: CN(CC(=O)NC(C)(C)C)c1nc(-c2cc(C#N)ccn2)nc2c1CCC2] | N-tert-butyl-2-{[2-(4-cyanopyridin-2-yl)-5H,6H,7H-cyclopenta[d]pyrimidin-4-yl](methyl)amino}acetamide | 365.2 |
| 159 | 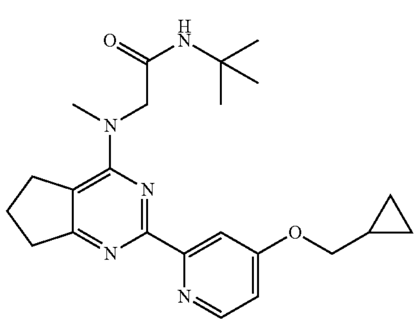 [SMILES: CN(CC(=O)NC(C)(C)C)c1nc(-c2cc(OCC3CC3)ccn2)nc2c1CCC2] | N-tert-butyl-2-({2-[4-(cyclopropylmethoxy)pyridin-2-yl]-5H,6H,7H-cyclopenta[d]pyrimidin-4-yl}(methyl)amino)acetamide | 410.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 160 | 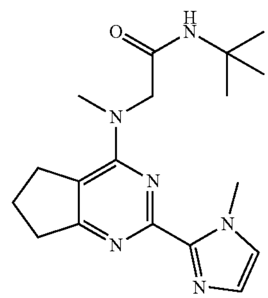 [SMILES: CN(CC(=O)NC(C)(C)C)c1nc(-c2nccn2C)nc2c1CCC2] | N-tert-butyl-2-{methyl[2-(1-methyl-1H-pyrazlo-3-yl)-5H,6H,7H-cyclopenta[d]pyrimidin-4-yl]amino}acetamide | 343.2 |
| 161 | 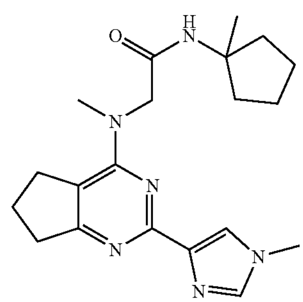 [SMILES: CN(CC(=O)NC1(C)CCCC1)c1nc(-c2cn(C)cn2)nc2c1CCC2] | 2-{methyl[2-(1-methyl-1H-imidazol-4-yl)-5H,6H,7H-cyclopenta[d]pyrimidin-4-yl]amino}-N-(1-methylcyclopentyl)acetamide | 369.2 |
| 162 | 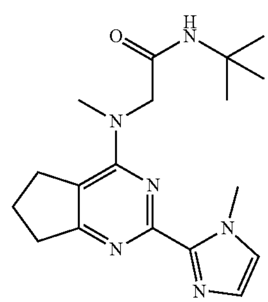 [SMILES: CN(CC(=O)NC(C)(C)C)c1nc(-c2nccn2C)nc2c1CCC2] | N-tert-butyl-2-{methyl[2-(1-methyl-1H-imidazol-2-yl)-5H,6H,7H-cyclopenta[d]pyrimidin-4-yl]amino}acetamide | 343.2 |
| 163 | 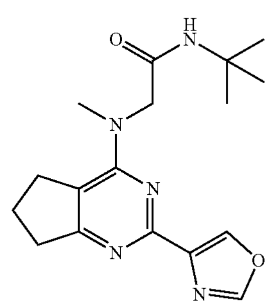 [SMILES: CN(CC(=O)NC(C)(C)C)c1nc(-c2cocn2)nc2c1CCC2] | N-tert-butyl-2-{methyl[2-(1,3-oxazol-4-yl)-5H,6H,7H-cyclopenta[d]pyrimidin-4-yl]amino}acetamide | 330.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 164 | 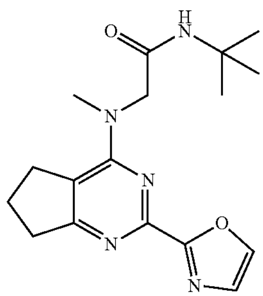 [SMILES: CN(CC(=O)NC(C)(C)C)c1nc(-c2ncco2)nc2c1CCC2] | N-tert-butyl-2-{methyl[2-(1,3-oxazol-2-yl)-5H,6H,7H-cyclopenta[d]pyrimidin-4-yl]amino}acetamide | 330.2 |
| 165 | 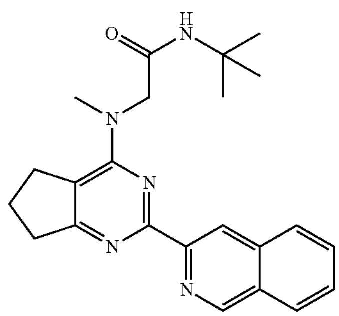 [SMILES: CN(CC(=O)NC(C)(C)C)c1nc(-c2cc3ccccc3cn2)nc2c1CCC2] | N-tert-butyl-2-{[2-(isoquinolin-3-yl)-5H,6H,7H-cyclopenta[d]pyrimidin-4-yl](methyl)amino}acetamide | 390.2 |
| 166 | 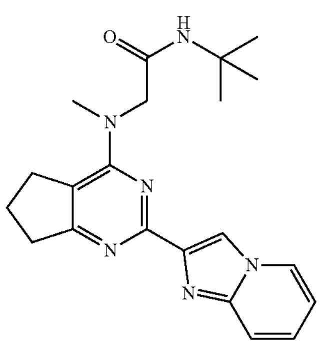 [SMILES: CN(CC(=O)NC(C)(C)C)c1nc(-c2cn3ccccc3n2)nc2c1CCC2] | N-tert-butyl-2-[(2-{imidazo[1,2-a]pyridin-2-yl}-5H,6H,7H-cyclopenta[d]pyrimidin-4-yl)(methyl)amino]acetamide | 379.2 |
| 167 | 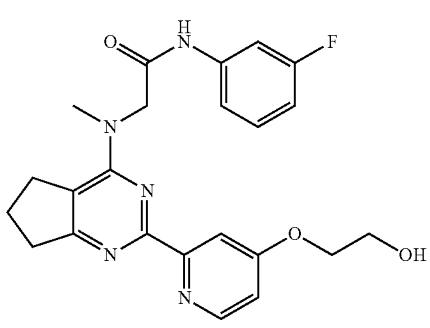 [SMILES: CN(CC(=O)Nc1cccc(F)c1)c1nc(-c2cc(OCCO)ccn2)nc2c1CCC2] | N-(3-fluorophenyl)-2-({2-[4-(2-hydroxyethoxy)pyridin-2-yl]-5H,6H,7H-cyclopenta[d]pyrimidin-4-yl}(methyl)amino)acetamide | 438.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 168 | 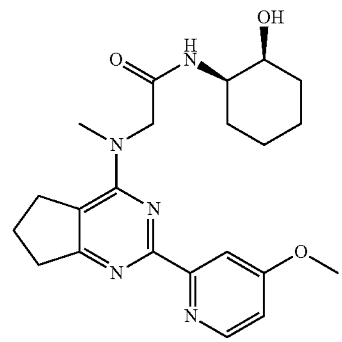 [SMILES: COc1ccnc(-c2nc3c(c(N(C)CC(=O)N[C@@H]4CCCC[C@@H]4O)n2)CCC3)c1] | N-[(1R,2S)-2-hydroxycyclohexyl]-2-{[2-(4-methoxypyridin-2-yl)-5H,6H,7H-cyclopenta[d]pyrimidin-4-yl](methyl)amino}acetamide | 412.2 |
| 169 | 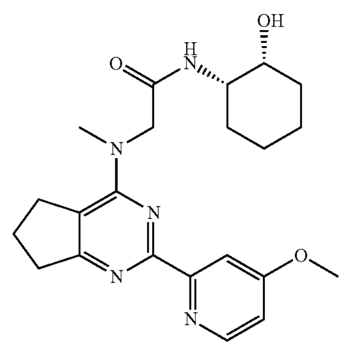 [SMILES: COc1ccnc(-c2nc3c(c(N(C)CC(=O)N[C@H]4CCCC[C@H]4O)n2)CCC3)c1] | N-[(1S,2R)-2-hydroxycyclohexyl]-2-{[2-(4-methoxypyridin-2-yl)-5H,6H,7H-cyclopenta[d]pyrimidin-4-yl](methyl)amino}acetamide | 412.2 |
| 170 | 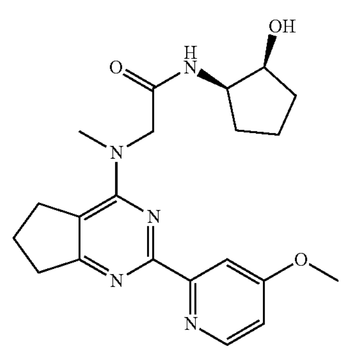 [SMILES: COc1ccnc(-c2nc3c(c(N(C)CC(=O)N[C@@H]4CCC[C@@H]4O)n2)CCC3)c1] | N-[(1R,2S)-2-hydroxycyclopentyl]-2-{[2-(4-methoxypyridin-2-yl)-5H,6H,7H-cyclopenta[d]pyrimidin-4-yl](methyl)amino}acetamide | 398.2 |
| 171 | 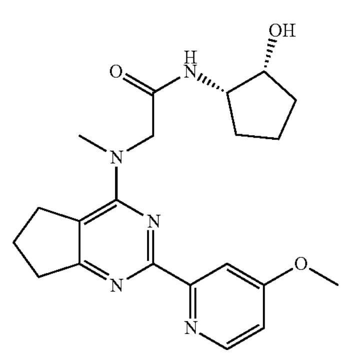 [SMILES: COc1ccnc(-c2nc3c(c(N(C)CC(=O)N[C@H]4CCC[C@H]4O)n2)CCC3)c1] | N-[(1S,2R)-2-hydroxycyclopentyl]-2-{[2-(4-methoxypyridin-2-yl)-5H,6H,7H-cyclopenta[d]pyrimidin-4-yl](methyl)amino}acetamide | 398.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 172 | 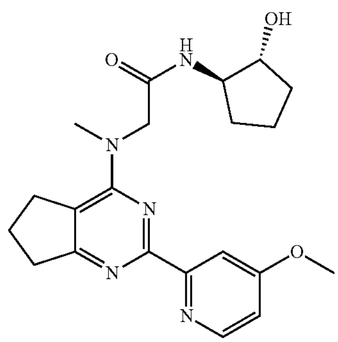 [SMILES: COc1ccnc(-c2nc3c(c(N(C)CC(=O)N[C@@H]4CCC[C@H]4O)n2)CCC3)c1] | N-[(1R,2R)-2-hydroxycyclopentyl]-2-{[2-(4-methoxypyridin-2-yl)-5H,6H,7H-cyclopenta[d]pyrimidin-4-yl](methyl)amino}acetamide | 398.2 |
| 173 | 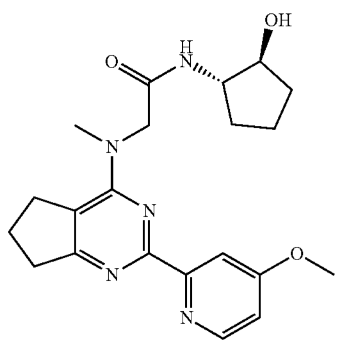 [SMILES: COc1ccnc(-c2nc3c(c(N(C)CC(=O)N[C@H]4CCC[C@@H]4O)n2)CCC3)c1] | N-[(1S,2S)-2-hydroxycyclopentyl]-2-{[2-(4-methoxypyridin-2-yl)-5H,6H,7H-cyclopenta[d]pyrimidin-4-yl](methyl)amino}acetamide | 398.2 |
| 174 | 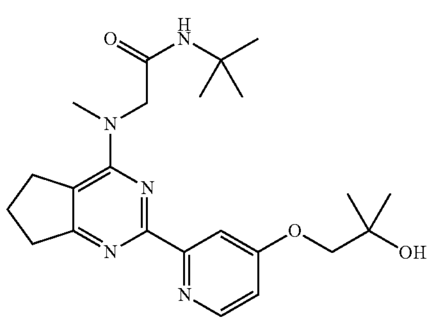 [SMILES: CN(CC(=O)NC(C)(C)C)c1nc(-c2cc(OCC(C)(C)O)ccn2)nc2c1CCC2] | N-tert-butyl-2-({2-[4-(2-hydroxy-2-methylpropoxy)pyridin-2-yl]-5H,6H,7H-cyclopenta[d]pyrimidin-4-yl}(methyl)amino)acetamide | 428.2 |
| 175 | 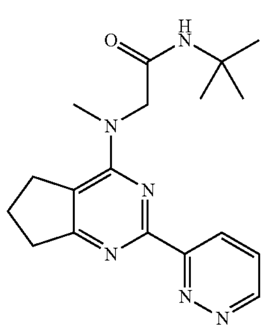 [SMILES: CN(CC(=O)NC(C)(C)C)c1nc(-c2cccnn2)nc2c1CCC2] | N-tert-butyl-2-{methyl[2-(pyridazin-3-yl)-5H,6H,7H-cyclopenta[d]pyrimidin-4-yl]amino}acetamide | 341.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 176 | 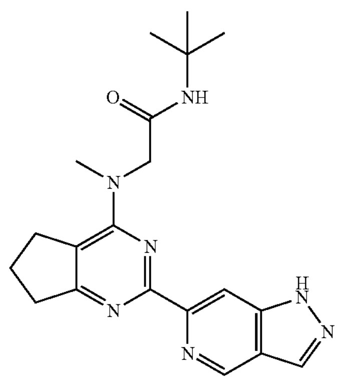 [SMILES: CN(CC(=O)NC(C)(C)C)c1nc(-c2cc3[nH]ncc3cn2)nc2c1CCC2] | N-tert-butyl-2-[methyl(2-{1H-pyrazolo[4,3-c]pyridin-6-yl}-5H,6H,7H-cyclopenta[d]pyrimidin-4-yl)amino]acetamide | 380.2 |
| 177 | 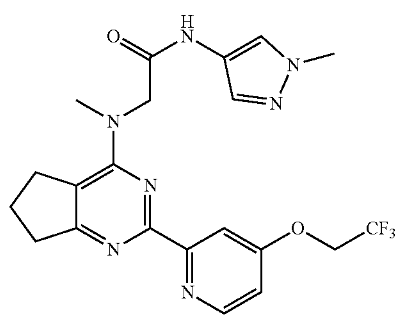 [SMILES: CN(CC(=O)Nc1cnn(C)c1)c1nc(-c2cc(OCC(F)(F)F)ccn2)nc2c1CCC2] | 2-[methyl({2-[4-(2,2,2-trifluoroethoxy)pyridin-2-yl]-5H,6H,7H-cyclopenta[d]pyrimidin-4-yl})amino]-N-(1-methyl-1H-pyrazol-4-yl)acetamide | 462.1 |
| 178 | 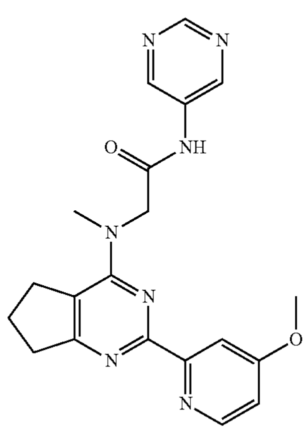 [SMILES: COc1ccnc(-c2nc3c(c(N(C)CC(=O)Nc4cncnc4)n2)CCC3)c1] | 2-{[2-(4-methoxypyridin-2-yl)-5H,6H,7H-cyclopenta[d]pyrimidin-4-yl](methyl)amino}-N-(pyrimidin-5-yl)acetamide | 392.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 179 | 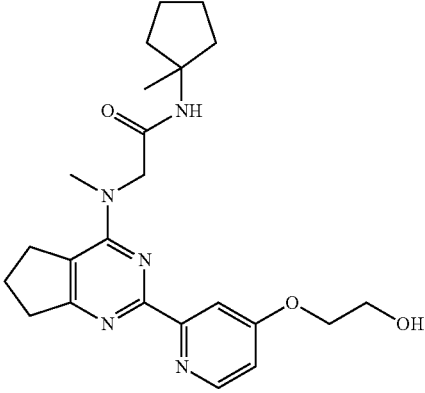 [SMILES: CN(CC(=O)NC1(C)CCCC1)c1nc(-c2cc(OCCO)ccn2)nc2c1CCC2] | 2-({2-[4-(2-hydroxyethoxy)pyridin-2-yl]-5H,6H,7H-cyclopenta[d]pyrimdiin-4-yl}(methyl)amino)-N-(1-methylcyclopentyl)acetamide | 426.3 |
| 180 | 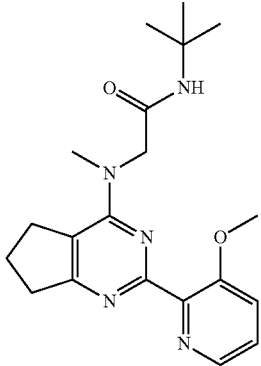 [SMILES: COc1cccnc1-c1nc2c(c(N(C)CC(=O)NC(C)(C)C)n1)CCC2] | N-tert-butyl-2-{[2-(4-methoxypyridin-2-yl)-5H,6H,7H-cyclopenta[d]pyrimidin-4-yl](methyl)amino}acetamide | 370.2 |
| 181 | 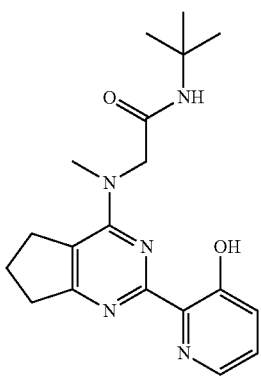 | N-tert-butyl-2-{[2-(3-hydroxypyridin-2-yl)-5H,6H,7H-cyclopenta[d]pyrimidin-4-yl](methyl)amino}acetamide | 356.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 182 | 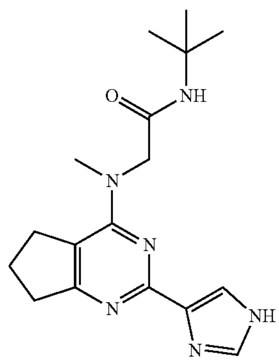 [SMILES: CN(CC(=O)NC(C)(C)C)c1nc(-c2c[nH]cn2)nc2c1CCC2] | N-tert-butyl-2-{[2-(1H-imidazol-4-yl)-5H,6H,7H-cyclopenta[d]pyrimidin-4-yl](methyl)amino}acetamide | 329.2 |
| 183 | 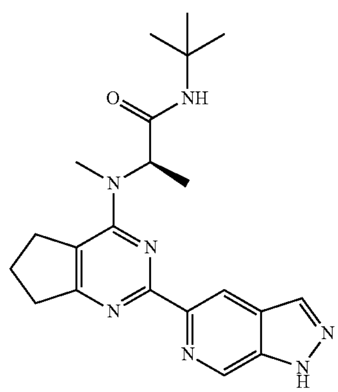 [SMILES: C[C@H](C(=O)NC(C)(C)C)N(C)c1nc(-c2cc3cn[nH]c3cn2)nc2c1CCC2] | (2R)-N-tert-butyl-2-[methyl(2-{1H-pyrazolo[3,4-c]pyridin-5-yl}-5H,6H,7H-cyclopenta[d]pyrimidni-4-yl)amino]propanamide | 394.2 |
| 184 | 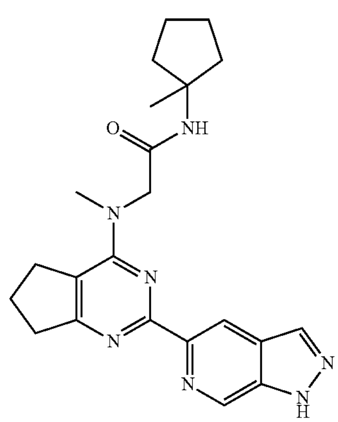 [SMILES: CN(CC(=O)NC1(C)CCCC1)c1nc(-c2cc3cn[nH]c3cn2)nc2c1CCC2] | 2-[methyl(2-{1H-pyrazolo[3,4-c]pyridin-5-yl}-5H,6H,7H-cyclopenta[d]pyrimidin-4-yl)amino]-N-(1-methylcyclopentyl)acetamide | 406.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 185 | 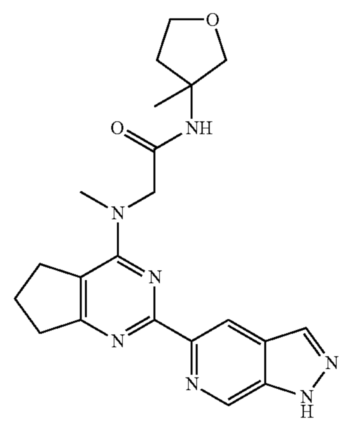 [SMILES: CN(CC(=O)NC1(C)CCOC1)c1nc(-c2cc3cn[nH]c3cn2)nc2c1CCC2] | 2-[methyl(2-{1H-pyrazolo[3,4-c]pyridin-5-yl}-5H,6H,7H-cyclopenta[d]pyrimidin-4-yl)amino]-N-(3-methyloxolan-3-yl)acetamide | 408.2 |
| 186 | 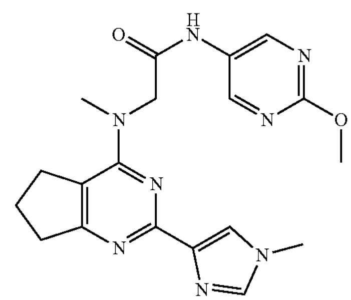 [SMILES: COc1ncc(NC(=O)CN(C)c2nc(-c3cn(C)cn3)nc3c2CCC3)cn1] | N-(2-methoxypyrimidin-5-yl)-2-{methyl[2-(1-methyl-1H-imidazol-4-yl)-5H,6H,7H-cyclopenta[d]pyrimidin-4-yl]amino}acetamide | 395.2 |
| 187 | 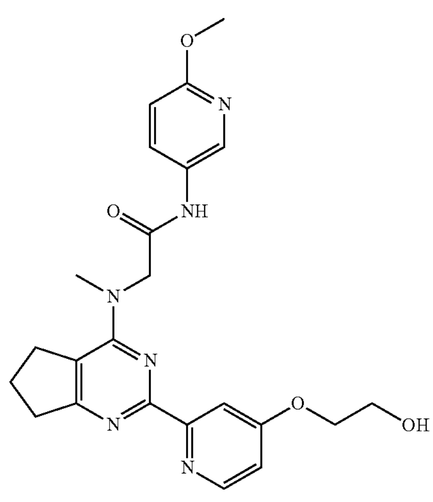 [SMILES: COc1ccc(NC(=O)CN(C)c2nc(-c3cc(OCCO)ccn3)nc3c2CCC3)cn1] | 2-({2-[4-(2-hydroxyethoxy)pyridin-2-yl]-5H,6H,7H-cyclopenta[d]pyrimidin-4-yl}(methyl)amino)-N-(6-methoxypyridin-3-yl)acetamide | 451.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 188 | 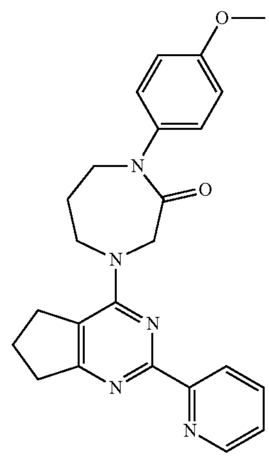 [SMILES: COc1ccc(N2CCCN(c3nc(-c4ccccn4)nc4c3CCC4)CC2=O)cc1] | 1-(4-methoxyphenyl)-4-[2-(pyridin-2-yl)-5H,6H,7H-cyclopenta[d]pyrimidin-4-yl]-1,4-diazepan-2-one | 416.1 |
| 189 | 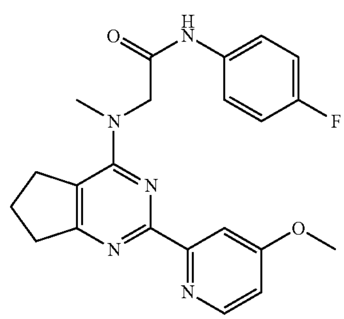 [SMILES: COc1ccnc(-c2nc3c(c(N(C)CC(=O)Nc4ccc(F)cc4)n2)CCC3)c1] | N-(4-fluorophenyl)-2-{[2-(4-methoxypyridin-2-yl)-5H,6H,7H-cyclopenta[d]pyrimidin-4-yl](methyl)amino}acetamide | 408.1 |
| 190 | 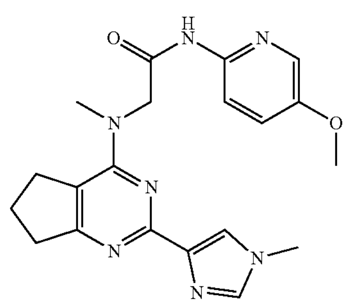 [SMILES: COc1ccc(NC(=O)CN(C)c2nc(-c3cn(C)cn3)nc3c2CCC3)nc1] | N-(5-methoxypyridin-2-yl)-2-{methyl[2-(1-methyl-1H-imidazol-4-yl)-5H,6H,7H-cyclopenta[d]pyrimidin-4-yl]amino}acetamide | 394.2 |
| 191 | 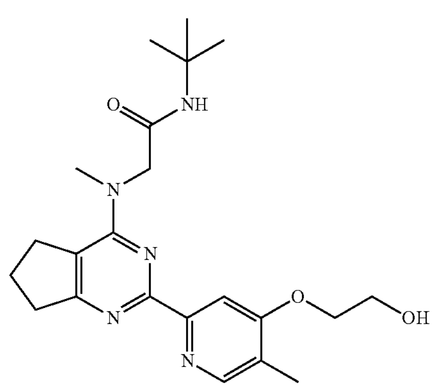 [SMILES: Cc1cnc(-c2nc3c(c(N(C)CC(=O)NC(C)(C)C)n2)CCC3)cc1OCCO] | N-tert-butyl-2-({2-[4-(2-hydroxyethoxy)-5-methylpyridin-2-yl]-5H,6H,7H-cyclopenta[d]pyrimidin-4-yl}(methyl)amino)acetamide | 414.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 192 | 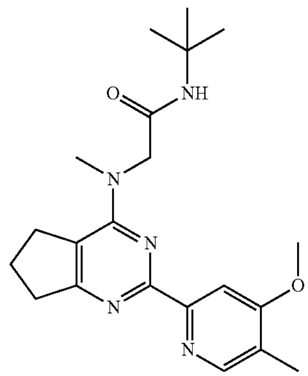 [SMILES: COc1cc(-c2nc3c(c(N(C)CC(=O)NC(C)(C)C)n2)CCC3)ncc1C] | N-tert-butyl-2-{[2-(4-methoxy-5-methylpyridin-2-yl)-5H,6H,7H-cyclopenta[d]pyrimidin-4-yl](methyl)amino}acetamide | 384.2 |
| 193 | 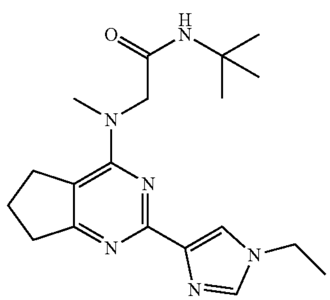 [SMILES: CCn1cnc(-c2nc3c(c(N(C)CC(=O)NC(C)(C)C)n2)CCC3)c1] | N-tert-butyl-2-{[2-(1-ethyl-1H-imidazol-4-yl)-5H,6H,7H-cyclopenta[d]pyrimidin-4-yl](methyl)amino}acetamide | 357.2 |
| 194 | 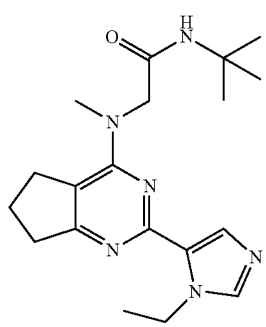 [SMILES: CCn1cncc1-c1nc2c(c(N(C)CC(=O)NC(C)(C)C)n1)CCC2] | N-tert-butyl-2-{[2-(1-ethyl-1H-imidazol-5-yl)-5H,6H,7H-cyclopenta[d]pyrimidin-4-yl](methyl)amino}acetamide | 357.2 |
| 195 | 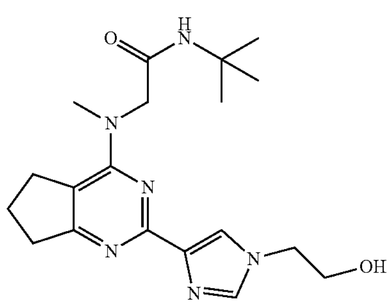 [SMILES: CN(CC(=O)NC(C)(C)C)c1nc(-c2cn(CCO)cn2)nc2c1CCC2] | N-tert-butyl-2-({2-[1-(2-hydroxyethyl)-1H-imidazol-4-yl]-5H,6H,7H-cyclopenta[d]pyrimidin-4-yl}(methyl)amino)acetamide | 373.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 196 | 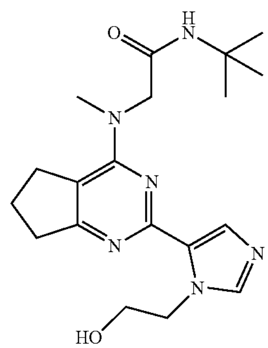 [SMILES: CN(CC(=O)NC(C)(C)C)c1nc(-c2cncn2CCO)nc2c1CCC2] | N-tert-butyl-2-({2-[1-(2-hydroxyethyl)-1H-imidazol-5-yl]-5H,6H,7H-cyclopenta[d]pyrimidin-4-yl}(methyl)amino)acetamide | 373.3 |
| 197 | 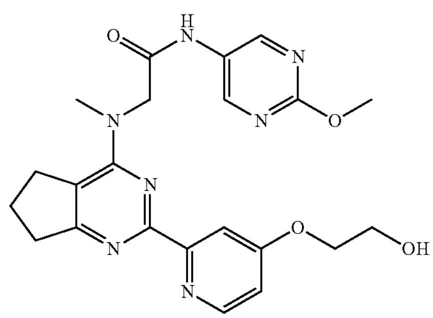 [SMILES: COc1ncc(NC(=O)CN(C)c2nc(-c3cc(OCCO)ccn3)nc3c2CCC3)cn1] | 2-({2-[4-(2-hydroxyethoxy)pyridin-2-yl]-5H,6H,7H-cyclopenta[d]pyrimidin-4-yl}(methyl)amino)-N-(2-methoxypyrimidin-5-yl)acetamide | 452.2 |
| 198 | 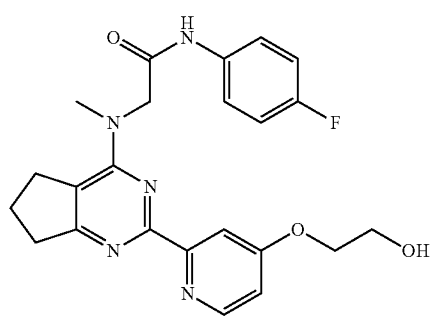 [SMILES: CN(CC(=O)Nc1ccc(F)cc1)c1nc(-c2cc(OCCO)ccn2)nc2c1CCC2] | N-(4-fluorophenyl)-2-({2-[4-(2-hydroxyethoxy)pyridin-2-yl]-5H,6H,7H-cyclopenta[d]pyrimidin-4-yl}(methyl)amino)acetamide | 438.2 |
| 199 | 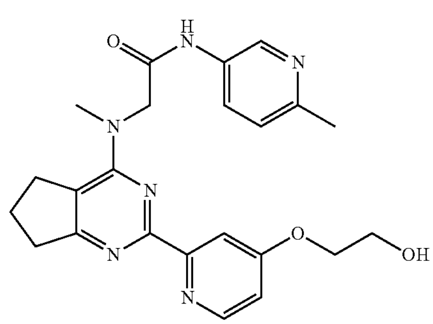 [SMILES: Cc1ccc(NC(=O)CN(C)c2nc(-c3cc(OCCO)ccn3)nc3c2CCC3)cn1] | 2-({2-[4-(2-hydroxyethoxy)pyridin-2-yl]-5H,6H,7H-cyclopenta[d]pyrimidin-4-yl}(methyl)amino)-N-(6-methylpyridin-3-yl)acetamide | 435.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 200 | 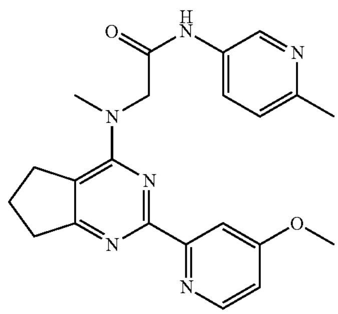 [SMILES: COc1ccnc(-c2nc3c(c(N(C)CC(=O)Nc4ccc(C)nc4)n2)CCC3)c1] | 2-{[2-(4-methoxypyridin-2-yl)-5H,6H,7H-cyclopenta[d]pyrimidin-4-yl](methyl)amino}-N-(6-methylpyridin-3-yl)acetamide | 405.2 |
| 201 | 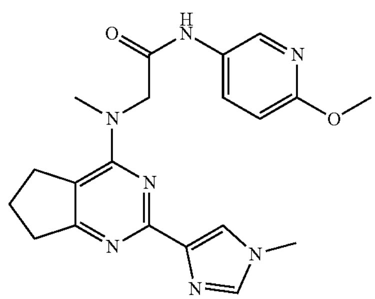 [SMILES: COc1ccc(NC(=O)CN(C)c2nc(-c3cn(C)cn3)nc3c2CCC3)cn1] | N-(6-methoxypyridin-3-yl)-2-{methyl[2-(1-methyl-1H-imidazol-4-yl)-5H,6H,7H-cyclopenta[d]pyrimidin-4-yl]amino}acetamide | 394.2 |
| 202 | 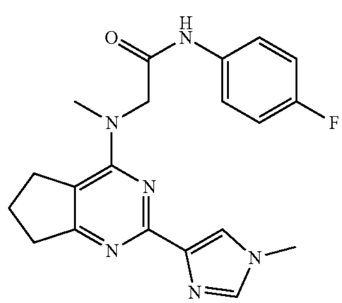 [SMILES: CN(CC(=O)Nc1ccc(F)cc1)c1nc(-c2cn(C)cn2)nc2c1CCC2] | N-(4-fluorophenyl)-2-{methyl[2-(1-methyl-1H-imidazol-4-yl)-5H,6H,7H-cyclopenta[d]pyrimidin-4-yl]amino}acetamide | 381.2 |
| 203 | 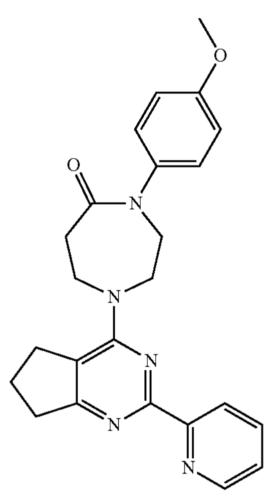 [SMILES: COc1ccc(N2CCN(c3nc(-c4ccccn4)nc4c3CCC4)CCC2=O)cc1] | 4-(4-methoxyphenyl)-1-[2-(pyridin-2-yl)-5H,6H,7H-cyclopenta[d]pyrimidin-4-yl]-1,4-diazepan-5-one | 416.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 204 | 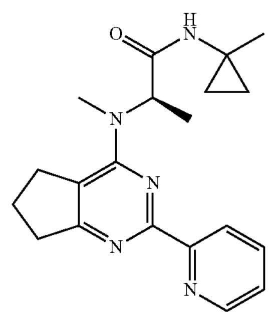 [SMILES: C[C@H](C(=O)NC1(C)CC1)N(C)c1nc(-c2ccccn2)nc2c1CCC2] | (2R)-2-{methyl[2-(pyridin-2-yl)-5H,6H,7H-cyclopenta[d]pyrimidin-4-yl]amino}-N-(1-methylcyclopropyl)propanamide | 352.1 |
| 205 | 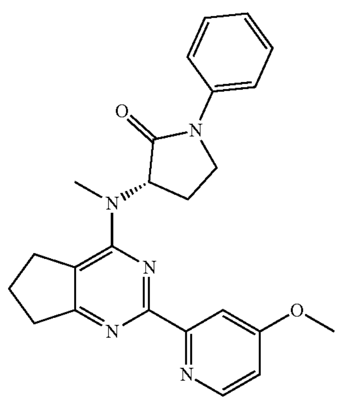 [SMILES: COc1ccnc(-c2nc3c(c(N(C)[C@H]4CCN(c5ccccc5)C4=O)n2)CCC3)c1] | (3S)-3-{[2-(4-methoxypyridin-2-yl)-5H,6H,7H-cyclopenta[d]pyrimidin-4-yl](methyl)amino}-1-phenylpyrrolidin-2-one | 416.3 |
| 206 | 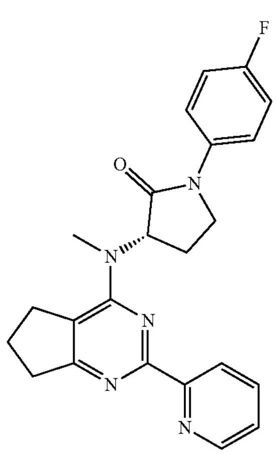 [SMILES: CN(c1nc(-c2ccccn2)nc2c1CCC2)[C@H]1CCN(c2ccc(F)cc2)C1=O] | (3S)-1-(4-fluorophenyl)-3-{methyl[2-(pyridin-2-yl)-5H,6H,7H-cyclopenta[d]pyrimidin-4-yl]amino}pyrrolidin-2-one | 404.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 207 | 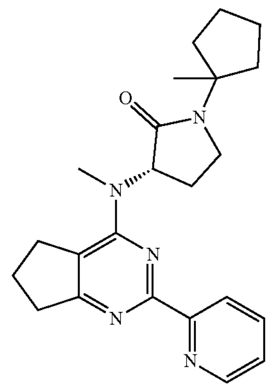 [SMILES: CN(c1nc(-c2ccccn2)nc2c1CCC2)[C@H]1CCN(C2(C)CCCC2)C1=O] | (3S)-3-{methyl[2-(pyridin-2-yl)-5H,6H,7H-cyclopenta[d]pyrimidin-4-yl]amino}-1-(1-methylcyclopentyl)pyrrolidin-2-one | 392.2 |
| 208 | 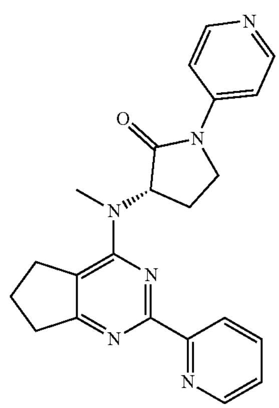 [SMILES: CN(c1nc(-c2ccccn2)nc2c1CCC2)[C@H]1CCN(c2ccncc2)C1=O] | (3S)-3-{methyl[2-(pyridin-2-yl)-5H,6H,7H-cyclopenta[d]pyrimidin-4-yl]amino}-1-(pyridin-4-yl)pyrrolidin-2-one | 386.9 |
| 209 | 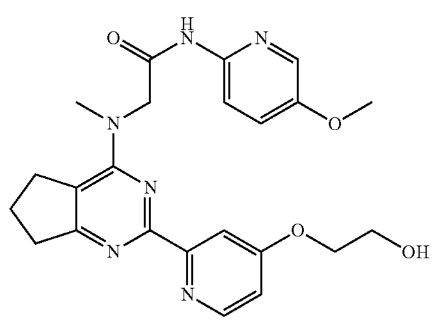 | 2-({2-[4-(2-hydroxyethoxy)pyridin-2-yl]-5H,6H,7H-cyclopenta[d]pyrimidin-4-yl}(methyl)amino)-N-(5-methoxypyridin-2-yl)acetamide | 451.2 |
| 210 | 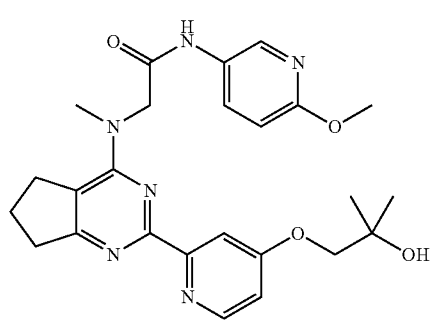 [SMILES: COc1ccc(NC(=O)CN(C)c2nc(-c3cc(OCC(C)(C)O)ccn3)nc3c2CCC3)cn1] | 2-({2-[4-(2-hydroxy-2-methylpropoxy)pyridin-2-yl]-5H,6H,7H-cyclopenta[d]pyrimidin-4-yl}(methyl)amino)-N-(6-methoxypyridin-3-yl)acetamide | 479.3 |

TABLE 1-continued

Where the mass for a compound is not provided in Table 1, the mass can be found
for the compound in the synthetic examples.

| Compound No. | Structure | IUPAC Name | Mass Found (M + 1) |
|---|---|---|---|
| 211 | 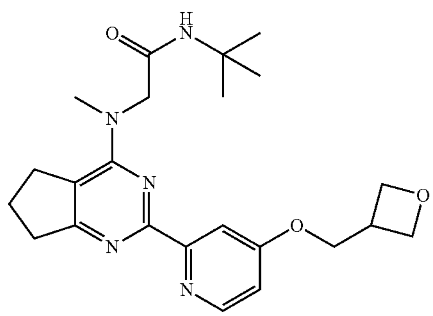 [SMILES: CN(CC(=O)NC(C)(C)C)c1nc(-c2cc(OCC3COC3)ccn2)nc2c1CCC2] | N-tert-butyl-2-[methyl(2-{4-[(oxetan-3-yl)methoxy]pyridin-2-yl}-5H,6H,7H-cyclopenta[d]pyrimidin-4-yl)amino]acetamide | 426.2 |
| 212 | 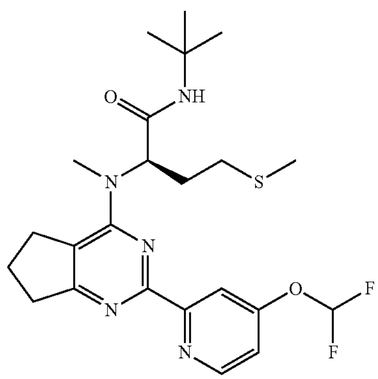 [SMILES: CSCC[C@H](C(=O)NC(C)(C)C)N(C)c1nc(-c2cc(OC(F)F)ccn2)nc2c1CCC2] | (2R)-N-tert-butyl-2-({2-[4-(difluoromethoxy)pyridin-2-yl]-5H,6H,7H-cyclopenta[d]pyrimidin-4-yl}(methyl)amino)-4-(methylsulfanyl)butanamide | 480.4 |
| 213 | 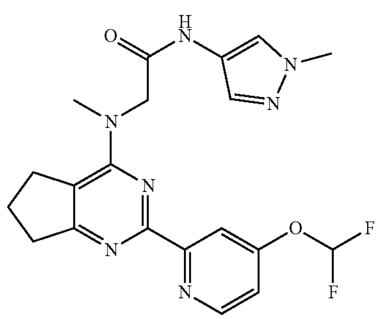 [SMILES: CN(CC(=O)Nc1cnn(C)c1)c1nc(-c2cc(OC(F)F)ccn2)nc2c1CCC2] | 2-({2-[4-(difluoromethoxy)pyridin-2-yl]-5H,6H,7H-cyclopenta[d]pyrimidin-4-yl}(methyl)amino)-N-(1-methyl-1H-pyrazol-4-yl)acetamide | 429.9 |
| 214 | 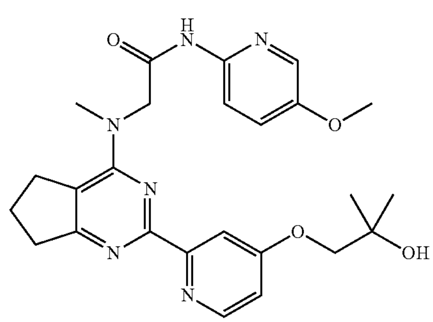 [SMILES: COc1ccc(NC(=O)CN(C)c2nc(-c3cc(OCC(C)(C)O)ccn3)nc3c2CCC3)nc1] | 2-({2-[4-(2-hydroxy-2-methylpropoxy)pyridin-2-yl]-5H,6H,7H-cyclopenta[d]pyrimidin-4-yl}(methyl)amino)-N-(5-methoxypyridin-2-yl)acetamide | 479.3 |

TABLE 1-continued

Where the mass for a compound is not provided in Table 1, the mass can be found for the compound in the synthetic examples.

| Compound No. | Structure | IUPAC Name | Mass Found (M + 1) |
| --- | --- | --- | --- |
| 215 | 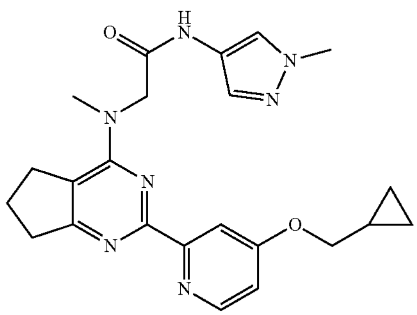 [SMILES: CN(CC(=O)Nc1cnn(C)c1)c1nc(-c2cc(OCC3CC3)ccn2)nc2c1CCC2] | 2-({2-[4-(cyclopropylmethoxy)pyridin-2-yl]-5H,6H,7H-cyclopenta[d]pyrimidin-4-yl}(methyl)amino)-N-(1-methyl-1H-pyrazol-4-yl)acetamide | 434.1 |
| 216 | 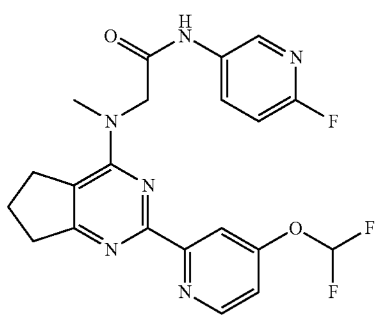 [SMILES: CN(CC(=O)Nc1ccc(F)nc1)c1nc(-c2cc(OC(F)F)ccn2)nc2c1CCC2] | 2-({2-[4-(difluoromethoxy)pyridin-2-yl]-5H,6H,7H-cyclopenta[d]pyrimidin-4-yl}(methyl)amino)-N-(6-fluoropyridin-3-yl)acetamide | 445.1 |
| 217 | 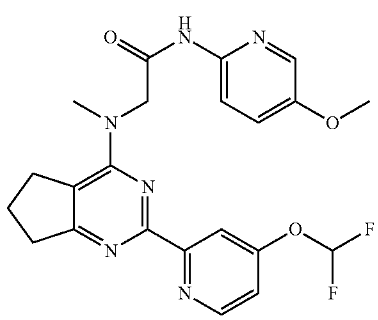 [SMILES: COc1ccc(NC(=O)CN(C)c2nc(-c3cc(OC(F)F)ccn3)nc3c2CCC3)nc1] | 2-({2-[4-(difluoromethoxy)pyridin-2-yl]-5H,6H,7H-cyclopenta[d]pyrimidin-4-yl}(methyl)amino)-N-(5-methoxypyridin-2-yl)acetamide | 456.9 |
| 218 | 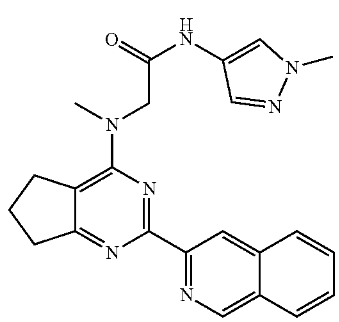 [SMILES: CN(CC(=O)Nc1cnn(C)c1)c1nc(-c2cc3ccccc3cn2)nc2c1CCC2] | 2-{[2-(isoquinolin-3-yl)-5H,6H,7H-cyclopenta[d]pyrimidin-4-yl](methyl)amino}-N-(1-methyl-1H-pyrazol-4-yl)acetamide | 414.0 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 219 | 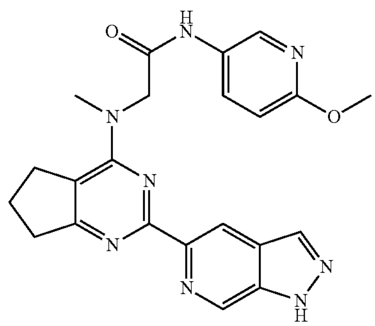 [SMILES: COc1ccc(NC(=O)CN(C)c2nc(-c3cc4cn[nH]c4cn3)nc3c2CCC3)cn1] | N-(6-methoxypyridin-3-yl)-2-[methyl(2-{1H-pyrazolo[3,4-c]pyridin-5-yl}-5H,6H,7H-cyclopenta[d]pyrimidin-4-yl)amino]acetamide | 431.2 |
| 220 | 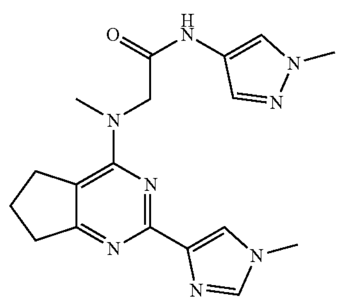 [SMILES: CN(CC(=O)Nc1cnn(C)c1)c1nc(-c2cn(C)cn2)nc2c1CCC2] | N-(1-methyl-1H-pyrazol-4-yl)-2-{methyl[2-(1-methyl-1H-imidazol-4-yl)-5H,6H,7H-cyclopenta[d]pyrimidin-4-yl]amino}acetamide | 367.2 |
| 221 | 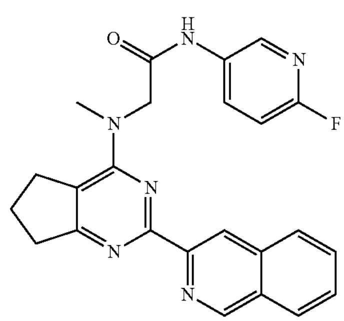 [SMILES: CN(CC(=O)Nc1ccc(F)nc1)c1nc(-c2cc3ccccc3cn2)nc2c1CCC2] | N-(6-fluoropyridin-3-yl)-2-{[2-(isoquinolin-3-yl)-5H,6H,7H-cyclopenta[d]pyrimidin-4-yl](methyl)amino}acetamide | 429.1 |
| 222 | 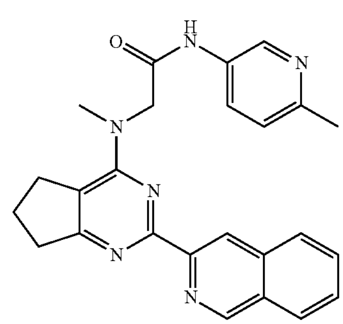 [SMILES: Cc1ccc(NC(=O)CN(C)c2nc(-c3cc4ccccc4cn3)nc3c2CCC3)cn1] | 2-{[2-(isoquinolin-3-yl)-5H,6H,7H-cyclopenta[d]pyrimidin-4-yl](methyl)amino}-N-(6-methylpyridin-3-yl)acetamide | 425.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 223 | 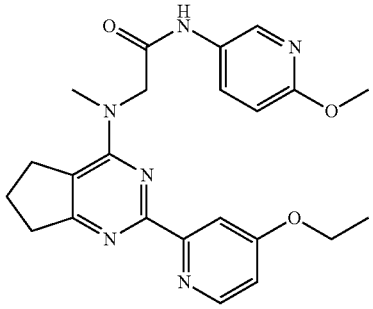 [SMILES: CCOc1ccnc(-c2nc3c(c(N(C)CC(=O)Nc4ccc(OC)nc4)n2)CCC3)c1] | 2-{[2-(4-ethoxypyridin-2-yl)-5H,6H,7H-cyclopenta[d]pyrimidin-4-yl](methyl)amino}-N-(6-methoxypyriidn-3-yl)acetamide | 435.2 |
| 224 | 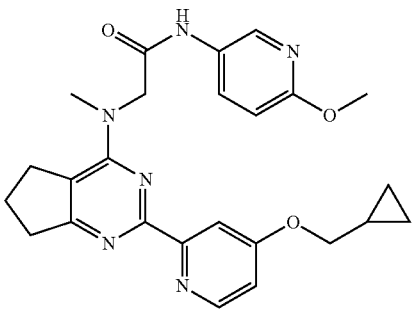 [SMILES: COc1ccc(NC(=O)CN(C)c2nc(-c3cc(OCC4CC4)ccn3)nc3c2CCC3)cn1] | 2-({2-[4-(cyclopropylmethoxy)pyridin-2-yl]-5H,6H,7H-cyclopenta[d]pyrimidin-4-yl}(methyl)amino)-N-(6-methoxypyridin-3-yl)acetamide | 461.3 |
| 225 | 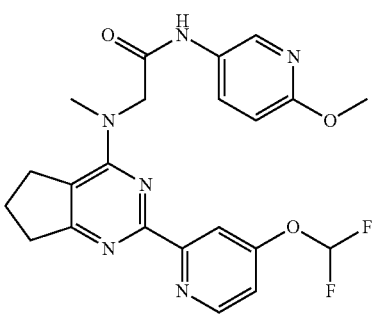 [SMILES: COc1ccc(NC(=O)CN(C)c2nc(-c3cc(OC(F)F)ccn3)nc3c2CCC3)cn1] | 2-({2-[4-(difluoromethoxy)pyridin-2-yl]-5H,6H,7H-cyclopenta[d]pyrimidin-4-yl}(methyl)amino)-N-(6-methoxypyridin-3-yl)acetamide | 457.2 |
| 226 | 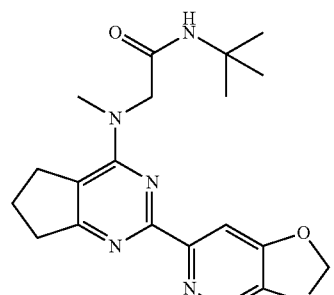 | N-tert-butyl-2-[(2-{2H-[1,3]dioxolo[4,5-c]pyridin-6-yl}-5H,6H,7H-cyclopenta[d]pyrimidin-4-yl)(methyl)amino]acetamide | 384.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 227 | 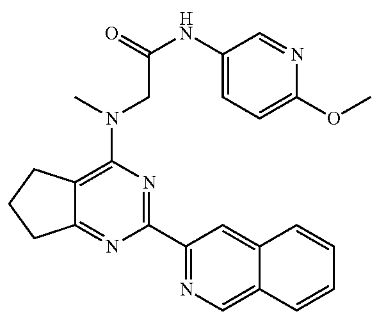 | 2-{[2-(isoquinolin-3-yl)-5H,6H,7H-cyclopenta[d]pyrimidin-4-yl](methyl)amino}-N-(6-methoxypyridin-3-yl)acetamide | 441.3 |
| 228 | 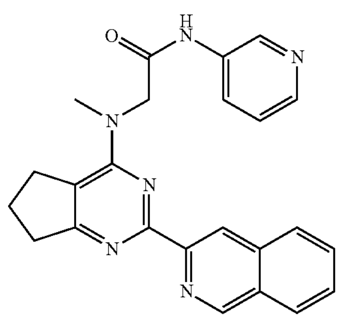 [SMILES: CN(CC(=O)Nc1cccnc1)c1nc(-c2cc3ccccc3cn2)nc2c1CCC2] | 2-{[2-(isoquinolin-3-yl)-5H,6H,7H-cyclopenta[d]pyrimidin-4-yl](methyl)amino}-N-(pyridin-3-yl)acetamide | 411.3 |
| 229 | 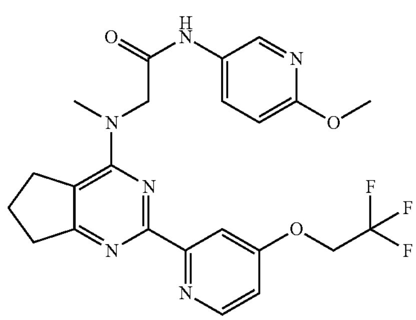 [SMILES: COc1ccc(NC(=O)CN(C)c2nc(-c3cc(OCC(F)(F)F)ccn3)nc3c2CCC3)cn1] | N-(6-methoxypyridin-3-yl)-2-[methyl({2-[4-(2,2,2-trifluoroethoxy)pyridin-2-yl]-5H,6H,7H-cyclopenta[d]pyrimidin-4-yl})amino]acetamide | 489.2 |
| 230 | 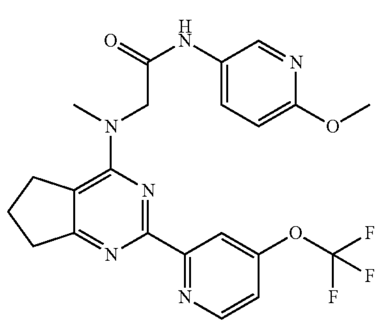 [SMILES: COc1ccc(NC(=O)CN(C)c2nc(-c3cc(OC(F)(F)F)ccn3)nc3c2CCC3)cn1] | N-(6-methoxypyridin-3-yl)-2-[methyl({2-[4-(trifluoromethoxy)pyridin-2-yl]-5H,6H,7H-cyclopenta[d]pyrimidin-4-yl})amino]acetamide | 475.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 231 | 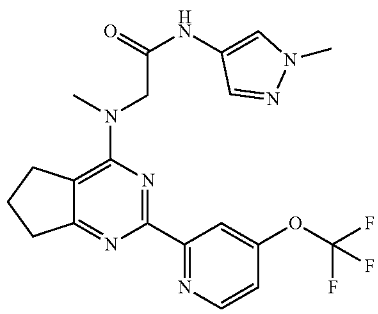 [SMILES: CN(CC(=O)Nc1cnn(C)c1)c1nc(-c2cc(OC(F)(F)F)ccn2)nc2c1CCC2] | 2-[methyl({2-[4-(trifluoromethoxy)pyridin-2-yl]-5H,6H,7H-cyclopenta[d]pyrimidin-4-yl}amino]-N-(1-methyl-1H-pyrazol-4-yl)acetamide | 448.2 |
| 232 | 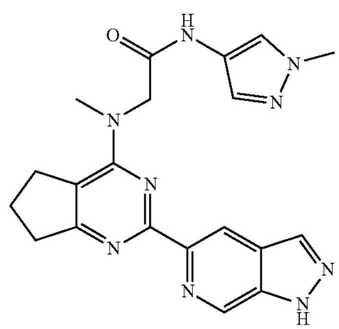 [SMILES: CN(CC(=O)Nc1cnn(C)c1)c1nc(-c2cc3cn[nH]c3cn2)nc2c1CCC2] | 2-[methyl(2-{1H-pyrazolo[3,4-c]pyridin-5-yl}-5H,6H,7H-cyclopenta[d]pyrimidin-4-yl)amino]-N-(1-methyl-1H-pyrazol-3-yl)acetamide | 404.3 |
| 233 | 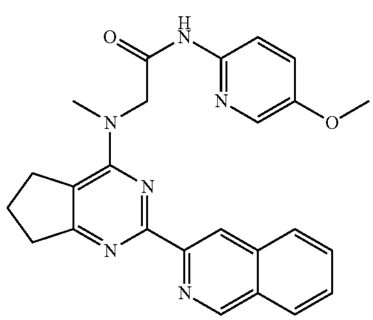 | 2-{[2-(isoquinolin-3-yl)-5H,6H,7H-cyclopenta[d]pyrimidin-4-yl](methyl)amino}-N-(5-methoxypyridin-2-yl)acetamide | 441.3 |
| 234 | 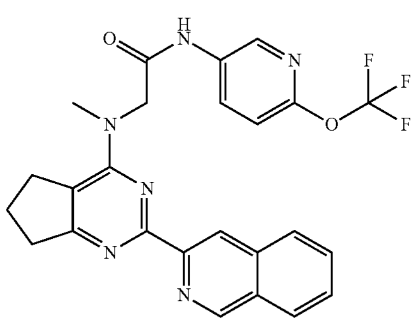 [SMILES: CN(CC(=O)Nc1ccc(OC(F)(F)F)nc1)c1nc(-c2cc3ccccc3cn2)nc2c1CCC2] | 2-{[2-(isoquinolin-3-yl)-5H,6H,7H-cyclopenta[d]pyrimidin-4-yl](methyl)amino}-N-[6-(trifluoromethoxy)pyridin-3-yl]acetamide | 495.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 235 | 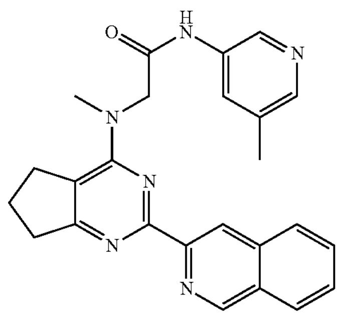 [SMILES: Cc1cncc(NC(=O)CN(C)c2nc(-c3cc4ccccc4cn3)nc3c2CCC3)c1] | 2-{[2-(isoquinolin-3-yl)-5H,6H,7H-cyclopenta[d]pyrimidin-4-yl](methyl)amino}-N-(5-methylpyridin-3-yl)acetamide | 425.2 |
| 236 | 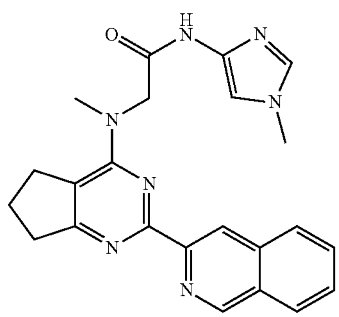 [SMILES: CN(CC(=O)Nc1cn(C)cn1)c1nc(-c2cc3ccccc3cn2)nc2c1CCC2] | 2-{[2-(isoquinolin-3-yl)-5H,6H,7H-cyclopenta[d]pyrimidin-4-yl](methyl)amino}-N-(1-methyl-1H-imidazol-4-yl)acetamide | 414.3 |
| 237 | 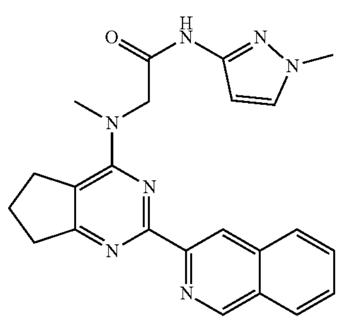 [SMILES: CN(CC(=O)Nc1ccn(C)n1)c1nc(-c2cc3ccccc3cn2)nc2c1CCC2] | 2-{[2-(isoquinolin-3-yl)-5H,6H,7H-cyclopenta[d]pyrimidin-4-yl](methyl)amino}-N-(1-methyl-1H-pyrazol-3-yl)acetamide | 414.3 |
| 238 | 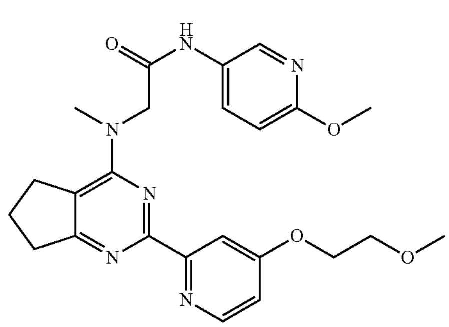 | 2-({2-[4-(2-methoxyethoxy)pyridin-2-yl]-5H,6H,7H-cyclopenta[d]pyrimidin-4-yl}(methyl)amino)-N-(6-methoxypyiridin-3-yl)acetamide | 465.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 239 | 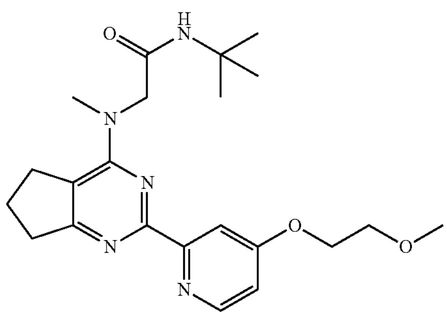 | N-tert-butyl-2-({2-[4-(2-methoxyethoxy)pyridin-2-yl]-5H,6H,7H-cyclopenta[d]pyrimidin-4-yl}(methyl)amino)acetamide | 414.3 |
| 240 | 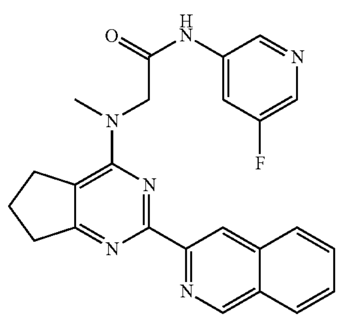 [SMILES: CN(CC(=O)Nc1cncc(F)c1)c1nc(-c2cc3ccccc3cn2)nc2c1CCC2] | N-(5-fluoropyridin-3-yl)-2-{[2-(isoquinolin-3-yl)-5H,6H,7H-cyclopenta[d]pyrimidin-4-yl](methyl)amino}acetamide | 429.2 |
| 241 | 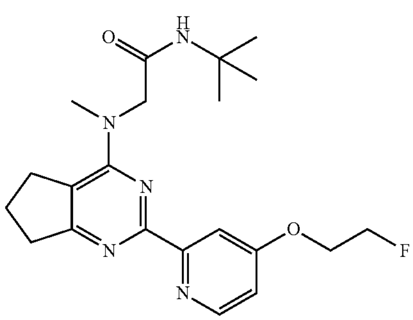 [SMILES: CN(CC(=O)NC(C)(C)C)c1nc(-c2cc(OCCF)ccn2)nc2c1CCC2] | N-tert-butyl-2-({2-[4-(2-fluoroethoxy)pyridin-2-yl]-5H,6H,7H-cyclopenta[d]pyrimidin-4-yl}(methyl)amino)acetamide | 402.3 |
| 242 | 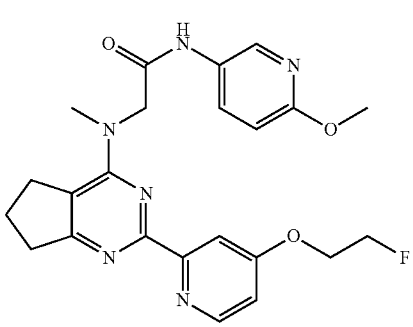 [SMILES: COc1ccc(NC(=O)CN(C)c2nc(-c3cc(OCCF)ccn3)nc3c2CCC3)cn1] | 2-({2-[4-(2-fluoroethoxy)pyridin-2-yl]-5H,6H,7H-cyclopenta[d]pyrimidin-4-yl}(methyl)amino)-N-(6-methoxypyridin-3-yl)acetamide | 453.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 243 | 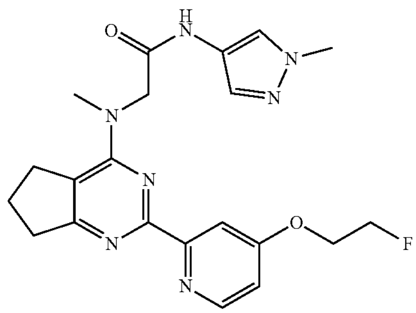 [SMILES: CN(CC(=O)Nc1cnn(C)c1)c1nc(-c2cc(OCCF)ccn2)nc2c1CCC2] | 2-({2-[4-(2-fluoroethoxy)pyridin-2-yl]-5H,6H,7H-cyclopenta[d]pyrimidin-4-yl}(methyl)amino)-N-(1-methyl-1H-pyrazol-4-yl)acetamide | 426.3 |
| 244 | 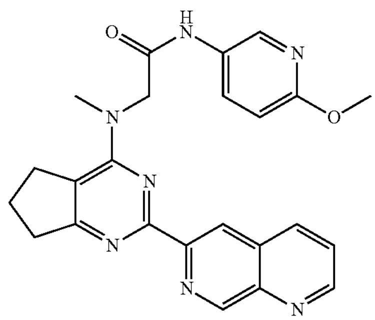 [SMILES: COc1ccc(NC(=O)CN(C)c2nc(-c3cc4cccnc4cn3)nc3c2CCC3)cn1] | N-(6-methoxypyridin-3-yl)-2-{methyl[2-(1,7-naphthyridin-6-yl)-5H,6H,7H-cyclopenta[d]pyrimidin-4-yl]amino}acetamide | 442.2 |
| 245 | 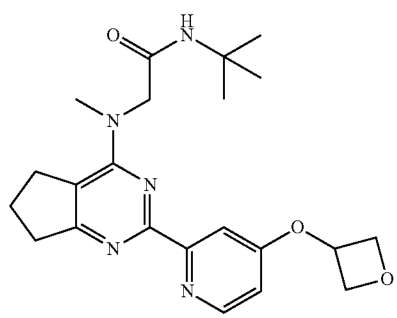 [SMILES: CN(CC(=O)NC(C)(C)C)c1nc(-c2cc(OC3COC3)ccn2)nc2c1CCC2] | N-tert-butyl-2-[methyl({2-[4-(oxetan-3-yloxy)pyridin-2-yl]-5H,6H,7H-cyclopenta[d]pyrimidin-4-yl})amino]acetamide | 412 |
| 246 | 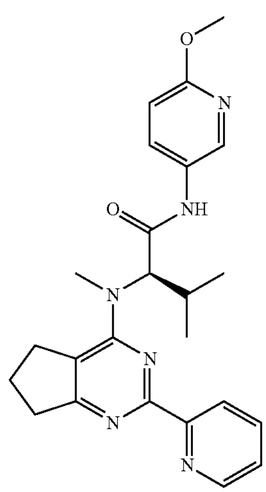 [SMILES: COc1ccc(NC(=O)[C@@H](C(C)C)N(C)c2nc(-c3ccccn3)nc3c2CCC3)cn1] | (2R)-N-(6-methoxypyridin-3-yl)-3-methyl-2-{methyl[2-(pyridin-2-yl)-5H,6H,7H-cyclopenta[d]pyrimidin-4-yl]amino}butanamide | 433.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 247 | 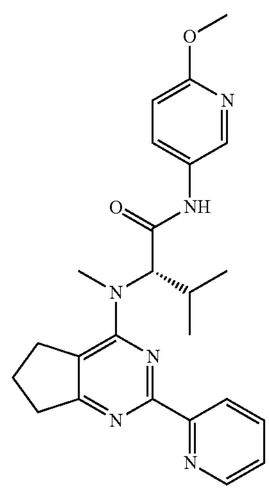 [SMILES: COc1ccc(NC(=O)[C@H](C(C)C)N(C)c2nc(-c3ccccn3)nc3c2CCC3)cn1] | (2S)-N-(6-methoxypyridin-3-yl)-3-methyl-2-{methyl[2-(pyridin-2-yl)-5H,6H,7H-cyclopenta[d]pyrimidin-4-yl]amino}butnamide | 433.2 |
| 248 | 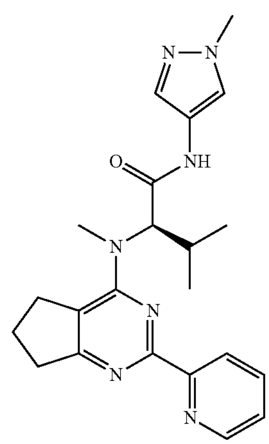 [SMILES: CC(C)[C@H](C(=O)Nc1cnn(C)c1)N(C)c1nc(-c2ccccn2)nc2c1CCC2] | (2R)-3-methyl-N-(1-methyl-1H-pyrazol-4-yl)-2-{methyl[2-(pyridin-2-yl)-5H,6H,7H-cyclopenta[d]pyrimidin-4-yl]amino}butanamide | 406.2 |
| 249 | 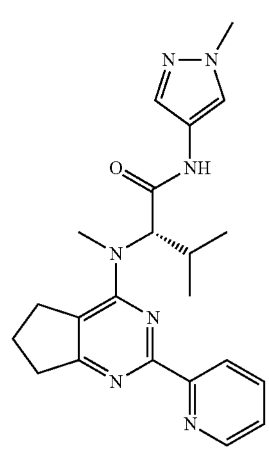 [SMILES: CC(C)[C@@H](C(=O)Nc1cnn(C)c1)N(C)c1nc(-c2ccccn2)nc2c1CCC2] | (2S)-3-methyl-N-(1-methyl-1H-pyrazol-4-yl)-2-{methyl[2-(pyridin-2-yl)-5H,6H,7H-cyclopenta[d]pyrimidin-4-yl]amino}butanamide | 406.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 250 | 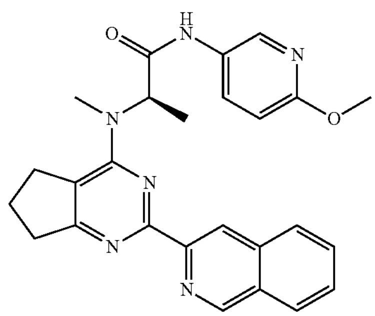 [SMILES: COc1ccc(NC(=O)[C@@H](C)N(C)c2nc(-c3cc4ccccc4cn3)nc3c2CCC3)cn1] | (2R)-2-{[2-(isoquinolin-3-yl)-5H,6H,7H-cyclopenta[d]pyrimidin-4-yl](methyl)amino}-N-(6-methoxypyridin-3-yl)propanamide | 455.2 |
| 251 | 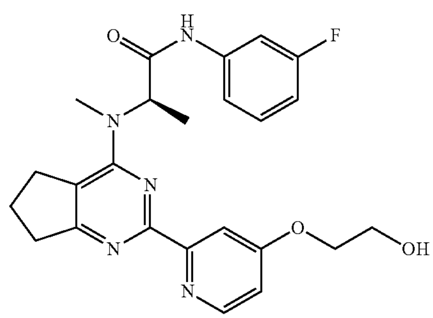 [SMILES: C[C@H](C(=O)Nc1cccc(F)c1)N(C)c1nc(-c2cc(OCCO)ccn2)nc2c1CCC2] | (2R)-N-(3-fluorophenyl)-2-({2-[4-(2-hydroxyethoxy)pyridin-2-yl]-5H,6H,7H-cyclopenta[d]pyrimidin-4-yl}(methyl)amino)propanamide | 452.3 |
| 252 | 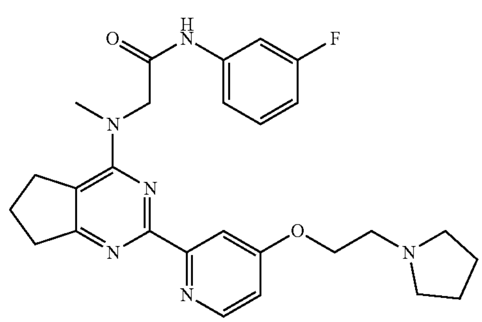 [SMILES: CN(CC(=O)Nc1cccc(F)c1)c1nc(-c2cc(OCCN3CCCC3)ccn2)nc2c1CCC2] | N-(3-fluorophenyl)-2-[methyl(2-{4-[2-(pyrrolidin-1-yl)ethoxy]pyridin-2-yl}-5H,6H,7H-cyclopenta[d]pyrimidin-4-yl)amino]acetamide | 491.3 |
| 253 | 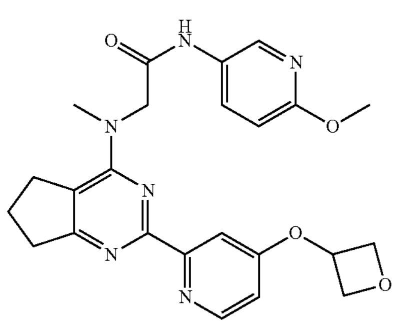 [SMILES: COc1ccc(NC(=O)CN(C)c2nc(-c3cc(OC4COC4)ccn3)nc3c2CCC3)cn1] | N-(6-methoxypyridin-3-yl)-2-[methyl({2-[4-(oxetan-3-yloxy)pyridin-2-yl]-5H,6H,7H-cyclopenta[d]pyrimidin-4-yl})amino]acetamide | 463.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 254 | 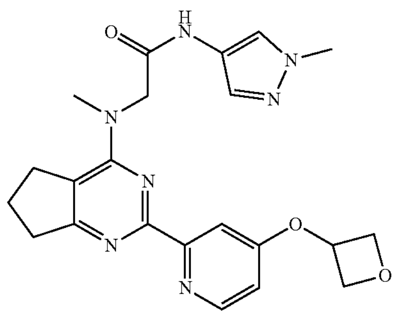 [SMILES: CN(CC(=O)Nc1cnn(C)c1)c1nc(-c2cc(OC3COC3)ccn2)nc2c1CCC2] | 2-[methyl({2-[4-(oxetan-3-yloxy)pyridin-2-yl]-5H,6H,7H-cyclopenta[d]pyrimidin-4-yl})amino]-N-(1-methyl-1H-pyrazol-4-yl)acetamide | 436.2 |
| 255 | 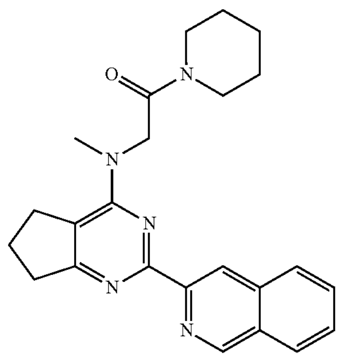 [SMILES: CN(CC(=O)N1CCCCC1)c1nc(-c2cc3ccccc3cn2)nc2c1CCC2] | 2-{[2-(isoquinolin-3-yl)-5H,6H,7H-cyclopenta[d]pyrimidin-4-yl](methyl)amino}-1-(piperidin-1-yl)ethan-1-one | 402.2 |
| 256 | 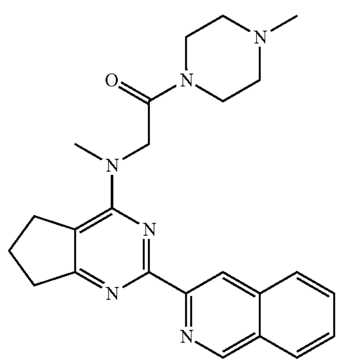 [SMILES: CN1CCN(C(=O)CN(C)c2nc(-c3cc4ccccc4cn3)nc3c2CCC3)CC1] | 2-{[2-(isoquinolin-3-yl)-5H,6H,7H-cyclopenta[d]pyrimidin-4-yl](methyl)amino}-1-(4-methylpiperazin-1-yl)ethan-1-one | 417.3 |
| 257 | 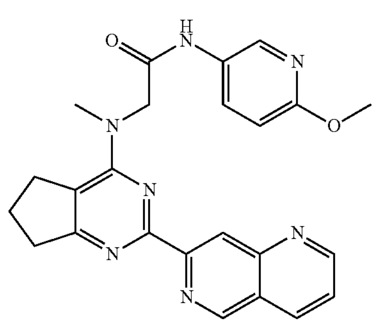 [SMILES: COc1ccc(NC(=O)CN(C)c2nc(-c3cc4ncccc4cn3)nc3c2CCC3)cn1] | N-(6-methoxypyridin-3-yl)-2-{methyl[2-(1,6-naphthyridin-7-yl)-5H,6H,7H-cyclopenta[d]pyrimidin-4-yl]amino}acetamide | 442.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 258 | 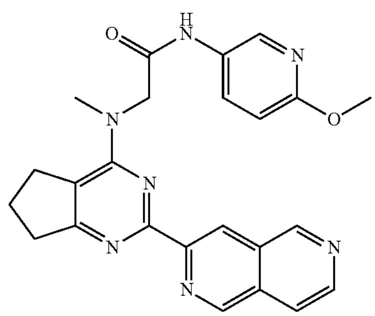 [SMILES: COc1ccc(NC(=O)CN(C)c2nc(-c3cc4cnccc4cn3)nc3c2CCC3)cn1] | N-(6-methoxypyridin-3-yl)-2-{methyl[2-(2,6-naphthyridin-3-yl)-5H,6H,7H-cyclopenta[d]pyrimidin-4-yl]amino}acetamide | 442.2 |
| 259 | 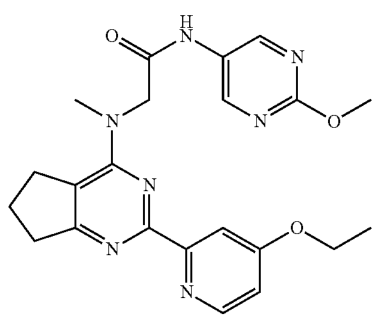 [SMILES: CCOc1ccnc(-c2nc3c(c(N(C)CC(=O)Nc4cnc(OC)nc4)n2)CCC3)c1] | 2-{[2-(4-ethoxypyridin-2-yl)-5H,6H,7H-cyclopenta[d]pyrimidin-4-yl](methyl)amino}-N-(2-methoxypyrimidin-5-yl)acetamide | 436.2 |
| 260 | 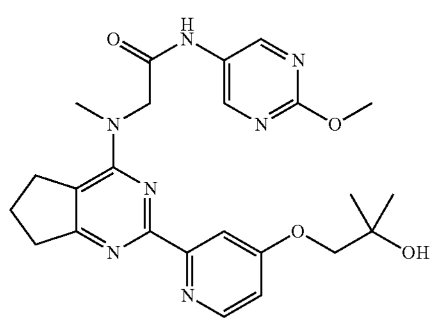 [SMILES: COc1ncc(NC(=O)CN(C)c2nc(-c3cc(OCC(C)(C)O)ccn3)nc3c2CCC3)cn1] | 2-({2-[4-(2-hydroxy-2-methylpropoxy)pyridin-2-yl]-5H,6H,7H-cyclopenta[d]pyrimidin-4-yl}(methyl)amino)-N-(2-methoxypyrimidin-5-yl)acetamide | 480.2 |
| 261 | 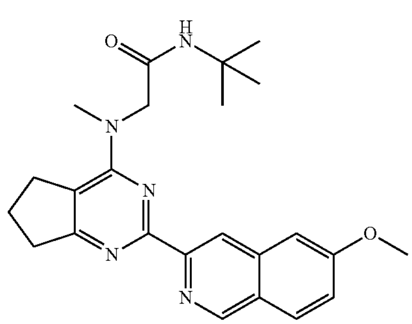 [SMILES: COc1ccc2cnc(-c3nc4c(c(N(C)CC(=O)NC(C)(C)C)n3)CCC4)cc2c1] | N-tert-butyl-2-{[2-(6-methoxyisoquinolin-3-yl)-5H,6H,7H-cyclopenta[d]pyrimidin-4-yl](methyl)amino}acetamide | 420.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 262 | 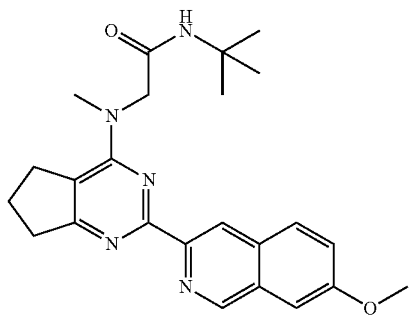 [SMILES: COc1ccc2cc(-c3nc4c(c(N(C)CC(=O)NC(C)(C)C)n3)CCC4)ncc2c1] | N-tert-butyl-2-{[2-(7-methoxyisoquinolin-3-yl)-5H,6H,7H-cyclopenta[d]pyrimidin-4-yl](methyl)amino}acetamide | 420.2 |
| 263 | 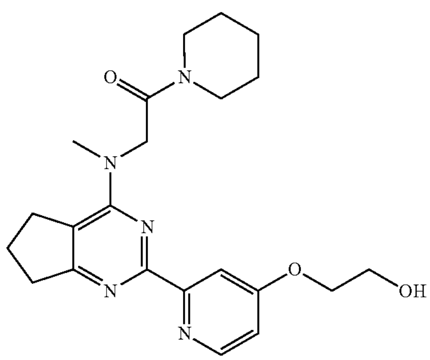 [SMILES: CN(CC(=O)N1CCCCC1)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-1-(piperidin-1-yl)ethan-1-one | 412.3 |
| 264 | 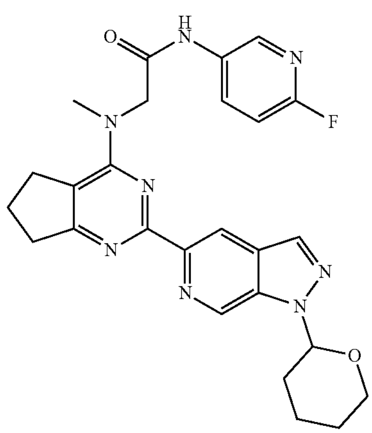 [SMILES: CN(CC(=O)Nc1ccc(F)nc1)c1nc(-c2cc3cnn(C4CCCCO4)c3cn2)nc2c1CCC2] | N-(6-fluoropyridin-3-yl)-2-[methyl({2-[1-(oxan-2-yl)-1H-pyrazolo[3,4-c]pyridin-5-yl]-5H,6H,7H-cyclopenta[d]pyrimidin-4-yl})amino]acetamide | 503.2 |
| 265 | 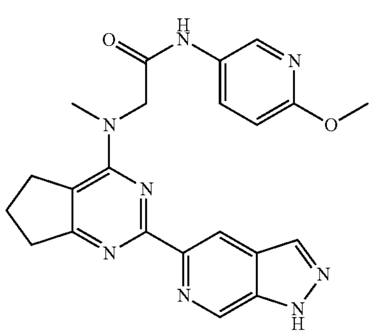 [SMILES: COc1ccc(NC(=O)CN(C)c2nc(-c3cc4cn[nH]c4cn3)nc3c2CCC3)cn1] | N-(5-methoxypyridin-2-yl)-2-[methyl(2-{1H-pyrazolo[3,4-c]pyridin-5-yl}-5H,6H,7H-cyclopenta[d]pyrimidin-4-yl)amino]acetamide | 431.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 266 | 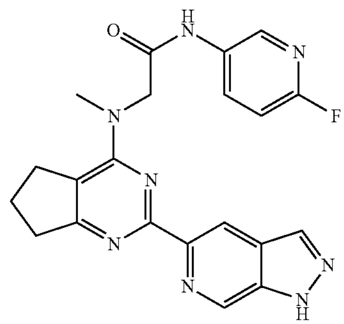 [SMILES: CN(CC(=O)Nc1ccc(F)nc1)c1nc(-c2cc3cn[nH]c3cn2)nc2c1CCC2] | N-(6-fluoropyridin-3-yl)-2-[methyl(2-{1H-pyrazolo[3,4-c]pyridin-5-yl}-5H,6H,7H-cyclopenta[d]pyrimidin-4-yl)amino]acetamide | 419.0 |
| 267 | 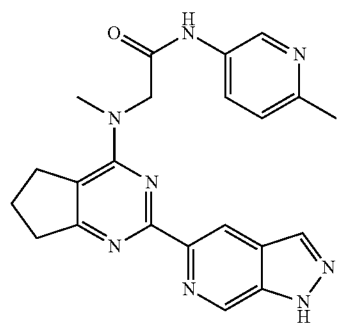 [SMILES: Cc1ccc(NC(=O)CN(C)c2nc(-c3cc4cn[nH]c4cn3)nc3c2CCC3)cn1] | 2-[methyl(2-{1H-pyrazolo[3,4-c]pyridin-5-yl}-5H,6H,7H-cyclopenta[d]pyrimidin-4-yl)amino]-N-(6-methylpyridin-3-yl)acetamide | 415.1 |
| 268 | 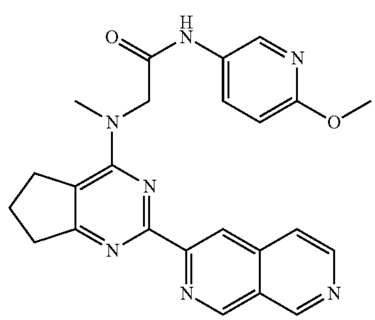 [SMILES: COc1ccc(NC(=O)CN(C)c2nc(-c3cc4ccncc4cn3)nc3c2CCC3)cn1] | N-(6-methoxypyridin-3-yl)-2-{methyl[2-(2,7-naphthyridin-3-yl)-5H,6H,7H-cyclopenta[d]pyrimidin-4-yl]amino}acetamide | 442.3 |
| 269 | 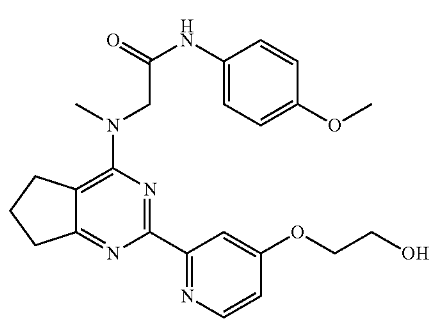 [SMILES: COc1ccc(NC(=O)CN(C)c2nc(-c3cc(OCCO)ccn3)nc3c2CCC3)cc1] | 2-({2-[4-(2-hydroxyethoxy)pyridin-2-yl]-5H,6H,7H-cyclopenta[d]pyrimidin-4-yl}(methyl)amino)-N-(4-methoxyphenyl)acetamide | 450.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 270 | 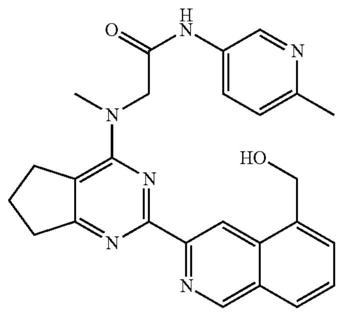 [SMILES: Cc1ccc(NC(=O)CN(C)c2nc(-c3cc4c(CO)cccc4cn3)nc3c2CCC3)cn1] | 2-({2-[5-(hydroxymethyl)isoquinolin-3-yl]-5H,6H,7H-cyclopenta[d]pyrimidin-4-yl}(methyl)amino)-N-(6-methylpyridin-3-yl)acetamide | 455.2 |
| 271 | 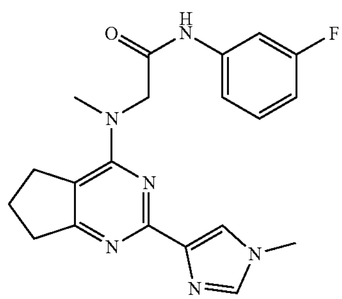 [SMILES: CN(CC(=O)Nc1cccc(F)c1)c1nc(-c2cn(C)cn2)nc2c1CCC2] | N-(3-fluorophenyl)-2-{methyl[2-(1-methyl-1H-imidazol-4-yl)-5H,6H,7H-cyclopenta[d]pyrimidin-4-yl]amino}acetamide | 381.2 |
| 272 | 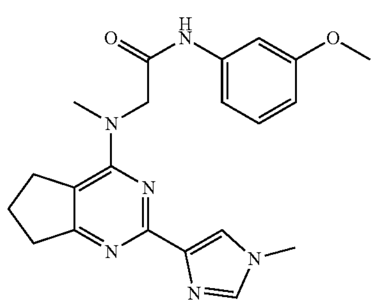 [SMILES: COc1cccc(NC(=O)CN(C)c2nc(-c3cn(C)cn3)nc3c2CCC3)c1] | N-(3-methoxyphenyl)-2-{methyl[2-(1-methyl-1H-imidazol-4-yl)-5H,6H,7H-cyclopenta[d]pyrimidin-4-yl]amino}acetamide | 393.2 |
| 273 | 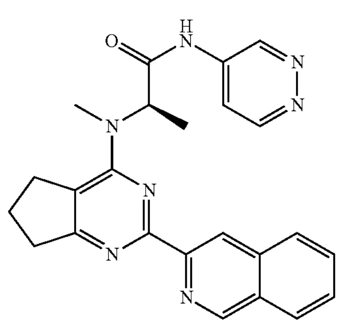 [SMILES: C[C@H](C(=O)Nc1ccnnc1)N(C)c1nc(-c2cc3ccccc3cn2)nc2c1CCC2] | (2R)-2-{[2-(isoquinolin-3-yl)-5H,6H,7H-cyclopenta[d]pyrimidin-4-yl](methyl)amino}-N-(pyridazin-4-yl)propanamide | 426.7 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 274 | 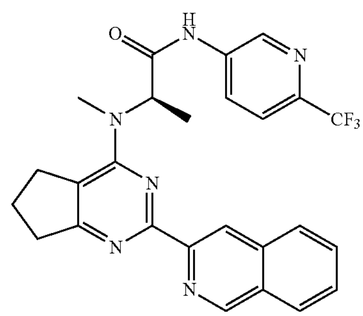 [SMILES: C[C@H](C(=O)Nc1ccc(C(F)(F)F)nc1)N(C)c1nc(-c2cc3ccccc3cn2)nc2c1CCC2] | (2R)-2-{[2-(isoquinolin-3-yl)-5H,6H,7H-cyclopenta[d]pyrimidin-4-yl](methyl)amino}-N-[6-(trifluoromethyl)pyridin-3-yl]propanamide | 493.7 |
| 275 | 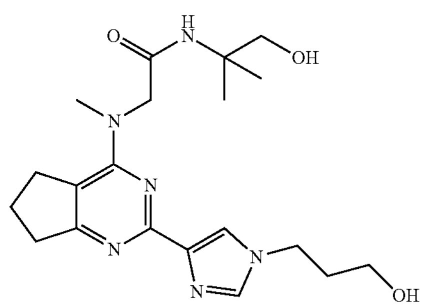 [SMILES: CN(CC(=O)NC(C)(C)CO)c1nc(-c2cn(CCCO)cn2)nc2c1CCC2] | N-(1-hydroxy-2-methylpropan-2-yl)-2-({2-[1-(3-hydroxypropyl)-1H-imidazol-4-yl]-5H,6H,7H-cyclopenta[d]pyrimidin-4-yl}(methyl)amino)acetamide | 403.3 |
| 276 | 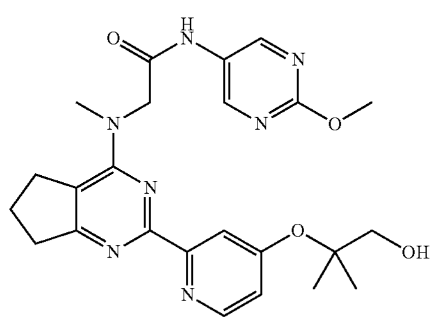 [SMILES: COc1ncc(NC(=O)CN(C)c2nc(-c3cc(OC(C)(C)CO)ccn3)nc3c2CCC3)cn1] | 2-[(2-{4-[(1-hydroxy-2-methylpropan-2-yl)oxy]pyridin-2-yl}-5H,6H,7H-cyclopenta[d]pyrimidin-4-yl)(methyl)amino]-N-(2-methoxypyrimidin-5-yl)acetamide | 480.3 |
| 277 | 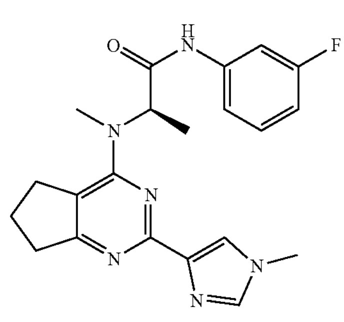 [SMILES: C[C@H](C(=O)Nc1cccc(F)c1)N(C)c1nc(-c2cn(C)cn2)nc2c1CCC2] | (2R)-N-(3-fluorophenyl)-2-{methyl[2-(1-methyl-1H-imidazol-4-yl)-5H,6H,7H-cyclopenta[d]pyrimidin-4-yl]amino}propanamide | 395.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 278 | 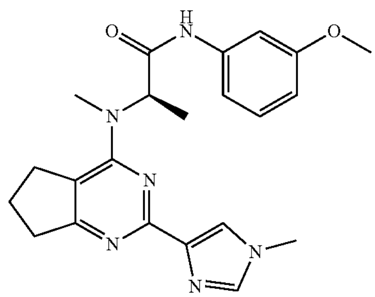 [SMILES: COc1cccc(NC(=O)[C@@H](C)N(C)c2nc(-c3cn(C)cn3)nc3c2CCC3)c1] | (2R)-N-(3-methoxyphenyl)-2-{methyl[2-(1-methyl-1H-imidazol-4-yl)-5H,6H,7H-cyclopenta[d]pyrimidin-4-yl]amino}propanamide | 407.2 |
| 279 | 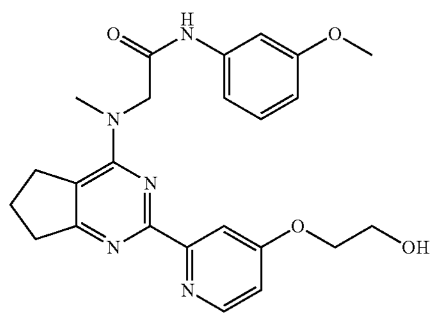 [SMILES: COc1cccc(NC(=O)CN(C)c2nc(-c3cc(OCCO)ccn3)nc3c2CCC3)c1] | 2-({2-[4-(2-hydroxyethoxy)pyridin-2-yl]-5H,6H,7H-cyclopenta[d]pyrimidin-4-yl}(methyl)amino)-N-(3-methoxyphenyl)acetamide | 450.2 |
| 280 | 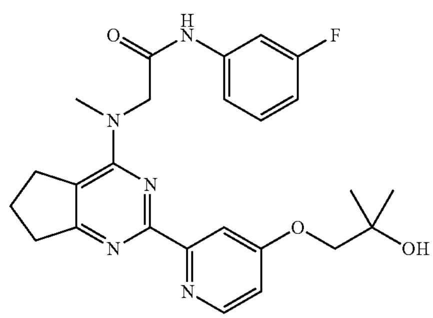 [SMILES: CN(CC(=O)Nc1cccc(F)c1)c1nc(-c2cc(OCC(C)(C)O)ccn2)nc2c1CCC2] | N-(3-fluorophenyl)-2-({2-[4-(2-hydroxy-2-methylpropoxy)pyridin-2-yl]-5H,6H,7H-cyclopenta[d]pyrimidin-4-yl}(methyl)amino)acetamide | 466.2 |
| 281 | 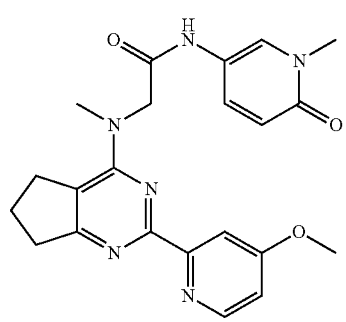 [SMILES: COc1ccnc(-c2nc3c(c(N(C)CC(=O)Nc4ccc(=O)n(C)c4)n2)CCC3)c1] | 2-{[2-(4-methoxypyridin-2-yl)-5H,6H,7H-cyclopenta[d]pyrimidin-4-yl](methyl)amino}-N-(1-methyl-6-oxo-1,6-dihydropyridin-3-yl)acetamide | 421.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 282 | 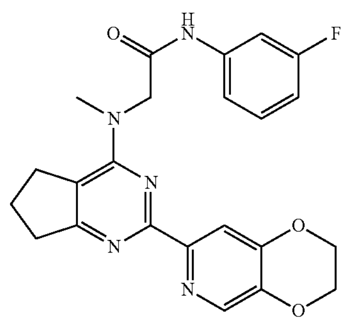 [SMILES: CN(CC(=O)Nc1cccc(F)c1)c1nc(-c2cc3c(cn2)OCCO3)nc2c1CCC2] | 2-[(2-{2H,3H-[1,4]dioxino[2,3-c]pyridin-7-yl}-5H,6H,7H-cyclopenta[d]pyrimidin-4-yl)(methyl)amino]-N-(3-fluorophenyl)acetamide | 436.2 |
| 283 | 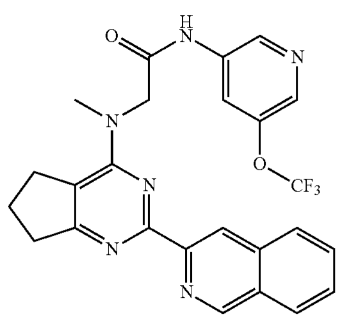 [SMILES: CN(CC(=O)Nc1cncc(OC(F)(F)F)c1)c1nc(-c2cc3ccccc3cn2)nc2c1CCC2] | 2-{[2-(isoquinolin-3-yl)-5H,6H,7H-cyclopenta[d]pyrimidin-4-yl](methyl)amino}-N-[5-(trifluoromethoxy)pyridin-3-yl]acetamide | 495.2 |
| 284 | 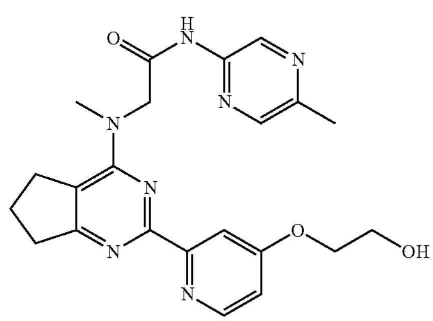 [SMILES: Cc1cnc(NC(=O)CN(C)c2nc(-c3cc(OCCO)ccn3)nc3c2CCC3)cn1] | 2-({2-[4-(2-hydroxyethoxy)pyridin-2-yl]-5H,6H,7H-cyclopenta[d]pyrimidin-4-yl}(methyl)amino)-N-(5-methylpyrazin-2-yl)acetamide | 436.2 |
| 285 | 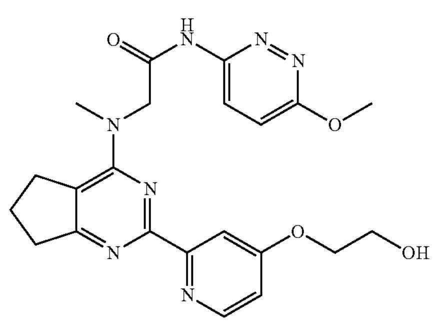 [SMILES: COc1ccc(NC(=O)CN(C)c2nc(-c3cc(OCCO)ccn3)nc3c2CCC3)nn1] | 2-({2-[4-(2-hydroxyethoxy)pyridin-2-yl]-5H,6H,7H-cyclopenta[d]pyrimidin-4-yl}(methyl)amino)-N-(6-methoxypyridazin-3-yl)acetamide | 452.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 286 | 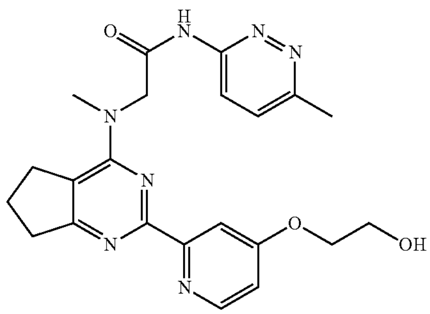 [SMILES: Cc1ccc(NC(=O)CN(C)c2nc(-c3cc(OCCO)ccn3)nc3c2CCC3)nn1] | 2-({2-[4-(2-hydroxyethoxy)pyridin-2-yl]-5H,6H,7H-cyclopenta[d]pyrimidin-4-yl}(methyl)amino)-N-(6-methylpyridazin-3-yl)acetamide | 436.2 |
| 287 | 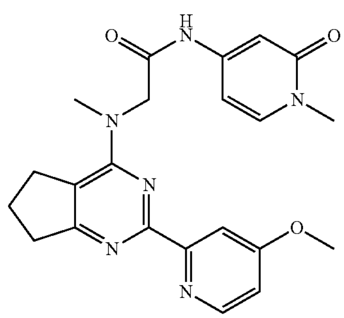 [SMILES: COc1ccnc(-c2nc3c(c(N(C)CC(=O)Nc4ccn(C)c(=O)c4)n2)CCC3)c1] | 2-{[2-(4-methoxypyridin-2-yl)-5H,6H,7H-cyclopenta[d]pyrimidin-4-yl](methyl)amino}-N-(1-methyl-2-oxo-1,2-dihydropyridin-4-yl)acetamide | 421.2 |
| 288 | 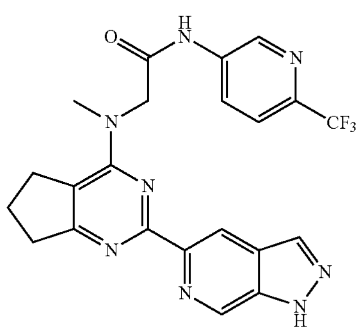 [SMILES: CN(CC(=O)Nc1ccc(C(F)(F)F)nc1)c1nc(-c2cc3cn[nH]c3cn2)nc2c1CCC2] | 2-[methyl(2-{1H-pyrazolo[3,4-c]pyridin-5-yl}-5H,6H,7H-cyclopenta[d]pyrimidin-4-yl)amino]-N-[6-(trifluoromethyl)pyridin-3-yl]acetamide | 469.1 |
| 289 | 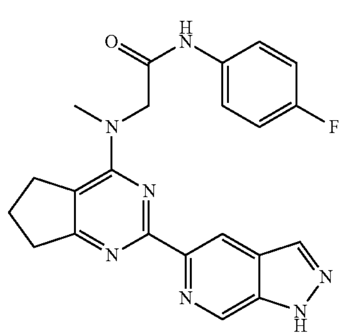 [SMILES: CN(CC(=O)Nc1ccc(F)cc1)c1nc(-c2cc3cn[nH]c3cn2)nc2c1CCC2] | N-(4-fluorophenyl)-2-[methyl(2-{1H-pyrazolo[3,4-c]pyridin-5-yl}-5H,6H,7H-cyclopenta[d]pyrimidin-4-yl)amino]acetamide | 418.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 290 | 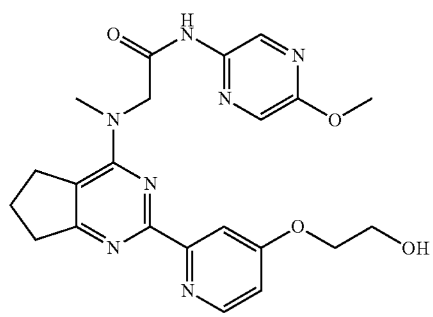 | 2-({2-[4-(2-hydroxyethoxy)pyridin-2-yl]-5H,6H,7H-cyclopenta[d]pyrimidin-4-yl}(methyl)amino)-N-(5-methoxypyrazin-2-yl)acetamide | 452.3 |
| 291 | 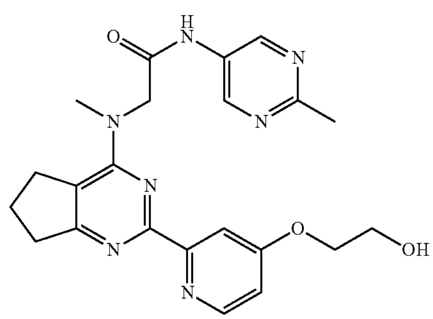 | 2-({2-[4-(2-hydroxyethoxy)pyridin-2-yl]-5H,6H,7H-cyclopenta[d]pyrimidin-4-yl}(methyl)amino)-N-(2-methylpyrimidin-5-yl)acetamide | 436.2 |
| 292 | 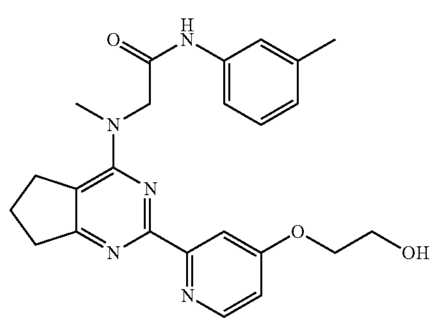 | 2-({2-[4-(2-hydroxyethoxy)pyridin-2-yl]-5H,6H,7H-cyclopenta[d]pyrimidin-4-yl}(methyl)amino)-N-(3-methylphenyl)acetamide | 434.2 |
| 293 | 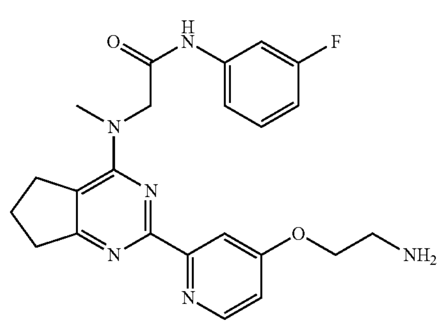 [SMILES: CN(CC(=O)Nc1cccc(F)c1)c1nc(-c2cc(OCCN)ccn2)nc2c1CCC2] | 2-({2-[4-(2-aminoethoxy)pyridin-2-yl]-5H,6H,7H-cyclopenta[d]pyrimidin-4-yl}(methyl)amino)-N-(3-fluoropehnyl)acetamide | 437.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 294 | 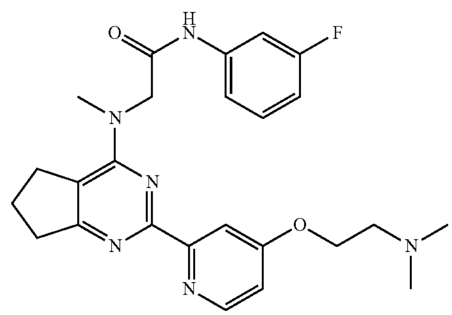 [SMILES: CN(C)CCOc1ccnc(-c2nc3c(c(N(C)CC(=O)Nc4cccc(F)c4)n2)CCC3)c1] | 2-[(2-{4-[2-(dimethylamino)ethoxy]pyridin-2-yl}-5H,6H,7H-cyclopenta[d]pyrimidin-4-yl)(methyl)amino]-N-(3-fluorophenyl)acetamide | 465.3 |
| 295 | 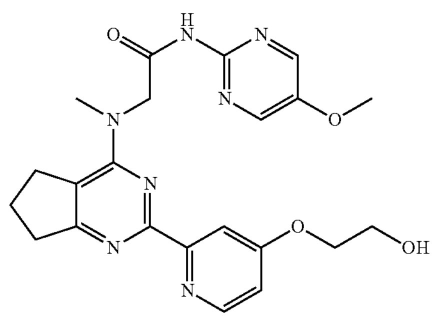 | 2-({2-[4-(2-hydroxyethoxy)pyridin-2-yl]-5H,6H,7H-cyclopenta[d]pyrimidin-4-yl}(methyl)amino)-N-(5-methoxypyrimidin-2-yl)acetamide | 452.3 |
| 296 | 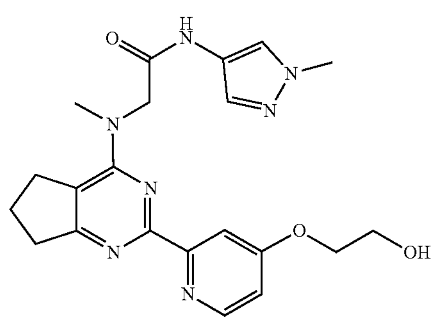 [SMILES: CN(CC(=O)Nc1cnn(C)c1)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-N-(1-methyl-1H-pyrazol-4-yl)acetamide | 424.2 |
| 297 | 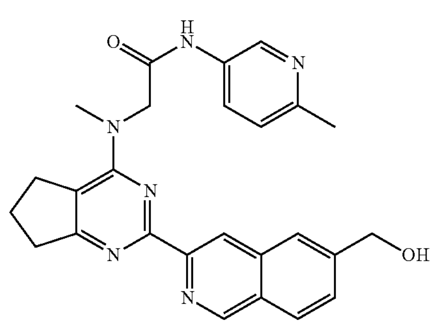 [SMILES: Cc1ccc(NC(=O)CN(C)c2nc(-c3cc4cc(CO)ccc4cn3)nc3c2CCC3)cn1] | 2-({2-[6-(hydroxymethyl)isoquinolin-3-yl]-5H,6H,7H-cyclopenta[d]pyrimidin-4-yl}(methyl)amino)-N-(6-methylpyridin-3-yl)acetamide | 455.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 298 | 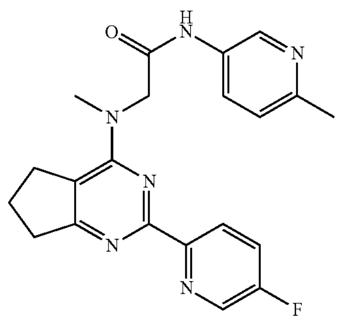 [SMILES: Cc1ccc(NC(=O)CN(C)c2nc(-c3ccc(F)cn3)nc3c2CCC3)cn1] | 2-{[2-(5-fluoropyridin-2-yl)-5H,6H,7H-cyclopenta[d]pyrimidin-4-yl](methyl)amino}-N-(6-methylpyridin-3-yl)acetamide | 393.1 |
| 299 | 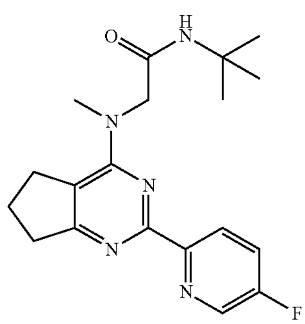 [SMILES: CN(CC(=O)NC(C)(C)C)c1nc(-c2ccc(F)cn2)nc2c1CCC2] | N-tert-butyl-2-{[2-(5-fluoropyridin-2-yl)-5H,6H,7H-cyclopenta[d]pyrimidin-4-yl](methyl)amino}acetamide | 358.1 |
| 300 | 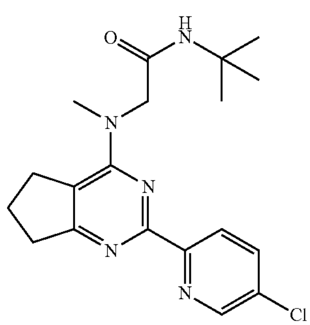 [SMILES: CN(CC(=O)NC(C)(C)C)c1nc(-c2ccc(Cl)cn2)nc2c1CCC2] | N-tert-butyl-2-{[2-(5-chloropyridin-2-yl)-5H,6H,7H-cyclopenta[d]pyrimidin-4-yl](methyl)amino}acetamide | 374.7, 376.7 |
| 301 | 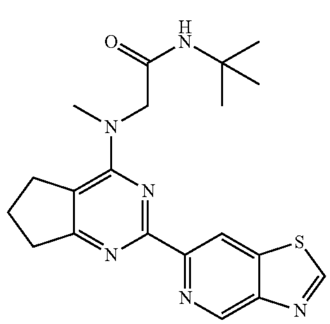 [SMILES: CN(CC(=O)NC(C)(C)C)c1nc(-c2cc3scnc3cn2)nc2c1CCC2] | N-tert-butyl-2-[methyl(2-{[1,3]thiazolo[4,5-c]pyridin-6-yl}-5H,6H,7H-cyclopenta[d]pyrimidin-4-yl)amino]acetamide | 397.2 |

TABLE 1-continued

Where the mass for a compound is not provided in Table 1, the mass can be found
for the compound in the synthetic examples.

| Compound No. | Structure | IUPAC Name | Mass Found (M + 1) |
|---|---|---|---|
| 302 | 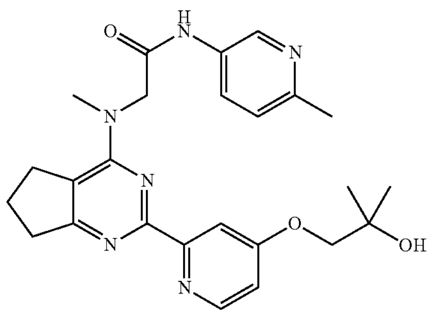 [SMILES: Cc1ccc(NC(=O)CN(C)c2nc(-c3cc(OCC(C)(C)O)ccn3)nc3c2CCC3)cn1] | 2-({2-[4-(2-hydroxy-2-methylpropoxy)pyridin-2-yl]-5H,6H,7H-cyclopenta[d]pyrimidin-4-yl}(methyl)amino)-N-(6-methylpyridin-3-yl)acetamide | 463.3 |
| 303 | 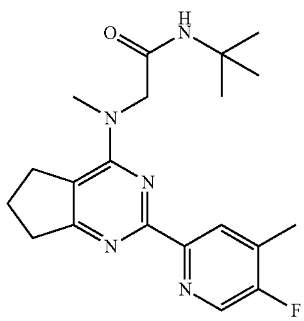 [SMILES: Cc1cc(-c2nc3c(c(N(C)CC(=O)NC(C)(C)C)n2)CCC3)ncc1F] | N-tert-butyl-2-{[2-(5-fluoro-4-methylpyridin-2-yl)-5H,6H,7H-cyclopenta[d]pyrimidin-4-yl](methyl)amino}acetamide | 372.2 |
| 304 | 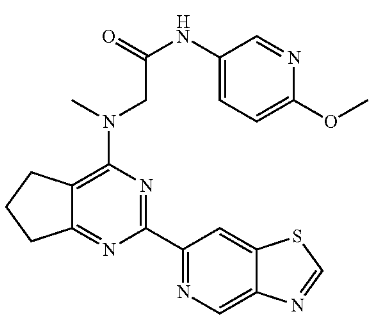 [SMILES: COc1ccc(NC(=O)CN(C)c2nc(-c3cc4scnc4cn3)nc3c2CCC3)cn1] | N-(6-methoxypyridin-3-yl)-2-[methyl(2-{[1,3]thiazolo[4,5-c]pyridin-6-yl}-5H,6H,7H-cyclopenta[d]pyrimidin-4-yl)amino]acetamide | 448.2 |
| 305 | 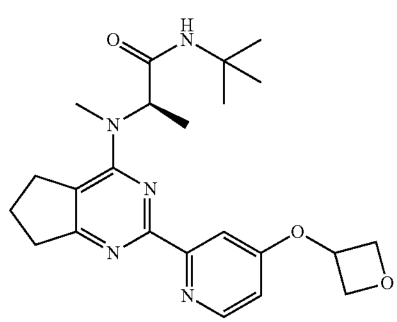 [SMILES: C[C@H](C(=O)NC(C)(C)C)N(C)c1nc(-c2cc(OC3COC3)ccn2)nc2c1CCC2] | (2R)-N-tert-butyl-2-[methyl({2-[4-(oxetan-3-yloxy-pyridin-2-yl]-5H,6H,7H-cyclopenta[d]pyrimidin-4-yl})amino]propanamide | 426.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 306 | 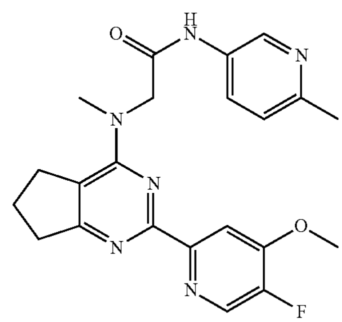 [SMILES: COc1cc(-c2nc3c(c(N(C)CC(=O)Nc4ccc(C)nc4)n2)CCC3)ncc1F] | 2-{[2-(5-fluoro-4-methoxypyridin-2-yl)-5H,6H,7H-cyclopenta[d]pyrimidin-4-yl](methyl)amino}-N-(6-methylpyridin-3-yl)acetamide | 423.1 |
| 307 | 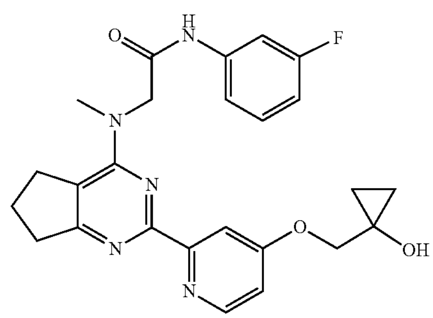 [SMILES: CN(CC(=O)Nc1cccc(F)c1)c1nc(-c2cc(OCC3(O)CC3)ccn2)nc2c1CCC2] | N-(3-fluorophenyl)-2-[(2-{4-[(1-hydroxycyclopropyl)methoxy]pyridin-2-yl}-5H,6H,7H-cyclopenta[d]pyrimidin-4-yl)(methyl)amino]acetamide | 464.2 |
| 308 | 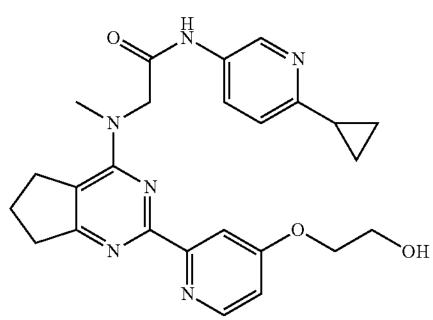 [SMILES: CN(CC(=O)Nc1ccc(C2CC2)nc1)c1nc(-c2cc(OCCO)ccn2)nc2c1CCC2] | N-(6-cyclopropylpyridin-3-yl)-2-({2-[4-(2-hydroxyethoxy)pyridin-2-yl]-5H,6H,7H-cyclopenta[d]pyrimidin-4-yl}(methyl)amino)acetamide | 461.2 |
| 309 | 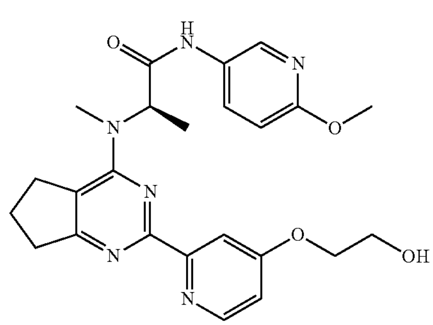 [SMILES: COc1ccc(NC(=O)[C@@H](C)N(C)c2nc(-c3cc(OCCO)ccn3)nc3c2CCC3)cn1] | (2R)-2-({2-[4-(2-hydroxyethoxy)pyridin-2-yl]-5H,6H,7H-cyclopenta[d]pyrimidin-4-yl}(methyl)amino)-N-(6-methoxypyridin-3-yl)propanamide | 465.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 310 | 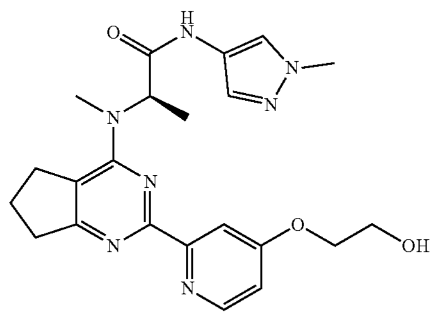 [SMILES: C[C@H](C(=O)Nc1cnn(C)c1)N(C)c1nc(-c2cc(OCCO)ccn2)nc2c1CCC2] | (2R)-2-({2-[4-(2-hydroxyethoxy)pyridin-2-yl]-5H,6H,7H-cyclopenta[d]pyrimidin-4-yl}(methyl)amino)-N-(1-methyl-1H-pyrazol-4-yl)propanamide | 438.2 |
| 311 | 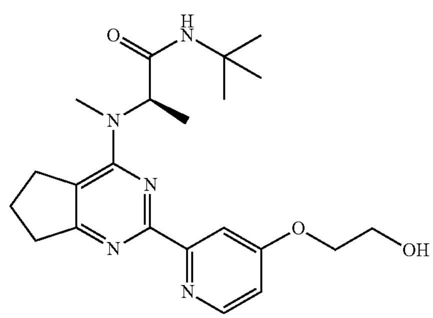 [SMILES: C[C@H](C(=O)NC(C)(C)C)N(C)c1nc(-c2cc(OCCO)ccn2)nc2c1CCC2] | (2R)-N-tert-butyl-2-({2-[4-(2-hydroxyethoxy)pyridin-2-yl]-5H,6H,7H-cyclopenta[d]pyrimidin-4-yl}(methyl)amino)propanamide | 414.3 |
| 312 | 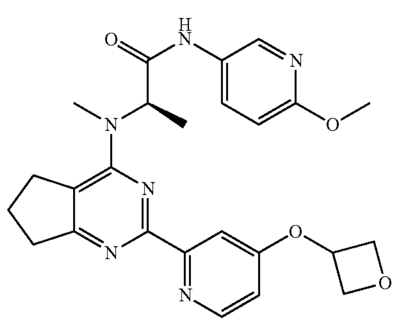 [SMILES: COc1ccc(NC(=O)[C@@H](C)N(C)c2nc(-c3cc(OC4COC4)ccn3)nc3c2CCC3)cn1] | (2R)-N-(6-methoxypyridin-3-yl)-2-[methyl({2-[4-(oxetan-3-yloxy)pyridin-2-yl]-5H,6H,7H-cyclopenta[d]pyrimidin-4-yl})amino]propanamide | 477.3 |
| 313 | 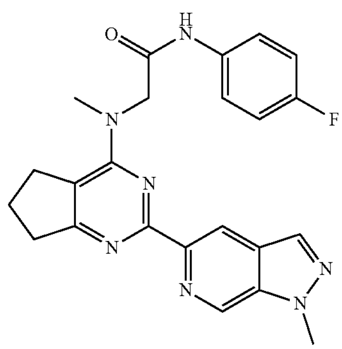 [SMILES: CN(CC(=O)Nc1ccc(F)cc1)c1nc(-c2cc3cnn(C)c3cn2)nc2c1CCC2] | N-(4-fluorophenyl)-2-[methyl(2-{1-methyl-1H-pyrazolo[3,4-c]pyridin-5-yl}-5H,6H,7H-cyclopenta[d]pyrimidin-4-yl)amino]acetamide | 432.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 314 | 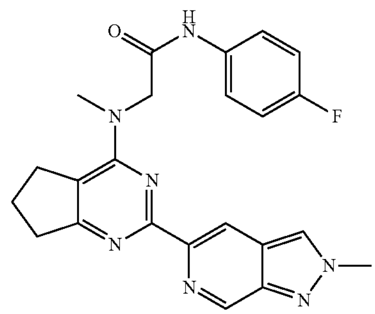 [SMILES: CN(CC(=O)Nc1ccc(F)cc1)c1nc(-c2cc3cn(C)nc3cn2)nc2c1CCC2] | N-(4-fluorophenyl)-2-[methyl(2-{2-methyl-2H-pyrazolo[3,4-c]pyridin-5-yl}-5H,6H,7H-cyclopenta[d]pyrimidin-4-yl)amino]acetamide | 432.1 |
| 315 | 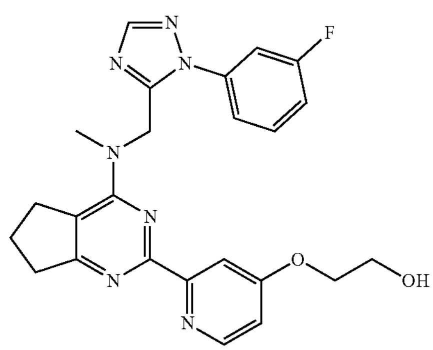 [SMILES: CN(Cc1ncnn1-c1cccc(F)c1)c1nc(-c2cc(OCCO)ccn2)nc2c1CCC2] | 2-({2-[4-({[1-(3-fluorophenyl)-1H-1,2,4-triazol-5-yl]methyl}(methyl)amino)-5H,6H,7H-cyclopenta[d]pyrimidin-2-yl]pyridin-4-yl}oxy)ethan-1-ol | 462.2 |
| 316 | 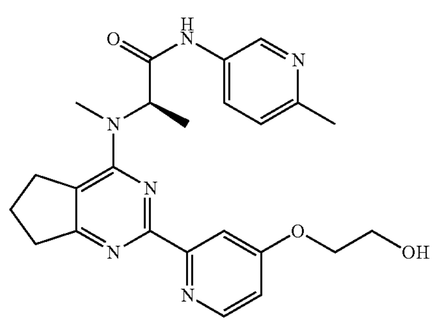 [SMILES: Cc1ccc(NC(=O)[C@@H](C)N(C)c2nc(-c3cc(OCCO)ccn3)nc3c2CCC3)cn1] | (2R)-2-({2-[4-(2-hydroxyethoxy)pyridin-2-yl]-5H,6H,7H-cyclopenta[d]pyrimidin-4-yl}(methyl)amino)-N-(6-methylpyridin-3-yl)propanamide | 449.3 |
| 317 | 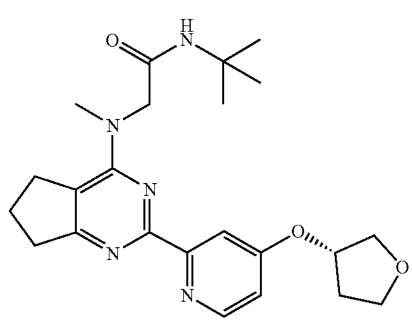 [SMILES: CN(CC(=O)NC(C)(C)C)c1nc(-c2cc(O[C@H]3CCOC3)ccn2)nc2c1CCC2] | N-tert-butyl-2-[methyl(2-{4-[(3S)-oxolan-3-yloxy]pyridin-2-yl}-5H,6H,7H-cyclopenta[d]pyrimidin-4-yl)amino]acetamide | 426.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 318 | 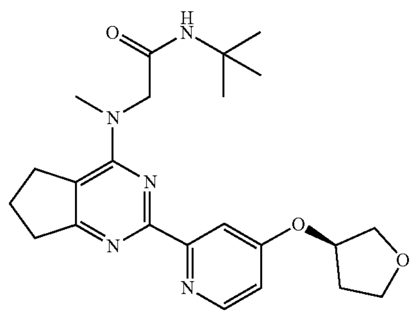 [SMILES: CN(CC(=O)NC(C)(C)C)c1nc(-c2cc(O[C@@H]3CCOC3)ccn2)nc2c1CCC2] | N-tert-butyl-2-[methyl(2-{4-[(3R)-oxolan-3-yloxy]pyridin-2-yl}-5H,6H,7H-cyclopenta[d]pyrimidin-4-yl)amino]acetamide | 426.3 |
| 319 | 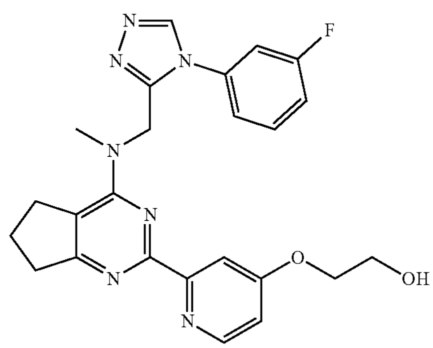 [SMILES: CN(Cc1nncn1-c1cccc(F)c1)c1nc(-c2cc(OCCO)ccn2)nc2c1CCC2] | 2-({2-[4-({[4-(difluorophenyl)-4H-1,2,4-triaozl-3-yl]methyl}(methyl)amino)-5H,6H,7H-cyclopenta[d]pyrimidin-2-yl]pyridin-4-yl}oxy)ethan-1-ol | 462.2 |
| 320 | 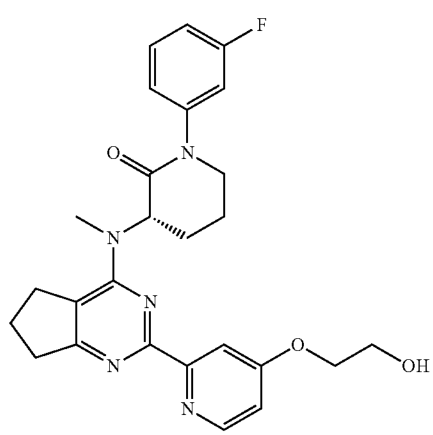 [SMILES: CN(c1nc(-c2cc(OCCO)ccn2)nc2c1CCC2)[C@H]1CCCN(c2cccc(F)c2)C1=O] | (3S)-1-(3-fluorophenyl)-3-({2-[4-(2-hydroxyethoxy)pyridin-2-yl]-5H,6H,7H-cyclopenta[d]pyrimidin-4-yl}(methyl)amino)piperidin-2-one | 478.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 321 | 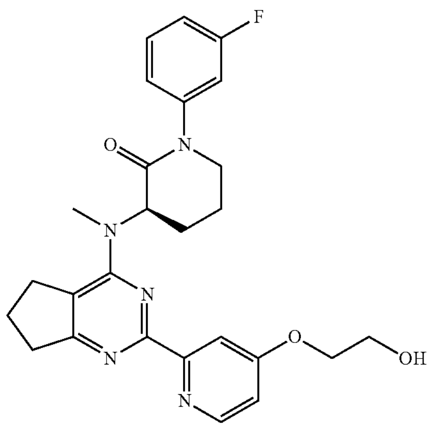 [SMILES: CN(c1nc(-c2cc(OCCO)ccn2)nc2c1CCC2)[C@@H]1CCCN(c2cccc(F)c2)C1=O] | (3R)-1-(3-fluorophenyl)-3-({2-[4-(2-hydroxyethoxy)pyridin-2-yl]-5H,6H,7H-cyclopenta[d]pyrimidin-4-yl}(methyl)amino)piperidin-2-one | 478.2 |
| 322 | 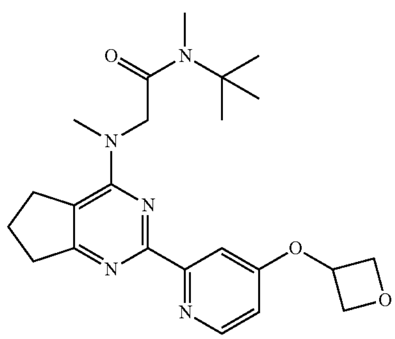 [SMILES: CN(CC(=O)N(C)C(C)(C)C)c1nc(-c2cc(OC3COC3)ccn2)nc2c1CCC2] | N-tert-butyl-N-methyl-2-[methyl({2-[4-(oxetan-3-yloxy)pyridin-2-yl]-5H,6H,7H-cyclopenta[d]pyrimidin-4-yl})amino]acetamide | 426.3 |
| 323 | 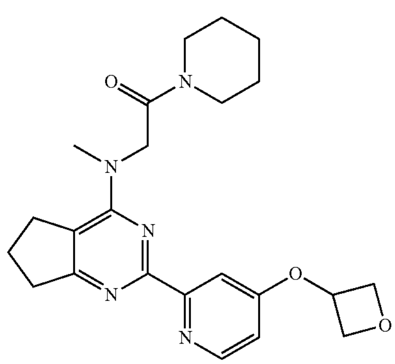 [SMILES: CN(CC(=O)N1CCCCC1)c1nc(-c2cc(OC3COC3)ccn2)nc2c1CCC2] | 2-[methyl({2-[4-(oxetan-3-yloxy)pyridin-2-yl]-5H,6H,7H-cyclopenta[d]pyrimidin-4-yl})amino]-1-(piperidin-1-yl)ethan-1-one | 424.3 |
| 324 | 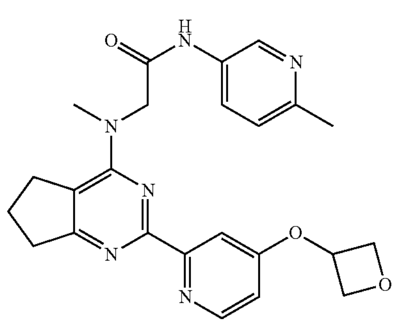 [SMILES: Cc1ccc(NC(=O)CN(C)c2nc(-c3cc(OC4COC4)ccn3)nc3c2CCC3)cn1] | 2-[methyl({2-[4-(oxetan-3-yloxy)pyridin-2-yl]-5H,6H,7H-cyclopenta[d]pyrimidin-4-yl})amino]-N-(6-methylpyridin-3-yl)acetamide | 447.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 325 | 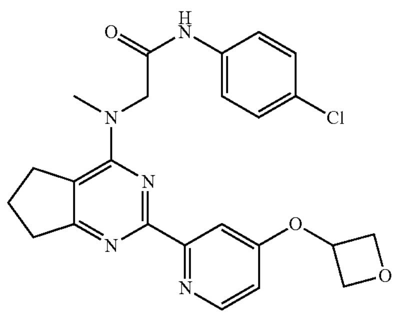 [SMILES: CN(CC(=O)Nc1ccc(Cl)cc1)c1nc(-c2cc(OC3COC3)ccn2)nc2c1CCC2] | N-(4-chlorophenyl)-2-[methyl({2-[4-(oxetan-3-yloxy)pyridin-2-yl]-5H,6H,7H-cyclopenta[d]pyrimidin-4-yl})amino]acetamide | 466.2 |
| 326 | 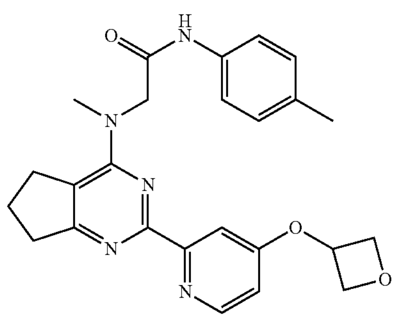 [SMILES: Cc1ccc(NC(=O)CN(C)c2nc(-c3cc(OC4COC4)ccn3)nc3c2CCC3)cc1] | 2-[methyl({2-[4-(oxetan-3-yloxy)pyridin-2-yl]-5H,6H,7H-cyclopenta[d]pyrimidin-4-yl})amino]-N-(4-methylphenyl)acetamide | 446.2 |
| 327 | 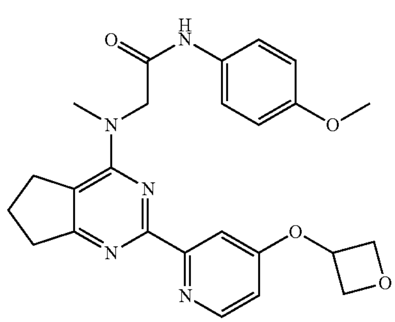 [SMILES: COc1ccc(NC(=O)CN(C)c2nc(-c3cc(OC4COC4)ccn3)nc3c2CCC3)cc1] | N-(4-methoxyphenyl)-2-[methyl({2-[4-(oxetan-3-yloxy)pyridin-2-yl]-5H,6H,7H-cyclopenta[d]pyrimidin-4-yl})amino]acetamide | 462.2 |
| 328 | 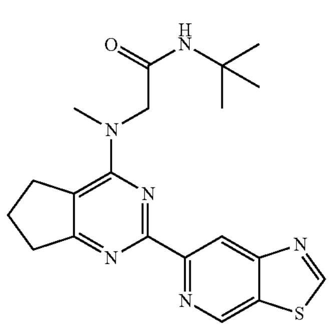 [SMILES: CN(CC(=O)NC(C)(C)C)c1nc(-c2cc3ncsc3cn2)nc2c1CCC2] | N-tert-butyl-2-[methyl(2-{[1,3]thiazolo[5,4-c]pyridin-6-yl}-5H,6H,7H-cyclopenta[d]pyrimidin-4-yl)amino]acetamide | 397.2 |

TABLE 1-continued

Where the mass for a compound is not provided in Table 1, the mass can be found
for the compound in the synthetic examples.

| Compound No. | Structure | IUPAC Name | Mass Found (M + 1) |
|---|---|---|---|
| 329 | 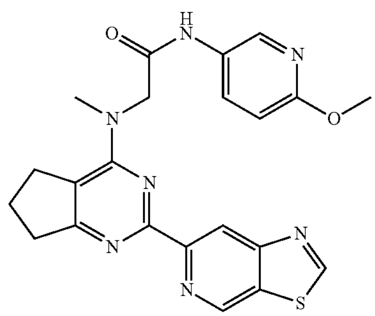 [SMILES: COc1ccc(NC(=O)CN(C)c2nc(-c3cc4ncsc4cn3)nc3c2CCC3)cn1] | N-(6-methoxypyridin-3-yl)-2-[methyl(2-{[1,3]thiazolo[5,4-c]pyridin-6-yl}-5H,6H,7H-cyclopenta[d]pyrimidin-4-yl)amino]acetamide | 448.2 |
| 330 | 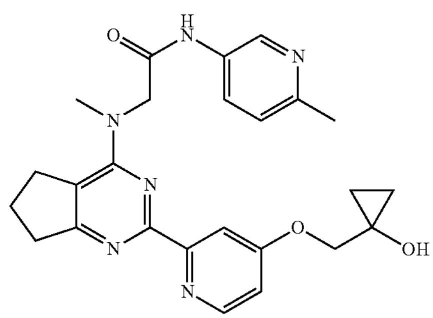 [SMILES: Cc1ccc(NC(=O)CN(C)c2nc(-c3cc(OCC4(O)CC4)ccn3)nc3c2CCC3)cn1] | 2-[(2-{4-[(1-hydroxycyclopropyl)methoxy]pyridin-2-yl}-5H,6H,7H-cyclopenta[d]pyrimidin-4-yl)(methyl)amino]-N-(6-methylpyridin-3-yl)acetamide | 461.2 |
| 331 | 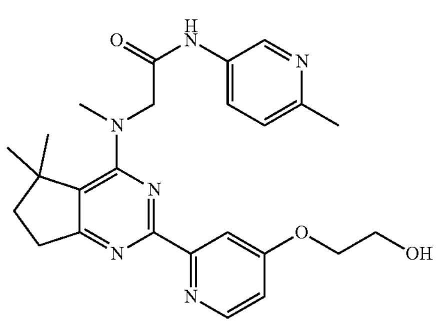 [SMILES: Cc1ccc(NC(=O)CN(C)c2nc(-c3cc(OCCO)ccn3)nc3c2C(C)(C)CC3)cn1] | 2-({2-[4-(2-hydroxyethoxy)pyridin-2-yl]-5,5-dimethyl-5H,6H,7H-cyclopenta[d]pyrimidin-4-yl}(methyl)amino)-N-(6-methylpyridin-3-yl)acetamide | 463.3 |
| 332 | 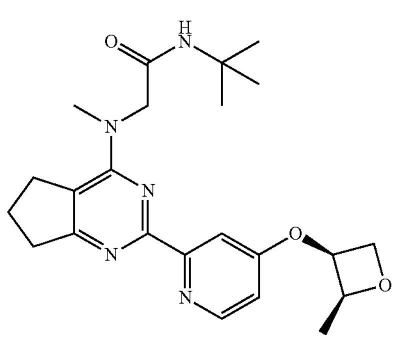 [SMILES: C[C@@H]1OC[C@@H]1Oc1ccnc(-c2nc3c(c(N(C)CC(=O)NC(C)(C)C)n2)CCC3)c1] | N-tert-butyl-2-{methyl[2-(4-{[(2S,3S)-2-methyloxetan-3-yl]oxy}pyridin-2-yl)-5H,6H,7H-cyclopenta[d]pyrimidin-4-yl]amino}acetamide | 426.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 333 | 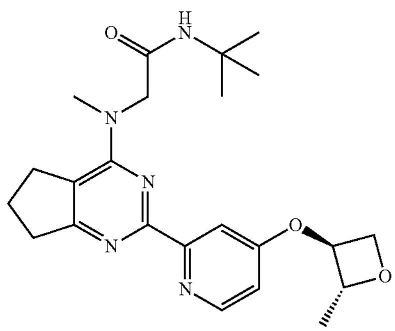 [SMILES: C[C@H]1OC[C@@H]1Oc1ccnc(-c2nc3c(c(N(C)CC(=O)NC(C)(C)C)n2)CCC3)c1] | N-tert-butyl-2-{methyl[2-(4-{[(2R,3S)-2-methyloxetan-3-yl]oxy}pyridin-2-yl)-5H,6H,7H-cyclopenta[d]pyrimidin-4-yl]amino}acetamide | 426.3 |
| 334 | 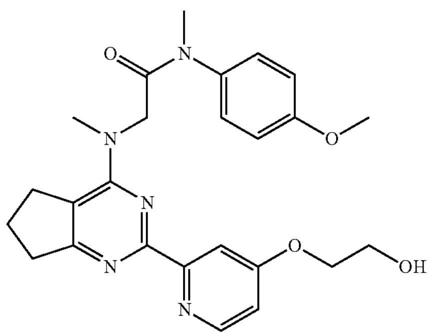 [SMILES: COc1ccc(N(C)C(=O)CN(C)c2nc(-c3cc(OCCO)ccn3)nc3c2CCC3)cc1] | 2-({2-[4-(2-hydroxyethoxy)pyridin-2-yl]-5H,6H,7H-cyclopenta[d]pyrimidin-4-yl}(methyl)amino)-N-(4-methoxyphenyl)-N-methylacetamide | 464.2 |
| 335 | 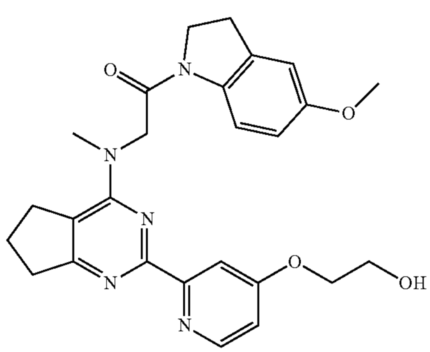 [SMILES: COc1ccc2c(c1)CCN2C(=O)CN(C)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-1-(5-methoxy-2,3-dihydro-1H-indol-1-yl)ethan-1-one | 476.2 |
| 336 | 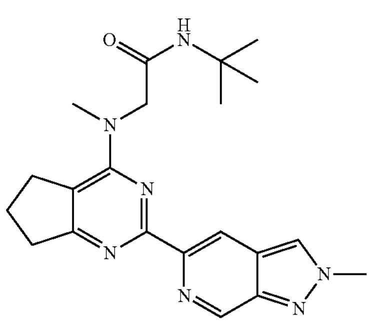 [SMILES: CN(CC(=O)NC(C)(C)C)c1nc(-c2cc3cn(C)nc3cn2)nc2c1CCC2] | N-tert-butyl-2-[methyl(2-{2-methyl-2H-pyrazolo[3,4-c]pyridin-5-yl}-5H,6H,7H-cyclopenta[d]pyrimidin-4-yl)amino]acetamide | 394.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 337 | 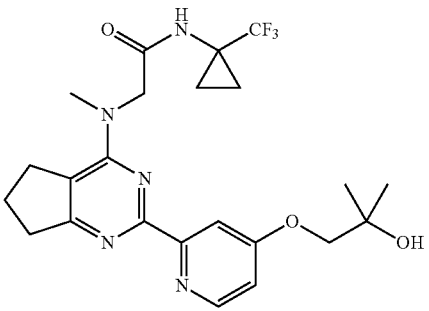 [SMILES: CN(CC(=O)NC1(C(F)(F)F)CC1)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-N-[1-(trifluoromethyl)cyclopropyl]acetamide | 480.2 |
| 338 | 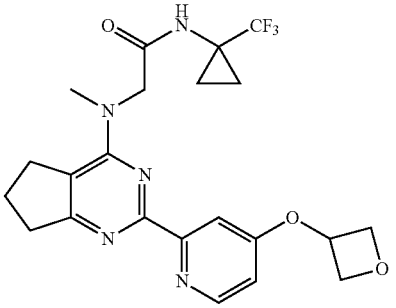 [SMILES: CN(CC(=O)NC1(C(F)(F)F)CC1)c1nc(-c2cc(OC3COC3)ccn2)nc2c1CCC2] | 2-[methyl({2-[4-(oxetan-3-yloxy)pyridin-2-yl]-5H,6H,7H-cyclopenta[d]pyrimidin-4-yl})amino]-N-[1-(trifluoromethyl)cyclopropyl]acetamide | 464.2 |
| 339 | 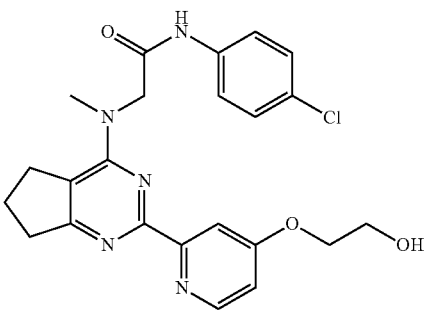 | N-(4-chloropehnyl)-2-({2-[4-(2-hydroxyethoxy)pyridin-2-yl]-5H,6H,7H-cyclopenta[d]pyrimidin-4-yl}(methyl)amino)acetamide | 454.2 |
| 340 | 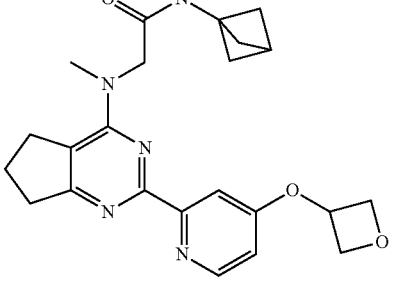 | N-{bicyclo[1.1.1]pentan-1-yl}-2-[methyl({2-[4-(oxetan-3-yloxy)pyridin-2-yl]-5H,6H,7H-cyclopenta[d]pyrimidin-4-yl})amino]acetamide | 422.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 341 | 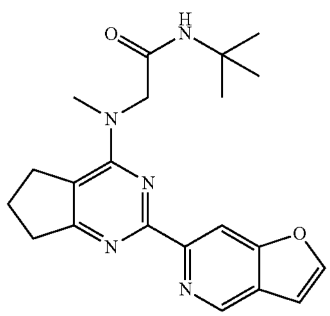 [SMILES: CN(CC(=O)NC(C)(C)C)c1nc(-c2cc3occc3cn2)nc2c1CCC2] | N-tert-butyl-2-[(2-{furo[3,2-c]pyridin-6-yl}-5H,6H,7H-cyclopenta[d]pyrimidin-4-yl)(methyl)amino]acetamide | 380.2 |
| 342 | 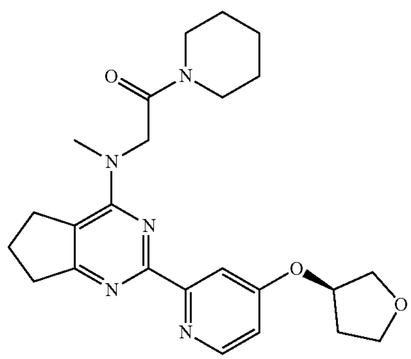 [SMILES: CN(CC(=O)N1CCCCC1)c1nc(-c2cc(O[C@@H]3CCOC3)ccn2)nc2c1CCC2] | 2-[methyl(2-{4-[(3R)-oxolan-3-yloxy]pyridin-2-yl}-5H,6H,7H-cyclopenta[d]pyrimidin-4-yl)amino]-1-(piperidin-1-yl)ethan-1-one | 438.3 |
| 343 | 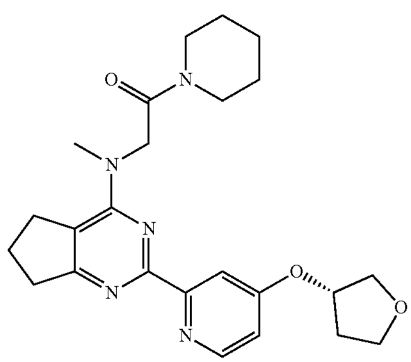 [SMILES: CN(CC(=O)N1CCCCC1)c1nc(-c2cc(O[C@H]3CCOC3)ccn2)nc2c1CCC2] | 2-[methyl(2-{4-[(3S)-oxolan-3-yloxy]pyridin-2-yl}-5H,6H,7H-cyclopenta[d]pyrimidin-4-yl)amino]-1-(piperidin-1-yl)ethan-1-one | 438.3 |
| 344 | 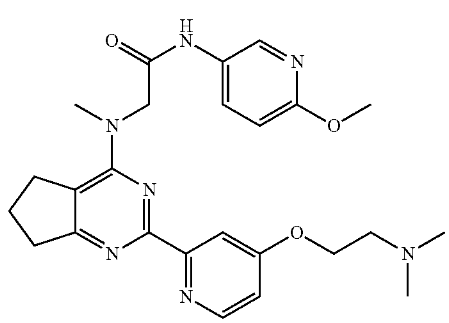 [SMILES: COc1ccc(NC(=O)CN(C)c2nc(-c3cc(OCCN(C)C)ccn3)nc3c2CCC3)cn1] | 2-[(2-{4-[2-(dimethylamino)ethoxy]pyridin-2-yl}-5H,6H,7H-cyclopenta[d]pyrimidin-4-yl)(methyl)amino]-N-(6-methoxypyridin-3-yl)acetamide | 478.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 345 | 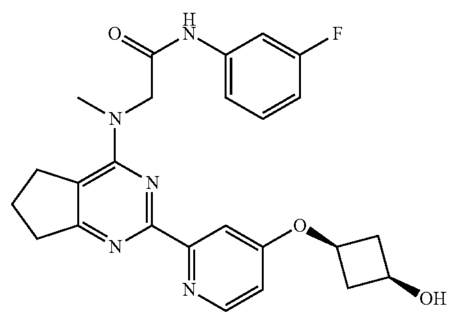 [SMILES: CN(CC(=O)Nc1cccc(F)c1)c1nc(-c2cc(O[C@H]3C[C@@H](O)C3)ccn2)nc2c1CCC2] | N-(3-fluorophenyl)-2-[methyl(2-{4-[(1s,3s)-3-hydroxycyclobutoxy]pyridin-2-yl}-5H,6H,7H-cyclopenta[d]pyrimidin-4-yl)amino]acetamide | 464.2 |
| 346 | 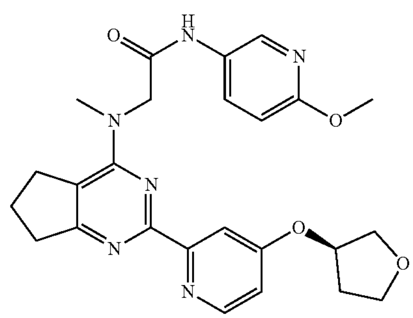 | N-(6-methoxypyridin-3-yl)-2-[methyl(2-{4-[(3R)-oxolan-3-yloxy]pyridin-2-yl}-5H,6H,7H-cyclopenta[d]pyrimidin-4-yl)amino]acetamide | 477.2 |
| 347 | 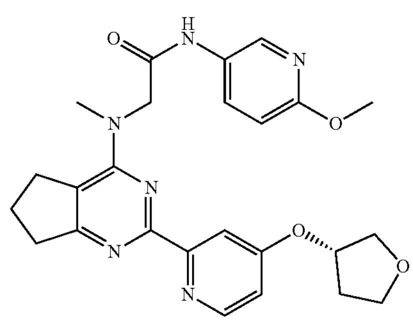 [SMILES: COc1ccc(NC(=O)CN(C)c2nc(-c3cc(O[C@H]4CCOC4)ccn3)nc3c2CCC3)cn1] | N-(6-methoxypyridin-3-yl)-2-[methyl(2-{4-[(3S)-oxolan-3-yloxy]pyridin-2-yl}-5H,6H,7H-cyclopenta[d]pyrimidin-4-ylamino]acetamide | 477.3 |
| 348 | 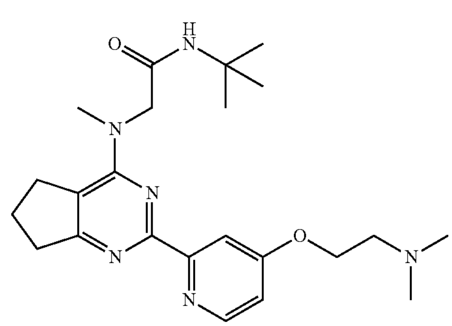 | N-tert-butyl-2-[(2-{4-[2-(dimethylamino)ethoxy]pyridin-2-yl}-5H,6H,7H-cyclopenta[d]pyrimidin-4-yl)(methyl)amino]acetamide | 427.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 349 | 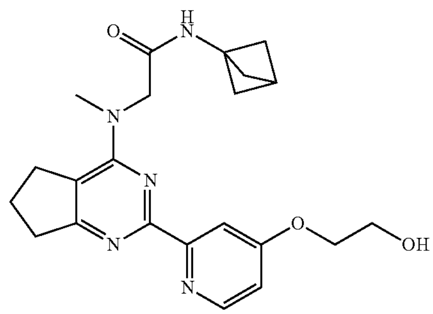 [SMILES: CN(CC(=O)NC12CC(C1)C2)c1nc(-c2cc(OCCO)ccn2)nc2c1CCC2] | N-{bicyclo[1.1.1]pentan-1-yl}-2-({2-[4-(2-hydroxyethoxy)pyridin-2-yl]-5H,6H,7H-cyclopenta[d]pyrimidin-4-yl}(methyl)amino)acetamide | 410.3 |
| 350 | 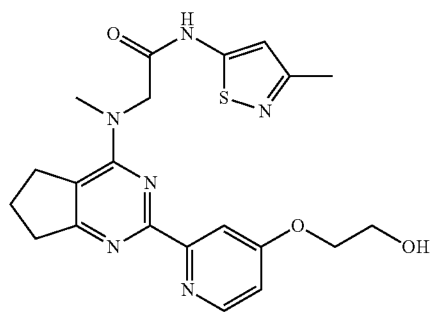 [SMILES: Cc1cc(NC(=O)CN(C)c2nc(-c3cc(OCCO)ccn3)nc3c2CCC3)sn1] | 2-({2-[4-(2-hydroxyethoxy)pyridin-2-yl]-5H,6H,7H-cyclopenta[d]pyrimidin-4-yl}(methyl)amino)-N-(3-methyl-1,2-thiaozl-5-yl)acetamide | 441.2 |
| 351 | 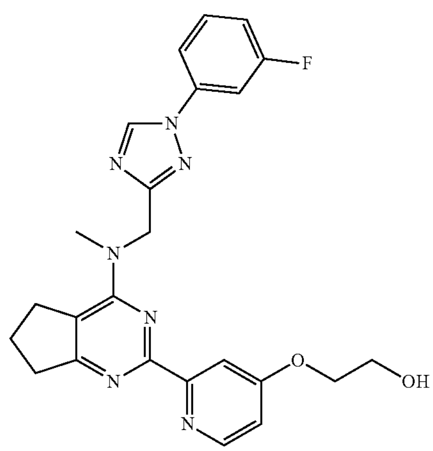 [SMILES: CN(Cc1ncn(-c2cccc(F)c2)n1)c1nc(-c2cc(OCCO)ccn2)nc2c1CCC2] | 2-({2-[4-({[1-(3-fluorophenyl)-1H-1,2,4-triazol-3-yl]methyl}(methyl)amino)-5H,6H,7H-cyclopenta[d]pyrimidin-2-yl]pyridin-4-yl}oxy)ethan-1-ol | 462.3 |
| 352 | 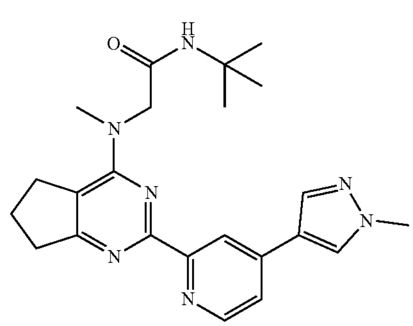 [SMILES: CN(CC(=O)NC(C)(C)C)c1nc(-c2cc(-c3cnn(C)c3)ccn2)nc2c1CCC2] | N-tert-butyl-2-[methyl({2-[4-(1-methyl-1H-pyrazol-4-yl)pyridin-2-yl]-5H,6H,7H-cyclopenta[d]pyrimidin-4-yl})amino]acetamide | 420.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 353 | 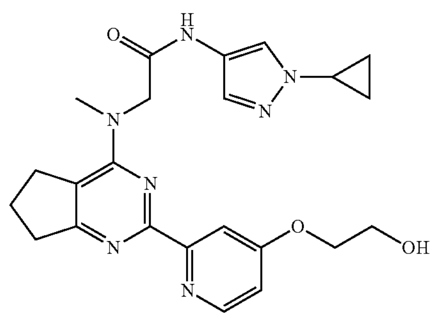 [SMILES: CN(CC(=O)Nc1cnn(C2CC2)c1)c1nc(-c2cc(OCCO)ccn2)nc2c1CCC2] | N-(1-cyclopropyl-1H-pyrazol-4-yl)-2-({2-[4-(2-hydroxyethoxy)pyridin-2-yl]-5H,6H,7H-cyclopenta[d]pyrimidin-4-yl}(methyl)amino)acetamide | 450.2 |
| 354 | 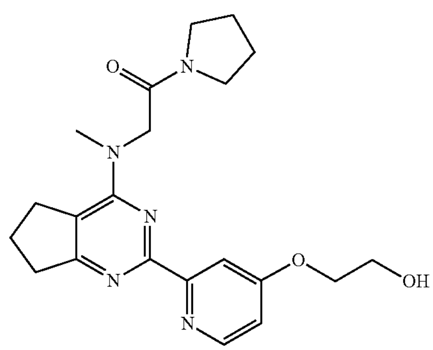 [SMILES: CN(CC(=O)N1CCCC1)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-1-(pyrrolidin-1-yl)ethan-1-one | 398.2 |
| 355 | 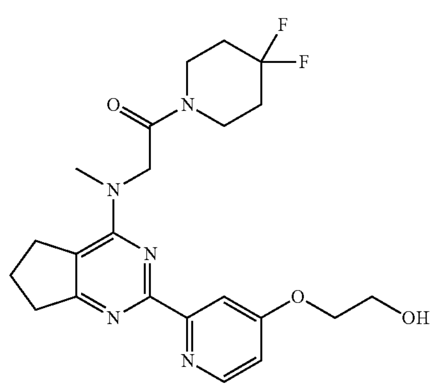 [SMILES: CN(CC(=O)N1CCC(F)(F)CC1)c1nc(-c2cc(OCCO)ccn2)nc2c1CCC2] | 1-(4,4-difluoropiperidin-1-yl)-2-({2-[4-(2-hydroxyethoxy)pyridin-2-yl]-5H,6H,7H-cyclopenta[d]pyrimidin-4-yl}(methyl)amino)ethan-1-one | 448.3 |
| 356 | 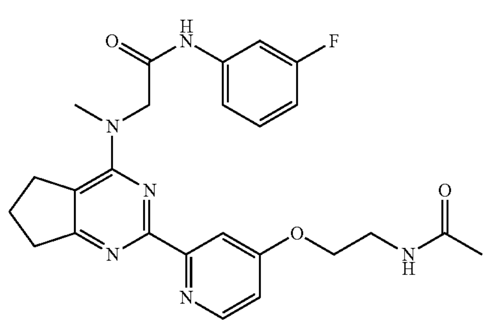 [SMILES: CC(=O)NCCOc1ccnc(-c2nc3c(c(N(C)CC(=O)Nc4cccc(F)c4)n2)CCC3)c1] | 2-({2-[4-(2-acetamidoethoxy)pyridin-2-yl]-5H,6H,7H-cyclopenta[d]pyrimidin-4-yl}(methyl)amino)-N-(3-fluorophenyl)acetamide | 479.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 357 | 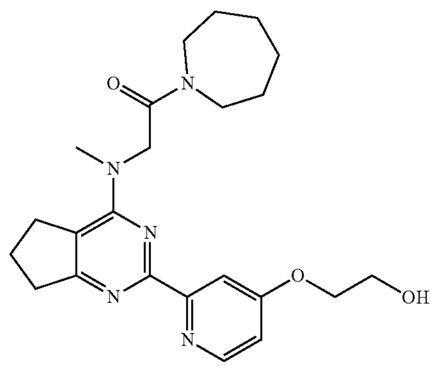 [SMILES: CN(CC(=O)N1CCCCCC1)c1nc(-c2cc(OCCO)ccn2)nc2c1CCC2] | 1-(azepan-1-yl)-2-({2-[4-(2-hydroxyethoxy)pyridin-2-yl]-5H,6H,7H-cyclopenta[d]pyrimidin-4-yl}(methyl)amino)ethan-1-one | 426.3 |
| 358 | 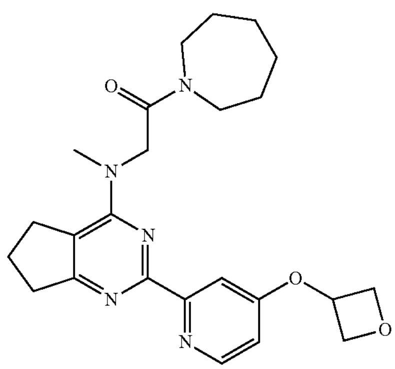 [SMILES: CN(CC(=O)N1CCCCCC1)c1nc(-c2cc(OC3COC3)ccn2)nc2c1CCC2] | 1-(azepan-1-yl)-2-[methyl({2-[4-(oxetan-3-yloxy)pyridin-2-yl]-5H,6H,7H-cyclopenta[d]pyrimidin-4-yl})amino]ethan-1-one | 438.3 |
| 359 | 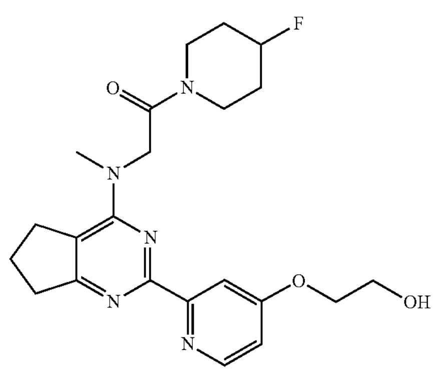 [SMILES: CN(CC(=O)N1CCC(F)CC1)c1nc(-c2cc(OCCO)ccn2)nc2c1CCC2] | 1-(4-fluoropiperidin-1-yl)-2-({2-[4-(2-hydroxyethoxy)pyridin-2-yl]-5H,6H,7H-cyclopenta[d]pyrimidin-4-yl}(methyl)amino)ethan-1-one | 430.2 |
| 360 | 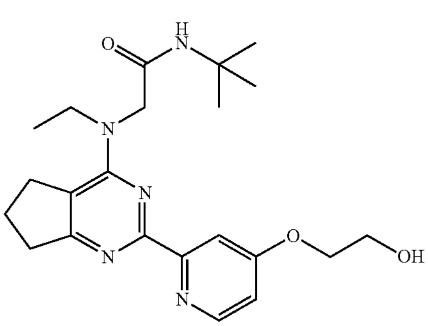 [SMILES: CCN(CC(=O)NC(C)(C)C)c1nc(-c2cc(OCCO)ccn2)nc2c1CCC2] | N-tert-butyl-2-[ethyl({2-[4-(2-hydroxyethoxy)pyridin-2-yl]-5H,6H,7H-cyclopenta[d]pyrimidin-4-yl})amino]acetamide | 414.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 361 | 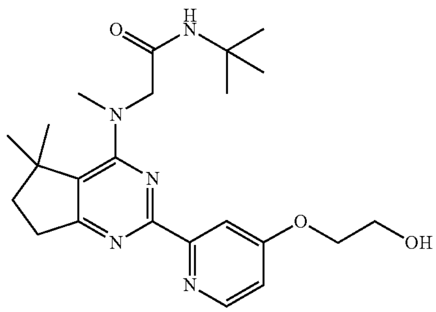 [SMILES: CN(CC(=O)NC(C)(C)C)c1nc(-c2cc(OCCO)ccn2)nc2c1C(C)(C)CC2] | N-tert-butyl-2-({2-[4-(2-hydroxyethoxy)pyridin-2-yl]-5,5-dimethyl-5H,6H,7H-cyclopenta[d]pyrimidin-4-yl}(methyl)amino)acetamide | 428.3 |
| 362 | 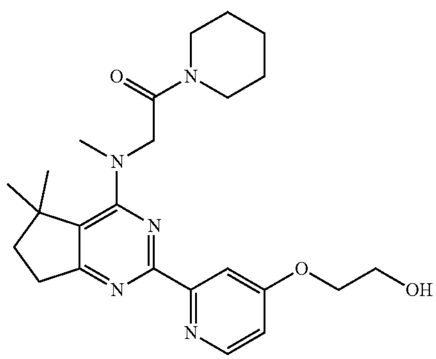 [SMILES: CN(CC(=O)N1CCCCC1)c1nc(-c2cc(OCCO)ccn2)nc2c1C(C)(C)CC2] | 2-({2-[4-(2-hydroxyethoxy)pyridin-2-yl]-5,5-dimethyl-5H,6H,7H-cyclopenta[d]pyrimidin-4-yl}(methyl)amino)-1-(piperidin-1-yl)ethan-1-one | 440.3 |
| 363 | 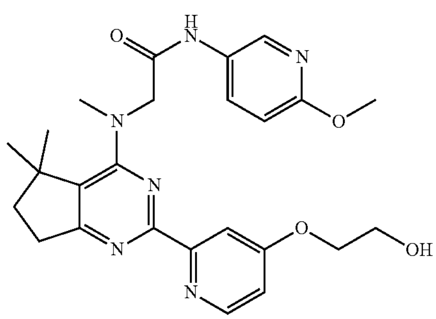 [SMILES: COc1ccc(NC(=O)CN(C)c2nc(-c3cc(OCCO)ccn3)nc3c2C(C)(C)CC3)cn1] | 2-({2-[4-(2-hydroxyethoxy)pyridin-2-yl]-5,5-dimethyl-5H,6H,7H-cyclopenta[d]pyrimidin-4-yl}(methyl)amino)-N-(6-methoxypyridin-3-yl)acetamide | 479.3 |
| 364 | 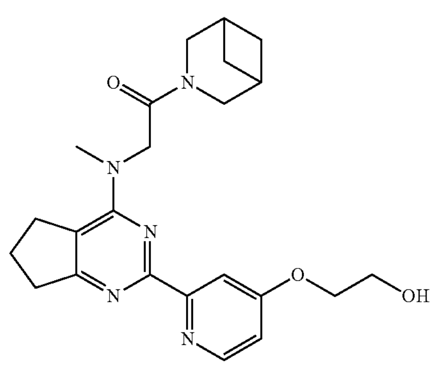 [SMILES: CN(CC(=O)N1CC2CC(C2)C1)c1nc(-c2cc(OCCO)ccn2)nc2c1CCC2] | 1-{3-azabicyclo[3.1.1]heptan-3-yl}-2-({2-[4-(2-hydroxyethoxy)pyridin-2-yl]-5H,6H,7H-cyclopenta[d]pyrimidin-4-yl}(methyl)amino)ethan-1-one | 424.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 365 | 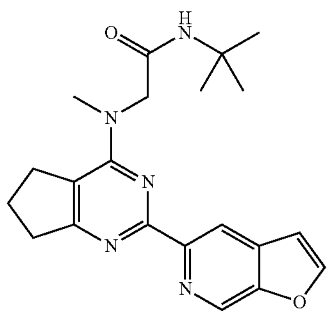 [SMILES: CN(CC(=O)NC(C)(C)C)c1nc(-c2cc3ccoc3cn2)nc2c1CCC2] | N-tert-butyl-2-[(2-{furo[2,3-c]pyridin-5-yl}-5H,6H,7H-cyclopenta[d]pyrimidin-4-yl)(methyl)amino]acetamide | 380.3 |
| 366 | 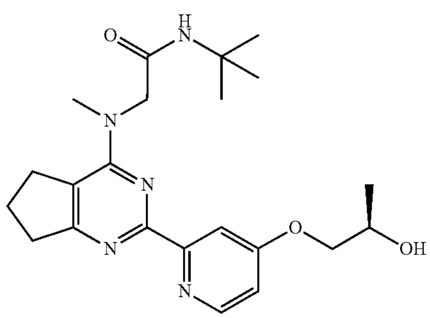 [SMILES: C[C@@H](O)COc1ccnc(-c2nc3c(c(N(C)CC(=O)NC(C)(C)C)n2)CCC3)c1] | N-tert-butyl-2-[(2-{4-[(2R)-2-hydroxypropoxy]pyridin-2-yl}-5H,6H,7H-cyclopenta[d]pyrimidin-4-yl)(methyl)amino]acetamide | 414.3 |
| 367 | 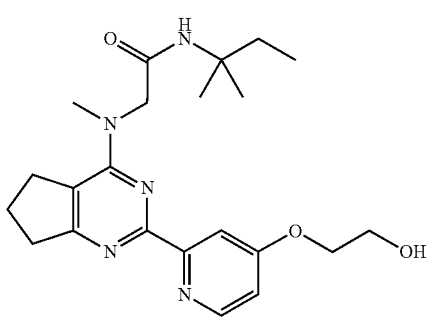 [SMILES: CCC(C)(C)NC(=O)CN(C)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-N-(2-methylbutan-2-yl)acetamide | 414.3 |
| 368 | 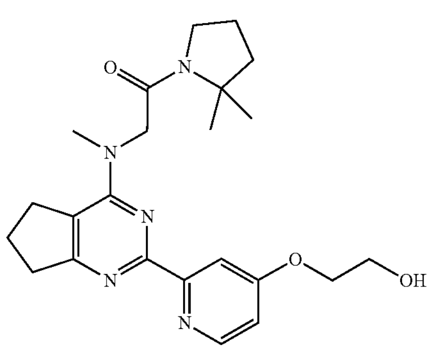 [SMILES: CN(CC(=O)N1CCCC1(C)C)c1nc(-c2cc(OCCO)ccn2)nc2c1CCC2] | 1-(2,2-dimethylpyrrolidin1--yl)-2-({2-[4-(2-hydroxyethoxy)pyridin-2-yl]-5H,6H,7H-cyclopenta[d]pyrimidin-4-yl}(methyl)amino)ethan-1-one | 426.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 369 | 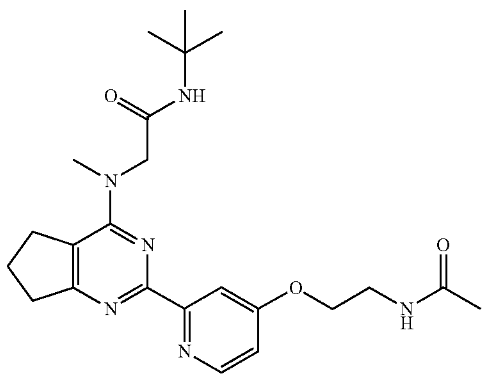 [SMILES: CC(=O)NCCOc1ccnc(-c2nc3c(c(N(C)CC(=O)NC(C)(C)C)n2)CCC3)c1] | N-tert-butyl-2-({2-[4-(2-acetamidoethoxy)pyridin-2-yl]-5H,6H,7H-cyclopenta[d]pyrimidin-4-yl}(methyl)amino)acetamide | 441.3 |
| 370 | 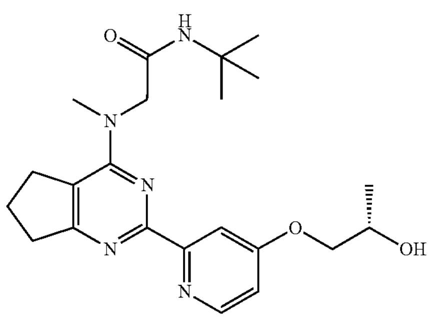 [SMILES: C[C@H](O)COc1ccnc(-c2nc3c(c(N(C)CC(=O)NC(C)(C)C)n2)CCC3)c1] | N-tert-butyl-2-[(2-{4-[(2S)-2-hydroxypropoxy]pyridin-2-yl}-5H,6H,7H-cyclopenta[d]pyrimidin-4-yl)(methyl)amino]acetamide | 414.3 |
| 371 | 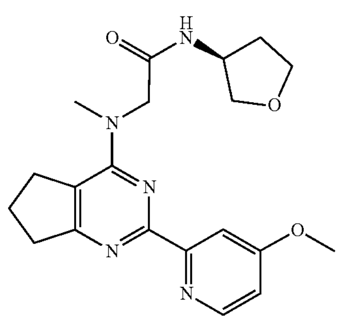 [SMILES: COc1ccnc(-c2nc3c(c(N(C)CC(=O)N[C@H]4CCOC4)n2)CCC3)c1] | 2-{[2-(4-methoxypyridin-2-yl)-5H,6H,7H-cyclopenta[d]pyrimidin-4-yl](methyl)amino}-N-[(3S)-oxolan-3-yl]acetamide | 384.2 |
| 372 | 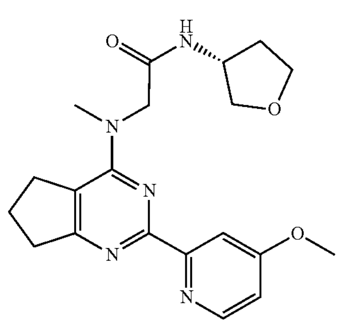 [SMILES: COc1ccnc(-c2nc3c(c(N(C)CC(=O)N[C@@H]4CCOC4)n2)CCC3)c1] | 2-{[2-(4-methoxypyridin-2-yl)-5H,6H,7H-cyclopenta[d]pyrimidin-4-yl](mehtyl)amino}-N-[(3R)-oxolan-3-yl]acetamide | 384.2 |

TABLE 1-continued

Where the mass for a compound is not provided in Table 1, the mass can be found for the compound in the synthetic examples.

| Compound No. | Structure | IUPAC Name | Mass Found (M + 1) |
| --- | --- | --- | --- |
| 373 | 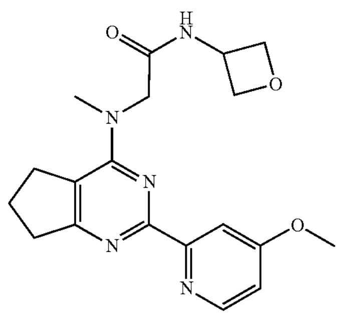 [SMILES: COc1ccnc(-c2nc3c(c(N(C)CC(=O)NC4COC4)n2)CCC3)c1] | 2-{[2-(4-methoxypyridin-2-yl)-5H,6H,7H-cyclopenta[d]pyrimidin-4-yl](methyl)amino}-N-(oxetan-3-yl)acetamide | 370.2 |
| 374 | 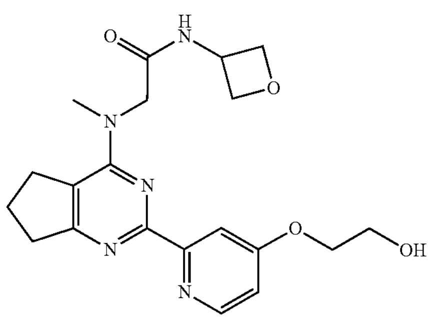 [SMILES: CN(CC(=O)NC1COC1)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-N-(oxetan-3-yl)acetamide | 400.2 |
| 375 | 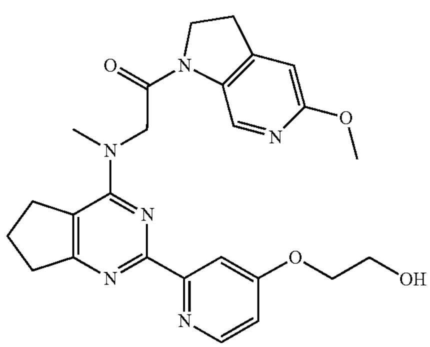 [SMILES: COc1cc2c(cn1)N(C(=O)CN(C)c1nc(-c3cc(OCCO)ccn3)nc3c1CCC3)CC2] | 2-({2-[4-(2-hydroxyethoxy)pyridin-2-yl]-5H,6H,7H-cyclopenta[d]pyrimidin-4-yl}(methyl)amino)-1-{5-methoxy-1H,2H,3H-pyrrolo[2,3-c]pyridin-1-yl}ethan-1-one | 477.2 |
| 376 | 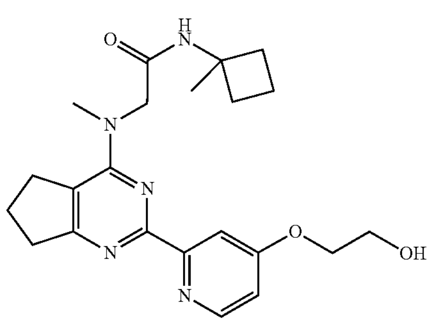 [SMILES: CN(CC(=O)NC1(C)CCC1)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-N-(1-methylcyclobutyl)acetamide | 412.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 377 | 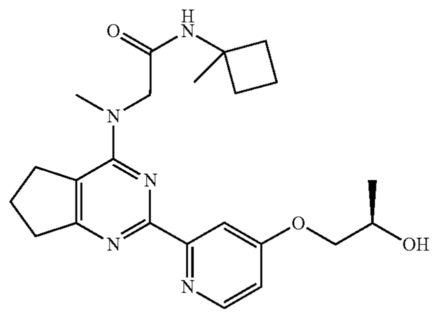 [SMILES: C[C@@H](O)COc1ccnc(-c2nc3c(c(N(C)CC(=O)NC4(C)CCC4)n2)CCC3)c1] | 2-[(2-{4-[(2R)-2-hydroxypropoxy]pyridin-2-yl}-5H,6H,7H-cyclopenta[d]pyrimidin-4-yl)(methyl)amino]-N-(1-methylcyclobutyl)acetamide | 426.3 |
| 378 | 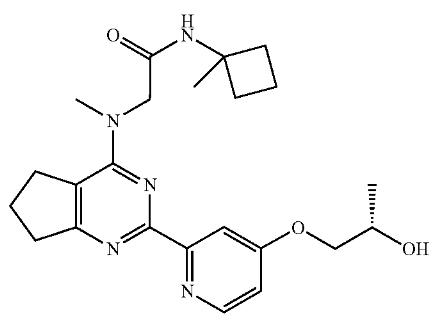 [SMILES: C[C@H](O)COc1ccnc(-c2nc3c(c(N(C)CC(=O)NC4(C)CCC4)n2)CCC3)c1] | 2-[(2-{4-[(2S)-2-hydroxypropoxy]pyridin-2-yl}-5H,6H,7H-cyclopenta[d]pyrimidin-4-yl)(methyl)amino]-N-(1-methylcyclobutyl)acetamide | 426.3 |
| 379 | 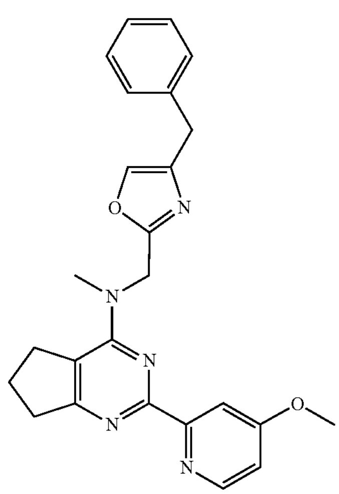 [SMILES: COc1ccnc(-c2nc3c(c(N(C)Cc4nc(Cc5ccccc5)co4)n2)CCC3)c1] | N-[(4-benzyl-1,3-oxazol-2-yl)methyl]-2-(4-methoxypyridin-2-yl)-N-methyl-5H,6H,7H-cyclopenta[d]pyrimidin-4-amine | 428.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 380 | 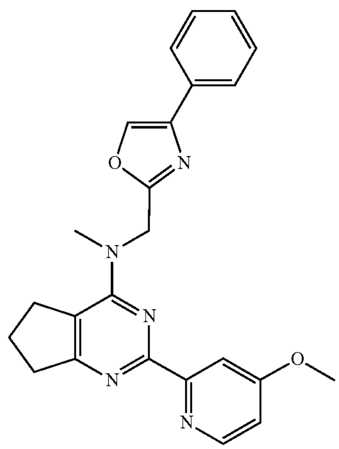 [SMILES: COc1ccnc(-c2nc3c(c(N(C)Cc4nc(-c5ccccc5)co4)n2)CCC3)c1] | 2-(4-methoxypyridin-2-yl)-N-methyl-N-[(4-phenyl-1,3-oxazol-2-yl)methyl]-5H,6H,7H-cyclopenta[d]pyrimidin-4-amine | 414.2 |
| 381 | 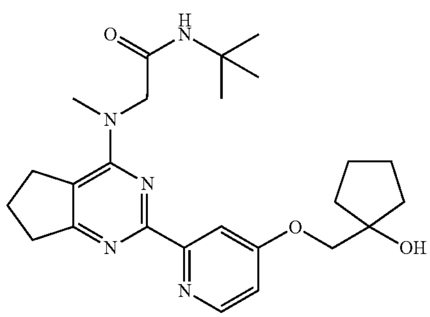 [SMILES: CN(CC(=O)NC(C)(C)C)c1nc(-c2cc(OCC3(O)CCCC3)ccn2)nc2c1CCC2] | N-tert-butyl-2-[(2-{4-[(1-hydroxycyclopentyl)methoxy]pyridin-2-yl}-5H,6H,7H-cyclopenta[d]pyrimidin-4-yl)(methyl)amino]acetamide | 454.3 |
| 382 | 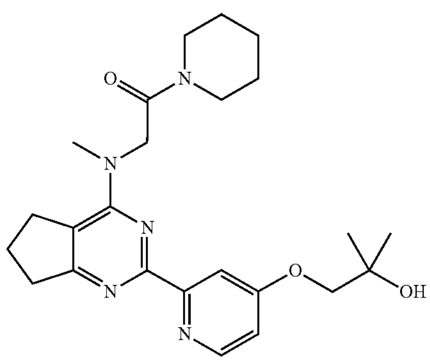 [SMILES: CN(CC(=O)N1CCCCC1)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-1-(piperidin-1-yl)ethan-1-one | 440.3 |
| 383 | 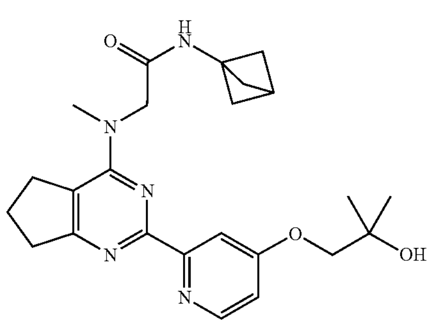 [SMILES: CN(CC(=O)NC12CC(C1)C2)c1nc(-c2cc(OCC(C)(C)O)ccn2)nc2c1CCC2] | N-{bicyclo[1.1.1]pentan-1-yl}-2-({2-[4-(2-hydroxy-2-methylpropoxy)pyridin-2-yl]-5H,6H,7H-cyclopenta[d]pyrimidin-4-yl}(methyl)amino)acetamide | 438.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 384 | 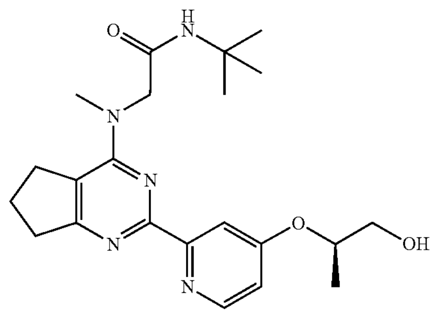 [SMILES: C[C@H](CO)Oc1ccnc(-c2nc3c(c(N(C)CC(=O)NC(C)(C)C)n2)CCC3)c1] | N-tert-butyl-2-{[2-(4-{[(2R)-1-hydroxypropan-2-yl]oxy}pyridin-2-yl)-5H,6H,7H-cyclopenta[d]pyrimidin-4-yl](methyl)amino}acetamide | 414.3 |
| 385 | 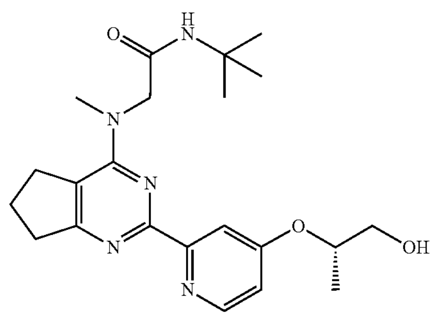 [SMILES: C[C@@H](CO)Oc1ccnc(-c2nc3c(c(N(C)CC(=O)NC(C)(C)C)n2)CCC3)c1] | N-tert-butyl-2-{[2-(4-{[(2S)-1-hydroxypropan-2-yl]oxy}pyridin-2-yl)-5H,6H,7H-cyclopenta[d]pyrimidin-4-yl](methyl)amino}acetamide | 414.3 |
| 386 | 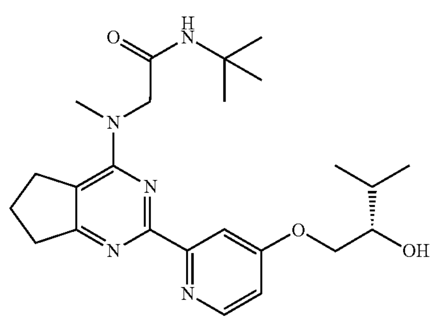 [SMILES: CC(C)[C@H](O)COc1ccnc(-c2nc3c(c(N(C)CC(=O)NC(C)(C)C)n2)CCC3)c1] | N-tert-butyl-2-[(2-{4-[(2S)-2-hydroxy-3-methylbutoxy]pyridin-2-yl}-5H,6H,7H-cyclopenta[d]pyrimidin-4-yl)(methyl)amino]acetamide | 442.3 |
| 387 | 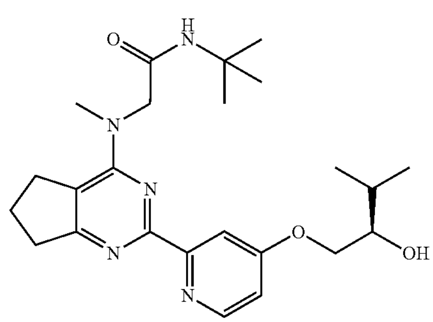 [SMILES: CC(C)[C@@H](O)COc1ccnc(-c2nc3c(c(N(C)CC(=O)NC(C)(C)C)n2)CCC3)c1] | N-tert-butyl-2-[(2-{4-[(2R)-2-hydroxy-3-methylbutoxy]pyridin-2-yl}-5H,6H,7H-cyclopenta[d]pyrimidin-4-yl)(methyl)amino]acetamide | 442.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 388 | 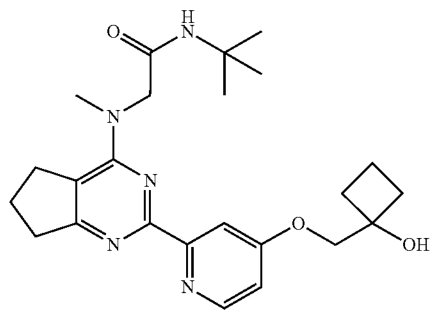 [SMILES: CN(CC(=O)NC(C)(C)C)c1nc(-c2cc(OCC3(O)CCC3)ccn2)nc2c1CCC2] | N-tert-butyl-2-[(2-{4-[(1-hydroxycyclobutyl)methoxy]pyridin-2-yl}-5H,6H,7H-cyclopenta[d]pyrimidin-4-yl)(methyl)amino]acetamide | 440.3 |
| 389 | 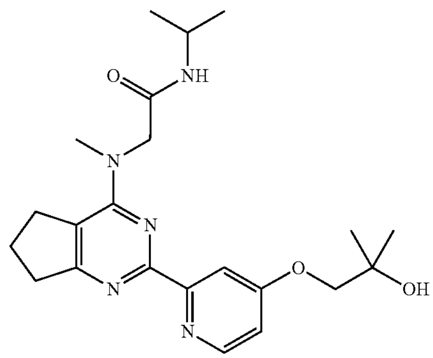 [SMILES: CC(C)NC(=O)CN(C)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-N-(propan-2-yl)acetamide | 414.3 |
| 390 | 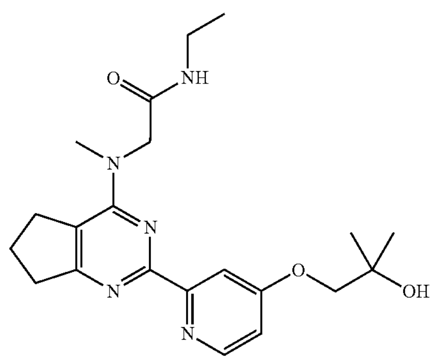 [SMILES: CCNC(=O)CN(C)c1nc(-c2cc(OCC(C)(C)O)ccn2)nc2c1CCC2] | N-ethyl-2-({2-[4-(2-hydroxy-2-methylpropoxy)pyridin-2-yl]-5H,6H,7H-cyclopenta[d]pyrimidin-4-yl}(methyl)amino)acetamide | 400.2 |
| 391 | 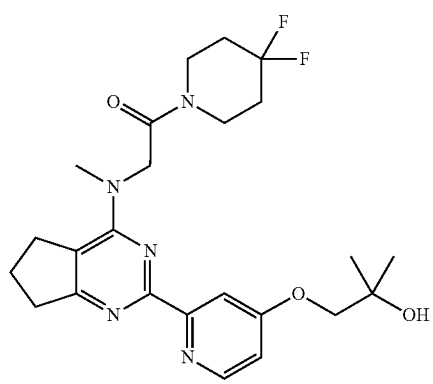 [SMILES: CN(CC(=O)N1CCC(F)(F)CC1)c1nc(-c2cc(OCC(C)(C)O)ccn2)nc2c1CCC2] | 1-(4,4-difluoropiperidin-1-yl)-2-({2-[4-(2-hydroxy-2-methylproopoxy)pyridin-2-yl]-5H,6H,7H-cyclopenta[d]pyrimidin-4-yl}(methyl)amino)ethan-1-one | 476.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 392 | 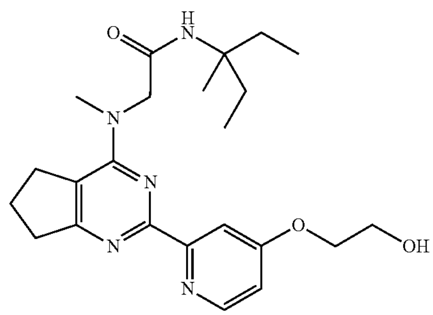 [SMILES: CCC(C)(CC)NC(=O)CN(C)c1nc(-c2cc(OCCO)ccn2)nc2c1CCC2] | 2-({2-[4-(2-hydroxyethoxy)pyridin-2-yl]-5H,6H,7H-cyclopenta[d]pyrimidin-4-yl}(methyl)amino)-N-(3-methylpentan-3-yl)acetamide | 428.3 |
| 393 | 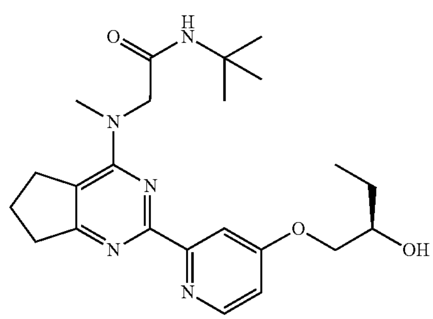 [SMILES: CC[C@@H](O)COc1ccnc(-c2nc3c(c(N(C)CC(=O)NC(C)(C)C)n2)CCC3)c1] | N-tert-butyl-2-[(2-{4-[(2R)-2-hydroxybutoxy]pyridin-2-yl}-5H,6H,7H-cyclopenta[d]pyrimidin-4-yl)(methyl)amino]acetamide | 428.3 |
| 394 | 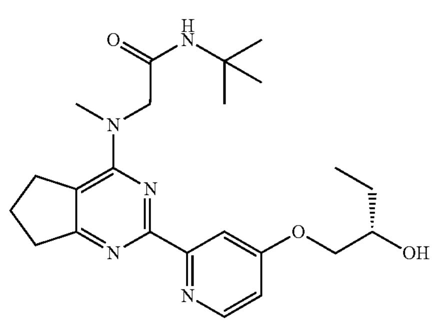 [SMILES: CC[C@H](O)COc1ccnc(-c2nc3c(c(N(C)CC(=O)NC(C)(C)C)n2)CCC3)c1] | N-tert-butyl-2-[(2-{4-[(2S)-2-hydroxybutoxy]pyridin-2-yl}-5H,6H,7H-cyclopenta[d]pyrimidin-4-yl)(methyl)amino]acetamide | 428.3 |
| 395 | 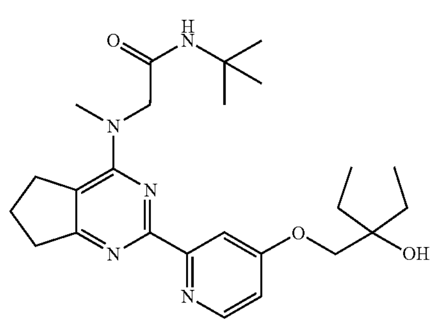 [SMILES: CCC(O)(CC)COc1ccnc(-c2nc3c(c(N(C)CC(=O)NC(C)(C)C)n2)CCC3)c1] | N-tert-butyl-2-({2-[4-(2-ethyl-2-hydroxybutoxy)pyridin-2-yl]-5H,6H,7H-cyclopenta[d]pyrimidin-4-yl}(methyl)amino)acetamide | 456.3 |

| Compound No. | Structure | IUPAC Name | Mass Found (M + 1) |
|---|---|---|---|
| 396 | 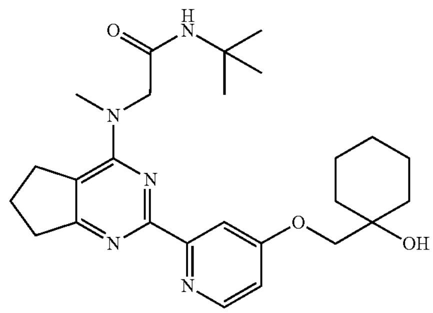 [SMILES: CN(CC(=O)NC(C)(C)C)c1nc(-c2cc(OCC3(O)CCCCC3)ccn2)nc2c1CCC2] | N-tert-butyl-2-[(2-{4-[(1-hydroxycyclohexyl)methoxy]pyridin-2-yl}-5H,6H,7H-cyclopenta[d]pyrimidin-4-yl)(methyl)amino]acetamide | 468.3 |
| 397 | 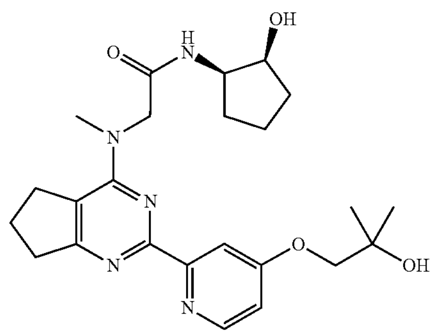 [SMILES: CN(CC(=O)N[C@@H]1CCC[C@@H]1O)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-N-[(1R,2S)-2-hydroxycyclopentyl]acetamide | 456.3 |
| 398 | 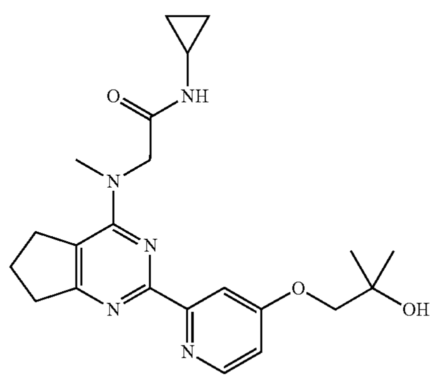 [SMILES: CN(CC(=O)NC1CC1)c1nc(-c2cc(OCC(C)(C)O)ccn2)nc2c1CCC2] | N-cyclopropyl-2-({2-[4-(2-hydroxy-2-methylpropoxy)pyridin-2-yl]-5H,6H,7H-cyclopenta[d]pyrimidin-4-yl}(methyl)amino)acetamide | 412.3 |
| 399 | 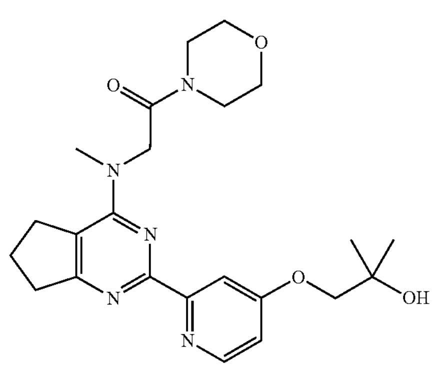 [SMILES: CN(CC(=O)N1CCOCC1)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-1-(morpholin-4-yl)ethan-1-one | 442.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 400 | 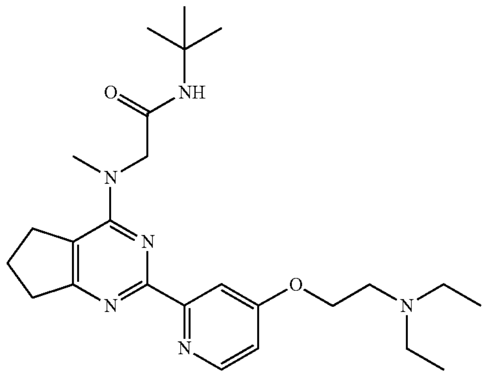 [SMILES: CCN(CC)CCOc1ccnc(-c2nc3c(c(N(C)CC(=O)NC(C)(C)C)n2)CCC3)c1] | N-tert-butyl-2-[(2-{4-[2-(diethylamino)ethoxy]pyridin-2-yl}-5H,6H,7H-cyclopenta[d]pyrimidin-4-yl)(methyl)amino]acetamide | 455.4 |
| 401 | 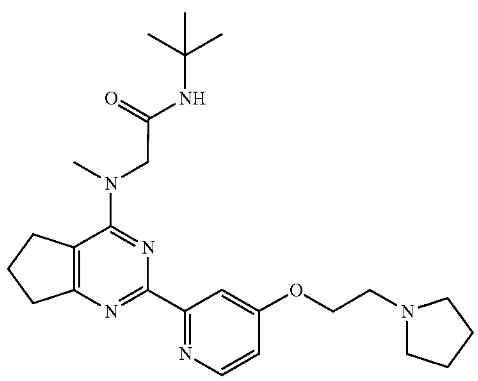 [SMILES: CN(CC(=O)NC(C)(C)C)c1nc(-c2cc(OCCN3CCCC3)ccn2)nc2c1CCC2] | N-tert-butyl-2-[methyl(2-{4-[2-(pyrrolidin-1-yl)ethoxy]pyridin-2-yl}-5H,6H,7H-cyclopenta[d]pyrimidin-4-yl)amino]acetamide | 453.4 |
| 402 | 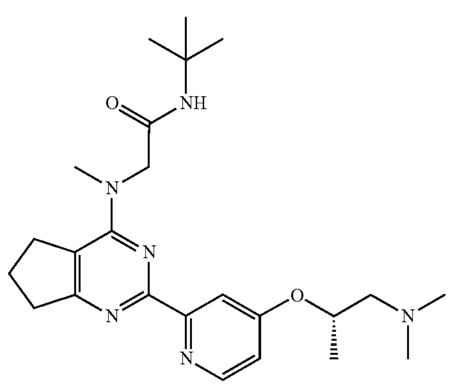 [SMILES: C[C@@H](CN(C)C)Oc1ccnc(-c2nc3c(c(N(C)CC(=O)NC(C)(C)C)n2)CCC3)c1] | N-tert-butyl-2-{[2-(4-{[(2S)-1-(dimethylamino)propan-2-yl]oxy}pyridin-2-yl)-5H,6H,7H-cyclopenta[d]pyrimidin-4-yl](methyl)amino}acetamide | 441.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 403 | 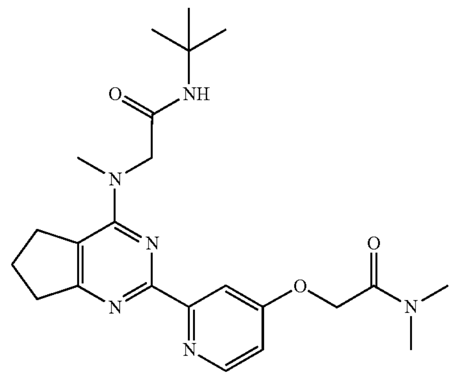 [SMILES: CN(C)C(=O)COc1ccnc(-c2nc3c(c(N(C)CC(=O)NC(C)(C)C)n2)CCC3)c1] | 2-{[2-(4-{[(tert-butylcarbamoyl)methyl](methyl)amino}-5H,6H,7H-cyclopenta[d]pyrimidin-2-yl)pyridin-4-yl]oxy}-N,N-dimethylacetamide | 441.3 |
| 404 | 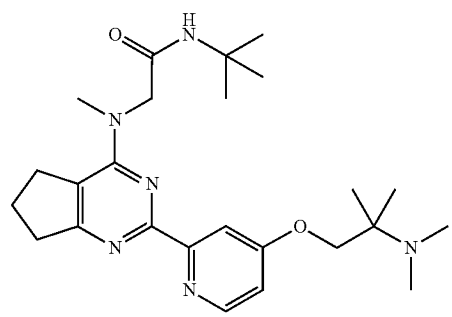 [SMILES: CN(CC(=O)NC(C)(C)C)c1nc(-c2cc(OCC(C)(C)N(C)C)ccn2)nc2c1CCC2] | N-tert-butyl-2-[(2-{4-[2-(dimethylamino)-2-methylpropoxy]pyridin-2-yl}-5H,6H,7H-cyclopenta[d]pyrimidin-4-yl)(methyl)amino]acetamide | 455.4 |
| 405 | 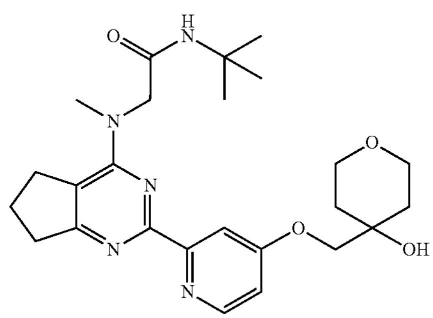 | N-tert-butyl-2-[(2-{4-[(4-hydroxyoxan-4-yl)methoxy]pyridin-2-yl}-5H,6H,7H-cyclopenta[d]pyrimidin-4-yl)(methyl)amino]acetamide | 470.3 |
| 406 | 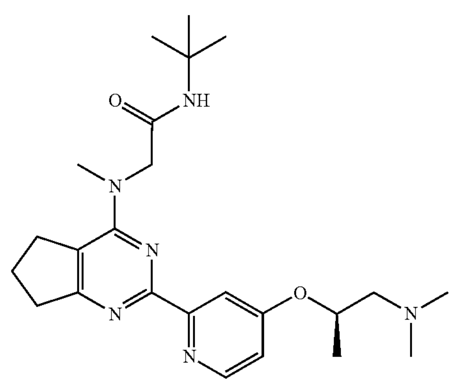 [SMILES: C[C@H](CN(C)C)Oc1ccnc(-c2nc3c(c(N(C)CC(=O)NC(C)(C)C)n2)CCC3)c1] | N-tert-butyl-2-{[2-(4-{[(2R)-1-(dimethylamino)propan-2-yl]oxy}pyridin-2-yl)-5H,6H,7H-cyclopenta[d]pyrimidin-4-yl](methyl)amino}acetamide | 441.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 407 | 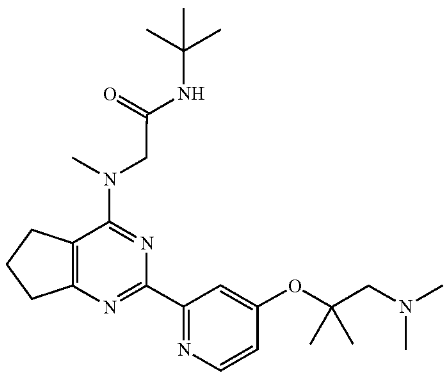 [SMILES: CN(C)CC(C)(C)Oc1ccnc(-c2nc3c(c(N(C)CC(=O)NC(C)(C)C)n2)CCC3)c1] | N-tert-butyl-2-{[2-(4-{[1-(dimethylamino)-2-methylpropan-2-yl]oxy}pyridin-2-yl)-5H,6H,7H-cyclopenta[d]pyrimidin-4-yl](methyl)amino}acetamide | 455.4 |
| 408 | 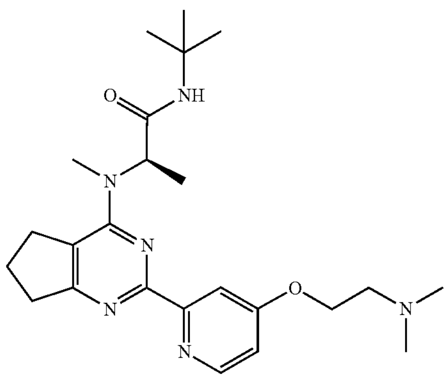 [SMILES: C[C@H](C(=O)NC(C)(C)C)N(C)c1nc(-c2cc(OCCN(C)C)ccn2)nc2c1CCC2] | (2R)-N-tert-butyl-2-[(2-{4-[2-(dimethylamino)ethoxy]pyridin-2-yl}-5H,6H,7H-cyclopenta[d]pyrimidin-4-yl)(methyl)amino]propanamide | 441.3 |
| 409 | 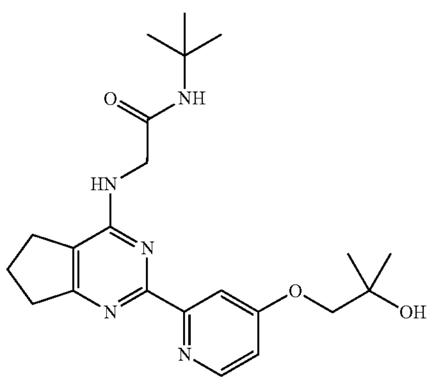 [SMILES: CC(C)(O)COc1ccnc(-c2nc3c(c(NCC(=O)NC(C)(C)C)n2)CCC3)c1] | N-tert-butyl-2-({2-[4-(2-hydroxy-2-methylpropoxy)pyridin-2-yl]-5H,6H,7H-cyclopenta[d]pyrimidin-4-yl}amino)acetamide | 414.3 |
| 410 | 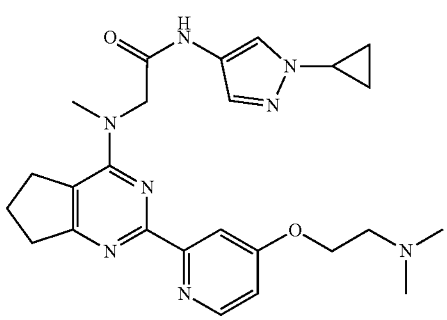 [SMILES: CN(C)CCOc1ccnc(-c2nc3c(c(N(C)CC(=O)Nc4cnn(C5CC5)c4)n2)CCC3)c1] | N-(1-cyclopropyl-1H-pyrazol-4-yl)-2-[(2-{4-[2-(dimethylamino)ethoxy]pyridin-2-yl}-5H,6H,7H-cyclopenta[d]pyrimidin-4-yl)(methyl)amino]acetamide | 477.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 411 | 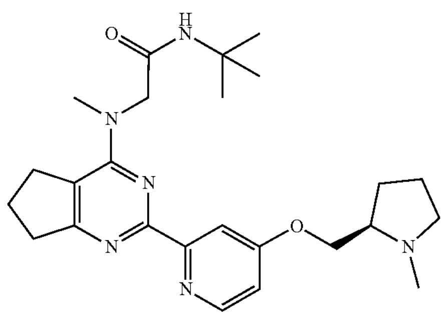 [SMILES: CN(CC(=O)NC(C)(C)C)c1nc(-c2cc(OC[C@H]3CCCN3C)ccn2)nc2c1CCC2] | N-tert-butyl-2-{methyl[2-(4-{[(2R)-1-methylpyrrolidin-2-yl]methoxy}pyridin-2-yl)-5H,6H,7H-cyclopenta[d]pyrimidin-4-yl]amino}acetamide | 453.4 |
| 412 | 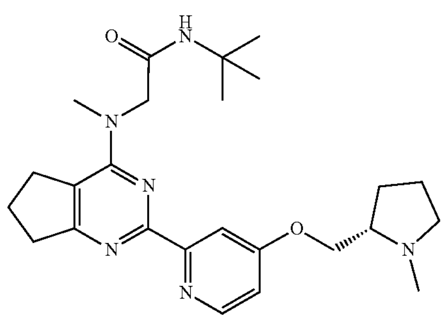 [SMILES: CN(CC(=O)NC(C)(C)C)c1nc(-c2cc(OC[C@@H]3CCCN3C)ccn2)nc2c1CCC2] | N-tert-butyl-2-{methyl[2-(4-{[(2S)-1-methylpyrrolidin-2-yl]methoxy}pyridin-2-yl)-5H,6H,7H-cyclopenta[d]pyrimidin-4-yl]amino}acetamide | 453.4 |
| 413 | 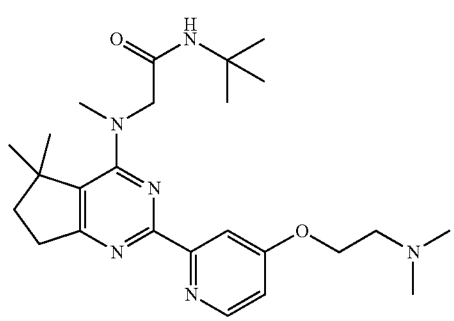 | N-tert-butyl-2-[(2-{4-[2-(dimethylamino)ethoxy]pyridin-2-yl}-5,5-dimethyl-5H,6H,7H-cyclopenta[d]pyrimidin-4-yl)(methyl)amino]acetamide | 455.3 |
| 414 | 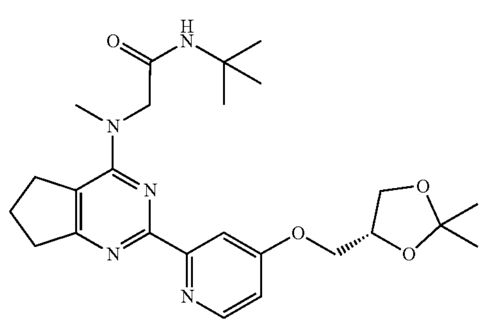 [SMILES: CN(CC(=O)NC(C)(C)C)c1nc(-c2cc(OC[C@@H]3COC(C)(C)O3)ccn2)nc2c1CCC2] | N-tert-butyl-2-{[2-(4-{[(4R)-2,2-dimethyl-1,3-dioxolan-4-yl]methoxy}pyridin-2-yl)-5H,6H,7H-cyclopenta[d]pyrimdin-4-yl](methyl)amino}acetamide | 470.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 415 | 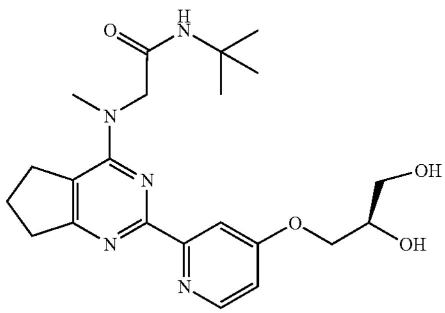 [SMILES: CN(CC(=O)NC(C)(C)C)c1nc(-c2cc(OC[C@H](O)CO)ccn2)nc2c1CCC2] | N-tert-butyl-2-[(2-{4-[(2R)-2,3-dihydroxypropoxy]pyridin-2-yl}-5H,6H,7H-cyclopenta[d]pyrimidin-4-yl)(methyl)amino]acetamide | 430.1 |
| 416 | 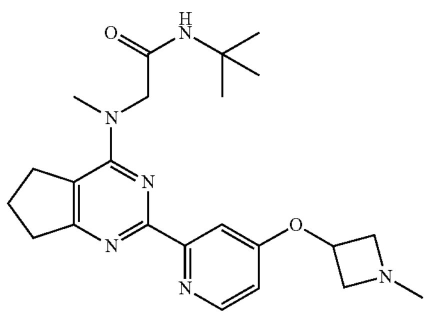 [SMILES: CN1CC(Oc2ccnc(-c3nc4c(c(N(C)CC(=O)NC(C)(C)C)n3)CCC4)c2)C1] | N-tert-butyl-2-[methyl(2-{4-[(1-methylazetidin1-3-yl)oxy]pyridin-2-yl}-5H,6H,7H-cyclopenta[d]pyrimidin-4-yl)amino]acetamide | 425.3 |
| 417 | 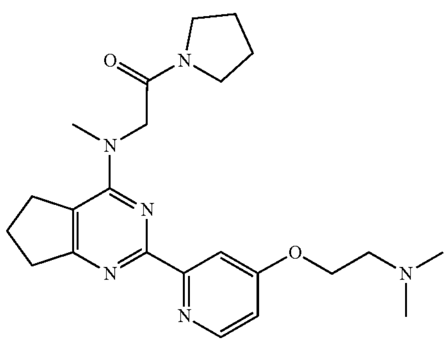 [SMILES: CN(C)CCOc1ccnc(-c2nc3c(c(N(C)CC(=O)N4CCCC4)n2)CCC3)c1] | 2-[(2-{4-[2-(dimethylamino)ethoxy]pyridin-2-yl}-5H,6H,7H-cyclopenta[d]pyrimidin-4-yl)(methyl)amino]-1-(pyrrolidin-1-yl)ethan-1-one | 425.3 |
| 418 | 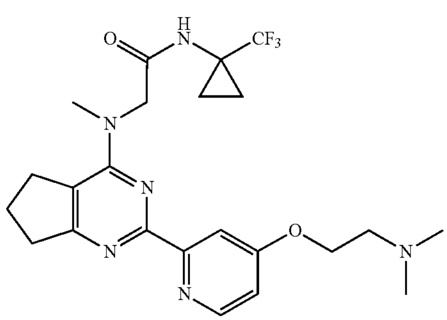 [SMILES: CN(C)CCOc1ccnc(-c2nc3c(c(N(C)CC(=O)NC4(C(F)(F)F)CC4)n2)CCC3)c1] | 2-[(2-{4-[2-(dimethylamino)ethoxy]pyridin-2-yl}-5H,6H,7H-cyclopenta[d]pyrimidin-4-yl)(methyl)amino]-N-[1-(trifluoromethyl)cyclopropyl]acetamide | 479.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 419 | 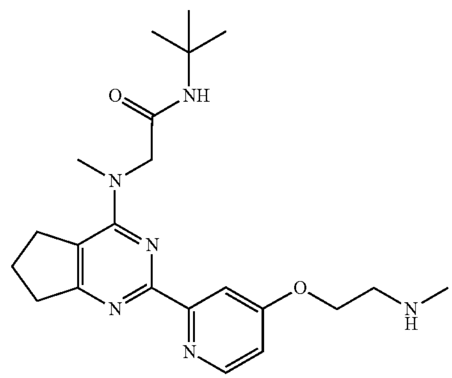 [SMILES: CNCCOc1ccnc(-c2nc3c(c(N(C)CC(=O)NC(C)(C)C)n2)CCC3)c1] | N-tert-butyl-2-[methyl(2-{4-[2-(methylamino)ethoxy]pyridin-2-yl}-5H,6H,7H-cyclopenta[d]pyrimidin-4-yl)amino]acetamide | 413.3 |
| 420 | 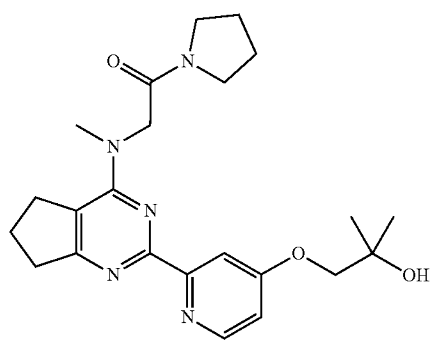 [SMILES: CN(CC(=O)N1CCCC1)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-1-(pyrrolidin-1-yl)ethan-1-one | 426.3 |
| 421 | 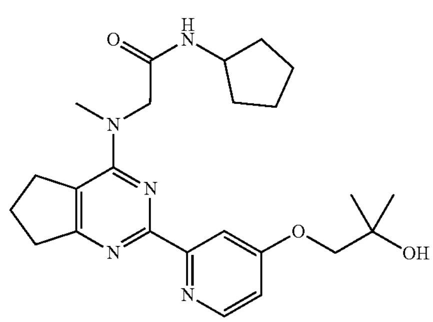 [SMILES: CN(CC(=O)NC1CCCC1)c1nc(-c2cc(OCC(C)(C)O)ccn2)nc2c1CCC2] | N-cyclopentyl-2-({2-[4-(2-hydroxy-2-methylpropoxy)pyridin-2-yl]-5H,6H,7H-cyclopenta[d]pyrimidin-4-yl}(methyl)amino)acetamide | 440.3 |
| 422 | 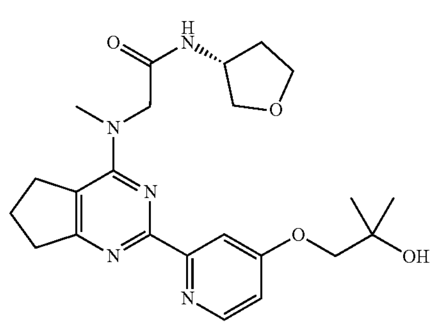 [SMILES: CN(CC(=O)N[C@@H]1CCOC1)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-N-[(3R)-oxolan-3-yl]acetamide | 442.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 423 | 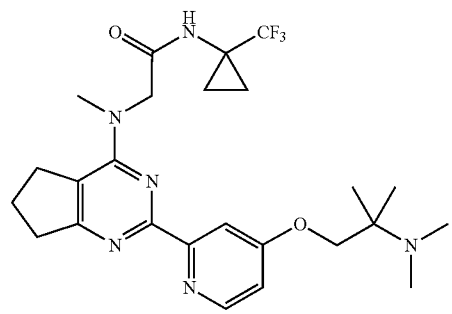 [SMILES: CN(CC(=O)NC1(C(F)(F)F)CC1)c1nc(-c2cc(OCC(C)(C)N(C)C)ccn2)nc2c1CCC2] | 2-[(2-{4-[2-(dimethylamino)-2-methylpropoxy]pyridin-2-yl}-5H,6H,7H-cyclopenta[d]pyrimidin-4-yl)(methyl)amino]-N[1-(trifluoromethyl)cyclopropyl]acetamide | 507.3 |
| 424 | 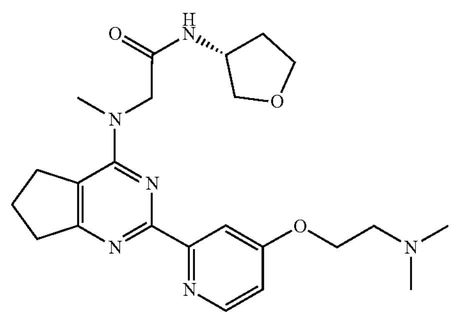 [SMILES: CN(C)CCOc1ccnc(-c2nc3c(c(N(C)CC(=O)N[C@@H]4CCOC4)n2)CCC3)c1] | 2-[(2-{4-[2-(dimethylamino)ethoxy]pyridin-2-yl}-5H,6H,7H-cyclopenta[d]pyrimidin-4-yl)(methyl)amino]-N-[(3R)-oxolan-3-yl]acetamide | 441.2 |
| 425 | 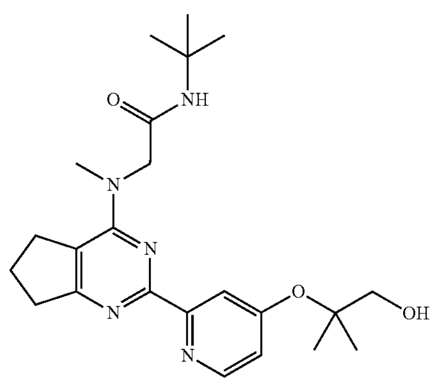 [SMILES: CN(CC(=O)NC(C)(C)C)c1nc(-c2cc(OC(C)(C)CO)ccn2)nc2c1CCC2] | N-tert-butyl-2-[(2-{4-[(1-hydroxy-2-methylpropan-2-yl)oxy]pyridin-2-yl}-5H,6H,7H-cyclopenta[d]pyrimidin-4-yl)(methyl)amino]acetamide | 428.1 |
| 426 | 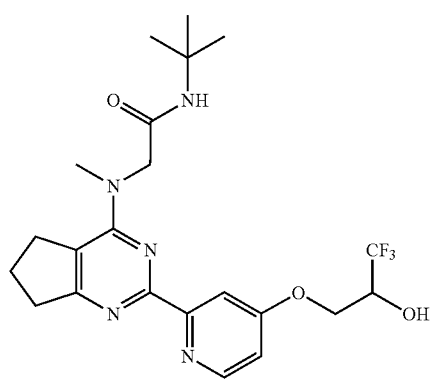 [SMILES: CN(CC(=O)NC(C)(C)C)c1nc(-c2cc(OCC(O)C(F)(F)F)ccn2)nc2c1CCC2] | N-tert-butyl-2-[methyl({2-[4-(3,3,3-trifluoro-2-hydroxypropoxy)pyridin-2-yl]-5H,6H,7H-cyclopenta[d]pyrimidin-4-yl})amino]acetamide | 468.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 427 | 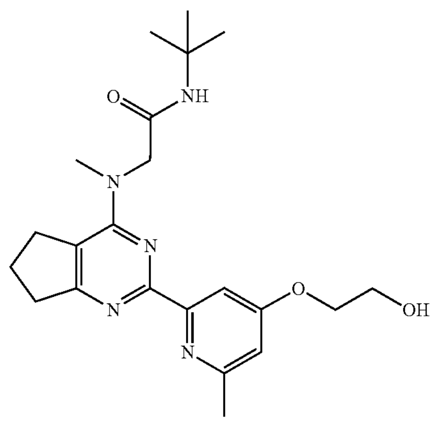 [SMILES: Cc1cc(OCCO)cc(-c2nc3c(c(N(C)CC(=O)NC(C)(C)C)n2)CCC3)n1] | N-tert-butyl-2-({2-[4-(2-hydroxyethoxy)-6-methylpyridin-2-yl]-5H,6H,7H-cyclopenta[d]pyrimidin-4-yl}(methyl)amino)acetamide | 414.3 |
| 428 | 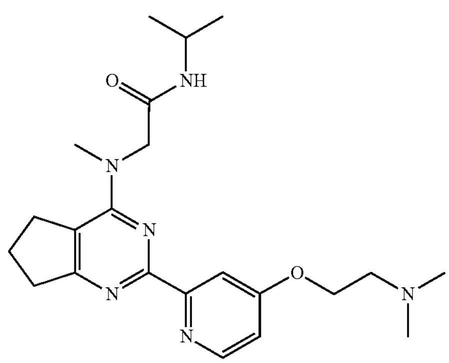 [SMILES: CC(C)NC(=O)CN(C)c1nc(-c2cc(OCCN(C)C)ccn2)nc2c1CCC2] | 2-[(2-{4-[2-(dimethylamino)ethoxy]pyridin-2-yl}-5H,6H,7H-cyclopenta[d]pyrimidin-4-yl)(methyl)amino]-N-(propan-2-yl)acetamide | 413.3 |
| 429 | 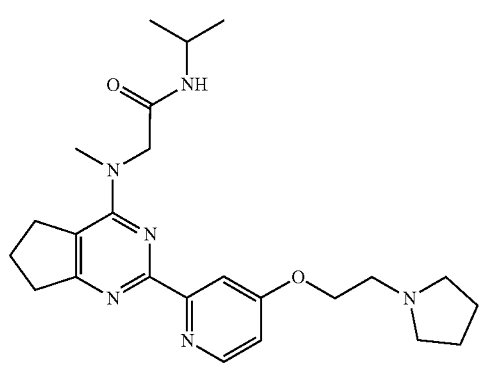 [SMILES: CC(C)NC(=O)CN(C)c1nc(-c2cc(OCCN3CCCC3)ccn2)nc2c1CCC2] | 2-[methyl(2-{4-[2-(pyrrolidi-1-yl)ethoxy]pyridin-2-yl}-5H,6H,7H-cyclopenta[d]pyrimidin-4-yl)amino]-N-(propan-2-yl)acetamide | 439.3 |
| 430 | 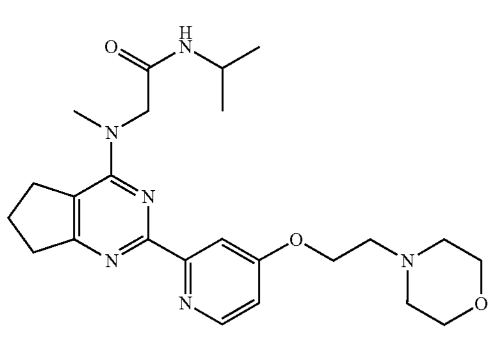 [SMILES: CC(C)NC(=O)CN(C)c1nc(-c2cc(OCCN3CCOCC3)ccn2)nc2c1CCC2] | 2-[methyl(2-{4-[2-(morpholin-4-yl)ethoxy]pyridin-2-yl}-5H,6H,7H-cyclopenta[d]pyrimidin-4-yl)amino]-N-(propan-2-yl)acetamide | 455.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 431 | 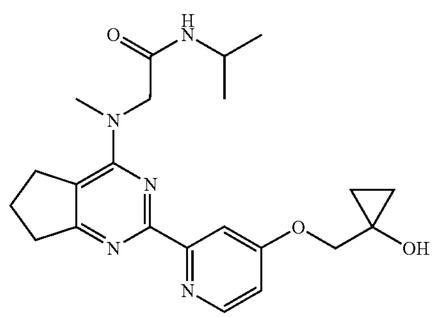 [SMILES: CC(C)NC(=O)CN(C)c1nc(-c2cc(OCC3(O)CC3)ccn2)nc2c1CCC2] | 2-[2-{4-[(1-hydroxycyclopropyl)methoxy]pyridin-2-yl}-5H,6H,7H-cyclopenta[d]pyrimidin-4-yl)(methyl)amino]-N-(propan-2-yl)acetamide | 412.3 |
| 432 | 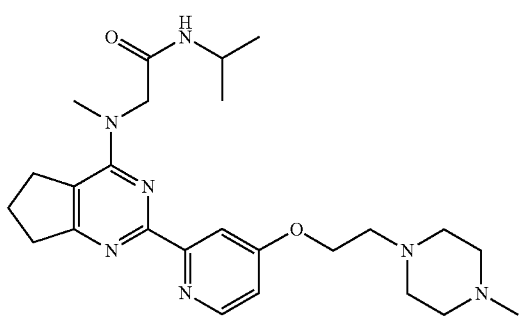 [SMILES: CC(C)NC(=O)CN(C)c1nc(-c2cc(OCCN3CCN(C)CC3)ccn2)nc2c1CCC2] | 2-[methyl(2-{4-[2-(4-methylpiperazin-1-yl)ethoxy]pyridin-2-yl}-5H,6H,7H-cyclopenta[d]pyrimidin-4-yl)amino]-N-(propan-2-yl)acetamide | 468.3 |
| 433 | 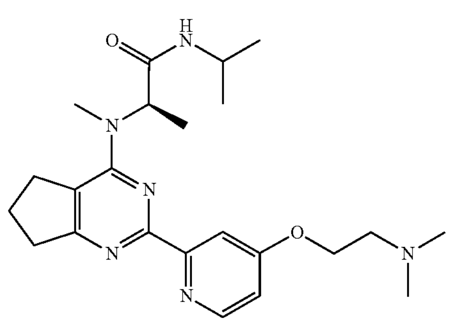 [SMILES: CC(C)NC(=O)[C@@H](C)N(C)c1nc(-c2cc(OCCN(C)C)ccn2)nc2c1CCC2] | (2R)-2-[(2-{4-[2-(dimethylamino)ethoxy]pyridin-2-yl}-5H,6H,7H-cyclopenta[d]pyrimidin-4-yl)(methyl)amino]-N-(propan-2-yl)propanamide | 427.3 |
| 434 | 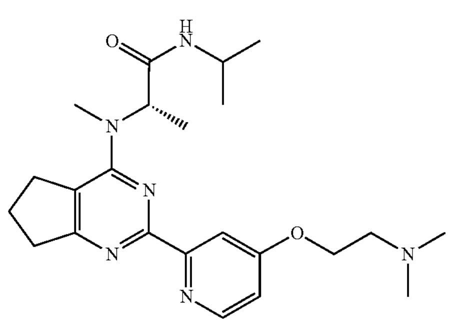 [SMILES: CC(C)NC(=O)[C@H](C)N(C)c1nc(-c2cc(OCCN(C)C)ccn2)nc2c1CCC2] | (2S)-2-[(2-{4-[2-(dimethylamino)ethoxy]pyridin-2-yl}-5H,6H,7H-cyclopenta[d]pyrimidin-4-yl)(methyl)amino]-N-(propan-2-yl)propanmide | 427.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 435 | 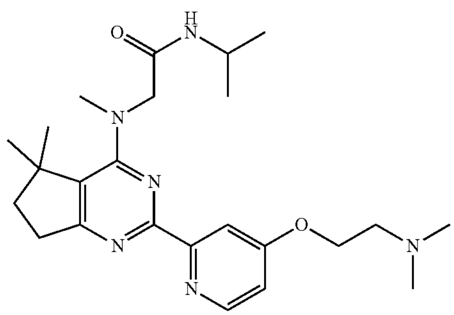 | 2-[(2-{4-[2-(dimethylamino)ethoxy]pyridin-2-yl}-5,5-dimethyl-5H,6H,7H-cyclopenta[d]pyrimidin-4-yl)(methyl)amino]-N-(propan-2-yl)acetamide | 441.3 |
| 436 | 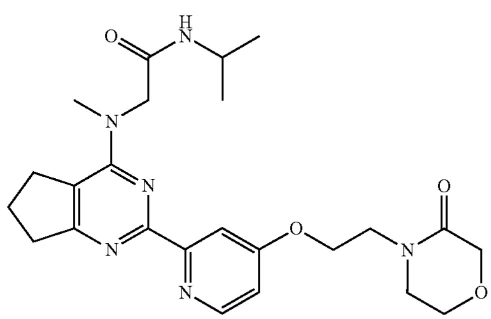 [SMILES: CC(C)NC(=O)CN(C)c1nc(-c2cc(OCCN3CCOCC3=O)ccn2)nc2c1CCC2] | 2-[methyl(2-{4-[2-(3-oxomorpholin-4-yl)ethoxy]pyridin-2-yl}-5H,6H,7H-cyclopenta[d]pyrimidin-4-yl)amino]-N-(propan-2-yl)acetamide | 469.3 |
| 437 | 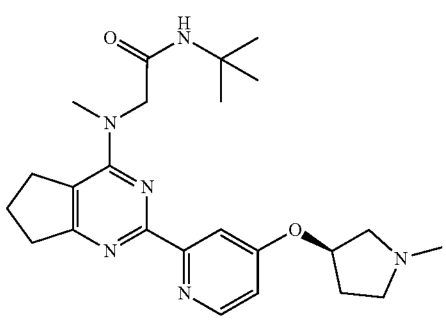 [SMILES: CN1CC[C@@H](Oc2ccnc(-c3nc4c(c(N(C)CC(=O)NC(C)(C)C)n3)CCC4)c2)C1] | N-tert-butyl-2-{methyl[2-(4-{[(3R)-1-methylpyrrolidin-3-yl]oxy}pyridin-2-yl)-5H,6H,7H-cyclopenta[d]pyrimidin-4-yl]amino}acetamide | 439.3 |
| 438 | 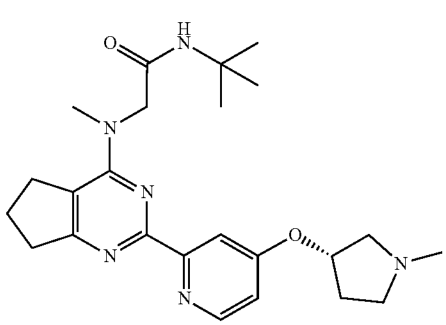 [SMILES: CN1CC[C@H](Oc2ccnc(-c3nc4c(c(N(C)CC(=O)NC(C)(C)C)n3)CCC4)c2)C1] | N-tert-butyl-2-{methyl[2-(4-{[(3S)-1-methylpyrrolidin-3-yl]oxy}pyridin-2-yl)-5H,6H,7H-cyclopenta[d]pyrimidin-4-yl]amino}acetamide | 439.4 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 440 | 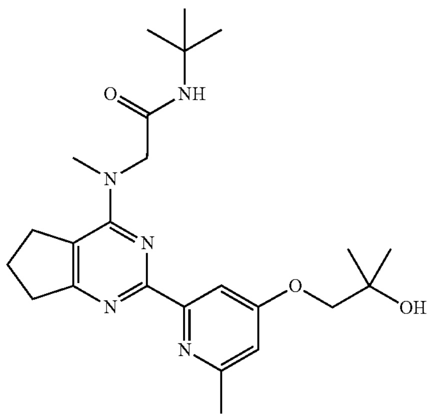 [SMILES: Cc1cc(OCC(C)(C)O)cc(-c2nc3c(c(N(C)CC(=O)NC(C)(C)C)n2)CCC3)n1] | N-tert-butyl-2-({2-[4-(2-hydroxy-2-methylpropoxy)-6-methylpyridin-2-yl]-5H,6H,7H-cyclopenta[d]pyrimidin-4-yl}(methyl)amino)acetamide | 442.3 |
| 441 | 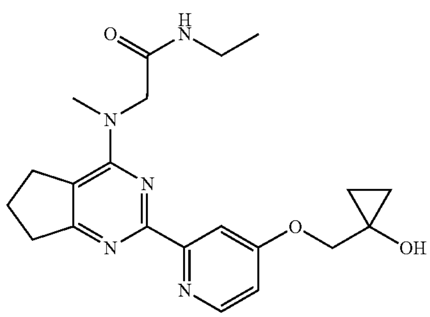 [SMILES: CCNC(=O)CN(C)c1nc(-c2cc(OCC3(O)CC3)ccn2)nc2c1CCC2] | N-ethyl-2-[(2-{4-[(1-hydroxycyclopropyl)methoxy]pyridin-2-l}-5H,6H,7H-cyclopenta[d]pyrimidin-4-yl)(methyl)amino]acetamide | 398.2 |
| 442 | 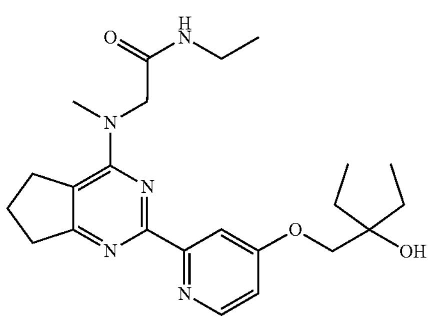 [SMILES: CCNC(=O)CN(C)c1nc(-c2cc(OCC(O)(CC)CC)ccn2)nc2c1CCC2] | N-ethyl-2-({2-[4-(2-ethyl-2-hydroxybutoxy)pyridin-2-yl]-5H,6H,7H-cyclopenta[d]pyrimidin-4-yl}(methyl)amino)acetamide | 428.3 |
| 443 | 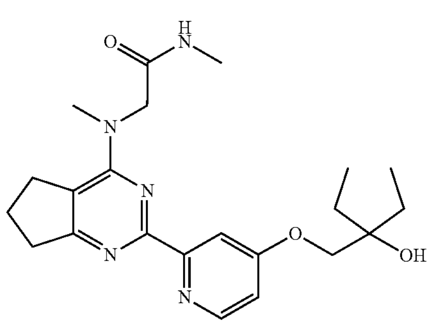 [SMILES: CCC(O)(CC)COc1ccnc(-c2nc3c(c(N(C)CC(=O)NC)n2)CCC3)c1] | 2-({2-[4-(2-ethyl-2-hydroxybutoxy)pyridin-2-yl]-5H,6H,7H-cyclopenta[d]pyrimidin-4-yl}(methyl)amino)-N-methylacetamide | 414.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 444 | 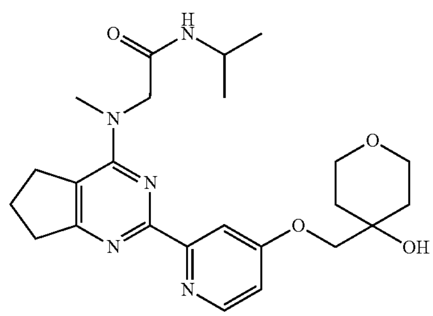 [SMILES: CC(C)NC(=O)CN(C)c1nc(-c2cc(OCC3(O)CCOCC3)ccn2)nc2c1CCC2] | 2-[(2-{4-[(4-hydroxyoxan-4-yl)methoxy]pyridin-2-yl}-5H,6H,7H-cyclopenta[d]pyrimidin-4-yl)(methyl)amino]-N-(propan-2-yl)acetamide | 456.3 |
| 445 | 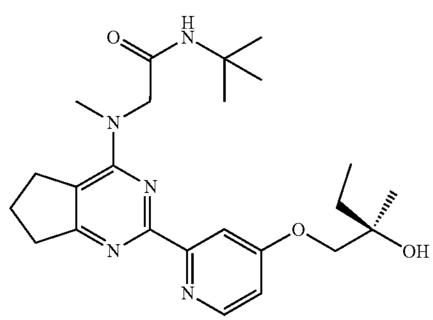 [SMILES: CC[C@@](C)(O)COc1ccnc(-c2nc3c(c(N(C)CC(=O)NC(C)(C)C)n2)CCC3)c1] | N-tert-butyl-2-[(2-{4-[(2R)-2-hydroxy-2-methylbutoxy]pyridin-2-yl}-5H,6H,7H-cyclopenta[d]pyrimidin-4-yl)(methyl)amino]acetamide | 442.3 |
| 446 | 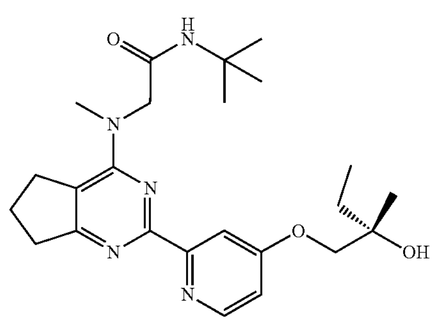 [SMILES: CC[C@](C)(O)COc1ccnc(-c2nc3c(c(N(C)CC(=O)NC(C)(C)C)n2)CCC3)c1] | N-tert-butyl-2-[(2-{4-[(2S)-2-hydroxy-2-methylbutoxy]pyridin-2-yl}-5H,6H,7H-cyclopenta[d]pyrimidin-4-yl)(methyl)amino]acetamide | 442.3 |
| 447 | 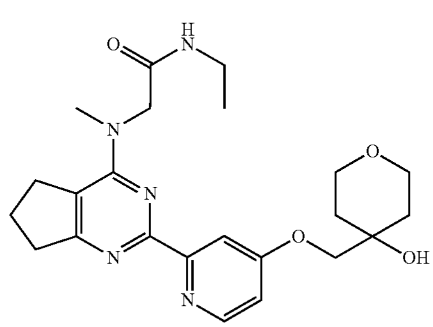 [SMILES: CCNC(=O)CN(C)c1nc(-c2cc(OCC3(O)CCOCC3)ccn2)nc2c1CCC2] | N-ethyl-2-[(2-{4-[(4-hydroxyoxan-4-yl)methoxy]pyridin-2-yl}-5H,6H,7H-cyclopenta[d]pyrimidin-4-yl)(methyl)amino]acetamide | 442.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 448 | 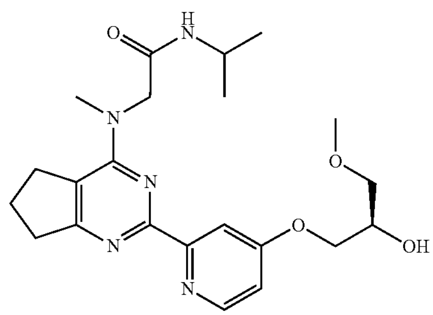 [SMILES: COC[C@@H](O)COc1ccnc(-c2nc3c(c(N(C)CC(=O)NC(C)C)n2)CCC3)c1] | 2-[(2-{4-[(2R)-2-hydroxy-3-methoxypropoxy]pyridin-2-yl}-5H,6H,7H-cyclopenta[d]pyrimidin-4-yl)(methyl)amino]-N-(propan-2-yl)acetamide | 430.2 |
| 449 | 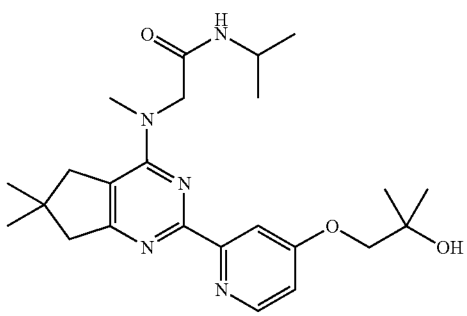 [SMILES: CC(C)NC(=O)CN(C)c1nc(-c2cc(OCC(C)(C)O)ccn2)nc2c1CC(C)(C)C2] | 2-({2-[4-(2-hydroxy-2-mehtylpropoxy)pyridin-2-yl]-6,6-dimethyl-5H,6H,7H-cyclopenta[d]pyrimidin-4-yl}(methyl)amino)-N-(propan-2-yl)acetamide | 442.3 |
| 450 | 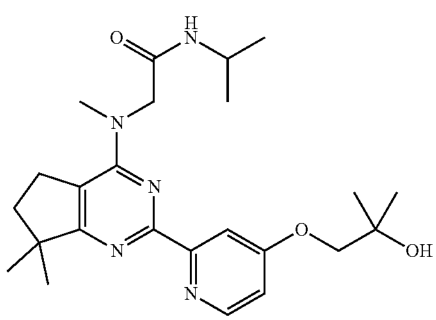 [SMILES: CC(C)NC(=O)CN(C)c1nc(-c2cc(OCC(C)(C)O)ccn2)nc2c1CCC2(C)C] | 2-({2-[4-(2-hydroxy-2-methylpropoxy)pyridin-2-yl]-7,7-dimethyl-5H,6H,7H-cyclopenta[d]pyrimidin-4-yl}(methyl)amino)-N-(propan-2-yl)acetamide | 442.3 |
| 451 | 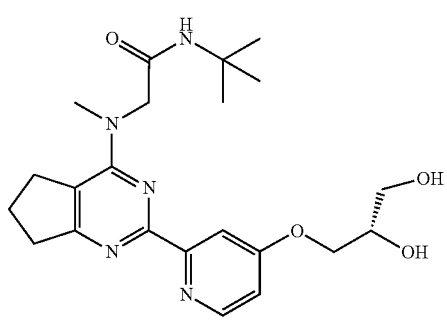 [SMILES: CN(CC(=O)NC(C)(C)C)c1nc(-c2cc(OC[C@@H](O)CO)ccn2)nc2c1CCC2] | N-tert-butyl-2-[(2-{4-[(2S)-2,3-dihydroxypropoxy]pyridin-2-yl}-5H,6H,7H-cyclopenta[d]pyrimdiin-4-yl)(methyl)amino]acetamide | 430.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 452 | 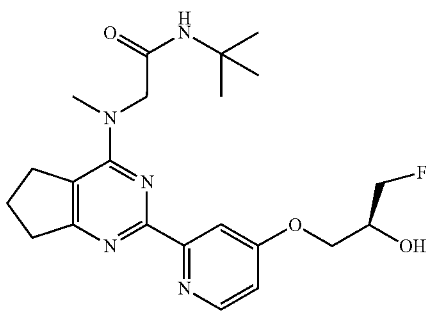 [SMILES: CN(CC(=O)NC(C)(C)C)c1nc(-c2cc(OC[C@H](O)CF)ccn2)nc2c1CCC2] | N-tert-butyl-2-[(2-{4-[(2S)-3-fluoro-2-hydroxypropoxy]pyridin-2-yl}-5H,6H,7H-cyclopenta[d]pyrimidin-4-yl)(methyl)amino]acetamide | 432.1 |
| 453 | 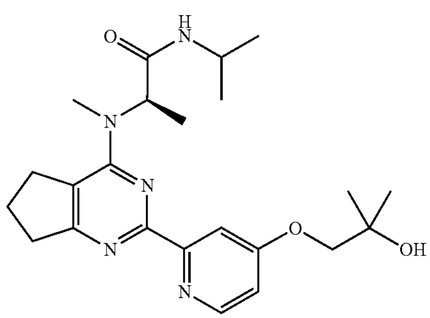 [SMILES: CC(C)NC(=O)[C@@H](C)N(C)c1nc(-c2cc(OCC(C)(C)O)ccn2)nc2c1CCC2] | (2R)-2-({2-[4-(2-hydroxy-2-methylpropoxy)pyridin-2-yl]-5H,6H,7H-cyclopenta[d]pyrimidin-4-yl}(methyl)amino)-N-(propan-2-yl)propanamide | 428.3 |
| 454 | 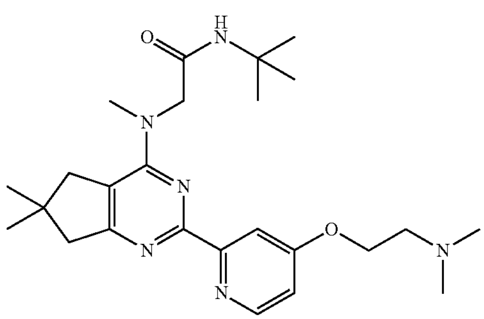 | N-tert-butyl-2-[(2-{4-[2-(dimethylamino)ethoxy]pyridin-2-yl}-6,6-dimethyl-5H,6H,7H-cyclopenta[d]pyrimidin-4-yl)(methyl)amino]acetamide | 455.3 |
| 455 | 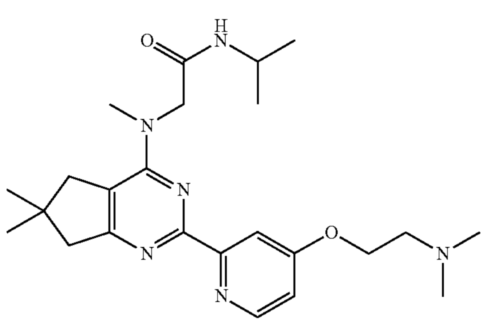 | 2-[(2-{4-[2-(dimethylamino)ethoxy]pyridin-2-yl}-6,6-dimethyl-5H,6H,7H-cyclopenta[d]pyrimidin-4-yl)(methyl)amino]-N-(propan-2-yl)acetamide | 441.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 456 | 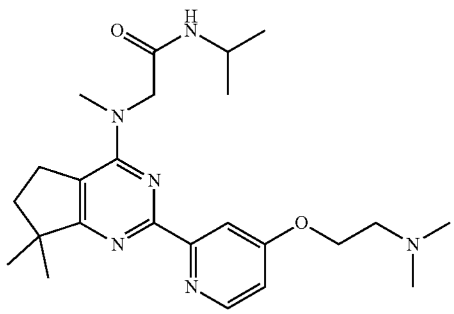 | 2-[(2-{4-[2-(dimethylamino)ethoxy]pyridin-2-yl}-7,7-dimethyl-5H,6H,7H-cyclopenta[d]pyrimidin-4-yl)(methyl)amino]-N-(propan-2-yl)acetamide | 441.3 |
| 457 | 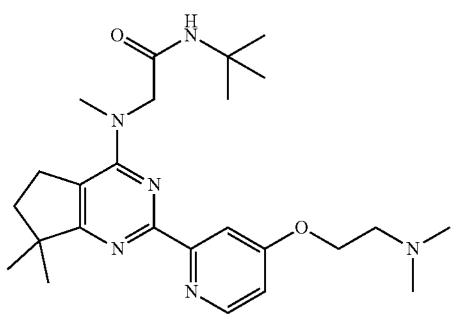 | N-tert-butyl-2-[(2-{4-[2-(dimethylamino)ethoxy]pyridin-2-yl}-7,7-dimethyl-5H,6H,7H-cyclopenta[d]pyrimidin-4-yl)(methyl)amino]acetamide | 455.3 |
| 458 | 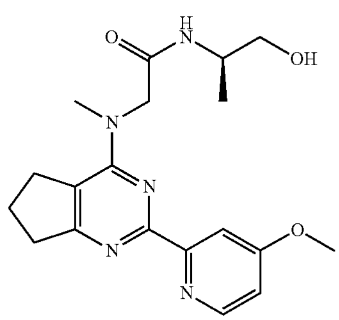 [SMILES: COc1ccnc(-c2nc3c(c(N(C)CC(=O)N[C@H](C)CO)n2)CCC3)c1] | N-[(2R)-1-hydroxypropan-2-yl]-2-{[2-(4-methoxypyridin-2-yl)-5H,6H,7H-cyclopenta[d]pyrimidin-4-yl](methyl)amino}acetamide | 372.2 |
| 459 | 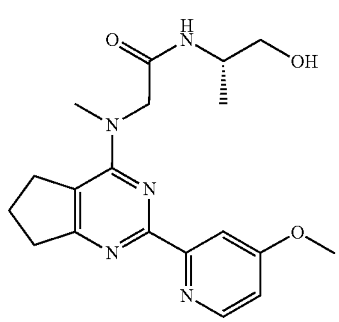 [SMILES: COc1ccnc(-c2nc3c(c(N(C)CC(=O)N[C@@H](C)CO)n2)CCC3)c1] | N-[(2S)-1-hydroxypropan-2-yl]-2-{[2-(4-methoxypyridin-2-yl)-5H,6H,7H-cyclopenta[d]pyrimidin-4-yl](methyl)amino}acetamide | 372.2 |

TABLE 1-continued

Where the mass for a compound is not provided in Table 1, the mass can be found
for the compound in the synthetic examples.

| Compound No. | Structure | IUPAC Name | Mass Found (M + 1) |
|---|---|---|---|
| 460 | 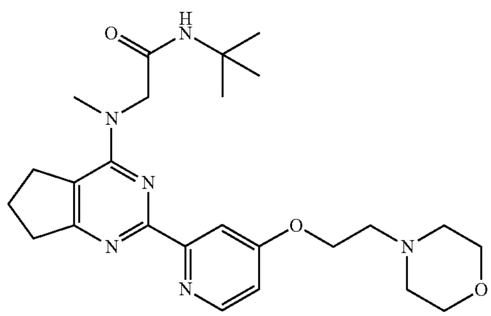 [SMILES: CN(CC(=O)NC(C)(C)C)c1nc(-c2cc(OCCN3CCOCC3)ccn2)nc2c1CCC2] | N-tert-butyl-2-[methyl(2-{4-[2-(morpholin-4-yl)ethoxy]pyridin-2-yl}-5H,6H,7H-cyclopenta[d]pyrimidin-4-yl)amino]acetamide | 469.3 |
| 461 | 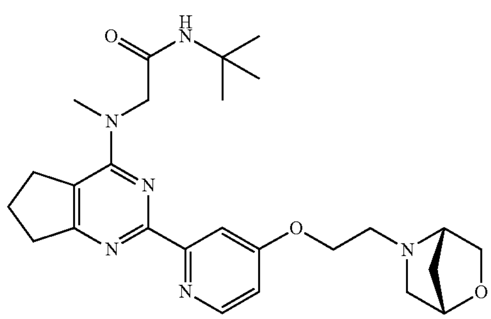 [SMILES: CN(CC(=O)NC(C)(C)C)c1nc(-c2cc(OCCN3C[C@@H]4C[C@H]3CO4)ccn2)nc2c1CCC2] | N-tert-butyl-2-{methyl[2-(4-{2-[(1S,4S)-2-oxa-5-azabicyclo[2.2.1]heptan-5-yl]ethoxy}pyridin-2-yl)-5H,6H,7H-cyclopenta[d]pyrimidin-4-yl]amino}acetamide | 481.3 |
| 462 | 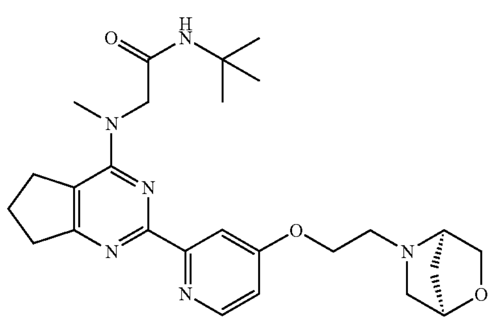 [SMILES: CN(CC(=O)NC(C)(C)C)c1nc(-c2cc(OCCN3C[C@H]4C[C@@H]3CO4)ccn2)nc2c1CCC2] | N-tert-butyl-2-{methyl[2-(4-{2-[(1R,4R)-2-oxa-5-azabicyclo[2.2.1]heptan-5-yl]ethoxy}pyridin-2-yl)-5H,6H,7H-cyclopenta[d]pyrimidin-4-yl]amino}acetamide | 481.3 |
| 463 | 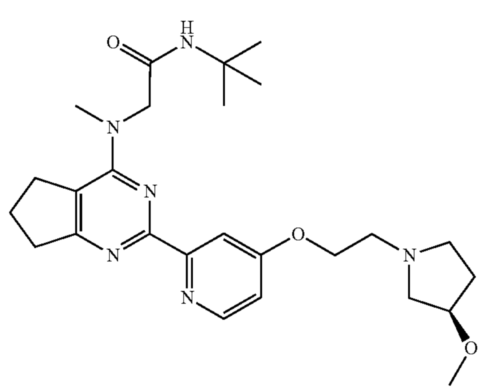 [SMILES: CO[C@@H]1CCN(CCOc2ccnc(-c3nc4c(c(N(C)CC(=O)NC(C)(C)C)n3)CCC4)c2)C1] | N-tert-butyl-2-{[2-(4-{2-[(3R)-3-methoxypyrrolidin-1-yl]ethoxy}pyridin-2-yl)-5H,6H,7H-cyclopenta[d]pyrimidin-4-yl](methyl)amino}acetamide | 483.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 464 | 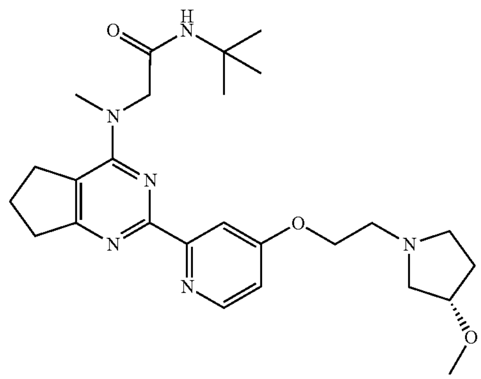 [SMILES: CO[C@H]1CCN(CCOc2ccnc(-c3nc4c(c(N(C)CC(=O)NC(C)(C)C)n3)CCC4)c2)C1] | N-tert-butyl-2-{[2-(4-{2-[(3S)-3-methoxypyrrolidin-1-yl]ethoxy}pyridin-2-yl)-5H,6H,7H-cyclopenta[d]pyrimidin-4-yl](methyl)amino}acetamide | 483.3 |
| 465 | 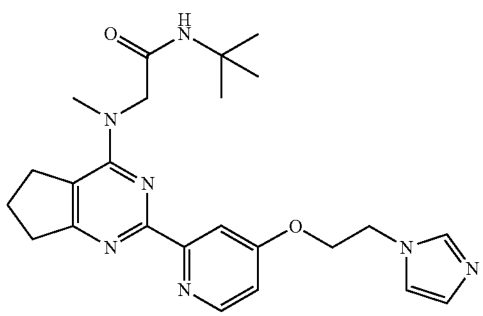 [SMILES: CN(CC(=O)NC(C)(C)C)c1nc(-c2cc(OCCn3ccnc3)ccn2)nc2c1CCC2] | N-tert-butyl-2-[(2-{4-[2-(1H-imidazol-1-yl)ethoxy]pyridin-2-yl})-5H,6H,7H-cyclopenta[d]pyrimidin-4-yl)(methyl)amino]acetamide | 450.2 |
| 466 | 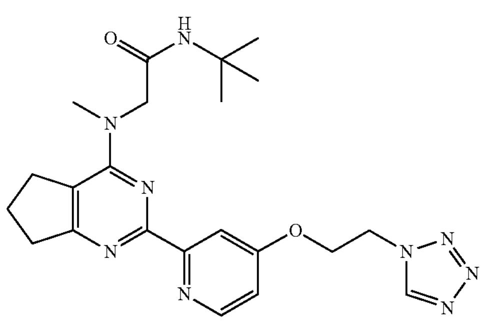 [SMILES: CN(CC(=O)NC(C)(C)C)c1nc(-c2cc(OCCn3cnnn3)ccn2)nc2c1CCC2] | N-tert-butyl-2-[methyl(2-{4-[2-(1H-1,2,3,4-tetrazol-1-yl)ethoxy]pyridin-2-yl}-5H,6H,7H-cyclopenta[d]pyrimidin-4-yl)amino]acetamide | 452.2 |
| 467 | 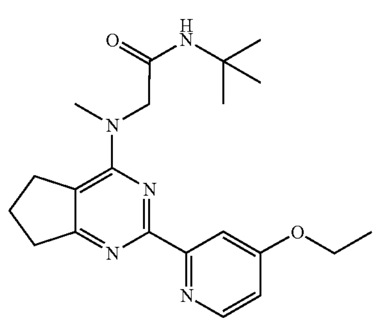 [SMILES: CCOc1ccnc(-c2nc3c(c(N(C)CC(=O)NC(C)(C)C)n2)CCC3)c1] | N-tert-butyl-2-{[2-(4-ethoxypyridin-2-yl)-5H,6H,7H-cyclopenta[d]pyrimidin-4-yl](methyl)amino}acetamide | 384.2 |

TABLE 1-continued

Where the mass for a compound is not provided in Table 1, the mass can be found
for the compound in the synthetic examples.

| Compound No. | Structure | IUPAC Name | Mass Found (M + 1) |
|---|---|---|---|
| 468 | 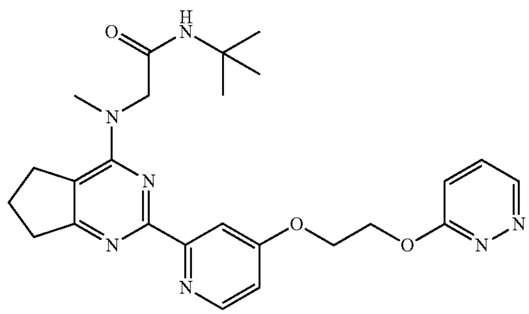 [SMILES: CN(CC(=O)NC(C)(C)C)c1nc(-c2cc(OCCOc3cccnn3)ccn2)nc2c1CCC2] | N-tert-butyl-2-[methyl(2-{4-[2-(pyridazin-3-yloxy)ethoxy]pyridin-2-yl}-5H,6H,7H-cyclopenta[d]pyrimidin-4-yl)amino]acetamide | 478.2 |
| 469 | 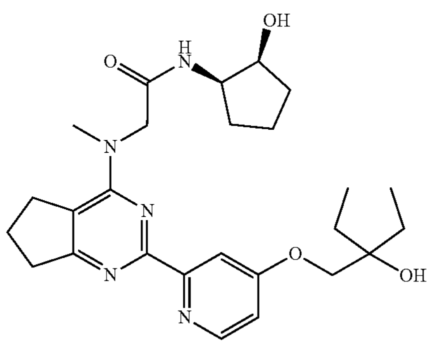 [SMILES: CCC(O)(CC)COc1ccnc(-c2nc3c(c(N(C)CC(=O)N[C@@H]4CCC[C@@H]4O)n2)CCC3)c1] | 2-({2-[4-(2-ethyl-2-hydroxybutoxy)pyridin-2-yl]-5H,6H,7H-cyclopenta[d]pyrimidin-4-yl}(methyl)amino)-N-[(1R,2S)-2-hydroxycyclopentyl]acetamide | 484.3 |
| 470 | 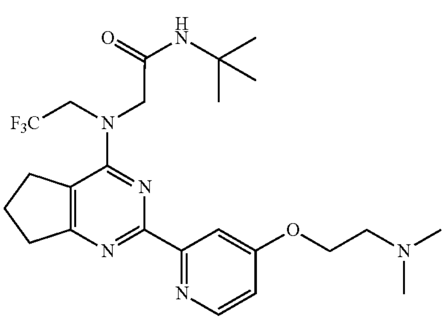 [SMILES: CN(C)CCOc1ccnc(-c2nc3c(c(N(CC(=O)NC(C)(C)C)CC(F)(F)F)n2)CCC3)c1] | N-tert-btuyl-2-[(2-{4-[2-(dimethylamino)ethoxy]pyridin-2-yl}-5H,6H,7H-cyclopenta[d]pyrimidin-4-yl)(2,2,2-trifluoroethyl)amino]acetamide | 495.3 |
| 471 | 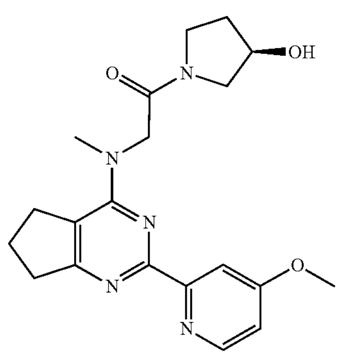 [SMILES: COc1ccnc(-c2nc3c(c(N(C)CC(=O)N4CC[C@@H](O)C4)n2)CCC3)c1] | 1-[(3R)-3-hydroxypyrrolidin-1-yl]-2-{[2-(4-methoxypyridin-2-yl)-5H,6H,7H-cyclopenta[d]pyrimidin-4-yl](methyl)amino}ethan-1-one | 384.2 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 472 | 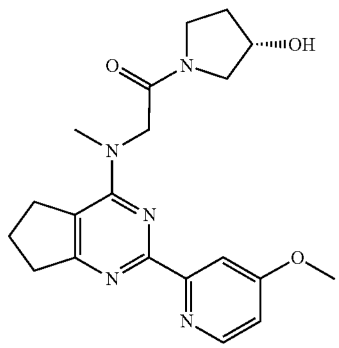 [SMILES: COc1ccnc(-c2nc3c(c(N(C)CC(=O)N4CC[C@H](O)C4)n2)CCC3)c1] | 1-[(3S)-3-hydroxypyrrolidin-1-yl]-2-{[2-(4-methoxypyridin-2-yl)-5H,6H,7H-cyclopenta[d]pyrimidin-4-yl](methyl)amino}ethan-1-one | 384.2 |
| 473 | 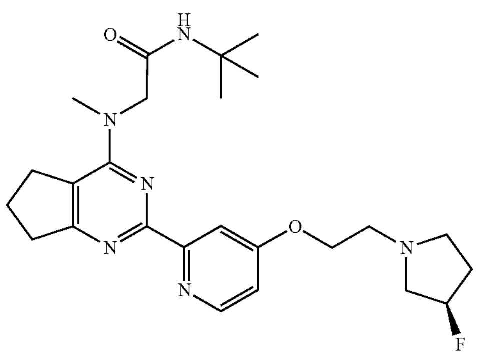 [SMILES: CN(CC(=O)NC(C)(C)C)c1nc(-c2cc(OCCN3CC[C@@H](F)C3)ccn2)nc2c1CCC2] | N-tert-butyl-2-{[2-(4-{2-[(3R)-3-fluoropyrrolidin-1-yl]ethoxy}pyridin-2-yl)-5H,6H,7H-cyclopenta[d]pyrimidin-4-yl](methyl)amino}acetamide | 471.2 |
| 474 | 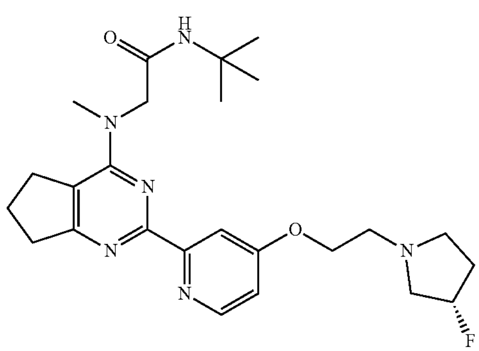 [SMILES: CN(CC(=O)NC(C)(C)C)c1nc(-c2cc(OCCN3CC[C@H](F)C3)ccn2)nc2c1CCC2] | N-tert-butyl-2-{[2-(4-{2-[(3S)-3-fluoropyrrolidin-1-yl]ethoxy}pyridin-2-yl)-5H,6H,7H-cyclopenta[d]pyrimidin-4-yl](methyl)amino}acetamide | 471.2 |
| 475 | 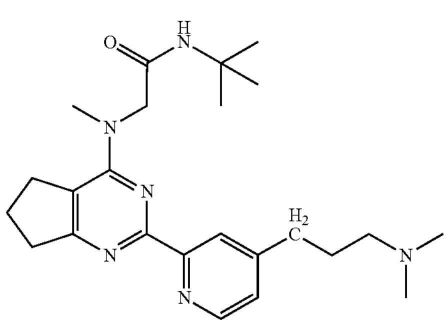 [SMILES: CN(C)CCCc1ccnc(-c2nc3c(c(N(C)CC(=O)NC(C)(C)C)n2)CCC3)c1] | N-tert-butyl-2-[(2-{4-[3-(dimethylamino)propyl]pyridin-2-yl}-5H,6H,7H-cyclopenta[d]pyrimidin-4-yl)(methyl)amino]acetamide | 425.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 476 | 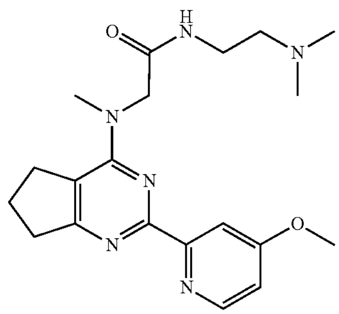 [SMILES: COc1ccnc(-c2nc3c(c(N(C)CC(=O)NCCN(C)C)n2)CCC3)c1] | N-[2-(dimethylamino)ethyl]-2-{[2-(4-methoxypyridin-2-yl)-5H,6H,7H-cyclopenta[d]pyrimidin-4-yl](methyl)amino}acetamide | 385.2 |
| 477 | 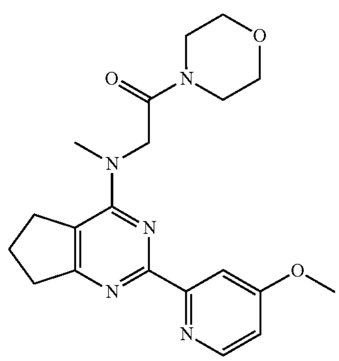 [SMILES: COc1ccnc(-c2nc3c(c(N(C)CC(=O)N4CCOCC4)n2)CCC3)c1] | 2-{[2-(4-methoxypyridin-2-yl)-5H,6H,7H-cyclopenta[d]pyrimidin-4-yl](methyl)amino}-1-(morpholin-4-yl)ethan-1-one | 384.2 |
| 478 | 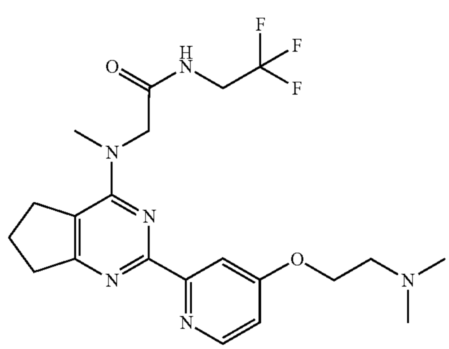 [SMILES: CN(C)CCOc1ccnc(-c2nc3c(c(N(C)CC(=O)NCC(F)(F)F)n2)CCC3)c1] | 2-[(2-{4-[2-(dimethylamino)ethoxy]pyridin-2-yl}-5H,6H,7H-cyclopenta[d]pyrimidin-4-yl)(methyl)amino]-N-(2,2,2-trifluoroethyl)acetamide | 453.2 |
| 479 | 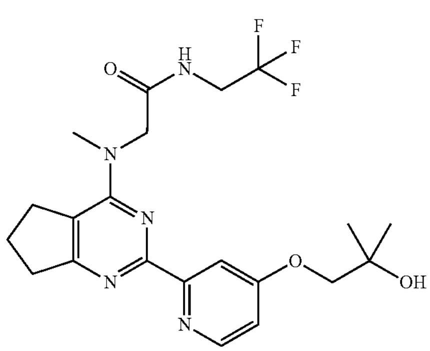 [SMILES: CN(CC(=O)NCC(F)(F)F)c1nc(-c2cc(OCC(C)(C)O)ccn2)nc2c1CCC2] | 2-({2-[4-(2-hydroxy-2-methylpropoxy)pyridin-2-yl]-5H,6H,7H-cyclopenta[d]pyrimidin-4-yl}(methyl)amino)-N-(2,2,2-trifluoroethyl)acetamide | 454.1 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 480 | 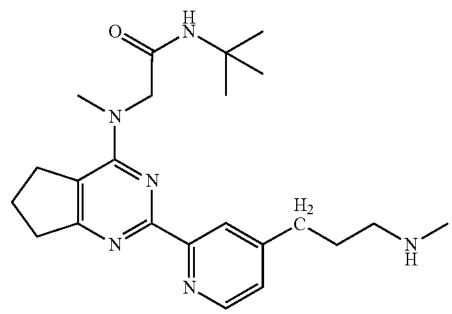 | N-tert-butyl-2-[methyl(2-{4-[3-(methylamino)propyl]pyridin-2-yl}-5H,6H,7H-cyclopenta[d]pyrimdin-4-yl)amino]acetamide | 411.3 |
| 481 | 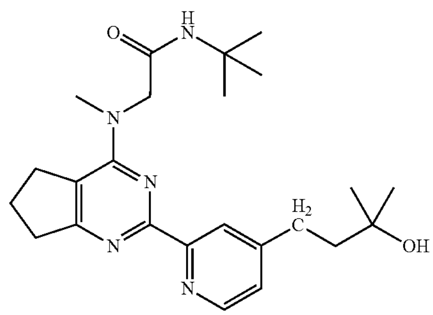 [SMILES: CN(CC(=O)NC(C)(C)C)c1nc(-c2cc(CCC(C)(C)O)ccn2)nc2c1CCC2] | N-tert-butyl-2-({2-[4-(3-hydroxy-3-methylbutyl)pyridin-2-yl]-5H,6H,7H-cyclopenta[d]pyrimidin-4-yl}(methyl)amino)acetamide | 426.3 |
| 482 | 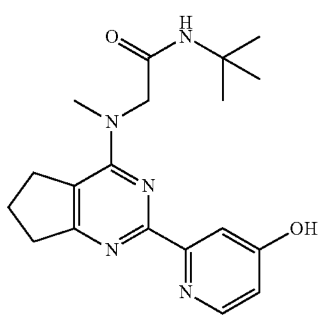 [SMILES: CN(CC(=O)NC(C)(C)C)c1nc(-c2cc(O)ccn2)nc2c1CCC2] | N-tert-butyl-2-{[2-(4-hydroxypyridin-2-yl)-5H,6H,7H-cyclopenta[d]pyrimidin-4-yl](methyl)amino}acetamide | 356.2 |
| 483 | 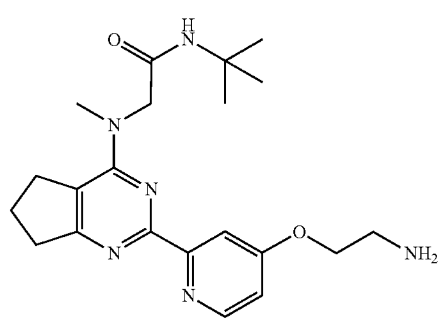 [SMILES: CN(CC(=O)NC(C)(C)C)c1nc(-c2cc(OCCN)ccn2)nc2c1CCC2] | 2-({2-[4-(2-aminoethoxy)pyridin-2-yl]-5H,6H,7H-cyclopenta[d]pyrimidin-4-yl}(methyl)amino)-N-tert-butylacetamide | 399.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 484 | 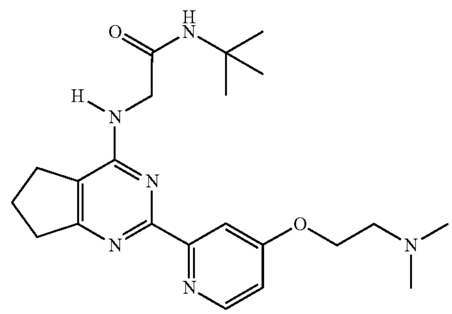 | N-tert-butyl-2-[(2-{4-[2-(dimethylamino)ethoxy]pyridin-2-yl}-5H,6H,7H-cyclopenta[d]pyrimidin-4-yl)amino]acetamide | 413.3 |
| 485 | 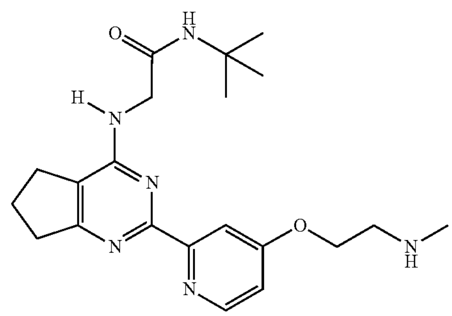 [SMILES: CNCCOc1ccnc(-c2nc3c(c(NCC(=O)NC(C)(C)C)n2)CCC3)c1] | N-tert-butyl-2-[2-{4-[2-(methylamino)ethoxy]pyridin-2-yl}-5H,6H,7H-cyclopenta[d]pyrimidin-4-yl)amino]acetamide | 399.2 |
| 486 | 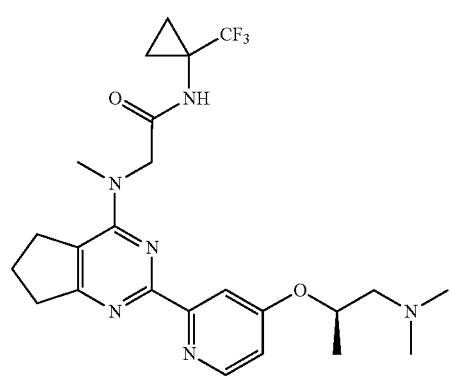 [SMILES: C[C@H](CN(C)C)Oc1ccnc(-c2nc3c(c(N(C)CC(=O)NC4(C(F)(F)F)CC4)n2)CCC3)c1] | 2-{[2-(4-{[(2R)-1-(dimethyamino)propan-2-yl]oxy}pyridin-2-yl)-5H,6H,7H-cyclopenta[d]pyrimidin-4-yl](methyl)amino}-N-[1-(trifluoromethyl)cyclopropyl]acetamide | 493.3 |
| 487 | 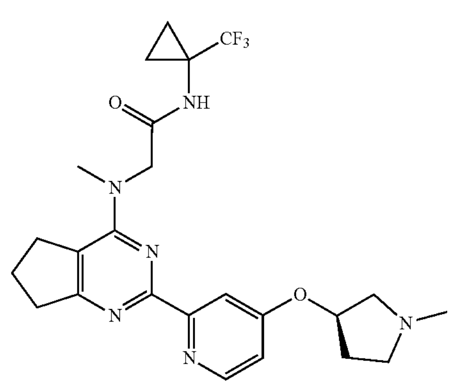 [SMILES: CN1CC[C@@H](Oc2ccnc(-c3nc4c(c(N(C)CC(=O)NC5(C(F)(F)F)CC5)n3)CCC4)c2)C1] | 2-{methyl[2-(4-{[(3R)-1-methylpyrrolidin-3-yl]oxy}pyridin-2-yl)-5H,6H,7H-cyclopenta[d]pyrimidin-4-yl]amino}-N-[1-(trifluoromethyl)cyclopropyl]acetamide | 491.3 |

US 11,746,100 B2

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 488 | 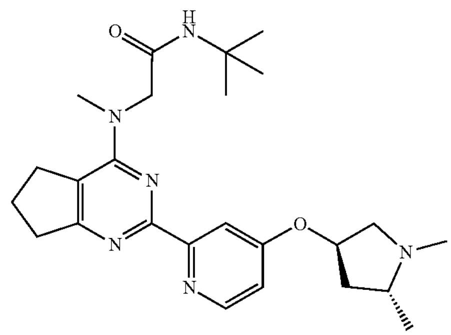 [SMILES: C[C@@H]1C[C@@H](Oc2ccnc(-c3nc4c(c(N(C)CC(=O)NC(C)(C)C)n3)CCC4)c2)CN1C] | N-tert-butyl-2-{[2-(4-{[(3R,5R)-1,5-dimethylpyrrolidin-3-yl]oxy}pyridin-2-yl)-5H,6H,7H-cyclopenta[d]pyrimidin-4-yl](methyl)amino}acetamide | 453.3 |
| 489 | 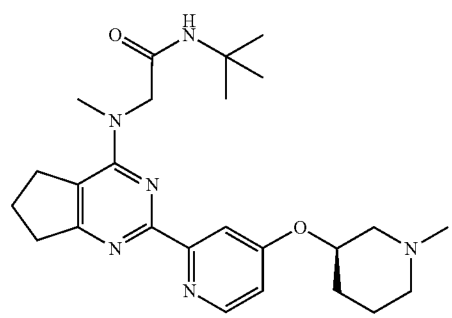 [SMILES: CN1CCC[C@@H](Oc2ccnc(-c3nc4c(c(N(C)CC(=O)NC(C)(C)C)n3)CCC4)c2)C1] | N-tert-butyl-2-{methyl[2-(4-{[(3R)-1-methylpiperidin-3-yl]oxy}pyridin-2-yl)-5H,6H,7H-cyclopenta[d]pyrimidin-4-yl]amino}acetamide | 453.3 |
| 490 | 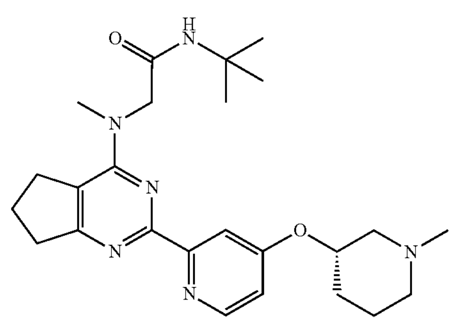 [SMILES: CN1CCC[C@H](Oc2ccnc(-c3nc4c(c(N(C)CC(=O)NC(C)(C)C)n3)CCC4)c2)C1] | N-tert-butyl-2-{methyl[2-(4-{[(3S)-1-methylpiperidin-3-yl]oxy}pyridin-2-yl)-5H,6H,7H-cyclopenta[d]pyrimidin-4-yl]amino}acetamide | 453.3 |
| 491 | 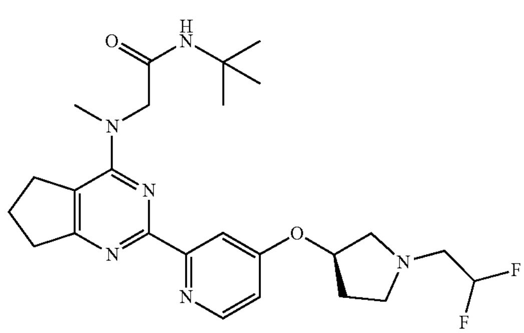 [SMILES: CN(CC(=O)NC(C)(C)C)c1nc(-c2cc(O[C@@H]3CCN(CC(F)F)C3)ccn2)nc2c1CCC2] | N-tert-butyl-2-{[2-(4-{[(3R)-1-(2,2-difluoroethyl)pyrrolidin-3-yl]oxy}pyridin-2-yl)-5H,6H,7H-cyclopenta[d]pyrimidin-4-yl](methyl)amino}acetamide | 489.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 492 | 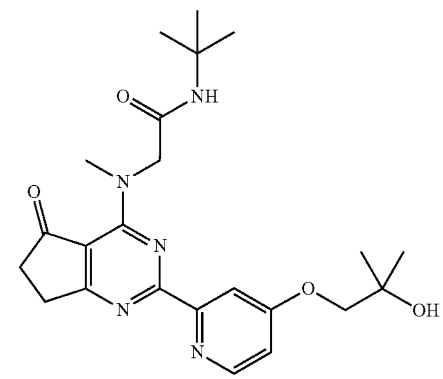 [SMILES: CN(CC(=O)NC(C)(C)C)c1nc(-c2cc(OCC(C)(C)O)ccn2)nc2c1C(=O)CC2] | N-tert-butyl-2-({2-[4-(2-hydroxy-2-methylpropoxy)pyridin-2-yl]-5-oxo-5H,6H,7H-cyclopenta[d]pyrimidin-4-yl}(methyl)amino)acetamide | 442.2 |
| 493 | 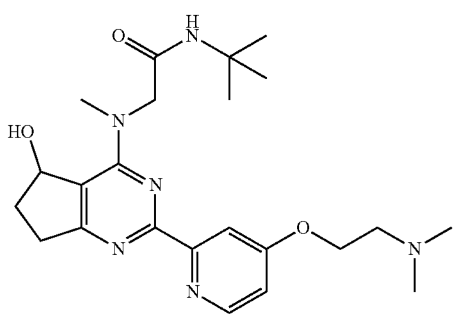 [SMILES: CN(C)CCOc1ccnc(-c2nc3c(c(N(C)CC(=O)NC(C)(C)C)n2)C(O)CC3)c1] | N-tert-butyl-2-[(2-{4-[2-(dimethylamino)ethoxy]pyridin-2-yl}-5-hydroxy-5H,6H,7H-cyclopenta[d]pyrimidin-4-yl)(methyl)amino]acetamide | 443.2 |
| 494 | 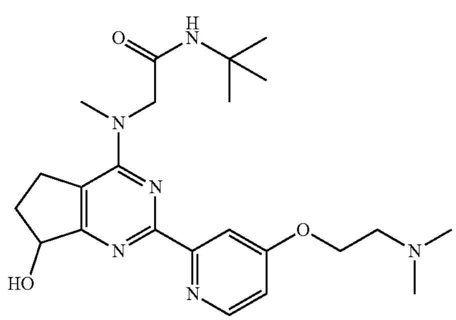 [SMILES: CN(C)CCOc1ccnc(-c2nc3c(c(N(C)CC(=O)NC(C)(C)C)n2)CCC3O)c1] | N-tert-butyl-2-[(2-{4-[2-(dimethylamino)ethoxy]pyridin-2-yl}-7-hydroxy-5H,6H,7H-cyclopenta[d]pyrimidin-4-yl)(methyl)amino]acetamide | 443.3 |
| 495 | 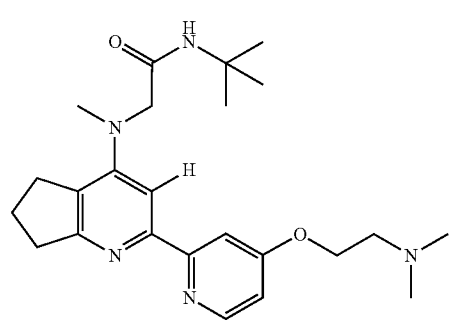 [SMILES: CN(C)CCOc1ccnc(-c2cc(N(C)CC(=O)NC(C)(C)C)c3c(n2)CCC3)c1] | N-tert-butyl-2-[(2-{4-[2-(dimethylamino)ethoxy]pyridin-2-yl}-5H,6H,7H-cyclopenta[b]pyridin-4-yl)(methyl)amino]acetamide | 426.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 496 | 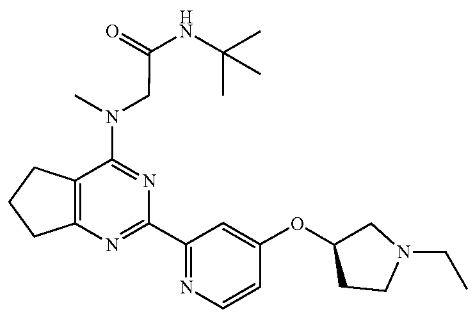 [SMILES: CCN1CC[C@@H](Oc2ccnc(-c3nc4c(c(N(C)CC(=O)NC(C)(C)C)n3)CCC4)c2)C1] | N-tert-butyl-2-{[2-(4-{[(3R)-1-ethylpyrrolidin-3-yl]oxy}pyridin-2-yl)-5H,6H,7H-cyclopenta[d]pyrimidin-4-yl](methyl)amino}acetamide | 453.3 |
| 497 | 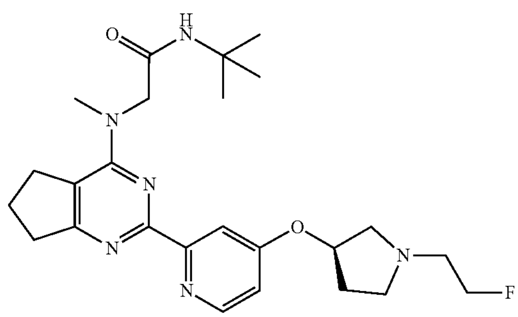 [SMILES: CN(CC(=O)NC(C)(C)C)c1nc(-c2cc(O[C@@H]3CCN(CCF)C3)ccn2)nc2c1CCC2] | N-tert-butyl-2-{[2-(4-{[(3R)-1-(2-fluoroethyl)pyrrolidin-3-yl]oxy}pyridin-2-yl)-5H,6H,7H-cyclopenta[d]pyrimidin-4-yl](methyl)amino}acetamide | 471.3 |
| 498 | 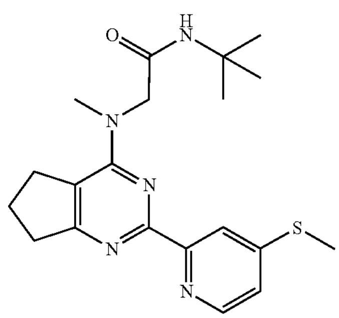 [SMILES: CSc1ccnc(-c2nc3c(c(N(C)CC(=O)NC(C)(C)C)n2)CCC3)c1] | N-tert-butyl-2-[methyl({2-[4-(methylsulfanyl)pyridin-2-yl]-5H,6H,7H-cyclopenta[d]pyrimidin-4-yl})amino]acetamide | 386.2 |
| 499 | 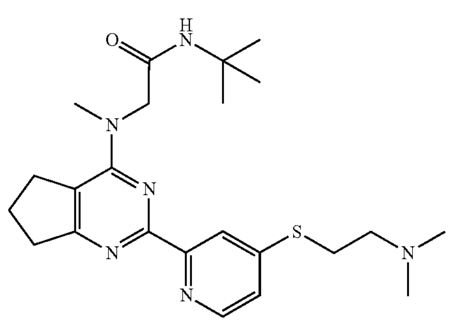 [SMILES: CN(C)CCSc1ccnc(-c2nc3c(c(N(C)CC(=O)NC(C)(C)C)n2)CCC3)c1] | N-tert-butyl-2-{[2-(4-{[2-(dimethylamino)ethyl]sulfanyl}pyridin-2-yl)-5H,6H,7H-cyclopenta[d]pyrimidin-4-yl](methyl)amino}acetamide | 443.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 500 | 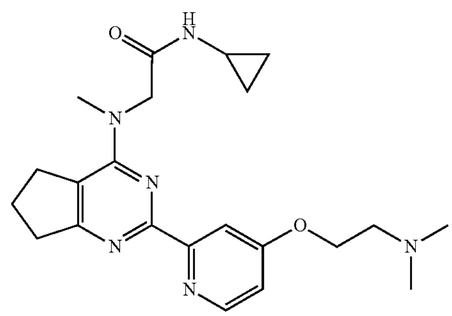 [SMILES: CN(C)CCOc1ccnc(-c2nc3c(c(N(C)CC(=O)NC4CC4)n2)CCC3)c1] | N-cyclopropyl-2-[(2-{4-[2-(dimethylamino)ethoxy]pyridin-2-yl}-5H,6H,7H-cyclopenta[d]pyrimidin-4-yl)(methyl)amino]acetamide | 411.3 |
| 501 | 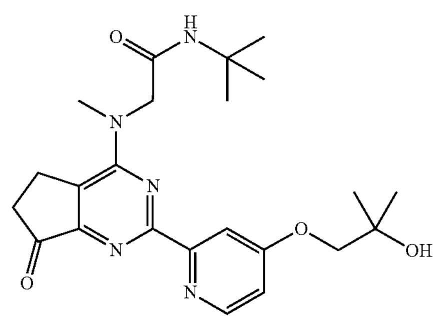 [SMILES: CN(CC(=O)NC(C)(C)C)c1nc(-c2cc(OCC(C)(C)O)ccn2)nc2c1CCC2=O] | N-tert-butyl-2-({2-[4-(2-hydroxy-2-methylpropoxy)pyridin-2-yl]-7-oxo-5H,6H,7H-cyclopenta[d]pyrimdin-4-yl}(methyl)amino)acetamide | 442.3 |
| 502 | 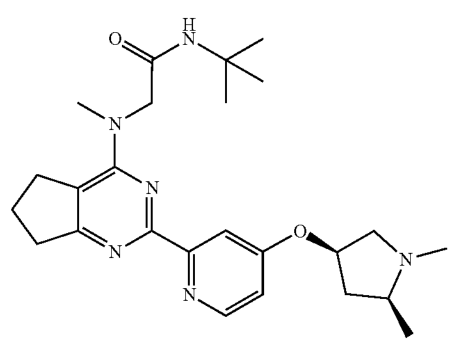 [SMILES: C[C@H]1C[C@@H](Oc2ccnc(-c3nc4c(c(N(C)CC(=O)NC(C)(C)C)n3)CCC4)c2)CN1C] | N-tert-butyl-2-{[2-(4-{[(3R,5S)-1,5-dimethylpyrrolidin-3-yl]oxy}pyridin-2-yl)-5H,6H,7H-cyclopenta[d]pyrimidin-4-yl](methyl)amino}acetamide | 453.4 |
| 503 | 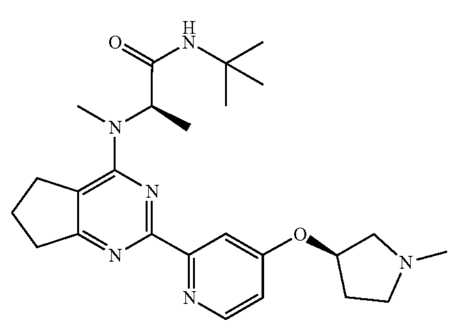 [SMILES: C[C@H](C(=O)NC(C)(C)C)N(C)c1nc(-c2cc(O[C@@H]3CCN(C)C3)ccn2)nc2c1CCC2] | (2R)-N-tert-butyl-2-{methyl[2-(4-{[(3R)-1-methylpyrrolidin-3-yl]oxy}pyridin-2-yl)-5H,6H,7H-cyclopenta[d]pyrimidin-4-yl]amino}propanamide | 453.4 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 504 | 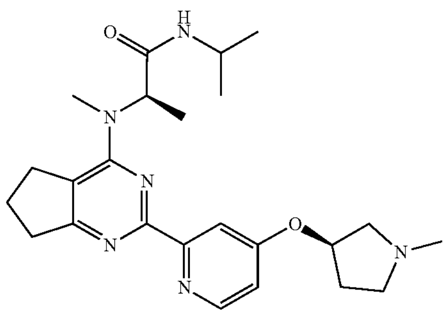 [SMILES: CC(C)NC(=O)[C@@H](C)N(C)c1nc(-c2cc(O[C@@H]3CCN(C)C3)ccn2)nc2c1CCC2] | (2R)-2-{methyl[2-(4-{[(3R)-1-methylpyrrolidin-3-yl]oxy}pyridin-2-yl)-5H,6H,7H-cyclopenta[d]pyrimidin-4-yl]amino}-N-(propan-2-yl)propanamide | 439.3 |
| 505 | 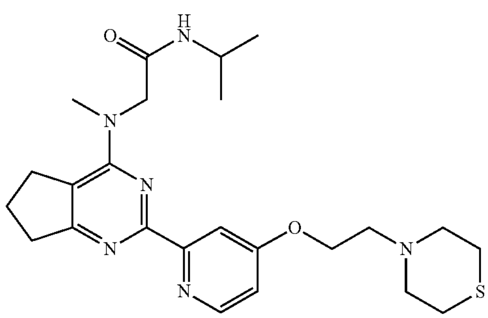 [SMILES: CC(C)NC(=O)CN(C)c1nc(-c2cc(OCCN3CCSCC3)ccn2)nc2c1CCC2] | 2-[methyl(2-{4-[2-(thiomorpholin-4-yl)ethoxy]pyridin-2-yl}-5H,6H,7H-cyclopenta[d]pyrimidin-4-yl)amino]-N-(propan-2-yl)acetamide | 471.3 |
| 506 | 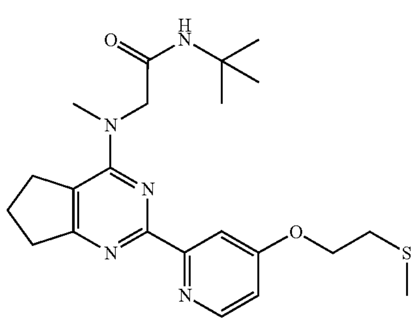 [SMILES: CSCCOc1ccnc(-c2nc3c(c(N(C)CC(=O)NC(C)(C)C)n2)CCC3)c1] | N-tert-butyl-2-[methyl(2-{4-[2-(methylsulfanyl)ethoxy]pyridin-2-yl}-5H,6H,7H-cyclopenta[d]pyrimidin-4-yl)amino]acetamide | 430.2 |
| 507 | 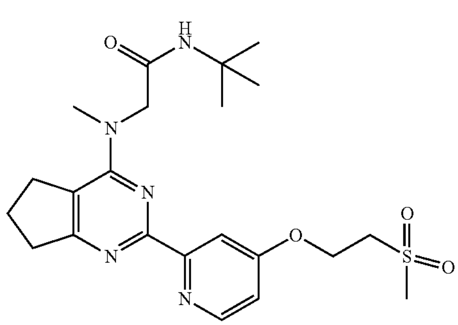 [SMILES: CN(CC(=O)NC(C)(C)C)c1nc(-c2cc(OCCS(C)(=O)=O)ccn2)nc2c1CCC2] | N-tert-butyl-2-({2-[4-(2-methanesulfonylethoxy)pyridin-2-yl]-5H,6H,7H-cyclopenta[d]pyrimidin-4-yl}(methyl)amino)acetamide | 462.3 |

TABLE 1-continued

Where the mass for a compound is not provided in Table 1, the mass can be found for the compound in the synthetic examples.

| Compound No. | Structure | IUPAC Name | Mass Found (M + 1) |
|---|---|---|---|
| 508 | 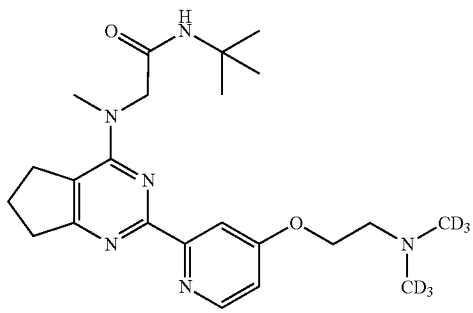 [SMILES: [2H]C([2H])([2H])N(CCOc1ccnc(-c2nc3c(c(N(C)CC(=O)NC(C)(C)C)n2)CCC3)c1)C([2H])([2H])[2H]] | N-tert-butyl-2-{[2-(4-{2-[di(2H3)methylamino]ethoxy}pyridin-2-yl)-5H,6H,7H-cyclopenta[d]pyrimidin-4-yl](methyl)amino}acetamide | 433.3 |
| 509 | 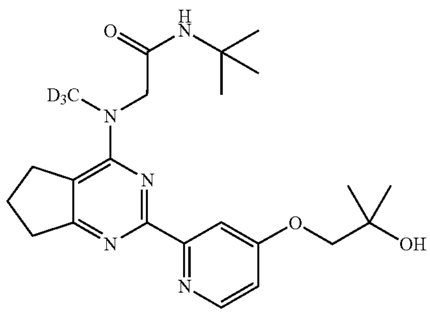 [SMILES: [2H]C([2H])([2H])N(CC(=O)NC(C)(C)C)c1nc(-c2cc(OCC(C)(C)O)ccn2)nc2c1CCC2] | N-tert-butyl-2-({2-[4-(2-hydroxy-2-methylpropoxy)pyridin-2-yl]-5H,6H,7H-cyclopenta[d]pyrimidin-4-yl}((2H3)methyl)amino)acetamide | 431 |

III. Pharmaceutical Compositions and Modes of Administration

Compounds provided herein are usually administered in the form of pharmaceutical compositions. Thus, provided herein are also pharmaceutical compositions that comprise one or more of the compounds described herein or a pharmaceutically acceptable salt, a stereoisomer, or a mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, a stereoisomer, or a mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, a stereoisomer, or a mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, a stereoisomer, or a mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

IV. Methods of Treatment

In certain embodiments, the subject matter described herein is directed to a method of inhibiting iron transport mediated by ferroportin in a subject, comprising administering to a subject an effective amount of a compound of Formula I or Formula I', or a pharmaceutically acceptable salt thereof.

In certain embodiments, the subject matter described herein is directed to a method of treating a subject afflicted with a disease related to or caused by reduced hepcidin levels, increased ferroportin levels, reduced sensitivity of ferroportin to hepcidin, increased iron levels, increased iron absorption, iron overload, increased erythropoiesis, stress erythropoiesis, or ineffective erythropoiesis, comprising administering to the subject an effective amount of a compound of Formula I or Formula I'.

In certain embodiments, the disease is related to or caused by reduced hepcidin levels, reduced sensitivity of ferroportin to hepcidin, a hemoglobinopathy, or iron overload.

In certain embodiments, the disease is related to or caused by reduced hepcidin levels or reduced sensitivity of ferroportin to hepcidin.

In certain embodiments, the disease is hemochromatosis.

In certain embodiments, the disease is related to or caused by a hemoglobinopathy.

In certain embodiments, the disease is thalassemia, hemoglobin E disease, hemoglobin H disease, or sickle cell disease.

In certain embodiments, the disease is sickle cell disease.

In certain embodiments, the sickle cell disease is sickle cell anemia.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The ferroportin inhibition activity of the compounds of Formula I or Formula I' and pharmaceutically acceptable salts thereof provide methods particularly suitable for the use in the inhibition of iron transport mediated by ferroportin. As such, the compounds of Formula I or Formula I' and pharmaceutically acceptable salts thereof are useful in the prophylaxis and/or treatment of a disease related to or caused by reduced hepcidin levels, increased ferroportin levels, reduced sensitivity of ferroportin to hepcidin, increased iron levels, increased iron absorption, iron overload, increased erythropoiesis, stress erythropoiesis, or ineffective erythropoiesis.

Further, the compounds of Formula I or Formula I' are suitable for the use in an adjunctive therapy by limiting the amount of iron available to pathogenic microorganisms, e.g. the siderophilic bacteria *Vibrio vulnificus* and *Yersinia enterocolitica*, and common pathogens (e.g. *Escherichia coli*), thereby preventing or treating infections, inflammation, sepsis, and septic shock caused by said pathogenic microorganisms.

In certain embodiments, the subject matter described herein is directed to a method of inhibiting iron transport mediated by ferroportin in a subject, comprising administering to the subject an effective amount of a compound of Formula I or Formula I' or a pharmaceutically acceptable salt thereof.

In certain embodiments, the subject matter described herein is directed to a method of treating a subject afflicted with a disease related to or caused by reduced hepcidin levels, increased ferroportin levels, reduced sensitivity of ferroportin to hepcidin, a hemoglobinopathy, increased iron levels, increased iron absorption, iron overload (e.g. due to blood transfusions), increased erythropoiesis, stress erythropoiesis, or ineffective erythropoiesis, comprising administering to the subject an effective amount of a compound of Formula I or Formula I' or a pharmaceutically acceptable salt thereof. In aspects of these embodiments, the treating comprises inhibiting iron transport mediated by ferroportin in the subject.

In certain embodiments, the subject matter described herein is directed to a method of treating a subject afflicted with a disease related to or caused by reduced hepcidin levels, reduced sensitivity of ferroportin to hepcidin, a hemoglobinopathy, or iron overload.

In certain embodiments, the subject matter described herein is directed to a method of treating a subject afflicted with a disease related to or caused by reduced hepcidin levels or reduced sensitivity of ferroportin to hepcidin. In a certain aspect of this embodiment, the disease is hemochromatosis.

In certain embodiments, the subject matter described herein is directed to a method of treating a subject afflicted with a disease related to or caused by a hemoglobinopathy. In a certain aspects of this embodiment, the disease is thalassemia, hemoglobin E disease, hemoglobin H disease, or sickle cell disease. In certain aspects of this embodiment, the disease is sickle cell disease. In certain aspect of this embodiment, the disease is sickle cell anemia.

In certain embodiments, the diseases being associated with, being related to, being caused by or leading to increased iron levels, increased iron absorption, iron overload (e.g., tissue iron overload) or ineffective erythropoiesis comprise thalassemia, hemoglobinopathy, such as hemoglobin E disease (HbE), hemoglobin H disease (HbH), haemochromatosis, hemolytic anemia, such as sickle cell anemia and congenital dyserythropoietic anemia. Additional diseases being associated with, being related to, being caused by or leading to increased iron levels, increased iron absorption, iron overload (e.g., tissue iron overload) include neurodegenerative diseases, such as for example Alzheimer's disease, Parkinson's disease, Huntington's disease, multiple sclerosis, Wilson's disease, amyotrophic lateral sclerosis (ALS), and Friedreich's Ataxia, wherein the compounds and methods are considered to be effective by limiting the deposition or increase of iron in tissue or cells; conditions associated with the formation of radicals, reactive oxygen species (ROS) and oxidative stress caused by excess iron or iron overload; cardiac, liver and endocrine damage caused by excess iron or iron overload; inflammation triggered by excess iron or iron overload; diseases associated with ineffective erythropoiesis, such as myelodysplastic syndromes (MDS, myelodysplasia), polycythemia vera, and congenital dyserythropoietic anemia; diseases, disorders and/or disease conditions that comprise iron overload caused by mutations in genes involved in sensing the systemic iron stores, such as hepcidin/hepcidin antimicrobial peptide (HAMP), hemochromatosis protein (HFE), hemojuvelin (HJV) and transferrin receptor 2 (TFR2), such as in particular diseases related to HFE and HJV gene mutations; diseases related to ferroportin mutations; chronic hemolysis associated diseases, sickle cell diseases (including sickle cell anemia (HbSS) as well as hemoglobin SC disease (HbSC), hemoglobin S beta-plus-thalassemia (HbS/β+), and hemoglobin S beta-zero-thalassemia (HbS/β0)), red cell membrane disorders, Glucose-6-phosphate dehydrogenase deficiency (G6PD deficiency), erythropoietic porphyria, Friedreich's Ataxia, as well as subgroups of iron overload such as transfusional iron overload, iron intoxication, pulmonary hemosiderosis, osteopenia, insulin resistance, African iron overload, Hallervordan Spatz disease, hyperferritinemia, ceruloplasmin deficiency, neonatal hemochromatosis and red blood cell disorders comprising thalassemia, including alpha thalassemia, beta thalassemia and delta thalassemia, thalassemia intermedia, sickle cell disease and myelodyplastic syndrome; liver diseases (e.g. hepatitis B virus infection, hepatitis C virus infection, alcoholic liver disease, autoimmune hepatitis), other conditions including ataxia, Friedreich's ataxia, age-related macular degeneration, age-related cataract, age-related retinal diseases and neurodegenerative disease, such as pantothenate kinase-associated neurodegeneration, restless leg syndrome and Huntington's disease. In certain embodiments, the disease is sickle cell anemia. The ferroportin inhibition activity, for instance by inducing internalization of ferroportin, of the compounds of Formula I and pharmaceutically acceptable salts thereof can be determined by the assays described herein as well as those described in WO2018/192973, incorporated herein by reference in its entirety.

The activity of the compounds of Formula I or Formula I' in the treatment of sickle cell anemia (sickle cell disease) can be determined by using a mouse model, such as e.g. described by Yulin Zhao et al. in "MEK1/2 inhibitors reverse acute vascular occlusion in mouse models of sickle cell disease"; The FASEB Journal Vol. 30, No. 3, pp 1171-1186, 2016. Said mouse model can be suitably adapted to determine the activity of the compounds of Formula I or Formula I' in the treatment of sickle cell anemia. In certain embodiments, the disease is caused by a lack of hepcidin or iron metabolism disorders, particularly iron overload states, such as thalassemia, sickle cell disease and hemochromatosis. In certain embodiments, the disease is related to or caused by reduced hepcidin levels, increased iron levels, increased iron absorption, iron overload, increased erythropoiesis, stress erythropoiesis, or ineffective erythropoiesis. In certain embodiments, the disease is selected from the group consisting of thalassemia, hemoglobinopathy, hemoglobin E disease, hemoglobin H disease, haemochromatosis, and hemolytic anemia.

In certain embodiments, the methods of administering and treating described herein further comprise co-administration of one or more additional pharmaceutically active compounds or in combination with a blood transfusion.

In a combination therapy, the pharmaceutically active compounds can be administered at the same time, in the same formulation, or at different times. Such combination therapy comprises co-administration of a compound of Formula I or Formula I' or a pharmaceutically acceptable salt thereof with at least one additional pharmaceutically active compound. Combination therapy in a fixed dose combination therapy comprises co-administration of a compound of Formula I or Formula I' or a pharmaceutically acceptable salt thereof with at least one additional pharmaceutically active compound in a fixed-dose formulation. Combination therapy in a free dose combination therapy comprises co-administration of a compound of Formula I or Formula I' or a pharmaceutically acceptable salt thereof and at least one additional pharmaceutically active compound in free doses of the respective compounds, either by simultaneous administration of the individual compounds or by sequential use of the individual compounds over a period of time.

The additional pharmaceutically active compound includes in particular drugs for reducing iron overload (e.g., Tmprss6-ASO or siRNA) or iron chelators, in particular curcumin, SSP-004184, Deferitrin, deferasirox, deferoxamine and/or deferiprone, or antioxidants such as n-acetyl cysteine, anti-diabetics such as GLP-1 receptor agonists, antibiotics such as penicillin, vancomycin (Van) or tobramycin, antifungal drugs, anti-viral drugs such as interferon-a or ribavirin, drugs for the treatment of malaria, anticancer agents, drugs for the treatment of neurodegenerative diseases such as Alzheimer's disease and Parkinson's disease (e.g., dopamine agonists such as Levodopa), or immunosuppressants (cyclosporine A or cyclosporine A derivatives), iron supplements, vitamin supplements, red cell production stimulators (e.g., erythropoietin, Epo), anti-inflammatory agents, anti-thrombolytics, statins, vasopressors and inotropic compounds. A further object of the present invention relates to the use of the above combinations for the prophylaxis and/or treatment of diseases caused by a lack of hepcidin or iron metabolism disorders, such as particularly iron overload states such as in particular thalassemia, sickle cell disease and hemochromatosis and other disorders as described in the present application.

In certain embodiments, the subject matter described herein is directed to a method of treating beta-thalassemia (b-thalassemia) in a subject, comprising administering to the subject an effective amount of a compound of Formula I or a pharmaceutically acceptable salt thereof. The compounds of Formula I as defined herein, act as ferroportin inhibitors and can be used for treating severe forms of b-thalassemia, such as transfusion-dependent b-thalassemia, including in particular b-thalassemia major and hemoglobin E b-thalassemia and the symptoms and pathological conditions associated therewith, such as in particular defective red blood cell production in the bone marrow, ineffective erythropoiesis, low hemoglobin levels/anemia, multiple organ dysfunction, iron overload, liver iron loading and cardiac iron overload, paleness, fatigue, jaundice, and splenomegaly.

In particular, a severe form of b-thalassemia is transfusion-dependent b-thalassemia (TDT), including in particular b-thalassemia major and severe forms of hemoglobin E b-thalassemia. Severe forms of b-thalassemia and hemoglobin E 13-thalassemia, require that patients suffering therefrom achieve regular blood transfusions/Red Blood Cell transfusions (RBC transfusions). Such severe forms of b-thalassemia are thus also summarized as transfUsion-dependent b-thalassemia (TDT). Thus the methods of treating severe forms of b-thalassemia, such as in particular transfusion-dependent b-thalassemia (TDT), include in particular b-thalassemia major and severe forms of hemoglobin E b-thalassemia by administering to a subject in need thereof one or more of the compounds of Formula I as described herein.

The subject may be: suffering from b-thalassemia or haemoglobin E b-thalassemia and requiring regular blood transfusion; suffering from b-thalassemia major and/or severe haemoglobin E b-thalassemia, more particularly to patients suffering from b-thalassemia major.

The methods of treating beta-thalassemia can result in: reduced NTBI levels in a subject; reduced LPI levels in a subject; reduced alpha globin aggregate levels in a subject; reduced ROS levels in RBCs of a subject; a decrease in liver iron concentration in the subject; a decrease in myocardial iron concentration in the subject; an improvement of at least one of the parameters Hct, MCV, MCH, ROW and reticulocyte numbers in the subject; in an erythroid response, which comprises a reduction in transfusion burden in the subject; a reduction of transfusion burden in the subject compared to the transfusion burden prior to treatment using the methods; achieving no longer requiring a transfusion in a transfusion-dependent b-thalassemia subject; reduced serum ferritin levels in the subject; a reduction of the symptoms associated with one or more transfusion-dependent b-thalassemia clinical complications. Nonlimiting examples of transfusion-dependent b-thalassemia symptoms include growth retardation, pallor, jaundice, poor musculature, genu valgum, hepatosplenomegaly, leg ulcers, development of masses from extramedullary hematopoiesis, skeletal changes resulting from expansion of the bone marrow, and clinical complications of chronic red blood cell transfusions, such as, for example hepatitis B virus infection, hepatitis C virus infection and human immunodeficiency virus infection, alloimmunization, and organ damage due to iron overload, such as, for example, liver damage, heart damage and endocrine gland damage. Although the compounds of the formula (I) are not expected to directly affect growth differentiation factor 11 (GDF11), decrease of skeletal deformities can also occur caused by reduced extramedullary erythropoiesis.

The following parameters can be determined to evaluate the efficacy of the compounds of the present invention in the new medical use: serum iron, NTBI levels, LPI (Labile Plasma Iron) levels, erythropoietin, TSAT (transferrin saturation), Hb (hemoglobin), Hct (haematocrit), MCV (Mean Cell Volume), MCH (Mean Cell Hemoglobin), RDW (Red Blood Cell Distribution Width) and reticulocyte numbers, complete blood counts, spleen and liver weight, erythropoiesis in spleen and bone marrow, spleen and liver iron content and alpha-globin aggregates in RBC membranes. The determination can be carried out using conventional methods of the art, in particular by those described below in more detail. The compounds (I) of the present invention are suitable to improve at least one of these parameters.

The methods can be prior to or accompanying blood transfusion to prevent or at least attenuate occurrence of transfusion-caused pathological conditions.

In certain embodiments, the subject matter described herein is directed to a method of preventing and treating kidney injuries in a subject, comprising administering to the subject an effective amount of a compound of Formula I or a pharmaceutically acceptable salt thereof. In certain aspects of these embodiments, the compound of Formula I can be co-administered with another pharmaceutically active compound. In certain aspects of these embodiments, the kidney injuries are those induced by catalytic free iron. In certain aspects of these embodiments, the kidney injuries are selected from renal ischemia-reperfusion injury (IRI), ischemic injury and acute kidney injuries. In a further aspect, kidney injuries are selected from acute kidney injury (AK!), renal ischemia-reperfusion injury (IRI), ischemic injury and AKI caused by ischemic injury, AKI following surgery or surgical intervention, such as in particular following cardiac surgery most often with procedures involving cardiopulmonary bypass, other major chest or abdominal surgery, and kidney injury associated with RBC transfusion.

The term "preventing" and the like includes the protection from ischemic renal injury, avoidance of occurrence of AKI or at least reducing the severity of AKI following ischemic injury, RBC transfusion or a surgery intervention e.g. by administering the compounds prior to or accompanying or shortly after an ischemic event, RBC transfusion or the surgery intervention to prevent or at least attenuate occurrence of kidney injuries induced by catalytic free iron.

Free catalytic iron or labile iron or NTBI is considered as a main cause of kidney injury, such as in particular AKI triggered by ischemia. The administration of the ferroportin inhibitor compounds of formula (I) as described herein can protect against the damaging effects of catalytic free iron. Without being bound to theory, the ferroportin inhibitors described herein can reduce or prevent the formation of catalytic free iron or NTBI by sequestering iron in macrophages of liver and spleen, therewith reducing its levels in plasma and reducing the risk of ROS formation. The compounds of Formula I described herein act as ferroportin inhibitors, and have the potential to sequester iron in macrophages, thereby interrupting the cycle of self-sustaining release of catalytic free iron. The compounds of the Formula I are suitable for the prevention and treatment of the kidney injuries described herein by limiting reactive oxygen species (ROS) to avoid kidney tissue injury. Further to catalytic free iron, NTBI and LPI (Labile Plasma Iron) can cause kidney injuries. NTBI encompasses all forms of serum iron that are not tightly associated with transferrin and is chemically and functionally heterogeneous. LPI represents a component of NTBI that is both redox active and chelatable, capable of permeating into organs and inducing tissue iron overload.

The following parameters can be determined to evaluate the efficacy of the compounds for treating kidney injuries: plasma creatinine, glomerular filtration rate (including estimated glomerular filtration rate eGFR), urine albumin excretion, urine neutrophil gelatinase-associated lipocalin (NGAL), NTBI, LPI, RBC hemolysis, blood urea nitrogen (BUN), plasma hemoglobin (Hb), total plasma iron, plasma hepcidin, renal neutrophil infiltration, serum IL-6, spleen, kidney and/or liver iron content, renal ferroportin, KIM-1 (Kidney Injury Molecule-1) as an acute marker for kidney injury in blood and urine, and H-ferritin. Additionally or alternatively, the efficacy of the compounds of the present invention can be determined via the kidney tubular injury score, such as e.g. the CSA-NGAL score (Cardiac Surgery Associated NGAL Score) for detecting acute tubular damage as described in more detail below, the KDIGO score described in more detail below or the EGTI score comprising Endothelial, Glomerular, Tubular and Interstitial (EGTI) components to evaluate histology (described e. g, by: Khalid et al. 'Kidney ischaemia reperfusion injury in the rat the EGTI scoring system as a valid and reliable tool for histological assessment" Journal of Histology & Histopatholoy, Vol. 3, 2016).

The methods of treating or preventing kidney injury can result in a decrease of serum creatinine (sCr) in the subject. The methods of treating or preventing kidney injury can result in a corrected (decreased) urine albumin excretion in the subject. The methods of treating or preventing kidney injury can result in a decrease of blood urea nitrogen (BUN) in the subject. The methods of treating or preventing kidney injury can result in a decrease of total plasma iron in the subject. The methods of treating or preventing kidney injury can result in a decrease of interleukin-6 (!L-6) levels in the subject. The methods of treating or preventing kidney injury can result in a decrease of KIM-1 levels in the subject. The methods of treating or preventing kidney injury can result in an increase in spleen and/or liver iron concentration in the subject. The methods of treating or preventing kidney injury can result in a decrease in kidney iron concentration in the subject. The methods of treating or preventing kidney injury can result in reduced NTBI levels. The methods of treating or preventing kidney injury can result in reduced LPI levels in the subject. The methods of treating or preventing kidney injury can result in an inhibition of tubular injury, such as tubular necrosis. The methods of treating or preventing kidney injury can result in an inhibition of apoptosis. The methods of treating or preventing kidney injury can result in a reduced IRI-induced renal neutrophil infiltration. The methods of treating or preventing kidney injury can result in reduced ROS levels in kidney tissue of the subject. The methods of treating or preventing kidney injury can result in corrected (increased) kidney H-ferritin levels in the subject. In particular, the methods of treating or preventing kidney injury can reduce the occurrence of AKI, renal ischemia-reperfusion injury and AKI caused by ischemic injury, AKI following surgery or surgical intervention, such as in particular following cardiac surgery most often with procedures involving cardiopulmonary bypass, other major chest or abdominal surgery, and kidney injury associated with RBC transfusion. The methods of treating or preventing kidney injury can comprise a) decrease, accelerated decrease or prevention of increase of serum creatinine; and/or b) increase or prevention of decrease of estimated glomerular filtration rate (eGFR); and/or c) decrease or prevention of increase of renal ferroportin; and/or d) increase or prevention of decrease of H-ferritin levels; and/or e) decrease or prevention of increase of renal neutrophil infiltration; and/or
f) decrease or prevention of increase of serum IL-6 levels.

V. Methods of Preparing Compounds of Formula I and Pharmaceutically Acceptable Salts Thereof Compounds can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g., Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database). DTT refers to dithiothreitol. DHAA refers to dehydroascorbic acid.

Synthetic chemistry transformations and protecting group methodologies (protection and deprotection) useful in synthesizing compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus, according to a further aspect, there is provided a compound library comprising at least 2 compounds, or pharmaceutically acceptable salts thereof.

The subject matter described herein is directed to the following embodiments.

1A. A compound of Formula (I):

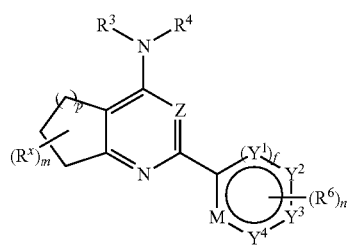

(I)

or a pharmaceutically acceptable salt thereof; wherein,
Z is N or CH;
$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$-alkyl, cyano, $C_3$-$C_7$ cycloalkyl-$C_1$-$C_3$ alkoxy, $NR^G R^H$, halo-$C_1$-$C_3$ alkoxy, and $C_3$-$C_6$ cycloalkyl;
  wherein $R^G$ and $R^H$ are each independently hydrogen or $C_1$-$C_3$ alkyl; or
two $R^6$ groups, taken together with the atom to which each is attached, form a 5- or 6-membered heterocyclyl, $C_3$-$C_7$ cycloalkyl, $C_6$-$C_{10}$ aryl, or 5- to 10-membered heteroaryl;
n is 0, 1, 2, or 3;
$Y^1$, $Y^2$, $Y^3$, and $Y^4$ are each independently selected from the group consisting of CH, N, NH, O, S, and C (when $R^6$ is attached thereto), provided that 1 or 2 of $Y^1$, $Y^2$, $Y^3$, and $Y^4$ can be N, NH, O, or S;
f is 0 or 1;
p is 1 or 2;
$R^x$, in each instance, is halogen, $C_1$-$C_6$ alkyl, $C_1$-$C_3$ alkoxy, hydroxy, or cyano;
m is 0, 1, or 2;
$R^3$ is selected from the group consisting of hydrogen, $C_1$-$C_3$ alkyl, hydroxy-$C_1$-$C_3$ alkyl, cyclopropyl, and phenyl;
$R^4$ is selected from the group consisting of:
  i. (5- to 10-membered monocyclic or bicyclic fused heteroaryl)-$C_1$-$C_3$ alkyl branched or linear, or (6- or 7-membered monocyclic heterocyclyl)-$C_1$-$C_3$ alkyl branched or linear;
    wherein,
      when p is 1, $C_1$-$C_3$ alkyl in the (5- to 10-membered monocyclic or bicyclic fused heteroaryl)-$C_1$-$C_3$ alkyl is linear;
  and,
  ii.

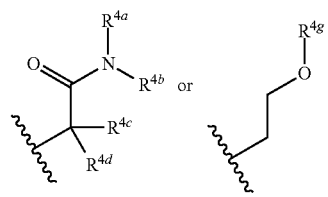

wherein,
  $R^{4a}$ and $R^{4g}$ are each independently selected from the group consisting of hydrogen, $C_1$-$C_6$ alkyl, hydroxy-$C_1$-$C_6$ alkyl, $C_1$-$C_3$ alkoxy-$C_1$-$C_6$ alkyl, $C_3$-$C_7$ cycloalkyl, 5- to 10-membered monocyclic, bicyclic fused, or spiro heterocyclyl, $C_6$-$C_{10}$ aryl, 5- to 10-membered monocyclic or bicyclic fused heteroaryl, ($C_6$-$C_{10}$ aryl)-$C_1$-$C_3$ alkyl, and (5- to 10-membered monocyclic heteroaryl)-$C_1$-$C_3$ alkyl;
    wherein the cycloalkyl, heterocyclyl, aryl, heteroaryl, arylalkyl, or heteroaryl-alkyl of $R^{4a}$ or $R^{4g}$ is optionally substituted with one, two, or three substituents, each independently selected from the group consisting of halogen, $C_1$-$C_6$ alkyl, haloalkyl, hydroxy, $C_1$-$C_3$ alkoxy, oxo, $C_3$-$C_7$ cycloalkyl, and 5- to 10-membered monocyclic, bicyclic fused, or spiro heterocyclyl;
  $R^{4b}$ is hydrogen or $C_1$-$C_6$ alkyl; or
  $R^{4a}$ and $R^{4b}$ taken together with the atom to which each is attached form a 5- to 7-membered heterocyclyl; or
  $R^{4b}$ and $R^{4c}$ taken together with the atom to which each is attached form a 5- to 7-membered heterocyclyl optionally substituted with one, two, or three substituents, each independently selected from the group consisting of hydroxy, halo, and $C_1$-$C_3$ alkyl; or $R^{4c}$ and $R^{4d}$ are each independently selected from the group consisting of hydrogen, $C_1$-$C_3$ alkoxy, hydroxy, $C_1$-$C_3$ alkyl-thio-$C_1$-$C_3$ alkyl, hydroxy-$C_1$-$C_6$ alkyl, $C_1$-$C_6$ alkoxy-$C_1$-$C_3$ alkyl, $C_3$-$C_7$ cycloalkyl, and $C_1$-$C_3$ alkyl; or $R^{4c}$ and $R^{4d}$ taken together with the atom to which each is attached form a $C_3$-$C_7$ cycloalkyl;

or, when p is 1, $R^3$ and $R^4$ taken together with the nitrogen atom to which each is attached can form a:
  i. 7-membered bicyclic fused heterocyclyl, 7-membered bridged heterocyclyl, or 7-membered monocyclic heterocyclyl containing one or two heteroatoms;
     wherein when said 7-membered monocyclic heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and,
     when said 7-membered monocyclic heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, haloalkyl, and $C_6$-$C_{10}$ aryl; and
       wherein said aryl is optionally substituted with one or two substituents, each individually selected from the group consisting of $C_1$-$C_3$ alkoxy, hydroxy, halogen, and $C_1$-$C_3$ alkyl;
  ii. 4- or 6-membered monocyclic heterocyclyl containing one heteroatom;
      wherein said 4-membered monocyclic heterocyclyl is optionally substituted with one or two substituents, each independently selected from the group consisting of halogen, $C_1$-$C_3$ alkoxy, oxo, and —$(CH_2)_sC(=O)NR^kR^l$;
      wherein, s is 0, 1, 2, or 3;
      $R^k$ is hydrogen or $C_1$-$C_3$ alkyl; and
      $R^l$ is selected from the group consisting of hydrogen, hydroxy, $C_1$—$C_3$ alkyl, $C_3$-$C_7$ cycloalkyl, and $C_6$-$C_{10}$ aryl;
      wherein said 6-membered monocyclic heterocyclyl is optionally substituted with one or two substituents, each independently selected from the group consisting of $C_1$-$C_3$ alkoxy, oxo, halogen, cyano, and $NR^qR^w$;
        wherein $R^q$ is hydrogen or $C_1$-$C_3$ alkyl, and $R^w$ is $C_6$-$C_{10}$ aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy;
or;
  iii. 8-, 9-, 10- or 11-membered bicyclic fused heterocyclyl, or 12-membered bicyclic bridged, fused heterocyclyl, wherein said 8-, 9-, or 11-membered heterocyclyl contains one heteroatom and said 10- or 12-membered heterocyclyl contains one or two heteroatoms; and wherein said 10-, 11-, or 12-membered heterocyclyl is optionally substituted with one, two, or three substituents, each independently selected from the group consisting of halogen, $C_1$-$C_3$ alkyl, $C_1$-$C_3$ alkoxy, and hydroxy;

or, when p is 2, $R^3$ and $R^4$ taken together with the nitrogen atom to which each is attached can form a:
  i. 6-membered monocyclic heterocyclyl containing one heteroatom, optionally with one or two substituents, each independently selected from the group consisting of halogen, hydroxy-($C_1$-$C_6$ alkyl), hydroxy, oxo, and $C_1$-$C_3$ alkoxy; or
  ii. 4- or 7-membered monocyclic heterocyclyl containing one or two heteroatoms, or 7-, 8-, 9, 10-, or 11-membered bicyclic bridged, fused, or spiro heterocyclyl containing one, two, or three heteroatoms, optionally substituted with one or two substituents, each independently selected from the group consisting of halogen, oxo, cyano, $C_1$-$C_3$ alkyl, hydroxy, $NR^GR^H$, and —$(CH_2)_sC(=O)NR^kR^l$;

provided that when the structure of Formula (I) is

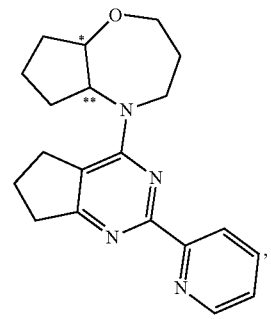 [SMILES: c1ccc(-c2nc3c(c(N4CCCOC5CCCC54)n2)CCC3)nc1]

* is ⦗H-wedge⦘ and ** is ⦗H-dash⦘; or

* is ⦗H-dash⦘ and ** is ⦗H-dash⦘;

and, wherein the compound of Formula (I) is not:
N-((1,4-dioxan-2-yl)methyl)-2-(pyridin-2-yl)-6,7-dihydro-5H-cyclopenta[d]pyrimidin-4-amine;
4-(piperidin-1-yl)-2-(pyridin-2-yl)-5,6,7,8-tetrahydroquinazoline;
4-(azepan-1-yl)-2-(6-propylpyridin-2-yl)-5,6,7,8-tetrahydroquinazoline;
1-propyl-4-(2-(pyridin-2-yl)-6,7-dihydro-5H-cyclopenta[d]pyrimidin-4-yl)-1,4-diazepan-2-one; or
2-(2-(pyridin-2-yl)-6,7-dihydro-5H-cyclopenta[d]pyrimidin-4-yl)-1,2-oxazepane; or a salt thereof.

2A. The compound of embodiment 1A,
wherein,
Z is N;
$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$-alkyl, and $NR^GR^H$;
  wherein $R^G$ and $R^H$ are each independently hydrogen or $C_1$-$C_3$ alkyl; or
  wherein two $R^6$ groups, taken together with the atom to which each is attached, form a 5- or 6-membered heterocyclyl, $C_6$-$C_{10}$ aryl, or 5- to 10-membered heteroaryl;
n is 0, 1, or 2;
$Y^1$, $Y^2$, $Y^3$, and $Y^4$ are each independently selected from the group consisting of CH, N, NH, and C (when $R^6$ is attached thereto), provided that 1 or 2 of $Y^1$, $Y^2$, $Y^3$, and $Y^4$ can be N or NH;

f is 0 or 1;
p is 1 or 2;
m is 0;
$R^3$ is selected from the group consisting of hydrogen, $C_1$-$C_3$ alkyl, and hydroxy-$C_1$-$C_3$-alkyl;
$R^4$ is selected from the group consisting of:
i. (5- to 10-membered monocyclic or bicyclic fused heteroaryl)-$C_1$-$C_3$ alkyl branched or linear;
wherein,
when p is 1, $C_1$-$C_3$ alkyl in the (5- to 10-membered monocyclic or bicyclic fused heteroaryl)-$C_1$-$C_3$ alkyl is linear;
and,
ii.

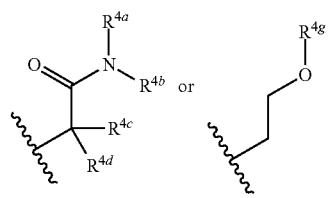

wherein,
$R^{4a}$ is selected from the group consisting of $C_1$-$C_6$ alkyl, hydroxy-$C_1$-$C_6$ alkyl, $C_1$-$C_3$ alkoxy-$C_1$-$C_6$ alkyl, $C_3$-$C_7$ cycloalkyl, 5- to 10-membered monocyclic heterocyclyl, $C_6$-$C_{10}$ aryl, 5- to 10-membered monocyclic or bicyclic fused heteroaryl, ($C_6$-$C_{10}$ aryl)-$C_1$-$C_3$ alkyl, and (5- to 10-membered monocyclic heteroaryl)-$C_1$-$C_3$ alkyl;
wherein the cycloalkyl, heterocyclyl, aryl, heteroaryl, arylalkyl, or heteroaryl-alkyl of $R^{4a}$ is optionally substituted with one or two substituents, each independently selected from the group consisting of halogen, $C_1$-$C_6$ alkyl, haloalkyl, hydroxy, $C_1$-$C_3$ alkoxy, oxo, $C_3$-$C_7$ cycloalkyl, and 5- to 10-membered monocyclic, bicyclic fused, or spiro heterocyclyl;
$R^{4g}$ is selected from the group consisting of $C_6$-$C_{10}$ aryl and $C_1$-$C_3$ alkyl;
$R^{4b}$ is hydrogen or $C_1$-$C_6$ alkyl;
or, $R^{4a}$ and $R^{4b}$ taken together with the atom to which each is attached form a 5- to 7-membered heterocyclyl;
or, $R^{4b}$ and $R^{4c}$ taken together with the atom to which each is attached form a 5- to 7-membered heterocyclyl optionally substituted with one or two substituents, each independently selected from $C_1$-$C_3$ alkyl;
$R^{4c}$ and $R^{4d}$ are each independently hydrogen or $C_1$-$C_3$ alkyl;
or, $R^{4c}$ and $R^{4d}$ taken together with the atom to which each is attached form a $C_3$-$C_5$ cycloalkyl;
or,
$R^3$ and $R^4$ taken together with the nitrogen atom to which each is attached form a:
i. 7-membered monocyclic heterocyclyl containing one or two heteroatoms;
wherein when said 7-membered monocyclic heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and when said 7-membered monocyclic heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, haloalkyl, and $C_6$-$C_{10}$ aryl; and
wherein said aryl is optionally substituted with one or two substituents, each individually selected from the group consisting of $C_1$-$C_3$ alkoxy, hydroxy, halogen, and $C_1$-$C_3$ alkyl;
ii. 4- or 6-membered monocyclic heterocyclyl containing one heteroatom;
wherein said 4-membered monocyclic heterocyclyl is optionally substituted with —$(CH_2)_sC(=O)NR^kR^l$;
wherein s is 0, 1, or 2;
$R^k$ is hydrogen or $C_1$-$C_3$ alkyl; and
$R^l$ is selected from the group consisting of hydrogen, methyl, phenyl, cyclopentyl, and cyclohexyl;
wherein said 6-membered monocyclic heterocyclyl is optionally substituted with one or two substituents, each independently selected from the group consisting of $C_1$-$C_3$ alkoxy, oxo, halogen, cyano, and $NR^qR^w$;
wherein $R^q$ is hydrogen or $C_1$-$C_3$ alkyl and $R^w$ is $C_6$-$C_{10}$ aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy; or
iii. 10- or 11-membered bicyclic fused heterocyclyl containing one heteroatom, optionally substituted with one, two, or three substituents, each independently selected from the group consisting of $C_1$-$C_3$ alkyl, $C_1$-$C_3$ alkoxy, hydroxy, and halogen.

3A. The compound of embodiment 1A or 2A, wherein $Y^1$, $Y^2$, $Y^3$, and $Y^4$ are each CH or C (to which $R^6$ is bound).

4A. The compound of embodiment 1A or 2A, wherein $Y^3$ is N and $Y^1$, $Y^2$, and $Y^4$ are each CH or C (to which $R^6$ is bound).

5A. The compound of embodiment 1A or 2A, wherein $Y^2$ is N and $Y^1$, $Y^3$, $Y^4$ are each CH or C (to which $R^6$ is bound).

6A. The compound of embodiment 1A or 2A, wherein $Y^1$ is N and $Y^2$, $Y^3$, and $Y^4$ are each CH or C (to which $R^6$ is bound).

7A. The compound of any one of embodiments 1A-6A, wherein $R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_3$ alkoxy, hydroxy-$C_1$-$C_3$-alkyl, and $NR^GR^H$;
wherein $R^G$ and $R^H$ are each independently hydrogen or $C_1$-$C_3$ alkyl.

8A. The compound of embodiment 7A, wherein $R^6$, in each instance, is selected from the group consisting of methoxy, methyl, fluoro, chloro, ethyl, $N(CH_3)_2$, hydroxy, —$OCH_2CH_2OH$, —$CH_2OH$, —$CH_2OCH_3$, and —$CH_2CH_2OH$.

9A. The compound of embodiment 8A, wherein $R^6$, in each instance, is methoxy or methyl.

10A. The compound of any one of embodiments 1A-6A, wherein two $R^6$ groups, taken together with the atom to which each is attached, form a 5- or 6-membered heterocyclyl, $C_6$-$C_{10}$ aryl, or 5- to 10-membered heteroaryl.

11A. The compound of embodiment 10A, wherein two $R^6$ groups, taken together with the atom to which each is attached, form a pyrazolyl, dioxanyl, pyridinyl, or phenyl ring.

12A. The compound of any one of embodiments 1A-11A, wherein n is 1.

13A. The compound of any one of embodiments 1A-11A, wherein n is 0.

14A. The compound of any one of embodiments 1A-13A, wherein f is 1.

15A. The compound of any one of embodiments 1A-13A, wherein f is 0.

16A. The compound of any one of embodiments 1A-15A, wherein $R^3$ is selected from the group consisting of hydrogen, methyl, and —$CH_2CH_2OH$.

17A. The compound of embodiment 16A, wherein $R^3$ is methyl.

18A. The compound of any one of embodiments 1A-17A, wherein $R^4$ is a (5- to 10-membered monocyclic or bicyclic fused heteroaryl)-methyl.

19A. The compound of embodiment 18A, wherein $R^4$ is a (5- to 10-membered monocyclic or bicyclic fused heteroaryl)-methyl, wherein at least one of the ring atoms ortho to the attachment point is a nitrogen or oxygen.

20A. The compound of embodiment 18A or 19A, wherein $R^4$ is selected from the group consisting of pyridinyl-methyl, pyrimidinyl-methyl, and benzoxazole-methyl.

21A. The compound of any one of embodiments 1A-17A, wherein, wherein $R^4$ is

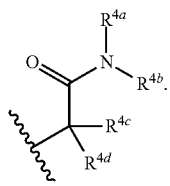

22A. The compound of embodiment 21A, wherein $R^{4c}$ and $R^{4d}$ are each independently hydrogen or methyl.

23A. The compound of embodiment 22A, wherein $R^{4c}$ and $R^{4d}$ are each hydrogen.

24A. The compound of any one of embodiments 21A-23A, wherein $R^{4b}$ is hydrogen.

25A. The compound of any one of embodiments 21A-24A, wherein $R^{4a}$ is $C_1$-$C_6$ alkyl.

26A. The compound of embodiment 25A, wherein $R^{4a}$ is tert-butyl.

27A. The compound of any one of embodiments 21A-24A, wherein $R^{4a}$ is $C_6$-$C_{10}$ aryl optionally substituted with one or two substituents, each independently selected from the group consisting of halogen, $C_1$-$C_6$ alkyl, haloalkyl, hydroxy, $C_1$-$C_3$ alkoxy, $C_3$-$C_7$ cycloalkyl, and 5- to 10-membered monocyclic, bicyclic fused, or spiro heterocyclyl.

28A. The compound of embodiment 27A, wherein $R^{4a}$ is phenyl optionally substituted with fluoro or methoxy.

29A. The compound of any one of embodiments 21A-24A, wherein $R^{4a}$ is 5- to 10-membered monocyclic or bicyclic fused heteroaryl optionally substituted with one or two substituents, each independently selected from the group consisting of halogen, $C_1$-$C_6$ alkyl, haloalkyl, hydroxy, $C_1$-$C_3$ alkoxy, $C_3$-$C_7$ cycloalkyl, and 5- to 10-membered monocyclic, bicyclic fused, or spiro heterocyclyl.

30A. The compound of embodiment 29A, wherein $R^{4a}$ is pyridinyl or quinolinyl, optionally substituted with fluoro, methoxy, or methyl.

31A. The compound of any one of embodiments 21A-24A, wherein $R^{4a}$ is $C_3$-$C_7$ cycloalkyl, optionally substituted with one or two substituents, each independently selected from the group consisting of halogen, $C_1$-$C_6$ alkyl, haloalkyl, hydroxy, $C_1$-$C_3$ alkoxy, $C_3$-$C_7$ cycloalkyl, and 5- to 10-membered monocyclic, bicyclic fused, or spiro heterocyclyl.

32A. The compound of embodiment 31A, wherein $R^{4a}$ is cyclopropyl, cyclobutyl, cyclopentyl, or cyclohexyl, optionally substituted with methyl, trifluoromethyl, fluoro, or hydroxy.

33A. The compound of any one of embodiments 21A-24A, wherein $R^{4a}$ is a 5- or 6-membered heterocyclyl, optionally substituted with one or two substituents, each independently selected from the group consisting of halogen, $C_1$-$C_6$ alkyl, haloalkyl, hydroxy, $C_1$-$C_3$ alkoxy, oxo, $C_3$-$C_7$ cycloalkyl, and 5- to 10-membered monocyclic, bicyclic fused, or spiro heterocyclyl.

34A. The compound of embodiment 33A, wherein $R^{4a}$ is selected from the group consisting of tetrahydrofuranyl, pyrrolidinyl, and tetrahydropyranyl, optionally substituted with one or two substituents, each independently selected from the group consisting of methyl and oxo.

35A. The compound of any one of embodiments 21A-24A, wherein $R^{4a}$ is ($C_6$-$C_{10}$ aryl)-$C_1$-$C_3$ alkyl or (5- to 10-membered monocyclic heteroaryl)-$C_1$-$C_3$ alkyl, optionally substituted with one or two substituents, each independently selected from the group consisting of halogen, $C_1$-$C_6$ alkyl, haloalkyl, hydroxy, $C_1$-$C_3$ alkoxy, $C_3$-$C_7$ cycloalkyl, and 5- to 10-membered monocyclic, bicyclic fused, or spiro heterocyclyl.

36A. The compound of embodiment 35A, wherein $R^{4a}$ is phenyl-methyl or pyridinyl-methyl.

37A. The compound of any one of embodiments 21A-23A, wherein $R^{4a}$ and $R^{4b}$ taken together with the atom to which each is attached form a 5- to 7-membered heterocyclyl.

38A. The compound of embodiment 37A, wherein $R^{4a}$ and $R^{4b}$ taken together with the atom to which each is attached form a 6-membered heterocyclyl selected from the group consisting of piperidinyl, morpholinyl, and piperazinyl.

39A. The compound of any one of embodiments 21A or 25A-36A, wherein $R^{4b}$ and $R^{4c}$ taken together with the atom to which each is attached form a 5- to 7-membered heterocyclyl optionally substituted one or two times with $C_1$-$C_3$ alkyl.

40A. The compound of embodiment 39A, wherein $R^{4b}$ and $R^{4c}$ taken together with the atom to which each is attached form a piperidin-2-one or a pyrrolidine-2-one, optionally substituted one or two times with $C_1$-$C_3$ alkyl.

41A. The compound of any one of embodiments 1A-17A, wherein $R^4$ is

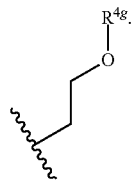

42A. The compound of embodiment 41A, wherein $R^{4g}$ is phenyl or methyl.

43A. The compound of any one of embodiments 1A-15A, wherein $R^3$ and $R^4$ taken together with the nitrogen atom to which each is attached form a 7-membered monocyclic heterocyclyl containing one or two heteroatoms.

44A. The compound of embodiment 43A, wherein $R^3$ and $R^4$ taken together with the nitrogen atom to which each is attached form a 7-membered monocyclic heterocyclyl containing one heteroatom, wherein said heterocyclyl is optionally substituted once with methyl or oxo.

45A. The compound of embodiment 43A, wherein $R^3$ and $R^4$ taken together with the nitrogen atom to which each is attached form a 7-membered monocyclic heterocyclyl containing two heteroatoms, wherein said heteroatoms are N or O, and said heterocyclyl is optionally substituted once with phenyl, methyl, or oxo, and wherein said phenyl is optionally substituted with methoxy.

46A. The compound of any one of embodiments 1A-15A, wherein $R^3$ and $R^4$ taken together with the nitrogen atom to which each is attached form an 11-membered bicyclic fused heterocyclyl containing one heteroatom, optionally substituted with methoxy.

47A. The compound of any one of embodiments 1A-46A, wherein p is 1.

1B. A compound of Formula (I'):

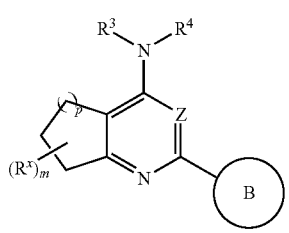

(I')

or a pharmaceutically acceptable salt thereof; wherein,

Z is N or CH;

Ring B is

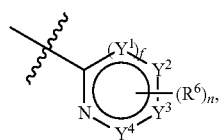

wherein $\{$ indicates the point of attachment to the remainder of the molecule;

$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$-alkyl, cyano, —$NR^G R^H$, halo-$C_1$-$C_3$ alkoxy, —O—$(CH_2)_u$—$R^{bb}$, halo-$C_1$-$C_3$ alkyl, —O—$R^{cc}$— O—$R^{dd}$, 5- to 7-membered monocyclic heteroaryl, and $C_3$-$C_6$ cycloalkyl; wherein, u is an integer from 0 to 6;

$R^{bb}$ is 4- to 7-membered monocyclic heterocyclyl, $C_3$-$C_7$ cycloalkyl, or —$NR^G R^H$;

$R^{cc}$ and $R^{dd}$ are each independently $C_1$-$C_3$ alkyl;

wherein, said cycloalkyl, heterocyclyl, or heteroaryl is optionally substituted with one or two substituents, each independently selected from the group consisting of hydroxy, $C_1$-$C_3$ alkoxy, and $C_1$-$C_3$ alkyl;

and, $R^G$ and $R^H$ are each independently hydrogen, —C(O) $R^{Ga}$, or $C_1$-$C_3$ alkyl; wherein, $R^{Ga}$ is $C_1$-$C_3$ alkyl or hydrogen;

or, two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- to 6-membered monocyclic heteroaryl fused with Ring B; wherein, said heterocyclyl, phenyl, cycloalkyl, or heteroaryl fused with ring B is optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl;

n is 0, 1, 2, or 3;

$Y^1$, $Y^2$, $Y^3$, and $Y^4$ are each independently selected from the group consisting of CH, N, NH, O, S, SH, S—$R^6$, N—$R^6$, and C—$R^6$, provided that 1 or 2 of $Y^1$, $Y^2$, $Y^3$, and $Y^4$ can be N, N—$R^6$, NH, O, SH or S—$R^6$;

f is 0 or 1;

p is 1 or 2;

$R^x$, in each instance, is halogen, $C_1$-$C_6$ alkyl, $C_1$-$C_3$ alkoxy, hydroxy, or cyano;

m is 0, 1, or 2;

$R^3$ is selected from the group consisting of hydrogen, $C_1$-$C_3$ alkyl, hydroxy-$C_1$-$C_3$ alkyl, cyclopropyl, and phenyl;

$R^4$ is selected from the group consisting of:

i. (5- to 10-membered monocyclic or fused bicyclic heteroaryl)-$C_1$-$C_3$ alkyl branched or linear, or (6- or 7-membered monocyclic heterocyclyl)-$C_1$-$C_3$ alkyl branched or linear; wherein, said heteroaryl or heterocyclyl is optionally substituted with one or two substituents, each independently selected from the group consisting of $C_6$-$C_{10}$ monocyclic or fused bicyclic aryl, $C_3$-$C_7$ cycloalkyl, 5- or 6-membered heteroaryl, and 5- to 7-membered monocyclic heterocyclyl, and wherein said aryl, cycloalkyl, heteroaryl, or heterocyclyl is optionally substituted with one or two substituents, each individually selected from the group consisting of $C_1$-$C_3$ alkyl, halogen, and hydroxy; and, when p is 1, $C_1$-$C_3$ alkyl in the (5- to 10-membered monocyclic or fused bicyclic heteroaryl)-$C_1$-$C_3$ alkyl is linear;

and, ii.

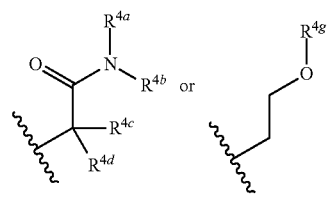

wherein, $R^{4a}$ and $R^{4g}$ are each independently selected from the group consisting of hydrogen, $C_1$-$C_6$ alkyl, hydroxy-$C_1$-$C_6$ alkyl, $C_1$-$C_3$ alkoxy-$C_1$-$C_6$ alkyl, $C_3$-$C_7$ cycloalkyl, 5- to 10-membered monocyclic, fused bicyclic, bridged bicyclic, or spiro heterocyclyl, $C_6$-$C_{10}$ monocyclic or fused bicyclic aryl, 5- to 10-membered monocyclic or fused bicyclic het eroaryl, ($C_6$-$C_{10}$ monocyclic or fused bicyclic aryl)-$C_1$-$C_3$ alkyl, and (5- to 10-membered monocyclic or fused bicyclic heteroaryl)-$C_1$-$C_3$ alkyl;
wherein the cycloalkyl, heterocyclyl, aryl, heteroaryl, aryl-alkyl, or heteroaryl-alkyl of $R^{4a}$ or $R^{4g}$ is optionally substituted with one, two, or three substituents, each independently selected from the group consisting of halogen, $C_1$-$C_6$ alkyl, halo-$C_1$-$C_3$ alkyl, hydroxy, $C_1$-$C_3$ alkoxy, halo-$C_1$-$C_3$ alkoxy, oxo, $C_3$-$C_7$ cycloalkyl, and 5- to 10-membered monocyclic, fused bicyclic, or spiro heterocyclyl;
$R^{4b}$ is hydrogen or $C_1$-$C_6$ alkyl; or
$R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy; or
$R^{4b}$ and $R^{4c}$ taken together with the atom to which each is attached form a 5- to 7-membered monocyclic heterocyclyl optionally substituted with one, two, or three substituents, each independently selected from the group consisting of hydroxy, halogen, and $C_1$-$C_3$ alkyl; or
$R^{4c}$ and $R^{4d}$ are each independently selected from the group consisting of hydrogen, $C_1$-$C_3$ alkoxy, hydroxy, $C_1$-$C_3$ alkyl-thio-$C_1$-$C_3$ alkyl, hydroxy-$C_1$-$C_6$ alkyl, $C_1$-$C_6$ alkoxy-$C_1$-$C_3$ alkyl, $C_3$-$C_7$ cycloalkyl, and $C_1$-$C_3$ alkyl; or
$R^{4c}$ and $R^{4d}$ taken together with the atom to which each is attached form a $C_3$-$C_7$ cycloalkyl;
or, when p is 1,
$R^3$ and $R^4$ taken together with the nitrogen atom to which each is attached can form a:
i. 7-membered fused bicyclic heterocyclyl, 7-membered bridged bicyclic heterocyclyl, or 7-membered monocyclic heterocyclyl containing one or two heteroatoms;
wherein when said 7-membered monocyclic heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and,
when said 7-membered monocyclic heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, halo-$C_1$-$C_3$ alkyl, and $C_6$-$C_{10}$ monocyclic or fused bicyclic aryl; and
wherein said aryl is optionally substituted with one or two substituents, each individually selected from the group consisting of $C_1$-$C_3$ alkoxy, hydroxy, halogen, and $C_1$-$C_3$ alkyl;
ii. 4- or 6-membered monocyclic heterocyclyl containing one heteroatom;
wherein said 4-membered monocyclic heterocyclyl is optionally substituted with one or two substituents, each independently selected from the group consisting of halogen, $C_1$-$C_3$ alkoxy, oxo, and —$(CH_2)_sC(=O)NR^kR^l$; wherein,
s is 0, 1, 2, or 3;
$R^k$ is hydrogen or $C_1$-$C_3$ alkyl; and
$R^l$ is selected from the group consisting of hydrogen, hydroxy, $C_1$-$C_3$ alkyl, $C_3$-$C_7$ cycloalkyl, and $C_6$-$C_{10}$ monocyclic or fused bicyclic aryl; wherein said 6-membered monocyclic heterocyclyl is optionally substituted with one or two substituents, each independently selected from the group consisting of $C_1$-$C_3$ alkoxy, oxo, halogen, cyano, and —$NR^qR^w$; wherein,
$R^q$ is hydrogen or $C_1$-$C_3$ alkyl; and
$R^w$ is $C_6$-$C_{10}$ monocyclic or fused bicyclic aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy;
or,
iii. 8-, 9-, 10- or 11-membered fused bicyclic heterocyclyl, or 12-membered bicyclic bridged and fused heterocyclyl, wherein said 8-, 9-, or 11-membered heterocyclyl contains one heteroatom and said 10- or 12-membered heterocyclyl contains one or two heteroatoms; and wherein said 10-, 11-, or 12-membered heterocyclyl is optionally substituted with one, two, or three substituents, each independently selected from the group consisting of halogen, $C_1$-$C_3$ alkyl, $C_1$-$C_3$ alkoxy, and hydroxy;
or, when p is 2,
$R^3$ and $R^4$ taken together with the nitrogen atom to which each is attached can form a:
i. 6-membered monocyclic heterocyclyl containing one heteroatom, optionally substituted with one or two substituents, each independently selected from the group consisting of halogen, hydroxy-($C_1$-$C_6$ alkyl), hydroxy, oxo, and $C_1$-$C_3$ alkoxy; or
ii. 4- or 7-membered monocyclic heterocyclyl containing one or two heteroatoms, or 7-, 8-, 9-, 10-, or 11-membered bridged bicyclic, fused bicyclic, or spiro heterocyclyl containing one, two, or three heteroatoms, optionally substituted with one or two substituents, each independently selected from the group consisting of halogen, oxo, cyano, $C_1$-$C_3$ alkyl, hydroxy, —$NR^GR^H$, and —$(CH_2)_sC(=O)NR^kR^l$;
provided that when the structure of Formula (I) is

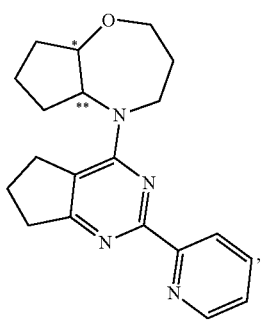 [SMILES: c1ccc(-c2nc3c(c(N4CCCOC5CCCC54)n2)CCC3)nc1]

* is ![wedge H] and ** is ![dash H]H; or
* is ![dash H] and ** is ![dash H]H;
and,
wherein the compound of Formula (I) is not:
N-((1,4-dioxan-2-yl)methyl)-2-(pyridin-2-yl)-6,7-dihydro-5H-cyclopenta[d]pyrimidin-4-amine;

4-(piperidin-1-yl)-2-(pyridin-2-yl)-5,6,7,8-tetrahydroquinazoline;

4-(azepan-1-yl)-2-(6-propylpyridin-2-yl)-5,6,7,8-tetrahydroquinazoline;

1-propyl-4-(2-(pyridin-2-yl)-6,7-dihydro-5H-cyclopenta[d]pyrimidin-4-yl)-1,4-diazepan-2-one; or 2-(2-(pyridin-2-yl)-6,7-dihydro-5H-cyclopenta[d]pyrimidin-4-yl)-1,2-oxazepane; or a salt thereof.

1C. A compound of Formula (I'):

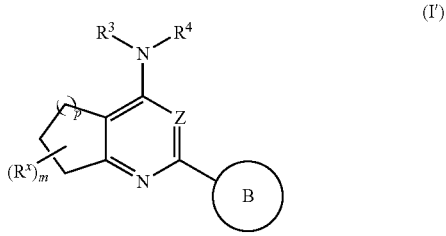

or a pharmaceutically acceptable salt thereof; wherein,

Z is N or CH;

Ring B is

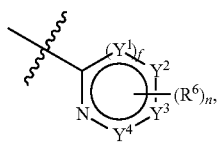

wherein ⁀ indicates the point of attachment to the remainder of the molecule;

$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_{10}$ alkoxy, hydroxy-$C_1$-$C_{10}$-alkyl, cyano, —$NR^G R^H$, halo-$C_1$-$C_3$ alkoxy, —O—($C_1$-$C_6$ alkyl)-$R^{bb}$, —O—$R^{bb}$, —($C_1$-$C_6$ alkyl)-$NR^{G1}R^{H1}$, —S—$C_1$-$C_3$ alkyl, —S—$C_1$-$C_3$ alkyl-$NR^{G1}R^{H1}$, halo-$C_1$-$C_3$ alkyl, —O—$R^{cc}$—O—$R^{dd}$, 5- to 7-membered monocyclic heteroaryl, and $C_3$-$C_6$ cycloalkyl; wherein, the alkyl moiety in hydroxy-$C_1$-$C_{10}$ alkoxy or —O—($C_1$-$C_6$ alkyl)-$R^{bb}$ is optionally substituted with cyano, hydroxy, hydroxy-$C_1$-$C_3$-alkyl, halogen, or $C_1$-$C_3$ alkoxy;

$R^{bb}$ is 4- to 7-membered monocyclic or bridged heterocyclyl, $C_3$-$C_7$ cycloalkyl, 5- or 6-membered monocyclic heteroaryl, —$SO_2$—$C_1$-$C_3$ alkyl, —S—$C_1$-$C_3$ alkyl, —C(O)$NR^{G1}R^{H1}$, or —$NR^G R^H$;

$R^{cc}$ is $C_1$-$C_3$ alkyl; and $R^{dd}$ is $C_1$-$C_3$ alkyl or a 6-membered heteroaryl;

wherein, said cycloalkyl, heterocyclyl, or heteroaryl of $R^6$, $R^{bb}$, or $R^{dd}$ is optionally substituted with one or two substituents, each independently selected from the group consisting of hydroxy, halogen, halo-$C_1$-$C_3$ alkyl, oxo, $C_1$-$C_3$ alkoxy, and $C_1$-$C_3$ alkyl;

$R^{G1}$ and $R^{H1}$ are each independently hydrogen or $C_1$-$C_3$ alkyl;

and, $R^G$ and $R^H$ are each independently hydrogen, —C(O)$R^{Ga}$, or optionally deuterated $C_1$-$C_3$ alkyl; wherein, $R^{Ga}$ is $C_1$-$C_3$ alkyl or hydrogen;

or, two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- to 6-membered monocyclic heteroaryl fused with Ring B; wherein, said heterocyclyl, phenyl, cycloalkyl, or heteroaryl fused with ring B is optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl;

n is 0, 1, 2, or 3;

$Y^1$, $Y^2$, $Y^3$, and $Y^4$ are each independently selected from the group consisting of CH, N, NH, O, S, SH, S—$R^6$, N—$R^6$, and C—$R^6$, provided that 1 or 2 of $Y^1$, $Y^2$, $Y^3$, and $Y^4$ can be N, N—$R^6$, NH, O, SH or S—$R^6$;

f is 0 or 1;

p is 1 or 2;

$R^x$, in each instance, is halogen, $C_1$-$C_6$ alkyl, $C_1$-$C_3$ alkoxy, hydroxy, oxo, or cyano;

m is 0, 1, or 2;

$R^3$ is selected from the group consisting of hydrogen, optionally deuterated $C_1$-$C_3$ alkyl, hydroxy-$C_1$-$C_3$ alkyl, halo-$C_1$-$C_3$ alkyl, cyclopropyl, and phenyl;

$R^4$ is selected from the group consisting of:

i. (5- to 10-membered monocyclic or fused bicyclic heteroaryl)-$C_1$-$C_3$ alkyl, or (6- or 7-membered monocyclic heterocyclyl)-$C_1$-$C_3$ alkyl; wherein, said heteroaryl or heterocyclyl is optionally substituted with one or two substituents, each independently selected from the group consisting of $C_6$-$C_{10}$ monocyclic or fused bicyclic aryl, $C_3$-$C_7$ cycloalkyl, 5- or 6-membered heteroaryl, —($C_1$-$C_3$ alkyl)-T, and 5- to 7-membered monocyclic heterocyclyl;

T is selected from the group consisting of $C_6$-$C_{10}$ monocyclic or fused bicyclic aryl, $C_3$-$C_7$ cycloalkyl, 5- or 6-membered heteroaryl, and 5- to 7-membered monocyclic heterocyclyl; and, wherein T or said aryl, cycloalkyl, heteroaryl, or heterocyclyl substituent of $R^4$ is optionally substituted with one or two substituents, each individually selected from the group consisting of $C_1$-$C_3$ alkyl, halogen, and hydroxy; and when p is 1, $C_1$-$C_3$ alkyl in the (5- to 10-membered monocyclic or fused bicyclic heteroaryl)-$C_1$-$C_3$ alkyl is linear;

and, ii.

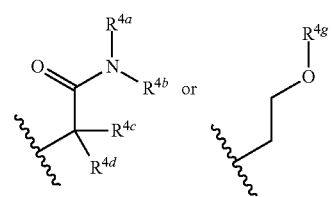

wherein,
R$^{4a}$ and R$^{4g}$ are each independently selected from the group consisting of hydrogen, C$_1$-C$_{10}$ alkyl, hydroxy-C$_1$-C$_6$ alkyl, halo-C$_1$-C$_3$ alkyl, C$_1$-C$_3$ alkoxy-C$_1$-C$_6$ alkyl, —C$_1$-C$_6$ alkyl-NR$^{J1}$R$^{J2}$, C$_3$-C$_7$ cycloalkyl, 4- to 10-membered monocyclic, fused bicyclic, bridged bicyclic, or spiro heterocyclyl, C$_6$-C$_{10}$ monocyclic or fused bicyclic aryl, 5- to 10-membered monocyclic or fused bicyclic heteroaryl, (C$_6$-C$_{10}$ monocyclic or fused bicyclic aryl)-C$_1$-C$_3$ alkyl, and (5- to 10-membered monocyclic or fused bicyclic heteroaryl)-C$_1$-C$_3$ alkyl;
R$^{J1}$ and R$^{J2}$ are independently hydrogen or C$_1$-C$_3$ alkyl;
wherein the cycloalkyl, heterocyclyl, aryl, heteroaryl, aryl-alkyl, or heteroaryl-alkyl of R$^{4a}$ or R$^{4g}$ is optionally substituted with one, two, or three substituents, each independently selected from the group consisting of halogen, C$_1$-C$_6$ alkyl, halo-C$_1$-C$_3$ alkyl, hydroxy, C$_1$-C$_3$ alkoxy, halo-C$_1$-C$_3$ alkoxy, oxo, C$_3$-C$_7$ cycloalkyl, and 5- to 10-membered monocyclic, fused bicyclic, or spiro heterocyclyl;
R$^{4b}$ is hydrogen or C$_1$-C$_6$ alkyl; or
R$^{4a}$ and R$^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, C$_1$-C$_6$ alkyl, halo-C$_1$-C$_3$ alkyl, hydroxy, and C$_1$-C$_3$ alkoxy; or
R$^{4b}$ and R$^{4c}$ taken together with the atom to which each is attached form a 5- to 7-membered monocyclic heterocyclyl optionally substituted with one, two, or three substituents, each independently selected from the group consisting of hydroxy, halogen, and C$_1$-C$_3$ alkyl; or
R$^{4c}$ and R$^{4d}$ are each independently selected from the group consisting of hydrogen, C$_1$-C$_3$ alkoxy, hydroxy, C$_1$-C$_3$ alkyl-thio-C$_1$-C$_3$ alkyl, hydroxy-C$_1$-C$_6$ alkyl, C$_1$-C$_6$ alkoxy-C$_1$-C$_3$ alkyl, C$_3$-C$_7$ cycloalkyl, and C$_1$-C$_3$ alkyl; or
R$^{4c}$ and R$^{4d}$ taken together with the atom to which each is attached form a C$_3$-C$_7$ cycloalkyl;
or, when p is 1,
R$^3$ and R$^4$ taken together with the nitrogen atom to which each is attached can form a:
i. 7-membered fused bicyclic heterocyclyl, 7-membered bridged bicyclic heterocyclyl, or 7-membered monocyclic heterocyclyl containing one or two heteroatoms;
wherein when said 7-membered monocyclic heterocyclyl contains one heteroatom, said heterocyclyl is optionally substituted with one, two, or three substituents, each independently selected from the group consisting of oxo, halogen, hydroxy, C$_1$-C$_3$ alkoxy, cyano, and C$_1$-C$_3$ alkyl; and,
when said 7-membered monocyclic heterocyclyl contains two heteroatoms, said heteroatoms are each independently N or O, and said heterocyclyl is optionally substituted with one, two, or three substituents, each independently selected from the group consisting of C$_1$-C$_3$ alkyl, cyano, oxo, halogen, halo-C$_1$-C$_3$ alkyl, and C$_6$-C$_{10}$ monocyclic or fused bicyclic aryl; and
wherein said aryl is optionally substituted with one or two substituents, each individually selected from the group consisting of C$_1$-C$_3$ alkoxy, hydroxy, halogen, and C$_1$-C$_3$ alkyl;

ii. 4- or 6-membered monocyclic heterocyclyl containing one heteroatom;
wherein said 4-membered monocyclic heterocyclyl is optionally substituted with one or two substituents, each independently selected from the group consisting of halogen, C$_1$-C$_3$ alkoxy, oxo, and —(CH$_2$)$_s$C(=O)NR$^k$R$^l$; wherein,
s is 0, 1, 2, or 3;
R$^k$ is hydrogen or C$_1$-C$_3$ alkyl; and
R$^l$ is selected from the group consisting of hydrogen, hydroxy, C$_1$-C$_3$ alkyl, C$_3$-C$_7$ cycloalkyl, and C$_6$-C$_{10}$ monocyclic or fused bicyclic aryl;
wherein said 6-membered monocyclic heterocyclyl is optionally substituted with one or two substituents, each independently selected from the group consisting of C$_1$-C$_3$ alkoxy, oxo, halogen, cyano, and —NR$^q$R$^w$; wherein,
R$^q$ is hydrogen or C$_1$-C$_3$ alkyl; and
R$^w$ is C$_6$-C$_{10}$ monocyclic or fused bicyclic aryl or C$_3$-C$_7$ cycloalkyl, wherein said aryl or cycloalkyl is optionally substituted with one or two substituents, each independently selected from the group consisting of halogen, C$_1$-C$_3$ alkyl, hydroxy, and C$_1$-C$_3$ alkoxy;

or,
iii. 8-, 9-, 10- or 11-membered fused bicyclic heterocyclyl, or 12-membered bicyclic bridged and fused heterocyclyl, wherein said 8-, 9-, or 11-membered heterocyclyl contains one heteroatom and said 10- or 12-membered heterocyclyl contains one or two heteroatoms; and wherein said 10-, 11-, or 12-membered heterocyclyl is optionally substituted with one, two, or three substituents, each independently selected from the group consisting of halogen, C$_1$-C$_3$ alkyl, C$_1$-C$_3$ alkoxy, and hydroxy;
or, when p is 2,
R$^3$ and R$^4$ taken together with the nitrogen atom to which each is attached can form a:
i. 6-membered monocyclic heterocyclyl containing one heteroatom, optionally substituted with one or two substituents, each independently selected from the group consisting of halogen, hydroxy-(C$_1$-C$_6$ alkyl), hydroxy, oxo, and C$_1$-C$_3$ alkoxy; or
ii. 4- or 7-membered monocyclic heterocyclyl containing one or two heteroatoms, or 7-, 8-, 9-, 10-, or 11-membered bridged bicyclic, fused bicyclic, or spiro heterocyclyl containing one, two, or three heteroatoms, optionally substituted with one or two substituents, each independently selected from the group consisting of halogen, oxo, cyano, C$_1$-C$_3$ alkyl, hydroxy, —NR$^G$R$^H$, and —(CH$_2$)$_s$C(=O)NR$^k$R$^l$;
provided that when the structure of Formula (I) is

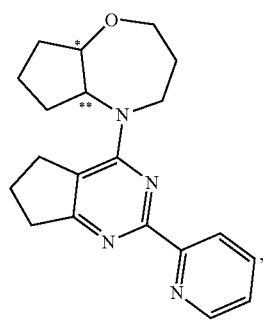 [SMILES: c1ccc(-c2nc3c(c(N4CCCOC5CCCC54)n2)CCC3)nc1]

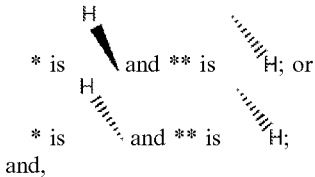

* is [wedge H] and ** is [dash H]; or
* is [dash H] and ** is [wedge H];

and,
wherein the compound of Formula (I) is not:
N-((1,4-dioxan-2-yl)methyl)-2-(pyridin-2-yl)-6,7-dihydro-5H-cyclopenta[d]pyrimidin-4-amine;
4-(piperidin-1-yl)-2-(pyridin-2-yl)-5,6,7,8-tetrahydroquinazoline;
4-(azepan-1-yl)-2-(6-propylpyridin-2-yl)-5,6,7,8-tetrahydroquinazoline;
1-propyl-4-(2-(pyridin-2-yl)-6,7-dihydro-5H-cyclopenta[d]pyrimidin-4-yl)-1,4-diazepan-2-one; or
2-(2-(pyridin-2-yl)-6,7-dihydro-5H-cyclopenta[d]pyrimidin-4-yl)-1,2-oxazepane; or a salt thereof.

2B. The compound of embodiment 1B or 1C, or a pharmaceutically acceptable salt thereof, wherein p is 1.

3B. The compound of embodiment 1B, 2B, or 1C, or a pharmaceutically acceptable salt thereof, wherein Z is N.

4B. The compound of any one of embodiments 1B-3B or 1C, or a pharmaceutically acceptable salt thereof, wherein $Y^1$, $Y^2$, $Y^3$, and $Y^4$ are each CH or C—$R^6$.

5C. The compound of embodiment 4B or 1C, or a pharmaceutically acceptable salt thereof, wherein $Y^1$ is CH, $Y^2$ is C—$R^6$, $Y^3$ is CH, and $Y^4$ is CH.

5B. The compound of any one of embodiments 1B-3B or 1C, or a pharmaceutically acceptable salt thereof, wherein $Y^3$ is N and $Y^1$, $Y^2$, and $Y^4$ are each CH or C—$R^6$.

6B. The compound of any one of embodiments 1B-3B or 1C, or a pharmaceutically acceptable salt thereof, wherein $Y^2$ is N and $Y^1$, $Y^3$, $Y^4$ are each CH or C—$R^6$.

7B. The compound of any one of embodiments 1B-3B or 1C, or a pharmaceutically acceptable salt thereof, wherein $Y^1$ is N and $Y^2$, $Y^3$, and $Y^4$ are each CH or C—$R^6$.

8B. The compound of any one of embodiments 1B-7B, or a pharmaceutically acceptable salt thereof, wherein $R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$ alkyl, —O—$(CH_2)_u$—$R^{bb}$, halo-$C_1$-$C_3$ alkoxy, —O—$R^{cc}$—O—$R^{dd}$, halo-$C_1$-$C_3$ alkyl, and —$NR^GR^H$; wherein,
$R^{bb}$ is —$NR^GR^H$;
u is an integer from 1 to 3;
$R^G$ and $R^H$ are each independently hydrogen or $C_1$-$C_3$ alkyl; and
$R^{cc}$ and $R^{dd}$ are each independently $C_1$-$C_3$ alkyl.

9C. The compound of any one of embodiments 1C, 2B-8B or 5C, or a pharmaceutically acceptable salt thereof, wherein $R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_{10}$ alkoxy, hydroxy-$C_1$-$C_{10}$-alkyl, —O—($C_1$-$C_6$ alkyl)-$R^{bb}$, halo-$C_1$-$C_3$ alkoxy, —O—$R^{cc}$—O—$R^{dd}$, halo-$C_1$-$C_3$ alkyl, —($C_1$-$C_6$ alkyl)- $NR^{GI}R^{HI}$, —S—$CH_3$, —$S(CH_2)_2N(CH_3)_2$, and —$NR^GR^H$; wherein,
$R^{bb}$ is —$NR^GR^H$, —$C(O)N(CH_3)_2$, —$S(O)_2CH_3$, or —$SCH_3$;
$R^G$ and $R^H$ are each independently hydrogen, optionally deuterated $C_1$-$C_3$ alkyl, or —$C(O)R^{Ga}$, wherein $R^{Ga}$ is $C_1$-$C_3$ alkyl;
$R^{GI}$ and $R^{HI}$ are each independently hydrogen or $C_1$-$C_3$ alkyl;
$R^{cc}$ and $R^{dd}$ are each independently $C_1$-$C_3$ alkyl; and, wherein the alkyl moiety in hydroxy-$C_1$-$C_{10}$ alkoxy is optionally substituted with hydroxy, halogen, or $C_1$-$C_3$ alkoxy.

9B. The compound of any one of embodiments 1B-8B, 5C, or 9C, or a pharmaceutically acceptable salt thereof, wherein $R^6$, in each instance, is selected from the group consisting of methoxy, ethoxy, methyl, fluoro, chloro, ethyl, —$N(CH_3)_2$, hydroxy, —$OCH_2CH_2OH$, —$CH_2OH$, —$CH_2OCH_3$, —$OCH_2CH_2NH_2$, —$OCH_2CH_2N(CH_3)_2$, —$OCH_2C(CH_3)_2OH$, —$OCH_2CF_3$, —$OCHF_2$, —$OCF_3$, —$OCH_2CH_2OCH_3$, —$OCH_2CH_2F$, —$OC(CH_3)_2CH_2OH$, and —$CH_2CH_2OH$.

10C. The compound of embodiment 9C, or a pharmaceutically acceptable salt thereof, wherein $R^6$, in each instance, is selected from the group consisting of methoxy, ethoxy, methyl, fluoro, chloro, ethyl, —$N(CH_3)_2$, hydroxy, —$OCH_2CH_2OH$, —$CH_2OH$, —$CH_2OCH_3$, —$OCH_2CH_2NH_2$, —$OCH_2CH_2N(CH_3)_2$, —$OCH_2C(CH_3)_2OH$, —$OCH_2CF_3$, —$OCHF_2$, —$OCF_3$, —$OCH_2CH_2OCH_3$, —$OCH_2CH_2F$, —$OC(CH_3)_2CH_2OH$, —$OCH_2CH(CH_3)OH$, —$OCH_2CH_2NHC(O)CH_3$, —$OC(CH_3)_2CH_2N(CH_3)_2$, —$OCH(CH_3)CH_2OH$, —$OCH_2CH(CH(CH_3)_2)OH$, —$OCH_2CH(CH_2CH_3)OH$, —$OCH_2C(CH_2CH_3)_2OH$, —$OCH_2CH_2N(CH_2CH_3)_2$, —$OCH(CH_3)CH_2N(CH_3)_2$, —$OCH_2C(O)N(CH_3)_2$, —$OCH_2C(CH_3)_2N(CH_3)_2$, —$OCH_2CH(CH_2OH)OH$, —$OCH_2CH_2NH(CH_3)$, —$OCH_2CH(CF_3)OH$, —$OCH_2C(CH_3)(CH_2CH_3)OH$, —$OCH_2CH(CH_2OCH_3)OH$, —$OCH_2CH(CH_2F)OH$, —$(CH_2)_3N(CH_3)_2$, —$(CH_2)_3N(CH_3)H$, —$O(CH_2)_2S(O)_2CH_3$, —$O(CH_2)_2SCH_3$, —$(CH_2)_2C(CH_3)_2OH$, —$OCH_2CH_2N(CD_3)_2$, and —$CH_2CH_2OH$.

10B. The compound of embodiment 9B, 9C, or 10C, or a pharmaceutically acceptable salt thereof, wherein $R^6$, in each instance, is methoxy, —$OCH_2CH_2OH$, or —$OCH_2C(CH_3)_2OH$.

11C. The compound of embodiment 10C, or a pharmaceutically acceptable salt thereof, wherein $R^6$, in each instance, is methoxy, —$OCH_2CH_2N(CH_3)_2$, —$OCH_2CH_2OH$, or —$OCH_2C(CH_3)_2OH$.

12C. The compound of embodiment 11C, or a pharmaceutically acceptable salt thereof, wherein $R^6$, in each instance, is —$OCH_2CH_2N(CH_3)_2$ or —$OCH_2C(CH_3)_2OH$.

11B. The compound of any one of embodiments 1B-7B, or a pharmaceutically acceptable salt thereof, wherein $R^6$, in each instance, is selected from the group consisting of —O—$(CH_2)_u$—$R^{bb}$, and $C_3$-$C_6$ cycloalkyl; wherein,
u is an integer from 0 to 3;
$R^{bb}$ is 4- to 7-membered monocyclic heterocyclyl or $C_3$-$C_7$ cycloalkyl; and
wherein said cycloalkyl or heterocyclyl is optionally substituted with one or two substituents, each independently selected from the group consisting of hydroxy, $C_1$-$C_3$ alkoxy, and $C_1$-$C_3$ alkyl.

12B. The compound of embodiment 11B, or a pharmaceutically acceptable salt thereof, wherein $R^6$, in each instance, is selected from the group consisting of cyclopropyl and —O—$(CH_2)_u$—$R^{bb}$; wherein,
u is 0, 1, or 2; and
$R^{bb}$ is selected from the group consisting of cyclopropyl, cyclobutyl, tetrahydrofuranyl, oxetanyl, and pyrrolidinyl, each optionally substituted with hydroxy or methyl.

13C. The compound of any one of embodiments 1C, 2B-8B or 5C, or a pharmaceutically acceptable salt thereof, wherein $R^6$, in each instance, is selected from the group consisting of —O—($C_1$-$C_6$ alkyl)-$R^{bb}$, —O—$R^{bb}$, —O—$R^{cc}$—O—$R^{dd}$, 5- to 7-membered monocyclic heteroaryl, and $C_3$-$C_6$ cycloalkyl; wherein, $R^{cc}$ is $C_1$-$C_3$ alkyl and $R^{dd}$ is 6-membered heteroaryl;

$R^{bb}$ is 4- to 7-membered monocyclic or bridged heterocyclyl, 5- or 6-membered monocyclic heteroaryl, or $C_3$-$C_7$ cycloalkyl; and wherein said cycloalkyl, heteroaryl, or heterocyclyl of $R^6$, $R^{bb}$, or $R^{dd}$ is optionally substituted with one or two substituents, each independently selected from the group consisting of hydroxy, halogen, $C_1$-$C_3$ alkoxy, oxo, halo-$C_1$-$C_3$ alkyl, and $C_1$-$C_3$ alkyl.

14C. The compound of embodiment 13C, or a pharmaceutically acceptable salt thereof, wherein $R^6$, in each instance, is selected from the group consisting of cyclopropyl, —O—$R^{bb}$, —O—$(CH_2)$—$R^{bb}$, and —O—$(CH_2)_2$—$R^{bb}$, —O—$(CH_2)_2$—O-pyridazinyl, optionally $C_1$-$C_3$ alkyl-substituted imidazolyl; wherein, $R^{bb}$ is selected from the group consisting of cyclopropyl, cyclobutyl, cyclopentyl, cyclohexyl, tetrahydrofuranyl, tetrahydropyranol, oxetanyl, dioxolanyl, azetidinyl, morpholinyl, piperazinyl, 2-oxa-5-azabicyclo[2.2.1]heptane, imidazolyl, tetrazolyl, pyridazinyl, piperidinyl, thiomorpholinyl, and pyrrolidinyl, each optionally substituted with hydroxy, oxo, fluoro, —$CF_3$, —$CH_2CF_3$, —$CH_2CHF_2$, —$CH_2CH_2F$, methoxy, ethyl, or methyl.

15C. The compound of embodiment 14C, or a pharmaceutically acceptable salt thereof, wherein $R^6$, in each instance, is selected from the group consisting of

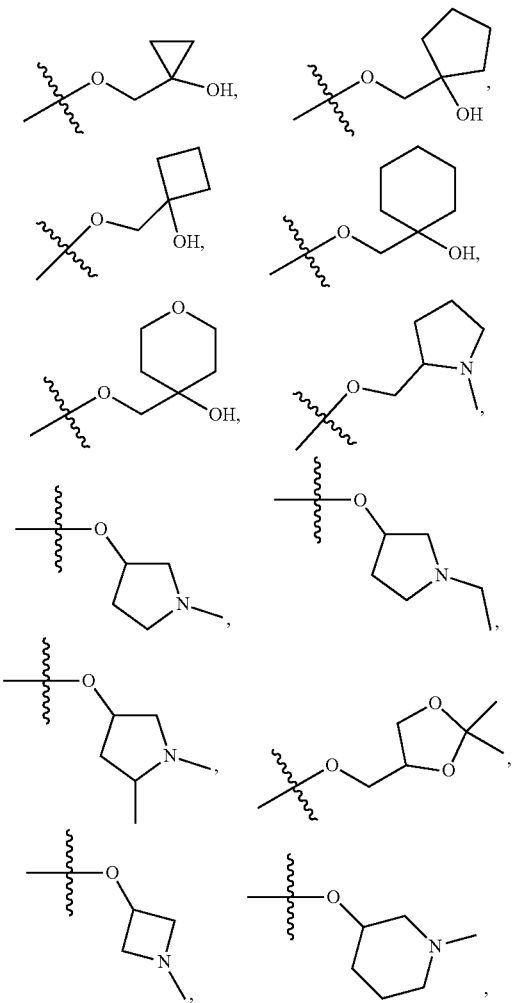


where ⁃ indicates the point of attachment to Ring B.

13B. The compound of embodiment 12B, 14C, or 15C, or a pharmaceutically acceptable salt thereof, wherein $R^6$, in each instance, is selected from the group consisting of

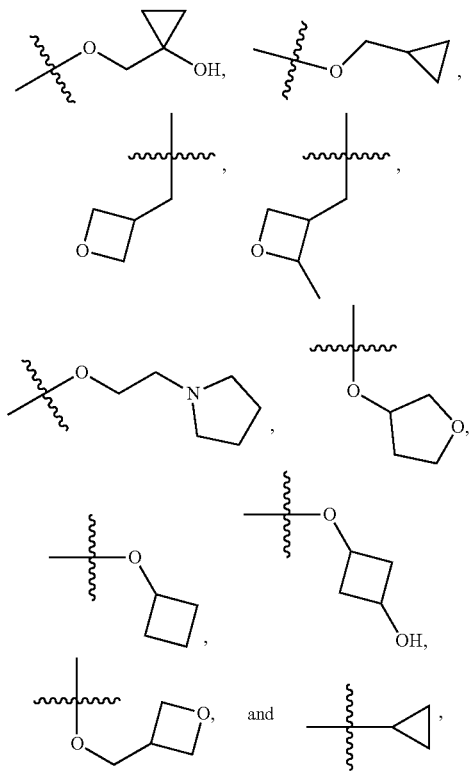

where ⌇ indicates the point of attachment to Ring B.

16C. The compound of embodiment 15C, or a pharmaceutically acceptable salt thereof, wherein $R^6$ is

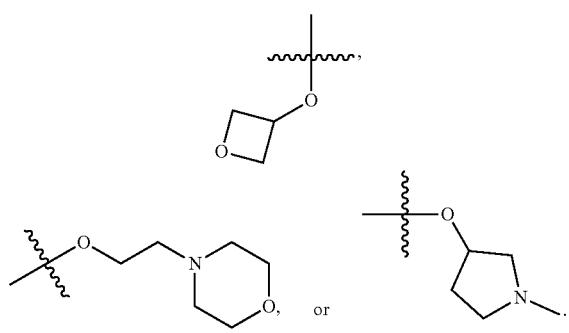

14B. The compound of embodiment 13B or 13-16C, or a pharmaceutically acceptable salt thereof, wherein $R^6$ is

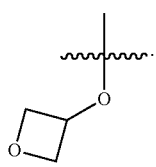 [SMILES: *OC1COC1]

15B. The compound of any one of embodiments 1B-7B or 1C, or a pharmaceutically acceptable salt thereof, wherein two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- or 6-membered monocyclic heteroaryl fused with Ring B, each optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl.

16B. The compound of any one of embodiments 1B-7B or 1C, or a pharmaceutically acceptable salt thereof, wherein two $R^6$ groups, taken together with the atom to which each is attached, form a pyrazolyl, dioxanyl, pyridinyl, pyrimidinyl, thiazolyl, furanyl, dioxolanyl, or phenyl ring fused with Ring B, wherein said ring is optionally substituted with one substituent selected from the group consisting of hydroxy, methoxy, tetrahydropyranyl, —$CH_2OH$, and methyl.

17B. The compound of embodiment 16B, or a pharmaceutically acceptable salt thereof, wherein two $R^6$ groups, taken together with the atom to which each is attached, form a ring selected from the group consisting of

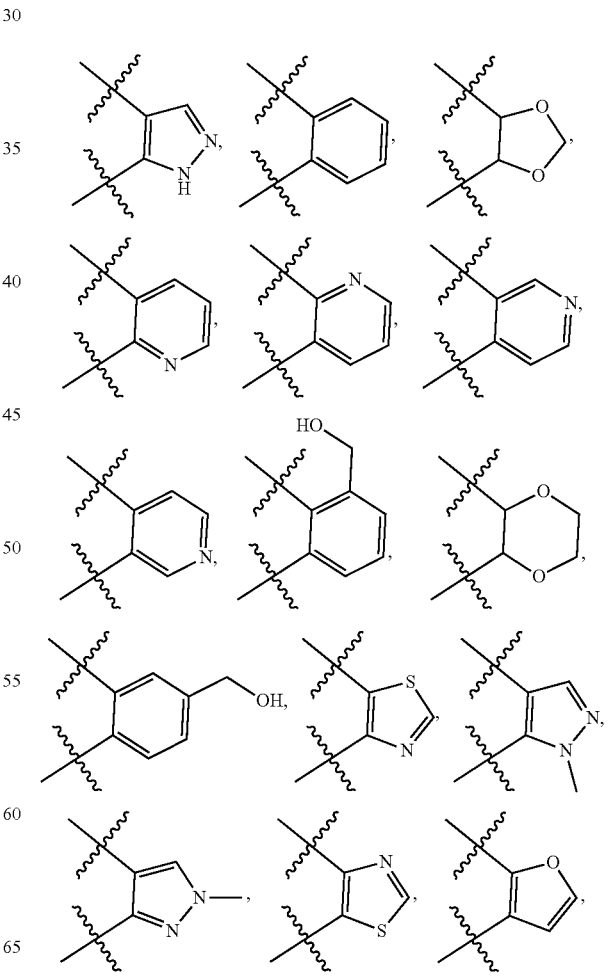

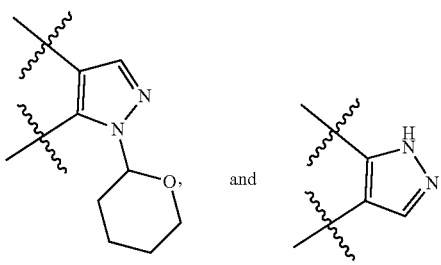

fused with ring B, wherein the pair of ⌇ represent the attachment of the ring with Ring B.

18B. The compound of embodiment 17B, or a pharmaceutically acceptable salt thereof, wherein two $R^6$ groups, taken together with the atom to which each is attached, form a form a ring selected from the group consisting of

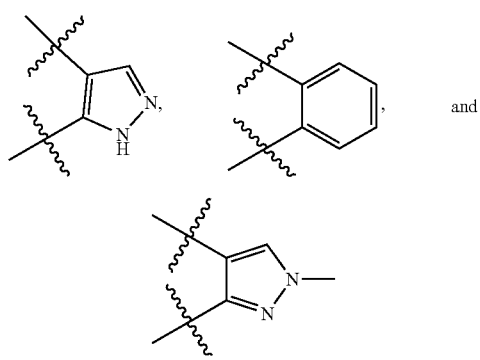

fused with Ring B.

18.bb The compound of any one of embodiments 15B-18B, wherein Ring B is selected from the group consisting of

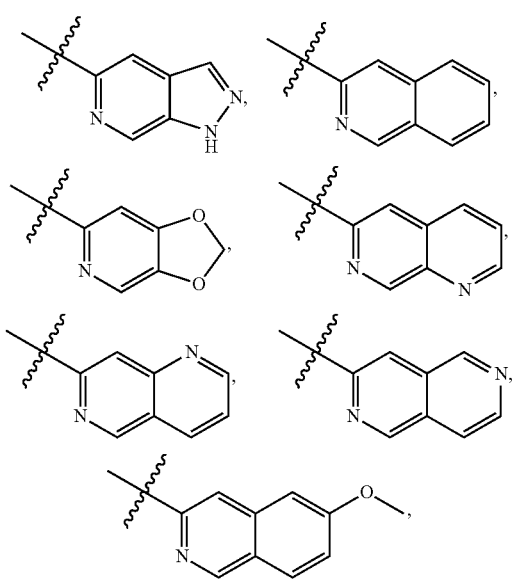

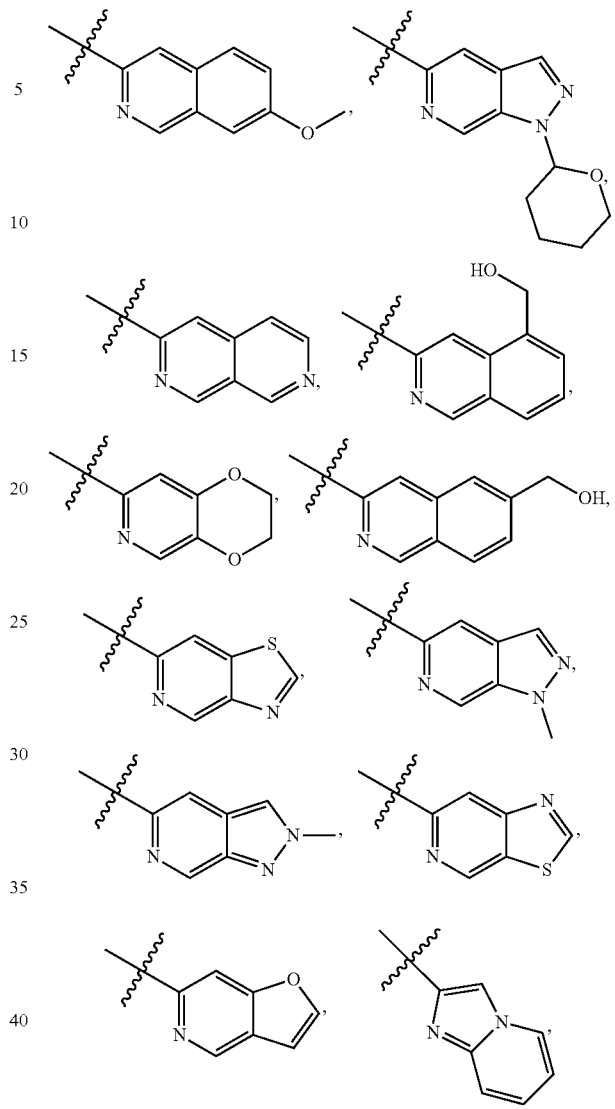

and

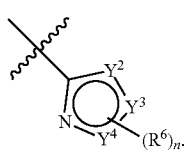

19B. The compound of any one of embodiments 1B-19B, 1C, 5C, 9C, 1° C., 11C, 12C, 13C, 14C, 15C, or 16C, or a pharmaceutically acceptable salt thereof, wherein f is 1.

20B. The compound of embodiment 1B, 2B, 3B, or 1C, or a pharmaceutically acceptable salt thereof, wherein f is 0, and Ring B is 21B. The compound of embodiment 20B, or a pharmaceutically acceptable salt thereof, wherein Ring B is

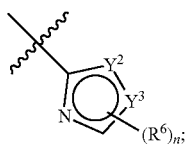

wherein,
n is 0 or 1; and
$Y^2$ and $Y^3$ are each independently selected from the group consisting of CH, N, NH, $NR^6$, S, O, and $CR^6$, provided that only one of $Y^2$ and $Y^3$ can be N, NH, $NR^6$, S, or O.

22B. The compound of embodiment 20B or 21B, or a pharmaceutically acceptable salt thereof, wherein Ring B is selected from the group consisting of

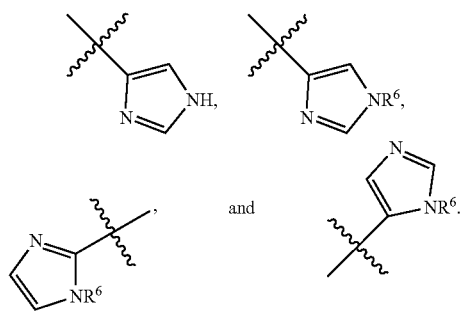

23B. The compound of any one of embodiments 20B-22B, or a pharmaceutically acceptable salt thereof, wherein $R^6$, in each instance, is selected from the group consisting of $C_1$-$C_3$ alkyl and hydroxy-$C_1$-$C_3$ alkyl.

24B. The compound of embodiment 23B, or a pharmaceutically acceptable salt thereof, wherein $R^6$, in each instance, is selected from the group consisting of methyl, ethyl, n-propyl, —$CH_2CH_2OH$, and —$CH_2CH_2CH_2OH$.

25B. The compound of any one of embodiments 1B-24B, 1C, 5C, 9C, 10C, 11C, 12C, 13C, 14C, 15C, or 16C, or a pharmaceutically acceptable salt thereof, wherein n is 1.

26B. The compound of any one of embodiments 1B-24B1C, 5C, 9C, 10C, 11C, 12C, 13C, 14C, 15C, or 16C, or a pharmaceutically acceptable salt thereof, wherein n is 0.

27B. The compound of any one of embodiments 1B-14B, 1C, 5C, 9C, 10C, 11C, 12C, 13C, 14C, 15C, or 16C, or a pharmaceutically acceptable salt thereof, wherein n is 2.

28B. The compound of embodiment 27B, wherein one $R^6$ is selected from the group consisting of methyl and methoxy and the other $R^6$ is selected from the group consisting of methyl, methoxy, halogen, and —$OCH_2CH_2OH$.

31C. The compound of any one of embodiments 1-28B or 1C, 5C, 9C, 10C, 11C, 12C, 13C, 14C, 15C, or 16C, or a pharmaceutically acceptable salt thereof, wherein $R^3$ is selected from the group consisting of hydrogen, methyl, ethyl, phenyl, —$CD_3$, —$CH_2CF_3$, and —$CH_2CH_2OH$.

29B. The compound of any one of embodiments 1B-28B1C, 5C, 9C, 10C, 11C, 12C, 13C, 14C, 15C, 16C, or 31C, or a pharmaceutically acceptable salt thereof, wherein $R^3$ is selected from the group consisting of hydrogen, methyl, ethyl, phenyl, and —$CH_2CH_2OH$.

30B. The compound of embodiment 29B or 31C, or a pharmaceutically acceptable salt thereof, wherein $R^3$ is methyl.

33C. The compound of any one of embodiments 1B-30B or 1C, 5C, 9C, 10C, 11C, 12C, 13C, 14C, 15C, 16C, or 31C, or a pharmaceutically acceptable salt thereof, wherein $R^4$ is a (5- to 10-membered monocyclic or fused bicyclic heteroaryl)-methyl, wherein said heteroaryl is optionally substituted with one or two substituents, each independently selected from the group consisting of phenyl, $C_3$-$C_7$ cycloalkyl, —($C_1$-$C_3$ alkyl)-phenyl, and 5- to 7-membered monocyclic heterocyclyl, and wherein said phenyl either alone or in —($C_1$-$C_3$ alkyl)-phenyl, cycloalkyl, or heterocyclyl is optionally substituted with one or two substituents, each individually selected from the group consisting of $C_1$-$C_3$ alkyl, halogen, and hydroxy.

31B. The compound of any one of embodiments 1B-30B or 33C, or a pharmaceutically acceptable salt thereof, wherein $R^4$ is a (5- to 10-membered monocyclic or fused bicyclic heteroaryl)-methyl, wherein said heteroaryl is optionally substituted with one or two substituents, each independently selected from the group consisting of phenyl, $C_3$-$C_7$ cycloalkyl, and 5- to 7-membered monocyclic heterocyclyl, and wherein said phenyl, cycloalkyl, or heterocyclyl is optionally substituted with one or two substituents, each individually selected from the group consisting of $C_1$-$C_3$ alkyl, halogen, and hydroxy.

32B. The compound of embodiment 31B or 33C, or a pharmaceutically acceptable salt thereof, wherein $R^4$ is a (6-membered heteroaryl)-methyl, wherein at least one of the ring atoms ortho to the attachment point in said 6-membered heteroaryl is a nitrogen.

35C. The compound of embodiment 33C or 32B, or a pharmaceutically acceptable salt thereof, wherein $R^4$ is selected from the group consisting of pyridinyl-methyl, pyrimidinyl-methyl, benzoxazole-methyl, oxazolyl-methyl, and triazolyl-methyl, each optionally substituted with phenyl or benzyl, and wherein said phenyl is optionally substituted with one substituent selected from the group consisting of fluoro, methyl, and chloro.

33B. The compound of embodiment 31B, 32B or 35C, or a pharmaceutically acceptable salt thereof, wherein $R^4$ is selected from the group consisting of pyridinyl-methyl, pyrimidinyl-methyl, benzoxazole-methyl, and triazolyl-methyl, each optionally substituted with phenyl, and wherein said phenyl is optionally substituted with one substituent selected from the group consisting of fluoro, methyl, and chloro.

36C. The compound of embodiment 35C, or a pharmaceutically acceptable salt thereof, wherein $R^4$ is selected from the group consisting of

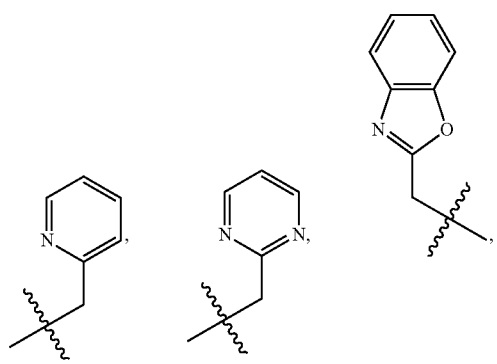

-continued

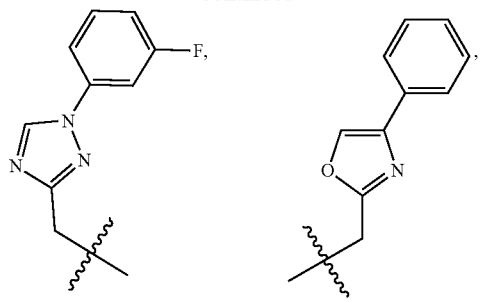

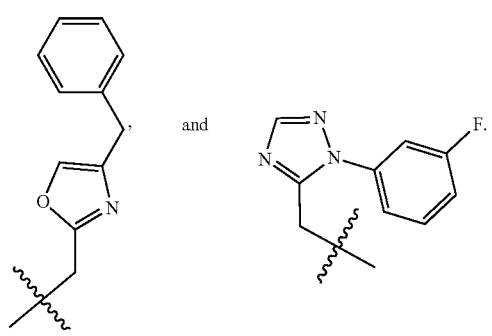

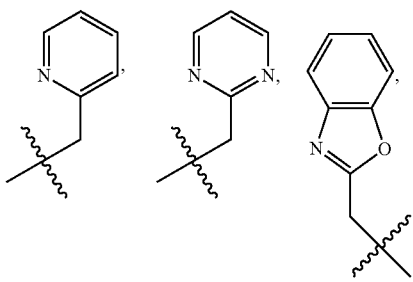

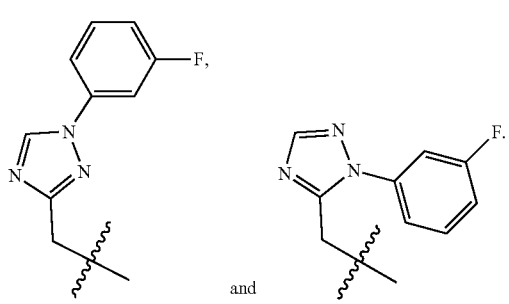

34B. The compound of embodiment 33B or 36C, or a pharmaceutically acceptable salt thereof, wherein $R^4$ is selected from the group consisting of 35B. The compound of any one of embodiments 1B-30B or 1C, 5C, 9C, 1° C., 11C, 12C, 13C, 14C, 15C, 16C, 31C, 33C, 35C, or 36C, or a pharmaceutically acceptable salt thereof, wherein, wherein $R^4$ is

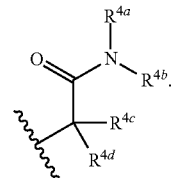

36B. The compound of embodiment 35B, or a pharmaceutically acceptable salt thereof, wherein $R^{4c}$ is selected from the group consisting of hydrogen, methyl, isopropyl, —CH$_2$OH, —CH$_2$OC(CH$_3$)$_3$, and —CH$_2$CH$_2$SCH$_3$; and $R^{4d}$ is selected from the group consisting of hydrogen and methyl; or, $R^{4c}$ and $R^{4d}$ taken together with the atom to which each is attached form a cyclopropyl ring.

37B. The compound of embodiment 36B, or a pharmaceutically acceptable salt thereof, wherein $R^{4c}$ and $R^{4d}$ are each hydrogen.

37bb. The compound of embodiment 36B, or a pharmaceutically acceptable salt thereof, wherein $R^{4c}$ is hydrogen or methyl; and $R^{4d}$ is hydrogen.

37bbb. The compound of embodiment 36B or 37bb, or a pharmaceutically acceptable salt thereof, wherein $R^{4c}$ is methyl; and $R^{4d}$ is hydrogen.

38B. The compound of any one of embodiments 35B-37B, or a pharmaceutically acceptable salt thereof, wherein $R^{4b}$ is hydrogen.

39B. The compound of any one of embodiments 35B-38B, or a pharmaceutically acceptable salt thereof, wherein $R^{4a}$ is $C_1$-$C_6$ alkyl.

42C. The compound of embodiment 39B, or a pharmaceutically acceptable salt thereof, wherein $R^{4a}$ is methyl, ethyl, isopropyl, tert-butyl, or 3-methylpentan-3-yl.

43C. The compound of embodiment 39B or 42C, or a pharmaceutically acceptable salt thereof, wherein $R^{4a}$ is tert-butyl or isopropyl.

40B. The compound of embodiment 39B or 42C, or a pharmaceutically acceptable salt thereof, wherein $R^{4a}$ is tert-butyl.

41B. The compound of any one of embodiments 35B-38B, or a pharmaceutically acceptable salt thereof, wherein $R^{4a}$ is phenyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic or fused bicyclic heterocyclyl.

42B. The compound of embodiment 41B, or a pharmaceutically acceptable salt thereof, wherein $R^{4a}$ is phenyl optionally substituted with one substituent selected from the group consisting of fluoro, chloro, methyl, and methoxy.

43B. The compound of embodiment 42B, wherein $R^{4a}$ is selected from the group consisting of

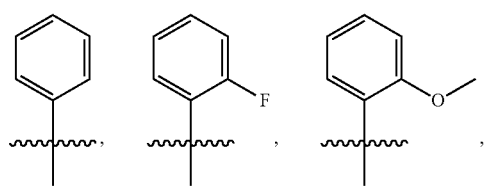

-continued

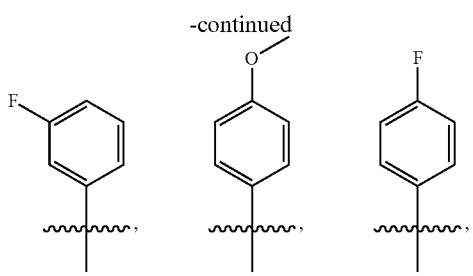

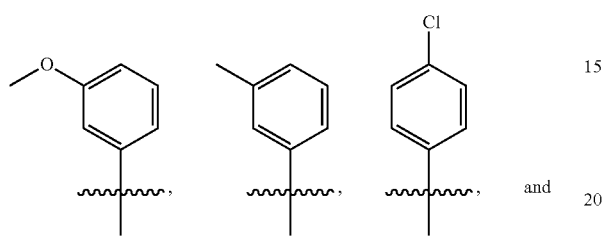

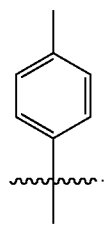

44B. The compound of any one of embodiments 35B-38B, or a pharmaceutically acceptable salt thereof, wherein $R^{4a}$ is 5- to 10-membered monocyclic or fused bicyclic heteroaryl optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic, fused bicyclic, or spiro heterocyclyl.

45B. The compound of embodiment 44B, or a pharmaceutically acceptable salt thereof, wherein $R^{4a}$ is pyridinyl, pyrimidinyl, pyrazolyl, isothiazolyl, pyridizinyl, or quinolinyl, optionally substituted with one substituent selected from the group consisting of fluoro, chloro, methoxy, azepanyl, cyclopropyl, —$CF_3$, —$OCF_3$, or methyl.

46B. The compound of embodiment 45B, or a pharmaceutically acceptable salt thereof, wherein $R^{4a}$ is selected from the group consisting of

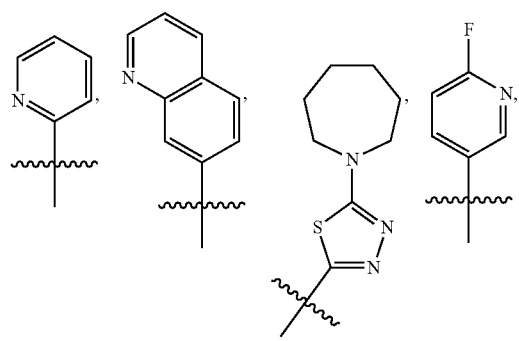

-continued

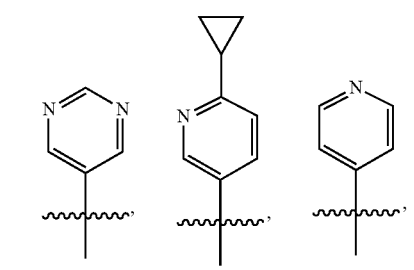

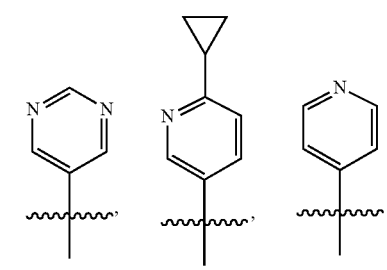

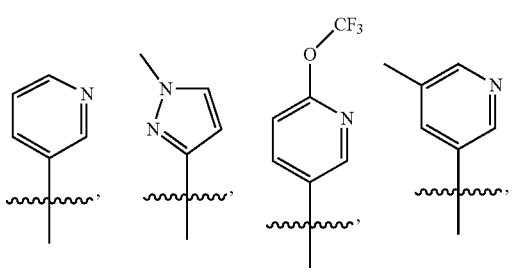

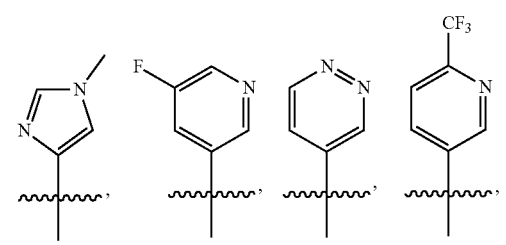

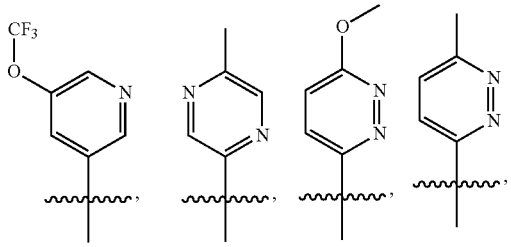

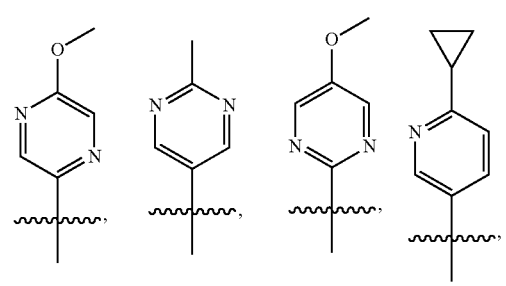

-continued

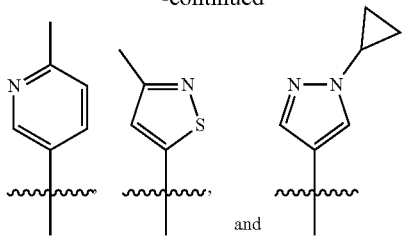
and

47B. The compound of any one of embodiments 35B-38B, or a pharmaceutically acceptable salt thereof, wherein $R^{4a}$ is $C_3$-$C_7$ cycloalkyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic or fused bicyclic heterocyclyl.

48B. The compound of embodiment 47B, or a pharmaceutically acceptable salt thereof, wherein $R^{4a}$ is selected from the group consisting of cyclopropyl, cyclobutyl, cyclopentyl, cyclohexyl, and bicyclo[1.1.1]pentan-1-yl, optionally substituted with one or two substituents, each independently selected from the group consisting of methyl, —$CF_3$, fluoro, or hydroxy.

52C. The compound of embodiment 48B, wherein $R^{4a}$ is selected from the group consisting of

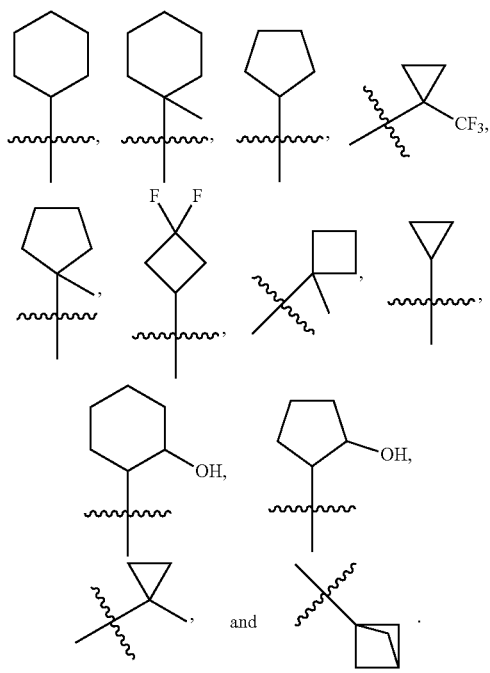
, and

49B. The compound of embodiment 48B or 52C, wherein $R^{4a}$ is selected from the group consisting of

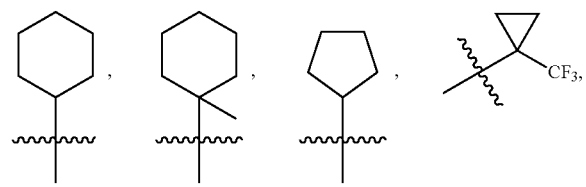

-continued

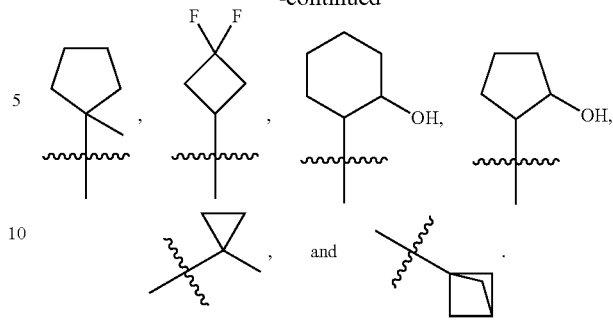
, and

53C. The compound of any one of embodiments 35B-38B, or a pharmaceutically acceptable salt thereof, wherein $R^{4a}$ is a 4- to 10-membered monocyclic or fused bicyclic heterocyclyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, oxo, $C_3$-$C_7$ cycloalkyl, and 5- to 10-membered monocyclic or fused bicyclic heterocyclyl.

50B. The compound of any one of embodiments 35B-38B or 53C, or a pharmaceutically acceptable salt thereof, wherein $R^{4a}$ is a 5- to 10-membered monocyclic or fused bicyclic heterocyclyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, oxo, $C_3$-$C_7$ cycloalkyl, and 5- to 10-membered monocyclic or fused bicyclic heterocyclyl.

54C. The compound of embodiment 53C, or a pharmaceutically acceptable salt thereof, wherein $R^{4a}$ is selected from the group consisting of tetrahydrofuranyl, pyrrolidinyl, benzo[d][1,3]dioxolyl, oxetanyl, and tetrahydropyranyl, optionally substituted with one or two substituents, each independently selected from the group consisting of methyl, methoxy, and oxo.

51B. The compound of embodiment 50B, or a pharmaceutically acceptable salt thereof, wherein $R^{4a}$ is selected from the group consisting of tetrahydrofuranyl, pyrrolidinyl, benzo[d][1,3]dioxolyl, and tetrahydropyranyl, optionally substituted with one or two substituents, each independently selected from the group consisting of methyl, methoxy, and oxo.

55C. The compound of embodiment 54C, wherein $R^{4a}$ is selected from the group consisting of

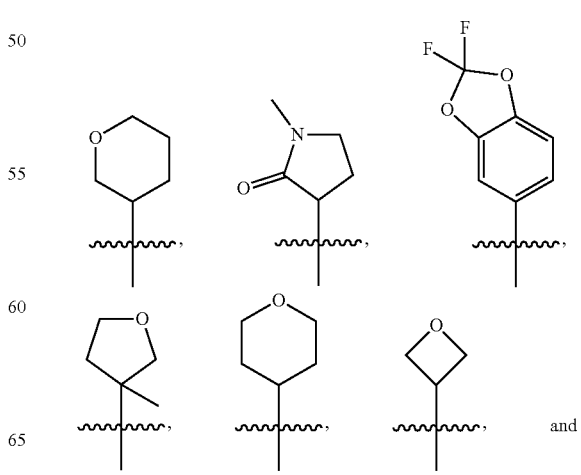
, and

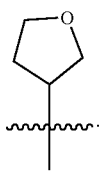

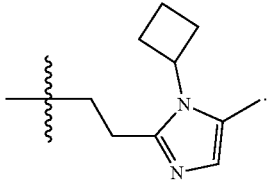

52B. The compound of embodiment 51B or 55C, wherein $R^{4a}$ is selected from the group consisting of

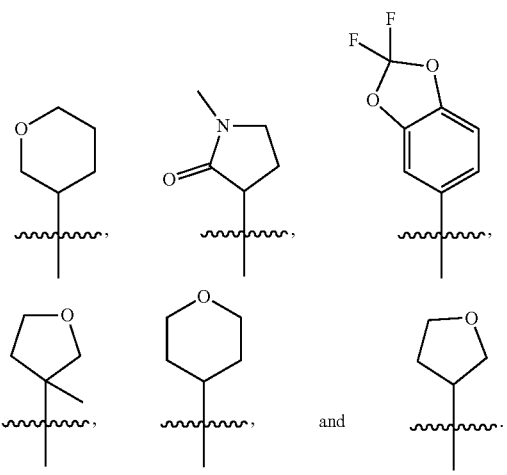

53B. The compound of any one of embodiments 35B-38B, or a pharmaceutically acceptable salt thereof, wherein $R^{4a}$ is ($C_6$-$C_{10}$ monocyclic or fused bicyclic aryl)-$C_1$-$C_3$ alkyl or (5- to 10-membered monocyclic or fused bicyclic heteroaryl)-$C_1$-$C_3$ alkyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic, fused bicyclic heterocyclyl.

54B. The compound of embodiment 53B, or a pharmaceutically acceptable salt thereof, wherein $R^{4a}$ is selected from the group consisting of phenyl-methyl, 1-cyclobutyl-2-ethyl-5-methyl-1H-imidazolyl, and pyridinyl-methyl.

57C. The compound of claim 53B, or a pharmaceutically acceptable salt thereof, wherein $R^{4a}$ is selected from the group consisting of benzyl, 2-(1-cyclobutyl-5-methyl-1H-imidazol-2-yl)ethyl, and pyridinyl-methyl.

55B. The compound of embodiment 54B or 57C, or a pharmaceutically acceptable salt thereof, wherein $R^{4a}$ is selected from the group consisting of

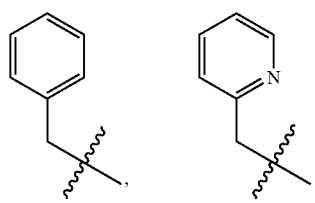

59C. The compound of any one of embodiments 35B-38B, or a pharmaceutically acceptable salt thereof, wherein $R^{4a}$ is selected from the group consisting of hydroxy-$C_1$-$C_6$ alkyl, halo-$C_1$-$C_3$ alkyl, $C_1$-$C_3$ alkoxy-$C_1$-$C_6$ alkyl, and —$C_1$-$C_6$ alkyl-$NR^{J1}R^{J2}$, wherein $R^{J1}$ and $R^{J2}$ are each independently hydrogen or $C_1$-$C_3$ alkyl.

60C. The compound of embodiment 59C, or a pharmaceutically acceptable salt thereof, wherein $R^{4a}$ is selected from the group consisting of —$C(CH_3)_2CH_2OH$, —$CH_2CH_2OH$, —$C(CH_3)_2CH_2OCH_3$, —$CH(CH_3)CH_2OH$, —$CH_2CH_2N(CH_3)_2$, —$CH_2CF_3$.

56B. The compound of any one of embodiments 35B-38B, or a pharmaceutically acceptable salt thereof, wherein $R^{4a}$ is selected from the group consisting of —$C(CH_3)_2CH_2OH$, —$CH_2CH_2OH$, and —$C(CH_3)_2CH_2OCH_3$.

61C. The compound of embodiment 59C, 60C, or 56B, or a pharmaceutically acceptable salt thereof, wherein $R^{4a}$ is —$C(CH_3)_2CH_2OH$.

57B. The compound of any one of embodiments 35B-38B, or a pharmaceutically acceptable salt thereof, wherein $R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy.

63C. The compound of embodiment 57B, or a pharmaceutically acceptable salt thereof, wherein $R^{4a}$ and $R^{4b}$ taken together with the atom to which each is attached form a piperidinyl, morpholinyl, pyrrolidinyl, azepanyl, indolinyl, azabicyclo[3.1.1]heptanyl, 2,3-dihydro-1H-pyrrolo[2,3-c]pyridine, or piperazinyl, optionally substituted with one or two substituents, each independently selected from the group consisting of hydroxy, methyl, fluoro, and methoxy.

58B. The compound of embodiment 57B or 63C, or a pharmaceutically acceptable salt thereof, wherein $R^{4a}$ and $R^{4b}$ taken together with the atom to which each is attached form a piperidinyl, morpholinyl, pyrrolidinyl, azepanyl, indolinyl, azabicyclo[3.1.1]heptanyl, or piperazinyl, optionally substituted with one or two substituents, each independently selected from the group consisting of methyl, fluoro, and methoxy.

64C. The compound of embodiment 63C or 58B, or a pharmaceutically acceptable salt thereof, wherein $R^{4a}$ and $R^{4b}$ taken together with the atom to which each is attached form a

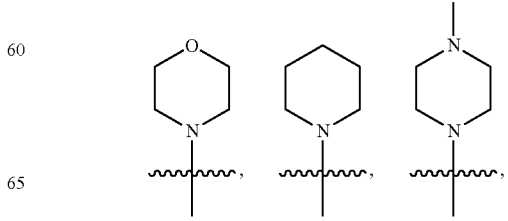

-continued

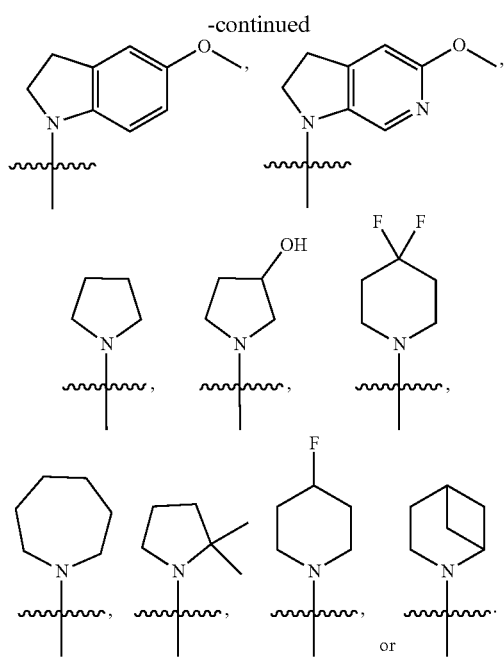

59B. The compound of embodiment 58B or 64C, or a pharmaceutically acceptable salt thereof, wherein $R^{4a}$ and $R^{4b}$ taken together with the atom to which each is attached form a

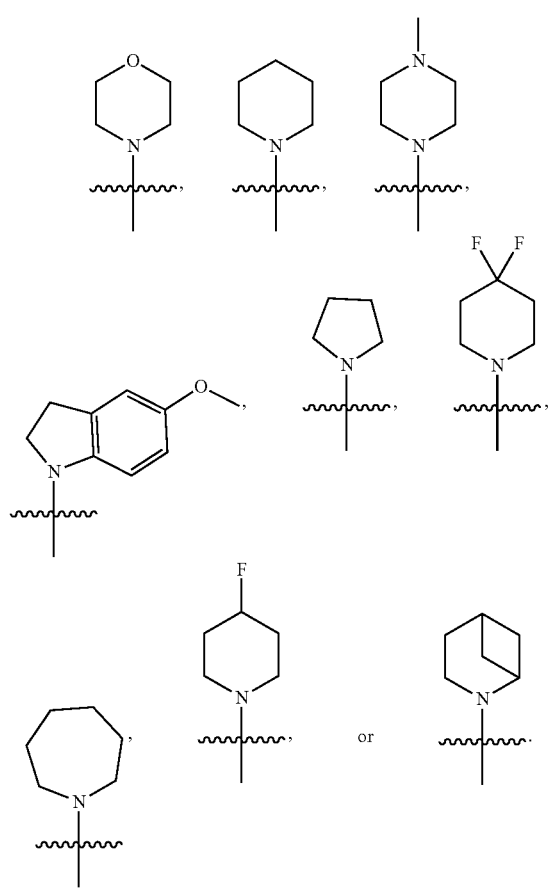

60B. The compound of any one of embodiments 35B, 39B-56B, 42C, 43C, 52C, 53C, 54C, 55C, 59C, 60C, or 61C, or a pharmaceutically acceptable salt thereof, wherein $R^{4b}$ and $R^{4c}$ taken together with the atom to which each is attached form a 5- to 7-membered monocyclic heterocyclyl, optionally substituted with one or two substituents, each independently selected from $C_1$-$C_3$ alkyl.

61B. The compound of embodiment 60B, or a pharmaceutically acceptable salt thereof, wherein $R^{4b}$ and $R^{4c}$ taken together with the atom to which each is attached form a piperidin-2-one or a pyrrolidine-2-one, optionally substituted one or two times with methyl.

62B. The compound of any one of embodiments 1B-30B, 1C, 5C, 9C, 10C, 11C, 12C, 13C, 14C, 15C, 16C, or 31C, or a pharmaceutically acceptable salt thereof, wherein $R^4$ is

wherein $R^{4g}$ is selected from the group consisting of $C_6$-$C_{10}$ monocyclic or fused bicyclic aryl and $C_1$-$C_3$ alkyl.

63B. The compound of claim 62B, or a pharmaceutically acceptable salt thereof, wherein $R^{4g}$ is selected from the group consisting of phenyl and methyl.

64B. The compound of claim any one of embodiments 1B-28B, 1C, 5C, 9C, 10C, 11C, 12C, 13C, 14C, 15C, 16C, or 31C, or a pharmaceutically acceptable salt thereof, wherein $R^3$ and $R^4$ taken together with the nitrogen atom to which each is attached form a 7-membered monocyclic or bridged bicyclic heterocyclyl containing one or two heteroatoms;
  wherein when said 7-membered heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and
  when said 7-membered heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, halo-$C_1$-$C_3$ alkyl, and $C_6$-$C_{10}$ monocyclic or fused bicyclic aryl; and
  wherein said aryl is optionally substituted with one or two substituents, each individually selected from the group consisting of $C_1$-$C_3$ alkoxy, hydroxy, halogen, and $C_1$-$C_3$ alkyl.

65B. The compound of embodiment 64B, or a pharmaceutically acceptable salt thereof, wherein $R^3$ and $R^4$ taken together with the nitrogen atom to which each is attached form a 7-membered heterocyclyl containing one heteroatom, wherein said heterocyclyl is optionally substituted once with methyl or oxo; or, a 7-membered monocyclic or bridged bicyclic heterocyclyl containing two heteroatoms, wherein said heteroatoms are N or O, and said heterocyclyl is optionally substituted with one or two substituents, each independently selected from the group consisting of phenyl, methyl, and oxo, and wherein said phenyl is optionally substituted with methoxy.

66B. The compound of embodiment 65B, or a pharmaceutically acceptable salt thereof, wherein $R^3$ and $R^4$ taken together with the nitrogen atom to which each is attached form a

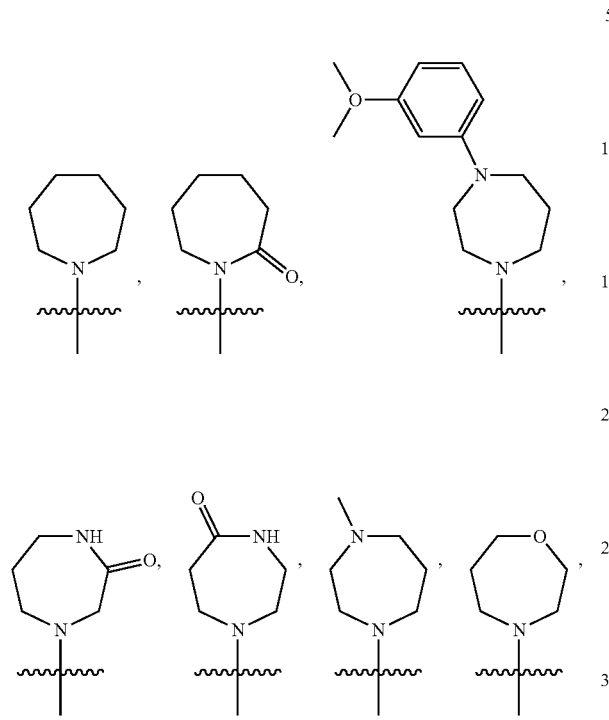

67B. The compound of any one of embodiments 1B-28B, 1C, 5C, 9C, 1° C., 11C, 12C, 13C, 14C, 15C, 16C, or 31C, or a pharmaceutically acceptable salt thereof, wherein $R^3$ and $R^4$ taken together with the nitrogen atom to which each is attached form a 10- or 11-membered fused bicyclic heterocyclyl containing one heteroatom, or a 12-membered bicyclic fused and bridged heterocyclyl, each optionally substituted with one, two, or three substituents, each independently selected from the group consisting of $C_1$-$C_3$ alkyl, $C_1$-$C_3$ alkoxy, hydroxy, and halogen.

68B. The compound of embodiment 67B, or a pharmaceutically acceptable salt thereof, wherein $R^3$ and $R^4$ taken together with the nitrogen atom to which each is attached form a

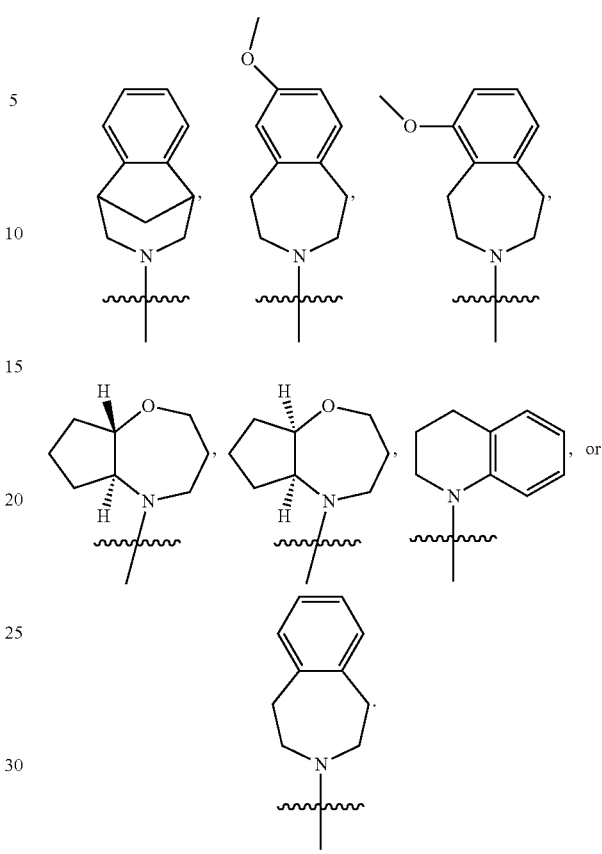

69B. The compound of any one of embodiments 1B-28B, 1C, 8C, 9C, 10C, 11C, 12C, 13C, 14C, 15C, 16C, or 31C, or a pharmaceutically acceptable salt thereof, wherein $R^3$ and $R^4$ taken together with the nitrogen atom to which each is attached form a 4- or 6-membered monocyclic heterocyclyl containing one heteroatom; wherein, said 4-membered monocyclic heterocyclyl is optionally substituted with —$(CH_2)_sC(\!=\!O)NR^kR^l$; wherein, s is 0, 1, or 2;

$R^k$ is hydrogen or $C_1$-$C_3$ alkyl; and $R^l$ is selected from the group consisting of hydrogen, methyl, phenyl, cyclopentyl, and cyclohexyl;

and, said 6-membered monocyclic heterocyclyl is optionally substituted with one or two substituents, each independently selected from the group consisting of $C_1$-$C_3$ alkoxy, oxo, halogen, cyano, and —$NR^qR^w$; wherein, $R^q$ is hydrogen or $C_1$-$C_3$ alkyl;

$R^w$ is $C_6$-$C_{10}$ monocyclic or fused bicyclic aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy.

70B. The compound of embodiment 69B, or a pharmaceutically acceptable salt thereof, wherein $R^3$ and $R^4$ taken together with the nitrogen atom to which each is attached form a

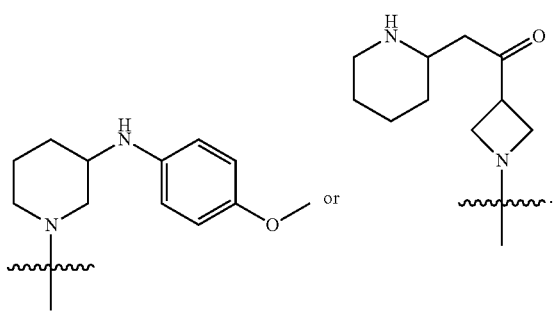 [SMILES: *N1CCCC(Nc2ccc(OC)cc2)C1 ; *N1CC(C(=O)CC2CCCCN2)C1]

71B. The compound of any one of embodiments 1B-70B, 1C, 5C, 9C, 10C, 11C, 12C, 13C, 14C, 15C, 16C, 31C, 33C, 35C, 36C, 42C, 52C, 53C, 54C, 55C, 61C, 63C, or 64C, or a pharmaceutically acceptable salt thereof, wherein $R^x$, in each instance, is methyl.

72B. The compound of any one of embodiments 1B-71B, 1C, 5C, 9C, 1° C., 11C, 12C, 13C, 14C, 15C, 16C, 31C, 33C, 35C, 36C, 42C, 52C, 53C, 54C, 55C, 61C, 63C, or 64C, or a pharmaceutically acceptable salt thereof, wherein m is 0.

73B. The compound of any one of embodiments 1B-71B, 1C, 5C, 9C, 1° C., 11C, 12C, 13C, 14C, 15C, 16C, 31C, 33C, 35C, 36C, 42C, 52C, 53C, 54C, 55C, 61C, 63C, or 64C, or a pharmaceutically acceptable salt thereof, wherein m is 2.

79C. The compound of claim 1, or a pharmaceutically acceptable salt thereof; wherein, Z is N;
p is 1;
f is 1;
$Y^1$, $Y^2$, $Y^3$, and $Y^4$ are each independently selected from the group consisting of CH, N, and C—$R^6$, provided that 1 or 2 of $Y^1$, $Y^2$, $Y^3$, and $Y^4$ can be N;
$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_{10}$ alkoxy, hydroxy-$C_1$-$C_{10}$-alkyl, cyano, —$NR^GR^H$, halo-$C_1$-$C_3$ alkoxy, —O—($C_1$-$C_6$ alkyl)-$R^{bb}$, —O—$R^{bb}$, —($C_1$-$C_6$ alkyl)-$NR^{GI}R^{HI}$, halo-$C_1$-$C_3$ alkyl, —O—$R^{cc}$—O—$R^{dd}$, 5- to 7-membered monocyclic heteroaryl, and $C_3$-$C_6$ cycloalkyl; wherein,
the alkyl moiety in hydroxy-$C_1$-$C_{10}$ alkoxy or —O—($C_1$-$C_6$ alkyl)-$R^{bb}$ is optionally substituted with hydroxy, hydroxy-$C_1$-$C_3$-alkyl, halogen, or $C_1$-$C_3$ alkoxy;
$R^{bb}$ is 4- to 7-membered monocyclic heterocyclyl, $C_3$-$C_7$ cycloalkyl, or —$NR^GR^H$;
$R^{cc}$ and $R^{dd}$ are each independently $C_1$-$C_3$ alkyl;
wherein, said cycloalkyl, heterocyclyl, or heteroaryl of $R^6$ or $R^{bb}$ is optionally substituted with one or two substituents, each independently selected from the group consisting of hydroxy, $C_1$-$C_3$ alkoxy, and $C_1$-$C_3$ alkyl; and,
$R^{G1}$ and $R^{H1}$ are each independently hydrogen or $C_1$-$C_3$ alkyl;
$R^G$ and $R^H$ are each independently hydrogen, —$C(O)R^{Ga}$, or optionally deuterated $C_1$-$C_3$ alkyl; wherein,
$R^{Ga}$ is $C_1$-$C_3$ alkyl or hydrogen;
or,
two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- to 6-membered monocyclic heteroaryl fused with Ring B; wherein, said heterocyclyl, phenyl, cycloalkyl, or heteroaryl fused with ring B is optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl;
n is 0, 1, or 2;
$R^3$ is selected from the group consisting of hydrogen, phenyl, —$CH_2CH_2OH$, and optionally deuterated methyl or ethyl;
$R^4$ is

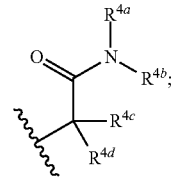

wherein,
$R^{4c}$ is selected from the group consisting of hydrogen, methyl, isopropyl, —$CH_2OH$, —$CH_2OC(CH_3)_3$, and —$CH_2CH_2SCH_3$;
$R^{4d}$ is selected from the group consisting of hydrogen and methyl;
or,
$R^{4c}$ and $R^{4d}$ taken together with the atom to which each is attached form a cyclopropyl ring;
$R^{4b}$ is hydrogen or methyl;
$R^{4a}$ is selected from the group consisting of hydrogen, $C_1$-$C_{10}$ alkyl, hydroxy-$C_1$-$C_6$ alkyl, $C_1$-$C_3$ alkoxy-$C_1$-$C_6$ alkyl, —$C_1$-$C_6$ alkyl-$NR^{J1}R^{J2}$, $C_3$-$C_7$ cycloalkyl, 5- to 10-membered monocyclic, fused bicyclic, or bridged bicyclic heterocyclyl, $C_6$-$C_{10}$ monocyclic or fused bicyclic aryl, 4- to 10-membered monocyclic or fused bicyclic heteroaryl, ($C_6$-$C_{10}$ monocyclic or fused bicyclic aryl)-$C_1$-$C_3$ alkyl, and (5- to 10-membered monocyclic or fused bicyclic heteroaryl)-$C_1$-$C_3$ alkyl;
wherein the cycloalkyl, heterocyclyl, aryl, heteroaryl, arylalkyl, or heteroaryl-alkyl of $R^{4a}$ is optionally substituted with one, two, or three substituents, each independently selected from the group consisting of halogen, $C_1$-$C_6$ alkyl, halo-$C_1$-$C_3$ alkyl, hydroxy, $C_1$-$C_3$ alkoxy, halo-$C_1$-$C_3$ alkoxy, oxo, $C_3$-$C_7$ cycloalkyl, and 5- to 10-membered monocyclic or fused bicyclic heterocyclyl;
$R^{J1}$ and $R^{J2}$ are independently hydrogen or $C_1$-$C_3$ alkyl;
or,
$R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy;
$R^x$, in each instance, is $C_1$-$C_3$ alkyl; and
m is 0, 1, or 2.

74B. The compound of embodiment 1B, or a pharmaceutically acceptable salt thereof, wherein,
Z is N;
p is 1;
f is 1;
$Y^1$, $Y^2$, $Y^3$, and $Y^4$ are each independently selected from the group consisting of CH, N, and C—$R^6$, provided that 1 or 2 of $Y^1$, $Y^2$, $Y^3$, and $Y^4$ can be N;

$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$ alkyl, cyano, —$NR^GR^H$, halo-$C_1$-$C_3$ alkoxy, —O—$(CH_2)_u$—$R^{bb}$, halo-$C_1$-$C_3$ alkyl, —O—$R^{cc}$—O—$R^{dd}$, 5- to 7-membered monocyclic heteroaryl, and $C_3$-$C_6$ cycloalkyl; wherein, u is an integer from 0 to 6;
$R^{bb}$ is 4- to 7-membered monocyclic heterocyclyl, $C_3$-$C_7$ cycloalkyl, or —$NR^GR^H$;
$R^{cc}$ and $R^{dd}$ are each independently $C_1$-$C_3$ alkyl;
wherein, said cycloalkyl, heterocyclyl, or heteroaryl is optionally substituted with one or two substituents, each independently selected from the group consisting of hydroxy, $C_1$-$C_3$ alkoxy, and $C_1$-$C_3$ alkyl; and,
$R^G$ and $R^H$ are each independently hydrogen, —C(O)$R^{Ga}$, or $C_1$-$C_3$ alkyl; wherein,
$R^{Ga}$ is $C_1$-$C_3$ alkyl or hydrogen;
or,
two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- to 6-membered monocyclic heteroaryl fused with Ring B; wherein,
said heterocyclyl, phenyl, cycloalkyl, or heteroaryl fused with ring B is optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl;
n is 0, 1, or 2;
$R^3$ is selected from the group consisting of hydrogen, methyl, ethyl, phenyl, and —$CH_2CH_2OH$;
$R^4$ is

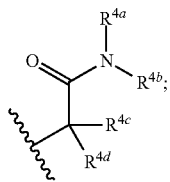

wherein,
$R^{4c}$ is selected from the group consisting of hydrogen, methyl, isopropyl, —$CH_2OH$, —$CH_2OC(CH_3)_3$, and —$CH_2CH_2SCH_3$;
$R^{4d}$ is selected from the group consisting of hydrogen and methyl;
or,
$R^{4c}$ and $R^{4d}$ taken together with the atom to which each is attached form a cyclopropyl ring;
$R^{4b}$ is hydrogen or methyl;
$R^{4a}$ is selected from the group consisting of hydrogen, $C_1$-$C_6$ alkyl, hydroxy-$C_1$-$C_6$ alkyl, $C_1$-$C_3$ alkoxy-$C_1$-$C_6$ alkyl, $C_3$-$C_7$ cycloalkyl, 5- to 10-membered monocyclic, fused bicyclic, or bridged bicyclic heterocyclyl, $C_6$-$C_{10}$ monocyclic or fused bicyclic aryl, 5- to 10-membered monocyclic or fused bicyclic heteroaryl, ($C_6$-$C_{10}$ monocyclic or fused bicyclic aryl)-$C_1$-$C_3$ alkyl, and (5- to 10-membered monocyclic or fused bicyclic heteroaryl)-$C_1$-$C_3$ alkyl; wherein the cycloalkyl, heterocyclyl, aryl, heteroaryl, arylalkyl, or heteroaryl-alkyl of $R^{4a}$ is optionally substituted with one, two, or three substituents, each independently selected from the group consisting of halogen, $C_1$-$C_6$ alkyl, halo-$C_1$-$C_3$ alkyl, hydroxy, $C_1$-$C_3$ alkoxy, halo-$C_1$-$C_3$ alkoxy, halo-$C_1$-$C_3$ alkyl, oxo, $C_3$-$C_7$ cycloalkyl, and 5- to 10-membered monocyclic or fused bicyclic heterocyclyl;
or,
$R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy;
$R^x$, in each instance, is $C_1$-$C_3$ alkyl; and
m is 0, 1, or 2.

75B. The compound of embodiment 74B or 79C, or a pharmaceutically acceptable salt thereof, wherein m is 0.
76B. The compound of embodiment 74B or 79C, or a pharmaceutically acceptable salt thereof, wherein m is 2 and $R^X$, in each instance, is methyl.
77B. The compound of any one of embodiments 74B-76B or 79C, or a pharmaceutically acceptable salt thereof, wherein, $Y^1$, $Y^2$, $Y^3$, and $Y^4$ are each CH or C—$R^6$;
$Y^3$ is N and $Y^1$, $Y^2$, and $Y^4$ are each CH or C—$R^6$;
$Y^2$ is N and $Y^1$, $Y^3$, $Y^4$ are each CH or C—$R^6$;
or
$Y^1$ is N and $Y^2$, $Y^3$, and $Y^4$ are each CH or C—$R^6$.
77bb. The compound of any one of embodiments 74B-77B or 79C, or a pharmaceutically acceptable salt thereof, wherein, $Y^1$ is CH, $Y^2$ is C—$R^6$, $Y^3$ is CH, and $Y^4$ is CH.
83C. The compound of any one of embodiments 79C or 75B-77bb, or a pharmaceutically acceptable salt thereof; wherein $R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_{10}$-alkyl, —O—$R^{bb}$, —O—($C_1$-$C_6$ alkyl)-$R^{bb}$, halo-$C_1$-$C_3$ alkoxy, —O—$R^{cc}$—O—$R^{dd}$, halo-$C_1$-$C_3$ alkyl, $C_3$-$C_6$ cycloalkyl, and —$NR^GR^H$; wherein,
$R^{bb}$ is —$NR^GR^H$, 4- to 6-membered monocyclic heterocyclyl, or $C_3$-$C_7$ cycloalkyl;
$R^G$ and $R^H$ are each independently hydrogen or $C_1$-$C_3$ alkyl;
$R^{cc}$ and $R^{dd}$ are each independently $C_1$-$C_3$ alkyl; and,
wherein,
said cycloalkyl or heterocyclyl of $R^6$ or $R^{bb}$ is optionally substituted with one or two substituents, each independently selected from the group consisting of hydroxy, $C_1$-$C_3$ alkoxy, and $C_1$-$C_3$ alkyl.
84C. The compound of embodiment 83C, wherein $R^{bb}$ is selected from the group consisting of cyclopropyl, cyclobutyl, tetrahydrofuranyl, oxetanyl, morpholinyl, and pyrrolidinyl, each optionally substituted with hydroxy or methyl; or, $R^{bb}$ is —$N(CH_3)_2$.
78B. The compound of any one of embodiments 74B-77B, or a pharmaceutically acceptable salt thereof; wherein $R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_6$ alkoxy, hydroxy-$C_1$-$C_3$ alkyl, —O—$(CH_2)_u$—$R^{bb}$, halo-$C_1$-$C_3$ alkoxy, —O—$R^{cc}$—O—$R^{dd}$, halo-$C_1$-$C_3$ alkyl, $C_3$-$C_6$ cycloalkyl, and —$NR^GR^H$; wherein,
$R^{bb}$ is —$NR^GR^H$, 4- or 5-membered monocyclic heterocyclyl, or $C_3$-$C_7$ cycloalkyl;
u is an integer from 0 to 3;
$R^G$ and $R^H$ are each independently hydrogen or $C_1$-$C_3$ alkyl;

$R^{cc}$ and $R^{dd}$ are each independently $C_1$-$C_3$ alkyl; and, wherein, said cycloalkyl or heterocyclyl is optionally substituted with one or two substituents, each independently selected from the group consisting of hydroxy, $C_1$-$C_3$ alkoxy, and $C_1$-$C_3$ alkyl.

79B. The compound of embodiment 78B, wherein $R^{bb}$ is selected from the group consisting of cyclopropyl, cyclobutyl, tetrahydrofuranyl, oxetanyl, and pyrrolidinyl, each optionally substituted with hydroxy or methyl.

85C. The compound of any one of embodiments 79C, 75B-77B, or 84C, or a pharmaceutically acceptable salt thereof, wherein $R^6$, in each instance, is selected from the group consisting of methoxy, ethoxy, methyl, fluoro, chloro, ethyl, —N(CH$_3$)$_2$, hydroxy, —OCH$_2$CH(CH$_3$)OH, —OCH$_2$CH$_2$N(CH$_2$CH$_3$)$_2$, —OCH$_2$C(CH$_3$)(CH$_2$CH$_3$)OH, —OCH$_2$CH(CH$_2$OCH$_3$)OH, —OCH$_2$CH$_2$OH, —CH$_2$OH, —CH$_2$OCH$_3$, —OCH$_2$CH$_2$NH$_2$, —OCH$_2$CH$_2$N(CH$_3$)$_2$, —OCH$_2$C(CH$_3$)$_2$OH, —OCH$_2$CF$_3$, —OCHF$_2$, —OCF$_3$, —OCH$_2$CH$_2$OCH$_3$, —OCH$_2$CH$_2$F, —OC(CH$_3$)$_2$CH$_2$OH, —CH$_2$CH$_2$OH,

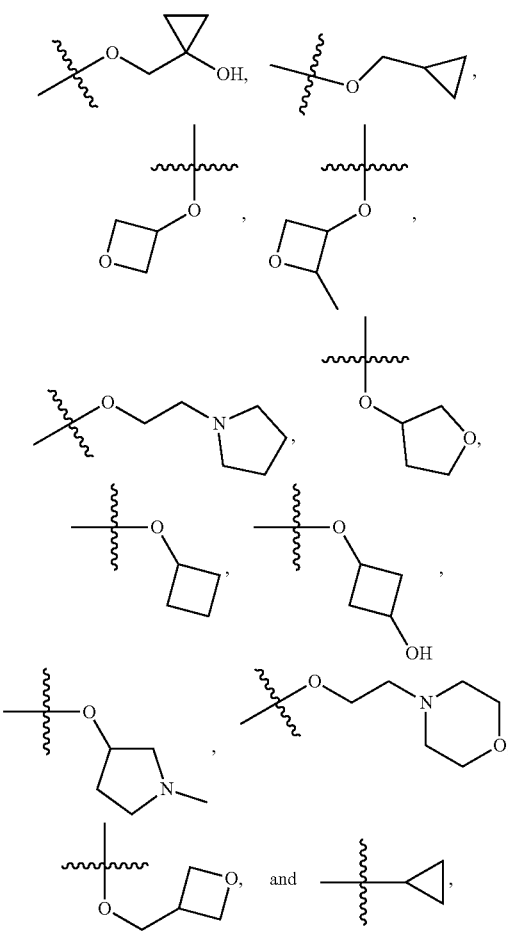

where ⟩ indicates the point of attachment to Ring B.

80B. The compound of any one of embodiments 74B-79B, or a pharmaceutically acceptable salt thereof, wherein $R^6$, in each instance, is selected from the group consisting of methoxy, ethoxy, methyl, fluoro, chloro, ethyl, —N(CH$_3$)$_2$, hydroxy, —OCH$_2$CH$_2$OH, —CH$_2$OH, —CH$_2$OCH$_3$, —OCH$_2$CH$_2$NH$_2$, —OCH$_2$CH$_2$N(CH$_3$)$_2$, —OCH$_2$C(CH$_3$)$_2$OH, —OCH$_2$CF$_3$, —OCHF$_2$, —OCF$_3$, —OCH$_2$CH$_2$OCH$_3$, —OCH$_2$CH$_2$F, —OC(CH$_3$)$_2$CH$_2$OH, —CH$_2$CH$_2$OH,

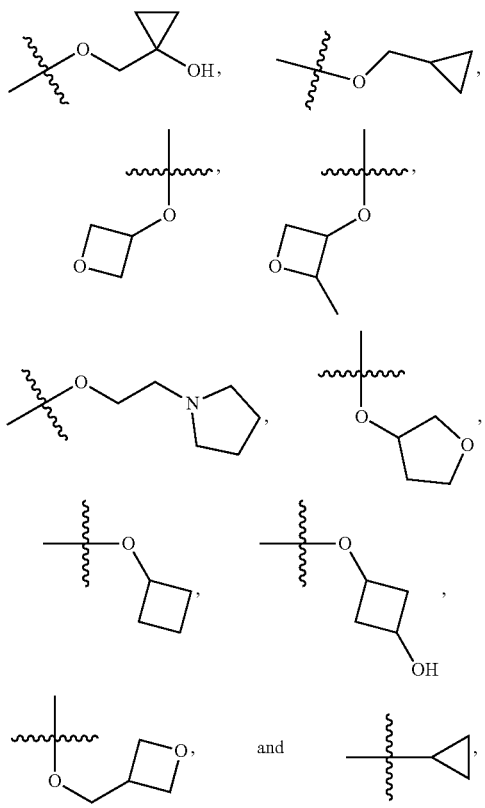

where ⟩ indicates the point of attachment to Ring B.

86C. The compound of embodiment 85C, or a pharmaceutically acceptable salt thereof, wherein $R^6$, in each instance, is methoxy, —OCH$_2$CH$_2$OH, —OCH$_2$CH$_2$N(CH$_3$)$_2$, —OCH$_2$C(CH$_3$)$_2$OH,

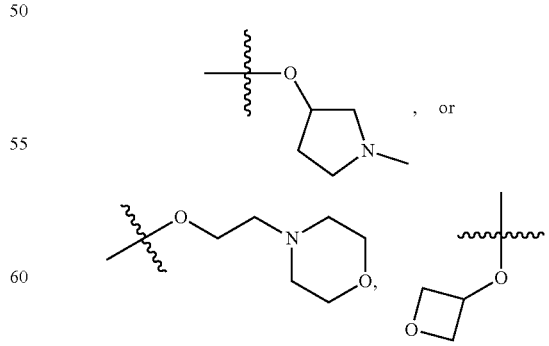

87C. The compound of embodiment 86C, or a pharmaceutically acceptable salt thereof, wherein $R^6$, in each instance, is methoxy, —OCH$_2$CH$_2$N(CH$_3$)$_2$, —OCH$_2$C(CH$_3$)$_2$OH,

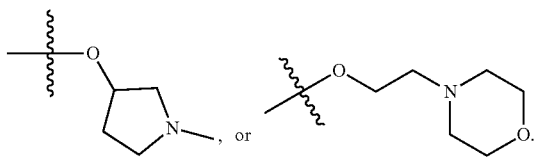

81B. The compound of embodiment 80B or 86C, or a pharmaceutically acceptable salt thereof, wherein $R^6$, in each instance is methoxy, —$OCH_2CH_2OH$, —$OCH_2CH_2N(CH_3)_2$, —$OCH_2C(CH_3)_2OH$, or

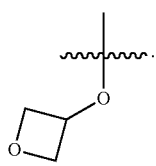 [SMILES: *OC1COC1]

82B. The compound of any one of embodiments 74B-77B, or a pharmaceutically acceptable salt thereof, wherein two $R^6$ groups, taken together with the atom to which each is attached, form a pyrazolyl, dioxanyl, pyridinyl, pyrimidinyl, thiazolyl, furanyl, dioxolanyl, or phenyl ring fused with Ring B, wherein said ring is optionally substituted with one substituent selected from the group consisting of hydroxy, methoxy, tetrahydropyranyl, —$CH_2OH$, and methyl.

83B. The compound of any one of embodiments 74B-82B, 79C, 83C, 84C, 85C, 86C, or 87C, or a pharmaceutically acceptable salt thereof, wherein $R^3$ is methyl.

84B. The compound of any one of embodiments 74B-82B, 79C, 83C, 84C, 85C, 86C, or 87C, or a pharmaceutically acceptable salt thereof, wherein n is 1.

85B. The compound of any one of embodiments 74B-84B, 79C, 83C, 84C, 85C, 86C, or 87C, or a pharmaceutically acceptable salt thereof, wherein $R^{4c}$ is hydrogen.

92C. The compound of any one of embodiments 79C, 83C, 84C, 85C, 86C, or 87C, or a pharmaceutically acceptable salt thereof, wherein $R^{4a}$ is selected from the group consisting of.
  i. tert-butyl or isopropyl;
  ii. phenyl optionally substituted with one substituent selected from the group consisting of fluoro, chloro, methyl, and methoxy;
  iii. pyridinyl, pyrimidinyl, pyrazolyl, isothiazolyl, pyridizinyl, or quinolinyl, optionally substituted with one substituent selected from the group consisting of fluoro, chloro, methoxy, azepanyl, cyclopropyl, —$CF_3$, —$OCF_3$, and methyl;
  iv. cyclopropyl, cyclobutyl, cyclopentyl, cyclohexyl, and bicyclo[1.1.1]pentan-1-yl, optionally substituted with one or two substituents, each independently selected from the group consisting of methyl, —$CF_3$, fluoro, and hydroxy;
  v. tetrahydrofuranyl, pyrrolidinyl, benzo[d][1,3]dioxolyl, and tetrahydropyranyl, optionally substituted with one or two substituents, each independently selected from the group consisting of methyl, methoxy, and oxo;
  vi. benzyl, 2-(1-cyclobutyl-5-methyl-1H-imidazol-2-yl)ethyl, and pyridinyl-methyl; and
  vii. —$C(CH_3)_2CH_2OH$, —$CH_2CH_2OH$, and —$C(CH_3)_2CH_2OCH_3$.

86B. The compound of any one of embodiments 74B-84B, 79C, 83C, 84C, 85C, 86C, or 87C, or a pharmaceutically acceptable salt thereof, wherein $R^{4a}$ is selected from the group consisting of.
  i. tert-butyl;
  ii. phenyl optionally substituted with one substituent selected from the group consisting of fluoro, chloro, methyl, and methoxy;
  iii. pyridinyl, pyrimidinyl, pyrazolyl, isothiazolyl, pyridizinyl, or quinolinyl, optionally substituted with one substituent selected from the group consisting of fluoro, chloro, methoxy, azepanyl, cyclopropyl, —$CF_3$, —$OCF_3$, or methyl;
  iv. cyclopropyl, cyclobutyl, cyclopentyl, cyclohexyl, and bicyclo[1.1.1]pentan-1-yl, optionally substituted with one or two substituents, each independently selected from the group consisting of methyl, —$CF_3$, fluoro, or hydroxy;
  v. tetrahydrofuranyl, pyrrolidinyl, benzo[d][1,3]dioxolyl, and tetrahydropyranyl, optionally substituted with one or two substituents, each independently selected from the group consisting of methyl, methoxy, and oxo;
  vi. phenyl-methyl, 1-cyclobutyl-2-ethyl-5-methyl-1H-imidazolyl, and pyridinyl-methyl; and
  vii. —$C(CH_3)_2CH_2OH$, —$CH_2CH_2OH$, and —$C(CH_3)_2CH_2OCH_3$.

87B. The compound of any one of embodiments 74B-84B, 79C, 83C, 84C, 85C, 86C, or 87C, wherein $R^{4a}$ and $R^{4b}$ taken together with the atom to which each is attached form a piperidinyl, morpholinyl, pyrrolidinyl, azepanyl, indolinyl, azabicyclo[3.1.1]heptanyl, or piperazinyl, optionally substituted with one or two substituents, each independently selected from the group consisting of methyl, fluoro, and methoxy.

88B. The compound of embodiment 1B or 1C, or a pharmaceutically acceptable salt thereof, wherein,
  Z is N;
  f is 1;
  $R^6$, in each instance, is selected from the group consisting of $C_1$-$C_3$ alkyl, —$NR^GR^H$, halogen, and $C_1$-$C_3$ alkoxy;
  p is 1
  n is 0 or 1
  $R^G$ and $R^H$ are each independently hydrogen or $C_1$-$C_3$ alkyl;
  $Y^1$, $Y^2$, $Y^3$, and $Y^4$ are each independently selected from the group consisting of CH, N, and C—$R^6$, provided that 1 or 2 of $Y^1$, $Y^2$, $Y^3$, and $Y^4$ can be N;
  $R^x$, in each instance, is halogen, $C_1$-$C_6$ alkyl, $C_1$-$C_3$ alkoxy, hydroxy, or cyano;
  m is 0; and
  $R^3$ and $R^4$ taken together with the nitrogen atom to which each is attached form a:
    i. 7-membered fused bicyclic heterocyclyl, 7-membered bridged bicyclic heterocyclyl, or 7-membered monocyclic heterocyclyl containing one or two heteroatoms;
      wherein when said 7-membered monocyclic heterocyclyl contains one heteroatom, said heterocyclyl is optionally substituted with one, two, or three substituents, each independently selected from the group consisting of oxo, halogen, hydroxy, $C_1$-$C_3$ alkoxy, cyano, and $C_1$-$C_3$ alkyl; and,
      when said 7-membered monocyclic heterocyclyl contains two heteroatoms, said heteroatoms are each independently N or O, and said heterocyclyl is optionally substituted with one, two, or three substituents, each independently selected from the group consisting of $C_1$-$C_3$ alkyl, cyano, oxo, halogen, halo-$C_1$-$C_3$ alkyl, and $C_6$-$C_{10}$ monocyclic or fused bicyclic aryl; and
      wherein said aryl is optionally substituted with one or two substituents, each individually selected from the group consisting of $C_1$-$C_3$ alkoxy, hydroxy, halogen, and $C_1$-$C_3$ alkyl;
ii. 4- or 6-membered monocyclic heterocyclyl containing one heteroatom;
wherein said 4-membered monocyclic heterocyclyl is optionally substituted with one or two substituents, each independently selected from the group consisting of halogen, $C_1$-$C_3$ alkoxy, oxo, and —(CH$_2$)$_s$C(=O)NR$^k$R$^l$; wherein,
s is 0, 1, 2, or 3;
R$^k$ is hydrogen or $C_1$-$C_3$ alkyl; and
R$^l$ is selected from the group consisting of hydrogen, hydroxy, $C_1$-$C_3$ alkyl, $C_3$-$C_7$ cycloalkyl, and $C_6$-$C_{10}$ monocyclic or fused bicyclic aryl;
wherein said 6-membered monocyclic heterocyclyl is optionally substituted with one or two substituents, each independently selected from the group consisting of $C_1$-$C_3$ alkoxy, oxo, halogen, cyano, and NR$^q$R$^w$; wherein,
R$^q$ is hydrogen or $C_1$-$C_3$ alkyl; and
R$^w$ is $C_6$-$C_{10}$ monocyclic or bicyclic aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy;
or,
iii. 8-, 9-, 10- or 11-membered fused bicyclic heterocyclyl, or 12-membered bicyclic bridged, fused heterocyclyl, wherein said 8-, 9-, or 11-membered heterocyclyl contains one heteroatom and said 10- or 12-membered heterocyclyl contains one or two heteroatoms; and wherein said 10-, 11-, or 12-membered heterocyclyl is optionally substituted with one, two, or three substituents, each independently selected from the group consisting of halogen, $C_1$-$C_3$ alkyl, $C_1$-$C_3$ alkoxy, and hydroxy.

89B. The compound of embodiment 88B, or a pharmaceutically acceptable salt thereof, wherein Y$^1$, Y$^2$, Y$^3$, and Y$^4$ are each CH or C—R$^6$.

90B. The compound of embodiment 88B or 89B, or a pharmaceutically acceptable salt thereof, wherein R$^6$, if present, is selected from the group consisting of —N(CH$_3$)$_2$, methyl, methoxy, fluoro, and chloro.

91B. The compound of any one of embodiments 88B-90B, or a pharmaceutically acceptable salt thereof, wherein R$^3$ and R$^4$ taken together with the nitrogen atom to which each is attached form a 7-membered heterocyclyl containing one heteroatom, wherein said heterocyclyl is optionally substituted once with methyl or oxo; or, a 7-membered monocyclic or bridged bicyclic heterocyclyl containing two heteroatoms, wherein said heteroatoms are N or O, and said heterocyclyl is optionally substituted with one or two substituents, each independently selected from the group consisting of phenyl, methyl, and oxo, and wherein said phenyl is optionally substituted with methoxy.

92B. The compound of any one of embodiments 88B-90B, or a pharmaceutically acceptable salt thereof, wherein R$^3$ and R$^4$ taken together with the nitrogen atom to which each is attached form a 10- or 11-membered fused bicyclic heterocyclyl containing one heteroatom, or a 12-membered bicyclic fused, bridged heterocyclyl, each optionally substituted with one, two, or three substituents, each independently selected from the group consisting of $C_1$-$C_3$ alkyl, $C_1$-$C_3$ alkoxy, hydroxy, and halogen.

93B. The compound of any one of embodiments 88B-90B, or a pharmaceutically acceptable salt thereof, wherein R$^3$ and R$^4$ taken together with the nitrogen atom to which each is attached form a 4- or 6-membered monocyclic heterocyclyl containing one heteroatom; wherein,
said 4-membered monocyclic heterocyclyl is optionally substituted with —(CH$_2$)$_s$C(=O)NR$^k$R$^l$; wherein,
s is 0, 1, or 2;
R$^k$ is hydrogen or $C_1$-$C_3$ alkyl; and
R$^l$ is selected from the group consisting of hydrogen, methyl, phenyl, cyclopentyl, and cyclohexyl;
and,
said 6-membered monocyclic heterocyclyl is optionally substituted with one or two substituents, each independently selected from the group consisting of $C_1$-$C_3$ alkoxy, oxo, halogen, cyano, and NR$^q$R$^w$; wherein,
R$^q$ is hydrogen or $C_1$-$C_3$ alkyl;
R$^w$ is $C_6$-$C_{10}$ monocyclic or fused bicyclic aryl or $C_3$-$C_7$ cycloalkyl, wherein said aryl or cycloalkyl is optionally substituted with one or two substituents, each independently selected from the group consisting of halogen, $C_1$-$C_3$ alkyl, hydroxy, and $C_1$-$C_3$ alkoxy.

94B. The compound of embodiment 1B, 74B, or 1C, or a pharmaceutically acceptable salt thereof, wherein,
Z is N;
p is 1;
f is 1;
Y$^1$, Y$^2$, Y$^3$, and Y$^4$ are each independently CH or C—R$^6$.
R$^6$, in each instance, is selected from the group consisting of $C_1$-$C_3$ alkyl, hydroxy, $C_1$-$C_3$ alkoxy, $C_1$-$C_3$ alkoxy-$C_1$-$C_3$ alkyl, hydroxy-$C_1$-$C_3$ alkyl, hydroxy-$C_1$-$C_6$ alkoxy, —O—(CH$_2$)$_u$—R$^{bb}$, halo-$C_1$-$C_3$ alkyl, —O—R$^{cc}$—O—R$^{dd}$, and $C_3$-$C_6$ cycloalkyl; or, R$^6$, in each instance, is —O—R$^{bb}$ or —O—($C_1$-$C_6$ alkoxy)-R$^{bb}$, wherein,
u is an integer from 0 to 6;
R$^{bb}$ is 4- to 7-membered monocyclic heterocyclyl, $C_3$-$C_7$ cycloalkyl, or —NR$^G$R$^H$;
R$^{cc}$ and R$^{dd}$ are each independently $C_1$-$C_3$ alkyl;
wherein, said cycloalkyl or heterocyclyl is optionally substituted with one or two substituents, each independently selected from the group consisting of hydroxy, $C_1$-$C_3$ alkoxy, and $C_1$-$C_3$ alkyl; and,
R$^G$ and R$^H$ are each independently hydrogen, —C(O)R$^{Ga}$, or $C_1$-$C_3$ alkyl; wherein,
R$^{Ga}$ is $C_1$-$C_3$ alkyl or hydrogen;
n is 0, 1, or 2;
R$^3$ is selected from the group consisting of hydrogen, methyl, ethyl, phenyl, and —CH$_2$CH$_2$OH;
R$^4$ is

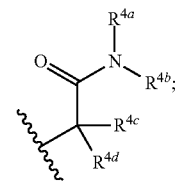

wherein,
R$^{4c}$ is selected from the group consisting of hydrogen, methyl, isopropyl, —CH$_2$OH, and —CH$_2$OC(CH$_3$)$_3$;
R$^{4d}$ is selected from the group consisting of hydrogen and methyl;
or,
R$^{4c}$ and R$^{4d}$ taken together with the atom to which each is attached form a cyclopropyl ring;
R$^{4b}$ is hydrogen or methyl;

$R^{4a}$ is selected from the group consisting of hydrogen, $C_1$-$C_6$ alkyl, hydroxy-$C_1$-$C_6$ alkyl, $C_1$-$C_3$ alkoxy-$C_1$-$C_6$ alkyl, $C_3$-$C_7$ cycloalkyl, 5- to 10-membered monocyclic, fused bicyclic, or bridged bicyclic heterocyclyl, $C_6$-$C_{10}$ monocyclic or fused bicyclic aryl, 5- to 10-membered monocyclic or fused bicyclic heteroaryl, ($C_6$-$C_{10}$ monocyclic or fused bicyclic aryl)-$C_1$-$C_3$ alkyl, and (5- to 10-membered monocyclic or fused bicyclic heteroaryl)-$C_1$-$C_3$ alkyl; wherein the cycloalkyl, heterocyclyl, aryl, heteroaryl, arylalkyl, or heteroaryl-alkyl of $R^{4a}$ is optionally substituted with one, two, or three substituents, each independently selected from the group consisting of halogen, $C_1$-$C_6$ alkyl, halo-$C_1$-$C_3$ alkyl, hydroxy, $C_1$-$C_3$ alkoxy, halo-$C_1$-$C_3$ alkoxy, halo-$C_1$-$C_3$ alkyl, oxo, $C_3$-$C_7$ cycloalkyl, and 5- to 10-membered monocyclic or fused bicyclic heterocyclyl; or, $R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy;

$R^x$, in each instance, is $C_1$-$C_3$ alkyl; and m is 0, 1, or 2.

95B. The compound of embodiment 94B, or a pharmaceutically acceptable salt thereof, wherein, $Y^1$ is CH, $Y^2$ is C—$R^6$, $Y^3$ is CH, and $Y^4$ is CH.

96B. The compound of embodiment 94B or 95B, or a pharmaceutically acceptable salt thereof, wherein $R^6$ is selected from the group consisting of hydroxy-$C_1$-$C_6$ alkoxy, and —O—$(CH_2)_u$—$R^{bb}$; wherein, u is an integer from 0 to 6;

$R^{bb}$ is 4- to 7-membered monocyclic heterocyclyl, $C_3$-$C_7$ cycloalkyl, or —$NR^GR^H$;

wherein, said cycloalkyl or heterocyclyl is optionally substituted with one or two substituents, each independently selected from the group consisting of hydroxy, $C_1$-$C_3$ alkoxy, and $C_1$-$C_3$ alkyl; and, $R^G$ and $R^H$ are each independently hydrogen or $C_1$-$C_3$ alkyl; and n is 0, 1, or 2.

97B. The compound of embodiment 96B, or a pharmaceutically acceptable salt thereof, wherein $R^6$ is selected from the group consisting of
—OCH$_2$CH$_2$OH, —OCH$_2$CH$_2$N(CH$_3$)$_2$, —OCH$_2$C(CH$_3$)$_2$OH, and

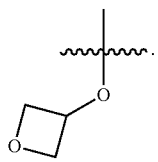 [SMILES: *OC1COC1]

98B. The compound of any one of embodiments 94B-97B, or a pharmaceutically acceptable salt thereof, wherein:
$R^3$ is methyl;
$R^{4c}$ and $R^{4d}$ are each hydrogen;
$R^{4b}$ is hydrogen; and,
$R^{4a}$ is selected from the group consisting of $C_1$-$C_6$ alkyl, $C_6$-$C_{10}$ monocyclic or fused bicyclic aryl, and 5- to 10-membered monocyclic or fused bicyclic heteroaryl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, and halo-$C_1$-$C_3$ alkoxy.

99B. The compound of embodiment 98B, or a pharmaceutically acceptable salt thereof, wherein $R^{4a}$ is selected from the group consisting of $C_1$-$C_6$ alkyl, phenyl, and pyridinyl, wherein said phenyl or pyrimidinyl is optionally substituted with $C_1$-$C_3$ alkoxy.

100B. The compound of embodiment 99B, or a pharmaceutically acceptable salt thereof, wherein $R^{4a}$ is selected from the group consisting of tert-butyl and

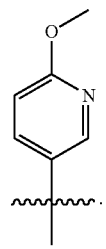

101B. The compound of embodiment 1A, 1B, or 1C selected from Table 1, or a pharmaceutically acceptable salt thereof.

102B. A pharmaceutical composition comprising a compound according to any one of embodiments 1B-101B, 1A-47A, 1C, 5C, 9C, 10C, 11C, 12C, 13C, 14C, 15C, 16C, 31C, 33C, 35C, 36C, 42C, 52C, 53C, 54C, 55C, 61C, 63C, 64C, 79C, 83C, 84C, 85C, 86C, or 87C, or a pharmaceutically acceptable salt thereof, and a pharmaceutically acceptable excipient.

103B. A method of inhibiting iron transport mediated by ferroportin in a subject, comprising administering to the subject an effective amount of a compound of any one of embodiments 1B-101B, 1A-47A, 1C, 5C, 9C, 10C, 11C, 12C, 13C, 14C, 15C, 16C, 31C, 33C, 35C, 36C, 42C, 52C, 53C, 54C, 55C, 61C, 63C, 64C, 79C, 83C, 84C, 85C, 86C, or 87C, or the pharmaceutical composition of embodiment 102B.

The General Procedures and Examples provide exemplary methods for preparing compounds. Those skilled in the art will appreciate that other synthetic routes may be used to synthesize the compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

General Synthetic Schemes

General synthetic approaches to FPN1 compounds 1a and 1b. In certain embodiments, compound 1a can be synthesized as shown in Scheme 1, the core intermediate 2a could be displaced by various substituted amine 3a via method A to give intermediate 4a, which was then coupled with various organometallic reagent 5a to provide final compound 1a. Alternatively, final compound 1a could be synthesized as shown in Scheme 2. Intermediate 2a could be displaced by primary amine 6a to give intermediate 7a, after coupling with organometallic reagent 5a, the resulting intermediate 8a could then be alkylated by a halide to give compound 1a. Final compound 1b could be synthesized according to scheme 3. Intermediate 2a was displaced by glycinate 9a to provide intermediate 10a, after coupling with organometallic reagent 5a, the resulting intermediate 11a was saponified. The corresponding carboxylic acid intermediate 12a was coupled with various amine to form compound 1b.

Modifications and variations to schemes 1-3 can be made based on the availability of starting materials and synthetic compatibility of reagents, starting materials, or intermediates. This should be obvious to those who are familiar with the art. For example, $R_1$ and $R_2$ could be hydrogen, halogen, simple alkyl or could join to form a ring; $R_3$ could be hydrogen or alkyl; $R_4$ could be alkyl substituted by aminocarbonyl, alkoxy; or $R_3$ and $R_4$ could join together to form a cyclic amine. For method B, another available heteroaromatic Suzuki or Stille reagent could be used to provide the final compound 1a.

Scheme 1 depicts a method for preparing exemplary compounds using Method A and Method B.


Scheme 2 depicts a method for preparing exemplary compounds using Method A, Method B, and Method C.

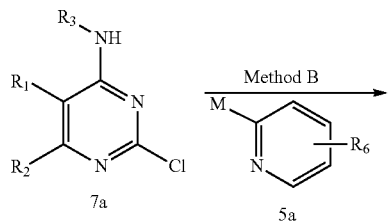

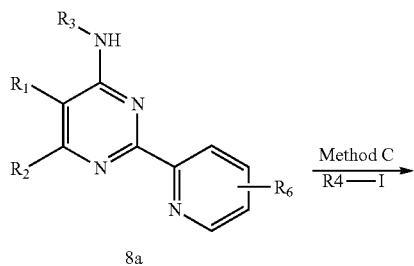

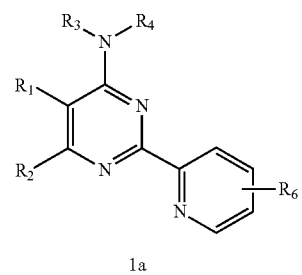

Scheme 3 depicts a method for preparing exemplary compounds using Method A, Method B, Method D, and Method E.

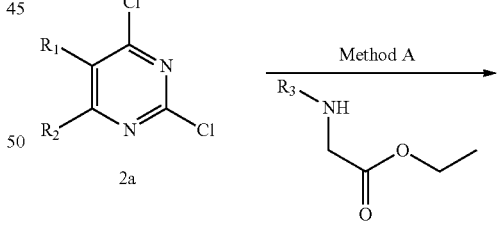

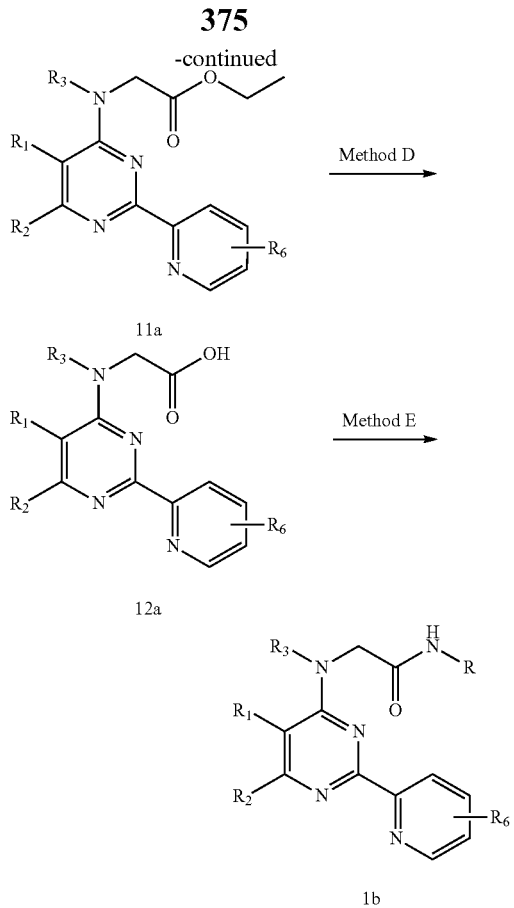

The conditions and reagents for Methods A-E are provided in the below Examples. The following examples are offered by way of illustration and not by way of limitation.

1. SYNTHETIC EXAMPLES

Example 1.1

Method A: General Synthetic Method for Nucleophilic Coupling of Amine to Intermediate 4a Into a 100-mL round-bottom flask, was placed dichloropyrimidine intermediate 2a (1.00 equiv), $CH_3CN$, amine 3a (1.10 equiv), and triethylamine (2.00 equiv). The resulting solution was stirred for 3 hr at 80° C. The resulting mixture was concentrated under vacuum. The residue was applied onto a silica gel column with ethyl acetate/petroleum ether to give intermediate 4a.

Example 1.2

Method B: General Synthetic Method for Metal Mediated Cross Coupling

Into a 100-mL round-bottom flask purged and maintained with an inert atmosphere of nitrogen, was placed intermediate 4a (1.00 equiv), dioxane, organometallic reagent 5 (2.0 equiv) and Pd(dppf)Cl$_2$ (0.05 equiv). The resulting solution was stirred overnight at 100° C. The resulting mixture was concentrated under vacuum. The residue was applied onto a silica gel column with ethyl acetate/petroleum ether (1:1) or subjected to preparative HPLC purification to give compound 1a, 8a, or 11a.

Example 1.3

Method C: General Synthetic Method for Alkylation with Halide to Give Compound 1a Intermediate 8a (1.00 eq.) was dissolved in DMF and cooled in an ice bath. Sodium hydride (2.00 eq.) (60%) was added in two portions and the reaction was stirred for 45 min. Halide (2.00 eq.) was added slowly and the mixture was stirred for 1.5 h more. Water (20 ml) and ethyl acetate (100 ml) were added, the phases were separated, and the aqueous phase was extracted with more ethyl acetate The combined organic phases were washed with some water and dried over sodium sulfate. After evaporation of solvent, the residue was purified by reverse phase chromatography (Waters XSelect CSH C18 column, 0-70% acetonitrile/0.1% aqueous formic acid gradient). The purified fractions were treated with 1 M HCl and freeze-dried to give compound 1a.

Example 1.4

Method D: General Synthetic Method for Saponification to Give 12a

Intermediate 11a (1.00 eq.) was dissolved in THF and methanol. Lithium hydroxide (5.00 eq.) was dissolved in water and was added dropwise to the solution. After 7 h, the mixture was acidified carefully with 6 M HCl to pH 3 and evaporated to dryness. The residue was co-evaporated with toluene and dried under high vacuum to give 12a.

Example 1.5

Method E: General Synthetic Method for Amide Formation to Give 1b

Intermediate 12a (1.00 eq.) was suspended in N,N-dimethylformamide, N,N-Diisopropylethylamine (2.50 eq.), amine (1.35 eq.) and then 1-[bis(dimethylamino)methylene]-1H-1,2,3-triazolo[4,5-b]pyridinium 3-oxid hexafluorophosphate (HATU, 1.35 eq.) were added. After 40 h, ethyl acetate (50 ml) and sodium bicarbonate solution (20 ml) were added, the phases were separated, and the aqueous phase was extracted with ethyl acetate (50 ml). The combined organic phases were washed with sodium chloride solution and dried over sodium sulfate. After evaporation of the solvents, the residue was purified by reverse phase chromatography (Waters XSelect CSH C18 column, 0-70% acetonitrile/0.1% aqueous formic acid gradient) to give compound 1b.

Example 1.6

Experimental Procedures for Common Intermediates

Scheme 4 Depicts a Method for Preparing Intermediate I

Scheme 4

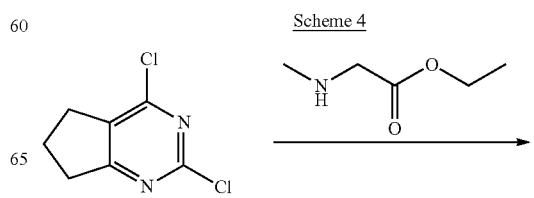

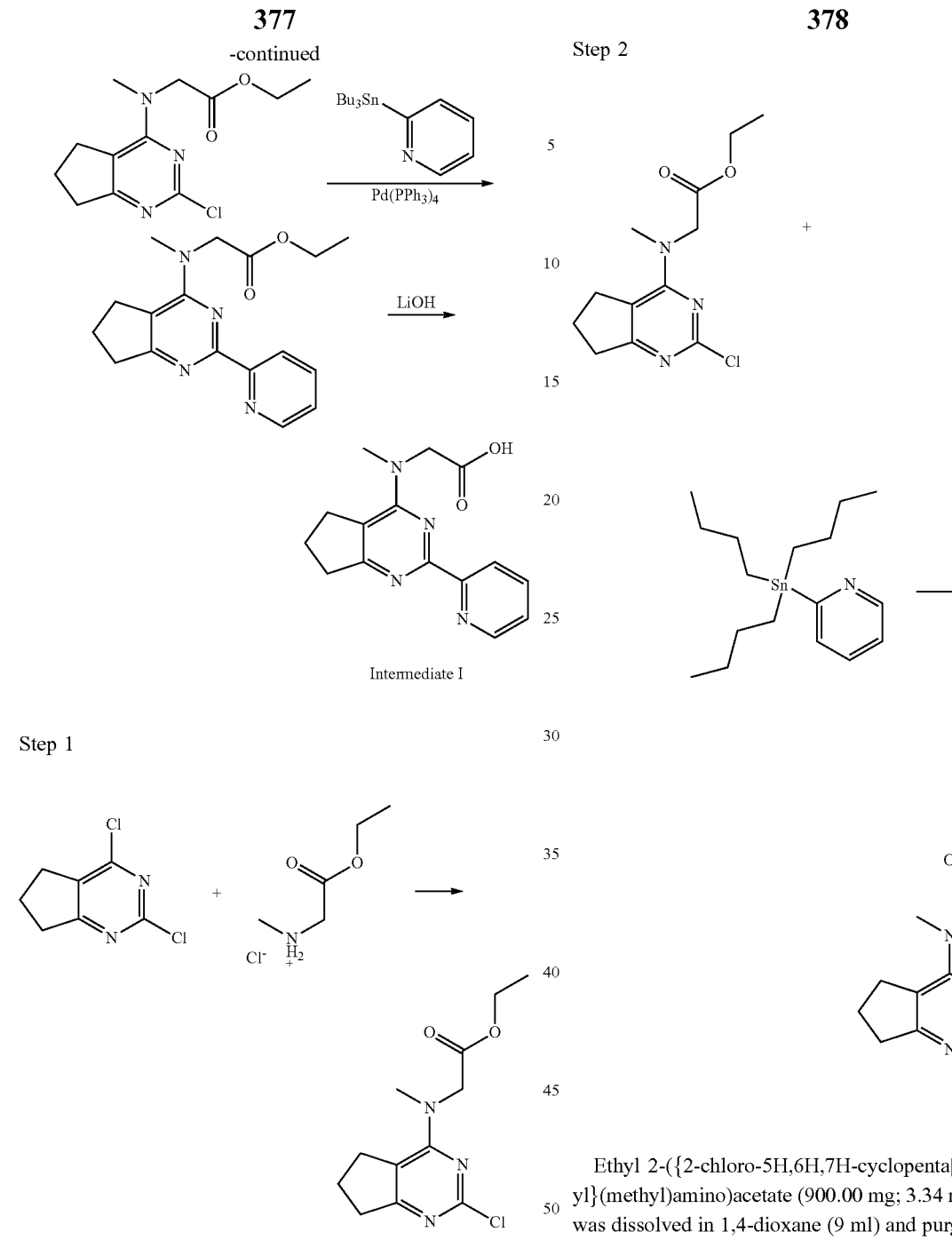

Step 1

2,4-Dichloro-6,7-dihydro-5H-cyclopenta[d]pyrimidine (2.00 g; 10.58 mmol; 1.00 eq.) was dissolved in acetonitrile (36 ml). (2-Ethoxy-2-oxoethyl)(methyl)azanium chloride (2.11 g; 13.75 mmol; 1.30 eq., sarcosine ethyl ester HCl) was added, followed by N,N-diisopropylethylamine (4.6 mL; 26.45 mmol; 2.50 eq.) slowly. The reaction was stirred at 25° C. for 22 h and then at 50° C. for 20 h. The solvent was evaporated and the residue was purified by silica gel chromatography (ethyl acetate/hexanes gradient) to give ethyl 2-({2-chloro-5H,6H,7H-cyclopenta[d]pyrimidin-4-yl}(methyl)amino)acetate (2.18 g, 76%) as a solid. $^1$H NMR (400 MHz, Chloroform-d) δ 4.30-4.19 (m, 4H), 3.31 (s, 3H), 3.11 (t, J=7.4 Hz, 2H), 2.88 (t, J=7.9 Hz, 2H), 2.12-2.02 (m, 2H), 1.30 (t, J=7.2 Hz, 3H).

Step 2

Ethyl 2-({2-chloro-5H,6H,7H-cyclopenta[d]pyrimidin-4-yl}(methyl)amino)acetate (900.00 mg; 3.34 mmol; 1.00 eq.) was dissolved in 1,4-dioxane (9 ml) and purged with argon. 2-(Tributylstannyl)pyridine (2.34 mL; 6.67 mmol; 2.00 eq.) and tetrakis(triphenylphosphane) palladium (385.58 mg; 0.33 mmol; 0.10 eq.) were added, the reaction vessel was sealed, and then stirred in a heat bath at 105° C. After 16 h, the solvent was evaporated and the residue was purified by silica gel chromatography (methanol/dichloromethane) to give ethyl 2-{methyl[2-(pyridin-2-yl)-5H,6H,7H-cyclopenta[d]pyrimidin-4-yl]amino}acetate (0.72 g, 62%) $^1$H NMR (400 MHz, Chloroform-d) δ 8.83 (d, J=4.8 Hz, 1H), 8.39-8.28 (m, 1H), 7.86-7.77 (m, 1H), 7.41-7.32 (m, 1H), 4.37 (s, 2H), 4.20 (q, J=7.2, 1.5 Hz, 2H), 3.42 (s, 3H), 3.23-3.12 (m, 4H), 2.15-2.07 (m, 2H), 1.27-1.23 (m, 3H). MS (ES+): (M+H)$^+$=269.9.

Step 3

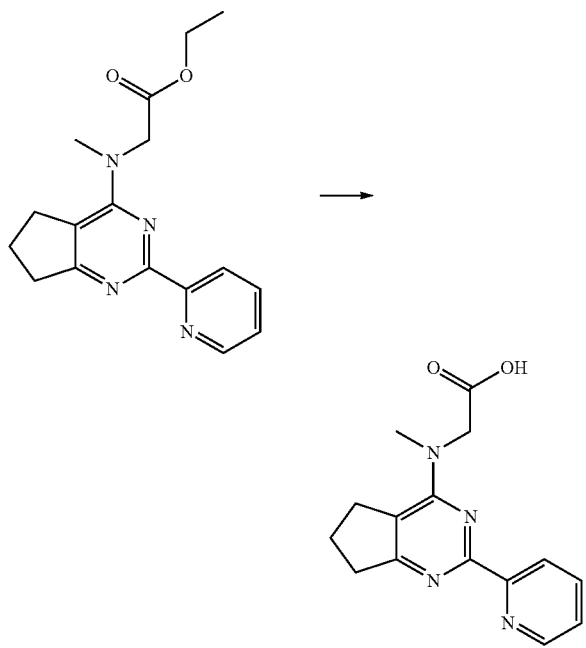

Intermediate I

Ethyl 2-{methyl[2-(pyridin-2-yl)-5H,6H,7H-cyclopenta[d]pyrimidin-4-yl]amino}acetate (0.72 g; 2.30 mmol; 1.00 eq.) was dissolved in THF (20 ml) and methanol (5 ml). Lithium hydroxide (0.28 g; 11.52 mmol; 5.00 eq.) dissolved in water (8 ml) was added dropwise to the solution. After 7 h, the mixture was acidified carefully with 6 M HCl to pH 3 and evaporated to dryness. The residue was co-evaporated with toluene and dried under high vacuum to give 2-{methyl[2-(pyridin-2-yl)-5H,6H,7H-cyclopenta[d]pyrimidin-4-yl]amino}acetic acid hydrochloride (Intermediate I) as an off-white solid. $^1$H NMR (400 MHz, DMSO-d6) δ 8.84 (d, J=4.7 Hz, 1H), 8.41 (d, J=7.9 Hz, 1H), 8.21-8.12 (m, 1H), 7.75 (dd, J=7.8, 4.8 Hz, 1H), 3.28-3.27 (m, 2H), 3.07-3.01 (m, 2H), 2.15-2.05 (m, 2H). MS (ES+): (M+H)$^+$=284.9.

Example 1.7

Scheme 5 Depicts a Method for Preparing Intermediate II

Scheme 5

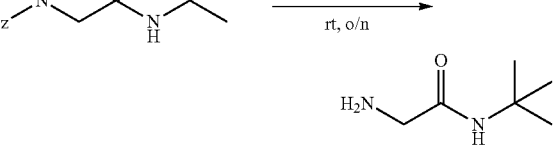

Step 1

Into a 1-L 3-necked round-bottom flask was placed 2-(benzyloxycarbonylamino)acetic acid (20.0 g, 95.6 mmol, 1.00 equiv), DCM (500 mL), HOBt (15.5 g, 114.7 mmol, 1.20 equiv), EDCI (22.0 g, 114.7 mmol, 1.20 equiv), and tert-butylamine (21.0 g, 286.8 mmol, 3.00 equiv). The resulting solution was stirred overnight at room temperature. The resulting mixture was concentrated. The residue was applied onto a silica gel column with PE/EA ether (0-50%). This resulted in 25.1 g (99%) of benzyl N-[(tert-butylcarbamoyl)methyl]-carbamate as a white solid. LCMS: (ES, m/z): [M+H]+265.

Into a 250-mL round-bottom flask, was placed benzyl N-[(tert-butylcarbamoyl)methyl]carbamate (7.0 g, 26.48 mmol, 1.00 equiv), MeOH (50 mL), and Pd/C (10%) (0.70 g, 10%). The resulting solution was stirred overnight at room temperature under H$_2$ (1 atm). The solids were filtered out. The resulting mixture was concentrated. This resulted in 3.3 g (95%) of 2-amino-N-tert-butylacetamide as a colorless oil. LCMS: (ES, m/z): [M+H]+: 131.

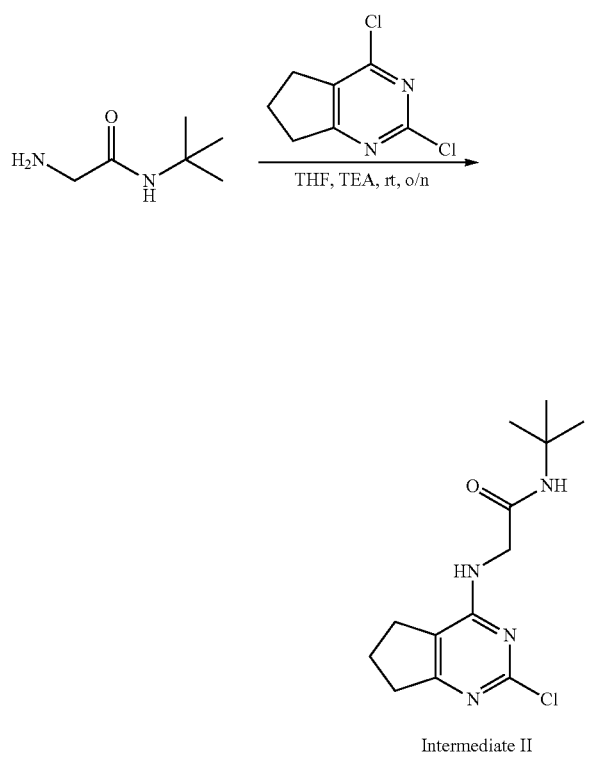

Intermediate II

Into a 50-mL round-bottom flask, was placed 2,4-dichloro-5H,6H,7H-cyclopenta[d]pyrimidine (0.80 g, 4.23 mmol, 1.00 equiv), THF (20 mL), TEA (0.51 g, 5.04 mmol, 1.19 equiv), and 2-amino-N-tert-butylacetamide (0.58 g, 4.44 mmol, 1.05 equiv). The resulting solution was stirred overnight at room temperature. The resulting mixture was concentrated. The residue was applied onto a silica gel column with ethyl acetate/hexane (0-50%). This resulted in 0.688 g (57%) of N-tert-butyl-2-([2-chloro-5H,6H,7H-cyclopenta[d]pyrimidin-4-yl]amino)acetamide as a white solid. LCMS (ES, m/z): [M+H]⁺: 283.1.

Example 1.8

Synthesis of 1-[2-(pyridin-2-yl)-5H,6H,7H-cyclopenta[d]pyrimidin-4-yl]azepane (Compound 92)

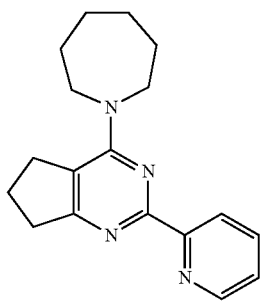 [SMILES: c1ccc(-c2nc3c(c(N4CCCCCC4)n2)CCC3)nc1]

Scheme 6 depicts a synthetic route for preparing an exemplary compound.

Scheme 6

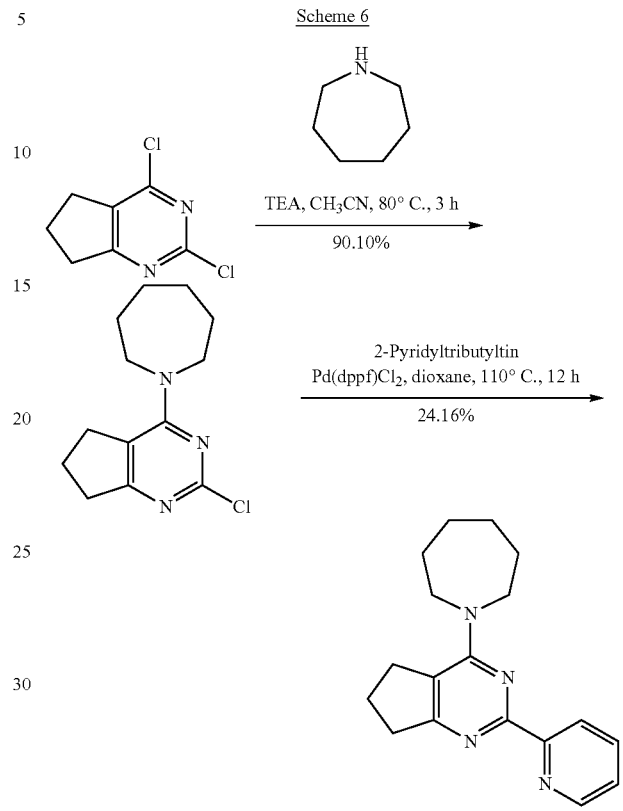

Step 1

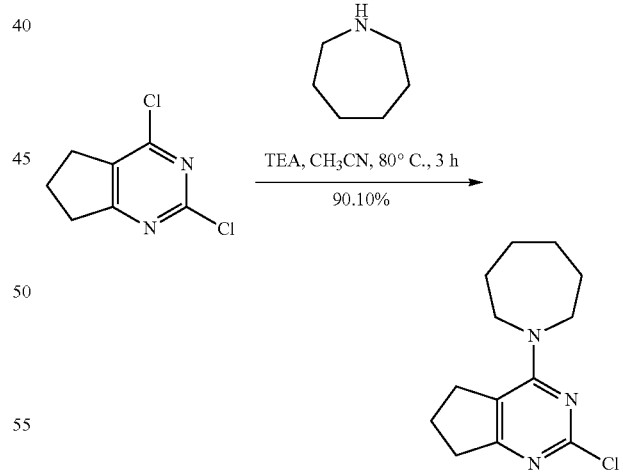

Into a 100-mL round-bottom flask, was placed 2,4-dichloro-5H,6H,7H-cyclopenta[d]pyrimidine (500.00 mg, 2.645 mmol, 1.00 equiv), acetonitrile (20.00 mL, 0.487 mmol, 0.18 equiv), azepane (314.78 mg, 3.174 mmol, 1.20 equiv), and TEA (321.17 mg, 3.174 mmol, 1.20 equiv). The resulting solution was stirred for 2 hr at 80° C. The resulting mixture was concentrated under vacuum. The residue was applied onto a silica gel column with ethyl acetate/petroleum ether (1:3) to give 600 mg (90.10%) of 1-[2-chloro-5H,6H,7H-cyclopenta[d]pyrimidin-4-yl]azepane as a solid.

Step 2

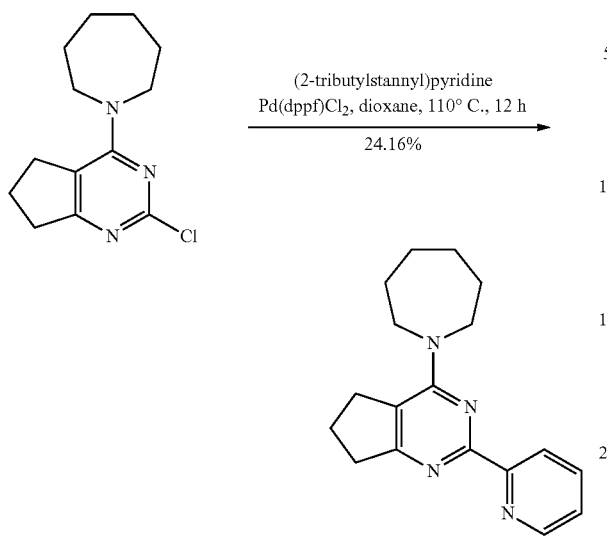

Into a 100-mL round-bottom flask purged and maintained in an inert atmosphere of nitrogen, was placed 1-[2-chloro-5H,6H,7H-cyclopenta[d]pyrimidin-4-yl]azepane (300.00 mg, 1.192 mmol, 1.00 equiv), dioxane (20.00 mL), 2-(tributylstannyl)pyridine (877.39 mg, 2.383 mmol, 2.0 equiv), and Pd(dppf)Cl$_2$ (43.60 mg, 0.060 mmol, 0.05 equiv). The resulting solution was stirred overnight at 100 degrees C. in an oil bath. The resulting mixture was concentrated. The residue was applied onto a silica gel column with ethyl acetate/petroleum ether (1:1). The crude product was purified by re-crystallization from EA (ethyl acetate). This resulted in 79 mg (24.16%) of 1-[2-(pyridin-2-yl)-5H,6H,7H-cyclopenta[d]pyrimidin-4-yl]azepane as a white solid. $^1$H NMR (300 MHz, DMSO-d$_6$): δ 8.66 (d, J=4.5 Hz, 1H), 8.25 (d, J=7.8 Hz, 1H), 7.882 (t, J=7.8 Hz, 1H), 7.42 (dd, J=5.1 Hz, 6.0 Hz, 1H), 3.78-3.64 (m, 4H), 3.11-3.00 (m, 2H), 2.83-2.78 (m, 2H), 2.08-1.97 (m, 2H), 1.76 (s, 4H), 1.49 (s, 2H). LCMS: (ES) [M+1]$^+$ m/z 295.2.

Example 1.9

Synthesis of 4-[2-(pyridin-2-yl)-5H,6H,7H-cyclopenta[d]pyrimidin-4-yl]-1,4-oxazepane (Compound 93)

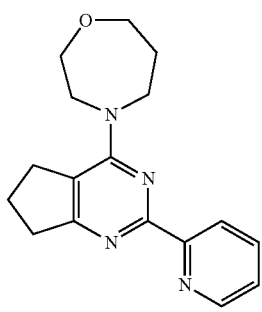 [SMILES: c1ccc(-c2nc3c(c(N4CCCOCC4)n2)CCC3)nc1]

Scheme 7 depicts a synthetic route for preparing an exemplary compound.

Scheme 7

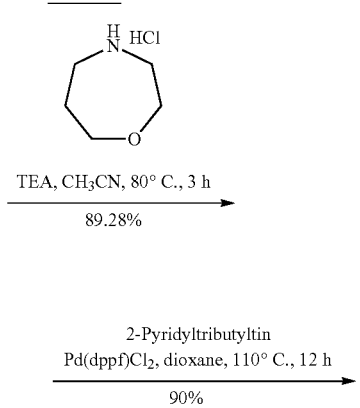

Step 1

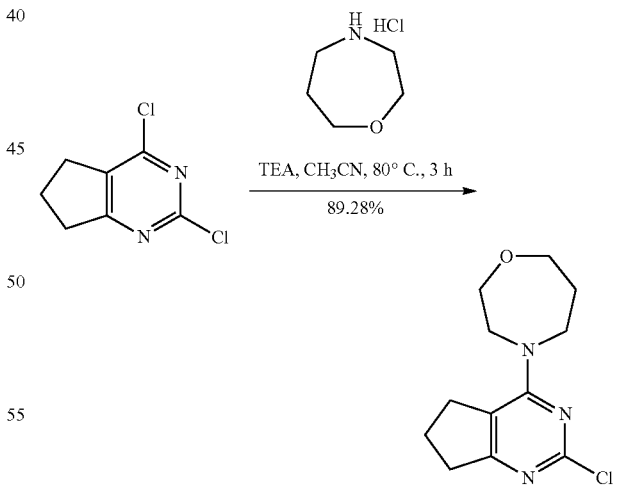

Into a 100-mL round-bottom flask, was placed 2,4-dichloro-5H,6H,7H-cyclopenta[d]pyrimidine (500.00 mg, 1.00 equiv), CH$_3$CN (10.00 mL), 1,4-oxazepane hydrochloride (402.00 mg, 1.10 equiv), and TEA (534.00 mg, 2.00 equiv). The resulting solution was stirred for 3 hr at 80 degrees C. The reaction progress was monitored by LCMS. The resulting mixture was concentrated under vacuum. The residue was applied onto a silica gel column with ethyl acetate/petroleum ether (1:2). This resulted in 600 mg (89.28%) of 4-[2-chloro-5H,6H,7H-cyclopenta[d]pyrimidin-4-yl]-1,4-oxazepane as a brown solid.
Step 2

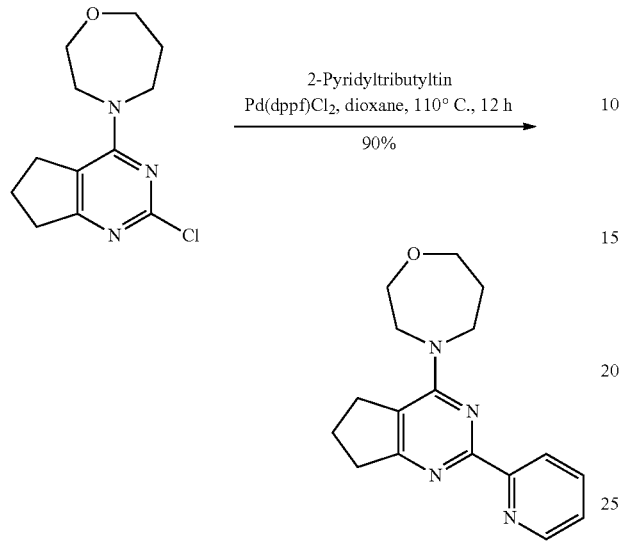

Into a 100-mL round-bottom flask purged and maintained in an inert atmosphere of nitrogen, was placed 4-[2-chloro-5H,6H,7H-cyclopenta[d]pyrimidin-4-yl]-1,4-oxazepane (0.30 g, 1.18 mmol, 1.00 equiv), dioxane (20 mL), 2-(tributylstannyl)pyridine (0.87 g, 2.36 mmol, 2.0 equiv), Pd(dppf)Cl$_2$ (0.04 g, 0.035 mmol, 0.05 equiv). The resulting solution was stirred overnight at 100° C. in an oil bath. The resulting mixture was concentrated under vacuum. The residue was applied onto a silica gel column with ethyl acetate/petroleum ether (1:1). The crude product was purified by re-crystallization from EA. This resulted in 358.1 mg (90%) of 4-[2-(pyridin-2-yl)-5H,6H,7H-1-λ-4-cyclopenta[d]pyrimidin-4-yl]-1,4-oxazepane as a light brown solid. 1H NMR (300 MHz, DMSO-d6): δ 8.66 (dd, J=0.9, 0.9 Hz, 1H), 8.25 (d, J=7.8 Hz, 1H), 7.91-7.86 (m, 1H), 7.45-7.41 (m, 1H), 3.97-3.87 (m, 4H), 3.85-3.75 (m, 2H), 3.66-3.62 (m, 2H), 3.08 (t, J=7.5 Hz, 2H), 2.85-2.80 (m, 2H), 2.06-1.96 (m, 4H). LCMS (ES) [M+1]+ m/z 297.2.

Example 1.10

Synthesis of 1-[2-(3-fluoropyridin-2-yl)-5H,6H,7H-cyclopenta[d]pyrimidin-4-yl]azepane (Compound 71)

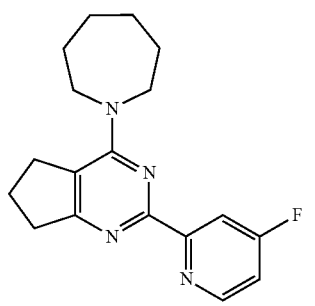 [SMILES: Fc1ccnc(-c2nc3c(c(N4CCCCCC4)n2)CCC3)c1]

Compound 71 was synthesized similar to compound 92 replacing 2-(tributylstannyl)pyridine with 4-fluoro-2-(tributylstannyl)pyridine. $^1$H NMR (400 MHz, Methanol-d$_4$) δ 8.46 (d, J=4.8 Hz, 1H), 7.77-7.68 (m, 1H), 7.54 (dt, J=8.5, 4.3 Hz, 1H), 3.82 (t, J=6.1 Hz, 4H), 3.19 (t, J=7.4 Hz, 2H), 2.89 (t, J=7.9 Hz, 2H), 2.11 (p, J=7.7 Hz, 2H), 1.80 (s, 4H), 1.59 (p, J=2.8 Hz, 4H). LCMS (ES) [M+1]$^+$ m/z 312.4.

Example 1.11

Synthesis of 5-[2-(pyridin-2-yl)-5H,6H,7H-cyclopenta[d]pyrimidin-4-yl]-2-oxa-5-azabicyclo[2.2.1]heptane (Compound 72)

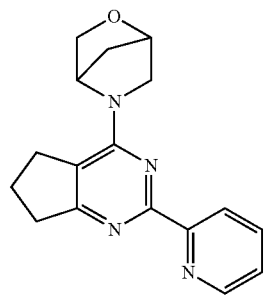 [SMILES: c1ccc(-c2nc3c(c(N4CC5CC4CO5)n2)CCC3)nc1]

Compound 72 was synthesized similar to compound 92 replacing azepane with 2-oxa-5-azabicyclo[2.2.1]heptane. LCMS (ES+): (M+H)$^+$=295.0. $^1$H NMR (400 MHz, Chloroform-d) δ 8.85 (d, J=4.8 Hz, 1H), 8.40 (d, J=7.9 Hz, 1H), 7.89-7.79 (m, 1H), 7.39 (dd, J=7.5, 4.9 Hz, 1H), 5.33 (s, 1H), 4.71 (s, 1H), 4.00-3.94 (m, 2H), 3.83-3.76 (m, 2H), 3.20-2.96 (m, 4H), 2.19-1.94 (m, 4H).

Example 1.12

Synthesis of N-methyl-2-(pyridin-2-yl)-N-[(pyridin-2-yl)methyl]-5H,6H,7H-cyclopenta[d]pyrimidin-4-amine (Compound 73)

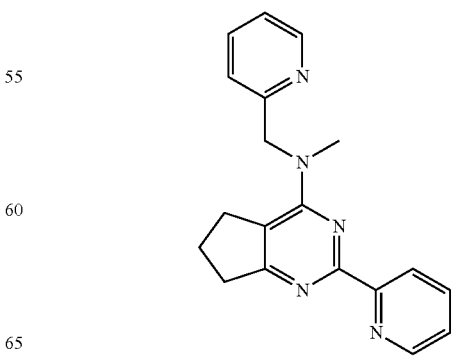

Scheme 8 depicts a synthetic route for preparing an exemplary compound.

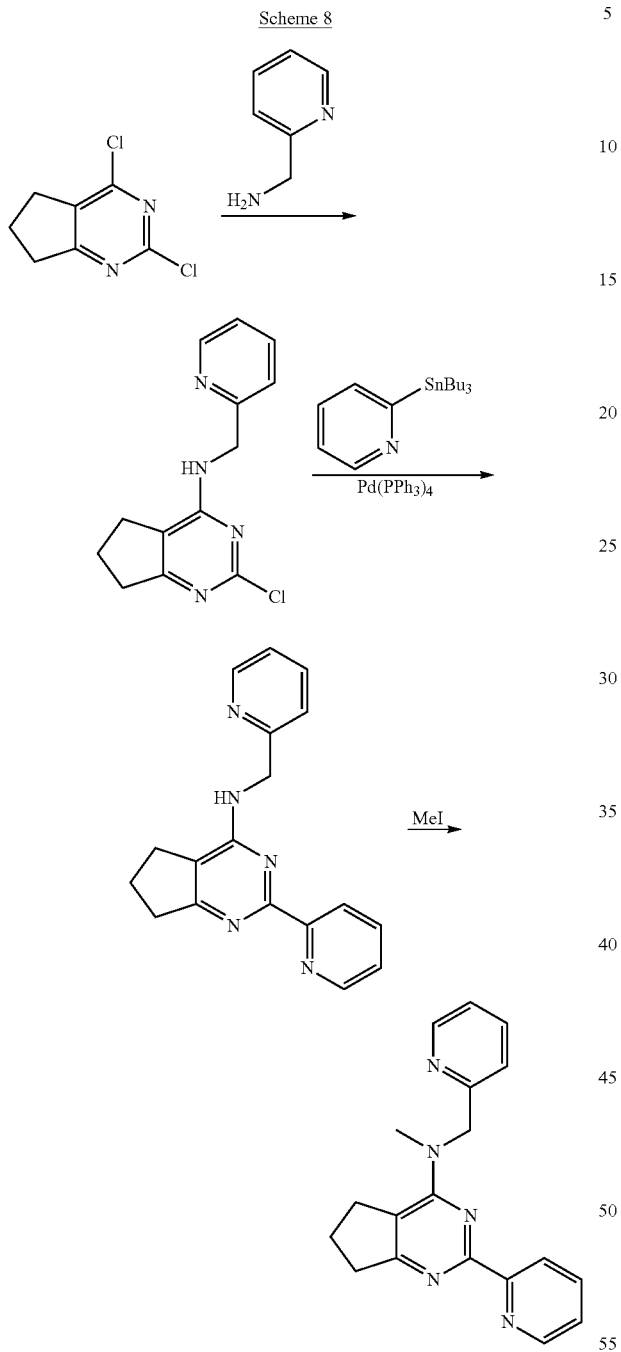

Step 1

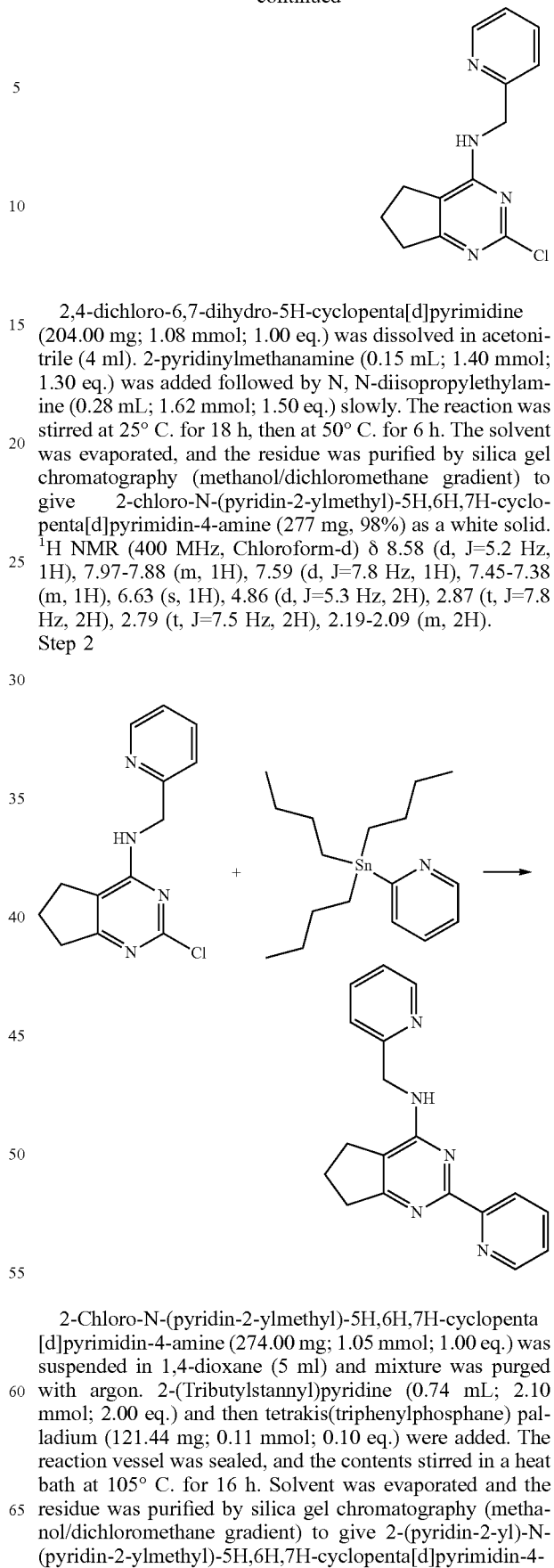

2,4-dichloro-6,7-dihydro-5H-cyclopenta[d]pyrimidine (204.00 mg; 1.08 mmol; 1.00 eq.) was dissolved in acetonitrile (4 ml). 2-pyridinylmethanamine (0.15 mL; 1.40 mmol; 1.30 eq.) was added followed by N, N-diisopropylethylamine (0.28 mL; 1.62 mmol; 1.50 eq.) slowly. The reaction was stirred at 25° C. for 18 h, then at 50° C. for 6 h. The solvent was evaporated, and the residue was purified by silica gel chromatography (methanol/dichloromethane gradient) to give 2-chloro-N-(pyridin-2-ylmethyl)-5H,6H,7H-cyclopenta[d]pyrimidin-4-amine (277 mg, 98%) as a white solid. $^1$H NMR (400 MHz, Chloroform-d) δ 8.58 (d, J=5.2 Hz, 1H), 7.97-7.88 (m, 1H), 7.59 (d, J=7.8 Hz, 1H), 7.45-7.38 (m, 1H), 6.63 (s, 1H), 4.86 (d, J=5.3 Hz, 2H), 2.87 (t, J=7.8 Hz, 2H), 2.79 (t, J=7.5 Hz, 2H), 2.19-2.09 (m, 2H).

Step 2

2-Chloro-N-(pyridin-2-ylmethyl)-5H,6H,7H-cyclopenta[d]pyrimidin-4-amine (274.00 mg; 1.05 mmol; 1.00 eq.) was suspended in 1,4-dioxane (5 ml) and mixture was purged with argon. 2-(Tributylstannyl)pyridine (0.74 mL; 2.10 mmol; 2.00 eq.) and then tetrakis(triphenylphosphane) palladium (121.44 mg; 0.11 mmol; 0.10 eq.) were added. The reaction vessel was sealed, and the contents stirred in a heat bath at 105° C. for 16 h. Solvent was evaporated and the residue was purified by silica gel chromatography (methanol/dichloromethane gradient) to give 2-(pyridin-2-yl)-N-(pyridin-2-ylmethyl)-5H,6H,7H-cyclopenta[d]pyrimidin-4- amine (161 mg, 50%) as a white solid. ¹H NMR (400 MHz, Chloroform-d) δ 8.87 (d, J=5.0 Hz, 1H), 8.57 (d, J=5.0 Hz, 1H), 8.49 (d, J=8.0 Hz, 1H), 7.94-7.88 (m, 1H), 7.80-7.73 (m, 1H), 7.65 (d, J=7.9 Hz, 1H), 7.45 (dd, J=7.4, 4.9 Hz, 1H), 7.30-7.26 (m, 1H), 7.13 (s, 1H), 5.07 (d, J=5.1 Hz, 2H), 3.11 (t, J=7.8 Hz, 2H), 2.95 (t, J=7.5 Hz, 2H), 2.24-2.16 (m, 2H). MS (ES+): (M+H)⁺=304.0.

Step 3

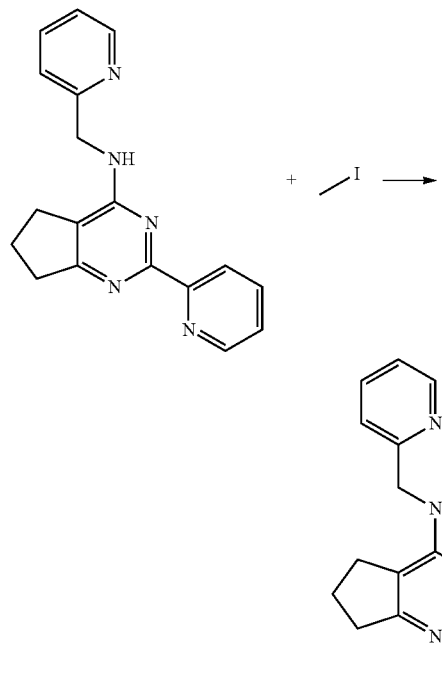

2-(Pyridin-2-yl)-N-(pyridin-2-ylmethyl)-5H,6H,7H-cyclopenta[d]pyrimidin-4-amine (0.16 g; 0.53 mmol; 1.00 eq.) was dissolved in DMF (10 ml) and cooled in an ice bath. Sodium hydride (42 mg; 1.05 mmol; 2.00 eq.) (60%) was added in two portions and the reaction was stirred for 45 m. Iodomethane (66 µL; 1.05 mmol; 2.00 eq.) was added slowly and the mixture was stirred for 1.5 h more. Water (20 ml) and ethyl acetate (100 ml) were added, the phases were separated, and the aqueous phase was extracted with more ethyl acetate (3×75 ml) and 3:1 chloroform:isopropanol (50 ml). The combined organic phases were washed with some water (5 ml) and dried over sodium sulfate. After evaporation of solvent, the residue was purified by reverse phase chromatography (Waters XSelect CSH C18 column, 0-70% acetonitrile/0.1% aqueous formic acid gradient). The purified fractions were treated with 1 M HCl and freeze-dried to give N-methyl-2-(pyridin-2-yl)-N-[(pyridin-2-yl)methyl]-5H,6H,7H-cyclopenta[d]pyrimidin-4-amine hydrochloride (90 mg, 48%) as a white solid. ¹H NMR (400 MHz, Chloroform-d) δ 9.08 (d, J=5.3 Hz, 1H), 8.69 (d, J=5.5 Hz, 1H), 8.62 (d, J=8.0 Hz, 1H), 8.29-7.98 (m, 3H), 7.75-7.68 (m, 1H), 7.55-7.47 (m, 1H), 5.68 (s, 2H), 3.67 (s, 3H), 3.52-3.37 (m, 2H), 3.26-3.14 (m, 2H), 2.23-2.12 (m, 2H). MS (ES+): (M+H)⁺=317.9.

Example 1.13

Synthesis of N-(4-methoxyphenyl)-2-{methyl[2-(pyridin-2-yl)pyrimidin-4-yl]amino}acetamide (Compound 75)

Scheme 9 depicts a synthetic route for preparing an exemplary compound.

Scheme 9

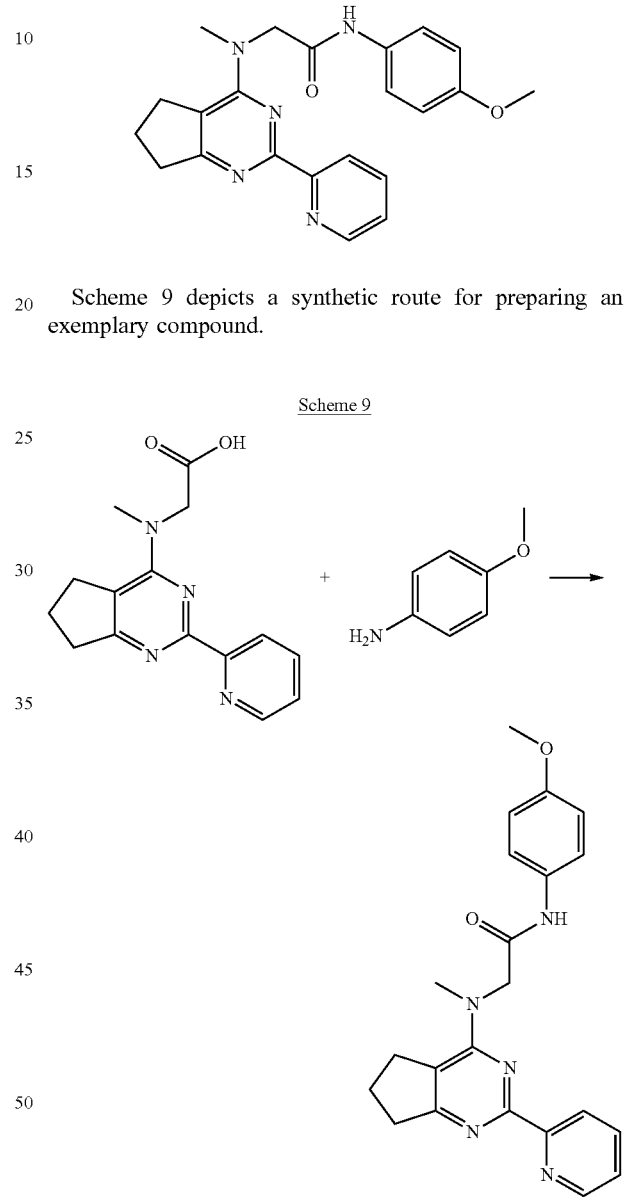

2-{4-[(Carboxymethyl)(methyl)amino]-5H,6H,7H-cyclopenta[d]pyrimidin-2-yl}pyridin-1-ium chloride (Intermediate I) (150.00 mg; 0.35 mmol; 1.00 eq.) was suspended in N,N-dimethylformamide (3.5 ml). N,N-Diisopropylethylamine (0.15 mL; 0.87 mmol; 2.50 eq.), 4-methoxyaniline (57.5 mg; 0.47 mmol; 1.35 eq.) and then 1-[bis(dimethylamino)methylene]-1H-1,2,3-triazolo[4,5-b]pyridinium 3-oxid hexafluorophosphate (HATU, 177.6 mg; 0.47 mmol; 1.35 eq.) were added. After 40 h, ethyl acetate (50 ml) and sodium bicarbonate solution (20 ml) were added, the phases were separated, and the aqueous phase was extracted with ethyl acetate (50 ml). The combined organic phases were washed with sodium chloride solution and dried over sodium sulfate. After evaporation of the solvents, the residue was purified by reverse phase chromatography (Waters XSelect CSH C18 column, 0-70% acetonitrile/0.1% aqueous formic acid gradient) to give N-(4-methoxyphenyl)-2-{methyl[2-(pyridin-2-yl)-5H,6H,7H-cyclopenta[d]pyrimidin-4-yl]amino}acetamide (formate salt, 46 mg, 34%) as a solid. $^1$H NMR (400 MHz, Chloroform-d) δ 10.18 (s, 1H), 8.86 (d, J=5.0 Hz, 1H), 8.53 (d, J=8.0 Hz, 1H), 8.22 (s, 1H), 8.04-7.93 (m, 1H), 7.56-7.46 (m, 3H), 6.76 (d, J=8.6 Hz, 2H), 4.56 (s, 2H), 3.74 (s, 3H), 3.50 (s, 3H), 3.24 (t, J=7.4 Hz, 2H), 2.99 (t, J=7.9 Hz, 2H), 2.12 (p, J=7.7 Hz, 2H). MS (ES+): (M+H)$^+$=390.1.

Example 1.14

Synthesis of N-(3-fluorophenyl)-2-{methyl[2-(pyridin-2-yl)-5H,6H,7H-cyclopenta[d]pyrimidin-4-yl]amino}acetamide (Compound 74)

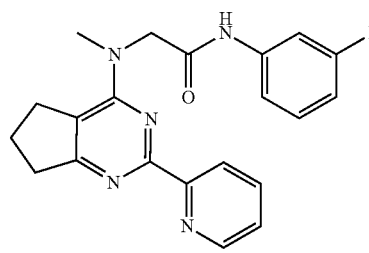

Compound 74 was synthesized similar to Compound 75 replacing 4-methoxyaniline with 3-fluoroaniline. LCMS (ES+): (M+H)$^+$=379.0. $^1$H NMR (400 MHz, Chloroform-d) δ 10.80 (s, 1H), 9.10-8.96 (m, 1H), 8.67 (d, J=7.9 Hz, 1H), 8.21-8.09 (m, 1H), 7.72-7.58 (m, 2H), 7.40 (d, J=8.2 Hz, 1H), 7.21-7.11 (m, 1H), 6.75-6.65 (m, 1H), 4.71 (s, 2H), 3.55 (s, 3H), 3.29 (t, J=7.4 Hz, 2H), 2.97 (t, J=7.9 Hz, 2H), 2.14 (p, J=7.7 Hz, 2H).

Example 1.15

Synthesis of 1-[2-(pyridin-2-yl)-5H,6H,7H-cyclopenta[d]pyrimidin-4-yl]-1,2,3,4-tetrahydroquinoline (Compound 76)

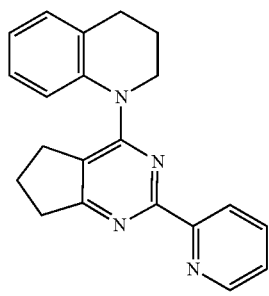 [SMILES: c1ccc(-c2nc3c(c(N4CCCc5ccccc54)n2)CCC3)nc1]

Scheme 10 depicts a synthetic route for preparing an exemplary compound.

Scheme 10

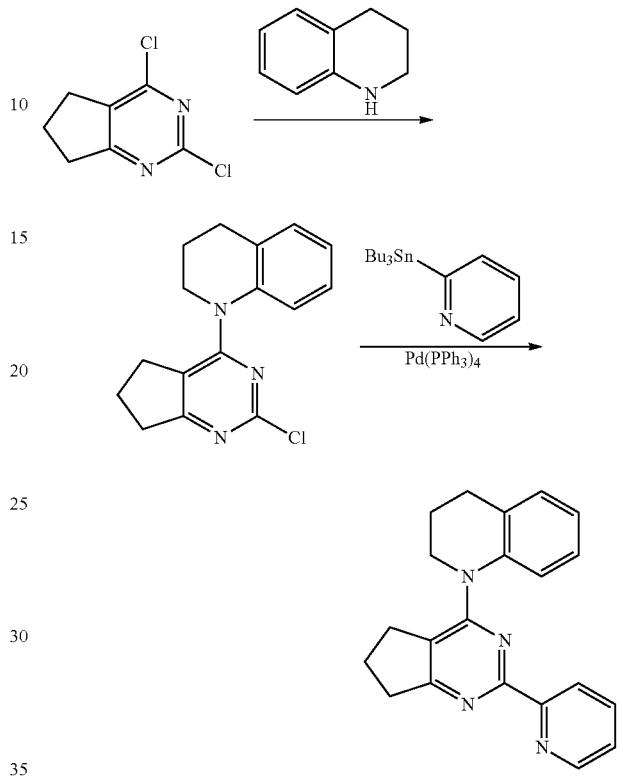

Step 1

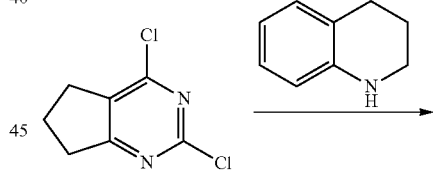

To a solution of 2,4-dichloro-6,7-dihydro-5H-cyclopenta[d]pyrimidine (100.00 mg; 0.53 mmol; 1.00 eq.) in AcCN (2 mL) was added 1,2,3,4-tetrahydroquinoline (73.98 mg; 0.56 mmol; 1.05 eq.) followed by Hunig's base (0.19 mL; 1.06 mmol; 2.00 eq.). The mixture was heated at 75° C. for 2 h, the mixture was cooled and concentrated, the residue was diluted with water, the resulting precipitate was collected by filtration, and dried under vacuum to give 1-{2-chloro-5H,6H,7H-cyclopenta[d]pyrimidin-4-yl}-1,2,3,4-tetrahydroquinoline (25 mg). LCMS (ES$^+$): (M+H)$^+$=286.2, 288.2.

Step 2

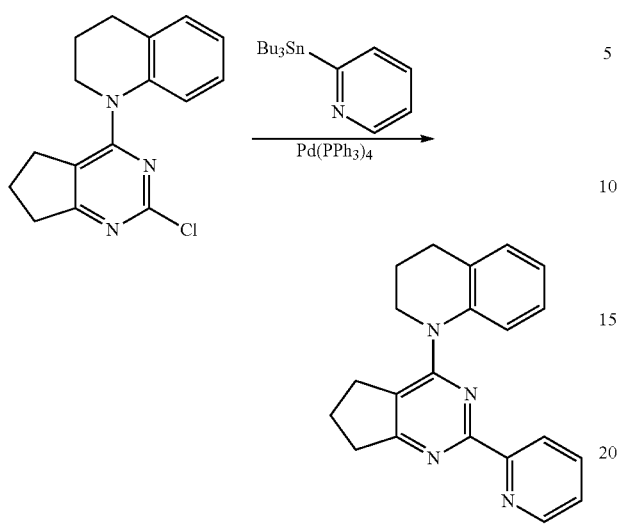

To a solution of 1-{2-chloro-5H,6H,7H-cyclopenta[d]pyrimidin-4-yl}-1,2,3,4-tetrahydroquinoline (25.00 mg; 0.09 mmol; 1.00 eq.) in toluene (1.5 mL) was added 2-(tributylstannyl)pyridine (48.31 mg; 0.13 mmol; 1.50 eq.) and tetrakis(triphenylphosphane) palladium (10.11 mg; 0.01 mmol; 0.10 eq.). The mixture was degassed and heated at 110° C. for 15 h. The mixture was cooled and concentrated, diluted with AcCN and water, and subjected to purification by preparative HPLC to give 1-[2-(pyridin-2-yl)-5H,6H,7H-cyclopenta[d]pyrimidin-4-yl]-1,2,3,4-tetrahydroquinoline (36 mg). $^1$H NMR (400 MHz, Methanol-$d_4$) δ 8.73-8.67 (m, 1H), 8.42 (dt, J=8.0, 1.2 Hz, 1H), 7.96 (td, J=7.8, 1.8 Hz, 1H), 7.50 (ddd, J=7.5, 4.9, 1.3 Hz, 1H), 7.17 (q, J=7.5 Hz, 2H), 7.03 (td, J=7.5, 1.3 Hz, 1H), 6.77 (d, J=7.9 Hz, 1H), 4.10 (t, J=6.5 Hz, 2H), 2.97 (t, J=7.7 Hz, 2H), 2.82 (t, J=6.6 Hz, 2H), 2.31 (t, J=7.3 Hz, 2H), 2.02 (dp, J=36.1, 7.5, 7.0 Hz, 4H). LCMS (ES+): (M+H)$^+$=329.1.

Example 1.16

Synthesis of 2-{methyl[2-(pyridin-2-yl)-5H,6H,7H-cyclopenta[d]pyrimidin-4-yl]amino}-N-phenylacetamide (Compound 77)

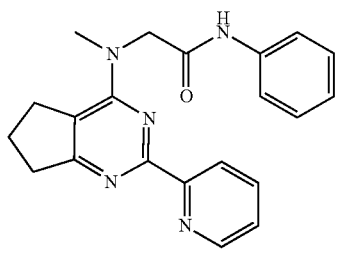 [SMILES: CN(CC(=O)Nc1ccccc1)c1nc(-c2ccccn2)nc2c1CCC2]

Compound 77 was synthesized similar to Compound 75 replacing 4-methoxyaniline with aniline. LC MS (ES+): (M+H)$^+$=360.0. $^1$H NMR (400 MHz, Chloroform-d) δ 10.39 (s, 1H), 8.98-8.87 (m, 1H), 8.58 (d, J=8.0 Hz, 1H), 8.08-7.96 (m, 1H), 7.62 (d, J=8.0 Hz, 2H), 7.59-7.51 (m, 1H), 7.25-7.17 (m, 2H), 7.01 (t, J=7.4 Hz, 1H), 4.61 (s, 2H), 3.52 (s, 3H), 3.26 (t, J=7.4 Hz, 2H), 2.98 (t, J=7.9 Hz, 2H), 2.18-2.07 (m, 2H).

Example 1.17

Synthesis of N-cyclohexyl-2-{methyl[2-(pyridin-2-yl)-5H,6H,7H-cyclopenta[d]pyrimidin-4-yl]amino}acetamide (Compound 78)

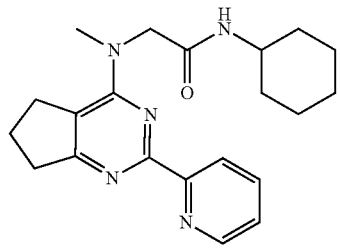 [SMILES: CN(CC(=O)NC1CCCCC1)c1nc(-c2ccccn2)nc2c1CCC2]

Compound 78 was synthesized similar to Compound 75 replacing 4-methoxyaniline with cyclohexanamine. $^1$H NMR (400 MHz, Chloroform-d) δ 9.07-8.93 (m, 1H), 8.59 (d, J=8.0 Hz, 1H), 8.12-8.01 (m, 1H), 7.83-7.64 (m, 1H), 7.59 (d, J=6.7 Hz, 1H), 4.47 (s, 2H), 3.78-3.68 (m, 1H), 3.47 (s, 3H), 3.24 (t, J=7.4 Hz, 2H), 3.00 (t, J=7.9 Hz, 2H), 2.17-2.07 (m, 2H), 1.75 (d, J=12.0 Hz, 2H), 1.65-1.58 (m, 2H), 1.56-1.49 (m, 1H), 1.28-1.06 (m, 5H). LCMS (ES+): (M+H)$^+$=366.0.

Example 1.18

Synthesis of 2-{methyl[2-(pyridin-2-yl)-5H,6H,7H-cyclopenta[d]pyrimidin-4-yl]amino}-N-(oxan-4-yl)acetamide (Compound 79)

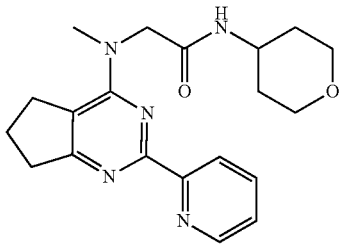 [SMILES: CN(CC(=O)NC1CCOCC1)c1nc(-c2ccccn2)nc2c1CCC2]

Compound 79 was synthesized similar to Compound 75 by replacing 4-methoxyaniline with 4-aminotetrahydropyran. LCMS (ES+): (M+H)$^+$=368.1. $^1$H NMR (400 MHz, Chloroform-d) δ 9.32 (s, 1H), 8.87 (d, J=8.0 Hz, 1H), 8.81-8.73 (m, 1H), 8.45-8.35 (m, 1H), 7.92-7.84 (m, 1H), 4.76 (s, 2H), 3.93-3.84 (m, 3H), 3.58 (s, 3H), 3.40-3.30 (m, 4H), 2.96 (t, J=7.9 Hz, 2H), 2.16-2.11 (m, 2H), 1.75-1.56 (m, 4H).

Example 1.19

Synthesis of N-ethyl-2-(pyridin-2-yl)-N-[(pyrimidin-2-yl)methyl]-5H,6H,7H-cyclopenta[d]pyrimidin-4-amine (Compound 80)

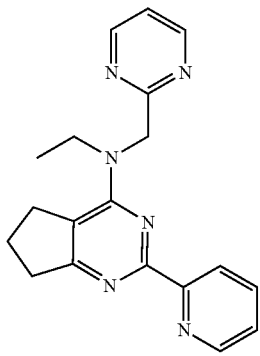 [SMILES: CCN(Cc1ncccn1)c1nc(-c2ccccn2)nc2c1CCC2]

Compound 80 was synthesized similar to Compound 73 by replacing 2-pyridinylmethanamine with 2-pyrimidinylmethylamine and replacing iodomethane with ethyl iodide. LCMS (ES+): (M+H)⁺=333.0. ¹H NMR (400 MHz, Chloroform-d) δ 8.96-8.82 (m, 3H), 8.52 (d, J=7.7 Hz, 1H), 8.18-8.09 (m, 1H), 7.75-7.68 (m, 1H), 7.55 (s, 1H), 5.43 (s, 2H), 4.01 (q, J=7.1 Hz, 2H), 3.32-3.13 (m, 4H), 2.28-2.17 (m, 2H), 1.37 (t, J=6.9 Hz, 3H).

Example 1.20

Synthesis of N-methyl-2-(pyridin-2-yl)-N-[(pyrimidin-2-yl)methyl]-5H,6H,7H-cyclopenta[d]pyrimidin-4-amine (Compound 81)

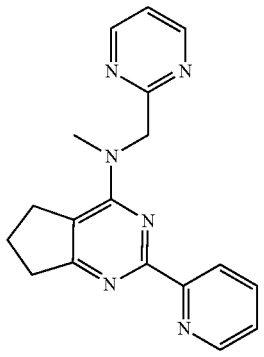 [SMILES: CN(Cc1ncccn1)c1nc(-c2ccccn2)nc2c1CCC2]

Compound 81 was synthesized similar to Compound 73 by replacing 2-pyridinylmethanamine with 2-pyrimidinylmethylamine. LCMS (ES+): (M+H)⁺=319.1. ¹H NMR (400 MHz, Chloroform-d) δ 8.78-8.69 (m, 3H), 8.33 (s, 1H), 8.18 (d, J=8.0 Hz, 1H), 7.79-7.72 (m, 1H), 7.38-7.31 (m, 1H), 7.22-7.17 (m, 1H), 5.14 (s, 2H), 3.53 (s, 3H), 3.21 (t, J=7.4 Hz, 2H), 3.15-3.10 (m, 2H), 2.13-2.07 (m, 2H).

Example 1.21

Synthesis of N-[(1,3-benzoxazol-2-yl)methyl]-N-methyl-2-(pyridin-2-yl)-5H,6H,7H-cyclopenta[d]pyrimidin-4-amine (Compound 82)

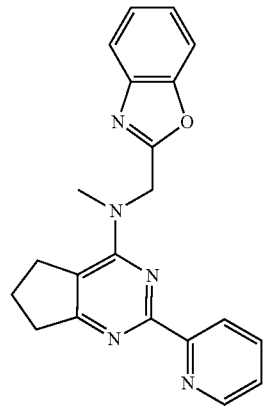 [SMILES: CN(Cc1nc2ccccc2o1)c1nc(-c2ccccn2)nc2c1CCC2]

Compound 82 was synthesized similar to Compound 73 by replacing 2-pyridinylmethanamine with 1,3-benzoxazol-2-ylmethanamine. LCMS (ES+): (M+H)⁺=358.0. ¹H NMR (400 MHz, Chloroform-d) δ 8.82 (d, J=5.4 Hz, 1H), 8.34 (d, J=8.0 Hz, 1H), 8.14 (s, 1H), 7.86-7.77 (m, 1H), 7.74-7.67 (m, 1H), 7.54-7.47 (m, 1H), 7.41-7.35 (m, 1H), 7.35-7.29 (m, 2H), 5.25 (s, 2H), 3.54 (s, 3H), 3.29 (t, J=7.3 Hz, 2H), 3.18-3.11 (m, 2H), 2.16-2.12 (m, 2H).

Example 1.22

Synthesis of 3-[2-(pyridin-2-yl)-5H,6H,7H-cyclopenta[d]pyrimidin-4-yl]-2,3,4,5-tetrahydro-1H-3-benzazepine (Compound 83)

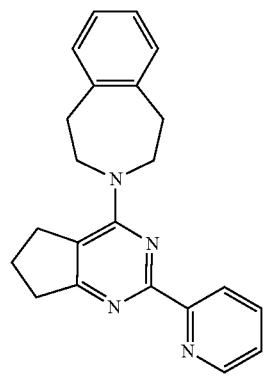 [SMILES: c1ccc(-c2nc3c(c(N4CCc5ccccc5CC4)n2)CCC3)nc1]

Compound 83 was synthesized similar to compound 92 by replacing azepane with 2,3,4,5-tetrahydro-1H-benzo[d]azepine. LCMS (ES+): (M+H)⁺=343.0. ¹H NMR (400 MHz, Chloroform-d) δ 8.81 (d, J=4.8 Hz, 1H), 8.41 (d, J=7.9 Hz, 1H), 7.89-7.80 (m, 1H), 7.39 (dd, J=7.5, 4.9 Hz, 1H), 7.15 (s, 4H), 6.10 (s, 2H), 4.08-3.99 (m, 4H), 3.15-3.02 (m, 8H), 2.19-2.08 (m, 2H).

Example 1.23

Synthesis of N-(2-methoxyethyl)-N-methyl-2-(pyridin-2-yl)-5H,6H,7H-cyclopenta[d]pyrimidin-4-amine (Compound 84)

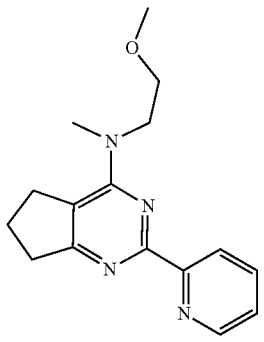 [SMILES: COCCN(C)c1nc(-c2ccccn2)nc2c1CCC2]

Compound 84 was synthesized similar to compound 92 by replacing azepane with N-(2-methoxyethyl)-N-methylamine. LCMS (ES+): (M+H)$^+$=285.0. $^1$H NMR (400 MHz, Chloroform-d) δ 8.81 (dd, J=4.7, 2.0 Hz, 1H), 8.45 (d, J=1.5 Hz, 1H), 8.34 (dd, J=8.2, 1.5 Hz, 1H), 7.89-7.80 (m, 1H), 7.50-7.27 (m, 3H), 3.97-3.90 (m, 2H), 3.70-3.63 (m, 2H), 3.41 (s, 3H), 3.36 (s, 3H), 3.23-3.14 (m, 4H), 2.16-2.07 (m, 2H).

Example 1.24

Synthesis of 1-methyl-4-[2-(pyridin-2-yl)-5H,6H,7H-cyclopenta[d]pyrimidin-4-yl]-1,4-diazepane (Compound 85)

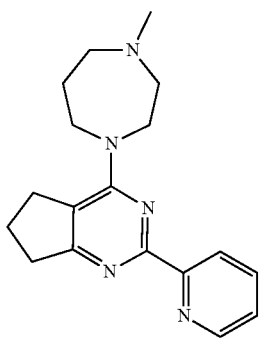 [SMILES: CN1CCCN(c2nc(-c3ccccn3)nc3c2CCC3)CC1]

Compound 85 was synthesized similar to compound 92 by replacing azepane with 1-methyl-1,4-diazepane. LCMS (ES+): (M+H)$^+$=310.1. $^1$H NMR (400 MHz, Chloroform-d) δ 8.79 (d, J=4.8 Hz, 1H), 8.29-8.21 (m, 1H), 7.86-7.76 (m, 1H), 7.40-7.34 (m, 1H), 4.36-4.22 (m, 2H), 3.98 (t, J=6.7 Hz, 2H), 3.50-3.40 (m, 2H), 3.28-3.18 (m, 2H), 3.11 (t, J=7.3 Hz, 2H), 3.03 (t, J=7.8 Hz, 2H), 2.82 (s, 3H), 2.56 (s, 2H), 2.15-2.04 (m, 2H).

Example 1.25

Synthesis of 2-{methyl[2-(pyridin-2-yl)-5H,6H,7H-cyclopenta[d]pyrimidin-4-yl]amino}-1-(morpholin-4-yl)ethan-1-one (Compound 86)

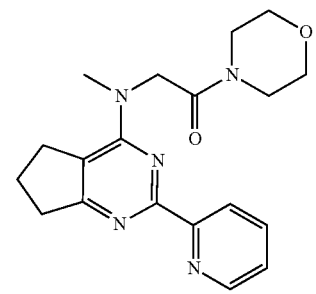 [SMILES: CN(CC(=O)N1CCOCC1)c1nc(-c2ccccn2)nc2c1CCC2]

Compound 86 was synthesized similar to Compound 75 by replacing 4-methoxyaniline with morpholine. LCMS (ES+): (M+H)$^+$=354.0. $^1$H NMR (400 MHz, Chloroform-d) δ 8.96-8.86 (m, 1H), 8.50-8.37 (m, 1H), 8.21-8.15 (m, 1H), 8.07-7.93 (m, 1H), 7.60-7.48 (m, 1H), 4.86-4.75 (m, 2H), 3.81-3.74 (m, 2H), 3.71-3.66 (m, 4H), 3.62-3.58 (m, 2H), 3.41 (s, 3H), 3.29-3.25 (m, 2H), 3.06-3.00 (m, 2H), 2.17-2.05 (m, 2H).

Example 1.26

Synthesis of N-methyl-N-(2-phenoxyethyl)-2-(pyridin-2-yl)-5H,6H,7H-cyclopenta[d]pyrimidin-4-amine (Compound 87)

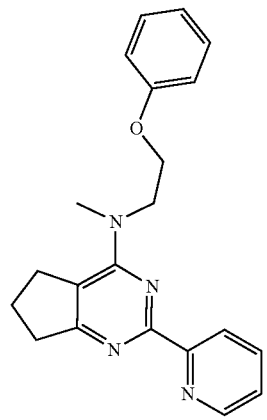 [SMILES: CN(CCOc1ccccc1)c1nc(-c2ccccn2)nc2c1CCC2]

Compound 87 was synthesized similar to compound 92 by replacing azepane with N-methyl-N-(2-phenoxyethyl)amine. LCMS (ES+): (M+H)$^+$=285.0. $^1$H NMR (400 MHz, Chloroform-d) δ 9.09 (d, J=4.9 Hz, 1H), 8.57 (d, J=7.8 Hz, 1H), 8.16-8.00 (m, 1H), 7.69-7.63 (m, 1H), 7.29-7.25 (m, 2H), 6.98-6.91 (m, 1H), 6.86 (d, J=8.0 Hz, 2H), 4.36 (s, 4H), 3.61 (s, 3H), 3.45 (t, J=7.8 Hz, 2H), 3.29 (t, J=7.3 Hz, 2H), 2.24-2.13 (m, 2H).

Example 1.27

Synthesis of 2-{methyl[2-(pyridin-2-yl)-5H,6H,7H-cyclopenta[d]pyrimidin-4-yl]amino}-1-(piperidin-1-yl)ethan-1-one (Compound 88)

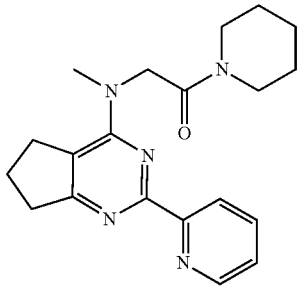 [SMILES: CN(CC(=O)N1CCCCC1)c1nc(-c2ccccn2)nc2c1CCC2]

Compound 88 was synthesized similar to Compound 75 replacing 4-methoxyaniline with piperidine. LCMS (ES+): (M+H)$^+$=352.1. $^1$H NMR (400 MHz, Chloroform-d) δ 9.03 (d, J=5.1 Hz, 1H), 8.69-8.55 (m, 1H), 8.23-8.07 (m, 1H), 7.74-7.64 (m, 1H), 5.17-4.78 (m, 2H), 3.64-3.56 (m, 2H), 3.52 (t, J=5.6 Hz, 2H), 3.44 (s, 3H), 3.33-3.20 (m, 4H), 2.20-2.10 (m, 2H), 1.73-1.62 (m, 4H), 1.57-1.49 (m, 2H).

Example 1.28

Synthesis of N-tert-butyl-2-{methyl[2-(pyridin-2-yl)-5H,6H,7H-cyclopenta[d]pyrimidin-4-yl]amino}acetamide (Compound 89)

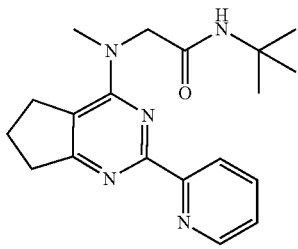 [SMILES: CN(CC(=O)NC(C)(C)C)c1nc(-c2ccccn2)nc2c1CCC2]

Compound 89 was synthesized similar to Compound 75 by replacing 4-methoxyaniline with tert-butylamine. $^1$H NMR (400 MHz, Chloroform-d) δ 9.33-9.18 (m, 1H), 8.87 (d, J=7.7 Hz, 1H), 8.43-8.33 (m, 1H), 8.28 (s, 1H), 7.91-7.79 (m, 1H), 4.71 (s, 2H), 3.55 (s, 3H), 3.29 (t, J=7.3 Hz, 2H), 3.00 (t, J=7.9 Hz, 2H), 2.17-2.07 (m, 2H), 1.27 (s, 9H). MS (ES+): (M+H)$^+$=340.0.

Example 1.29

Synthesis of N-cyclohexyl-2-{methyl[2-(pyridin-2-yl)-5H,6H,7H-cyclopenta[d]pyrimidin-4-yl]amino}propanamide (Compound 91)

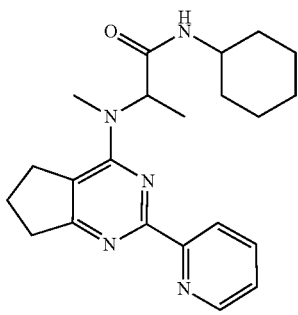 [SMILES: CC(C(=O)NC1CCCCC1)N(C)c1nc(-c2ccccn2)nc2c1CCC2]

Step 1

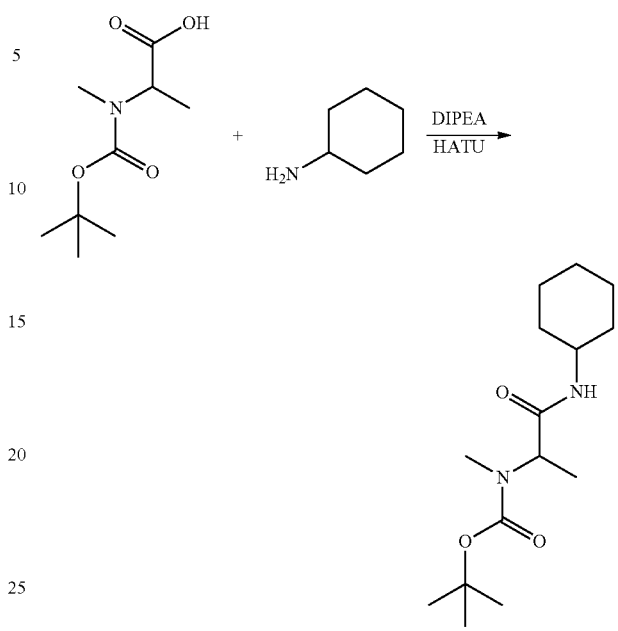

2-{[(Tert-butoxy)carbonyl](methyl)amino}propanoic acid (500 mg; 2.5 mmol; 1 eq.) was dissolved in DMF (6 ml). N, N-diisopropylethylamine (1.1 mL; 6.15 mmol; 2.5 eq.) and then 1-[bis(dimethylamino)methylene]-1H-1,2,3-triazolo[4,5-b]pyridinium 3-oxid hexafluorophosphate (HATU, 1262 mg; 3.3 mmol; 1.35 eq.) were added. Cyclohexanamine (0.38 mL; 3.3 mmol; 1.35 eq.) was added and the reaction mixture was stirred at 25° C. After 14 h, the reaction was diluted with ethyl acetate (50 ml), water (15 ml) and sodium bicarbonate solution (30 ml). The phases were separated, and the aqueous phase was extracted with ethyl acetate (50 ml). the combined organics were washed with sodium chloride solution (50 ml) and dried over sodium sulfate. After evaporation, the residue was purified by silica gel chromatography (ethyl acetate/hexanes gradient) to give tert-butyl N-[1-(cyclohexylcarbamoyl)ethyl]-N-methylcarbamate (0.48 g, 68%) as white crystals. LCMS (ES+): (M+H)$^+$=285.0.

Step 2

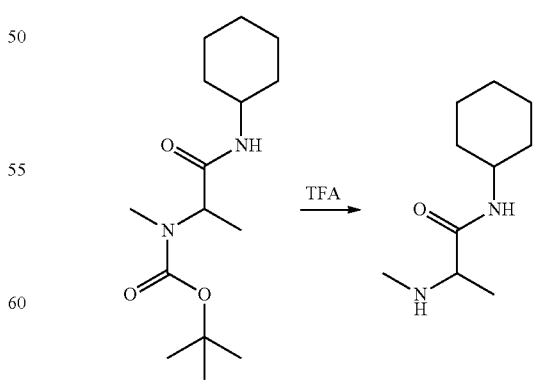

Tert-butyl N-[1-(cyclohexylcarbamoyl)ethyl]-N-methylcarbamate (0.48 g; 1.7 mmol; 1 eq.) was dissolved in dichloromethane (12 ml) and cooled in an ice bath. Trifluoroacetic acid (6 mL) was added slowly and the reaction was stirred at 20° C. After 1.6 h, the reaction was evaporated to a residue and then co-evaporated from toluene (40 ml). The crude product of N-cyclohexyl-2-(methylamino)propanamide; trifluoroacetic acid salt was used directly in the next step.

Step 3

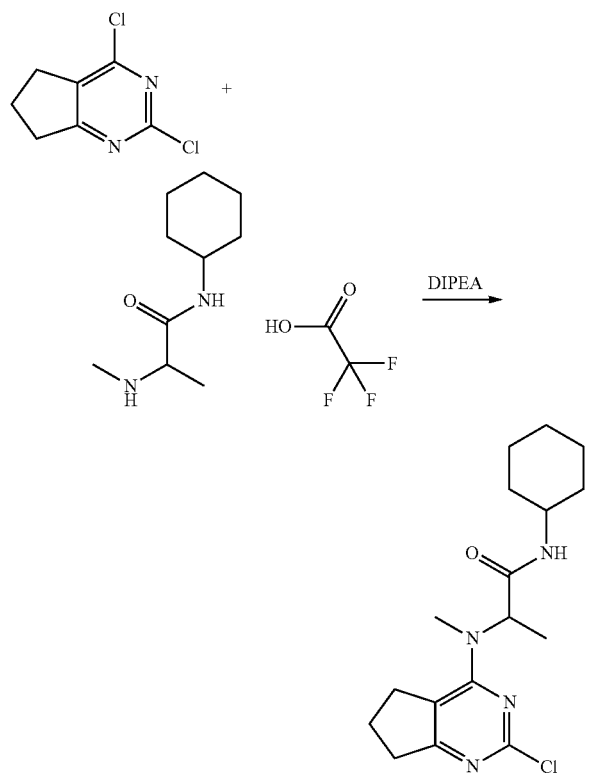

2,4-Dichloro-6,7-dihydro-5H-cyclopenta[d]pyrimidine (150 mg; 0.79 mmol; 1 eq.) was dissolved in acetonitrile (3 ml) containing N-cyclohexyl-2-(methylamino)propanamide trifluoroacetic acid salt (355 mg; 1.19 mmol; 1.5 eq.). N,N-diisopropylethylamine (0.55 mL; 3.2 mmol; 4 eq.) was added and the reaction was stirred at 50° C. for 14 h, then at 60° C. for 6 h, and to 30° C. over 18 h. After evaporation, the residue was purified by silica gel chromatography (ethyl acetate/hexanes gradient) to give 2-({2-chloro-5H,6H,7H-cyclopenta[d]pyrimidin-4-yl}(methyl)amino)-N-cyclohexylpropanamide (174 mg, 65%) as a film. LCMS (ES+): (M+H)$^+$=337.2.

Step 4

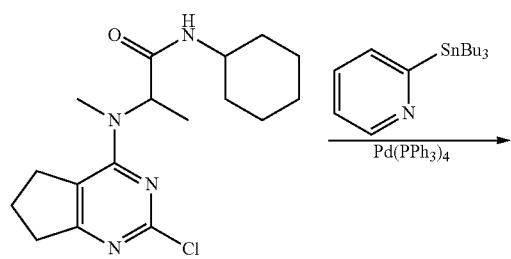

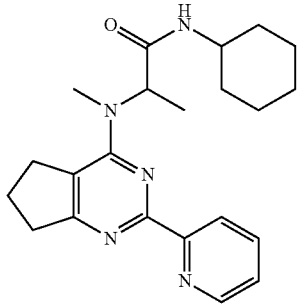

2-({2-Chloro-5H,6H,7H-cyclopenta[d]pyrimidin-4-yl}(methyl)amino)-N-cyclohexylpropanamide (174 mg; 0.52 mmol; 1 eq.) was dissolved in 1,4-dioxane (4 ml). and the solution was purged with Ar gas. 2-(Tributylstannyl)pyridine (0.39 mL; 1.03 mmol; 2 eq.) was added followed by tetrakis(triphenylphosphane) palladium (60 mg; 0.05 mmol; 0.1 eq.) The reaction vessel was sealed and stirred in a heat bath at 110° C. for 15 h. After evaporation, the residue was purified by reverse phase chromatography (Waters XSelect CSH C18 column, 0-70% acetonitrile/0.1% aqueous formic acid gradient) to give N-cyclohexyl-2-{methyl[2-(pyridin-2-yl)-5H,6H,7H-cyclopenta[d]pyrimidin-4-yl]amino}propenamide (86 mg, 43%) as an off-white solid. LCMS (ES+): (M+H)$^+$=380.0. $^1$H NMR (400 MHz, DMSO-d6) δ 8.69 (d, J=4.8 Hz, 1H), 8.34 (d, J=7.9 Hz, 1H), 8.19 (d, J=8.3 Hz, 1H), 7.96-7.84 (m, 1H), 7.53-7.42 (m, 1H), 5.16 (q, J=7.0 Hz, 1H), 3.63-3.49 (m, 1H), 3.25-3.16 (m, 1H), 3.14-3.06 (m, 4H), 2.93-2.76 (m, 2H), 1.74 (s, 1H), 1.65 (s, 1H), 1.59-1.44 (m, 3H), 1.33 (d, J=7.0 Hz, 3H), 1.25-1.12 (m, 3H), 1.07-0.93 (m, 2H).

Example 1.30

Synthesis of N-tert-butyl-2-{methyl[2-(pyridin-2-yl)-5H,6H,7H-cyclopenta[d]pyrimidin-4-yl]amino}propanamide (Compound 90)

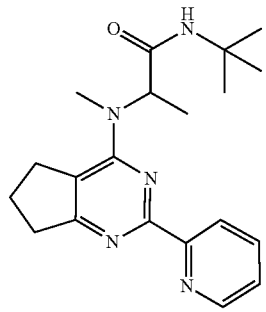 [SMILES: CC(C(=O)NC(C)(C)C)N(C)c1nc(-c2ccccn2)nc2c1CCC2]

Compound 90 was synthesized similar to Compound 91 by replacing cyclohexanamine with tert-butylamine. LCMS (ES+): (M+H)$^+$=354.4. $^1$H NMR (400 MHz, DMSO-d6) δ 8.80-8.74 (m, 1H), 8.50 (d, J=7.9 Hz, 1H), 8.09-8.01 (m, 1H), 7.81 (s, 1H), 7.66-7.59 (m, 1H), 5.14 (q, J=7.0 Hz, 1H), 3.26 (s, 3H), 3.24-3.10 (m, 2H), 3.05-2.88 (m, 2H), 2.15-1.97 (m, 3H), 1.40 (d, J=7.1 Hz, 3H), 1.21 (s, 9H).

Example 1.31

Synthesis of 10-[2-(pyridin-2-yl)-5H,6H,7H-cyclopenta[d]pyrimidin-4-yl]-10-azatricyclo[6.3.1.0^{2,7}]dodeca-2,4,6-triene (Compound 1)

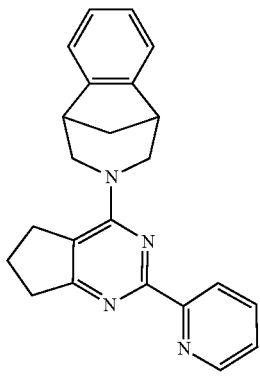 [SMILES: c1ccc(-c2nc3c(c(N4CC5CC(C4)c4ccccc45)n2)CCC3)nc1]

Compound 1 was synthesized similar to compound 92 by replacing azepane with 10-azatricyclo[6.3.1.0$^2$,7]dodeca-2(7),3,5-triene. LCMS (ES+): (M+H)$^+$=355.0. $^1$H NMR (400 MHz, Chloroform-d) δ 8.66 (s, 1H), 8.45-8.12 (m, 1H), 7.71 (s, 1H), 7.26-6.87 (m, 5H), 4.46-4.19 (m, 2H), 3.52-3.10 (m, 4H), 2.99-2.74 (m, 4H), 2.34 (s, 1H), 2.01-1.76 (m, 3H).

Example 1.32

Synthesis of 7-methoxy-3-[2-(pyridin-2-yl)-5H,6H,7H-cyclopenta[d]pyrimidin-4-yl]-2,3,4,5-tetrahydro-1H-3-benzazepine (Compound 2)

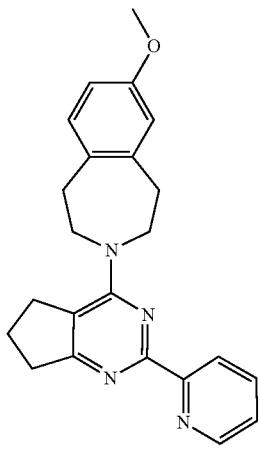 [SMILES: COc1ccc2c(c1)CCN(c1nc(-c3ccccn3)nc3c1CCC3)CC2]

Compound 2 was synthesized similar to compound 92 by replacing azepane with 7-methoxy-2,3,4,5-tetrahydro-1H-3-benzazepine. LCMS (ES+): (M+H)$^+$=373.1 $^1$H NMR (400 MHz, Chloroform-d) δ 8.90-8.70 (m, 1H), 8.40 (d, J=7.1 Hz, 2H), 7.90-7.76 (m, 1H), 7.43-7.31 (m, 1H), 7.07 (d, J=8.2 Hz, 1H), 6.77-6.60 (m, 2H), 4.10-3.91 (m, 4H), 3.79 (s, 3H), 3.15-2.91 (m, 8H), 2.19-2.07 (m, 2H).

Example 1.33

Synthesis of 6-methoxy-3-[2-(pyridin-2-yl)-5H,6H,7H-cyclopenta[d]pyrimidin-4-yl]-2,3,4,5-tetrahydro-1H-3-benzazepine (Compound 3)

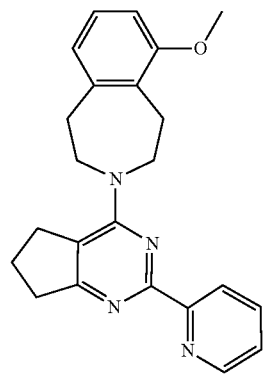 [SMILES: COc1cccc2c1CCN(c1nc(-c3ccccn3)nc3c1CCC3)CC2]

Compound 3 was synthesized similar to compound 92 by replacing azepane with 6-methoxy-2,3,4,5-tetrahydro-1H-3-benzazepine. LCMS (ES+): (M+H)$^+$=373.0. $^1$H NMR (400 MHz, Chloroform-d) δ 8.81 (dd, J=4.8, 1.8 Hz, 1H), 8.42 (d, J=7.9 Hz, 1H), 7.86-7.77 (m, 1H), 7.39-7.31 (m, 1H), 7.14-7.07 (m, 1H), 6.79-6.74 (m, 2H), 4.00 (dt, J=25.4, 4.9 Hz, 4H), 3.81 (s, 3H), 3.17-3.03 (m, 8H), 2.15-2.06 (m, 2H).

Example 1.34

Synthesis of 1-(3-methoxyphenyl)-4-[2-(pyridin-2-yl)-5H,6H,7H-cyclopenta[d]pyrimidin-4-yl]-1,4-diazepane (Compound 4)

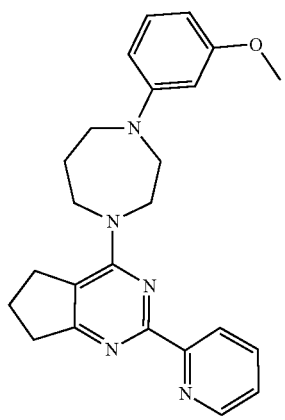 [SMILES: COc1cccc(N2CCCN(c3nc(-c4ccccn4)nc4c3CCC4)CC2)c1]

Scheme 11 depicts a synthetic route for preparing an exemplary compound.

Scheme 11

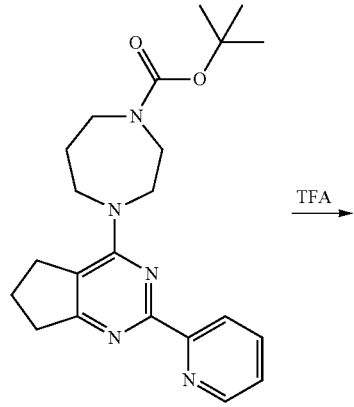

Step 1

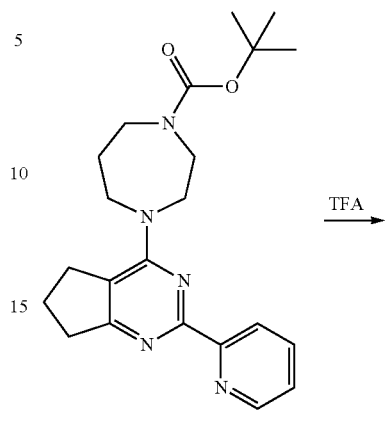

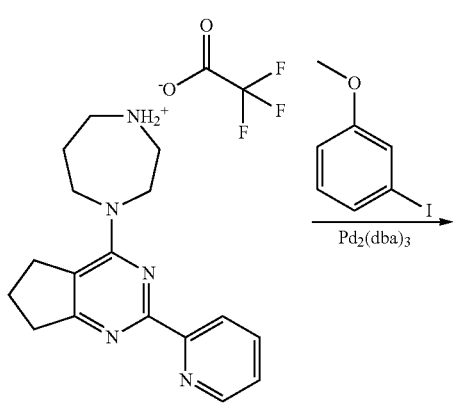

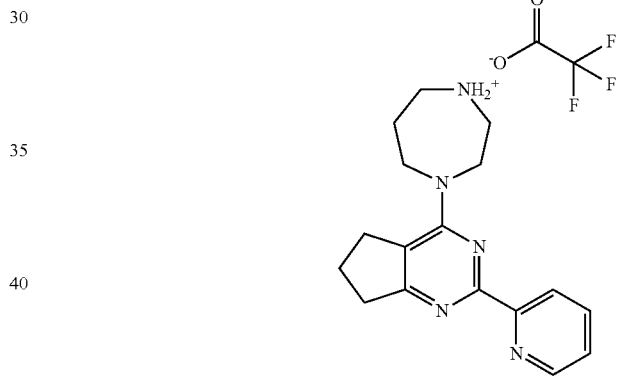

Tert-butyl 4-[2-(pyridin-2-yl)-5H,6H,7H-cyclopenta[d]pyrimidin-4-yl]-1,4-diazepane-1-carboxylate (200 mg; 0.51 mmol; 1 eq.) was dissolved in dichloromethane (5 ml). Trifluoroacetic acid (2.5 mL) was added slowly and the reaction was stirred at 25° C. After 1 h, the reaction was evaporated to dryness and the residue was co-evaporated with toluene. LCMS (ES+): (M+H)⁺=296.

Step 2

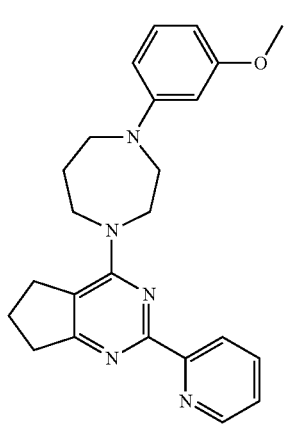

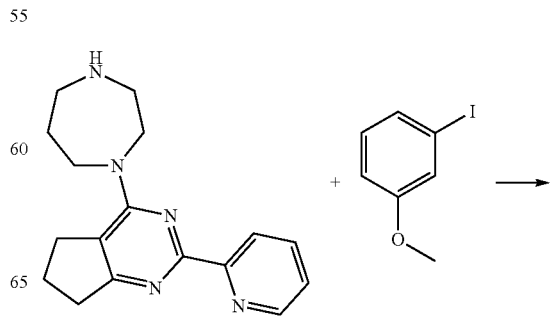

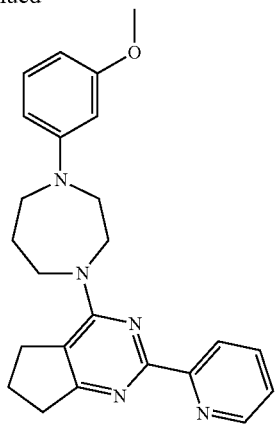

1-[2-(Pyridin-2-yl)-5H,6H,7H-cyclopenta[d]pyrimidin-4-yl]-1,4-diazepane (108 mg; 0.37 mmol; 1.15 eq.) and 1-iodo-3-methoxybenzene (75 mg; 0.32 mmol; 1 eq.) were mixed with 1,4-dioxane (1 ml) and tert-butanol (0.5 ml). The mixture was purged with Ar gas. 2-[2-(Dicyclohexylphosphanyl)phenyl]-N,N-dimethylaniline (25 mg; 0.06 mmol; 0.20 eq.), tris(dibenzylideneacetone)dipalladium(0) (15 mg; 0.02 mmol; 0.05 eq.) and sodium tert-butoxide (46 mg; 0.48 mmol; 1.50 eq.) were added and the reaction vessel was sealed and stirred at 100° C. After 19 h, additional portions of reagents (iodide, ligand, palladium catalyst and base) were added to drive product formation. The reaction mixture was then filtered, concentrated and purified by reverse phase chromatography (Waters XSelect CSH C18 column, 0-50% acetonitrile/0.1% aqueous formic acid gradient) to give 1-(3-methoxyphenyl)-4-[2-(pyridin-2-yl)-5H,6H,7H-cyclopenta[d]pyrimidin-4-yl]-1,4-diazepane (19 mg, 15%) as a yellow solid.

MS (ES+): (M+H)$^+$=402.1. $^1$H NMR (400 MHz, Chloroform-d) δ 8.94-8.87 (m, 1H), 8.34 (d, J=7.9 Hz, 1H), 8.02-7.92 (m, 1H), 7.62-7.53 (m, 1H), 7.19-7.10 (m, 1H), 6.41 (d, J=8.3 Hz, 1H), 6.35-6.28 (m, 2H), 4.30-4.22 (m, 2H), 3.92-3.86 (m, 2H), 3.81-3.76 (m, 5H), 3.64 (t, J=6.2 Hz, 2H), 3.36 (t, J=8.0 Hz, 2H), 3.18 (t, J=7.4 Hz, 2H), 2.27-2.15 (m, 4H).

Example 1.35

Synthesis of N-(pyridin-2-yl)-2-{[2-(pyridin-2-yl)-5H,6H,7H-cyclopenta[d]pyrimidin-4-yl]amino}acetamide (Compound 5)

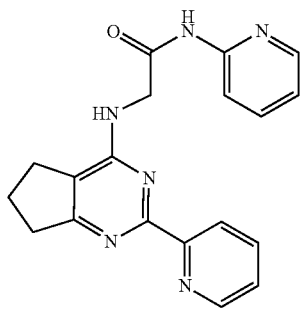 [SMILES: O=C(CNc1nc(-c2ccccn2)nc2c1CCC2)Nc1ccccn1]

Scheme 12 depicts a synthetic route for preparing an exemplary compound.

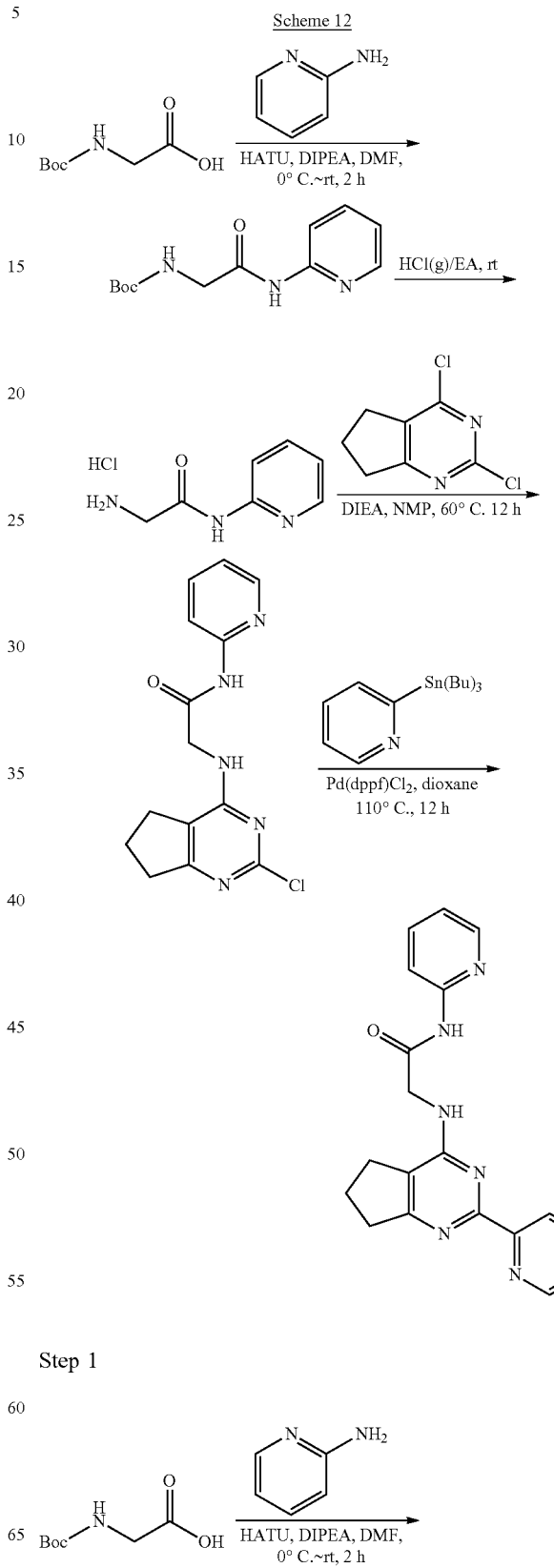

Step 1

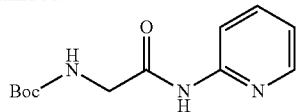

Into a 50-mL 3-necked round-bottom flask, was placed [(tert-butoxycarbonyl)amino]acetic acid (2.0 g, 11.42 mmol, 1.0 equiv), DMF (20.0 mL), 2-aminopyridine (1.29 g, 13.71 mmol, 1.2 equiv) and DIPEA (3.69 g, 28.54 mmol, 2.5 equiv). This was followed by the addition of HATU (5.21 g, 13.70 mmol, 1.2 equiv) in several batches at 0° C. The reaction solution was stirred for 2 h at room temperature. The reaction was then quenched by the addition of 50 mL of H₂O, filtered and the collected solid was dried under infrared lamp. 2.4 g (84% yield) of tert-butyl N-[[(pyridin-2-yl)carbamoyl]methyl]carbamate was obtained as white solid. LCMS (ES) [M+1]⁺ m/z: 252.
Step 2

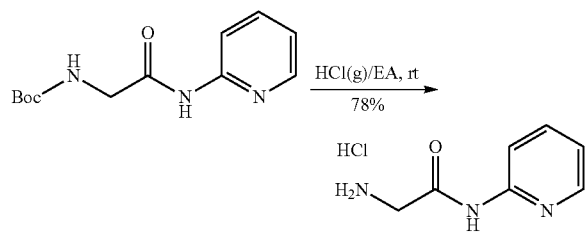

Into a 50-mL round-bottom flask, was placed tert-butyl N-[[(pyridin-2-yl)carbamoyl]methyl]carbamate (2.40 g, 9.55 mmol, 1.0 equiv) and DCM (20.0 mL). To the above mixture was added HCl (g) (2 M in EA) (19.0 mL) at 0° C. The mixture was stirred for 2 h at room temperature. The mixture was concentrated to remove the solvent, 1.4 g (78% yield) of 2-amino-N-(pyridin-2-yl)acetamide hydrochloride was obtained as white solid. LCMS (ES) [M−HCl+1]⁺ m/z: 152.
Step 3

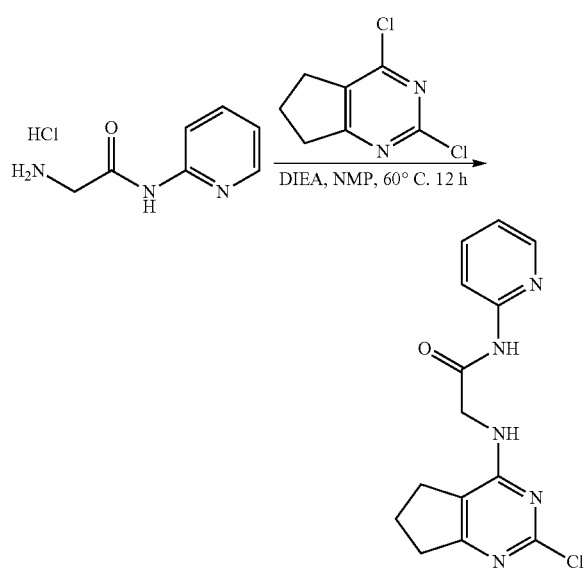

Into a 100-mL round-bottom flask, was placed 2-amino-N-(pyridin-2-yl)acetamide hydrochloride (1.40 g, 7.46 mmol, 1.0 equiv), NMP (30.0 mL), 2,4-dichloro-5H,6H,7H-cyclopenta[d]pyrimidine (1.30 g, 6.88 mmol, 0.9 equiv), DIEA (2.70 g, 20.89 mmol, 2.80 equiv). The mixture was stirred for 12 h at 60° C. in an oil bath. After being cooled to room temperature, the reaction was diluted with H₂O (50 mL) and extracted with 3×40 mL of ethyl acetate. The combined organic phase was washed with 3×40 ml of brine, dried over anhydrous sodium sulfate, filtered, and the filtrate was concentrated under reduced pressure. The residue was purified by silica gel column with ethyl acetate/petroleum ether (1:2). 320 mg (14% yield) of 2-([2-chloro-5H,6H,7H-cyclopenta[d]pyrimidin-4-yl]amino)-N-(pyridin-2-yl)acetamide was obtained as a white solid. LCMS (ES) [M+1]⁺ m/z: 304.
Step 4

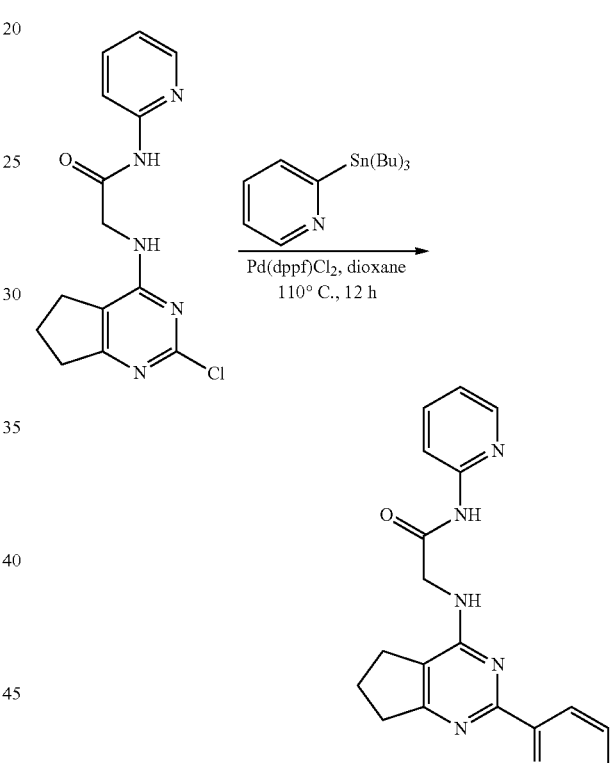

Into a 50-mL round-bottom flask, was placed 2-([2-chloro-5H,6H,7H-cyclopenta[d]pyrimidin-4-yl]amino)-N-(pyridin-2-yl)acetamide (320 mg, 1.05 mmol, 1.0 equiv), dioxane (20.0 mL), 2-(tributylstannyl)pyridine (465 mg, 1.26 mmol, 1.2 equiv), and Pd(dppf)Cl₂ (86 mg, 0.11 mmol, 0.1 equiv). The mixture was stirred for 12 h at 110° C. in an oil bath under N₂ atmosphere. The reaction mixture was cooled to room temperature and concentrated to remove the solvent. The residue was purified by silica gel column with ethyl acetate/petroleum ether (3:1). The crude product was further purified by Flash-Prep-HPLC with the following conditions: Column: HPH C18, 50*3.0 mm, 2.6 um, Mobile Phase A: Water/0.05% NH₃·H₂O, Mobile Phase B: CH₃CN, Flow rate: 1.2 mL/min, Gradient: 5% B to 100% B within 1.1 min, hold 0.7 min. 78.9 mg (22% yield) of N-(pyridin-2-yl)-2-[[2-(pyridin-2-yl)-5H,6H,7H-cyclopenta[d]pyrimidin-4-yl]amino]acetamide was obtained as off-white solid.

¹H-NMR (300 MHz, DMSO-d₆, ppm): δ 10.60 (s, 1H), 8.61 (d, J=4.6 Hz, 1H), 8.33 (dd, J=4.9, 1.1 Hz, 1H) 8.23 (d, J=8.1 Hz, 1H), 8.03 (d, J=8.4 Hz, 1H), 7.78-7.69 (m, 2H), 7.40-7.35 (m, 2H), 7.09 (ddd, J=7.3, 4.8, 1.0 Hz, 1H), 4.31 (d, J=5.8 Hz, 2H), 2.86 (t, J=7.7 Hz, 2H), 2.79 (t, J=7.4 Hz, 2H), 2.09 (p, J=7.5 Hz, 2H). LCMS: (ES, m/z): [M+H]⁺: 347.1.

Example 1.36

Synthesis of N-(2-fluorophenyl)-2-{[2-(pyridin-2-yl)-5H,6H,7H-cyclopenta[d]pyrimidin-4-yl]amino}acetamide (Compound 6)

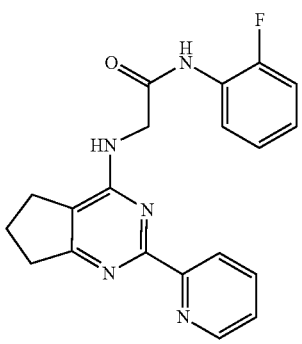 [SMILES: O=C(CNc1nc(-c2ccccn2)nc2c1CCC2)Nc1ccccc1F]

Scheme 13 depicts a synthetic route for preparing an exemplary compound.

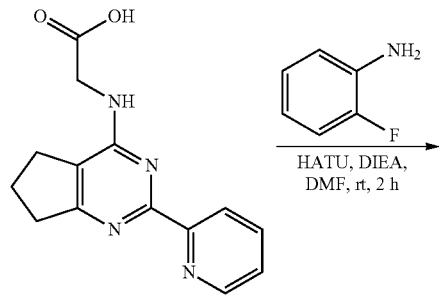

Into a 50-mL round-bottom flask, was placed [[2-(pyridin-2-yl)-5H,6H,7H-cyclopenta[d]pyrimidin-4-yl]amino]acetic acid (160 mg, 0.59 mmol, 1.0 equiv), DMF (3.0 mL), 2-fluoroaniline (98 mg, 0.88 mmol, 1.5 equiv), DIEA (153 mg, 1.18 mmol, 2.0 equiv) and HATU (337 mg, 0.88 mmol, 1.5 equiv). The resulting solution was stirred for 2 h at room temperature. The reaction solution was diluted with 5 mL of CH₃CN and filtered. The filtrate was purified by Prep-HPLC with the following conditions (SHIMADZU (HPLC-01)): Column, Welch Xtimate C18, 21.2*250 mm, 5 um, mobile phase, Water (10 mmol/L NH₄HCO₃) and MeOH:CH₃CN=1:1 (25% Phase B up to 65% in 15 min), Detector, UV, 254 nm. This provided 117.3 mg of N-(2-fluorophenyl)-2-[[2-(pyridin-2-yl)-5H,6H,7H-cyclopenta[d]pyrimidin-4-yl]amino]acetamide as light yellow solid. ¹H NMR (300 MHz, DMSO-d₆) δ 10.03 (br, 1H), 8.63-8.61 (m, 1H), 8.31-8.28 (m, 1H), 7.88-7.75 (m, 2H), 7.50-7.37 (m, 2H), 7.29-7.18 (m, 1H), 7.18-7.08 (m, 2H), 4.28 (d, J=5.4 Hz, 2H), 2.86 (t, J=7.8 Hz, 2H), 2.78 (t, J=7.4 Hz, 2H), 2.14-2.04 (m, 2H). LCMS (ES)[M+1]⁺ m/z: 364.1.

Example 1.37

Synthesis of 2-{[2-(pyridin-2-yl)-5H,6H,7H-cyclopenta[d]pyrimidin-4-yl]amino}-N-(quinolin-7-yl)acetamide (Compound 7)

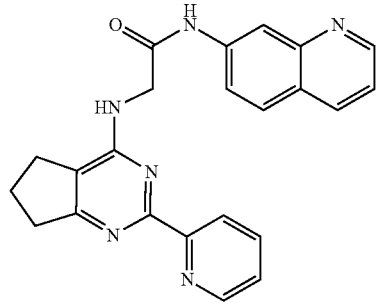 [SMILES: O=C(CNc1nc(-c2ccccn2)nc2c1CCC2)Nc1ccc2cccnc2c1]

Scheme 14 depicts a synthetic route for preparing an exemplary compound.

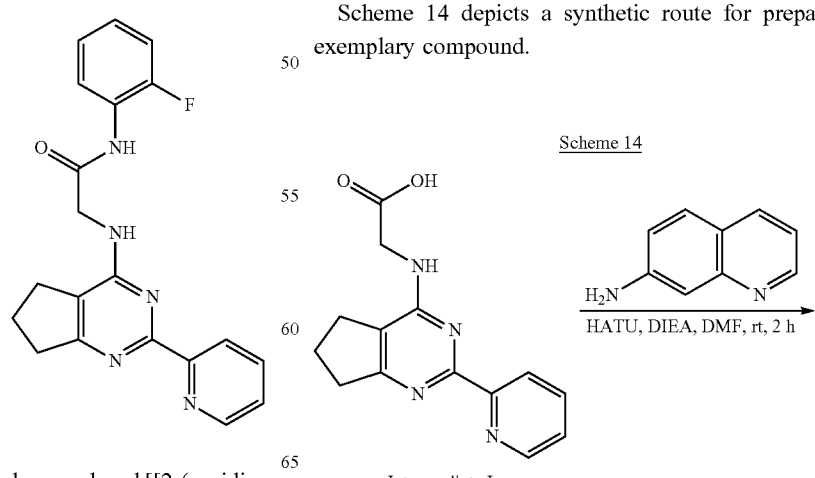

-continued

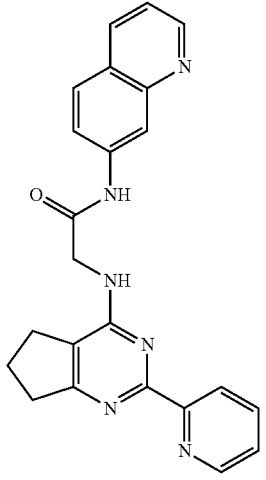

Into a 50-mL round-bottom flask at 0° C. was placed [[2-(pyridin-2-yl)-5H,6H,7H-cyclopenta[d]pyrimidin-4-yl] amino]acetic acid (160 mg, 0.59 mmol, 1.0 equiv), DMF (3.0 mL), quinolin-7-amine (128 mg, 0.88 mmol, 1.5 equiv), DIEA (153 mg, 1.18 mmol, 2.0 equiv) and HATU (337 mg, 0.88 mmol, 1.5 equiv). After addition, the mixture was stirred for 2 h at room temperature. The reaction solution was diluted with 5 mL of CH$_3$CN and filtered. The filtrate was purified by Prep-HPLC with the following conditions: Column, Welch Xtimate C18, 21.2*250 mm, 5 um, mobile phase, Water (10 mmol/L NH$_4$HCO$_3$) and MeOH: CH$_3$CN=1:1 (25% Phase B up to 70% in 15 min); Detector, UV 254 nm. This provided 118.0 mg (50%) of 2-((2-(pyridin-2-yl)-6,7-dihydro-5H-cyclopenta[d]pyrimidin-4-yl)amino)-N-(quinolin-7-yl)acetamide was obtained as grey solid. $^1$H NMR (300 MHz, DMSO-d$_6$) δ 10.64 (s, 1H), 8.82 (dd, J=4.2, 1.8 Hz, 1H), 8.64-8.61 (m, 1H), 8.43 (d, J=1.8 Hz, 1H), 8.29-8.25 (m, 2H), 7.92 (d, J=8.7 Hz, 1H), 7.81-7.69 (m, 2H), 7.54-7.50 (m, 1H), 7.43-7.36 (m, 2H), 4.30 (d, J=5.7 Hz, 2H), 2.90-2.76 (m, 4H), 2.15-2.05 (m, 2H). LCMS: (ES, m/z): [M+1]$^+$ m/z: 397.1.

Example 1.38

Synthesis of N-tert-butyl-2-{[2-(pyrimidin-4-yl)-5H, 6H,7H-cyclopenta[d]pyrimidin-4-yl] amino}acetamide (Compound 8)

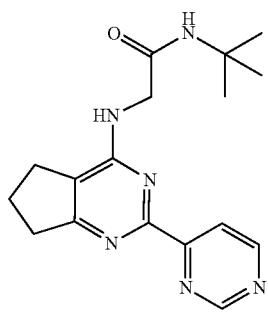 [SMILES: CC(C)(C)NC(=O)CNc1nc(-c2ccncn2)nc2c1CCC2]

Scheme 15 depicts a synthetic route for preparing an exemplary compound.

Scheme 15

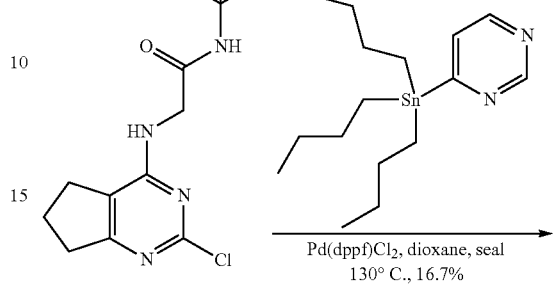

Pd(dppf)Cl$_2$, dioxane, seal
130° C., 16.7%

Into a 10-mL sealed tube purged and maintained in an inert atmosphere of nitrogen, was placed N-tert-butyl-2-([2-chloro-5H,6H,7H-cyclopenta[d]pyrimidin-4-yl]amino)acetamide (0.30 g, 1.06 mmol, 1.00 equiv), dioxane (10 mL), 4-(tributylstannyl)pyrimidine (0.47 g, 1.27 mmol, 1.20 equiv), and Pd(dppf)Cl$_2$·CH$_2$Cl$_2$ (0.17 g, 0.20 equiv). The resulting solution was stirred overnight at 130° C. The resulting mixture was concentrated. The residue was applied onto a silica gel column with MeOH/EA (1:9). The crude product was purified by Prep-HPLC with the following conditions: Column, welch Xtimate C18, 21.2*250 mm, 5 um; mobile phase; phase A water (10 mmol/L NH$_4$HCO$_3$), phase B CH$_3$CN/MeOH (1:1) (15% B up to 60% in 15 min); Detector, 220 nm. This resulted in 57.7 mg (16.7%) of N-tert-butyl-2-[[2-(pyrimidin-4-yl)-5H,6H,7H-cyclopenta[d]pyrimidin-4-yl]amino]acetamide as a white solid. $^1$H-NMR: (300 MHz, DMSO-d6, ppm): δ 9.28 (s, 1H), 8.93 (d, J=5.1 Hz), 8.32 (d, J=5.1 Hz, 1H), 7.67 (s, 1H), 7.29 (t, J=6.0 Hz, 1H), 3.97 (d, J=5.7 Hz, 2H), 2.87 (q, J=7.8 Hz, 2H), 2.76 (q, J=7.2 Hz, 2H), 2.13-2.06 (m, 2H), 1.24 (s, 9H). LCMS: (ES, m/z): [M+H]$^+$: 327.2.

Example 1.39

Synthesis of N-tert-butyl-2-{[2-(pyridin-2-yl)-5H,6H,7H-cyclopenta[b]pyridin-4-yl]amino}acetamide (Compound 9)

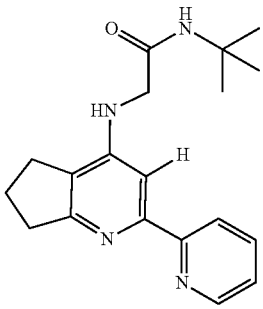 [SMILES: CC(C)(C)NC(=O)CNc1cc(-c2ccccn2)nc2c1CCC2]

Scheme 16 depicts a synthetic route for preparing an exemplary compound.

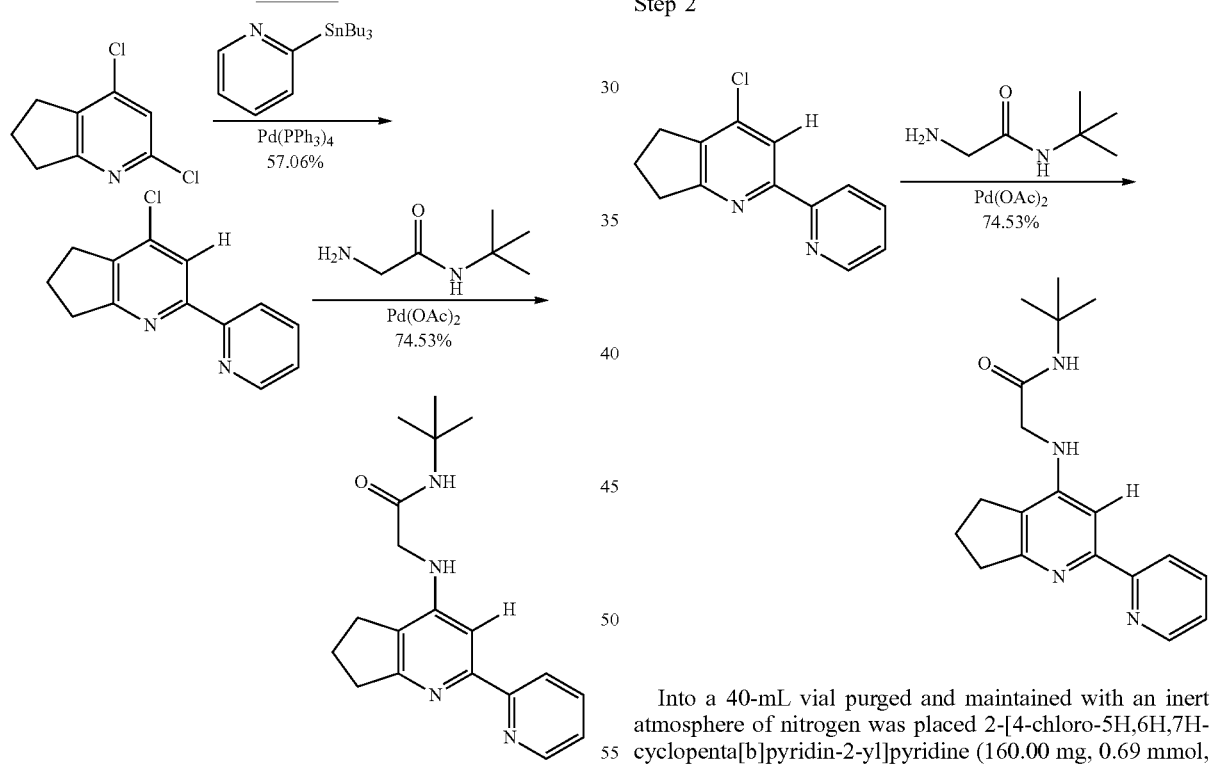

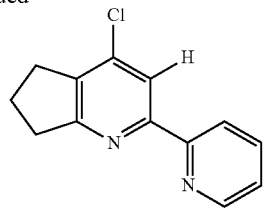

Into a 40-mL vial purged and maintained with an inert atmosphere of nitrogen was placed 2,4-dichloro-5H,6H,7H-cyclopenta[b]pyridine (500.00 mg, 2.66 mmol, 1.00 equiv), 2-(tributylstannyl)pyridine (1272.53 mg, 3.46 mmol, 1.30 equiv), dioxane (10.00 mL), and Pd(PPh3)4 (307.25 mg, 0.26 mmol, 0.10 equiv). The resulting solution was stirred overnight at 110° C. The reaction mixture was cooled to room temperature. The resulting mixture was concentrated. The crude product (1 g) was purified by Prep-HPLC with the following conditions: Column, XBridge Prep C18 OBD Column, 19 cm, 150 mm, 5 um; mobile phase, Water (0.1% NH3·H2O) and CAN (50% Phase B up to 80% in 11 min); Detector, 254. This resulted in 350 mg (57.06%) of 2-[4-chloro-5H,6H,7H-cyclopenta[b]pyridin-2-yl]pyridine as white solid. LCMS (ES) [M+H]+ m/z: 231.

Step 2

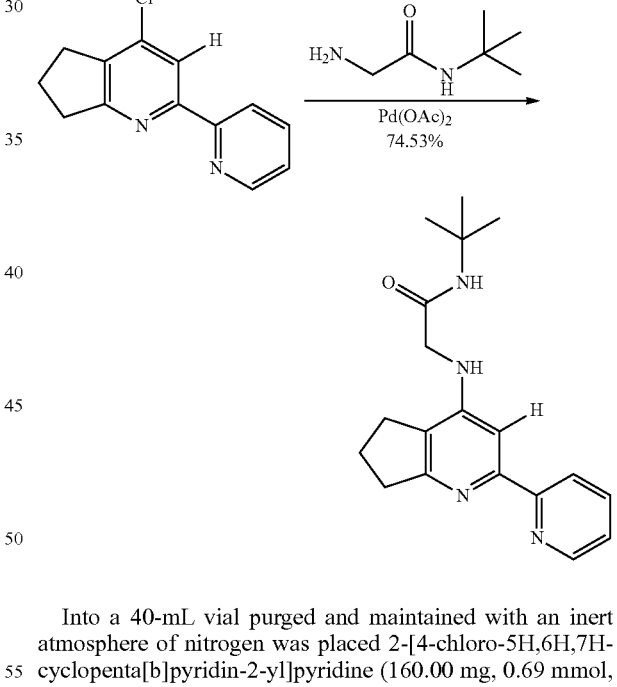

Into a 40-mL vial purged and maintained with an inert atmosphere of nitrogen was placed 2-[4-chloro-5H,6H,7H-cyclopenta[b]pyridin-2-yl]pyridine (160.00 mg, 0.69 mmol, 1.00 equiv), 2-amino-N-tert-butylacetamide (99.32 mg, 0.76 mmol, 1.10 equiv), Pd(OAc)2 (15.57 mg, 0.069 mmol, 0.10 equiv), Cs2CO3 (451.94 mg, 1.38 mmol, 2.00 equiv), BINAP (86.37 mg, 0.14 mmol, 0.20 equiv), dioxane (10.00 mL). The resulting solution was stirred for overnight at 100° C. The reaction mixture was cooled to room temperature. The resulting mixture was concentrated. The crude product (300 mg) was purified by Prep-HPLC with the following conditions: Column, XBridge Prep C18 OBD Column, 19 cm, 150 mm, 5 um; mobile phase, Water (0.1% NH4HCO3) and CAN (20% Phase B up to 50% in 11 min); Detector, 254 nm. This resulted in 167.7 mg (74.53%) of N-tert-butyl-2-

Step 1

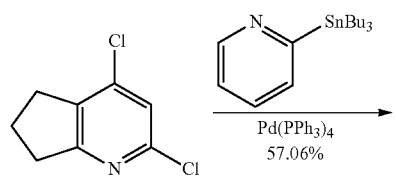

[[2-(pyridin-2-yl)-5H,6H,7H-cyclopenta[b]pyridin-4-yl]amino]acetamide as off-white solid. 1HNMR (300 MHz, DMSO-d6) δ 8.59 (ddd, J=4.8, 1.9, 0.9 Hz, 1H), 8.30 (dt, J=8.0, 1.1 Hz, 1H), 7.84 (td, J=7.7, 1.8 Hz, 1H), 7.66 (s, 1H), 7.41-7.30 (m, 2H), 6.00 (t, J=5.7 Hz, 1H), 3.77 (d, J=5.7 Hz, 2H), 2.88 (t, J=7.6 Hz, 2H), 2.75 (t, J=7.3 Hz, 2H), 2.12-2.02 (m, 2H), 1.27 (s, 9H). LCMS (ES, m/z): [M+H]+: 325.1.

Example 1.40

Synthesis of N-tert-butyl-2-{[2-(pyridin-2-yl)-5,6,7,8-tetrahydroquinazolin-4-yl]amino}acetamide (Compound 10)

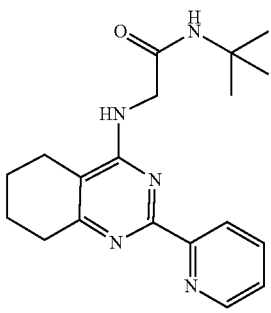 [SMILES: CC(C)(C)NC(=O)CNc1nc(-c2ccccn2)nc2c1CCCC2]

Scheme 17 depicts a synthetic route for preparing an exemplary compound.

Scheme 17

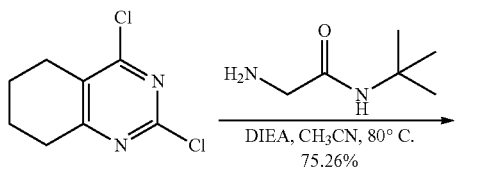

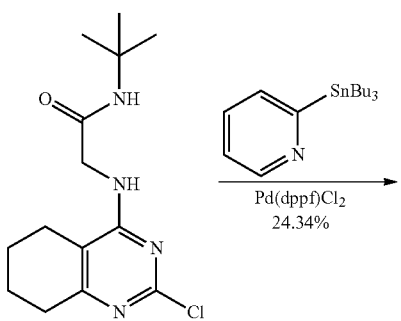

Step 1

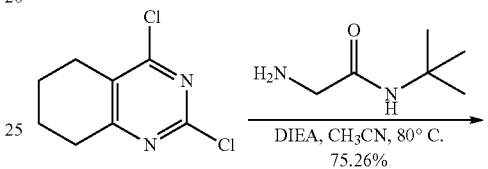

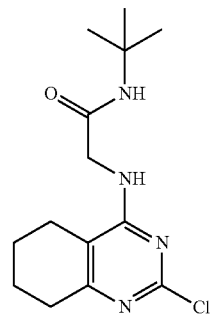

Into a 40-mL vial, was placed 2,4-dichloro-5,6,7,8-tetrahydroquinazoline (1.00 g, 4.92 mmol, 1.00 equiv), 2-amino-N-tert-butylacetamide (0.71 g, 5.47 mmol, 1.11 equiv), DIEA (1.27 g, 9.85 mmol, 2.00 equiv), and CH₃CN (10.00 mL). The resulting solution was stirred overnight at 80° C. The reaction mixture was cooled to room temperature. The crude product (2 g) was purified by Prep-HPLC with the following conditions: Column, XBridge Prep C18 OBD Column, 19 cm, 150 mm, 5 um; mobile phase, Water (0.1% NH3·H2O) and CAN (20% Phase B up to 60% in 11 min); Detector, 254. This resulted in 1.1 g (75.26%) of N-tert-butyl-2-[(2-chloro-5,6,7,8-tetrahydroquinazolin-4-yl)amino]acetamide as a white solid. LCMS (ES) [M+H]+ m/z: 297.

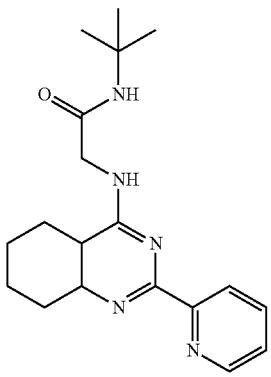

Step 2

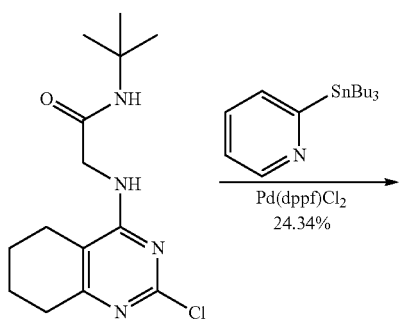

Into a 40-mL vial purged and maintained with an inert atmosphere of nitrogen, was placed N-tert-butyl-2-[(2-chloro-5,6,7,8-tetrahydroquinazolin-4-yl)amino]acetamide (500.00 mg, 1.68 mmol, 1.00 equiv), 2-(tributylstannyl)pyridine (806.26 mg, 2.19 mmol, 1.30 equiv), dioxane (10.00 mL) and Pd(dppf)Cl$_2$ (123.26 mg, 0.17 mmol, 0.10 equiv). The resulting solution was stirred for overnight at 110° C. The reaction mixture was cooled to room temperature. The resulting mixture was concentrated. The crude product (800 mg) was purified by Prep-HPLC with the following conditions: Column, XBridge Prep C18 OBD Column, 19 cm, 150 mm, 5 um; mobile phase, Water (0.1% NH$_4$HCO$_3$) and CAN (20% Phase B up to 50% in 11 min); Detector, 254 nm. This resulted in 139.2 mg (24.34%) of N-tert-butyl-2-[[2-(pyridin-2-yl)-5,6,7,8-tetrahydroquinazolin-4-yl]amino]acetamide as white solid. $^1$H-NMR (300 MHz, DMSO-d6) δ8.65 (ddd, J=4.8, 1.8, 0.9 Hz, 1H), 8.33 (dt, J=8.0, 1.1 Hz, 1H), 7.87 (td, J=7.7, 1.8 Hz, 1H), 7.71 (s, 1H), 7.45-7.40 (m, 1H), 6.88 (t, J=5.6 Hz, 1H), 3.95 (d, J=5.6 Hz, 2H), 2.73-2.63 (m, 2H), 2.46-2.38 (m, 2H), 1.81-1.78 (m, 4H), 1.24 (s, 9H). LCMS (ES, m/z): [M+H]$^+$: 340.1

Example 1.41

Synthesis of N-(4-methoxyphenyl)-1-[2-(pyridin-2-yl)-5H,6H,7H-cyclopenta[d]pyrimidin-4-yl]piperidin-3-amine (Compound 11)

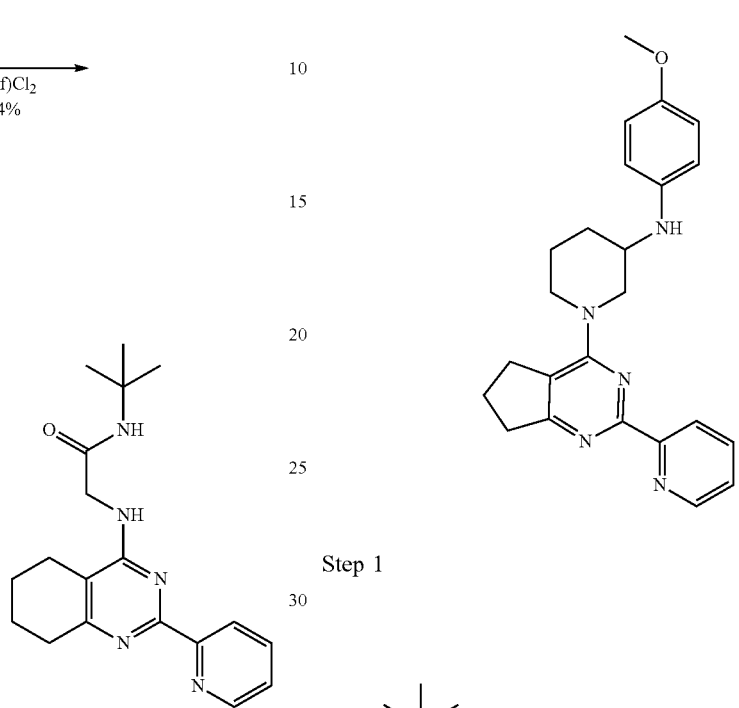

Step 1

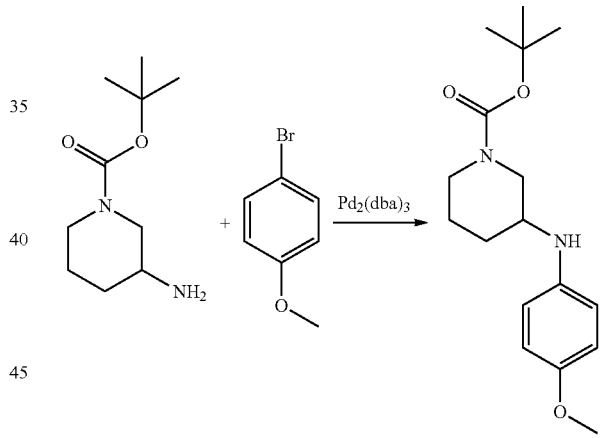

1-Bromo-4-methoxybenzene (0.25 g; 1.34 mmol; 1 eq.) and tert-butyl 3-amino-1-piperidinecarboxylate (0.32 g; 1.6 mmol; 1.2 eq.) were dissolved in 1,4-dioxane (5 ml) and tert-butanol (2.5 ml). The solution was purged with Ar gas, and sodium tert-butoxide (0.26 g; 2.67 mmol; 2 eq.), 2-[2-(dicyclohexylphosphanyl)phenyl]-N,N-dimethylaniline (52.6 mg; 0.13 mmol; 0.1 eq.) and tris(dibenzylideneacetone)dipalladium(0) (61.2 mg; 0.07 mmol; 0.05 eq.) were added. The sealed reaction vessel was stirred in a heat bath at 100° C. for 6 h. After cooling and evaporation, the residue was purified by silica gel chromatography (ethyl acetate/hexanes gradient) to give tert-butyl 3-[(4-methoxyphenyl)amino]piperidine-1-carboxylate (178 mg, 43%) as a solid. LCMS (ES+): (M+H)$^+$=307.0. $^1$H NMR (400 MHz, Chloroform-d) δ 6.82-6.76 (m, 2H), 6.76-6.60 (m, 2H), 4.09-3.93 (m, 1H), 3.76-3.67 (m, 4H), 3.33-3.22 (m, 1H), 3.09-2.95 (m, 1H), 2.95-2.75 (m, 1H), 2.07-1.95 (m, 1H), 1.76-1.68 (m, 1H), 1.45 (s, 9H).

Step 2

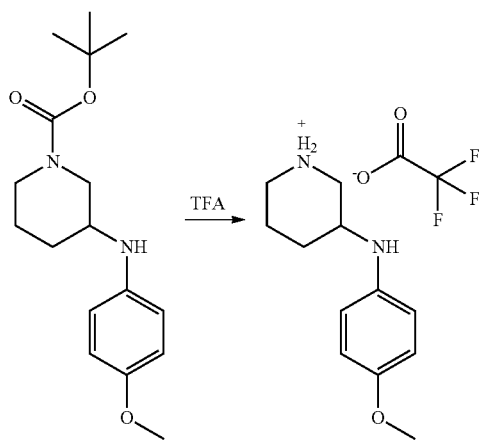

Tert-butyl 3-[(4-methoxyphenyl)amino]piperidine-1-carboxylate (178 mg; 0.58 mmol; 1 eq.) was dissolved in DCM (5 ml) and cooled in an ice bath. Trifluoroacetic acid (2.55 mL) was added slowly and the reaction was stirred at 20° C. for 1 h. The reaction was evaporated, and the residue was co-evaporated with toluene to give 3-[(4-methoxyphenyl)amino]piperidin-1-ium trifluoroacetate, which was used directly in the next step.

Step 3

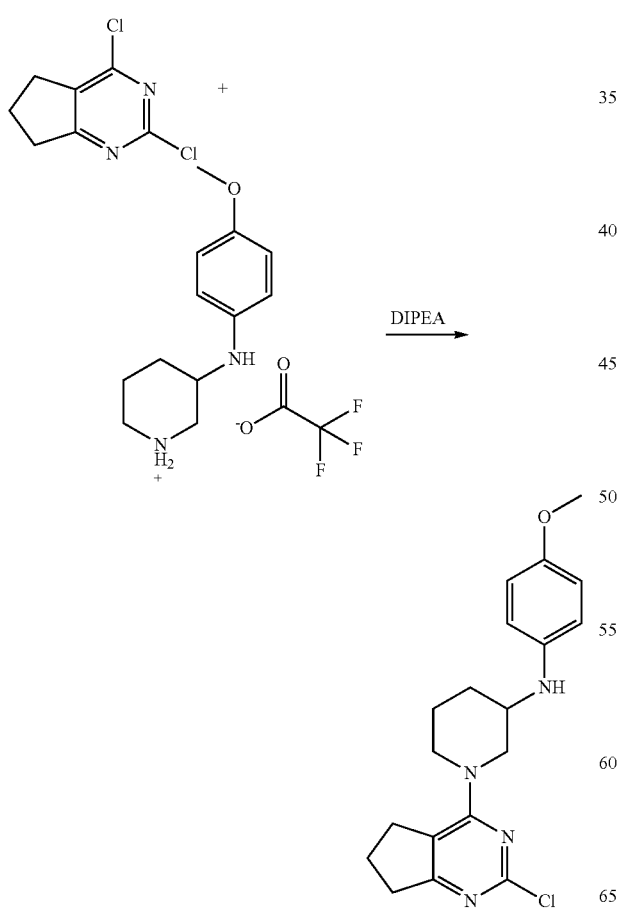

In a round bottom flask was added 2,4-dichloro-6,7-dihydro-5H-cyclopenta[d]pyrimidine (100.00 mg; 0.53 mmol; 1.00 eq.), acetonitrile (3.5 ml), 3-[(4-methoxyphenyl)amino]piperidin-1-ium trifluoroacetate (186.38 mg; 0.58 mmol; 1.10 eq.) Hunig's base (0.38 mL; 2.17 mmol; 4.10 eq.). The mixture was stirred at ~70° C. After cooling and evaporation, the residue was purified by silica gel chromatography (0 to 50% ethyl acetate/hexanes gradient) to give 1-{2-chloro-5H,6H,7H-cyclopenta[d]pyrimidin-4-yl}-N-(4-methoxyphenyl)piperidin-3-amine (144 mg, 76%). LCMS (ES+): (M+H)$^+$=402.4.

Step 4

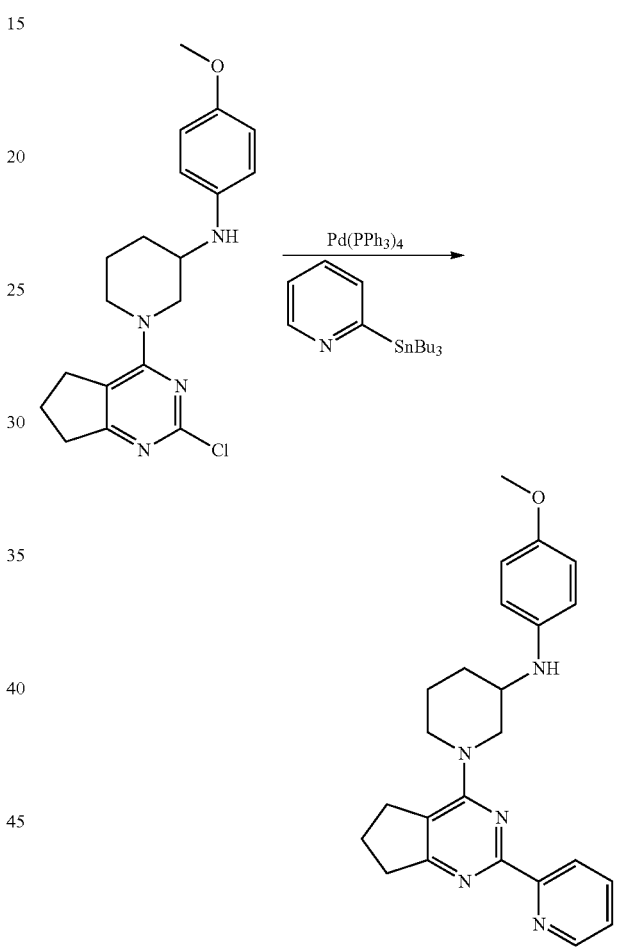

In a round bottom flask was added 1-{2-chloro-5H,6H,7H-cyclopenta[d]pyrimidin-4-yl}-N-(4-methoxyphenyl)piperidin-3-amine (144.00 mg; 0.40 mmol; 1.00 eq.) in 1,4-dioxane (dry, ~3 ml). The solution was purged with Ar. To the mixture was added 2-(tributylstannyl)pyridine (0.26 mL; 0.80 mmol; 2.00 eq.) and tetrakis(triphenylphosphane) palladium (46.37 mg; 0.04 mmol; 0.10 eq.) After being stirred in a heat block at 105° C. for 15 h, the mixture was concentrated and the residue was purified by preparative HPLC to give N-(4-methoxyphenyl)-1-[2-(pyridin-2-yl)-5H,6H,7H-cyclopenta[d]pyrimidin-4-yl]piperidin-3-amine (52 mg) as a yellow solid. LCMS (ES+): (M+H)$^+$=402.4. $^1$H NMR (400 MHz, Chloroform-d) δ 9.01-8.83 (m, 1H), 8.38 (d, J=8.6 Hz, 1H), 8.00-7.86 (m, 1H), 7.55-7.43 (m, 1H), 7.08-6.87 (m, 2H), 6.87-6.69 (m, 2H), 4.79 (s, 1H), 4.16-

4.00 (m, 1H), 3.74 (s, 3H), 3.62-3.44 (m, 3H), 3.17-2.87 (m, 4H), 2.17-1.99 (m, 3H), 1.99-1.75 (m, 2H), 1.70-1.52 (m, 1H).

Example 1.42

Synthesis of N-tert-butyl-2-{[2-(5-methoxypyrazin-2-yl)-5H,6H,7H-cyclopenta[d]pyrimidin-4-yl](methyl)amino}acetamide (Compound 12)

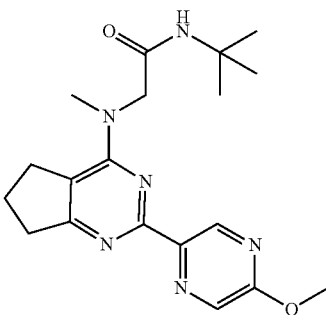 [SMILES: COc1cnc(-c2nc3c(c(N(C)CC(=O)NC(C)(C)C)n2)CCC3)cn1]

Scheme 18 depicts a synthetic route for preparing an exemplary compound.

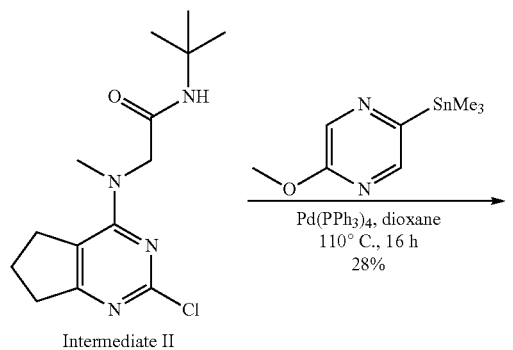

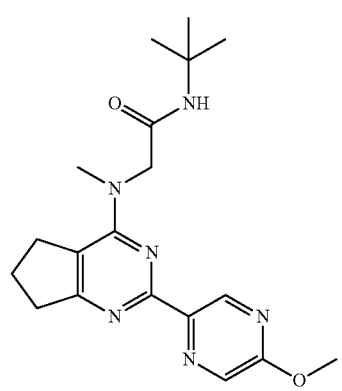

Into a 40-mL vial purged and maintained in an inert atmosphere of nitrogen was placed a mixture of N-(tert-butyl)-2-((2-chloro-6,7-dihydro-5H-cyclopenta[d]pyrimidin-4-yl)(methyl)amino)acetamide (200 mg, 0.674 mmol, 1.00 equiv), dioxane (10.0 ml), 2-methoxy-5-(trimethylstannyl)pyrazine (275 mg, 1.01 mmol, 1.50 equiv), and Pd(PPh₃)₄ (155 mg, 0.135 mmol, 0.20 equiv). The resulting solution was stirred for 16 hours at 110° C. The resulting mixture was concentrated. The crude reaction mixture was filtered and subjected to reverse phase preparative MPLC (Prep-C18, 20-45 mM, 120 g, Tianjin Bonna-Agela Technologies; gradient elution of 5% MeCN in water to 35% MeCN in water over a 15 min period, where both solvents contain 0.1% formic acid). This resulted in 71.7 mg (28%) of N-(tert-butyl)-2-((2-(5-methoxypyrazin-2-yl)-6,7-dihydro-5H-cyclopenta[d]pyrimidin-4-yl)(methyl)amino)acetamide as an off-white solid. ¹H NMR (300 MHz, DMSO-d₆, ppm): δ 9.12 (d, J=1.4 Hz, 1H), 8.36 (d, J=1.3 Hz, 1H), 7.68 (s, 1H), 4.13 (s, 2H), 3.98 (s, 3H), 3.27 (s, 3H), 3.14 (t, J=7.3 Hz, 2H), 2.81 (t, J=7.8 Hz, 2H), 2.00-1.95 (m, 2H), 1.25-1.22 (m, 9H). LCMS (ES) [M+1]⁺ m/z: 371.2.

Example 1.43A

Synthesis of N-tert-butyl-2-({2-[4-(2-hydroxy-2-methylpropoxy)pyridin-2-yl]-5H,6H,7H-cyclopenta[d]pyrimidin-4-yl}(methyl)amino)acetamide (Compound 174)

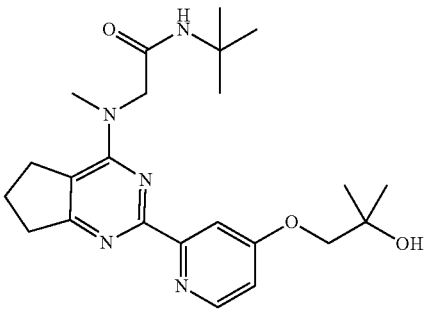 [SMILES: CN(CC(=O)NC(C)(C)C)c1nc(-c2cc(OCC(C)(C)O)ccn2)nc2c1CCC2]

Scheme 19A depicts a synthetic route for preparing an exemplary compound.

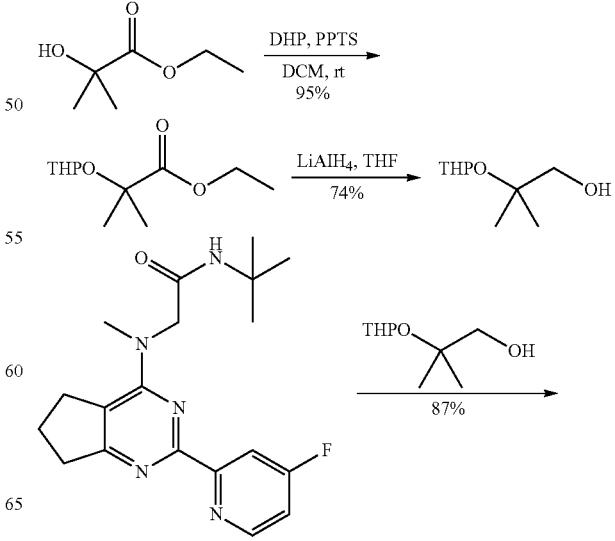

425

-continued

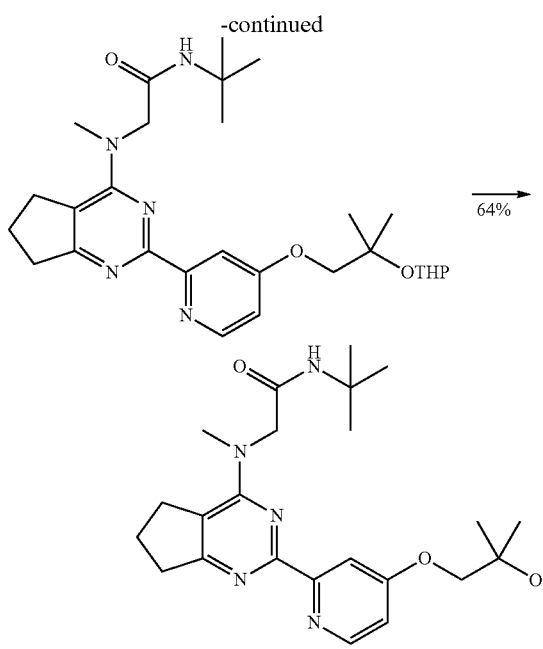

Step 1

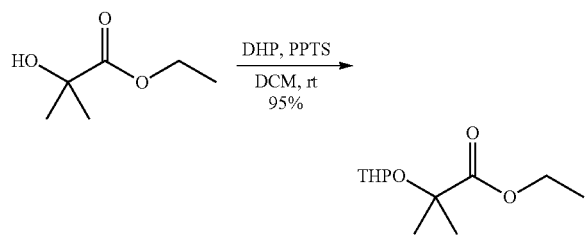

Into a 250-mL 3-necked round-bottom flask was placed ethyl 2-hydroxy-2-methylpropanoate (10.0 g, 75.8 mmol, 1.00 equiv), 3,4-dihydro-2H-pyran (9.54 g, 113.7 mmol, 1.50 equiv) in dichloromethane (100 mL), and pyridine 4-methylbenzenesulfonate (0.95 g, 3.79 mmol, 0.05 equiv). The resulting solution was stirred for 3 h at room temperature. The reaction mixture was poured into water and extracted with Et₂O. The organic layers were dried over Na₂SO₄, filtered, and the filtrate was concentrated in vacuo. The crude residue was purified by silica gel chromatography (hexane/ethyl acetate, 100:0 to 5:1) to give 15.6 g (95%) of ethyl 2-methyl-2-((tetrahydro-2H-pyran-2-yl)oxy)propanoate as a colorless oil.

Step 2

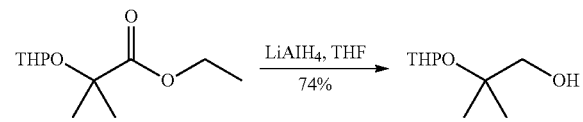

Into a 500-mL 3-round-bottom flask was placed ethyl 2-methyl-2-((tetrahydro-2H-pyran-2-yl)oxy)propanoate (15.0 g, 69.4 mmol, 1.00 equiv) in THF (150.00 mL). Lithium aluminium hydride (69.4 mL, 1 mol/L, 69.4 mmol, 1.00 equiv) was added portion-wise at 0° C. The reaction mixture was stirred for 5 h, followed by the slow addition of Na₂SO₄.10H₂O (22.3 g, 69.4 mmol, 1.00 equiv). After 30 minutes of stirring at 0° C., the mixture was filtered and the filtrate was concentrated in vacuo to give 2-methyl-2-((tetrahydro-2H-pyran-2-yl)oxy)propan-1-ol (8.9 g, 74%) as a colorless oil which was used in the next step without further purification.

Step 3

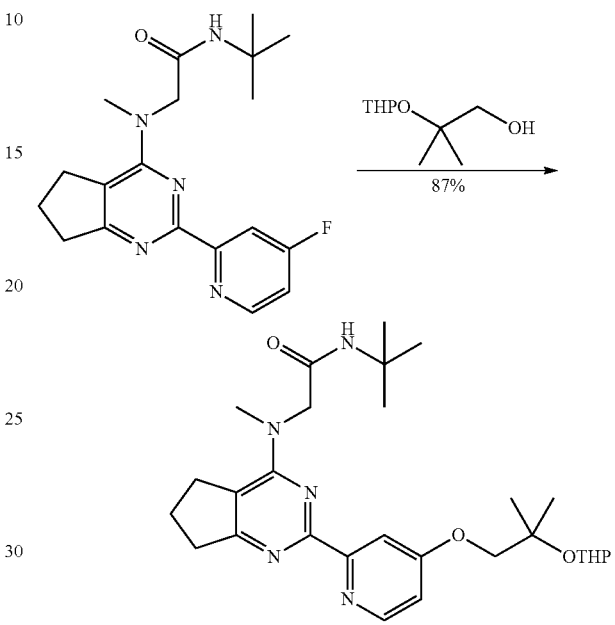

Into a 250 mL 3-neck flask was placed 2-methyl-2-((tetrahydro-2H-pyran-2-yl)oxy)propan-1-ol (3.9 g, 22.4 mmol, 2.0 equiv) and DMF (50 mL), NaH (60% in mineral oil) (896 mg, 22.4 mmol, 2.0 equiv) was added portion-wise at 0-5° C. The mixture was stirred for 1 h at room temperature. After that, N-(tert-butyl)-2-((2-(4-fluoropyridin-2-yl)-6,7-dihydro-5H-cyclopenta[d]pyrimidin-4-yl)(methyl)amino)acetamide (4 g, 11.2 mmol, 1.00 equiv) was added at 0-5° C. The reaction mixture was stirred for 5 h at 50° C. (The reaction was repeated in 2 batches). The reaction mixture was cooled to room temperature, diluted with 150 mL of water, and extracted with 3×100 mL of ethyl acetate. The combined organic phase was washed with 3×150 mL of water and brine 1×100 mL, dried over anhydrous sodium sulfate, and concentrated to afford 10 g crude product (87% yield). This was directly used in the next step without purification. LCMS (ES) [M+1]⁺ m/z: 512.

Step 4

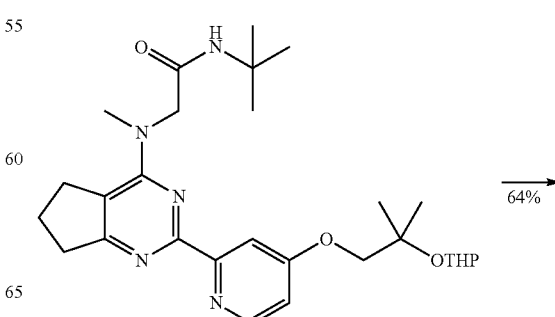

427

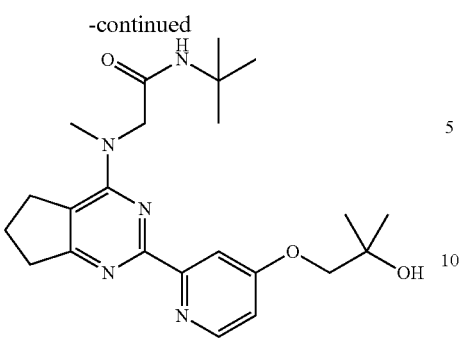

Into a 250 mL 3-neck flask was placed N-(tert-butyl)-2-(methyl(2-(4-(2-methyl-2-((tetrahydro-2H-pyran-2-yl)oxy)propoxy)pyridin-2-yl)-6,7-dihydro-5H-cyclopenta[d]pyrimidin-4-yl)amino)acetamide (crude product from step 3, 10 g, 19.5 mmol, 1.00 equiv) and MeOH (50 mL). HCl (20 mL, 1N) was added in portion wise at 0-5° C. The mixture was stirred for 3 h at room temperature. The reaction mixture was concentrated, and the residue was purified by Prep-HPLC with the following conditions: column, C18-800 g, Mobile phase, $CH_3CN/H_2O$ (0.05% FA), from 10% increased to 70% within 27 min, Flow rate, 180 mL/min, Detector, 254 nm. The pH value of the fraction was adjusted to 7~8 with $K_2CO_3$ solid, and extracted with dichloromethane (3×300 mL). The combined organic phase was dried over anhydrous sodium sulfate, filtered, and the filtrate was concentrated under reduced pressure. The residue was freezing dried, and this resulted in 5.3 g (64%) of N-(tert-butyl)-2-((2-(4-(2-hydroxy-2-methylpropoxy)pyridin-2-yl)-6,7-dihydro-5H-cyclopenta[d]pyrimidin-4-yl)(methyl)amino)acetamide as a white solid. LCMS: (ES, m/z): $[M+H]^+$: 428.3. $^1$H NMR (300 MHz, DMSO-$d_6$): δ 8.47 (d, J=5.6 Hz, 1H), 7.82 (d, J=2.5 Hz, 1H), 7.67 (s, 1H), 7.04 (dd, J=5.7, 2.6 Hz, 1H), 4.69 (s, 1H), 4.14 (s, 2H), 3.86 (s, 2H), 3.26 (s, 3H), 3.15 (t, J=7.4 Hz, 2H), 2.81 (t, J=7.8 Hz, 2H), 2.04-1.94 (m, 2H), 1.25-1.24 (m, 15H).

Example 1.43B (Alternative Method for Preparing Compound 174)

Scheme 19B

428

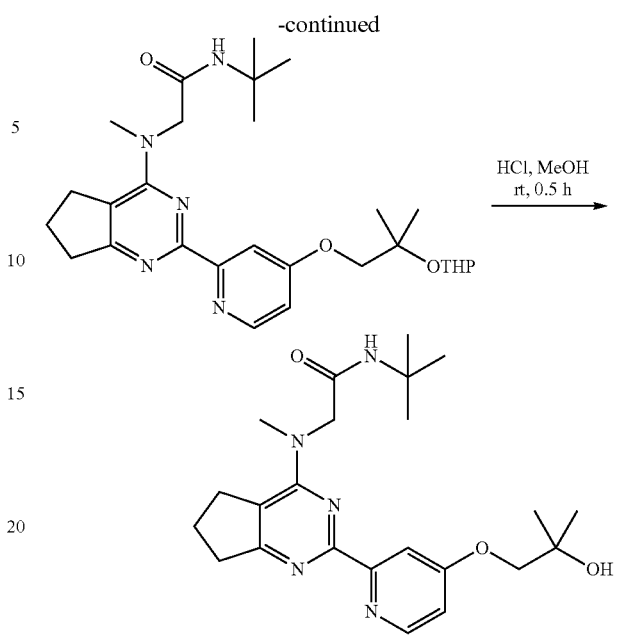

Into a 250 mL three-necked round bottom flask were added N-(tert-butyl)-2-((2-(4-chloropyridin-2-yl)-6,7-dihydro-5H-cyclopenta[d]pyrimidin-4-yl)(methyl)amino)acetamide (7.2 g, 19.3 mmol, 1.00 equiv) and DMSO (80 mL). This was followed by the addition of NaH (60% in mineral oil) (1.5 g, 38.6 mmol, 2.00 equiv) at room temperature. The mixture was stirred for 0.5 h, and 2-methyl-2-((tetrahydro-2H-pyran-2-yl)oxy)propan-1-ol (6.7 g, 38.6 mmol, 2.00 equiv) was added to the above mixture and stirred for an additional 3 h at 40° C. The reaction mixture was cooled to room temperature, quenched with $H_2O$ (100 mL), and extracted with ethyl acetate (100 mL*2). The combined organic phases were washed with brine (100 mL*2), dried over anhydrous sodium sulfate, and filtered. The filtrate was concentrated under reduced pressure and the residue was purified by Prep-HPLC with the following conditions: C18-500 g, $CH_3CN/H_2O$ ($NH_4HCO_3$ 0.1%), from 15% to 70% in 30 min, Flow rate, 150 mL/min, Detector, UV 254 nm. This resulted in 7.0 g (71%) N-(tert-butyl)-2-(methyl(2-(4-(2-methyl-2-((tetrahydro-2H-pyran-2-yl)oxy)propoxy)pyridin-2-yl)-6,7-dihydro-5H-cyclopenta[d]pyrimidin-4-yl)amino)acetamide as a brown solid. LCMS (ES, m/z): $[M+H]^+$: 512.

Into a 250 mL three-necked round bottom flask were added N-(tert-butyl)-2-(methyl(2-(4-(2-methyl-2-((tetrahydro-2H-pyran-2-yl)oxy)propoxy)pyridin-2-yl)-6,7-dihydro-5H-cyclopenta[d]pyrimidin-4-yl)amino)acetamide (7.0 g, 13.7 mmol, 1.00 equiv) and methanol (70 mL), HCl (c) (5 mL). The mixture was stirred for 0.5 h, diluted with $H_2O$ (200 mL), and the pH value was adjusted to 9 with $K_2CO_3$ solid. The mixture was extracted with dichloromethane (300 mL*2), the combined organic phase was dried over anhydrous sodium sulfate, filtered, and the filtrate was concentrated under reduced pressure. The residue 5.8 g (purity: 96.7%) was triturated in $CH_3CN$ (120 mL), filtered, and 5.5 g (98.8% purity) was obtained. The crude product was dissolved in $CH_3CN$ (110 mL) at 60° and then cooled to 20° C. in 20 min. The solid was collected by filtration and dried under an infrared lamp for 1 h. This resulted in 3.1 g (99.94% purity, 56.3% yield) N-(tert-butyl)-2-((2-(4-(2-hydroxy-2-methylpropoxy)pyridin-2-yl)-6,7-dihydro-5H-cyclopenta[d]pyrimidin-4-yl)(methyl)amino)acetamide as a white solid. LCMS: (ES, m/z): [M+H]⁺: 428. ¹H-NMR (300 MHz, DMSO-d₆, ppm): δ 8.48 (d, J=5.4 Hz, 1H), 7.83 (d, J=2.7 Hz, 1H), 7.67 (s, 1H), 7.05 (dd, J=5.7, 2.7 Hz, 1H), 4.69 (s, 1H), 4.14 (s, 2H), 3.86 (s, 2H), 3.26 (s, 3H), 3.15 (t, J=7.2 Hz, 2H), 2.82 (t, J=7.8 Hz, 2H), 2.04-1.94 (m, 2H), 1.25 (s, 9H), 1.24 (s, 6H).

Example 1.44

Synthesis of 2-[4-(azepan-1-yl)-5H,6H,7H-cyclopenta[d]pyrimidin-2-yl]-N,N-dimethylpyridin-4-amine (Compound 13)

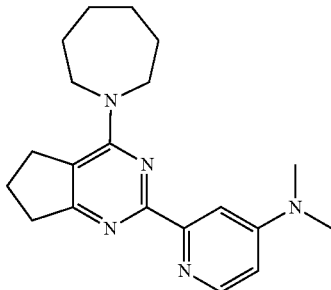

Compound 13 was synthesized similar to Compound 92, by replacing (2-tributylstannyl)pyridine with N,N-dimethyl-2-(tributylstannyl)pyridin-4-amine. ¹H NMR (400 MHz, DMSO-d₆) δ 8.19 (d, J=7.2 Hz, 1H), 7.75 (d, J=3.1 Hz, 1H), 7.05 (dd, J=7.3, 2.9 Hz, 1H), 3.86 (d, J=3.4 Hz, 1H), 3.86-3.72 (m, 3H), 3.26 (s, 6H), 3.12 (hept, J=7.3, 6.7 Hz, 2H), 3.00-2.80 (m, J=8.0 Hz, 2H), 2.04 (h, J=8.2, 7.8 Hz, 2H), 1.73 (dq, J=18.9, 7.4, 6.4 Hz, 4H), 1.48 (dq, J=7.4, 4.6, 3.7 Hz, 4H). LCMS (ES+): (M+H)⁺=338.1.

Example 1.45

Synthesis of 1-[2-(4-methylpyridin-2-yl)-5H,6H,7H-cyclopenta[d]pyrimidin-4-yl]azepane (Compound 14)

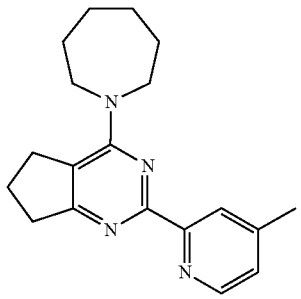 [SMILES: Cc1ccnc(-c2nc3c(c(N4CCCCCC4)n2)CCC3)c1]

Compound 14 was synthesized similar to Compound 92 replacing (2-tributylstannyl)pyridine with 4-methyl-2-(tributylstannyl)pyridine. ¹H NMR (400 MHz, DMSO-d₆) δ 8.69 (d, J=5.0 Hz, 1H), 8.27 (d, J=1.7 Hz, 1H), 7.64-7.58 (m, 1H), 3.97 (s, 4H), 3.22-3.10 (m, 2H), 3.03 (t, J=7.9 Hz, 2H), 2.51 (s, 3H), 2.09 (p, J=7.7 Hz, 2H), 1.82 (s, 4H), 1.54 (s, 4H). LCMS (ES+): (M+H)⁺=309.2.

Example 1.46

Synthesis of N-(2-methoxyphenyl)-2-{methyl[2-(pyridin-2-yl)-5H,6H,7H-cyclopenta[d]pyrimidin-4-yl]amino}acetamide (Compound 15)

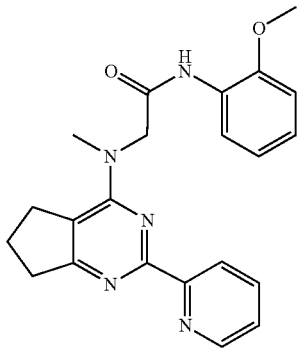 [SMILES: COc1ccccc1NC(=O)CN(C)c1nc(-c2ccccn2)nc2c1CCC2]

Scheme 20 depicts a synthetic route for preparing an exemplary compound.

Scheme 20

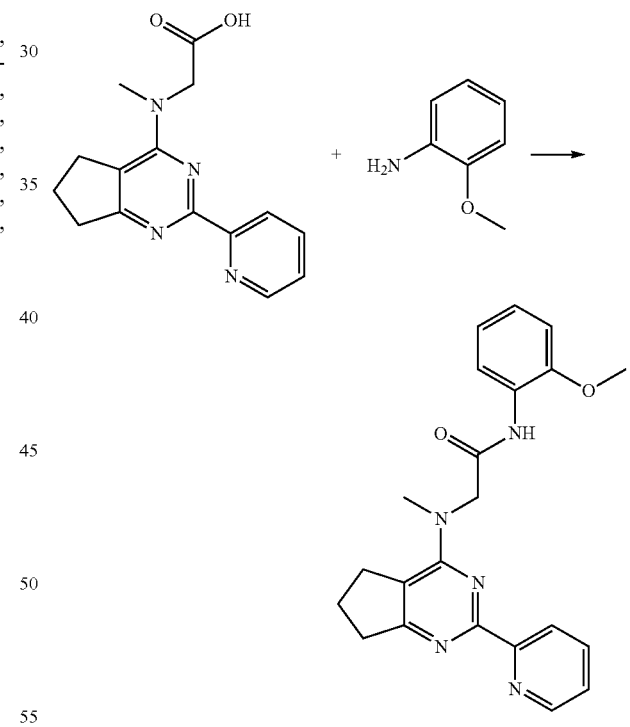

To a solution of 2-{methyl[2-(pyridin-2-yl)-5H,6H,7H-cyclopenta[d]pyrimidin-4-yl]amino}acetic acid (65.00 mg; 0.23 mmol; 1.00 eq.) in DMF (1.5 mL) was added 2-methoxyaniline (33.79 mg; 0.27 mmol; 1.20 eq.) followed by Hunig's base (0.08 mL; 0.46 mmol; 2.00 eq.), and HATU (86.93 mg; 0.23 mmol; 1.00 eq.). After being stirred for 1 h at room temperature, it was diluted with water and acetonitrile and the mixture was subjected to purification by preparative HPLC to give N-(2-methoxyphenyl)-2-{methyl[2-(pyridin-2-yl)-5H,6H,7H-cyclopenta[d]pyrimidin-4-yl]amino}acetamide (9 mg). ¹H NMR (400 MHz, DMSO-d₆)

δ 9.39 (s, 1H), 8.66-8.59 (m, 1H), 8.31-8.24 (m, 1H), 7.92 (d, J=8.0 Hz, 1H), 7.78 (td, J=7.7, 1.8 Hz, 1H), 7.40 (ddd, J=7.5, 4.7, 1.2 Hz, 1H), 7.07-6.95 (m, 2H), 6.85 (td, J=7.5, 7.0, 1.7 Hz, 1H), 4.49 (s, 2H), 3.68 (s, 3H), 3.31 (s, 3H), 3.18 (t, J=7.3 Hz, 2H), 2.83 (t, J=7.8 Hz, 2H), 2.00 (dq, J=15.2, 8.3, 7.8 Hz, 2H). LCMS (ES+): (M+H)+=390.3.

Example 1.47

Synthesis of N-tert-butyl-2-{methyl[2-(pyridin-2-yl)-5H,6H,7H-cyclopenta[b]pyridin-4-yl]amino}acetamide (Compound 16)

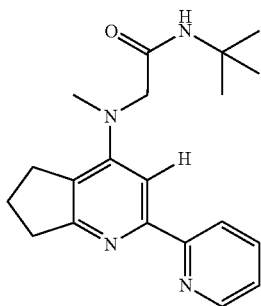 [SMILES: CN(CC(=O)NC(C)(C)C)c1cc(-c2ccccn2)nc2c1CCC2]

Scheme 21 depicts a synthetic route for preparing an exemplary compound.

Scheme 21

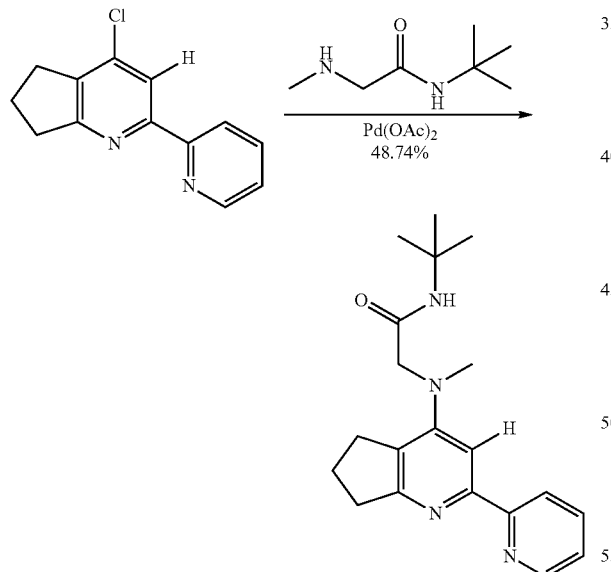

Into a 40-mL vial purged and maintained in an inert atmosphere of nitrogen, was placed 2-[4-chloro-5H,6H,7H-cyclopenta[b]pyridin-2-yl]pyridine (100.00 mg, 0.43 mmol, 1.00 equiv), N-tert-butyl-2-(methylamino)acetamide (81.27 mg, 0.56 mmol, 1.30 equiv), Pd(OAc)$_2$ (9.73 mg, 0.04 mmol, 0.10 equiv), BINAP (53.98 mg, 0.08 mmol, 0.20 equiv), Cs$_2$CO$_3$ (282.46 mg, 0.86 mmol, 2.00 equiv) and dioxane (6.00 mL). The resulting solution was stirred overnight at 100° C. The reaction mixture was cooled to room temperature. The resulting mixture was concentrated. The crude product (200 mg) was purified by Prep-HPLC with the following conditions: Column, XBridge Prep C18 OBD Column, 19 cm, 150 mm, 5 um; mobile phase, Water (0.1% NH$_4$HCO$_3$) and AcCN (30% Phase B up to 60% in 11 min); Detector, 254 nm. This resulted in 71.5 mg (48.74%) of N-tert-butyl-2-[methyl[2-(pyridin-2-yl)-5H,6H,7H-cyclopenta[b]pyridin-4-yl]amino]acetamide as off-white solid. $^1$H-NMR (300 MHz, DMSO-d6) δ 8.62 (dd, J=4.8, 1.7 Hz, 2H), 8.31 (dt, J=8.0, 1.2 Hz, 1H), 7.86 (td, J=7.7, 1.9 Hz, 1H), 7.57 (s, 1H), 7.55 (s, 1H), 7.37 (ddd, J=7.5, 4.7, 1.2 Hz, 1H), 3.94 (s, 2H), 3.07 (s, 3H), 3.03 (t, J=7.2 Hz, 2H), 2.86 (t, J=7.7 Hz, 2H), 2.05-1.95 (m, 2H), 1.28 (s, 9H). LCMS (ES, m/z): [M+H]+: 339.2.

Example 1.48

Synthesis of N-tert-butyl-2-[methyl({2-[4-(oxetan-3-yloxy)pyridin-2-yl]-5H,6H,7H-cyclopenta[d]pyrimidin-4-yl})amino]acetamide (Compound 245)

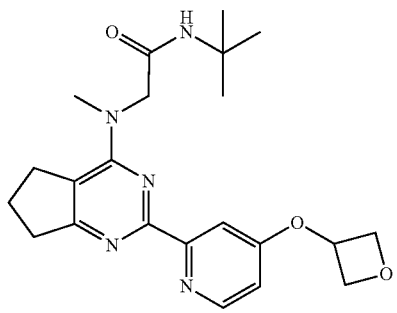 [SMILES: CN(CC(=O)NC(C)(C)C)c1nc(-c2cc(OC3COC3)ccn2)nc2c1CCC2]

Scheme 22 depicts a synthetic route for preparing an exemplary compound.

Scheme 22

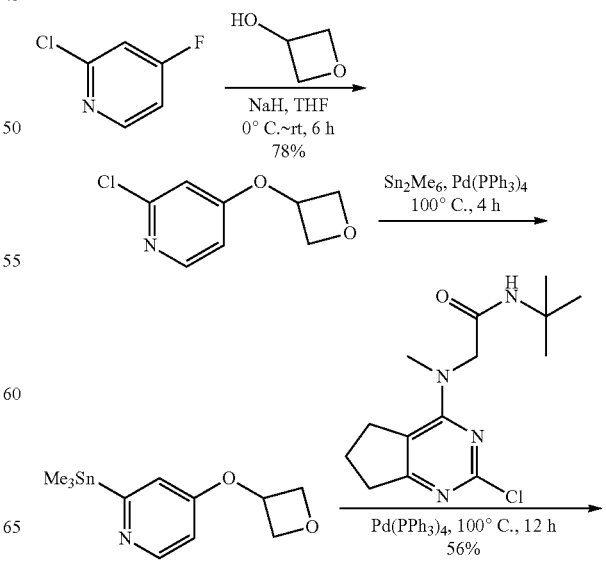

Step 1

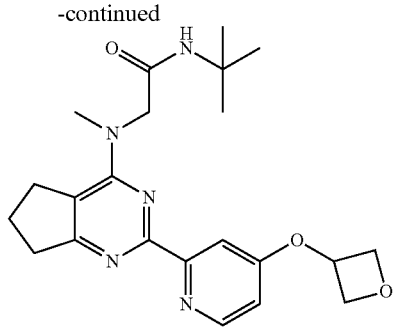

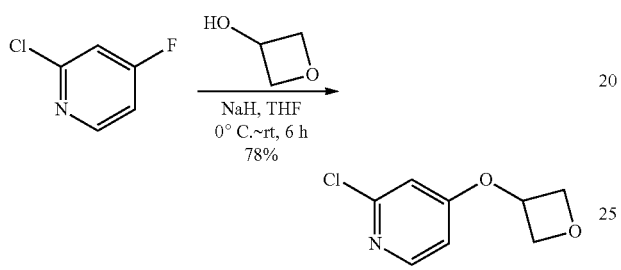

Into a 500-mL 3-necked round-bottom flask purged and maintained with an inert atmosphere of nitrogen was placed oxetan-3-ol (8.45 g, 114.04 mmol, 1.50 equiv) and THF (100.00 mL). This was followed by the addition of NaH (60% in mineral oil) (6.84 g, 171.06 mmol, 1.50 equiv) in several batches at 0° C. The mixture was stirred at 0° C. for 30 min. 2-chloro-4-fluoropyridine (10.00 g, 76.02 mmol, 1.00 equiv) was added dropwise with stirring at 0° C. After addition, the resulting solution was stirred for 6 h at room temperature. The reaction mixture was cooled to 0° C. again, quenched carefully by the addition of 30 mL of water, extracted with 3×100 mL of ethyl acetate. The combined organic phase was dried over anhydrous sodium sulfate, filtered and the filtrate was concentrated under reduced pressure. The residue was purified by silica gel column with ethyl acetate/petroleum ether (1:2). This resulted in 11 g (78%) of 2-chloro-4-(oxetan-3-yloxy)pyridine as a white solid. LCMS (ES) [M+1]+ m/z: 186.

Step 2

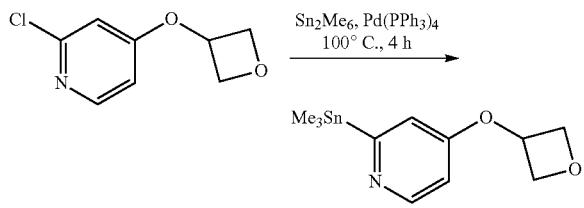

Into a 100-mL 3-necked round-bottom flask purged and maintained with an inert atmosphere of nitrogen was placed 2-chloro-4-(oxetan-3-yloxy)pyridine (2.00 g, 10.81 mmol, 1.00 equiv), toluene (60.00 mL), Sn$_2$Me$_6$ (3.71 g, 11.31 mmol, 1.05 equiv), Pd(PPh$_3$)$_4$ (1.25 g, 1.08 mmol, 0.10 equiv). The reaction mixture was stirred for 4 h at 100° C. in oil bath. The reaction mixture was cooled to room temperature and used to the next step without purification. This reaction was repeated three times. LCMS (ES) [M+1]+ m/z: 316.

Step 3

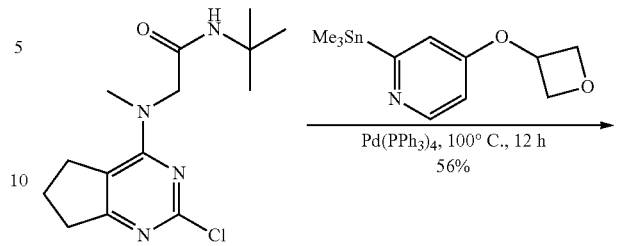

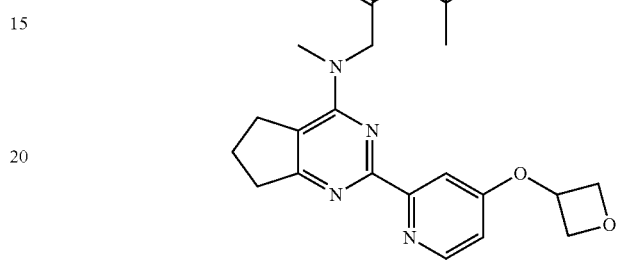

Into the reaction solution of step 3 purged and maintained with an inert atmosphere of nitrogen, N-tert-butyl-2-([2-chloro-5H,6H,7H-cyclopenta[d]pyrimidin-4-yl](methyl) amino)acetamide (2.23 g, 7.54 mmol, 0.70 equiv) and Pd(PPh$_3$)$_4$ (1.24 g, 1.07 mmol, 0.10 equiv) were added. The resulting solution was stirred for 12 h at 100° C. in oil bath. This parallel reaction was repeated three times. The reaction mixture was cooled and concentrated to remove the solvent. The residue was purified by silica gel column with ethyl acetate/petroleum ether (from 10% to 100%). This resulted in 7.2 g crude compound, which was further purified by Prep-HPLC with conditions: column, C18-800 g, Mobile phase, CH$_3$CN/H$_2$O (0.05% FA), from 10% increased to 70% within 27 min, Flow rate, 180 mL/min, Detector, 254 nm. The pH value of the fraction was adjusted to 7~8 with K$_2$CO$_3$ solid, extracted with dichloromethane (3×300 mL). The combined organic phase was dried over anhydrous sodium sulfate and filtered. The filtrate was concentrated under reduced pressure. The residue was triturated in dichloromethane/hexane (1:10, 30 mL), filtered and the solid was freezing dried to give 5.2 g (56%) of N-tert-butyl-2-[methyl ([2-[4-(oxetan-3-yloxy)pyridin-2-yl]-5H,6H,7H-cyclopenta[d]pyrimidin-4-yl])amino]acetamide as a white solid. LCMS: (ES, m/z): [M+H]+: 412. $^1$H-NMR: (300 MHz, DMSO-d$_6$, ppm): δ 8.49 (d, J=5.4 Hz, 1H), 7.77 (d, J=2.4 Hz, 1H), 7.70 (s, 1H), 6.87 (dd, J=5.7, 2.4 Hz, 1H), 5.52-5.45 (m, 1H), 4.99 (t, J=6.6 Hz, 2H), 4.58 (dd, J=7.2, 4.8 Hz, 2H), 4.13 (s, 2H), 3.29 (s, 3H), 3.15 (t, J=7.2 Hz, 2H), 2.82 (t, J=7.8 Hz, 2H), 2.05-1.94 (m, 2H), 1.26 (s, 9H).

Example 1.49

Synthesis of N-cyclohexyl-1-{methyl[2-(pyridin-2-yl)-5H,6H,7H-cyclopenta[d]pyrimidin-4-yl]amino}cyclopropane-1-carboxamide (Compound 17)

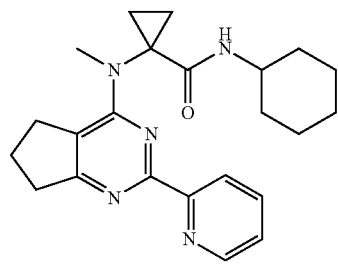 [SMILES: CN(c1nc(-c2ccccn2)nc2c1CCC2)C1(C(=O)NC2CCCCC2)CC1]

Scheme 23 depicts a synthetic route for preparing an exemplary compound.

Scheme 23

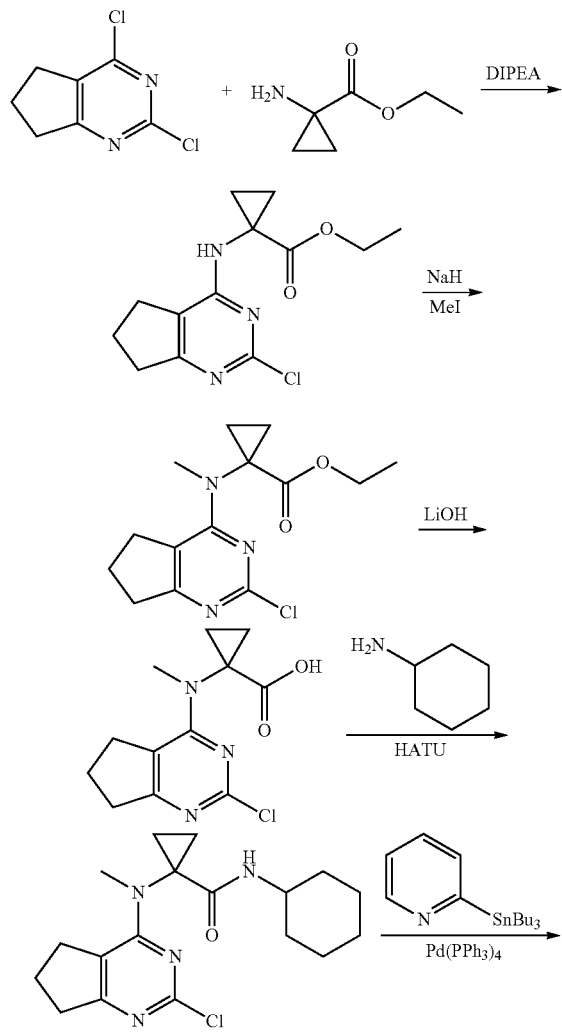

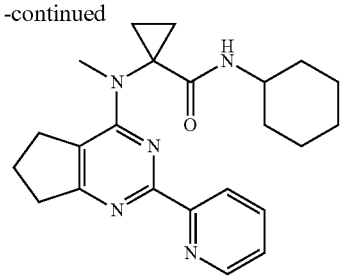

Step 1

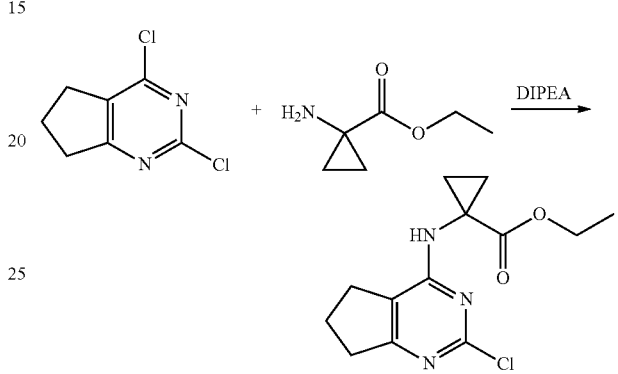

To a solution of 2,4-dichloro-6,7-dihydro-5H-cyclopenta[d]pyrimidine (500.00 mg; 2.64 mmol; 1.00 eq.) in AcCN (5 mL) was added DIPEA (1.15 mL; 6.61 mmol; 2.50 eq.) and ethyl 1-aminocyclopropane-1-carboxylate (409.93 mg; 3.17 mmol; 1.20 eq.). The mixture was heated at 60° C. for 24 h, and 80° C. for an additional 4 days (HPLC showed the conversion to be about 50%). The reaction was stopped and the mixture was concentrated, the resulting crude residue was purified by column chromatography (hexanes/EtOAc=1:1) to give ethyl 1-({2-chloro-5H,6H,7H-cyclopenta[d]pyrimidin-4-yl}amino)cyclopropane-1-carboxylate (135 mg). LCMS (ES⁺): (M+H)⁺=282.0, 284.1.

Step 2

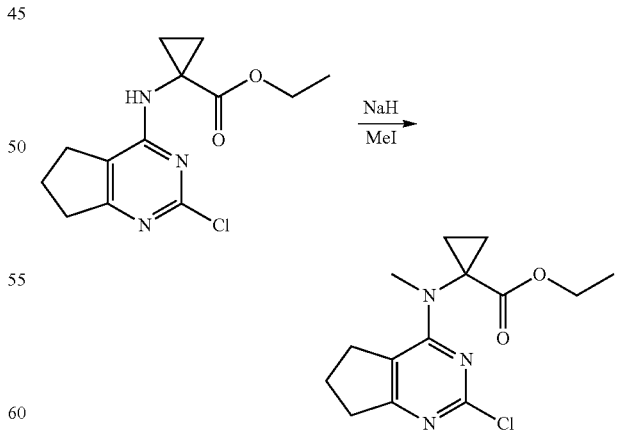

To a solution of ethyl 1-({2-chloro-5H,6H,7H-cyclopenta[d]pyrimidin-4-yl}amino)cyclopropane-1-carboxylate (135.00 mg; 0.48 mmol; 1.00 eq.) in DMF (2 mL) was added sodium hydride (57.49 mg; 1.44 mmol; 3.00 eq.) at 0° C. After being stirred for 10 min, to the mixture was added iodomethane (0.04 mL; 0.72 mmol; 1.50 eq.) and the solution was further stirred at ambient temperature until finished. The mixture was diluted with Sat. NaHCO₃ and EtOAc, the organic layer was separated, and the aqueous layer was further extracted with EtOAc (2×). The combined organic layer was washed with brine, dried, and concentrated to give ethyl 1-({2-chloro-5H,6H,7H-cyclopenta[d]pyrimidin-4-yl}(methyl)amino)cyclopropane-1-carboxylate (66 mg), which was used for the next step without further purification. LCMS (ES⁺): (M+H)⁺=296.1, 298.4.
Step 3

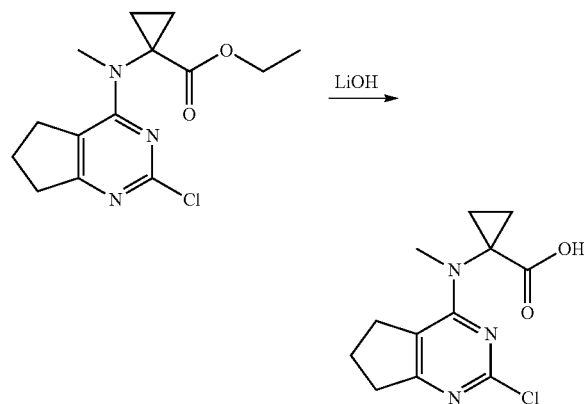

To a solution of ethyl 1-({2-chloro-5H,6H,7H-cyclopenta[d]pyrimidin-4-yl}(methyl)amino)cyclopropane-1-carboxylate (66.00 mg; 0.22 mmol; 1.00 eq.) in THF (1 mL) was added MeOH (0.5 mL) and water (0.5 mL) followed by lithium hydroxide monohydrate (18.73 mg; 0.45 mmol; 2.00 eq.). The mixture was stirred for 2 h at room temperature and was heated to 60° C. and stirred for an additional 2 h. The mixture was cooled and concentrated under vacuum, the residue was acidified with 1N HCl to pH=3, and the aqueous layer was freeze-dried to give 1-({2-chloro-5H,6H,7H-cyclopenta[d]pyrimidin-4-yl}(methyl)amino)cyclopropane-1-carboxylic acid, which was used for the next step without purification. LCMS (ES⁺): (M+H)⁺=268.1, 270.2.
Step 4

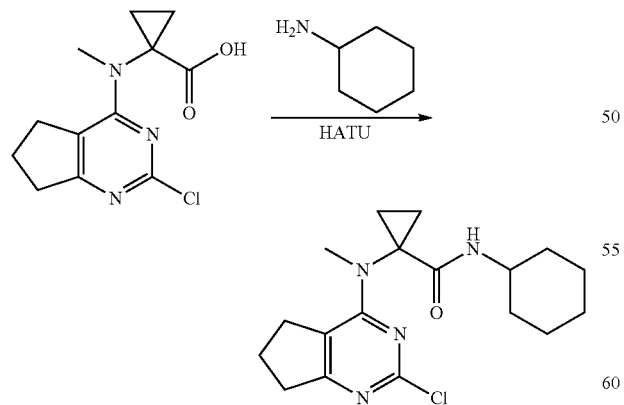

To a solution of 1-({2-chloro-5H,6H,7H-cyclopenta[d]pyrimidin-4-yl}(methyl)amino)cyclopropane-1-carboxylic acid (100.00 mg; 0.37 mmol; 1.00 eq.) and cyclohexanamine (0.05 mL; 0.45 mmol; 1.20 eq.) in DMF (1 mL) was added DIPEA (0.13 mL; 0.75 mmol; 2.00 eq.) and HATU (142.03 mg; 0.37 mmol; 1.00 eq.). After being stirred at room temperature for 1 h, the mixture was diluted with water and the precipitate was collected by filtration, and dried under vacuum to give 1-({2-chloro-5H,6H,7H-cyclopenta[d]pyrimidin-4-yl}(methyl)amino)-N-cyclohexylcyclopropane-1-carboxamide (73 mg). LCMS (ES⁺): (M+H)⁺=268.1, 270.2.
Step 5

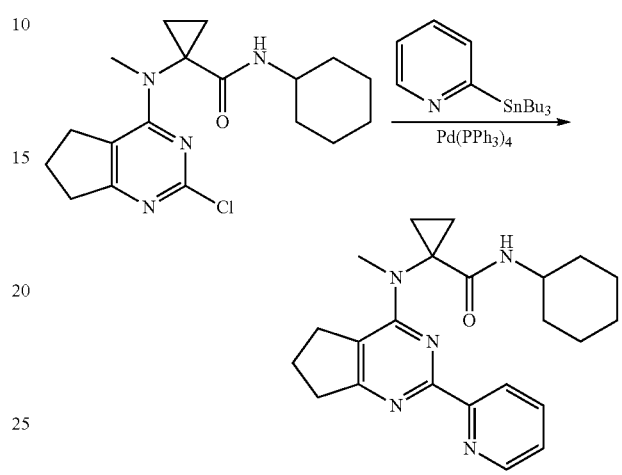

To a solution of 1-({2-chloro-5H,6H,7H-cyclopenta[d]pyrimidin-4-yl}(methyl)amino)-N-cyclohexylcyclopropane-1-carboxamide (70.00 mg; 0.20 mmol; 1.00 eq.) and 2-(tributylstannyl)pyridine (110.80 mg; 0.30 mmol; 1.50 eq.) in Toluene (1 mL) was added tetrakis(triphenylphosphane) palladium (23.19 mg; 0.02 mmol; 0.10 eq.). The solution was degassed with N₂ and heated at 105° C. for 15 h. The mixture was cooled and concentrated, and the residue was subjected to purification by preparative HPLC to give N-cyclohexyl-1-{methyl[2-(pyridin-2-yl)-5H,6H,7H-cyclopenta[d]pyrimidin-4-yl]amino}cyclopropane-1-carboxamide (23 mg). ¹H NMR (400 MHz, DMSO-d₆) δ 8.69-8.62 (m, 1H), 8.27 (d, J=7.9 Hz, 1H), 7.88 (td, J=7.7, 1.8 Hz, 2H), 7.58 (ddd, J=18.1, 10.7, 6.9 Hz, 1H), 7.42 (ddd, J=7.5, 4.7, 1.2 Hz, 1H), 3.62 (s, 1H), 3.13 (s, 3H), 2.93-2.81 (m, 1H), 2.76 (s, 2H), 2.02 (s, 1H), 1.84 (s, 1H), 1.64 (m, 4H), 1.56 (t, J=14.5 Hz, 2H), 1.33 (dd, J=24.0, 10.8 Hz, 2H), 1.19 (m, 4H), 1.02 (m, 2H). LCMS (ES⁺). (M+H)⁺=392.2.

Example 1.50

Synthesis of N-tert-butyl-2-methyl-2-{methyl[2-(pyridin-2-yl)-5H,6H,7H-cyclopenta[d]pyrimidin-4-yl]amino}propanamide (Compound 19)

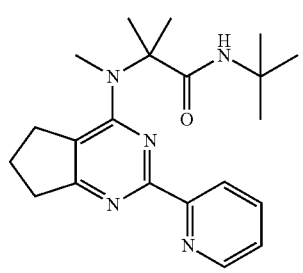 [SMILES: CN(c1nc(-c2ccccn2)nc2c1CCC2)C(C)(C)C(=O)NC(C)(C)C]

Scheme 24 depicts a synthetic route for preparing an exemplary compound.

Scheme 24

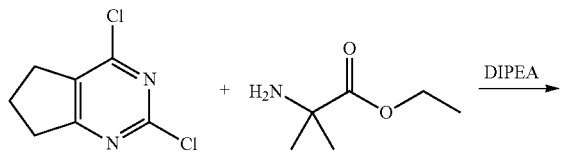

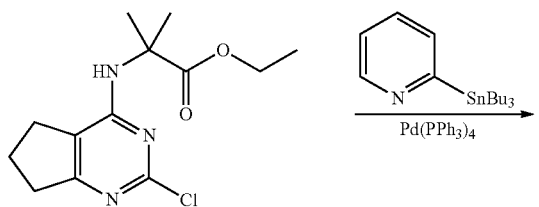

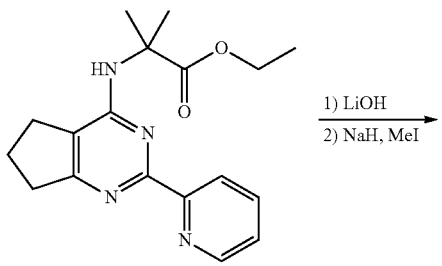

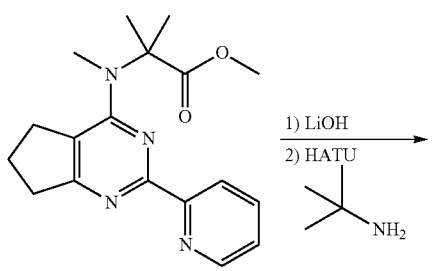

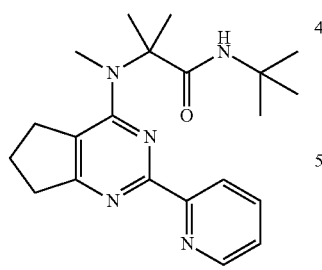

Step 1

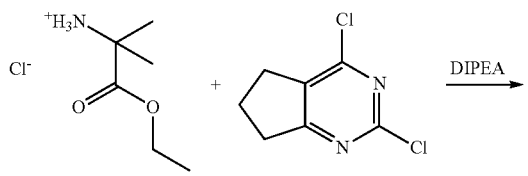

-continued

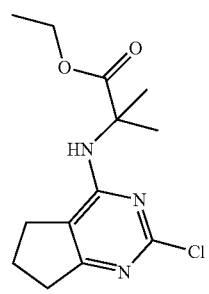

In a vial was added 2,4-dichloro-6,7-dihydro-5H-cyclopenta[d]pyrimidine (150.00 mg; 0.79 mmol; 1.00 eq.), acetonitrile (3 ml), 1-ethoxy-2-methyl-1-oxopropan-2-aminium chloride (159.62 mg; 0.95 mmol; 1.20 eq.), and Hunig's base (0.58 mL; 3.33 mmol; 4.20 eq.). After being stirred in a heat block at 60° C. for 15 h, the mixture was evaporated and the residue was subjected to column chromatography eluting with (0 to 50% EtOAc in Hexanes) to give ethyl 2-({2-chloro-5H,6H,7H-cyclopenta[d]pyrimidin-4-yl}amino)-2-methylpropanoate (88 mg). LCMS (ES+): $(M+H)^+=283.9$.

Step 2

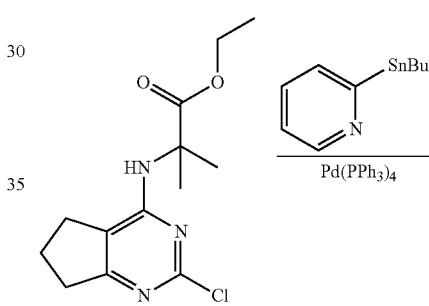

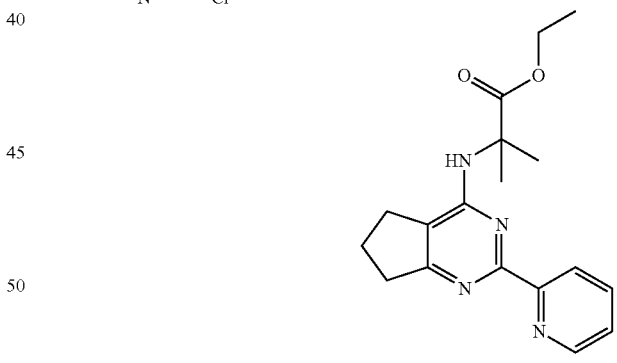

In an round bottom flask was added ethyl 2-({2-chloro-5H,6H,7H-cyclopenta[d]pyrimidin-4-yl}amino)-2-methylpropanoate (88.00 mg; 0.31 mmol; 1.00 eq.) in 1,4-dioxane (dry, ~2 ml). The mixture was purged with Ar. To the mixture was added 2-(tributylstannyl)pyridine (0.20 mL; 0.62 mmol; 2.00 eq.) and tetrakis(triphenylphosphane) palladium (35.84 mg; 0.03 mmol; 0.10 eq.) After being stirred in a heat block at 108° C. for 15 h, the mixture was cooled and concentrated, and the residue was purified by column chromatography (0-5% MeOH/DCM) to give Ethyl 2-methyl-2-{[2-(pyridin-2-yl)-5H,6H,7H-cyclopenta[d]pyrimidin-4-yl]amino}propanoate. LCMS (ES+): $(M+H)^+=327.0$.

Step 3

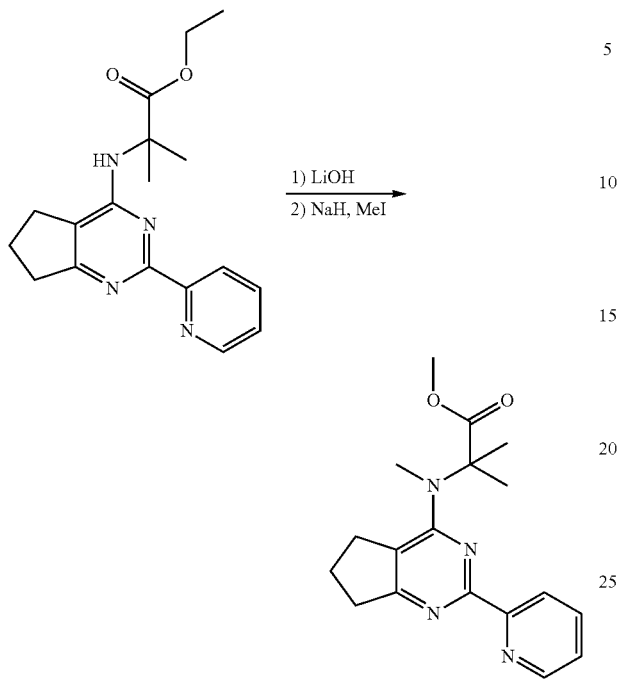

Ethyl 2-methyl-2-{[2-(pyridin-2-yl)-5H,6H,7H-cyclopenta[d]pyrimidin-4-yl]amino}propanoate (67 mg; 0.21 mmol; 1 eq.) was dissolved in tetrahydrofuran (2 ml) and methanol (0.5 ml). Lithium hydroxide (anhydrous, 25 mg; 1.03 mmol; 5 eq.) was dissolved in water (~0.8 ml) was added dropwise and stirred at 25° C. After 4.5 h, the reaction was acidified carefully with 6 M HCl to pH<3 and evaporated to dryness. The residue of 2-methyl-2-{[2-(pyridin-2-yl)-5H,6H,7H-cyclopenta[d]pyrimidin-4-yl]amino}propanoic acid hydrochloride was co-evaporated with toluene and dried under a high vacuum. This material was dissolved in N, N-dimethylformamide (3 ml) and cooled in an ice bath. Iodomethane (39 µL; 0.62 mmol; 3 eq.) and potassium carbonate (142 mg; 1.03 mmol; 5 eq.) were added and the mixture was stirred at 60° C. After 7 h, additional portions of iodomethane and potassium carbonate were added several times to drive the reaction to product. The reaction was taken up in ethyl acetate (50 ml) and water (25 ml), the phases were separated, and the aqueous phase was extracted with ethyl acetate (50 ml). The combined organics were washed with water (10 ml) and sodium chloride solution (10 ml). The combined aqueous phases were extracted with 1:3 isopropanol chloroform (6×20 ml), combined with the organics, and dried over sodium sulfate. The residue from concentration was purified by reverse phase chromatography (Waters XSelect CSH C18 column, 0-80% acetonitrile/0.1% aqueous formic acid gradient) to give methyl 2-methyl-2-{methyl[2-(pyridin-2-yl)-5H,6H,7H-cyclopenta[d]pyrimidin-4-yl]amino}propanoate (10 mg, 15%) as a yellow solid. LCMS (ES+): (M+H)$^+$=327.0.

Step 4

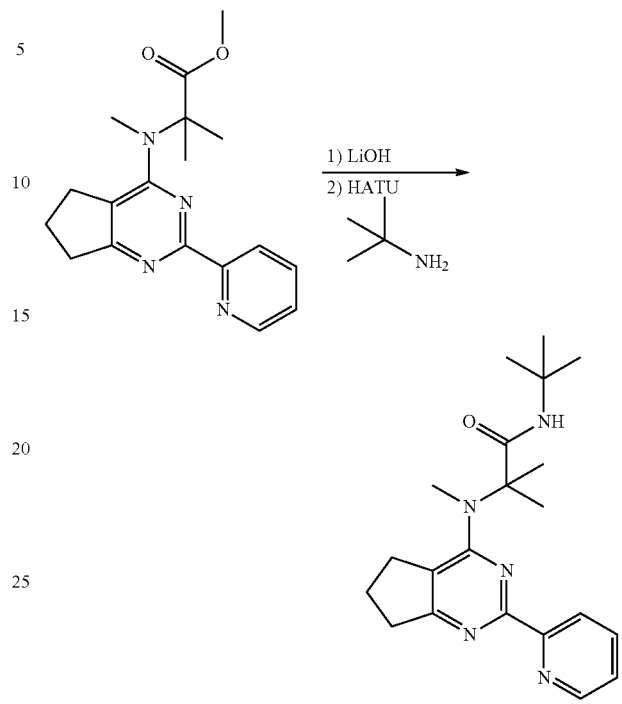

Methyl 2-methyl-2-{methyl[2-(pyridin-2-yl)-5H,6H,7H-cyclopenta[d]pyrimidin-4-yl]amino}propanoate (10 mg; 30.64 µmol; 1 eq.) was dissolved in tetrahydrofuran (0.5 ml) and methanol (0.2 ml). Lithium hydroxide (anhydrous, 3.67 mg; 0.15 mmol; 5 eq.) dissolved in water (~0.2 ml) was added dropwise and the mixture was stirred for 2 h at 25° C. The reaction was then acidified carefully with 6 M HCl to pH<3 and evaporated to dryness. The residue was co-evaporated with toluene and dried under high vacuum. The residue of 2-{4-[(1-carboxy-1-methylethyl)(methyl)amino]-5H,6H,7H-cyclopenta[d]pyrimidin-2-yl}pyridin-1-ium chloride (10.7 mg; 0.03 mmol; 1 eq.) was dissolved in N,N-dimethylformamide (1.5 ml). N, N-diisopropylethylamine (19 µL; 0.11 mmol; 3.5 eq.) and 1-[bis(dimethylamino)methylene]-1H-1,2,3-triazolo[4,5-b]pyridinium 3-oxid hexafluorophosphate (HATU, 23 mg; 0.06 mmol; 2 eq.) were added, followed by tert-butylamine (6 µL; 0.05 mmol; 1.5 eq.) After 15 h, additional portions of tert-butylamine, HATU and N, N-diisopropylethylamine were added to drive the reaction to completion. The reaction was partitioned into water (5 ml), ethyl acetate (50 ml) and sodium bicarbonate solution (10 ml). The phases were separated and the aqueous phase was extracted with ethyl acetate (50 ml) and 1:3 isopropanol:chloroform (50 ml). The combined organic phases were dried over sodium sulfate, evaporated, and purified by reverse phase chromatography (Waters XSelect CSH C18 column, 0-90% acetonitrile/0.1% aqueous formic acid gradient) to give N-tert-butyl-2-methyl-2-{methyl[2-(pyridin-2-yl)-5H,6H,7H-cyclopenta[d]pyrimidin-4-yl]amino}propenamide (6 mg, 50%) as a brown solid. LCMS (ES+): (M+H)$^+$=368.1. $^1$H NMR (400 MHz, Chloroform-d) δ 8.77-8.67 (m, 1H), 8.52-8.43 (m, 2H), 8.11-8.00 (m, 1H), 7.74-7.65 (m, 1H), 6.79-6.71 (m, 1H), 4.73 (s, 3H), 3.00-2.91 (m, 4H), 2.21-2.12 (m, 2H), 1.62 (s, 6H), 1.18 (s, 9H).

Example 1.51

Synthesis of N-tert-butyl-2-{phenyl[2-(pyridin-2-yl)-5H,6H,7H-cyclopenta[d]pyrimidin-4-yl]amino}propanamide (Compound 20)

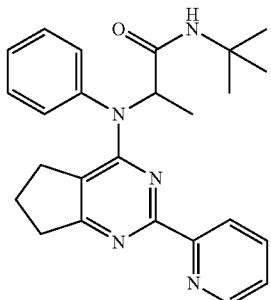

Scheme 25 depicts a synthetic route for preparing an exemplary compound.

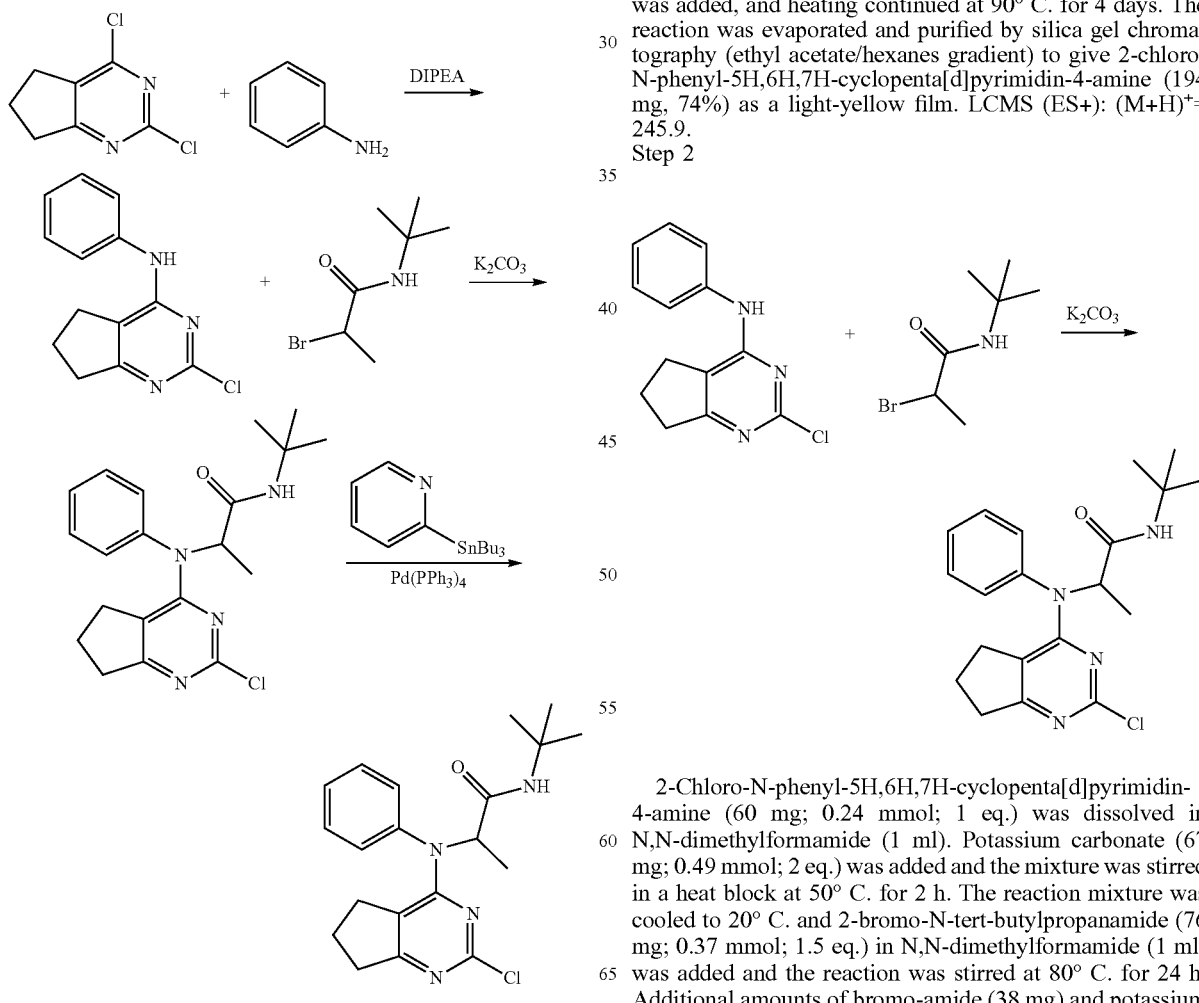

Step 1

2,4-Dichloro-6,7-dihydro-5H-cyclopenta[d]pyrimidine (200 mg; 1.06 mmol; 1 eq.) was dissolved in acetonitrile (9.5 ml). Aniline (0.12 mL; 1.27 mmol; 1.2 eq.) and N,N-diisopropylethylamine (0.55 mL; 3.17 mmol; 3 eq.) were added. The reaction was sealed and heated in a microwave reactor at 120° C. for 1 h. Additional aniline (1.2 eq.) and N,N-diisopropylamine (1.5 eq.) were added and heating continued at 100° C. for 4 h, and then 90° C. in a heat block for 10 h. The reaction was then concentrated to approximately 2 ml in volume, more N,N-diisopropylethylamine (0.75 ml) was added, and heating continued at 90° C. for 4 days. The reaction was evaporated and purified by silica gel chromatography (ethyl acetate/hexanes gradient) to give 2-chloro-N-phenyl-5H,6H,7H-cyclopenta[d]pyrimidin-4-amine (194 mg, 74%) as a light-yellow film. LCMS (ES+): (M+H)$^+$= 245.9.

Step 2

2-Chloro-N-phenyl-5H,6H,7H-cyclopenta[d]pyrimidin-4-amine (60 mg; 0.24 mmol; 1 eq.) was dissolved in N,N-dimethylformamide (1 ml). Potassium carbonate (67 mg; 0.49 mmol; 2 eq.) was added and the mixture was stirred in a heat block at 50° C. for 2 h. The reaction mixture was cooled to 20° C. and 2-bromo-N-tert-butylpropanamide (76 mg; 0.37 mmol; 1.5 eq.) in N,N-dimethylformamide (1 ml) was added and the reaction was stirred at 80° C. for 24 h. Additional amounts of bromo-amide (38 mg) and potassium carbonate (33 mg) were added and the reaction was heated for 24 h more. The reaction mixture was taken up in ethyl acetate (50 ml), water (10 ml), and sodium bicarbonate solution (10 ml). The phases were separated, and the aqueous phase was extracted with ethyl acetate (50 ml). The combined organics were washed with water (10 ml) and sodium chloride solution (10 ml), dried over sodium sulfate, and evaporated. The residue was purified by silica gel chromatography (ethyl acetate/hexanes gradient) to give N-tert-butyl-2-({2-chloro-5H,6H,7H-cyclopenta[d]pyrimidin-4-yl}(phenyl)amino)propenamide (48 mg, 52%) as a white solid. LCMS (ES+): (M+H)⁺=372.9.
Step 3

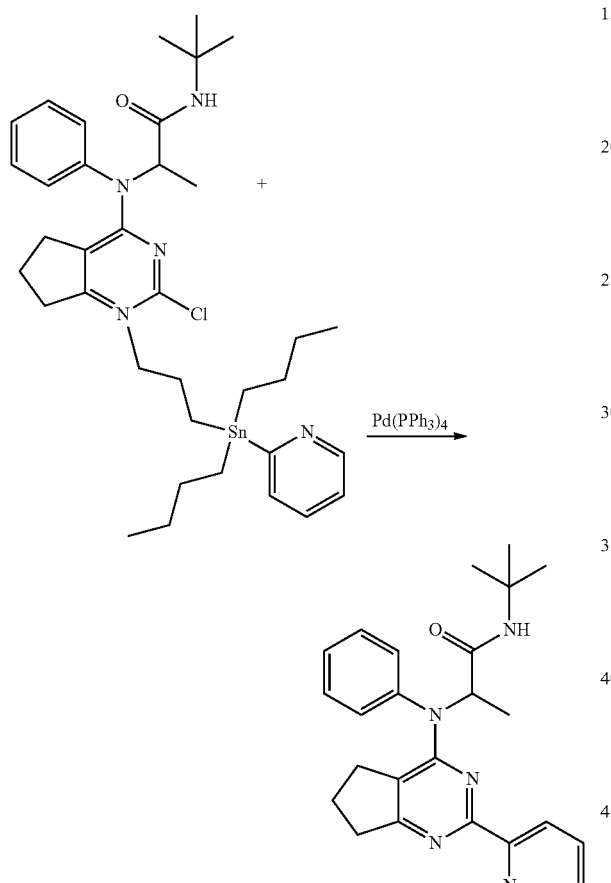

N-tert-butyl-2-({2-chloro-5H,6H,7H-cyclopenta[d]pyrimidin-4-yl}(phenyl)amino)propanamide (48 mg; 0.13 mmol; 1 eq.) was suspended in 1,4-dioxane (2 ml). The mixture was purged with Ar gas. 2-(Tributylstannyl)pyridine (0.08 mL; 0.26 mmol; 2 eq.) and tetrakis(triphenylphosphane) palladium (15 mg; 0.01 mmol; 0.1 eq.) were added and the mixture was stirred in a heat block at 108° C. for 18 h. Additional amounts of tin reagent (0.08 ml) and palladium catalyst (15 mg) were added and heating continued for 14 h. The reaction was evaporated, filtered, and purified by reverse phase chromatography (Waters XSelect CSH C18 column, 5-80% acetonitrile/0.1% aqueous formic acid gradient) to give N-tert-butyl-2-{phenyl[2-(pyridin-2-yl)-5H,6H,7H-cyclopenta[d]pyrimidin-4-yl]amino}propenamide (19 mg, 35%) as a white solid. LCMS (ES+): (M+H)⁺= 415.8. ¹H NMR (400 MHz, Chloroform-d) δ 8.82 (d, J=4.8 Hz, 1H), 8.49 (d, J=8.0 Hz, 1H), 7.92-7.83 (m, 1H), 7.43-7.33 (m, 4H), 7.33-7.26 (m, 2H), 7.26-7.21 (m, 1H), 5.44 (s, 1H), 2.92 (t, J=7.8 Hz, 2H), 1.99-1.92 (m, 1H), 1.80-1.63 (m, 3H), 1.33 (d, J=7.1 Hz, 3H), 1.19 (s, 9H).

Example 1.52

Synthesis of 2-{methyl[2-(pyridin-2-yl)-5H,6H,7H-cyclopenta[d]pyrimidin-4-yl]amino}-N-(quinolin-7-yl)acetamide (Compound 21)

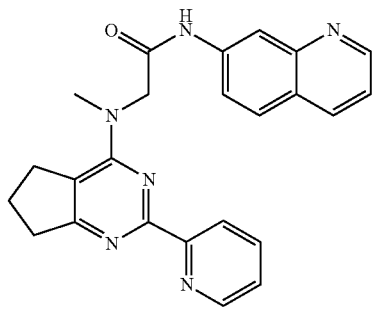 [SMILES: CN(CC(=O)Nc1ccc2cccnc2c1)c1nc(-c2ccccn2)nc2c1CCC2]

Scheme 26 depicts a synthetic route for preparing an exemplary compound.

Scheme 26

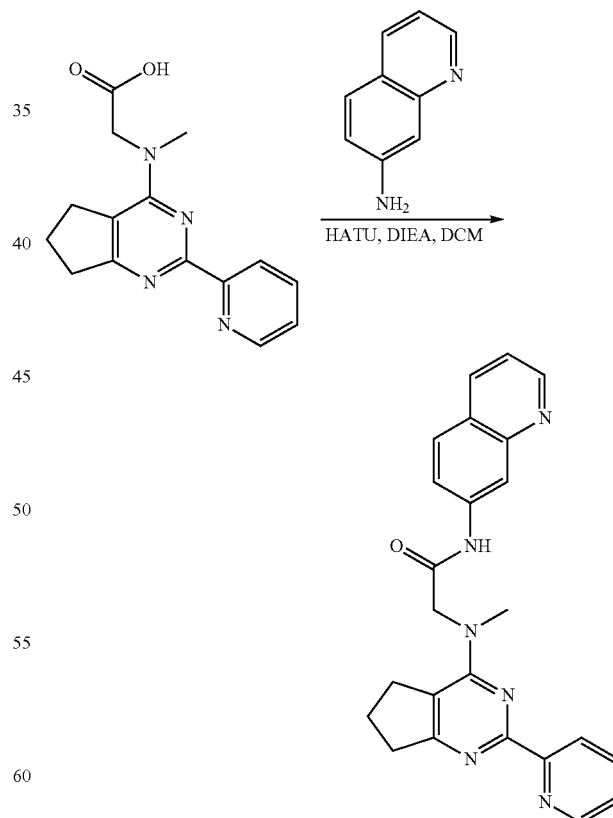

Into a 100-mL round-bottom flask, was placed N-methyl-N-(2-(pyridin-2-yl)-6,7-dihydro-5H-cyclopenta[d]pyrimidin-4-yl)glycine (250 mg, 0.879 mmol, 1.00 equiv), quinolin-7-amine (190.16 mg, 1.319 mmol, 1.5 equiv), HATU (501.50 mg, 1.319 mmol, 1.50 equiv), DIEA (227.29 mg, 1.759 mmol, 2 equiv), DCM (10.00 mL). The resulting solution was stirred for 4 hr at room temperature. The resulting solution was extracted with 3×20 mL of dichloromethane and the organic layers were combined and dried over anhydrous sodium sulfate and concentrated under vacuum. The crude product was purified by Prep-HPLC with the following conditions (2 #SHIMADZU (HPLC-01)): Column, Atlantis HILIC OBD Column, 19*150 mm*5 um; mobile phase, Water (0.05% NH$_3$H$_2$O) and ACN (25% PhaseB up to 42% in 14 min. This resulted in 137.7 mg (38.2%) of 2-(methyl(2-(pyridin-2-yl)-6,7-dihydro-5H-cyclopenta[d]pyrimidin-4-yl)amino)-N-(quinolin-7-yl)acetamide as an off-white solid. $^1$H NMR (300 MHz, DMSO-d$_6$) δ 10.61 (s, 1H), 8.86-8.80 (m, 1H), 8.67-8.60 (m, 1H), 8.39 (s, 1H), 8.32-8.22 (m, 2H), 7.92 (d, J=8.8 Hz, 1H), 7.83-7.66 (m, 2H), 7.39 (td, J=7.6, 4.5 Hz, 2H), 4.52 (s, 2H), 3.42 (s, 3H), 3.24 (t, J=7.3 Hz, 2H), 2.85 (t, J=7.8 Hz, 2H), 2.02 (p, J=7.7 Hz, 2H). LCMS (ES) [M+1]$^+$ m/z: 411.2.

Example 1.53

Synthesis of N-(2-fluorophenyl)-2-{methyl[2-(pyridin-2-yl)-5H,6H,7H-cyclopenta[d]pyrimidin-4-yl]amino}acetamide (Compound 22)

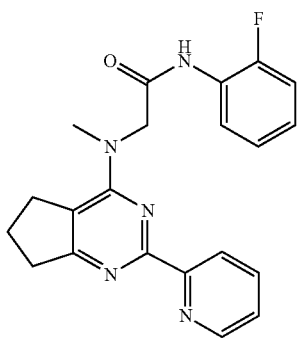 [SMILES: CN(CC(=O)Nc1ccccc1F)c1nc(-c2ccccn2)nc2c1CCC2]

Scheme 27 depicts a synthetic route for preparing an exemplary compound.

Scheme 27

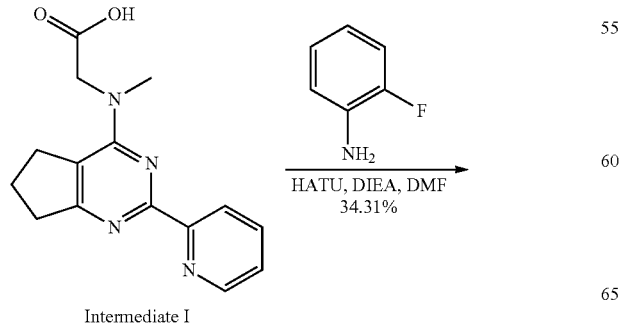

Intermediate I

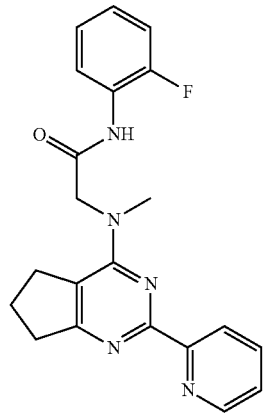

Into a 50-mL round-bottom flask, was placed 2-[methyl[2-(pyridin-2-yl)-5H,6H,7H-cyclopenta[d]pyrimidin-4-yl]amino]acetamide (Intermediate I, 100.00 mg, 0.353 mmol, 1.00 equiv), dimethylformamide (8 mL), 2-fluoroaniline (39.22 mg, 0.353 mmol, 1.00 equiv), HATU (201.30 mg, 0.529 mmol, 1.50 equiv) and DIEA (136.84 mg, 1.059 mmol, 3.00 equiv). The resulting solution was stirred for 2 hr at 25° C. The crude reaction mixture was filtered and subjected to reverse phase preparative HPLC (Prep-C18, 20-45M, 120 g, Tianjin Bonna-Agela Technologies; gradient elution of 30% MeCN in water to 40% MeCN in water over a 10 min period, water contains 0.1% FA) to provide N-(2-fluorophenyl)-2-{methyl[2-(pyridin-2-yl)-5H,6H,7H-cyclopenta[d]pyrimidin-4-yl]amino}acetamide as a brown solid (45.7 mg, 34.31%). $^1$H NMR (300 MHz, DMSO-d6) δ 10.05 (s, 1H), 8.63 (d, J=4.4 Hz, 1H), 8.29 (d, J=7.8 Hz, 1H), 7.89-7.64 (m, 2H), 7.47-7.34 (m, 1H), 7.32-7.20 (m, 1H), 7.14 (dt, J=6.4, 3.2 Hz, 2H), 4.50 (s, 2H), 3.36-3.32 (m, 3H), 3.21 (t, J=7.4 Hz, 2H), 2.84 (t, J=7.8 Hz, 2H), 2.01 (p, J=7.6 Hz, 2H). LCMS (ES) [M+1]$^+$ m/z 378.2.

Example 1.54

Synthesis of N-tert-butyl-2-{methyl[2-(pyridin-2-yl)-5,6,7,8-tetrahydroquinazolin-4-yl]amino}acetamide (Compound 23)

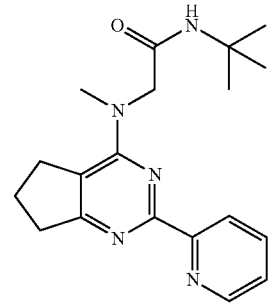 [SMILES: CN(CC(=O)NC(C)(C)C)c1nc(-c2ccccn2)nc2c1CCC2]

Scheme 28 depicts a synthetic route for preparing an exemplary compound.

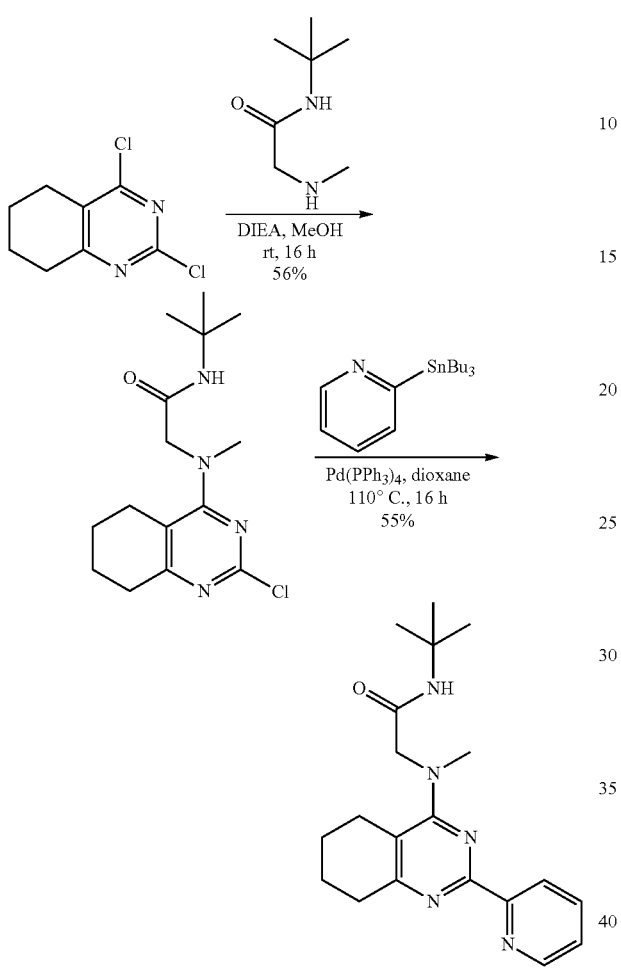

Step 1

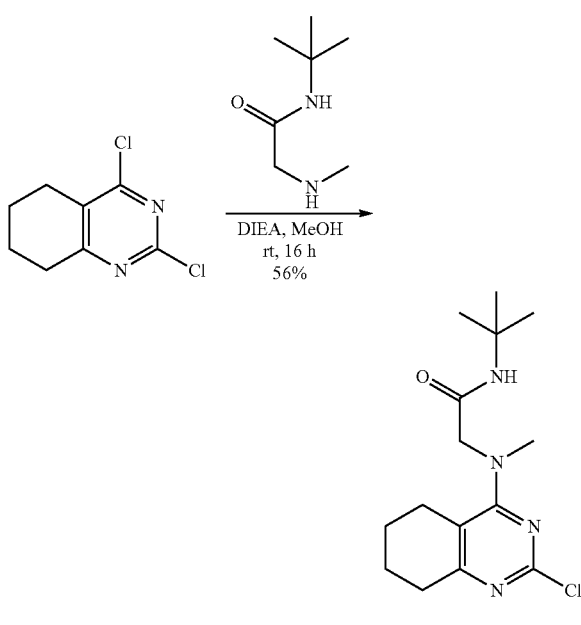

Into a 50-mL round-bottom flask, was placed a mixture of 2,4-dichloro-5,6,7,8-tetrahydroquinazoline (300 mg, 1.477 mmol, 1.00 equiv), MeOH (10.00 mL), N-tert-butyl-2-(methylamino)acetamide (319 mg, 2.21 mmol, 1.50 equiv), and DIEA (286 mg, 2.21 mmol, 1.50 equiv). The resulting solution was stirred for 16 hours at room temperature. The resulting mixture was concentrated. The residue was applied onto a silica gel column with ethyl acetate/petroleum ether (1/3). This resulted in 260 mg (56.62%) of N-tert-butyl-2-[(2-chloro-5,6,7,8-tetrahydroquinazolin-4-yl)(methyl)amino]acetamide as a white solid. LCMS (ES) [M+1]+ m/z: 311.

Step 2

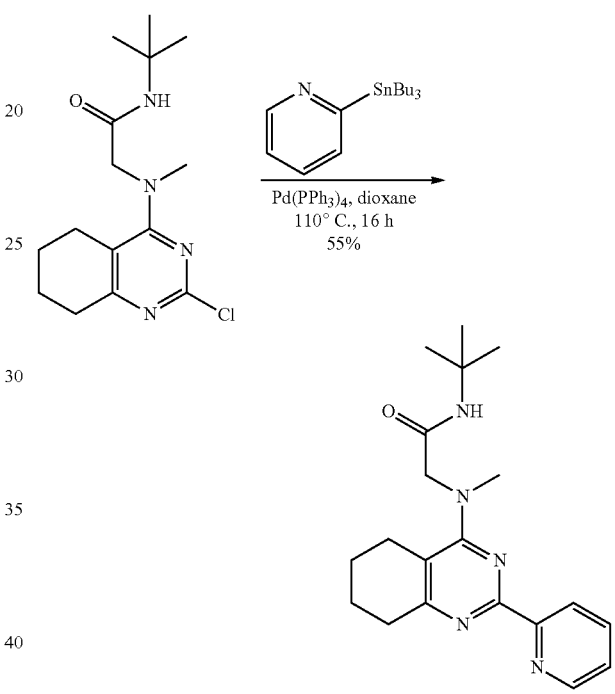

Into a 40-mL vial purged and maintained in an inert atmosphere of nitrogen, was placed a mixture of N-tert-butyl-2-[(2-chloro-5,6,7,8-tetrahydroquinazolin-4-yl)(methyl)amino]acetamide (200 mg, 0.643 mmol, 1.00 equiv), dioxane (15.0 mL), 2-(tributylstannyl)pyridine (473 mg, 1.28 mmol, 2.00 equiv), and Pd(PPh3)4 (223 mg, 0.193 mmol, 0.30 equiv). The resulting solution was stirred for 16 hours at 110° C. The crude reaction mixture was filtered and subjected to reverse phase preparative MPLC (Prep-C18, 20-45 mM, 120 g, Tianjin Bonna-Agela Technologies; gradient elution of 5% MeCN in water to 26% MeCN in water over a 12 min period, where both solvents contain 0.1% formic acid). This resulted in 127.1 mg (55.88%) of N-tert-butyl-2-[methyl[2-(pyridin-2-yl)-5,6,7,8-tetrahydroquinazolin-4-yl]amino]acetamide as an off-white solid. $^1$H NMR (300 MHz, DMSO-d6, ppm): δ 8.70 (d, J=4.3 Hz, 1H), 8.37 (d, J=7.9 Hz, 1H), 7.93 (td, J=7.7, 1.8 Hz, 1H), 7.77 (s, 1H), 7.52-7.47 (m, 1H), 4.04 (s, 2H), 3.21 (s, 3H), 2.83-2.79 (m, 2H), 2.73-2.70 (m, 2H), 1.82-1.80 (m, 2H), 1.69-1.67 (m, 2H), 1.23 (s, 9H). LCMS (ES) [M+1]+ m/z: 354.2.

Example 1.55

Synthesis of N-tert-butyl-2-{methyl[2-(4-methylpyridin-2-yl)-5H,6H,7H-cyclopenta[d]pyrimidin-4-yl]amino}acetamide (Compound 24)

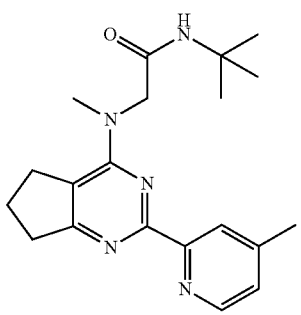 [SMILES: Cc1ccnc(-c2nc3c(c(N(C)CC(=O)NC(C)(C)C)n2)CCC3)c1]

Scheme 29 depicts a synthetic route for preparing an exemplary compound.

Scheme 29

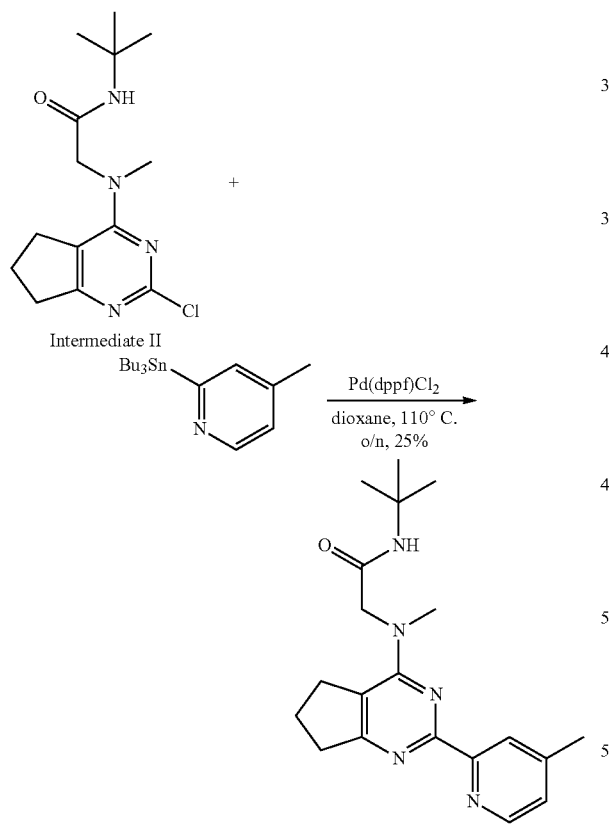

Into a 40-mL vial purged and maintained in an inert atmosphere of nitrogen, was placed N-tert-butyl-2-([2-chloro-5H,6H,7H-cyclopenta[d]pyrimidin-4-yl](methyl)amino)acetamide (Intermediate II, 0.30 g, 1.01 mmol, 1.00 equiv), dioxane (15 mL), Pd(dppf)Cl$_2$·CH$_2$Cl$_2$ (0.22 g, 0.30 mmol, 0.30 equiv), and 4-methyl-2-(tributylstannyl)-pyridine (0.58 g, 1.52 mmol, 1.50 equiv). The resulting solution was stirred overnight at 110° C. The resulting mixture was concentrated. The crude product was purified by Flash-Prep-HPLC with the following conditions (IntelFlash-1): Column, C18 silica gel; mobile phase, Phase A: Water (0.05% FA), Phase B CH$_3$CN (0-30% in 6 min); Detector, 220&254 nm. This resulted in 0.1 g crude product. The crude product (0.1 g) was further purified by Prep-HPLC with the following conditions: Column, X-Bridge C18 OBD, 5 um, 19*150 mm; mobile phase, Phase A: Water (0.05% NH$_4$OH), Phase B CH$_3$CN (25% B up to 45% in 8 min); Detector, 220 nm; Flow rate 20 mL/min. This resulted in 88.9 mg (24.88%) of (N-tert-butyl)-2-(methyl(2-(4-methylpyridin-2-yl)-5H,6H,7H-cyclopenta[d]pyrimidin-4-yl)amino)acetamide as an off-white solid. $^1$H-NMR: (300 MHz, DMSO-d6, ppm): δ 8.50 (d, J=4.9 Hz, 1H), 8.16 (s, 1H), 7.71 (s, 1H), 7.26 (d, J=4.2 Hz, 1H), 4.14 (s, 2H), 3.27 (s, 3H), 3.14 (t, J=7.2 Hz, 2H), 2.81 (t, J=7.8 Hz, 2H), 2.41 (s, 3H), 2.0-1.99 (m, 2H), 1.23 (s, 9H). LCMS: (ES, m/z): [M+H]$^+$: 354.2.

Example 1.56

Synthesis of 2-{methyl[2-(pyridin-2-yl)-5H,6H,7H-cyclopenta[d]pyrimidin-4-yl]amino}-N-(1-methylcyclohexyl)acetamide (Compound 25)

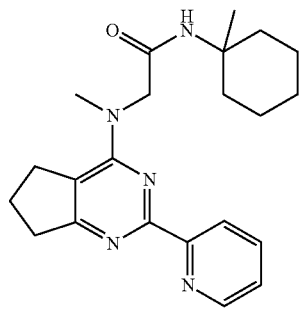 [SMILES: CN(CC(=O)NC1(C)CCCCC1)c1nc(-c2ccccn2)nc2c1CCC2]

Scheme 30 depicts a synthetic route for preparing an exemplary compound.

Scheme 30

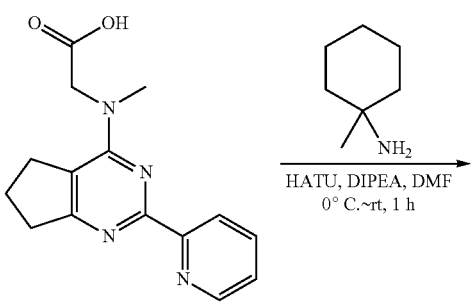

-continued

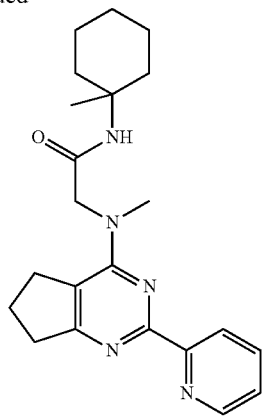

Into a 8-mL vial, was placed [methyl[2-(pyridin-2-yl)-5H,6H,7H-cyclopenta[d]pyrimidin-4-yl]amino]acetic acid (Intermediate I, 150 mg, 0.53 mmol, 1.0 equiv), DMF (3.0 mL), 1-methylcyclohexylamine (66 mg, 0.58 mmol, 1.1 equiv), and DIPEA (341 mg, 2.64 mmol, 5.0 equiv). This was followed by the addition of HATU (301 mg, 0.79 mmol, 1.5 equiv) at 0° C. The mixture was stirred for 1 h at room temperature. The mixture was filtered, and the filtrate was purified by Prep-HPLC with the following conditions: 120 g $C_{18}$ column, $CH_3CN/H_2O$ (0.05% $NH_4OH$), from 5% to 80% with 15 min, flow rate, 70 mL/min, detector, 254 nm. 101.6 mg (51%) of 2-[methyl[2-(pyridin-2-yl)-5H,6H,7H-cyclopenta[d]pyrimidin-4-yl]amino]-N-(1-methylcyclohexyl)acetamide was obtained as light yellow solid. $^1$H-NMR (300 MHz, DMSO-$d_6$, ppm): δ 8.66 (dd, J=4.7, 1.8 Hz, 1H), 8.34 (dt, J=8.0, 1.1 Hz, 1H), 7.86 (td, J=7.7, 1.8 Hz, 1H), 7.43 (ddd, J=7.5, 4.7, 1.2 Hz, 1H), 7.37 (s, 1H), 4.20 (s, 2H), 3.28 (s, 3H), 3.16 (t, J=7.2 Hz, 2H), 2.82 (t, J=7.8 Hz, 2H), 2.02-1.96 (m, 4H), 1.33-1.24 (m, 8H), 1.19 (s, 3H). LCMS: (ES, m/z): [M+H]$^+$: 380.3.

Example 1.57

Synthesis of 2-{methyl[2-(pyridin-2-yl)-5H,6H,7H-cyclopenta[d]pyrimidin-4-yl]amino}-N-(oxan-3-yl)acetamide (Compound 26)

Scheme 31 depicts a synthetic route for preparing an exemplary compound.

Scheme 31

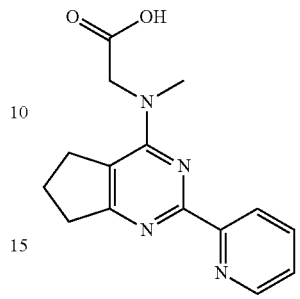 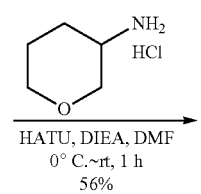

HATU, DIEA, DMF
0° C.~rt, 1 h
56%

Intermediate I

Into an 8-mL vial, was placed [methyl[2-(pyridin-2-yl)-5H,6H,7H-cyclopenta[d]pyrimidin-4-yl]amino]acetic acid (Intermediate I, 150 mg, 0.53 mmol, 1.0 equiv), DMF (3.0 mL), oxan-3-amine hydrochloride (80 mg, 0.58 mmol, 1.1 equiv), and DIEA (341 mg, 2.64 mmol, 5.0 equiv). This was followed by the addition of HATU (301 mg, 0.79 mmol, 1.5 equiv) at 0° C. The mixture was stirred for 1 h at room temperature, filtered, and the filtrate was purified by Prep-HPLC with conditions: C18-120 g column, $CH_3CN/H_2O$ (0.05% $NH_4OH$), from 5% to 80% with 15 min, flow rate, 70 mL/min, detector, 254 nm. This provided 108.5 mg (56%) of 2-[methyl[2-(pyridin-2-yl)-5H,6H,7H-cyclopenta[d]pyrimidin-4-yl]amino]-N-(oxan-3-yl)acetamide as an off-white solid. $^1$H-NMR: (300 MHz, DMSO-$d_6$, ppm): δ 8.67 (d, J=4.2 Hz, 1H), 8.29 (d, J=7.8 Hz, 1H), 8.09 (d, J=7.5 Hz, 1H), 7.90-7.85 (m, 1H), 7.46-7.42 (m, 1H), 4.20 (s, 2H), 3.71-3.63 (m, 3H), 3.33-3.29 (m, 1H), 3.26 (s, 3H) 3.15-3.05 (m, 3H), 2.82 (t, J=7.8 Hz, 2H), 2.04-1.94 (m, 2H), 1.79-1.71 (m, 1H), 1.64-1.55 (m, 1H), 1.49-1.43 (m, 2H). LCMS: (ES, m/z): [M+H]$^+$: 368.2.

Example 1.58

Synthesis of N-benzyl-2-{methyl[2-(pyridin-2-yl)-5H,6H,7H-cyclopenta[d]pyrimidin-4-yl]amino}acetamide (Compound 27)

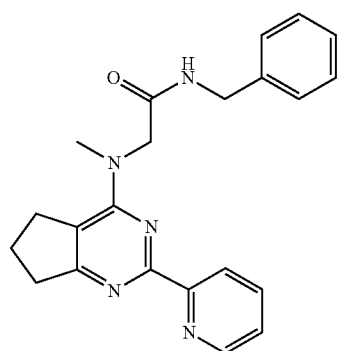

Scheme 32 depicts a synthetic route for preparing an exemplary compound.

Scheme 32

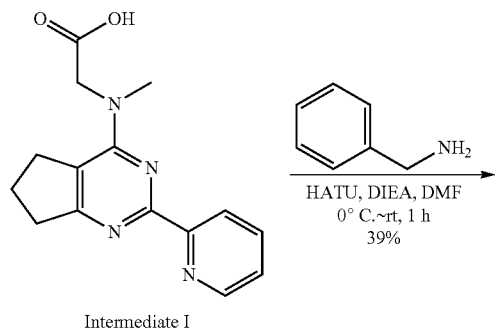

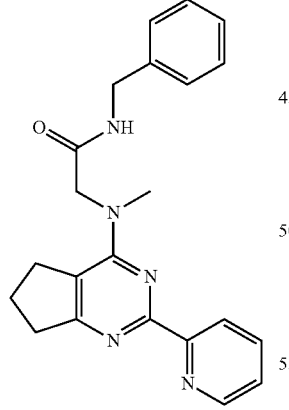

Into an 8-mL vial, was placed [methyl[2-(pyridin-2-yl)-5H,6H,7H-cyclopenta[d]pyrimidin-4-yl]amino]acetic acid (200 mg, 0.70 mmol, 1.0 equiv), DMF (3.00 mL), benzylamine (83 mg, 0.77 mmol, 1.1 equiv), and DIEA (455 mg, 3.52 mmol, 5.0 equiv). This was followed by the addition of HATU (321 mg, 0.84 mmol, 1.2 equiv) at 0° C. The reaction solution was stirred for 1 h at room temperature, filtered, and the filtrate was purified by Prep-HPLC with conditions: C18-120 g column, CH$_3$CN/H$_2$O (0.05% NH$_4$OH), from 5% to 80% with 15 min, flow rate, 70 mL/min, detector, 254 nm. This provided 101.6 mg (39%) of N-benzyl-2-[methyl[2-(pyridin-2-yl)-5H,6H,7H-cyclopenta[d]pyrimidin-4-yl]amino]acetamide as an off-white solid. 1H-NMR (300 MHz, DMSO-d6, ppm): δ 8.64 (d, J=5.4 Hz 2H), 8.26 (d, J=7.8 Hz, 1H), 7.83 (td, J=7.7, 1.9 Hz, 1H), 7.43 (dd, J=7.5, 4.9 Hz, 1H), 7.22-7.10 (m, 5H), 4.31 (s, 2H), 4.30 (s, 2H), 3.32 (s, 3H), 3.17 (t, J=7.2 Hz, 2H), 2.82 (t, J=7.8 Hz, 2H), 2.03-1.93 (m, 2H). LCMS: (ES, m/z): [M+H]+: 374.2

Example 1.59

Synthesis of N-tert-butyl-2-{[2-(5-hydroxypyrazin-2-yl)-5H,6H,7H-cyclopenta[d]pyrimidin-4-yl](methyl)amino}acetamide (Compound 28)

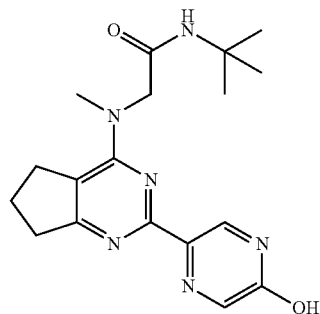 [SMILES: CN(CC(=O)NC(C)(C)C)c1nc(-c2cnc(O)cn2)nc2c1CCC2]

Scheme 33 depicts a synthetic route for preparing an exemplary compound.

Scheme 33

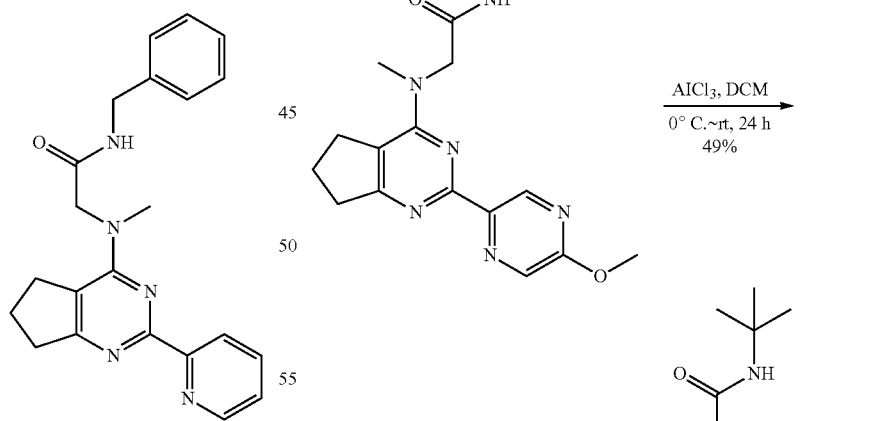

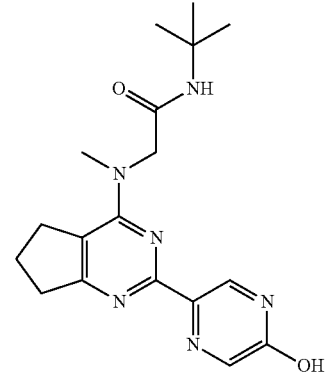

Into a 50-mL round-bottom flask, was placed a mixture of N-(tert-butyl)-2-((2-(5-methoxypyrazin-2-yl)-6,7-dihydro-5H-cyclopenta[d]pyrimidin-4-yl)(methyl)amino)acetamide (120 mg, 0.324 mmol, 1.00 equiv), DCM (20.0 mL), and AlCl₃ (431 mg, 3.23 mmol, 10.00 equiv). The resulting solution was stirred for 24 hours at room temperature. The reaction was then quenched by the addition of 100 mL of water/ice. The resulting solution was extracted with 3×50 mL of dichloromethane. The organic layer was separated, dried over anhydrous magnesium sulfate, and concentrated. The crude product was purified by Prep-HPLC with the following conditions: Column, Xbridge Prep C18 OBD Column, 19×150 mm, 5 um; mobile phase, phase A: H₂O (0.05% NH₃H₂O); phase B: CH₃CN (10% CH₃CN up to 30% CH₃CN in 8 min). This resulted in 57.2 mg (49.54%) of N-(tert-butyl)-2-((2-(5-hydroxypyrazin-2-yl)-6,7-dihydro-5H-cyclopenta[d]pyrimidin-4-yl)(methyl)amino)acetamide as a white solid. ¹H NMR (300 MHz, DMSO-d₆, ppm): δ12.63 (br, 1H), 8.26 (br, 1H), 8.05 (d, J=1.3 Hz 1H), 7.61 (s, 1H), 4.08 (s, 2H), 3.3 (s, 3H), 3.10 (t, J=7.3 Hz, 2H), 2.76 (t, J=7.8 Hz, 2H), 2.05-1.93 (m, 2H), 1.24 (s, 9H). LCMS (ES) [M+1]⁺ m/z: 357.2.

Example 1.60

Synthesis of N-cyclohexyl-1-[2-(pyridin-2-yl)-5H,6H,7H-cyclopenta[d]pyrimidin-4-yl]azetidine-3-carboxamide (Compound 29)

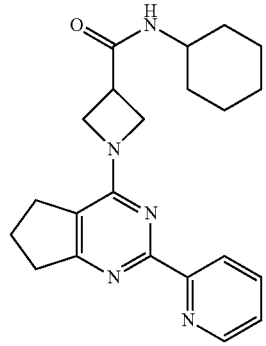 [SMILES: O=C(NC1CCCCC1)C1CN(c2nc(-c3ccccn3)nc3c2CCC3)C1]

Scheme 34 depicts a synthetic route for preparing an exemplary compound.

Scheme 34

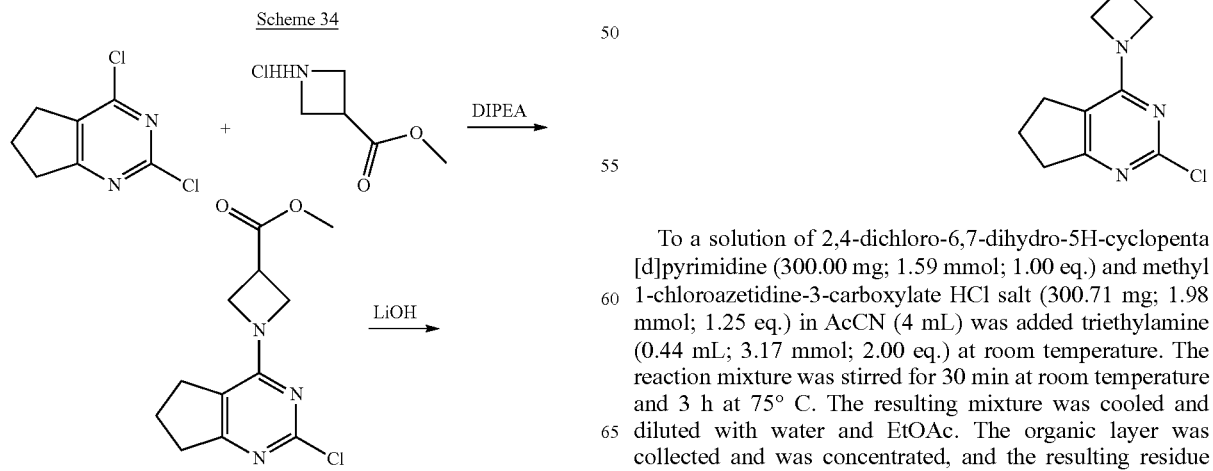

Step 1

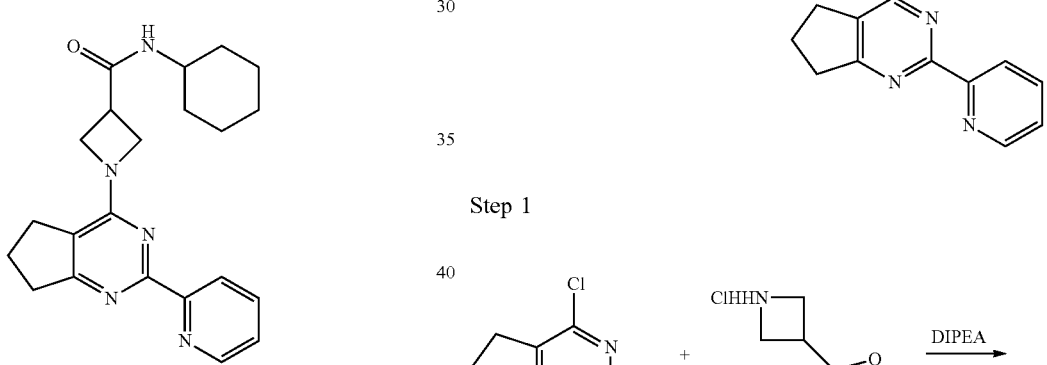

To a solution of 2,4-dichloro-6,7-dihydro-5H-cyclopenta[d]pyrimidine (300.00 mg; 1.59 mmol; 1.00 eq.) and methyl 1-chloroazetidine-3-carboxylate HCl salt (300.71 mg; 1.98 mmol; 1.25 eq.) in AcCN (4 mL) was added triethylamine (0.44 mL; 3.17 mmol; 2.00 eq.) at room temperature. The reaction mixture was stirred for 30 min at room temperature and 3 h at 75° C. The resulting mixture was cooled and diluted with water and EtOAc. The organic layer was collected and was concentrated, and the resulting residue was purified by column chromatography (Hexanes/

EtOAc=30:70) to give methyl 1-{2-chloro-5H,6H,7H-cyclopenta[d]pyrimidin-4-yl}azetidine-3-carboxylate (390 mg). LCMS (ES+): (M+H)+=268.1, 270.1.

Step 2

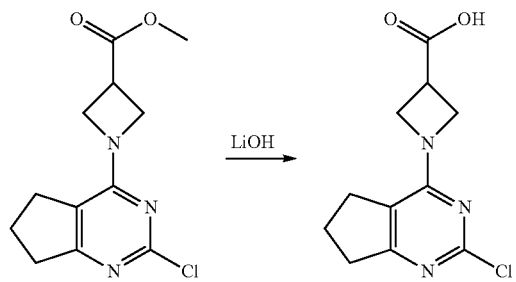 [SMILES: COC(=O)C1CN(c2nc(Cl)nc3c2CCC3)C1 ; "LiOH" ; O=C(O)C1CN(c2nc(Cl)nc3c2CCC3)C1]

To a solution of methyl 1-{2-chloro-5H,6H,7H-cyclopenta[d]pyrimidin-4-yl}azetidine-3-carboxylate (390.00 mg; 1.46 mmol; 1.00 eq.) in THF (2 mL) was added MeOH (1 mL) and water (1 mL), followed by lithium hydroxide monohydrate (122.26 mg; 2.91 mmol; 2.00 eq.). The mixture was stirred for 2 h and concentrated and the residue was acidified with 1N HCl to pH=3. The resulting precipitates were collected by filtration to give 1-{2-chloro-5H,6H,7H-cyclopenta[d]pyrimidin-4-yl}azetidine-3-carboxylic acid (339 mg). LCMS (ES+): (M+H)+=254.0, 256.2.

Step 3

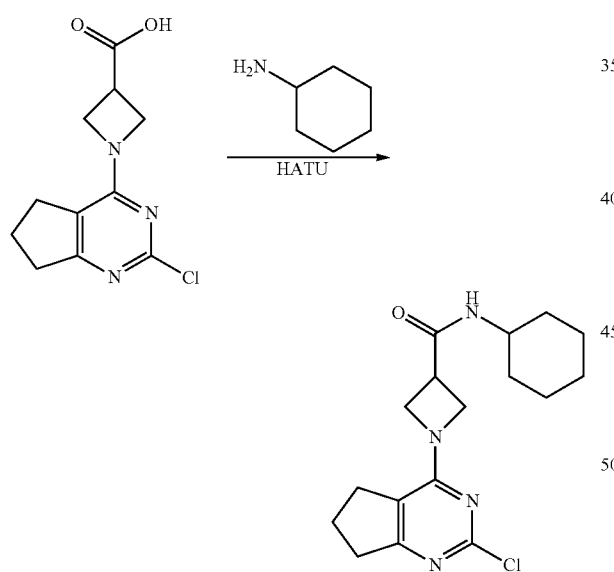

To a solution of 1-{2-chloro-5H,6H,7H-cyclopenta[d]pyrimidin-4-yl}azetidine-3-carboxylic acid (156.00 mg; 0.61 mmol; 1.00 eq.) and cyclohexanamine (0.11 mL; 0.92 mmol; 1.50 eq.) in DMF (2 mL) was added DIPEA (0.27 mL; 1.54 mmol; 2.50 eq.) and HATU (257.20 mg; 0.68 mmol; 1.10 eq.). The reaction was stirred until completion, and the mixture was poured over Sat. NaHCO3 and water. The resulting precipitates were collected by filtration to give 1-{2-chloro-5H,6H,7H-cyclopenta[d]pyrimidin-4-yl}-N-cyclohexylazetidine-3-carboxamide (198 mg). LCMS (ES+): (M+H)+=335.0, 337.1.

Step 4

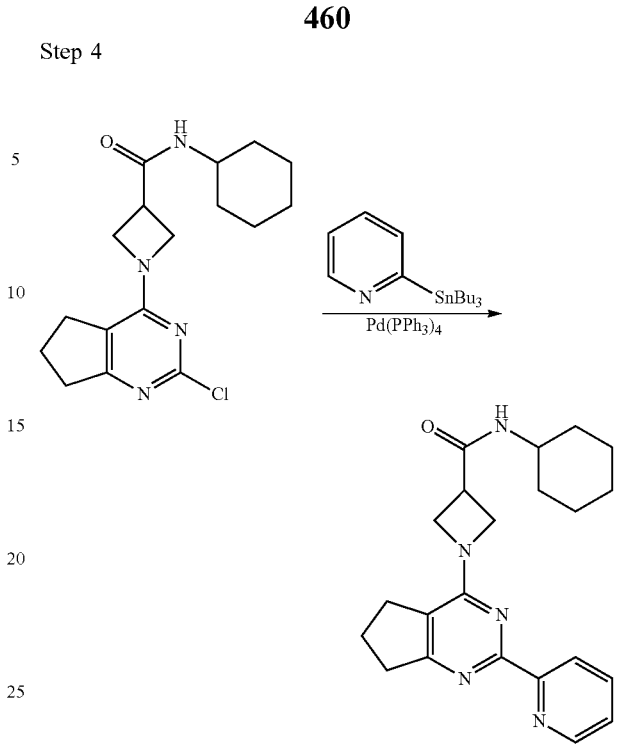

To a suspension of 1-{2-chloro-5H,6H,7H-cyclopenta[d]pyrimidin-4-yl}-N-cyclohexylazetidine-3-carboxamide (100.00 mg; 0.30 mmol; 1.00 eq.) in DMF (2 mL) was added 2-(tributylstannyl)pyridine (164.92 mg; 0.45 mmol; 1.50 eq.) and tetrakis(triphenylphosphane) palladium (34.51 mg; 0.03 mmol; 0.10 eq.). The mixture was heated at 115° C. for 15 h, the mixture was cooled and diluted with water and AcCN, the insoluble material was filtered off, and the filtrate was purified by preparative HPLC to give N-cyclohexyl-1-[2-(pyridin-2-yl)-5H,6H,7H-cyclopenta[d]pyrimidin-4-yl]azetidine-3-carboxamide (63 mg). 1H NMR (400 MHz, DMSO-d6) δ 8.66 (ddd, J=4.8, 1.8, 0.9 Hz, 1H), 8.25 (dt, J=7.9, 1.2 Hz, 1H), 7.89 (td, J=7.7, 1.8 Hz, 2H), 7.45 (ddd, J=7.6, 4.7, 1.2 Hz, 1H), 4.33 (t, J=8.6 Hz, 2H), 4.24 (t, J=7.4 Hz, 2H), 3.58-3.50 (m, 1H), 3.48-3.39 (m, 1H), 2.93 (t, J=7.4 Hz, 2H), 2.81 (t, J=7.8 Hz, 2H), 2.01 (p, J=7.7 Hz, 2H), 1.77-1.62 (m, 4H), 1.53 (d, J=12.3 Hz, 1H), 1.32-1.03 (m, 5H). LCMS (ES+): (M+H)+=378.3.

Example 1.61

Synthesis of N-cyclohexyl-1-[2-(4-methylpyridin-2-yl)-5H,6H,7H-cyclopenta[d]pyrimidin-4-yl]azetidine-3-carboxamide (Compound 30)

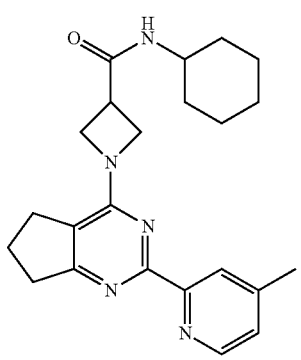 [SMILES: Cc1ccnc(-c2nc3c(c(N4CC(C(=O)NC5CCCCC5)C4)n2)CCC3)c1]

Compound 30 was synthesized similar to Compound 29 by replacing 2-(tributylstannyl)pyridine with 4-methyl-2-(tributylstannyl)pyridine. $^1$H NMR (400 MHz, DMSO-d$_6$) δ 8.51-8.46 (m, 1H), 8.06 (dd, J=1.8, 0.9 Hz, 1H), 7.88 (d, J=7.8 Hz, 1H), 7.27-7.21 (m, 1H), 4.29 (t, J=8.5 Hz, 2H), 4.21 (t, J=7.3 Hz, 2H), 3.60-3.48 (m, 1H), 3.48-3.38 (m, 1H), 2.92 (t, J=7.4 Hz, 2H), 2.78 (t, J=7.8 Hz, 2H), 2.37 (s, 3H), 1.99 (p, J=7.7 Hz, 2H), 1.77-1.73 (m, 2H), 1.66 (dt, J=12.6, 3.7 Hz, 2H), 1.53 (d, J=12.8 Hz, 1H), 1.33-1.18 (m, 2H), 1.22-1.03 (m, 3H). LCMS (ES+): (M+H)$^+$=392.4.

Example 1.62

Synthesis of N-(1-methyl-2-oxopyrrolidin-3-yl)-2-{methyl[2-(pyridin-2-yl)-5H,6H,7H-cyclopenta[d]pyrimidin-4-yl]amino}acetamide (Compound 31)

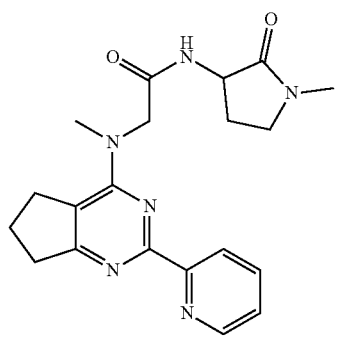 [SMILES: CN1CCC(NC(=O)CN(C)c2nc(-c3ccccn3)nc3c2CCC3)C1=O]

Compound 31 was synthesized similar to compound 75 by replacing 4-methoxyaniline with 3-amino-1-methylpyrrolidin-2-one. LCMS (ES+): (M+H)$^+$=381.3. $^1$H NMR (400 MHz, Acetonitrile-d3) δ 8.60-8.55 (m, 1H), 8.37 (d, J=8.0 Hz, 1H), 8.02 (d, J=8.3 Hz, 1H), 7.90-7.84 (m, 1H), 7.40 (ddd, J=7.6, 4.8, 1.2 Hz, 1H), 4.43 (q, J=9.0 Hz, 1H), 4.31-4.10 (m, 2H), 3.34 (s, 3H), 3.23-3.14 (m, 4H), 2.89-2.85 (m, 2H), 2.74 (s, 3H), 2.28 (dddd, J=12.5, 9.0, 6.9, 2.2 Hz, 1H), 2.10-1.99 (m, 2H), 1.79-1.67 (m, 1H).

Example 1.63

Synthesis of N-(2,2-difluoro-2H-1,3-benzodioxol-5-yl)-2-{methyl[2-(pyridin-2-yl)-5H,6H,7H-cyclopenta[d]pyrimidin-4-yl]amino}acetamide (Compound 32)

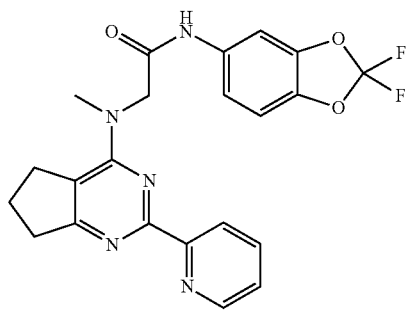 [SMILES: CN(CC(=O)Nc1ccc2c(c1)OC(F)(F)O2)c1nc(-c2ccccn2)nc2c1CCC2]

Compound 32 was synthesized similar to compound 75 by replacing 4-methoxyaniline with 2,2-difluoro-1,3-benzodioxol-5-amine. LCMS (ES+): (M+H)$^+$=440.3. $^1$H NMR (400 MHz, Acetonitrile-d3) δ 9.91 (s, 1H), 8.68 (d, J=4.7 Hz, 1H), 8.39 (d, J=8.0 Hz, 1H), 7.92-7.84 (m, 1H), 7.69 (d, J=2.1 Hz, 1H), 7.46 (dd, J=7.6, 4.9 Hz, 1H), 7.24 (dd, J=8.7, 2.1 Hz, 1H), 7.07 (d, J=8.7 Hz, 1H), 4.35 (s, 2H), 3.43 (s, 3H), 3.28-3.22 (m, 2H), 2.96-2.90 (m, 2H), 2.11-2.06 (m, 2H).

Example 1.64

Synthesis of N-tert-butyl-2-{[2-(pyrimidin-2-yl)-5H,6H,7H-cyclopenta[d]pyrimidin-4-yl]amino}acetamide (Compound 33)

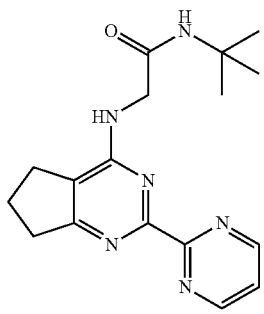 [SMILES: CC(C)(C)NC(=O)CNc1nc(-c2ncccn2)nc2c1CCC2]

Scheme 35 depicts a synthetic route for preparing an exemplary compound.

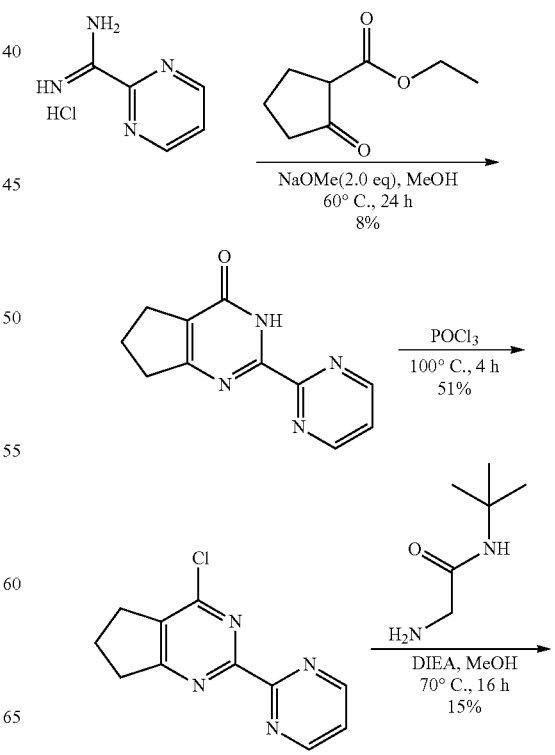

-continued

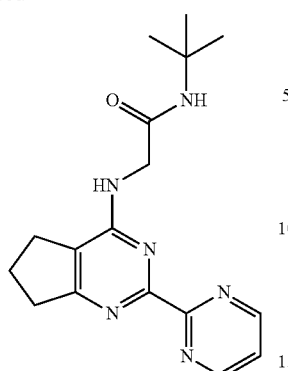

Step 1

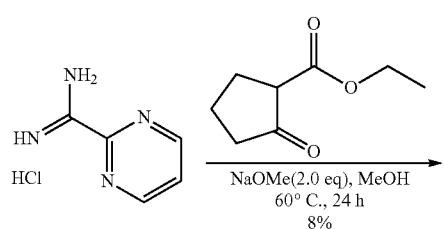

Into a 500-mL round-bottom flask, was placed a mixture of pyrimidine-2-carboximidamide hydrochloride (10.0 g, 63.0 mmol, 1.00 equiv), MeOH (200 mL), ethyl 2-oxocyclopentane-1-carboxylate (14.7 g, 94.5 mmol, 1.50 equiv), and NaOMe (6.81 g, 126 mmol, 2.00 equiv). The resulting solution was stirred for 16 hours at 60° C. The resulting mixture was concentrated. The reaction was then quenched by the addition of 200 mL of water. The pH value of the solution was adjusted to 3 with HCl (2 mol/L). The resulting solution was extracted with 3×150 mL of dichloromethane, the organic layers were separated and combined, dried over anhydrous sodium sulfate, and concentrated. This resulted in 1.1 g (8.14%) of 2-(pyrimidin-2-yl)-3,5,6,7-tetrahydro-4H-cyclopenta[d]pyrimidin-4-one as an off-white oil. LCMS (ES) [M+1]+ m/z: 215.

Step 2

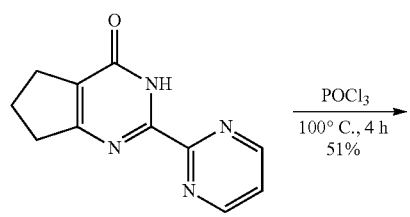

-continued

Into a 20-mL vial was placed 2-(pyrimidin-2-yl)-3,5,6,7-tetrahydro-4H-cyclopenta[d]pyrimidin-4-one (1.00 g, 4.66 mmol, 1.00 equiv) and phosphorus oxychloride (10 mL). The resulting solution was stirred for 4 hours at 100° C. The resulting mixture was concentrated. The reaction was then quenched by the addition of 50 mL of water. The pH value of the solution was adjusted to 9 with saturated sodium carbonate solution. The resulting solution was extracted with 3×50 mL of dichloromethane, the organic layer was separated and dried in an oven under reduced pressure. This resulted in 560 mg (51.56%) of 4-chloro-2-(pyrimidin-2-yl)-6,7-dihydro-5H-cyclopenta[d]pyrimidine as black oil. LCMS (ES) [M+1]+ m/z: 233.

Step 3

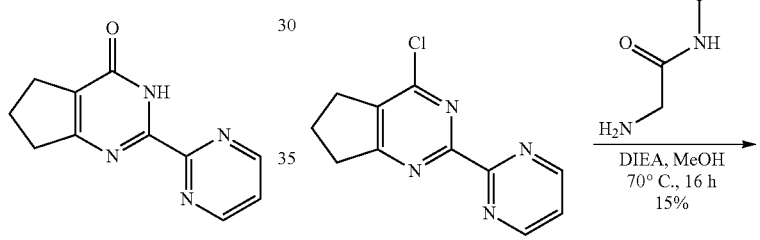

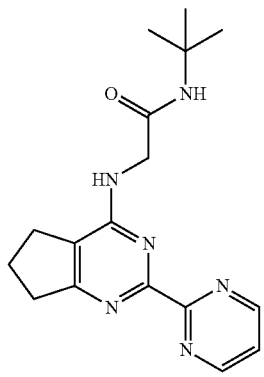

Into a 40-mL vial was placed 4-chloro-2-(pyrimidin-2-yl)-6,7-dihydro-5H-cyclopenta[d]pyrimidine (500 mg, 2.14 mmol, 1.00 equiv), MeOH (10.0 mL), 2-amino-N-tert-butylacetamide (419 mg, 3.22 mmol, 1.50 equiv) and DIEA (416 mg, 3.22 mmol, 1.50 equiv). The resulting solution was stirred for 16 hours at 80° C. The resulting mixture was concentrated. The crude product was purified by Prep-HPLC with the following conditions: Column, SunFire Prep C18 OBD Column, 19×150 mm, 5 um; mobile phase, phase A: H2O (0.1% FA); phase B: CH3CN (5% CH3CN up to 35% CH3CN in 10 min). This resulted in 111 mg (15.82%) of N-(tert-butyl)-2-((2-(pyrimidin-2-yl)-6,7-dihydro-5H-cyclopenta[d]Pyrimidin-4-yl)amino)acetamide. 1H NMR (300 MHz, DMSO-d6, ppm): δ 8.91 (d, J=4.9 Hz, 2H), 7.63 (s, 1H), 7.56 (t, J=4.9 Hz, 1H), 7.08 (t, J=5.8 Hz, 1H), 3.97 (d, J=5.8 Hz, 2H), 2.84 (t, J=7.7 Hz, 2H), 2.76 (t, J=7.4 Hz, 2H), 2.10-2.05 (m, 2H), 1.22 (s, 9H). LCMS (ES) [M+1]+ m/z: 327.2.

Example 1.65

Synthesis of N-tert-butyl-2-{[2-(4-methoxypyridin-2-yl)-5H,6H,7H-cyclopenta[d]pyrimidin-4-yl](methyl)amino}acetamide (Compound 34)

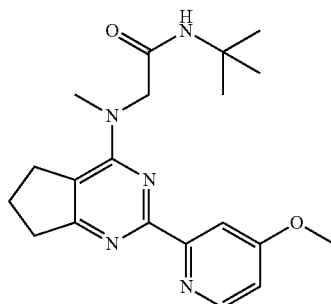

Scheme 36 depicts a synthetic route for preparing an exemplary compound.

Step 1

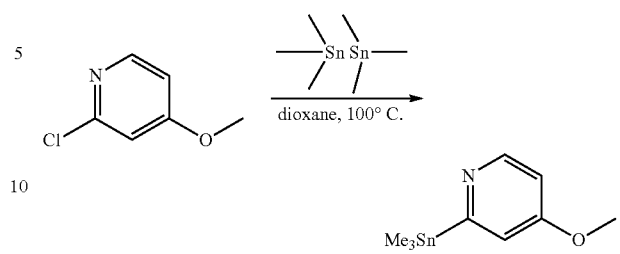

Into a 100-mL 3-necked round-bottom flask purged and maintained in an inert atmosphere of argon, was placed 2-chloro-4-methoxypyridine (500 mg, 3.48 mmol, 1.00 equiv), hexamethyldistannane (1.48 g, 4.527 mmol, 1.3 equiv), dioxane (20 mL), and Pd(PPh$_3$)$_4$ (804 mg, 0.69 mmol, 0.2 equiv). The resulting solution was stirred for 16 h at 110° C. in an oil bath. The solids were filtered out. The filtrate was concentrated to give 950 mg of 4-methoxy-2-(trimethylstannyl)pyridine. The crude product was used for next step without further purification. LCMS (ES) [M+1]$^+$ m/z: 274.02.

Step 2

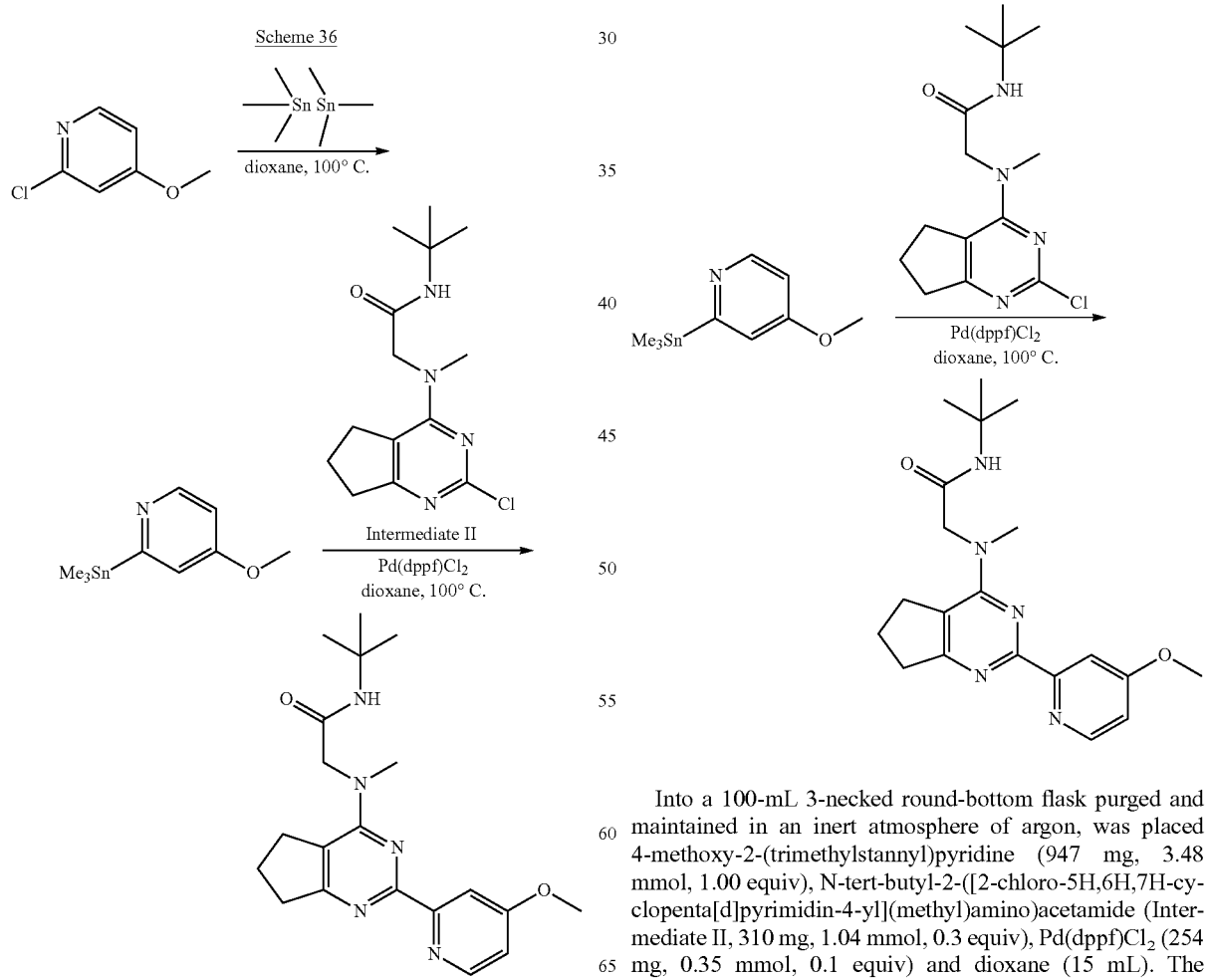

Into a 100-mL 3-necked round-bottom flask purged and maintained in an inert atmosphere of argon, was placed 4-methoxy-2-(trimethylstannyl)pyridine (947 mg, 3.48 mmol, 1.00 equiv), N-tert-butyl-2-([2-chloro-5H,6H,7H-cyclopenta[d]pyrimidin-4-yl](methyl)amino)acetamide (Intermediate II, 310 mg, 1.04 mmol, 0.3 equiv), Pd(dppf)Cl$_2$ (254 mg, 0.35 mmol, 0.1 equiv) and dioxane (15 mL). The resulting solution was stirred for 16 hr at 100° C. The resulting mixture was concentrated under vacuum. The residue was applied onto a silica gel column with ethyl acetate/petroleum ether (1:50 to 3:1). The crude product (160 mg) was purified by Flash-Prep-HPLC. This resulted in 50 mg (3.9%) of N-tert-butyl-2-[[2-(4-methoxypyridin-2-yl)-5H,6H,7H-cyclopenta[d]pyrimidin-4-yl](methyl)amino]acetamide as a white solid. $^1$H NMR (300 MHz, DMSO-d$_6$) δ 8.49 (d, J=5.4 Hz, 1H), 7.86 (d, J=2.4 Hz, 1H), 7.69 (s, 1H), 7.06 (dd, J=5.7, 2.4 Hz, 1H), 4.14 (s, 2H), 3.92 (s, 3H), 3.27 (s, 3H), 3.14 (t, J=7.2 Hz, 2H), 2.82 (t, J=7.8 Hz, 2H), 1.99 (t, J=7.5 Hz, 2H), 1.23 (s, 9H). LCMS (ES) [M+1]$^+$ m/z: 370.2.

Example 1.66

Synthesis of N-tert-butyl-2-({2-[4-(methoxymethyl)pyridin-2-yl]-5H,6H,7H-cyclopenta[d]pyrimidin-4-yl}(methyl)amino)acetamide (Compound 35)

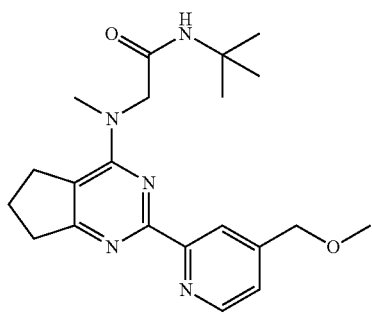 [SMILES: COCc1ccnc(-c2nc3c(c(N(C)CC(=O)NC(C)(C)C)n2)CCC3)c1]

Scheme 37 depicts a synthetic route for preparing an exemplary compound.

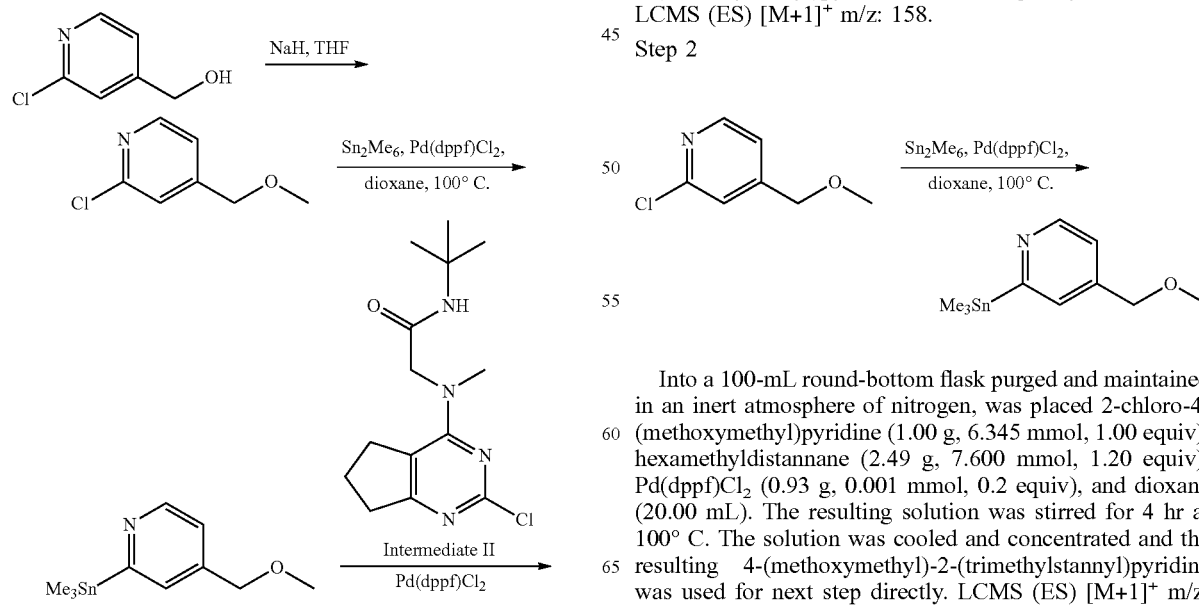

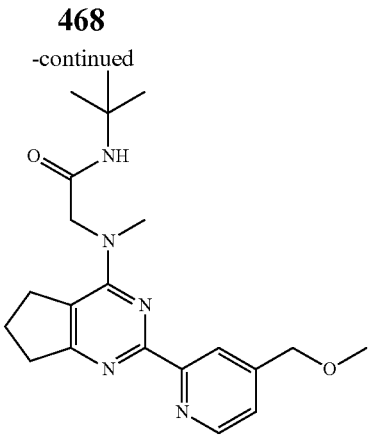

Step 1

Into a 100-mL round-bottom flask purged and maintained in an inert atmosphere of nitrogen, was placed (2-chloropyridin-4-yl)methanol (5.00 g, 34.826 mmol, 1.00 equiv), THF (20 mL). The resulting solution was stirred for 40 min at 0° C., and NaH (1.25 g, 52.088 mmol, 1.50 equiv) was added. The resulting solution was allowed to stir for an additional 4 hr at room temperature. The reaction was quenched by the addition of water. The resulting mixture was extracted with ethyl acetate (3×30 mL), the organic layers were combined, dried over anhydrous sodium sulfate and concentrated under vacuum. The residue was purified by silica gel column chromatography with ethyl acetate/petroleum ether (1:4). This resulted in 3.1 g (56.5%) of 2-chloro-4-(methoxymethyl)pyridine as a light yellow solid. LCMS (ES) [M+1]$^+$ m/z: 158.

Step 2

Into a 100-mL round-bottom flask purged and maintained in an inert atmosphere of nitrogen, was placed 2-chloro-4-(methoxymethyl)pyridine (1.00 g, 6.345 mmol, 1.00 equiv), hexamethyldistannane (2.49 g, 7.600 mmol, 1.20 equiv), Pd(dppf)Cl$_2$ (0.93 g, 0.001 mmol, 0.2 equiv), and dioxane (20.00 mL). The resulting solution was stirred for 4 hr at 100° C. The solution was cooled and concentrated and the resulting 4-(methoxymethyl)-2-(trimethylstannyl)pyridine was used for next step directly. LCMS (ES) [M+1]$^+$ m/z: 288.

Step 3

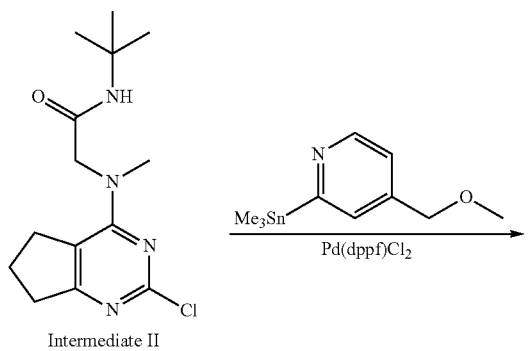

Intermediate II

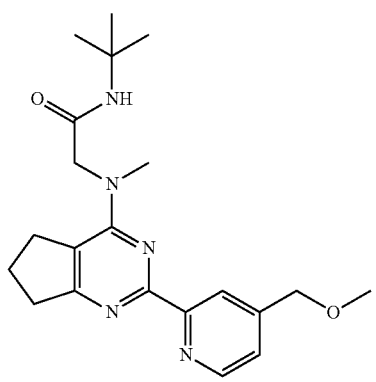

Into a 100-mL round-bottom flask purged and maintained in an inert atmosphere of nitrogen, was placed 4-(methoxymethyl)-2-(trimethylstannyl)pyridine (Intermediate II, 500.00 mg, 1.748 mmol, 1.00 equiv), N-(tert-butyl)-2-((2-chloro-6,7-dihydro-5H-cyclopenta[d]pyrimidin-4-yl)(methyl)amino)acetamide (415.16 mg, 1.399 mmol, 0.8 equiv), Pd(dppf)Cl$_2$ (255.87 mg, 0.350 mmol, 0.20 equiv), and dioxane (20.00 mL). The resulting solution was stirred for 16 seconds at 100° C. The resulting solution was cooled and extracted with ethyl acetate (3×20 mL). The organic layers were combined, dried over anhydrous sodium sulfate, and concentrated under vacuum. The crude product was purified by Prep-HPLC with the following conditions (2 #SHIMADZU (HPLC-01)): Column, Welch Xtimate C18, 21.2*250 mm, 5 um; mobile phase, Water (0.05% TFA) and MeOH:ACN=1:1 (10% PhaseB up to 60% in 17 min. This resulted in 51.2 mg (7.6%) of N-(tert-butyl)-2-((2-(4-(methoxymethyl)pyridin-2-yl)-6,7-dihydro-5H-cyclopenta[d]pyrimidin-4-yl)(methyl)amino)acetamide as a pink solid. $^1$H NMR (300 MHz, DMSO-d$_6$) δ 8.83 (dd, J=5.0, 0.8 Hz, 1H), 8.46-8.39 (m, 1H), 7.97 (s, 1H), 7.73 (dd, J=5.0, 1.7 Hz, 1H), 4.64 (s, 2H), 4.41 (s, 2H), 3.49 (s, 3H), 3.42 (s, 3H), 3.32-3.18 (m, 2H), 3.07 (t, J=7.9 Hz, 2H), 2.11 (p, J=7.7 Hz, 2H), 1.25 (s, 9H). LCMS (ES) [M+1]$^+$ m/z: 384.2.

Example 1.67

Synthesis of N-tert-butyl-2-{ethyl[2-(pyridin-2-yl)-5H,6H,7H-cyclopenta[d]pyrimidin-4-yl]amino}acetamide (Compound 36)

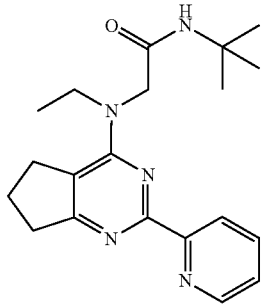 [SMILES: CCN(CC(=O)NC(C)(C)C)c1nc(-c2ccccn2)nc2c1CCC2]

Scheme 38 depicts a synthetic route for preparing an exemplary compound.

Scheme 38

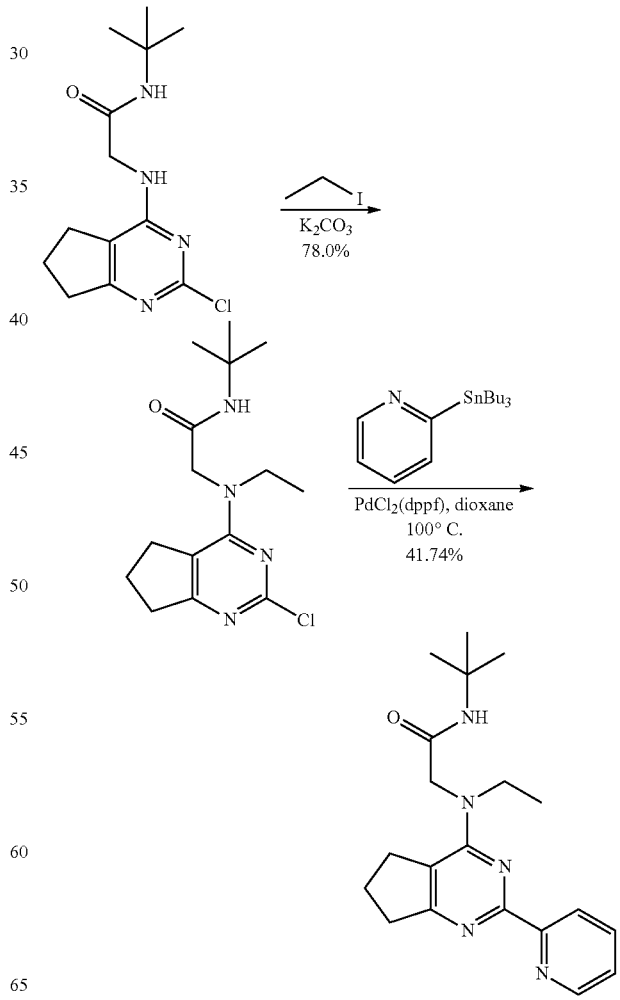

Step 1

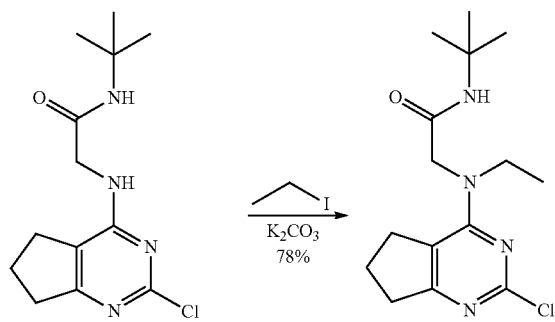

Into a 50-mL round-bottom flask, was placed a solution of N-(tert-butyl)-2-((2-chloro-6,7-dihydro-5H-cyclopenta[d]pyrimidin-4-yl)amino)acetamide (500.00 mg, 1.768 mmol, 1.00 equiv) in DMF (10 mL), ethyl iodide (303.36 mg, 1.945 mmol, 1.1 equiv) and K$_2$CO$_3$ (366.57 mg, 2.652 mmol, 1.5 equiv). The resulting solution was stirred for 3 hr at room temperature. The resulting solution was diluted with 50 mL of H$_2$O and extracted with 2×50 mL of ethyl acetate. Organic layers were combined, dried over anhydrous sodium sulfate, and concentrated under vacuum. This resulted in 390 mg (78.00%) of N-(tert-butyl)-2-((2-chloro-6,7-dihydro-5H-cyclopenta[d]pyrimidin-4-yl)(ethyl)amino)acetamide as a light yellow solid. LCMS (ES) [M+1]$^+$ m/z: 311.

Step 2

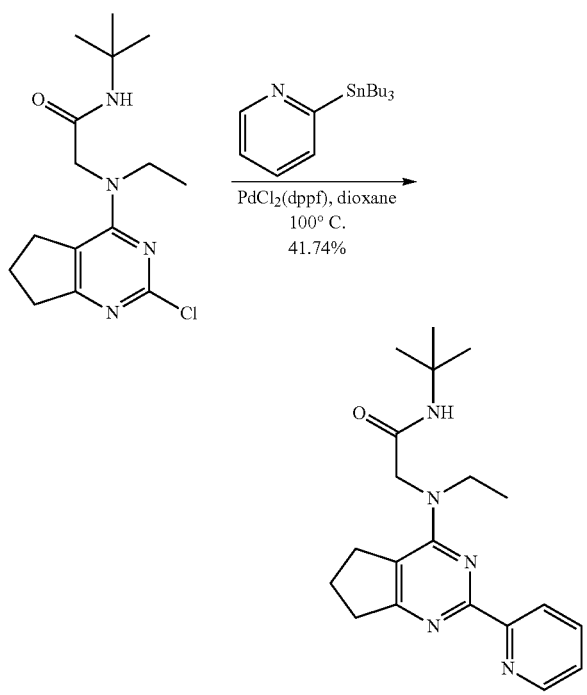

Into a 25-mL round-bottom flask purged and maintained in an inert atmosphere of nitrogen was placed a solution of N-(tert-butyl)-2-((2-chloro-6,7-dihydro-5H-cyclopenta[d]pyrimidin-4-yl)(ethyl)amino)acetamide (230.00 mg, 0.813 mmol, 1.00 equiv) in Tol (8 mL), 2-(tributylstannyl)pyridine (359.34 mg, 0.976 mmol, 1.2 equiv) and Pd(PPh$_3$)$_4$ (93.99 mg, 0.081 mmol, 0.1 equiv). The resulting solution was stirred for 12 hr at 100° C. in an oil bath. The resulting solution was diluted with 10 mL of H$_2$O and extracted with 2×15 mL of ethyl acetate. Organic layers were combined, dried over anhydrous sodium sulfate, and concentrated. The residue was applied onto a silica gel column with ethyl acetate/petroleum ether (1:1). The collected crude product was further purified by Flash-Prep-HPLC with the following conditions (IntelFlash-1): Column, C18 silica gel; mobile phase, CAN:H$_2$O=1:20 increasing to ACN:H$_2$O=1:4 within 15; Detector, 254 nm. product was obtained and concentrated. This resulted in 120 mg (41.74%) of N-(tert-butyl)-2-((2-chloro-6,7-dihydro-5H-cyclopenta[d]pyrimidin-4-yl)(ethyl)amino)acetamide as a solid. $^1$H NMR (300 MHz, DMSO-d$_6$) δ8.67 (dd, J=4.8, 1.9 Hz, 1H), 8.35 (d, J=8.1 Hz, 1H), 7.88 (td, J=7.7, 1.9 Hz, 1H), 7.71 (s, 1H), 7.44 (ddd, J=7.5, 4.7, 1.2 Hz, 1H), 4.10 (s, 2H), 3.66 (q, J=7.1 Hz, 2H), 3.09 (t, J=7.3 Hz, 2H), 2.83 (t, J=7.8 Hz, 2H), 2.08-1.95 (m, 2H), 1.23 (s, 9H), 1.19 (t, J=7.0 Hz, 3H). LCMS (ES) [M+1]$^+$ m/z 354.2.

Example 1.68

Synthesis of N-tert-butyl-2-[(2-hydroxyethyl)[2-(pyridin-2-yl)-5H,6H,7H-cyclopenta[d]pyrimidin-4-yl]amino]acetamide (Compound 37)

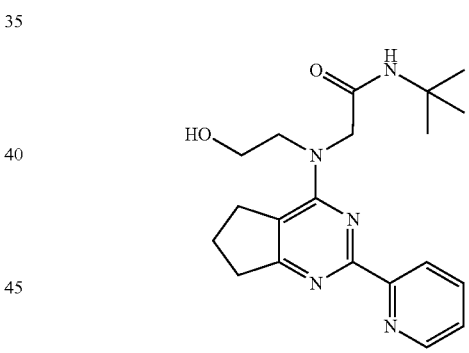

Scheme 39 depicts a synthetic route for preparing an exemplary compound.

Scheme 39

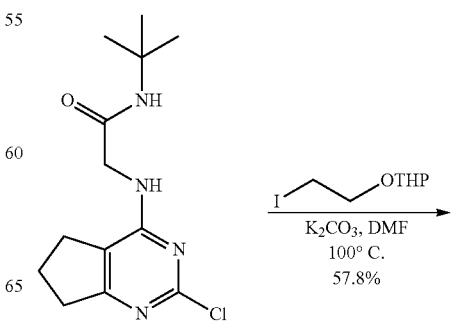

473
-continued

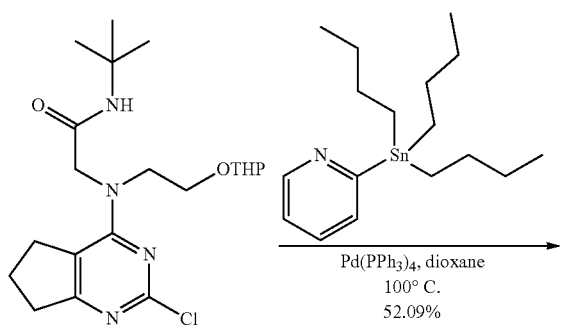

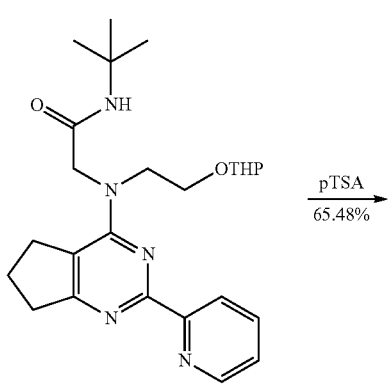

Step 1

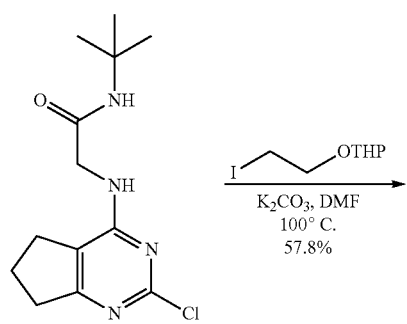

474
-continued

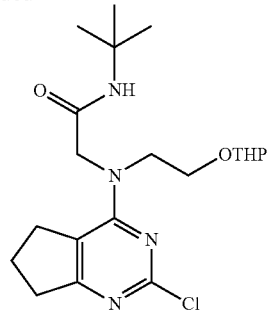

Into a 25-mL round-bottom flask purged and maintained in an inert atmosphere of nitrogen, was placed N-(tert-butyl)-2-((2-chloro-6,7-dihydro-5H-cyclopenta[d]pyrimidin-4-yl)amino)acetamide. The resulting solution was stirred for 12 hr at room temperature in an oil bath. The resulting solution was diluted with 25 mL of H$_2$O. The resulting solution was extracted with 2×25 mL of ethyl acetate, dried over anhydrous sodium sulfate, and concentrated. The residue was applied onto a silica gel column with ethyl acetate/petroleum ether (1:3). The collected fractions were combined and concentrated. This resulted in 420 mg (57.8%) of N-(tert-butyl)-2-((2-chloro-6,7-dihydro-5H-cyclopenta[d]pyrimidin-4-yl)(2-((tetrahydro-2H-pyran-2-yl)oxy)ethyl)amino)acetamide. LCMS (ES) [M+1]$^+$ m/z: 411.

Step 2

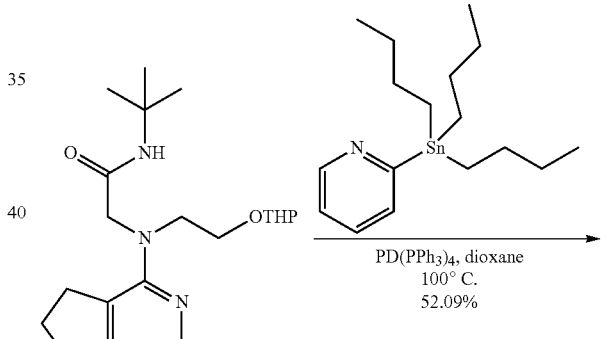

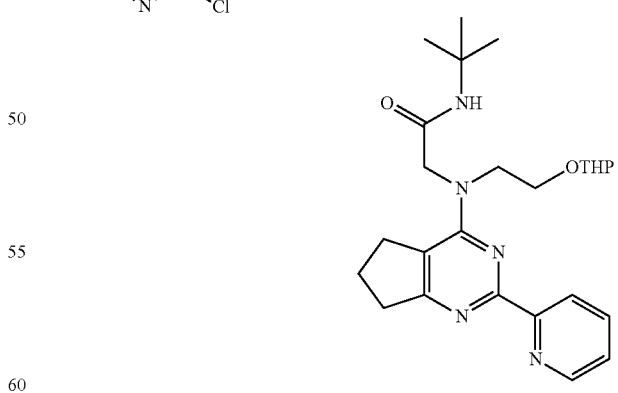

Into a 25-mL round-bottom flask purged and maintained in an inert atmosphere of nitrogen, was placed a solution of N-(tert-butyl)-2-((2-chloro-6,7-dihydro-5H-cyclopenta[d]pyrimidin-4-yl)(2-((tetrahydro-2H-pyran-2-yl)oxy)ethyl)amino)acetamide (400 mg, 0.97 mmol, 1.00 equiv) in dioxene (8 mL), 2-(tributylstannyl)pyridine (243 mg, 0.97 mmol, 1 equiv), and Pd(PPh₃)₄ (112 mg, 0.097 mmol, 0.1 equiv). The resulting solution was stirred for 12 hr at 100° C. in an oil bath. The resulting solution was diluted with 20 mL of H₂O and extracted with 3×20 mL of ethyl acetate. The organic layers were combined and concentrated. The residue was applied onto a silica gel column with ethyl acetate/petroleum ether (1:1). The collected fractions were combined and concentrated. This resulted in 230 mg (52.09%) of N-(tert-butyl)-2-((2-chloro-6,7-dihydro-5H-cyclopenta[d]pyrimidin-4-yl)(ethyl)amino)acetamide as a solid. LCMS (ES) [M+1]⁺ m/z: 454.

Step 3

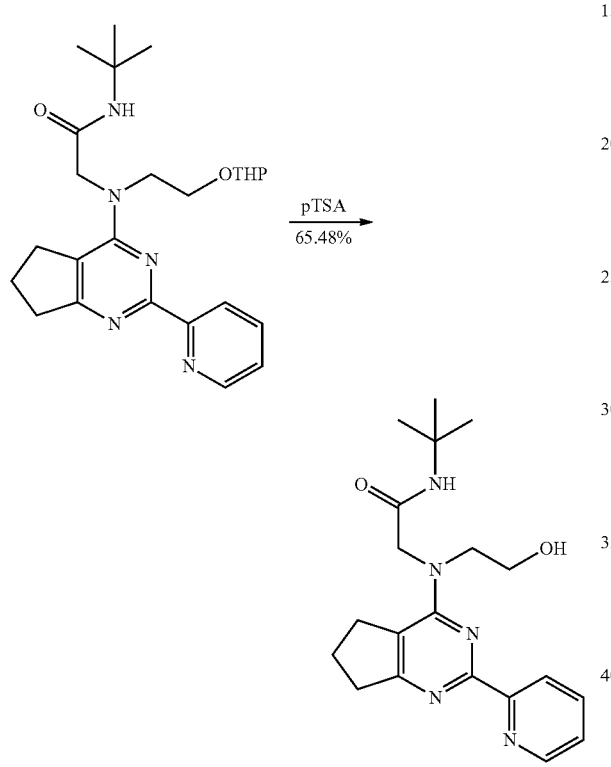

Into a 25-mL round-bottom flask, was placed a solution of N-(tert-butyl)-2-((2-chloro-6,7-dihydro-5H-cyclopenta[d]pyrimidin-4-yl)(ethyl)amino)acetamide (150.00 mg, 0.331 mmol, 1.00 equiv) in MeOH (7 mL), pTSA (5.69 mg, 0.033 mmol, 0.1 equiv). The resulting solution was stirred for 12 hr at room temperature. The resulting mixture was concentrated. The crude product was purified by Flash-Prep-HPLC with the following conditions (IntelFlash-1): Column, silica gel; mobile phase, ACN:H₂O (0.01% TFA)=1:15 increasing to ACN:H₂O (0.01% TFA)=1:3 within 9; Detector, UV 254 nm. This resulted in 80 mg (65.48%) of N-(tert-butyl)-2-((2-hydroxyethyl)(2-(pyridin-2-yl)-6,7-dihydro-5H-cyclopenta[d]pyrimidin-4-yl)amino)acetamide. LCMS (ES) [M+1]⁺ m/z: 370.2. ¹H NMR (300 MHz, DMSO-d₆) δ 8.67 (d, J=4.9 Hz, 1H), 8.36 (d, J=7.9 Hz, 1H), 7.93-7.80 (m, 2H), 7.48-7.40 (m, 1H), 5.15 (t, J=5.5 Hz, 1H), 4.16 (s, 2H), 3.78-3.61 (m, 4H), 3.10 (t, J=7.3 Hz, 2H), 2.83 (t, J=7.8 Hz, 2H), 2.06-1.96 (m, 2H), 1.22 (s, 9H).

Example 1.69

Synthesis of 2-{methyl[2-(pyridin-2-yl)-5H,6H,7H-cyclopenta[d]pyrimidin-4-yl]amino}-N-[(pyridin-2-yl)methyl]acetamide (Compound 38)

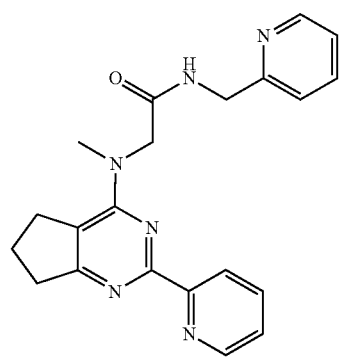 [SMILES: CN(CC(=O)NCc1ccccn1)c1nc(-c2ccccn2)nc2c1CCC2]

Scheme 40 depicts a synthetic route for preparing an exemplary compound.

Scheme 40

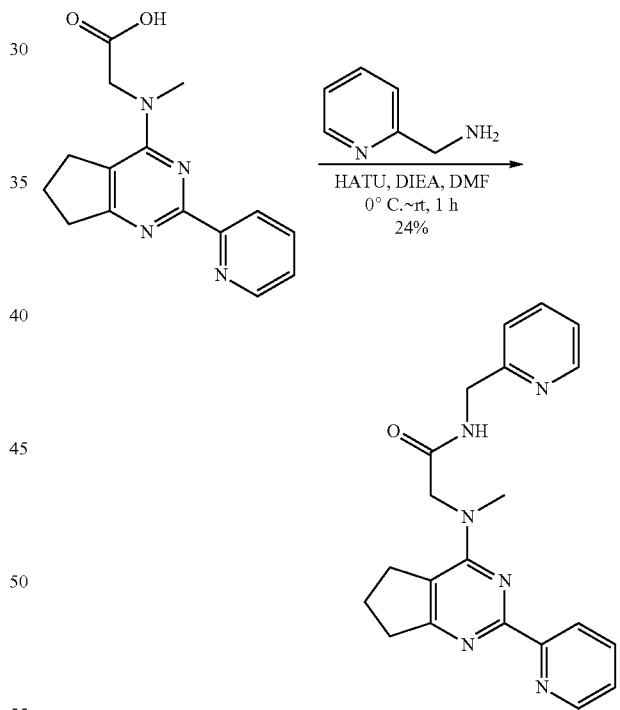

Into an 8-mL vial was placed [methyl[2-(pyridin-2-yl)-5H,6H,7H-cyclopenta[d]pyrimidin-4-yl]amino]acetic acid (200 mg, 0.70 mmol, 1.0 equiv), DMF (3.0 mL), 2-pyridinemethanamine (84 mg, 0.77 mmol, 1.1 equiv), and DIEA (455 mg, 3.52 mmol, 5.0 equiv). This was followed by the addition of HATU (401 mg, 1.06 mmol, 1.5 equiv) at 0° C. The mixture was stirred for 1 h at room temperature, filtered, and the filtrate was purified by Prep-HPLC with conditions: C18-120 g column, CH₃CN/H₂O (0.05% NH₄OH), from 5% to 80% with 15 min, flow rate, 70 mL/min, detector, 254 nm. This resulted in 62.8 mg (24%) of 2-[methyl[2-(pyridin-2- yl)-5H,6H,7H-cyclopenta[d]pyrimidin-4-yl]amino]-N-(pyridin-2-ylmethyl)acetamide formate as light brown solid. 1H-NMR (300 MHz, DMSO-d6, ppm): δ8.72 (t, J=6.0 Hz, 1H), 8.64 (dd, J=4.7, 1.8 Hz, 1H), 8.43 (dd, J=4.8, 1.9 Hz, 1H), 8.28 (dt, J=8.0, 1.1 Hz, 1H), 8.16 (s, 1H), 7.85 (td, J=7.7, 1.8 Hz, 1H), 7.44 (ddd, J=7.5, 4.7, 1.2 Hz, 1H), 7.35 (td, J=7.7, 1.8 Hz, 1H), 7.21-7.14 (m, 2H), 4.37 (d, J=6.0 Hz, 2H), 4.34 (s, 2H), 3.34 (s, 3H), 3.20 (t, J=7.2 Hz, 2H), 2.83 (t, J=7.8 Hz, 2H), 1.99 (p, J=7.7 Hz, 2H). LCMS: (ES, m/z): [M+H]+: 375.2.

Example 1.70

Synthesis of N-tert-butyl-2-({2-[6-(2-hydroxyethoxy)pyridin-2-yl]-5H,6H,7H-cyclopenta[d]pyrimidin-4-yl}(methyl)amino)acetamide (Compound 39)

Scheme 41 depicts a synthetic route for preparing an exemplary compound.

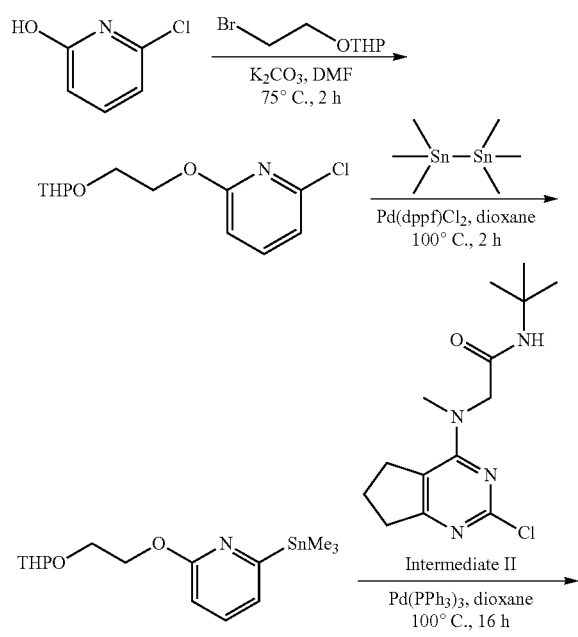

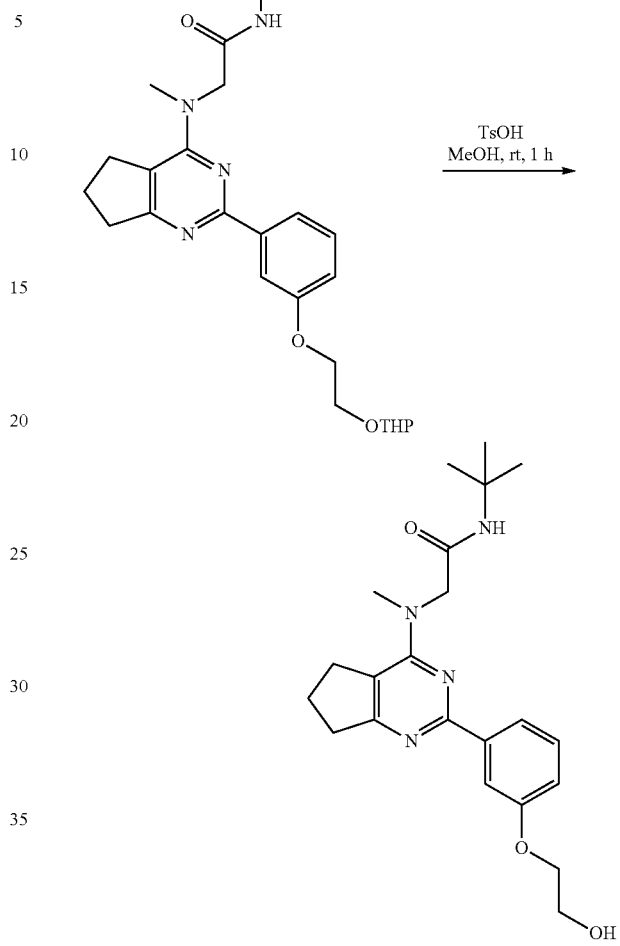

Step 1

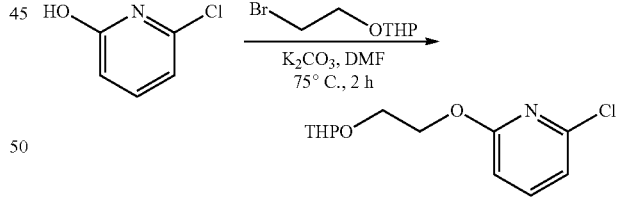

Into a 100-mL round-bottom flask, was placed 6-chloropyridin-2-ol (5.00 g, 38.59 mmol, 1.00 equiv), DMF (50.0 mL), 2-(2-bromoethoxy)oxane (9.68 g, 46.31 mmol, 1.20 equiv), and K$_2$CO$_3$ (10.67 g, 77.19 mmol, 2.00 equiv). The mixture was stirred for 2 h at 70° C. The reaction mixture was cooled and diluted with 200 mL of H$_2$O, and extracted with 3×50 mL of ethyl acetate. The organic layers were combined and dried over anhydrous sodium sulfate, filtered, and the filtrate was concentrated under reduced pressure. The residue was purified by silica gel column with ethyl acetate/petroleum ether (1/3) to give 9.0 g (90%) of 2-chloro-6-[2-(oxan-2-yloxy)ethoxy]pyridine as colorless oil. LCMS (ES) [M+1]$^+$ m/z: 258.

Step 2

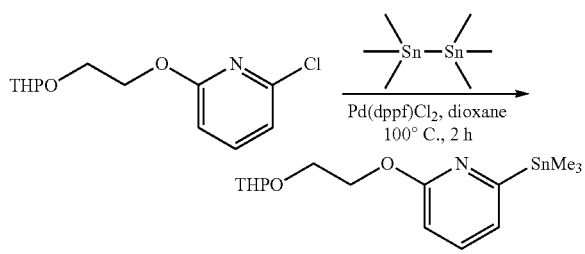

Into a 100-mL round-bottom flask purged and maintained in an inert atmosphere of nitrogen was placed 2-chloro-6-[2-(oxan-2-yloxy)ethoxy]pyridine (600 mg, 2.42 mmol, 1.00 equiv), dioxane (10.0 mL), hexamethyldistannane (872 mg, 2.66 mmol, 1.10 equiv) and Pd(dppf)Cl$_2$ (177 mg, 0.24 mmol, 0.10 equiv). The mixture was stirred for 2 h at 100° C. The reaction mixture was cooled and diluted with 20 mL of H$_2$O, and extracted with 3×10 mL of ethyl acetate. The organic layers were combined and dried over anhydrous sodium sulfate, filtered, and the filtrate was concentrated under reduced pressure. This resulted in 500 mg of 2-[2-(oxan-2-yloxy)ethoxy]-6-(trimethylstannyl)pyridine as brown oil and the crude product was used to the next step directly without purification. LCMS (ES) [M+1]$^+$ m/z: 388.

Step 3

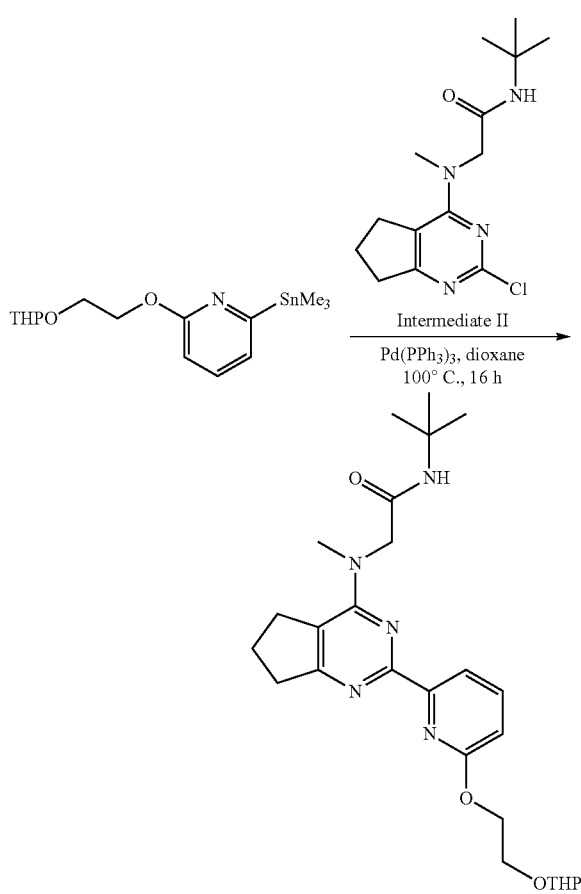

Into a 100-mL round-bottom flask purged and maintained in an inert atmosphere of nitrogen, was placed 2-[2-(oxan-2-yloxy)ethoxy]-6-(trimethylstannyl)pyridine (468 mg, 1.21 mmol, 1.20 equiv), dioxane (5.0 mL), N-tert-butyl-2-([2-chloro-5H,6H,7H-cyclopenta[d]pyrimidin-4-yl](methyl)amino)acetamide (300 mg, 1.01 mmol, 1.00 equiv), and Pd(PPh$_3$)$_4$ (116 mg, 0.10 mmol, 0.10 equiv). The mixture was stirred for 16 h at 100° C. The reaction mixture was cooled and diluted with 20 mL of EA, filtered, and the filtrate was concentrated under reduced pressure. The residue was purified by silica gel column with ethyl acetate/petroleum ether (4/1). This resulted in 400 mg (82%) of N-tert-butyl-2-[methyl(2-[6-[2-(oxan-2-yloxy)ethoxy]pyridin-2-yl]-5H,6H,7H-cyclopenta[d]pyrimidin-4-yl)amino]acetamide as brown solid. LCMS (ES) [M+1]$^+$ m/z: 484.

Step 4

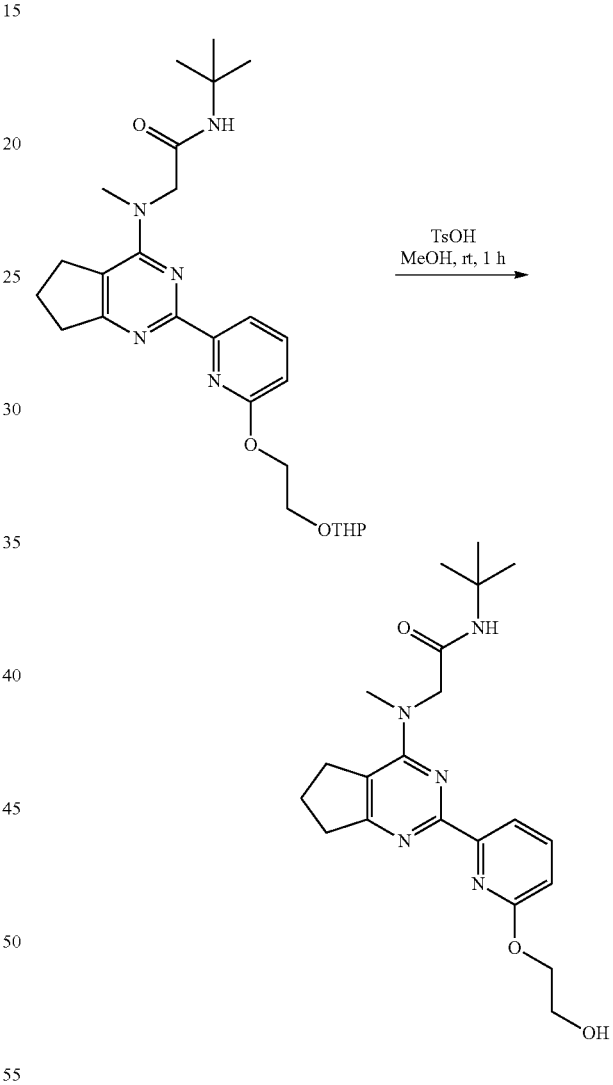

Into a 100-mL round-bottom flask was placed N-tert-butyl-2-[methyl(2-[6-[2-(oxan-2-yloxy)ethoxy]pyridin-2-yl]-5H,6H,7H-cyclopenta[d]pyrimidin-4-yl)amino]acetamide (400 mg, 0.82 mmol, 1.00 equiv), MeOH (5.0 mL), and TsOH (142 mg, 0.82 mmol, 1.00 equiv). The resulting solution was stirred for 1 h at room temperature. The resulting mixture was concentrated and diluted with 5 mL of H$_2$O. The pH value of the solution was adjusted to 8 with NH$_3$·H$_2$O (30%). The mixture was extracted with 3×5 mL of ethyl acetate, the organic layers were combined, dried over anhydrous sodium sulfate, filtered, and the filtrate was concentrated. The residue was purified by Prep-HPLC with the following conditions: Column, Welch XB-C18, 21.2*250 mm, 5 um, Mobile phase, Water (0.05% NH₄OH) and CH₃CN (10% Phase B up to 65% in 15 min), Detector, UV 254 nm. This resulted in 121.1 mg (36.6%) of N-tert-butyl-2-([2-[6-(2-hydroxyethoxy)pyridin-2-yl]-5H,6H,7H-cyclopenta[d]pyrimidin-4-yl](methyl)amino)acetamide as white solid. ¹H NMR (300 MHz, DMSO-d₆) δ 7.96 (d, J=7.2 Hz, 1H), 7.79 (t, J=7.8 Hz, 1H), 7.63 (s, 1H), 6.89 (d, J=8.1 Hz, 1H), 5.18 (br, 1H), 4.43-4.39 (m, 2H), 4.16 (s, 2H), 3.79-3.75 (m, 2H), 3.27 (s, 3H), 3.13 (t, J=7.5 Hz, 2H), 2.82 (t, J=7.8 Hz, 2H), 2.04-1.96 (m, 2H), 1.23 (s, 9H). LCMS (ES) [M+1]⁺ m/z: 400.2.

Example 1.71

Synthesis of N-tert-butyl-2-({2-[5-(2-hydroxy-ethoxy)pyridin-2-yl]-5H,6H,7H-cyclopenta[d]py-rimidin-4-yl}(methyl)amino)acetamide (Compound 40)

Scheme 42 depicts a synthetic route for preparing an exemplary compound.

Scheme 42

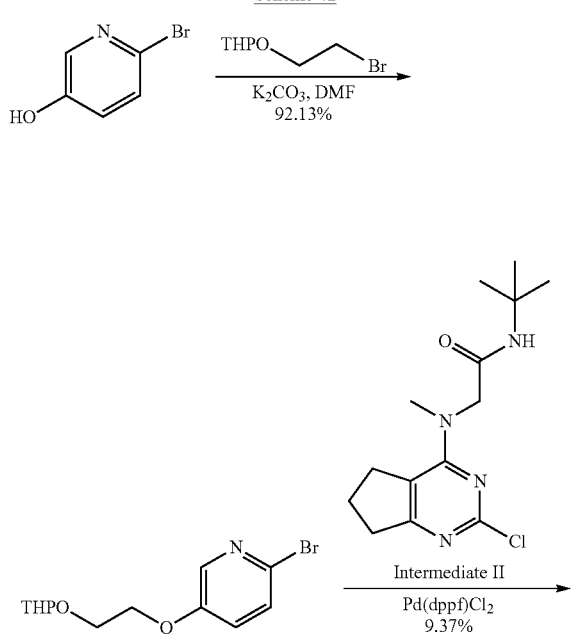

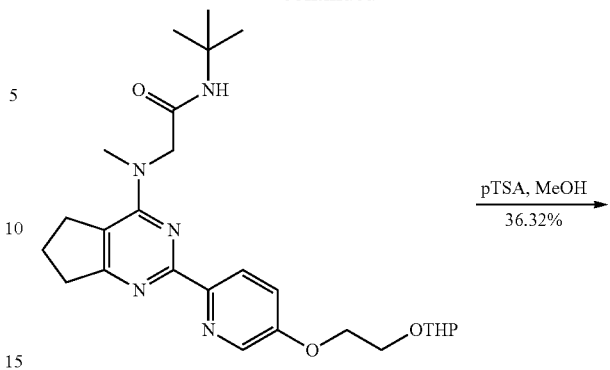

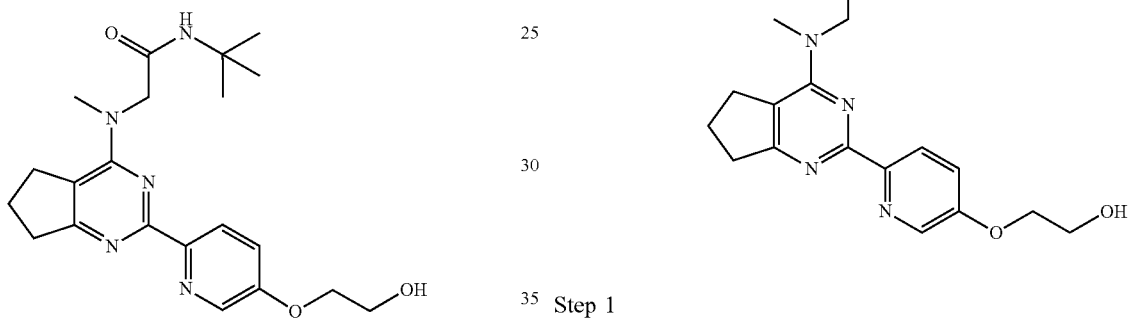

Step 1

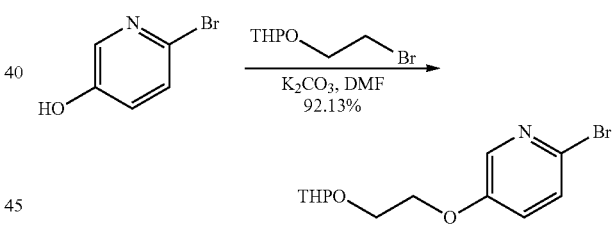

Into a 250-mL round-bottom flask was placed 6-bromopyridin-3-ol (2.00 g, 11.49 mmol, 1.00 equiv), DMF (30.00 mL), 2-(2-bromoethoxy)oxane (2.88 g, 13.79 mmol, 1.20 equiv), and K₂CO₃ (3.18 g, 22.99 mmol, 2.00 equiv). The resulting solution was stirred for 2 h at 70° C. The reaction mixture was cooled to room temperature. The reaction was then quenched by the addition of 50 mL of water. The resulting mixture was extracted with 3×50 mL of ethyl acetate, the organic layers were combined, dried over anhydrous sodium sulfate, and concentrated. The residue was applied onto a silica gel column with ethyl acetate/petroleum ether (15%). This resulted in 3.2 g (92.13%) of 2-bromo-5-[2-(oxan-2-yloxy)ethoxy]pyridine as a yellow oil. LCMS (ES) [M+H]+ m/z: 302.

Step 2

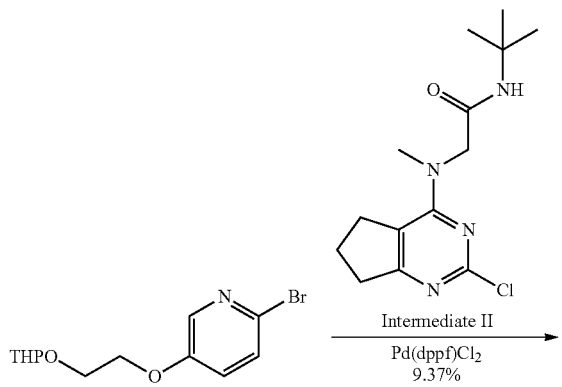

Step 3

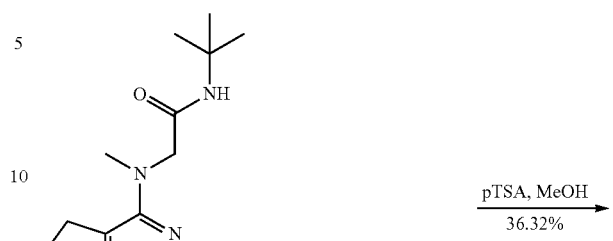

Into a 100-mL round-bottom flask, was placed 2-bromo-5-[2-(oxan-2-yloxy)ethoxy]pyridine (1.00 g, 3.31 mmol, 1.00 equiv), hexamethyldistannane (1.30 g, 3.97 mmol, 1.20 equiv), Pd(PPh3)4 (0.38 g, 0.33 mmol, 0.1 equiv), and dioxane (10.00 mL). The resulting solution was stirred for 3 h at 100° C. The reaction mixture was cooled to room temperature and was added N-tert-butyl-2-([2-chloro-5H,6H,7H-cyclopenta[d]pyrimidin-4-yl](methyl)amino)acetamide (Intermediate II, 0.49 g, 1.65 mmol, 0.50 equiv) and Pd(dppf)Cl$_2$ (0.24 g, 0.33 mmol, 0.10 equiv). The resulting solution was stirred for 5 h at 100° C. The reaction mixture was cooled to room temperature. The crude product (1 g) was purified by Prep-HPLC with the following conditions: Column, XBridge Prep C18 OBD Column, 19 cm, 150 mm, 5 um; mobile phase, Water (0.1% NH4HCO3) and CAN (30% Phase B up to 60% in 11 min); Detector, 254 nm. This resulted in 150 mg (9.37%) of N-tert-butyl-2-[methyl(2-[5-[2-(oxan-2-yloxy)ethoxy]pyridin-2-yl]-5H,6H,7H-cyclopenta[d]pyrimidin-4-yl)amino]acetamide as yellow solid. LCMS (ES) [M+H]+ m/z: 484.

Into an 8-mL vial was placed N-tert-butyl-2-[methyl(2-[5-[2-(oxan-2-yloxy)ethoxy]pyridin-2-yl]-5H,6H,7H-cyclopenta[d]pyrimidin-4-yl)amino]acetamide (150.00 mg, 0.31 mmol, 1.00 equiv), MeOH (5.00 mL) and PTSA (10.68 mg, 0.06 mmol, 0.20 equiv). The resulting solution was stirred for 1 h at room temperature. The crude product (150 mg) was purified by Prep-HPLC with the following conditions: Column, XBridge Prep C18 OBD Column, 19 cm, 150 mm, 5 um; mobile phase, Water (0.1% NH$_4$HCO$_3$) and CAN (20% Phase B up to 50% in 11 min); Detector, 254 nm. This resulted in 45.0 mg (36.32%) of N-tert-butyl-2-([2-[5-(2-hydroxyethoxy)pyridin-2-yl]-5H,6H,7H-cyclopenta[d]pyrimidin-4-yl](methyl)amino)acetamide as a white solid. 1H-NMR (300 MHz, DMSO-d6) δ 8.38-8.27 (m, 2H), 7.68 (s, 1H), 7.43 (dd, J=8.8, 3.0 Hz, 1H), 4.94 (t, J=5.5 Hz, 1H), 4.18-4.09 (m, 4H), 3.78-3.73 (m, 2H), 3.25 (s, 3H), 3.12 (t, J=7.3 Hz, 2H), 2.79 (t, J=7.8 Hz, 2H), 2.10-1.89 (m, 2H), 1.24 (s, 9H). LCMS: (ES, m/z): [M+H]+: 400.3.

Example 1.72

Synthesis of N-tert-butyl-2-({2-[4-(hydroxymethyl)pyridin-2-yl]-5H,6H,7H-cyclopenta[d]pyrimidin-4-yl}(methyl)amino)acetamide (Compound 41)

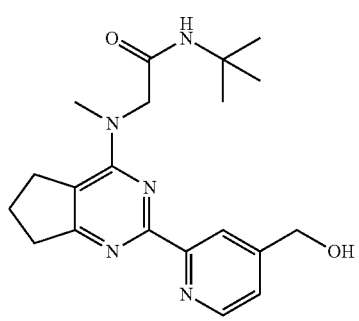 [SMILES: CN(CC(=O)NC(C)(C)C)c1nc(-c2cc(CO)ccn2)nc2c1CCC2]

Scheme 43 depicts a synthetic route for preparing an exemplary compound.

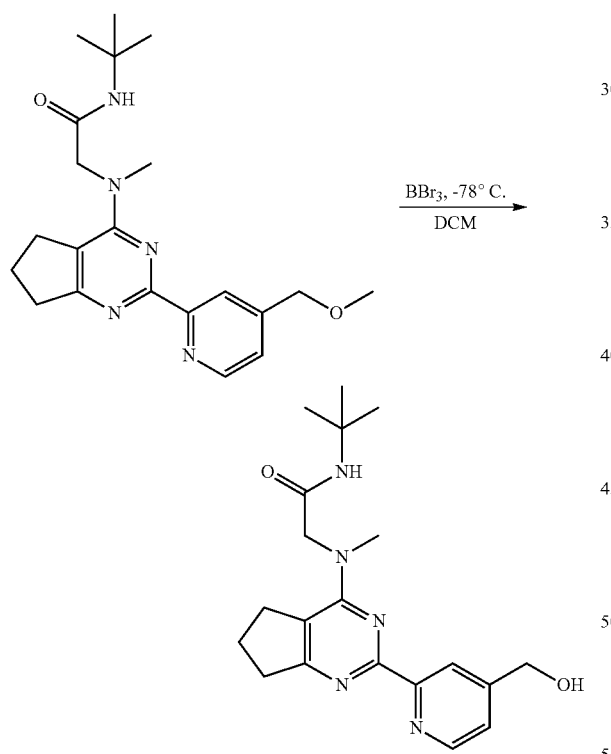

Into a 50-mL round-bottom flask purged and maintained in an inert atmosphere of nitrogen, was placed N-(tert-butyl)-2-((2-(4-(methoxymethyl)pyridin-2-yl)-6,7-dihydro-5H-cyclopenta[d]pyrimidin-4-yl)(methyl)amino)acetamide (100 mg, 0.261 mmol, 1.00 equiv), BBr$_3$ (0.78 mL, 0.780 mmol, 2.99 equiv), and DCM (10.00 mL). The resulting solution was stirred for 4 hr at −78° C. The reaction was quenched by the addition of water. The resulting solution was extracted with dichloromethane (3×20 mL), the organic layers were combined, dried over anhydrous sodium sulfate, and concentrated under vacuum. The crude product was purified by Prep-HPLC with the following conditions (2 #SHIMADZU (HPLC-01)): Column, Welch XB-C18, 21.2*250 mm, 5 um; mobile phase, Water (0.05% NH$_3$H$_2$O) and AcCN (5% Phase B up to 50% in 16 min). This resulted in 30.2 mg (31.4%) of N-(tert-butyl)-2-((2-(4-(hydroxymethyl)pyridin-2-yl)-6,7-dihydro-5H-cyclopenta[d]pyrimidin-4-yl)(methyl)amino)acetamide as a white solid. $^1$H NMR (300 MHz, DMSO-d$_6$) δ 8.60 (d, J=4.9 Hz, 1H), 8.26 (s, 1H), 7.68 (s, 1H), 7.39 (d, J=5.0 Hz, 1H), 5.48 (br, 1H), 4.62 (s, 2H), 4.16 (s, 2H), 3.32 (s, 3H), 3.14 (t, J=7.3 Hz, 2H), 2.82 (t, J=7.8 Hz, 2H), 1.99 (p, J=7.5 Hz, 2H), 1.24 (s, 9H). LCMS (ES) [M+1]$^+$ m/z: 370.2.

Example 1.73

Synthesis of N-tert-butyl-2-{methyl[2-(4-methylpyridin-2-yl)-5,6,7,8-tetrahydroquinazolin-4-yl]amino}acetamide (Compound 42)

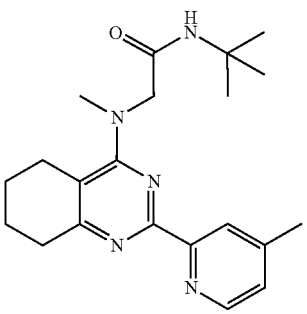 [SMILES: Cc1ccnc(-c2nc3c(c(N(C)CC(=O)NC(C)(C)C)n2)CCCC3)c1]

Scheme 44 depicts a synthetic route for preparing an exemplary compound.

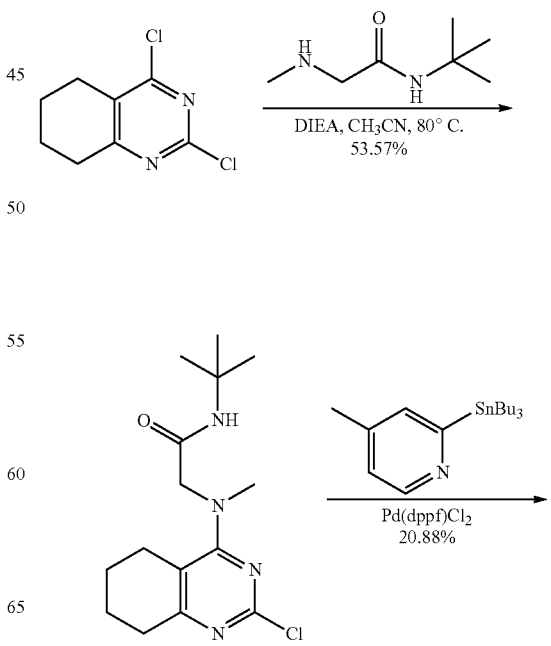

Step 2

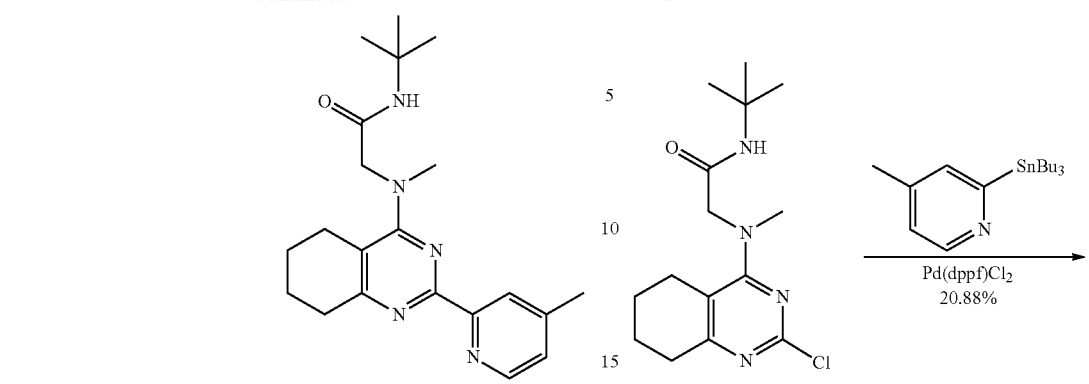

Step 1

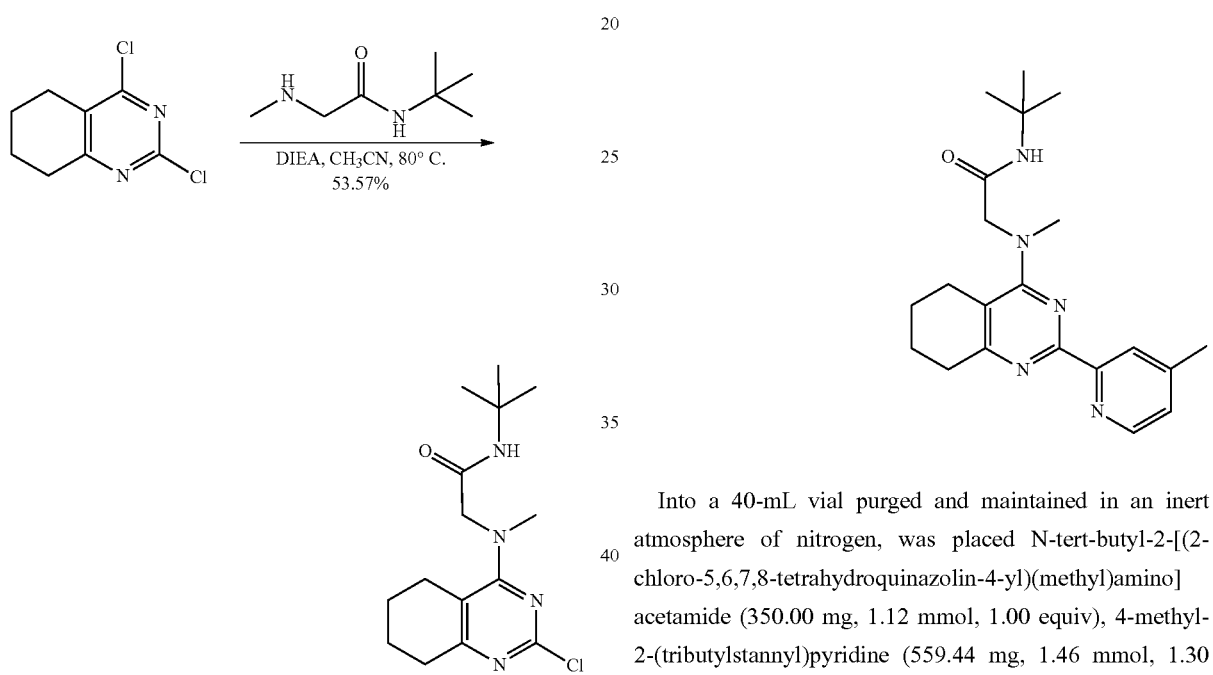

Into a 40-mL vial, was placed 2,4-dichloro-5,6,7,8-tetrahydroquinazoline (500.00 mg, 2.46 mmol, 1.00 equiv), $CH_3CN$ (8.00 mL), DIEA (636.45 mg, 4.92 mmol, 2.00 equiv), and N-tert-butyl-2-(methylamino)acetamide (390.60 mg, 2.71 mmol, 1.10 equiv). The resulting solution was stirred for 3 h at 80° C. The reaction mixture was cooled to room temperature. The crude product (1 g) was purified by Prep-HPLC with the following conditions: Column, XBridge Prep C18 OBD Column, 19 cm, 150 mm, 5 um; mobile phase, Water (0.1% $NH_4HCO_3$) and CAN (30% Phase B up to 60% in 11 min); Detector, 254. This resulted in 410 mg (53.57%) of N-tert-butyl-2-[(2-chloro-5,6,7,8-tetrahydroquinazolin-4-yl)(methyl)amino]acetamide as a white solid. LCMS (ES) [M+H]⁺ m/z: 311.

Into a 40-mL vial purged and maintained in an inert atmosphere of nitrogen, was placed N-tert-butyl-2-[(2-chloro-5,6,7,8-tetrahydroquinazolin-4-yl)(methyl)amino]acetamide (350.00 mg, 1.12 mmol, 1.00 equiv), 4-methyl-2-(tributylstannyl)pyridine (559.44 mg, 1.46 mmol, 1.30 equiv), and dioxane (8.00 mL), Pd(dppf)Cl₂ (82.39 mg, 0.11 mmol, 0.10 equiv). The resulting solution was stirred for overnight at 110° C. The reaction mixture was cooled to room temperature. The resulting mixture was concentrated. The crude product (500 mg) was purified by Prep-HPLC with the following conditions: Column, XBridge Prep C18 OBD Column, 19 cm, 150 mm, 5 um; mobile phase, Water (0.1% $NH_4HCO_3$) and CAN (30% Phase B up to 60% in 11 min); Detector, 254. This resulted in 86.4 mg (20.88%) of N-tert-butyl-2-[methyl[2-(4-methylpyridin-2-yl)-5,6,7,8-tetrahydroquinazolin-4-yl]amino]acetamide as an off-white solid. ¹H-NMR (300 MHz, DMSO-d6) δ 8.51 (d, J=4.9 Hz, 1H), 8.15 (d, J=1.6 Hz, 1H), 7.77 (s, 1H), 7.31-7.23 (m, 1H), 3.99 (s, 2H), 3.15 (s, 3H), 2.78 (t, J=6.4 Hz, 2H), 2.69 (t, J=6.0 Hz, 2H), 2.40 (s, 3H), 1.82 (s, 2H), 1.68 (d, J=6.9 Hz, 2H), 1.22 (s, 9H). LCMS (ES, m/z): [M+H]⁺: 368.2.

Example 1.74

Synthesis of N-tert-butyl-2-({2-[5-(2-hydroxyethyl)pyridin-2-yl]-5H,6H,7H-cyclopenta[d]pyrimidin-4-yl}(methyl)amino)acetamide (Compound 43)

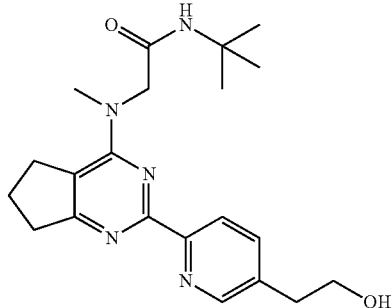 [SMILES: CN(CC(=O)NC(C)(C)C)c1nc(-c2ccc(CCO)cn2)nc2c1CCC2]

Scheme 45 depicts a synthetic route for preparing an exemplary compound.

Scheme 45

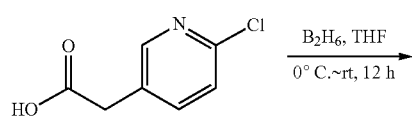

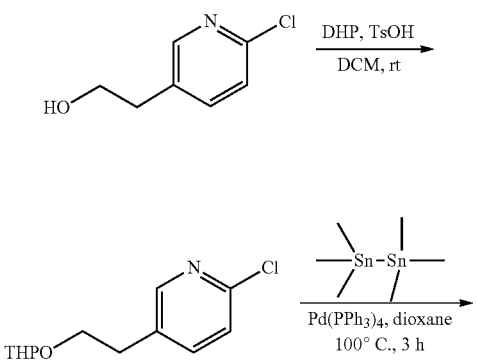

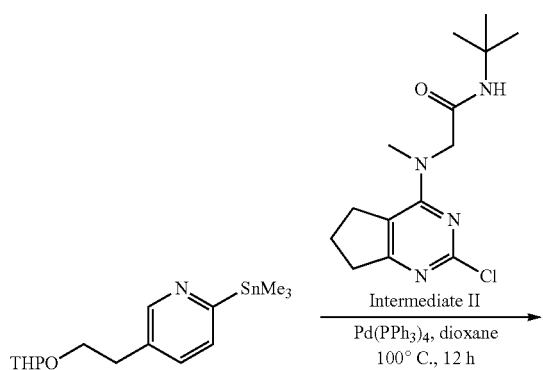

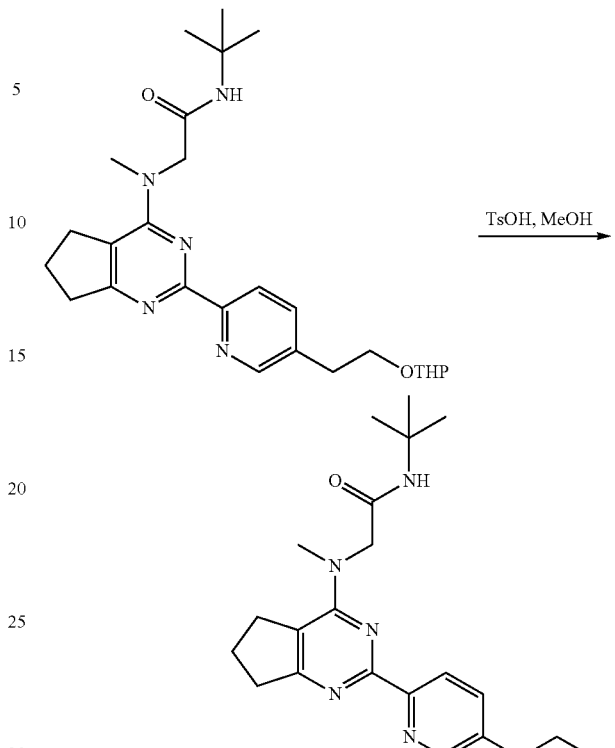

Step 1

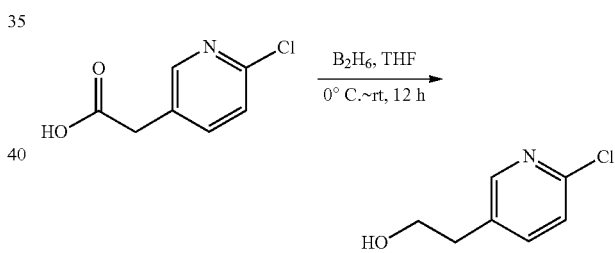

Into a 250-mL 3-necked round-bottom flask, was placed (6-chloropyridin-3-yl)acetic acid (5.0 g, 29.14 mmol, 1.0 equiv), THF (50.0 mL). This was followed by the addition of B₂H₆ (1 M in THF) (88.0 mL, 3.0 eq) at 0° C. After addition, the mixture was stirred for 12 h at room temperature. The reaction was then quenched by the addition of MeOH (30 mL), diluted with of H₂O (100 mL), and extracted with 3×100 mL of dichloromethane. The combined organic phase was dried over anhydrous sodium sulfate, filtered, and the filtrate was concentrated under reduced pressure. This resulted in 3.09 g (67%) of 2-(6-chloropyridin-3-yl)ethanol as yellow oil. LCMS (ES) [M+1]⁺ m/z: 158.

Step 2

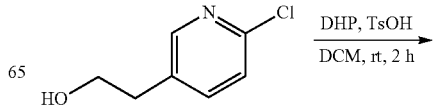

-continued

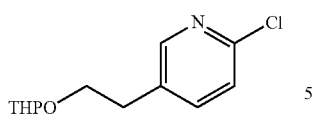

Into a 100-mL round-bottom flask, was placed 2-(6-chloropyridin-3-yl)ethanol (3.09 g, 19.61 mmol, 1.0 equiv), DCM (30.0 mL), DHP (3.30 g, 39.23 mmol, 2.0 equiv), and TsOH (340 mg, 1.97 mmol, 0.10 equiv). The reaction solution was stirred for 2 h at room temperature. The mixture was diluted with of saturated Na$_2$CO$_3$ (20.0 mL), and extracted with 3×50 mL of dichloromethane. The combined organic phase was dried over anhydrous sodium sulfate, filtered, and the filtrate was concentrated under reduced pressure. The residue was purified by silica gel column with ethyl acetate/petroleum ether (7%). This resulted in 3.0 g (63%) of 2-chloro-5-(2-((tetrahydro-2H-pyran-2-yl)oxy)ethyl)pyridine as a yellow oil. LCMS (ES) [M+1]$^+$ m/z: 242.

Step 3

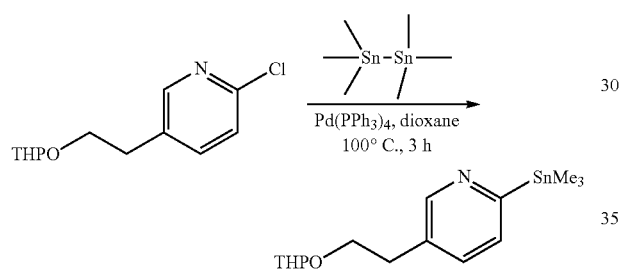

Into a 100-mL round-bottom flask purged and maintained in an inert atmosphere of nitrogen, was placed 2-chloro-5-[2-(oxan-2-yloxy)ethyl]pyridine (1.17 g, 4.84 mmol, 1.0 equiv), dioxane (30.0 mL), hexamethyldistannane (1.60 g, 4.88 mmol, 1.0 equiv), and Pd(PPh$_3$)$_4$ (1.44 g, 1.25 mmol, 0.26 equiv). The mixture was stirred for 2 h at 100° C. The reaction was cooled to room temperature, filtered, and the filtrate was concentrated under reduced pressure. The crude product was used to the next step directly without further purification. LCMS (ES) [M+1]$^+$ m/z: 372.

Step 4

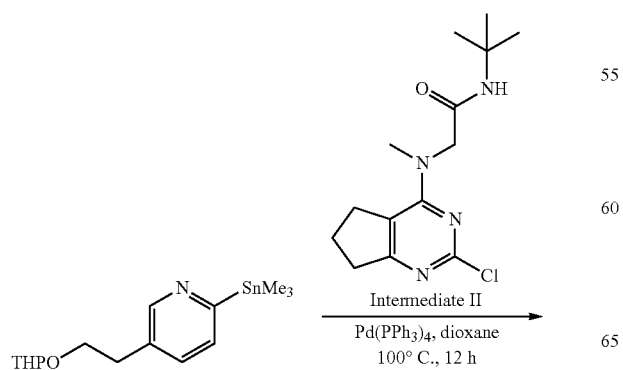

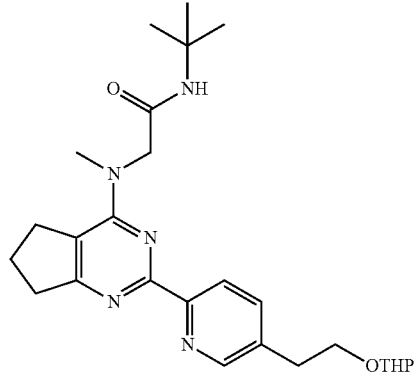

Into a 100-mL round-bottom flask purged and maintained in an inert atmosphere of nitrogen, was placed 5-[2-(oxan-2-yloxy)ethyl]-2-(trimethylstannyl)pyridine (1.50 g, 4.05 mmol, 1.0 equiv), dioxane (20.0 mL), N-tert-butyl-2-([2-chloro-5H,6H,7H-cyclopenta[d]pyrimidin-4-yl](methyl)amino)acetamide (Intermediate II, 700 mg, 2.36 mmol, 0.58 equiv), and Pd(PPh$_3$)$_4$ (932.00 mg, 0.81 mmol, 0.20 equiv). The mixture was stirred for 12 h at 100° C. The mixture was concentrated to remove the solvent, and the residue was purified by silica gel column with THF/petroleum ether (70%). This resulted in 184 mg (9.7%) of N-(tert-butyl)-2-(methyl(2-(5-(2-((tetrahydro-2H-pyran-2-yl)oxy)ethyl)pyridin-2-yl)-6,7-dihydro-5H-cyclopenta[d]pyrimidin-4-yl)amino)acetamide as yellow oil. LCMS (ES) [M+1]$^+$ m/z: 468.

Step 5

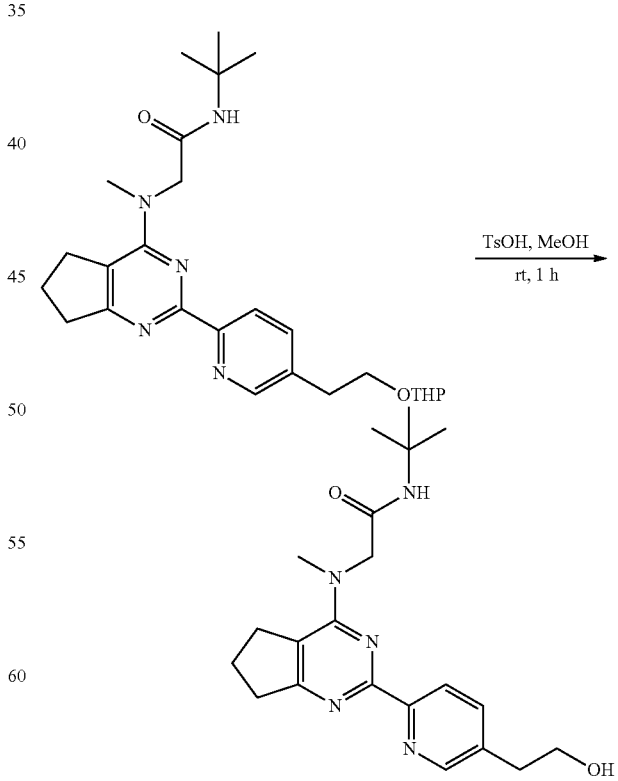

Into a 20-mL vial, was placed N-tert-butyl-2-[methyl(2-[5-[2-(oxan-2-yloxy)ethyl]pyridin-2-yl]-5H,6H,7H-cyclopenta[d]pyrimidin-4-yl)amino]acetamide (184 mg, 0.39 mmol, 1.0 equiv), methanol (5.0 mL), and TsOH (68 mg, 0.40 mmol, 1.0 equiv). The mixture was stirred for 1 h at room temperature. The crude product was purified by Prep-HPLC with the following conditions: Column, Atlantis HILIC OBD Column, 19*150 mm*5 um, mobile phase, Water (10 mmol/L NH₄HCO₃) and MeOH:CH₃CN=1:1 (33% Phase B up to 45% within 9 min); Detector, UV 254 nm. This resulted in 89.2 mg (59%) of N-(tert-butyl)-2-((2-(5-(2-hydroxyethyl)pyridin-2-yl)-6,7-dihydro-5H-cyclopenta[d]pyrimidin-4-yl)(methyl)amino)acetamide as an off-white solid. ¹H-NMR (300 MHz, DMSO-d₆, ppm): δ 8.51 (d, J=1.8 Hz, 1H), 8.25 (d, J=8.1 Hz, 1H), 7.72 (dd, J=8.1, 2.1 Hz, 1H), 7.68 (s, 1H), 4.72 (t, J=5.1 Hz, 1H), 4.13 (s, 2H), 3.70-3.63 (m, 2H), 3.26 (s, 3H), 3.14 (t, J=7.2 Hz, 2H), 2.84-2.78 (m, 4H), 2.04-1.96 (m, 2H), 1.25 (s, 9H). LCMS: (ES, m/z): [M+H]⁺: 384.2.

Example 1.75

Synthesis of N-tert-butyl-2-({2-[4-(2-hydroxyethoxy)pyridin-2-yl]-5H,6H,7H-cyclopenta[d]pyrimidin-4-yl}(methyl)amino)acetamide (Compound 44)

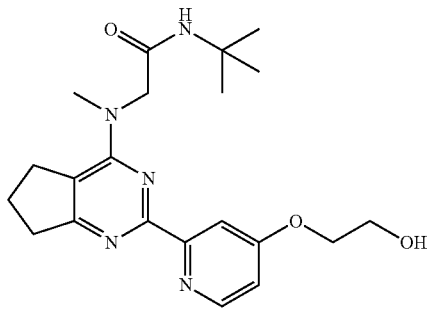 [SMILES: CN(CC(=O)NC(C)(C)C)c1nc(-c2cc(OCCO)ccn2)nc2c1CCC2]

Scheme 46a depicts a synthetic route for preparing an exemplary compound.

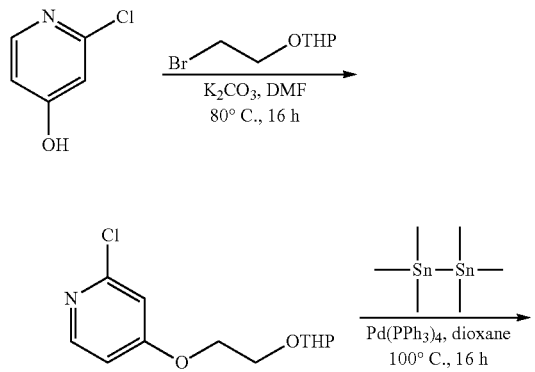

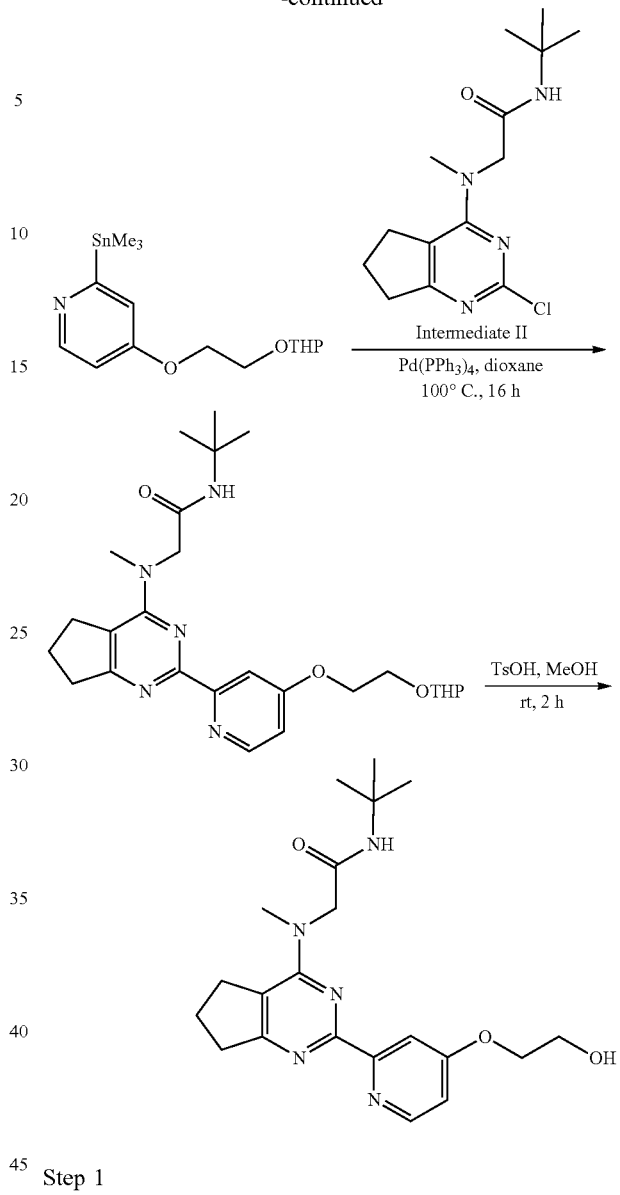

Step 1

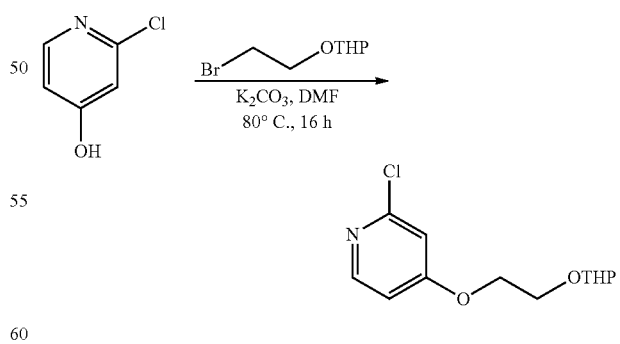

Into a 50-mL round-bottom flask was placed a mixture of 2-chloropyridin-4-ol (2.00 g, 15.439 mmol, 1.00 equiv), DMF (20 ml), K₂CO₃ (4.27 g, 30.878 mmol, 2.00 equiv), and 2-(2-bromoethoxy)oxane (4.84 g, 23.159 mmol, 1.50 equiv). The resulting solution was stirred for 16 hours at 70° C. The resulting solution was diluted with 100 mL of H₂O. The resulting solution was extracted with 3×100 mL of ethyl acetate. The organic layers were combined, washed with 100 ml of brine, dried over anhydrous sodium sulfate, and concentrated. This resulted in 2.15 g (54.04%) of 2-chloro-4-[2-(oxan-2-yloxy)ethoxy]pyridine as a light yellow oil. LCMS (ES) [M+1]+ m/z: 258.

Step 2

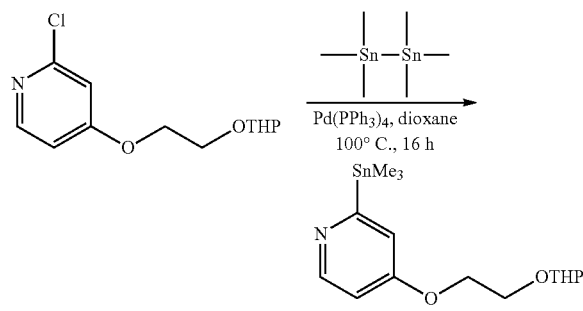

Into a 40-mL vial, was placed a mixture of 2-chloro-4-[2-(oxan-2-yloxy)ethoxy]pyridine (1.00 g, 3.88 mmol, 1.00 equiv), dioxane (10.0 mL), hexamethyldistannane (1.91 g, 5.82 mmol, 1.50 equiv), and Pd(PPh3)4 (896 mg, 0.776 mmol, 0.20 equiv). The resulting solution was stirred for 2 hours at 100° C. The resulting mixture was concentrated. This resulted product was used directly in the next step. LCMS (ES) [M+1]+ m/z: 388.

Step 3

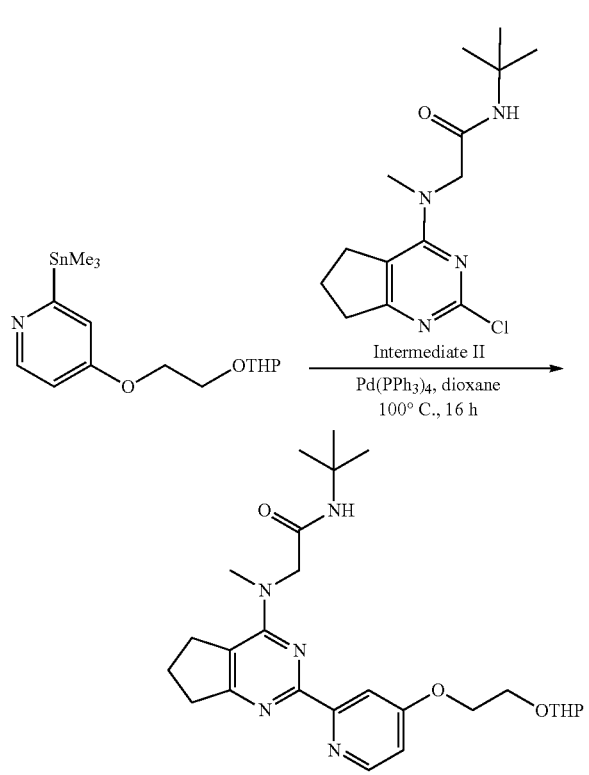

Into a 40-mL vial, was placed a mixture of 4-[2-(oxan-2-yloxy)ethoxy]-2-(trimethylstannyl)pyridine (800 mg, 2.07 mmol, 1.00 equiv), dioxane (10.00 mL), N-(tert-butyl)-2-((2-chloro-6,7-dihydro-5H-cyclopenta[d]pyrimidin-4-yl)(methyl)amino)acetamide (Intermediate II, 430 mg, 1.45 mmol, 0.70 equiv), and Pd(PPh3)4 (478 mg, 0.414 mmol, 0.20 equiv). The resulting solution was stirred for 16 hours at 100° C. The crude reaction mixture was filtered and subjected to reverse phase preparative MPLC (Prep-C18, 20-45 mM, 120 g, Tianjin Bonna-Agela Technologies; gradient elution of 10% MeCN in water to 48% MeCN in water over a 15 min period, where both solvents contain 0.1% NH4HCO3). The resulting mixture was concentrated. This resulted in 280 mg (27.94%) of N-(tert-butyl)-2-(methyl(2-(4-(2-((tetrahydro-2H-pyran-2-yl)oxy)ethoxy)pyridin-2-yl)-6,7-dihydro-5H-cyclopenta[d]pyrimidin-4-yl)amino)acetamide as a off-white solid. LCMS (ES) [M+1]+ m/z: 484.

Step 4

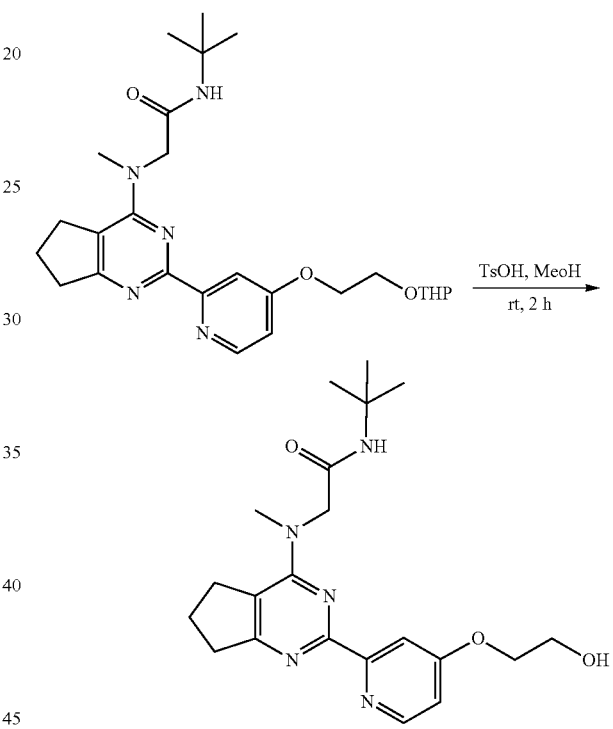

Into a 40-mL vial was placed a mixture of N-(tert-butyl)-2-(methyl(2-(4-(2-((tetrahydro-2H-pyran-2-yl)oxy)ethoxy)pyridin-2-yl)-6,7-dihydro-5H-cyclopenta[d]pyrimidin-4-yl)amino)acetamide (250 mg, 0.517 mmol, 1.00 equiv), MeOH (10.0 mL) and TsOH (89 mg, 0.52 mmol, 1.0 equiv). The resulting solution was stirred for 2 hours at room temperature. The resulting mixture was concentrated. The crude product was purified by Prep-HPLC with the following conditions: Column, Xbridge Prep C18 OBD Column, 19×150 mm, 5 um; mobile phase, phase A: H2O (0.05% NH3H2O); phase B: CH3CN (20% CH3CN up to 70% CH3CN in 13 min). This resulted in 72.6 mg (35.15%) of N-(tert-butyl)-2-((2-(4-(2-hydroxyethoxy)pyridin-2-yl)-6,7-dihydro-5H-cyclopenta[d]pyrimidin-4-yl)(methyl)amino)acetamide as a white solid. 1H NMR (300 MHz, DMSO-d6, ppm): δ 8.47 (d, J=5.6 Hz, 1H), 7.85 (d, J=2.5 Hz, 1H), 7.68 (s, 1H), 7.04 (dd, J=5.7, 2.6 Hz, 1H), 4.92 (t, J=5.4 Hz, 1H), 4.19-4.10 (m, 4H), 3.76 (q, J=5.1 Hz, 2H), 3.26 (s, 3H), 3.14 (t, J=7.3 Hz, 2H), 2.81 (t, J=7.8 Hz, 2H), 2.01-1.96 (m, 2H), 1.24 (s, 9H). LCMS (ES) [M+1]+ m/z: 400.2.

Scheme 46b depicts a synthetic route for preparing an exemplary compound.

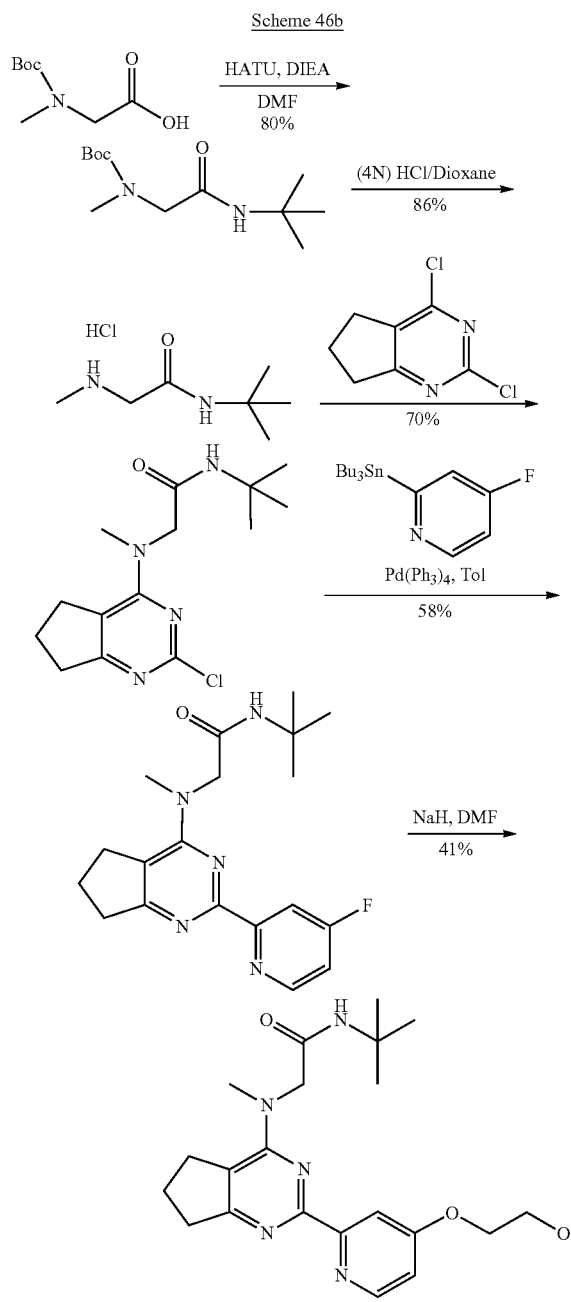

Step 1

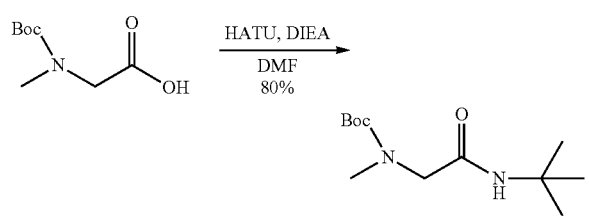

Into a 50-mL 3-necked round-bottom flask was placed N-(tert-butoxycarbonyl)-N-methylglycine (20.0 g, 0.105 mol, 1.00 equiv), DMF (200.00 mL), 2-methylpropan-2-amine (8.43 g, 0.115 mol, 1.10 equiv) and DIEA (27.21 g, 0.211 mmol, 2.00 equiv). This was followed by the addition of HATU (44.08 g, 0.115 mol, 1.10 equiv) in several batches at 0° C. After addition, the resulting solution was stirred for 16 h at room temperature. The reaction was quenched with 200 mL of water, extracted with 3×100 mL of ethyl acetate. The combined organic phase was washed with 2×200 mL of water and 1×200 mL brine, dried over anhydrous sodium sulfate and filtered. The filtrate was concentrated under reduced pressure, the residue was purified by silica gel column with ethyl acetate/petroleum ether (1:1) to give 20.6 g (80%) of tert-butyl (2-(tert-butylamino)-2-oxoethyl)(methyl)carbamate as an off white solid. LCMS (ES) [M+1]+ m/z: 245.

Step 2

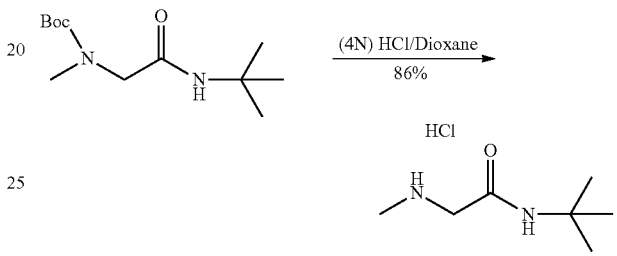

Into a 500-mL 3-round-bottom flask was placed tert-butyl (2-(tert-butylamino)-2-oxoethyl)(methyl)carbamate (25 g, 102.4 mmol, 1.00 equiv) and DCM (100.00 mL). This was followed by the addition of HCl (g) (4 M in dioxane) (200.00 mL) dropwise with stirring at 0° C. The resulting solution was stirred for 16 h at room temperature, concentrated in vacuum to remove the solvent and washed with ethyl acetate (150 mL). This resulted in 16 g (86%) of N-(tert-butyl)-2-(methylamino)acetamide hydrochloride. LCMS (ES) [M−HCl+1]+ m/z: 145.

Step 3

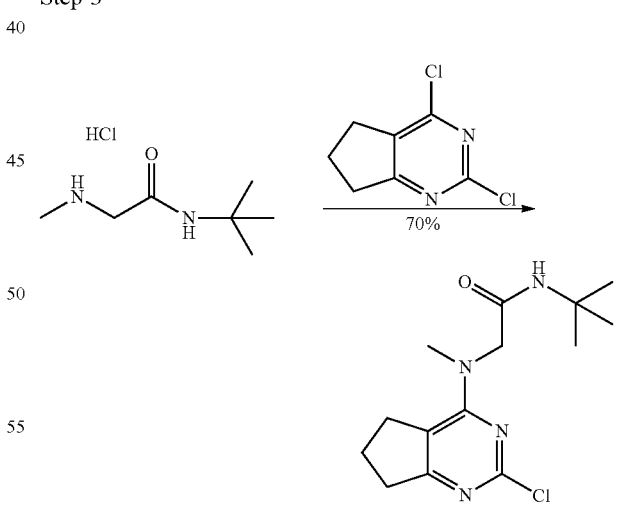

Into a 500-mL 3 neck round-bottom flask was placed N-(tert-butyl)-2-(methylamino)acetamide hydrochloride (16 g, 88.9 mmol, 1.00 equiv), NMP (200.00 mL), 2,4-dichloro-6,7-dihydro-5H-cyclopenta[d]pyrimidine (16.8 g, 88.9 mmol, 1.00 equiv) and DIEA (40.6 g, 0.315 mol, 3.00 equiv). The resulting solution was stirred for 6 h at 50° C. in oil bath. The reaction mixture was cooled to room temperature, diluted with 200 mL of water and extracted with 3×200 mL of ethyl acetate. The combined organic phase was washed with 3×300 mL of water and brine 1×200 mL, dried over anhydrous sodium sulfate and filtered. The filtrate was concentrated under reduced pressure, the residue was triturated with ethyl acetate and filtered. This resulted in 18.4 g (70%) of N-(tert-butyl)-2-((2-chloro-6,7-dihydro-5H-cyclopenta[d]pyrimidin-4-yl)(methyl)amino)acetamide as a white solid. LCMS (ES) [M+1]+ m/z: 297.

Step 4

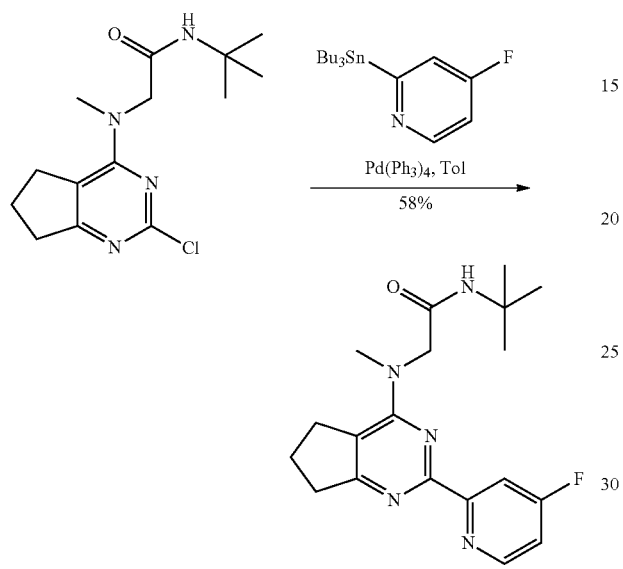

4-fluoro-2-(tributylstannyl)pyridine was synthesized as following: To a solution of 2-bromo-4-fluoropyridine (25 g, 142 mmol, 1.00 eq.) in Toluene (300 mL) was added butyllithium (62.5 mL, 2.50 mol/L, 156 mmol, 1.10 eq.) at −78° C., after stirred for 1 h, the mixture was added tributyl(chloro)stannane (50.7 g, 156 mmol, 1.10 eq.) and was further stirred for 30 min at −78° C. and 3 h. at room temperature The mixture was quenched with ice water, extracted with hexane, organic layers were combined and washed with Sat. NaHCO₃, brine, dried and filtered. The filtrate was concentrated to give crude product (51 g) as clear yellow oil, which was used without purification. LCMS (ES) [M+1]+ m/z: 388.

Into a 250-mL three necked round bottom flask purged and maintained with an inert atmosphere of nitrogen was placed N-(tert-butyl)-2-((2-chloro-6,7-dihydro-5H-cyclopenta[d]pyrimidin-4-yl)(methyl)amino)acetamide (10 g, 33.8 mmol, 1.00 equiv), toluene (150.00 mL), 4-fluoro-2-(tributylstannyl)pyridine (21.7 g, 60.84 mmol, 1.8 equiv) and Pd(PPh₃)₄ (3.57 g, 3.38 mmol, 0.10 equiv). The mixture was stirred for 60 h at 110° C. in oil bath. The reaction mixture was cooled to room temperature, concentrated to remove the solvent; the residue was purified by silica gel column with dichloromethane/methanol (10:1). This resulted in 7 g (58%) of N-(tert-butyl)-2-((2-(4-fluoropyridin-2-yl)-6,7-dihydro-5H-cyclopenta[d]pyrimidin-4-yl)(methyl)amino)acetamide as yellow solid. LCMS (ES) [M+1]+ m/z: 358.

Step 5

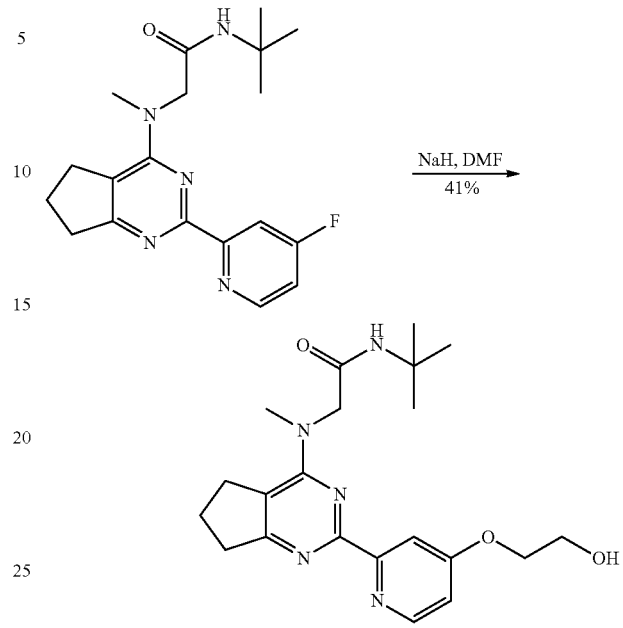

Into a 250 mL 3-neck flask was placed ethane-1,2-diol (9.55 g, 154 mmol, 10.0 equiv) and DMF (100 mL), NaH (60% in mineral oil) (6.16 g, 154 mmol, 10.0 equiv) was added in portion wise at 0-5° C. The mixture was stirred for 1 h at room temperature and N-(tert-butyl)-2-((2-(4-fluoropyridin-2-yl)-6,7-dihydro-5H-cyclopenta[d]pyrimidin-4-yl)(methyl)amino)acetamide (5.5 g, 15.4 mmol, 1.00 equiv) was added at 0-5° C. The reaction mixture was stirred for 5 h at 50° C. (The reaction was repeated in 2 batches). The reaction mixture was cooled to room temperature, diluted with 200 mL of water, extracted with 3×200 mL of ethyl acetate. The combined organic phase was washed with 3×300 ml of water and brine 1×200 mL, dried over anhydrous sodium sulfate. The residue was purified by Prep-HPLC with conditions: column, C18-800 g, Mobile phase, CH₃CN/H₂O (0.05% FA), from 10% increased to 70% within 27 min, Flow rate, 180 mL/min, Detector, 254 nm. The pH value of the fraction was adjusted to 7~8 with K₂CO₃ solid, extracted with dichloromethane (3×300 mL). The combined organic phase was dried over anhydrous sodium sulfate and filtered. The filtrate was concentrated under reduced pressure and the residue was freezing dried, this resulted in 5.03 g (41%) of N-(tert-butyl)-2-((2-(4-(2-hydroxyethoxy)pyridin-2-yl)-6,7-dihydro-5H-cyclopenta[d]pyrimidin-4-yl)(methyl)amino)acetamide as a white solid. LCMS: (ES, m/z): [M+H]+: 400. ¹H-NMR: (300 MHz, DMSO-d6, ppm): δ 8.47 (d, J=5.6 Hz, 1H), 7.86 (d, J=2.5 Hz, 1H), 7.68 (s, 1H), 7.04 (dd, J=5.6, 2.6 Hz, 1H), 4.92 (t, J=5.4 Hz, 1H), 4.19-4.10 (m, 4H), 3.77 (q, J=5.1 Hz, 2H), 3.26 (s, 3H), 3.13 (t, J=7.3 Hz, 2H), 2.81 (t, J=7.9 Hz, 2H), 2.01-1.96 (m, 2H), 1.24 (s, 9H).

501

Synthesis of Compound 44—Route 2

Scheme 4-1

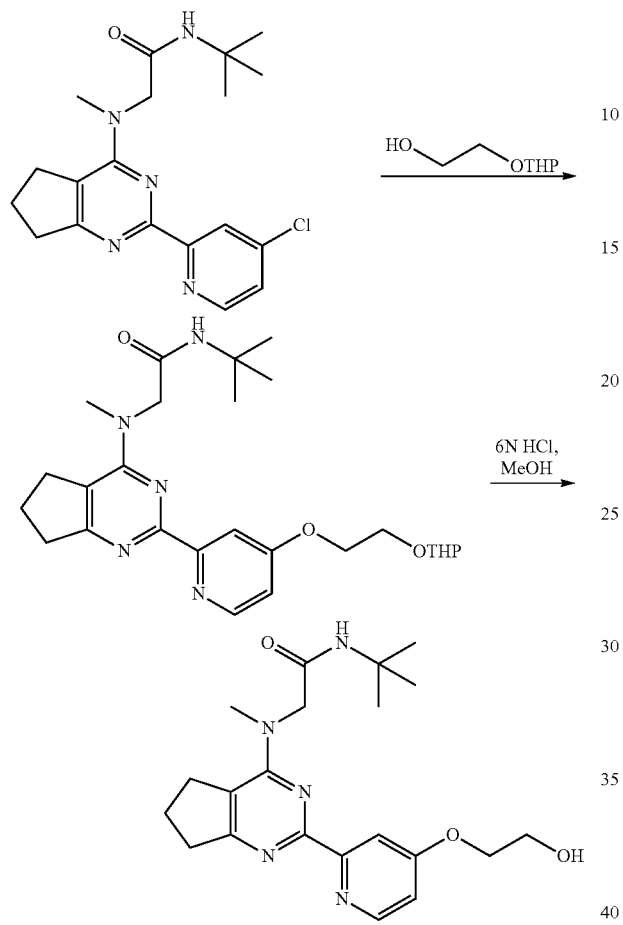

Into a 250-mL round-bottom flask were placed N-tert-butyl-2-[[2-(4-chloropyridin-2-yl)-5H,6H,7H-cyclopenta[d]pyrimidin-4-yl](methyl)amino]acetamide (7.40 g, 19.79 mmol, 1.00 equiv), 2-(oxan-2-yloxy)ethanol (4.34 g, 29.69 mmol, 1.50 equiv), DMF (150.00 mL) and t-BuOK (6.66 g, 59.37 mmol, 3.00 equiv). The resulting solution was stirred for overnight at 25° C. The reaction was then quenched by the addition of water/ice. The resulting solution was extracted with 3×200 mL of ethyl acetate and the organic layers combined, dried over anhydrous sodium sulfate and concentrated. The crude product (8 g) was purified by Prep-HPLC with the following conditions: Column, XBridge Prep C18 OBD Column, 19 cm, 150 mm, 5 um; mobile phase, Water (0.1% NH$_3$·H$_2$O) and CAN (20% Phase B up to 60% in 11 min); Detector, 254. This resulted in 6 g (62.69%) of N-tert-butyl-2-[methyl(2-[4-[2-(oxan-2-yloxy)ethoxy]pyridin-2-yl]-5H,6H,7H-cyclopenta[d]pyrimidin-4-yl)amino]acetamide as yellow solid. LCMS (ES) [M+1]$^+$ m/z: 484.

Into a 40-mL vial were placed N-tert-butyl-2-[methyl(2-[4-[2-(oxan-2-yloxy)ethoxy]pyridin-2-yl]-5H,6H,7H-cyclopenta[d]pyrimidin-4-yl)amino]acetamide (1.00 g, 2.07 mmol, 1.00 equiv), MeOH (10.00 mL) and HCl (6M) (1.00 mL). The resulting solution was stirred for 1 h at room temperature. The crude product (1 g) was purified by Prep-HPLC with the following conditions: Column, XBridge Prep C18 OBD Column, 19 cm, 150 mm, 5 um; mobile phase, Water (0.1% NH$_3$·H$_2$O) and ACN (15% Phase B up to 60% in 11 min); Detector, 254 nm. This resulted in 613.5 mg (74.27%) of N-tert-butyl-2-([2-[4-(2-hydroxyethoxy)pyridin-2-yl]-5H,6H,7H-cyclopenta[d]pyrimidin-4-yl](methyl)amino)acetamide as white solid. LCMS (ES, m/z): [M+H]$^+$: 400. $^1$H-NMR (300 MHz, DMSO-d$_6$, ppm): δ 8.47 (d, J=5.6 Hz, 1H), 7.85 (d, J=2.5 Hz, 1H), 7.68 (s, 1H), 7.04 (dd, J=5.7, 2.6 Hz, 1H), 4.92 (t, J=5.4 Hz, 1H), 4.21-4.07 (m, 4H), 3.76 (q, J=5.1 Hz, 2H), 3.26 (s, 3H), 3.14 (t, J=7.3 Hz, 2H), 2.81 (t, J=7.8 Hz, 2H), 2.01-1.96 (m, 2H), 1.24 (s, 9H).

Example 1.76

Synthesis of 4-[2-(pyridin-2-yl)-5H,6H,7H-cyclopenta[d]pyrimidin-4-yl]-1,4-diazepan-2-one (Compound 47)

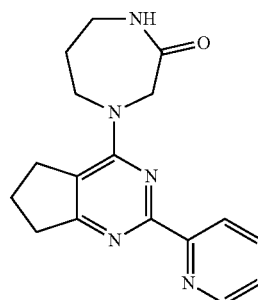

Compound 47 was synthesized similar to compound 92 by replacing azapane with 1,4-diazepan-2-one. LCMS (ES+): (M+H)$^+$=310.0. $^1$H NMR (400 MHz, DMSO-d6) δ 8.82-8.76 (m, 1H), 8.52 (d, J=7.9 Hz, 1H), 8.12-8.05 (m, 1H), 7.70-7.61 (m, 2H), 6.52 (s, 1H), 4.48 (s, 2H), 4.16-4.06 (m, 2H), 3.27-3.22 (m, 4H), 2.99 (t, J=7.9 Hz, 2H), 2.14-2.03 (m, 2H), 1.92-1.83 (m, 2H).

Example 1.77

Synthesis of 1-[2-(pyridin-2-yl)-5H,6H,7H-cyclopenta[d]pyrimidin-4-yl]-1,4-diazepan-5-one (Compound 50)

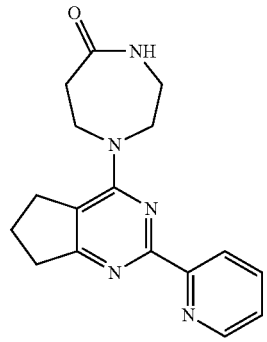 [SMILES: O=C1CCN(c2nc(-c3ccccn3)nc3c2CCC3)CCN1]

Compound 50 was synthesized similar to compound 92 by replacing azapane with 1,4-diazepan-5-one. LCMS (ES+): (M+H)$^+$=309.9. $^1$H NMR (400 MHz, DMSO-d6) δ

8.76-8.69 (m, 1H), 8.34 (d, J=7.9 Hz, 1H), 8.01-7.92 (m, 1H), 7.73-7.64 (m, 1H), 7.57-7.48 (m, 1H), 3.98-3.92 (m, 4H), 3.29-3.26 (m, 2H), 3.10-3.03 (m, 2H), 2.93-2.87 (m, 2H), 2.65-2.60 (m, 2H), 2.09-2.00 (m, 2H).

Example 1.78

Synthesis of (2R)—N-tert-butyl-2-{methyl[2-(pyridin-2-yl)-5H,6H,7H-cyclopenta[d]pyrimidin-4-yl]amino}propanamide (Compound 51)

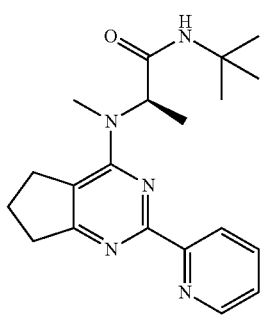 [SMILES: C[C@H](C(=O)NC(C)(C)C)N(C)c1nc(-c2ccccn2)nc2c1CCC2]

Scheme 47 depicts a synthetic route for preparing an exemplary compound.

Scheme 47

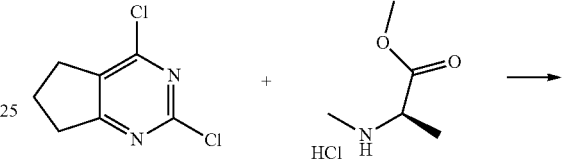

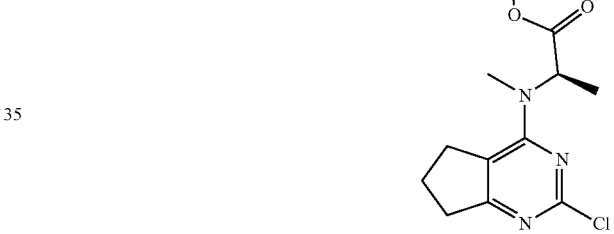

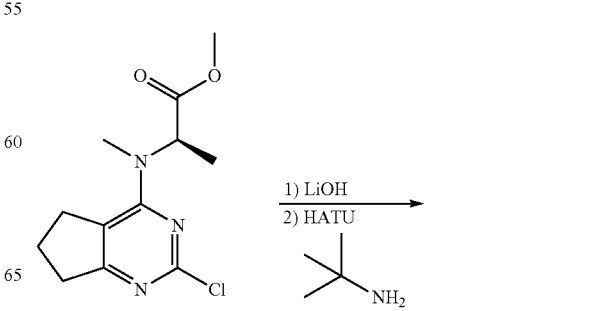

Step 1

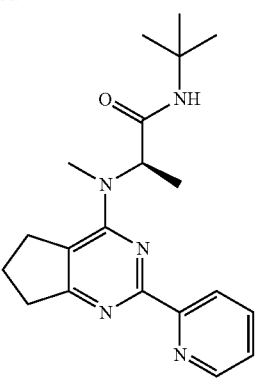

2,4-dichloro-6,7-dihydro-5H-cyclopenta[d]pyrimidine (130.00 mg; 0.69 mmol; 1.00 eq.) was dissolved in acetonitrile (2.5 ml), and to the solution was added methyl (2R)-2-(methylamino)propanoate hydrochloride (126.76 mg; 0.83 mmol; 1.20 eq.) and Hunig's base (0.48 mL; 2.75 mmol; 4.00 eq.). After being stirred at ~55° C. for 15 h, the mixture was evaporated and the residue was subjected to column chromatography to give methyl (2R)-2-({2-chloro-5H,6H,7H-cyclopenta[d]pyrimidin-4-yl}(methyl)amino)propanoate (54 mg, 31%) as a film. LCMS (ES+): (M+H)$^+$= 270.2.

-continued

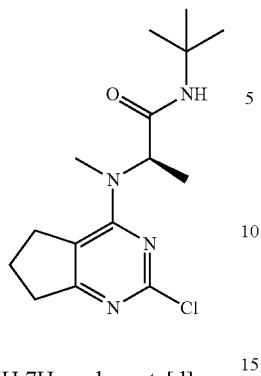

Methyl (2R)-2-({2-chloro-5H,6H,7H-cyclopenta[d]pyrimidin-4-yl}(methyl)amino)propanoate (54 mg; 0.20 mmol; 1 eq.) was dissolved in THF (2 ml) and methanol (0.5 ml). Lithium hydroxide (anhydrous, 19 mg; 0.8 mmol; 4 eq.) dissolved in ~0.8 ml of water was added dropwise and the reaction was stirred at 25° C. for 1.5 h. 6 M HCl was added carefully to acidify the reaction to pH<3. The solvents were evaporated and the residue was dried on high vacuum. The residue of (2R)-2-({2-chloro-5H,6H,7H-cyclopenta[d]pyrimidin-4-yl}(methyl)amino)propanoic acid (51 mg; 0.2 mmol; 1 eq.) was dissolved in N,N-dimethylformamide (2 ml). N, N-diisopropylethylamine (0.12 mL; 0.7 mmol; 3.5 eq.) was added and the reaction was stirred in an ice bath. Tert-butylamine (32 µL; 0.3 mmol; 1.5 eq.) and 1-[bis(dimethylamino)methylene]-1H-1,2,3-triazolo[4,5-b]pyridinium 3-oxid hexafluorophosphate (HATU, (152 mg; 0.4 mmol; 2 eq.) were added. After 4 h, ethyl acetate (50 ml), water (10 ml), and sodium bicarbonate solution (10 ml) were added. The phases were separated, and the aqueous phase was extracted with ethyl acetate (50 ml). The organic phases were washed with water (10 ml) and sodium chloride solution (20 ml), and dried over sodium sulfate. After evaporation, the product was purified by silica gel chromatography (ethyl acetate/hexanes gradient) to give (2R)—N-tert-butyl-2-({2-chloro-5H,6H,7H-cyclopenta[d]pyrimidin-4-yl}(methyl)amino)propenamide (12.5 mg, 20%). MS (ES+): (M+H)$^+$=310.9.

Step 3

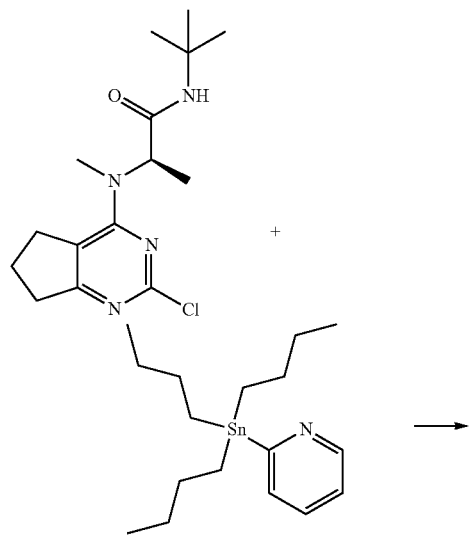

-continued

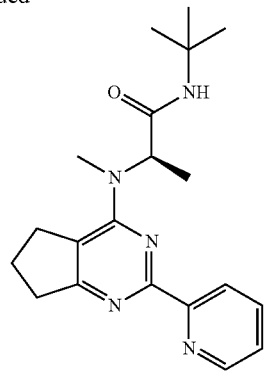

(2R)—N-tert-butyl-2-({2-chloro-5H,6H,7H-cyclopenta[d]pyrimidin-4-yl}(methyl)amino)propanamide (30.00 mg; 0.10 mmol; 1.00 eq.) was dissolved in 1,4-dioxane (1 ml) and the solution was purged with Ar gas. 2-(tributylstannyl)pyridine (0.06 mL; 0.19 mmol; 2.00 eq.) and tetrakis(triphenylphosphane) palladium (11.15 mg; 0.01 mmol; 0.10 eq.) were added The reaction vessel was sealed and stirred in a heat bath at 110° C. for 15 h. After evaporation, the residue was purified by reverse phase chromatography (Waters XSelect CSH C18 column, 0-70% acetonitrile/0.1% aqueous formic acid gradient) to give (2R)—N-tert-butyl-2-{methyl[2-(pyridin-2-yl)-5H,6H,7H-cyclopenta[d]pyrimidin-4-yl]amino}propanamide (11 mg, 32%) as an off-white solid. LCMS (ES+): (M+H)$^+$=354.4. $^1$H NMR (400 MHz, Methanol-d4) δ 8.72 (ddd, J=4.9, 1.8, 0.9 Hz, 1H), 8.46-8.41 (m, 1H), 8.02-7.95 (m, 1H), 7.68 (s, 1H), 7.57-7.50 (m, 1H), 5.26 (q, J=7.1 Hz, 1H), 3.38-3.33 (m, 1H), 3.28-3.18 (m, 1H), 3.08-2.91 (m, 2H), 2.24-2.06 (m, 2H), 1.48 (d, J=7.1 Hz, 3H), 1.25 (s, 9H).

Example 1.79

Synthesis of (2S)—N-tert-butyl-2-{methyl[2-(pyridin-2-yl)-5H,6H,7H-cyclopenta[d]pyrimidin-4-yl]amino}propanamide (Compound 52)

Compound 52 was synthesized similar to compound 51 by replacing (2R)-2-(methylamino)propanoate with (2S)-2-(methylamino)propanoate. LCMS (ES+): (M+H)$^+$=354.4. $^1$H NMR (400 MHz, Methanol-d4) δ 8.72 (ddd, J=4.8, 1.8, 0.9 Hz, 1H), 8.46-8.40 (m, 1H), 8.02-7.95 (m, 1H), 7.68 (s, 1H), 7.54 (ddd, J=7.6, 4.8, 1.2 Hz, 1H), 5.26 (q, J=7.1 Hz, 1H), 3.38-3.32 (m, 1H), 3.28-3.18 (m, 1H), 3.09-2.91 (m, 2H), 2.23-2.04 (m, 2H), 1.48 (d, J=7.2 Hz, 3H), 1.25 (s, 9H).

Example 1.80

Synthesis of 1-[2-(4-methoxypyridin-2-yl)-5H,6H,7H-cyclopenta[d]pyrimidin-4-yl]azepane (Compound 53)

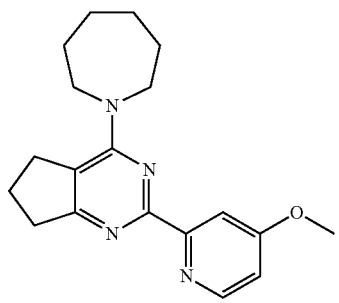 [SMILES: COc1ccnc(-c2nc3c(c(N4CCCCCC4)n2)CCC3)c1]

Compound 53 was synthesized similar to Compound 92 by replacing (2-tributylstannyl)pyridine with 4-methoxy-2-(tributylstannyl)pyridine. $^1$H NMR (400 MHz, Methanol-d$_4$) δ 8.48 (d, J=5.8 Hz, 1H), 7.86 (d, J=2.6 Hz, 1H), 7.06 (dd, J=5.8, 2.6 Hz, 1H), 3.94 (s, 3H), 3.86 (t, J=6.1 Hz, 4H), 3.15 (t, J=7.3 Hz, 2H), 2.92 (t, J=7.9 Hz, 2H), 2.16-2.04 (m, 2H), 1.83 (q, J=5.5 Hz, 4H), 1.59 (p, J=2.7 Hz, 4H). LCMS (ES+): (M+H)$^+$=325.1.

Example 1.81

Synthesis of (3R)-6,6-dimethyl-3-{[2-(pyridin-2-yl)-5H,6H,7H-cyclopenta[d]pyrimidin-4-yl]amino}piperidin-2-one (Compound 55)

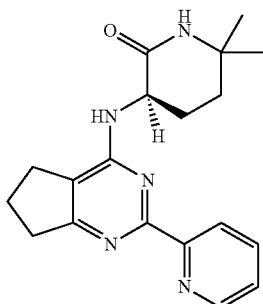

Scheme 48 depicts a synthetic route for preparing an exemplary compound.

Scheme 48

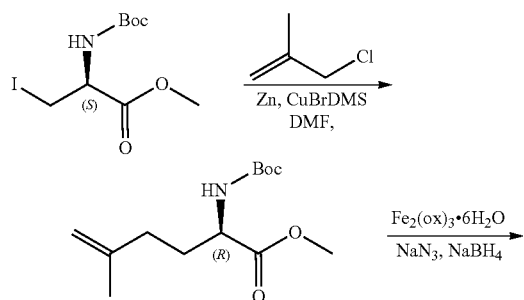

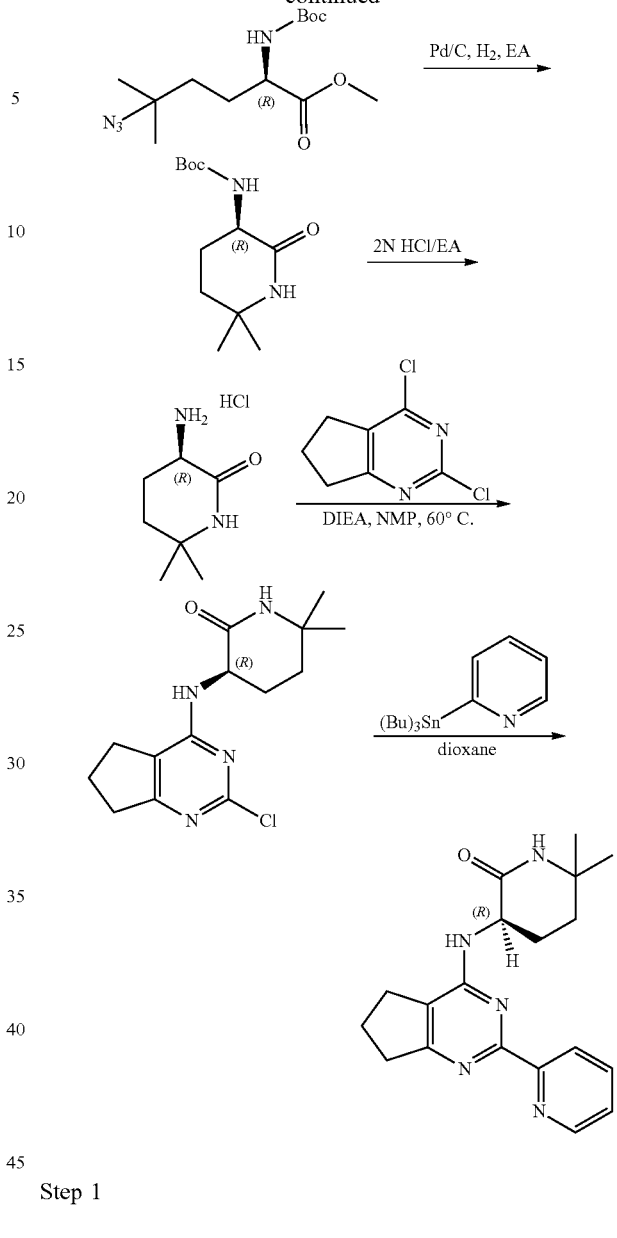

Step 1

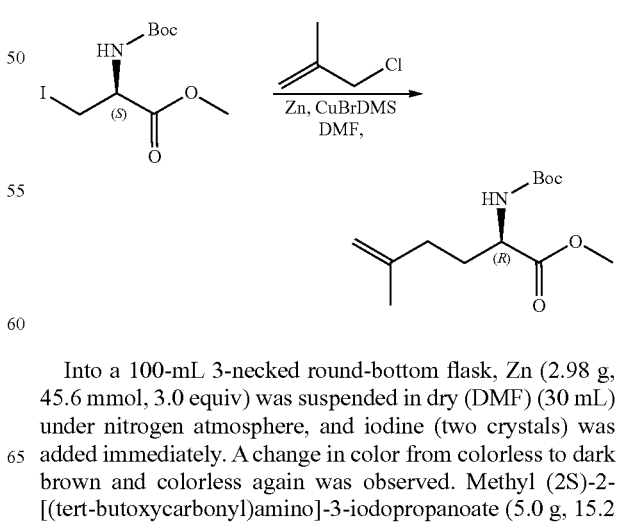

Into a 100-mL 3-necked round-bottom flask, Zn (2.98 g, 45.6 mmol, 3.0 equiv) was suspended in dry (DMF) (30 mL) under nitrogen atmosphere, and iodine (two crystals) was added immediately. A change in color from colorless to dark brown and colorless again was observed. Methyl (2S)-2-[(tert-butoxycarbonyl)amino]-3-iodopropanoate (5.0 g, 15.2 mmol, 1.0 equiv), was added followed immediately by iodine (three crystals), the aforementioned color change was observed once more, and the insertion process was allowed to proceed for 2 h. A flask containing CuBr-Me₂S (0.31 g, 1.53 mmol, 0.1 equiv), was placed under vacuum and heated vigorously until the gray CuBr-Me₂S became light green/yellow. The flask was then placed under a flow of nitrogen and allowed to cool to room temperature. This was repeated once more, and the flask was allowed to cool to room temperature. A prepared solution of Zn Reagent in DMF was transferred to the flask containing CuBr-Me₂S (2.06 g, 22.78 mmol, 2.0 equiv), and the reaction was stirred for 72 h at room temperature. The reaction mixture was then filtered through a silica plug eluting with EtOAc. The organic phase was washed with water (2×50 mL) and brine (50 mL). The organic phase was dried with Na₂SO₄, filtered, and the solvent removed under reduced pressure. The residue was applied onto a silica gel column with ethyl acetate/petroleum ether (1:50 to 1:1). This resulted in 3 g (76.7%) of methyl (2R)-2-[(tert-butoxycarbonyl)amino]-5-methylhex-5-enoate as an oil. LCMS (ES) [M+1]⁺ m/z: 258.2.

Step 2

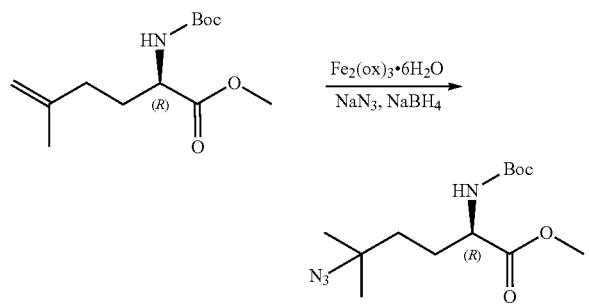

Into a 500-mL 3-necked round-bottom flask, Fe₂ (OX)₃·6H₂O (3.76 g, 7.77 mmol, 2.0 equiv) was stirred in H₂O (150 mL) until completely dissolved (typically 2 h). The clear yellow solution was cooled to 0° C. and degassed with Ar for 10 min. NaN₃ (0.76 g, 11.66 mmol, 3.0 equiv) and ethanol (75 mL) were added. After 20 min, a solution of methyl (2R)-2-[(tert-butoxycarbonyl)amino]-5-methylhex-5-enoate (1.00 g, 3.886 mmol, 1.00 equiv) in EtOH (75 mL) was added to the reaction mixture, followed by NaBH₄ (1.03 g, 27.202 mmol, 7 equiv) at 0° C. The resulting mixture was stirred for 30 min before being quenched by the addition of 30% aqueous NH₄OH (4 mL). The mixture was extracted with 10% MeOH in CH₂Cl₂, the organic layer was dried over Na₂SO₄ and concentrated. The residue was purified by flash chromatography (SiO₂, 20% EtOAc/PE) to give methyl (2R)-5-azido-2-[(tert-butoxycarbonyl)amino]-5-methylhexanoate (450 mg, 38.5%) as a colorless oil. LCMS (ES) [M+1]⁺ m/z: 301.2.

Step 3

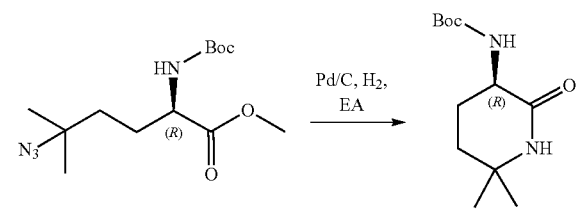

To a solution of methyl (2R)-5-azido-2-[(tert-butoxycarbonyl)amino]-5-methylhexanoate (450 mg, 1.50 mmol, 1.0 equiv) in EtOAc (15 mL) was added Pd/C (200 mg) at room temperature. After the addition, the reaction was purged with H₂ three times. The resulting mixture was stirred for 16 hr at 25° C. under a H₂ atmosphere. The resulting mixture was filtered, and the filtrate was concentrated to give 220 mg (60.6%) of tert-butyl N-[(3R)-6,6-dimethyl-2-oxopiperidin-3-yl]carbamate as an off white solid. LCMS (ES) [M+1]⁺ m/z: 243.3.

Step 4

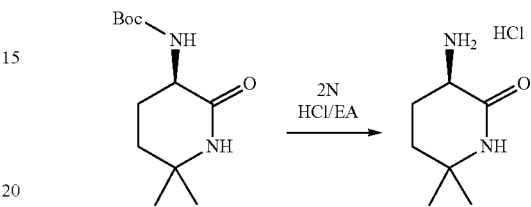

Into a 100-mL round-bottom flask, was placed tert-butyl N-[(3R)-6,6-dimethyl-2-oxopiperidin-3-yl]carbamate (220 mg, 0.91 mmol, 1.0 equiv), EtOAc (5 mL), and HCl/EtOAc (2 mL, 2 M, 4.0 mmol, 4.4 equiv). The resulting solution was stirred for 5 h at 25° C. The resulting mixture was concentrated under vacuum. This resulted in 150 mg (100%) of (3R)-3-amino-6,6-dimethylpiperidin-2-one as an off white solid. LCMS (ES) [M+1]⁺ m/z: 143.

Step 5

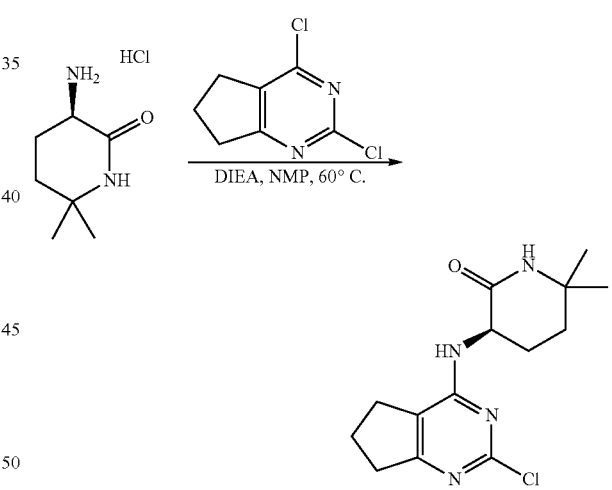

Into a 50-mL round-bottom flask, was placed (3R)-3-amino-6,6-dimethylpiperidin-2-one (150 mg, 1.05 mmol, 1.0 equiv), 2,4-dichloro-5H,6H,7H-cyclopenta[d]pyrimidine (199 mg, 1.05 mmol, 1.0 equiv), NMP (5 mL), and DIPEA (409 mg, 3.16 mmol, 3.0 equiv). The resulting solution was stirred for 16 h at 60° C. in an oil bath. The reaction mixture was cooled to room temperature. The reaction was then quenched by the addition of 20 mL of water. The resulting solution was extracted with 3×30 mL of ethyl acetate, dried over anhydrous sodium sulfate, and concentrated. The residue was applied onto a silica gel column with ethyl acetate/petroleum ether (1:50 to 1:1). This resulted in 160 mg (51.5%) of (3R)-3-([2-chloro-5H,6H,7H-cyclopenta[d]pyrimidin-4-yl]amino)-6,6-dimethylpiperidin-2-one as a white solid. LCMS (ES) [M+1]⁺ m/z: 295.2.

Step 6

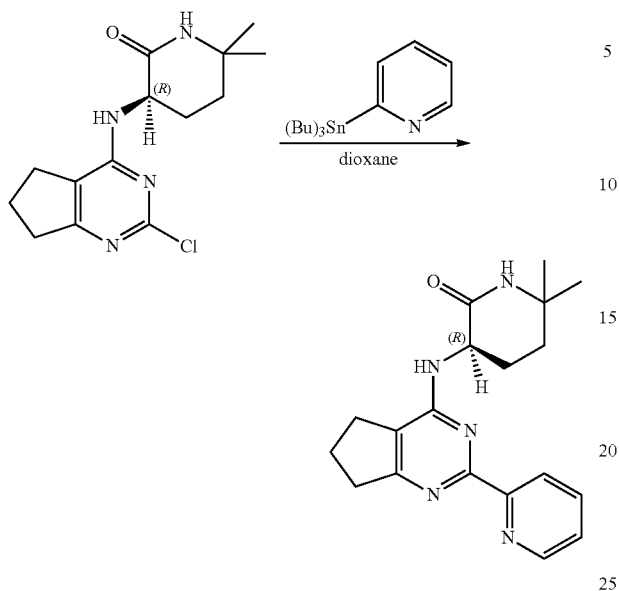

To a solution of (3R)-3-([2-chloro-5H,6H,7H-cyclopenta[d]pyrimidin-4-yl]amino)-6,6-dimethylpiperidin-2-one (160 mg, 0.54 mmol, 1.0 equiv) and 2-(tributylstannyl)pyridine (200 mg, 0.54 mmol, 1.0 equiv) in dioxane (5 mL) was added Pd(PPh₃)₄ (62 mg, 0.05 mmol, 0.1 equiv) at 25° C. in one portion. After the addition, the resulting solution was stirred for 16 hr at 100° C. under an Ar atmosphere. The resulting mixture was concentrated under vacuum. The residue was applied onto a silica gel column with ethyl acetate/petroleum ether (1:50 to 10:1). The crude product (150 mg) was purified by Flash-Prep-HPLC with the following conditions (IntelFlash-1): Column, C18 silica gel; mobile phase, MeCN=10/90 increasing to MeCN=90/10 within 15 min; Detector, 220. This resulted in 57.5 mg (31.4%) of (3R)-6,6-dimethyl-3-[[2-(pyridin-2-yl)-5H,6H,7H-cyclopenta[d]pyrimidin-4-yl]amino]piperidin-2-one as a white solid. ¹H NMR (300 MHz, DMSO-d₆, ppm) δ 8.65 (d, J=3.9 Hz, 1H), 8.23 (d, J=7.8 Hz, 1H), 7.89 (dd, J=1.5 Hz, 7.5 Hz, 1H), 7.57 (s, 1H), 7.44 (dd, J=1.2 Hz, 6.0 Hz, 1H), 7.06 (d, J=8.1 Hz, 1H), 4.67-4.52 (m, 1H), 2.84 (t, J=7.5 Hz, 2H), 2.72 (t, J=7.2 Hz, 2H), 2.12-1.96 (m, 4H), 1.78-1.76 (m, 2H), 1.23 (d, J=10.8 Hz, 6H). LCMS (ES) [M+1]⁺ m/z: 338.2.

Example 1.82

Synthesis of (3S)-6,6-dimethyl-3-{[2-(pyridin-2-yl)-5H,6H,7H-cyclopenta[d]pyrimidin-4-yl]amino}piperidin-2-one (Compound 56)

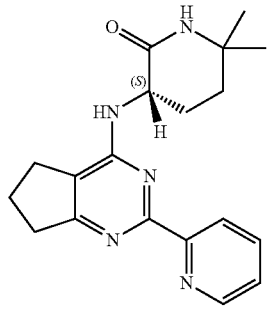

Compound 56 was synthesized similar to Compound 55 by replacing Methyl (2S)-2-[(tert-butoxycarbonyl)amino]-3-iodopropanoate with Methyl (2R)-2-[(tert-butoxycarbonyl)amino]-3-iodopropanoate. ¹H NMR (300 MHz, DMSO-d₆, ppm) δ 8.65 (d, J=3.6 Hz, 1H), 8.23 (d, J=7.8 Hz, 1H), 7.89 (dd, J=1.8 Hz, 7.8 Hz, 1H), 7.57 (s, 1H), 7.44 (dd, J=0.9 Hz, 4.8 Hz, 1H), 7.06 (d, J=8.1 Hz, 1H), 4.71-4.53 (m, 1H), 2.84 (t, J=8.1 Hz, 2H), 2.72 (t, J=7.2 Hz, 2H), 2.15-1.95 (m, 4H), 1.79-1.76 (m, 2H), 1.25 (d, J=10.8 Hz, 6H). LCMS (ES) [M+1]⁺ m/z: 338.2.

Example 1.83

Synthesis of N-tert-butyl-2-{[2-(4-cyclopropylpyridin-2-yl)-5H,6H,7H-cyclopenta[d]pyrimidin-4-yl](methyl)amino}acetamide (Compound 57)

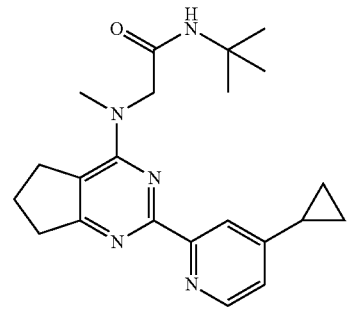 [SMILES: CN(CC(=O)NC(C)(C)C)c1nc(-c2cc(C3CC3)ccn2)nc2c1CCC2]

Scheme 49 depicts a synthetic route for preparing an exemplary compound.

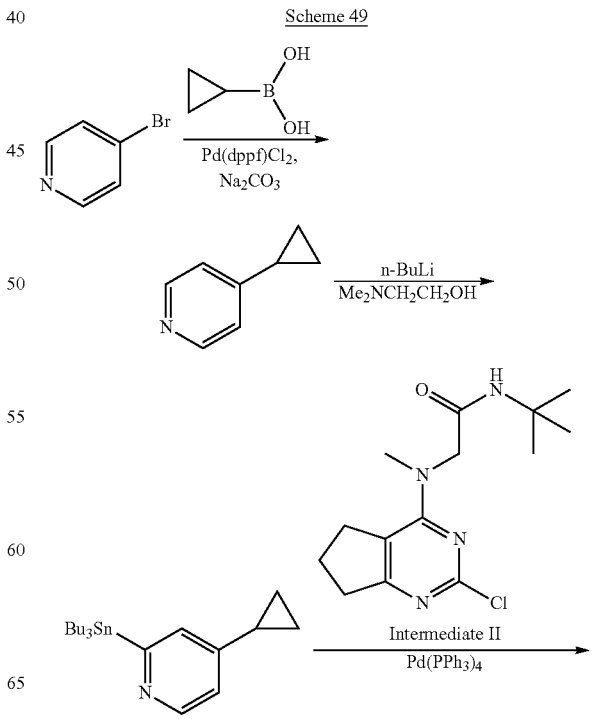

513

-continued

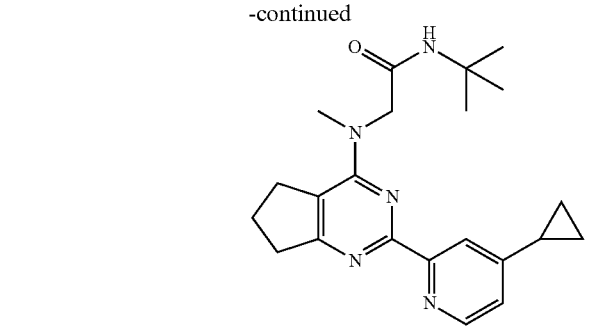

Step 1

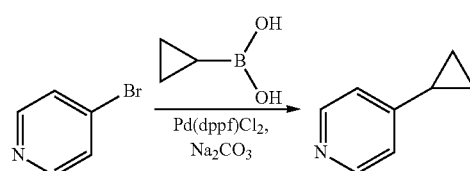

To a mixture of 2-chloro-4-methoxypyridine (1.0 g, 6.32 mmol, 1.00 equiv), cyclopropylboronic acid (0.68 g, 6.9 mmol, 1.25 equiv) and Na$_2$CO$_3$ (1.68 g, 15.8 mmol, 2.50 equiv) in dioxane (20 mL)/H$_2$O (1 mL) was added Pd(dppf)Cl$_2$·CH$_2$Cl$_2$ (50 mg, 0.064 mmol, 0.01 equiv) at room temperature. The resulting mixture was stirred for 16 h at 80° C. in an oil bath under an Ar atmosphere. The resulting mixture was concentrated. The residue was applied onto a silica gel column with ethyl acetate/petroleum ether (1:100 to 1:10). This resulted in 500 mg (66.29%) of 4-cyclopropylpyridine as a solid. LCMS (ES) [M+1]$^+$ m/z: 120.1. $^1$H NMR (300 MHz, CDCl3, ppm) δ 8.45 (d, J=5.1 Hz, 2H), 6.98 (dd, J=4.5, 1.5 Hz, 2H), 1.92-1.84 (m, 1H), 1.28-1.10 (m, 2H), 0.84-0.81 (m, 2H).

Step 2

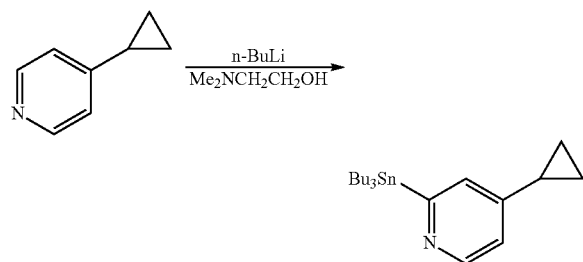

To a mixture of 2-(dimethylamino)ethan-1-ol (523 mg, 5.87 mmol, 2.0 equiv) in hexane (20 mL), was added n-BuLi (2.3 mL, 2.5 M, 5.87 mmol, 2.0 equiv) at −78° C. under a N$_2$ atmosphere. After the reaction was stirred at −78° C. for 20 min, Bu$_3$SnCl (1.9 g, 5.8 mmol, 2.0 equiv) and 4-cyclopropylpyridine (350 mg, 2.94 mmol, 1.0 equiv) were added. The resulting mixture was stirred for 2 h between −78° C. to room temperature. The reaction was then quenched by the addition of water. The resulting solution was extracted with 3×50 mL of ethyl acetate, the organic layers were combined, dried over Na$_2$SO$_4$, and concentrated under vacuum to give 600 mg of the crude 4-cyclopropyl-2-(tributylstannyl)pyridine as a yellow gum. LCMS (ES) [M+1]$^+$ m/z: 410.1.

514

Step 3

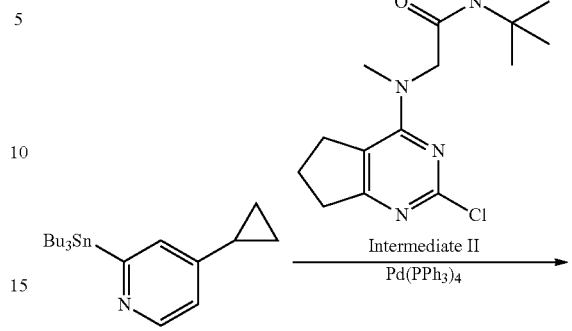

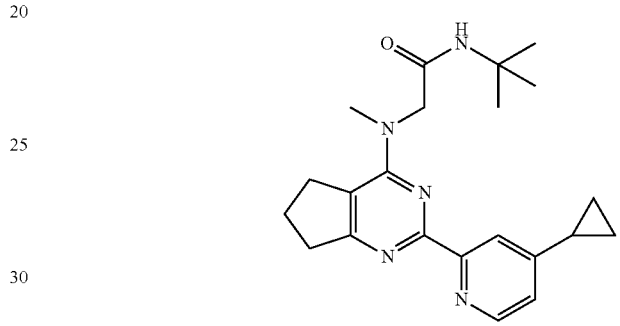

Into a 50-mL 3-necked round-bottom flask purged and maintained in an inert atmosphere of argon was placed 4-cyclopropyl-2-(tributylstannyl)pyridine (200 mg, 0.49 mmol, 1.00 equiv), N-tert-butyl-2-([2-chloro-5H,6H,7H-cyclopenta[d]pyrimidin-4-yl](methyl)amino)acetamide (Intermediate II, 72.7 mg, 0.25 mmol, 0.5 equiv), Pd(PPh$_3$)$_4$ (56.6 mg, 0.05 mmol, 0.1 equiv) and dioxane (5 mL). The resulting solution was stirred for 16 hr at 100° C. The resulting mixture was concentrated. The residue was applied onto a silica gel column with ethyl acetate/petroleum ether (1:10 to 10:1). The crude product (150 mg) was purified by Flash-Prep-HPLC with the following conditions (IntelFlash-1): Column, C18; mobile phase, Mobile phase: MeCN=5/1B: Water Flow rate: 20 mL/min Column: DAICEL CHIRALPAK IC, 250*20 mm, 220 nm Gradient: 50% B in 20 min; 220 nm; This resulted in 87.6 mg (47.11%) of N-tert-butyl-2-[[2-(4-cyclopropylpyridin-2-yl)-5H,6H,7H-cyclopenta[d]pyrimidin-4-yl](methyl)amino]acetamide as a white solid. $^1$H NMR (300 MHz, DMSO-d$_6$) δ 8.47 (d, J=5.1 Hz, 1H), 8.16 (s, 1H), 8.08 (d, J=1.8 Hz, 1H), 7.68 (s, 1H), 7.06 (dd, J=5.1, 1.8 Hz, Hz, 1H), 4.15 (s, 2H), 3.50 (s, 3H), 3.15 (t, J=7.3 Hz, 2H), 2.82 (t, J=7.8 Hz, 2H), 2.28-1.97 (m, 3H), 1.23 (s, 9H), 1.13-1.07 (m, 2H), 0.88-0.82 (m, 2H). LCMS (ES) [M+1]$^+$ m/z: 380.2.

Example 1.84

Synthesis of N-tert-butyl-2-{[2-(4-fluoropyridin-2-yl)-5H,6H,7H-cyclopenta[d]pyrimidin-4-yl](methyl)amino}acetamide (Compound 58)

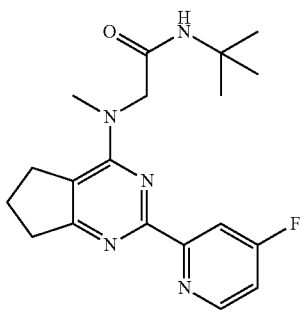 [SMILES: CN(CC(=O)NC(C)(C)C)c1nc(-c2cc(F)ccn2)nc2c1CCC2]

Scheme 50 depicts a synthetic route for preparing an exemplary compound.

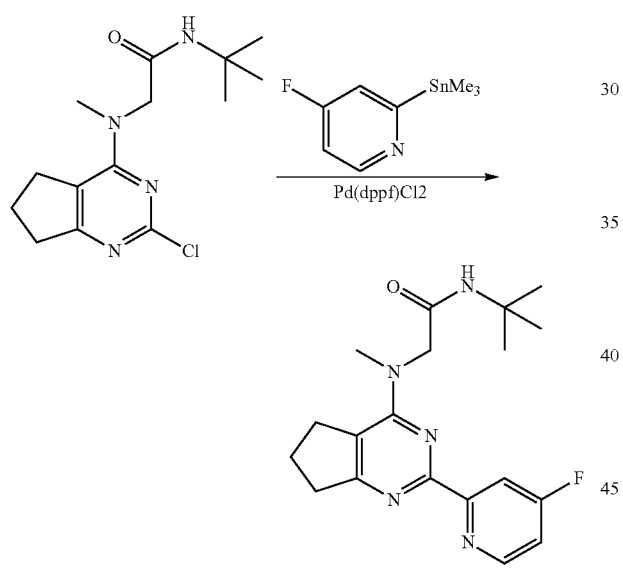

Into a 50-mL round-bottom flask purged and maintained in an inert atmosphere of nitrogen, was placed 4-fluoro-2-(trimethylstannyl)pyridine (1.00 g, 3.85 mmol, 1.00 equiv), N-tert-butyl-2-[5H,6H,7H-cyclopenta[d]pyrimidin-4-yl(methyl)amino]acetamide (Intermediate II, 500 mg, 1.91 mmol, 0.50 equiv), Pd(dppf)Cl₂ (350 mg, 0.43 mmol, 0.10 equiv), and dioxane (20.0 mL). The mixture was stirred for 12 h at 100° C. The mixture was concentrated to remove the solvent, the resulting residue was purified by silica gel column with THF/PE (70%) and the collected product was further purified by Prep-HPLC with conditions: Column, Welch Xtimate C18, 21.2*250 mm, 5 um, mobile phase, Water (10 mmol/L NH₄HCO₃) and MeOH:CH₃CN=1:1 (25% Phase B up to 65% in 15 min), Detector, UV, 254 nm. This resulted in 42.9 mg (3%) of N-(tert-butyl)-2-((2-(4-fluoropyridin-2-yl)-6,7-dihydro-5H-cyclopenta[d]pyrimidin-4-yl)(methyl)amino)acetamide as a white solid. ¹H-NMR (300 MHz, DMSO-d₆, ppm): δ 8.69 (dd, J=9.0, 5.4 Hz, 1H), 8.16 (dd, J=10.8, 2.7 Hz, 1H), 7.73 (s, 1H), 7.42-7.37 (m, 1H), 4.12 (s, 2H), 3.30 (s, 3H), 3.17 (t, J=7.2 Hz, 2H), 2.82 (t, J=7.8 Hz, 2H), 2.05-1.95 (m, 2H), 1.24 (s, 9H).

LCMS (ES, m/z): [M+H]⁺: 358.1.

Example 1.85

Synthesis of -tert-butyl-2-{methyl[2-(6-methylpyridin-2-yl)-5H,6H,7H-cyclopenta[d]pyrimidin-4-yl]amino}acetamide (Compound 59)

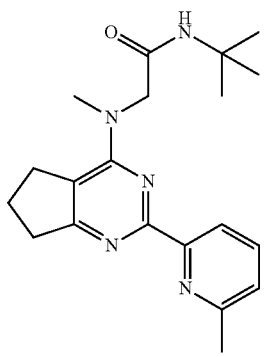 [SMILES: Cc1cccc(-c2nc3c(c(N(C)CC(=O)NC(C)(C)C)n2)CCC3)n1]

Scheme 51 depicts a synthetic route for preparing an exemplary compound.

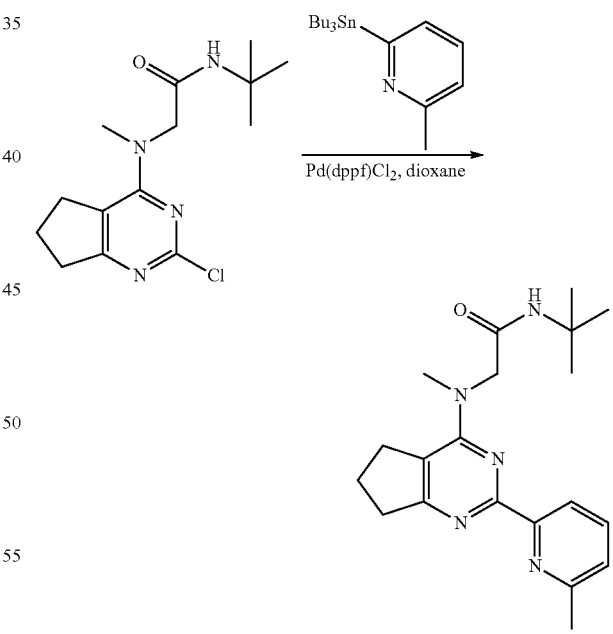

To a solution of N-tert-butyl-2-([2-chloro-5H,6H,7H-cyclopenta[d]pyrimidin-4-yl](methyl)amino)acetamide (Intermediate II, 200.00 mg, 0.674 mmol, 1.00 equiv) and 2-methyl-6-(tributylstannyl)pyridine (386.30 mg, 1.011 mmol, 1.5 equiv) in dioxane (4 ml) was added Pd(dppf)Cl₂ (49.31 mg, 0.067 mmol, 0.10 equiv). After stirring for 4 h at 100° C. under a nitrogen atmosphere, the resulting mixture was concentrated under reduced pressure. The residue was purified by silica gel column chromatography and eluted with PE/THF (1:5) to afford N-tert-butyl-2-[methyl[2-(6-methylpyridin-2-yl)-5H,6H,7H-cyclopenta[d]pyrimidin-4-yl]amino]acetamide (125 mg, 52.48%) as a white solid. ¹H NMR (300 MHz, DMSO-d₆) 1H NMR (300 MHz, DMSO-d6) δ 8.15 (d, J=7.8 Hz, 1H), 7.75 (t, J=7.7 Hz, 1H), 7.66 (s, 1H), 7.29 (d, J=7.6 Hz, 1H), 4.13 (s, 2H), 3.27 (s, 3H), 3.14 (t, J=7.4 Hz, 2H), 2.83 (t, J=7.8 Hz, 2H), 2.55 (s, 3H), 2.14-1.83 (m, 2H), 1.24 (s, 9H). LCMS (ES) [M+1]⁺ m/z: 354.3.

Example 1.86

Synthesis of N-tert-butyl-2-{[2-(4,5-dimethylpyridin-2-yl)-5H,6H,7H-cyclopenta[d]pyrimidin-4-yl](methyl)amino}acetamide (Compound 60)

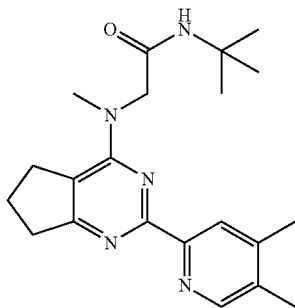 [SMILES: Cc1cnc(-c2nc3c(c(N(C)CC(=O)NC(C)(C)C)n2)CCC3)cc1C]

Scheme 52 depicts a synthetic route for preparing an exemplary compound.

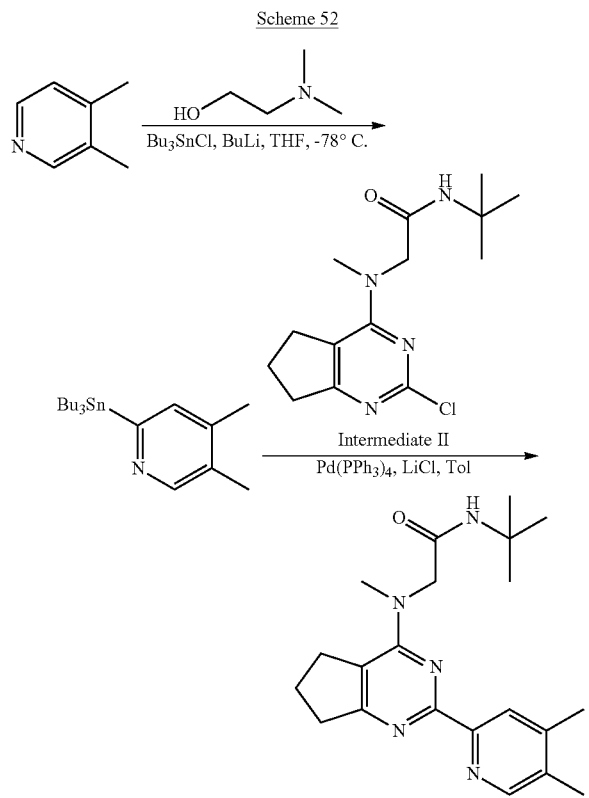

Step 1

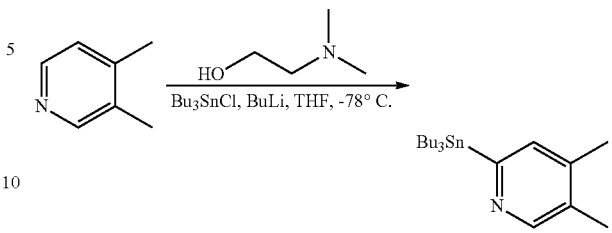

Into a 250-mL 3-necked round-bottom flask purged and maintained in an inert atmosphere of nitrogen was placed 3,4-dimethylpyridine (1.00 g, 9.332 mmol, 1.00 equiv) and THF (20.00 mL). The mixture was stirred at 0° C., then butyllithium (1.76 mL, 27.448 mmol, 2 equiv) was added dropwise. The resulting solution was stirred at 0° C. for 1 hr and dimethylaminoethanol (1.25 g, 14.023 mmol, 1.50 equiv) was added dropwise. The resulting solution was stirred for an additional 1 hr at 0° C., cooled down to −78° C. and tributyltin chloride (4.56 g, 13.998 mmol, 1.5 equiv) was added dropwise. The resulting solution was stirred for an additional 1 h at −78° C. The reaction was then quenched by the addition of water. The resulting mixture was extracted with 3×30 mL of ethyl acetate and the organic layers were combined and dried over anhydrous sodium sulfate and concentrated under vacuum. This resulted in 400 mg (10.82%) of 4,5-dimethyl-2-(tributylstannyl)pyridine as a solid. LCMS (ES) [M+1]⁺ m/z: 398.

Step 2

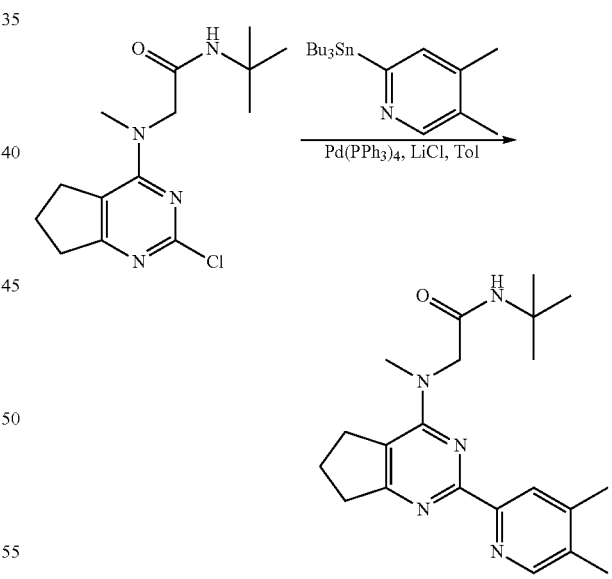

Into a 100-mL round-bottom flask purged and maintained in an inert atmosphere of nitrogen, was placed 4,5-dimethyl-2-(tributylstannyl)pyridine (400.48 mg, 1.011 mmol, 1.20 equiv), N-(tert-butyl)-2-((2-chloro-6,7-dihydro-5H-cyclopenta[d]pyrimidin-4-yl)(methyl)amino)acetamide (Intermediate II, 250.00 mg, 0.842 mmol, 1.00 equiv), Pd(PPh₃)₄ (97.33 mg, 0.084 mmol, 0.10 equiv), LiCl (35.71 mg, 0.842 mmol, 1.00 equiv), and Toluene (10.00 mL). The resulting solution was stirred for 16 hr at 100° C. The reaction mixture was cooled and concentrated. The residue was applied onto a silica gel column and eluted with dichloromethane/methanol (10:1). The collected crude product was further purified by Prep-HPLC with the following conditions (2 #SHIMADZU (HPLC-01)): Column, Welch Xtimate C18, 21.2*250 mm, 5 um; mobile phase, Water (0.05% TFA) and MeOH:ACN=1:1 (10% PhaseB up to 60% in 17 min. This resulted in 68.3 mg (22.06%) of N-(tert-butyl)-2-((2-(4,5-dimethylpyridin-2-yl)-6,7-dihydro-5H-cyclopenta[d]pyrimidin-4-yl)(methyl)amino)acetamide as a white solid. $^1$H NMR (300 MHz, DMSO-$d_6$) δ 8.37 (s, 1H), 8.14 (s, 1H), 7.72 (s, 1H), 4.14 (s, 2H), 3.27 (s, 3H), 3.14 (t, J=7.3 Hz, 2H), 2.80 (t, J=7.8 Hz, 2H), 2.34 (s, 3H), 2.27 (s, 3H), 2.03-1.92 (m, 2H), 1.24 (s, 9H). LCMS (ES) [M+1]$^+$ m/z: 368.2

Example 1.87

Synthesis of N-(1-hydroxy-2-methylpropan-2-yl)-2-{methyl[2-(pyridin-2-yl)-5H,6H,7H-cyclopenta[d]pyrimidin-4-yl]amino}acetamide (Compound 61)

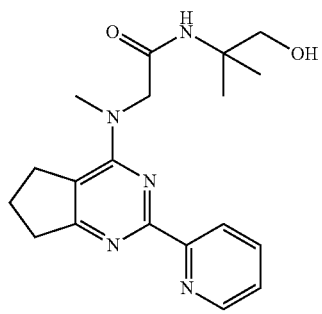 [SMILES: CN(CC(=O)NC(C)(C)CO)c1nc(-c2ccccn2)nc2c1CCC2]

Scheme 53 depicts a synthetic route for preparing an exemplary compound.

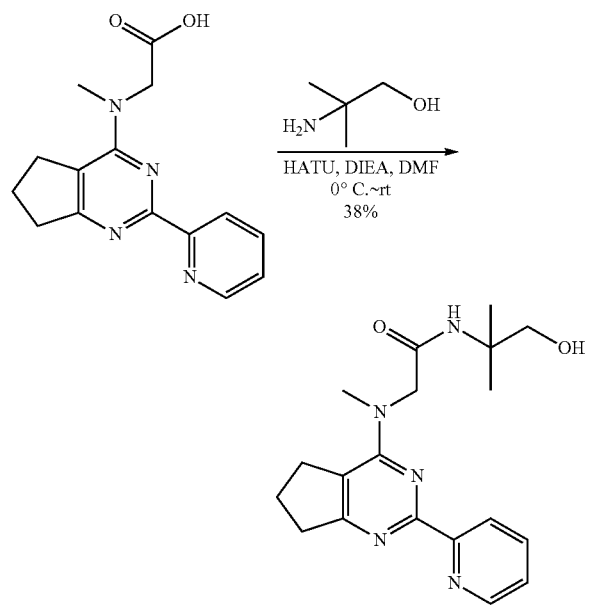

Into a 20-mL vial was placed [methyl[2-(pyridin-2-yl)-5H,6H,7H-cyclopenta[d]pyrimidin-4-yl]amino]acetic acid (Intermediate I, 200 mg, 0.70 mmol, 1.0 equiv), DMF (3.0 mL), 2-amino-2-methyl-1-propanol (69 mg, 0.77 mmol, 1.1 equiv), and DIEA (455 mg, 3.52 mmol, 5.0 equiv). This was followed by the addition of HATU (401 mg, 1.06 mmol, 1.5 equiv) at 0° C. The reaction solution was stirred for 1 h at room temperature. The reaction solution was directly purified by C18-120 g column eluted with CH$_3$CN/H$_2$O (1% NH$_4$OH), from 5% to 80% within 12 min, flow rate, 70 mL/min, detector, 254 nm. This resulted in 93.9 mg (38%) of N-(1-hydroxy-2-methylpropan-2-yl)-2-[methyl[2-(pyridin-2-yl)-5H,6H,7H-cyclopenta[d]pyrimidin-4-yl]amino]acetamide as white solid. $^1$H-NMR (300 MHz, DMSO-$d_6$, ppm): δ 8.66 (dd, J=4.7, 1.8 Hz, 1H), 8.33 (dt, J=8.0, 1.1 Hz, 1H), 7.88 (td, J=7.7, 1.8 Hz, 1H), 7.51 (s, 1H), 7.44 (ddd, J=7.5, 4.8, 1.2 Hz, 1H), 4.82 (t, J=6.0 Hz, 1H), 4.16 (s, 2H), 3.37 (d, J=5.7 Hz, 2H), 3.27 (s, 3H), 3.15 (t, J=7.2 Hz, 2H), 2.82 (t, J=7.8 Hz, 2H), 2.03-1.97 (m, 2H), 1.17 (s, 6H). LCMS (ES, m/z): [M+H]$^+$: 356.2.

Example 1.88

Synthesis of N-(1-hydroxy-2-methylpropan-2-yl)-2-{methyl[2-(4-methylpyridin-2-yl)-5H,6H,7H-cyclopenta[d]pyrimidin-4-yl]amino}acetamide (Compound 62)

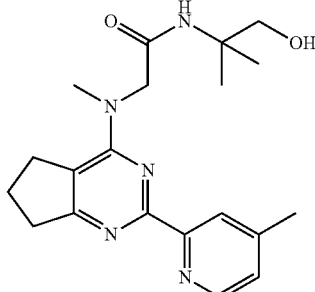

Scheme 54 depicts a synthetic route for preparing an exemplary compound.

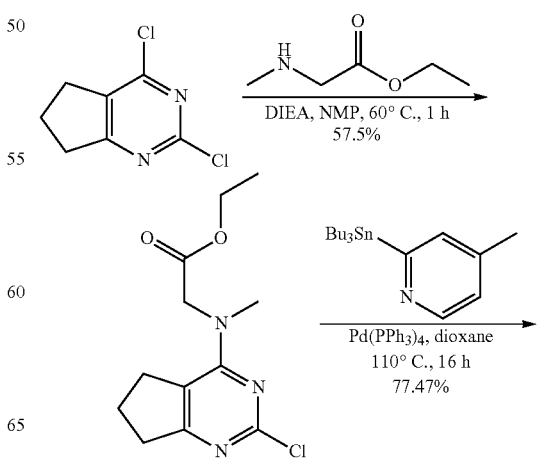

-continued

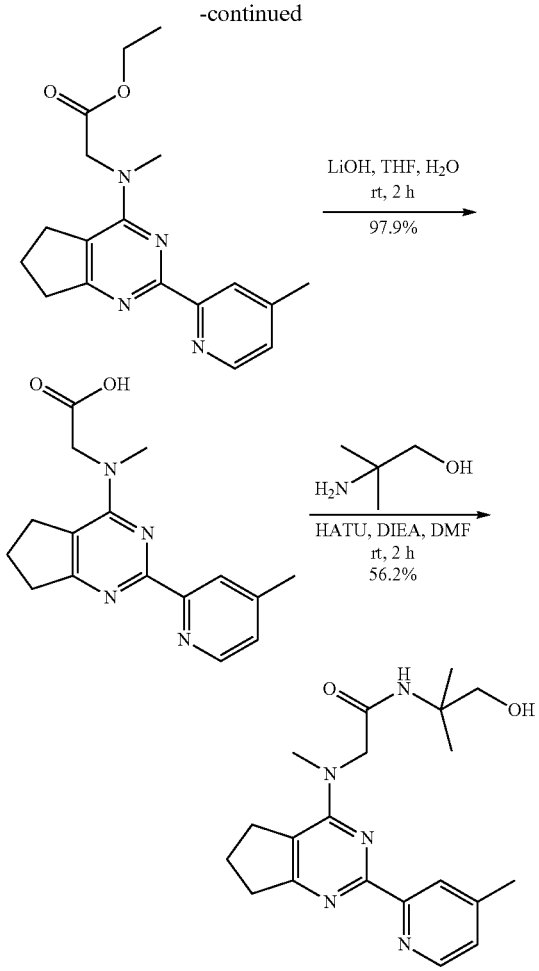

Step 1

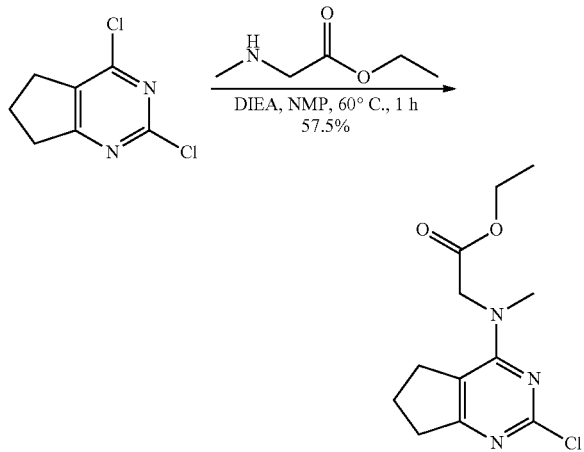

Into a 250-mL round-bottom flask, was placed 2,4-dichloro-6,7-dihydro-5H-cyclopenta[d]pyrimidine (10.00 g, 52.899 mmol, 1.00 equiv), NMP (100.00 mL), ethyl 2-(methylamino)acetate hydrochloride (8.13 g, 52.899 mmol, 1.00 equiv), and DIEA (13.67 g, 105.798 mmol, 2.00 equiv). The resulting solution was stirred for 1 hr at 60° C. The mixture was poured into 200 mL of ethyl acetate. The organic layer was separated and washed with 3×100 ml of water. The organic layer was dried over anhydrous sodium sulfate and concentrated under vacuum. The residue was applied onto a silica gel column and eluted with ethyl acetate/petroleum ether (1:3). The collected fractions were combined and concentrated. This resulted in 8.2 g (57.47%) of ethyl N-(2-chloro-6,7-dihydro-5H-cyclopenta[d]pyrimidin-4-yl)-N-methylglycinate as a yellow solid. LCMS (ES) [M+1]$^+$ m/z 270.

Step 2

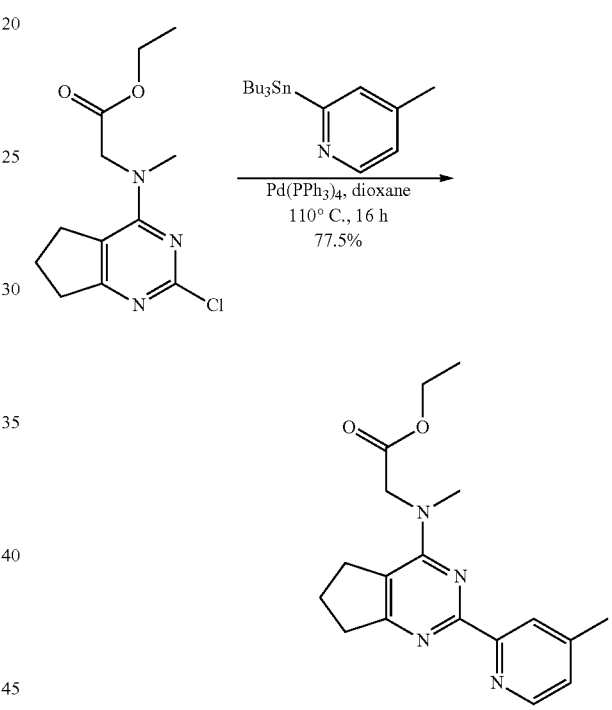

Into a 250-mL round-bottom flask, was placed ethyl N-(2-chloro-6,7-dihydro-5H-cyclopenta[d]pyrimidin-4-yl)-N-methylglycinate (8.00 g, 29.659 mmol, 1.00 equiv), dioxane (100.00 mL), 4-methyl-2-(tributylstannyl)pyridine (13.60 g, 35.591 mmol, 1.20 equiv), and tetrakis(triphenylphosphine)palladium(0) (3.43 g, 2.966 mmol, 0.10 equiv). The resulting solution was stirred for 16 hr at 110° C. The resulting mixture was concentrated. The residue was applied onto a silica gel column and eluted with ethyl acetate/petroleum ether (1:3). The collected fractions were combined and concentrated. This resulted in 7.5 g (77.5%) of ethyl N-methyl-N-(2-(4-methylpyridin-2-yl)-6,7-dihydro-5H-cyclopenta[d]pyrimidin-4-yl)glycinate as a yellow solid. LCMS (ES) [M+1]$^+$ m/z 327.

Step 3

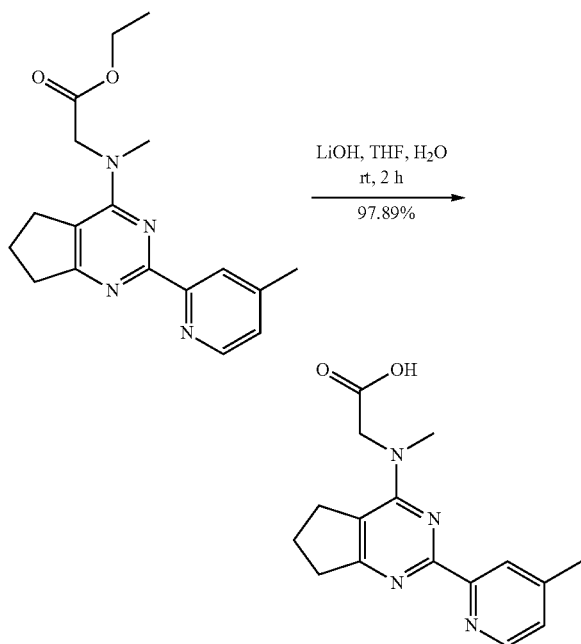

Into a 250-mL round-bottom flask was placed ethyl N-methyl-N-(2-(4-methylpyridin-2-yl)-6,7-dihydro-5H-cyclopenta[d]pyrimidin-4-yl)glycinate (3.80 g, 11.642 mmol, 1 equiv), tetrahydrofuran (30 mL), water (30 mL), and lithium hydroxide (0.56 g, 23.284 mmol, 2.00 equiv). The resulting solution was stirred for 2 hr at 25° C. The resulting mixture was concentrated. The resulting solution was diluted with 50 mL of water. The pH value of the solution was adjusted to 4 with HCl (1 mol/L). The precipitated solids were collected by filtration. This resulted in 3.4 g (97.89%) of N-methyl-N-(2-(4-methylpyridin-2-yl)-6,7-dihydro-5H-cyclopenta[d]pyrimidin-4-yl)glycine as an off-white solid. LCMS (ES) [M+1]+ m/z 299.

Step 4

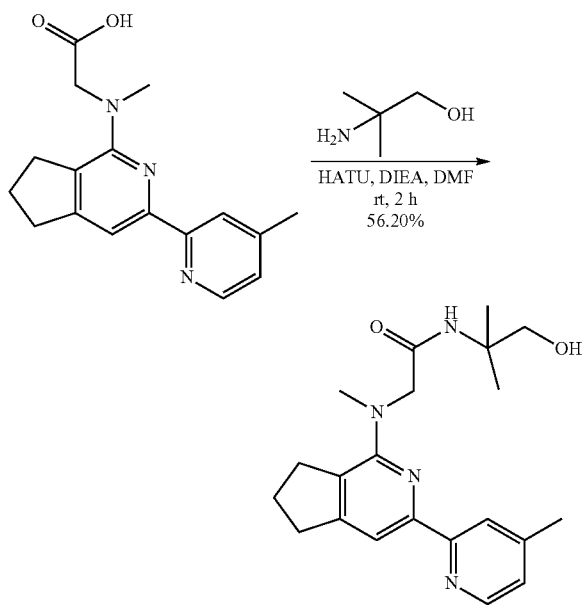

Into a 50-mL round-bottom flask, was placed N-methyl-N-(2-(4-methylpyridin-2-yl)-6,7-dihydro-5H-cyclopenta[d]pyrimidin-4-yl)glycine (100.00 mg, 0.335 mmol, 1.00 equiv), dimethylformamide (4.00 mL), 2-amino-2-methyl-1-propanol (29.88 mg, 0.335 mmol, 1.00 equiv), HATU (191.17 mg, 0.503 mmol, 1.50 equiv), and DIEA (129.96 mg, 1.006 mmol, 3.00 equiv). The resulting solution was stirred for 2 hr at 25° C. The crude reaction mixture was filtered and subjected to reverse phase preparative HPLC (Prep-C18, 20-45M, 120 g, Tianjin Bonna-Agela Technologies; gradient elution of 25% MeCN in water to 35% MeCN in water over a 10 min period, water contains 0.1% NH₃H₂O) to provide N-(1-hydroxy-2-methylpropan-2-yl)-2-{methyl[2-(4-methylpyridin-2-yl)-5H,6H,7H-cyclopenta[d]pyrimidin-4-yl]amino}acetamide as a yellow solid (69.6 mg, 56.20%). ¹H NMR (300 MHz, DMSO-d6) δ 8.61 (d, J=5.0 Hz, 1H), 8.28 (s, 1H), 7.72 (s, 1H), 7.46 (d, J=4.9 Hz, 1H), 4.83 (s, 1H), 4.30 (s, 2H), 3.32 (s, 5H), 3.21 (t, J=7.4 Hz, 2H), 2.93 (t, J=7.8 Hz, 2H), 2.47 (s, 3H), 2.11-1.97 (m, 2H), 1.17 (s, 6H). LCMS (ES) [M+1]+ m/z 370.1.

Example 1.89

Synthesis of N-(4-hydroxy-2-methylbutan-2-yl)-2-{methyl[2-(pyridin-2-yl)-5H,6H,7H-cyclopenta[d]pyrimidin-4-yl]amino}acetamide (Compound 63)

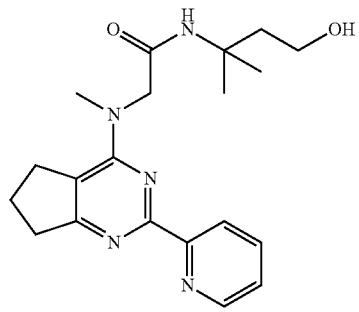 [SMILES: CN(CC(=O)NC(C)(C)CCO)c1nc(-c2ccccn2)nc2c1CCC2]

Scheme 55 depicts a synthetic route for preparing an exemplary compound.

Scheme 55

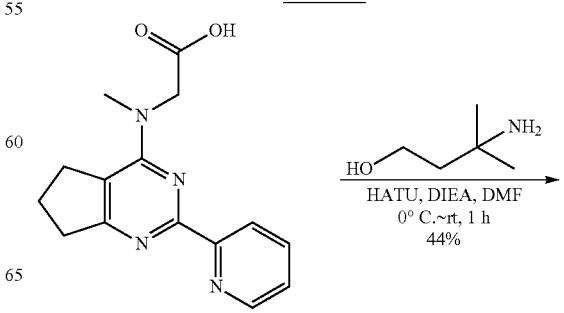

-continued

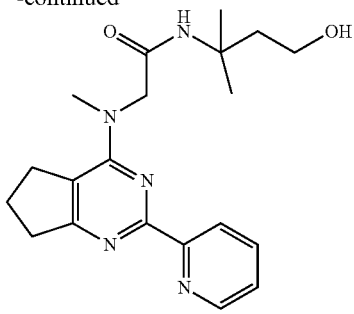

Into a 20-mL vial was placed [methyl[2-(pyridin-2-yl)-5H,6H,7H-cyclopenta[d]pyrimidin-4-yl]amino]acetic acid (150 mg, 0.53 mmol, 1.0 equiv), DMF (3.0 mL), 3-amino-3-methylbutan-1-ol (60 mg, 0.58 mmol, 1.10 equiv), and DIEA (341 mg, 2.64 mmol, 5.0 equiv). This was followed by the addition of HATU (301 mg, 0.79 mmol, 1.5 equiv) at 0° C. The reaction solution was stirred for 1 h at room temperature. The reaction solution was purified by Prep-HPLC with conditions: C18-120 g column, $CH_3CN/H_2O$ (0.5% $NH_4OH$) from 5% to 80% within 15 min, flow rate: 70 mL/min, detector, 254 nm. This resulted in 86.5 mg (44%) of N-(4-hydroxy-2-methylbutan-2-yl)-2-[methyl[2-(pyridin-2-yl)-5H,6H,7H-cyclopenta[d]pyrimidin-4-yl]amino] acetamide as an off-white solid. $^1$H-NMR (300 MHz, DMSO-$d_6$, ppm): δ 8.67 (ddd, J=4.8, 1.8, 0.9 Hz, 1H), 8.32 (dt, J=7.9, 1.1 Hz, 1H), 7.88 (td, J=7.7, 1.8 Hz, 1H), 7.69 (s, 1H), 7.44 (ddd, J=7.5, 4.8, 1.3 Hz, 1H), 4.40 (t, J=4.8 Hz, 1H), 4.14 (s, 2H), 3.47-3.41 (m, 2H), 3.26 (s, 3H), 3.14 (t, J=7.2 Hz, 2H), 2.82 (t, J=7.8 Hz, 2H), 2.05-1.95 (m, 2H), 1.76 (t, J=6.9 Hz, 2H), 1.23 (s, 6H). LCMS (ES, m/z): [M+H]$^+$: 370.3.

Example 1.90

Synthesis of N-cyclopentyl-2-{methyl[2-(4-methylpyridin-2-yl)-5H,6H,7H-cyclopenta[d]pyrimidin-4-yl]amino}acetamide (Compound 64)

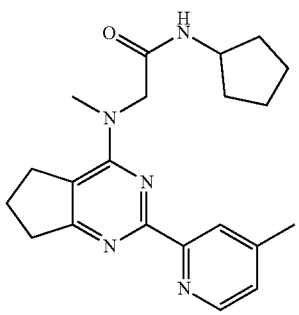 [SMILES: Cc1ccnc(-c2nc3c(c(N(C)CC(=O)NC4CCCC4)n2)CCC3)c1]

Compound 64 was synthesized similar to compound 62 by replacing 2-amino-2-methyl-1-propanol with cyclopentanamine. $^1$H NMR (300 MHz, DMSO-d6) δ 8.51 (d, J=4.9 Hz, 1H), 8.16-8.07 (m, 2H), 7.31-7.23 (m, 1H), 4.17 (s, 2H), 4.06-3.95 (m, 1H), 3.30-3.20 (m, 3H), 3.15 (t, J=7.3 Hz, 2H), 2.82 (t, J=7.8 Hz, 2H), 2.40 (s, 3H), 2.03-1.93 (m, 2H), 1.85-1.68 (m, 2H), 1.70-1.30 (m, 6H). LCMS (ES) [M+1]$^+$ m/z 366.2.

Example 1.91

Synthesis of 2-{methyl[2-(4-methylpyridin-2-yl)-5H,6H,7H-cyclopenta[d]pyrimidin-4-yl]amino}-N-(3-methyloxolan-3-yl)acetamide (Compound 65)

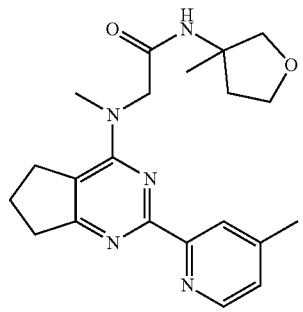 [SMILES: Cc1ccnc(-c2nc3c(c(N(C)CC(=O)NC4(C)CCOC4)n2)CCC3)c1]

Compound 65 was synthesized similar to compound 62 by replacing 2-amino-2-methyl-1-propanol with 3-methyloxolan-3-amine. $^1$H NMR (300 MHz, DMSO-$d_6$) δ 8.51 (d, J=4.9 Hz, 1H), 8.20 (s, 1H), 8.16 (d, J=1.8 Hz, 1H), 7.27 (dd, J=5.1, 1.4 Hz, 1H), 4.18 (s, 2H), 3.80 (d, J=8.7 Hz, 1H), 3.77-3.67 (m, 2H), 3.49 (d, J=8.7 Hz, 1H), 3.29 (s, 3H), 3.16 (t, J=7.4 Hz, 2H), 2.82 (t, J=7.8 Hz, 2H), 2.40 (s, 3H), 2.12-2.28 (m, 1H), 1.81-2.02 (m, 2H), 1.71-1.79 (m, 1H), 1.31 (s, 3H). LCMS (ES) [M+1]$^+$ m/z: 382.3.

Example 1.92

Synthesis of N-(3-fluorophenyl)-2-{methyl[2-(4-methylpyridin-2-yl)-5H,6H,7H-cyclopenta[d]pyrimidin-4-yl]amino}acetamide (Compound 66)

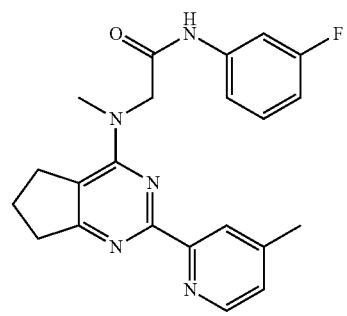 [SMILES: Cc1ccnc(-c2nc3c(c(N(C)CC(=O)Nc4cccc(F)c4)n2)CCC3)c1]

Compound 66 was synthesized similar to compound 62 by replacing 2-amino-2-methyl-1-propanol with 3-fluoroaniline. $^1$H NMR (300 MHz, DMSO-$d_6$) δ 10.49 (s, 1H), 8.47 (d, J=4.9 Hz, 1H), 8.03 (s, 1H), 7.65-7.55 (m, 1H), 7.39-7.26 (m, 2H), 7.25-7.17 (m, 1H), 6.93-6.80 (m, 1H), 4.40 (s, 2H), 3.39 (s, 3H), 3.22 (t, J=7.3 Hz, 2H), 2.83 (t, J=7.8 Hz, 2H), 2.18 (s, 3H), 2.11-1.94 (m, 2H). LCMS (ES) [M+1]$^+$ m/z 392.1.

Example 1.93

Synthesis of N-tert-butyl-2-{methyl[2-(pyrimidin-2-yl)-5H,6H,7H-cyclopenta[b]pyridin-4-yl]amino}acetamide (Compound 67)

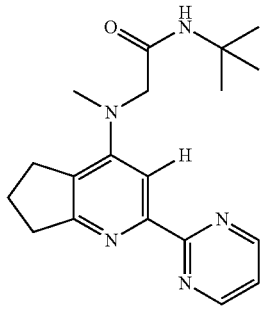 [SMILES: CN(CC(=O)NC(C)(C)C)c1cc(-c2ncccn2)nc2c1CCC2]

Scheme 56 depicts a synthetic route for preparing an exemplary compound.

Scheme 56

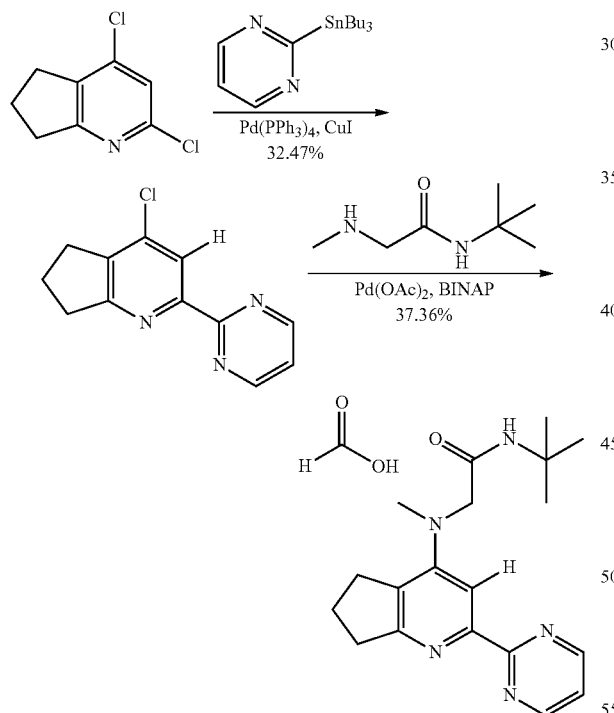

Step 1

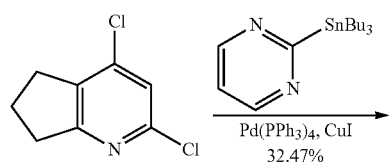

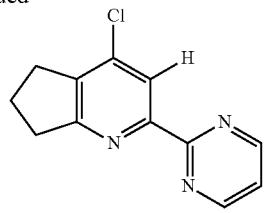

Into a 40-mL vial purged and maintained in an inert atmosphere of nitrogen was placed 2,4-dichloro-5H,6H,7H-cyclopenta[b]pyridine (500.00 mg, 2.66 mmol, 1.00 equiv), 2-(tributylstannyl)pyrimidine (1275.94 mg, 3.46 mmol, 1.30 equiv), CsF (807.78 mg, 5.32 mmol, 2.00 equiv), Pd(PPh$_3$)$_4$ (307.25 mg, 0.26 mmol, 0.10 equiv), CuI (50.64 mg, 0.26 mmol, 0.10 equiv), and DMF (10.00 mL). The resulting solution was stirred for 8 h at 110° C. The reaction mixture was cooled to room temperature. The crude product (1 g) was purified by Prep-HPLC with the following conditions: Column, XBridge Prep C18 OBD Column, 19 cm, 150 mm, 5 um; mobile phase, Water (0.1% NH$_4$HCO$_3$) and CAN (30% Phase B up to 60% in 11 min); Detector, 254 nm. This resulted in 200 mg (32.47%) of 2-[4-chloro-5H,6H,7H-cyclopenta[b]pyridin-2-yl]pyrimidine as a brown solid. LCMS (ES) [M+H]$^+$ m/z: 232.

Step 2

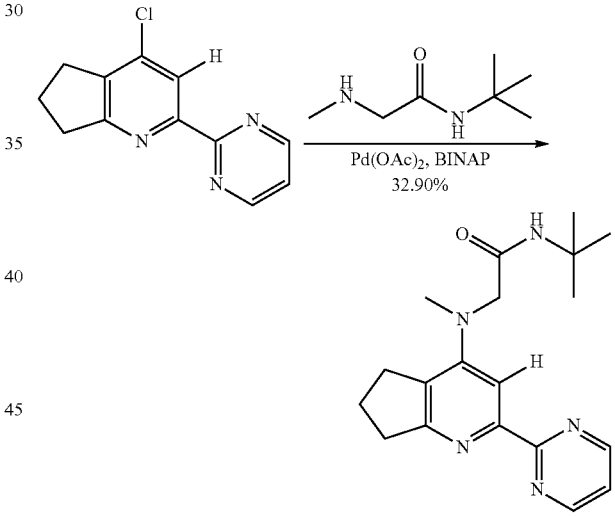

Into a 40-mL vial purged and maintained in an inert atmosphere of nitrogen, was placed 2-[4-chloro-5H,6H,7H-cyclopenta[b]pyridin-2-yl]pyrimidine (150.00 mg, 0.65 mmol, 1.00 equiv), N-tert-butyl-2-(methylamino)acetamide (121.39 mg, 0.84 mmol, 1.30 equiv), Pd(OAc)$_2$ (14.54 mg, 0.06 mmol, 0.10 equiv), BINAP (80.63 mg, 0.13 mmol, 0.20 equiv), Cs$_2$CO$_3$ (421.90 mg, 1.29 mmol, 2.00 equiv), and dioxane (8.00 mL). The resulting solution was stirred overnight at 100° C. The reaction mixture was cooled to room temperature. The resulting mixture was concentrated. The crude product (500 mg) was purified by Prep-HPLC with the following conditions: Column, XBridge Prep C18 OBD Column, 19 cm, 150 mm, 5 um; mobile phase, Water (0.1% HCOOH) and CAN (20% Phase B up to 50% in 11 min); Detector, 254 nm. This resulted in 82.1 mg (32.90%) of N-tert-butyl-2-[methyl[2-(pyrimidin-2-yl)-5H,6H,7H-cyclopenta[b]pyridin-4-yl]amino]acetamide formate as a yellow oil. $^1$H-NMR (300 MHz, DMSO-d6) δ 8.91 (d, J=4.8 Hz, 2H), 8.17 (s, 1H), 7.61 (s, 1H), 7.57-7.45 (m, 2H), 3.98 (s, 2H), 3.09 (s, 3H), 3.04 (t, J=7.2 Hz, 2H), 2.88 (t, J=7.7 Hz, 2H), 2.09-1.93 (m, 2H), 1.27 (s, 9H). LCMS (ES, m/z): [M+H]$^+$: 340.1.

Example 1.94

Synthesis of N-tert-butyl-2-{methyl[2-(4-methylpyridin-2-yl)-5H,6H,7H-cyclopenta[b]pyridin-4-yl]amino}acetamide (Compound 68)

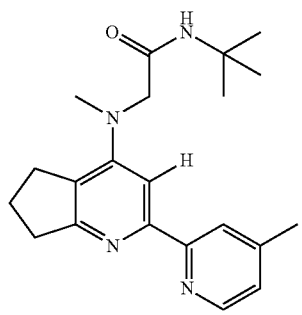 [SMILES: Cc1ccnc(-c2cc(N(C)CC(=O)NC(C)(C)C)c3c(n2)CCC3)c1]

Scheme 57 depicts a synthetic route for preparing an exemplary compound.

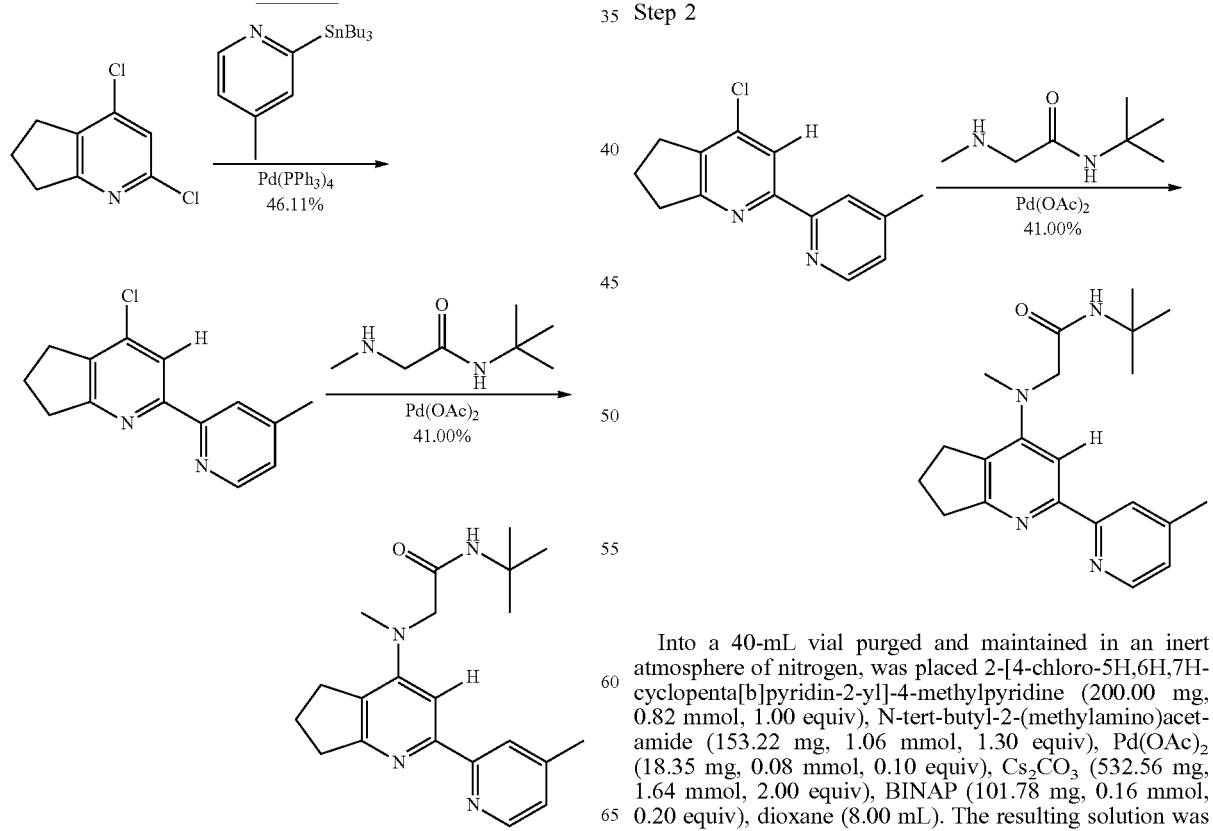

Step 1

Into a 40-mL vial purged and maintained in an inert atmosphere of nitrogen, was placed 2,4-dichloro-5H,6H,7H-cyclopenta[b]pyridine (500.00 mg, 2.66 mmol, 1.00 equiv), 4-methyl-2-(tributylstannyl)pyridine (1321.01 mg, 3.46 mmol, 1.30 equiv), Pd(PPh$_3$)$_4$ (307.25 mg, 0.26 mmol, 0.10 equiv), and dioxane (10.00 mL). The resulting solution was stirred overnight at 110° C. The reaction mixture was cooled to room temperature. The resulting mixture was concentrated. The crude product (1 g) was purified by Prep-HPLC with the following conditions: Column, XBridge Prep C18 OBD Column, 19 cm, 150 mm, 5 um; mobile phase, Water (0.1% NH$_4$HCO$_3$) and CAN (40% Phase B up to 70% in 11 min); Detector, 254. This resulted in 300 mg (46.11%) of 2-[4-chloro-5H,6H,7H-cyclopenta[b]pyridin-2-yl]-4-methylpyridine as a white solid. LCMS (ES) [M+H]$^+$ m/z: 245.

Step 2

Into a 40-mL vial purged and maintained in an inert atmosphere of nitrogen, was placed 2-[4-chloro-5H,6H,7H-cyclopenta[b]pyridin-2-yl]-4-methylpyridine (200.00 mg, 0.82 mmol, 1.00 equiv), N-tert-butyl-2-(methylamino)acetamide (153.22 mg, 1.06 mmol, 1.30 equiv), Pd(OAc)$_2$ (18.35 mg, 0.08 mmol, 0.10 equiv), Cs$_2$CO$_3$ (532.56 mg, 1.64 mmol, 2.00 equiv), BINAP (101.78 mg, 0.16 mmol, 0.20 equiv), dioxane (8.00 mL). The resulting solution was stirred overnight at 100° C. The reaction mixture was cooled to room temperature. The resulting mixture was concentrated. The crude product (0.5 g) was purified by Prep-HPLC with the following conditions: Column, XBridge Prep C18 OBD Column, 19 cm, 150 mm, 5 um; mobile phase, Water (0.1% NH$_4$HCO$_3$) and CAN (40% Phase B up to 70% in 11 min); Detector, 254 nm. This resulted in 118.1 mg (41.00%) of N-tert-butyl-2-[methyl[2-(4-methylpyridin-2-yl)-5H,6H,7H-cyclopenta[b]pyridin-4-yl]amino]acetamide as a white solid. $^1$H-NMR (300 MHz, DMSO-d6) δ 8.46 (d, J=4.9 Hz, 1H), 8.16 (d, J=1.8 Hz, 1H), 7.56 (s, 1H), 7.54 (s, 1H), 7.19 (dd, J=5.0, 1.8 Hz, 1H), 3.93 (s, 2H), 3.06 (s, 3H), 3.02 (t, J=7.1 Hz, 2H), 2.85 (t, J=7.7 Hz, 2H), 2.39 (s, 3H), 2.08-1.95 (m, 2H), 1.27 (s, 9H). LCMS (ES, m/z): [M+H]$^+$: 353.2.

Example 1.95

Synthesis of N-[2-(1-cyclobutyl-5-methyl-1H-imidazol-2-yl)ethyl]-2-{methyl[2-(pyridin-2-yl)-5H,6H,7H-cyclopenta[d]pyrimidin-4-yl]amino}acetamide (Compound 69)

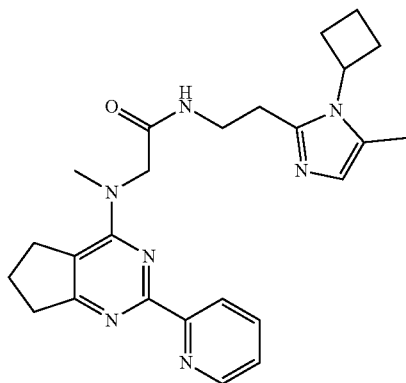 [SMILES: Cc1cnc(CCNC(=O)CN(C)c2nc(-c3ccccn3)nc3c2CCC3)n1C1CCC1]

Scheme 58 depicts a synthetic route for preparing an exemplary compound.

Scheme 58

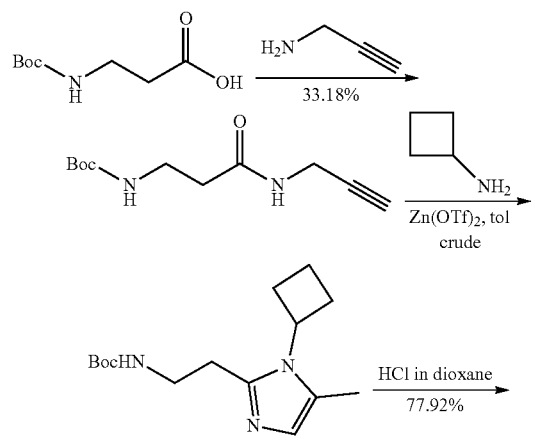

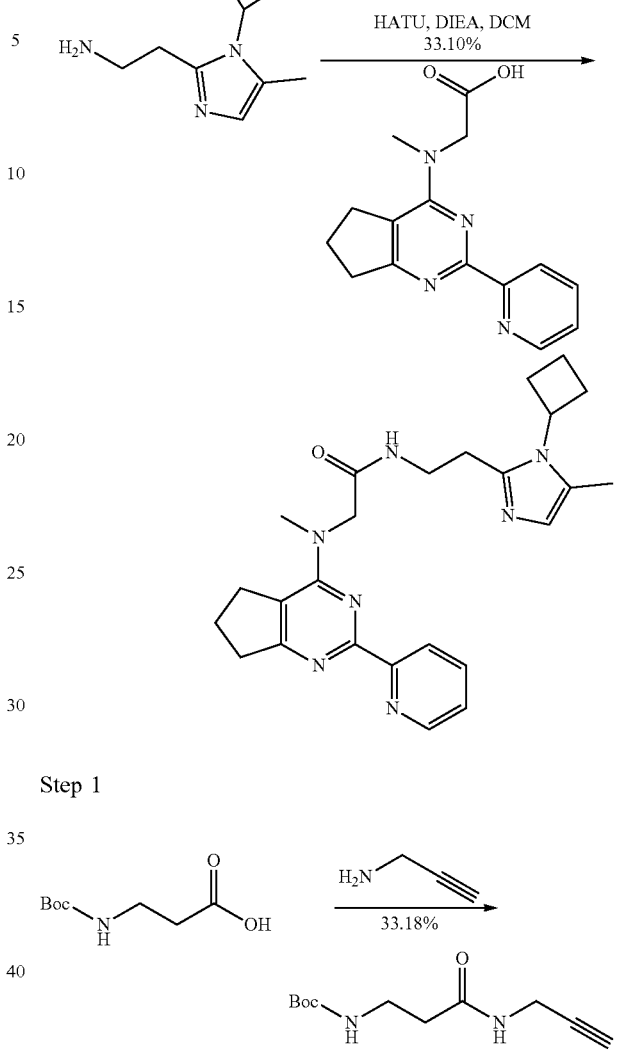

Step 1

Into a 250-mL round-bottom flask purged and maintained in an inert atmosphere of nitrogen, was placed 3-((tert-butoxycarbonyl)amino)propanoic acid (7.56 g, 39.955 mmol, 1.00 equiv), DCM (100.00 mL), and CDI (6.48 g, 39.955 mmol, 1 equiv). The resulting solution was stirred for 2 h at room temperature. This was followed by the addition of 2-propynylamine (2.20 g, 39.942 mmol, 1.00 equiv) dropwise with stirring at room temperature. The resulting solution was stirred overnight at room temperature. The resulting mixture was concentrated. The residue was applied onto a silica gel column and eluted with PE/THF (50% THF). This resulted in 3 g (33.18%) of tert-butyl (3-oxo-3-(prop-2-yn-1-ylamino)propyl)carbamate as an off-white solid. LCMS (ES) [M+1]$^+$ m/z 227.

Step 2

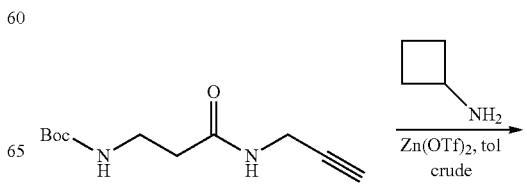

-continued

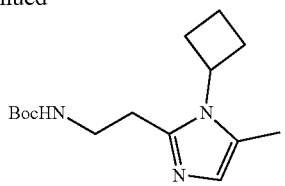

Into a 100-mL round-bottom flask purged and maintained in an inert atmosphere of nitrogen, was placed tert-butyl (3-oxo-3-(prop-2-yn-1-ylamino)propyl)carbamate (500.00 mg, 2.210 mmol, 1.00 equiv), cyclobutylamine (188.59 mg, 2.652 mmol, 1.20 equiv), zinc trifluoromethanesulfonate (160.67 mg, 0.442 mmol, 0.20 equiv), and Toluene (30.00 mL). The resulting solution was stirred overnight at 100° C. in an oil bath. The reaction mixture was cooled to room temperature with a water bath. The pH value of the solution was adjusted to 8 with $K_2CO_3$ (10%). The resulting solution was extracted with 3×100 mL of ethyl acetate, he organic layers were combined, dried over anhydrous sodium sulfate, and concentrated. This resulted in 600 mg (crude) of tert-butyl (2-(1-cyclobutyl-5-methyl-1H-imidazol-2-yl)ethyl) carbamate as a yellow oil. LCMS (ES) [M+1]$^+$ m/z 280.

Step 3

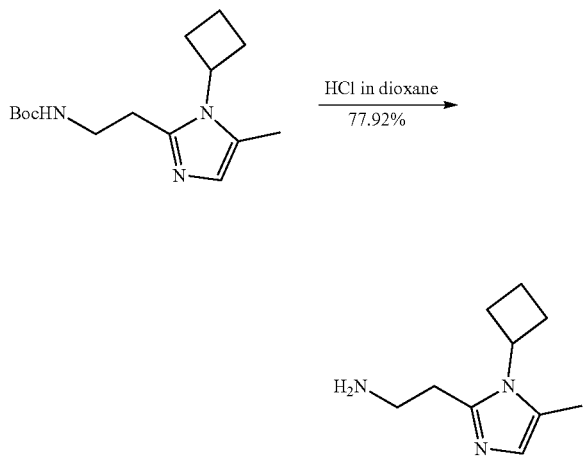

Into a 100-mL round-bottom flask purged and maintained in an inert atmosphere of nitrogen, was placed tert-butyl (2-(1-cyclobutyl-5-methyl-1H-imidazol-2-yl)ethyl)carbamate (600.00 mg, 2.148 mmol, 1.00 equiv), HCl (gas) in EA (10.00 mL). The resulting solution was stirred overnight at room temperature. The resulting mixture was concentrated. The solids were isolated by filtration and dried over vacuum. This resulted in 300 mg (77.92%) of 2-(1-cyclobutyl-5-methyl-1H-imidazol-2-yl)ethan-1-amine as a yellow solid. LCMS (ES) [M+1]$^+$ m/z 180.

Step 4

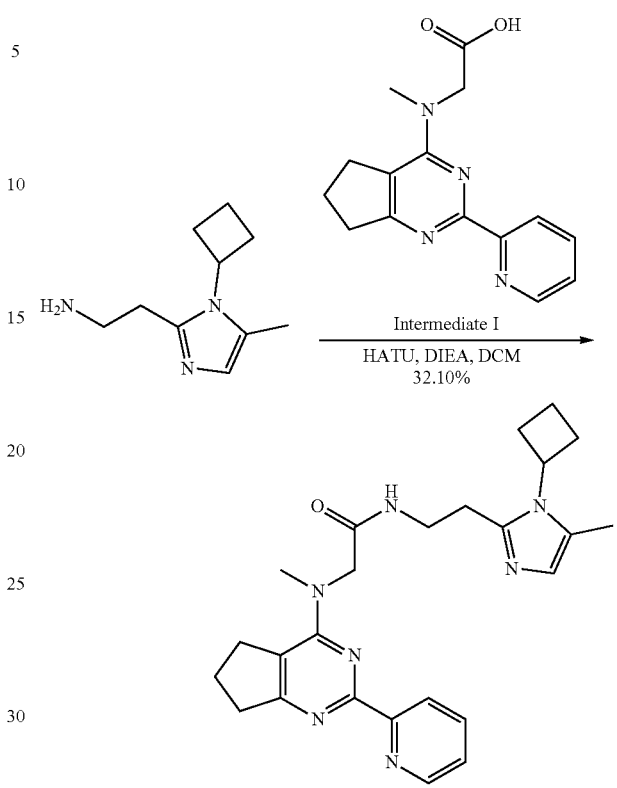

Into a 100-mL round-bottom flask, was placed N-methyl-N-(2-(pyridin-2-yl)-6,7-dihydro-5H-cyclopenta[d]pyrimidin-4-yl)glycine (200.00 mg, 0.703 mmol, 1.00 equiv), 2-(1-cyclobutyl-5-methyl-1H-imidazol-2-yl)ethan-1-amine (151.32 mg, 0.844 mmol, 1.20 equiv), HATU (294.21 mg, 0.774 mmol, 1.10 equiv), DIEA (272.74 mg, 2.110 mmol, 3.00 equiv), and DCM (20.00 mL). The resulting solution was stirred for 4 hr at room temperature. The resulting mixture was concentrated. The crude product was purified by Flash-Prep-HPLC (Prep-C18, 20-45M, 120 g, Tianjin Bonna-Agela Technologies; gradient elution of 35% MeCN in water to 60% MeCN in water over a 10 min period, where both solvents contain 0.1% $NH_3H_2O$). This resulted in 100.6 mg (32.10%) of N-(2-(1-cyclobutyl-5-methyl-1H-imidazol-2-yl)ethyl)-2-(methyl(2-(pyridin-2-yl)-6,7-dihydro-5H-cyclopenta[d]pyrimidin-4-yl)amino)acetamide as a white solid. $^1$H NMR (300 MHz, DMSO-$d_6$, ppm) δ 8.66 (d, J=3.6 Hz, 1H), 8.22-8.35 (m, 2H), 7.86 (td, J=7.7, 1.9 Hz, 1H), 7.49-7.38 (m, 1H), 6.40 (s, 1H), 4.41-4.56 (m, 1H), 4.19 (s, 2H), 3.25-3.39 (m, 2H), 3.28 (s, 3H), 3.15 (t, J=7.4 Hz, 2H), 2.82 (t, J=7.9 Hz, 2H), 2.70 (t, J=7.3 Hz, 2H), 2.45-2.23 (m, 4H), 2.18 (s, 3H), 1.87-2.05 (m, 2H), 1.55-1.71 (m, 2H). LCMS (ES) [M+1]$^+$ m/z 446.2.

Example 1.96

Synthesis of N-[5-(azepan-1-yl)-1,3,4-thiadiazol-2-yl]-2-{methyl[2-(pyridin-2-yl)-5H,6H,7H-cyclopenta[d]pyrimidin-4-yl]amino}acetamide (Compound 70)

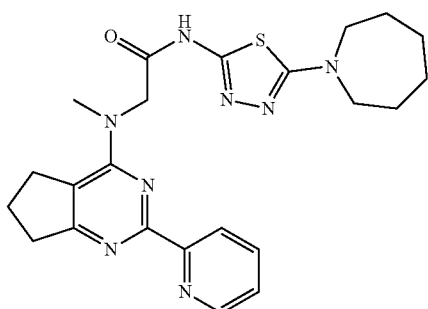

Scheme 59 depicts a synthetic route for preparing an exemplary compound.

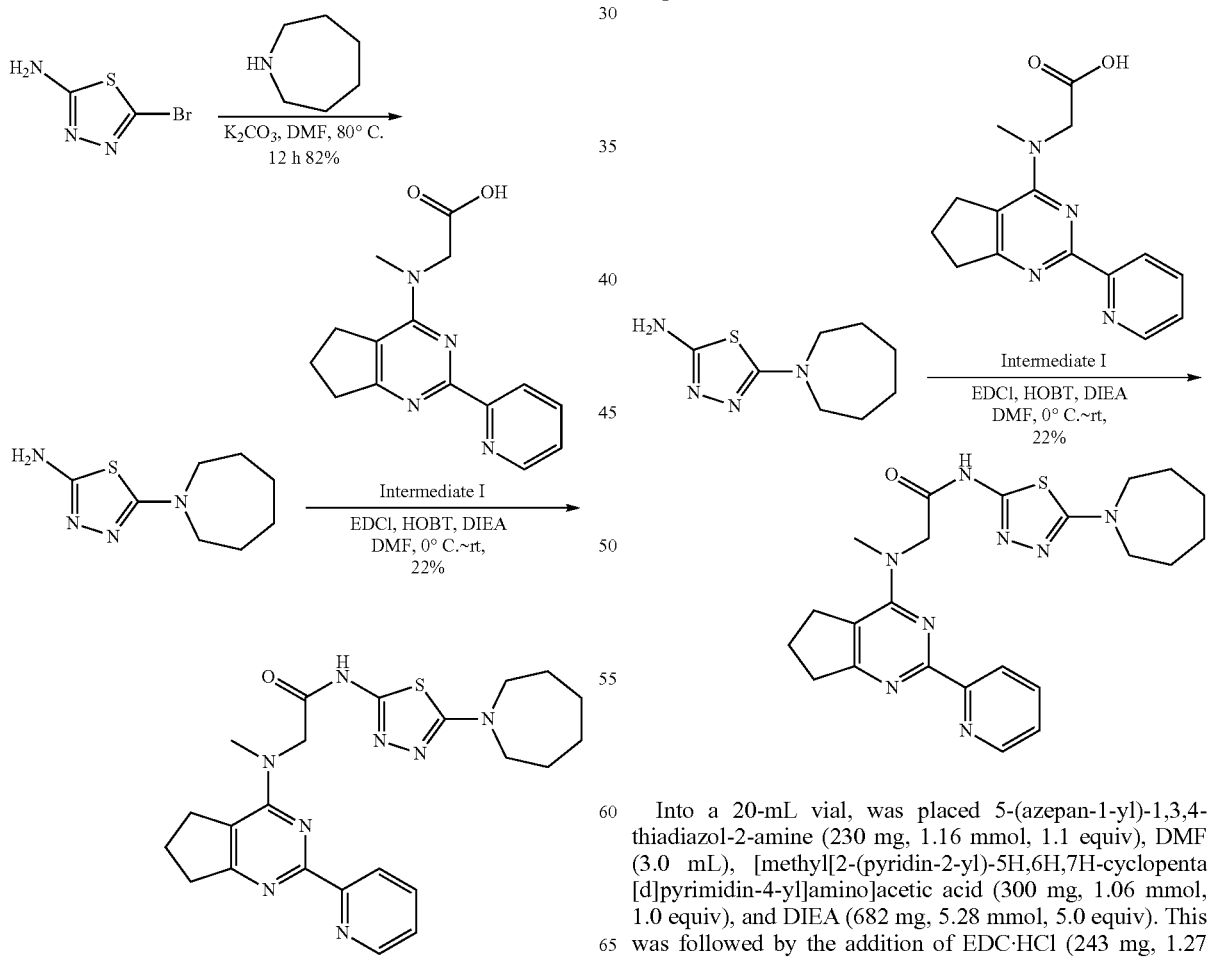

Step 1

Into a 50-mL round-bottom flask was placed 5-bromo-1,3,4-thiadiazol-2-amine (500 mg, 2.78 mmol, 1.0 equiv), DMF (10.0 mL), $K_2CO_3$ (1.15 g, 8.33 mmol, 3.0 equiv), and hexamethyleneimine (276 mg, 2.78 mmol, 1.0 equiv). The mixture was stirred for 12 h at 80° C. in an oil bath. After being cooled to room temperature, the reaction was diluted with 20 mL of water and extracted with 3×20 mL of ethyl acetate. The combined organic phase was washed with 3×20 ml of brine, dried over anhydrous sodium sulfate, filtered, and the filtrate was concentrated under reduced pressure. The residue was purified by silica gel column with ethyl acetate/petroleum ether (1:1). This resulted in 450 mg (82%) of 5-(azepan-1-yl)-1,3,4-thiadiazol-2-amine obtained as a pink solid.

Step 2

Into a 20-mL vial, was placed 5-(azepan-1-yl)-1,3,4-thiadiazol-2-amine (230 mg, 1.16 mmol, 1.1 equiv), DMF (3.0 mL), [methyl[2-(pyridin-2-yl)-5H,6H,7H-cyclopenta[d]pyrimidin-4-yl]amino]acetic acid (300 mg, 1.06 mmol, 1.0 equiv), and DIEA (682 mg, 5.28 mmol, 5.0 equiv). This was followed by the addition of EDC·HCl (243 mg, 1.27 mmol, 1.2 equiv) and HOBt (171 mg, 1.27 mmol, 1.2 equiv) at 0° C. The mixture was stirred for 1 h at room temperature.

The reaction solution was purified by Prep-HPLC with conditions: C18-120 g column, CH$_3$CN/H$_2$O (0.5% NH$_4$OH) from 5% to 80% within 15 min, flow rate: 70 mL/min, detector, 254 nm. 106.6 mg (22%) of N-[5-(azepan-1-yl)-1,3,4-thiadiazol-2-yl]-2-[methyl[2-(pyridin-2-yl)-5H,6H,7H-cyclopenta[d]pyrimidin-4-yl]amino]acetamide was obtained as off-white solid. $^1$H NMR (300 MHz, DMSO-d$_6$, ppm): δ 12.19 (br, 1H), 8.64 (ddd, J=4.8, 1.8, 0.9 Hz, 1H), 8.19 (dt, J=7.9, 1.1 Hz, 1H), 7.77 (td, J=7.7, 1.8 Hz, 1H), 7.41 (ddd, J=7.5, 4.7, 1.2 Hz, 1H), 4.50 (s, 2H), 3.48 (t, J=5.7 Hz, 4H), 3.36 (s, 3H), 3.20 (t, J=7.2 Hz, 2H), 2.84 (t, J=7.8 Hz, 2H), 2.06-1.96 (m, 2H), 1.73-1.67 (m, 4H), 1.50-1.46 (m, 4H). LCMS (ES, m/z): [M+H]$^+$: 465.3.

Example 1.97

Synthesis of 1-[2-(1,3-thiazol-4-yl)-5H,6H,7H-cyclopenta[d]pyrimidin-4-yl]azepane (Compound 94)

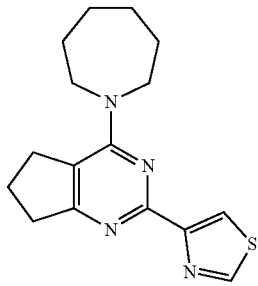 [SMILES: c1nc(-c2nc3c(c(N4CCCCCC4)n2)CCC3)cs1]

Compound 94 was synthesized similar to Compound 92 by replacing 2-(tributylstannyl)pyridine with 4-(tributylstannyl)thiazole. $^1$H NMR (400 MHz, DMSO-d$_6$) δ 9.13 (d, J=2.1 Hz, 1H), 8.32 (d, J=2.1 Hz, 1H), 3.75 (t, J=6.1 Hz, 4H), 3.05 (t, J=7.3 Hz, 2H), 2.78 (t, J=7.9 Hz, 2H), 1.97 (p, J=7.7 Hz, 2H), 1.73 (q, J=5.5 Hz, 4H), 1.47 (p, J=2.8 Hz, 4H). LCMS (ES) [M+1]$^+$ m/z: 301.2.

Example 1.98

Synthesis of 3-{methyl[2-(pyridin-2-yl)-5H,6H,7H-cyclopenta[d]pyrimidin-4-yl]amino}-1-phenylpyrrolidin-2-one (Compound 95)

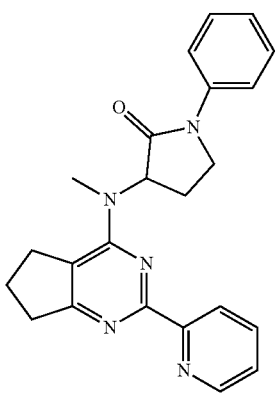 [SMILES: CN(c1nc(-c2ccccn2)nc2c1CCC2)C1CCN(c2ccccc2)C1=O]

Compound 95 was synthesized similar to Compound 73 by replacing 2-pyridinylmethanamine with 3-amino-1-phenylpyrrolidin-2-one LCMS (ES+): (M+H)$^+$=386.3. $^1$H NMR (400 MHz, DMSO-d6) δ 8.65-8.45 (m, 1H), 8.23-8.06 (m, 1H), 7.79-7.56 (m, 3H), 7.44-7.08 (m, 4H), 5.48-5.17 (m, 1H), 4.01-3.85 (m, 2H), 3.24 (s, 5H), 2.90-2.79 (m, 2H), 2.44-2.27 (m, 2H), 2.09-1.95 (m, 2H).

Example 1.99

Synthesis of 1-[2-(4-chloropyridin-2-yl)-5H,6H,7H-cyclopenta[d]pyrimidin-4-yl]azepane (Compound 96)

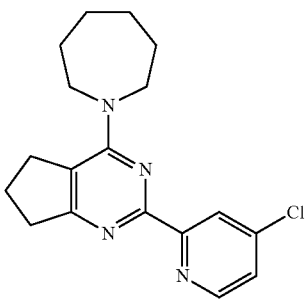 [SMILES: Clc1ccnc(-c2nc3c(c(N4CCCCCC4)n2)CCC3)c1]

Compound 96 was synthesized similar to Compound 92 by replacing 2-(tributylstannyl)pyridine with 4-chloro-2-(tributylstannyl)pyridine. $^1$H NMR (400 MHz, Methanol-d$_4$) δ 8.59 (d, J=5.3 Hz, 1H), 8.30 (d, J=2.0 Hz, 1H), 7.50 (dd, J=5.3, 2.1 Hz, 1H), 3.81 (t, J=6.1 Hz, 4H), 3.11 (t, J=7.3 Hz, 2H), 2.89 (t, J=7.9 Hz, 2H), 2.07 (p, J=7.7 Hz, 2H), 1.81 (dq, J=9.2, 4.0 Hz, 4H), 1.51 (m, 4H). LCMS (ES) [M+1]$^+$ m/z: 329.3, 331.4.

Example 1.100

Synthesis of 1-[2-(1-methyl-1H-imidazol-4-yl)-5H,6H,7H-cyclopenta[d]pyrimidin-4-yl]azepane (Compound 97)

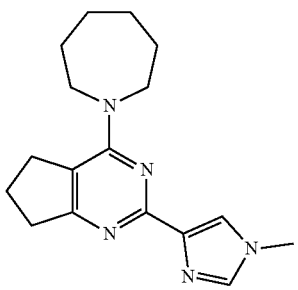 [SMILES: Cn1cnc(-c2nc3c(c(N4CCCCCC4)n2)CCC3)c1]

Compound 97 was synthesized similar to Compound 92 by replacing 2-(tributylstannyl)pyridine with 1-methyl-4-(tributylstannyl)-1H-imidazole. $^1$H NMR (400 MHz, Methanol-d4) δ 7.86 (d, J=1.3 Hz, 1H), 7.73 (d, J=1.3 Hz, 1H), 3.88 (t, J=6.1 Hz, 4H), 3.80 (s, 3H), 3.12 (t, J=7.4 Hz, 2H), 2.91 (t, J=7.9 Hz, 2H), 2.09 (h, J=8.1 Hz, 2H), 1.82 (q, J=5.7 Hz, 4H), 1.58 (p, J=2.7 Hz, 4H). LCMS (ES) [M+1]$^+$ m/z: 298.2.

Example 1.101

Synthesis of 2-{methyl[2-(pyridin-2-yl)-5H,6H,7H-cyclopenta[d]pyrimidin-4-yl]amino}-N-[1-(trifluoromethyl)cyclopropyl]acetamide (Compound 98)

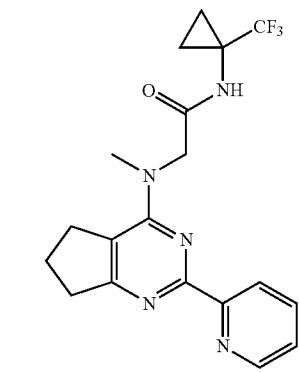 [SMILES: CN(CC(=O)NC1(C(F)(F)F)CC1)c1nc(-c2ccccn2)nc2c1CCC2]

Scheme 60 depicts a synthetic route for preparing an exemplary compound.

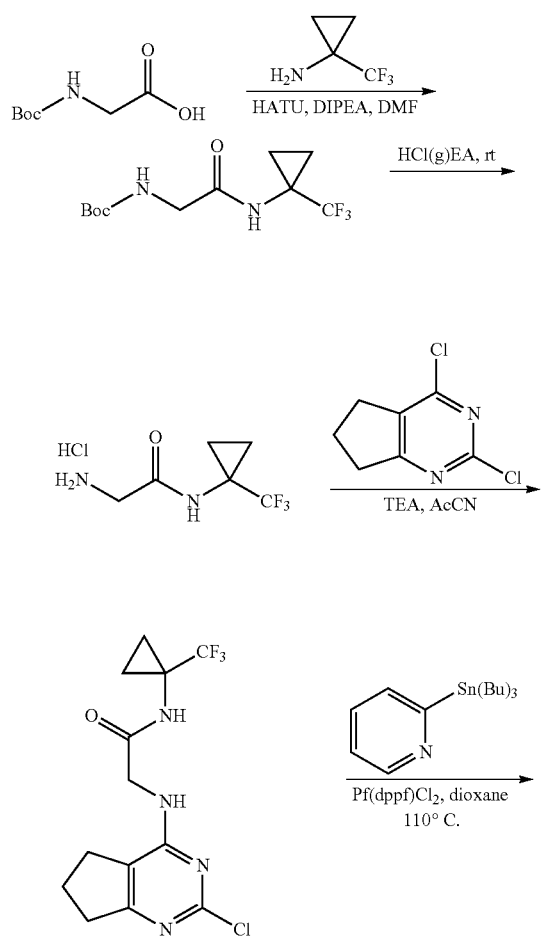

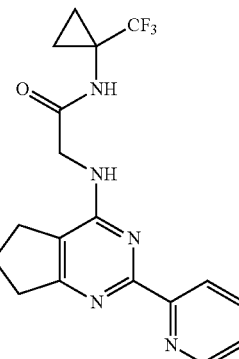

Step 1

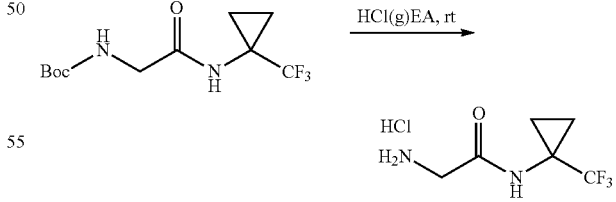

To a solution of [(tert-butoxycarbonyl)(methyl)amino] acetic acid (302.51 mg; 1.60 mmol; 1.00 eq.) in DMF (2.5 mL) was added 1-(trifluoromethyl)cyclopropan-1-amine (200.00 mg; 1.60 mmol; 1.00 eq.), followed by DIPEA (0.42 mL; 2.40 mmol; 1.50 eq.) and HATU (607.92 mg; 1.60 mmol; 1.00 eq.). After being stirred for 15 h at room temperature, it was diluted with water, and extracted with EtOAc. The organic layers were combined, dried, and concentrated to give tert-butyl N-methyl-N-({[1-(trifluoromethyl)cyclopropyl]carbamoyl}methyl)carbamate, which was used for the next step without purification. LCMS (ES) [M+1]+ m/z: 297.5.

Step 2

To a solution of tert-butyl N-methyl-N-({[1-(trifluoromethyl)cyclopropyl]carbamoyl}methyl)carbamate (0.47 g; 1.60 mmol; 1.00 eq.) in DCM (4 mL) was added 4N HCl in dioxane (4 mL). The mixture was stirred further, concentrated, and lyophilized to give 2-[chloro(methyl)amino]-N-[1-(trifluoromethyl)cyclopropyl]acetamide, which was used directly for the next step without purification. LCMS (ES) [M+1]+ m/z: 197.3.

Step 3

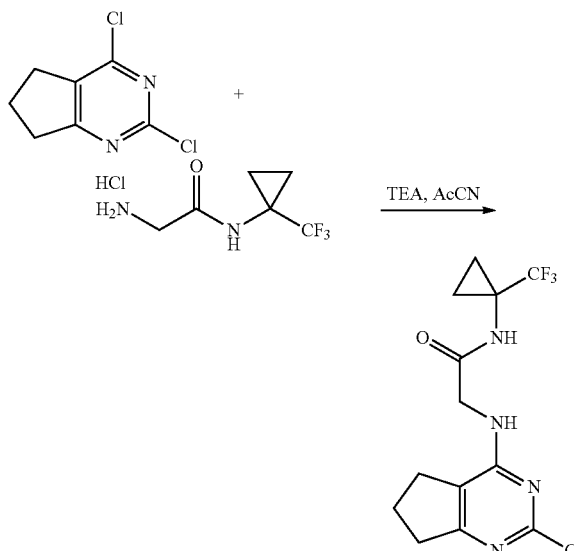

To a solution of 2,4-dichloro-6,7-dihydro-5H-cyclopenta[d]pyrimidine (0.13 g; 0.70 mmol; 1.00 eq.) in AcCN (2 mL) was added 2-[chloro(methyl)amino]-N-[1-(trifluoromethyl)cyclopropyl]acetamide (0.19 g; 0.80 mmol; 1.15 eq.), and triethylamine (0.29 mL; 2.10 mmol; 3.00 eq.). After being heated at 75° C. for 4 h, the mixture was cooled and concentrated, diluted with water, and the resulting precipitates were collected by filtration and dried to give 2-({2-chloro-5H,6H,7H-cyclopenta[d]pyrimidin-4-yl}(methyl)amino)-N-[1-(trifluoromethyl)cyclopropyl]acetamide (200 mg). LCMS (ES) [M+1]+ m/z: 349.0, 351.1.

Step 4

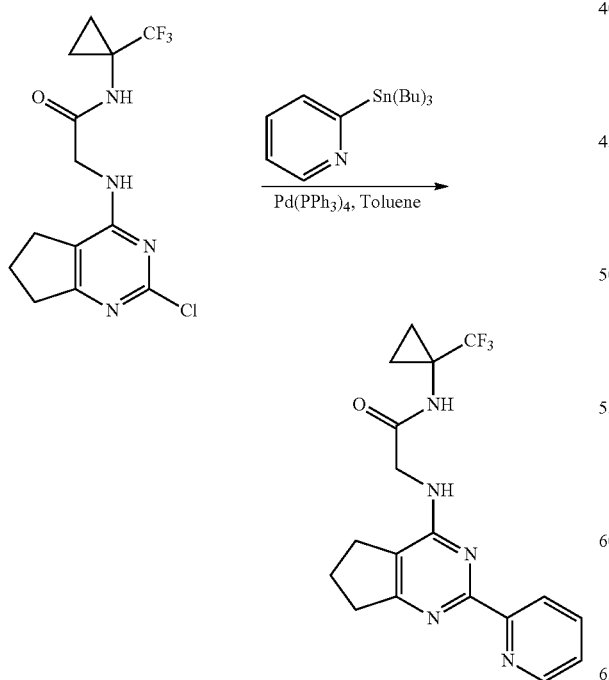

To a solution of 2-({2-chloro-5H,6H,7H-cyclopenta[d]pyrimidin-4-yl}(methyl)amino)-N-[1-(trifluoromethyl)cyclopropyl]acetamide (50.00 mg; 0.20 mmol; 1.00 eq.) and 2-(tributylstannyl)pyridine (190.01 mg; 0.52 mmol; 2.00 eq.) in toluene (1 mL) was added tetrakis(triphenylphosphane) palladium (29.82 mg; 0.03 mmol; 0.10 eq.). The mixture was heated at 115° C. for 15 h. The mixture was cooled and concentrated, and the crude residue was purified by preparative HPLC to give 2-{methyl[2-(pyridin-2-yl)-5H,6H,7H-cyclopenta[d]pyrimidin-4-yl]amino}-N-[1-(trifluoromethyl)cyclopropyl]acetamide (49.8 mg). $^1$H NMR (400 MHz, DMSO-d$_6$) δ 9.05 (s, 1H), 8.80 (d, J=4.7 Hz, 1H), 8.35 (d, J=8.2 Hz, 1H), 8.07 (s, 1H), 7.70 (s, 1H), 4.37 (s, 2H), 3.44 (s, 3H), 3.20 (m, 2H), 3.00 (t, J=7.9 Hz, 2H), 2.11-2.03 (m, 2H), 1.25-1.17 (m, 2H), 0.96 (s, 2H). LCMS (ES) [M+1]+ m/z: 392.0.

Example 1.102

Synthesis of 2-{[2-(4-methoxypyridin-2-yl)-5H,6H,7H-cyclopenta[d]pyrimidin-4-yl](methyl)amino}-N-[1-(trifluoromethyl)cyclopropyl]acetamide (Compound 99)

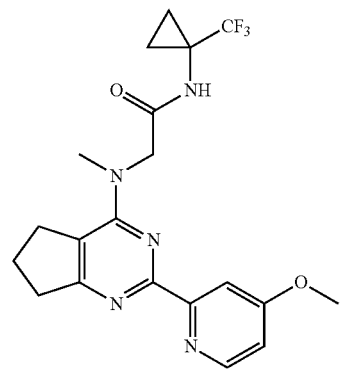 [SMILES: COc1ccnc(-c2nc3c(c(N(C)CC(=O)NC4(C(F)(F)F)CC4)n2)CCC3)c1]

Compound 99 was synthesized similar to Compound 98 by replacing 2-(tributylstannyl)pyridine with 4-methoxy-2-(tributylstannyl)pyridine. $^1$H NMR (400 MHz, DMSO-d$_6$) δ 9.04 (s, 1H), 8.65 (d, J=6.1 Hz, 1H), 7.91 (d, J=2.6 Hz, 1H), 7.41 (dd, J=6.2, 2.6 Hz, 1H), 4.35 (s, 2H), 4.02 (s, 3H), 3.40 (s, 3H), 3.22 (m, 2H), 2.96 (t, J=7.9 Hz, 2H), 2.11-1.99 (m, 2H), 1.23-1.09 (m, 2H), 0.96 (s, 2H). LCMS (ES) [M+1]+ m/z: 421.7.

Example 1.103

Synthesis of N-tert-butyl-2-{[2-(4-ethylpyridin-2-yl)-5H,6H,7H-cyclopenta[d]pyrimidin-4-yl](methyl)amino}acetamide (Compound 100)

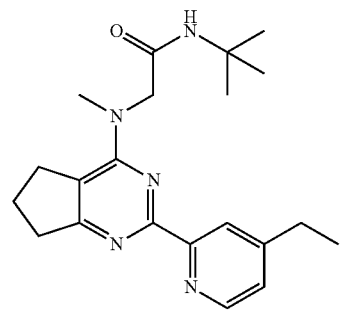 [SMILES: CCc1ccnc(-c2nc3c(c(N(C)CC(=O)NC(C)(C)C)n2)CCC3)c1]

Scheme 61 depicts a synthetic route for preparing an exemplary compound.

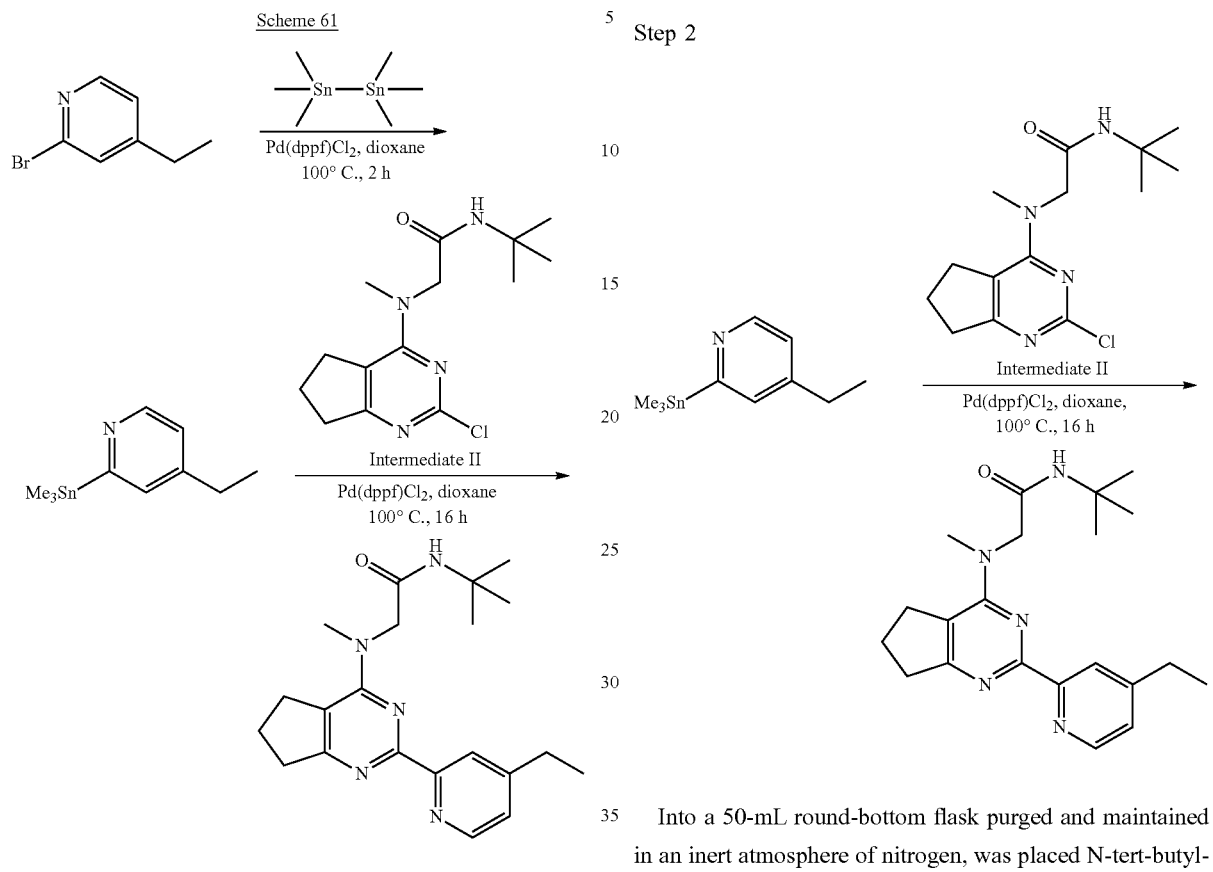

Step 1

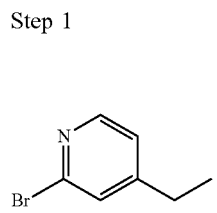

Into a 100-mL round-bottom flask purged and maintained in an inert atmosphere of nitrogen, was placed 2-bromo-4-ethylpyridine (500 mg, 2.68 mmol, 1.00 equiv), dioxane (5.0 mL), hexamethyldistannane (1.06 g, 3.22 mmol, 1.20 equiv), and Pd(dppf)Cl₂ (196 mg, 0.26 mmol, 0.10 equiv). The mixture was stirred for 2 h at 100° C. The reaction mixture was cooled and diluted with 20 mL of H₂O and extracted with 3×10 mL of ethyl acetate. The combined organic phase was dried over anhydrous sodium sulfate, filtered, and the filtrate was concentrated under reduced pressure. This resulted in 600 mg crude product of 4-ethyl-2-(trimethylstannyl)pyridine as a brown oil, which was used in the next step directly without further purification. LCMS (ES): [M+1]⁺ m/z: 272.

Step 2

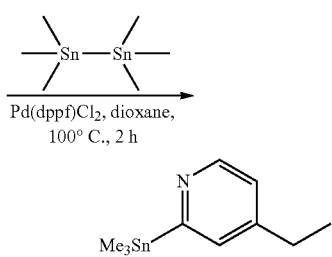

Into a 50-mL round-bottom flask purged and maintained in an inert atmosphere of nitrogen, was placed N-tert-butyl-2-([2-chloro-5H,6H,7H-cyclopenta[d]pyrimidin-4-yl] (methyl)amino)acetamide (300 mg, 1.01 mmol, 1.00 equiv), dioxane (5.0 mL), 4-ethyl-2-(trimethylstannyl)pyridine (409 mg, 1.51 mmol, 1.50 equiv), and Pd(dppf)Cl₂ (73 mg, 0.10 mmol, 0.10 equiv). The mixture was stirred for 16 h at 100° C. The reaction mixture was cooled and diluted with 20 mL of H₂O and extracted with 3×10 mL of ethyl acetate. The combined organic phase was dried over anhydrous sodium sulfate, filtered, and the filtrate was concentrated. The crude residue was purified by Prep-HPLC with the following conditions: Column, Kinetex EVO C18 Column, 21.2*150, 5 um, mobile phase, Water (0.1% FA) and CH₃CN (10% Phase B up to 50% in 15 min); Detector, UV 254 nm. 29.6 mg (7.9%) of N-tert-butyl-2-[[2-(4-ethylpyridin-2-yl)-5H,6H,7H-cyclopenta[d]pyrimidin-4-yl](methyl)amino]acetamide was obtained as a pink solid. ¹H NMR (300 MHz, DMSO-d₆) δ 8.54 (d, J=4.8 Hz, 1H), 8.16 (s, 1H), 7.69 (s, 1H), 7.30 (dd, J=5.1, 1.7 Hz, 1H), 4.16 (s, 2H), 3.27 (s, 3H), 3.15 (t, J=7.5 Hz, 2H), 2.82 (t, J=7.8 Hz, 2H), 2.72 (q, J=7.5 Hz, 2H), 2.08-1.91 (m, 2H), 1.30-1.19 (m, 12H). LCMS (ES) [M+1]⁺ m/z: 368.2.

Example 1.104
Synthesis of (2R)—N-tert-butyl-2-{[2-(4-methoxy-pyridin-2-yl)-5H,6H,7H-cyclopenta[d]pyrimidin-4-yl](methyl)amino}propanamide (Compound 101)
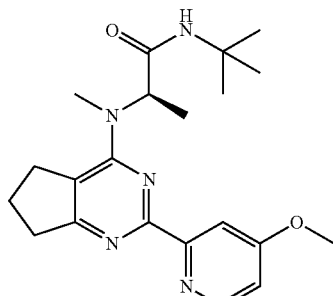
Scheme 62 depicts a synthetic route for preparing an exemplary compound.
Scheme 62
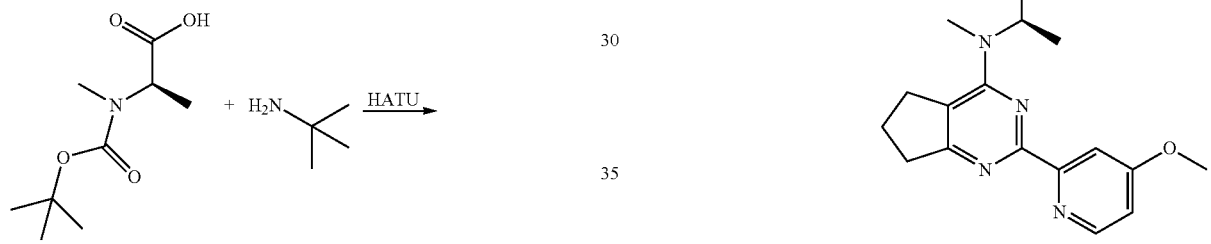
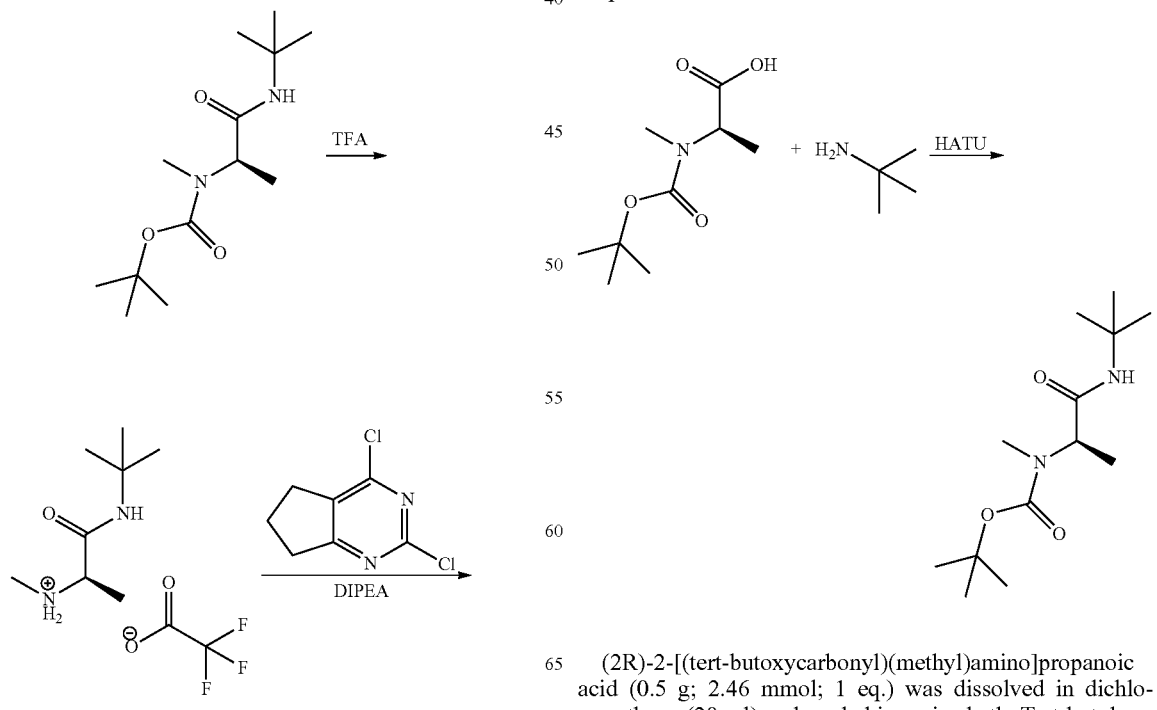
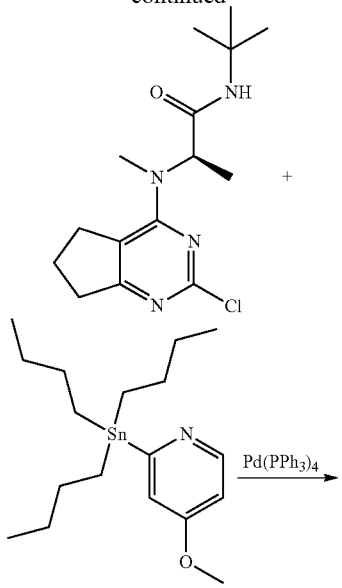
Step 1
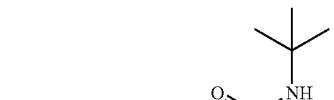
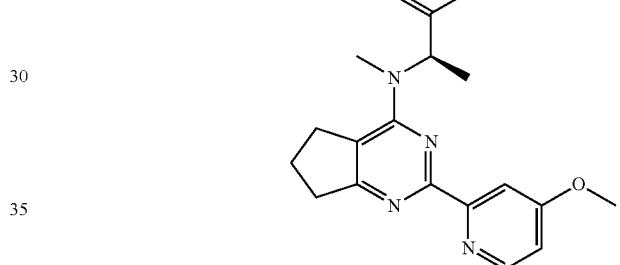
(2R)-2-[(tert-butoxycarbonyl)(methyl)amino]propanoic acid (0.5 g; 2.46 mmol; 1 eq.) was dissolved in dichloromethane (20 ml) and cooled in an ice bath. Tert-butylamine (0.28 mL; 2.71 mmol; 1.1 eq.), 1-[bis(dimethylamino)methylene]-1H-1,2,3-triazolo[4,5-b]pyridinium 3-oxid hexafluorophosphate (HATU, 1.03 g; 2.71 mmol; 1.1 eq.) and N,N-diisopropylethylamine (0.90 mL; 5.17 mmol; 2.1 eq.) were then added. The reaction was stirred to 25° C. over 20 h and then taken up in ethyl acetate (100 ml), water (10 ml), and sodium bicarbonate solution (50 ml). The phases were separated, and the aqueous phase was extracted with more ethyl acetate (100 ml). The combined organics were washed with sodium chloride solution (30 ml), dried over sodium sulfate, and evaporated. The residue was purified by silica gel chromatography (ethyl acetate/hexanes gradient) to give tert-butyl N-[(1R)-1-(tert-butylcarbamoyl)ethyl]-N-methylcarbamate (0.61 g, 96%) as a white solid. LCMS (ES+): (M+Na)$^+$=281.0.

Step 2

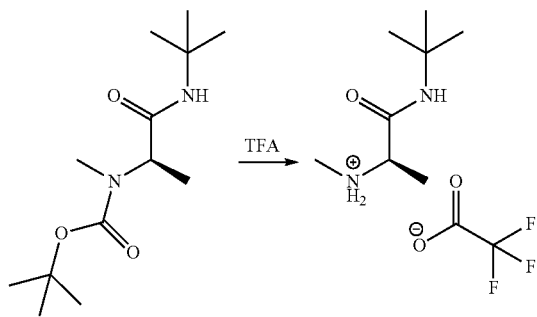 [SMILES: C[C@H](C(=O)NC(C)(C)C)N(C)C(=O)OC(C)(C)C ; C[NH2+][C@H](C)C(=O)NC(C)(C)C ; O=C([O-])C(F)(F)F]

Tert-butyl N-{1-[(1-hydroxy-3-phenylpropan-2-yl)carbamoyl]ethyl}-N-methylcarbamate (0.56 g; 1.66 mmol; 1 eq.) was dissolved in dichloromethane (8 ml) and cooled in an ice bath. Trifluoroacetic acid (4 ml) was added slowly and the reaction was stirred to 25° C. over 3 h. The reaction was evaporated, and the residue was co-evaporated with toluene and dried under high vacuum to give (2R)—N-tert-butyl-2-(methylamino)propanamide; trifluoroacetic acid, which was used directly in the next step. LCMS (ES+): (M+Na)$^+$=159.0.

Step 3

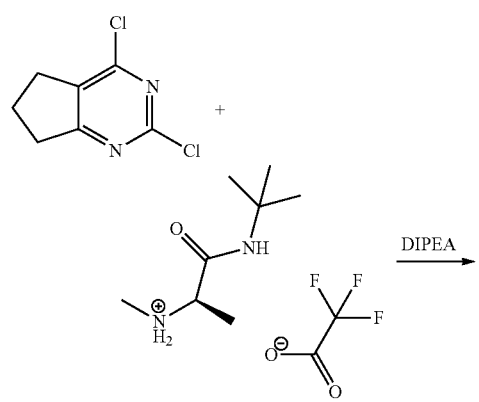

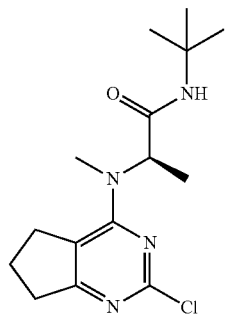

2,4-dichloro-6,7-dihydro-5H-cyclopenta[d]pyrimidine (400.00 mg; 2.12 mmol; 1.00 eq.) (Combi-Blocks) was dissolved in acetonitrile (7 ml), and to this was added (2R)—N-tert-butyl-2-(methylamino)propanamide; trifluoroacetic acid (633.70 mg; 2.33 mmol; 1.10 eq.), and Hunig's base (1.84 mL; 10.58 mmol; 5.00 eq.). The mixture was stirred at 70° C. for 15 h, the solvent was then evaporated under reduced pressure, and the residue was purified by column chromatography (50% EtOAc in Hexanes) to give (2R)—N-tert-butyl-2-({2-chloro-5H,6H,7H-cyclopenta[d]pyrimidin-4-yl}(methyl)amino)propenamide (480 mg, 73%). LCMS (ES+): (M+H)$^+$=310.9.

Step 4

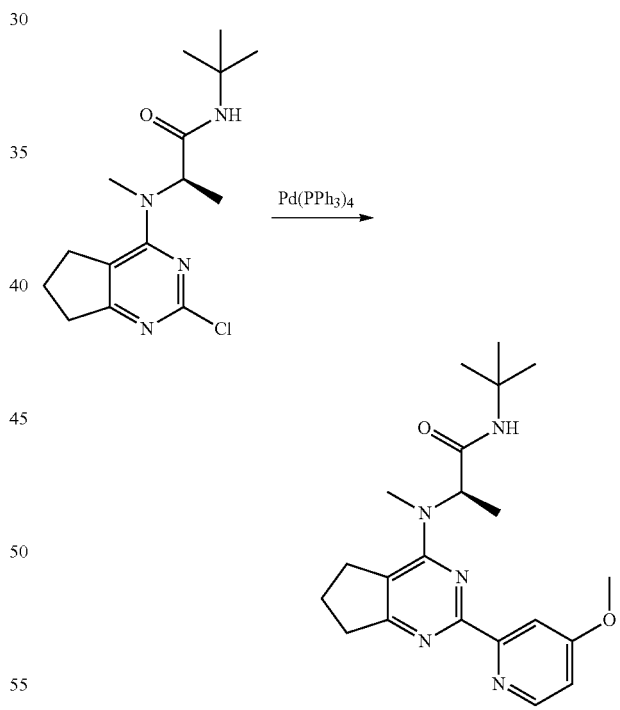

(2R)—N-tert-butyl-2-({2-chloro-5H,6H,7H-cyclopenta[d]pyrimidin-4-yl}(methyl)amino)propanamide (140.00 mg; 0.45 mmol; 1.00 eq.) was dissolved in 1,4-dioxane (3.5 ml) and the solution was purged with Ar gas. 4-methoxy-2-(tributylstannyl)pyridine (0.36 g; 0.90 mmol; 2.00 eq.) and tetrakis(triphenylphosphane) palladium (52.05 mg; 0.05 mmol; 0.10 eq.) were added. The reaction vessel was sealed and stirred in a heat bath at 110° C. for 15 h. After evaporation, the residue was purified by reverse phase chromatography (Waters XSelect CSH C18 column, 0-70% acetonitrile/0.1% aqueous formic acid gradient) to give (2R)—N-tert-butyl-2-{[2-(4-methoxypyridin-2-yl)-5H,6H,7H-cyclopenta[d]pyrimidin-4-yl](methyl)amino}propanamide (67 mg, 39%) as a white solid. LCMS (ES+): (M+H)+= 384.4. ¹H NMR (400 MHz, Methanol-d4) δ 8.51 (d, J=5.8 Hz, 1H), 7.95 (d, J=2.6 Hz, 1H), 7.63 (s, 1H), 7.09 (dd, J=5.8, 2.6 Hz, 1H), 5.24 (q, J=7.1 Hz, 1H), 3.98 (s, 3H), 3.30-3.15 (m, 5H), 3.04-2.86 (m, 2H), 2.21-2.01 (m, 2H), 1.45 (d, J=7.1 Hz, 3H), 1.23 (s, 9H).

Example 1.105

Synthesis of N-tert-butyl-2-({2-[4-(dimethylamino)pyridin-2-yl]-5H,6H,7H-cyclopenta[d]pyrimidin-4-yl}(methyl)amino)acetamide (Compound 102)

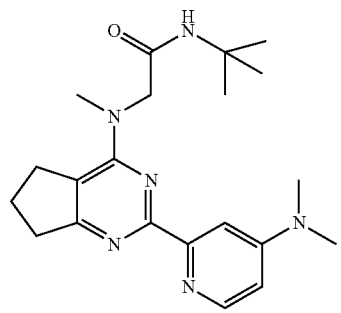 [SMILES: CN(C)c1ccnc(-c2nc3c(c(N(C)CC(=O)NC(C)(C)C)n2)CCC3)c1]

Scheme 63 depicts a synthetic route for preparing an exemplary compound.

Scheme 63

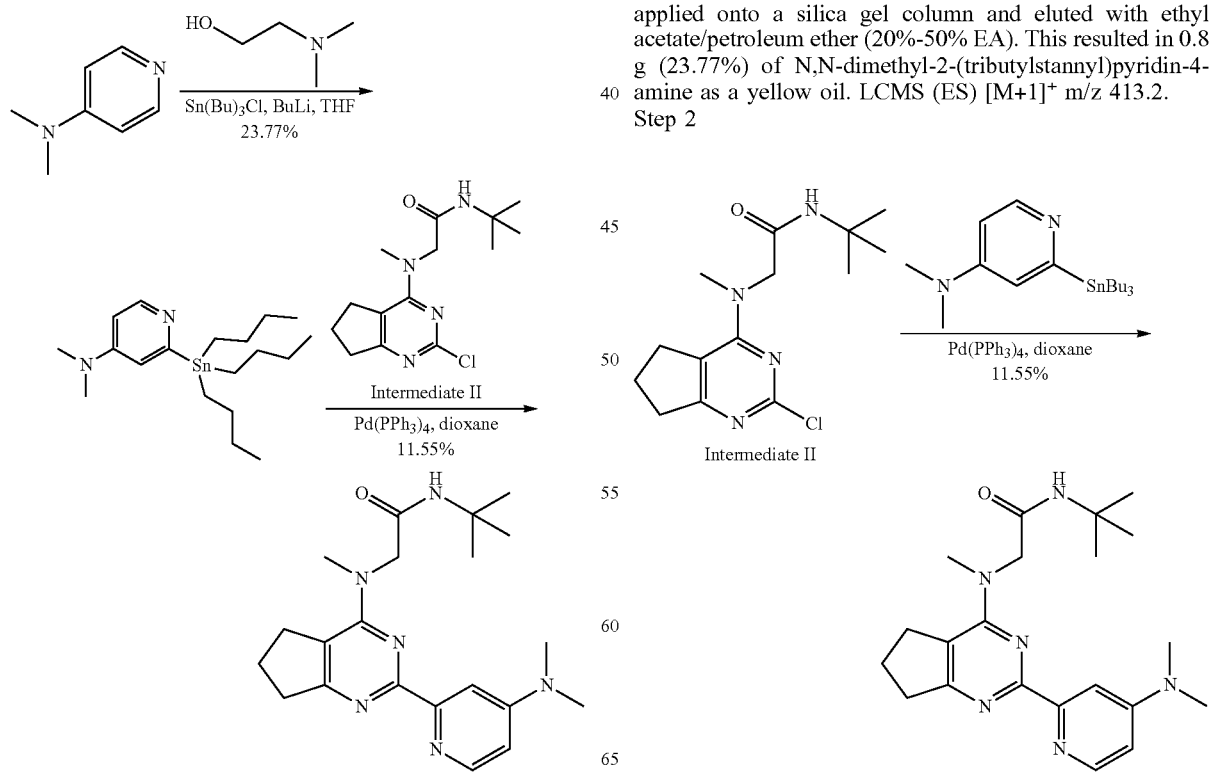

Step 1

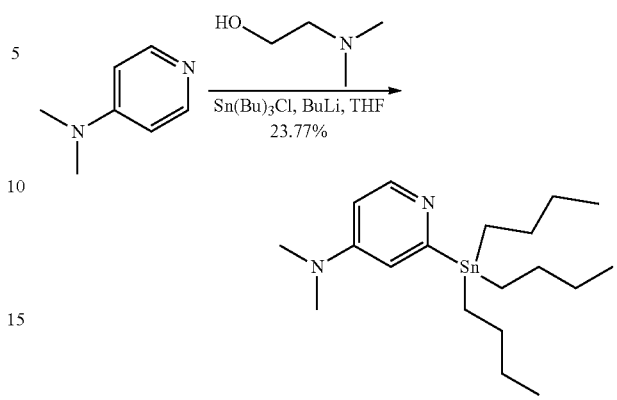

Into a 100-mL 3-necked round-bottom flask purged and maintained in an inert atmosphere of nitrogen was placed ethanolamine (1.00 g, 16.371 mmol, 2.00 equiv) and THF (40.00 mL). This was followed by the addition of n-BuLi (13.00 mL, 138.006 mmol, 16.86 equiv) dropwise with stirring at 0° C. in 10 min. The resulting solution was stirred for 0.5 h at 0° C. To this was added a solution of 4-dimethylaminopyridine (1.00 g, 8.185 mmol, 1.00 equiv) in THF (5 mL) dropwise with stirring at 0° C. in 5 min. The resulting solution was stirred for 1 h at 0° C. The resulting solution was stirred for 0.5 h at room temperature. To the mixture was added tributyltin chloride (6.66 g, 20.460 mmol, 2.50 equiv) dropwise with stirring at −78° C. in 10 min. The resulting solution was then stirred overnight at room temperature. The resulting solution was diluted with 50 mL of H₂O and extracted with 3×50 mL of dichloromethane. The organic layers were combined, dried over anhydrous sodium sulfate, and concentrated. The residue was applied onto a silica gel column and eluted with ethyl acetate/petroleum ether (20%-50% EA). This resulted in 0.8 g (23.77%) of N,N-dimethyl-2-(tributylstannyl)pyridin-4-amine as a yellow oil. LCMS (ES) [M+1]+ m/z 413.2.

Step 2

Into a 40-mL round-bottom flask purged and maintained in an inert atmosphere of argon, was placed N,N-dimethyl-2-(tributylstannyl)pyridin-4-amine (418.00 mg, 1.016 mmol, 1.00 equiv), N-(tert-butyl)-2-((2-chloro-6,7-dihydro-5H-cyclopenta[d]pyrimidin-4-yl)(methyl)amino)acetamide (301.69 mg, 1.016 mmol, 1.00 equiv), Pd(PPh$_3$)$_4$ (117.46 mg, 0.102 mmol, 0.10 equiv), and dioxane (10.00 mL). The resulting solution was stirred for 24 hr at 100° C. in an oil bath. The resulting mixture was concentrated. The residue was applied onto a silica gel column and eluted with dichloromethane/methanol (10%-30% MeOH). The collected crude product was purified by Flash-Prep-HPLC (Prep-C18, 20-45M, 120 g, Tianjin Bonna-AgelaTechnologies; gradient elution of 20% MeCN in water to 45% MeCN in water over a 10 min period, where both solvents contain 0.1% FA). This resulted in 44.9 mg (11.55%) of N-(tert-butyl)-2-((2-(4-(dimethylamino)pyridin-2-yl)-6,7-dihydro-5H-cyclopenta[d]pyrimidin-4-yl)(methyl)amino)acetamide formate as a light yellow solid. $^1$H NMR (300 MHz, DMSO-d$_6$, ppm) δ 8.23 (s, 1H), 8.21 (d, J=6.0 Hz, 1H), 7.68 (s, 1H), 7.59 (d, J=2.7 Hz, 1H), 6.72 (dd, J=6.2, 2.8 Hz, 1H), 4.17 (s, 2H), 3.13 (t, J=7.3 Hz, 2H), 3.07 (s, 6H), 2.82 (t, J=7.7 Hz, 2H), 1.89-2.08 (m, 2H), 1.22 (s, 9H). LCMS (ES) [M+1]$^+$ m/z 383.2.

Example 1.106

Synthesis of N-tert-butyl-2-{methyl[2-(3-methylpyridin-2-yl)-5H,6H,7H-cyclopenta[d]pyrimidin-4-yl]amino}acetamide (Compound 103)

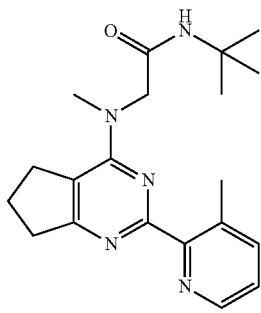 [SMILES: Cc1cccnc1-c1nc2c(c(N(C)CC(=O)NC(C)(C)C)n1)CCC2]

Scheme 64 depicts a synthetic route for preparing an exemplary compound.

Scheme 64

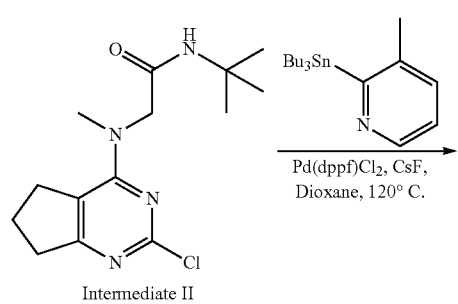

Intermediate II

Into a 100-mL round-bottom flask purged and maintained in an inert atmosphere of nitrogen, was placed N-tert-butyl-2-([2-chloro-5H,6H,7H-cyclopenta[d]pyrimidin-4-yl](methyl)amino)acetamide (800.00 mg, 2.695 mmol, 1.00 equiv), 3-methyl-2-(tributylstannyl)pyridine (1.23 g, 3.235 mmol, 1.20 equiv), Pd(dppf)Cl$_2$ (197.22 mg, 0.270 mmol, 0.10 equiv), CsF (409.44 mg, 2.695 mmol, 1.00 equiv), and dioxane (20.00 mL). The resulting solution was stirred for 16 hr at 120° C. The reaction mixture was cooled. The resulting solution was extracted with 3×50 mL of dichloromethane. The organic layers were combined, dried over anhydrous sodium sulfate, and concentrated under vacuum. The crude product was purified by Prep-HPLC with the following conditions (Prep-HPLC-002): Column, XBridge BEH130 Prep C18 OBD Column, 19*150 mm 5 um 13 nm; mobile phase, Water (0.05% FA) and ACN (10% PhaseB up to 50% in 8 min). This resulted in 41.3 mg (4.3%) of N-tert-butyl-2-[methyl[2-(3-methylpyridin-2-yl)-5H,6H,7H-cyclopenta[d]pyrimidin-4-yl]amino]acetamide formate as a pink solid. $^1$H NMR (300 MHz, DMSO-d$_6$) δ 8.41 (d, J=4.7 Hz, 1H), 8.19 (s, 1H), 7.68 (d, J=7.7 Hz, 1H), 7.49 (s, 1H), 7.31 (dd, J=7.7, 4.7 Hz, 1H), 4.11 (s, 2H), 3.18 (s, 3H), 3.14 (d, J=7.4 Hz, 2H), 2.78 (t, J=7.8 Hz, 2H), 2.28 (s, 3H), 2.05-1.95 (m, 2H), 1.22 (s, 9H). LCMS (ES) [M+1]$^+$ m/z: 354.2.

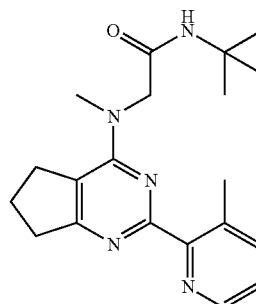

Example 1.107

Synthesis of N-tert-butyl-2-{methyl[2-(5-methylpyridin-2-yl)-5H,6H,7H-cyclopenta[d]pyrimidin-4-yl]amino}acetamide (Compound 104)

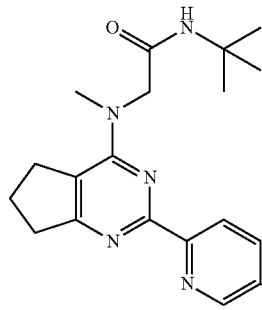

Scheme 65 depicts a synthetic route for preparing an exemplary compound.

Scheme 65

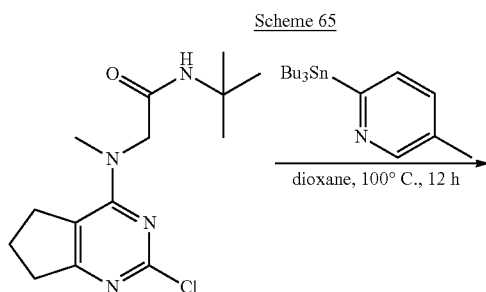

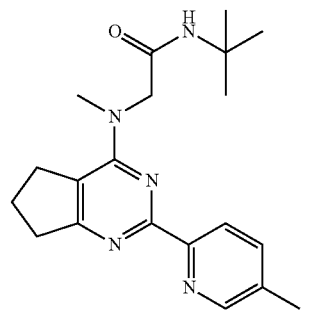 [SMILES: Cc1ccc(-c2nc3c(c(N(C)CC(=O)NC(C)(C)C)n2)CCC3)nc1]

Into a 40-mL vial purged and maintained in an inert atmosphere of nitrogen, was placed N-tert-butyl-2-([2-chloro-5H,6H,7H-cyclopenta[d]pyrimidin-4-yl](methyl)amino)acetamide (500 mg, 1.69 mmol, 1.0 equiv), 5-methyl-2-(tributylstannyl)pyridine (712 mg, 1.86 mmol, 1.1 equiv), dioxane (5.0 mL), and Pd(PPh$_3$)$_4$ (391 mg, 0.34 mmol, 0.2 equiv). The mixture was stirred for 12 h at 100° C. It was then concentrated to remove the solvent, and the crude product was purified by Prep-HPLC with the following conditions: Column, Atlantis HILIC OBD Column, 19*150 mm*5 um, Mobile phase, Water (0.1% FA) and CH$_3$CN (5% Phase B up to 35% in 8 min), Detector, UV 254 nm. This resulted 48.3 mg (7%) of N-(tert-butyl)-2-(methyl(2-(5-methylpyridin-2-yl)-6,7-dihydro-5H-cyclopenta[d]pyrimidin-4-yl)amino)acetamide formate as a light brown solid. $^1$HNMR (300 MHz, DMSO-d$_6$, ppm): δ 8.50 (d, J=2.1 Hz, 1H), 8.26 (d, J=8.1 Hz, 1H), 8.18 (s, 1H), 7.70-7.68 (m, 2H), 4.13 (s, 2H), 3.26 (s, 3H), 3.14 (t, J=7.2 Hz, 2H), 2.81 (t, J=7.8 Hz, 2H), 2.36 (s, 3H), 2.01-1.96 (m, 2H), 1.24 (s, 9H). LCMS (ES, m/z): [M+H]$^+$: 354.1.

Example 1.108

Synthesis of 2-{methyl[2-(4-methylpyridin-2-yl)-5H,6H,7H-cyclopenta[d]pyrimidin-4-yl]amino}-N-(1-methylcyclopentyl)acetamide (Compound 105)

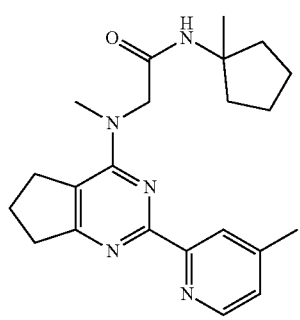 [SMILES: Cc1ccnc(-c2nc3c(c(N(C)CC(=O)NC4(C)CCCC4)n2)CCC3)c1]

Compound 105 was synthesized similar to compound 62 by replacing 2-amino-2-methyl-1-propanol with 1-methylcyclopentanamine. $^1$H NMR (300 MHz, DMSO-d$_6$, ppm) δ 8.51 (d, J=4.9 Hz, 1H), 8.16 (s, 1H), 7.76 (s, 1H), 7.27 (dd, J=5.2, 1.7 Hz, 1H), 4.16 (s, 2H), 3.28 (s, 3H), 3.15 (t, J=7.3 Hz, 2H), 2.82 (t, J=7.8 Hz, 2H), 2.41 (s, 3H), 2.07-1.89 (m, 4H), 1.60-1.40 (m, 6H), 1.28 (s, 3H). LCMS (ES) [M+1]$^+$ m/z 380.2.

Example 1.109

Synthesis of N-tert-butyl-2-{methyl[2-(pyrimidin-2-yl)-5H,6H,7H-cyclopenta[d]pyrimidin-4-yl]amino}acetamide (Compound 106)

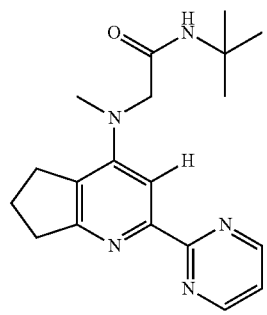 [SMILES: CN(CC(=O)NC(C)(C)C)c1cc(-c2ncccn2)nc2c1CCC2]

Scheme 66 depicts a synthetic route for preparing an exemplary compound.

Scheme 66

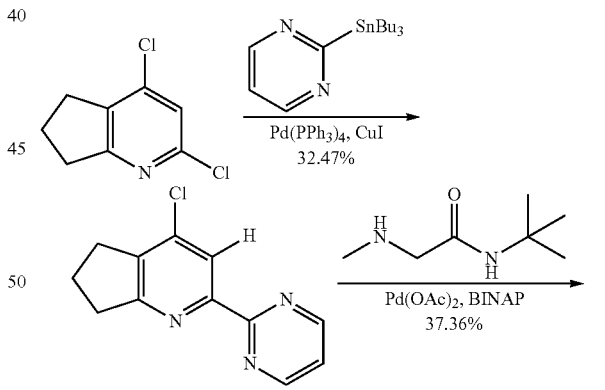

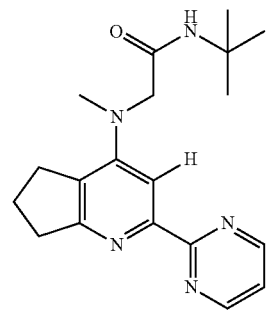

Step 1

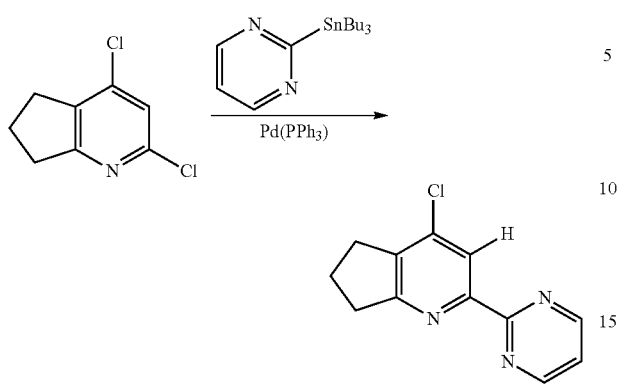

Into a 40-mL vial purged and maintained in an inert atmosphere of nitrogen, was placed 2,4-dichloro-5H,6H,7H-cyclopenta[b]pyridine (500.00 mg, 2.66 mmol, 1.00 equiv), 2-(tributylstannyl)pyrimidine (1275.94 mg, 3.46 mmol, 1.30 equiv), CsF (807.78 mg, 5.32 mmol, 2.00 equiv), Pd(PPh$_3$)$_4$ (307.25 mg, 0.26 mmol, 0.10 equiv), CuI (50.64 mg, 0.26 mmol, 0.10 equiv), and DMF (10.00 mL). The resulting solution was stirred for 8 h at 110° C. The reaction mixture was cooled to room temperature. The crude product (1 g) was purified by Prep-HPLC with the following conditions: Column, XBridge Prep C18 OBD Column, 19 cm, 150 mm, 5 um; mobile phase, Water (0.1% NH$_4$HCO$_3$) and CAN (30% Phase B up to 60% in 11 min); Detector, 254. This resulted in 200 mg (32.47%) of 2-[4-chloro-5H,6H,7H-cyclopenta[b]pyridin-2-yl]pyrimidine as a brown solid. LCMS (ES) [M+H]$^+$ m/z: 232.

Step 2

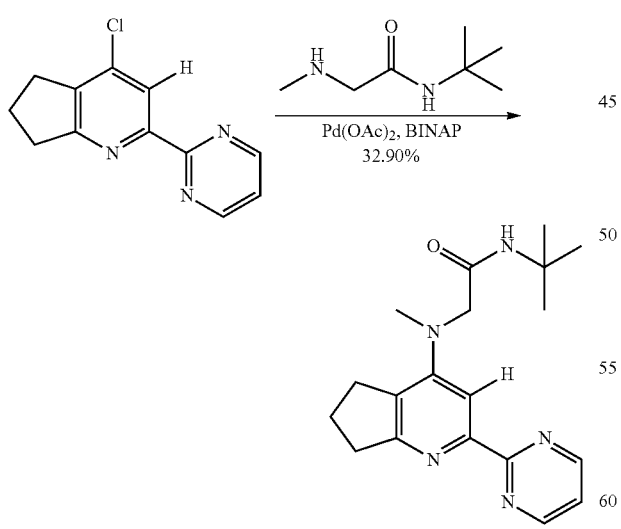

Into a 40-mL vial purged and maintained in an inert atmosphere of nitrogen was placed 2-[4-chloro-5H,6H,7H-cyclopenta[b]pyridin-2-yl]pyrimidine (150.00 mg, 0.65 mmol, 1.00 equiv), N-tert-butyl-2-(methylamino)acetamide (121.39 mg, 0.84 mmol, 1.30 equiv), Pd(OAc)$_2$ (14.54 mg, 0.06 mmol, 0.10 equiv), BINAP (80.63 mg, 0.13 mmol, 0.20 equiv), Cs$_2$CO$_3$ (421.90 mg, 1.29 mmol, 2.00 equiv), and dioxane (8.00 mL). The resulting solution was stirred overnight at 100° C. The reaction mixture was cooled to room temperature and concentrated. The crude product (500 mg) was purified by Prep-HPLC with the following conditions: Column, XBridge Prep C18 OBD Column, 19 cm, 150 mm, 5 um; mobile phase, Water (0.1% HCOOH) and CAN (20% Phase B up to 50% in 11 min); Detector, 254. This resulted in 82.1 mg (32.90%) of N-tert-butyl-2-[methyl[2-(pyrimidin-2-yl)-5H,6H,7H-cyclopenta[b]pyridin-4-yl]amino]acetamide formate as a yellow oil. $^1$HNMR (300 MHz, DMSO-d6) δ 8.91 (d, J=4.8 Hz, 2H), 8.17 (s, 1H), 7.61 (s, 1H), 7.57-7.45 (m, 2H), 3.98 (s, 2H), 3.09 (s, 3H), 3.04 (t, J=7.2 Hz, 2H), 2.88 (t, J=7.7 Hz, 2H), 2.09-1.93 (m, 2H), 1.27 (s, 9H). LCMS (ES, m/z): [M+H]$^+$: 341.2.

Example 1.110

Synthesis of N-tert-butyl-2-({2-[5-(2-hydroxyethyl)-1,3-thiazol-2-yl]-5H,6H,7H-cyclopenta[d]pyrimidin-4-yl}(methyl)amino)acetamide (Compound 107)

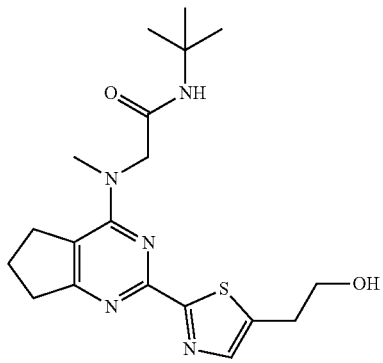 [SMILES: CN(CC(=O)NC(C)(C)C)c1nc(-c2ncc(CCO)s2)nc2c1CCC2]

Scheme 67 depicts a synthetic route for preparing an exemplary compound.

Scheme 67

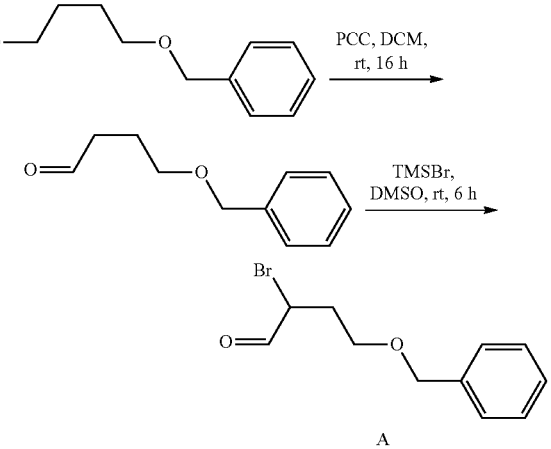

A

557

-continued

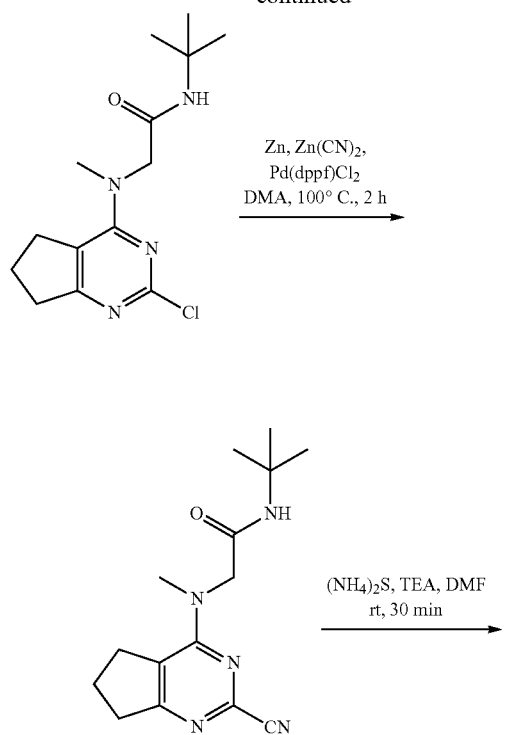

558

-continued

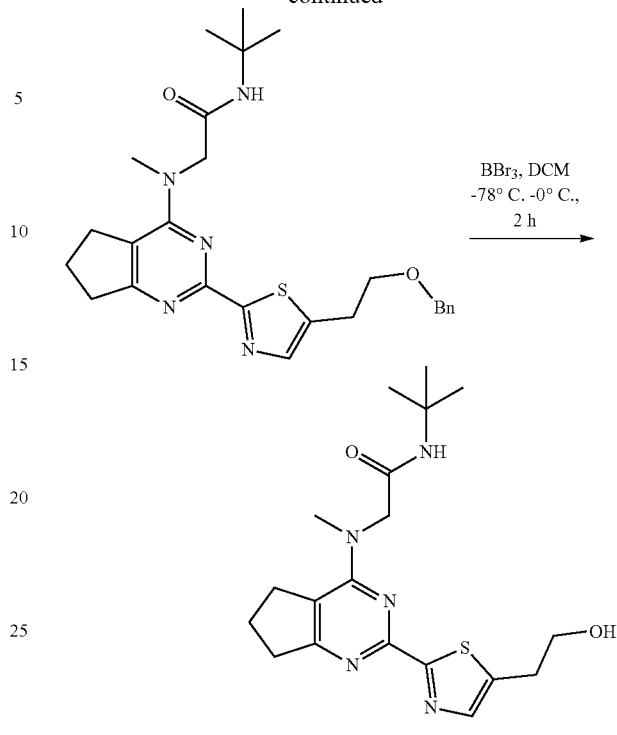

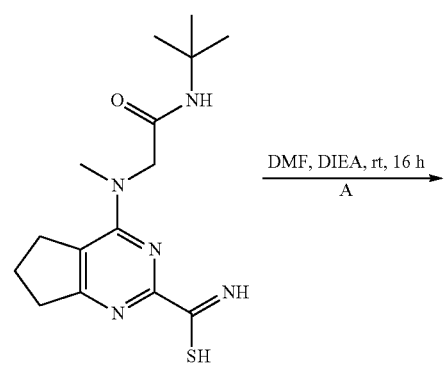

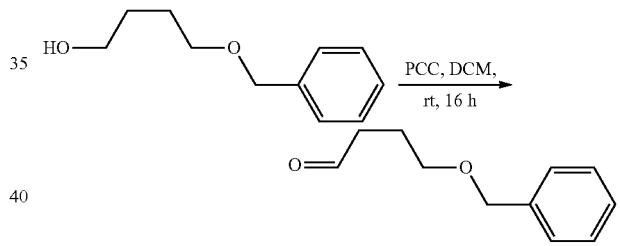

Step 1

Into a 250-mL round-bottom flask, was placed 4-(benzyloxy)butan-1-ol (5.00 g, 27.74 mmol, 1.00 equiv), DCM (100 mL), and PCC (11.96 g, 55.47 mmol, 2.00 equiv). The mixture was stirred for 16 h at room temperature, filtered, and the filtrate was concentrated under reduced pressure. The residue was purified by silica gel column and eluted with ethyl acetate/petroleum ether (1/10). This resulted in 2.5 g (50%) of 4-(benzyloxy)butanal was obtained as a colorless solid. LCMS (ES)[M+1]$^+$ m/z: 179.

Step 2

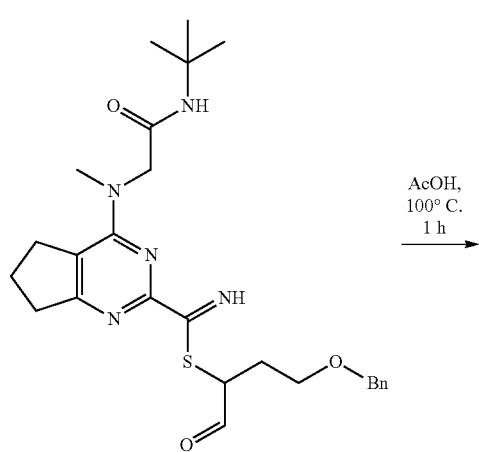

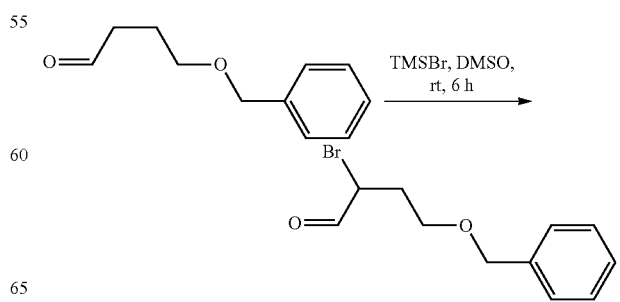

Into a 100-mL 3-necked round-bottom flask, was placed 4-(cyclohexylmethoxy)butan-1-ol (2.50 g, 13.42 mmol, 1.00 equiv), DMSO (30 mL). This was followed by the addition of bromotrimethylsilane (2.05 g, 13.42 mmol, 1.00 equiv) dropwise with stirring at 0° C. The resulting solution was stirred for 6 h at room temperature. The reaction was quenched with 100 mL of H$_2$O, extracted with 3×30 mL of ethyl acetate, the organic layers were combined and dried over anhydrous sodium sulfate, filtered, and the filtrate was concentrated. The residue was purified by silica gel column with ethyl acetate/petroleum ether (1/10). This resulted in 1.5 g (43.4%) of 4-(benzyloxy)-2-bromobutanal as light brown oil. LCMS (ES) [M+1]$^+$ m/z: 257.

Step 3

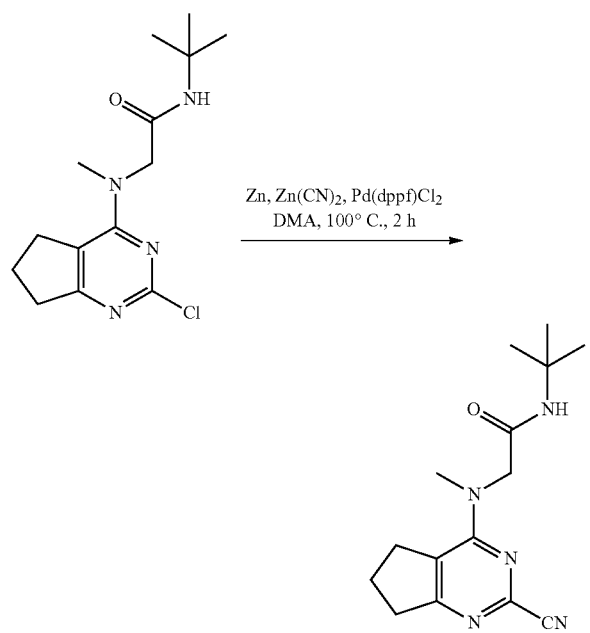

Into a 100-mL round-bottom flask purged and maintained in an inert atmosphere of nitrogen was placed N-tert-butyl-2-([2-chloro-5H,6H,7H-cyclopenta[d]pyrimidin-4-yl] (methyl)amino)acetamide (600 mg, 2.02 mmol, 1.00 equiv), DMA (6.0 mL), Zn(CN)$_2$ (474 mg, 4.04 mmol, 2.00 equiv), Zn (264 mg, 4.04 mmol, 2.00 equiv), and Pd(dppf)Cl$_2$ (147 mg, 0.20 mmol, 0.10 equiv). The mixture was stirred for 2 h at 100° C. The reaction mixture was cooled and filtered. The filtrate was diluted with 20 mL of H$_2$O, extracted with 3×20 mL of ethyl acetate, the organic layers were combined and dried over anhydrous sodium sulfate, filtered, and the filtrate was concentrated. The residue was purified by silica gel column with ethyl acetate/petroleum ether (1/1). This resulted in 550 mg (95%) of N-tert-butyl-2-([2-cyano-5H,6H,7H-cyclopenta[d]pyrimidin-4-yl](methyl)amino)acetamide as a yellow solid. $^1$H NMR (300 MHz, DMSO-d$_6$) δ 7.64 (s, 1H), 4.10 (s, 2H), 3.18 (s, 3H), 3.13 (t, J=7.5 Hz, 2H), 2.78 (t, J=7.8 Hz, 2H), 2.04-1.88 (m, 2H), 1.27 (s, 9H). LCMS (ES) [M+1]$^+$ m/z: 288.

Step 4

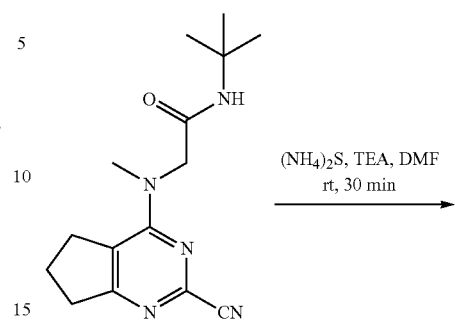

Into a 100-mL round-bottom flask was placed N-tert-butyl-2-([2-cyano-5H,6H,7H-cyclopenta[d]pyrimidin-4-yl] (methyl)amino)acetamide (530 mg, 1.84 mmol, 1.00 equiv), DMF (6.0 mL), (NH$_4$)$_2$S (251 mg, 3.68 mmol, 2.00 equiv), and TEA (373 mg, 3.68 mmol, 2.00 equiv). The resulting solution was stirred for 0.5 h at room temperature. The reaction solution was diluted with 20 mL of H$_2$O, extracted with 3×20 mL of ethyl acetate, the organic layers were combined and dried over anhydrous sodium sulfate, filtered, and the filtrate was concentrated. The crude product was washed with 30 ml of hexane. This resulted in 500 mg (84.3%) of N-tert-butyl-2-([2-carbamothioyl-5H,6H,7H-cyclopenta[d]pyrimidin-4-yl](methyl)amino)acetamide as a yellow solid. $^1$H NMR (300 MHz, DMSO-d$_6$) δ 10.10 (br, 1H), 9.45 (br, 1H), 7.60 (s, 1H), 4.01 (s, 2H), 3.25 (s, 3H), 3.12 (t, J=7.5 Hz, 2H), 2.79 (t, J=7.8 Hz, 2H), 2.04-1.88 (m, 2H), 1.25 (s, 9H). LCMS (ES) [M+1]$^+$ m/z: 322.

Step 5

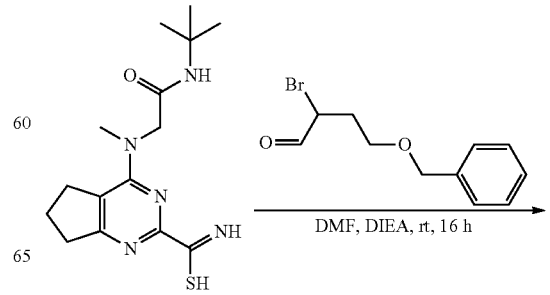

561

-continued

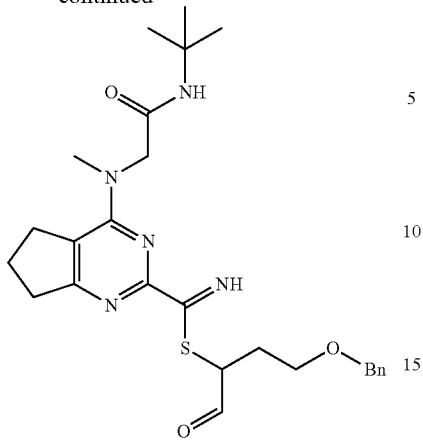

Into a 100-mL round-bottom flask, was placed N-tert-butyl-2-([2-carbamothioyl-5H,6H,7H-cyclopenta[d]pyrimidin-4-yl](methyl)amino)acetamide (400 mg, 1.24 mmol, 1.00 equiv), DMF (5.0 mL), DIEA (321 mg, 2.48 mmol, 2.00 equiv), and 4-(benzyloxy)-2-bromobutanal (383 mg, 1.49 mmol, 1.20 equiv). The resulting solution was stirred for 16 h at room temperature. The reaction was diluted with 20 mL of H₂O, extracted with 3×20 mL of ethyl acetate, the organic layers were combined and dried over anhydrous sodium sulfate, filtered, and the filtrate was concentrated. The residue was purified by silica gel column with ethyl acetate/petroleum ether (1/10). This resulted in 380 mg (61%) of 2-[[2-([[4-(benzyloxy)-1-oxobutan-2-yl]sulfanyl]methanimidoyl)-5H,6H,7H-cyclopenta[d]pyrimidin-4-yl](methyl)amino]-N-tert-butylacetamide as a brown solid. LCMS (ES) [M+1]⁺ m/z: 498.

Step 5

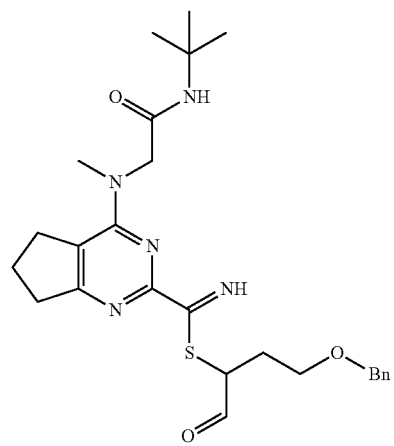

562

-continued

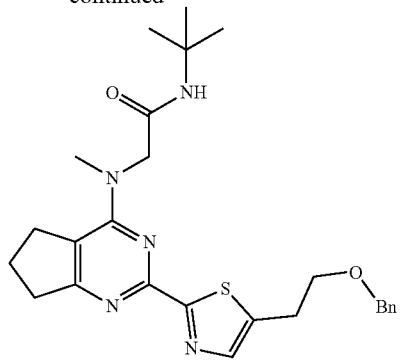

Into a 100-mL round-bottom flask, was placed 2-[[2-([[4-(benzyloxy)-1-oxobutan-2-yl]sulfanyl]methanimidoyl)-5H,6H,7H-cyclopenta[d]pyrimidin-4-yl](methyl)amino]-N-tert-butylacetamide (380 mg, 0.76 mmol, 1.00 equiv), and AcOH (4.0 mL). The mixture was stirred for 1 h at 100° C. The reaction mixture was cooled to room temperature, and diluted with 10 mL of H₂O. The pH value of the solution was adjusted to 8 with NaHCO₃ (10%), extracted with 3×10 mL of ethyl acetate, the organic layers were combined and dried over anhydrous sodium sulfate, filtered, and the filtrate was concentrated. The residue was purified by silica gel column with ethyl acetate/petroleum ether (1/1). 180 mg (49%) of 2-[(2-[5-[2-(benzyloxy)ethyl]-1,3-thiazol-2-yl]-5H,6H,7H-cyclopenta[d]pyrimidin-4-yl)(methyl)amino]-N-tert-butylacetamide was obtained as a brown solid. LCMS (ES) [M+1]⁺ m/z: 480.

Step 6

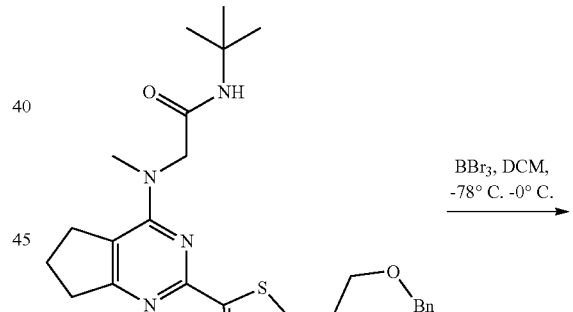

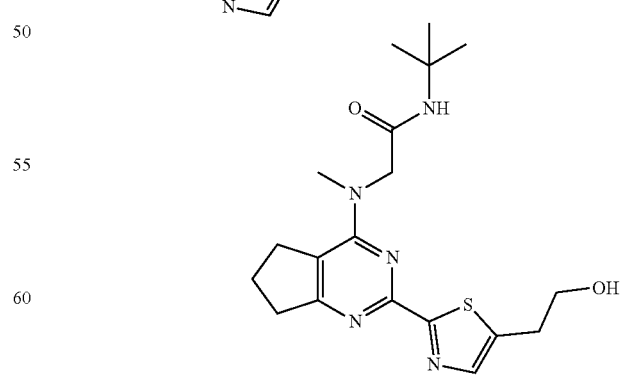

Into a 50-mL 3-necked round-bottom flask purged and maintained in an inert atmosphere of nitrogen was placed 2-[(2-[5-[2-(benzyloxy)ethyl]-1,3-thiazol-2-yl]-5H,6H,7H- cyclopenta[d]pyrimidin-4-yl)(methyl)amino]-N-tert-butylacetamide (180 mg, 0.37 mmol, 1.00 equiv), and DCM (3.0 mL). This was followed by the addition of BBr₃ (1.8 mL, 1.80 mmol, 4.80 equiv) dropwise with stirring at −78° C. The resulting solution was stirred for 2 h at 0° C. The reaction was then quenched by the addition of 10 mL of water, and extracted with 3×5 mL of dichloromethane. The organic layers were combined, dried over anhydrous sodium sulfate, filtered, and the filtrate was concentrated. The crude product was purified by Prep-HPLC with the following conditions: Column, Welch XB-C18, 21.2*250 mm, 5 um, Mobile phase, Water (0.05% NH₄OH) and CH₃CN (10% Phase B up to 65% in 15 min), Detector, UV 254 nm. This resulted in 53.0 mg (36.2%) of N-tert-butyl-2-([2-[5-(2-hydroxyethyl)-1,3-thiazol-2-yl]-5H,6H,7H-cyclopenta[d]pyrimidin-4-yl](methyl)amino)acetamide as a white solid. ¹H NMR (300 MHz, DMSO-d₆) δ 7.68 (s, 1H), 7.62 (s, 1H), 4.91 (t, J=5.1 Hz, 1H), 4.14 (s, 2H), 3.65 (q, J=6.3 Hz, 2H), 3.22 (s, 3H), 3.10 (t, J=7.5 Hz, 2H), 2.98 (t, J=6.3 Hz, 2H), 2.79 (t, J=7.8 Hz, 2H), 2.06-1.90 (m, 2H), 1.26 (s, 9H). LCMS (ES) [M+1]⁺ m/z: 390.2.

Example 1.111

Synthesis of (2R)—N-cyclohexyl-2-{methyl[2-(pyridin-2-yl)-5H,6H,7H-cyclopenta[d]pyrimidin-4-yl]amino}propanamide (Compound 108)

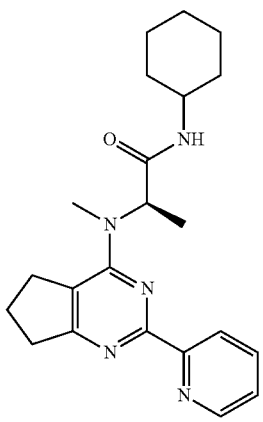 [SMILES: C[C@H](C(=O)NC1CCCCC1)N(C)c1nc(-c2ccccn2)nc2c1CCC2]

Step 1

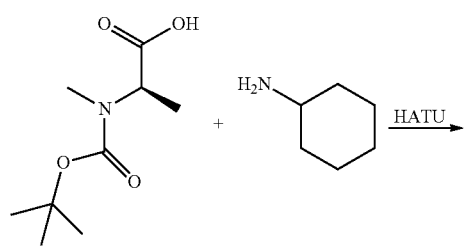

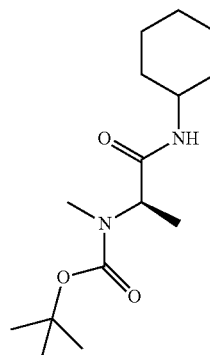

(2R)-2-[(tert-butoxycarbonyl)(methyl)amino]propanoic acid (0.50 g; 2.46 mmol; 1.00 eq.) was dissolved in dichloromethane (20 ml) and cooled in an ice bath. Cyclohexanamine (0.31 mL; 2.71 mmol; 1.10 eq.), 1-[bis(dimethylamino)methylene]-1H-1,2,3-triazolo[4,5-b]pyridinium 3-oxid hexafluorophosphate (HATU, 1.03 g; 2.71 mmol; 1.10 eq.)), and Hunig's base (0.90 mL; 5.17 mmol; 2.10 eq.) were then added. The reaction was stirred to 25° C. over 20 h and then taken up in ethyl acetate (100 ml), water (10 ml), and sodium bicarbonate solution (50 ml). The phases were separated, and the aqueous phase was extracted with more ethyl acetate (100 ml). The combined organics were washed with sodium chloride solution (30 ml), dried over sodium sulfate, and evaporated. The residue was purified by silica gel chromatography (ethyl acetate/hexanes gradient) to give tert-butyl N-{1-[(1-hydroxy-3-phenylpropan-2-yl)carbamoyl]ethyl}-N-methylcarbamate (0.7 g, 99%) as a white solid. LCMS (ES+): (M+Na)⁺=307.0.

Step 2

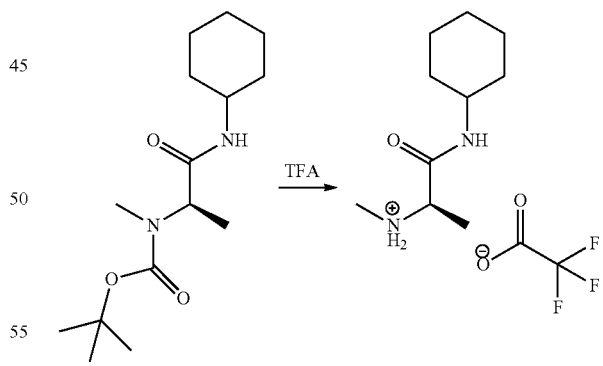

Tert-butyl N-{1-[(1-hydroxy-3-phenylpropan-2-yl)carbamoyl]ethyl}-N-methylcarbamate (0.56 g; 1.66 mmol; 1.00 eq.) was dissolved in dichloromethane (8 ml) and cooled in an ice bath. Trifluoroacetic acid (4 ml) was added slowly and the reaction was stirred to 25° C. over 3 h. The reaction was evaporated, and the residue was co-evaporated with toluene and dried under high vacuum to give (2R)—N-cyclohexyl-2-(methylamino)propanamide; trifluoroacetic acid which was used directly in the next step.

Step 3

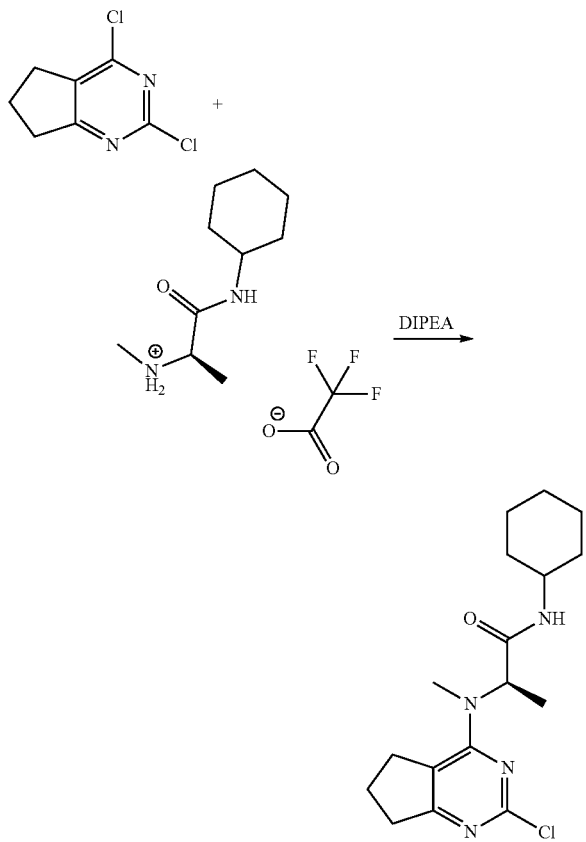

2,4-dichloro-6,7-dihydro-5H-cyclopenta[d]pyrimidine (420.00 mg; 2.22 mmol; 1.00 eq.) was dissolved in acetonitrile (7 ml), and to this was added (2R)—N-cyclohexyl-2-(methylamino)propanamide; trifluoroacetic acid (729.02 mg; 2.44 mmol; 1.10 eq.), and Hunig's base (1.93 mL; 11.11 mmol; 5.00 eq.). The mixture was stirred at 70° C. for 15 h, the solvent was then evaporated under reduced pressure, and the residue was purified by column chromatography (50% EtOAc in Hexanes) to give (2R)—N-tert-butyl-2-({2-chloro-5H,6H,7H-cyclopenta[d]pyrimidin-4-yl}(methyl)amino)propenamide (480 mg, 73%). LCMS (ES+): (M+H)+= 336.9.

Step 4

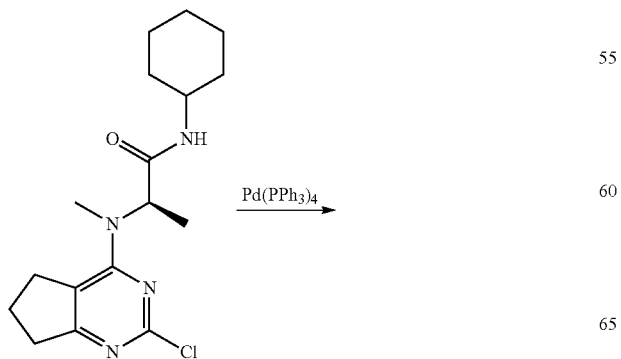

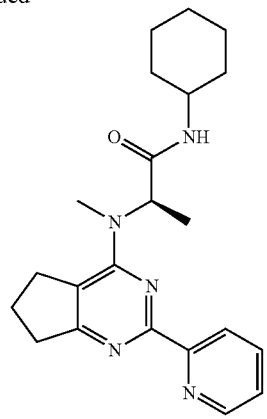

(2R)-2-({2-chloro-5H,6H,7H-cyclopenta[d]pyrimidin-4-yl}(methyl)amino)-N-cyclohexylpropanamide (150.00 mg; 0.45 mmol; 1.00 eq.) was dissolved in 1,4-dioxane (3.5 ml), and the solution was purged with Ar gas. 2-(tributylstannyl)pyridine (0.29 mL; 0.89 mmol; 2.00 eq.) and tetrakis(triphenylphosphane) palladium (51.46 mg; 0.04 mmol; 0.10 eq.) were added. The reaction vessel was sealed and stirred in a heat bath at 110° C. for 15 h. After evaporation, the residue was purified by reverse phase chromatography (Waters XSelect CSH C18 column, 0-70% acetonitrile/0.1% aqueous formic acid gradient) to give (2R)—N-cyclohexyl-2-{methyl[2-(pyridin-2-yl)-5H,6H,7H-cyclopenta[d]pyrimidin-4-yl]amino}propanamide (132 mg) as a white solid. LCMS (ES+): (M+H)+=380.4. $^1$H NMR (400 MHz, DMSO-d6) δ 8.82-8.56 (m, 1H), 8.44-8.27 (m, 1H), 8.27-8.07 (m, 1H), 7.99-7.77 (m, 1H), 7.57-7.36 (m, 1H), 5.26-5.04 (m, 1H), 3.65-3.50 (m, 1H), 3.23-3.15 (m, 2H), 3.09 (s, 3H), 2.93-2.72 (m, 2H), 2.11-1.89 (m, 2H), 1.78-1.61 (m, 2H), 1.61-1.47 (m, 3H), 1.35-1.12 (m, 6H), 1.06-0.89 (m, 2H).

Example 1.112

Synthesis of (2R)—N-(3,3-difluorocyclobutyl)-2-{methyl[2-(pyridin-2-yl)-5H,6H,7H-cyclopenta[d]pyrimidin-4-yl]amino}propanamide (Compound 109)

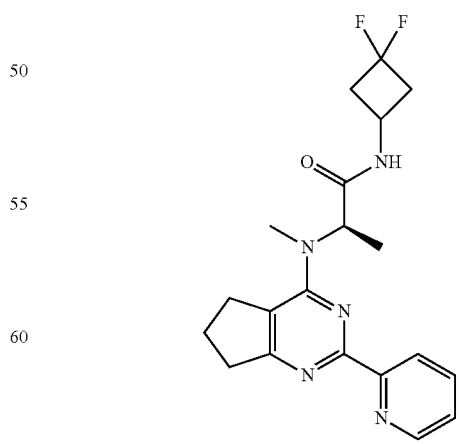

Compound 109 was synthesized similar to Compound 108 by replacing cyclohexylamine with 3,3-difluorocyclobutanamine. LCMS (ES+): (M+H)⁺=388.3. ¹H NMR (400 MHz, DMSO-d6) δ 8.82 (d, J=7.1 Hz, 1H), 8.72-8.66 (m, 1H), 8.31 (d, J=7.9 Hz, 1H), 7.95-7.88 (m, 1H), 7.51-7.43 (m, 1H), 5.15 (q, J=7.0 Hz, 1H), 4.17-4.04 (m, 1H), 3.24-3.14 (m, 2H), 3.10 (s, 3H), 2.95-2.58 (m, 5H), 2.49-2.41 (m, 1H), 2.09-1.90 (m, 2H), 1.34 (d, J=7.0 Hz, 3H).

Example 1.113

Synthesis of N-tert-butyl-2-[methyl(2-{1H-pyrazolo[3,4-c]pyridin-5-yl}-5H,6H,7H-cyclopenta[d]pyrimidin-4-yl)amino]acetamide (Compound 110)

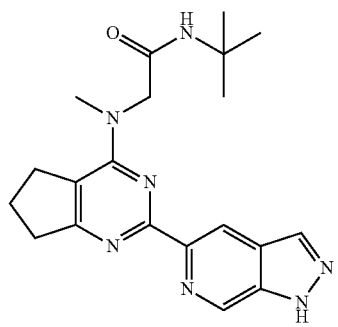 [SMILES: CN(CC(=O)NC(C)(C)C)c1nc(-c2cc3cn[nH]c3cn2)nc2c1CCC2]

Scheme 68 depicts a synthetic route for preparing an exemplary compound.

Scheme 68

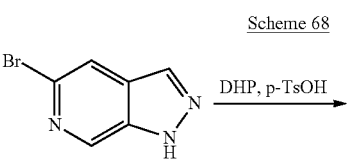

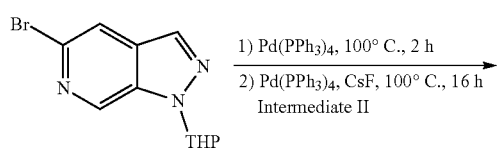

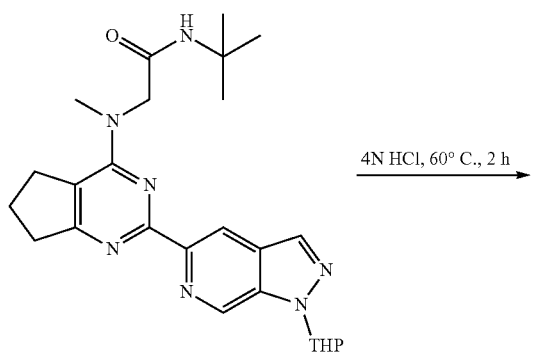

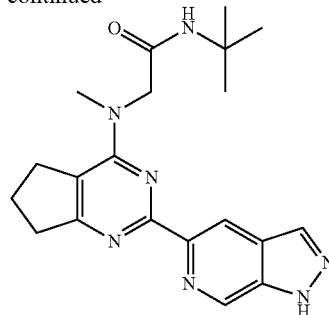

Step 2

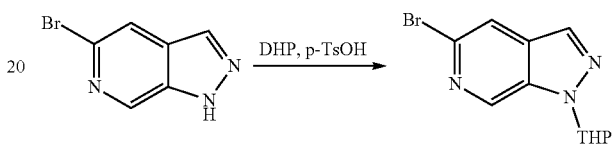

To a stirred solution of 5-bromo-1H-pyrazolo[3,4-c]pyridine (4.00 g, 20.200 mmol, 1.00 equiv) in DCM (32.00 mL), THF (32.00 mL), and DMF (2.00 mL) were added DHP (3.80 g, 45.175 mmol, 2.24 equiv) and p-Toluenesulfonic acid (0.35 g, 0.002 mmol, 0.10 equiv) at room temperature under an air atmosphere. The resulting mixture was stirred for 12 h at 50° C. under an air atmosphere. The mixture was allowed to cool down to room temperature. The resulting mixture was concentrated under reduced pressure. The residue was dissolved in 10% NaHCO₃ (100 mL). The resulting mixture was extracted with EtOAc (3×100 mL). The combined organic layers were washed with brine (1×100 mL) and dried over anhydrous Na₂SO₄. After filtration, the filtrate was concentrated under reduced pressure. This resulted in 5-bromo-1-(oxan-2-yl)pyrazolo[3,4-c]pyridine (3 g, 52.64%) as a yellow solid. LCMS (ES) [M+1]⁺ m/z: 282.

Step 3

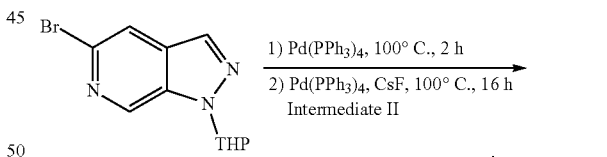

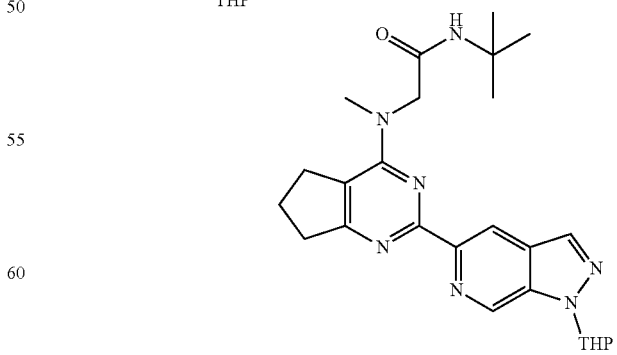

To a solution of 5-bromo-1-(oxan-2-yl)pyrazolo[3,4-c]pyridine (71.30 mg, 0.253 mmol, 1.5 equiv) and Sn₂Me₆ (91.07 mg, 0.278 mmol, 1.65 equiv) in dioxane (2.00 mL)

was added Pd(PPh₃)₄ (19.5 mg, 0.017 mmol, 0.1 equiv) after stirring for 2 h at 100° C. under a nitrogen atmosphere. The mixture was cooled to room temperature. To the above mixture was added N-tert-butyl-2-([2-chloro-5H,6H,7H-cyclopenta[d]pyrimidin-4-yl](methyl)amino)acetamide (Intermediate II, 50.00 mg, 0.168 mmol, 1.00 equiv), CsF (51.18 mg, 0.337 mmol, 2 equiv), and Pd(PPh₃)₄ (19.5 mg, 0.017 mmol, 0.1 equiv) at room temperature. The resulting mixture was stirred for an additional 16 h at 100° C. under a nitrogen atmosphere. The resulting mixture was concentrated under reduced pressure. The residue was purified by silica gel column chromatography and eluted with PE/THF (1:1) to afford N-tert-butyl-2-[methyl([2-[1-(oxan-2-yl)pyrazolo[3,4-c]pyridin-5-yl]-5H,6H,7H-cyclopenta[d]pyrimidin-4-yl])amino]acetamide (50 mg, 64.02%) as a yellow solid. LCMS (ES) [M+1]⁺ m/z: 464.

Step 4

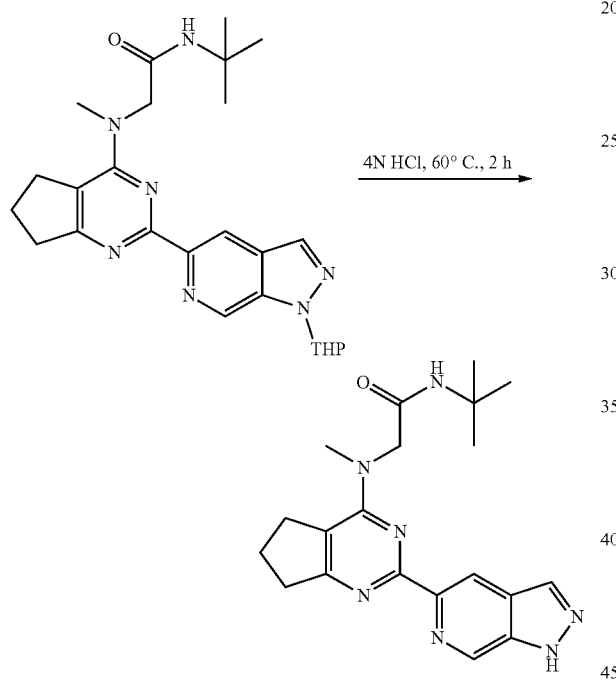

A solution of N-tert-butyl-2-[methyl([2-[1-(oxan-2-yl)pyrazolo[3,4-c]pyridin-5-yl]-5H,6H,7H-cyclopenta[d]pyrimidin-4-yl])amino]acetamide (400.00 mg, 0.863 mmol, 1.00 equiv) in 4NHCl (g) in MeOH (4.00 mL, 131.648 mmol, 152.57 equiv) was stirred for 2 h at 60° C. under an air atmosphere. The mixture was cooled to room temperature. The resulting mixture was concentrated under reduced pressure. The crude product (500 mg) was purified by Prep-HPLC to afford N-tert-butyl-2-[methyl(2-[1H-pyrazolo[3,4-c]pyridin-5-yl]-5H,6H,7H-cyclopenta[d]pyrimidin-4-yl)amino]acetamide formate (76 mg, 23.21%) as a white solid. ¹H NMR (300 MHz, DMSO-d₆) ¹H NMR (300 MHz, DMSO-d₆) δ 13.71 (br, 3H), 9.09 (s, 1H), 8.81 (d, J=1.2 Hz, 1H), 8.28 (s, 1H), 8.15 (s, 1H), 7.77 (s, 1H), 4.15 (s, 2H), 3.30 (s, 3H), 3.15 (t, J=7.3 Hz, 2H), 2.83 (t, J=7.8 Hz, 2H), 2.06-1.92 (m, 2H), 1.22 (s, 9H). LCMS (ES) [M+1]⁺ m/z: 380.2.

Example 1.114

Synthesis of 2-{methyl[2-(1-methyl-1H-imidazol-4-yl)-5H,6H,7H-cyclopenta[d]pyrimidin-4-yl]amino}-N-[1-(trifluoromethyl)cyclopropyl]acetamide (Compound 111)

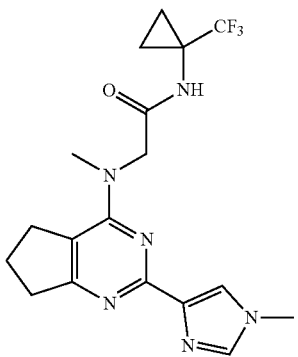 [SMILES: CN(CC(=O)NC1(C(F)(F)F)CC1)c1nc(-c2cn(C)cn2)nc2c1CCC2]

Compound 111 was synthesized similar to Compound 98 by replacing 2-(tributylstannyl)pyridine with 1-methyl-4-(tributylstannyl)-1H-imidazole. ¹H NMR (400 MHz, DMSO-d₆) δ 9.15 (s, 1H), 8.34 (s, 1H), 8.22 (s, 1H), 4.35 (s, 2H), 3.80 (s, 3H), 3.36 (s, 3H), 3.14 (s, 2H), 2.92 (t, J=7.9 Hz, 2H), 2.02 (p, J=7.9 Hz, 2H), 1.24-1.16 (m, 2H), 0.98 (s, 2H). LCMS (ES) [M+1]⁺ m/z: 395.2.

Example 1.115

Synthesis of (2R)—N-tert-butyl-2-{methyl[2-(1-methyl-1H-imidazol-4-yl)-5H,6H,7H-cyclopenta[d]pyrimidin-4-yl]amino}propanamide (Compound 112)

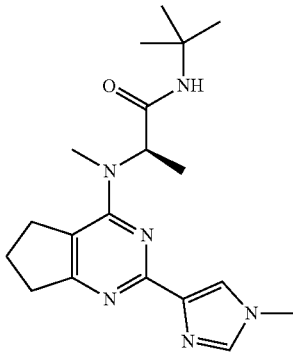 [SMILES: C[C@H](C(=O)NC(C)(C)C)N(C)c1nc(-c2cn(C)cn2)nc2c1CCC2]

Compound 112 was synthesized similar to Compound 101 replacing with 1-methyl-4-(tributylstannyl)-1H-imidazole. ¹H NMR (400 MHz, DMSO-d₆) δ 8.09 (s, 1H), 8.02 (s, 1H), 7.75 (s, 1H), 5.17 (q, J=7.0 Hz, 1H), 3.75 (s, 3H), 3.15 (s, 3H), 3.24-3.01 (m, 3H), 2.87-2.78 (m, 2H), 2.06-1.90 (m, 1H), 1.31 (d, J=7.1 Hz, 3H), 1.20 (d, J=1.1 Hz, 9H). LCMS (ES) [M+1]⁺ m/z: 357.4.

Example 1.116

Synthesis of N-tert-butyl-2-({2-[4-(2-hydroxyethyl)pyridin-2-yl]-5H,6H,7H-cyclopenta[d]pyrimidin-4-yl}(methyl)amino)acetamide (Compound 113)

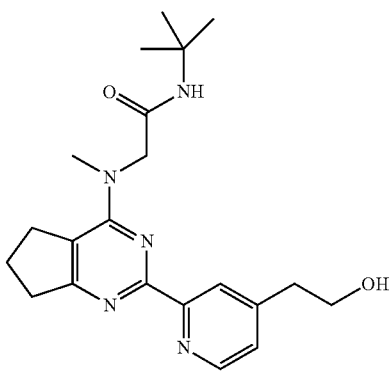 [SMILES: CN(CC(=O)NC(C)(C)C)c1nc(-c2cc(CCO)ccn2)nc2c1CCC2]

Scheme 69 depicts a synthetic route for preparing an exemplary compound.

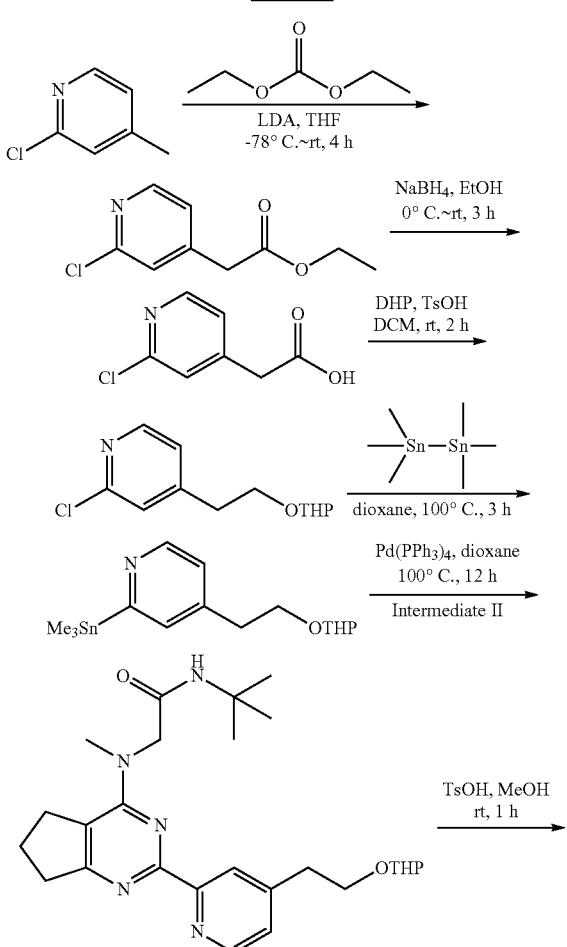

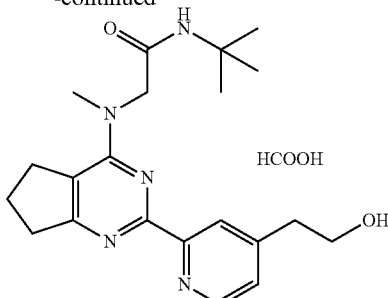

Step 1

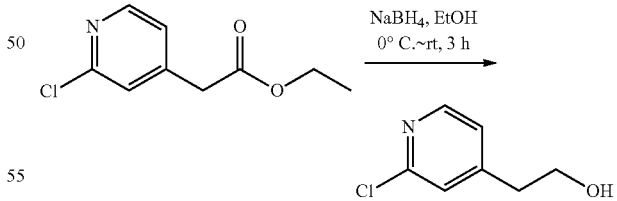

Into a 250-mL 3-necked round-bottom flask purged and maintained in an inert atmosphere of nitrogen, was placed 2-chloro-4-methylpyridine (10.0 g, 78.39 mmol, 1.0 equiv) and THF (100 mL). This was followed by the addition of LDA (2 M in THF) (117.5 mL, 235.17 mmol, 3.0 equiv) at −78° C. After addition, the reaction solution was stirred for 2 hr at −78° C. To this, diethyl carbonate (13.9 g, 117.66 mmol, 1.50 equiv) was added. The mixture was stirred for 3 h at room temperature. The reaction was then quenched by the addition of NH$_4$Cl (aq) (200 mL) and extracted with 3×100 mL of ethyl acetate. The combined organic phase was dried over anhydrous sodium sulfate, filtered, and the filtrate was concentrated under reduced pressure. The residue was purified by silica gel column with ethyl acetate/petroleum ether (4:1). This resulted in 10.0 g (64%) of ethyl 2-(2-chloropyridin-4-yl)acetate was obtained as a yellow oil. LCMS (ES) [M+1]$^+$ m/z: 200.

Step 2

Into a 250-mL 3-necked round-bottom flask was placed ethyl 2-(2-chloropyridin-4-yl)acetate (10.0 g, 50.09 mmol, 1.0 equiv) and EtOH (100 mL). This was followed by the addition of NaBH$_4$ (9.50 g, 251.10 mmol, 5.0 equiv) in several batches at 0° C. After addition, the mixture was stirred for 3 h at room temperature. The reaction was then quenched by the addition of water (300 mL) and extracted with 3×100 mL of dichloromethane. The combined organic phase was dried over anhydrous sodium sulfate, filtered, and the filtrate was concentrated under reduced pressure. This resulted in 7.5 g (95%) of 2-(2-chloropyridin-4-yl)ethan-1-ol as a yellow oil, which was used in the next step directly without further purification. LCMS (ES) [M+1]+ m/z: 158.
Step 3

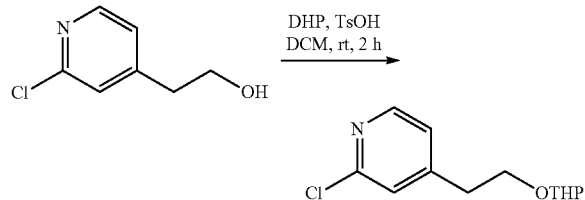

Into a 100-mL round-bottom flask was placed 2-(2-chloropyridin-4-yl)ethan-1-ol (4.78 g, 30.33 mmol, 1.0 equiv), DCM (40 mL), DHP (5.10 g, 60.63 mmol, 2.0 equiv), and TsOH (524 mg, 3.04 mmol, 0.1 equiv). The reaction was stirred for 2 h at room temperature. The solution was concentrated to remove the solvent, and the residue was purified by silica gel column with ethyl acetate/petroleum ether (1/3) to yield 2.0 g (27%) of 2-chloro-4-(2-((tetrahydro-2H-pyran-2-yl)oxy)ethyl)pyridine as a colorless oil. LCMS (ES) [M+1]+ m/z: 242.
Step 4

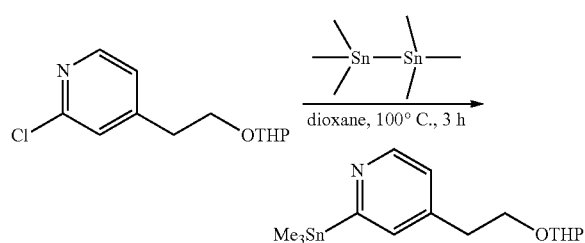

Into a 50-mL round-bottom flask purged and maintained in an inert atmosphere of nitrogen was placed 2-chloro-4-(2-((tetrahydro-2H-pyran-2-yl)oxy)ethyl)pyridine (800 mg, 3.31 mmol, 1.0 equiv), dioxane (10.0 mL), hexamethyldistannane (1.3 g, 3.97 mmol, 1.2 equiv), and Pd(PPh3)4 (765 mg, 0.66 mmol, 0.2 equiv). The mixture was stirred for 2 h at 100° C. After being cooled to room temperature, the reaction solution was used in the next step directly without purification. LCMS (ES) [M+1]+ m/z: 372.
Step 5

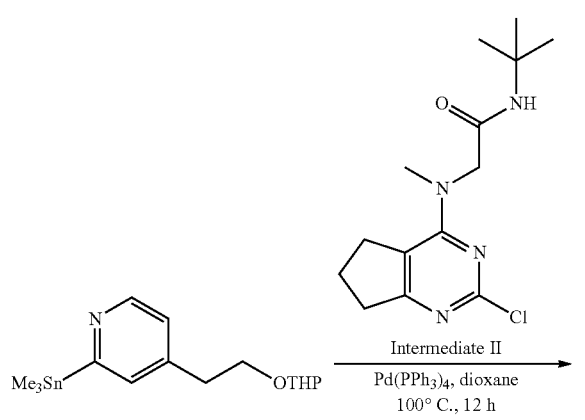

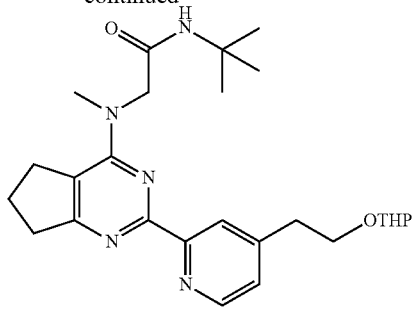

Into a 40-mL vial purged and maintained in an inert atmosphere of nitrogen was placed 4-(2-((tetrahydro-2H-pyran-2-yl)oxy)ethyl)-2-(trimethylstannyl)pyridine (the reaction solution of last step), dioxane (10.0 mL), N-tert-butyl-2-([2-chloro-5H,6H,7H-cyclopenta[d]pyrimidin-4-yl](methyl)amino)acetamide (Intermediate II, 385 mg, 1.30 mmol, 0.6 equiv), and Pd(PPh3)4 (500 mg, 0.43 mmol, 0.2 equiv). The mixture was stirred for 12 h at 100° C. The mixture was cooled and concentrated to remove the solvent, and the residue was purified by silica gel column with THF/PE (2/1) to yield 500 mg (50%) of N-(tert-butyl)-2-(methyl(2-(4-(2-((tetrahydro-2H-pyran-2-yl)oxy)ethyl)pyridin-2-yl)-6,7-dihydro-5H-cyclopenta[d]pyrimidin-4-yl)amino)acetamide as a yellow oil. LCMS (ES) [M+1]+ m/z: 468.
Step 6

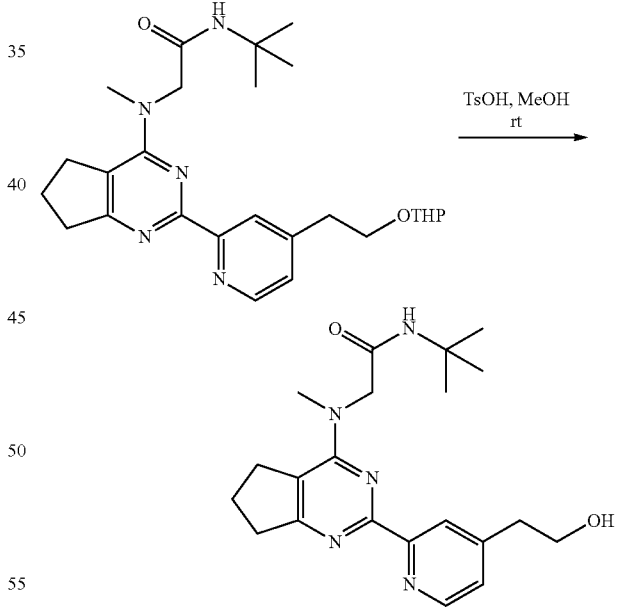

Into a 20-mL vial was placed N-(tert-butyl)-2-(methyl(2-(4-(2-((tetrahydro-2H-pyran-2-yl)oxy)ethyl)pyridin-2-yl)-6,7-dihydro-5H-cyclopenta[d]pyrimidin-4-yl)amino)acetamide (184 mg, 0.39 mmol, 1.0 equiv), methanol (5.0 mL), and para-toluene sulfonic acid (68 mg, 0.39 mmol, 1.0 equiv). The reaction solution was stirred for 1 h at room temperature. The reaction solution was purified by Prep-HPLC with the following conditions: Column, Atlantis HILIC OBD Column, 19*150 mm*5 um, mobile phase, Water (10 mmol/L) with (0.5 HCOOH) and MeOH:

ACN=1:1 (33% Phase B up to 45% within 9 min), Detector, UV 254 nm. This resulted in 89.2 mg (59%) of N-(tert-butyl)-2-((2-(4-(2-hydroxyethyl)pyridin-2-yl)-6,7-dihydro-5H-cyclopenta[d]pyrimidin-4-yl)(methyl)amino)acetamide formate as an off-white solid. $^1$H NMR (300 MHz, DMSO-$d_6$, ppm): δ 8.53 (d, J=4.8 Hz, 1H), 8.24 (br, 1H), 8.17 (s, 1H), 7.70 (s, 1H), 7.32 (d, J=3.6 Hz, 1H), 4.16 (s, 2H), 3.70 (t, J=6.6 Hz, 2H), 3.27 (s, 3H), 3.15 (t, J=7.2 Hz, 2H), 2.86-2.79 (m, 4H), 2.04-1.94 (m, 2H), 1.23 (s, 9H). LCMS (ES, m/z): [M+H]$^+$: 384.2.

Example 1.117

Synthesis of (2R)—N-tert-butyl-3-methyl-2-{methyl[2-(pyridin-2-yl)-5H,6H,7H-cyclopenta[d]pyrimidin-4-yl]amino}butanamide (Compound 114)

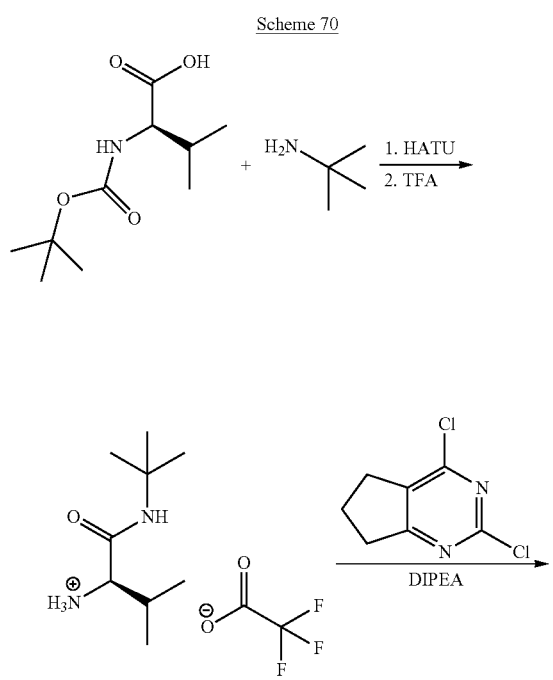

Scheme 70 depicts a synthetic route for preparing an exemplary compound.

Scheme 70

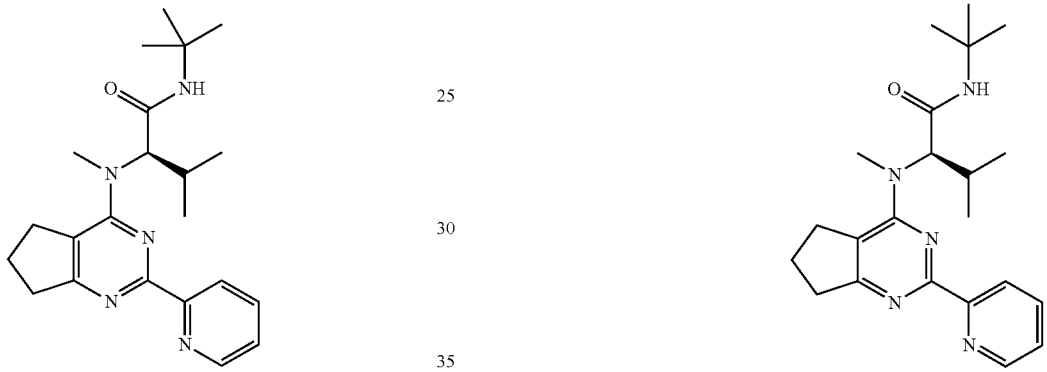

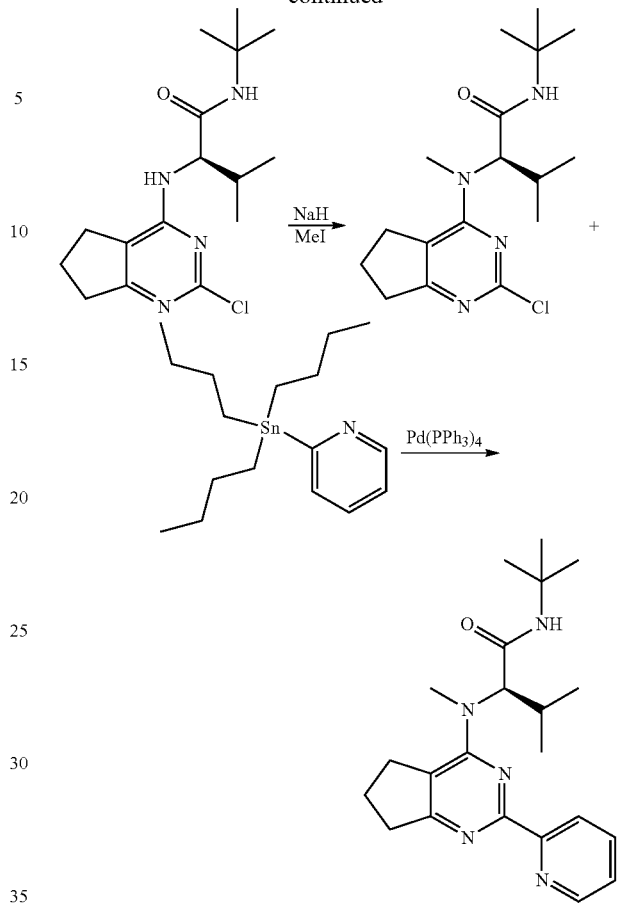

Step 1

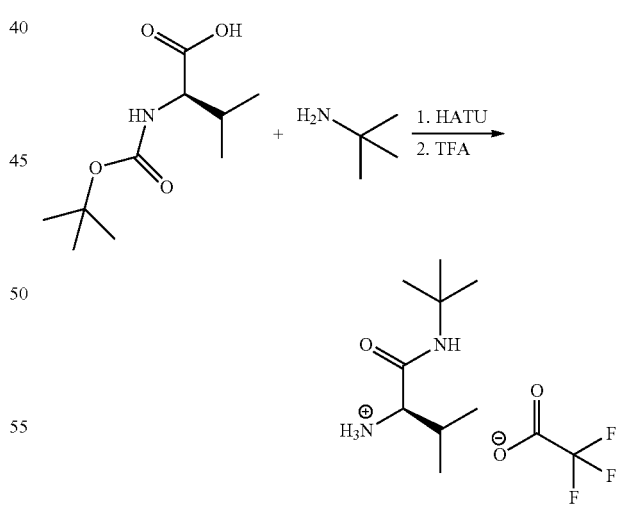

(2R)-2-[(tert-butoxycarbonyl)amino]-3-methylbutanoic acid (0.50 g; 2.30 mmol; 1.00 eq.) was dissolved in dichloromethane (23 ml) and cooled in an ice bath. Tert-butylamine (0.27 mL; 2.53 mmol; 1.10 eq.), 1-[bis(dimethylamino)methylene]-1H-1,2,3-triazolo[4,5-b]pyridinium 3-oxid hexafluorophosphate (HATU, 0.96 g; 2.53 mmol; 1.10 eq.), and Hunig's base (0.84 mL; 4.83 mmol; 2.10 eq.) were then added. The reaction was stirred to 25° C. over 20 h and then taken up in ethyl acetate (100 ml), water (10 ml), and sodium bicarbonate solution (50 ml). The phases were separated, and the aqueous phase was extracted with more ethyl acetate (100 ml). The combined organics were washed with sodium chloride solution (30 ml), dried over sodium sulfate, and evaporated. The residue was purified by silica gel chromatography (ethyl acetate/hexanes gradient) to give tert-butyl N-{1-[(1-hydroxy-3-phenylpropan-2-yl)carbamoyl]ethyl}-N-methylcarbamate (0.6 g, 96%) as a white solid.

Tert-butyl N-{1-[(1-hydroxy-3-phenylpropan-2-yl)carbamoyl]ethyl}-N-methylcarbamate (0.56 g; 1.66 mmol; 1.00 eq.) was dissolved in dichloromethane (7 ml) and cooled in an ice bath. Trifluoroacetic acid (3.7 ml) was added slowly and the reaction was stirred to 25° C. over 3 h. The reaction was evaporated, and the residue was co-evaporated with toluene and dried under high vacuum to give (2R)-2-amino-N-tert-butyl-3-methylbutanamide; trifluoroacetic acid, which was used directly in the next step. LCMS (ES+): $(M+H)^+=172.9$.

Step 2

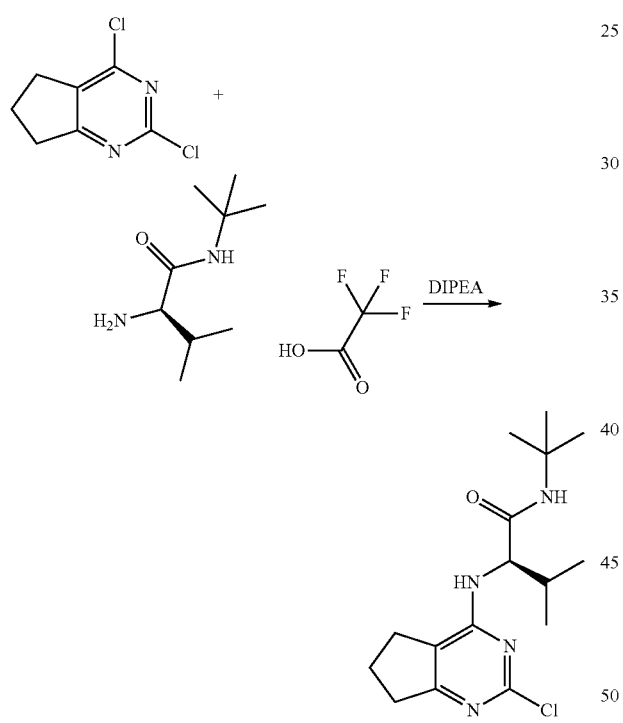

2,4-dichloro-6,7-dihydro-5H-cyclopenta[d]pyrimidine (200.00 mg; 1.06 mmol; 1.00 eq.) was dissolved in acetonitrile (4 ml), and to this was added (2R)-2-amino-N-tert-butyl-3-methylbutanamide; trifluoroacetic acid (333.18 mg; 1.16 mmol; 1.10 eq.), and Hunig's base (0.92 mL; 5.29 mmol; 5.00 eq.). The mixture was stirred at 70° C. for 15 h, the solvent was then evaporated under reduced pressure, and the residue was purified by column chromatography (50% EtOAc in Hexanes) to give (2R)—N-tert-butyl-2-({2-chloro-5H,6H,7H-cyclopenta[d]pyrimidin-4-yl}amino)-3-methylbutanamide (266 mg, 77%). LCMS (ES+): $(M+H)^+=$ 324.9. $^1$H NMR (400 MHz, DMSO-d6) δ 7.64 (s, 1H), 6.85 (d, J=8.3 Hz, 1H), 4.32-4.24 (m, 1H), 2.75-2.65 (m, 4H), 2.09-1.96 (m, 3H), 1.25 (s, 9H), 0.92-0.86 (m, 6H).

Step 3

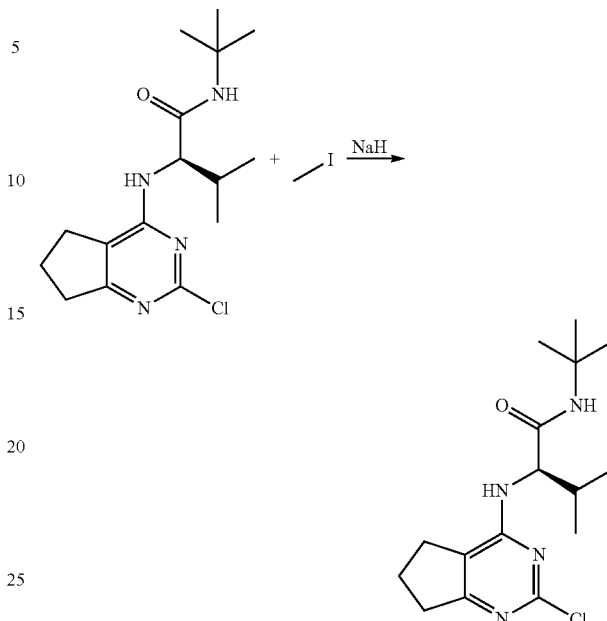

(2R)—N-tert-butyl-2-({2-chloro-5H,6H,7H-cyclopenta[d]pyrimidin-4-yl}amino)-3-methylbutanamide (262 mg; 0.81 mmol; 1 eq.) was dissolved in N,N-dimethylformamide (15 ml) and cooled in an ice bath. Sodium hydride (34 mg; 0.85 mmol; 1.05 eq., 60%) was added and the mixture was stirred for 20 min. Iodomethane (53 µL; 0.85 mmol; 1.05 eq.) was then added and the reaction was stirred to 25° C. over 1.5 h. The reaction was quenched by the addition of water (90 ml) and then extracted with ethyl acetate (2×100 ml). The combined organic phases were washed with water (30 ml) and sodium chloride solution (30 ml), and then dried over sodium sulfate. After evaporation, the residue was purified by silica gel chromatography (ethyl acetate/hexanes gradient) to give (2R)—N-tert-butyl-2-({2-chloro-5H,6H,7H-cyclopenta[d]pyrimidin-4-yl}(methyl)amino)-3-methylbutanamide (255 mg, 93%) as a film. MS (ES+): $(M+H)^+=$ 339.3.

Step 4

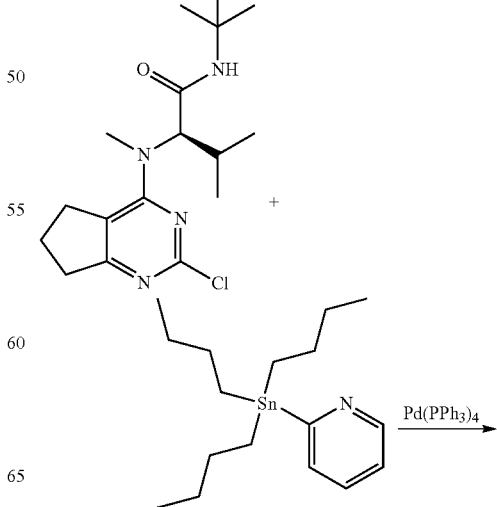

-continued

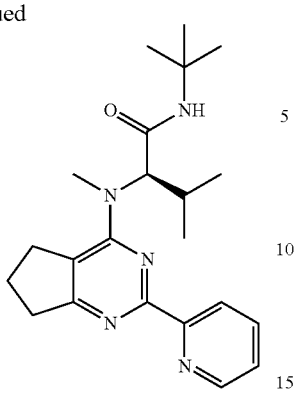

(2R)—N-tert-butyl-2-({2-chloro-5H,6H,7H-cyclopenta[d]pyrimidin-4-yl}(methyl)amino)-3-methylbutanamide (147.00 mg; 0.43 mmol; 1.00 eq.) was dissolved in 1,4-dioxane (3.5 ml), and the solution was purged with Ar gas. 2-(tributylstannyl)pyridine (0.28 mL; 0.87 mmol; 2.00 eq.) and tetrakis(triphenylphosphane) palladium (50.13 mg; 0.04 mmol; 0.10 eq.) were added The reaction vessel was sealed and stirred in a heat bath at 110° C. for 15 h. After evaporation, the residue was purified by reverse phase chromatography (Waters XSelect CSH C18 column, 0-70% acetonitrile/0.1% aqueous formic acid gradient) to give (2R)—N-tert-butyl-3-methyl-2-{methyl[2-(pyridin-2-yl)-5H,6H,7H-cyclopenta[d]pyrimidin-4-yl]amino}butanamide (98 mg, 59%) as a light yellow solid. LCMS (ES+): (M+H)⁺= 382.0. ¹H NMR (400 MHz, DMSO-d6) δ 8.72 (ddd, J=4.8, 1.8, 0.9 Hz, 1H), 8.41 (dt, J=8.0, 1.1 Hz, 1H), 7.98-7.89 (m, 2H), 7.52-7.46 (m, 1H), 4.56 (d, J=11.0 Hz, 1H), 3.27-3.20 (m, 1H), 3.14 (s, 3H), 3.10-3.00 (m, 1H), 2.99-2.88 (m, 1H), 2.85-2.76 (m, 1H), 2.36-2.25 (m, 1H), 2.06-1.89 (m, 2H), 1.18 (s, 9H), 0.95 (d, J=6.4 Hz, 3H), 0.86 (d, J=6.6 Hz, 3H).

Example 1.118

Synthesis of (2S)—N-tert-butyl-3-methyl-2-{methyl[2-(pyridin-2-yl)-5H,6H,7H-cyclopenta[d]pyrimidin-4-yl]amino}butanamide (Compound 115)

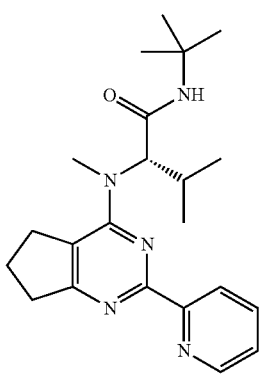 [SMILES: CC(C)[C@@H](C(=O)NC(C)(C)C)N(C)c1nc(-c2ccccn2)nc2c1CCC2]

Compound 115 was synthesized similar to compound 114 by replacing (2R)-2-[(tert-butoxycarbonyl)amino]-3-methylbutanoic acid with (2S)-2-[(tert-butoxycarbonyl)amino]-3-methylbutanoic acid. LCMS (ES+): (M+H)⁺=382.0. ¹H NMR (400 MHz, DMSO-d6) δ 8.73 (ddd, J=4.8, 1.8, 0.9 Hz, 1H), 8.45-8.40 (m, 1H), 7.98-7.90 (m, 2H), 7.51 (ddd, J=7.5, 4.8, 1.2 Hz, 1H), 4.57 (d, J=11.0 Hz, 1H), 3.28-3.21 (m, 1H), 3.16 (s, 3H), 3.10-3.00 (m, 1H), 2.99-2.88 (m, 1H), 2.86-2.76 (m, 1H), 2.37-2.26 (m, 1H), 2.15-1.91 (m, 2H), 1.19 (s, 9H), 0.95 (d, J=6.5 Hz, 3H), 0.86 (d, J=6.6 Hz, 3H).

Example 1.119

Synthesis of (2R)—N-tert-butyl-2-{methyl[2-(pyridin-2-yl)-5H,6H,7H-cyclopenta[d]pyrimidin-4-yl]amino}-4-(methylsulfanyl)butanamide (Compound 116)

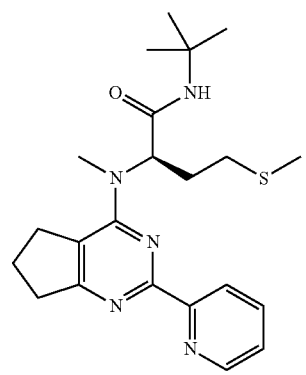 [SMILES: CSCC[C@H](C(=O)NC(C)(C)C)N(C)c1nc(-c2ccccn2)nc2c1CCC2]

Compound 116 was synthesized similar to Compound 114 by replacing (2R)-2-[(tert-butoxycarbonyl)amino]-3-methylbutanoic acid in with (2R)-2-[(tert-butoxycarbonyl)amino]-4-(methylsulfanyl)butanoic acid. LCMS (ES+): (M+H)⁺=414.0. ¹H NMR (400 MHz, DMSO-d6) δ 8.70 (ddd, J=4.7, 1.8, 0.9 Hz, 1H), 8.43-8.35 (m, 1H), 7.97-7.88 (m, 2H), 7.48 (ddd, J=7.5, 4.8, 1.2 Hz, 1H), 5.11 (dd, J=8.9, 6.2 Hz, 1H), 3.26-3.17 (m, 1H), 3.13-3.04 (m, 4H), 2.97-2.87 (m, 1H), 2.87-2.77 (m, 1H), 2.48-2.36 (m, 2H), 2.15-1.92 (m, 7H), 1.20 (s, 9H).

Example 1.120

Synthesis of (2S)—N-tert-butyl-2-{methyl[2-(pyridin-2-yl)-5H,6H,7H-cyclopenta[d]pyrimidin-4-yl]amino}-4-methylsulfanyl)butanamide (Compound 117)

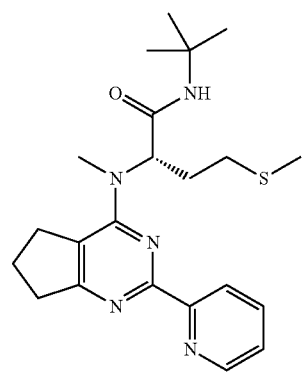 [SMILES: CSCC[C@@H](C(=O)NC(C)(C)C)N(C)c1nc(-c2ccccn2)nc2c1CCC2]

Compound 117 was synthesized similar to Compound 114 by replacing (2R)-2-[(tert-butoxycarbonyl)amino]-3-methylbutanoic acid in with (2S)-2-[(tert-butoxycarbonyl)

amino]-4-(methylsulfanyl)butanoic acid. LCMS (ES+): (M+H)⁺=414.1. ¹H NMR (400 MHz, DMSO-d6) δ 8.72 (ddd, J=4.8, 1.8, 0.9 Hz, 1H), 8.45-8.36 (m, 1H), 7.99-7.87 (m, 2H), 7.51 (ddd, J=7.5, 4.7, 1.2 Hz, 1H), 5.13 (dd, J=8.9, 6.1 Hz, 1H), 3.25-3.19 (m, 1H), 3.15-3.05 (m, 4H), 3.00-2.78 (m, 2H), 2.48-2.37 (m, 2H), 2.16-1.93 (m, 7H), 1.20 (s, 9H).

Example 1.121

Synthesis of (2R)—N-cyclohexyl-2-{methyl[2-(1-methyl-1H-imidazol-4-yl)-5H,6H,7H-cyclopenta[d]pyrimidin-4-yl]amino}propanamide (Compound 118)

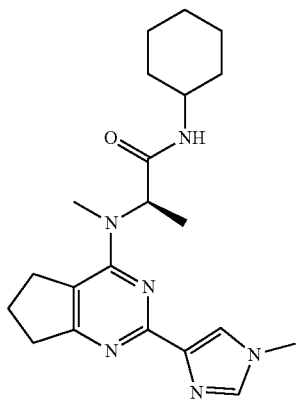 [SMILES: C[C@H](C(=O)NC1CCCCC1)N(C)c1nc(-c2cn(C)cn2)nc2c1CCC2]

Scheme 71 depicts a synthetic route for preparing an exemplary compound.

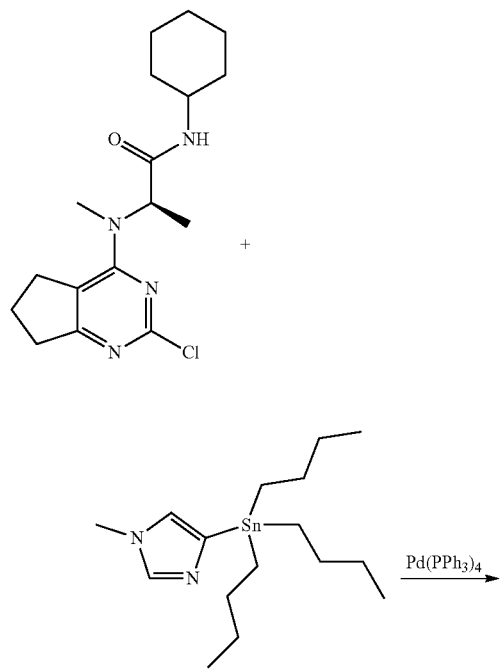

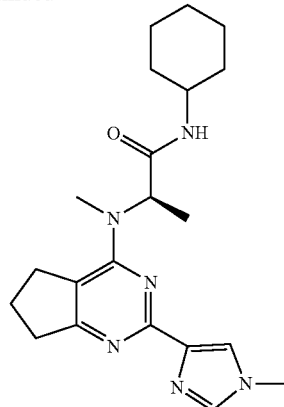

To a solution of (2R)-2-({2-chloro-5H,6H,7H-cyclopenta[d]pyrimidin-4-yl}(methyl)amino)-N-cyclohexylpropanamide (134.00 mg; 0.40 mmol; 1.00 eq.) and 1-methyl-4-(tributylstannyl)-1H-imidazole (251.17 mg; 0.63 mmol; 2.00 eq.) in Toluene (2 mL) was added tetrakis(triphenylphosphane) palladium (45.97 mg; 0.04 mmol; 0.10 eq.). The solution was heated at 105° C. for 15 h, cooled to room temperature, and concentrated to remove solvent. The residue was purified by preparative HPLC to give (2R)—N-cyclohexyl-2-{methyl[2-(1-methyl-1H-imidazol-4-yl)-5H,6H,7H-cyclopenta[d]pyrimidin-4-yl]amino}propanamide (135 mg). ¹H NMR (400 MHz, DMSO-d₆) δ 8.15-8.05 (m, 2H), 8.01 (d, J=8.1 Hz, 1H), 5.23 (q, J=6.9 Hz, 1H), 3.76 (s, 3H), 3.52 (s, 1H), 3.15 (s, 3H), 3.24-3.03 (m, 2H), 2.94-2.76 (m, 2H), 1.99 (ddt, J=20.4, 13.0, 5.5 Hz, 2H), 1.72-1.62 (m, 2H), 1.62-1.54 (m, 2H), 1.51 (d, J=12.3 Hz, 1H), 1.33 (d, J=7.0 Hz, 3H), 1.30-1.12 (m, 3H), 1.08 (ddd, J=19.3, 14.8, 8.6 Hz, 2H). LCMS (ES, m/z): [M+H]⁺: 383.2.

Example 1.122

Synthesis of (2R)—N-cyclohexyl-2-{[2-(4-methoxypyridin-2-yl)-5H,6H,7H-cyclopenta[d]pyrimidin-4-yl](methyl)amino}propanamide (Compound 119)

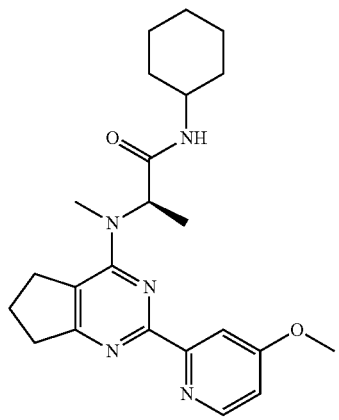 [SMILES: COc1ccnc(-c2nc3c(c(N(C)[C@H](C)C(=O)NC4CCCCC4)n2)CCC3)c1]

Scheme 72 depicts a synthetic route for preparing an exemplary compound.

Scheme 72

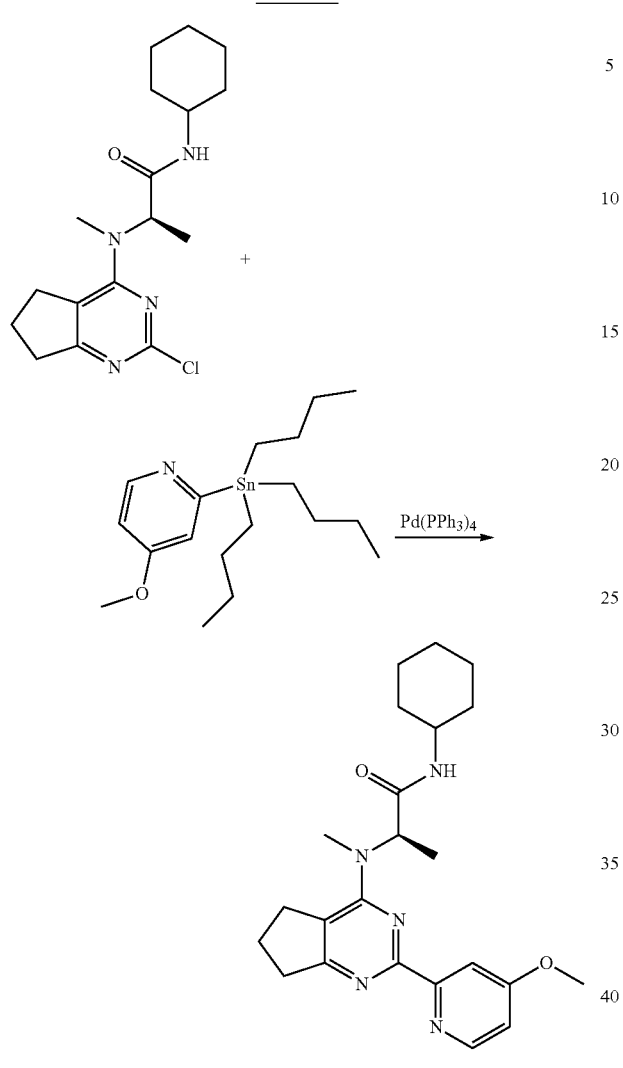

To a solution of (2R)-2-({2-chloro-5H,6H,7H-cyclopenta[d]pyrimidin-4-yl}(methyl)amino)-N-cyclohexylpropanamide (125.00 mg; 0.37 mmol; 1.00 eq.) and 4-methoxy-2-(tributylstannyl)pyridine (251.17 mg; 0.63 mmol; 2.00 eq.) in Toluene (2 mL) was added tetrakis(triphenylphosphane)palladium (42.88 mg; 0.04 mmol; 0.10 eq.). The solution was heated at 105° C. for 15 h, cooled to room temperature, and concentrated to remove solvent. The residue was purified by preparative HPLC to give (2R)—N-cyclohexyl-2-{[2-(4-methoxypyridin-2-yl)-5H,6H,7H-cyclopenta[d]pyrimidin-4-yl](methyl)amino}propenamide (62 mg). $^1$H NMR (400 MHz, DMSO-d$_6$) δ 8.54 (d, J=5.8 Hz, 1H), 8.11 (d, J=8.0 Hz, 1H), 7.91 (d, J=2.6 Hz, 1H), 7.16 (dd, J=5.8, 2.6 Hz, 1H), 5.07 (q, J=7.0 Hz, 1H), 3.94 (s, 3H), 3.53 (d, J=6.6 Hz, 1H), 3.25-3.17 (m, 1H), 3.15 (s, 3H), 3.15-3.05 (m, 1H), 2.87 (tdd, J=16.9, 13.0, 7.0 Hz, 2H), 2.12-1.90 (m, 2H), 1.71 (s, 1H), 1.51 (d, J=12.2 Hz, 1H), 1.50 (s, 3H), 1.34 (d, J=7.1 Hz, 3H), 1.20 (t, J=9.7 Hz, 2H), 1.16-1.06 (m, 1H), 0.99 (s, 2H). LCMS (ES, m/z): [M+H]$^+$: 410.1.

Example 1.123

Synthesis of (2S)-3-(tert-butoxy)-N-tert-butyl-2-{methyl[2-(pyridin-2-yl)-5H,6H,7H-cyclopenta[d]pyrimidin-4-yl]amino}propanamide (Compound 120)

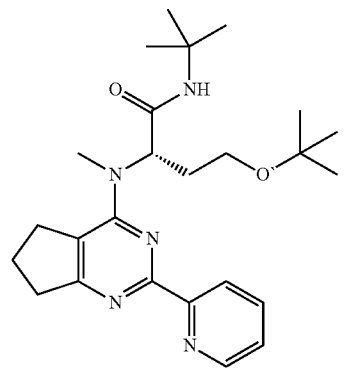

Compound 120 was synthesized similar to Compound 114 by replacing (2R)-2-[(tert-butoxycarbonyl)amino]-3-methylbutanoic acid with (2S)-3-tert-butoxy-2-{[(9H-fluoren-9-ylmethoxy)carbonyl]amino}propanoic acid. MS (ES+): (M+H)$^+$=426.1. $^1$H NMR (400 MHz, DMSO-d6) δ 8.68 (ddd, J=4.8, 1.8, 0.9 Hz, 1H), 8.41-8.33 (m, 1H), 7.94-7.86 (m, 1H), 7.81 (s, 1H), 7.46 (ddd, J=7.5, 4.7, 1.2 Hz, 1H), 5.00 (dd, J=8.0, 5.9 Hz, 1H), 3.83-3.75 (m, 1H), 3.73-3.65 (m, 1H), 3.29-3.20 (m, 2H), 3.18 (s, 3H), 3.12-3.02 (m, 1H), 2.93-2.74 (m, 2H), 2.10-1.90 (m, 2H), 1.19 (s, 9H), 1.14 (s, 9H).

Example 1.124

Synthesis of (2R)-3-(tert-butoxy)-N-tert-butyl-2-{methyl[2-(pyridin-2-yl)-5H,6H,7H-cyclopenta[d]pyrimidin-4-yl]amino}propanamide (Compound 121)

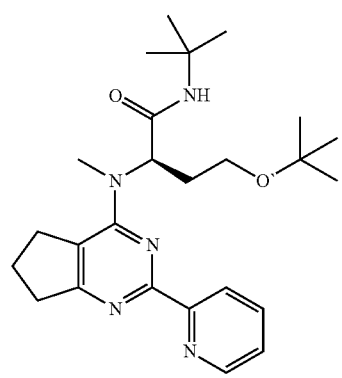

Compound 121 was synthesized similar to Compound 114 by replacing (2R)-2-[(tert-butoxycarbonyl)amino]-3-methylbutanoic acid with (2R)-3-tert-butoxy-2-{[(9H-fluoren-9-ylmethoxy)carbonyl]amino}propanoic acid. MS (ES+): (M+H)$^+$=426.1. $^1$H NMR (400 MHz, DMSO-d6) δ 8.69 (ddd, J=4.7, 1.8, 0.9 Hz, 1H), 8.41-8.33 (m, 1H), 7.94-7.85 (m, 1H), 7.81 (s, 1H), 7.46 (ddd, J=7.5, 4.7, 1.2 Hz, 1H), 5.00 (dd, J=7.9, 5.9 Hz, 1H), 3.82-3.76 (m, 1H), 3.70 (dd, J=9.5, 8.0 Hz, 1H), 3.26-3.20 (m, 1H), 3.18 (s, 3H), 3.12-3.02 (m, 1H), 2.93-2.75 (m, 2H), 2.10-1.90 (m, 2H), 1.19 (s, 9H), 1.14 (s, 9H).

Example 1.125

Synthesis of N-tert-butyl-2-[(2-{2H,3H-[1,4]dioxino[2,3-c]pyridin-7-yl}-5H,6H,7H-cyclopenta[d]pyrimidin-4-yl)(methyl)amino]acetamide (Compound 122)

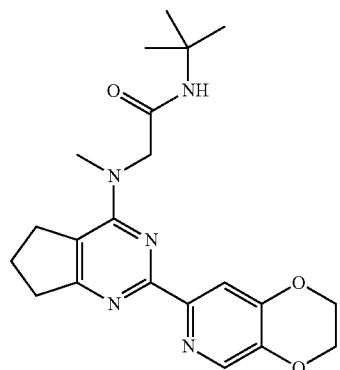

Scheme 73 depicts a synthetic route for preparing an exemplary compound.

Scheme 73

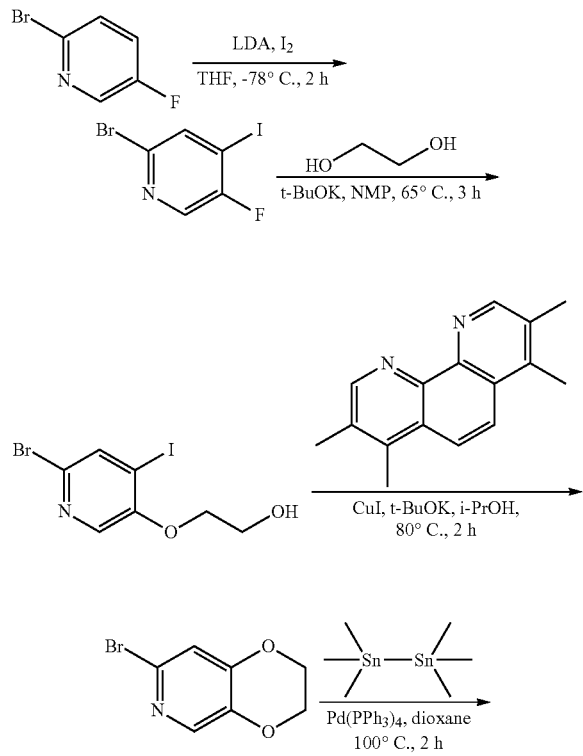

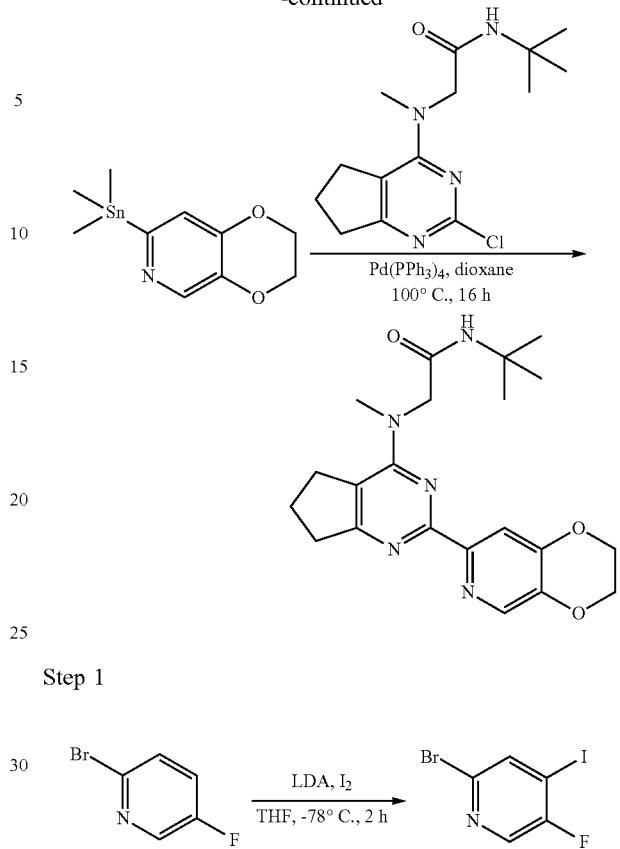

Step 1

Into a 250-mL 3-necked round-bottom flask purged and maintained in an inert atmosphere of nitrogen was placed 2-bromo-5-fluoropyridine (9.80 g, 55.68 mmol, 1.00 equiv) and THF (100 mL). This was followed by the addition of LDA (33.4 mL, 66.80 mmol, 1.20 equiv) dropwise with stirring at −78° C. The reaction solution was stirred for 0.5 hr at −78° C. To this was added a solution of iodine (14.13 g, 55.68 mmol, 1.00 equiv) in THF (20 mL) dropwise with stirring at −78° C. and stirred for 1.5 hr at −78° C. The reaction was then quenched by the addition of 100 mL of NH₄Cl (aq) and extracted with 3×50 mL of ethyl acetate. The combined organic layers were dried over anhydrous sodium sulfate, filtered, and the filtrate was concentrated under reduced pressure. The residue was purified by silica gel column with petroleum ether/THF (10/1) to give 16.0 g (95%) of 2-bromo-5-fluoro-4-iodopyridine as a white solid. LCMS (ES)[M+1]⁺ m/z: 302.

Step 2

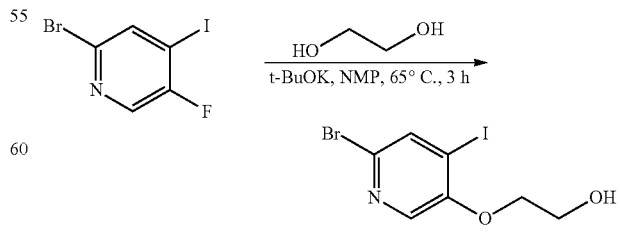

Into a 250-mL round-bottom flask was placed 2-bromo-5-fluoro-4-iodopyridine (8.0 g, 26.50 mmol, 1.00 equiv), ethylene glycol (50.0 mL), NMP (50.0 mL), and t-BuOK (5.95 g, 53.00 mmol, 2.0 equiv). The reaction was stirred for 3 h at 65° C. The mixture was cooled and diluted with 100 mL of H₂O and extracted with 3×50 mL of ethyl acetate. The combined organic layers were dried over anhydrous sodium sulfate, filtered, and the filtrate was concentrated under reduced pressure. The residue was purified by silica gel column with petroleum ether/THF (3/1) to yield 4.9 g (53.7%) of 2-[(6-bromo-4-iodopyridin-3-yl)oxy]ethanol as an off-white solid. LCMS (ES) [M+1]⁺ m/z: 344.
Step 3

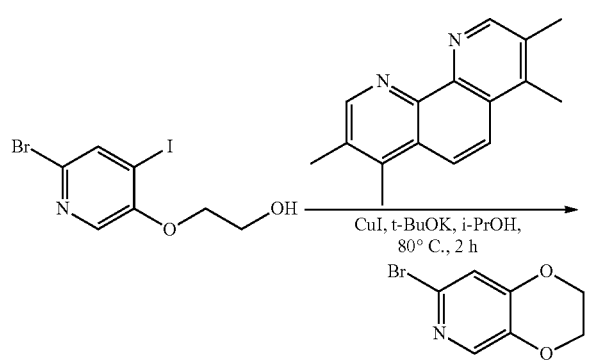

Into a 100-mL round-bottom flask purged and maintained in an inert atmosphere of nitrogen was placed 2-[(6-bromo-4-iodopyridin-3-yl)oxy]ethanol (4.90 g, 14.24 mmol, 1.00 equiv), isopropyl alcohol (50.00 mL), 3,4,7,8-tetramethyl-1,10-phenanthroline (673 mg, 2.84 mmol, 0.20 equiv), tert-butoxypotassium (3.20 g, 28.49 mmol, 2.00 equiv), and copper(I) iodide (542 mg, 2.84 mmol, 0.20 equiv). The mixture was stirred for 2 h at 80° C. After being cooled to room temperature, the reaction solution was diluted with 50 mL of H₂O and extracted with 3×50 mL of dichloromethane. The combined organic layers were dried over anhydrous sodium sulfate, filtered, and the filtrate was concentrated under reduced pressure. The residue was purified by silica gel column with petroleum ether/THF (4/1) to give 2.0 g (65%) of 7-bromo-2H,3H-[1,4]dioxino[2,3-c]pyridine as a light yellow solid. LCMS (ES) [M+1]⁺ m/z: 216.
Step 4

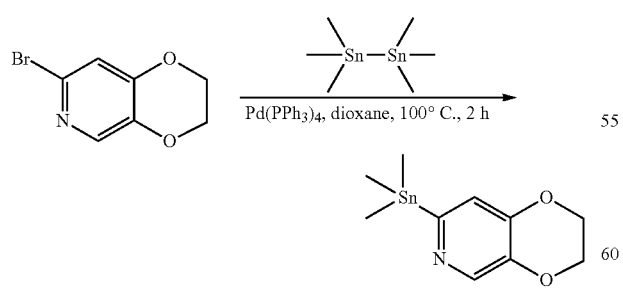

Into a 100-mL round-bottom flask purged and maintained in an inert atmosphere of nitrogen, was placed 7-bromo-2H, 3H-[1,4]dioxino[2,3-c]pyridine (500 mg, 2.31 mmol, 1.00 equiv), dioxane (8.0 mL), hexamethyldistannane (909 mg, 2.77 mmol, 1.20 equiv), and Pd(PPh₃)₄ (267 mg, 0.23 mmol, 0.10 equiv). The mixture was stirred for 2 h at 100° C. The reaction mixture was cooled and diluted with 10 mL of H₂O, and extracted with 3×10 mL of ethyl acetate. The combined organic phase was dried over anhydrous sodium sulfate, filtered, and the filtrate was concentrated under reduced pressure. 600 mg crude product of 7-(trimethylstannyl)-2H, 3H-[1,4]dioxino[2,3-c]pyridine was obtained as a brown oil and used to the next step without purification. LCMS (ES) [M+1]⁺ m/z: 302.
Step 5

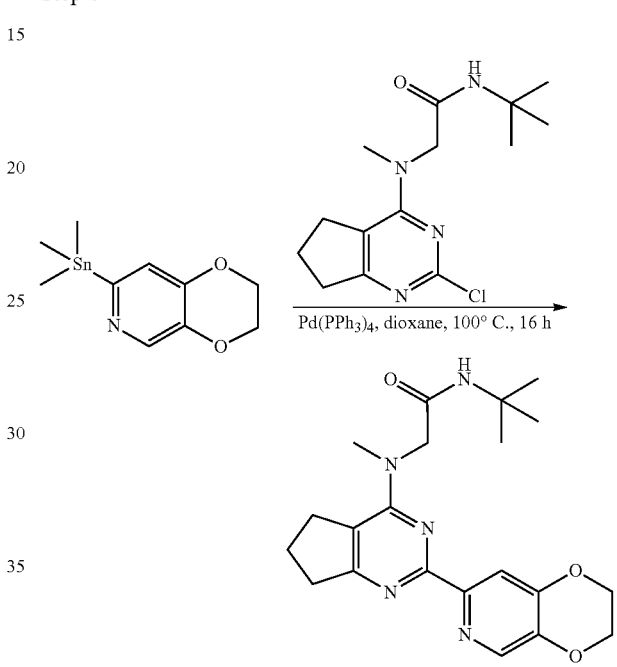

Into a 100-mL round-bottom flask purged and maintained in an inert atmosphere of nitrogen, was placed 7-(trimethylstannyl)-2H,3H-[1,4]dioxino[2,3-c]pyridine (454 mg, 1.51 mmol, 1.50 equiv), dioxane (5.0 mL), N-tert-butyl-2-([2-chloro-5H,6H,7H-cyclopenta[d]pyrimidin-4-yl](methyl)amino)acetamide (300 mg, 1.01 mmol, 1.00 equiv), and Pd(PPh₃)₄ (116 mg, 0.10 mmol, 0.10 equiv). The mixture was stirred for 16 h at 100° C. The reaction mixture was cooled and concentrated. The residue was purified by silica gel column with dichloromethane/methanol (10/1). The collected crude product was further purified by Prep-HPLC with the following conditions: Column, Atlantis HILIC OBD Column, 19*150 mm*5 um, Mobile phase, Water (0.05% NH₄OH) and CH₃CN (20% Phase B up to 45% in 15 min, hold 45% in 5 min), Detector, UV 254 nm. This resulted in 98.1 mg (24.4%) of N-tert-butyl-2-[(2-[2H,3H-[1,4]dioxino[2,3-c]pyridin-7-yl]-5H,6H,7H-cyclopenta[d]pyrimidin-4-yl)(methyl)amino]acetamide as a white solid. ¹H NMR (300 MHz, DMSO-d₆) δ 8.17 (s, 1H), 7.86 (s, 1H), 7.69 (s, 1H), 4.40-4.36 (m, 4H), 4.10 (s, 2H), 3.26 (s, 3H), 3.12 (t, J=7.5 Hz, 2H), 2.79 (t, J=7.8 Hz, 2H), 2.02-1.95 (m, 2H), 1.25 (s, 9H). LCMS (ES) [M+1]⁺ m/z: 398.2.

Example 1.126

Synthesis of (2S)—N-tert-butyl-3-hydroxy-2-{methyl[2-(pyridin-2-yl)-5H,6H,7H-cyclopenta[d]pyrimidin-4-yl]amino}propanamide (Compound 123)

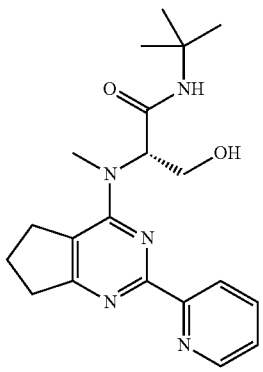 [SMILES: CN(c1nc(-c2ccccn2)nc2c1CCC2)[C@@H](CO)C(=O)NC(C)(C)C]

Scheme 74 depicts a synthetic route for preparing an exemplary compound.

Scheme 74

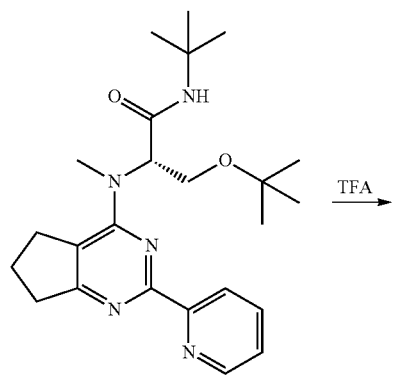

(2S)-3-(tert-butoxy)-N-tert-butyl-2-{methyl[2-(pyridin-2-yl)-5H,6H,7H-cyclopenta[d]pyrimidin-4-yl]amino}propanamide and formic acid (62.5 mg; 0.13 mmol; 1 eq.) were dissolved in dichloromethane (1 ml) and cooled in an ice bath. Trifluoroacetic acid (0.75 mL; 0.2 mol/L; 0.15 mmol; 1.13 eq.) (1 ml) was added and the reaction was stirred at 25° C. for 3.5 h. The solution was then evaporated, the residue was co-evaporated with toluene and purified by reverse phase chromatography (Waters XSelect CSH C18 column, 0-90% acetonitrile/0.1% aqueous formic acid gradient) to give (2S)—N-tert-butyl-3-hydroxy-2-{methyl[2-(pyridin-2-yl)-5H,6H,7H-cyclopenta[d]pyrimidin-4-yl]amino}propanamide (40 mg, 81%) as an off-white solid. LCMS (ES+): (M+H)$^+$=369.9. $^1$H NMR (400 MHz, DMSO-d6) δ 8.79-8.74 (m, 1H), 8.48 (d, J=7.9 Hz, 1H), 8.07-7.99 (m, 1H), 7.87 (s, 1H), 7.61 (ddd, J=7.6, 4.7, 1.2 Hz, 1H), 5.10 (t, J=7.3 Hz, 1H), 5.01 (s, 1H), 3.91-3.81 (m, 2H), 3.31-3.26 (m, 4H), 3.17-3.10 (m, 1H), 3.02-2.87 (m, 2H), 2.15-1.96 (m, 2H), 1.20 (s, 9H).

Example 1.127

Synthesis of (2R)—N-tert-butyl-3-hydroxy-2-{methyl[2-(pyridin-2-yl)-5H,6H,7H-cyclopenta[d]pyrimidin-4-yl]amino}propanamide (Compound 124)

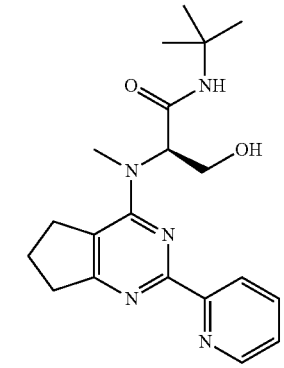 [SMILES: CN(c1nc(-c2ccccn2)nc2c1CCC2)[C@H](CO)C(=O)NC(C)(C)C]

Scheme 75 depicts a synthetic route for preparing an exemplary compound.

Scheme 75

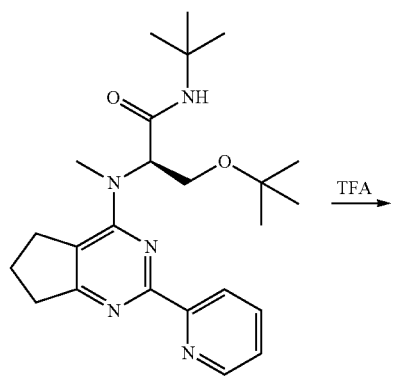

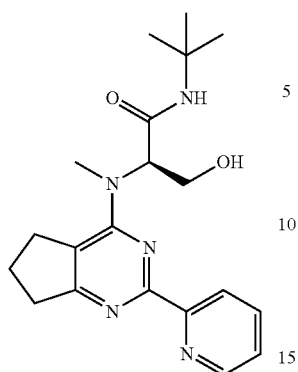

Compound 124 was synthesized similar to compound 123 by replacing (2S)-3-(tert-butoxy)-N-tert-butyl-2-{methyl[2-(pyridin-2-yl)-5H,6H,7H-cyclopenta[d]pyrimidin-4-yl]amino}propenamide with (2R)-3-(tert-butoxy)-N-tert-butyl-2-{methyl[2-(pyridin-2-yl)-5H,6H,7H-cyclopenta[d]pyrimidin-4-yl]amino}propenamide. LCMS (ES+): (M+H)+= 370.0. ¹H NMR (400 MHz, DMSO-d6) δ 8.88-8.81 (m, 1H), 8.59 (d, J=7.8 Hz, 1H), 8.19-8.12 (m, 1H), 7.89 (s, 1H), 7.76 (ddd, J=7.6, 4.8, 1.2 Hz, 1H), 5.34-5.00 (m, 2H), 3.92 (d, J=7.1 Hz, 2H), 3.45 (s, 3H), 3.36-3.34 (m, 1H), 3.23-3.16 (m, 1H), 3.08-3.01 (m, 2H), 2.20-2.02 (m, 2H), 1.22 (s, 9H).

Example 1.128

Synthesis of N-tert-butyl-2-{methyl[2-(1-methyl-1H-imidazol-4-yl)-5H,6H,7H-cyclopenta[d]pyrimidin-4-yl]amino}acetamide (Compound 125)

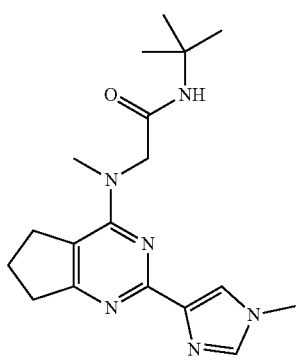 [SMILES: CN(CC(=O)NC(C)(C)C)c1nc(-c2cn(C)cn2)nc2c1CCC2]

Scheme 76 depicts a synthetic route for preparing an exemplary compound.

Scheme 76

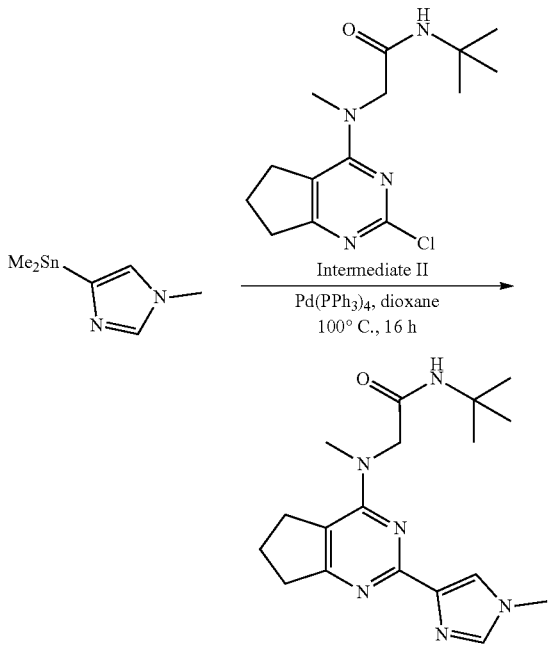

Step 1

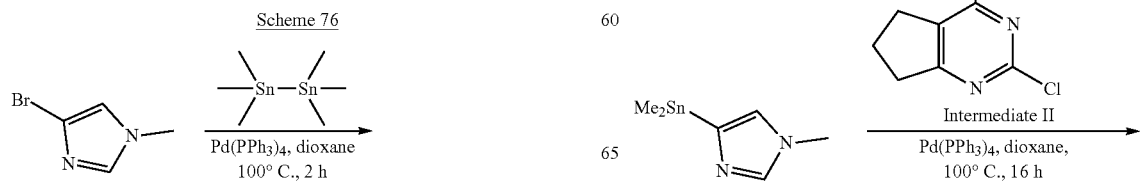

Into a 100-mL round-bottom flask purged and maintained in an inert atmosphere of nitrogen was placed 4-bromo-1-methylimidazole (500 mg, 3.10 mmol, 1.00 equiv), dioxane (8.0 mL), hexamethyldistannane (1.22 g, 3.72 mmol, 1.20 equiv), and Pd(PPh₃)₄ (358 mg, 0.31 mmol, 0.10 equiv). The mixture was stirred for 4 h at 100° C. The reaction mixture was cooled and concentrated. This resulted in 600 mg crude product of 1-methyl-4-(trimethylstannyl)imidazole as brown oil. LCMS (ES) [M+1]+ m/z: 247.

Step 2

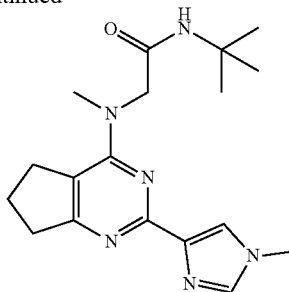

Into a 100-mL round-bottom flask purged and maintained in an inert atmosphere of nitrogen was placed N-tert-butyl-2-([2-chloro-5H,6H,7H-cyclopenta[d]pyrimidin-4-yl](methyl)amino)acetamide (300 mg, 1.01 mmol, 1.00 equiv), dioxane (5.0 mL), 1-methyl-4-(trimethylstannyl)imidazole (371 mg, 1.51 mmol, 1.50 equiv), and Pd(PPh$_3$)$_4$ (116 mg, 0.10 mmol, 0.10 equiv). The mixture was stirred for 20 h at 100° C. The reaction mixture was cooled and concentrated to remove the solvent. The residue was purified by silica gel column with dichloromethane/methanol (10/1). The product was further purified by Prep-HPLC with the following conditions: Column, Welch Xtimate C18, 21.2*250 mm, 5 um, Mobile phase, Water (10 mmol/L NH$_4$HCO$_3$) and MeOH:CH$_3$CN=1:1 (25% Phase B up to 65% in 15 min); Detector, UV 254 nm. This resulted in 47.0 mg (13.5%) of N-tert-butyl-2-[methyl[2-(1-methylimidazol-4-yl)-5H,6H,7H-cyclopenta[d]pyrimidin-4-yl]amino]acetamide as a white solid. $^1$H NMR (300 MHz, DMSO-d$_6$) δ 7.73 (d, J=1.5 Hz, 1H), 7.67-7.52 (m, 2H), 4.09 (s, 2H), 3.69 (s, 3H), 3.21 (s, 3H), 3.06 (t, J=7.5 Hz, 2H), 2.73 (t, J=7.8 Hz, 2H), 2.02-1.86 (m, 2H), 1.25 (s, 9H). LCMS (ES) [M+1]$^+$ m/z: 343.2.

Example 1.129

Synthesis of N-tert-butyl-2-{ethyl[2-(4-methoxypyridin-2-yl)-5H,6H,7H-cyclopenta[d]pyrimidin-4-yl]amino}acetamide (Compound 126)

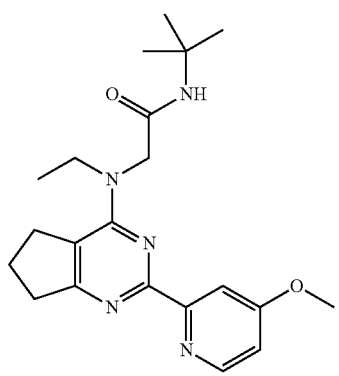 [SMILES: CCN(CC(=O)NC(C)(C)C)c1nc(-c2cc(OC)ccn2)nc2c1CCC2]

Scheme 77 depicts a synthetic route for preparing an exemplary compound.

Scheme 77

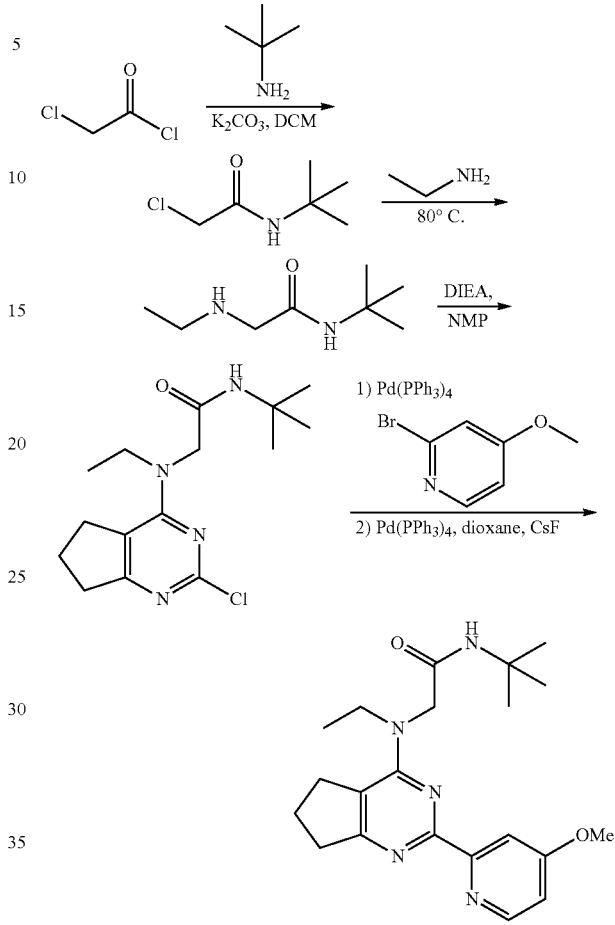

Step 1

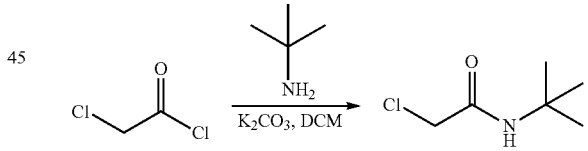

To a stirred solution of tert-butylamine (3.89 g, 53.186 mmol, 1.00 equiv) and K$_2$CO$_3$ (7.34 g, 53.126 mmol, 1.00 equiv) in DCM (120.00 mL) was added chloroacetyl chloride (6.00 g, 53.126 mmol, 1.00 equiv) dropwise at 0° C. under an air atmosphere. The resulting mixture was stirred for 16 h at room temperature under an air atmosphere. The reaction was quenched with water at room temperature. The resulting mixture was extracted with CH$_2$Cl$_2$ (2×100 mL). The combined organic layers were washed with brine (1×100 mL), dried over anhydrous Na$_2$SO$_4$, and filtered. The filtrate was concentrated under reduced pressure to afford N-tert-butyl-2-chloroacetamide (4 g, 50.32%) as a yellow solid. LCMS (ES) [M+1]$^+$ m/z: 150.

Step 2

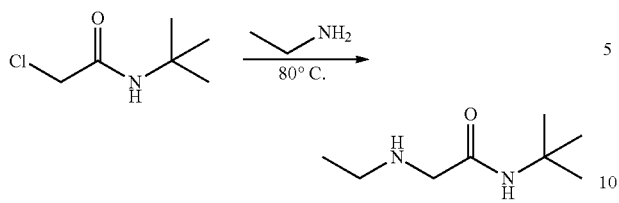

A solution of N-tert-butyl-2-chloroacetamide (4.00 g, 26.734 mmol, 1.00 equiv) and ethylamine in EtOH (80 mL) was stirred for 16 h at 80° C. under an air atmosphere. The resulting mixture was concentrated under reduced pressure. The resulting mixture was diluted with water (50 mL) and extracted with DCM:MeOH=10:1 (3×100 mL). The combined organic layers were washed with brine (1×100 mL), dried over anhydrous Na$_2$SO$_4$, and filtered. The filtrate was concentrated under reduced pressure to yield N-tert-butyl-2-(ethylamino)acetamide (3.3 g, 78.00%) as a yellow solid. LCMS (ES) [M+1]$^+$ m/z: 159.

Step 3

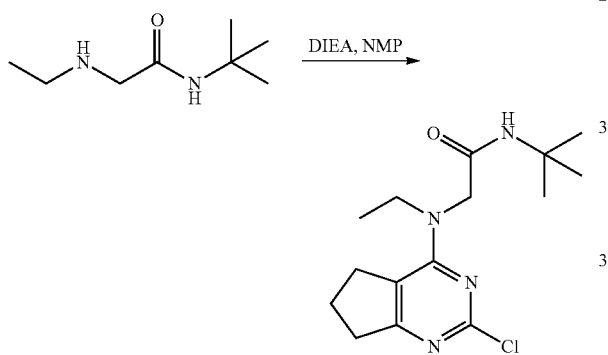

A solution of 2,4-dichloro-5H,6H,7H-cyclopenta[d]pyrimidine (3.00 g, 15.870 mmol, 1.00 equiv), DIEA (6.15 g, 47.609 mmol, 3 equiv) and N-tert-butyl-2-(ethylamino)acetamide (3.01 g, 19.044 mmol, 1.20 equiv) in NMP (30.00 mL, 311.103 mmol, 19.60 equiv) was stirred for 2 h at 60° C. under an air atmosphere. The mixture was cooled to room temperature. The resulting mixture was extracted with EtOAc (3×100 mL). The combined organic layers were washed with brine (1×100 mL), dried over anhydrous Na$_2$SO$_4$, and filtered. The filtrate was concentrated under reduced pressure. The residue was purified by silica gel column chromatography eluting with PE/EtOAc (1:1) to yield N-tert-butyl-2-([2-chloro-5H,6H,7H-cyclopenta[d]pyrimidin-4-yl](ethyl)amino)acetamide (2.2 g, 44.60%) as a white solid. LCMS (ES) [M+1]$^+$ m/z: 311.

Step 4

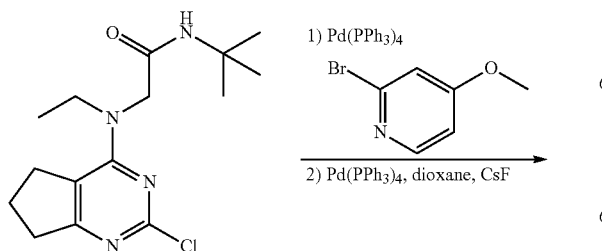

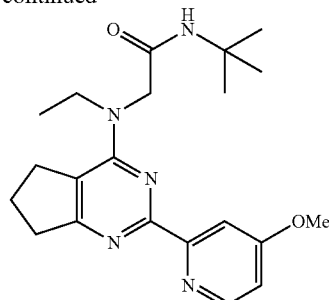

To a solution of 2-bromo-4-methoxypyridine (453.68 mg, 2.413 mmol, 1.5 equiv) and 2-tert-butyl-1,1,1-trimethyldistannane (906.82 mg, 2.654 mmol, 1.65 equiv) in dioxane (2.00 mL) were added Pd(PPh$_3$)$_4$ (186 mg, 0.161 mmol, 0.1 equiv). After being stirred for 2 h at 100° C. under a nitrogen atmosphere, the mixture was cooled to room temperature. To the above mixture was added N-tert-butyl-2-([2-chloro-5H,6H,7H-cyclopenta[d]pyrimidin-4-yl](ethyl)amino)acetamide (500.00 mg, 1.609 mmol, 1.00 equiv), CsF (488.70 mg, 3.217 mmol, 2.00 equiv), and Pd(PPh$_3$)$_4$ (186 mg, 0.161 mmol, 0.1 equiv) at room temperature. The resulting mixture was stirred for an additional 16 h at 100° C. under a nitrogen atmosphere. The resulting mixture was cooled and concentrated under reduced pressure. The residue was purified by silica gel column chromatography eluting with PE/THF (1:1) to afford N-tert-butyl-2-[ethyl[2-(4-methoxypyridin-2-yl)-5H,6H,7H-cyclopenta[d]pyrimidin-4-yl]amino]acetamide (89 mg, 13%) as a yellow solid. $^1$H NMR (300 MHz, DMSO-d$_6$) δ 8.49 (d, J=5.6 Hz, 1H), 7.87 (d, J=2.6 Hz, 1H), 7.68 (s, 1H), 7.16-6.82 (m, 1H), 4.09 (s, 2H), 3.90 (s, 3H), 3.65 (q, J=7.0 Hz, 2H), 3.08 (t, J=7.2 Hz, 2H), 2.82 (t, J=7.8 Hz, 2H), 2.23-1.92 (m, 2H), 1.23 (s, 9H), 3.65 (t, J=7.0 Hz, 3H). LCMS (ES) [M+1]$^+$ m/z: 384.1.

Example 1.130

Synthesis of N-(6-fluoropyridin-3-yl)-2-{methyl[2-(pyridin-2-yl)-5H,6H,7H-cyclopenta[d]pyrimidin-4-yl]amino}acetamide (Compound 127)

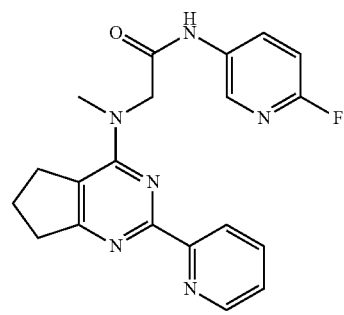 [SMILES: CN(CC(=O)Nc1ccc(F)nc1)c1nc(-c2ccccn2)nc2c1CCC2]

Scheme 78 depicts a synthetic route for preparing an exemplary compound.

Scheme 78

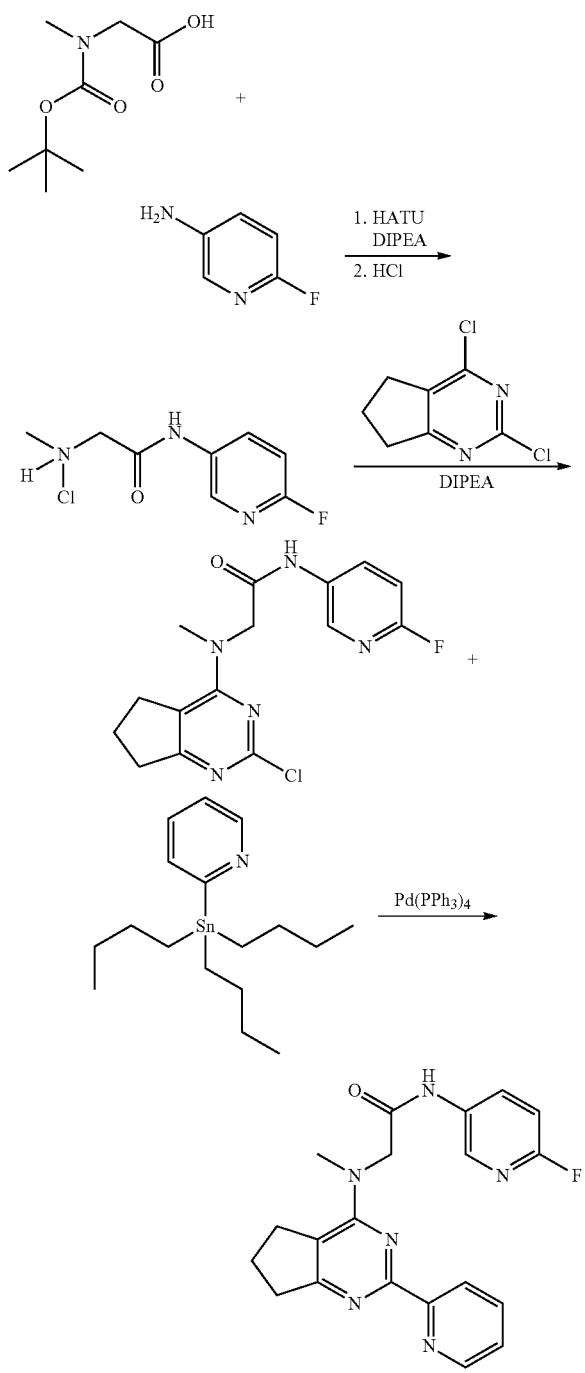

Step 1

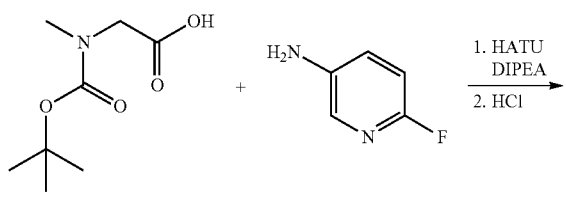

-continued

To a solution of [(tert-butoxycarbonyl)(methyl)amino]acetic acid (2.00 g; 10.57 mmol; 1.00 eq.) in DMF (15 mL) was added 6-fluoro-3-pyridinylamine (1.18 g; 10.57 mmol; 1.00 eq.) followed by Hunig's base (2.77 mL; 0.02 mol; 1.50 eq.) and HATU (4.02 g; 0.01 mol; 1.00 eq.). After being stirred for 15 h at room temperature, it was extracted with EtOAc. The organic layers were combined, dried, and concentrated to give tert-butyl (2-((6-fluoropyridin-3-yl)amino)-2-oxoethyl)(methyl)carbamate as a crude product (5.6 g). The crude product was diluted with DCM (10 mL), to which 4N HCl in dioxane (10 mL) was added. After completion, the mixture was concentrated and diluted with Sat. NaHCO$_3$. The aqueous layer was extracted with EtOAc, the organic layers were combined, dried, and concentrated to give 2-[chloro(methyl)amino]-N-(6-fluoropyridin-3-yl)acetamide (2.5 g). LCMS (ES) [M+1]$^+$ m/z: 184.

Step 2

To a solution of 2,4-dichloro-6,7-dihydro-5H-cyclopenta[d]pyrimidine (1.00 g; 5.29 mmol; 1.00 eq.) in AcCN (15 mL) was added triethylamine (1.48 mL; 10.58 mmol; 2.00 eq.) and 2-[chloro(methyl)amino]-N-(6-fluoropyridin-3-yl)acetamide (1.74 g; 7.93 mmol; 1.50 eq.). After being heated at 80° C. for 15 h, it was concentrated and diluted with Sat. NaHCO$_3$, and extracted with EtOAc. The organic layers were combined, washed with brine, dried, and concentrated to give the crude product, which was purified by column chromatography (0 to 100% EtOAc) to give 2-({2-chloro-5H,6H,7H-cyclopenta[d]pyrimidin-4-yl}(methyl)amino)-N-(6-fluoropyridin-3-yl)acetamide (1.78 g). LCMS (ES) [M+1]$^+$ m/z: 336.0.

Step 3

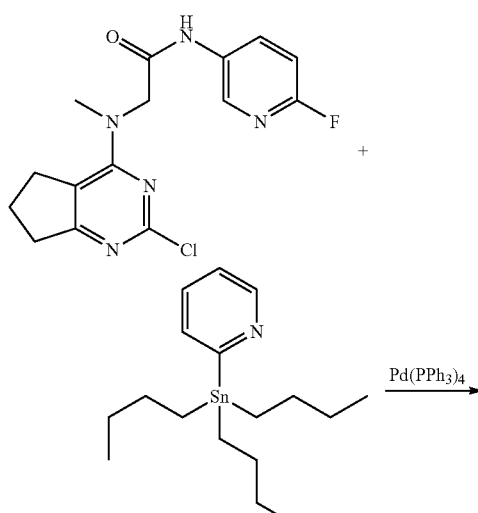

To a solution of 2-({2-chloro-5H,6H,7H-cyclopenta[d]pyrimidin-4-yl}(methyl)amino)-N-(6-fluoropyridin-3-yl)acetamide (95.00 mg; 0.28 mmol; 1.00 eq.) in Toluene (2 mL) was added 2-(tributylstannyl)pyridine (156.24 mg; 0.42 mmol; 1.50 eq.) and tetrakis(triphenylphosphane) palladium (32.70 mg; 0.03 mmol; 0.10 eq.). After being heated at 105° C. overnight, HPLC indicated starting material left. The mixture was concentrated and was added DMF (1 mL), additional tetrakis(triphenylphosphane) palladium (32.70 mg; 0.03 mmol; 0.10 eq.), and 2-(tributylstannyl)pyridine (156.24 mg; 0.42 mmol; 1.50 eq.). The mixture was heated for 5 h at 105° C. It was diluted with water and subjected to purification by prep HPLC to give N-tert-butyl-2-{ethyl[2-(4-methoxypyridin-2-yl)-5H,6H,7H-cyclopenta[d]pyrimidin-4-yl]amino}acetamide (28.7 mg). $^1$H NMR (400 MHz, DMSO-$d_6$) δ 10.83 (s, 1H), 8.81 (d, J=4.9 Hz, 1H), 8.47-8.40 (m, 2H), 8.19-8.10 (m, 1H), 8.05 (t, J=7.5 Hz, 1H), 7.71 (dd, J=7.7, 4.8 Hz, 1H), 7.15 (dd, J=8.8, 3.2 Hz, 1H), 4.69 (s, 2H), 3.54 (s, 3H), 3.04 (t, J=7.9 Hz, 2H), 2.49 (m, 2H), 2.16-2.03 (m, 2H). LCMS (ES) [M+1]$^+$ m/z: 379.1.

Example 1.131

Synthesis of N-(6-fluoropyridin-3-yl)-2-{[2-(4-methoxypyridin-2-yl)-5H,6H,7H-cyclopenta[d]pyrimidin-4-yl](methyl)amino}acetamide (Compound 128)

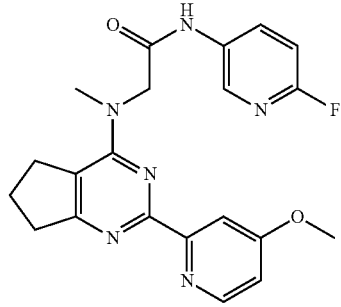 [SMILES: COc1ccnc(-c2nc3c(c(N(C)CC(=O)Nc4ccc(F)nc4)n2)CCC3)c1]

Scheme 79 depicts a synthetic route for preparing an exemplary compound.

Scheme 79

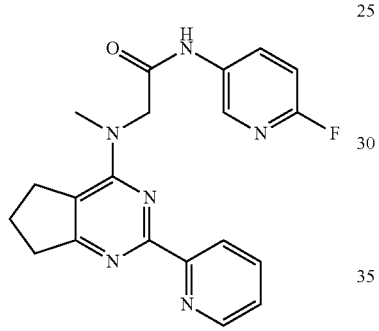

To a solution of 2-({2-chloro-5H,6H,7H-cyclopenta[d]pyrimidin-4-yl}(methyl)amino)-N-(6-fluoropyridin-3-yl)acetamide (95.00 mg; 0.28 mmol; 1.00 eq.) in DMF (1 mL) was added 4-methoxy-2-(tributylstannyl)pyridine (168.99 mg; 0.42 mmol; 1.50 eq.) and tetrakis(triphenylphosphane) palladium (32.70 mg; 0.03 mmol; 0.10 eq.). After being heated at 110° C. overnight, the mixture was cooled to room temperature and diluted with water and AcCN, and subjected to purification by preparative HPLC to give N-(6-fluoropyridin-3-yl)-2-{[2-(4-methoxypyridin-2-yl)-5H,6H,7H-cyclopenta[d]pyrimidin-4-yl](methyl)amino}acetamide (25.9 mg). $^1$H NMR (400 MHz, DMSO-d$_6$) δ 10.56 (s, 1H), 8.45 (d, J=5.7 Hz, 1H), 8.39 (d, J=3.3 Hz, 1H), 8.12 (td, J=8.4, 7.9, 2.7 Hz, 1H), 7.77 (d, J=2.6 Hz, 1H), 7.13 (dt, J=8.8, 3.5 Hz, 1H), 7.05 (dd, J=5.7, 2.6 Hz, 1H), 4.44 (s, 2H), 3.79 (s, 3H), 3.21 (t, J=7.4 Hz, 2H), 3.11 (t, J=7.3 Hz, 1H), 2.85 (t, J=7.9 Hz, 3H), 2.72 (t, J=7.9 Hz, 1H), 2.04 (d, J=11.3 Hz, 2H). LCMS (ES) [M+1]$^+$ m/z: 409.2.

Example 1.132

Synthesis of N-(6-fluoropyridin-3-yl)-2-{methyl[2-(1-methyl-1H-imidazol-4-yl)-5H,6H,7H-cyclopenta[d]pyrimidin-4-yl]amino}acetamide (Compound 129)

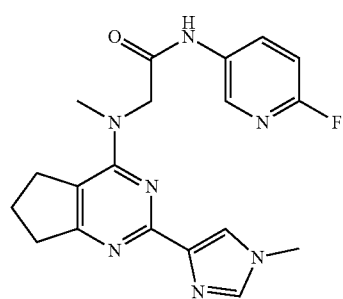 [SMILES: CN(CC(=O)Nc1ccc(F)nc1)c1nc(-c2cn(C)cn2)nc2c1CCC2]

Scheme 80 depicts a synthetic route for preparing an exemplary compound.

Scheme 80

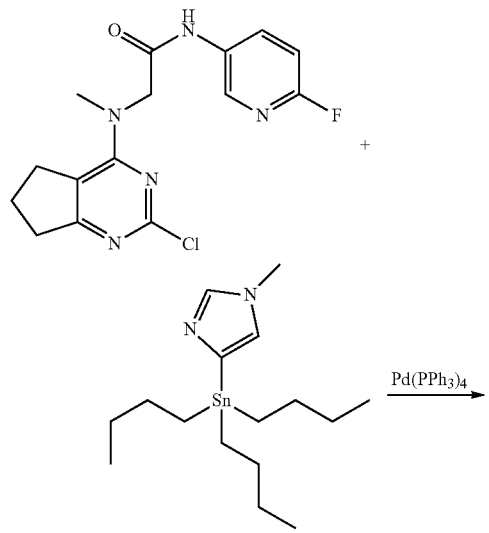

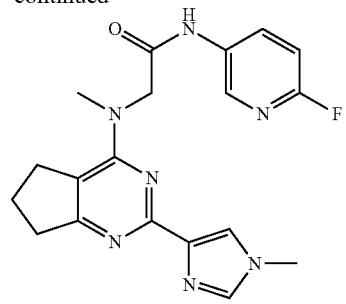

To a solution of 2-({2-chloro-5H,6H,7H-cyclopenta[d]pyrimidin-4-yl}(methyl)amino)-N-(6-fluoropyridin-3-yl)acetamide (95.00 mg; 0.28 mmol; 1.00 eq.) in DMF (1 mL) was added 1-methyl-4-(tributylstannyl)-1H-imidazole (157.52 mg; 0.42 mmol; 1.50 eq.) and tetrakis(triphenylphosphane) palladium (32.70 mg; 0.03 mmol; 0.10 eq.). After being heated at 110° C. overnight, the mixture was cooled to room temperature and diluted with water and AcCN. The mixture was subjected to purification by preparative HPLC to give N-(6-fluoropyridin-3-yl)-2-{methyl[2-(1-methyl-1H-imidazol-4-yl)-5H,6H,7H-cyclopenta[d]pyrimidin-4-yl]amino}acetamide. $^1$H NMR (400 MHz, DMSO-d$_6$) δ 10.86 (s, 1H), 10.76 (s, 1H), 8.47 (s, 1H), 8.30 (s, 1H), 8.18 (s, 2H), 7.16 (dd, J=8.8, 3.2 Hz, 1H), 4.62 (d, J=4.0 Hz, 2H), 3.75 (s, 4H), 3.19 (s, 1H), 2.91 (t, J=7.9 Hz, 2H), 2.78 (s, 1H), 2.09-1.97 (m, 2H). LCMS (ES) [M+1]$^+$ m/z: 382.2.

Example 1.133

Synthesis of (3R)-3-{methyl[2-(pyridin-2-yl)-5H,6H,7H-cyclopenta[d]pyrimidin-4-yl]amino}-1-phenylpyrrolidin-2-one (Compound 130)

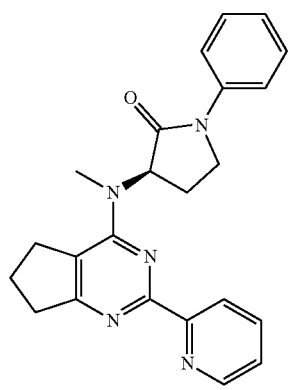 [SMILES: CN(c1nc(-c2ccccn2)nc2c1CCC2)[C@@H]1CCN(c2ccccc2)C1=O]

Scheme 81 depicts a synthetic route for preparing an exemplary compound.

Scheme 81
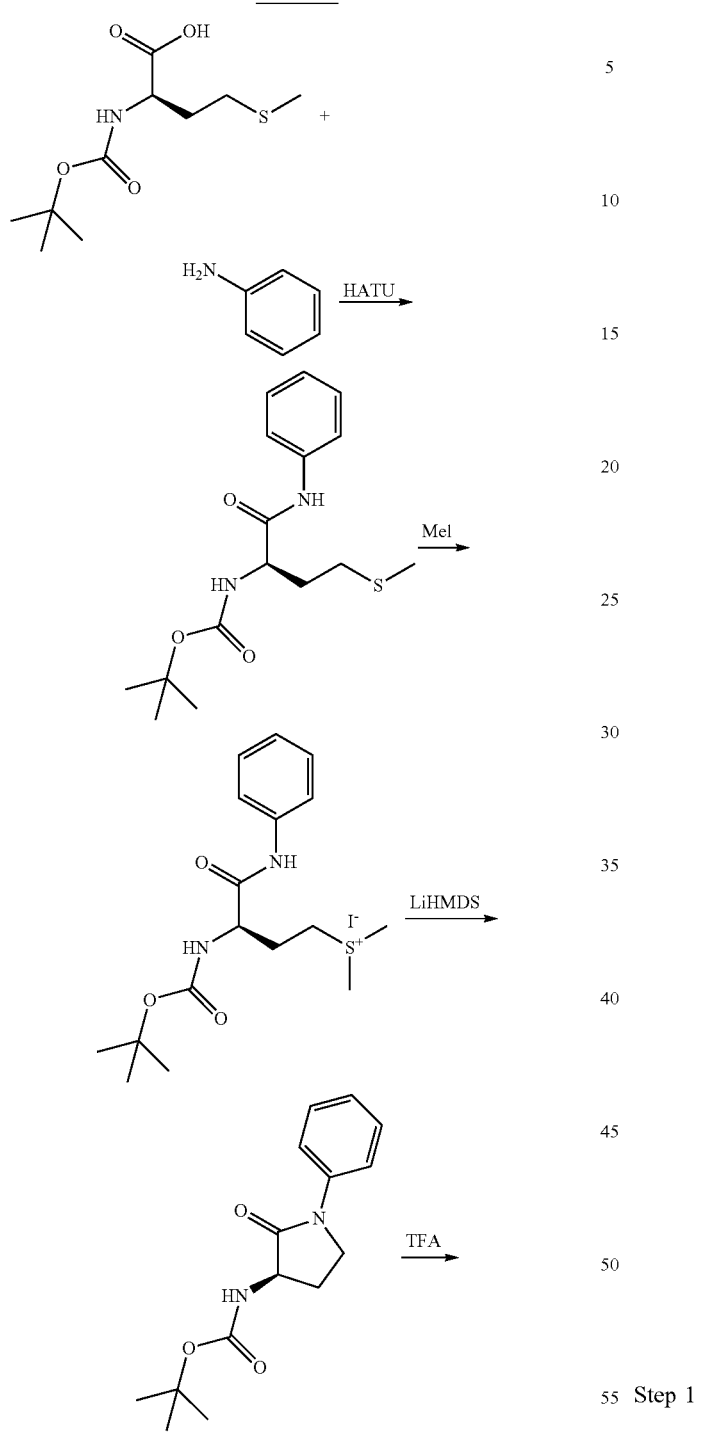
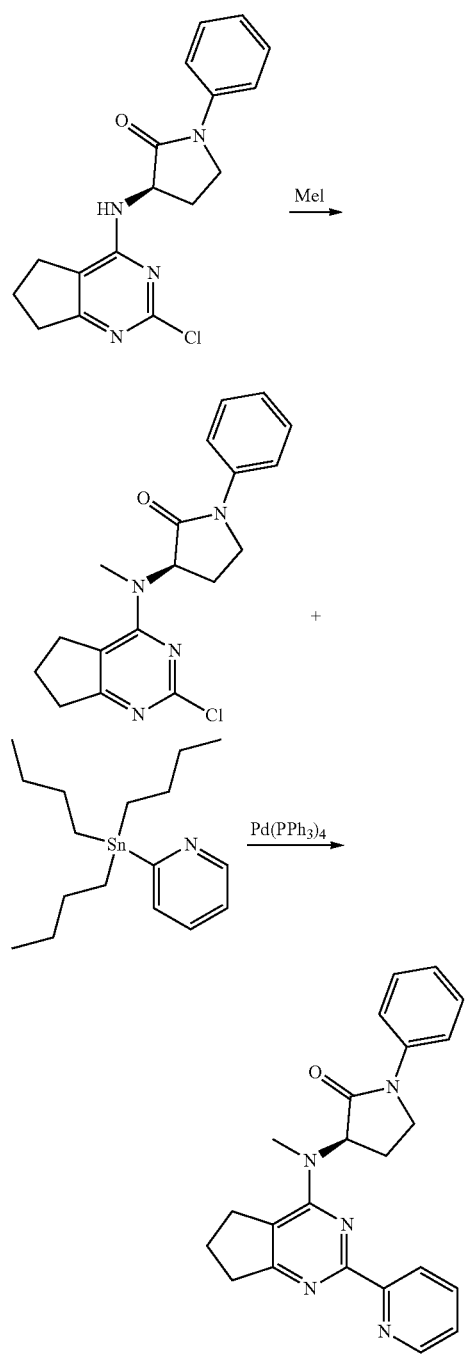
Step 1
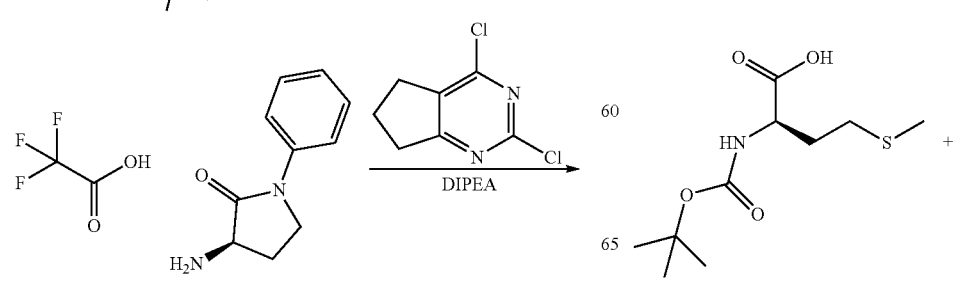

-continued

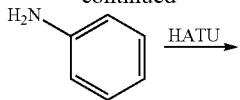
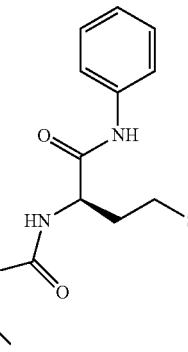

(2R)-2-[(tert-butoxycarbonyl)amino]-4-(methylsulfanyl) butanoic acid (0.50 g; 2.01 mmol; 1.00 eq.) was dissolved in DCM (20 ml). The mixture was cooled in an ice water bath and HATU (0.84 g; 2.21 mmol; 1.10 eq.), Hunig's base (0.73 mL; 4.21 mmol; 2.10 eq.) and aniline (0.20 mL; 2.21 mmol; 1.10 eq.) were added. After being stirred at 0° C. to r.t for 15 h, the mixture was diluted with water and extracted with EtOAc. The combined organic phase was washed with brine, dried, and concentrated. The residue was purified by column chromatography (Hexanes/EtOAc=3:1) to give tert-butyl N-[(1R)-3-(methylsulfanyl)-1-(phenylcarbamoyl)propyl] carbamate (0.58 g, 89%) as a solid. LCMS (ES+): (M+Na)+= 347.1.

Step 2

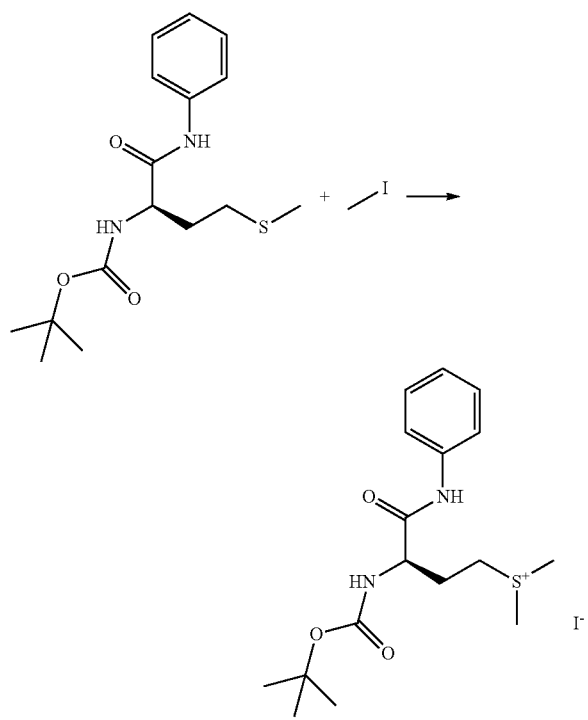

Tert-butyl N-[(1R)-3-(methylsulfanyl)-1-(phenylcarbamoyl)propyl]carbamate (0.58 g; 1.78 mmol; 1 eq.) was dissolved in iodomethane (2.66 mL; 43 mmol; 24 eq.) and the solution was stirred at 25° C. After 19 h, the residue was dried under vacuum and used directly in the next step. LCMS (ES+): (M+H)+=338.8.

Step 3

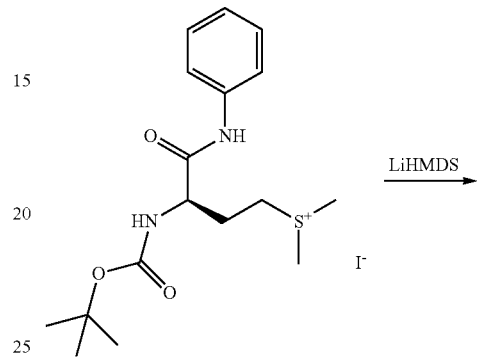
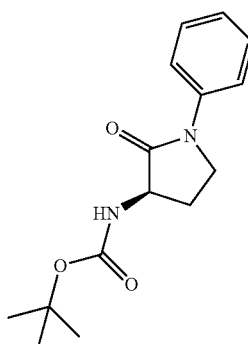

Tert-butyl N-[(1R)-3-(dimethylsulfaniumyl)-1-(phenylcarbamoyl)propyl]carbamate iodide (0.83 g; 1.78 mmol; 1 eq.) was suspended in tetrahydrofuran (35 ml) and cooled in an ice bath. Lithium bis(trimethylsilyl)azanide (1.78 mL; 1 mol/L; 1.78 mmol; 1 eq.) was added dropwise slowly. After stirring at 0° C. for 3 h, ammonium chloride solution (10 ml) was added slowly. The solvent was evaporated and the remainder was taken up in dichloromethane (100 ml) and sodium bicarbonate solution (50 ml). The phases were separated, the aqueous phase was extracted with dichloromethane (2×50 ml), and the combined organic phases were dried over sodium sulfate. After evaporation, the residue was purified by silica gel chromatography (ethyl acetate/hexanes gradient) to give tert-butyl N-[(3R)-2-oxo-1-phenylpyrrolidin-3-yl]carbamate (0.41 g, 82%) as a white solid. MS (ES+): (M+Na)+=299.0. $^1$H NMR (400 MHz, Chloroform-d) δ 7.67-7.60 (m, 2H), 7.42-7.34 (m, 2H), 7.21-7.14 (m, 1H), 5.28-5.17 (m, 1H), 4.41-4.27 (m, 1H), 3.85-3.76 (m, 2H), 2.85-2.74 (m, 1H), 2.06-1.93 (m, 1H), 1.47 (s, 9H).

Step 4

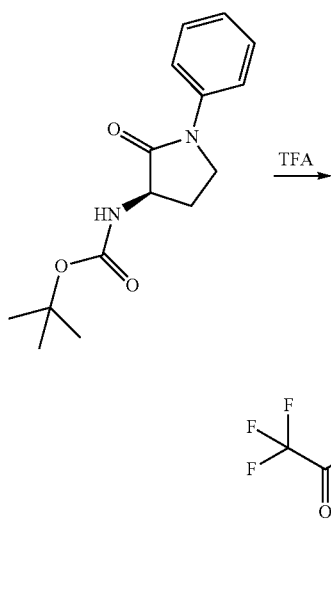

Tert-butyl N-[(3R)-2-oxo-1-phenylpyrrolidin-3-yl]carbamate (0.41 g; 1.48 mmol; 1 eq.) was dissolved in dichloromethane (5 ml) and cooled in an ice bath. Trifluoroacetic acid (2.5 mL) was added slowly and the reaction was stirred at 25° C. After 1.5 h. the reaction was evaporated, the residue was co-evaporated with toluene and then dried under high vacuum to give (3R)-3-amino-1-phenylpyrrolidin-2-one; trifluoroacetic acid.

Step 5

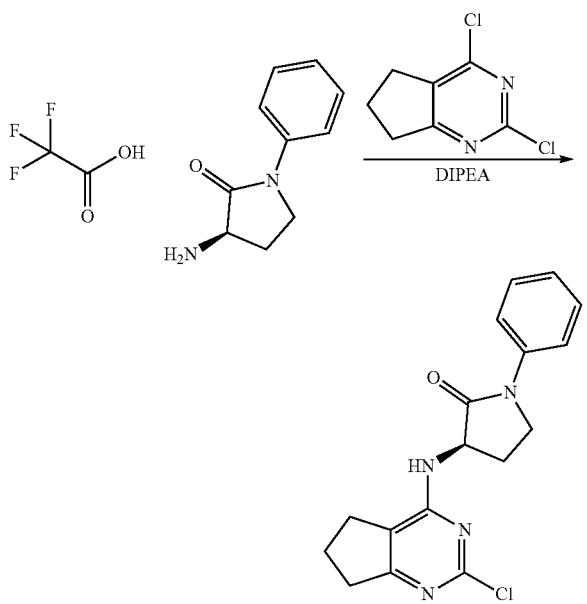

2,4-dichloro-6,7-dihydro-5H-cyclopenta[d]pyrimidine (0.25 g; 1.32 mmol; 1.00 eq.) was dissolved in acetonitrile (4.5 ml, dry), and to the solution was added (3R)-3-amino-1-phenylpyrrolidin-2-one; trifluoroacetic acid (0.42 g; 1.45 mmol; 1.10 eq.) and Hunig's base (1.15 mL; 6.61 mmol; 5.00 eq.) (dry). After being stirred at ~70° C. for 20 h, the mixture was cooled and the solvent was evaporated, the residue was purified by column chromatography (Hexanes/EtOAc=1:1) to give (3R)-3-({2-chloro-5H,6H,7H-cyclopenta[d]pyrimidin-4-yl}amino)-1-phenylpyrrolidin-2-one (170 mg, 39%). LCMS (ES+): (M+H)⁺=342.9.

Step 6

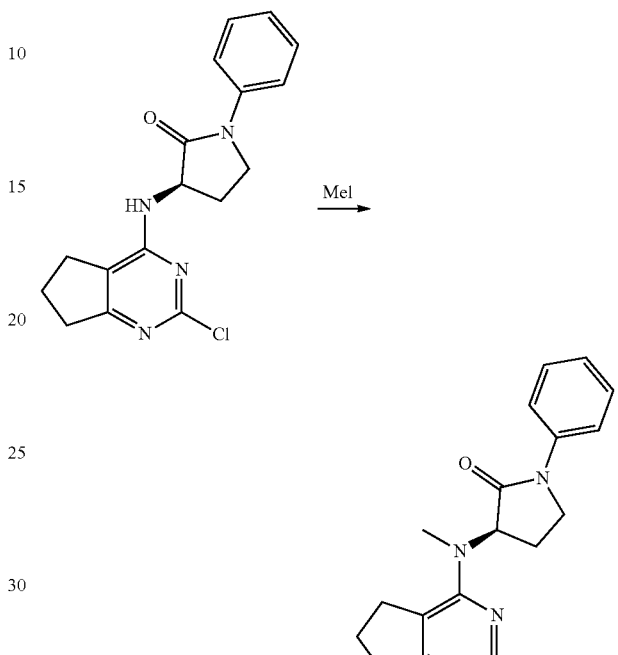

(3R)-3-({2-chloro-5H,6H,7H-cyclopenta[d]pyrimidin-4-yl}amino)-1-phenylpyrroiid-2-one (170.00 mg; 0.52 mmol; 1.00 eq.) was dissolved in DMF (3 ml) and cooled in an ice bath. Sodium hydride (62.04 mg; 1.55 mmol; 3.00 eq.) was added and the mixture was stirred in an ice bath for 30 min before iodomethane (96.56 µL; 1.55 mmol; 3.00 eq.) was added. After being stirred at room temperature for 1.5 h, the mixture was diluted with water and extracted with EtOAc. The combined organic phase was washed with brine, dried, and concentrated. The residue was purified by column chromatography (Hexanes/EtOAc=1:1) to give (3R)-3-({2-chloro-5H,6H,7H-cyclopenta[d]pyrimidin-4-yl}(methyl)amino)-1-phenylpyrrolidin-2-one (161 mg, 91%). LCMS (ES+): (M+H)⁺=342.9.

Step 7

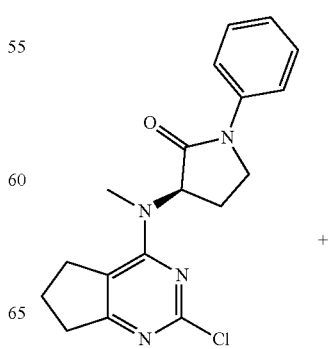

+

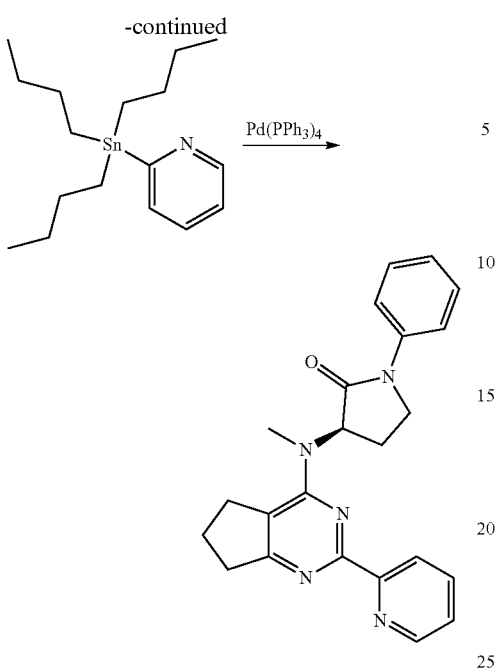

(3R)-3-({2-chloro-5H,6H,7H-cyclopenta[d]pyrimidin-4-yl}(methyl)amino)-1-phenylpyrrolidin-2-one (100.00 mg; 0.29 mmol; 1.00 eq.) was dissolved in 1,4-dioxane (2.4 ml) and purged with Ar gas. 2-(tributylstannyl)pyridine (0.19 mL; 0.58 mmol; 2.00 eq.) and tetrakis(triphenylphosphane)palladium (33.71 mg; 0.03 mmol; 0.10 eq.) were added and the mixture was stirred in a heat bath at 108° C. for 20 h. The solvent was evaporated, the residue taken up in acetonitrile, filtered, and purified by reverse phase chromatography (Waters XSelect CSH C18 column, 0-70% acetonitrile/0.1% aqueous formic acid gradient) to give (3R)-3-{methyl[2-(pyridin-2-yl)-5H,6H,7H-cyclopenta[d]pyrimidin-4-yl]amino}-1-phenylpyrrolidin-2-one (64 mg, 57%) as a white solid. LCMS (ES+): (M+H)$^+$=386.0. $^1$H NMR (400 MHz, DMSO-d6) δ 8.57 (dd, J=4.8, 1.8 Hz, 1H), 8.17 (d, J=7.9 Hz, 1H), 7.75-7.68 (m, 2H), 7.67-7.58 (m, 1H), 7.43-7.34 (m, 3H), 7.20-7.12 (m, 1H), 5.46-5.25 (m, 1H), 4.00-3.82 (m, 2H), 3.27-3.22 (m, 5H), 2.86 (dd, J=8.7, 7.0 Hz, 2H), 2.45-2.30 (m, 2H), 2.07-1.97 (m, 2H).

Example 1.134

Synthesis of (3S)-3-{methyl[2-(pyridin-2-yl)-5H,6H,7H-cyclopenta[d]pyrimidin-4-yl]amino}-1-phenylpyrrolidin-2-one (Compound 131)

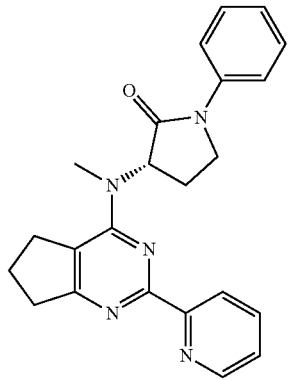 [SMILES: CN(c1nc(-c2ccccn2)nc2c1CCC2)[C@H]1CCN(c2ccccc2)C1=O]

Compound 131 was synthesized similar to compound 130 by replacing (2R)-2-[(tert-butoxycarbonyl)amino]-4-(methylsulfanyl)butanoic acid with (2S)-2-[(tert-butoxycarbonyl)amino]-4-(methylsulfanyl)butanoic acid. LCMS (ES+): (M+H)$^+$=386.0. $^1$H NMR (400 MHz, DMSO-d6) δ 8.57 (dd, J=4.9, 1.8 Hz, 1H), 8.17 (d, J=7.9 Hz, 1H), 7.74-7.68 (m, 2H), 7.66-7.57 (m, 1H), 7.43-7.33 (m, 3H), 7.19-7.12 (m, 1H), 5.44-5.26 (m, 1H), 3.92 (dtd, J=18.6, 9.5, 7.4 Hz, 2H), 3.26-3.21 (m, 5H), 2.86 (dd, J=8.7, 7.0 Hz, 2H), 2.47-2.29 (m, 2H), 2.08-1.98 (m, 2H).

Example 1.135

Synthesis of (3R)-3-{[2-(4-methoxypyridin-2-yl)-5H,6H,7H-cyclopenta[d]pyrimidin-4-yl](methyl)amino}-1-phenylpyrrolidin-2-one (Compound 132)

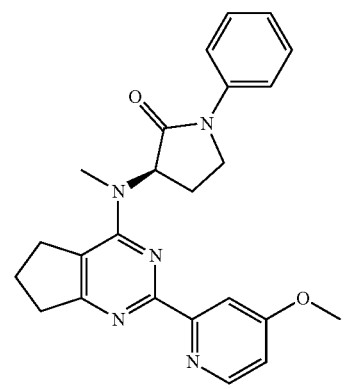 [SMILES: COc1ccnc(-c2nc3c(c(N(C)[C@@H]4CCN(c5ccccc5)C4=O)n2)CCC3)c1]

Scheme 82 depicts a synthetic route for preparing an exemplary compound.

Scheme 82

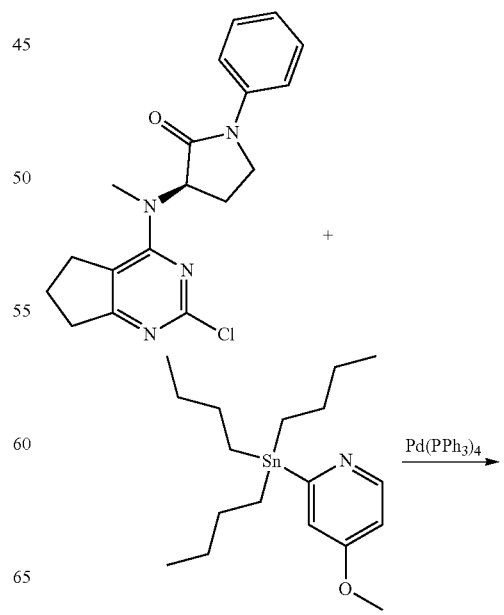

-continued

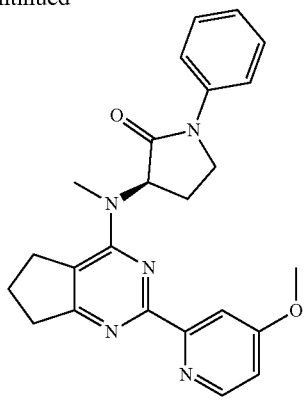

(3R)-3-({2-chloro-5H,6H,7H-cyclopenta[d]pyrimidin-4-yl}(methyl)amino)-1-phenylpyrrolidin-2-one (60 mg; 0.18 mmol; 1 eq.) was dissolved in 1,4-dioxane (2 ml) and purged with Ar gas. 4-Methoxy-2-(tributylstannyl)pyridine (0.14 g; 0.35 mmol; 2 eq.) and then tetrakis(triphenylphosphane) palladium (20 mg; 0.02 mmol; 0.1 eq.) were added and the mixture was stirred in a heat bath at 108° C. for 20 h. The solvent was evaporated, the residue taken up in acetonitrile, filtered, and purified by reverse phase chromatography (Waters XSelect CSH C18 column, 0-70% acetonitrile/0.1% aqueous formic acid gradient) to give (3R)-3-{[2-(4-methoxypyridin-2-yl)-5H,6H,7H-cyclopenta[d]pyrimidin-4-yl](methyl)amino}-1-phenylpyrrolidin-2-one (25 mg, 35%) as a white solid. LCMS (ES+): (M+H)⁺=415.9. $^1$H NMR (400 MHz, DMSO-d6) δ 8.37 (d, J=5.6 Hz, 1H), 7.72 (d, J=2.6 Hz, 1H), 7.71-7.65 (m, 2H), 7.41-7.33 (m, 2H), 7.18-7.11 (m, 1H), 6.97 (dd, J=5.6, 2.6 Hz, 1H), 5.40 (s, 1H), 3.92 (dtd, J=16.7, 9.4, 7.3 Hz, 2H), 3.78 (s, 3H), 3.24-3.19 (m, 5H), 2.84 (td, J=7.5, 1.6 Hz, 2H), 2.48-2.29 (m, 2H), 2.06-1.97 (m, 2H).

Example 1.136

Synthesis of N-(2-hydroxyethyl)-2-{[2-(4-methoxypyridin-2-yl)-5H,6H,7H-cyclopenta[d]pyrimidin-4-yl](methyl)amino}acetamide (Compound 133)

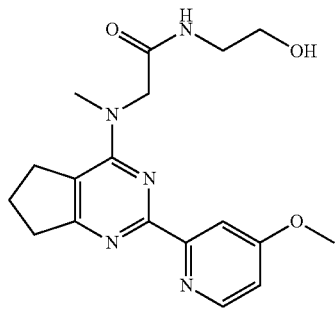 [SMILES: COc1ccnc(-c2nc3c(c(N(C)CC(=O)NCCO)n2)CCC3)c1]

Scheme 83 depicts a synthetic route for preparing an exemplary compound.

Scheme 83

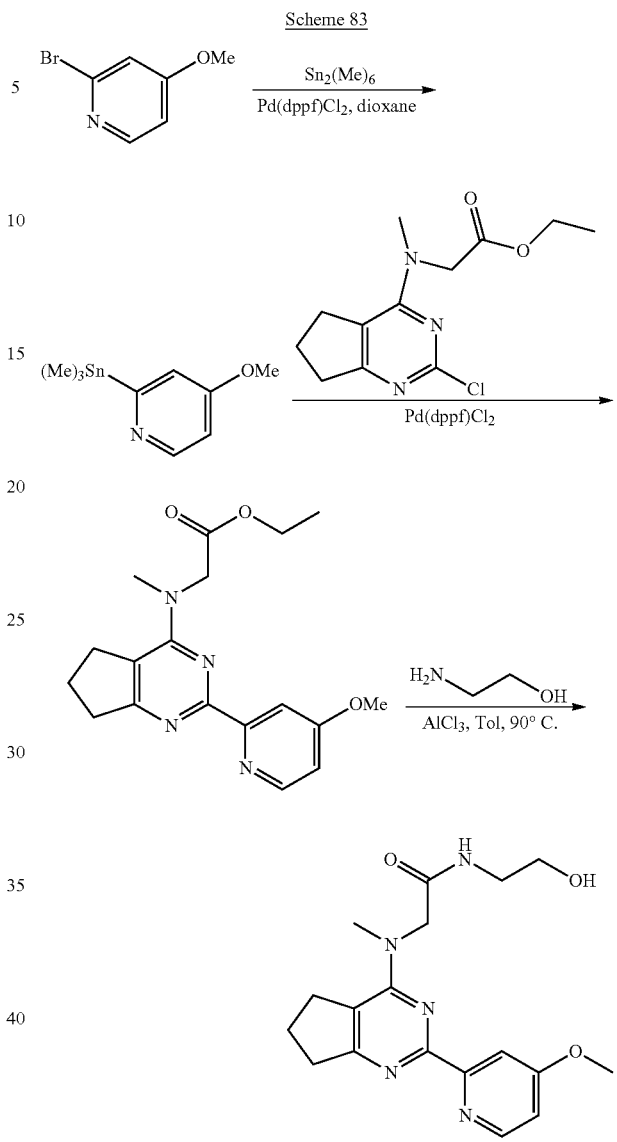

Step 1

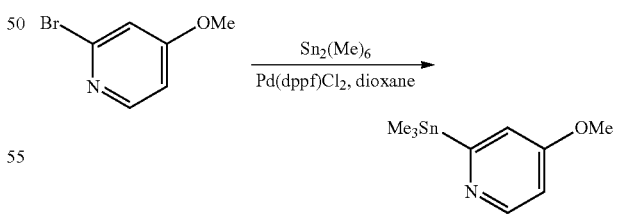

Into a 100-mL round-bottom flask purged and maintained in an inert atmosphere of nitrogen, was placed 2-bromo-4-methoxypyridine (500.00 mg, 2.659 mmol, 1.00 equiv), hexamethyldistannane (1045.49 mg, 3.191 mmol, 1.20 equiv), Pd(dppf)Cl₂ (194.58 mg, 0.266 mmol, 0.1 equiv), and dioxane (20.00 mL). The resulting solution was stirred for 4 hr at 100° C. The solution was cooled and then used for the next step directly. LCMS (ES) [M+1]⁺ m/z: 274.

Step 2

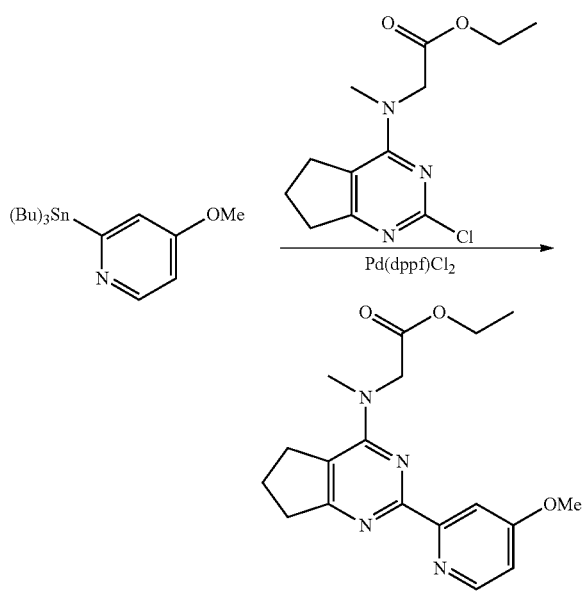

Into a 100-mL round-bottom flask purged and maintained in an inert atmosphere of nitrogen, was placed 4-methoxy-2-(tributylstannyl)pyridine (590.48 mg, 1.483 mmol, 1.00 equiv), ethyl 2-([2-chloro-5H,6H,7H-cyclopenta[d]pyrimidin-4-yl](methyl)amino)acetate (400.00 mg, 1.483 mmol, 1.00 equiv), Pd(dppf)Cl$_2$ (108.51 mg, 0.148 mmol, 0.10 equiv), and dioxane (20.00 mL). The resulting solution was stirred for 16 hr at 100° C. The reaction mixture was cooled. The resulting solution was extracted with 3×30 mL of ethyl acetate and the organic layers were combined, dried over anhydrous sodium sulfate, and concentrated under vacuum. The residue was applied onto a silica gel column and eluted with dichloromethane/methanol (10:1). This resulted in 300 mg (59.08%) of ethyl N-(2-(4-methoxypyridin-2-yl)-6,7-dihydro-5H-cyclopenta[d]pyrimidin-4-yl)-N-methylglycinate as brown oil. LCMS (ES) [M+1]$^+$ m/z: 343.

Step 3

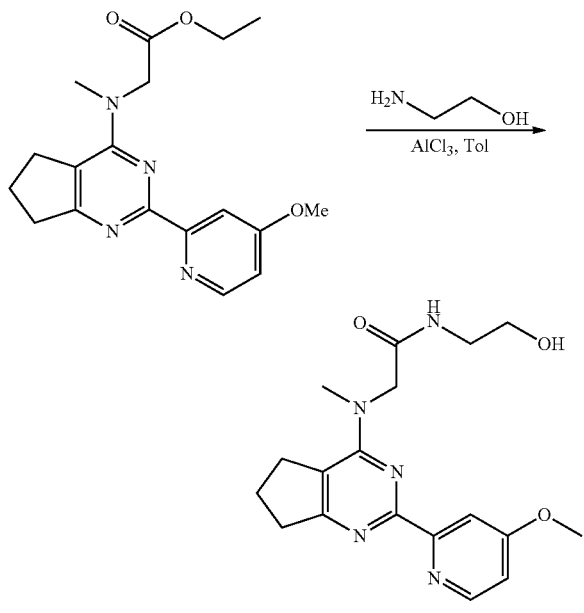

Into a 50-mL round-bottom flask, was placed ethyl N-(2-(4-methoxypyridin-2-yl)-6,7-dihydro-5H-cyclopenta[d]pyrimidin-4-yl)-N-methylglycinate (300.00 mg, 0.876 mmol, 1.00 equiv), ethanolamine (64.22 mg, 1.051 mmol, 1.20 equiv), AlCl$_3$ (11.68 mg, 0.088 mmol, 0.10 equiv), and toluene (20.00 mL). The resulting solution was stirred for 16 hr at 90° C. The reaction mixture was cooled. The resulting solution was extracted with 3×30 mL of ethyl acetate and the organic layers were combined, dried over anhydrous sodium sulfate, and concentrated under vacuum. The crude product was purified by Prep-HPLC with the following conditions (2 #SHIMADZU (HPLC-01)): Column, Atlantis HILIC OBD Column, 19*150 mm*5 um; mobile phase, Water (0.05% NH$_3$H$_2$O) and ACN (5% PhaseB up to 18% in 8 min). This resulted in 47.2 mg (15.07%) of N-(2-hydroxyethyl)-2-((2-(4-methoxypyridin-2-yl)-6,7-dihydro-5H-cyclopenta[d]pyrimidin-4-yl)(methyl)amino)acetamide as a white solid. $^1$H NMR (300 MHz, DMSO-d$_6$) δ 8.48 (d, J=5.7 Hz, 1H), 8.14 (t, J=5.7 Hz, 1H), 7.81 (d, J=2.6 Hz, 1H), 7.04 (dd, J=5.6, 2.6 Hz, 1H), 4.65 (s, 1H), 4.20 (s, 2H), 3.90 (s, 3H), 3.44-3.35 (m, 2H), 3.28 (s, 3H), 3.21-3.11 (m, 4H), 2.83 (t, J=7.8 Hz, 2H), 2.01-1.96 (m, 2H). LCMS (ES) [M+1]$^+$ m/z: 358.2.

Example 1.137

Synthesis of 2-{[2-(4-methoxypyridin-2-yl)-5H,6H,7H-cyclopenta[d]pyrimidin-4-yl](methyl)amino}-N-(oxan-4-yl)acetamide (Compound 134)

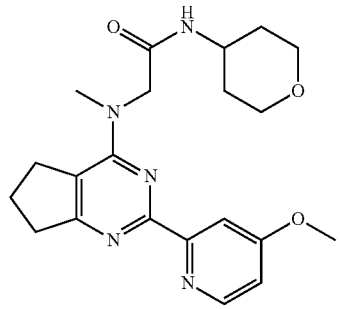 [SMILES: COc1ccnc(-c2nc3c(c(N(C)CC(=O)NC4CCOCC4)n2)CCC3)c1]

Scheme 84 depicts a synthetic route for preparing an exemplary compound.

Scheme 84

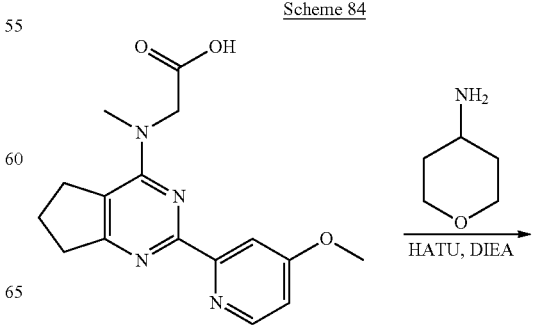

615
-continued

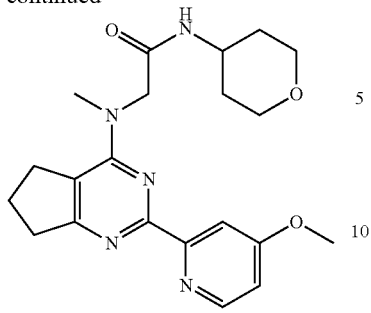

To a stirred solution of [[2-(4-methoxypyridin-2-yl)-5H,6H,7H-cyclopenta[d]pyrimidin-4-yl](methyl)amino]acetic acid (200 mg, 0.63 mmol, 1.0 equiv), DIEA (411 mg, 3.18 mmol, 5.0 equiv), and HATU (1.21 g, 3.181 mmol, 5.0 equiv) in THF (10 mL) was added oxan-4-amine (321 mg, 3.18 mmol, 5.0 equiv) in portions at 20° C. The resulting mixture was stirred for 5 h at 60° C. The reaction was concentrated under reduced pressure. The residue was purified by Flash-Prep-HPLC with the following conditions (IntelFlash-1): Column, C18; mobile phase, Mobile phase: MeCN=5/1B: Water Flow rate: 20 mL/min Column: DAICEL CHIRALPAK IC, 250*20 mm, 220 nm Gradient: 50% B in 20 min; 220 nm. This resulted in 47 mg (18.5%) 2-[[2-(4-methoxypyridin-2-yl)-5H,6H,7H-cyclopenta[d]pyrimidin-4-yl](methyl)amino]-N-(oxan-4-yl)acetamide as a white solid. $^1$H NMR (300 MHz, DMSO-d$_6$) δ 8.49 (d, J=5.7 Hz, 1H), 8.13 (d, J=7.5 Hz, 1H), 7.81 (d, J=2.4 Hz, 1H), 7.05 (dd, J=2.4 Hz, 5.7 Hz, 1H), 4.18 (s, 2H), 3.89 (s, 3H), 3.81-3.77 (m, 3H), 3.31-3.28 (m, 2H), 3.18-3.16 (m, 3H), 3.15 (t, J=7.2 Hz, 2H), 2.82 (t, J=7.8 Hz, 2H), 2.04-1.94 (m, 2H), 1.67-1.63 (m, 2H), 1.47-1.39 (m, 2H). LCMS (ES) [M+1]$^+$ m/z: 398.2.

Example 1.138

Synthesis of 2-{[2-(4-methoxypyridin-2-yl)-5H,6H,7H-cyclopenta[d]pyrimidin-4-yl](methyl)amino}-N-(oxolan-3-yl)acetamide (Compound 135)

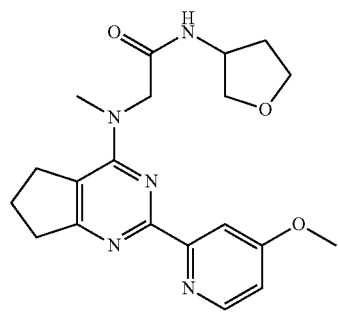 [SMILES: COc1ccnc(-c2nc3c(c(N(C)CC(=O)NC4CCOC4)n2)CCC3)c1]

616

Scheme 85

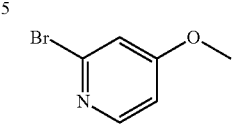

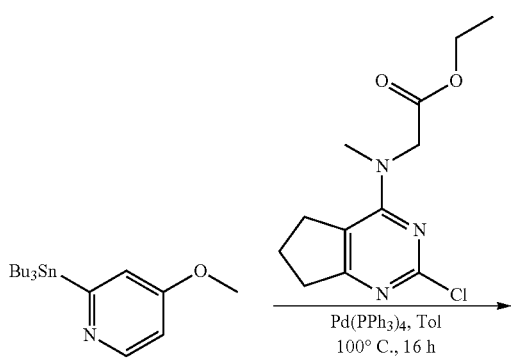

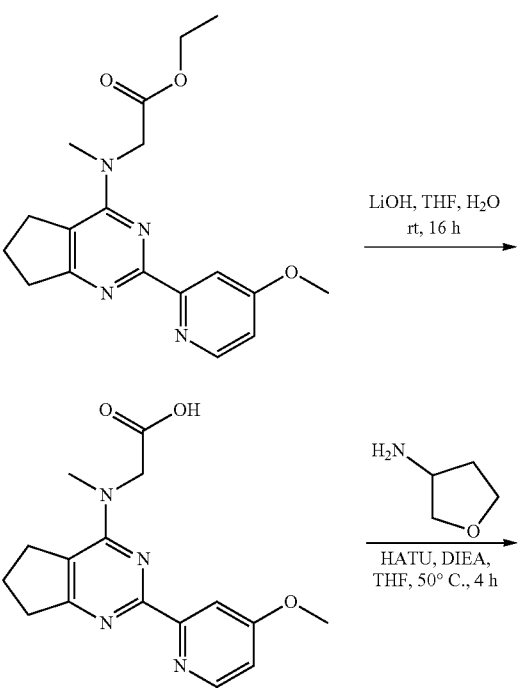

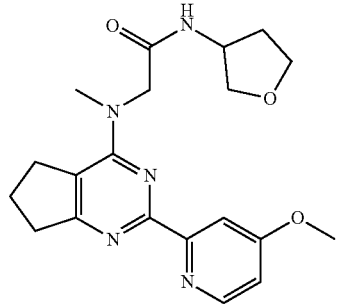

Scheme 85 depicts a synthetic route for preparing an exemplary compound.

Step 1

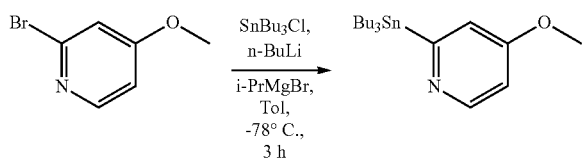

Into a 250-mL 3-necked round-bottom flask purged and maintained in an inert atmosphere of nitrogen was placed 2-bromo-4-methoxypyridine (7.0 g, 37.22 mmol, 1.0 equiv) and toluene (70.0 mL). This was followed by the addition of n-BuLi (16.4 mL, 41.0 mmol, 1.10 equiv) and i-PrMgBr (22.3 mL, 22.30 mmol, 0.60 equiv) dropwise with stirring at −78° C. After addition, the resulting solution was stirred for 2 hr at −78° C. To the mixture tributyltin chloride (14.54 g, 44.68 mmol, 1.20 equiv) was added at −78° C. The reaction was stirred for 1 h at room temperature. The reaction was then quenched by the addition of 200 mL of NH₄Cl (aq), and extracted with 3×100 mL of toluene. The combined organic phase was dried over anhydrous sodium sulfate, filtered, and the filtrate was concentrated under reduced pressure. 16.0 g crude product of 4-methoxy-2-(tributylstannyl)pyridine was obtained as a brown oil and used in the next step without purification. LCMS (ES) [M+1]⁺ m/z: 400.

Step 2

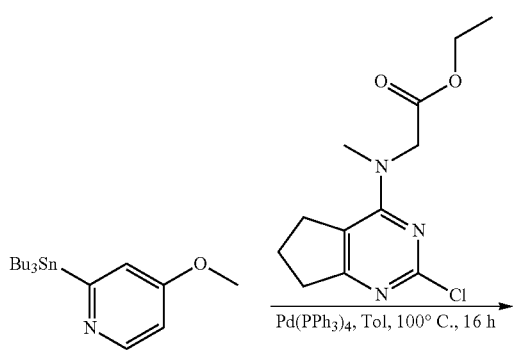

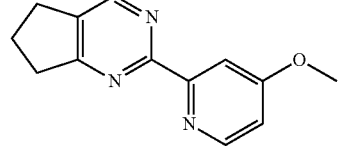

Into a 250-mL round-bottom flask purged and maintained in an inert atmosphere of nitrogen was placed ethyl 2-([2-chloro-5H,6H,7H-cyclopenta[d]pyrimidin-4-yl](methyl) amino)acetate (7.0 g, 25.95 mmol, 1.00 equiv), toluene (100.0 mL), 4-methoxy-2-(tributylstannyl)pyridine (15.5 g, 38.92 mmol, 1.50 equiv), and Pd(PPh₃)₄ (3.0 g, 2.59 mmol, 0.10 equiv). The mixture was stirred for 16 h at 100° C. The reaction mixture was cooled and concentrated to remove the solvent. The residue was purified by silica gel column with dichloromethane/methanol (10/1). This resulted in 3.5 g (39%) of ethyl 2-[[2-(4-methoxypyridin-2-yl)-5H,6H,7H-cyclopenta[d]pyrimidin-4-yl](methyl)amino]acetate as a brown oil. LCMS (ES) [M+1]⁺ m/z: 343.

Step 3

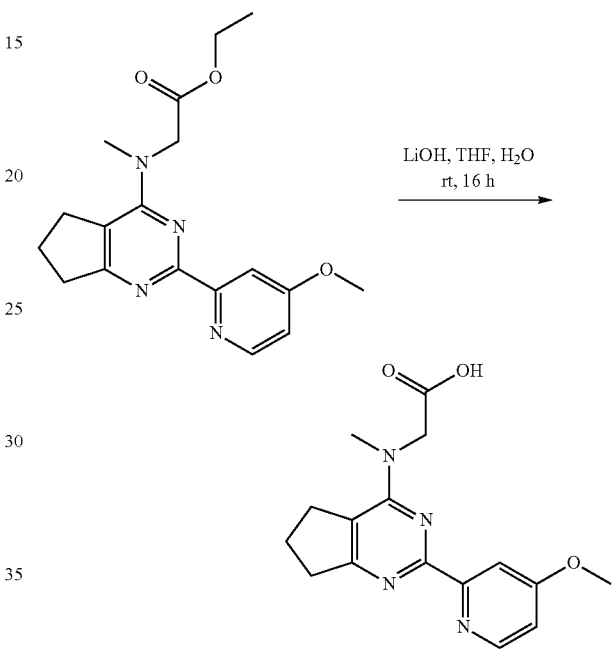

Into a 100-mL round-bottom flask, was placed ethyl 2-[[2-(4-methoxypyridin-2-yl)-5H,6H,7H-cyclopenta[d]pyrimidin-4-yl](methyl)amino]acetate (3.5 g, 10.22 mmol, 1.00 equiv), THF (30.0 mL), H₂O (10.0 mL), and LiOH H₂O (857 mg, 20.44 mmol, 2.00 equiv). The reaction solution was stirred for 16 h at room temperature. The solids were collected by filtration and dried under an infrared lamp. 2.5 g (77%) of N-(2-(4-methoxypyridin-2-yl)-6,7-dihydro-5H-cyclopenta[d]pyrimidin-4-yl)-N-methylglycine was obtained as a yellow solid. LCMS (ES)[M+1]⁺ m/z: 315.

Step 4

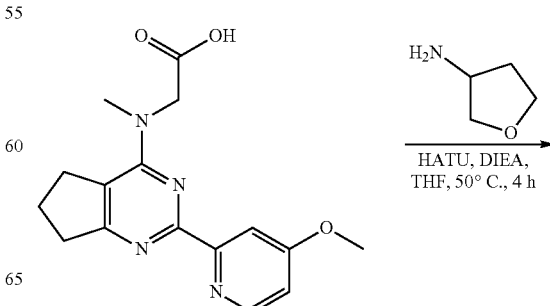

-continued

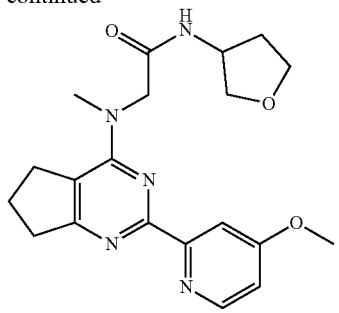

Into a 50-mL round-bottom flask, was placed N-(2-(4-methoxypyridin-2-yl)-6,7-dihydro-5H-cyclopenta[d]pyrimidin-4-yl)-N-methylglycine (200 mg, 0.63 mmol, 1.00 equiv), THF (5.0 mL), oxolan-3-amine (83 mg, 0.95 mmol, 1.50 equiv), DIEA (246 mg, 1.90 mmol, 3.00 equiv), and HATU (362 mg, 0.95 mmol, 1.50 equiv). The mixture was stirred for 4 h at 50° C. The reaction mixture was cooled and concentrated to remove the solvent. The residue was diluted with 5 mL of MeOH and purified by Prep-HPLC with the following conditions: Column, Welch Xtimate C18, 21.2*250 mm, 5 um, Mobile phase, Water (10 mmol/L NH$_4$HCO$_3$) and MeOH:CH$_3$CN=1:1 (25% Phase B up to 65% in 15 min), Detector, UV 254 nm. This resulted in 30 mg (12%) of 2-[[2-(4-methoxypyridin-2-yl)-5H,6H,7H-cyclopenta[d]pyrimidin-4-yl](methyl)amino]-N-(oxolan-3-yl)acetamide as a white solid. $^1$H NMR (300 MHz, DMSO-d$_6$) δ 8.47 (d, J=5.7 Hz, 1H), 8.35 (d, J=6.9 Hz, 1H), 7.80 (d, J=2.7 Hz, 1H), 7.03 (dd, J=5.7, 2.7 Hz, 1H), 4.33-4.22 (m, 1H), 4.18 (d, J=2.4 Hz, 2H), 3.89 (s, 3H), 3.80-3.67 (m, 2H), 3.70-3.57 (m, 1H), 3.43 (dd, J=8.7, 3.9 Hz, 1H), 3.27 (s, 3H), 3.16 (t, J=7.5 Hz, 2H), 2.82 (t, J=7.8 Hz, 2H), 2.13-1.91 (m, 3H), 1.77-1.67 (m, 1H). LCMS (ES)[M+1]$^+$ m/z: 384.1.

Example 1.139

Synthesis of N-(1-hydroxy-2-methylpropan-2-yl)-2-{[2-(4-methoxypyridin-2-yl)-5H,6H,7H-cyclopenta[d]pyrimidin-4-yl](methyl)amino}acetamide (Compound 136)

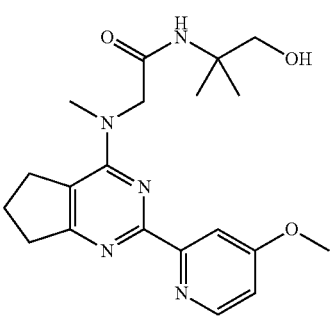 [SMILES: COc1ccnc(-c2nc3c(c(N(C)CC(=O)NC(C)(C)CO)n2)CCC3)c1]

Scheme 86 depicts a synthetic route for preparing an exemplary compound.

Scheme 86

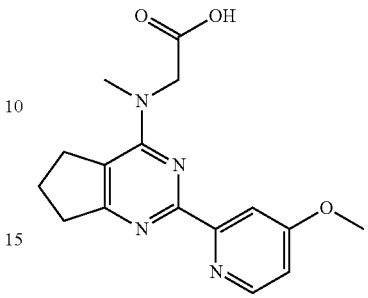 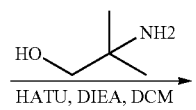

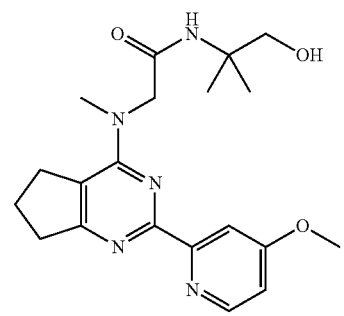

Into a 100-mL round-bottom flask was placed N-(2-(4-methoxypyridin-2-yl)-6,7-dihydro-5H-cyclopenta[d]pyrimidin-4-yl)-N-methylglycine (150.00 mg, 0.477 mmol, 1.00 equiv), 2-amino-2-methyl-1-propanol (85.07 mg, 0.954 mmol, 2.00 equiv), HATU (272.16 mg, 0.716 mmol, 1.50 equiv), DIEA (185.02 mg, 1.432 mmol, 3.00 equiv), and DCM (20.00 mL). The resulting solution was stirred for 6 hr at room temperature. The resulting solution was extracted with 3×20 mL of dichloromethane and the organic layers were combined, dried over anhydrous sodium sulfate, and concentrated. The crude product was purified by Prep-HPLC with the following conditions (2 #SHIMADZU (HPLC-01)): Column, Atlantis HILIC OBD Column, 19*150 mm*5 um; mobile phase, Water (0.05% NH$_3$H$_2$O) and ACN (5% PhaseB up to 18% in 8 min). This resulted in 66.9 mg (36.37%) of N-(1-hydroxy-2-methylpropan-2-yl)-2-((2-(4-methoxypyridin-2-yl)-6,7-dihydro-5H-cyclopenta[d]pyrimidin-4-yl)(methyl)amino)acetamide as a white solid. $^1$H NMR (300 MHz, DMSO-d$_6$) δ 8.68 (d, J=6.1 Hz, 1H), 8.04 (d, J=2.7 Hz, 1H), 7.69 (s, 1H), 7.44 (dd, J=6.1, 2.6 Hz, 1H), 4.88 (br, 1H), 4.35 (s, 2H), 4.06 (s, 3H), 3.52-3.41 (s, 3H), 3.39-3.25 (m, 2H), 3.22-3.17 (m, 2H), 3.01 (t, J=7.9 Hz, 2H), 2.15-1.99 (m, 2H), 1.17 (s, 6H). LCMS (ES) [M+1]$^+$ m/z: 386.2.

Example 1.140

Synthesis of N-cyclohexyl-2-{[2-(4-methoxypyridin-2-yl)-5H,6H,7H-cyclopenta[d]pyrimidin-4-yl](methyl)amino}acetamide (Compound 137)

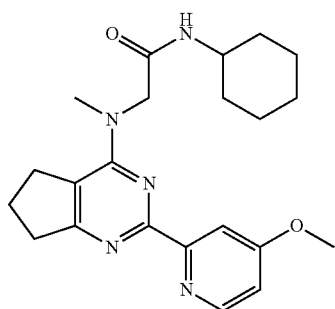

Scheme 87 depicts a synthetic route for preparing an exemplary compound.

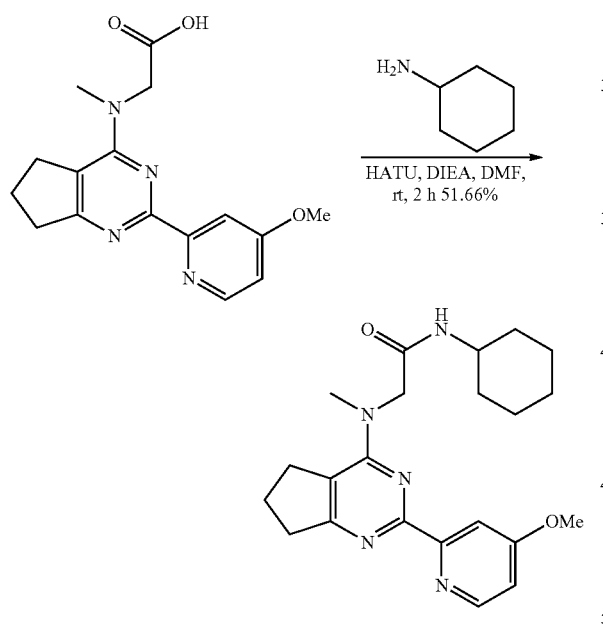

Into a 50-mL round-bottom flask, was placed [[2-(4-methoxypyridin-2-yl)-5H,6H,7H-cyclopenta[d]pyrimidin-4-yl](methyl)amino]acetic acid (100.00 mg, 0.318 mmol, 1.00 equiv), dimethylformamide (4 mL), cyclohexylamine (31.55 mg, 0.318 mmol, 1.00 equiv), HATU (181.44 mg, 0.477 mmol, 1.50 equiv), and DIEA (123.35 mg, 0.954 mmol, 3.00 equiv). The resulting solution was stirred for 2 hr at 25° C. The crude reaction mixture was filtered and subjected to reverse phase preparative HPLC (Prep-C18, 20-45 uM, 120 g, Tianjin Bonna-Agela Technologies; gradient elution of 25% MeCN in water to 35% MeCN in water over a 10 min period, water contains 0.1% $NH_3H_2O$) to provide N-cyclohexyl-2-{[2-(4-methoxypyridin-2-yl)-5H,6H,7H-cyclopenta[d]pyrimidin-4-yl](methyl)amino}acetamide as a white solid (65 mg, 51.66%). $^1$H NMR (300 MHz, DMSO-d6) δ 8.48 (d, J=5.6 Hz, 1H), 7.98 (d, J=8.0 Hz, 1H), 7.81 (d, J=2.6 Hz, 1H), 7.04 (dd, J=5.6, 2.7 Hz, 1H), 4.16 (s, 2H), 3.89 (s, 3H), 3.54 (s, 1H), 3.26 (s, 3H), 3.14 (t, J=7.2 Hz, 2H), 2.82 (t, J=7.8 Hz, 2H), 1.89-2.07 (m, 2H), 1.81-1.45 (m, 5H), 1.12-1.32 (m, 5H). LCMS (ES) [M+1]$^+$ m/z 396.2.

Example 1.141

Synthesis of N-(3-fluorophenyl)-2-{[2-(4-methoxypyridin-2-yl)-5H,6H,7H-cyclopenta[d]pyrimidin-4-yl](methyl)amino}acetamide (Compound 138)

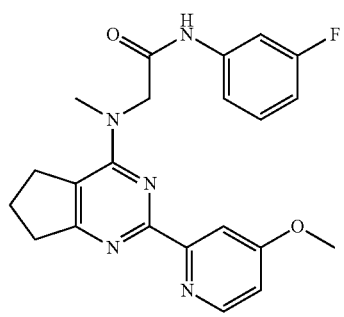 [SMILES: COc1ccnc(-c2nc3c(c(N(C)CC(=O)Nc4cccc(F)c4)n2)CCC3)c1]

Scheme 88 depicts a synthetic route for preparing an exemplary compound.

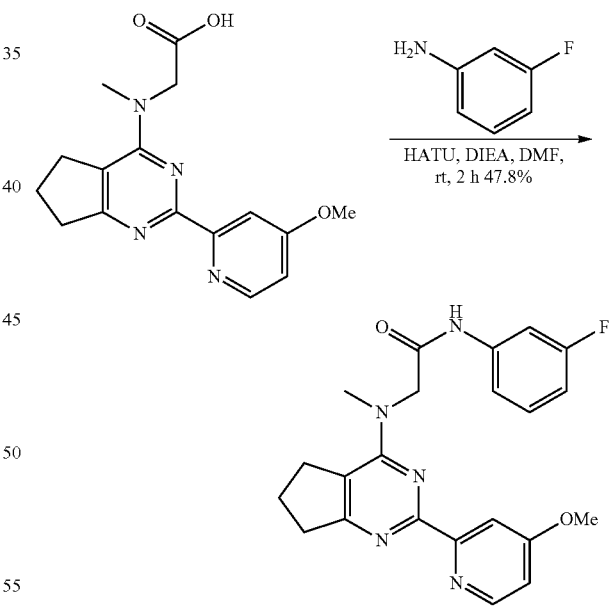

Into a 50-mL round-bottom flask, was placed [[2-(4-methoxypyridin-2-yl)-5H,6H,7H-cyclopenta[d]pyrimidin-4-yl](methyl)amino]acetic acid (100.00 mg, 0.318 mmol, 1.00 equiv), dimethylformamide (4 mL), 3-fluoroaniline (35.35 mg, 0.318 mmol, 1.00 equiv), HATU (181.44 mg, 0.477 mmol, 1.50 equiv), and DIEA (123.35 mg, 0.954 mmol, 3.00 equiv). The resulting solution was stirred for 2 hr at 25° C. The crude reaction mixture was filtered and subjected to reverse phase preparative HPLC (Prep-C18, 20-45 uM, 120 g, Tianjin Bonna-Agela Technologies; gradient elution of 25% MeCN in water to 35% MeCN in water over a 10 min period, water contains 0.1% NH₃H₂O) to provide N-(3-fluorophenyl)-2-{[2-(4-methoxypyridin-2-yl)-5H,6H,7H-cyclopenta[d]pyrimidin-4-yl](methyl)amino} acetamide as a white solid (62 mg, 47.83%). ¹H NMR (300 MHz, DMSO-d6) δ 10.43 (s, 1H), 8.44 (d, J=5.6 Hz, 1H), 7.77 (d, J=2.6 Hz, 1H), 7.57 (d, J=11.5 Hz, 1H), 7.40-7.28 (m, 2H), 6.99 (dd, J=5.6, 2.6 Hz, 1H), 6.86-6.92 (m, 1H), 4.43 (s, 2H), 3.76 (s, 3H), 3.37 (s, 3H), 3.21 (t, J=7.4 Hz, 2H), 2.84 (t, J=7.8 Hz, 2H), 1.94-2.09 (m, 2H). LCMS (ES) [M+1]⁺ m/z 408.2.

Example 1.142

Synthesis of N-(1-methoxy-2-methylpropan-2-yl)-2-{[2-(4-methoxypyridin-2-yl)-5H,6H,7H-cyclopenta[d]pyrimidin-4-yl](methyl)amino}acetamide (Compound 139)

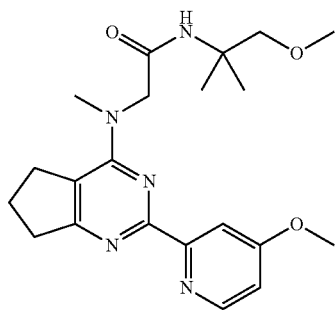 [SMILES: COCC(C)(C)NC(=O)CN(C)c1nc(-c2cc(OC)ccn2)nc2c1CCC2]

Scheme 89 depicts a synthetic route for preparing an exemplary compound.

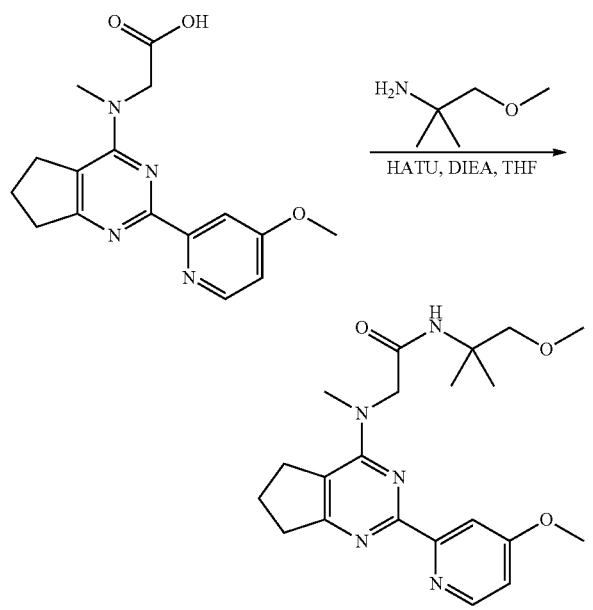

Into a 100-mL round-bottom flask, was placed N-(2-(4-methoxypyridin-2-yl)-6,7-dihydro-5H-cyclopenta[d]pyrimidin-4-yl)-N-methylglycine (150.00 mg, 0.493 mmol, 1.00 equiv), 1-methoxy-tert-butylamine (76.27 mg, 0.739 mmol, 1.5 equiv), HATU (281.10 mg, 0.739 mmol, 1.5 equiv), DIEA (191.09 mg, 1.479 mmol, 3 equiv), and THF (20.00 mL). The resulting solution was stirred for 4 hr at room temperature. The resulting solution was extracted with 3×20 mL of ethyl acetate and the organic layers were combined, dried over anhydrous sodium sulfate, and concentrated under vacuum. The crude product was purified by Prep-HPLC with the following conditions (2 #SHIMADZU (HPLC-01)): Column, Welch Xtimate C18, 21.2*250 mm, 5 um; mobile phase, Water (0.05% FA) and MeOH:ACN=1:1 (10% PhaseB up to 60% in 17 min. This resulted in 55.8 mg (29.07%) of N-(1-hydroxy-2-methylpropan-2-yl)-2-((2-(4-methoxypyridin-2-yl)-6,7-dihydro-5H-cyclopenta[d]pyrimidin-4-yl)(methyl)amino)acetamide as an off-white solid. ¹H NMR (300 MHz, DMSO-d₆) δ 8.48 (d, J=5.6 Hz, 1H), 7.85 (d, J=2.5 Hz, 1H), 7.57 (s, 1H), 7.04 (dd, J=5.6, 2.6 Hz, 1H), 4.17 (s, 2H), 3.90 (s, 3H), 3.34 (s, 2H), 3.25 (s, 3H), 3.18 (s, 3H), 3.14 (t, J=7.3 Hz, 2H), 2.82 (t, J=7.9 Hz, 2H), 2.09-1.92 (m, 2H), 1.19 (s, 6H). LCMS (ES) [M+1]⁺ m/z: 400.2.

Example 1.143

Synthesis of 2-({2-[4-(2-hydroxyethoxy)pyridin-2-yl]-5H,6H,7H-cyclopenta[d]pyrimidin-4-yl}(methyl)amino)-N-(oxan-4-yl)acetamide (Compound 140)

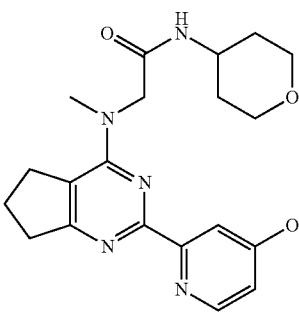

Scheme 90 depicts a synthetic route for preparing an exemplary compound.

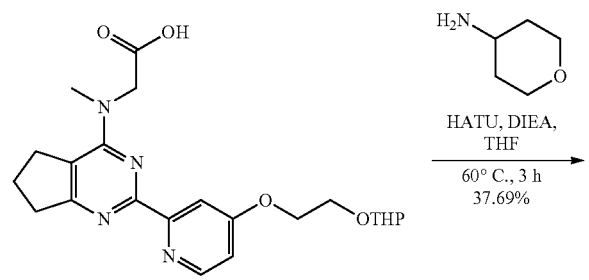

Step 2

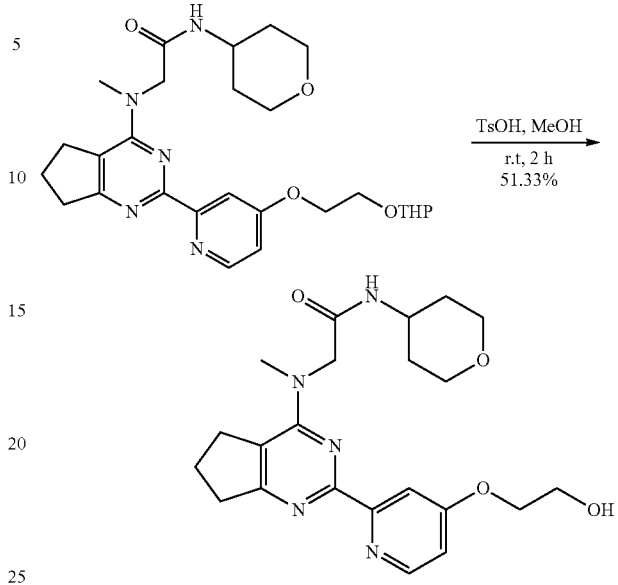

Into a 50-mL round-bottom flask, was placed 2-[methyl (2-[4-[2-(oxan-2-yloxy)ethoxy]pyridin-2-yl]-5H,6H,7H-cyclopenta[d]pyrimidin-4-yl)amino]-N-(oxan-4-yl)acetamide (90 mg, 0.17 mmol, 1.00 equiv), MeOH (3 mL), and TsOH (15 mg, 0.08 mmol, 0.5 equiv). The resulting solution was stirred for 2 hr at 25° C. The crude product was purified by Prep-HPLC with the following conditions (Waters I): Column, Xbridge Prep C18 OBD column, 5 um, 19*150 mm; mobile phase, Water (0.1% FA) and CH$_3$CN (30% CH$_3$CN up to 42% in 15 min); Detector, UV 254 nm. This resulted in 38.6 mg (51.33%) of 2-([2-[4-(2-hydroxyethoxy)pyridin-2-yl]-5H,6H,7H-cyclopenta[d]pyrimidin-4-yl](methyl) amino)-N-(oxan-4-yl)acetamide as a yellow solid. $^1$H NMR (300 MHz, DMSO-d$_6$) δ 8.47 (d, J=5.6 Hz, 1H), 8.29-8.05 (m, 2H), 7.81 (d, J=2.6 Hz, 1H), 7.05 (dd, J=5.7, 2.6 Hz, 1H), 4.24-4.09 (m, 4H), 3.84-3.72 (m, 5H), 3.36-3.30 (m, 2H), 3.28 (s, 3H), 3.15 (t, J=7.2 Hz, 2H), 2.82 (t, J=7.8 Hz, 2H), 2.00 (q, J=7.6 Hz, 2H), 1.67 (d, J=11.3 Hz, 2H), 1.49-1.37 (m, 2H). LCMS (ES) [M+1]$^+$ m/z 428.2.

Example 1.144

Synthesis of N-[(1R,2R)-2-hydroxycyclohexyl]-2-{[2-(4-methoxypyridin-2-yl)-5H,6H,7H-cyclopenta[d] pyrimidin-4-yl](methyl)amino}acetamide (Compound 141)

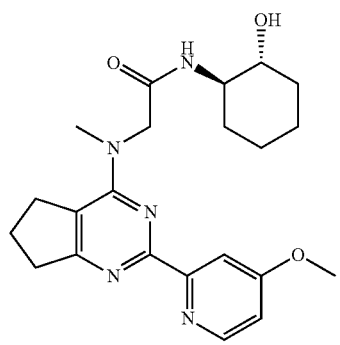 [SMILES: COc1ccnc(-c2nc3c(c(N(C)CC(=O)N[C@@H]4CCCC[C@H]4O)n2)CCC3)c1]

-continued

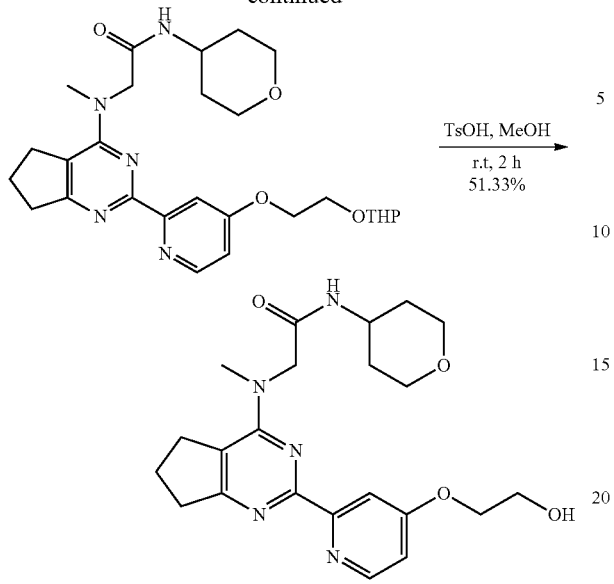

Step 1

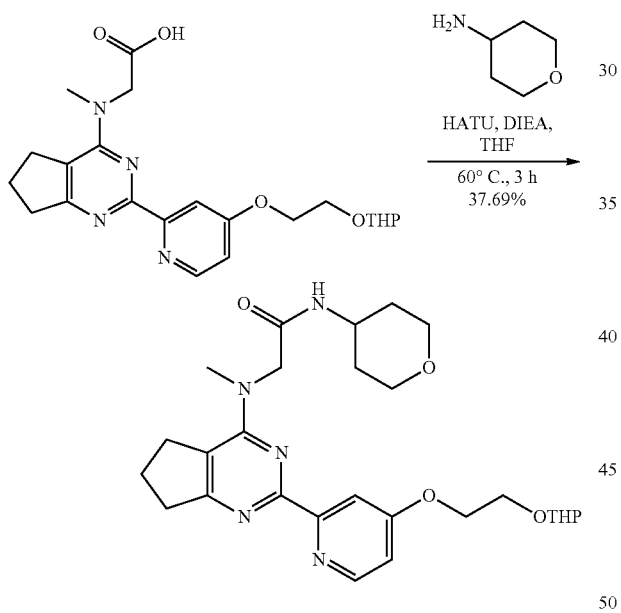

Into a 50-mL round-bottom flask was placed [methyl(2-[4-[2-(oxan-2-yloxy)ethoxy]pyridin-2-yl]-5H,6H,7H-cyclopenta[d]pyrimidin-4-yl)amino]acetic acid (200 mg, 0.46 mmol, 1.00 equiv), THF (5 mL), HATU (266 mg, 0.70 mmol, 1.50 equiv), DIEA (180 mg, 1.40 mmol, 3.00 equiv), and oxan-4-amine (70 mg, 0.70 mmol, 1.50 equiv). The resulting solution was stirred for 3 hr at 60° C. The reaction was then quenched by the addition of 50 mL of water. The resulting solution was extracted with 3×100 mL of ethyl acetate and the organic layers were combined, washed with 3×100 ml of brine, dried over anhydrous sodium sulfate, and concentrated under vacuum. This resulted in 90 mg (37.69%) of 2-[methyl(2-[4-[2-(oxan-2-yloxy)ethoxy]pyridin-2-yl]-5H,6H,7H-cyclopenta[d]pyrimidin-4-yl)amino]-N-(oxan-4-yl)acetamide as a yellow oil. LCMS (ES) [M+1]$^+$ m/z 512.

627

Scheme 91 depicts a synthetic route for preparing an exemplary compound.

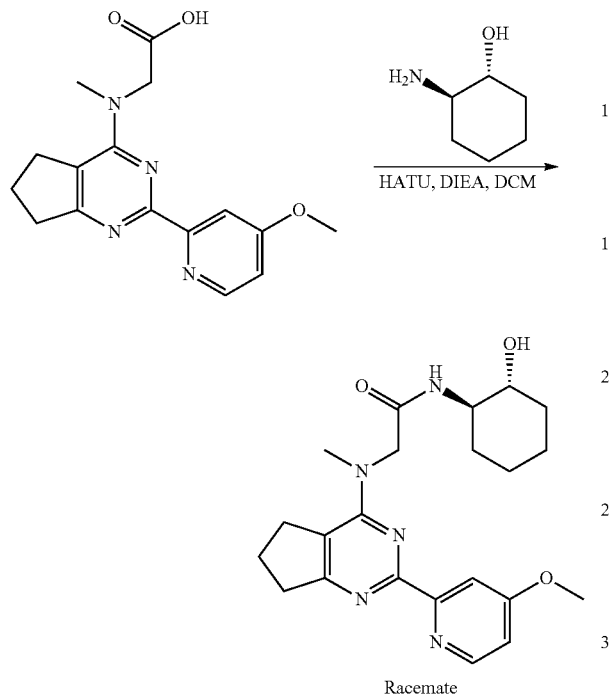

Into a 100-mL round-bottom flask, was placed N-(2-(4-methoxypyridin-2-yl)-6,7-dihydro-5H-cyclopenta[d]pyrimidin-4-yl)-N-methylglycine (150.00 mg, 0.477 mmol, 1.00 equiv), 2-aminocyclohexan-1-ol (82.44 mg, 0.716 mmol, 1.50 equiv), HATU (272.16 mg, 0.716 mmol, 1.5 equiv), DIEA (185.02 mg, 1.432 mmol, 3 equiv), and DCM (20.00 mL). The resulting solution was stirred for 4 hr at 4° C. The resulting solution was extracted with 3×20 mL of dichloromethane and the organic layers were combined, dried in an oven under reduced pressure, and concentrated under vacuum. The crude product was purified by Prep-HPLC with the following conditions (2 #SHIMADZU (HPLC-01)): Column, Atlantis HILIC OBD Column, 19*150 mm*5 um; mobile phase, Water (0.05% NNH$_3$H$_2$O) and ACN (5% PhaseB up to 18% in 8 min). This resulted in 95.2 mg (48.48%) of N-((1R,2R)-2-hydroxycyclohexyl)-2-((2-(4-methoxypyridin-2-yl)-6,7-dihydro-5H-cyclopenta[d]pyrimidin-4-yl)(methyl)amino)acetamide as a white solid. $^1$H NMR (300 MHz, DMSO-d$_6$) δ 8.48 (d, J=5.6 Hz, 1H), 7.91 (d, J=8.1 Hz, 1H), 7.82 (d, J=2.6 Hz, 1H), 7.04 (dd, J=5.7, 2.6 Hz, 1H), 4.54 (d, J=4.8 Hz, 1H), 4.25 (d, J=16.4 Hz, 1H), 4.15 (d, J=16.3 Hz, 1H), 3.89 (s, 3H), 3.48-3.36 (m, 1H), 3.31-3.22 (m, 4H), 3.14 (t, J=4.7 Hz, 2H), 2.82 (t, J=7.9 Hz, 2H), 2.03-1.93 (m, 2H), 1.86-1.49 (m, 4H), 1.32-1.05 (m, 4H). LCMS (ES) [M+1]$^+$ m/z: 412.3.

628

Example 1.145

Synthesis of N-cyclohexyl-2-{methyl[2-(1-methyl-1H-imidazol-4-yl)-5H,6H,7H-cyclopenta[d]pyrimidin-4-yl]amino}acetamide (Compound 142)

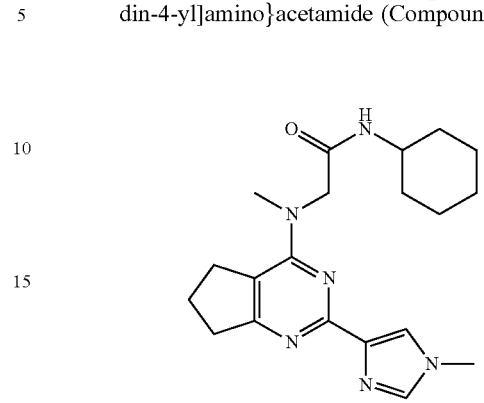

Scheme 92 depicts a synthetic route for preparing an exemplary compound.

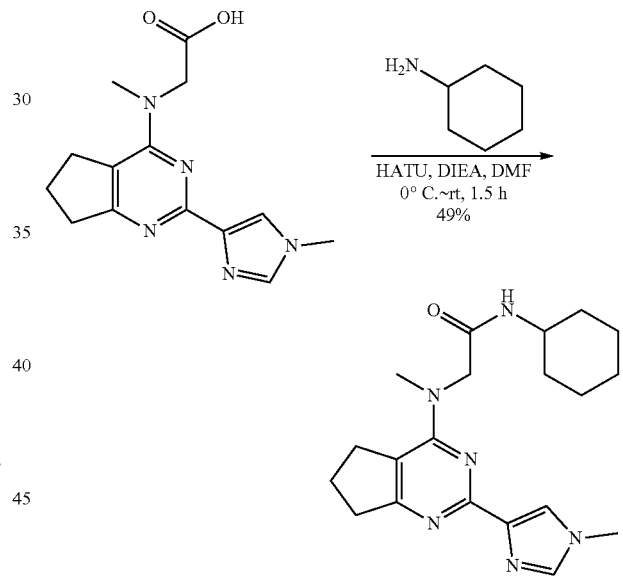

Into a 20-mL vial, was placed [methyl[2-(1-methylimidazol-4-yl)-5H,6H,7H-cyclopenta[d]pyrimidin-4-yl]amino]acetic acid hydrochloride (150 mg, 0.46 mmol, 1.00 equiv), DMF (3.0 mL), cyclohexylamine (51 mg, 0.51 mmol, 1.10 equiv), and DIEA (240 mg, 1.85 mmol, 4.00 equiv). This was followed by the addition of HATU (264 mg, 0.69 mmol, 1.50 equiv) at 0° C. The reaction solution was stirred for 2 h at room temperature. The crude product was purified by Flash-Prep-HPLC with the following conditions: Column, C18-120 g, CH$_3$CN/H$_2$O (0.05% NH$_4$OH) from 10% to 80% within 12 min, flow rate, 70 ml/min, Detector, UV 254 nm. 83.8 mg (49%) of N-cyclohexyl-2-[methyl[2-(1-methylimidazol-4-yl)-5H,6H,7H-cyclopenta[d]pyrimidin-4-yl]amino]acetamide was obtained as a white solid. $^1$HNMR (300 MHz, DMSO-d$_6$, ppm): δ 7.95 (d, J=8.1 Hz, 1H), 7.71 (d, J=1.5 Hz, 1H), 7.60 (d, J=1.5 Hz, 1H), 4.12 (s, 2H), 3.69 (s, 3H), 3.57-3.53 (m, 1H), 3.21 (s, 3H), 3.06 (t, J=7.5 Hz, 2H), 2.73 (t, J=7.8 Hz, 2H), 1.99-1.89 (m, 2H), 1.68 (t, J=10.8 Hz, 4H), 1.54 (d, J=12.3 Hz, 1H), 1.27-1.07 (m, 5H). LCMS (ES, m/z): [M+H]⁺: 369.2.

Example 1.146

Synthesis of N-(1-hydroxy-2-methylpropan-2-yl)-2-{methyl[2-(1-methyl-1H-imidazol-4-yl)-5H,6H,7H-cyclopenta[d]pyrimidin-4-yl]amino}acetamide (Compound 143)

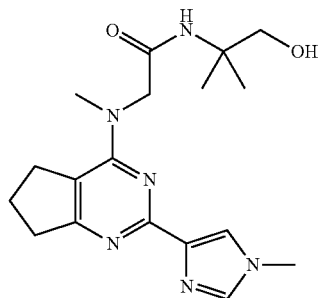 [SMILES: CN(CC(=O)NC(C)(C)CO)c1nc(-c2cn(C)cn2)nc2c1CCC2]

Scheme 93 depicts a synthetic route for preparing an exemplary compound.

Scheme 93

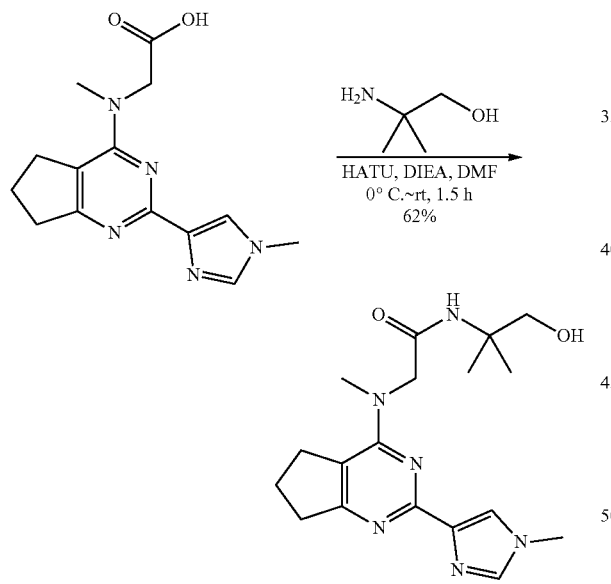

Into a 20-mL vial, was placed [methyl[2-(1-methylimidazol-4-yl)-5H,6H,7H-cyclopenta[d]pyrimidin-4-yl]amino]acetic acid hydrochloride (150 mg, 0.46 mmol, 1.00 equiv), DMF (3.00 mL), 2-amino-2-methyl-1-propanol (45 mg, 0.51 mmol, 1.10 equiv), and DIEA (240 mg, 1.85 mmol, 4.00 equiv). This was followed by the addition of HATU (264 mg, 0.69 mmol, 1.50 equiv) at 0° C. The resulting solution was stirred for 2 h at room temperature. The crude product was purified by Flash-Prep-HPLC with the following conditions: Column, C18-120 g, CH₃CN/H₂O (0.05% NH₄OH) from 10% to 80% within 12 min, flow rate, 70 ml/min, Detector, UV 254 nm. 102.8 mg (62%) of N-(1-hydroxy-2-methylpropan-2-yl)-2-[methyl[2-(1-methylimidazol-4-yl)-5H,6H,7H-cyclopenta[d]pyrimidin-4-yl]amino]acetamide was obtained as a white solid. ¹H-NMR (300 MHz, DMSO-d₆, ppm): δ 7.74 (d, J=1.5 Hz, 1H), 7.59 (d, J=1.5 Hz, 1H), 7.46 (s, 1H), 4.93 (br, 1H), 4.10 (s, 2H), 3.69 (s, 3H), 3.37 (d, J=3.9 Hz, 2H), 3.21 (s, 3H), 3.07 (t, J=7.5 Hz, 2H), 2.73 (t, J=7.8 Hz, 2H), 1.99-1.89 (m, 2H), 1.18 (s, 6H). LCMS (ES, m/z): [M+H]⁺: 359.2.

Example 1.147

Synthesis of N-cyclohexyl-2-({2-[4-(2-hydroxyethoxy)pyridin-2-yl]-5H,6H,7H-cyclopenta[d]pyrimidin-4-yl}(methyl)amino)acetamide (Compound 144)

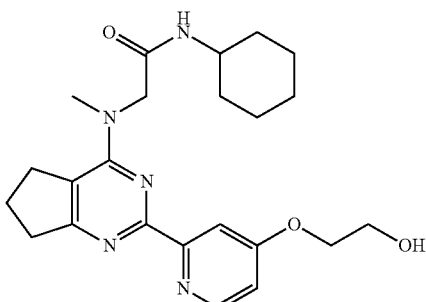

Scheme 94 depicts a synthetic route for preparing an exemplary compound.

Scheme 94

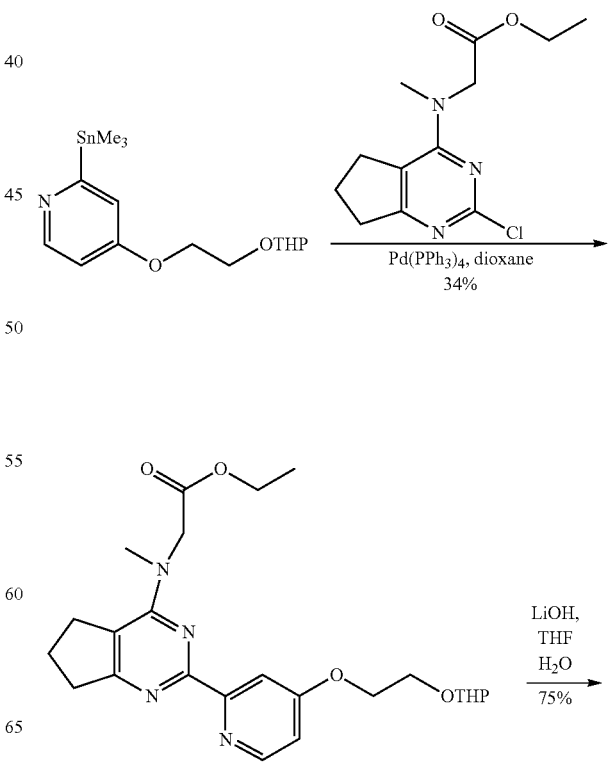

-continued

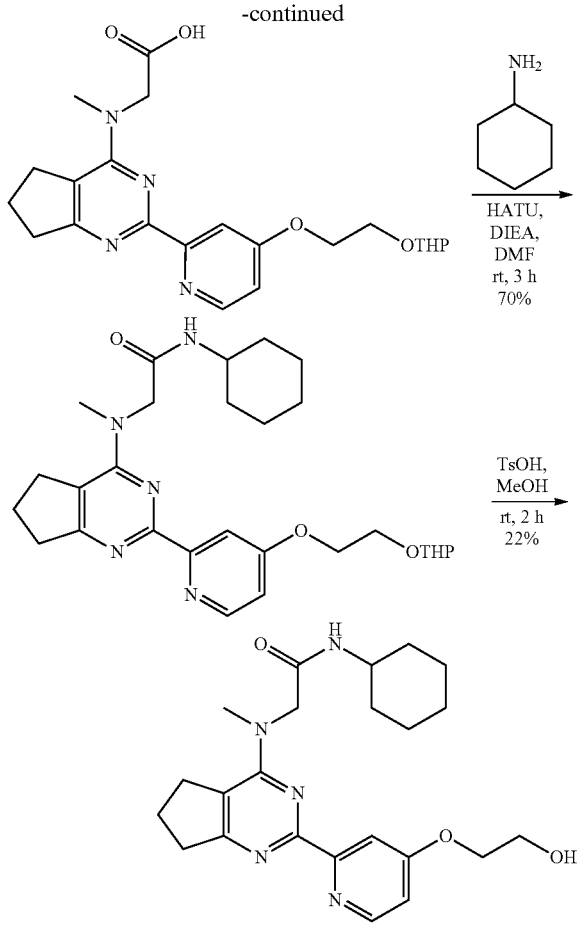

Step 1

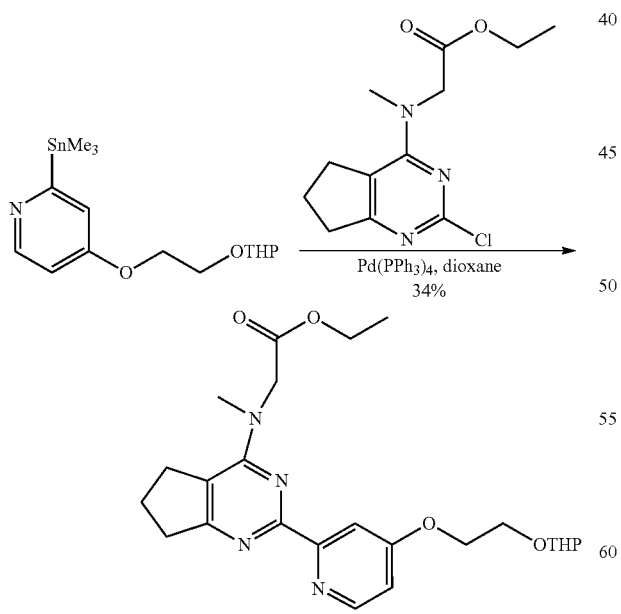

Into a 100-mL round-bottom flask purged and maintained in an inert atmosphere of nitrogen was placed a mixture of 4-[2-(oxan-2-yloxy)ethoxy]-2-(trimethylstannyl)pyridine (2.00 g, 5.18 mmol, 1.00 equiv), dioxane (40.0 mL, 454 mmol), ethyl N-(2-chloro-6,7-dihydro-5H-cyclopenta[d]pyrimidin-4-yl)-N-methylglycinate (1.40 g, 5.180 mmol, 1.00 equiv), and Pd(PPh$_3$)$_4$ (598 mg, 0.518 mmol, 0.10 equiv). The resulting solution was stirred for 16 hours at 100° C. After cooling, the solution was concentrated. The residue was applied onto a silica gel column eluting with dichloromethane/methanol (10/1). This resulted in 826 mg (34.93%) of ethyl N-methyl-N-(2-(4-(2-((tetrahydro-2H-pyran-2-yl)oxy)ethoxy)pyridin-2-yl)-6,7-dihydro-5H-cyclopenta[d]pyrimidin-4-yl)glycinate as a brown crude oil. LCMS (ES) [M+1]$^+$ m/z: 457.

Step 2

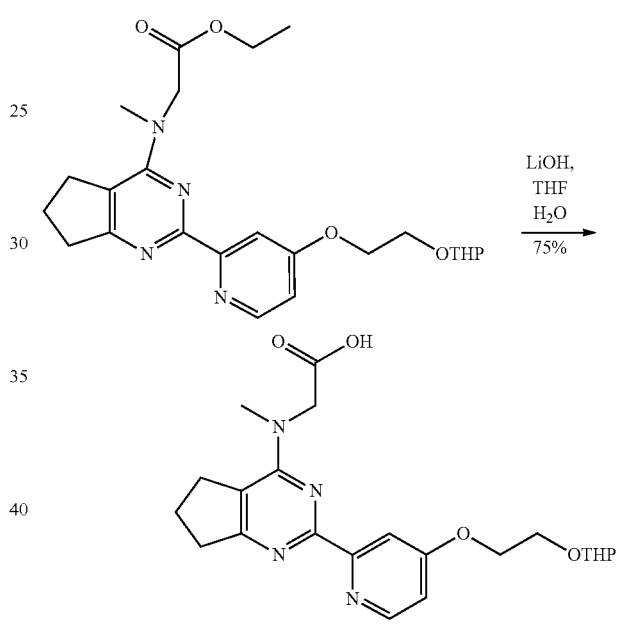

Into a 20-mL vial was placed a mixture of ethyl N-methyl-N-(2-(4-(2-((tetrahydro-2H-pyran-2-yl)oxy)ethoxy)pyridin-2-yl)-6,7-dihydro-5H-cyclopenta[d]pyrimidin-4-yl)glycinate (800 mg, 1.75 mmol, 1.00 equiv), MeOH (8.00 mL), H$_2$O (2.00 mL), and LiOH (83.9 mg, 3.50 mmol, 2.00 equiv). The resulting solution was stirred for 2 hours at room temperature. The crude reaction mixture was filtered and subjected to reverse phase preparative MPLC (Prep-C18, 20-45 mM, 120 g, Tianjin Bonna-Agela Technologies; gradient elution of 5% MeCN in water to 27% MeCN in water over a 12 min period, where both solvents contain 0.1% NH$_3$H$_2$O). This resulted in 568 mg (75.65%) of N-methyl-N-(2-(4-(2-((tetrahydro-2H-pyran-2-yl)oxy)ethoxy)pyridin-2-yl)-6,7-dihydro-5H-cyclopenta[d]pyrimidin-4-yl)glycine as a red solid. LCMS (ES) [M+1]$^+$ m/z: 429.

633

Step 3

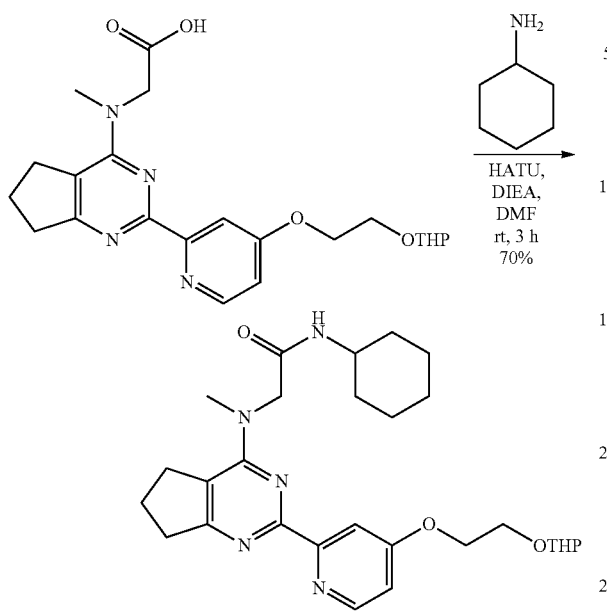

Into an 8-mL vial, was placed N-methyl-N-(2-(4-(2-((tetrahydro-2H-pyran-2-yl)oxy)ethoxy)pyridin-2-yl)-6,7-dihydro-5H-cyclopenta[d]pyrimidin-4-yl)glycine (150 mg, 0.350 mmol, 1.00 equiv), DMF (2.00 mL), cyclohexylamine (34.7 mg, 0.350 mmol, 1.00 equiv), DIEA (135 mg, 1.05 mmol, 3.00 equiv) and HATU (159 mg, 0.420 mmol, 1.20 equiv). The resulting solution was stirred for 3 hours at room temperature. The crude reaction mixture was filtered and the filtrate was subjected to reverse phase preparative MPLC (Prep-C18, 20-45 mM, 120 g, Tianjin Bonna-Agela Technologies; gradient elution of 8% MeCN in water to 33% MeCN in water over a 12 min period, where both solvents contain 0.1% NH$_3$H$_2$O). This resulted in 126 mg (70.62%) of N-cyclohexyl-2-(methyl(2-(4-(2-((tetrahydro-2H-pyran-2-yl)oxy)ethoxy)pyridin-2-yl)-6,7-dihydro-5H-cyclopenta[d]pyrimidin-4-yl)amino)acetamide as a brown oil. LCMS (ES) [M+1]$^+$ m/z: 510.

Step 4

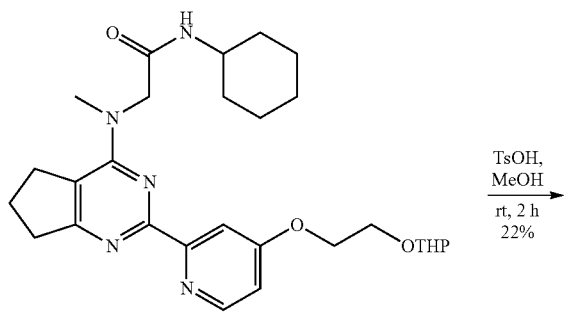

634

-continued

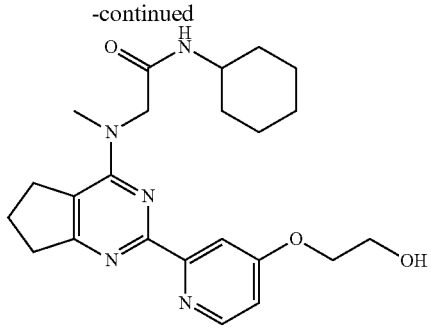

Into an 8-mL vial was placed a mixture of N-cyclohexyl-2-(methyl(2-(4-(2-((tetrahydro-2H-pyran-2-yl)oxy)ethoxy)pyridin-2-yl)-6,7-dihydro-5H-cyclopenta[d]pyrimidin-4-yl)amino)acetamide (120 mg, 0.235 mmol, 1.00 equiv), MeOH (3.00 mL), and TsOH (20.2 mg, 0.118 mmol, 0.50 equiv). The resulting solution was stirred for 2 hours at room temperature. The crude product was purified by Prep-HPLC with the following conditions: SunFire Prep C18 OBD Column, 19×150 mm, 5 um; mobile phase, phase A: H$_2$O (0.1% FA); phase B: CH$_3$CN (5% CH$_3$CN up to 20% CH$_3$CN in 8 min). This resulted in 22.5 mg (22.46%) of N-cyclohexyl-2-((2-(4-(2-hydroxyethoxy)pyridin-2-yl)-6,7-dihydro-5H-cyclopenta[d]pyrimidin-4-yl)(methyl)amino)acetamide as an off-white solid. $^1$H NMR (300 MHz, DMSO-d$_6$, ppm): δ 8.55 (d, J=5.9 Hz, 1H), 8.14 (s, OH), 8.03 (d, J=7.9 Hz, 1H), 7.89 (d, J=2.6 Hz, 1H), 7.22 (dd, J=5.9, 2.6 Hz, 1H), 4.96 (br, 1H), 4.24-4.20 (m, 4H), 3.77-3.68 (m, 2H), 3.62-3.47 (m, 1H), 3.33 (s, 3H), 3.18 (t, J=7.3 Hz, 2H), 2.89 (t, J=7.8 Hz, 2H), 2.07-1.97 (m, 2H), 1.72-1.52 (m, 5H), 1.31-1.07 (m, 5H). LCMS (ES) [M+1]$^+$ m/z: 426.2.

Example 1.148

Synthesis of N-tert-butyl-2-{[2-(4,5-dimethoxypyridin-2-yl)-5H,6H,7H-cyclopenta[d]pyrimidin-4-yl](methyl)amino}acetamide (Compound 145)

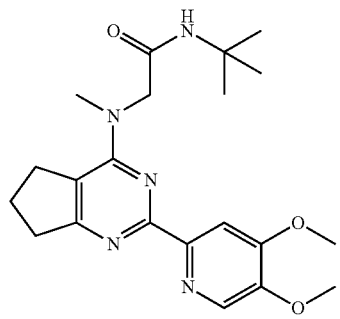 [SMILES: COc1cnc(-c2nc3c(c(N(C)CC(=O)NC(C)(C)C)n2)CCC3)cc1OC]

Scheme 95 depicts a synthetic route for preparing an exemplary compound.

Scheme 95

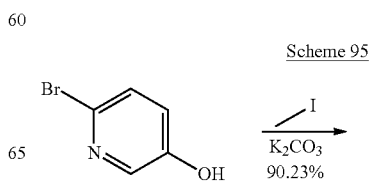

-continued

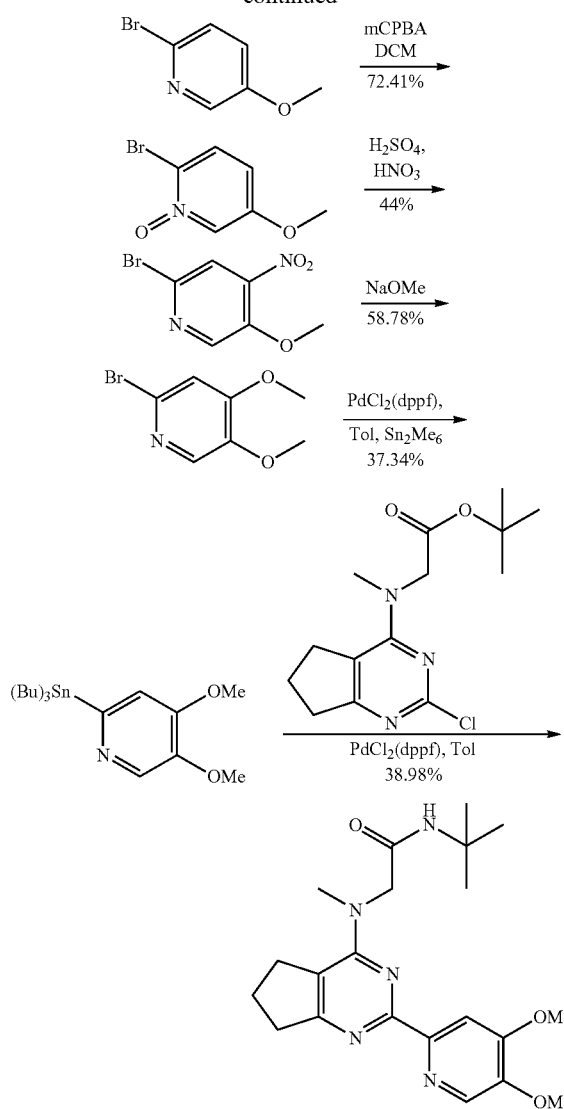

Step 1

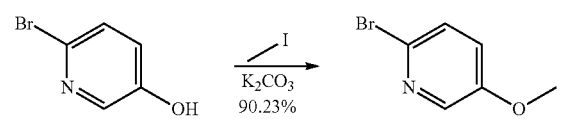

Into a 25-mL round-bottom flask was placed a solution of 6-bromopyridin-3-ol (800.00 mg, 4.598 mmol, 1.00 equiv) in DMF (10 mL), methyl iodide (717.86 mg, 5.058 mmol, 1.10 equiv), and $K_2CO_3$ (762.53 mg, 5.517 mmol, 1.2 equiv). The resulting solution was stirred for 12 hr at room temperature. The resulting solution was diluted with 50 mL of $H_2O$, extracted with 2×50 mL of ethyl acetate, the organic layers were combined, dried over anhydrous sodium sulfate, and concentrated. This resulted in 780 mg (90.23%) of 2-bromo-5-methoxypyridine as a light yellow oil. LCMS (ES) [M+1]$^+$ m/z: 188.

Step 2

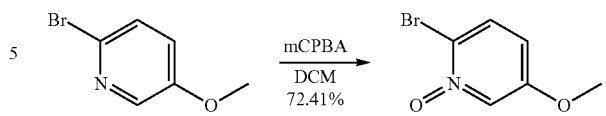

Into a 25-mL round-bottom flask, was placed a solution of 2-bromo-5-methoxypyridine (700.00 mg, 3.723 mmol, 1.00 equiv) in DCM (15 mL), and mCPBA (770.94 mg, 4.468 mmol, 1.2 equiv). The resulting solution was stirred for 10 hr at room temperature. The reaction was then quenched by the addition of 20 mL of water/ice. The resulting solution was extracted with 2×20 mL of dichloromethane. The combined organic layers were washed with 3×20 mL of aq $Na_2SO_3$, dried over anhydrous sodium sulfate, and concentrated. The residue was applied onto a silica gel column with ethyl acetate/petroleum ether (1:2). This resulted in 550 mg (72.41%) of 2-bromo-5-methoxypyridine 1-oxide as a light yellow solid. LCMS (ES) [M+1]$^+$ m/z: 204.

Step 3

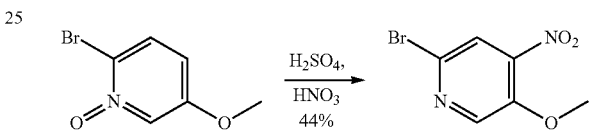

Into a 50-mL round-bottom flask, was placed $H_2SO_4$ (12.00 mL), 2-bromo-5-methoxypyridine 1-oxide (500.00 mg, 2.451 mmol, 1.00 equiv). This was followed by the addition of $HNO_3$ (8.00 mL, 0.127 mmol, 0.05 equiv) dropwise with stirring at 0° C. in 30 min. The resulting solution was stirred for 30 min at 0° C. in an ice/salt bath. The resulting solution was stirred for an additional 12 hr while the temperature was maintained at 100° C. in an oil bath. The resulting solution was diluted with 100 mL of ice water. The pH value of the solution was adjusted to 10 with NaOH (5 mol/L). The resulting mixture was extracted with 3×30 mL of ethyl acetate, and the combined organic layers were dried and concentrated. The residue was applied onto a silica gel column with ethyl acetate/petroleum ether (1:1). This resulted in 220 mg of 2-bromo-5-methoxy-4-nitropyridine as a light yellow solid. LCMS (ES) [M+1]$^+$ m/z: 233.

Step 4

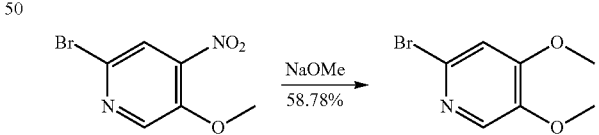

Into a 20-mL round-bottom flask was placed a solution of 2-bromo-5-methoxy-4-nitropyridine (200.00 mg, 0.858 mmol, 1.00 equiv) in MeOH (5 mL) and sodium methoxide (69.55 mg, 1.287 mmol, 1.50 equiv). The resulting solution was stirred for 3 hr at room temperature. The resulting solution was diluted with 20 mL of $H_2O$, extracted with 2×20 mL of dichloromethane. The combined organic layers were dried over anhydrous sodium sulfate and concentrated. This resulted in 110 mg (58.78%) of 2-bromo-4,5-dimethoxypyridine as an off-white solid. LCMS (ES) [M+1]$^+$ m/z: 218.

Step 5

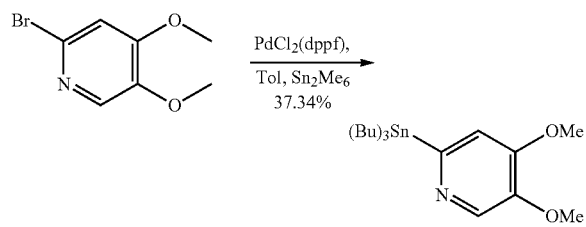

Into a 25-mL round-bottom flask purged and maintained in an inert atmosphere of nitrogen was placed a solution of 2-bromo-4,5-dimethoxypyridine (300.00 mg, 1.376 mmol, 1.00 equiv) in Tol (mL), Sn₂Me₆ (450.76 mg, 1.376 mmol, 1.00 equiv), and Pd(dppf)Cl₂ (1006.70 mg, 1.376 mmol, 1 equiv). The resulting solution was stirred for 3 hr at 100° C. in an oil bath. The resulting solution was diluted with 20 mL of H₂O, extracted with 2×20 mL of ethyl acetate. The combined organic layers were dried over anhydrous sodium sulfate and concentrated under vacuum. This resulted in 220 mg (37.34%) of 4,5-dimethoxy-2-(tributylstannyl)pyridine as a brown solid. LCMS (ES) [M+1]⁺ m/z: 430.

Step 6

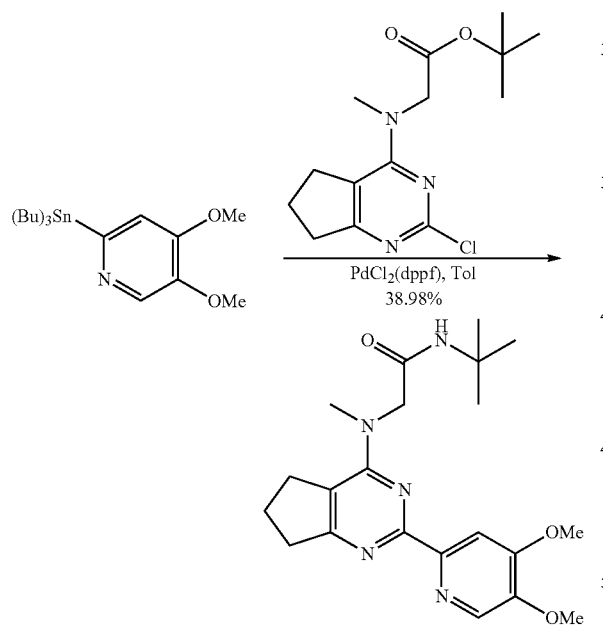

Into a 20-mL round-bottom flask purged and maintained in an inert atmosphere of nitrogen was placed a solution of 4,5-dimethoxy-2-(tributylstannyl)pyridine (220.00 mg, 0.514 mmol, 1.00 equiv) in Tol (6 mL), tert-butyl 2-([2-chloro-5H,6H,7H-cyclopenta[d]pyrimidin-4-yl](methyl) amino)acetate (152.99 mg, 0.514 mmol, 1 equiv), and Pd(dppf)Cl₂ (37.59 mg, 0.051 mmol, 0.10 equiv). The resulting solution was stirred for 12 hr at 100° C. in an oil bath. The resulting mixture was concentrated. The residue was applied onto a silica gel column with ethyl acetate/petroleum ether (1:1). The collected fractions were combined and concentrated. The crude product was purified by Flash-Prep-HPLC with the following conditions (IntelFlash-1): Column C18; mobile phase, ACN:H₂O (0.01% TFA)=1:20 increasing to ACN:H₂O (0.01% TFA)=1:5 within 15 min; Detector, UV 254 nm. This resulted in 80 mg (38.98%) of N-(tert-butyl)-2-((2-(4,5-dimethoxypyridin-2-yl)-6,7-dihydro-5H-cyclopenta[d]pyrimidin-4-yl)(methyl)amino)acetamide as a white solid. H NMR (300 MHz, DMSO-d₆) δ 8.24 (s, 1H), 7.92 (s, 1H), 7.64 (s, 1H), 4.16 (s, 2H), 3.93 (s, 3H), 3.91 (s, 3H), 3.25 (s, 3H), 3.13 (t, J=7.3 Hz, 2H), 2.81 (t, J=7.8 Hz, 2H), 2.03-1.95 (m, 2H), 1.22 (s, 9H). LCMS (ES) [M+1]⁺ m/z: 400.2.

Example 1.149

Synthesis of 2-{[2-(4-methoxypyridin-2-yl)-5H,6H,7H-cyclopenta[d]pyrimidin-4-yl](methyl)amino}-N-(3-methyloxolan-3-yl)acetamide (Compound 146)

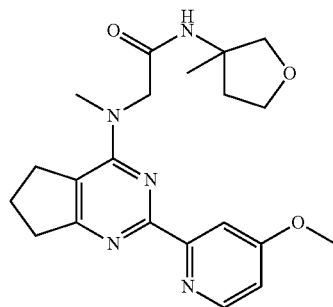

Scheme 96 depicts a synthetic route for preparing an exemplary compound.

Scheme 96

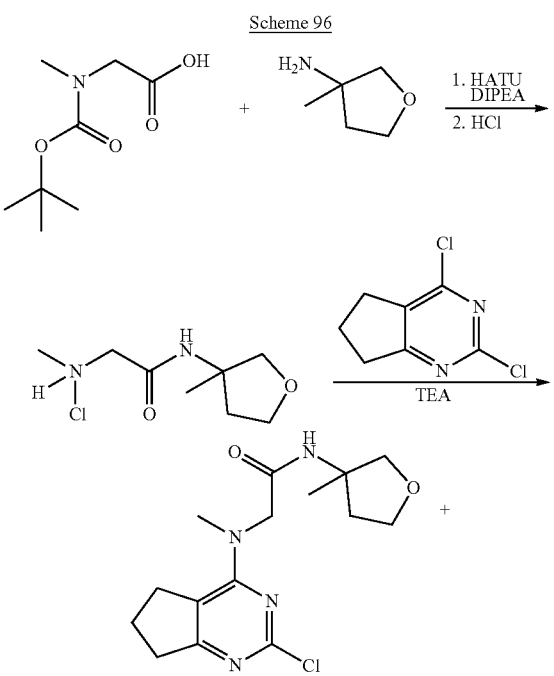

-continued

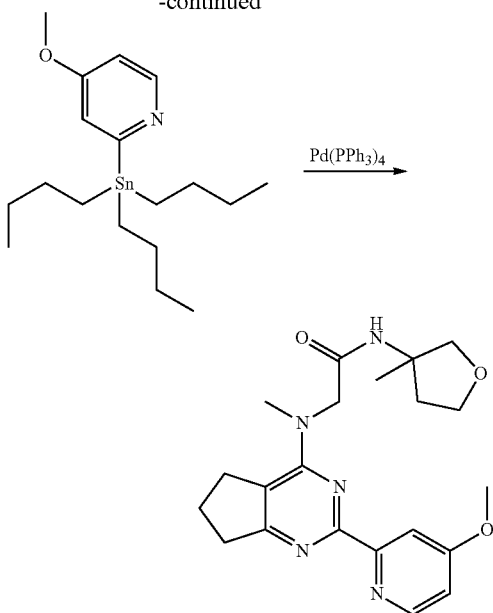

Step 1

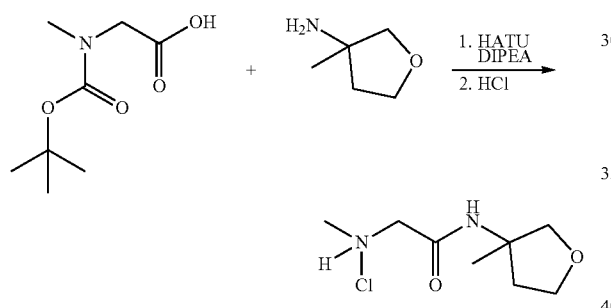

To a solution of [(tert-butoxycarbonyl)(methyl)amino]acetic acid (1.00 g; 5.29 mmol; 1.00 eq.) in DMF (15 mL) was added 3-methyloxolan-3-amine (0.53 g; 5.29 mmol; 1.00 eq.), followed by Hunig's base (1.38 mL; 0.01 mol; 1.50 eq.) and HATU (2.01 g; 0.01 mol; 1.00 eq.). After being stirred for 15 h at room temperature, the mixture was extracted with EtOAc, the organic layers were combined, dried, and concentrated to give desired crude product. The crude product was diluted with DCM (10 mL), to which was added 4N HCl in dioxane (10 mL). After completion, the mixture was concentrated and diluted with Sat. NaHCO₃. The aqueous layer was extracted with EtOAc, and then the organic layers were combined and concentrated to give 2-[chloro(methyl)amino]-N-(3-methyloxolan-3-yl)acetamide (2.80 g). LCMS (ES) [M+1]⁺ m/z: 173.4.
Step 2

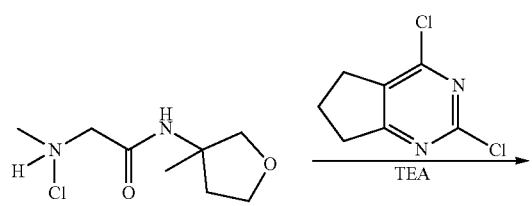

-continued

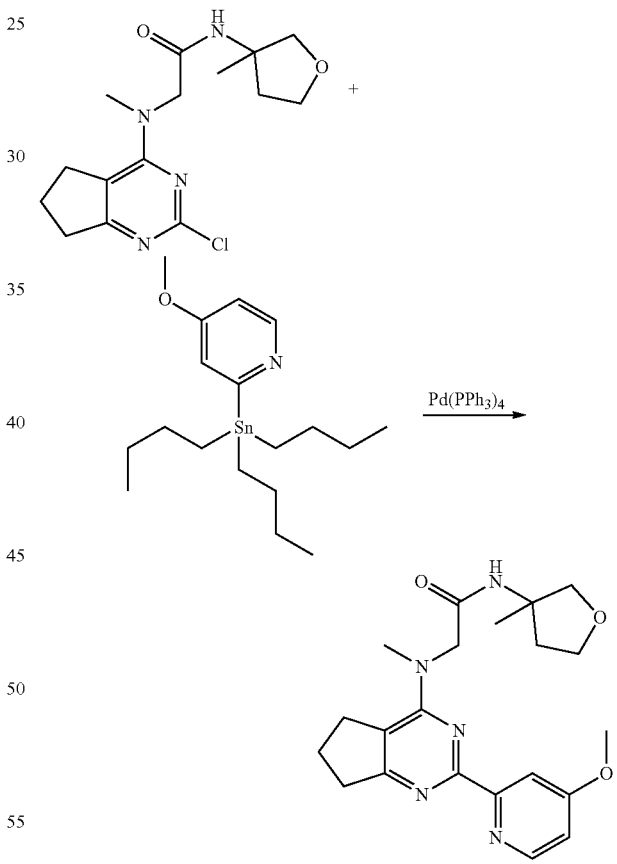

To a solution of 2,4-dichloro-6,7-dihydro-5H-cyclopenta[d]pyrimidine (0.66 g; 3.50 mmol; 1.00 eq.) in AcCN (10 mL) was added 2-[chloro(methyl)amino]-N-(3-methyloxolan-3-yl)acetamide (1.10 g; 5.25 mmol; 1.50 eq.) and triethylamine (1.96 mL; 14.00 mmol; 4.00 eq.). After being stirred at 80° C. for 15 h, the mixture was cooled to room temperature and concentrated to remove solvent. The residue was purified by column chromatography (DCM/MeOH=10:1) to give 2-({2-chloro-5H,6H,7H-cyclopenta[d]pyrimidin-4-yl}(methyl)amino)-N-(3-methyloxolan-3-yl)acetamide. LCMS (ES) [M+1]⁺ m/z: 325.1, 327.2.
Step 3

To a solution of 4-methoxy-2-(tributylstannyl)pyridine (183.88 mg; 0.46 mmol; 1.50 eq.) and 2-({2-chloro-5H,6H,7H-cyclopenta[d]pyrimidin-4-yl}(methyl)amino)-N-(3-methyloxolan-3-yl)acetamide (100.00 mg; 0.31 mmol; 1.00 eq.) in Toluene (1.0 mL) was added tetrakis(triphenylphosphane) palladium (35.58 mg; 0.03 mmol; 0.10 eq.). The mixture was degassed and heated at 105° C. for 15 h. HPLC indicated slow conversion. The mixture was concentrated and was added DMF (1 mL) more 4-methoxy-2-(tributylstannyl)pyridine (183.88 mg; 0.46 mmol; 1.50 eq.) and tetrakis(triphenylphosphane) palladium (35.58 mg; 0.03 mmol; 0.10 eq.). The mixture was heated further for 15 hr at 100° C., cooled. and diluted with water and AcCN and was subjected to purification by preparative HPLC to give N-tert-butyl-2-{ethyl[2-(4-methoxypyridin-2-yl)-5H,6H,7H-cyclopenta[d]pyrimidin-4-yl]amino}acetamide (16 mg). $^1$H NMR (400 MHz, Methanol-d$_4$) δ 8.62 (d, J=6.1 Hz, 1H), 8.06 (d, J=2.6 Hz, 1H), 7.35 (dd, J=6.1, 2.7 Hz, 1H), 4.49-4.33 (m, 2H), 4.07 (s, 3H), 3.96 (dd, J=13.9, 8.8 Hz, 1H), 3.94-3.81 (m, 2H), 3.61 (t, J=8.3 Hz, 1H), 3.51 (s, 3H), 3.33 (d, J=7.3 Hz, 2H), 3.13-2.94 (m, 2H), 2.30 (dq, J=13.3, 6.7 Hz, 1H), 2.26-2.13 (m, 2H), 2.07-1.86 (m, 1H), 1.45 (d, J=15.2 Hz, 3H). LCMS (ES) [M+1]$^+$ m/z: 398.0.

Example 1.150

Synthesis of 2-{methyl[2-(1-methyl-1H-imidazol-4-yl)-5H,6H,7H-cyclopenta[d]pyrimidin-4-yl]amino}-N-(3-methyloxolan-3-yl)acetamide (Compound 147)

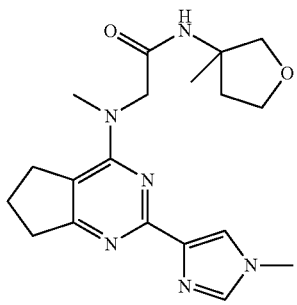 [SMILES: CN(CC(=O)NC1(C)CCOC1)c1nc(-c2cn(C)cn2)nc2c1CCC2]

Scheme 97 depicts a synthetic route for preparing an exemplary compound.

Scheme 97

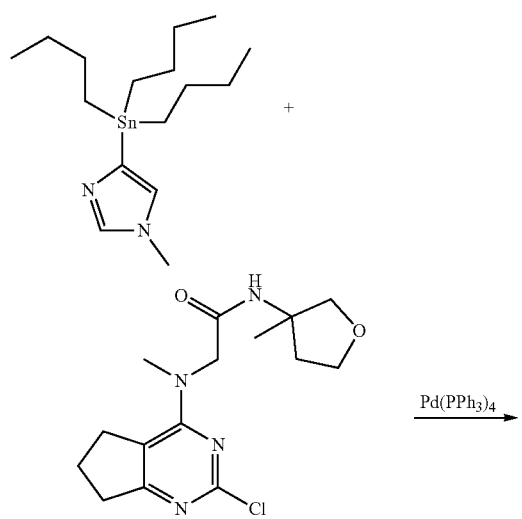

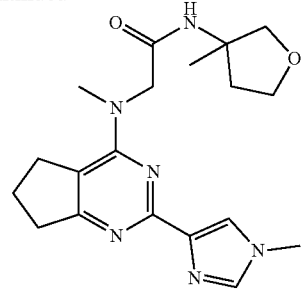

To a solution of 1-methyl-4-(tributylstannyl)-1H-imidazole (171.40 mg; 0.46 mmol; 1.50 eq.) and 2-({2-chloro-5H,6H,7H-cyclopenta[d]pyrimidin-4-yl}(methyl)amino)-N-(3-methyloxolan-3-yl)acetamide (100.00 mg; 0.31 mmol; 1.00 eq.) in DMF (1.0 mL) was added tetrakis(triphenylphosphane) palladium (35.58 mg; 0.03 mmol; 0.10 eq.). The mixture was degassed and heated at 105° C. for 15 h. The solution was cooled to room temperature and diluted with water and AcCN, and purified by preparative HPLC to give 2-{methyl[2-(1-methyl-1H-imidazol-4-yl)-5H,6H,7H-cyclopenta[d]pyrimidin-4-yl]amino}-N-(3-methyloxolan-3-yl)acetamide (26.6 mg). $^1$H NMR (400 MHz, Methanol-d$_4$) δ 8.74 (s, 1H), 8.37 (s, 1H), 4.60 (d, J=16.7 Hz, 1H), 4.52 (d, J=16.7 Hz, 1H), 4.02 (d, J=9.0 Hz, 1H), 4.00 (s, 3H), 3.96-3.82 (m, 2H), 3.56 (d, J=9.0 Hz, 1H), 3.51 (s, 3H), 3.30 (d, J=12.2 Hz, 2H), 3.10 (t, J=7.9 Hz, 2H), 2.33 (ddd, J=12.9, 7.6, 5.3 Hz, 1H), 2.23 (p, J=7.8 Hz, 2H), 1.95 (dt, J=12.9, 8.1 Hz, 1H), 1.46 (s, 3H). LCMS (ES) [M+1]$^+$ m/z: 371.0.

Example 1.151

Synthesis of 2-[methyl({2-[4-(2,2,2-trifluoroethoxy)pyridin-2-yl]-5H,6H,7H-cyclopenta[d]pyrimidin-4-yl})amino]-N-(1-methyl-1H-pyrazol-4-yl)acetamide (Compound 177)

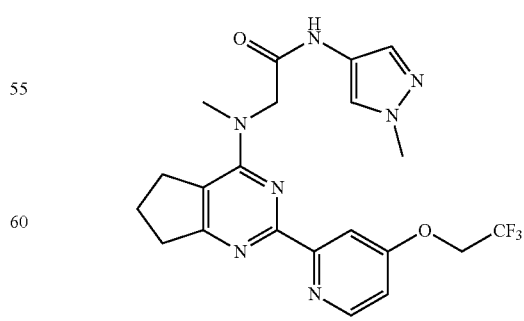

Scheme 98 depicts a synthetic route for preparing an exemplary compound.

Scheme 98

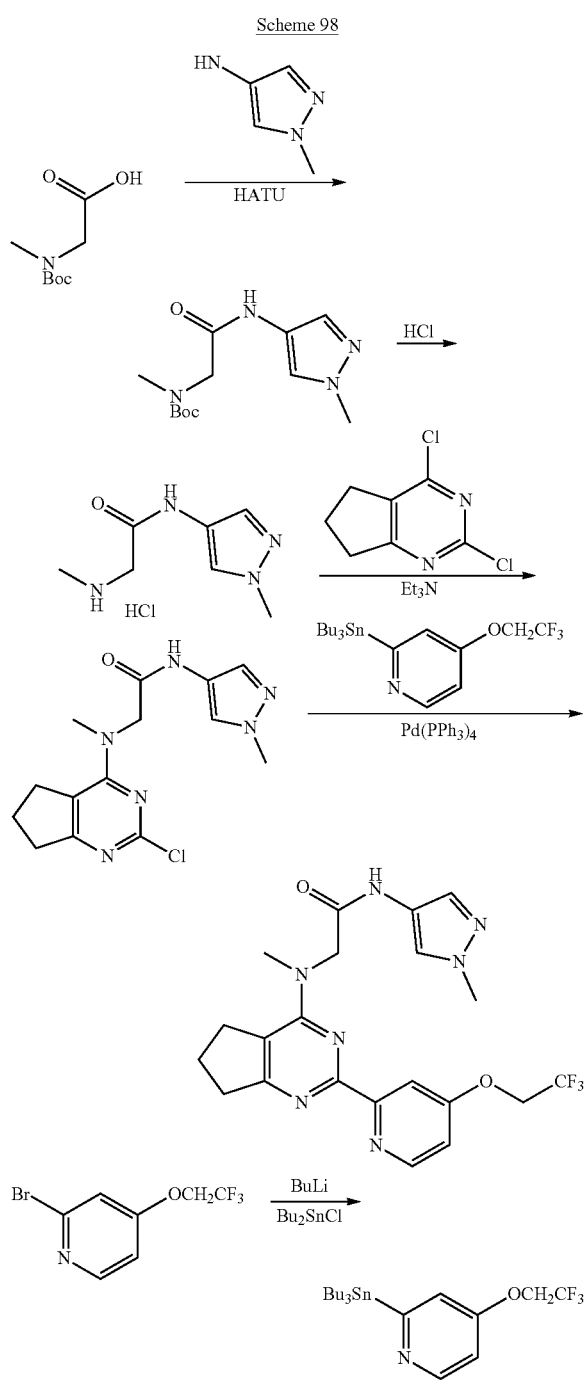

Step 1

To a solution of [(tert-butoxycarbonyl)(methyl)amino] acetic acid (2.00 g; 10.57 mmol; 1.00 eq.) in DMF (15 mL) was added 1-methyl-1H-pyrazol-4-ylamine (1.54 g; 15.86 mmol; 1.50 eq.), followed by Hunig's base (2.77 mL; 15.86 mmol; 1.50 eq.) and HATU (4.82 g; 12.68 mmol; 1.20 eq.). After being stirred for 4 h, the mixture was diluted with Sat. NaHCO₃, and the aqueous layer was extracted with EtOAc. The organic layers were combined, washed with brine, dried, and concentrated to give the crude product, which was purified by silica gel column chromatography (Hexanes/EtOAc=1:3) to give tert-butyl N-methyl-N-{[(1-methyl-1H-pyrazol-4-yl)carbamoyl]methyl}carbamate (2.75 g, 97% yield). LCMS (ES⁺): (M+Na)⁺=291.1.

Step 2

To a solution of tert-butyl N-methyl-N-{[(1-methyl-1H-pyrazol-4-yl)carbamoyl]methyl}carbamate (2.75 g; 10.25 mmol; 1.00 eq.) in DCM (5 mL) was added 4N HCl in dioxane (5 mL). The mixture was stirred for 2 h. HPLC was used to check that the reaction was finished. The suspension was concentrated to give 2-[chloro(methyl)amino]-N-(1-methyl-1H-pyrazol-4-yl)acetamide (2.15 g). LCMS (ES⁺): (M+H)⁺=169.1.

Step 3

To a solution of 2,4-dichloro-6,7-dihydro-5H-cyclopenta[d]pyrimidine (1.32 g; 7.00 mmol; 1.00 eq.) in AcCN (15 ml) was added triethylamine (2.94 mL; 21.01 mmol; 3.00 eq.) and 2-[chloro(methyl)amino]-N-(1-methyl-1H-pyrazol-4-yl)acetamide (2.15 g; 10.51 mmol; 1.50 eq.). The mixture was heated at 80° C. for 3 h and diluted with water. AcCN was removed under vacuum and the aqueous layer was extracted with EtOAc. The organic layers were combined, washed with brine, dried and concentrated. The resulting crude solid was washed with EtOAc, filtered, and dried to give 2-({2-chloro-5H,6H,7H-cyclopenta[d]pyrimidin-4-yl}(methyl)amino)-N-(1-methyl-1H-pyrazol-4-yl)acetamide as a white solid (1.61 g). LCMS (ES⁺): (M+H)⁺=321.1.

Step 4

Synthesis of the Stille tin reagent: To a solution of 2-bromo-4-(2,2,2-trifluoroethoxy)pyridine (310.00 mg; 1.21 mmol; 1.00 eq.) in toluene (10 ml) at −78° C. was added butyllithium (0.54 mL; 2.70 mol/L; 1.45 mmol; 1.20 eq.). After being stirred for 30 min at −78° C., to the mixture was added tributyl(chloro)stannane (0.36 mL; 1.33 mmol; 1.10 eq.). After being stirred for 30 min at −78° C., the solution was warmed to room temperature and further stirred for 2 h. The mixture was quenched with ice water and brine and extracted with hexane. The organic layers were combined, dried, and concentrated to give 2-(tributylstannyl)-4-(2,2,2-trifluoroethoxy)pyridine (590 mg).

To a solution of 2-({2-chloro-5H,6H,7H-cyclopenta[d]pyrimidin-4-yl}(methyl)amino)-N-(1-methyl-1H-pyrazol-4-yl)acetamide (175.00 mg; 0.55 mmol; 1.00 eq.) in DMF (2 mL) was added the above synthesized 2-(tributylstannyl)-4-(2,2,2-trifluoroethoxy)pyridine (508.64 mg; 1.09 mmol; 2.00 eq.) and tetrakis(triphenylphosphane) palladium (63.04 mg; 0.05 mmol; 0.10 eq.). After being degassed with N₂, the mixture was heated at 110 degree for 15 h. The mixture was cooled and diluted with AcCN/water, filtered, and the filtrate was subjected to purification by preparative HPLC to give 2-[methyl({2-[4-(2,2,2-trifluoroethoxy)pyridin-2-yl]-5H,6H,7H-cyclopenta[d]pyrimidin-4-yl})amino]-N-(1-methyl-1H-pyrazol-4-yl)acetamide (11.4 mg). LCMS (ES⁺): (M+H)⁺=462.1. ¹H NMR (400 MHz, DMSO-d₆) δ 10.74 (s, 1H), 8.68 (d, J=5.8 Hz, 1H), 7.94 (s, 1H), 7.50 (d, J=2.3 Hz, 1H), 7.43 (dd, J=5.8, 2.6 Hz, 1H), 6.33 (d, J=2.2 Hz, 1H), 5.01 (dd, J=9.3, 4.1 Hz, 2H), 4.61 (s, 2H), 3.69 (s, 3H), 3.51 (s, 3H), 3.31 (m, 2H), 3.01 (t, J=7.9 Hz, 2H), 2.14-2.03 (m, 2H).

Example 1.152

Synthesis of 2-({2-[4-(2-hydroxyethoxy)pyridin-2-yl]-5H,6H,7H-cyclopenta[d]pyrimidin-4-yl}(methyl)amino)-N-(6-methoxypyridin-3-yl)acetamide (Compound 187)

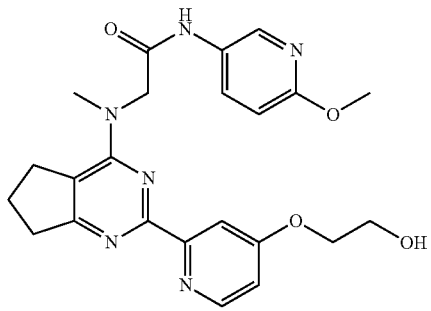 [SMILES: COc1ccc(NC(=O)CN(C)c2nc(-c3cc(OCCO)ccn3)nc3c2CCC3)cn1]

Scheme 99 depicts a synthetic route for preparing an exemplary compound.

Scheme 99

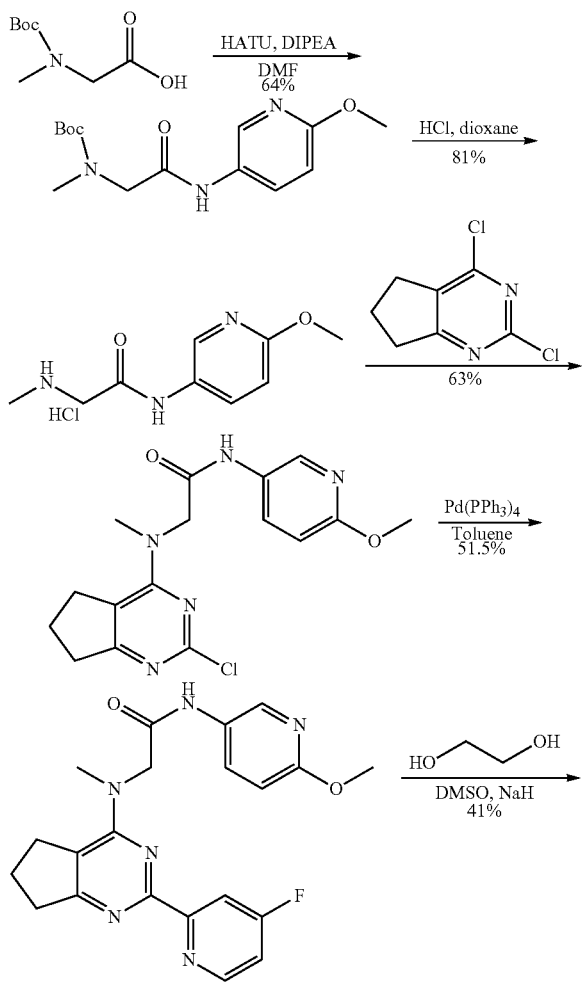

Step 1

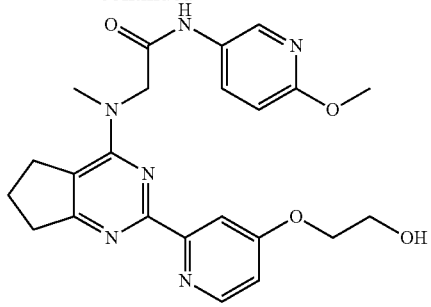

Into a 1 L 3-necked round-bottom flask was placed N-(tert-butoxycarbonyl)-N-methylglycine (40.0 g, 0.211 mol, 1.00 equiv), DMF (300 mL), 6-methoxypyridin-3-amine (28.8 g, 0.232 mol, 1.10 equiv), DIEA (54.4 g, 0.422 mmol, 2.00 equiv). This was followed by the addition of HATU (88.16 g, 0.232 mol, 1.10 equiv) in several batches at 0° C. After addition, the resulting solution was stirred for 16 h at room temperature. The reaction was quenched with 400 mL of water, extracted with 3×200 mL of ethyl acetate. The combined organic phase was washed with 2×400 mL of water and 1×400 mL brine, dried over anhydrous sodium sulfate and filtered. The filtrate was concentrated under reduced pressure, the residue was purified by silica gel column with ethyl acetate/petroleum ether (1:1). This resulted in 40 g (4%) of tert-butyl (2-((6-methoxypyridin-3-yl)amino)-2-oxoethyl)(methyl)carbamate as an off white solid. LCMS (ES) [M+1]$^+$ m/z: 296.

Step 2

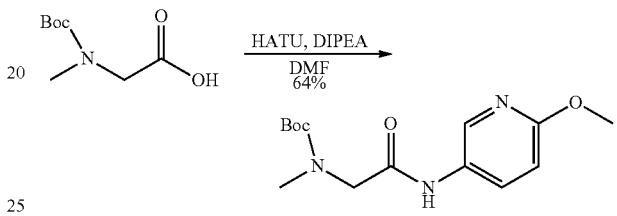

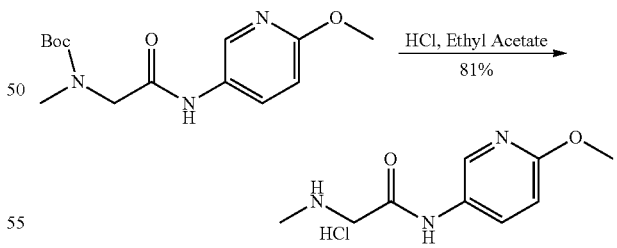

Into a 500-mL 3-round-bottom flask was placed tert-butyl (2-((6-methoxypyridin-3-yl)amino)-2-oxoethyl)(methyl)carbamate (40 g, 0.101 mol, 1.00 equiv), DCM (200.00 mL). This was followed by the addition of HCl (g) (2 M in ethyl acetate) (300.00 mL) dropwise with stirring at 0° C. The resulting solution was stirred for 16 h at room temperature, concentrated in vacuum to remove the solvent and washed with ethyl acetate (150 mL). This resulted in 25.5 g (81%) of N-(6-methoxypyridin-3-yl)-2-(methylamino)acetamide hydrochloride. LCMS (ES) [M−HCl+1]$^+$ m/z: 196.

Step 3

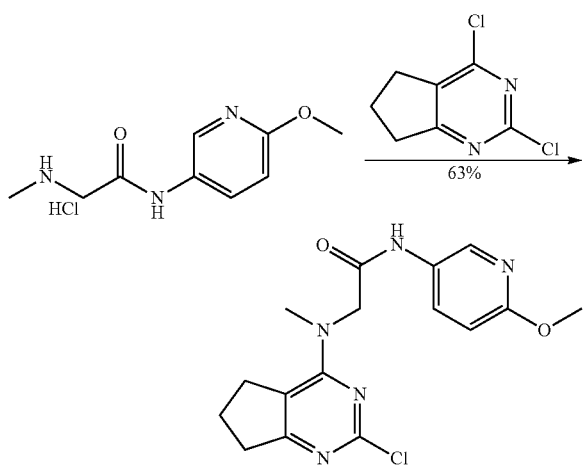

Into a 1 L 3 neck round-bottom flask was placed N-(6-methoxypyridin-3-yl)-2-(methylamino)acetamide hydrochloride (38.6 g, 0.167 mol, 1.05 equiv), NMP (300.00 mL), 2,4-dichloro-6,7-dihydro-5H-cyclopenta[d]pyrimidine (30 g, 0.158 mol, 1.00 equiv), DIEA (61.15 g, 0.474 mol, 3.00 equiv). The resulting solution was stirred for 18 h at 50° C. in oil bath. The reaction mixture was cooled to room temperature, diluted with 200 mL of water, extracted with 3×200 mL of ethyl acetate. The combined organic phase was washed with 3×300 ml of water and brine 200 mL, dried over anhydrous sodium sulfate and filtered. The filtrate was concentrated under reduced pressure, the residue was purified by silica gel column with THF/petroleum ether (1:1). This resulted in 35 g (63%) of 2-((2-chloro-6,7-dihydro-5H-cyclopenta[d]pyrimidin-4-yl)(methyl)amino)-N-(6-methoxypyridin-3-yl)acetamide as a white solid. LCMS (ES) [M+1]$^+$ m/z: 348.

Step 4

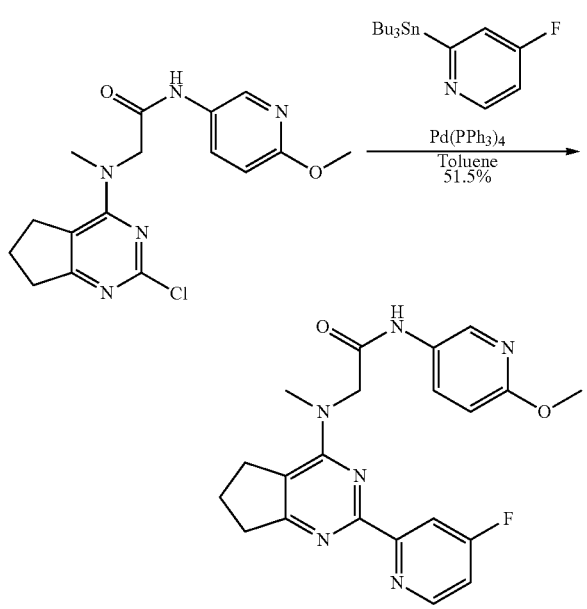

Into a 500-mL three necked round bottom flask purged and maintained with an inert atmosphere of nitrogen was placed 2-((2-chloro-6,7-dihydro-5H-cyclopenta[d]pyrimidin-4-yl)(methyl)amino)-N-(6-methoxypyridin-3-yl)acetamide (10 g, 28.8 mmol, 1.00 equiv), toluene (150 mL), 4-fluoro-2-(tributylstannyl)pyridine (20 g, 51.84 mmol, 1.8 equiv) and Pd(PPh$_3$)$_4$ (3.04 g, 2.88 mmol, 0.10 equiv). The mixture was stirred for 36 h at 110° C. in oil bath. The reaction was repeated in 2 batches. The reaction mixture was cooled to room temperature, concentrated to remove the solvent, the residue was purified by silica gel column with PE/THF (100:1 to 1:10). This resulted in 12.1 g (51.5%) of 2-((2-(4-fluoropyridin-2-yl)-6,7-dihydro-5H-cyclopenta[d]pyrimidin-4-yl)(methyl)amino)-N-(6-methoxypyridin-3-yl)acetamide as yellow oil. LCMS (ES) [M+1]$^+$ m/z: 409.

Step 5

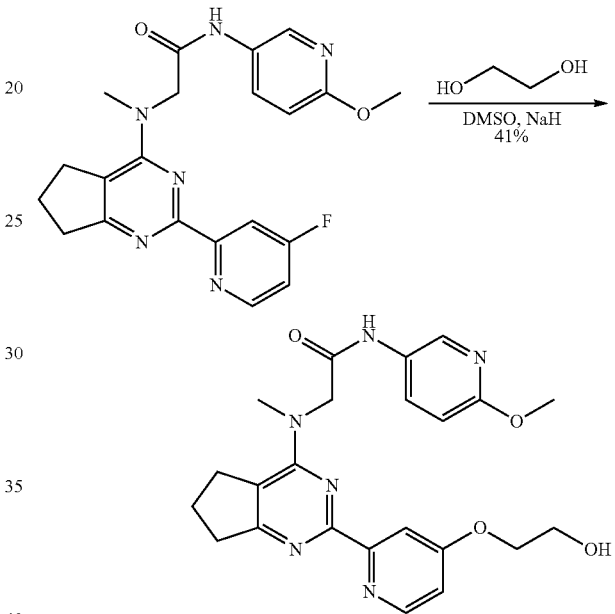

Into a 250 mL 3-neck flask was placed ethane-1,2-diol (4.78 g, 77.0 mmol, 5.0 equiv) and DMSO (100 mL), NaH (60% in mineral oil) (3.08 g, 77.0 mmol, 5.0 equiv) was added in portion wise at 5° C. The mixture was stirred for 1 h at room temperature. After which 2-((2-(4-fluoropyridin-2-yl)-6,7-dihydro-5H-cyclopenta[d]pyrimidin-4-yl)(methyl)amino)-N-(6-methoxypyridin-3-yl)acetamide (6.3 g, 15.4 mmol, 1.00 equiv) was added at 5° C. The reaction mixture was stirred for 5 h at room temperature. (The reaction was repeated in 2 batches). The reaction mixture was poured into 200 mL of stirred water, extracted with 3×200 mL of ethyl acetate. The combined organic phase was washed with 3×300 ml of water and brine 1×200 mL, dried over anhydrous sodium sulfate. The residue was purified by Prep-HPLC with conditions: column, C18-800 g, Mobile phase, CH$_3$CN/H$_2$O (0.05% FA), from 10% increased to 70% within 27 min, Flow rate, 180 mL/min, Detector, 254 nm. The pH value of the fraction was adjusted to 7~8 with K$_2$CO$_3$ solid, extracted with dichloromethane (3×300 mL). The combined organic phase was dried over anhydrous sodium sulfate and filtered. The filtrate was concentrated under reduced pressure. The residue was freeze dried to give 5.7 g (41%) of 2-((2-(4-(2-hydroxyethoxy)pyridin-2-yl)-6,7-dihydro-5H-cyclopenta[d]pyrimidin-4-yl)(methyl)amino)-N-(6-methoxypyridin-3-yl)acetamide as a white solid. LCMS: (ES, m/z): [M+H]$^+$: 451.2. $^1$H-NMR: (300

MHz, DMSO-d$_6$, ppm): δ 10.27 (s, 1H), 8.44 (d, J=5.6 Hz, 1H), 8.35 (d, J=2.6 Hz, 1H), 7.89 (dd, J=8.9, 2.7 Hz, 1H), 7.79 (d, J=2.5 Hz, 1H), 7.01 (dd, J=5.7, 2.6 Hz, 1H), 6.78 (d, J=8.9 Hz, 1H), 4.91 (t, J=5.4 Hz, 1H), 4.41 (s, 2H), 4.04 (t, J=4.8 Hz, 2H), 3.80 (s, 3H), 3.69 (q, J=5.1 Hz, 2H), 3.37 (s, 3H), 3.20 (t, J=7.3 Hz, 2H), 2.83 (t, J=7.8 Hz, 2H), 2.08-1.96 (m, 2H).
Example 1.153
Synthesis of N-tert-butyl-2-[(2-{4-[2-(dimethyl-amino)ethoxy]pyridin-2-yl}-5H,6H,7H-cyclopenta[d]pyrimidin-4-yl)(methyl)amino]acetamide (Compound 348)
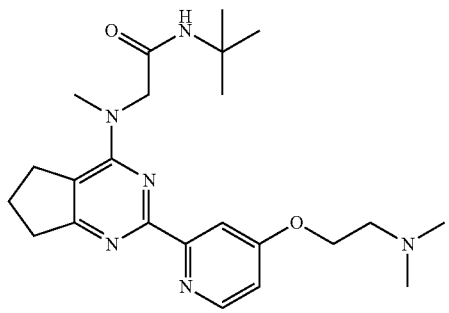 [SMILES: CN(C)CCOc1ccnc(-c2nc3c(c(N(C)CC(=O)NC(C)(C)C)n2)CCC3)c1]
Scheme 100 depicts a synthetic route for preparing an exemplary compound.
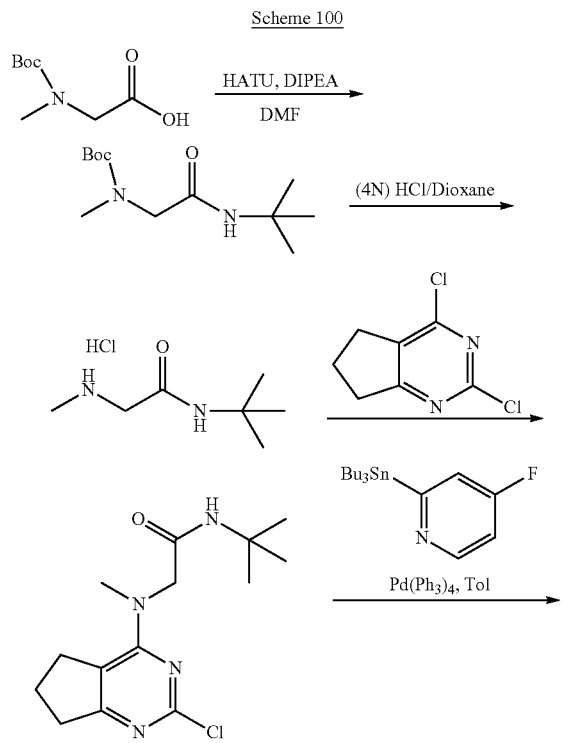
Step 1: Addition of Fluoropyridine
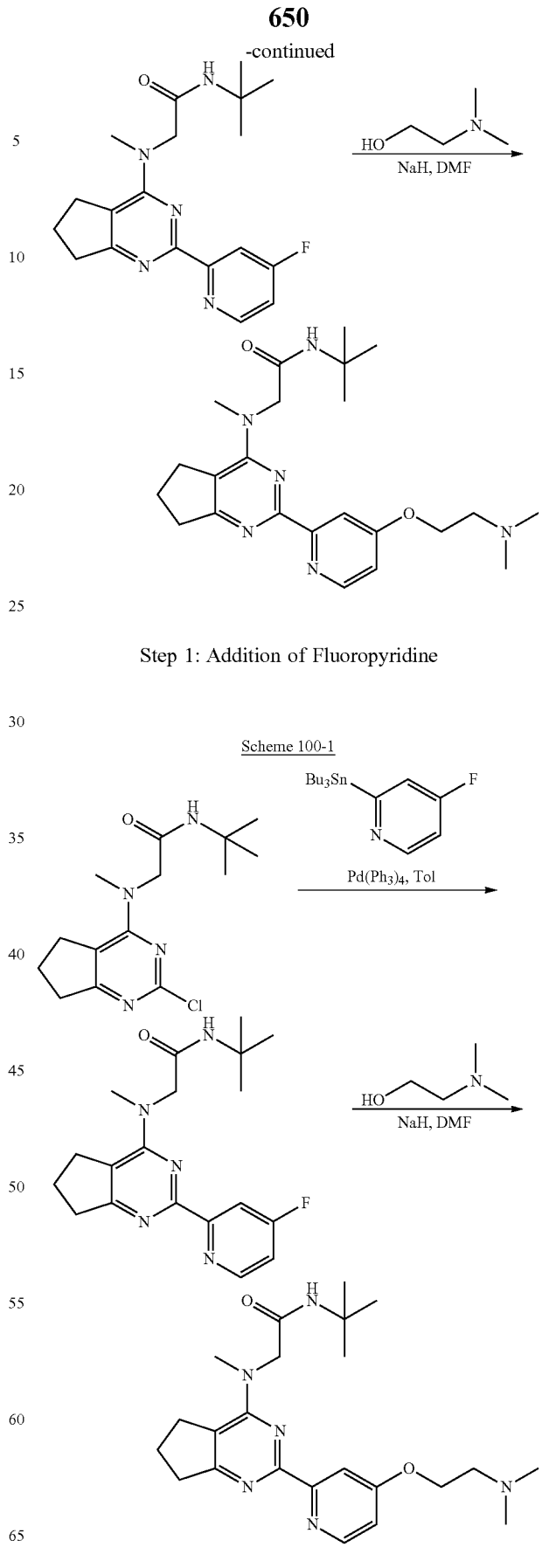

Into a 250-mL three-necked round bottom flask purged and maintained with an inert atmosphere of nitrogen were placed N-(tert-butyl)-2-((2-chloro-6,7-dihydro-5H-cyclopenta[d]pyrimidin-4-yl)(methyl)amino)acetamide (10 g, 33.8 mmol, 1.00 equiv), toluene (150.00 mL), 4-fluoro-2-(tributylstannyl)pyridine (21.7 g, 60.84 mmol, 1.8 equiv), and Pd(PPh$_3$)$_4$ (3.57 g, 3.38 mmol, 0.10 equiv). After being stirred for 60 h at 110° C. in an oil bath, the reaction mixture was cooled to room temperature, and concentrated to remove the solvent; the residue was purified by silica gel column with dichloromethane/methanol (10:1). This resulted in 7 g (58%) of N-(tert-butyl)-2-((2-(4-fluoropyridin-2-yl)-6,7-dihydro-5H-cyclopenta[d]pyrimidin-4-yl)(methyl) amino)acetamide as a yellow solid. LCMS (ES) [M+1]$^+$ m/z: 358.

Step 2: Addition of 2-(dimethylamino)ethan-1-ol

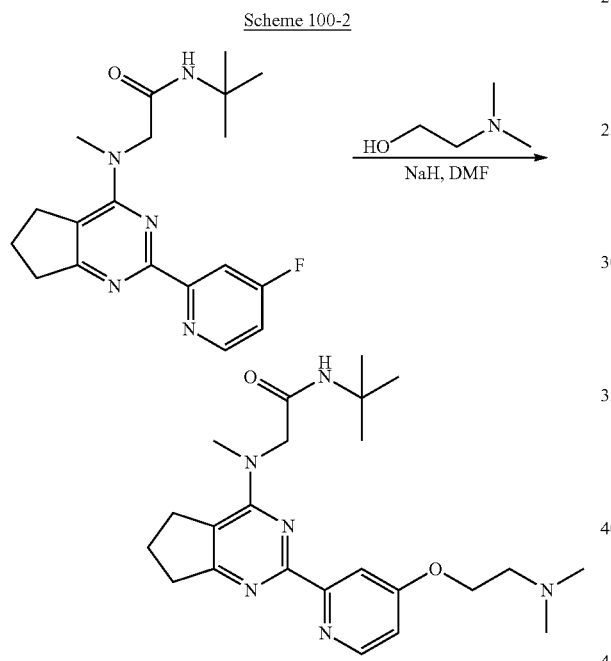

Scheme 100-2

Into a 50 mL 3-neck flask were placed 2-(dimethylamino)ethan-1-ol (112 mg, 1.26 mmol, 3.0 equiv) and DMF (2 mL). NaH (60% in mineral oil) (33.6 mg, 0.84 mmol, 2.0 equiv) was added portion-wise at 0-5° C. After being stirred for 1 h, to the mixture was added N-(tert-butyl)-2-((2-(4-fluoropyridin-2-yl)-6,7-dihydro-5H-cyclopenta[d]pyrimidin-4-yl)(methyl)amino)acetamide (150 mg, 0.42 mmol, 1.00 equiv) at 0-5° C. The reaction mixture was then stirred for 5 h at 50° C. After being cooled down to ambient temperature, the reaction mixture was concentrated, and the residue was purified by Prep-HPLC with the following conditions: column, C18-800 g, Mobile phase, CH$_3$CN/H$_2$O (0.05% FA), from 10% increased to 70% within 27 min, Flow rate, 80 mL/min, Detector, 254 nm. The pH value of the fraction was adjusted to 7~8 with Na$_2$CO$_3$, and the mixture was extracted with dichloromethane (3×300 mL). The combined organic phases were dried over anhydrous sodium sulfate, filtered, and the filtrate was concentrated under reduced pressure. This resulted in 100.9 mg (56%) of N-(tert-butyl)-2-((2-(4-(2-(dimethylamino)ethoxy)pyridin-2-yl)-6,7-dihydro-5H-cyclopenta[d]pyrimidin-4-yl)(methyl)amino)acetamide as a white solid. LCMS (ES, m/z): [M+H]$^+$: 427. $^1$H NMR (300 MHz, DMSO-d$_6$) δ 8.47 (d, J=5.6 Hz, 1H), 7.83 (d, J=2.5 Hz, 1H), 7.67 (s, 1H), 7.05 (dd, J=5.6, 2.6 Hz, 1H), 4.20 (t, J=5.7 Hz, 2H), 4.12 (s, 2H), 3.31 (s, 3H), 3.15 (t, J=7.2 Hz, 2H), 2.81 (t, J=7.8 Hz, 2H), 2.66 (t, J=5.7 Hz, 2H), 2.23 (s, 6H), 2.05-1.94 (m, 2H), 1.25 (s, 9H).

Alternative Method: For Preparing Compound 348

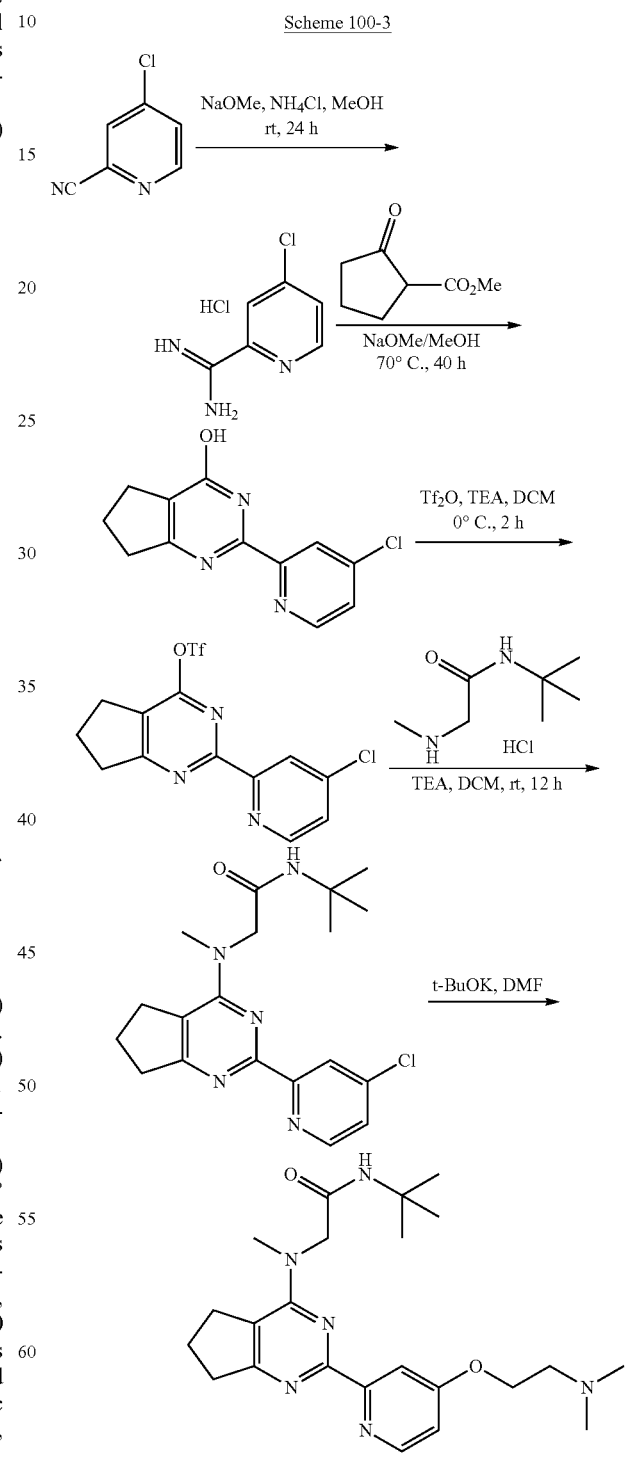

Scheme 100-3

Into a 500 mL round-bottom flask were added 4-chloropicolinonitrile (50 g, 360 mmol, 1.00 equiv) in MeOH and NaOMe (1.95 g, 36.1 mmol, 0.1 equiv). The mixture was stirred for 8 hours at room temperature under a nitrogen atmosphere, and NH$_4$Cl (29.0 g, 541 mmol, 1.5 equiv) was added. The resulting mixture was further stirred for 16 hours at room temperature under a nitrogen atmosphere. The resulting mixture was filtered, the filtrate was concentrated under reduced pressure. This resulted in 4-chloropicolinimidamide hydrochloride (63.0 g, 90.90%) as a brown solid. LCMS (ES) [M−HCl+1]$^+$ m/z 156.

Scheme 100-4

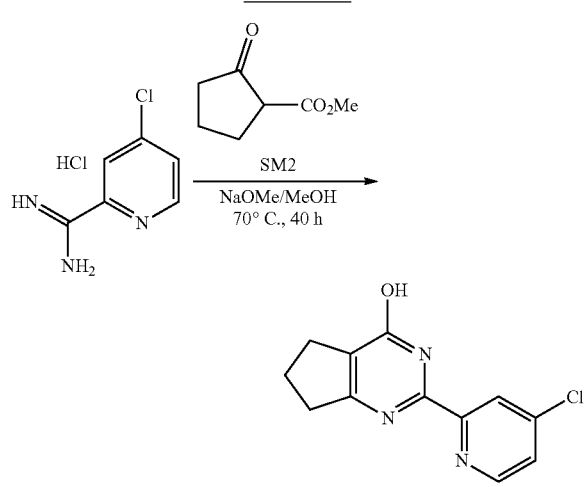

Into a 1 L round-bottom flask were added 4-chloropicolinimidamide hydrochloride (60.0 g, 312 mmol, 1.00 equiv) in MeOH (600 mL), methyl 2-oxocyclopentane-1-carboxylate (66.6 g, 468 mmol, 1.5 equiv), and NaOMe (42.18 g, 781 mmol, 2.5 equiv) in MeOH at room temperature. The mixture was stirred for 40 hours at 70° C. under a nitrogen atmosphere. The precipitated solids were collected by filtration and washed with MeOH (1×1 500 mL). This resulted in 2-(4-chloropyridin-2-yl)-6,7-dihydro-5H-cyclopenta[d]pyrimidin-4-ol (62 g, 80.12%) as a brown solid. LCMS (ES) [M+1]$^+$ m/z 248.

Scheme 100-5

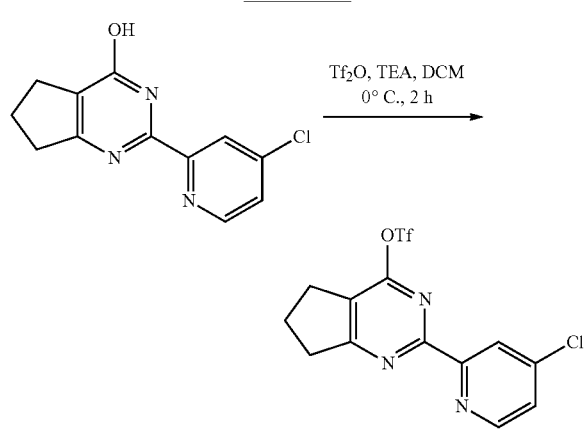

Into a 1 L 3-necked round-bottom flask were added 2-(4-chloropyridin-2-yl)-6,7-dihydro-5H-cyclopenta[d]pyrimidin-4-ol (60 g, 242 mmol, 1.00 equiv) in DCM and TEA (123 g, 1211 mmol, 5.0 equiv). A stirred mixture of Tf$_2$O (137 g, 484 mmol, 2.0 equiv) in DCM was added dropwise at 0° C. The resulting mixture was stirred for an additional 2 hours at 0° C. The reaction was quenched by the addition of NH$_4$Cl (aq. 500 mL) at room temperature. The resulting mixture was extracted with DCM (3×600 mL), and the organic layers were combined and dried over anhydrous Na$_2$SO$_4$. The resulting mixture was filtered, and the filtrate was concentrated under reduced pressure. The residue was purified by silica gel column chromatography, eluted with PE/EA (3.1) to afford 2-(4-chloropyridin-2-yl)-6,7-dihydro-5H-cyclopenta[d]pyrimidin-4-yl trifluoromethanesulfonate (63 g, 68.48) as an off-white solid. LCMS (ES) [M+1]$^+$ m/z 380.

Scheme 100-6

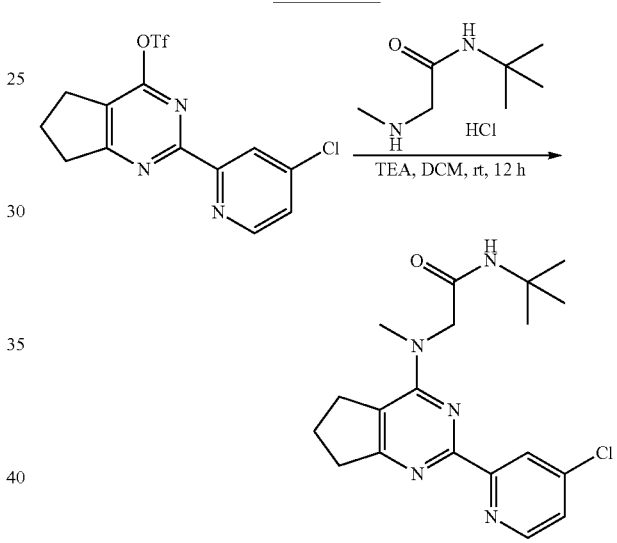

Into a 500 mL three-necked round bottom flask were added 2-(4-chloropyridin-2-yl)-6,7-dihydro-5H-cyclopenta[d]pyrimidin-4-yl trifluoromethanesulfonate (24.0 g, 63.3 mmol, 1.00 equiv), TEA (25.6 g, 253.2 mmol, 4.00 equiv), and dichloromethane (300 mL). This was followed by the addition of N-(tert-butyl)-2-(methylamino)acetamide hydrochloride (14.8 g, 82.3 mmol, 1.30 equiv) at room temperature. After being stirred for 12 h, the reaction was quenched with H$_2$O (200 mL), extracted with dichloromethane (100 mL*1), and the organic layer was separated and dried over anhydrous sodium sulfate. The mixture was filtered, and the filtrate was concentrated under reduced pressure. The residue was triturated in ethyl acetate/hexane (1:3). The solid was collected by filtration and dried under an infrared lamp for 3 h. This resulted in 21.3 g (90%) N-(tert-butyl)-2-((2-(4-chloropyridin-2-yl)-6,7-dihydro-5H-cyclopenta[d]pyrimidin-4-yl)(methyl)amino)acetamide as an off-white solid. LCMS (ES, m/z): [M+H]$^+$: 374.

Scheme 100-7

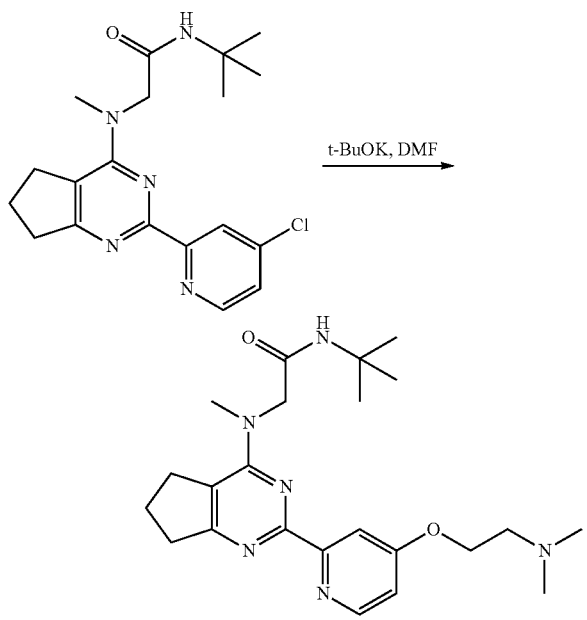

Into a 250 mL three-necked round bottom flask were added 2-(dimethylamino)ethan-1-ol (2.86 g, 32.17 mmol, 2.00 equiv) and DMF (80 mL). This was followed by the addition of t-BuOK (3.6 g, 32.17 mmol, 2.00 equiv) at room temperature. The mixture was stirred for 0.5 h, N-(tert-butyl)-2-((2-(4-chloropyridin-2-yl)-6,7-dihydro-5H-cyclopenta[d]pyrimidin-4-yl)(methyl)amino)acetamide (6.0 g, 16.08 mmol, 1.00 equiv) was added to the above mixture and stirred for additional 5 h at 60° C. The reaction mixture was cooled to room temperature, quenched with H₂O (100 mL), and extracted with ethyl acetate (100 mL*2). The combined organic phases were washed with brine (100 mL*2) and dried over anhydrous sodium sulfate. The mixture was filtered, and the filtrate was concentrated under reduced pressure. The residue was purified by Prep-HPLC with the following conditions: C18-500 g, CH₃CN/H₂O (NH₄HCO₃ 0.1%), from 15% to 70% in 30 min, Flow rate, 150 mL/min, Detector, UV 254 nm. This resulted in 5.5 g (80.29%) N-(tert-butyl)-2-((2-(4-(2-(dimethylamino)ethoxy)pyridin-2-yl)-6,7-dihydro-5H-cyclopenta[d]pyrimidin-4-yl)(methyl)amino)acetamide as a brown solid. The solid was triturated in CH₃CN (120 mL), collected by filtration and dried to give N-tert-butyl-2-[(2-{4-[2-(dimethylamino)ethoxy]pyridin-2-yl}-5H,6H,7H-cyclopenta[d]pyrimidin-4-yl)(methyl)amino]acetamide (5.5 g, 98.8%). LCMS (ES, m/z): [M+H]⁺: 427. ¹H NMR (300 MHz, DMSO-d6) δ 8.47 (d, J=5.6 Hz, 1H), 7.84 (d, J=2.5 Hz, 1H), 7.68 (s, 1H), 7.05 (dd, J=5.7, 2.6 Hz, 1H), 4.20 (t, J=5.7 Hz, 2H), 4.12 (s, 2H), 3.26 (s, 3H), 3.14 (t, J=7.3 Hz, 2H), 2.81 (t, J=7.8 Hz, 2H), 2.67 (t, J=5.6 Hz, 2H), 2.23 (s, 6H), 2.01-1.96 (m, 2H), 1.24 (s, 9H).

Example 1.154

Synthesis of N-(2,3-dihydro-1H-inden-1-yl)-N-methyl-2-(pyridin-2-yl)-5H,6H,7H-cyclopenta[d]pyrimidin-4-amine

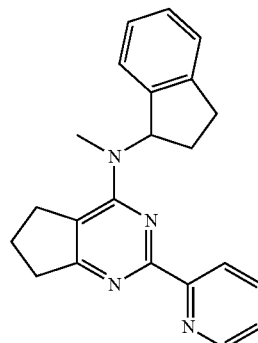

The title compound was synthesized in a similar manner to that of compound 92 by replacing azapane with N-methyl-1-indanamine. MS (ES+): (M+H)⁺=342.9. ¹H NMR (400 MHz, Chloroform-d) δ 8.78 (d, J=5.6 Hz, 1H), 8.38 (d, J=7.9 Hz, 1H), 7.83-7.74 (m, 1H), 7.36 (dd, J=7.6, 4.8 Hz, 1H), 7.32-7.27 (m, 1H), 7.25-7.14 (m, 2H), 6.44 (t, J=8.2 Hz, 1H), 3.21 (t, J=7.3 Hz, 2H), 3.14-3.03 (m, 3H), 3.03-2.91 (m, 4H), 2.56-2.43 (m, 1H), 2.18-2.05 (m, 3H).

Example 1.155

Synthesis of 2-{4-[(5aS,8aS)-octahydro-2H-cyclopenta[b][1,4]oxazepin-5-yl]-5H,6H,7H-cyclopenta[d]pyrimidin-2-yl}pyridine (Compound 18)

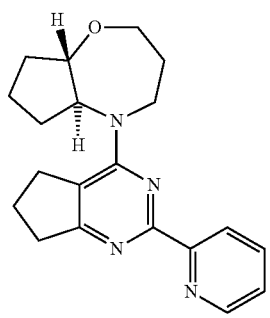

Scheme 101

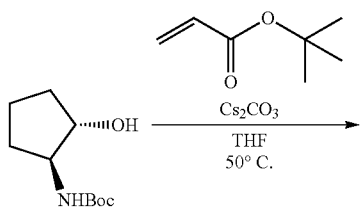

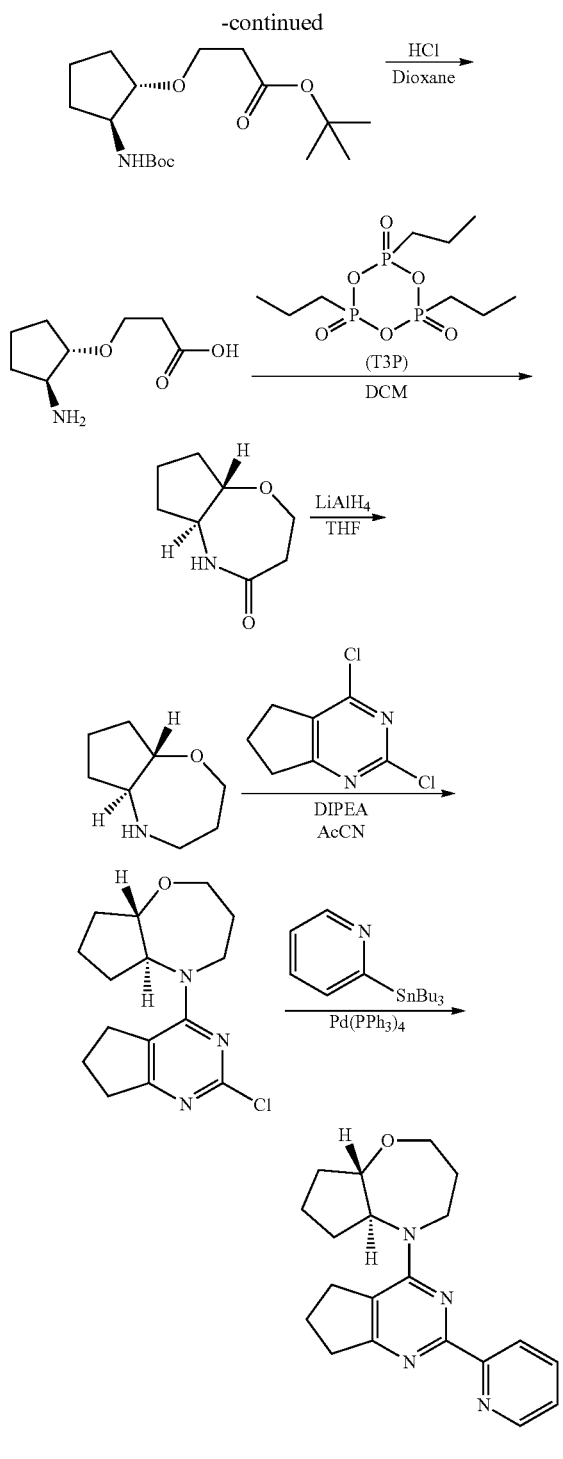

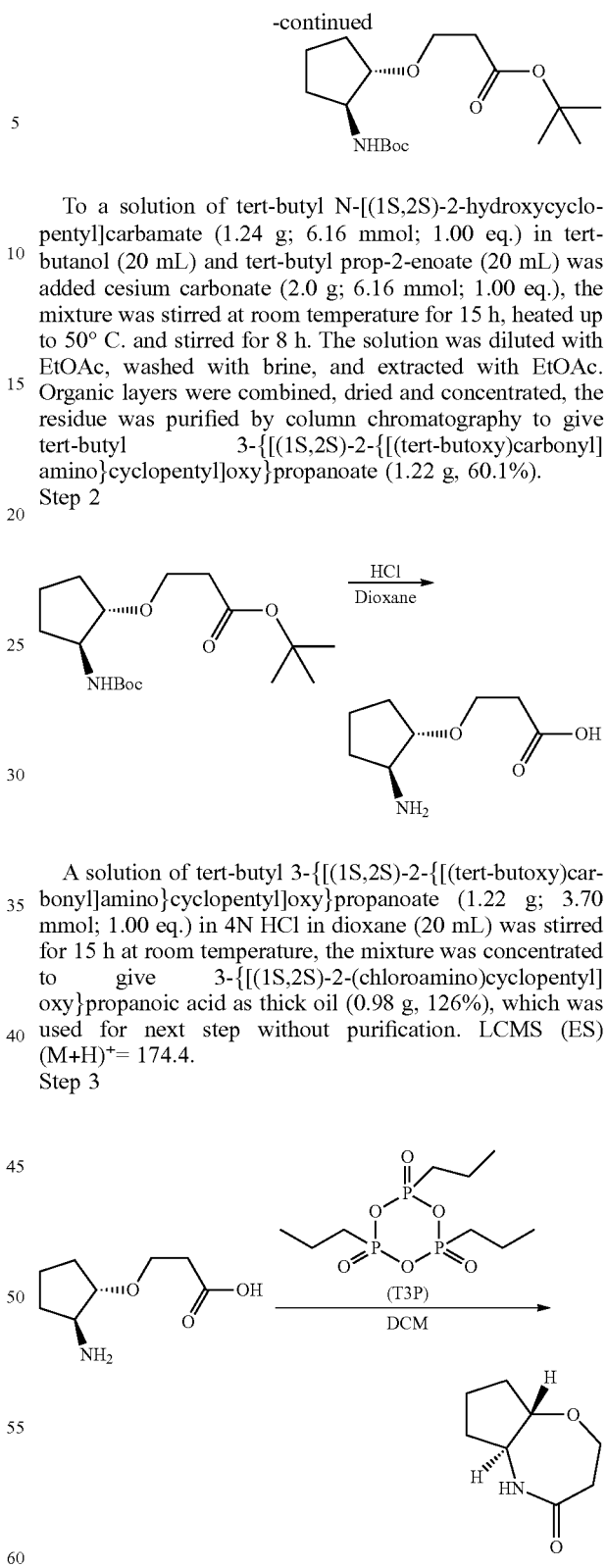

To a solution of tert-butyl N-[(1S,2S)-2-hydroxycyclopentyl]carbamate (1.24 g; 6.16 mmol; 1.00 eq.) in tert-butanol (20 mL) and tert-butyl prop-2-enoate (20 mL) was added cesium carbonate (2.0 g; 6.16 mmol; 1.00 eq.), the mixture was stirred at room temperature for 15 h, heated up to 50° C. and stirred for 8 h. The solution was diluted with EtOAc, washed with brine, and extracted with EtOAc. Organic layers were combined, dried and concentrated, the residue was purified by column chromatography to give tert-butyl 3-{[(1S,2S)-2-{[(tert-butoxy)carbonyl]amino}cyclopentyl]oxy}propanoate (1.22 g, 60.1%).

Step 2

A solution of tert-butyl 3-{[(1S,2S)-2-{[(tert-butoxy)carbonyl]amino}cyclopentyl]oxy}propanoate (1.22 g; 3.70 mmol; 1.00 eq.) in 4N HCl in dioxane (20 mL) was stirred for 15 h at room temperature, the mixture was concentrated to give 3-{[(1S,2S)-2-(chloroamino)cyclopentyl]oxy}propanoic acid as thick oil (0.98 g, 126%), which was used for next step without purification. LCMS (ES) $(M+H)^+$= 174.4.

Step 3

To a solution of 3-{[(1S,2S)-2-aminocyclopentyl]oxy}propanoic acid (1.00 g; 5.77 mmol; 1.00 eq.) in DCM (125 mL) was added Hunig's base (5.03 mL; 28.87 mmol; 5.00 eq.) and 2,4,6-tripropyl-1,3,5,2,4,6-trioxatriphosphinane 2,4,6-trioxide (5.16 mL; 8.66 mmol; 1.50 eq.), after stirred at room temperature for 15 h, HPLC check desired Step 1

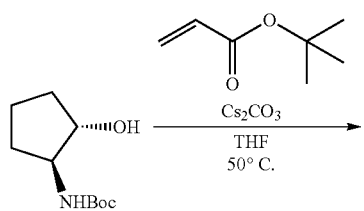

mass found. The mixture was concentrated and the residue was purified by column chromatography (DCM/MeOH=10:1) to give (5aS,8aS)-octahydro-2H-cyclopenta[b][1,4]oxazepin-4-one (460 mg, 51%). LCMS (ES) (M+H)$^+$=156.2.

Step 4

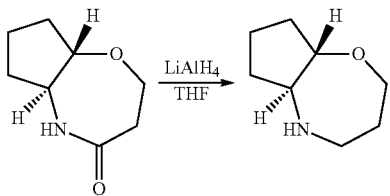

To a solution of (5aS,8aS)-octahydro-2H-cyclopenta[b][1,4]oxazepin-4-one (200.00 mg; 1.29 mmol; 1.00 eq.) in THF (4.5 mL) was added lithium aluminum hydride (1.29 mL; 2.00 mol/L; 2.58 mmol; 2.00 eq.) at room temperature. The mixture was then heated at 55° C. for 2 h, additional 1 eq of LiAH$_4$ was added. After 30 min, 1 more eq of LiAH$_4$ was added, after stirred for another 30 min, the mixture was cooled in ice batch, added 0.4 mL of water and 0.1 mL of 4M NaOH, the suspension was diluted with EtOAc (30 mL) and filtered through celite, the filtrate was concentrated to give (5aS,8aS)-octahydro-2H-cyclopenta[b][1,4]oxazepane (175 mg, 96%), which was used for next step without further purification. LCMS (ES) (M+H)$^+$=142.2.

Step 5

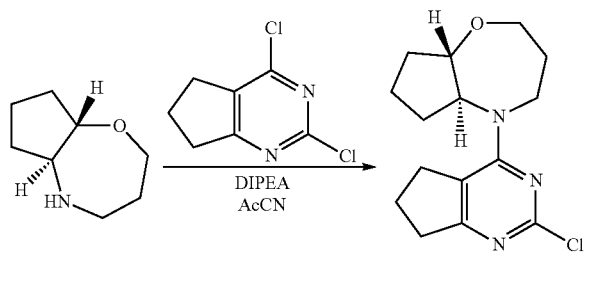

To a solution of 2,4-dichloro-6,7-dihydro-5H-cyclopenta[d]pyrimidine (100.00 mg; 0.53 mmol; 1.00 eq.) and (5aS,8aS)-octahydro-2H-cyclopenta[b][1,4]oxazepine (93.37 mg; 0.66 mmol; 1.25 eq.) in AcCN (1 mL) was added DIPEA (0.18 mL; 1.06 mmol; 2.00 eq.) at room temperature. The reaction mixture was stirred for 30 min at ambient temperature, and 80° C. degree for overnight. The solution was concentrated and the crude oil was purified by column chromatography (Hexanes/EtOAc=2:1) to give 4-[(5aS,8aS)-octahydro-2H-cyclopenta[b][1,4]oxazepin-5-yl]-2-chloro-5H,6H,7H-cyclopenta[d]pyrimidine (130 mg, 83.6% yield). LCMS (ES) (M+H)$^+$=293.5.

Step 6

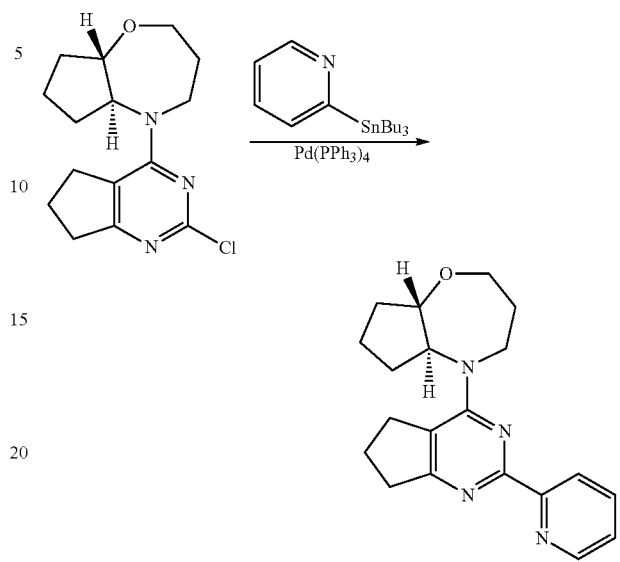

To a solution of 4-[(5aS,8aS)-octahydro-2H-cyclopenta[b][1,4]oxazepin-5-yl]-2-chloro-5H,6H,7H-cyclopenta[d]pyrimidine (136.00 mg; 0.46 mmol; 1.00 eq.) in Toluene (2 mL) was added 2-(tributylstannyl)pyridine (255.63 mg; 0.69 mmol; 1.50 eq.) followed by tetrakis(triphenylphosphane)palladium (53.49 mg; 0.05 mmol; 0.10 eq.). The solution was heated at 105° C. for 15 h, cooled and concentrated to give crude product, which was purified by preparative HPLC to give 2-{4-[(5aS,8aS)-octahydro-2H-cyclopenta[b][1,4]oxazepin-5-yl]-5H,6H,7H-cyclopenta[d]pyrimidin-2-yl}pyridine (101 mg, 64.5%). LCMS (ES) (M+H)$^+$=337.3.
$^1$H NMR (400 MHz, DMSO-d6) δ 8.74 (d, J=4.7 Hz, 1H), 8.31 (d, J=7.9 Hz, 1H), 8.01 (td, J=7.7, 1.8 Hz, 1H), 7.57 (dd, J=7.5, 4.8 Hz, 1H), 4.40 (dd, J=15.3, 5.9 Hz, 1H), 4.23 (tt, J=17.0, 10.0 Hz, 2H), 3.91-3.83 (m, 1H), 3.73 (dd, J=15.4, 10.9 Hz, 1H), 3.52 (td, J=12.1, 2.5 Hz, 1H), 3.12 (dp, J=29.5, 7.3, 6.9 Hz, 2H), 2.91 (t, J=7.9 Hz, 2H), 2.44-2.32 (m, 1H), 2.03 (dd, J=10.8, 5.0 Hz, 2H), 2.01-1.83 (m, 2H), 1.78 (q, J=9.5, 8.4 Hz, 1H), 1.71 (t, J=4.3 Hz, 1H), 1.70-1.63 (m, 1H), 1.56 (p, J=10.2 Hz, 1H), 1.44-1.30 (m, 1H).

Example 1.156

Synthesis of 2-{4-[(5aS,8aS)-octahydro-2H-cyclopenta[b][1,4]oxazepin-5-yl]-5H,6H,7H-cyclopenta[d]pyrimidin-2-yl}-4-methylpyridine (Compound 45)

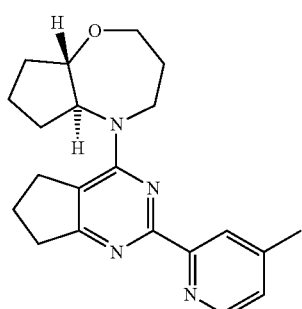

Compound 45 was synthesized similar to Compound 18 by replacing 2-(tributylstannyl)pyridine with 2-(tributylstannyl)pyridine. LCMS (ES) [M+1]+ m/z 351. ¹H NMR (400 MHz, DMSO-d6) δ 8.52 (d, J=4.9 Hz, 1H), 8.10 (d, J=15.7 Hz, 1H), 7.28 (d, J=4.9 Hz, 1H), 4.38 (dd, J=15.1, 5.9 Hz, 1H), 4.18 (dtd, J=23.0, 10.0, 7.0 Hz, 2H), 3.91-3.82 (m, 1H), 3.64 (dd, J=15.3, 10.8 Hz, 1H), 3.49 (td, J=12.0, 2.5 Hz, 1H), 3.16-3.00 (m, 2H), 2.83 (dd, J=8.7, 7.1 Hz, 2H), 2.41 (s, 1H), 2.39 (s, 3H), 2.00 (p, J=7.6 Hz, 2H), 1.94-1.84 (m, 2H), 1.79-1.63 (m, 3H), 1.55 (p, J=10.3 Hz, 1H), 1.40-1.25 (m, 1H).

Example 1.157

Synthesis of 1-[2-(pyridin-2-yl)-5H,6H,7H-cyclopenta[d]pyrimidin-4-yl]azepan-2-one (Compound 46)

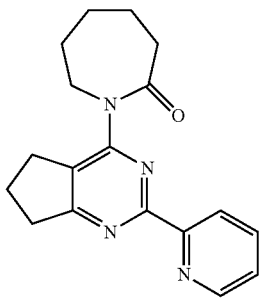 [SMILES: O=C1CCCCCN1c1nc(-c2ccccn2)nc2c1CCC2]

Scheme 102

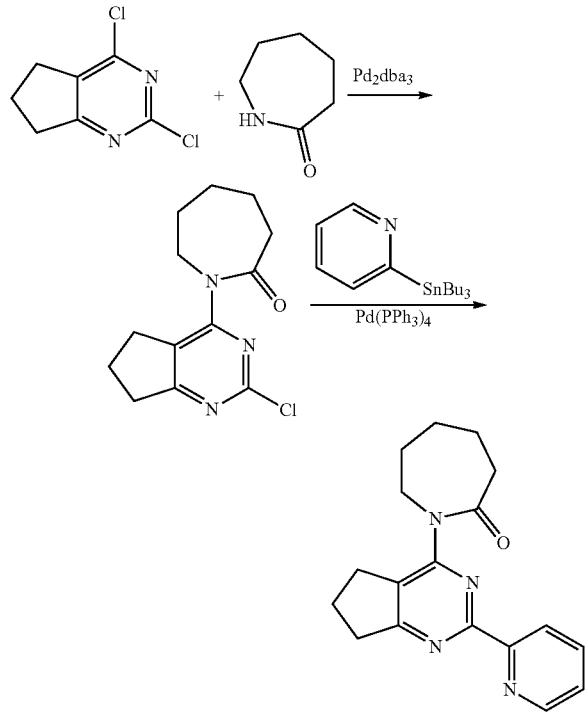

Step 1

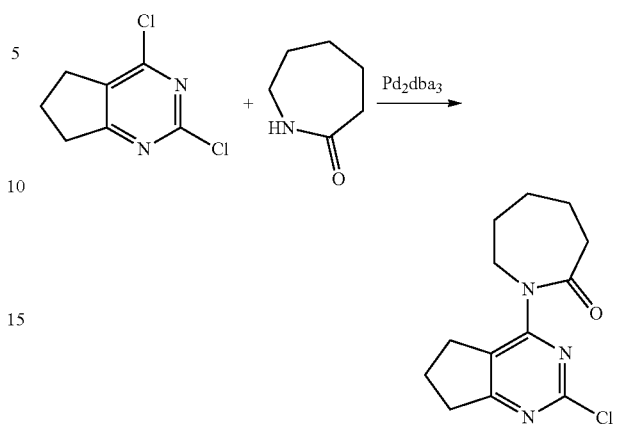

To a solution of 2,4-dichloro-6,7-dihydro-5H-cyclopenta[d]pyrimidine (100.00 mg; 0.53 mmol; 1.00 eq.) and 2-azepanone (65.84 mg; 0.58 mmol; 1.10 eq.) in Dioxane (2 mL) was added Cesium carbonate (258.53 mg; 0.79 mmol; 1.50 eq.), Xantphos (30.61 mg; 0.05 mmol; 0.10 eq.) and Tris(dibenzylideneacetone)dipalladium(0) (24.22 mg; 0.03 mmol; 0.05 eq.). After heated at 100° C. for 3 h, the mixture was diluted with AcCN, filtered through celite, the filtrate was concentrated and purified by preparative HPLC to give 1-{2-chloro-5H,6H,7H-cyclopenta[d]pyrimidin-4-yl}azepan-2-one (16 mg, 11% yield). LCMS (ES) (M+H)+= 342.7.

Step 2

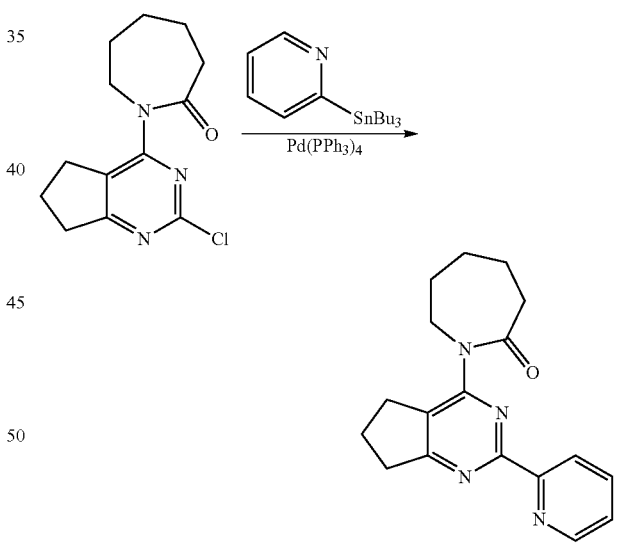

To a solution of 2-(tributylstannyl)pyridine (44.33 mg; 0.12 mmol; 2.00 eq.) and 1-{2-chloro-5H,6H,7H-cyclopenta[d]pyrimidin-4-yl}azepan-2-one (16.00 mg; 0.06 mmol; 1.00 eq.) in toluene (1 mL) was added tetrakis(triphenylphosphane) palladium (6.96 mg; 0.01 mmol; 0.10 eq.), after degassed and heated at 100° C. overnight, it was concentrated and the residue was subjected to purification by preparative HPLC to give 1-[2-(pyridin-2-yl)-5H,6H,7H-cyclopenta[d]pyrimidin-4-yl]azepan-2-one (5.4 mg, 29.1%). LCMS (ES) (M+H)+=308.9. ¹H NMR (400 MHz, DMSO-d₆) δ 8.77-8.71 (m, 1H), 8.30 (d, J=8.0 Hz, 1H), 7.99 (dd, J=8.5, 6.8 Hz, 1H), 7.54-7.47 (m, 1H), 3.92 (d, J=8.4 Hz, 2H), 2.95 (t, J=7.8 Hz, 2H), 2.64 (d, J=10.5 Hz, 2H), 2.15-2.03 (m, 2H), 1.80-1.68 (m, 8H).

Example 1.158

Synthesis of 2-{4-[(5aS,8aR)-octahydro-2H-cyclopenta[b][1,4]oxazepin-5-yl]-5H,6H,7H-cyclopenta[d]pyrimidin-2-yl}pyridine (Compound 48)

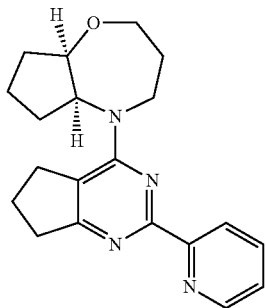 [SMILES: c1ccc(-c2nc3c(c(N4CCCO[C@@H]5CCC[C@@H]54)n2)CCC3)nc1]

Compound 48 was synthesized similar to Compound 18 by replacing tert-butyl N-[(1S,2S)-2-hydroxycyclopentyl]carbamate with tert-butyl N-[(1S,2R)-2-hydroxycyclopentyl]carbamate. LCMS (ES) [M+1]$^+$ m/z: 337.1. $^1$H NMR (400 MHz, Methanol-d$_4$) δ 8.69 (dt, J=4.8, 1.3 Hz, 1H), 8.33 (dd, J=8.0, 1.1 Hz, 1H), 7.95 (td, J=7.8, 1.8 Hz, 1H), 7.50 (ddd, J=7.6, 4.8, 1.2 Hz, 1H), 5.04-4.93 (m, 1H), 4.16 (dt, J=14.1, 4.1 Hz, 1H), 4.00 (s, 1H), 4.02-3.92 (m, 1H), 3.68 (ddd, J=15.2, 10.6, 5.2 Hz, 1H), 3.43 (ddd, J=12.5, 9.9, 6.2 Hz, 1H), 3.22-3.11 (m, 2H), 3.14-3.04 (m, 1H), 2.97 (t, J=7.9 Hz, 2H), 2.23-1.84 (m, 7H), 1.81-1.58 (m, 2H).

Example 1.159

Synthesis of 2-{4-[(5aS,8aR)-octahydro-2H-cyclopenta[b][1,4]oxazepin-5-yl]-5H,6H,7H-cyclopenta[d]pyrimidin-2-yl}-4-methylpyridine (Compound 49)

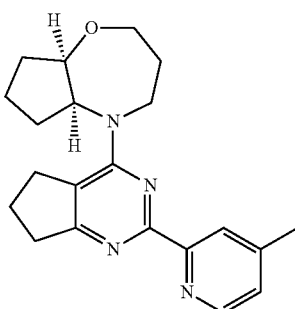

Compound 49 was synthesized similar to Compound 18 by replacing tert-butyl N-[(1S,2S)-2-hydroxycyclopentyl]carbamate with tert-butyl N-[(1S,2R)-2-hydroxycyclopentyl]carbamate and replacing 2-(tributylstannyl)pyridine with 2-(tributylstannyl)pyridine. LCMS (ES) [M+1]$^+$ m/z: 351.3. $^1$H NMR (400 MHz, Methanol-d$_4$) δ 8.54 (d, J=5.0 Hz, 1H), 8.15 (s, 1H), 7.37 (dd, J=5.2, 1.6 Hz, 1H), 5.00 (dq, J=10.5, 4.5 Hz, 1H), 4.19 (dt, J=14.6, 4.2 Hz, 1H), 3.99 (ddd, J=15.8, 6.6, 3.4 Hz, 2H), 3.69 (ddd, J=15.2, 10.5, 5.3 Hz, 1H), 3.44 (ddd, J=12.5, 9.9, 6.3 Hz, 1H), 3.23-3.12 (m, 1H), 3.16-3.05 (m, 2H), 2.98 (t, J=7.9 Hz, 2H), 2.47 (s, 3H), 2.24-1.85 (m, 7H), 1.82-1.58 (m, 2H).

Example 1.160

Synthesis of 2-{4-[(5aS,8aR)-octahydro-2H-cyclopenta[b][1,4]oxazepin-5-yl]-5H,6H,7H-cyclopenta[d]pyrimidin-2-yl}-4-methoxypyridine (Compound 54)

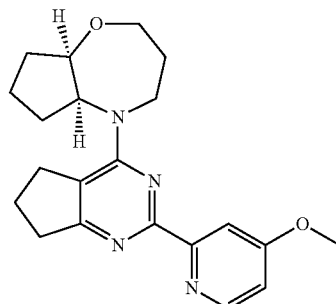

Compound 54 was synthesized similar to Compound 18 by replacing tert-butyl N-[(1S,2S)-2-hydroxycyclopentyl]carbamate with tert-butyl N-[(1S,2R)-2-hydroxycyclopentyl]carbamate and replacing 2-(tributylstannyl)pyridine with 4-methoxy-2-(tributylstannyl)pyridine. LCMS (ES) [M+1]$^+$ m/z: 367.2. $^1$H NMR (400 MHz, Methanol-d$_4$) δ 8.50 (d, J=5.8 Hz, 1H), 7.87 (d, J=2.6 Hz, 1H), 7.10 (dd, J=5.9, 2.6 Hz, 1H), 4.98 (td, J=9.7, 8.9, 4.3 Hz, 1H), 4.14 (dt, J=14.6, 4.2 Hz, 1H), 4.05-3.93 (m, 2H), 3.96 (s, 3H), 3.68 (ddd, J=15.2, 10.5, 5.2 Hz, 1H), 3.44 (ddd, J=12.5, 10.0, 6.2 Hz, 1H), 3.22-3.12 (m, 1H), 3.14-3.04 (m, 1H), 2.95 (t, J=7.9 Hz, 2H), 2.23-1.84 (m, 5H), 2.03 (s, 3H), 1.81-1.69 (m, 1H), 1.69-1.59 (m, 1H).

Example 1.161

Synthesis of N-(1-hydroxy-2-methylpropan-2-yl)-2-({2-[4-(2-hydroxyethoxy)pyridin-2-yl]-5H,6H,7H-cyclopenta[d]pyrimidin-4-yl}(methyl)amino)acetamide (Compound 148)

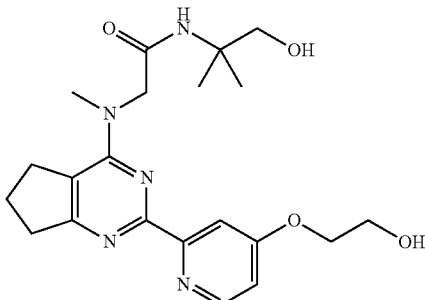

Compound 148 was synthesized similar to Compound 144 by replacing cyclohexylamine with 2-amino-2-methyl-1-propanol. LCMS (ES) [M+1]$^+$ m/z 416. $^1$H NMR (300 MHz, DMSO-d$_6$) δ 8.47 (d, J=5.6 Hz, 1H), 7.84 (d, J=2.6 Hz, 1H), 7.50 (s, 1H), 7.04 (dd, J=5.6, 2.6 Hz, 1H), 4.90 (br, 1H), 4.28-4.07 (m, 4H), 3.76 (t, J=5.0 Hz, 2H), 3.37 (s, 2H), 3.25 (s, 3H), 3.14 (t, J=7.3 Hz, 2H), 2.82 (t, J=7.8 Hz, 2H), 2.05-1.94 (m, 2H), 1.18 (s, 6H).

Example 1.162

Synthesis of 2-({2-[4-(2-hydroxyethoxy)pyridin-2-yl]-5H,6H,7H-cyclopenta[d]pyrimidin-4-yl}(methyl)amino)-N-(oxolan-3-yl)acetamide (Compound 149)

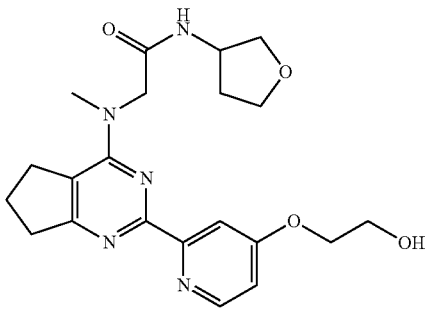 [SMILES: CN(CC(=O)NC1CCOC1)c1nc(-c2cc(OCCO)ccn2)nc2c1CCC2]

Compound 149 was synthesized similar to Compound 144 by replacing cyclohexylamine with oxolan-3-amine hydrochloride. LCMS (ES) [M+1]⁺ m/z 414. ¹H NMR (300 MHz, DMSO-d$_6$, ppm): δ 8.46 (d, J=5.6 Hz, 1H), 8.37 (d, J=6.9 Hz, 1H), 7.80 (d, J=2.6 Hz, 1H), 7.04 (dd, J=5.6, 2.6 Hz, 1H), 5.22-4.75 (m, 1H), 4.34-4.12 (m, 5H), 3.83-3.52 (m, 5H), 3.49-3.39 (m, 1H), 3.27 (s, 3H), 3.15 (t, J=7.3 Hz, 2H), 2.82 (t, J=7.8 Hz, 2H), 2.15-1.89 (m, 3H), 1.79-1.68 (m, 1H).

Example 1.163

Synthesis of N-cyclopentyl-2-{methyl[2-(1-methyl-1H-imidazol-4-yl)-5H,6H,7H-cyclopenta[d]pyrimidin-4-yl]amino}acetamide (Compound 150)

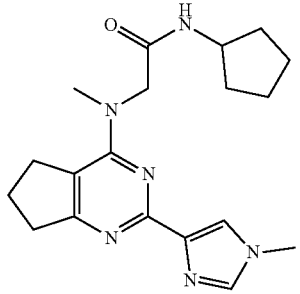 [SMILES: CN(CC(=O)NC1CCCC1)c1nc(-c2cn(C)cn2)nc2c1CCC2]

Compound 150 was synthesized similar to Compound 142 by replacing cyclohexylamine with cyclopentanamine. LCMS (ES, m/z): [M+H]⁺: 355. ¹H-NMR (300 MHz, DMSO-d$_6$, ppm): δ 8.05 (d, J=7.5 Hz, 1H), 7.71 (s, 1H), 7.60 (s, 1H), 4.11 (s, 2H), 4.02 (q, J=6.6, 13.5 Hz, 1H), 3.69 (s, 3H), 3.22 (s, 3H), 3.07 (t, J=7.5 Hz, 2H), 2.73 (t, J=7.8 Hz, 2H), 1.99-1.89 (m, 2H), 1.80-1.72 (m, 2H), 1.63-1.34 (m, 6H).

Example 1.164

Synthesis of 2-{[2-(4-methoxypyridin-2-yl)-5H,6H,7H-cyclopenta[d]pyrimidin-4-yl](methyl)amino}-N-(6-methoxypyridin-3-yl)acetamide (Compound 151)

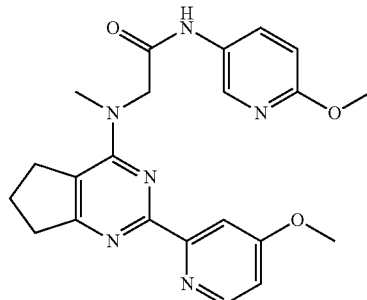

Compound 151 was synthesized similar to Compound 135 by replacing oxolan-3-amine with 5-amino-2-methoxypyridine. LCMS (ES, m/z): [M+H]⁺: 421. ¹H-NMR (300 MHz, DMSO-d$_6$, ppm): δ 10.26 (s, 1H), 8.45 (d, J=5.4 Hz, 1H), 8.34 (d, J=2.7 Hz, 1H), 7.87 (dd, J=9.0, 2.7 Hz, 1H), 7.79 (d, J=2.7 Hz, 1H), 7.01 (dd, J=5.4, 2.4 Hz, 1H), 6.78 (d, J=9.0 Hz, 1H), 4.40 (s, 2H), 3.80 (s, 3H), 3.79 (s, 3H), 3.37 (s, 3H), 3.21 (t, J=7.5 Hz, 2H), 2.83 (t, J=7.8 Hz, 2H), 2.08-1.94 (m, 2H).

Example 1.165

Synthesis of N-(5-methoxypyridin-2-yl)-2-{[2-(4-methoxypyridin-2-yl)-5H,6H,7H-cyclopenta[d]pyrimidin-4-yl](methyl)amino}acetamide (Compound 152)

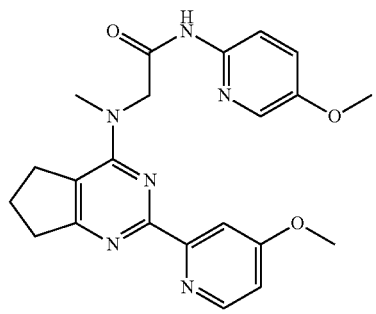 [SMILES: COc1ccc(NC(=O)CN(C)c2nc(-c3cc(OC)ccn3)nc3c2CCC3)nc1]

Compound 152 was synthesized similar to Compound 135 by replacing oxolan-3-amine with 5-methoxypyridin-2-amine. LCMS (ES, m/z): [M+H]⁺: 421. ¹H-NMR (300 MHz, DMSO-d$_6$, ppm): δ 10.55 (s, 1H), 8.43 (d, J=5.7 Hz, 1H), 8.03 (d, J=3.0 Hz, 1H), 7.96 (d, J=8.7 Hz, 1H), 7.76 (d, J=2.7 Hz, 1H), 7.39 (dd, J=9.0, 3.0 Hz, 1H), 6.96 (dd, J=5.7, 2.7 Hz, 1H), 4.49 (s, 2H), 3.79 (s, 3H), 3.73 (s, 3H), 3.35 (s, 3H), 3.20 (t, J=7.5 Hz, 2H), 2.83 (t, J=7.8 Hz, 2H), 2.08-1.95 (m, 2H).

Example 1.166

Synthesis of 2-{[2-(4-methoxypyridin-2-yl)-5H,6H,7H-cyclopenta[d]pyrimidin-4-yl](methyl)amino}-N-(2-methoxypyrimidin-5-yl)acetamide (Compound 153)

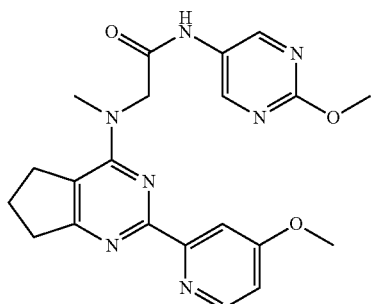

Compound 153 was synthesized similar to Compound 135 by replacing oxolan-3-amine with 5-methoxypyridin-2-amine. LCMS (ES, m/z): [M+H]$^+$: 421. $^1$H-NMR (300 MHz, DMSO-d$_6$, ppm): δ 10.55 (s, 1H), 8.43 (d, J=5.7 Hz, 1H), 8.03 (d, J=3.0 Hz, 1H), 7.96 (d, J=8.7 Hz, 1H), 7.76 (d, J=2.7 Hz, 1H), 7.39 (dd, J=9.0, 3.0 Hz, 1H), 6.96 (dd, J=5.7, 2.7 Hz, 1H), 4.49 (s, 2H), 3.79 (s, 3H), 3.73 (s, 3H), 3.35 (s, 3H), 3.20 (t, J=7.5 Hz, 2H), 2.83 (t, J=7.8 Hz, 2H), 2.08-1.95 (m, 2H).

Example 1.167

Synthesis of 2-{[2-(4-methoxypyridin-2-yl)-5H,6H,7H-cyclopenta[d]pyrimidin-4-yl](methyl)amino}-N-(1-methyl-1H-pyrazol-4-yl)acetamide (Compound 154)

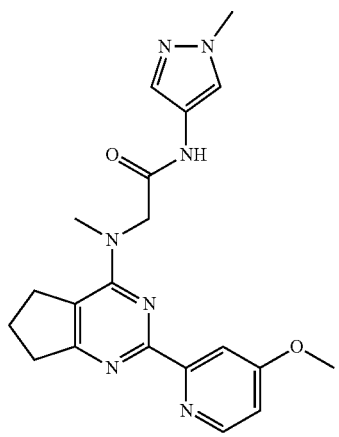 [SMILES: COc1ccnc(-c2nc3c(c(N(C)CC(=O)Nc4cnn(C)c4)n2)CCC3)c1]

Compound 154 was synthesized similar to Compound 135 by replacing oxolan-3-amine with 1-methylpyrazol-4-amine. LCMS (ES, m/z): [M+H]$^+$: 394. $^1$H NMR (300 MHz, DMSO-d$_6$) δ 10.24 (s, 1H), 8.47 (d, J=5.4 Hz, 1H), 7.83 (s, 1H), 7.78 (d, J=2.4 Hz, 1H), 7.38 (s, 1H), 7.01 (dd, J=5.7, 2.4 Hz, 1H), 4.35 (s, 2H), 3.82 (s, 3H), 3.76 (s, 3H), 3.34 (s, 3H), 3.19 (t, J=7.5 Hz, 2H), 2.83 (t, J=7.8 Hz, 2H), 2.08-1.95 (m, 2H).

Example 1.168

Synthesis of 2-{[2-(4-methoxypyridin-2-yl)-5H,6H,7H-cyclopenta[d]pyrimidin-4-yl](methyl)amino}-N-(1-methylcyclopentyl)acetamide (Compound 155)

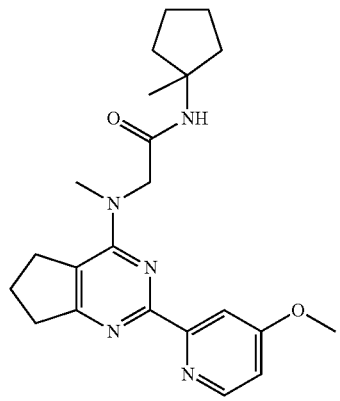 [SMILES: COc1ccnc(-c2nc3c(c(N(C)CC(=O)NC4(C)CCCC4)n2)CCC3)c1]

Compound 155 was synthesized similar to Compound 135 by replacing 2 oxolan-3-amine with 1-methylcyclopentan-1-amine hydrochloride. LCMS (ES, m/z): [M+H]$^+$: 396. $^1$H NMR (300 MHz, DMSO-d$_6$) δ 8.48 (d, J=5.7 Hz, 1H), 7.84 (d, J=2.4 Hz, 1H), 7.74 (s, 1H), 7.04 (dd, J=5.7, 2.7 Hz, 1H), 4.14 (s, 2H), 3.89 (s, 3H), 3.26 (s, 3H), 3.14 (t, J=7.5 Hz, 2H), 2.82 (t, J=7.8 Hz, 2H), 2.06-1.87 (m, 4H), 1.63-1.38 (m, 6H), 1.27 (s, 3H).

Example 1.169

Synthesis of N-tert-butyl-2-{[2-(4-methoxypyridin-2-yl)-5H,6H,7H-cyclopenta[d]pyrimidin-4-yl](methyl)amino}-N-methylacetamide (Compound 156)

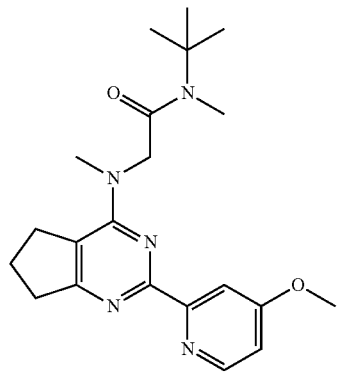 [SMILES: COc1ccnc(-c2nc3c(c(N(C)CC(=O)N(C)C(C)(C)C)n2)CCC3)c1]

Compound 156 was synthesized similar to Compound 135 by replacing oxolan-3-amine with tert-butyl(methyl)amine. LCMS (ES, m/z): [M+H]$^+$: 384. $^1$H NMR (300 MHz, DMSO-d$_6$) δ 8.48 (d, J=5.7 Hz, 1H), 7.79 (d, J=2.4 Hz, 1H), 7.03 (dd, J=5.7, 2.7 Hz, 1H), 4.43 (s, 2H), 3.89 (s, 3H), 3.25 (s, 3H), 3.11 (t, J=7.5 Hz, 2H), 2.93 (s, 3H), 2.80 (t, J=7.8 Hz, 2H), 2.08-1.95 (m, 2H), 1.32 (s, 9H).

Example 1.170

Synthesis of 2-{[2-(4-methoxypyridin-2-yl)-5H,6H,7H-cyclopenta[d]pyrimidin-4-yl](methyl)amino}-N,N-dimethylacetamide (Compound 157)

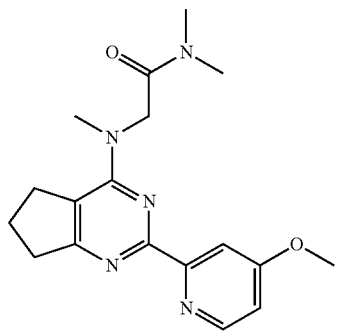 [SMILES: COc1ccnc(-c2nc3c(c(N(C)CC(=O)N(C)C)n2)CCC3)c1]

Compound 157 was synthesized similar to Compound 135 by replacing oxolan-3-amine with dimethylamine hydrochloride. LCMS (ES, m/z): [M+H]$^+$: 342. $^1$H NMR (300 MHz, DMSO-d$_6$) δ 8.47 (d, J=5.7 Hz, 1H), 7.74 (d, J=2.4 Hz, 1H), 7.02 (dd, J=5.7, 2.7 Hz, 1H), 4.51 (s, 2H), 3.89 (s, 3H), 3.25 (s, 3H), 3.12 (t, J=7.5 Hz, 2H), 3.05 (s, 3H), 2.85 (s, 3H), 2.81 (t, J=7.8 Hz, 2H), 2.03-1.93 (m, 2H).

Example 1.171

Synthesis of N-tert-butyl-2-{[2-(4-cyanopyridin-2-yl)-5H,6H,7H-cyclopenta[d]pyrimidin-4-yl](methyl)amino}acetamide (Compound 158)

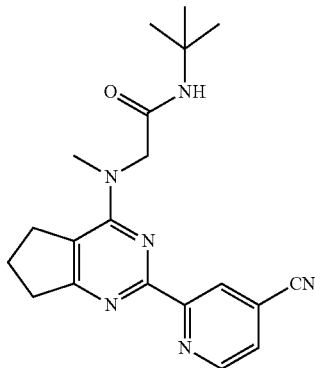 [SMILES: CN(CC(=O)NC(C)(C)C)c1nc(-c2cc(C#N)ccn2)nc2c1CCC2]

Compound 158 was synthesized similar to Compound 24 by replacing 4-methyl-2-(tributylstannyl)-pyridine with 2-(trimethylstannyl)pyridine-4-carbonitrile. LCMS (ES) [M+1]$^+$ m/z 365. $^1$H NMR (300 MHz, DMSO-d$_6$) δ 8.92 (d, J=4.9 Hz, 1H), 8.66 (s, 1H), 7.92 (dd, J=5.0, 1.6 Hz, 1H), 7.76 (s, 1H), 4.14 (s, 2H), 3.32 (s, 3H), 3.19 (t, J=7.3 Hz, 2H), 2.84 (t, J=7.8 Hz, 2H), 2.01 (t, J=7.6 Hz, 2H).

Example 1.172

Synthesis of N-tert-butyl-2-({2-[4-(cyclopropylmethoxy)pyridin-2-yl]-5H,6H,7H-cyclopenta[d]pyrimidin-4-yl}(methyl)amino)acetamide (Compound 159)

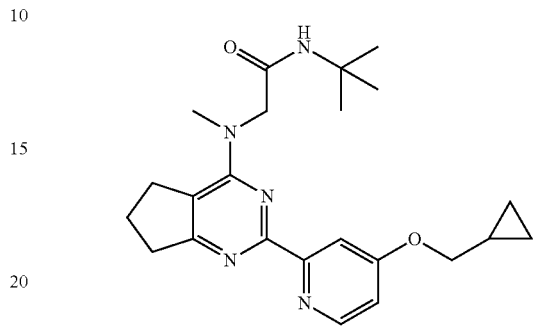

Compound 159 was synthesized similar to Compound 24 by replacing 4-methyl-2-(tributylstannyl)-pyridine with 4-(cyclopropylmethoxy)-2-(trimethylstannyl)pyridine. LCMS (ES) [M+1]$^+$ m/z 410. $^1$H NMR (300 MHz, DMSO-d$_6$) δ 8.45 (d, J=5.6 Hz, 1H), 7.85 (d, J=2.5 Hz, 1H), 7.69 (s, 1H), 7.01 (dd, J=5.7, 2.6 Hz, 1H), 4.12 (s, 2H), 3.97 (d, J=7.1 Hz, 2H), 3.27 (s, 3H), 3.15 (t, J=7.3 Hz, 2H), 2.81 (t, J=7.9 Hz, 2H), 2.04-1.88 (m, 2H), 1.25 (s, 9H), 1.25-1.20 (m, 1H), 0.66-0.54 (m, 2H), 0.43-0.32 (m, 2H).

Example 1.173

Synthesis of N-tert-butyl-2-{methyl[2-(1-methyl-1H-pyrazol-3-yl)-5H,6H,7H-cyclopenta[d]pyrimidin-4-yl]amino}acetamide (Compound 160)

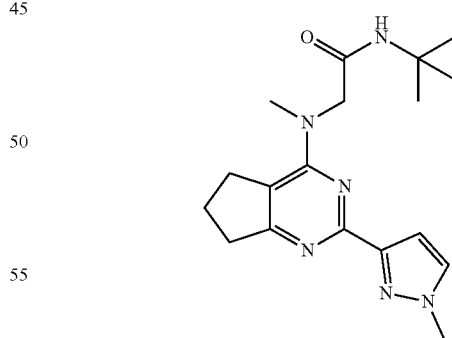

Compound 160 was synthesized similar to Compound 24 by replacing 4-methyl-2-(tributylstannyl)-pyridine with 1-methyl-3-(4,4,5,5-tetramethyl-1,3,2-dioxaborolan-2-yl)pyrazole. LCMS (ES) [M+1]$^+$ m/z: 343. $^1$H NMR (300 MHz, DMSO-d6) δ 7.69 (d, J=2.2 Hz, 1H), 7.60 (s, 1H), 6.81 (d, J=2.2 Hz, 1H), 4.09 (s, 2H), 3.89 (s, 3H), 3.21 (s, 3H), 3.08 (t, J=7.3 Hz, 2H), 2.75 (t, J=7.8 Hz, 2H), 2.13-1.84 (m, 2H), 1.24 (s, 9H).

Example 1.174

Synthesis of 2-{methyl[2-(1-methyl-1H-imidazol-4-yl)-5H,6H,7H-cyclopenta[d]pyrimidin-4-yl]amino}-N-(1-methylcyclopentyl)acetamide (Compound 161)

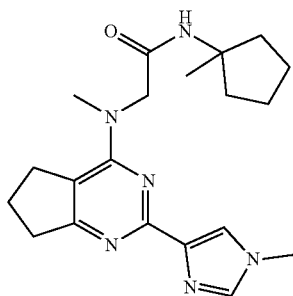

Compound 161 was synthesized similar to Compound 142 by replacing cyclohexylamine with 1-methylcyclopentan-1-amine. LCMS (ES, m/z): [M+H]$^+$: 369. $^1$H-NMR (300 MHz, DMSO-d$_6$, ppm): δ 8.16 (s, 1H), 7.74 (d, J=1.5 Hz, 1H), 7.71 (br, 1H), 7.61 (d, J=1.5 Hz, 1H), 4.10 (s, 2H), 3.69 (s, 3H), 3.22 (s, 3H), 3.07 (t, J=7.5 Hz, 2H), 2.74 (t, J=7.8 Hz, 2H), 1.99-1.89 (m, 4H), 1.60-1.44 (m, 6H), 1.29 (s, 3H).

Example 1.175

Synthesis of N-tert-butyl-2-{methyl[2-(1-methyl-1H-imidazol-2-yl)-5H,6H,7H-cyclopenta[d]pyrimidin-4-yl]amino}acetamide (Compound 162)

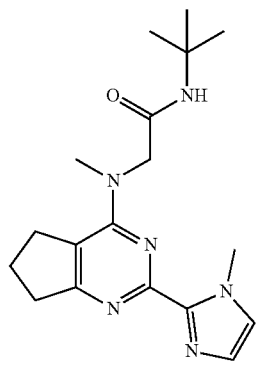 [SMILES: CN(CC(=O)NC(C)(C)C)c1nc(-c2nccn2C)nc2c1CCC2]

Compound 162 was synthesized similar to Compound 24 by replacing 4-methyl-2-(tributylstannyl)-pyridine with 1-methyl-2-(tributylstannyl)-1H-imidazole. LCMS (ES) [M+1]$^+$ m/z: 343. $^1$H NMR (300 MHz, DMSO-d6) δ 7.68 (d, J=1.2 Hz, 1H), 7.62-7.54 (m, 2H), 4.11 (s, 2H), 3.97 (s, 3H), 3.21 (s, 3H), 3.09 (t, J=7.2 Hz, 2H), 2.75 (t, J=7.8 Hz, 2H), 1.95 (m, 2H), 1.25 (s, 9H).

Example 1.176

Synthesis of N-tert-butyl-2-{methyl[2-(1,3-oxazol-4-yl)-5H,6H,7H-cyclopenta[d]pyrimidin-4-yl]amino}acetamide (Compound 163)

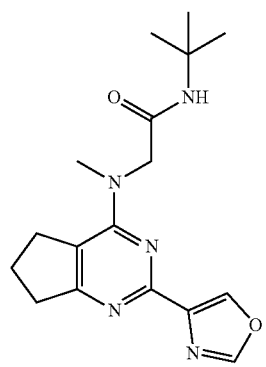 [SMILES: CN(CC(=O)NC(C)(C)C)c1nc(-c2cocn2)nc2c1CCC2]

Compound 163 was synthesized similar to Compound 24 by replacing 4-methyl-2-(tributylstannyl)-pyridine with 2-(triisopropylsilyl)-4-(trimethylstannyl)oxazole. LCMS (ES) [M+1]$^+$ m/z: 330. $^1$H NMR (300 MHz, DMSO-d6) δ 8.62 (d, J=1.1 Hz, 1H), 8.42 (d, J=1.1 Hz, 1H), 7.60 (s, 1H), 4.10 (s, 2H), 3.23 (s, 3H), 3.10 (t, J=7.3 Hz, 2H), 2.77 (t, J=7.9 Hz, 2H), 2.05-1.92 (m, 2H), 1.24 (s, 9H).

Example 1.177

Synthesis of N-tert-butyl-2-{methyl[2-(1,3-oxazol-2-yl)-5H,6H,7H-cyclopenta[d]pyrimidin-4-yl]amino}acetamide (Compound 164)

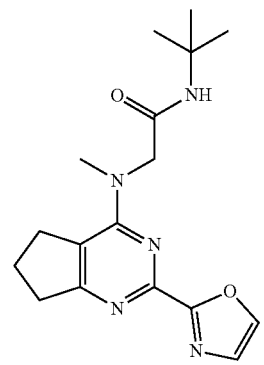 [SMILES: CN(CC(=O)NC(C)(C)C)c1nc(-c2ncco2)nc2c1CCC2]

Compound 164 was synthesized similar to Compound 24 by replacing 4-methyl-2-(tributylstannyl)-pyridine with 2-(trimethylstannyl)-1,3-oxazole. LCMS (ES) [M+1]$^+$ m/z: 330. $^1$H NMR (300 MHz, DMSO-d6) δ 8.23 (d, J=0.7 Hz, 1H), 7.60 (s, 1H), 7.40 (d, J=0.8 Hz, 1H), 4.16 (s, 2H), 3.20 (s, 3H), 3.11 (t, J=7.3 Hz, 2H), 2.80 (t, J=7.9 Hz, 2H), 1.98-1.85 (m, 2H), 1.25 (s, 9H).

Example 1.178

Synthesis of N-tert-butyl-2-{[2-(isoquinolin-3-yl)-5H,6H,7H-cyclopenta[d]pyrimidin-4-yl](methyl)amino}acetamide (Compound 165)

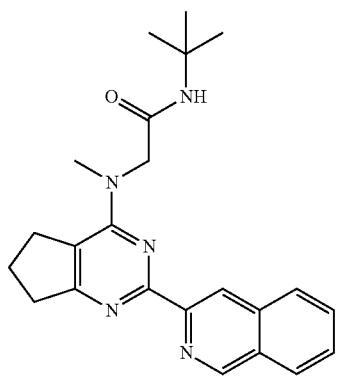 [SMILES: CN(CC(=O)NC(C)(C)C)c1nc(-c2cc3ccccc3cn2)nc2c1CCC2]

Compound 165 was synthesized similar to Compound 24 by replacing 4-methyl-2-(tributylstannyl)-pyridine with 3-(trimethylstannyl)isoquinoline. LCMS (ES) [M+1]$^+$ m/z: 390. $^1$H NMR (300 MHz, DMSO-d$_6$) δ 9.40 (s, 1H), 8.86 (s, 1H), 8.21-8.16 (m, 2H), 8.12 (d, J=8.2 Hz, 1H), 7.87-7.69 (m, 3H), 4.20 (s, 2H), 3.32 (s, 3H), 3.18 (t, J=7.3 Hz, 2H), 2.86 (t, J=7.8 Hz, 2H), 2.10-1.93 (m, 2H), 1.23 (s, 9H).

Example 1.179

Synthesis of N-tert-butyl-2-[(2-{imidazo[1,2-a]pyridin-2-yl}-5H,6H,7H-cyclopenta[d]pyrimidin-4-yl)(methyl)amino]acetamide (Compound 166)

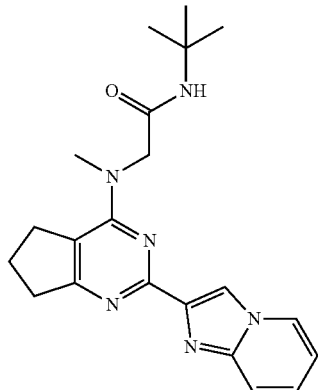 [SMILES: CN(CC(=O)NC(C)(C)C)c1nc(-c2cn3ccccc3n2)nc2c1CCC2]

Compound 166 was synthesized similar to Compound 24 by replacing 4-methyl-2-(tributylstannyl)-pyridine with 2-(trimethylstannyl)imidazo[1,2-a]pyridine. LCMS (ES) [M+1]$^+$ m/z 379. $^1$H NMR (300 MHz, DMSO-d6) δ 8.52 (d, J=7.1 Hz, 2H), 7.68 (s, 1H), 7.57 (d, J=9.1 Hz, 1H), 7.31-7.19 (m, 1H), 6.92 (td, J=6.7, 1.2 Hz, 1H), 4.16 (s, 2H), 3.25 (s, 3H), 3.11 (t, J=7.3 Hz, 2H), 2.79 (t, J=7.9 Hz, 2H), 1.99-1.85 (m, 2H), 1.25 (s, 9H).

Example 1.180

Synthesis of N-(3-fluorophenyl)-2-({2-[4-(2-hydroxyethoxy)pyridin-2-yl]-5H,6H,7H-cyclopenta[d]pyrimidin-4-yl}(methyl)amino)acetamide (Compound 167)

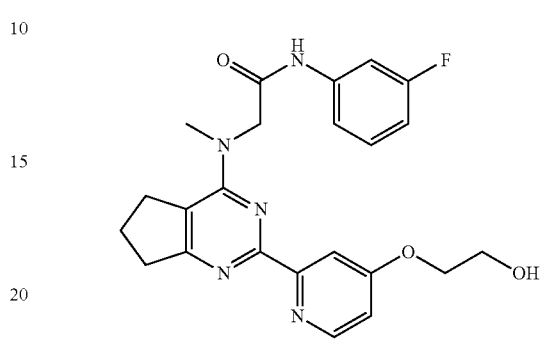

Compound 167 was synthesized similar to Compound 144 by replacing 1-cyclohexylamine with 3-fluoroaniline. LCMS (ES) [M+1]$^+$ m/z 438. $^1$H NMR (300 MHz, DMSO-d6) δ 10.46 (br, 1H), 8.43 (d, J=5.6 Hz, 1H), 7.78 (s, 1H), 7.57 (d, J=11.2 Hz, 1H), 7.41-7.25 (m, 2H), 7.04-6.96 (m, 1H), 6.85 (dd, J=8.4, 4.9 Hz, 1H), 5.18-4.62 (br, 1H), 4.55-4.31 (m, 2H), 4.15-3.95 (m, 2H), 3.71-3.62 (m, 2H), 3.35 (s, 3H), 3.21 (t, J=7.2 Hz, 2H) 2.83 (t, J=7.9 Hz, 2H), 2.22-1.98 (m, 2H).

Example 1.181

Synthesis of N-[(1R,2S)-2-hydroxycyclohexyl]-2-{[2-(4-methoxypyridin-2-yl)-5H,6H,7H-cyclopenta[d]pyrimidin-4-yl](methyl)amino}acetamide (Compound 168)

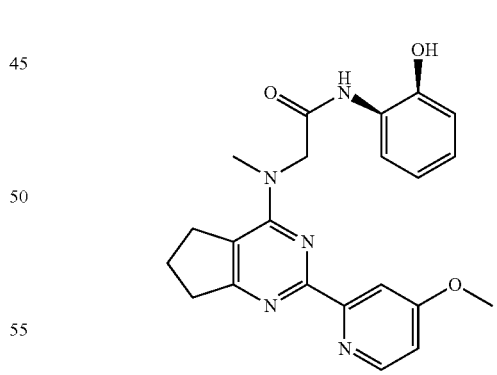

Compound 168 was synthesized similar to Compound 135 by replacing oxolan-3-amine with (1R,2S)-2-aminocyclohexan-1-ol. LCMS (ES) [M+1]$^+$ m/z: 412. $^1$H NMR (300 MHz, DMSO-d$_6$) δ 8.48 (d, J=5.6 Hz, 1H), 7.80 (d, J=2.6 Hz, 1H), 7.61 (d, J=7.9 Hz, 1H), 7.03 (dd, J=5.6, 2.6 Hz, 1H), 4.59 (d, J=3.9 Hz, 1H), 4.31 (d, J=16.6 Hz, 1H), 4.18 (d, J=16.6 Hz, 1H), 3.89 (s, 3H), 3.71-3.58 (m, 2H), 3.25 (s 3H), 3.14 (t, J=7.1 Hz, 2H), 2.82 (t, J=7.9 Hz, 2H), 2.03-1.91 (m, 2H), 1.67-1.15 (m, 8H).

Example 1.182

Synthesis of N-[(1S,2R)-2-hydroxycyclohexyl]-2-{[2-(4-methoxypyridin-2-yl)-5H,6H,7H-cyclopenta[d]pyrimidin-4-yl](methyl)amino}acetamide (Compound 169)

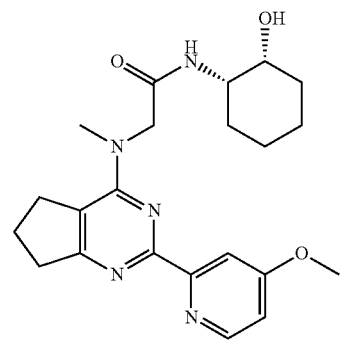 [SMILES: COc1ccnc(-c2nc3c(c(N(C)CC(=O)N[C@H]4CCCC[C@H]4O)n2)CCC3)c1]

Compound 169 was synthesized similar to Compound 135 by replacing oxolan-3-amine with (1S,2R)-2-aminocyclohexan-1-ol. LCMS (ES) [M+1]$^+$ m/z: 412. $^1$H NMR (300 MHz, DMSO-d$_6$) δ 8.48 (d, J=5.6 Hz, 1H), 7.80 (d, J=2.6 Hz, 1H), 7.61 (d, J=8.0 Hz, 1H), 7.03 (dd, J=5.6, 2.6 Hz, 1H), 4.59 (d, J=3.9 Hz, 1H), 4.31 (d, J=16.7 Hz, 1H), 4.18 (d, J=16.7 Hz, 1H), 3.89 (s, 3H), 3.71-3.63 (m, 2H), 3.25 (s, 3H), 3.14 (t, J=7.5 Hz, 2H), 2.82 (t, J=7.9 Hz, 2H), 2.06-1.92 (m, 2H), 1.69-1.32 (m, 6H), 1.31-1.14 (m, 2H).

Example 1.183a and Example 1.183b

Synthesis of N-[(1R,2S)-2-hydroxycyclopentyl]-2-{[2-(4-methoxypyridin-2-yl)-5H,6H,7H-cyclopenta[d]pyrimidin-4-yl](methyl)amino}acetamide (Compound 170) and N-[(1S,2R)-2-hydroxycyclopentyl]-2-{[2-(4-methoxypyridin-2-yl)-5H,6H,7H-cyclopenta[d]pyrimidin-4-yl](methyl)amino}acetamide (Compound 171)

assumed Compound 170

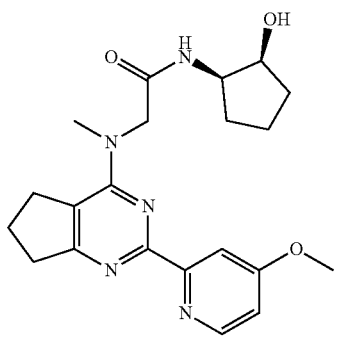

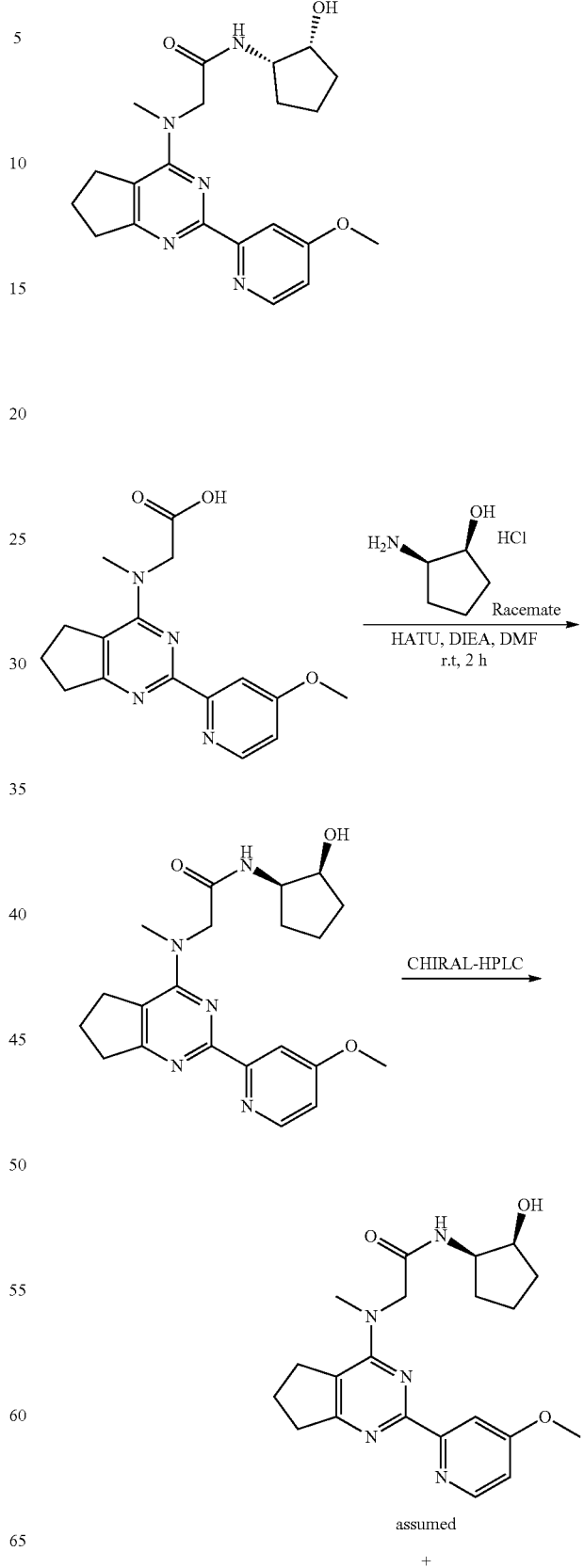

677
-continued

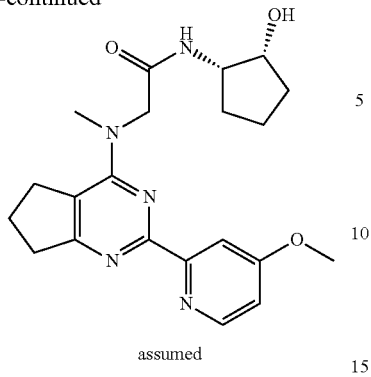

assumed

Into a 50-mL round-bottom flask were placed [[2-(4-methoxypyridin-2-yl)-5H,6H,7H-cyclopenta[d]pyrimidin-4-yl](methyl)amino]acetic acid (120 mg, 0.38 mmol, 1.00 equiv), DMF (5.00 mL), HATU (174 mg, 0.45 mmol, 1.20 equiv), DIEA (148 mg, 1.145 mmol, 3.00 equiv), and (1S,2R)-2-aminocyclopentan-1-ol hydrochloride (63.04 mg, 0.45 mmol, 1.20 equiv). The resulting solution was stirred for 3 hr at 25° C. The crude product was purified by Prep-HPLC with the following conditions: Column, Xbridge Prep C18 OBD column, 5 um, 19*150 mm; mobile phase, Water (0.05% NH₃·H₂O) and CH₃CN (35% CH₃CN up to 50% in 10 min); Detector, UV 254 nm. The collected fractions were combined and concentrated under vacuum.

The resulting product was separated by Chiral HPLC with the following conditions: Column: CHIRALPAK IC, 20*250 mm, 5 um; Mobile phase: A: n-Hexane/DCM=5:1, B: Ethanol+0.1% DEA; Flow rate: 90 mL/min; Gradient: 30% B in 20 min. This resulted in 35.1 mg (23.13%) of N-[(1R,2S)-2-hydroxycyclopentyl]-2-[[2-(4-methoxypyridin-2-yl)-5H,6H,7H-cyclopenta[d]pyrimidin-4-yl](methyl)amino]acetamide as a white solid and 37.2 mg (24.52%) of N-[(1S,2R)-2-hydroxycyclopentyl]-2-[[2-(4-methoxypyridin-2-yl)-5H,6H,7H-cyclopenta[d]pyrimidin-4-yl](methyl)amino]acetamide as a white solid. The compounds were analyzed by analytical chiral HPLC with the following conditions: Column: CHIRALPAK IC, 4.6*50 mm, 3 um; Mobile phase: A: n-Hexane/DCM=5:1, B: Ethanol+0.1% DEA; Flow rate: 1 mL/min; Gradient: 30% B in 6 min.

Compound 170: CHIRAL_HPLC: Retention time 3.09 min. LCMS (ES, m/z): [M+H]⁺: 398. ¹H-NMR (300 MHz, DMSO-d6, ppm): δ 8.48 (d, J=5.6 Hz, 1H), 7.81 (d, J=2.6 Hz, 1H), 7.65 (d, J=7.8 Hz, 1H), 7.03 (dd, J=5.6, 2.6 Hz, 1H), 4.65 (d, J=3.9 Hz, 1H), 4.32 (d, J=16.7 Hz, 1H), 4.19 (d, J=16.7 Hz, 1H), 3.89 (s, 3H), 3.98-3.79 (m, 2H), 3.26 (s, 3H), 3.15 (t, J=7.5 Hz, 2H), 2.82 (t, J=7.8 Hz, 2H), 2.05-1.94 (m, 2H), 1.74-1.68 (m, 3H), 1.58-1.39 (m, 3H). Compound 171: CHIRAL_HPLC: Retention time 3.88 min. LCMS (ES, m/z): [M+H]⁺: 398. ¹H-NMR (300 MHz, DMSO-d6, ppm): δ ¹H-NMR: (300 MHz, DMSO-d6, ppm): δ 8.48 (d, J=5.6 Hz, 1H), 7.81 (d, J=2.6 Hz, 1H), 7.65 (d, J=7.8 Hz, 1H), 7.03 (dd, J=5.6, 2.6 Hz, 1H), 4.65 (d, J=3.9 Hz, 1H), 4.32 (d, J=16.7 Hz, 1H), 4.19 (d, J=16.7 Hz, 1H), 3.89 (s, 3H), 3.98-3.79 (m, 2H), 3.26 (s, 3H), 3.15 (t, J=7.5 Hz, 2H), 2.82 (t, J=7.8 Hz, 2H), 2.05-1.94 (m, 2H), 1.74-1.68 (m, 3H), 1.58-1.39 (m, 3H).

678

Example 1.183c and Example 1.183d

Synthesis of N-[(1R,2R)-2-hydroxycyclopentyl]-2-{[2-(4-methoxypyridin-2-yl)-5H,6H,7H-cyclopenta[d]pyrimidin-4-yl](methyl)amino}acetamide (Compound 172) and N-[(1S,2S)-2-hydroxycyclopentyl]-2-{[2-(4-methoxypyridin-2-yl)-5H,6H,7H-cyclopenta[d]pyrimidin-4-yl](methyl)amino}acetamide (Compound 173)

Assumed Compound 172

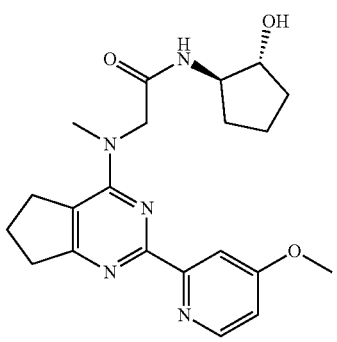

Assumed Compound 173

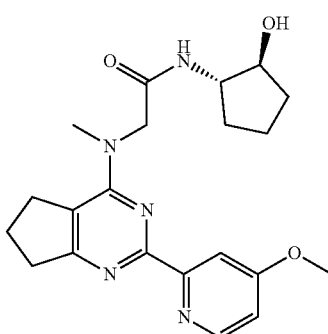

Scheme 103

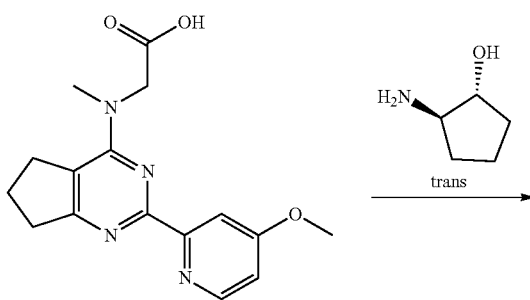

trans

-continued

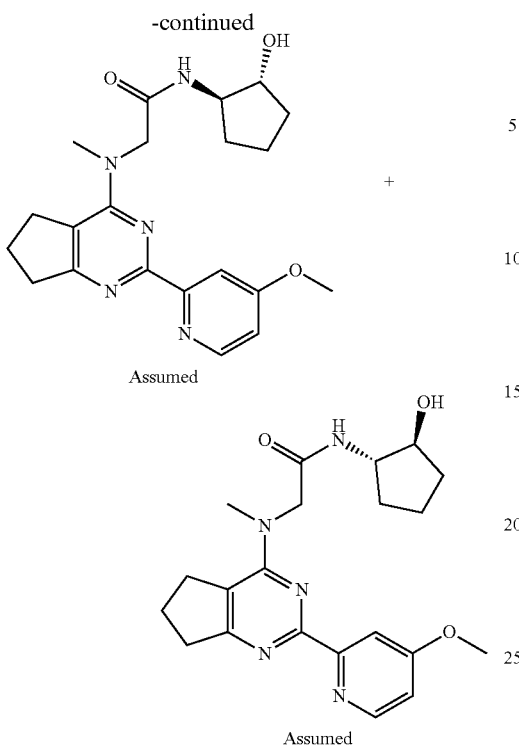

Assumed

To a stirred solution of [[2-(4-methoxypyridin-2-yl)-5H, 6H,7H-cyclopenta[d]pyrimidin-4-yl](methyl)amino]acetic acid (300 mg, 0.95 mmol, 1.0 equiv), DIEA (616 mg, 4.77 mmol, 5.0 equiv), and HATU (1.819 g, 4.77 mmol, 5.0 equiv) in THF (30 mL) was added (1R,2R)-2-aminocyclopentan-1-ol (482 mg, 4.77 mmol, 5.0 equiv) in portions at 20° C. The resulting mixture was stirred for 5 h at 60° C. The reaction was concentrated under reduced pressure. The residue was purified by Flash-Prep-HPLC with the following conditions (IntelFlash-1): Column, C18; mobile phase A: CH$_3$CN, Mobile phase B: Water; Flow rate: 20 mL/min Column to give 200 mg of the racemate product, which was separated by Chiral-HPLC with the following conditions: Column: Lux Amylose-1, 50*250 mm, 10 um; Mobile phase A: n-Hexane, Mobile phase B: Ethanol; Flow rate: 90 mL/min; Gradient: 50% B in 36 min; 220 nm. This resulted in N-[(1R,2R)-2-hydroxycyclopentyl]-2-[[2-(4-methoxypyridin-2-yl)-5H,6H,7H-cyclopenta[d]pyrimidin-4-yl](methyl)amino]acetamide (85 mg, 22.41%) and N-[(1S,2S)-2-hydroxycyclopentyl]-2-[[2-(4-methoxypyridin-2-yl)-5H, 6H,7H-cyclopenta[d]pyrimidin-4-yl](methyl)amino] acetamide (80 mg, 21.09%) as a white solid. The compounds were subjected to analytical chiral HPLC with the following conditions: CHIRALPAK IC, 4.6*50 mm, 3 um; Mobile phase: A: n-Hexane, Mobile phase B: Ethanol; Flow rate: 1 mL/min; Gradient: 50% B in 6 min.

Compound 172: CHIRAL_HPLC: Retention time 4.594 min. LCMS (ES, m/z): [M+H]$^+$: 398.2; $^1$H NMR (300 MHz, CDCl$_3$, ppm): δ 8.53 (d, J=5.7 Hz, 1H), 8.21 (s, 1H), 7.95 (d, J=2.4 Hz, 1H), 6.88 (dd, J=5.4, 2.4 Hz, 1H), 4.46 (br, 1H), 4.22 (s, 2H), 3.90 (s, 3H), 3.89-3.82 (m, 1H), 3.80-3.78 (m, 1H), 3.40 (s, 3H), 3.19 (t, J=7.2 Hz, 2H), 2.99 (t, J=7.8 Hz, 2H), 2.15-2.08 (m, 2H), 2.05-1.96 (m, 2H), 1.71-1.57 (m, 3H), 1.48-1.38 (m, 1H).

Compound 173: CHIRAL_HPLC: Retention time 5.942 min. LCMS (ES, m/z): [M+H]$^+$: 398.2; $^1$H NMR (300 MHz, CDCl$_3$, ppm): δ 8.52 (d, J=8.7 Hz, 1H), 8.20 (s, 1H), 7.95 (d, J=2.4 Hz, 1H), 6.88 (dd, J=2.7, 5.7 Hz, 1H), 4.48 (br, 1H), 4.22 (br, 2H), 3.90 (s, 3H), 3.89-3.82 (m, 1H), 3.80-3.78 (m, 1H), 3.40 (s, 3H), 3.18 (t, J=8.4 Hz, 2H), 2.99 (t, J=6.6 Hz, 2H), 2.15-2.07 (m, 2H), 2.05-1.94 (m, 2H), 1.71-1.55 (m, 3H), 1.48-1.38 (m, 1H).

Example 1.184

Synthesis of N-tert-butyl-2-{methyl[2-(pyridazin-3-yl)-5H,6H,7H-cyclopenta[d]pyrimidin-4-yl] amino}acetamide (Compound 175)

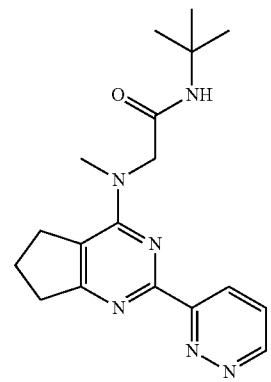 [SMILES: CN(CC(=O)NC(C)(C)C)c1nc(-c2cccnn2)nc2c1CCC2]

Compound 175 was synthesized similar to Compound 24 by replacing 4-methyl-2-(trimethylstannyl)pyridine with 3-(tributylstannyl)pyridazine. LCMS (ES) [M+1]$^+$ m/z: 341, $^1$H-NMR (300 MHz, DMSO-d6) δ 10.00 (dd, J=2.3, 1.3 Hz, 1H), 9.36 (dd, J=5.3, 1.3 Hz, 1H), 8.37 (dd, J=5.3, 2.3 Hz, 1H), 7.77 (s, 1H), 4.15 (s, 2H), 3.32 (s, 3H), 3.18 (t, J=7.3 Hz, 2H), 2.85 (t, J=7.9 Hz, 2H), 2.15-1.82 (m, 2H), 1.25 (s, 9H).

Example 1.185

Synthesis of N-tert-butyl-2-[methyl(2-{1H-pyrazolo [4,3-c]pyridin-6-yl}-5H,6H,7H-cyclopenta[d]pyrimidin-4-yl)amino]acetamide (Compound 176)

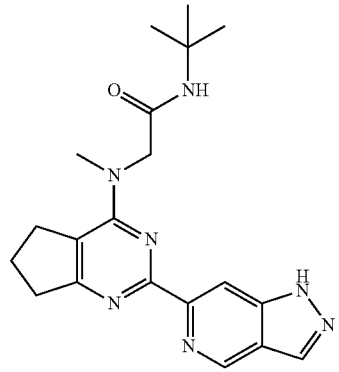 [SMILES: CN(CC(=O)NC(C)(C)C)c1nc(-c2cc3[nH]ncc3cn2)nc2c1CCC2]

Compound 176 was synthesized similar to Compound 24 by replacing 4-methyl-2-(trimethylstannyl)pyridine with 6-(trimethylstannyl)-1H-pyrazolo[4,3-c]pyridine. LCMS (ES) [M+1]$^+$ m/z: 380.2. $^1$H NMR (300 MHz, DMSO-d6, ppm): 9.16 (s, 1H), 8.45 (s, 1H), 8.33 (s, 1H), 7.69 (s, 1H), 4.18 (s, 2H), 3.26 (s, 3H), 3.13 (t, J=7.2 Hz, 2H), 2.84 (t, J=7.9 Hz, 2H), 2.06-1.93 (m, 2H), 1.25 (s, 9H).

Example 1.186

Synthesis of 2-[methyl({2-[4-(2,2,2-trifluoroethoxy)pyridin-2-yl]-5H,6H,7H-cyclopenta[d]pyrimidin-4-yl})amino]-N-(1-methyl-1H-pyrazol-4-yl)acetamide (Compound 178)

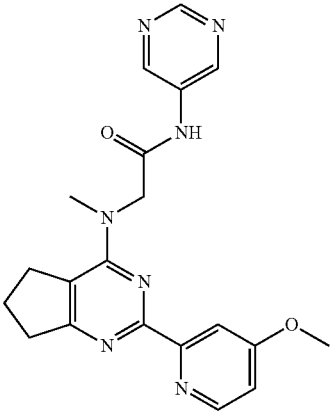 [SMILES: COc1ccnc(-c2nc3c(c(N(C)CC(=O)Nc4cncnc4)n2)CCC3)c1]

Compound 178 was synthesized similar to Compound 135 by replacing oxolan-3-amine with 5-pyrimidinamine. LCMS (ES) [M+1]+ m/z: 392. $^1$H NMR (300 MHz, DMSO-d$_6$) δ 10.69 (s, 1H), 9.00 (s, 2H), 8.87 (s, 1H), 8.42 (d, J=5.4 Hz, 1H), 7.74 (d, J=2.4 Hz, 1H), 7.00 (dd, J=5.4, 2.4 Hz, 1H), 4.45 (s, 2H), 3.78 (s, 3H), 3.39 (s, 3H), 3.22 (t, J=7.5 Hz, 2H), 2.84 (t, J=7.8 Hz, 2H), 2.10-1.95 (m, 2H).

Example 1.187

Synthesis of 2-({2-[4-(2-hydroxyethoxy)pyridin-2-yl]-5H,6H,7H-cyclopenta[d]pyrimidin-4-yl}(methyl)amino)-N-(1-methylcyclopentyl)acetamide (Compound 179)

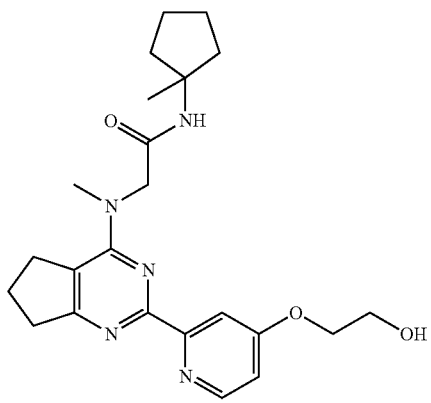 [SMILES: CN(CC(=O)NC1(C)CCCC1)c1nc(-c2cc(OCCO)ccn2)nc2c1CCC2]

Compound 179 was synthesized similar to Compound 144 by replacing cyclohexylamine with 1-methylcyclopentan-1-amine hydrochloride. LCMS (ES) [M+1]+ m/z: 426.3. $^1$H NMR (300 MHz, DMSO-d$_6$) δ 8.46 (d, J=5.4 Hz, 1H), 7.84 (d, J=2.4 Hz, 1H), 7.74 (s, 1H), 7.04 (dd, J=5.4, 2.4 Hz, 1H), 4.93 (br, 1H), 4.21-4.09 (m, 4H), 3.76 (t, J=4.8 Hz, 2H), 3.26 (s, 3H), 3.14 (t, J=7.5 Hz, 2H), 2.81 (t, J=7.8 Hz, 2H), 2.07-1.89 (m, 4H), 1.60-1.40 (m, 6H), 1.28 (s, 3H).

Example 1.188

Synthesis of N-tert-butyl-2-{[2-(3-methoxypyridin-2-yl)-5H,6H,7H-cyclopenta[d]pyrimidin-4-yl](methyl)amino}acetamide (Compound 180)

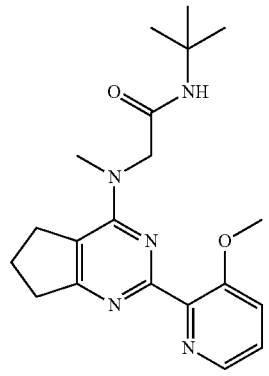 [SMILES: COc1cccnc1-c1nc2c(c(N(C)CC(=O)NC(C)(C)C)n1)CCC2]

Compound 180 was synthesized similar to Compound 24 by replacing 4-methyl-2-(trimethylstannyl)pyridine with 3-methoxy-2-(trimethylstannyl)pyridine. LCMS (ES) [M+1]+ m/z: 370. $^1$H NMR (300 MHz, DMSO-d$_6$) δ 8.12 (dd, J=4.6, 1.3 Hz, 1H), 7.55-7.36 (m, 3H), 4.09 (s, 2H), 3.74 (s, 3H), 3.15-3.07 (m, 5H), 2.74 (t, J=7.8 Hz, 2H), 2.06-1.87 (m, 2H), 1.22 (s, 9H).

Example 1.189

Synthesis of N-tert-butyl-2-{[2-(3-hydroxypyridin-2-yl)-5H,6H,7H-cyclopenta[d]pyrimidin-4-yl](methyl)amino}acetamide (Compound 181)

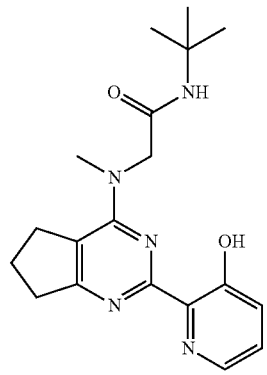 [SMILES: CN(CC(=O)NC(C)(C)C)c1nc(-c2ncccc2O)nc2c1CCC2]

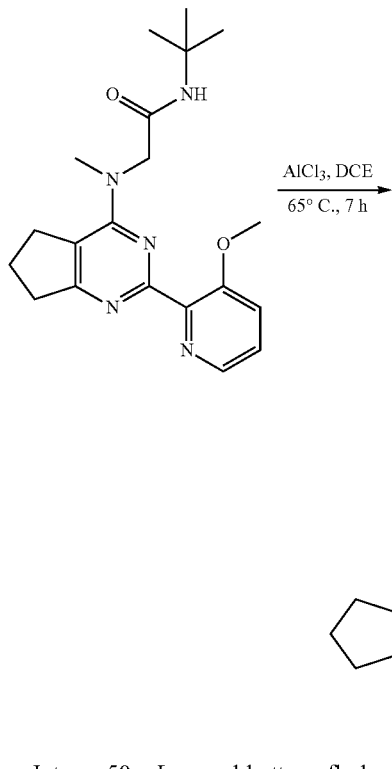

Into a 50-mL round-bottom flask were placed N-tert-butyl-2-[[2-(3-methoxypyridin-2-yl)-5H,6H,7H-cyclopenta[d]pyrimidin-4-yl](methyl)amino]acetamide (50 mg, 0.135 mmol, 1.00 equiv), DCE (5 mL) and AlCl₃ (54 mg, 0.406 mmol, 3.00 equiv). The resulting solution was stirred for 7 h at 65° C. The resulting mixture was concentrated under vacuum. The residue was dissolved in 4 mL of MeOH and purified by Prep-HPLC with the following conditions (Waters I): Column, Xbridge Prep C18 OBD column, 5 um, 19*150 mm; mobile phase, Water (0.05% FA) and CH₃CN (5% CH3CN up to 35% in 15 min); Detector, UV 254 nm. This resulted in 17.1 mg (35.6%) of N-tert-butyl-2-[[2-(3-hydroxypyridin-2-yl)-5H,6H,7H-cyclopenta[d]pyrimidin-4-yl](methyl)amino]acetamide as a white solid. LCMS (ES) [M+1]⁺ m/z 356. ¹H NMR (300 MHz, DMSO-d6) δ 14.21 (s, 1H), 8.31-8.13 (m, 1H), 7.88-7.69 (m, 1H), 7.38-7.31 (m, 2H), 4.21 (s, 2H), 3.25 (s, 3H), 3.21-3.09 (m, 2H), 2.99-2.81 (m, 2H), 2.11-1.89 (m, 2H), 1.25 (s, 9H).

Example 1.190

Synthesis of N-tert-butyl-2-{[2-(1H-imidazol-4-yl)-5H,6H,7H-cyclopenta[d]pyrimidin-4-yl](methyl)amino}acetamide (Compound 182)

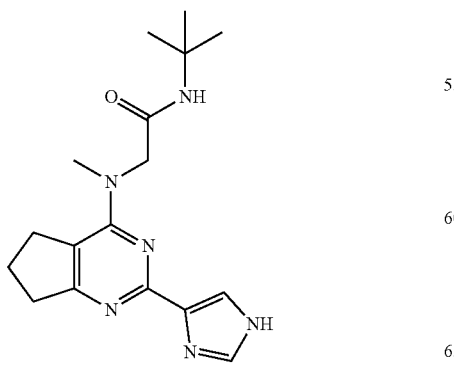

Compound 182 was synthesized similar to Compound 24 by replacing 4-methyl-2-(trimethylstannyl)pyridine with 1-(triphenylmethyl)imidazol-4-ylboronic acid. LCMS (ES) [M+1]⁺ m/z: 329; ¹H NMR (300 MHz, DMSO-d6) δ 12.44 (br, 1H), 7.67 (s, 1H), 7.61 (s, 1H), 7.55 (s, 1H), 4.12 (s, 2H), 3.25 (s, 3H), 3.09 (t, J=7.4 Hz, 2H), 2.76 (t, J=7.8 Hz, 2H), 2.15-1.77 (m, 2H), 1.24 (s, 9H).

Example 1.191

Synthesis of (2R)—N-tert-butyl-2-[methyl(2-{1H-pyrazolo[3,4-c]pyridin-5-yl}-5H,6H,7H-cyclopenta[d]pyrimidin-4-yl)amino]propanamide (Compound 183)

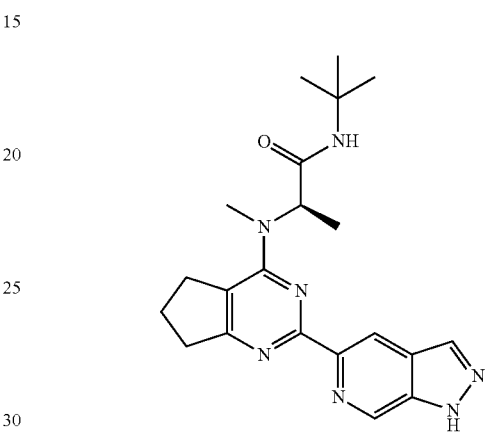

Compound 183 was synthesized similar to Compound 101 by replacing 4-methoxy-2-(trimethylstannyl)pyridine with 5-(trimethylstannyl)-1H-pyrazolo[3,4-c]pyridine. LCMS (ES) [M+1]⁺ m/z: 394.2; ¹H NMR (300 MHz, DMSO-d₆, ppm) δ 13.75 (s, 1H), 9.12 (s, 1H), 8.85 (d, J=1.3 Hz, 1H), 8.30 (d, J=0.9 Hz, 1H), 7.92 (s, 1H), 5.17 (q, J=7.0 Hz, 1H), 3.22 (dt, J=15.6, 7.9 Hz, 1H), 3.16-3.08 (m, 4H), 2.99-2.72 (m, 2H), 2.11-1.88 (m, 2H), 1.34 (d, J=7.1 Hz, 3H), 1.20 (s, 9H).

Example 1.192

Synthesis of 2-[methyl(2-{1H-pyrazolo[3,4-c]pyridin-5-yl}-5H,6H,7H-cyclopenta[d]pyrimidin-4-yl)amino]-N-(1-methylcyclopentyl)acetamide (Compound 184)

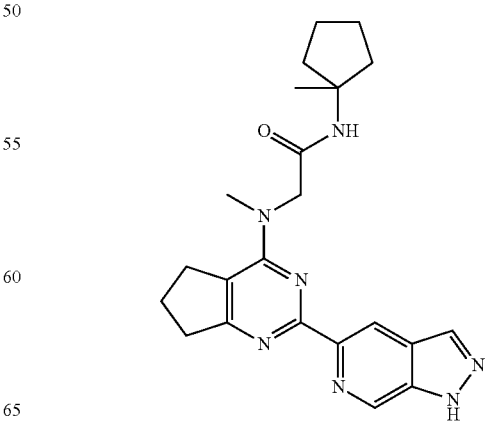

Compound 184 was synthesized similar to Compound 135 by replacing oxolan-3-amine with 1-methylcyclopentan-1-amine hydrochloride and by replacing 4-methoxy-2-(trimethylstannyl)pyridine with 5-(trimethylstannyl)-1H-pyrazolo[3,4-c]pyridine. LCMS (ES) [M+1]+ m/z: 406.2; 1HNMR (300 MHz, DMSO-d6, ppm) δ 13.40 (s, 1H), 9.09 (d, J=1.1 Hz, 1H), 8.80 (d, J=1.3 Hz, 1H), 8.26 (d, J=0.9 Hz, 1H), 7.82 (s, 1H), 4.17 (s, 2H), 3.30 (s, 3H), 3.15 (t, J=7.3 Hz, 2H), 2.83 (t, J=7.8 Hz, 2H), 2.09-1.97 (m, 4H), 1.48 (dt, J=16.7, 7.2 Hz, 6H), 1.28 (s, 3H).

Example 1.193

Synthesis of 2-[methyl(2-{1H-pyrazolo[3,4-c]pyridin-5-yl}-5H,6H,7H-cyclopenta[d]pyrimidin-4-yl)amino]-N-(3-methyloxolan-3-yl)acetamide (Compound 185)

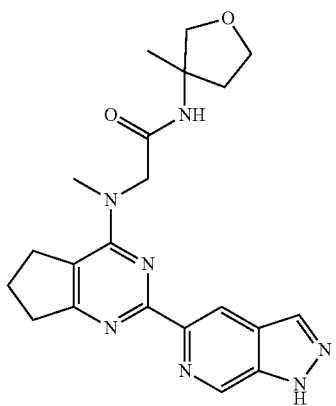 [SMILES: CN(CC(=O)NC1(C)CCOC1)c1nc(-c2cc3cn[nH]c3cn2)nc2c1CCC2]

Compound 185 was synthesized similar to Compound 135 by replacing oxolan-3-amine with 3-methyloxolan-3-amine and by replacing 4-methoxy-2-(trimethylstannyl)pyridine with 5-(trimethylstannyl)-1H-pyrazolo[3,4-c]pyridine. LCMS (ES) [M+1]+ m/z: 408.2; 1H NMR (300 MHz, DMSO-d6, ppm) δ13.71 (br, 1H), 9.09 (s, 1H), 8.78 (d, J=1.3 Hz, 1H), 8.26 (d, J=7.9 Hz, 2H), 4.19 (s, 2H), 3.82 (d, J=8.7 Hz, 1H), 3.77-3.66 (m, 2H), 3.49 (d, J=8.7 Hz, 1H), 3.31 (s, 3H), 3.15 (t, J=7.4 Hz, 2H), 2.83 (t, J=7.8 Hz, 2H), 2.25 (dt, J=12.9, 6.5 Hz, 1H), 2.01 (h, J=8.1, 7.5 Hz, 2H), 1.80 (dt, J=12.5, 7.6 Hz, 1H), 1.32 (s, 3H).

Example 1.194

Synthesis of N-(2-methoxypyrimidin-5-yl)-2-{methyl[2-(1-methyl-1H-imidazol-4-yl)-5H,6H,7H-cyclopenta[d]pyrimidin-4-yl]amino}acetamide (Compound 186)

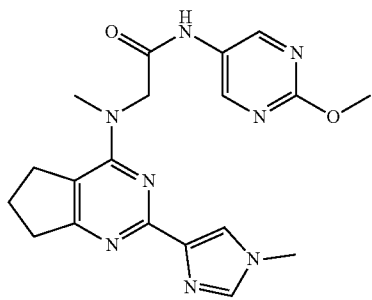 [SMILES: COc1ncc(NC(=O)CN(C)c2nc(-c3cn(C)cn3)nc3c2CCC3)cn1]

Compound 186 was synthesized similar to Compound 142 by replacing cyclohexylamine with 2-methoxypyrimidin-5-amine. LCMS (ES) [M+1]+ m/z: 395; 1H-NMR: (300 MHz, DMSO-d6, ppm): δ 10.49 (s, 1H), 8.79 (s, 2H), 7.69 (d, J=1.2 Hz, 1H), 7.61 (d, J=1.2 Hz, 1H), 4.37 (s, 2H), 3.87 (s, 3H), 3.66 (s, 3H), 3.32 (s, 3H), 3.12 (t, J=7.2 Hz, 2H), 2.74 (t, J=7.8 Hz, 2H), 2.00-1.90 (m, 2H).

Example 1.195

Synthesis of 1-(4-methoxyphenyl)-4-[2-(pyridin-2-yl)-5H,6H,7H-cyclopenta[d]pyrimidin-4-yl]-1,4-diazepan-2-one (Compound 188)

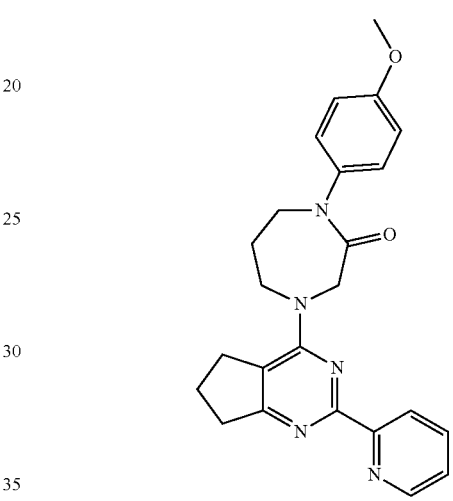

Scheme 104

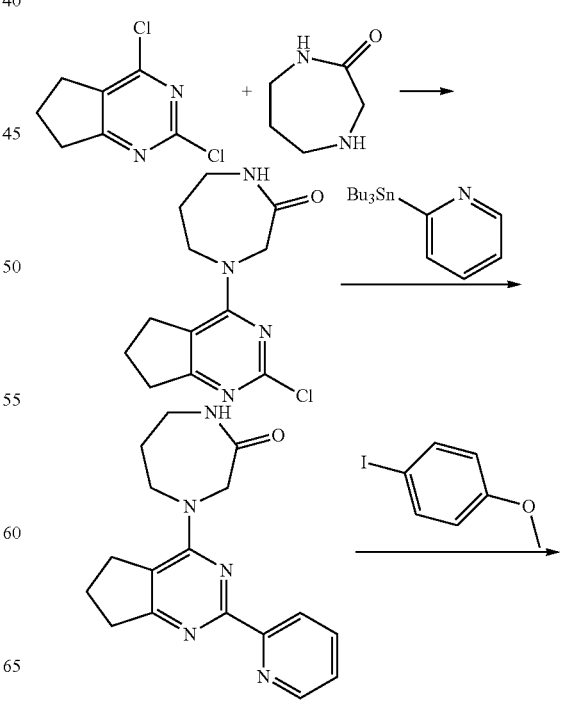

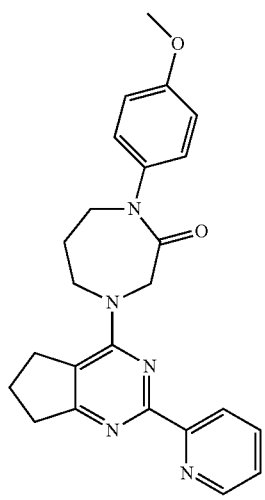

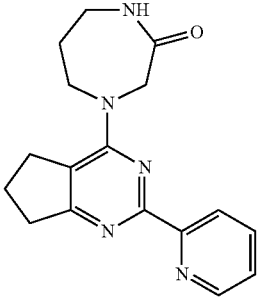

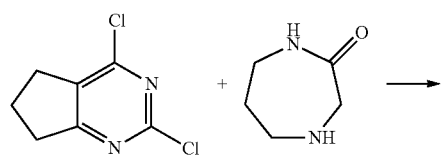

To a solution of 2,4-Dichloro-6,7-dihydro-5H-cyclopenta[d]pyrimidine (200 mg; 1.06 mmol; 1 eq.) in acetonitrile (3.5 ml) was added 1,4-Diazepan-2-one hydrochloride (191 mg; 1.27 mmol; 1.2 eq.) and Hunig's base (0.74 mL; 4.23 mmol; 4 eq.). The reaction was stirred at 70° C. for 24 h. The reaction was evaporated, and the residue was purified by silica gel chromatography (methanol/dichloromethane gradient) to give 4-{2-chloro-5H,6H,7H-cyclopenta[d]pyrimidin-4-yl}-1,4-diazepan-2-one (279 mg, 98%) as a white solid. LCMS (ES+): [M+H]⁺=266.9.

Step 2

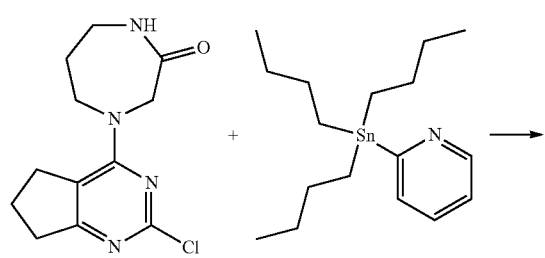

4-{2-Chloro-5H,6H,7H-cyclopenta[d]pyrimidin-4-yl}-1,4-diazepan-2-one (279 mg; 1.05 mmol; 1 eq.) was suspended in 1,4-dioxane (4 ml) and the mixture was purged with Argon gas. 2-(Tributylstannyl)pyridine (0.68 mL; 2.09 mmol; 2 eq.) and tetrakis(triphenylphosphane) palladium (121 mg; 0.1 mmol; 0.1 eq.) were added and the reaction was stirred in a heat block at 108° C. for 18 h. The reaction mixture was evaporated and purified by reverse phase chromatography (C18, acetonitrile/0.1% HCOOH-water gradient) to give 4-[2-(pyridin-2-yl)-5H,6H,7H-cyclopenta[d]pyrimidin-4-yl]-1,4-diazepan-2-one (66 mg) as a white solid. LCMS (ES+): [M+H]⁺=310.0.

Step 3

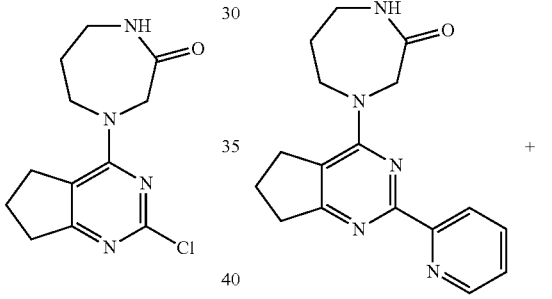

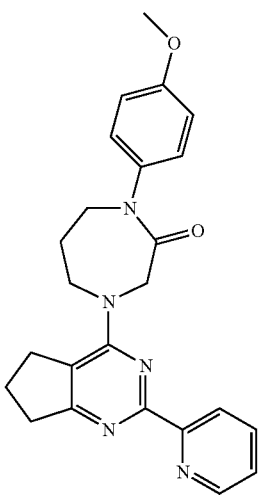

4-[2-(Pyridin-2-yl)-5H,6H,7H-cyclopenta[d]pyrimidin-4-yl]-1,4-diazepan-2-one (59 mg; 0.19 mmol; 1 eq.), 1-iodo-4-methoxybenzene (54 mg; 0.23 mmol; 1.2 eq.), 1-N,2-N-dimethylcyclohexane-1,2-diamine (13.5 mg; 0.1 mmol; 0.5 eq.), potassium phosphate tribasic (121 mg; 0.57 mmol; 3 eq.) were suspended in 1,4-dioxane (3.5 ml). The mixture was purged with Argon gas. Copper(I) iodide (12.7 mg; 0.07 mmol; 0.35 eq.) was added, the vessel was sealed and stirred in a heat block at 120° C. for 48 h. The reaction was cooled, filtered, evaporated and the residue was purified by reverse phase chromatography (Waters XSelect CSH C18 column, 0-100% acetonitrile/0.1% aqueous formic acid gradient) to give 1-(4-methoxyphenyl)-4-[2-(pyridin-2-yl)-5H,6H,7H-cyclopenta[d]pyrimidin-4-yl]-1,4-diazepan-2-one (33 mg, 42%) as a brown solid. LCMS (ES+): [M+H]⁺=416.1. ¹H NMR (400 MHz, DMSO-d₆, 80° C.) δ 7.18-6.65 (m, 8H), 4.43-4.11 (m, 2H), 3.87-3.54 (m, 11H), 2.15-1.96 (m, 4H).

Example 1.196

Synthesis of N-(4-fluorophenyl)-2-{[2-(4-methoxypyridin-2-yl)-5H,6H,7H-cyclopenta[d]pyrimidin-4-yl](methyl)amino}acetamide (Compound 189)

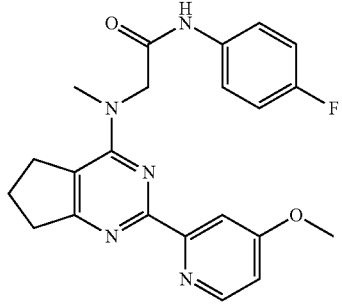 [SMILES: COc1ccnc(-c2nc3c(c(N(C)CC(=O)Nc4ccc(F)cc4)n2)CCC3)c1]

Compound 189 was synthesized similar to Compound 135 by replacing oxolan-3-amine with 4-fluoroaniline. LCMS (ES) [M+1]⁺ m/z: 408. ¹H NMR (300 MHz, DMSO-d₆) δ 10.34 (s, 1H), 8.45 (d, J=5.4 Hz, 1H), 7.79 (d, J=2.7 Hz, 1H), 7.72-7.47 (m, 2H), 7.16-7.10 (m, 2H), 7.00 (dd, J=5.7, 2.7 Hz, 1H), 4.42 (s, 2H), 3.77 (s, 3H), 3.37 (s, 3H), 3.21 (t, J=7.2 Hz, 2H), 2.84 (t, J=7.8 Hz, 2H), 2.08-1.95 (m, 2H).

Example 1.197

Synthesis of N-(5-methoxypyridin-2-yl)-2-{methyl[2-(1-methyl-1H-imidazol-4-yl)-5H,6H,7H-cyclopenta[d]pyrimidin-4-yl]amino}acetamide (Compound 190)

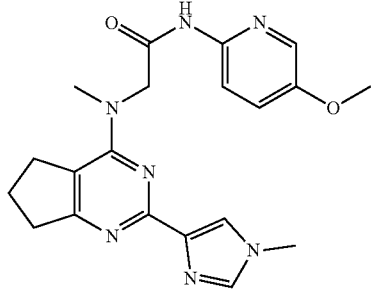 [SMILES: COc1ccc(NC(=O)CN(C)c2nc(-c3cn(C)cn3)nc3c2CCC3)nc1]

Compound 190 was synthesized similar to Compound 142 by replacing cyclohexylamine with 4-methoxypyridin-2-amine. LCMS (ES) [M+1]⁺ m/z: 394; ¹H NMR: (300 MHz, DMSO-d₆, ppm): δ 10.51 (s, 1H), 8.06 (d, J=2.7 Hz, 1H), 7.95 (d, J=9.0 Hz, 1H), 7.66 (d, J=1.2 Hz, 1H), 7.55 (d, J=1.2 Hz, 1H), 7.41 (dd, J=9.0, 3.0 Hz, 1H), 4.43 (s, 2H), 3.80 (s, 3H), 3.62 (s, 3H), 3.30 (s, 3H), 3.12 (t, J=7.2 Hz, 2H), 2.74 (t, J=7.8 Hz, 2H), 2.00-1.90 (m, 2H).

Example 1.198

Synthesis of N-tert-butyl-2-({2-[4-(2-hydroxyethoxy)-5-methylpyridin-2-yl]-5H,6H,7H-cyclopenta[d]pyrimidin-4-yl}(methyl)amino)acetamide (Compound 191)

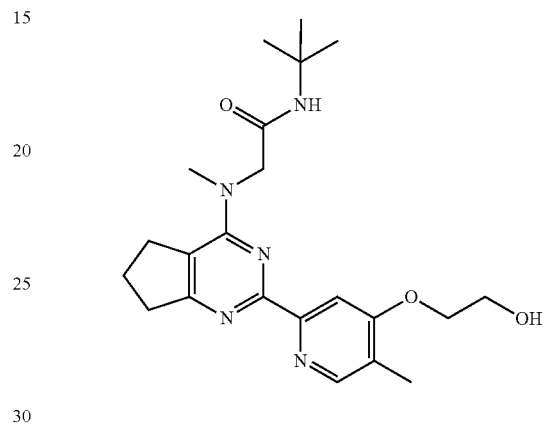

Compound 191 was synthesized similar to Compound 44 by replacing 2-chloropyridin-4-ol with 2-chloro-5-methylpyridin-4-ol. LCMS (ES) [M+1]⁺ m/z: 414. ¹H NMR (300 MHz, DMSO-d₆) δ 8.31 (s, 1H), 7.85 (s, 1H), 7.65 (s, 1H), 4.93 (t, J=5.5 Hz, 1H), 4.20-4.17 (m, 4H), 3.83-3.78 (m, 2H), 3.25 (s, 3H), 3.14 (t, J=7.3 Hz, 2H), 2.82 (t, J=7.8 Hz, 2H), 2.20 (s, 3H), 2.11-1.93 (m, 2H), 1.23 (s, 9H).

Example 1.199

Synthesis of N-tert-butyl-2-{[2-(4-methoxy-5-methylpyridin-2-yl)-5H,6H,7H-cyclopenta[d]pyrimidin-4-yl](methyl)amino}acetamide (Compound 192)

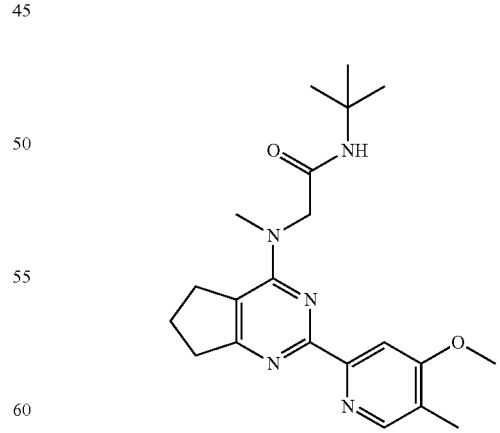

Compound 192 was synthesized similar to Compound 24 by replacing 4-methyl-2-(trimethylstannyl)pyridine with 4-methoxy-5-methyl-2-(trimethylstannyl)pyridine. LCMS (ES) [M+1]⁺ m/z: 384. ¹H NMR (300 MHz, DMSO-d₆) δ 8.31 (s, 1H), 7.88 (s, 1H), 7.65 (s, 1H), 4.17 (s, 2H), 3.96 (s, 3H), 3.26 (s, 3H), 3.14 (t, J=7.4 Hz, 2H), 2.82 (t, J=7.8 Hz, 2H), 2.18 (s, 3H), 2.04-1.94 (m, 2H), 1.23 (s, 9H).

Example 1.200 and Example 1.201

Synthesis of N-tert-butyl-2-{[2-(1-ethyl-1H-imidazol-4-yl)-5H,6H,7H-cyclopenta[d]pyrimidin-4-yl](methyl)amino}acetamide (Compound 193) and N-tert-butyl-2-{[2-(1-ethyl-1H-imidazol-5-yl)-5H,6H,7H-cyclopenta[d]pyrimidin-4-yl](methyl)amino}acetamide (Compound 194)

Compound 193

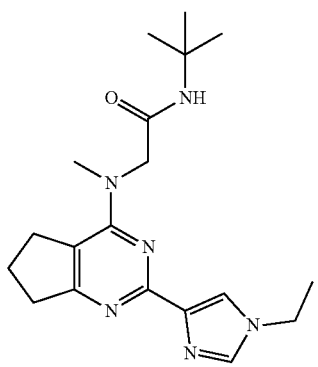

Compound 194

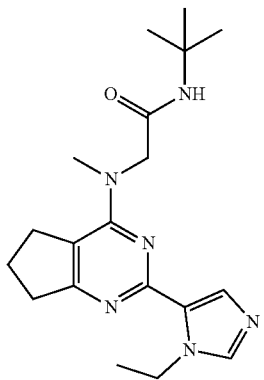

Scheme 105

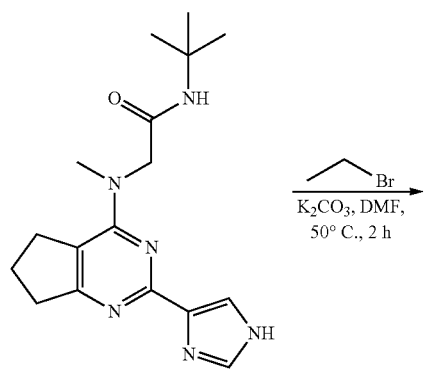

-continued

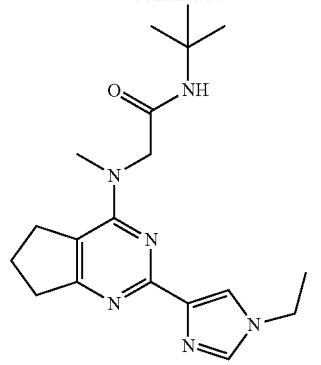

A solution of N-tert-butyl-2-[[2-(3H-imidazol-4-yl)-5H,6H,7H-cyclopenta[d]pyrimidin-4-yl](methyl)amino]acetamide (300.00 mg, 0.913 mmol, 1.00 equiv), $K_2CO_3$ (252.49 mg, 1.827 mmol, 2 equiv) and bromoethane (149.30 mg, 1.370 mmol, 1.50 equiv) in DMF (5.00 mL) was stirred for 2 h at 50° C. under air atmosphere. The crude product was purified by Prep-HPLC to afford N-tert-butyl-2-[[2-(3-ethylimidazol-4-yl)-5H,6H,7H-cyclopenta[d]pyrimidin-4-yl](methyl)amino]acetamide (Compound 192, 86 mg, 26.41%) and N-tert-butyl-2-[[2-(1-ethylimidazol-4-yl)-5H,6H,7H-cyclopenta[d]pyrimidin-4-yl](methyl)amino]acetamide (Compound 193, 102 mg, 31.32%) as a white solid.

Compound 193: LCMS (ES) [M+1]$^+$ m/z: 357; $^1$H NMR (300 MHz, DMSO-$d_6$) δ 7.80 (d, J=1.4 Hz, 1H), 7.66 (d, J=1.4 Hz, 1H), 7.64 (br, 1H), 4.09 (s, 2H), 4.03 (q, J=7.3 Hz, 2H), 3.22 (s, 3H), 3.08 (t, J=7.2 Hz, 2H), 2.73 (t, J=7.8 Hz, 2H), 2.05-1.86 (m, 2H), 1.39 (t, J=7.3 Hz, 3H), 1.25 (s, 9H).

Compound 194: LCMS (ES) [M+1]$^+$ m/z: 357; $^1$H NMR (300 MHz, DMSO-$d_6$) δ 7.75 (d, J=1.3 Hz, 1H), 7.61 (d, J=1.2 Hz, 1H), 7.58 (br, 1H), 4.53 (q, J=7.1 Hz, 2H), 4.11 (s, 2H), 3.19 (s, 3H), 3.08 (t, J=7.3 Hz, 2H), 2.75 (t, J=7.8 Hz, 2H), 2.03-1.82 (m, 2H), 1.31 (t, J=7.1 Hz, 3H), 1.24 (s, 9H).

Example 1.202 and Example 1.203

Synthesis of N-tert-butyl-2-({2-[1-(2-hydroxyethyl)-1H-imidazol-4-yl]-5H,6H,7H-cyclopenta[d]pyrimidin-4-yl}(methyl)amino)acetamide (Compound 195) and N-tert-butyl-2-({2-[1-(2-hydroxyethyl)-1H-imidazol-5-yl]-5H,6H,7H-cyclopenta[d]pyrimidin-4-yl}(methyl)amino)acetamide (Compound 196)

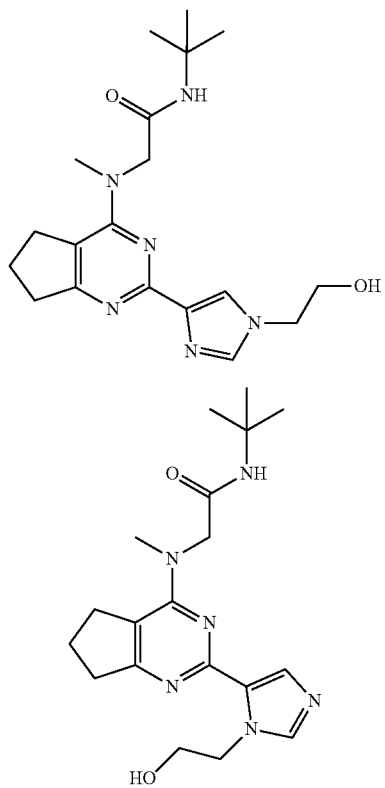

Compound 195

Compound 196

Compound 195 and Compound 196 were synthesized similar to Compound 193 and Compound 194 by replacing bromoethane with 2-(2-iodoethoxy)oxane.

Compound 195: LCMS (ES) [M+1]$^+$ m/z: 373; $^1$H NMR (300 MHz, DMSO-d$_6$) δ7.77 (d, J=1.4 Hz, 1H), 7.62 (br, 1H), 7.61 (d, J=1.4 Hz, 1H), 5.00 (t, J=4.5 Hz, 1H), 4.10 (s, 2H), 4.03 (t, J=5.4 Hz, 2H), 3.69 (q, J=5.1 Hz, 2H), 3.20 (s, 3H), 3.06 (t, J=7.3 Hz, 2H), 2.73 (t, J=7.8 Hz, 2H), 2.02-1.79 (m, 2H), 1.25 (s, 9H).

Compound 196: LCMS (ES) [M+1]$^+$ m/z: 373; $^1$H NMR (300 MHz, DMSO-d$_6$) δ7.66 (d, J=1.2 Hz, 1H), 7.62 (d, J=1.2 Hz, 1H), 7.57 (s, 1H), 4.89 (t, J=5.3 Hz, 1H), 4.56 (t, J=5.5 Hz, 2H), 4.09 (s, 2H), 3.67 (d, J=5.3 Hz, 2H), 3.18 (s, 3H), 3.08 (t, J=7.3 Hz, 2H), 2.75 (t, J=7.8 Hz, 2H), 2.00-1.90 (m, 2H), 1.26 (s, 9H).

Example 1.204

Synthesis of 2-({2-[4-(2-hydroxyethoxy)pyridin-2-yl]-5H,6H,7H-cyclopenta[d]pyrimidin-4-yl}(methyl)amino)-N-(2-methoxypyrimidin-5-yl)acetamide (Compound 197)

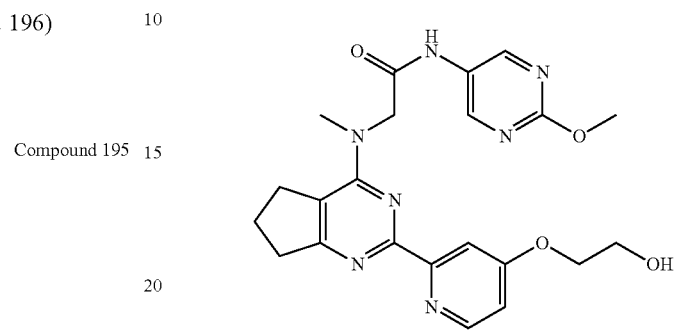

Compound 197 was synthesized similar to Compound 144 by replacing cyclohexylamine with 2-methoxypyrimidin-5-amine. LCMS (ES) [M+1]$^+$ m/z: 452. $^1$H NMR (300 MHz, DMSO-d$_6$) δ 10.51 (s, 1H), 8.77 (s, 2H), 8.44-8.42 (d, J=5.6 Hz, 1H), 7.77-7.76 (d, J=2.5 Hz, 1H), 7.03-7.01 (dd, J=5.6, 2.6 Hz, 1H), 4.92 (t, J=5.4 Hz, 1H), 4.42 (br, 2H), 4.05 (t, J=4.9 Hz, 2H), 3.88 (s, 3H), 3.70 (q, J=5.1 Hz, 2H), 3.38 (s, 3H), 3.21 (t, J=7.2 Hz, 2H), 2.83 (t, J=7.9 Hz, 2H), 2.10-2.00 (m, 2H).

Example 1.205

Synthesis of N-(4-fluorophenyl)-2-({2-[4-(2-hydroxyethoxy)pyridin-2-yl]-5H,6H,7H-cyclopenta[d]pyrimidin-4-yl}(methyl)amino)acetamide (Compound 198)

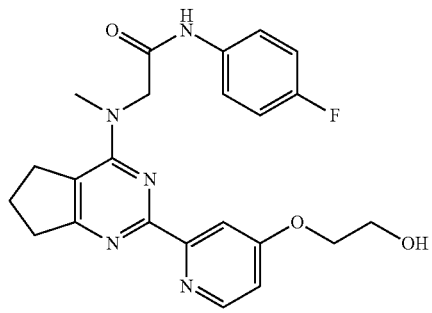 [SMILES: CN(CC(=O)Nc1ccc(F)cc1)c1nc(-c2cc(OCCO)ccn2)nc2c1CCC2]

Compound 198 was synthesized similar to Compound 144 by replacing cyclohexylamine with 4-fluoroaniline. LCMS (ES) [M+1]$^+$ m/z: 438. $^1$H NMR (300 MHz, DMSO-d$_6$) δ 10.28 (s, 1H), 8.43 (d, J=5.6 Hz, 1H), 7.78 (d, J=2.5 Hz, 1H), 7.60 (dd, J=9.1, 5.1 Hz, 2H), 7.12 (t, J=8.9 Hz, 2H), 7.00 (dd, J=5.6, 2.6 Hz, 1H), 4.90 (s, 1H), 4.41 (s, 2H), 4.02 (t, J=4.8 Hz, 2H), 3.67 (t, J=4.8 Hz, 2H), 3.36 (s, 3H), 3.21 (t, J=7.3 Hz, 2H), 2.83 (t, J=7.9 Hz, 2H), 2.08-1.95 (m, 2H).

Example 1.206

Synthesis of 2-({2-[4-(2-hydroxyethoxy)pyridin-2-yl]-5H,6H,7H-cyclopenta[d]pyrimidin-4-yl}(methyl)amino)-N-(6-methylpyridin-3-yl)acetamide (Compound 199)

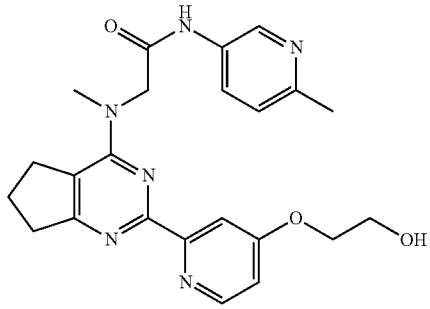 [SMILES: Cc1ccc(NC(=O)CN(C)c2nc(-c3cc(OCCO)ccn3)nc3c2CCC3)cn1]

Compound 199 was synthesized similar to Compound 144 by replacing cyclohexylamine with 6-methylpyridin-3-amine. LCMS (ES) [M+1]+ m/z: 435. $^1$H NMR (300 MHz, DMSO-d$_6$) δ 10.37 (s, 1H), 8.62 (d, J=2.5 Hz, 1H), 8.43 (d, J=5.6 Hz, 1H), 7.91 (dd, J=8.4, 2.6 Hz, 1H), 7.77 (d, J=2.5 Hz, 1H), 7.18 (d, J=8.4 Hz, 1H), 7.01 (dd, J=5.7, 2.6 Hz, 1H), 5.02 (t, J=5.5 Hz, 1H), 4.42 (s, 2H), 4.03 (t, J=4.8 Hz, 2H), 3.69 (q, J=5.1 Hz, 2H), 3.38 (s, 3H), 3.21 (t, J=7.3 Hz, 2H), 2.83 (t, J=7.8 Hz, 2H), 2.40 (s, 3H), 2.08-2.01 (m, 2H).

Example 1.207

Synthesis of 2-{[2-(4-methoxypyridin-2-yl)-5H,6H,7H-cyclopenta[d]pyrimidin-4-yl](methyl)amino}-N-(6-methylpyridin-3-yl)acetamide (Compound 200)

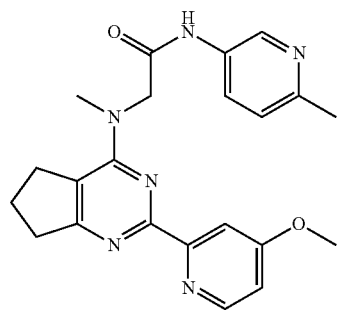 [SMILES: COc1ccnc(-c2nc3c(c(N(C)CC(=O)Nc4ccc(C)nc4)n2)CCC3)c1]

Compound 200 was synthesized similar to Compound 135 by replacing oxolan-3-amine with 6-methylpyridin-3-amine. LCMS (ES) [M+1]+ m/z: 405. $^1$H NMR (300 MHz, DMSO-d$_6$) δ 10.36 (s, 1H), 8.60 (d, J=2.7 Hz, 1H), 8.44 (d, J=5.7 Hz, 1H), 7.89 (dd, J=8.4, 2.7 Hz, 1H), 7.78 (d, J=2.1 Hz, 1H), 7.17 (d, J=8.4 Hz, 1H), 7.00 (dd, J=5.7, 2.7 Hz, 1H), 4.43 (s, 2H), 3.78 (s, 3H), 3.37 (s, 3H), 3.21 (t, J=7.2 Hz, 2H), 2.84 (t, J=7.8 Hz, 2H), 2.40 (s, 3H), 2.11-1.96 (m, 2H).

Example 1.208

Synthesis of N-(6-methoxypyridin-3-yl)-2-{methyl[2-(1-methyl-1H-imidazol-4-yl)-5H,6H,7H-cyclopenta[d]pyrimidin-4-yl]amino}acetamide (Compound 201)

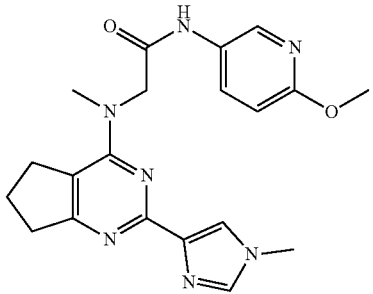 [SMILES: COc1ccc(NC(=O)CN(C)c2nc(-c3cn(C)cn3)nc3c2CCC3)cn1]

Compound 201 was synthesized similar to Compound 142 by replacing cyclohexylamine with 5-amino-2-methoxypyridine. LCMS (ES) [M+1]+ m/z: 394; $^1$H-NMR: (300 MHz, DMSO-d$_6$, ppm): δ 10.27 (s, 1H), 8.38 (d, J=2.7 Hz, 1H), 7.92 (dd, J=8.7, 2.7 Hz, 1H), 7.69 (d, J=1.2 Hz, 1H), 7.60 (d, J=1.2 Hz, 1H), 6.79 (d, J=8.7 Hz, 1H), 4.35 (s, 2H), 3.80 (s, 3H), 3.64 (s, 3H), 3.31 (s, 3H), 3.13 (t, J=7.2 Hz, 2H), 2.74 (t, J=7.8 Hz, 2H), 2.00-1.90 (m, 2H).

Example 1.209

Synthesis of N-(4-fluorophenyl)-2-{methyl[2-(1-methyl-1H-imidazol-4-yl)-5H,6H,7H-cyclopenta[d]pyrimidin-4-yl]amino}acetamide (Compound 202)

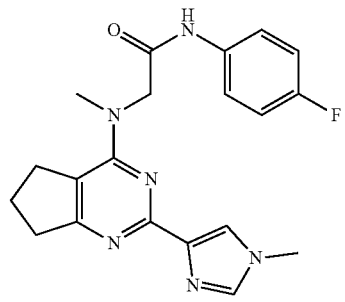 [SMILES: CN(CC(=O)Nc1ccc(F)cc1)c1nc(-c2cn(C)cn2)nc2c1CCC2]

Compound 202 was synthesized similar to Compound 142 by replacing cyclohexylamine with 4-fluoroaniline. LCMS (ES) [M+1]+ m/z: 381; $^1$H-NMR: (300 MHz, DMSO-d$_6$, ppm): δ 10.28 (s, 1H), 7.70-7.60 (m, 4H), 7.17-7.11 (m, 2H), 4.35 (s, 2H), 3.63 (s, 3H), 3.31 (s, 3H), 3.12 (t, J=7.2 Hz, 2H), 2.74 (t, J=7.8 Hz, 2H), 2.00-1.90 (m, 2H).

Example 1.210

Synthesis of 4-(4-methoxyphenyl)-1-[2-(pyridin-2-yl)-5H,6H,7H-cyclopenta[d]pyrimidin-4-yl]-1,4-diazepan-5-one (Compound 203)

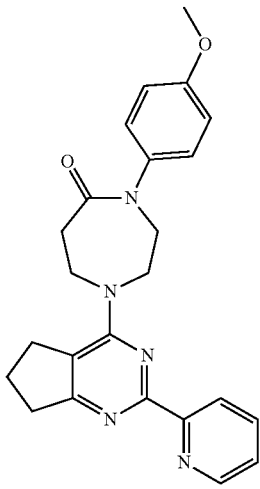 [SMILES: COc1ccc(N2CCN(c3nc(-c4ccccn4)nc4c3CCC4)CCC2=O)cc1]

Compound 203 was synthesized similar to Compound 188 by replacing 1,4-diazepan-2-one hydrochloride with 1,4-diazepan-5-one hydrochloride. LCMS (ES+): [M+H]+= 416.1. ¹H NMR (400 MHz, Methanol-d₄) δ 7.16-6.73 (m, 8H), 4.29-3.76 (m, 11H), 3.06-2.85 (m, 6H).

Example 1.211

Synthesis of (2R)-2-{methyl[2-(pyridin-2-yl)-5H,6H,7H-cyclopenta[d]pyrimidin-4-yl]amino}-N-(1-methylcyclopropyl)propanamide (Compound 204)

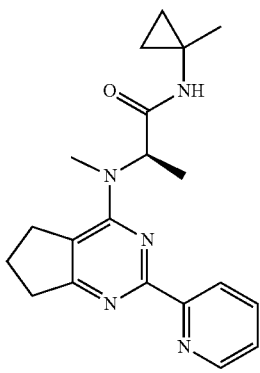 [SMILES: C[C@H](C(=O)NC1(C)CC1)N(C)c1nc(-c2ccccn2)nc2c1CCC2]

Compound 204 was synthesized similar to Compound 108 by replacing cyclohexylamine with 1-methylcyclopropan-1-amine. LCMS (ES+): [M+H]+=352.1. ¹H NMR (400 MHz, DMSO-d₆) δ 8.78-8.71 (m, 1H), 8.51 (s, 1H), 8.43-8.35 (m, 1H), 8.06-7.96 (m, 1H), 7.59 (ddd, J=7.6, 4.7, 1.2 Hz, 1H), 5.02 (q, J=7.0 Hz, 1H), 3.25-3.14 (m, 5H), 2.99-2.87 (m, 2H), 2.14-1.93 (m, 2H), 1.37 (d, J=7.0 Hz, 3H), 1.17 (s, 3H), 0.61-0.41 (m, 4H).

Example 1.212

Synthesis of (3S)-3-{[2-(4-methoxypyridin-2-yl)-5H,6H,7H-cyclopenta[d]pyrimidin-4-yl](methyl)amino}-1-phenylpyrrolidin-2-one (Compound 205)

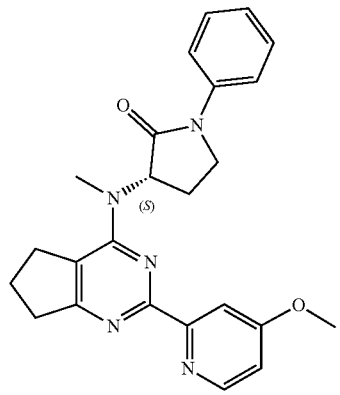

Compound 205 was synthesized similar to Compound 130 by replacing (2R)-2-[(tert-butoxycarbonyl)amino]-4-(methylsulfanyl)butanoic acid with (2S)-2-[(tert-butoxycarbonyl)amino]-4-(methylsulfanyl)butanoic acid and replacing 2-(tributylstannyl)pyridine with 4-methoxy-2-(tributylstannyl)pyridine. LCMS (ES+): [M+H]+=416.3. ¹H NMR (400 MHz, DMSO-d₆) δ 8.37 (d, J=5.6 Hz, 1H), 8.15 (s, 1H), 7.72 (d, 1H), 7.70-7.66 (m, 2H), 7.40-7.34 (m, 2H), 7.17-7.12 (m, 1H), 6.97 (dd, J=5.6, 2.6 Hz, 1H), 5.49-5.31 (m, 1H), 3.99-3.86 (m, 2H), 3.78 (s, 3H), 3.24-3.19 (m, 5H), 2.87-2.81 (m, 2H), 2.46-2.30 (m, 2H), 2.07-1.97 (m, 2H).

Example 1.213

Synthesis of (3S)-1-(4-fluorophenyl)-3-{methyl[2-(pyridin-2-yl)-5H,6H,7H-cyclopenta[d]pyrimidin-4-yl]amino}pyrrolidin-2-one (Compound 206)

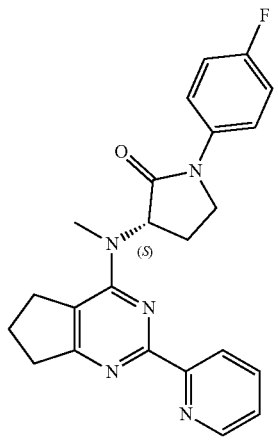

Compound 206 was synthesized similar to Compound 130 by replacing (2R)-2-[(tert-butoxycarbonyl)amino]-4-(methylsulfanyl)butanoic acid with (2S)-2-[(tert-butoxycarbonyl)amino]-4-(methylsulfanyl)butanoic acid and replacing aniline with 4-fluoroaniline. LCMS (ES+): [M+H]+=

404.2. $^1$H NMR (400 MHz, DMSO-d$_6$) δ 8.54 (d, J=4.7 Hz, 1H), 8.15 (d, J=2.5 Hz, 1H), 7.73 (dd, J=9.0, 4.9 Hz, 2H), 7.68-7.56 (m, 1H), 7.39-7.33 (m, 1H), 7.26-7.18 (m, 2H), 5.29 (s, 1H), 3.99-3.84 (m, 2H), 3.25-3.21 (m, 5H), 2.88-2.80 (m, 2H), 2.46-2.27 (m, 2H), 2.06-1.96 (m, 2H).

Example 1.214

Synthesis of (3S)-3-{methyl[2-(pyridin-2-yl)-5H,6H,7H-cyclopenta[d]pyrimidin-4-yl]amino}-1-(1-methylcyclopentyl)pyrrolidin-2-one (Compound 207)

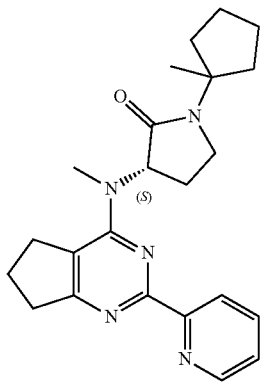

Compound 207 was synthesized similar to Compound 130 by replacing (2R)-2-[(tert-butoxycarbonyl)amino]-4-(methylsulfanyl)butanoic acid with (2S)-2-[(tert-butoxycarbonyl)amino]-4-(methylsulfanyl)butanoic acid and replacing aniline with 1-methylcyclopentan-1-aminium chloride. LCMS (ES+): [M+H]$^+$=392.2. $^1$H NMR (400 MHz, DMSO-d$_6$) δ 8.77-8.56 (m, 1H), 8.25 (d, J=7.8 Hz, 1H), 7.95-7.79 (m, 1H), 7.51-7.34 (m, 1H), 5.36-5.12 (m, 1H), 3.63-3.46 (m, 2H), 3.22-3.14 (m, 2H), 3.06 (s, 3H), 2.82 (t, J=8.0 Hz, 2H), 2.33-2.22 (m, 1H), 2.14-1.93 (m, 5H), 1.78-1.54 (m, 6H), 1.21 (s, 3H).

Example 1.215

Synthesis of (3S)-3-{methyl[2-(pyridin-2-yl)-5H,6H,7H-cyclopenta[d]pyrimidin-4-yl]amino}-1-(pyridin-4-yl)pyrrolidin-2-one (Compound 208)

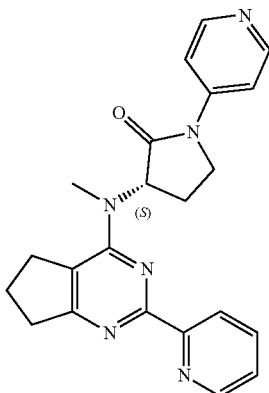

Compound 208 was synthesized similar to Compound 130 by replacing (2R)-2-[(tert-butoxycarbonyl)amino]-4-(methylsulfanyl)butanoic acid with (2S)-2-[(tert-butoxycarbonyl)amino]-4-(methylsulfanyl)butanoic acid and replacing aniline with 4-pyridinamine. LCMS (ES+): [M+H]$^+$=386.9. $^1$H NMR (400 MHz, Methanol-d$_4$) δ 8.53 (d, J=4.9 Hz, 1H), 8.48-8.44 (m, 2H), 7.97 (d, J=7.9 Hz, 1H), 7.84-7.78 (m, 2H), 7.49-7.42 (m, 1H), 7.35-7.29 (m, 1H), 4.14-3.91 (m, 3H), 3.44 (s, 3H), 2.99-2.93 (m, 2H), 2.62-2.51 (m, 2H), 2.17-2.11 (m, 2H).

Example 1.216

Synthesis of 2-({2-[4-(2-hydroxyethoxy)pyridin-2-yl]-5H,6H,7H-cyclopenta[d]pyrimidin-4-yl}(methyl)amino)-N-(5-methoxypyridin-2-yl)acetamide (Compound 209)

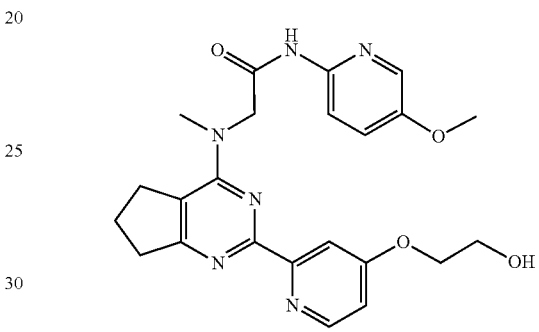

Compound 209 was synthesized similar to Compound 144 by replacing cyclohexylamine with 5-methoxyl-2-aminopyridine. LCMS (ES) [M+1]$^+$ m/z: 451. $^1$H NMR (300 MHz, DMSO-d$_6$) δ 10.54 (s, 1H), 8.44-8.42 (d, J=5.6 Hz, 1H), 8.04-8.03 (d, J=3.0 Hz, 1H), 7.98-7.95 (d, J=9.1 Hz, 1H), 7.77-7.76 (d, J=2.5 Hz, 1H), 7.42-7.38 (dd, J=9.1, 3.0 Hz, 1H), 6.99-6.96 (dd, J=5.6, 2.7 Hz, 1H), 4.90-4.87 (t, J=5.4 Hz, 1H), 4.50 (s, 2H), 4.02-3.96 (q, J=7.4 Hz, 2H), 3.80 (s, 3H), 3.69-3.64 (q, J=5.4 Hz, 2H), 3.34 (s, 3H), 3.22-3.17 (t, J=7.3 Hz, 2H), 2.85-2.80 (t, J=7.8 Hz, 2H), 2.05-1.98 (m, 2H).

Example 1.217

Synthesis of 2-({2-[4-(2-hydroxy-2-methylpropoxy)pyridin-2-yl]-5H,6H,7H-cyclopenta[d]pyrimidin-4-yl}(methyl)amino)-N-(6-methoxypyridin-3-yl)acetamide (Compound 210)

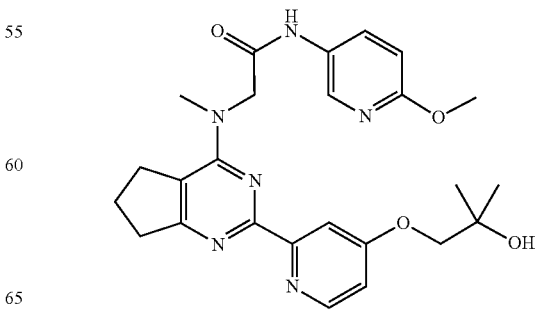

Scheme 106

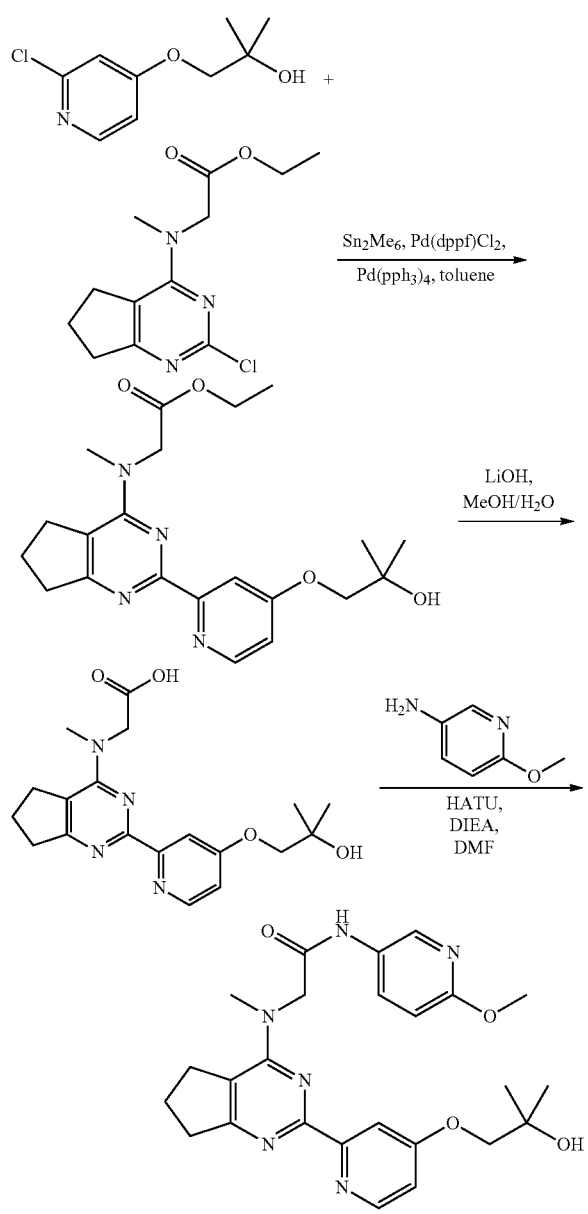

Step 1

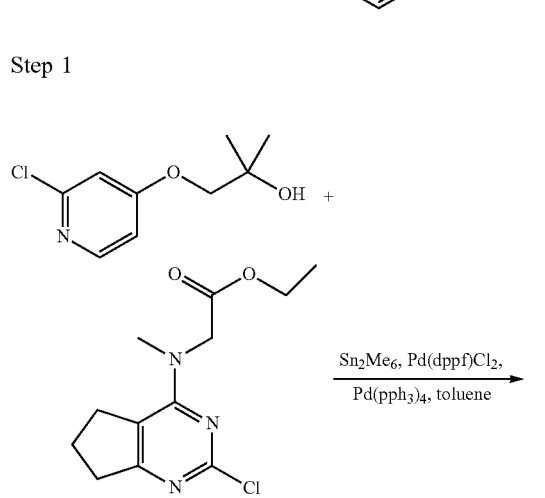

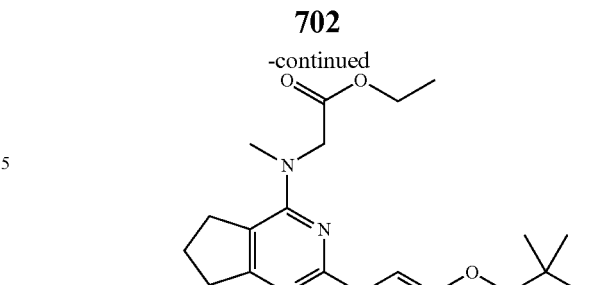

Into a 50-mL 3-necked round-bottom flask purged and maintained with an inert atmosphere of nitrogen were placed 1-[(2-chloropyridin-4-yl)oxy]-2-methylpropan-2-ol (1.00 g, 4.96 mmol, 1.00 equiv), Toluene (30 mL), $Sn_2Me_6$ (1.71 g, 5.22 mmol, 1.05 equiv) and $Pd(PPh_3)_4$ (0.57 g, 0.49 mmol, 0.10 equiv). The resulting solution was stirred for 2 h at 100° C. To this mixture was added ethyl 2-([2-chloro-5H,6H,7H-cyclopenta[d]pyrimidin-4-yl](methyl)amino)acetate (0.94 g, 3.48 mmol, 0.70 equiv) and $Pd(PPh_3)_4$ (0.57 g, 0.49 mmol, 0.10 equiv). The resulting solution was stirred overnight at 100° C. After cooled to ambient temperature the resulting mixture was concentrated under vacuum. The residue was applied onto a silica gel column with dichloromethane/methanol (20:1). This resulted in 300 mg (15.11%) of ethyl 2-([2-[4-(2-hydroxy-2-methylpropoxy)pyridin-2-yl]-5H, 6H,7H-cyclopenta[d]pyrimidin-4-yl](methyl)amino)acetate as brown oil. LCMS (ES) [M+1]$^+$ m/z 401.

Step 2

Into a 50-mL round-bottom flask were placed ethyl 2-([2-[4-(2-hydroxy-2-methylpropoxy)pyridin-2-yl]-5H,6H,7H-cyclopenta[d]pyrimidin-4-yl](methyl)amino)acetate (300 mg, 0.75 mmol, 1.00 equiv) and MeOH (3 mL). This was followed by the addition of a solution of LiOH (36 mg, 1.50 mmol, 2.00 equiv) in $H_2O$ (1 mL) dropwise with stirring at 25° C. The resulting solution was stirred for 2 hr at 25° C. and concentrated under vacuum. The resulting solution was extracted with 2×20 mL of dichloromethane and the aqueous was separated and concentrated under vacuum. This resulted

703 in 150 mg (52.92%) of lithio 2-([2-[4-(2-hydroxy-2-methylpropoxy)pyridin-2-yl]-5H,6H,7H-cyclopenta[d]pyrimidin-4-yl](methyl)amino)acetate as a brown solid. LCMS (ES) [M−Li+H+1]+ m/z 373.

Step 3

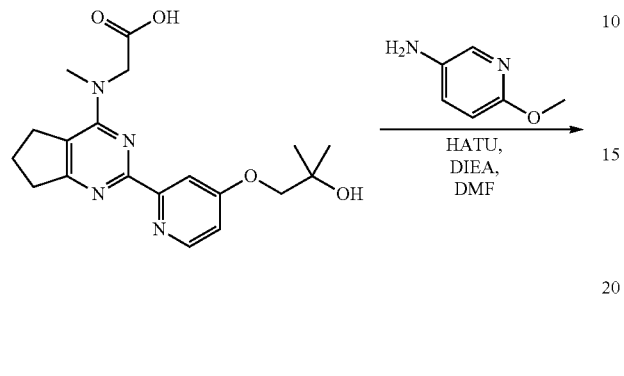

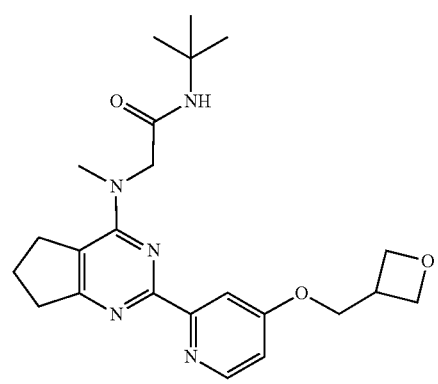 [SMILES: CN(CC(=O)NC(C)(C)C)c1nc(-c2cc(OCC3COC3)ccn2)nc2c1CCC2]

To a stirred solution of ([2-[4-(2-hydroxy-2-methylpropoxy)pyridin-2-yl]-5H,6H,7H-cyclopenta[d]pyrimidin-4-yl](methyl)amino)acetic acid (200.00 mg, 0.537 mmol, 1.00 equiv), 5-amino-2-methoxypyridine (80 mg, 0.64 mmol, 1.2 equiv) and DIEA (138.8 mg, 1.07 mmol, 2.0 equiv) in DMF (3 mL) was added HATU (265.4 mg, 0.69 mmol, 1.3 equiv) in one portion at 0° C. After stirred for 5 h at 0-25° C., the resulting mixture was purified by preparative HPLC (Column, C18; mobile phase A: CH$_3$CN, Mobile phase B: Water. Flow rate: 20 mL/min) to give 2-[2-[(2S)-2-(2-formyl-3-hydroxyphenoxymethyl)piperidine-1-carbonyl]phenyl]acetamide (123.1 mg, 12.3%) as an off white solid. LCMS (ES) [M+1]+ m/z: 479. $^1$H NMR (300 MHz, DMSO-d6) δ 10.27 (s, 1H), 8.45 (d, J=5.6 Hz, 1H), 8.34 (d, J=2.6 Hz, 1H), 7.87 (dd, J=8.9, 2.7 Hz, 1H), 7.79 (d, J=2.6 Hz, 1H), 7.03 (dd, J=5.7, 2.6 Hz, 1H), 6.77 (d, J=8.9 Hz, 1H), 4.67 (s, 1H), 4.41 (s, 2H), 3.82-3.78 (m, 5H), 3.37 (s, 3H), 3.21 (t, J=7.3 Hz, 2H), 2.84 (t, J=7.8 Hz, 2H), 2.04-1.99 (m, 2H), 1.17 (s, 6H).

704

Example 1.218

Synthesis of N-tert-butyl-2-[methyl(2-{4-[(oxetan-3-yl)methoxy]pyridin-2-yl}-5H,6H,7H-cyclopenta[d]pyrimidin-4-yl)amino]acetamide (Compound 211)

Compound 211 was synthesized similar to Compound 24 replacing 4-methyl-2-(tributylstannyl)-pyridine with 4-(oxetan-3-ylmethoxy)-2-(tributylstannyl)pyridine. LCMS (ES+): [M+H]+=426.2. $^1$H NMR (400 MHz, DMSO-d6) δ 8.60 (d, J=5.8 Hz, 1H), 7.95 (d, J=2.6 Hz, 1H), 7.82 (s, 1H), 7.29 (dd, J=5.9, 2.6 Hz, 1H), 4.77-4.69 (m, 2H), 4.51-4.42 (m, 4H), 4.22 (s, 2H), 3.48-3.43 (m, 1H), 3.37 (s, 3H), 3.22-3.17 (m, 2H), 2.96-2.87 (m, 2H), 2.09-1.98 (m, 2H), 1.24 (s, 9H).

Example 1.219

Synthesis of (2R)—N-tert-butyl-2-({2-[4-(difluoromethoxy)pyridin-2-yl]-5H,6H,7H-cyclopenta[d]pyrimidin-4-yl}(methyl)amino)-4-(methylsulfanyl)butanamide (Compound 212)

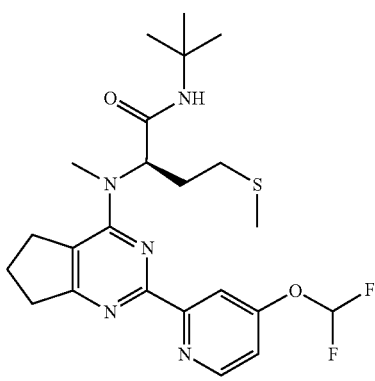 [SMILES: CSCC[C@H](C(=O)NC(C)(C)C)N(C)c1nc(-c2cc(OC(F)F)ccn2)nc2c1CCC2]

Compound 212 was synthesized similar to Compound 114 by replacing (2R)-2-[(tert-butoxycarbonyl)amino]-3-methylbutanoic acid with (2R)-2-[(tert-butoxycarbonyl)amino]-4-(methylsulfanyl)butanoic acid and by replacing 4-(tributylstannyl)pyridine with 4-(difluoromethoxy)-2-(tributylstannyl)pyridine. LCMS (ES+): [M+H]+=480.4. $^1$H NMR (400 MHz, DMSO-d$_6$) δ ppm 1.16-1.20 (m, 9H) 1.89-2.15 (m, 7H) 2.34-2.46 (m, 2H) 2.74-2.95 (m, 2H)

3.00-3.14 (m, 4H) 3.18-3.25 (m, 2H) 4.97-5.09 (m, 1H) 7.29 (dd, J=5.48, 2.35 Hz, 1H) 7.57 (t, J=72.78 Hz, 1H) 7.81-7.87 (m, 1H) 8.09 (d, J=1.96 Hz, 1H) 8.68 (d, J=5.87 Hz, 1H).

Example 1.220

Synthesis of 2-({2-[4-(difluoromethoxy)pyridin-2-yl]-5H,6H,7H-cyclopenta[d]pyrimidin-4-yl}(methyl)amino)-N-(1-methyl-1H-pyrazol-4-yl)acetamide (Compound 213)

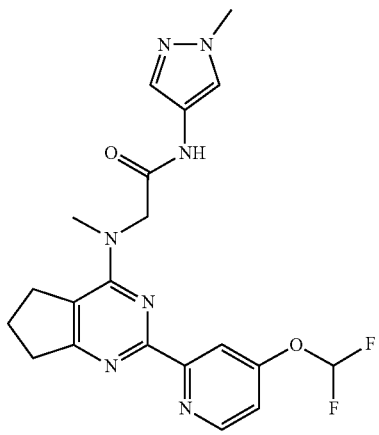 [SMILES: CN(CC(=O)Nc1cnn(C)c1)c1nc(-c2cc(OC(F)F)ccn2)nc2c1CCC2]

Compound 213 was synthesized similar to Compound 177 by replacing 2-(tributylstannyl)-4-(2,2,2-trifluoroethoxy)pyridine with 4-(difluoromethoxy)-2-(tributylstannyl)pyridine. LCMS (ES+): [M+H]⁺=429.9. ¹H NMR (400 MHz, DMSO-d₆) δ ppm 2.04-2.16 (m, 2H) 3.04 (br t, J=7.83 Hz, 2H) 3.26-3.28 (m, 2H) 3.52 (s, 3H) 3.70-3.74 (m, 3H) 4.61-4.69 (m, 2H) 6.32-6.38 (m, 1H) 6.36 (d, J=1.57 Hz, 1H) 7.42-7.47 (m, 1H) 7.43-7.83 (m, 2H) 7.63 (t, J=73.17 Hz, 1H) 8.04-8.12 (m, 1H) 8.77-8.85 (m, 1H) 10.78-10.86 (m, 1H).

Example 1.221

Synthesis of 2-({2-[4-(2-hydroxy-2-methylpropoxy)pyridin-2-yl]-5H,6H,7H-cyclopenta[d]pyrimidin-4-yl}(methyl)amino)-N-(5-methoxypyridin-2-yl)acetamide (Compound 214)

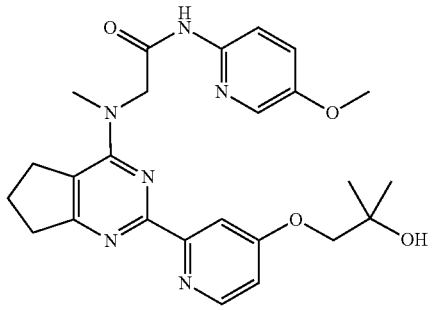 [SMILES: COc1ccc(NC(=O)CN(C)c2nc(-c3cc(OCC(C)(C)O)ccn3)nc3c2CCC3)nc1]

Compound 214 was synthesized similar to Compound 210 replacing 5-amino-2-methoxypyridine with 5-methoxypyridin-2-amine. LCMS (ES) [M+1]⁺ m/z: 479.3. ¹H NMR (300 MHz, DMSO-d6) δ 10.51 (s, 1H), 8.44 (d, J=5.6 Hz, 1H), 8.28 (s, 1H), 8.02 (d, J=3.1 Hz, 1H), 7.95 (d, J=9.1 Hz, 1H), 7.76 (d, J=2.5 Hz, 1H), 7.39 (dd, J=9.1, 3.1 Hz, 1H), 7.00 (dd, J=5.7, 2.5 Hz, 1H), 4.51 (s, 2H), 3.81-3.76 (m, 5H), 3.34 (s, 3H), 3.19 (t, J=7.3 Hz, 2H), 2.83 (t, J=7.9 Hz, 2H), 2.08-1.95 (m, 2H), 1.15 (s, 6H).

Example 1.222

Synthesis of 2-({2-[4-(cyclopropylmethoxy)pyridin-2-yl]-5H,6H,7H-cyclopenta[d]pyrimidin-4-yl}(methyl)amino)-N-(1-methyl-1H-pyrazol-4-yl)acetamide (Compound 215)

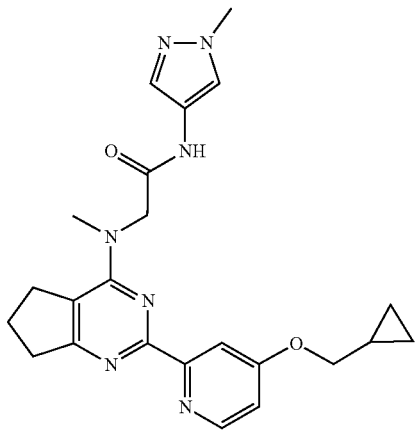 [SMILES: CN(CC(=O)Nc1cnn(C)c1)c1nc(-c2cc(OCC3CC3)ccn2)nc2c1CCC2]

Compound 215 was synthesized similar to Compound 177 replacing 2-bromo-4-(2,2,2-trifluoroethoxy)pyridine with 2-bromo-4-(cyclopropylmethoxy)pyridine. LCMS (ES) [M+1]⁺ m/z: 443.1. ¹H NMR (400 MHz, DMSO-d₆) δ 10.58 (s, 1H), 8.47 (d, J=5.8 Hz, 1H), 7.78 (d, J=2.6 Hz, 1H), 7.50 (d, J=2.2 Hz, 1H), 7.10 (dd, J=5.9, 2.6 Hz, 1H), 6.34 (d, J=2.2 Hz, 1H), 4.46 (s, 2H), 3.92 (d, J=7.1 Hz, 2H), 3.71 (s, 3H), 3.36 (s, 3H), 3.20 (d, J=14.8 Hz, 2H), 2.87 (t, J=7.9 Hz, 2H), 2.09-1.94 (m, 2H), 1.21 (s, 1H), 0.63-0.52 (m, 2H), 0.40-0.29 (m, 2H).

Example 1.223

Synthesis of 2-({2-[4-(difluoromethoxy)pyridin-2-yl]-5H,6H,7H-cyclopenta[d]pyrimidin-4-yl}(methyl)amino)-N-(6-fluoropyridin-3-yl)acetamide (Compound 216)

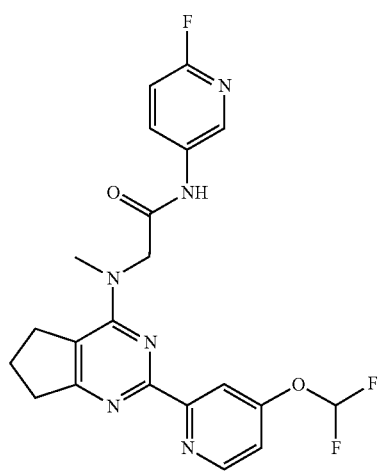 [SMILES: CN(CC(=O)Nc1ccc(F)nc1)c1nc(-c2cc(OC(F)F)ccn2)nc2c1CCC2]

Compound 216 was synthesized similar to Compound 24 replacing 4-methyl-2-(tributylstannyl)-pyridine with 4-(difluoromethoxy)-2-(tributylstannyl)pyridine and by replacing tert-butylamine with 6-fluoro-3-pyridinylamine. LCMS (ES+): [M+H]⁺=445.1. ¹H NMR (400 MHz, DMSO-d₆) δ ppm 2.03-2.16 (m, 2H) 3.02 (br t, J=7.83 Hz, 2H) 3.26-3.29 (m, 2H) 3.53 (s, 2H) 4.62-4.70 (m, 2H) 7.11-7.18 (m, 1H) 7.60 (t, J=71.99 Hz, 1H) 7.45-7.51 (m, 1H) 8.05 (br s, 1H) 8.10-8.18 (m, 1H) 8.45 (br s, 1H) 8.73-8.81 (m, 1H) 10.80-10.89 (m, 1H).

Example 1.224

Synthesis of 2-({2-[4-(difluoromethoxy)pyridin-2-yl]-5H,6H,7H-cyclopenta[d]pyrimidin-4-yl}(methyl)amino)-N-(5-methoxypyridin-2-yl)acetamide (Compound 217)

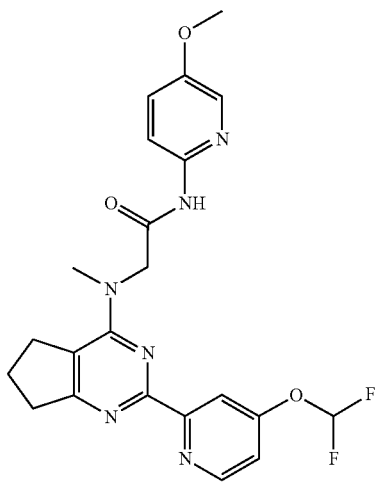 [SMILES: COc1ccc(NC(=O)CN(C)c2nc(-c3cc(OC(F)F)ccn3)nc3c2CCC3)nc1]

Compound 217 was synthesized similar to Compound 24 replacing 4-methyl-2-(tributylstannyl)-pyridine with 4-(difluoromethoxy)-2-(tributylstannyl)pyridine and by replacing tert-butylamine with 5-methoxypyridin-2-amine. LCMS (ES+): [M+H]⁺=456.9. ¹H NMR (400 MHz, DMSO-d₆) δ ppm 2.04-2.13 (m, 2H) 3.00 (br t, J=7.83 Hz, 2H) 3.28 (br d, J=7.04 Hz, 2H) 3.50 (s, 3H) 3.77-3.80 (m, 3H) 4.65-4.72 (m, 2H) 7.39 (dd, J=9.00, 3.13 Hz, 1H) 7.41-7.80 (m, 1H) 7.46 (dd, J=5.48, 2.35 Hz, 1H) 7.87-7.96 (m, 1H) 8.03 (d, J=2.74 Hz, 1H) 8.04-8.08 (m, 1H) 8.77 (d, J=5.87 Hz, 1H) 10.73-10.79 (m, 1H).

Example 1.225

Synthesis of 2-{[2-(isoquinolin-3-yl)-5H,6H,7H-cyclopenta[d]pyrimidin-4-yl](methyl)amino}-N-(1-methyl-1H-pyrazol-4-yl)acetamide (Compound 218)

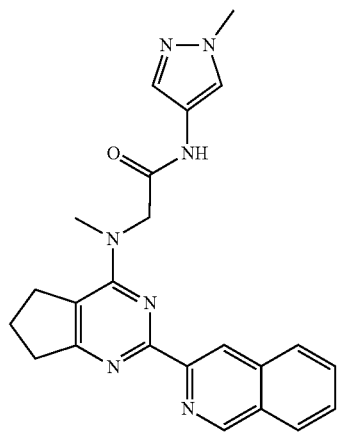 [SMILES: CN(CC(=O)Nc1cnn(C)c1)c1nc(-c2cc3ccccc3cn2)nc2c1CCC2]

Compound 218 was synthesized similar to Compound 177 by replacing 2-(tributylstannyl)-4-(2,2,2-trifluoroethoxy)pyridine with 3-(tributylstannyl)isoquinoline. LCMS (ES+): [M+H]⁺=414.0. ¹H NMR (400 MHz, DMSO-d₆) δ ppm 2.08-2.19 (m, 2H) 3.10 (br t, J=7.83 Hz, 2H) 3.30-3.36 (m, 2H) 3.61 (br s, 3H) 3.75-3.83 (m, 3H) 4.61-4.72 (m, 2H) 6.32-6.42 (m, 1H) 7.45-7.54 (m, 1H) 7.86-7.95 (m, 1H) 7.95-8.08 (m, 2H) 8.33 (br d, J=8.22 Hz, 1H) 8.79-8.98 (m, 1H) 9.52-9.62 (m, 1H) 10.98-11.15 (m, 1H)

Example 1.226

Synthesis of N-(6-methoxypyridin-3-yl)-2-[methyl(2-{1H-pyrazolo[3,4-c]pyridin-5-yl}-5H,6H,7H-cyclopenta[d]pyrimidin-4-yl)amino]acetamide (Compound 219)

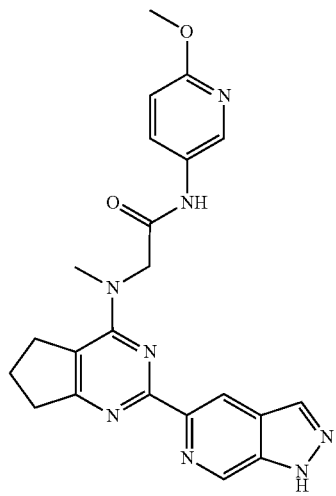 [SMILES: COc1ccc(NC(=O)CN(C)c2nc(-c3cc4cn[nH]c4cn3)nc3c2CCC3)cn1]

Compound 219 was synthesized similar to Compound 135 by replacing oxolan-3-amine with 5-amino-2-methoxypyridine and by replacing 4-methoxy-2-(trimethylstannyl)pyridine with 5-(trimethylstannyl)-1H-pyrazolo[3,4-c]pyridine. LCMS (ES) [M+1]+ m/z: 431.2; ¹HNMR (300 MHz, DMSO-d₆, ppm) δ 13.70 (s, 1H), 10.37 (s, 1H), 9.06 (s, 1H), 8.70 (d, J=1.2 Hz, 1H), 8.41 (t, J=2.4 Hz, 1H), 8.09 (s, 1H), 7.95 (ddd, J=8.9, 2.8, 1.5 Hz, 1H), 6.80 (d, J=8.9 Hz, 1H), 4.42 (s, 2H), 3.80 (s, 3H), 3.39 (s, 3H), 3.20 (t, J=7.3 Hz, 2H), 2.84 (t, J=7.8 Hz, 2H), 2.11-1.93 (m, 2H).

Example 1.227

Synthesis of N-(1-methyl-1H-pyrazol-4-yl)-2-{methyl[2-(1-methyl-1H-imidazol-4-yl)-5H,6H,7H-cyclopenta[d]pyrimidin-4-yl]amino}acetamide (Compound 220)

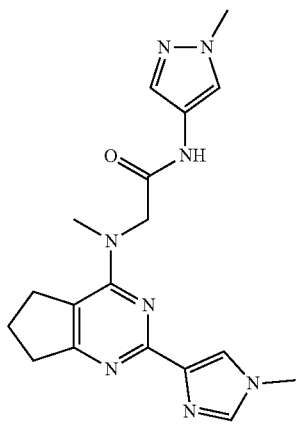 [SMILES: CN(CC(=O)Nc1cnn(C)c1)c1nc(-c2cn(C)cn2)nc2c1CCC2]

Compound 220 was synthesized similar to Compound 177 by replacing 2-(tributylstannyl)-4-(2,2,2-trifluoroethoxy)pyridine with 1-methyl-4-(tributylstannyl)-1H-imidazole. LCMS (ES) [M+1]+ m/z: 367.2; ¹H NMR (400 MHz, dmso) δ 10.73 (s, 1H), 8.29 (s, 1H), 8.16 (s, 1H), 7.53 (d, J=2.2 Hz, 1H), 6.35 (d, J=2.2 Hz, 1H), 4.58 (s, 3H), 4.55 (s, 2H), 3.77 (s, 3H), 3.73 (s, 3H), 3.16 (s, 2H), 2.92 (t, J=7.9 Hz, 2H), 2.09-1.96 (m, 2H).

Example 1.228

Synthesis of N-(6-fluoropyridin-3-yl)-2-{[2-(isoquinolin-3-yl)-5H,6H,7H-cyclopenta[d]pyrimidin-4-yl](methyl)amino}acetamide (Compound 221)

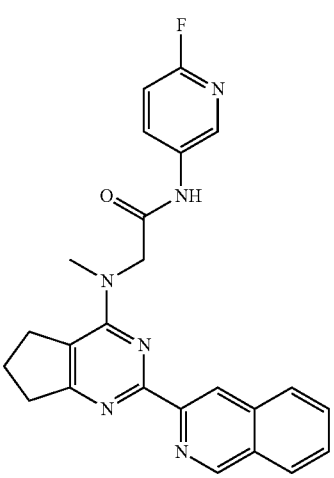 [SMILES: CN(CC(=O)Nc1ccc(F)nc1)c1nc(-c2cc3ccccc3cn2)nc2c1CCC2]

Compound 221 was synthesized similar to Compound 135 by replacing 4-methoxy-2-(trimethylstannyl)pyridine with 3-(tributylstannyl)isoquinoline and by replacing oxolan-3-amine with 6-fluoro-3-pyridinylamine. LCMS (ES+): [M+H]+=429.2. ¹H NMR (400 MHz, DMSO-d₆) δ ppm 1.99-2.08 (m, 2H) 2.84-2.91 (m, 2H) 3.20-3.26 (m, 2H) 3.42 (s, 3H) 4.46-4.51 (m, 2H) 7.10-7.16 (m, 1H) 7.67-7.73 (m, 1H) 7.73-7.79 (m, 1H) 7.81-7.86 (m, 1H) 8.13-8.17 (m, 1H) 8.17-8.24 (m, 1H) 8.43-8.48 (m, 1H) 8.71-8.75 (m, 1H) 9.32-9.37 (m, 1H) 10.67-10.74 (m, 1H)

Example 1.229

Synthesis of 2-{[2-(isoquinolin-3-yl)-5H,6H,7H-cyclopenta[d]pyrimidin-4-yl](methyl)amino}-N-(6-methylpyridin-3-yl)acetamide (Compound 222)

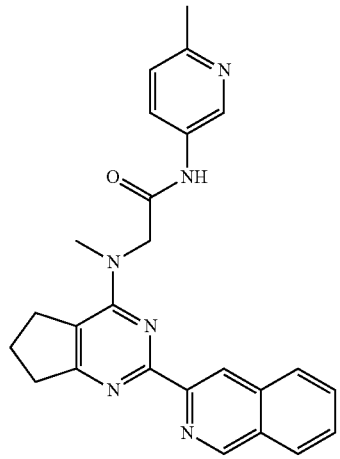 [SMILES: Cc1ccc(NC(=O)CN(C)c2nc(-c3cc4ccccc4cn3)nc3c2CCC3)cn1]

Compound 222 was synthesized similar to Compound 135 by replacing 4-methoxy-2-(trimethylstannyl)pyridine with 3-(tributylstannyl)isoquinoline and by replacing oxolan-3-amine with 5-methyl-2-pyridinamine. LCMS (ES+): [M+H]+=425.2. ¹H NMR (400 MHz, DMSO-d₆) δ ppm 2.09-2.19 (m, 2H) 2.52-2.60 (m, 3H) 3.11 (br t, J=7.83 Hz, 2H) 3.35-3.37 (m, 2H) 3.64 (s, 3H) 4.84-4.97 (m, 2H) 7.66-7.75 (m, 1H) 7.85-7.93 (m, 1H) 7.93-8.00 (m, 1H) 8.28-8.37 (m, 2H) 8.45-8.65 (m, 1H) 9.02-9.10 (m, 1H) 9.18-9.28 (m, 1H) 9.51-9.60 (m, 1H) 12.14-12.47 (m, 1H)

Example 1.230

Synthesis of 2-{[2-(4-ethoxypyridin-2-yl)-5H,6H,7H-cyclopenta[d]pyrimidin-4-yl](methyl)amino}-N-(6-methoxypyridin-3-yl)acetamide (Compound 223)

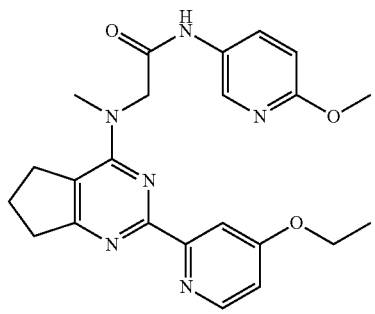 [SMILES: CCOc1ccnc(-c2nc3c(c(N(C)CC(=O)Nc4ccc(OC)nc4)n2)CCC3)c1]

Compound 223 was synthesized similar to Compound 135 by replacing 4-methoxy-2-(trimethylstannyl)pyridine with in situ made 4-ethoxy-2-(trimethylstannyl)pyridine and replacing oxolan-3-amine with 5-amino-2-methoxypyridine. LCMS (ES) [M+1]+ m/z: 435. ¹H NMR (300 MHz, DMSO-d6) δ 10.28 (s, 1H), 8.46 (d, J=5.7 Hz, 1H), 8.35 (d, J=2.6 Hz, 1H), 7.89 (dd, J=8.9, 2.7 Hz, 1H), 7.78 (d, J=2.6 Hz, 1H), 7.06 (dd, J=5.6, 2.6 Hz, 1H), 6.78 (d, J=8.8 Hz, 1H), 4.42 (s, 2H), 4.06 (q, J=7.0 Hz, 2H), 3.80 (s, 3H), 3.40 (s, 3H), 3.23 (t, J=7.3 Hz, 2H), 2.86 (t, J=7.7 Hz, 2H), 2.11-1.97 (m, 2H), 1.28 (t, J=6.9 Hz, 3H).

Example 1.231

Synthesis of 2-({2-[4-(cyclopropylmethoxy)pyridin-2-yl]-5H,6H,7H-cyclopenta[d]pyrimidin-4-yl}(methyl)amino)-N-(6-methoxypyridin-3-yl)acetamide (Compound 224)

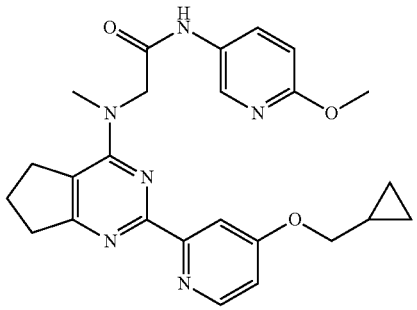 [SMILES: COc1ccc(NC(=O)CN(C)c2nc(-c3cc(OCC4CC4)ccn3)nc3c2CCC3)cn1]

Compound 224 was synthesized similar to Compound 135 by replacing 4-methoxy-2-(trimethylstannyl)pyridine with in situ made 4-cyclopropylmethoxy-2-(trimethylstannyl)pyridine and replacing oxolan-3-amine with 5-amino-2-methoxypyridine. LCMS (ES) [M+1]+ m/z: 461. ¹H NMR (300 MHz, DMSO-d6) δ 10.25 (s, 1H), 8.42 (d, J=5.6 Hz, 1H), 8.33 (d, J=2.7 Hz, 1H), 7.86 (dd, J=8.9, 2.7 Hz, 1H), 7.76 (d, J=2.5 Hz, 1H), 6.98 (dd, J=5.6, 2.6 Hz, 1H), 6.77 (d, J=8.9 Hz, 1H), 4.39 (s, 2H), 3.86 (d, J=7.1 Hz, 2H), 3.80 (s, 3H), 3.37 (s, 3H), 3.21 (t, J=7.2 Hz, 2H), 2.83 (t, J=7.8 Hz, 2H), 2.10-1.911 (m, 2H), 1.38-1.09 (m, 1H), 0.56 (q, J=5.5 Hz, 2H), 0.30 (d, J=5.2 Hz, 2H).

Example 1.232

Synthesis of 2-({2-[4-(difluoromethoxy)pyridin-2-yl]-5H,6H,7H-cyclopenta[d]pyrimidin-4-yl}(methyl)amino)-N-(6-methoxypyridin-3-yl)acetamide (Compound 225)

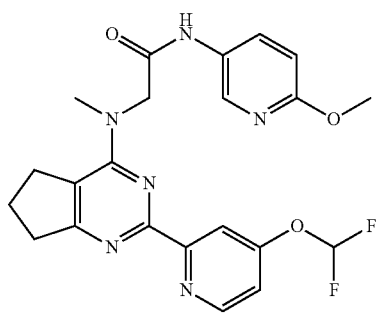 [SMILES: COc1ccc(NC(=O)CN(C)c2nc(-c3cc(OC(F)F)ccn3)nc3c2CCC3)cn1]

Compound 225 was synthesized similar to Compound 135 by replacing 4-methoxy-2-(trimethylstannyl)pyridine with in situ made 4-(difluoromethoxy)-2-(trimethylstannyl)pyridine and replacing oxolan-3-amine with 5-amino-2-methoxypyridine. LCMS (ES) [M+1]+ m/z: 457. ¹H NMR (300 MHz, DMSO-d6) δ 10.23 (br, 1H), 8.63 (d, J=5.7 Hz, 1H), 8.35 (d, J=2.7 Hz, 1H), 7.98 (d, J=2.4 Hz, 1H), 7.88 (dd, J=9.0, 2.7 Hz, 1H), 7.49 (t, J=72.6 Hz 1H, CHF2), 7.26 (dd, J=5.7, 2.4 Hz, 1H), 6.75 (d, J=9.0 Hz, 1H), 4.43 (s, 2H), 3.80 (s, 3H), 3.37 (s, 3H), 3.21 (t, J=7.5 Hz, 2H), 2.82 (t, J=7.8 Hz, 2H), 2.07-1.96 (m, 2H).

Example 1.233

Synthesis of N-tert-butyl-2-[(2-{2H-[1,3]dioxolo[4,5-c]pyridin-6-yl}-5H,6H,7H-cyclopenta[d]pyrimidin-4-yl)(methyl)amino]acetamide (Compound 226)

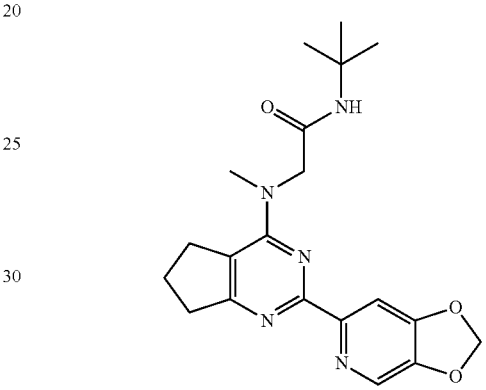

Compound 226 was synthesized similar to Compound 24 by replacing 4-methyl-2-(tributylstannyl)pyridine with 6-(trimethylstannyl)-[1,3]dioxolo[4,5-c]pyridine. LCMS (ES) [M+1]+ m/z: 384. ¹H NMR (300 MHz, DMSO-d6) δ 8.20 (s, 1H), 7.95 (s, 1H), 7.71 (s, 1H), 6.20 (s, 2H), 4.10 (s, 2H), 3.32 (s, 3H), 3.14 (t, J=7.4 Hz, 2H), 2.79 (t, J=7.9 Hz, 2H), 2.05-1.89 (m, 2H), 1.25 (s, 9H).

Example 1.234

Synthesis of 2-{[2-(isoquinolin-3-yl)-5H,6H,7H-cyclopenta[d]pyrimidin-4-yl](methyl)amino}-N-(6-methoxypyridin-3-yl)acetamide (Compound 227)

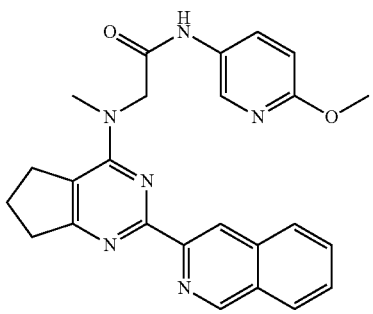 [SMILES: COc1ccc(NC(=O)CN(C)c2nc(-c3cc4ccccc4cn3)nc3c2CCC3)cn1]

Compound 227 was synthesized similar to Compound 135 by replacing 4-methoxy-2-(trimethylstannyl)pyridine with 3-(tributylstannyl)isoquinoline and replacing oxolan- 3-amine with 5-amino-2-methoxypyridine. LCMS (ES) [M+1]⁺ m/z: 457. ¹H NMR (300 MHz, DMSO-d6) δ 10.23 (br, 1H), 8.63 (d, J=5.7 Hz, 1H), 8.35 (d, J=2.7 Hz, 1H), 7.98 (d, J=2.4 Hz, 1H), 7.88 (dd, J=9.0, 2.7 Hz, 1H), 7.49 (t, J=72.6 Hz 1H, CHF2), 7.26 (dd, J=5.7, 2.4 Hz, 1H), 6.75 (d, J=9.0 Hz, 1H), 4.43 (s, 2H), 3.80 (s, 3H), 3.37 (s, 3H), 3.21 (t, J=7.5 Hz, 2H), 2.82 (t, J=7.8 Hz, 2H), 2.07-1.96 (m, 2H).

Example 1.235

Synthesis of 2-{[2-(isoquinolin-3-yl)-5H,6H,7H-cyclopenta[d]pyrimidin-4-yl](methyl)amino}-N-(6-methoxypyridin-3-yl)acetamide (Compound 228)

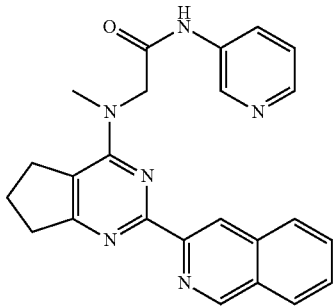 [SMILES: CN(CC(=O)Nc1cccnc1)c1nc(-c2cc3ccccc3cn2)nc2c1CCC2]

Compound 228 was synthesized similar to Compound 135 by replacing 4-methoxy-2-(trimethylstannyl)pyridine with 3-(tributylstannyl)isoquinoline and replacing oxolan-3-amine with 3-aminopyridine. LCMS (ES) [M+1]⁺ m/z: 411. ¹H NMR (300 MHz, DMSO-d6) δ 9.48 (s, 1H), 9.28 (d, J=2.4 Hz, 1H), 9.14 (s, 1H), 8.82 (s, 1H), 8.52 (s, 1H), 8.33-8.20 (m, 2H), 8.00 (t, J=7.1 Hz, 1H), 7.93-7.79 (m, 2H), 4.90 (s, 2H), 3.57 (s, 3H), 3.38-3.19 (s, 2H), 3.18-2.99 (m, 2H), 2.09-2.00 (m, 2H).

Example 1.236

Synthesis of N-(6-methoxypyridin-3-yl)-2-[methyl({2-[4-(trifluoromethoxy)pyridin-2-yl]-5H,6H,7H-cyclopenta[d]pyrimidin-4-yl})amino]acetamide (Compound 229)

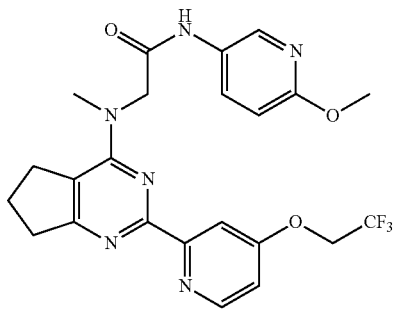 [SMILES: COc1ccc(NC(=O)CN(C)c2nc(-c3cc(OCC(F)(F)F)ccn3)nc3c2CCC3)cn1]

Compound 229 was synthesized similar to Compound 135 by replacing 4-methoxy-2-(trimethylstannyl)pyridine with 4-(trifluoromethoxy)-2-(trimethylstannyl)pyridine and replacing oxolan-3-amine with 5-amino-2-methoxypyridine. LCMS (ES) [M+1]⁺ m/z: 475. ¹H NMR (300 MHz, DMSO-d6) δ 10.22 (s, 1H), 8.75 (d, J=5.5 Hz, 1H), 8.36 (t, J=2.2 Hz, 1H), 8.09 (d, J=2.37 Hz 1H), 7.87 (ddd, J=8.9, 2.8, 1.3 Hz, 1H), 7.46 (dd, J=5.3, 2.1 Hz, 1H), 6.77 (d, J=8.8 Hz, 1H), 4.41 (s, 2H), 3.80 (s, 3H), 3.38 (s, 3H), 3.22 (t, J=7.3 Hz, 2H), 2.85 (t, J=7.8 Hz, 2H), 2.10-1.922 (m, 2H).

Example 1.237

Synthesis of N-(6-methoxypyridin-3-yl)-2-[methyl({2-[4-(trifluoromethoxy)pyridin-2-yl]-5H,6H,7H-cyclopenta[d]pyrimidin-4-yl})amino]acetamide (Compound 230)

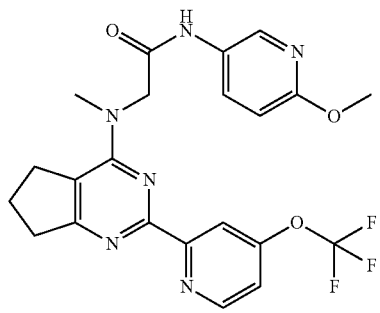 [SMILES: COc1ccc(NC(=O)CN(C)c2nc(-c3cc(OC(F)(F)F)ccn3)nc3c2CCC3)cn1]

Compound 230 was synthesized similar to Compound 135 by replacing 4-methoxy-2-(trimethylstannyl)pyridine with 4-(trifluoromethoxy)-2-(trimethylstannyl)pyridine and replacing oxolan-3-amine with 5-amino-2-methoxypyridine. LCMS (ES) [M+1]⁺ m/z: 475. ¹H NMR (300 MHz, DMSO-d6) δ 10.22 (s, 1H), 8.75 (d, J=5.5 Hz, 1H), 8.36 (t, J=2.2 Hz, 1H), 8.09 (d, J=2.37 Hz 1H), 7.87 (ddd, J=8.9, 2.8, 1.3 Hz, 1H), 7.46 (dd, J=5.3, 2.1 Hz, 1H), 6.77 (d, J=8.8 Hz, 1H), 4.41 (s, 2H), 3.80 (s, 3H), 3.38 (s, 3H), 3.22 (t, J=7.3 Hz, 2H), 2.85 (t, J=7.8 Hz, 2H), 2.10-1.922 (m, 2H).

Example 1.238

Synthesis of 2-[methyl({2-[4-(trifluoromethoxy)pyridin-2-yl]-5H,6H,7H-cyclopenta[d]pyrimidin-4-yl})amino]-N-(1-methyl-1H-pyrazol-4-yl)acetamide (Compound 231)

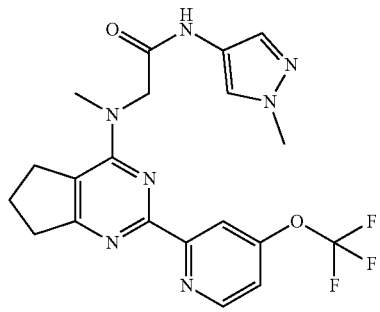 [SMILES: CN(CC(=O)Nc1cnn(C)c1)c1nc(-c2cc(OC(F)(F)F)ccn2)nc2c1CCC2]

Compound 231 was synthesized similar to Compound 135 by replacing 4-methoxy-2-(trimethylstannyl)pyridine with 4-(trifluoromethoxy)-2-(trimethylstannyl)pyridine and replacing oxolan-3-amine with 1-methylpyrazol-4-amine. LCMS (ES) [M+1]⁺ m/z: 448. ¹H NMR (300 MHz, DMSO-d6) δ 10.16 (s, 1H), 8.78 (d, J=5.6 Hz, 1H), 8.10 (d, J=2.3 Hz, 1H), 7.82 (s, 1H), 7.47 (dd, J=5.7, 1.4 Hz, 1H), 7.39 (s, 1H), 4.36 (s, 2H), 3.75 (s, 3H), 3.28 (s, 3H), 3.26-3.13 (m, 2H), 2.85 (t, J=7.8 Hz, 2H), 2.10-1.93 (m, 2H).

Example 1.239

Synthesis of 2-[methyl(2-{1H-pyrazolo[3,4-c]pyridin-5-yl}-5H,6H,7H-cyclopenta[d]pyrimidin-4-yl)amino]-N-(1-methyl-1H-pyrazol-3-yl)acetamide (Compound 232)

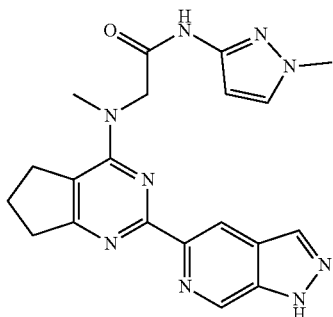 [SMILES: CN(CC(=O)Nc1ccn(C)n1)c1nc(-c2cc3cn[nH]c3cn2)nc2c1CCC2]

Compound 232 was synthesized similar to Compound 135 by replacing 4-methoxy-2-(trimethylstannyl)pyridine with 5-(trimethylstannyl)-1H-pyrazolo[3,4-c]pyridine and replacing oxolan-3-amine with 2-methylpyrimidin-5-amine. LCMS (ES) [M+1]⁺ m/z: 404. ¹H NMR (300 MHz, DMSO-d6) δ13.67 (s, 1H), 10.68 (s, 1H), 9.08 (s, 1H), 8.68 (d, J=1.4 Hz, 1H), 8.12 (s, 1H), 7.52 (d, J=2.3 Hz, 1H), 6.41 (d, J=2.3 Hz, 1H), 4.41 (s, 2H), 3.76 (s, 3H), 3.38 (s, 3H), 3.18 (t, J=7.4 Hz, 2H), 2.83 (t, J=7.8 Hz, 2H), 2.03-1.98 (m, 2H).

Example 1.240

Synthesis of 2-{[2-(isoquinolin-3-yl)-5H,6H,7H-cyclopenta[d]pyrimidin-4-yl](methyl)amino}-N-(5-methoxypyridin-2-yl)acetamide (Compound 233)

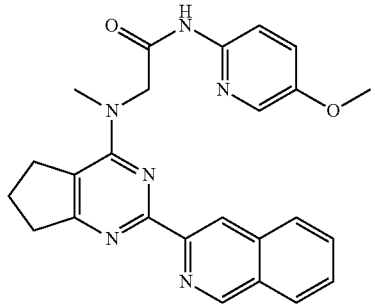 [SMILES: COc1ccc(NC(=O)CN(C)c2nc(-c3cc4ccccc4cn3)nc3c2CCC3)nc1]

Compound 233 was synthesized similar to Compound 135 by replacing 4-methoxy-2-(trimethylstannyl)pyridine with 3-(tributylstannyl)isoquinoline and replacing oxolan-3-amine with 5-methoxypyridin-2-amine. LCMS (ES) [M+1]⁺ m/z: 441. ¹H NMR (300 MHz, DMSO-d6) δ 10.71 (s, 1H), 9.35 (s, 1H), 8.72 (s, 1H), 8.16 (0.4 HCOOH), 8.14 (d, J=7.8 Hz, 1H), 8.10 (d, J=3.0 Hz, 1H), 7.99 (d, J=9.0 Hz, 1H), 7.85-7.63 (m, 3H), 7.38 (dd, J=9.1, 3.1 Hz, 1H), 4.51 (s, 2H), 3.79 (s, 3H), 3.41 (s, 3H), 3.22 (t, J=7.3 Hz, 2H), 2.87 (t, J=7.8 Hz, 2H), 2.07-1.98 (m, 2H).

Example 1.241

Synthesis of 2-{[2-(isoquinolin-3-yl)-5H,6H,7H-cyclopenta[d]pyrimidin-4-yl](methyl)amino}-N-[6-(trifluoromethoxy)pyridin-3-yl]acetamide (Compound 234)

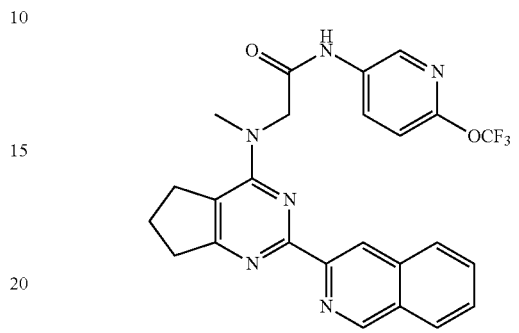

Compound 234 was synthesized similar to Compound 135 by replacing 4-methoxy-2-(trimethylstannyl)pyridine with 3-(tributylstannyl)isoquinoline and replacing oxolan-3-amine with 6-(trifluoromethoxy)pyridin-3-amine. LCMS (ES) [M+1]⁺ m/z: 495. ¹H NMR (300 MHz, DMSO-d6) δ 11.51 (br, 1H), 9.56 (s, 1H), 9.10 (s, 1H), 8.70 (s, 1H), 8.32 (d, J=8.1 Hz, 2H), 8.10 (s, 1H), 7.98-7.85 (m, 2H), 7.27 (d, J=8.8 Hz, 1H), 4.83 (s, 2H), 3.63 (s, 3H), 3.37-3.22 (m, 2H), 3.11 (t, J=8.0 Hz, 2H), 2.20-2.09 (m, 2H).

Example 1.242

Synthesis of 2-{[2-(isoquinolin-3-yl)-5H,6H,7H-cyclopenta[d]pyrimidin-4-yl](methyl)amino}-N-(5-methylpyridin-3-yl)acetamide (Compound 235)

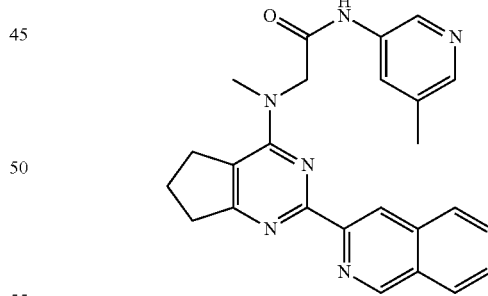

Compound 235 was synthesized similar to Compound 135 by replacing 4-methoxy-2-(trimethylstannyl)pyridine with 3-(tributylstannyl)isoquinoline and replacing oxolan-3-amine with 5-methylpyridin-3-amine. LCMS (ES) [M+1]⁺ m/z: 425. ¹H NMR (300 MHz, DMSO-d6) δ 10.52 (s, 1H), 9.36 (s, 1H), 8.72 (s, 1H), 8.61 (d, J=2.4 Hz, 1H), 8.20-8.11 (m, 2H), 8.08 (d, J=1.9 Hz, 1H), 7.92 (s, 1H), 7.85-7.64 (m, 3H), 4.48 (s, 2H), 3.43 (s, 3H), 3.24 (s, 2H), 2.88 (t, J=7.8 Hz, 2H), 2.21 (s, 3H), 2.07-2.01 (m, 2H).

Example 1.243

Synthesis of 2-{[2-(isoquinolin-3-yl)-5H,6H,7H-cyclopenta[d]pyrimidin-4-yl](methyl)amino}-N-(1-methyl-1H-imidazol-4-yl)acetamide (Compound 236)

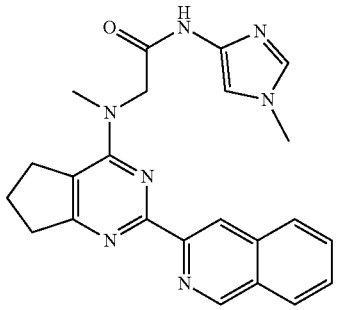 [SMILES: CN(CC(=O)Nc1cn(C)cn1)c1nc(-c2cc3ccccc3cn2)nc2c1CCC2]

Compound 236 was synthesized similar to Compound 135 by replacing 4-methoxy-2-(trimethylstannyl)pyridine with 3-(tributylstannyl)isoquinoline and replacing oxolan-3-amine with 1-methylimidazol-4-amine. LCMS (ES) [M+1]⁺ m/z: 414.3. ¹H NMR (300 MHz, DMSO-d6) δ 10.61 (s, 1H), 9.37 (d, J=3.1 Hz, 1H), 8.71 (d, J=2.9 Hz, 1H), 8.15 (dd, J=8.1, 3.1 Hz, 1H), 7.95-7.86 (m, 1H), 7.82-7.64 (m, 2H), 7.41 (t, J=2.1 Hz, 1H), 7.20-7.11 (m, 1H), 4.44 (s, 2H), 3.57 (s, 3H), 3.38 (s, 3H), 3.19 (t, J=7.4 Hz, 2H), 2.86 (d, J=7.7 Hz, 2H), 2.05-2.01 (m, 2H).

Example 1.244

Synthesis of 2-{[2-(isoquinolin-3-yl)-5H,6H,7H-cyclopenta[d]pyrimidin-4-yl](methyl)amino}-N-(1-methyl-1H-pyrazol-3-yl)acetamide (Compound 237)

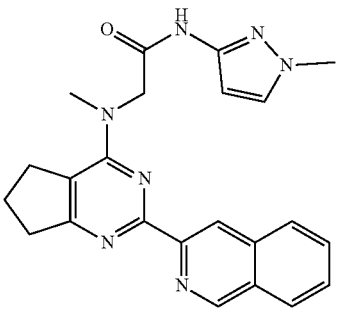 [SMILES: CN(CC(=O)Nc1ccn(C)n1)c1nc(-c2cc3ccccc3cn2)nc2c1CCC2]

Compound 237 was synthesized similar to Compound 135 by replacing 4-methoxy-2-(trimethylstannyl)pyridine with 3-(tributylstannyl)isoquinoline and replacing oxolan-3-amine with 1-methylpyrazol-3-amine. LCMS (ES) [M+1]⁺ m/z: 414. ¹H NMR (300 MHz, DMSO-d6) δ 10.75 (s, 1H), 9.37 (s, 1H), 8.69 (s, 1H), 8.15 (d, J=8.3 Hz, 1H), 7.88 (d, J=8.1 Hz, 1H), 7.83-7.74 (m, 1H), 7.74-7.66 (m, 1H), 7.52 (d, J=2.3 Hz, 1H), 6.42 (d, J=2.2 Hz, 1H), 4.42 (s, 2H), 3.77 (s, 3H), 3.40 (s, 3H), 3.21 (t, J=7.2 Hz, 2H), 2.86 (t, J=7.8 Hz, 2H), 2.08-2.00 (m, 2H).

Example 1.245

Synthesis of 2-({2-[4-(2-methoxyethoxy)pyridin-2-yl]-5H,6H,7H-cyclopenta[d]pyrimidin-4-yl}(methyl)amino)-N-(6-methoxypyridin-3-yl)acetamide (Compound 238)

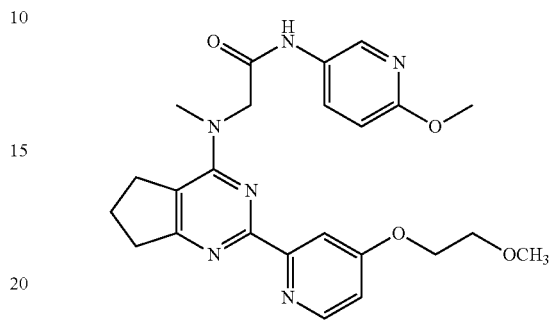

Compound 238 was synthesized similar to Compound 135 by replacing 4-methoxy-2-(trimethylstannyl)pyridine with 4-(2-methoxyethoxy)-2-(trimethylstannyl)pyridine and replacing oxolan-3-amine with 5-amino-2-methoxypyridine. LCMS (ES) [M+1]⁺ m/z: 465. ¹H NMR (300 MHz, DMSO-d6) δ 10.29 (s, 1H), 8.46 (d, J=5.7 Hz, 1H), 8.35 (d, J=2.7 Hz, 1H), 8.14 (s, HCOOH), 7.89 (dd, J=9.0, 2.7 Hz, 1H), 7.79 (d, J=2.7 Hz, 1H), 7.05 (dd, J=5.7, 2.7 Hz, 1H), 6.78 (d, J=9.0 Hz, 1H), 4.42 (s, 2H), 4.16-4.09 (m, 2H), 3.81 (s, 3H), 3.62-3.60 (m, 2H), 3.39 (s, 3H), 3.29 (s, 3H), 3.22 (t, J=7.2 Hz, 2H), 2.85 (t, J=7.8 Hz, 2H), 2.07-1.96 (m, 2H).

Example 1.246

Synthesis of N-tert-butyl-2-({2-[4-(2-methoxyethoxy)pyridin-2-yl]-5H,6H,7H-cyclopenta[d]pyrimidin-4-yl}(methyl)amino)acetamide (Compound 239)

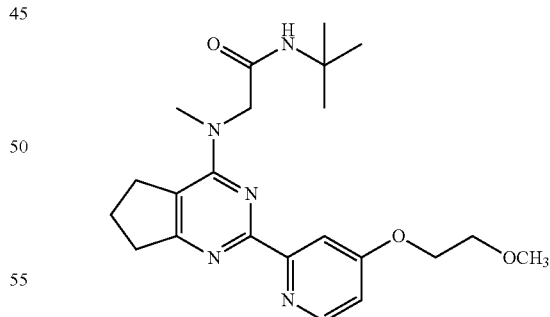

Compound 239 was synthesized similar to Compound 24 by replacing 4-methyl-2-(trimethylstannyl)pyridine with 4-(2-methoxyethoxy)-2-(trimethylstannyl)pyridine. LCMS (ES) [M+1]⁺ m/z: 414. ¹H NMR (300 MHz, DMSO-d6) δ 8.48 (d, J=5.7 Hz, 1H), 8.14 (s, HCOOH), 7.86 (d, J=2.4 Hz, 1H), 7.69 (s, 1H), 7.06 (dd, J=5.7, 2.7 Hz, 1H), 4.27-4.24 (m, 2H), 4.13 (s, 2H), 3.72-3.69 (m, 2H), 3.32 (s, 3H), 3.27 (s, 3H), 3.15 (t, J=7.2 Hz, 2H), 2.82 (t, J=7.8 Hz, 2H), 2.05-1.94 (m, 2H), 1.25 (s, 9H).

Example 1.247

Synthesis of N-(5-fluoropyridin-3-yl)-2-{[2-(isoquinolin-3-yl)-5H,6H,7H-cyclopenta[d]pyrimidin-4-yl](methyl)amino}acetamide (Compound 240)

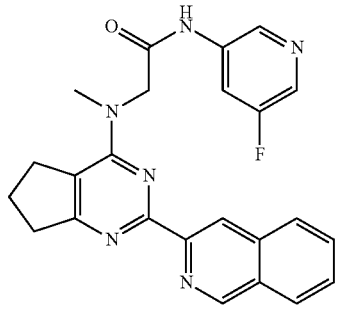 [SMILES: CN(CC(=O)Nc1cncc(F)c1)c1nc(-c2cc3ccccc3cn2)nc2c1CCC2]

Compound 240 was synthesized similar to Compound 135 by replacing 4-methoxy-2-(trimethylstannyl)pyridine with 4-(2-methoxyethoxy)-2-(trimethylstannyl)pyridine and replacing oxolan-3-amine with 5-fluoropyridin-3-amine. LCMS (ES) [M+1]$^+$ m/z: 429.2. $^1$H NMR (300 MHz, DMSO-d6) δ 10.87 (s, 1H), 9.35 (s, 1H), 8.71 (s, 1H), 8.63 (t, J=1.7 Hz, 1H), 8.25 (d, J=2.6 Hz, 1H), 8.20-8.03 (m, 3H), 7.81 (d, J=8.3 Hz, 1H), 7.82-7.64 (m, 2H), 4.51 (s, 2H), 3.43 (s, 3H), 3.24 (t, J=7.3 Hz, 2H), 2.88 (t, J=7.8 Hz, 2H), 2.04 (p, J=7.6 Hz, 2H).

Example 1.248

Synthesis of N-tert-butyl-2-({2-[4-(2-fluoroethoxy)pyridin-2-yl]-5H,6H,7H-cyclopenta[d]pyrimidin-4-yl}(methyl)amino)acetamide (Compound 241)

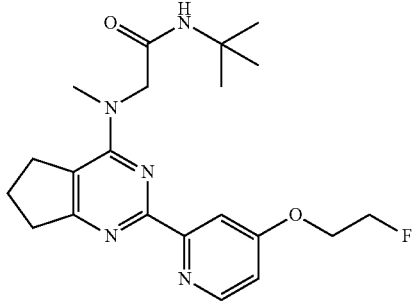 [SMILES: CN(CC(=O)NC(C)(C)C)c1nc(-c2cc(OCCF)ccn2)nc2c1CCC2]

Compound 241 was synthesized similar to Compound 24 by replacing 4-methyl-2-(trimethylstannyl)pyridine with 4-(2-fluoroethoxy)-2-(trimethylstannyl)pyridine. LCMS (ES) [M+1]$^+$ m/z: 429.2. $^1$H NMR (300 MHz, DMSO-d6) δ 8.50 (d, J=5.6 Hz, 1H), 7.89 (d, J=2.6 Hz, 1H), 7.69 (s, 1H), 7.08 (dd, J=5.6, 2.6 Hz, 1H), 4.91-4.82 (m, 1H), 4.75-4.66 (m, 1H), 4.48-4.44 (m, 1H), 4.40-4.31 (m, 1H), 4.12 (s, 2H), 3.27 (s, 3H), 3.15 (t, J=7.4 Hz, 2H), 2.81 (t, J=7.9 Hz, 2H), 2.02-1.97 (m, 2H), 1.24 (s, 9H).

Example 1.249

Synthesis of 2-({2-[4-(2-fluoroethoxy)pyridin-2-yl]-5H,6H,7H-cyclopenta[d]pyrimidin-4-yl}(methyl)amino)-N-(6-methoxypyridin-3-yl)acetamide (Compound 242)

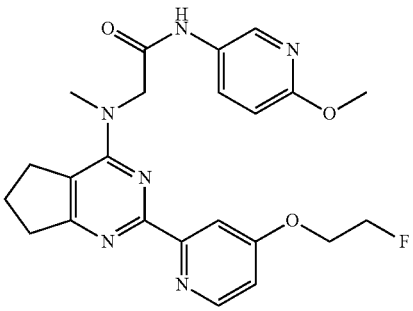 [SMILES: COc1ccc(NC(=O)CN(C)c2nc(-c3cc(OCCF)ccn3)nc3c2CCC3)cn1]

Compound 242 was synthesized similar to Compound 135 by replacing 4-methoxy-2-(trimethylstannyl)pyridine with 4-(2-fluoroethoxy)-2-(trimethylstannyl)pyridine and replacing oxolan-3-amine with 5-amino-2-methoxypyridine. LCMS (ES) [M+1]$^+$ m/z: 453. $^1$H NMR (300 MHz, DMSO-d6) δ 10.27 (s, 1H), 8.46 (d, J=5.6 Hz, 1H), 8.36 (d, J=2.6 Hz, 1H), 7.88 (dd, J=8.9, 2.7 Hz, 1H), 7.80 (d, J=2.6 Hz, 1H), 7.04 (dd, J=5.6, 2.6 Hz, 1H), 6.77 (d, J=8.9 Hz, 1H), 4.84-4.75 (m, 1H), 4.65-4.62 (m, 1H), 4.40 (s, 2H), 4.37-4.30 (m, 1H), 4.28-4.19 (m, 1H), 3.80 (s, 3H), 3.38 (s, 3H), 3.22 (t, J=7.2 Hz, 2H), 2.84 (t, J=7.8 Hz, 2H), 2.04-1.99 (m, 2H).

Example 1.250

Synthesis of 2-({2-[4-(2-fluoroethoxy)pyridin-2-yl]-5H,6H,7H-cyclopenta[d]pyrimidin-4-yl}(methyl)amino)-N-(1-methyl-1H-pyrazol-4-yl)acetamide (Compound 243)

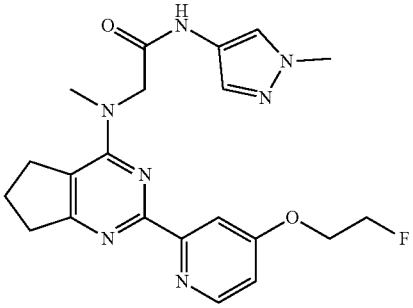 [SMILES: CN(CC(=O)Nc1cnn(C)c1)c1nc(-c2cc(OCCF)ccn2)nc2c1CCC2]

Compound 243 was synthesized similar to Compound 135 by replacing 4-methyl-2-(trimethylstannyl)pyridine with 4-(2-fluoroethoxy)-2-(trimethylstannyl)pyridine and replacing oxolan-3-amine with 1-methylpyrazol-4-amine. LCMS (ES) [M+1]$^+$ m/z: 426. $^1$H NMR (300 MHz, DMSO-d6) δ10.23 (s, 1H), 8.48 (d, J=5.6 Hz, 1H), 7.84 (s, 1H), 7.78 (d, J=2.6 Hz, 1H), 7.40 (s, 1H), 7.05 (dd, J=5.6, 2.6 Hz, 1H), 4.85-4.79 (m, 1H), 4.69-4.62 (m, 1H), 4.36-4.32 (m, 3H), 4.28-4.21 (m, 1H), 3.76 (s, 3H), 3.35 (s, 3H), 3.20 (t, J=7.4 Hz, 2H), 2.83 (t, J=7.9 Hz, 2H), 2.05-1.95 (m, 2H).

Example 1.251

Synthesis of N-(6-methoxypyridin-3-yl)-2-{methyl[2-(1,7-naphthyridin-6-yl)-5H,6H,7H-cyclopenta[d]pyrimidin-4-yl]amino}acetamide (Compound 244)

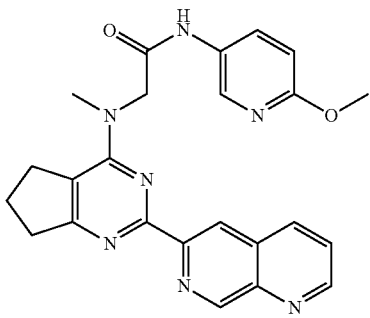 [SMILES: COc1ccc(NC(=O)CN(C)c2nc(-c3cc4cccnc4cn3)nc3c2CCC3)cn1]

Scheme 107

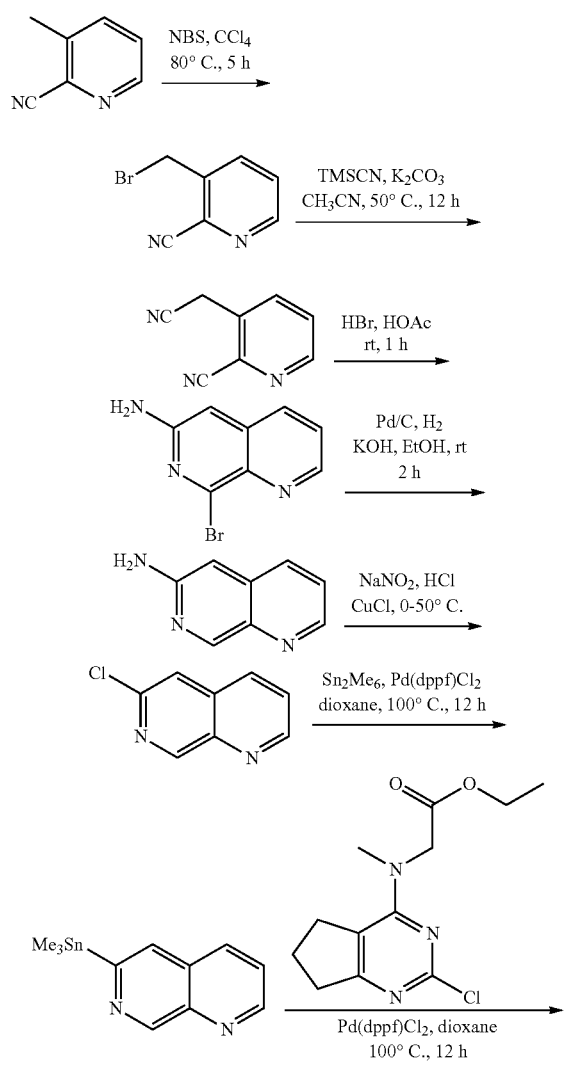

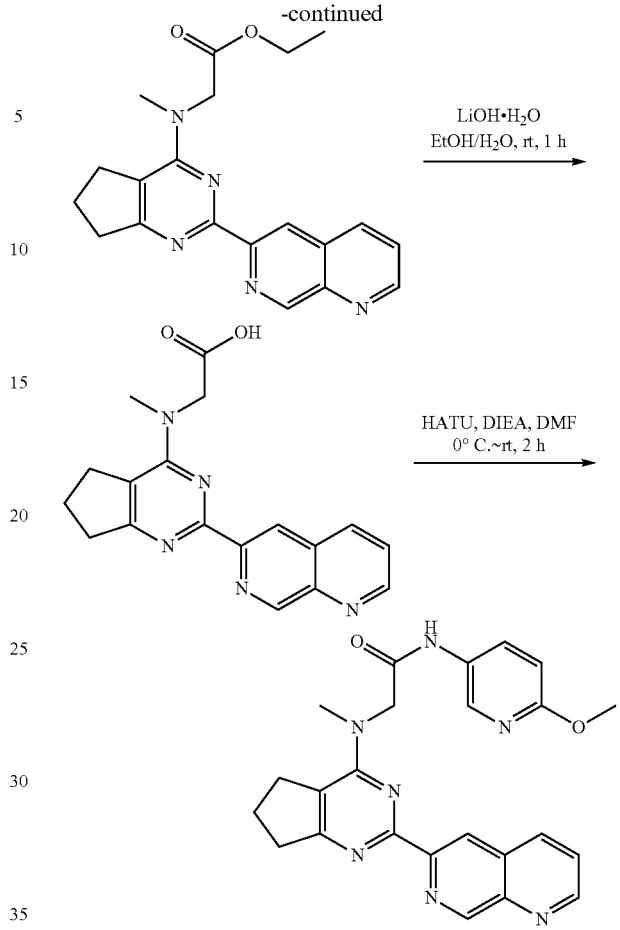

Step 1

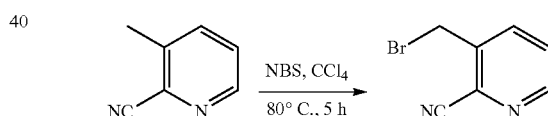

Into a 1 L round-bottom flask were placed 3-methylpyridine-2-carbonitrile (12.00 g, 101.58 mmol, 1.00 equiv), NBS (36.10 g, 203.16 mmol, 2.00 equiv), CCl₄ (500.00 mL) and AIBN (1.67 g, 10.16 mmol, 0.10 equiv). The resulting solution was stirred for 5 h at 80° C. The reaction solution was cooled to room temperature, concentrated to remove the solvent. The residue was purified by silica gel column with ethyl acetate/petroleum ether (1/2). This resulted in 9.0 g (45%) of 3-(bromomethyl)pyridine-2-carbonitrile as yellow oil. LCMS (ES) [M+1]⁺ m/z: 197.

Step 2

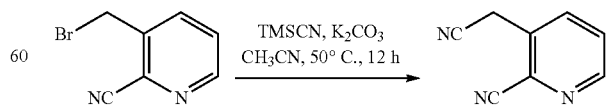

Into a 250-mL round-bottom flask were placed 3-(bromomethyl)pyridine-2-carbonitrile (9.00 g, 45.68 mmol, 1.00 equiv), CH₃CN (100.00 mL), TMSCN (13.59 g, 136.99 mmol, 3.00 equiv) and K₂CO₃ (12.62 g, 91.31 mmol, 2.00 equiv). The resulting solution was stirred for 12 h at 50° C. The reaction was cooled to room temperature, filtered and the filtrate was concentrated, the residue was purified by silica gel column with ethyl acetate/petroleum ether (2/3). This resulted in 3.0 g (46%) of 3-(cyanomethyl)pyridine-2-carbonitrile as a yellow solid. LCMS (ES) [M+1]⁺ m/z: 144.
Step 3

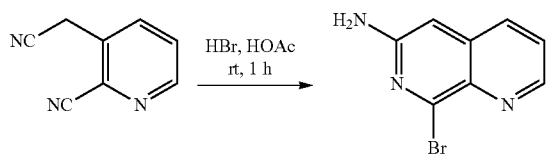 [SMILES: N#CCc1cccnc1C#N ; Nc1cc2cccnc2c(Br)n1]

Into a 100-mL 3-necked round-bottom flask were placed HBr (40% in H₂O) (20.00 mL), HOAc (20.00 mL), 3-(cyanomethyl)pyridine-2-carbonitrile (3.00 g, 20.96 mmol, 1.00 equiv). The resulting solution was stirred for 1 h at room temperature. The solution was filtered, and the filtrate was diluted with of H₂O (20.00 mL), the pH value of the solution was adjusted to 7 with NaHCO₃ solid, extracted with 3×50 mL of ethyl acetate. The combined organic phase was dried over anhydrous sodium sulfate, filtered and the filtrate was concentrated in vacuum. This resulted in 2.2 g (47%) of 8-bromo-1,7-naphthyridin-6-amine as yellow oil. LCMS (ES) [M+1]⁺ m/z: 224.
Step 4

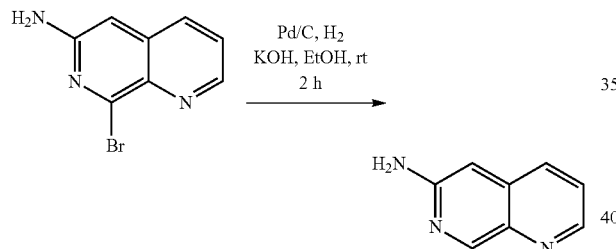

Into a 250-mL round-bottom flask were placed 8-bromo-1,7-naphthyridin-6-amine (2.20 g, 9.82 mmol, 1.00 equiv), EtOH (100.00 mL), KOH (663 mg, 11.82 mmol, 1.20 equiv), Pd/C (300 mg). The mixture was stirred for 2 h at room temperature under atmosphere of hydrogen at pressure at 2-3 atm, filtered through the celite and the filtrate was concentrated in vacuum. This resulted in 1.3 g (92%) of 1,7-naphthyridin-6-amine as yellow oil. LCMS (ES) [M+1]⁺ m/z: 146.
Step 5

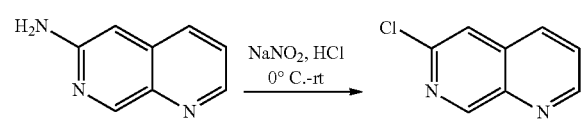 [SMILES: Nc1cc2cccnc2cn1 ; Clc1cc2cccnc2cn1]

Into a 250-mL 3-necked round-bottom flask were placed 1,7-naphthyridin-6-amine (1.30 g, 8.97 mmol, 1.00 equiv), HCl (c) (40.00 mL). This was followed by the addition of NaNO₂ (1.36 g, 19.73 mmol, 2.20 equiv) at 0° C. and stirred for 30 min. To this mixture was added CuCl (897 mg, 8.97 mmol, 1.00 equiv), the resulting solution was stirred for an additional 2 h at room temperature. The pH value of the solution was adjusted to 7 with NaOH (4 N) at 0° C., extracted with 3×50 mL of ethyl acetate. The combined organic phases were dried over anhydrous sodium sulfate, filtered and the filtrate was concentrated under reduced pressure. The residue was purified by silica gel column with ethyl acetate/petroleum ether (40%). This resulted in 530 mg (36%) of 6-chloro-1,7-naphthyridine as yellow oil. LCMS (ES) [M+1]⁺ m/z: 165.
Step 6

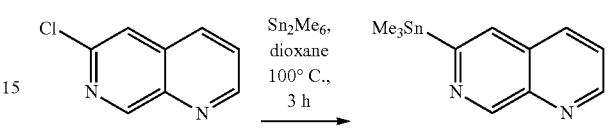

Into a 40-mL vial purged and maintained with an inert atmosphere of nitrogen were placed 6-chloro-1,7-naphthyridine (530 mg, 3.22 mmol, 1.00 equiv), dioxane (10.00 mL), Sn₂Me₆ (1.16 g, 3.54 mmol, 1.10 equiv) and Pd(dppf)Cl₂ (234 mg, 0.32 mmol, 0.10 equiv). The mixture was stirred for 3 h at 100° C. The mixture was used to the next step directly without purification. LCMS (ES) [M+1]⁺ m/z: 295.
Step 7

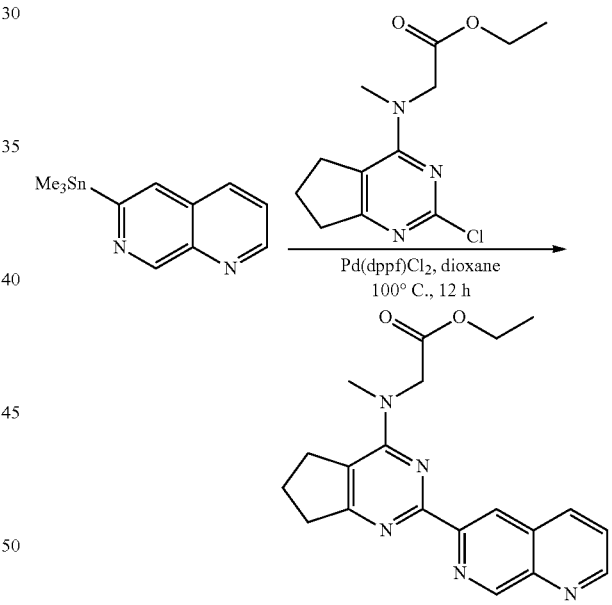

Into a 40-mL vial purged and maintained with an inert atmosphere of nitrogen were placed 6-(trimethylstannyl)-1,7-naphthyridine (reaction solution of last step), dioxane (5.00 mL), ethyl 2-([2-chloro-5H,6H,7H-cyclopenta[d]pyrimidin-4-yl](methyl)amino)acetate (350 mg, 1.30 mmol, 0.70 equiv) and Pd(dppf)Cl₂ (139 mg, 0.19 mmol, 0.10 equiv). The mixture was stirred for 12 h at 100° C. The resulting mixture was cooled to room temperature, concentrated to remove the solvent. The residue was purified by silica gel column with THF/PE (80%). This resulted in 507 mg (75%) of ethyl N-(2-(1,7-naphthyridin-6-yl)-6,7-dihydro-5H-cyclopenta[d]pyrimidin-4-yl)-N-methylglycinate as yellow oil. LCMS (ES) [M+1]⁺ m/z: 364.

Step 8

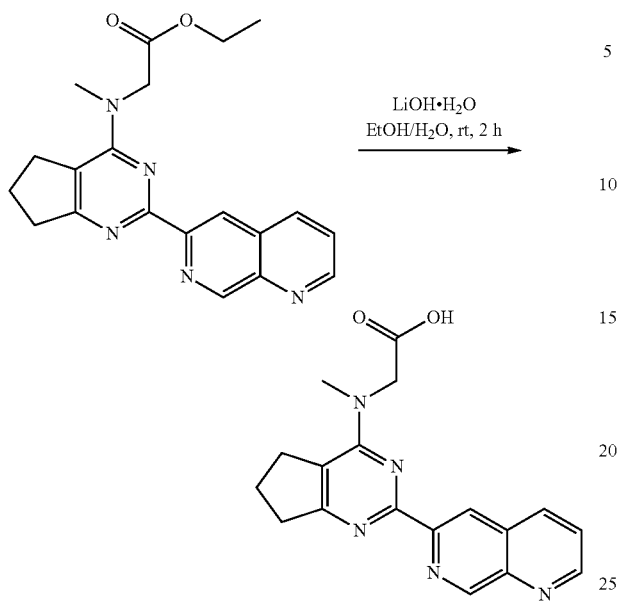

Into a 40-mL vial were placed ethyl 2-[methyl[2-(1,7-naphthyridin-6-yl)-5H,6H,7H-cyclopenta[d]pyrimidin-4-yl]amino]acetate (507 mg, 1.40 mmol, 1.00 equiv), EtOH (5.00 mL), LiOH·H₂O (117 mg, 2.79 mmol, 2.00 equiv) and H₂O (10.00 mL). The resulting solution was stirred for 1 h at room temperature. The reaction solution was concentrated and purified by Prep-HPLC with the following conditions: Column, C 18-120 g, Mobile phase, Water and CH₃CN 5% increased to 10% within 9 min, Detector, 254 nm. The fraction was freezing dried, this resulted in 161 mg (34%) of lithio 2-[methyl[2-(1,7-naphthyridin-6-yl)-5H,6H,7H-cyclopenta[d]pyrimidin-4-yl]amino]acetate as a white solid. LCMS (ES) [M−Li+1]⁺ m/z: 336.

Step 9

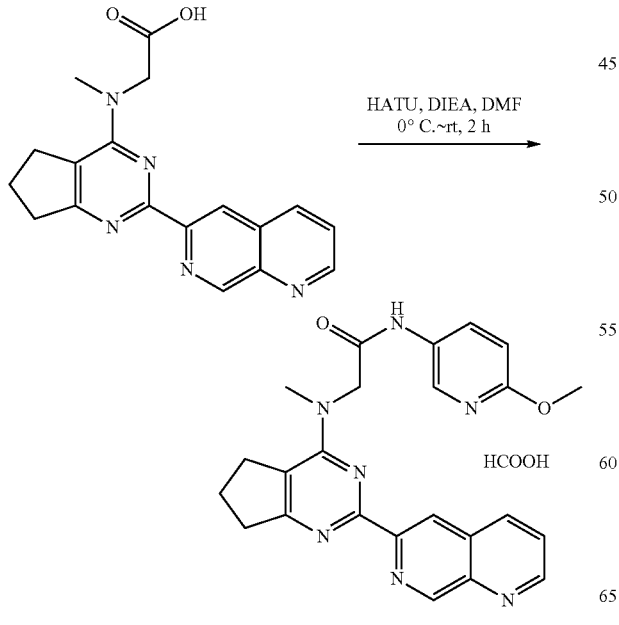

Into a 8-mL vial were placed lithio 2-[methyl[2-(1,7-naphthyridin-6-yl)-5H,6H,7H-cyclopenta[d]pyrimidin-4-yl]amino]acetate (161 mg, 0.47 mmol, 1.00 equiv), DMF (4.00 mL), 5-amino-2-methoxypyridine (70 mg, 0.57 mmol, 1.20 equiv), DIEA (122 mg, 0.95 mmol, 2.00 equiv) and HATU (215 mg, 0.57 mmol, 1.20 equiv). The resulting solution was stirred for 2 h at room temperature. The reaction solution was purified by Prep-HPLC with the following conditions: Column, Sunfire Prep C18 OBD Column, 50*250 mm 5 um, Mobile phase, Water (0.1% FA) and CH₃CN (5% Phase B up to 30% in 15 min), Detector, UV 254 nm. This resulted in 89.6 mg (43.02%) of N-(6-methoxypyridin-3-yl)-2-{methyl [2-(1,7-naphthyridin-6-yl)-5H,6H,7H-cyclopenta[d]pyrimidin-4-yl]amino}acetamide as an off-white solid. LCMS: (ES, m/z) [M+H]⁺: 442. ¹H NMR (300 MHz, DMSO-d6) δ 10.35 (s, 1H), 9.44 (s, 1H), 9.07 (dd, J=4.2, 1.5 Hz, 1H), 8.82 (s, 1H), 8.39 (d, J=2.7 Hz, 1H), 8.33 (d, J=8.4 Hz, 1H), 8.15 (s, 1H), 7.93 (dd, J=9.0, 2.7 Hz, 1H), 7.79 (dd, J=8.4, 4.2 Hz, 1H), 6.77 (d, J=9.0 Hz, 1H), 4.48 (s, 2H), 3.79 (s, 3H), 3.42 (s, 3H), 3.24 (t, J=7.5 Hz, 2H), 2.88 (t, J=7.8 Hz, 2H), 2.09-1.98 (m, 2H).

Example 1.252

Synthesis of (2R)-3-methyl-N-(1-methyl-1H-pyrazol-4-yl)-2-{methyl[2-(pyridin-2-yl)-5H,6H,7H-cyclopenta[d]pyrimidin-4-yl]amino}butanamide
(Compound 246)

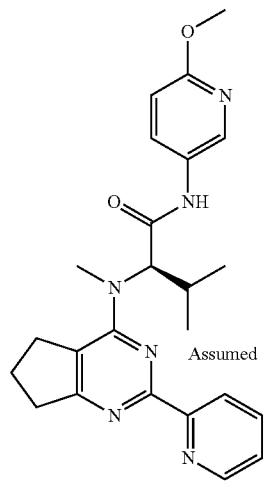 [SMILES: COc1ccc(NC(=O)[C@@H](C(C)C)N(C)c2nc(-c3ccccn3)nc3c2CCC3)cn1]

Scheme 108

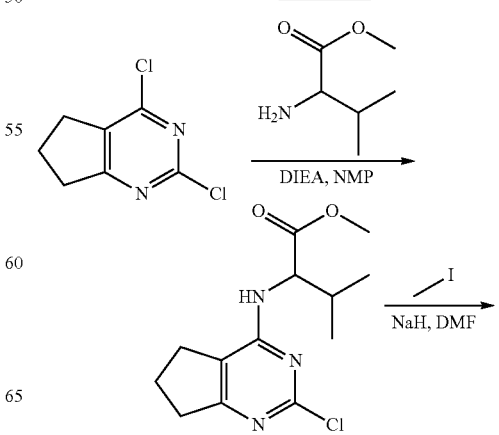

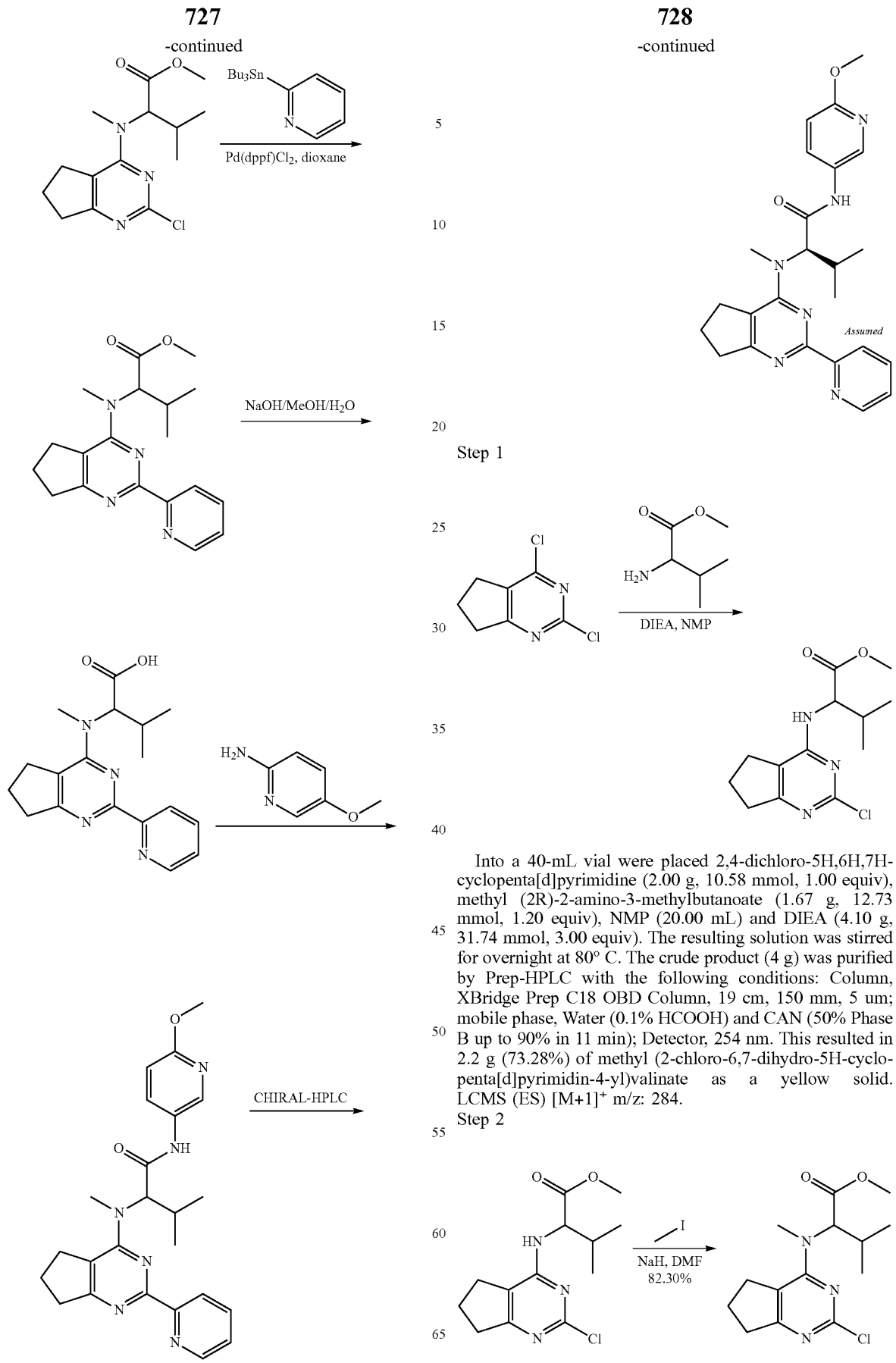

Into a 40-mL vial were placed 2,4-dichloro-5H,6H,7H-cyclopenta[d]pyrimidine (2.00 g, 10.58 mmol, 1.00 equiv), methyl (2R)-2-amino-3-methylbutanoate (1.67 g, 12.73 mmol, 1.20 equiv), NMP (20.00 mL) and DIEA (4.10 g, 31.74 mmol, 3.00 equiv). The resulting solution was stirred for overnight at 80° C. The crude product (4 g) was purified by Prep-HPLC with the following conditions: Column, XBridge Prep C18 OBD Column, 19 cm, 150 mm, 5 um; mobile phase, Water (0.1% HCOOH) and CAN (50% Phase B up to 90% in 11 min); Detector, 254 nm. This resulted in 2.2 g (73.28%) of methyl (2-chloro-6,7-dihydro-5H-cyclopenta[d]pyrimidin-4-yl)valinate as a yellow solid. LCMS (ES) [M+1]⁺ m/z: 284.

Step 2

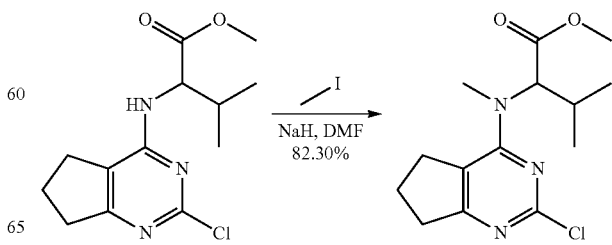

729

Into a 100-mL 3-necked round-bottom flask were placed methyl (2-chloro-6,7-dihydro-5H-cyclopenta[d]pyrimidin-4-yl)valinate (2.20 g, 7.75 mmol, 1.00 equiv), DMF (30.00 mL). This was followed by the addition of NaH (0.28 g, 11.67 mmol, 1.50 equiv) in portions at 0° C. To this was added methyl iodide (1.32 g, 9.30 mmol, 1.20 equiv) dropwise with stirring at 0° C. The resulting solution was stirred for 2 h at room temperature. The reaction was then quenched by the addition of 20 mL of water/ice, extracted with 3×30 mL of ethyl acetate. The organic layers were combined, dried over anhydrous sodium sulfate and concentrated. The residue was applied onto a silica gel column with THF/PE (6%). This resulted in 1.9 g (82.30%) of methyl N-(2-chloro-6,7-dihydro-5H-cyclopenta[d]pyrimidin-4-yl)-N-methyl-valinate as yellow solid. LCMS (ES) [M+1]⁺ m/z: 298.
Step 3

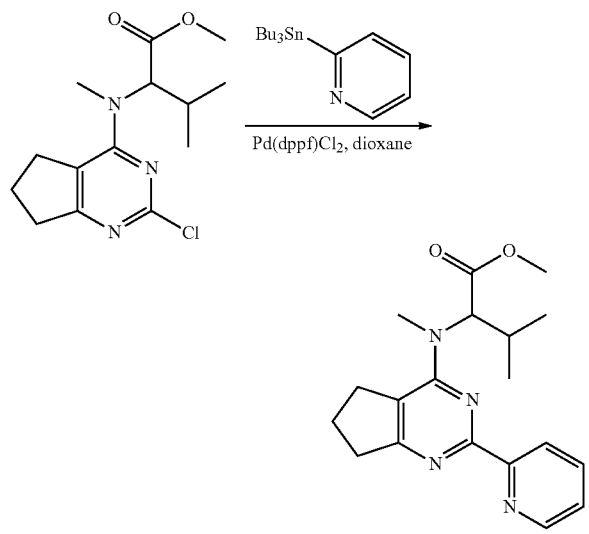

Into a 100-mL round-bottom flask were placed methyl N-(2-chloro-6,7-dihydro-5H-cyclopenta[d]pyrimidin-4-yl)-N-methylvalinate (1.90 g, 6.38 mmol, 1.00 equiv), 2-(tributylstannyl)pyridine (3.05 g, 8.28 mmol, 1.30 equiv), dioxane (30.00 mL) and Pd(dppf)Cl₂ (0.47 g, 0.64 mmol, 0.10 equiv). The resulting solution was stirred for overnight at 100° C. The resulting mixture was concentrated. The residue was applied onto a silica gel column with THF/PE (70-100%). This resulted in 1.5 g (69.06%) of methyl N-methyl-N-(2-(pyridin-2-yl)-6,7-dihydro-5H-cyclopenta[d]pyrimidin-4-yl)valinate as yellow oil. LCMS (ES) [M+1]+ m/z: 341.
Step 4

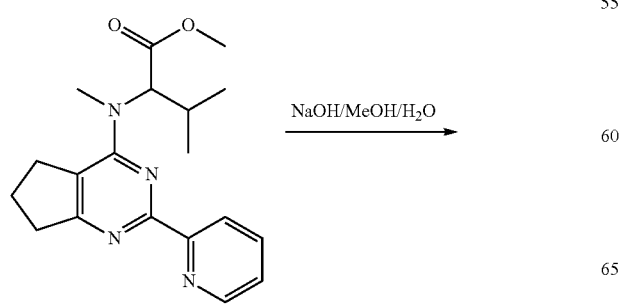

730

-continued

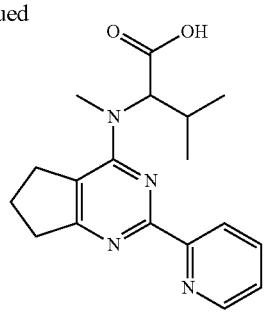

Into a 100-mL round-bottom flask were placed methyl N-methyl-N-(2-(pyridin-2-yl)-6,7-dihydro-5H-cyclopenta[d]pyrimidin-4-yl)valinate (1.50 g, 4.41 mmol, 1.00 equiv), MeOH (10.00 mL), H₂O (10.00 mL). This was followed by the addition of NaOH (0.35 g, 8.85 mmol, 2.00 equiv), in portions at 0° C. The resulting solution was stirred for overnight at room temperature. The pH value of the solution was adjusted to 5-6 with citric acid. The crude product (1 g) was purified by Prep-HPLC with the following conditions: Column, XBridge Prep C18 OBD Column, 19 cm, 150 mm, 5 um; mobile phase, Water (0.1% HCOOH) and CAN (10% Phase B up to 40% in 11 min); Detector, 254 nm. This resulted in 800 mg (55.63%) of 3-methyl-2-[methyl[2-(pyridin-2-yl)-5H,6H,7H-cyclopenta[d]pyrimidin-4-yl]amino]butanoic acid as yellow solid. LCMS (ES) [M+1]⁺ m/z: 327.
Step 5

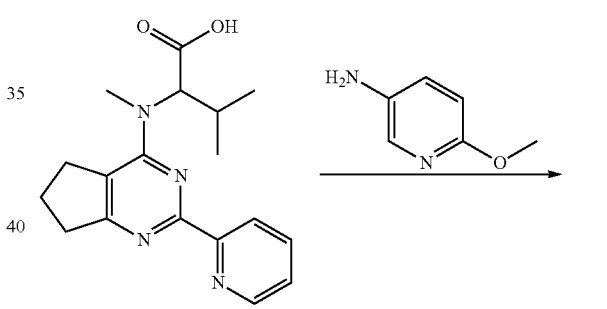

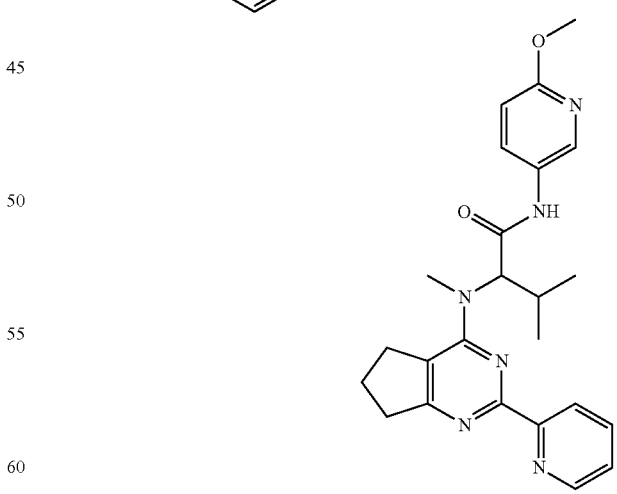

Into a 40-mL vial were placed 3-methyl-2-[methyl[2-(pyridin-2-yl)-5H,6H,7H-cyclopenta[d]pyrimidin-4-yl]amino]butanoic acid (330.00 mg, 1.01 mmol, 1.00 equiv), 5-amino-2-methoxypyridine (125.51 mg, 1.01 mmol, 1.00 equiv), DMF (5.00 mL) and DIEA (261.34 mg, 2.02 mmol, 2.00 equiv). This was followed by the addition of T₃P (386.03 mg, 1.21 mmol, 1.20 equiv) in portions at 0° C. The resulting solution was stirred for 3 h at room temperature. The crude product (1 g) was purified by Prep-HPLC with the following conditions: Column, XBridge Prep C18 OBD Column, 19 cm, 150 mm, 5 um; mobile phase, Water (0.1% NH₃·H₂O) and CAN (50% Phase B up to 90% in 11 min); Detector, 254 nm. This resulted in 310 mg (70.89%) of N-(6-methoxypyridin-3-yl)-3-methyl-2-[methyl[2-(pyridin-2-yl)-5H,6H,7H-cyclopenta[d]pyrimidin-4-yl]amino]butanamide as white solid. LCMS (ES) [M+1]⁺ m/z: 433.

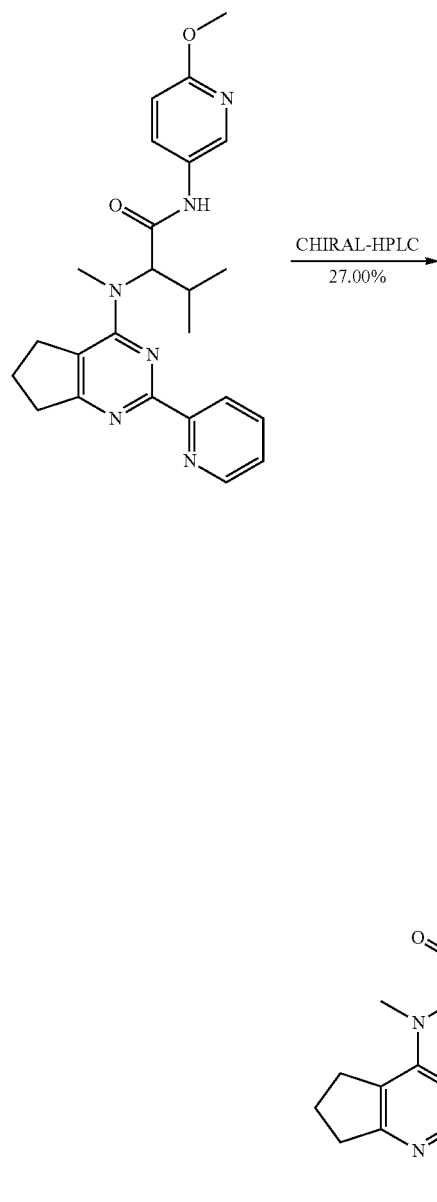

The crude product (310 mg) was purified by Prep-CHIRAL-HPLC with the following conditions: Column, CHIRALPAK IC, 20*250 mm, 5 μm; mobile phase, n-Hexane/DCM=5/1 and IPA (15% in 25 min); Detector, 254 nM. This resulted in 83.7 mg (27.00%) of (2R)-3-methyl-N-(1-methyl-1H-pyrazol-4-yl)-2-{methyl[2-(pyridin-2-yl)-5H,6H,7H-cyclopenta[d]pyrimidin-4-yl]amino}butanamide as white solid. Chiral HPLC retention time: 3.83 min (condition: Column, YMC Cellulose-SB, 100*4.6 mm, 3 μm; mobile phase, n-Hexane/DCM=5/1 and isopropanol (10% in 6 min)). LCMS (ES, m/z): [M+H]⁺: 433. ¹H NMR (300 MHz, DMSO-d6) δ 10.75 (s, 1H), 8.80-8.71 (m, 1H), 8.42 (d, J=7.9 Hz, 1H), 8.31 (d, J=2.6 Hz, 1H), 8.04-7.87 (m, 2H), 7.60-7.50 (m, 1H), 6.76 (d, J=8.9 Hz, 1H), 4.75 (d, J=11.1 Hz, 1H), 3.78 (s, 3H), 3.29-3.21 (m, 1H), 3.18 (s, 3H), 3.15-3.01 (m, 1H), 3.01-2.74 (m, 2H), 2.49-2.39 (m, 1H), 2.14-1.95 (m, 2H), 1.02 (d, J=6.4 Hz, 3H), 0.94 (d, J=6.6 Hz, 3H).

Example 1.253

Synthesis of (2S)—N-(6-methoxypyridin-3-yl)-3-methyl-2-{methyl[2-(pyridin-2-yl)-5H,6H,7H-cyclopenta[d]pyrimidin-4-yl]amino}butanamide (Compound 247)

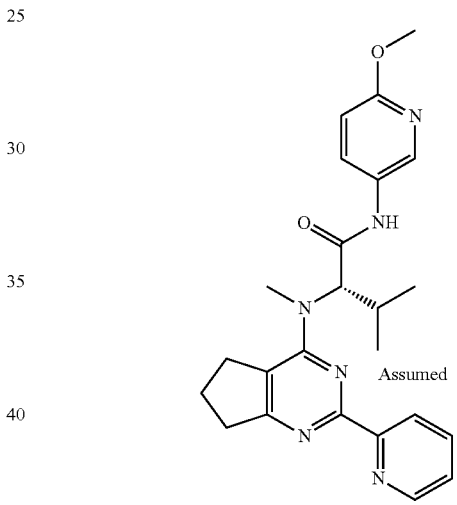

Reaction Scheme

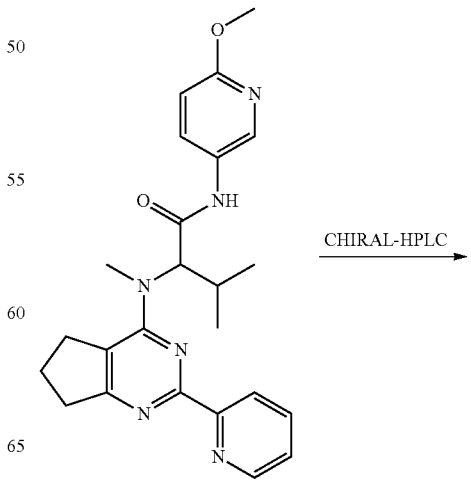

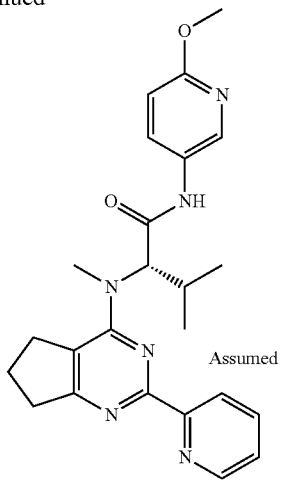

The crude product from compound 246 step 1 (310 mg) was purified by Prep-CHIRAL-HPLC with the following conditions: Column, CHIRALPAK IC, 30*250 mm, 5 μm; mobile phase, n-Hexane/DCM=5/1 and IPA (15% in 25 min); Detector, 254. This resulted in 105.5 mg (34.03%) (2S)—N-(6-methoxypyridin-3-yl)-3-methyl-2-{methyl[2-(pyridin-2-yl)-5H,6H,7H-cyclopenta[d]pyrimidin-4-yl]amino}butanamide as white solid. Chiral HPLC retention time: 5.19 min (condition: Column, YMC Cellulose-SB, 100*4.6 mm, 3 μm; mobile phase, n-Hexane/DCM=5/1 and isopropanol (10% in 6 min)). LCMS (ES, m/z): [M+H]$^+$: 433. $^1$H NMR (300 MHz, DMSO-d6) δ 10.74 (s, 1H), 8.75 (dt, J=4.6, 1.5 Hz, 1H), 8.42 (dt, J=8.0, 1.2 Hz, 1H), 8.31 (d, J=2.6 Hz, 1H), 8.04-7.87 (m, 2H), 7.55 (ddd, J=7.5, 4.8, 1.3 Hz, 1H), 6.76 (d, J=8.9 Hz, 1H), 4.75 (d, J=11.0 Hz, 1H), 3.78 (s, 3H), 3.30-3.20 (m, 1H), 3.18 (s, 3H), 3.15-3.01 (m, 1H), 3.01-2.74 (m, 2H), 2.51-2.37 (m, 1H), 2.17-1.91 (m, 2H), 1.02 (d, J=6.4 Hz, 3H), 0.94 (d, J=6.6 Hz, 3H).

Example 1.254

Synthesis of (2R)-3-methyl-N-(1-methyl-1H-pyrazol-4-yl)-2-{methyl[2-(pyridin-2-yl)-5H,6H,7H-cyclopenta[d]pyrimidin-4-yl]amino}butanamide (Compound 248)

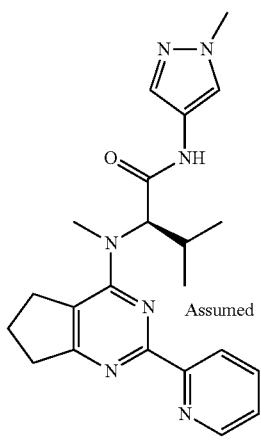 [SMILES: CC(C)[C@H](C(=O)Nc1cnn(C)c1)N(C)c1nc(-c2ccccn2)nc2c1CCC2]

Compound 248 was synthesized similar to Compound 246 replacing 5-amino-2-methoxypyridine with 1-methylpyrazol-4-amine. Chiral HPLC retention time: 3.68 min (condition: Column, YMC Cellulose-SB, 100*4.6 mm, 3 μm; mobile phase, n-Hexane and ethanol (10% in 8 min)). LCMS (ES) [M+1]$^+$ m/z: 406. $^1$H NMR (300 MHz, DMSO-d6) δ 10.78 (s, 1H), 8.85 (ddd, J=4.8, 1.7, 0.7 Hz, 1H), 8.41 (dt, J=7.9, 1.2 Hz, 1H), 7.99 (td, J=7.7, 1.8 Hz, 1H), 7.88 (s, 1H), 7.57 (ddd, J=7.5, 4.8, 1.3 Hz, 1H), 7.34 (s, 1H), 4.70 (d, J=11.1 Hz, 1H), 3.75 (s, 3H), 3.23 (dt, J=15.9, 8.0 Hz, 1H), 3.16 (s, 3H), 3.14-3.00 (m, 1H), 3.00-2.74 (m, 2H), 2.49-2.35 (m, 1H), 2.15-1.90 (m, 2H), 0.97 (d, J=6.4 Hz, 3H), 0.93 (d, J=6.6 Hz, 3H).

Example 1.255

Synthesis of (2R)-3-methyl-N-(1-methyl-1H-pyrazol-4-yl)-2-{methyl[2-(pyridin-2-yl)-5H,6H,7H-cyclopenta[d]pyrimidin-4-yl]amino}butanamide (Compound 249)

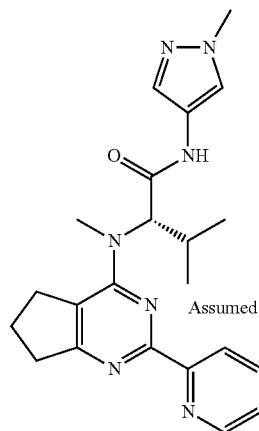

Compound 249 was synthesized similar to Compound 247 replacing 5-amino-2-methoxypyridine with 1-methylpyrazol-4-amine. Chiral HPLC retention time: 4.82 min (condition: Column, YMC Cellulose-SB, 100*4.6 mm, 3 μm; mobile phase, n-Hexane and ethanol (10% in 8 min)). LCMS (ES) [M+1]$^+$ m/z: 406. $^1$H NMR (300 MHz, DMSO-d6) δ 10.78 (s, 1H), 8.85 (dt, J=5.1, 1.2 Hz, 1H), 8.41 (dt, J=7.9, 1.1 Hz, 1H), 7.99 (td, J=7.7, 1.7 Hz, 1H), 7.88 (s, 1H), 7.57 (ddd, J=7.5, 4.7, 1.3 Hz, 1H), 7.35 (s, 1H), 4.70 (d, J=11.0 Hz, 1H), 3.75 (s, 3H), 3.23 (dt, J=16.0, 8.1 Hz, 1H), 3.16 (s, 3H), 3.14-3.00 (m, 1H), 3.00-2.74 (m, 2H), 2.49-2.35 (m, 1H), 2.16-1.90 (m, 2H), 0.97 (d, J=6.4 Hz, 3H), 0.93 (d, J=6.6 Hz, 3H).

Example 1.256

Synthesis of (2R)-2-{[2-(isoquinolin-3-yl)-5H,6H,7H-cyclopenta[d]pyrimidin-4-yl](methyl)amino}-N-(6-methoxypyridin-3-yl)propanamide (Compound 250)

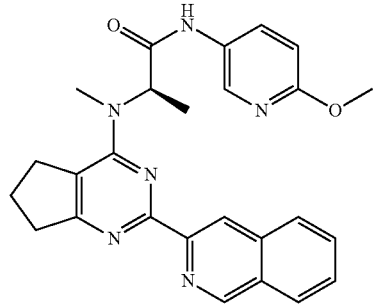 [SMILES: COc1ccc(NC(=O)[C@@H](C)N(C)c2nc(-c3cc4ccccc4cn3)nc3c2CCC3)cn1]

Compound 250 was synthesized similar to Compound 108 replacing Cyclohexanamine with 5-amino-2-methoxypyridine and replacing 2-(tributylstannyl)pyridine with 3-(trimethylstannyl)isoquinoline. LCMS (ES) [M+1]+ m/z: 455. $^1$H NMR (300 MHz, DMSO-d6) δ 10.61 (s, 1H), 9.42 (s, 1H), 8.85 (s, 1H), 8.38 (d, J=2.7 Hz, 1H), 8.20 (d, J=8.4 Hz, 1H), 8.17 (s, HCOOH), 8.03 (d, J=8.1 Hz, 1H), 7.94 (dd, J=8.7, 2.7 Hz, 1H), 7.84-7.72 (m, 2H), 6.75 (d, J=8.7 Hz, 1H), 5.38 (q, J=6.9 Hz, 1H), 3.77 (s, 3H), 3.29-3.13 (m, 2H), 3.25 (s, 3H), 2.95-2.86 (m, 2H), 2.08-1.98 (m, 2H), 1.50 (d, J=6.9 Hz, 3H).

Example 1.257

Synthesis of (2R)—N-(3-fluorophenyl)-2-({2-[4-(2-hydroxyethoxy)pyridin-2-yl]-5H,6H,7H-cyclopenta[d]pyrimidin-4-yl}(methyl)amino)propanamide (Compound 251)

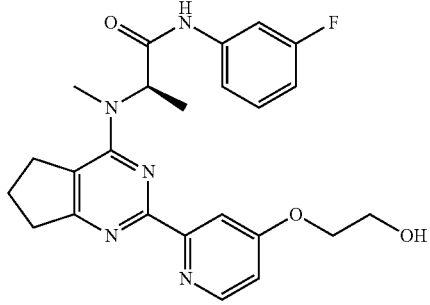 [SMILES: C[C@H](C(=O)Nc1cccc(F)c1)N(C)c1nc(-c2cc(OCCO)ccn2)nc2c1CCC2]

Scheme 108

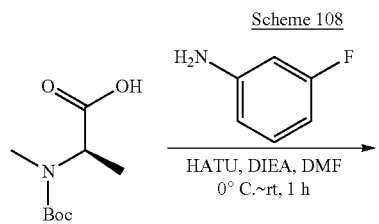

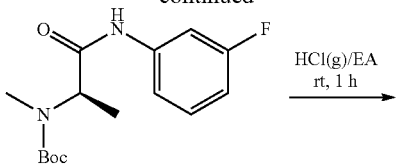

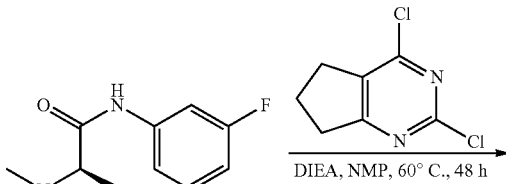

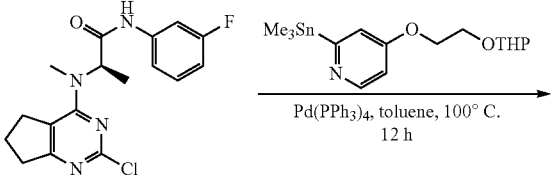

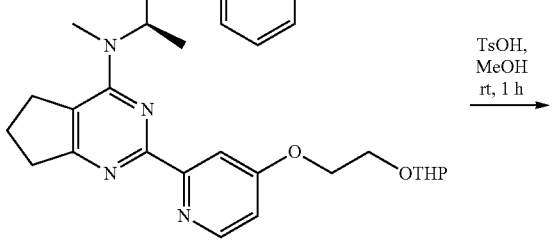

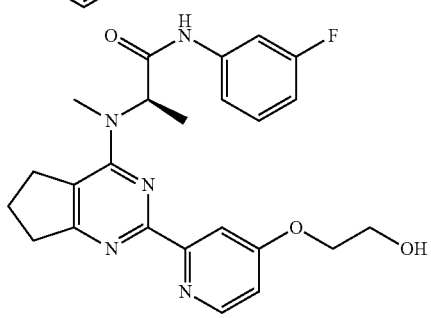

Step 1

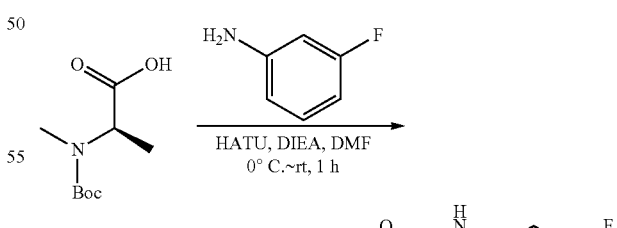

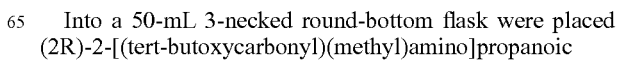

Into a 50-mL 3-necked round-bottom flask were placed (2R)-2-[(tert-butoxycarbonyl)(methyl)amino]propanoic acid (2.00 g, 9.84 mmol, 1.00 equiv), DMF (20.00 mL), 3-fluoroaniline (1.20 g, 10.82 mmol, 1.10 equiv) and DIEA (2.54 g, 19.68 mmol, 2.00 equiv). This was followed by the addition of HATU (4.12 g, 10.82 mmol, 1.10 equiv) in several batches at 0° C. After addition, the resulting solution was stirred for 1 h at room temperature. The reaction was quenched with 20 mL of water, extracted with 3×20 mL of ethyl acetate. The combined organic phase was washed with 3×20 ml of brine, dried over anhydrous sodium sulfate and filtered. The filtrate was concentrated under reduced pressure, the residue was purified by silica gel column with ethyl acetate/petroleum ether (1:1). This resulted in 2.2 g (75%) of tert-butyl N-[(1R)-1-[(3-fluorophenyl)carbamoyl]ethyl]-N-methylcarbamate as a white solid. LCMS (ES) [M+1]+ m/z: 297.

Step 2

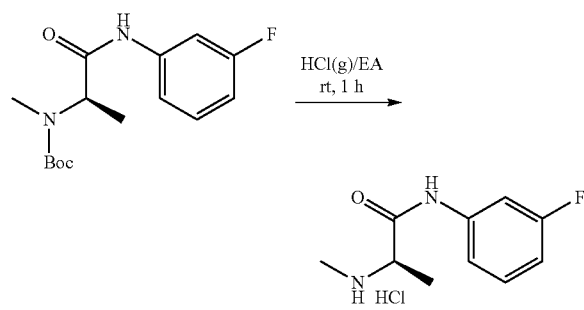

Into a 50-mL round-bottom flask were placed tert-butyl N-[(1R)-1-[(3-fluorophenyl)carbamoyl]ethyl]-N-methylcarbamate (2.20 g, 7.42 mmol, 1.00 equiv) and DCM (10.00 mL). This was followed by the addition of HCl (g) (2 M in EA) (19.00 mL, 37.10 mmol, 5.00 equiv) dropwise with stirring at 0° C. The resulting solution was stirred for 1 h at room temperature. The mixture was concentrated in vacuum to remove the solvent. This resulted in 1.6 g (93%) of (2R)—N-(3-fluorophenyl)-2-(methylamino)propanamide hydrochloride as a white solid. LCMS (ES) [M−HCl+1]+ m/z: 197.

Step 3

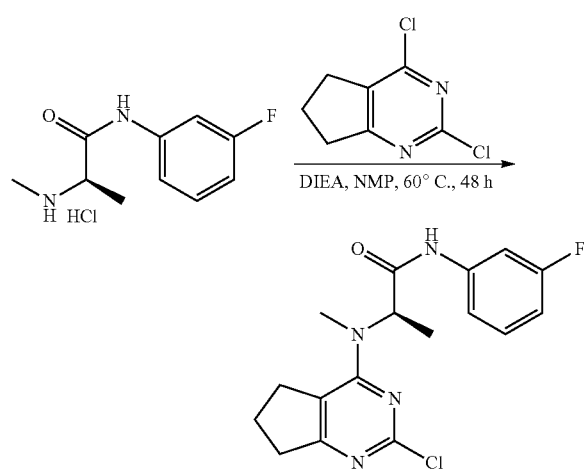

Into a 50-mL round-bottom flask were placed (2R)—N-(3-fluorophenyl)-2-(methylamino)propanamide hydrochloride (1.00 g, 4.29 mmol, 1.00 equiv), NMP (20.00 mL), 2,4-dichloro-5H,6H,7H-cyclopenta[d]pyrimidine (1.06 g, 5.58 mmol, 1.30 equiv) and DIEA (2.78 g, 21.49 mmol, 5.00 equiv). The resulting solution was stirred for 48 h at 60° C. in oil bath. The reaction mixture was cooled to room temperature, diluted with 20 mL of water and extracted with 3×20 mL of ethyl acetate. The combined organic phases were washed with 3×20 ml of brine, dried over anhydrous sodium sulfate and filtered. The filtrate was concentrated under reduced pressure, the residue was purified by silica gel column with ethyl acetate/petroleum ether (1:1). This resulted in 1.0 g (67%) of (2R)-2-([2-chloro-5H,6H,7H-cyclopenta[d]pyrimidin-4-yl](methyl)amino)-N-(3-fluorophenyl)propanamide as a white solid. LCMS (ES) [M+1]+ m/z: 349.

Step 4

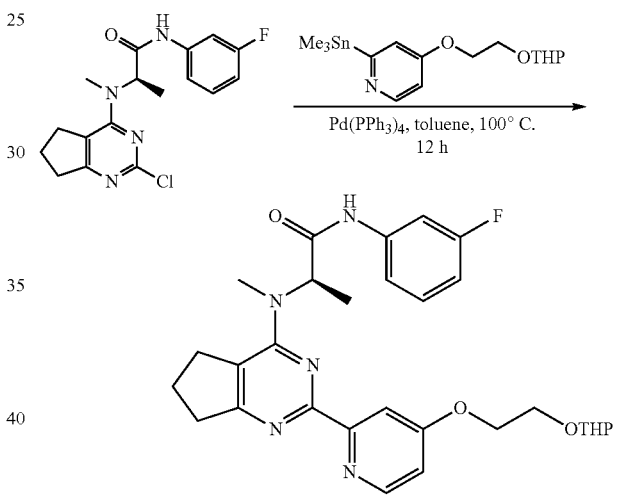

Into a 100-mL three necked round bottom flask purged and maintained with an inert atmosphere of nitrogen were placed 4-[2-(oxan-2-yloxy)ethoxy]-2-(trimethylstannyl) pyridine (Made in-situ from 2-chloro-4-(2-((tetrahydro-2H-pyran-2-yl)oxy)ethoxy)pyridine with hexamethyldistannane) (1.60 g, 4.14 mmol, 1.00 equiv), toluene (60.00 mL), (2R)-2-([2-chloro-5H,6H,7H-cyclopenta[d]pyrimidin-4-yl](methyl)amino)-N-(3-fluorophenyl)propanamide (1.01 g, 2.90 mmol, 0.70 equiv), Pd(PPh3)4 (479 mg, 0.41 mmol, 0.10 equiv). The mixture was stirred for 12 h at 105° C. in oil bath. The reaction mixture was cooled to room temperature, concentrated to remove the solvent, the residue was purified by silica gel column with dichloromethane/methanol (10:1). This resulted in 190 mg (9%) of (2R)—N-(3-fluorophenyl)-2-[methyl([2-[(2E)-3-[2-(oxan-2-yloxy)ethoxy]but-2-enimidoyl]-5H,6H,7H-cyclopenta[d]pyrimidin-4-yl])amino]propanamide as yellow oil. LCMS (ES) [M+1]+ m/z: 536.

Step 5

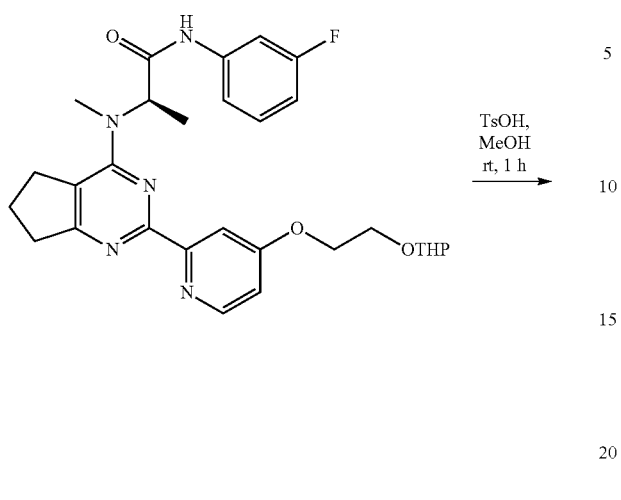

Example 1.258

Synthesis of N-(3-fluorophenyl)-2-[methyl(2-{4-[2-(pyrrolidin-1-yl)ethoxy]pyridin-2-yl}-5H,6H,7H-cyclopenta[d]pyrimidin-4-yl)amino]acetamide (Compound 252)

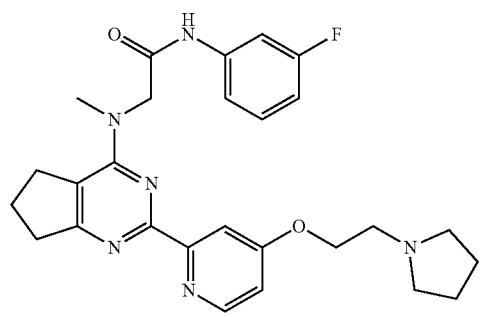 [SMILES: CN(CC(=O)Nc1cccc(F)c1)c1nc(-c2cc(OCCN3CCCC3)ccn2)nc2c1CCC2]

Into a 8-mL vial were placed (2R)—N-(3-fluorophenyl)-2-[methyl(2-4-[2-(oxan-2-yloxy)ethoxy]pyridin-2-yl]-5H,6H,7H-cyclopenta[d]pyrimidin-4-yl)amino]propanamide (190 mg, 0.35 mmol, 1.00 equiv), MeOH (4.00 mL) and TsOH (73 mg, 0.42 mmol, 1.20 equiv). The resulting solution was stirred for 1 h at room temperature. The reaction solution was purified by Flash-Prep-HPLC with the following conditions: Column, Welch XB-C18, 21.2*250 mm, 5 um, Mobile phase, Phase A: Water (0.05% NH$_4$OH) and Phase B: CH$_3$CN (10% Phase B up to 65% in 15 min), Detector, UV 254 nm. The fraction was freezing dried, this resulted in 108.1 mg (68%) of (2R)—N-(3-fluorophenyl)-2-({2-[4-(2-hydroxyethoxy)pyridin-2-yl]-5H,6H,7H-cyclopenta[d]pyrimidin-4-yl}(methyl)amino)propanamide as a white solid. LCMS (ES, m/z): [M+H]$^+$: 452. $^1$H-NMR (300 MHz, DMSO-d$_6$, ppm): δ 10.58 (br, 1H), 8.49 (d, J=5.7 Hz, 1H), 7.88 (d, J=2.7 Hz, 1H), 7.57-7.52 (m, 1H), 7.36-7.22 (m, 2H), 7.07 (dd, J=5.7, 2.7 Hz, 1H), 6.86-6.80 (m, 1H), 5.28 (q, J=7.2 Hz, 1H), 4.92 (t, J=5.4 Hz, 1H), 4.13 (t, J=4.2 Hz, 2H), 3.77-3.72 (m, 2H), 3.30-3.06 (m, 5H), 2.94-2.77 (m, 2H), 2.06-1.95 (m, 2H), 1.46 (d, J=7.2 Hz, 3H).

Scheme 109

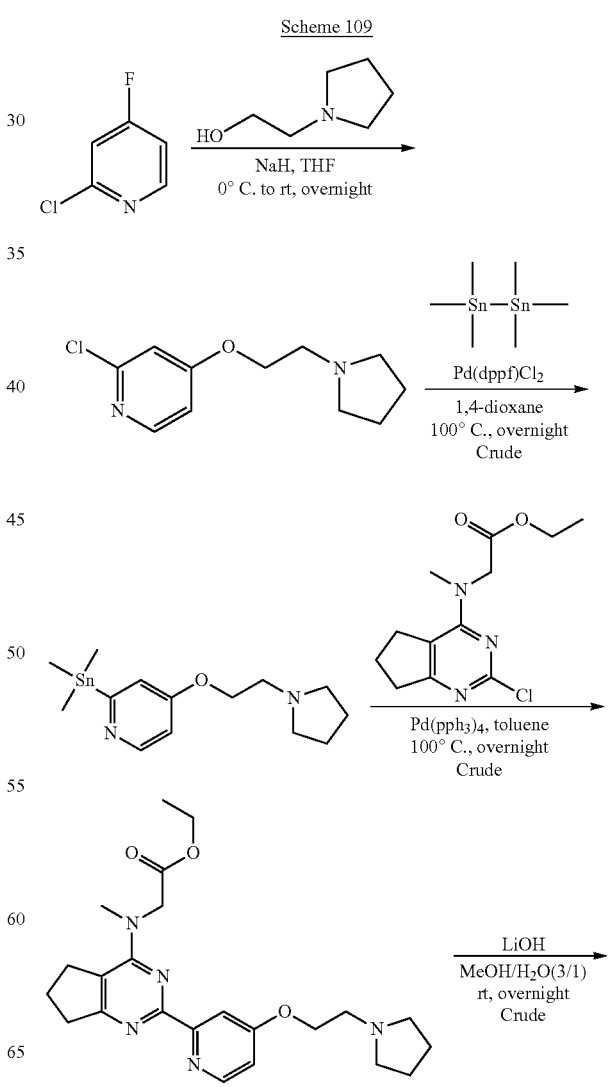

741
-continued

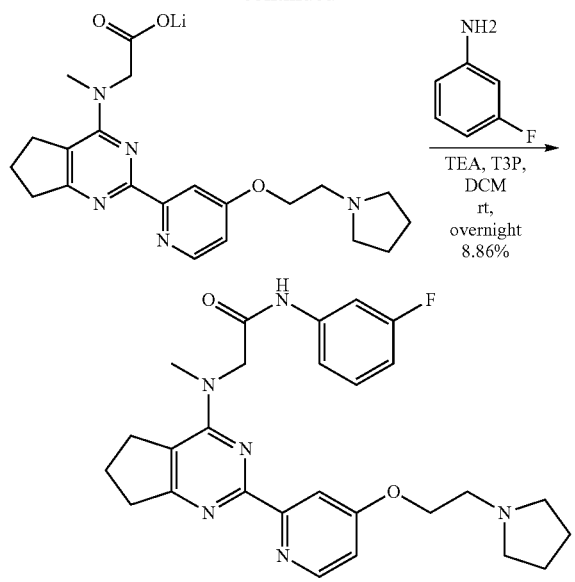

Step 1

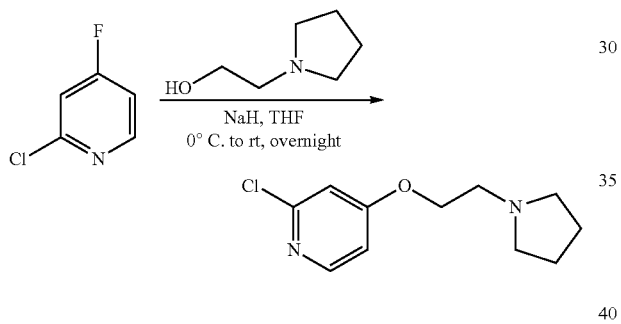

Into a 100-mL 3-necked round-bottom flask purged and maintained with an inert atmosphere of nitrogen was placed a solution of 1-(2-hydroxyethyl)pyrrolidine (4.82 g, 41.816 mmol, 1.1 equiv) in THF (50 mL). This was followed by the addition of NaH (60%) (1.83 g, 45.750 mmol, 1.2 equiv), in portions at 0° C. in 15 min. The resulting solution was stirred for 1 hr at 0° C. To this was added 2-chloro-4-fluoropyridine (5.00 g, 38.014 mmol, 1.00 equiv) dropwise with stirring at 0° C. in 20 min. The resulting solution was stirred overnight at room temperature. The reaction was then quenched by the addition of 50 mL of water/ice. The resulting solution was extracted with 3×50 mL of ethyl acetate and the organic layers combined, washed with 1×100 mL of brine. After filtration, the filtrate was dried over anhydrous sodium sulfate and concentrated. The residue was purified by silica gel column eluted with ethyl acetate/petroleum ether (1/4). This resulted in 5.5 g (63.95%) of 2-chloro-4-[2-(pyrrolidin-1-yl)ethoxy]pyridine as brown oil. LCMS (ES) [M+1]+ m/z: 227.

742

Step 2

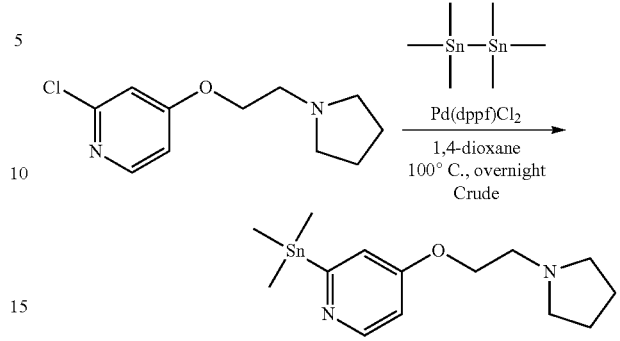

Into a 40-mL round-bottom flask purged and maintained with an inert atmosphere of nitrogen were placed a solution of 2-chloro-4-[2-(pyrrolidin-1-yl)ethoxy]pyridine (1.80 g, 7.940 mmol, 1.00 equiv) in 1,4-Dioxane (20 mL), hexamethyldistannane (2.86 g, 8.734 mmol, 1.1 equiv) and Pd(dppf)Cl$_2$ (400.00 mg, 0.547 mmol, 0.07 equiv). The resulting solution was stirred overnight at 100° C. in an oil bath. The resulting mixture was concentrated under vacuum. This resulted in 5.0 g (crude) of 4-[2-(pyrrolidin-1-yl)ethoxy]-2-(trimethylstannyl)pyridine as a solid. It was used directly in next step. LCMS (ES) [M+1]+ m/z: 357.

Step 3


Into a 100-mL round-bottom flask purged and maintained with an inert atmosphere of nitrogen were placed a solution of 4-[2-(pyrrolidin-1-yl)ethoxy]-2-(trimethylstannyl)pyridine (5.00 g crude, 14.082 mmol, 1.00 equiv) in toluene (50 mL), ethyl 2-([2-chloro-5H,6H,7H-cyclopenta[d]pyrimidin-4-yl](methyl)amino)acetate (2.28 g, 8.449 mmol, 0.6 equiv) and Pd(PPh$_3$)$_4$ (1.00 g, 0.865 mmol, 0.06 equiv). The resulting solution was stirred overnight at 100° C. in an oil bath. The resulting mixture was concentrated. The residue was purified by silica gel column eluted with dichloromethane/methanol (10/1). This resulted in 400 mg (crude) of ethyl 2-[methyl(2-[4-[2-(pyrrolidin-1-yl)ethoxy]pyridin-2-yl]-

5H,6H,7H-cyclopenta[d]pyrimidin-4-yl)amino]acetate as brown oil. LCMS (ES) [M+1]⁺ m/z: 426.
Step 4

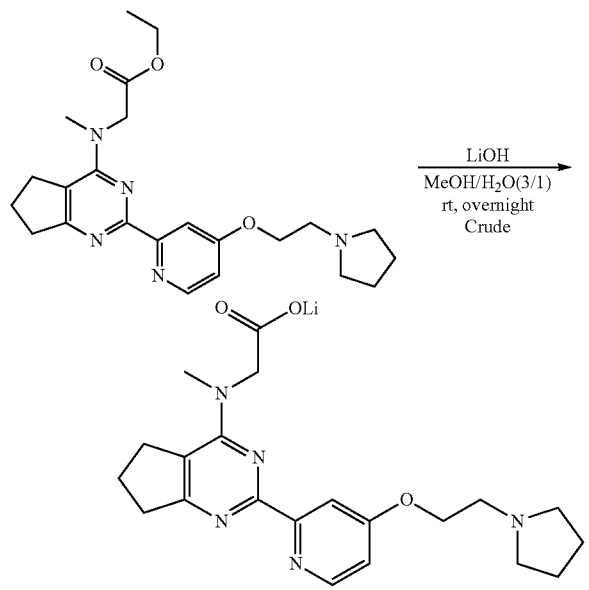

Into a 40-mL round-bottom flask were placed ethyl 2-[methyl(2-[4-[2-(pyrrolidin-1-yl)ethoxy]pyridin-2-yl]-5H,6H,7H-cyclopenta[d]pyrimidin-4-yl)amino]acetate (390.00 mg, 0.916 mmol, 1.00 equiv), MeOH/H₂O (3/1) (4 mL) and LiOH·H₂O (76.92 mg, 1.833 mmol, 2 equiv). The resulting solution was stirred overnight at room temperature. The resulting mixture was concentrated. This resulted in 350 mg (crude) of lithio 2-[methyl(2-[4-[2-(pyrrolidin-1-yl)ethoxy]pyridin-2-yl]-5H,6H,7H-cyclopenta[d]pyrimidin-4-yl)amino]acetate as a brown solid. LCMS (ES) [M−Li+H+1]⁺ m/z: 398.
Step 5

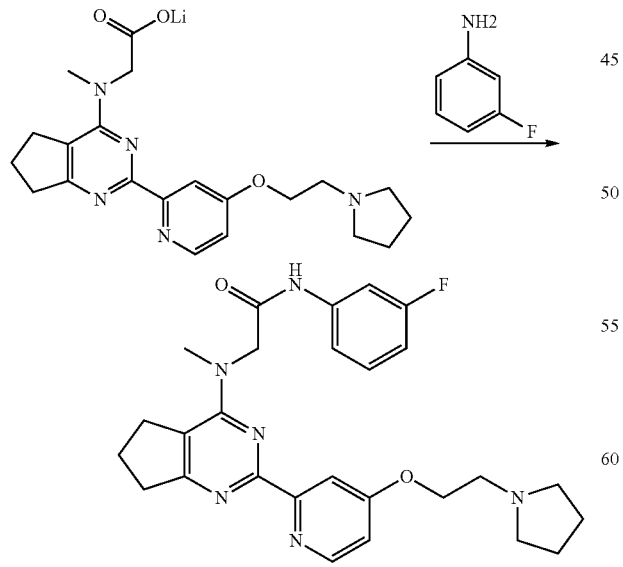

Into a 40-mL round-bottom flask were placed a solution of lithio 2-[methyl(2-[4-[2-(pyrrolidin-1-yl)ethoxy]pyridin-2-yl]-5H,6H,7H-cyclopenta[d]pyrimidin-4-yl)amino]acetate (320.00 mg, 0.805 mmol, 1.00 equiv) in DCM (4 mL), TEA (162.93 mg, 1.610 mmol, 2 equiv), T3P (512.32 mg, 1.610 mmol, 2 equiv) and 3-fluoroaniline (107.35 mg, 0.966 mmol, 1.2 equiv). The resulting solution was stirred overnight at room temperature. The resulting mixture was concentrated under vacuum. The residue was purified by silica gel column with THF/petroleum ether (10:1). The collected fractions were combined and concentrated under vacuum. The residue was dissolved in 4 mL of MeOH and was further purified by Prep-HPLC with the following conditions (Waters I): Column, Xbridge Prep C18 OBD column, 5 um, 19*150 mm; mobile phase, Water (0.1% TFA) and CH₃CN (30% CH₃CN up to 40% in 13 min); Detector, UV 254 nm. This resulted in 35.0 mg (8.99%) of N-(3-fluorophenyl)-2-[methyl(2-{4-[2-(pyrrolidin-1-yl)ethoxy]pyridin-2-yl}-5H,6H,7H-cyclopenta[d]pyrimidin-4-yl)amino]acetamide as a light yellow solid. LCMS (ES) [M+1]⁺ m/z: 491. ¹H NMR (300 MHz, Chloroform-d) δ 10.68 (s, 1H), 8.64 (s, 1H), 8.12 (s, 1H), 7.56 (d, J=11.4 Hz, 1H), 7.43 (d, J=8.3 Hz, 1H), 7.24-7.14 (m, 1H), 7.14 (s, 1H), 6.77-6.72 (m, 1H), 4.70 (s, 2H), 4.56 (s, 2H), 3.83 (s, 2H), 3.64 (s, 3H), 3.58 (s, 2H), 3.42-3.26 (m, 2H), 3.11-3.06 (m, 4H), 2.23-2.16 (m, 6H).

Example 1.259

Synthesis of N-(6-methoxypyridin-3-yl)-2-[methyl({2-[4-(oxetan-3-yloxy)pyridin-2-yl]-5H,6H,7H-cyclopenta[d]pyrimidin-4-yl})amino]acetamide (Compound 253)

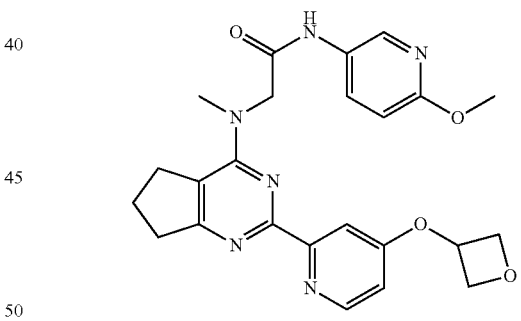

Scheme 110

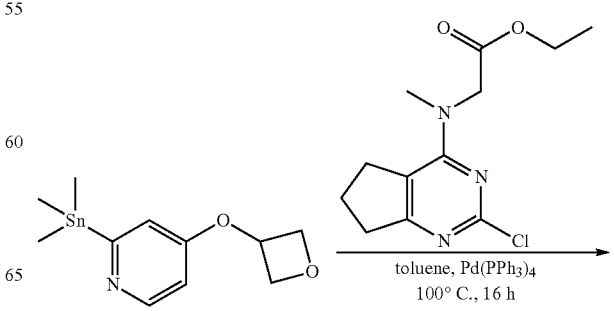

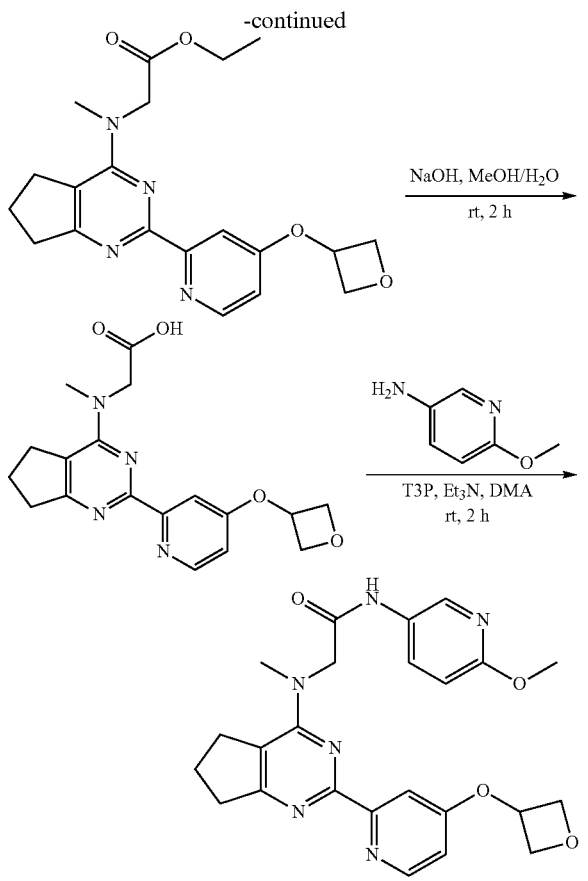

Step 1

Into a 40-mL vial purged and maintained with an inert atmosphere of nitrogen were placed a mixture of 4-(oxetan-3-yloxy)-2-(trimethylstannyl)pyridine (1.00 g, 3.185 mmol, 1.00 equiv), toluene (20.0 mL), ethyl 2-([2-chloro-5H,6H,7H-cyclopenta[d]pyrimidin-4-yl](methyl)amino)acetate (859 mg, 0.003 mmol, 1.00 equiv), Pd(PPh₃)₄ (368 mg, 0.319 mmol, 0.10 equiv). The resulting solution was stirred for 16 hours at 100° C. The resulting mixture was concentrated. The residue was applied onto a silica gel column with dichloromethane/methanol (10/1). This resulted in 540 mg (44.10%) of ethyl N-methyl-N-(2-(4-(oxetan-3-yloxy)pyridin-2-yl)-6,7-dihydro-5H-cyclopenta[d]pyrimidin-4-yl)glycinate as brown oil. LCMS (ES) [M+1]⁺ m/z 385.

Step 2

Into a 20-mL vial were placed a mixture of ethyl N-methyl-N-(2-(4-(oxetan-3-yloxy)pyridin-2-yl)-6,7-dihydro-5H-cyclopenta[d]pyrimidin-4-yl)glycinate (500 mg, 1.30 mmol, 1.00 equiv), MeOH (10.00 mL), H₂O (2.00 mL) and NaOH (104.04 mg, 2.602 mmol, 2.00 equiv). The resulting solution was stirred for 2 hours at room temperature. The resulting mixture was concentrated and diluted with 20 mL of H₂O. The pH value of the solution was adjusted to 6 with HCl (2 mol/L). The resulting solids were collected by filtration. This resulted in 420 mg (90.61%) of N-methyl-N-(2-(4-(oxetan-3-yloxy)pyridin-2-yl)-6,7-dihydro-5H-cyclopenta[d]pyrimidin-4-yl)glycine as a white solid. LCMS (ES) [M+1]⁺ m/z 357.

Step 3

Into a 8-mL vial were placed a mixture of N-methyl-N-(2-(4-(oxetan-3-yloxy)pyridin-2-yl)-6,7-dihydro-5H-cyclopenta[d]pyrimidin-4-yl)glycine (150 mg, 0.421 mmol, 1.00 equiv), DMA (5.00 mL), 5-amino-2-methoxypyridine (104 mg, 0.842 mmol, 2.00 equiv), T3P (267 mg, 0.842 mmol, 2.00 equiv) and Et₃N (127 mg, 1.26 mmol, 3.00 equiv). The resulting solution was stirred for 2 hours at room temperature. The crude product was purified by Prep-HPLC with the following conditions: Column, Xbridge Prep C18 OBD Column, 19×150 mm, 5 um; mobile phase, phase A: H₂O (0.05% NH₃H₂O); phase B: CH₃CN/MeOH=1/1 (15% CH₃CN/MeOH up to 65% CH₃CN/MeOH in 15 min). This resulted in 52.7 mg (27.1%) of N-(6-methoxypyridin-3-yl)-2-[methyl({2-[4-(oxetan-3-yloxy)pyridin-2-yl]-5H,6H,7H-cyclopenta[d]pyrimidin-4-yl})amino]acetamide as an off-white solid. LCMS (ES) [M+1]⁺ m/z: 463. ¹H NMR (300 MHz, DMSO-d6) δ 8.46 (d, J=5.6 Hz, 1H), 8.37 (d, J=2.7 Hz, 1H), 7.91 (dd, J=8.9, 2.8 Hz, 1H), 7.64 (d, J=2.6 Hz, 1H), 6.85 (dd, J=5.6, 2.6 Hz, 1H), 6.78 (d, J=8.8 Hz, 1H), 5.38-5.32 (m, 1H), 4.91 (t, J=6.7 Hz, 2H), 4.53 (dd, J=7.4, 4.8 Hz, 2H), 4.39 (s, 2H), 3.80 (s, 3H), 3.37 (s, 3H) 3.21 (t, J=7.3 Hz, 2H), 2.83 (t, J=7.8 Hz, 2H), 2.07-1.96 (m. 2H).

Example 1.260

Synthesis of 2-[methyl({2-[4-(oxetan-3-yloxy)pyridin-2-yl]-5H,6H,7H-cyclopenta[d]pyrimidin-4-yl})amino]-N-(1-methyl-1H-pyrazol-4-yl)acetamide (Compound 254)

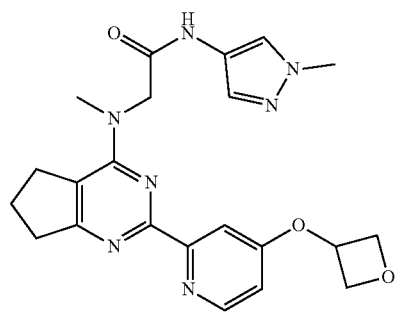 [SMILES: CN(CC(=O)Nc1cnn(C)c1)c1nc(-c2cc(OC3COC3)ccn2)nc2c1CCC2]

Compound 254 was synthesized similar to Compound 135 replacing of 4-methoxy-2-(tributylstannyl)pyridine with 4-(oxetan-3-yloxy)-2-(trimethylstannyl)pyridine and replacing oxolan-3-amine with 1-methyl-1H-pyrazol-4-amine. LCMS (ES) [M+1]⁺ m/z: 436. ¹H NMR (300 MHz, DMSO-d6) δ 8.48 (d, J=5.5 Hz, 1H), 7.86 (s, 1H), 7.58 (d, J=2.6 Hz, 1H), 7.42 (s, 1H), 6.88 (dd, J=5.9, 2.6 Hz, 1H), 5.48-5.35 (m, 1H), 4.92 (t, J=6.7 Hz, 2H), 4.55 (dd, J=7.4, 4.8 Hz, 2H), 4.35 (s, 2H), 3.76 (s, 3H), 3.41 (s, 3H), 3.19 (t, J=7.5 Hz, 2H), 2.83 (t, J=7.8 Hz, 2H), 2.13-1.95 (m, 2H), 1.86 (s, 1H).

Example 1.261

Synthesis of 2-{[2-(isoquinolin-3-yl)-5H,6H,7H-cyclopenta[d]pyrimidin-4-yl](methyl)amino}-1-(piperidin-1-yl)ethan-1-one (Compound 255)

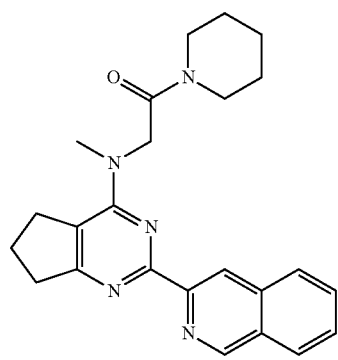 [SMILES: CN(CC(=O)N1CCCCC1)c1nc(-c2cc3ccccc3cn2)nc2c1CCC2]

Compound 255 was synthesized similar to Compound 135 replacing of 4-methoxy-2-(tributylstannyl)pyridine with 3-(trimethylstannyl)isoquinoline and replacing oxolan-3-amine with piperidine. LCMS (ES) [M+1]+ m/z: 402. $^1$H NMR (300 MHz, DMSO-d6) δ 9.39 (s, 1H), 8.71 (s, 1H), 8.23-8.15 (m, 1H), 8.05 (d, J=8.1 Hz, 1H), 7.82 (ddd, J=8.2, 6.9, 1.3 Hz, 1H), 7.73 (ddd, J=8.1, 6.9, 1.3 Hz, 1H), 4.59 (s, 2H), 3.54-3.39 (m, 4H), 3.30 (s, 3H), 3.16 (t, J=7.2 Hz, 2H), 2.92-2.80 (m, 2H), 2.05-1.95 (m, 2H), 1.72-1.59 (m, 4H), 1.48-1.38 (m, 2H).

Example 1.262

Synthesis of 2-{[2-(isoquinolin-3-yl)-5H,6H,7H-cyclopenta[d]pyrimidin-4-yl](methyl)amino}-1-(4-methylpiperazin-1-yl)ethan-1-one (Compound 256)

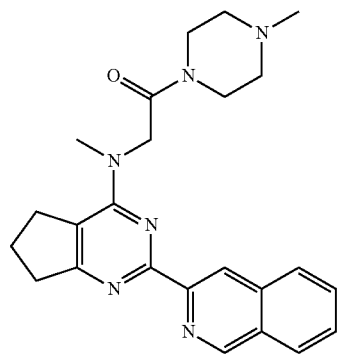 [SMILES: CN1CCN(C(=O)CN(C)c2nc(-c3cc4ccccc4cn3)nc3c2CCC3)CC1]

Compound 256 was synthesized similar to Compound 135 replacing of 4-methoxy-2-(tributylstannyl)pyridine with 3-(trimethylstannyl)isoquinoline and replacing oxolan-3-amine with 4-methylpiperazine. LCMS (ES) [M+1]+ m/z: 417. $^1$H NMR (300 MHz, DMSO-d6) δ 9.40 (s, 1H), 8.71 (s, 1H), 8.19 (d, J=8.0 Hz, 1H), 8.09 (d, J=8.1 Hz, 1H), 7.82 (ddd, J=8.2, 6.9, 1.3 Hz, 1H), 7.73 (ddd, J=8.1, 6.9, 1.2 Hz, 1H), 4.60 (s, 2H), 3.57 (s, 2H), 3.45 (s, 2H), 3.30 (s, 3H), 3.16 (t, J=7.3 Hz, 2H), 2.86 (t, J=8.1 Hz, 2H), 2.42 (s, 2H), 2.24 (s, 2H), 2.18 (s, 3H), 2.02 (td, J=14.8, 14.1, 6.5 Hz, 2H).

Example 1.263

Synthesis of N-(6-methoxypyridin-3-yl)-2-{methyl[2-(1,6-naphthyridin-7-yl)-5H,6H,7H-cyclopenta[d]pyrimidin-4-yl]amino}acetamide (Compound 257)

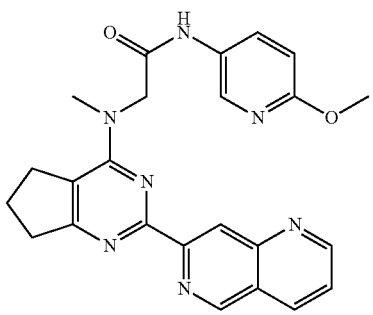 [SMILES: COc1ccc(NC(=O)CN(C)c2nc(-c3cc4ncccc4cn3)nc3c2CCC3)cn1]

Scheme 111

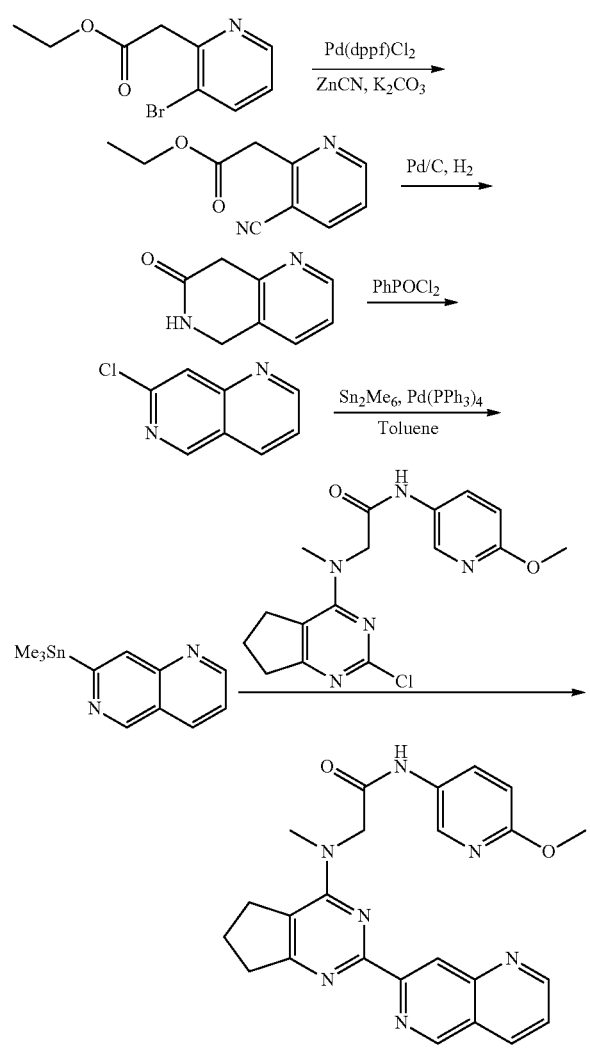

Step 1

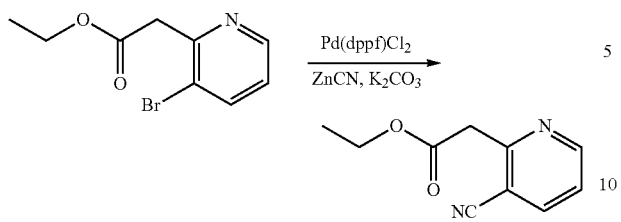

To a stirred mixture of ethyl 2-(3-bromopyridin-2-yl)acetate (14 g, 57.3 mmol, 1.0 equiv), Zn(CN)$_2$ (10.1 g, 86.03 mmol, 1.5 equiv) and K$_2$CO$_3$ (15.8 g, 114.7 mmol, 2.0 equiv) in NMP (100 mL) was added Pd(dppf)Cl$_2$·CH$_2$Cl$_2$ (4.7 g, 5.73 mmol, 0.10 equiv) at 20° C. The resulting mixture was heated to 70° C. and stirred at this temperature for 16 h under N$_2$ atmosphere. The resulting mixture was cooled to 25° C. and quenched with water, extracted with EtOAc (100 mL×3), organic layer was combined, concentrated, the residue was purified by silica gel column chromatography to give ethyl 2-(3-cyanopyridin-2-yl)acetate (9.0 g, 81.8% yield) as a yellow gum. LCMS (ES) [M+1]$^+$ m/z: 191.

Step 2

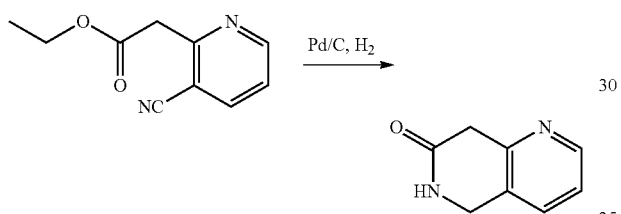

To a stirred mixture of ethyl 2-(3-cyanopyridin-2-yl)acetate (6.0 g, 31.5 mmol, 1.0 equiv) in AcOH (12 mL) and EtOH (60 mL) was added Pd/C (600 mg) at 20° C. The resulting mixture was heated to 40° C. and stirred at that temperature for 16 h under H$_2$ atmosphere (10 atm). The resulting mixture was cooled to 25° C., filtered and concentrated. The residue was purified by silica gel column chromatography to give 6,8-dihydro-5H-1,6-naphthyridin-7-one (4.0 g, 85.6%) as a yellow solid. LCMS (ES) [M+1]$^+$ m/z: 149.

Step 3

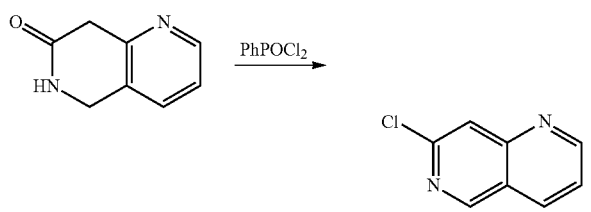

To a stirred solution of 6,8-dihydro-5H-1,6-naphthyridin-7-one (1.5 g) in phenylphosphonic dichloride (10 mL) was heated to 130° C. and stirred at this temperature for 16 h. The resulting mixture was cooled to 25° C., poured into 50 mL of water and adjusted pH to 8 with solid NaHCO$_3$. The mixture was extracted with EtOAc, organic layer was separated and concentrated. The residue was purified by silica gel column chromatography to give 7-chloro-1,6-naphthyridine (400 mg, 25.5% yield) as a yellow solid. LCMS (ES) [M+1]$^+$ m/z: 165.

Step 4

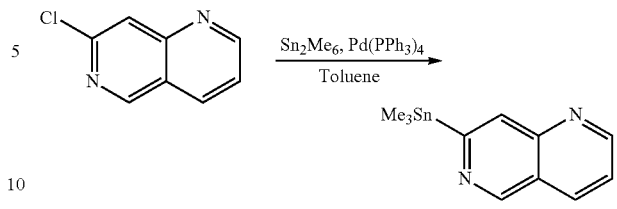

To a stirred solution of 7-chloro-1,6-naphthyridine (200 mg, 1.21 mmol, 1.0 equiv) in Toluene (5 mL) was added Sn$_2$Me$_6$ (438 mg, 1.33 mmol, 1.1 equiv) and Pd(dppf)Cl$_2$·CH$_2$Cl$_2$ (89 mg, 0.12 mmol, 0.1 equiv) at room temperature. The reaction was stirred at 100° C. for 3 h under N$_2$ atmosphere. The reaction mixture was used for next step without further purification (7-(trimethylstannyl)-1,6-naphthyridine: theoretical weight 358 mg). LCMS (ES) [M+1]$^+$ m/z: 295.

Step 5

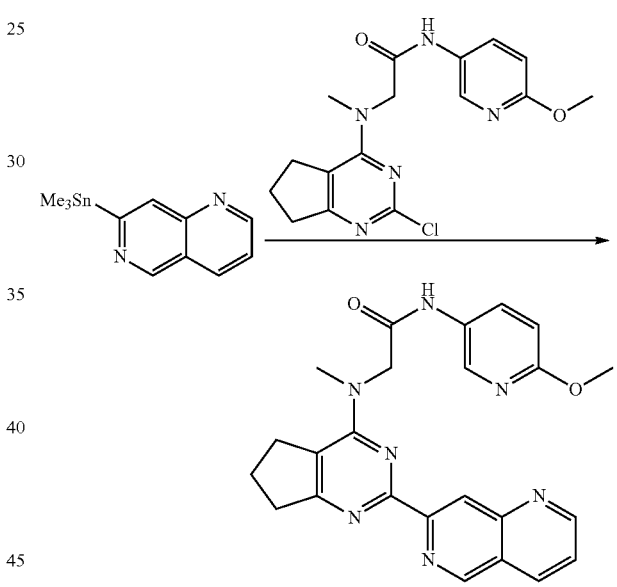

To a mixture of 7-(trimethylstannyl)-1,6-naphthyridine (358 mg, 1.21 mmol, 1.0 equiv) in toluene (10 mL) were added 2-([2-chloro-5H,6H,7H-cyclopenta[d]pyrimidin-4-yl](methyl)amino)-N-(6-methoxypyridin-3-yl)acetamide (296 mg, 0.85 mmol, 0.70 equiv) and Pd(PPh$_3$)$_4$ (140 mg, 0.12 mmol, 0.1 equiv) at room temperature. The reaction was purged and maintained with an inert atmosphere of argon for 2 min. The resulting solution was stirred for 16 hr at 100° C., cooled and concentrated under vacuum. The residue was applied onto a silica gel column with THF/petroleum ether (1:50 to 10:1) to give 150 mg crude product, which was further purified by preparatory HPLC (Column, C18; Flow rate: 20 mL/min Column: DAICEL CHIRALPAK IC, 250*20 mm, 220 nm) to give N-(6-methoxypyridin-3-yl)-2-[methyl[2-(1,6-naphthyridin-7-yl)-5H,6H,7H-cyclopenta[d]pyrimidin-4-yl]amino]acetamide (55 mg, 10.24%) as an off white solid. LCMS (ES) [M+1]$^+$ m/z: 442. $^1$H NMR (300 MHz, DMSO-d$_6$) δ 10.31 (s, 1H), 9.46 (s, 1H), 9.16 (d, J=4.2 Hz, 1H), 8.82 (s, 1H), 8.62 (d, J=8.3 Hz, 1H), 8.38 (d, J=2.7 Hz, 1H), 7.92 (dd, J=8.6, 2.7 Hz, 1H), 7.72 (dd, J=8.3, 4.2 Hz, 1H), 6.75 (d, J=8.9 Hz, 1H), 4.49 (s, 2H), 3.78 (s, 3H), 3.40 (s, 3H), 3.23 (t, J=7.4 Hz, 2H), 2.88 (t, J=7.8 Hz, 2H), 2.09-2.02 (m, 2H).

Example 1.264

Synthesis of N-(6-methoxypyridin-3-yl)-2-{methyl[2-(2,6-naphthyridin-3-yl)-5H,6H,7H-cyclopenta[d]pyrimidin-4-yl]amino}acetamide (Compound 258)

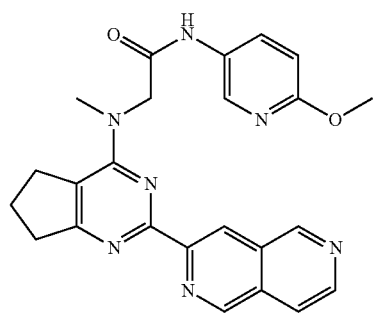 [SMILES: COc1ccc(NC(=O)CN(C)c2nc(-c3cc4cnccc4cn3)nc3c2CCC3)cn1]

Scheme 12

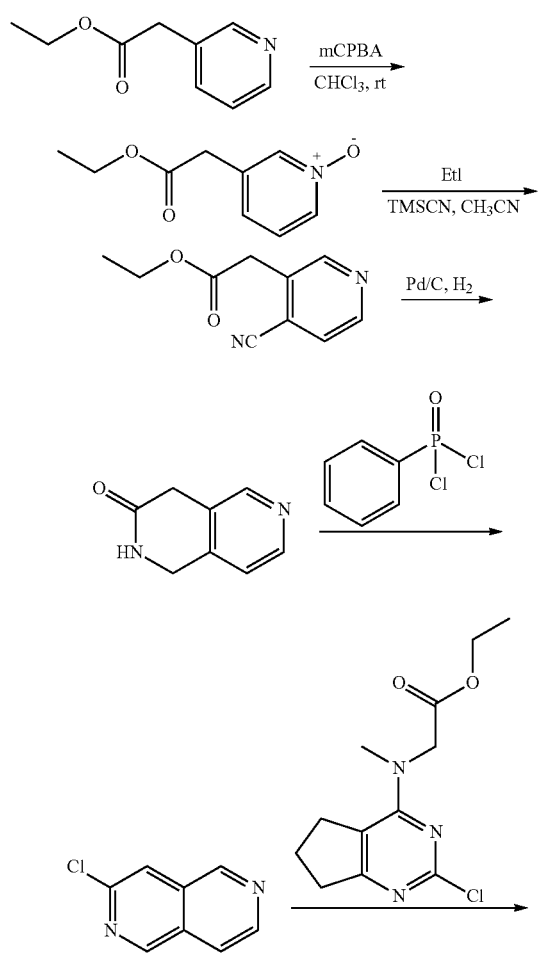

-continued

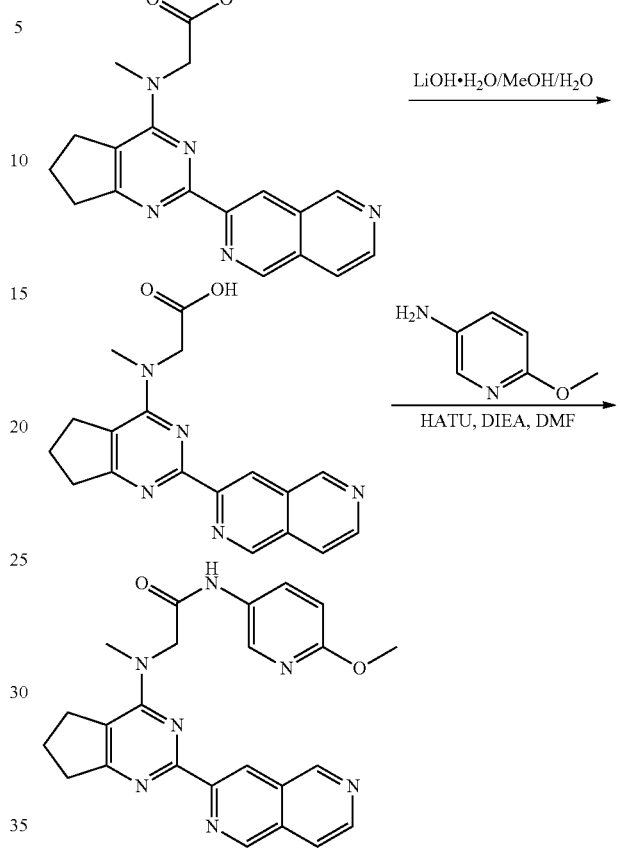

Step 1

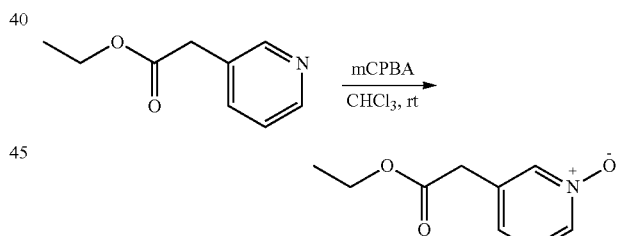

Into a 500 mL 3-necked round-bottom flask were placed ethyl 2-(pyridin-3-yl)acetate (20.00 g, 121.07 mmol, 1.00 equiv) and CHCl₃ (300.00 mL). This was followed by the addition of mCPBA (31.34 g, 181.61 mmol, 1.50 equiv) in portions at 0° C. The resulting solution was stirred for 5 h at room temperature. The reaction was then quenched by the addition of Sat. Na₂SO₃. The pH value of the solution was adjusted to 8-9 with Sat. Na₂CO₃. The resulting solution was extracted with 3×300 mL of dichloromethane and the organic layers were combined, dried over anhydrous sodium sulfate and concentrated. The residue was applied onto a silica gel column with dichloromethane/methanol (100/5). This resulted in 20 g (91.17%) of 3-(2-ethoxy-2-oxoethyl)pyridin-1-ium-1-olate as off-white solid. LCMS (ES) [M+1]⁺ m/z: 182.

Step 2

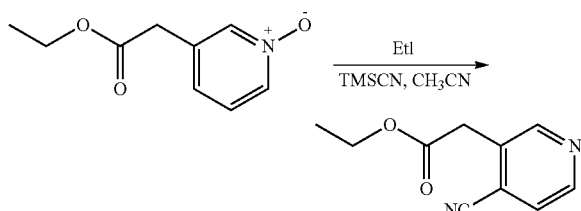

Into a 500 mL round-bottom flask, was placed 3-(2-ethoxy-2-oxoethyl)pyridin-1-ium-1-olate (20.00 g, 110.38 mmol, 1.00 equiv), ethyl iodide (51.65 g, 331.16 mmol, 3.00 equiv). The resulting solution was stirred for 6 h at 45° C. The resulting solution was added CH$_3$CN (350.00 mL), K$_2$CO$_3$ (45.77 g, 331.14 mmol, 3.00 equiv), TMSCN (32.85 g, 331.14 mmol, 3.00 equiv). The resulting solution was stirred for overnight at 50° C. The reaction mixture was cooled to room temperature. The solids were filtered out and the filtrate was concentrated. The residue was applied onto a silica gel column with THF/PE (10%). This resulted in 10 g (47.63%) of ethyl 2-(4-cyanopyridin-3-yl)acetate as yellow oil. LCMS (ES) [M+1]$^+$ m/z: 191.

Step 3

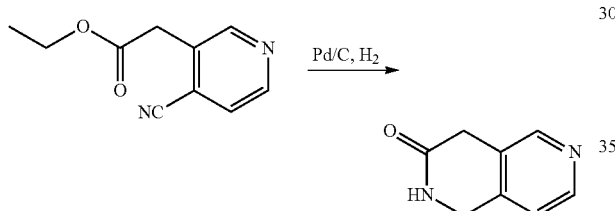

Into a 250 mL pressure tank reactor were placed ethyl 2-(4-cyanopyridin-3-yl)acetate (10.00 g, 52.57 mmol, 1.00 equiv), EtOH (80.00 mL), AcOH (20.00 mL) and Pd/C (0.56 g, 5.26 mmol, 0.10 equiv). The resulting solution was stirred for 6 h at 35° C. The solids were filtered out and the filtrate was concentrated. The crude product (10 g) was purified by Prep-HPLC with the following conditions: Column, XBridge Prep C18 OBD Column, 19 cm, 150 mm, 5 um; mobile phase, Water (0.1% NH$_3$·H$_2$O) and CAN (10% Phase B up to 30% in 11 min); Detector, 254 nM. This resulted in 6 g (77%) of 2,4-dihydro-1H-2,6-naphthyridin-3-one as yellow solid. LCMS (ES) [M+1]+ m/z: 149.

Step 4

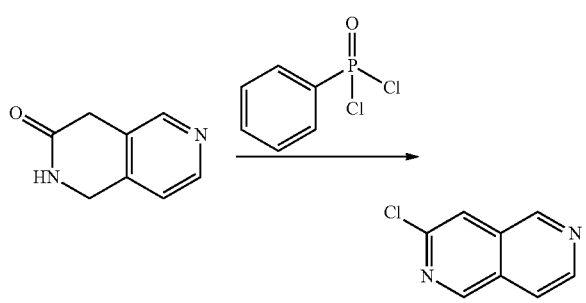

Into a 250 mL round-bottom flask were placed 2,4-dihydro-1H-2,6-naphthyridin-3-one (6.00 g, 40.49 mmol, 1.00 equiv) and phenylphosphonic dichloride (60.00 mL). The resulting solution was stirred for 3 h at 125° C. The reaction mixture was cooled to room temperature. The pH value of the solution was adjusted to 8 with Sat. NaHCO$_3$. The resulting solution was extracted with 3×300 mL of dichloromethane and the organic layers combined, dried over anhydrous sodium sulfate and concentrated. The residue was applied onto a silica gel column with THF/PE (30%). This resulted in 350 mg (5.25%) of 3-chloro-2,6-naphthyridine as yellow solid. LCMS (ES) [M+1]$^+$ m/z: 165.

Step 5

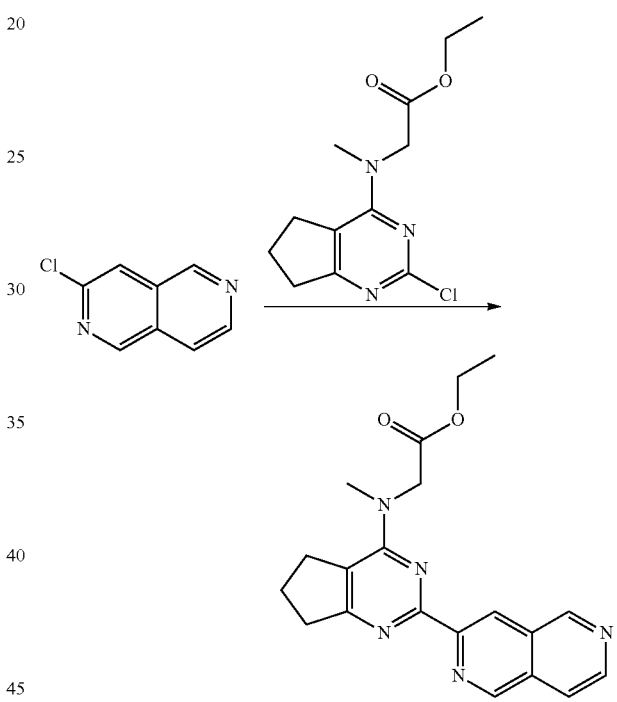

Into a 40-mL vial were placed 3-chloro-2,6-naphthyridine (350.00 mg, 2.13 mmol, 1.00 equiv), hexamethyldistannane (905.72 mg, 2.76 mmol, 1.30 equiv), toluene (10.00 mL) and Pd(dppf)Cl$_2$ (155.60 mg, 0.21 mmol, 0.10 equiv). The resulting solution was stirred for 3 h at 100° C. The reaction mixture was cooled to room temperature and added ethyl 2-([2-chloro-5H,6H,7H-cyclopenta[d]pyrimidin-4-yl](methyl)amino)acetate (401.51 mg, 1.49 mmol, 0.70 equiv). The resulting solution was then stirred for overnight at 100° C. The reaction mixture was cooled to room temperature and concentrated. The residue was applied onto a silica gel column with THF/PE (50%). This resulted in 300 mg (38.82%) of ethyl 2-[methyl[2-(2,6-naphthyridin-3-yl)-5H,6H,7H-cyclopenta[d]pyrimidin-4-yl]amino]acetate as yellow solid. LCMS (ES) [M+1]$^+$ m/z: 364.

Step 6

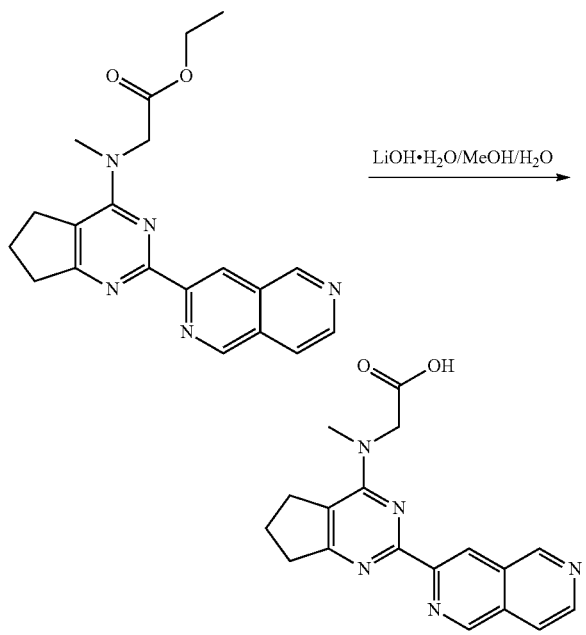

Into a 100-mL round-bottom flask were placed ethyl 2-[methyl[2-(2,6-naphthyridin-3-yl)-5H,6H,7H-cyclopenta[d]pyrimidin-4-yl]amino]acetate (300.00 mg, 0.83 mmol, 1.00 equiv), MeOH (5.00 mL) and H$_2$O (5.00 mL). This was followed by the addition of LiOH·H$_2$O (69.28 mg, 1.65 mmol, 2.00 equiv) in portions at 0° C. The resulting solution was stirred for 3 h at room temperature and the pH value of the solution was adjusted to 7 with citric acid. The crude product (0.5 g) was purified by Prep-HPLC with the following conditions: Column, XBridge Prep C18 OBD Column, 19 cm, 150 mm, 5 um; mobile phase, Water and AcCN (10% Phase B up to 30% in 11 min); Detector, 254 nm. This resulted in 160 mg (57.79%) of [methyl[2-(2,6-naphthyridin-3-yl)-5H,6H,7H-cyclopenta[d]pyrimidin-4-yl]amino]acetic acid as yellow solid. LCMS (ES) [M+1]$^+$ m/z: 336.

Step 7

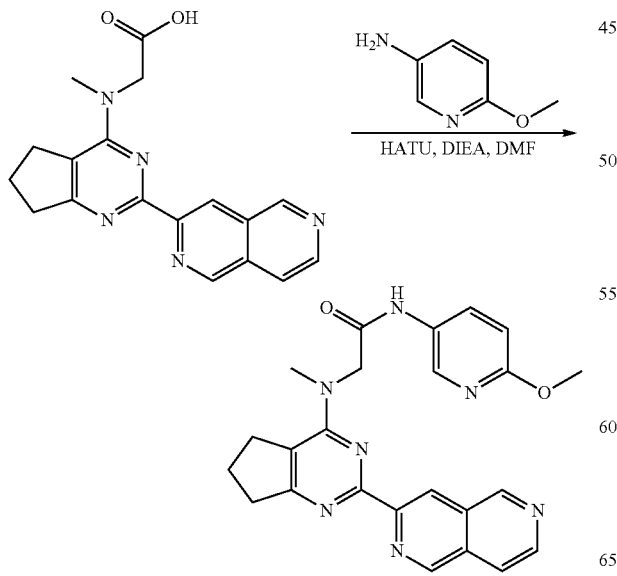

Into a 40 mL vial was placed [methyl[2-(2,6-naphthyridin-3-yl)-5H,6H,7H-cyclopenta[d]pyrimidin-4-yl]amino]acetic acid (160.00 mg, 0.47 mmol, 1.00 equiv), DMF (5.00 mL), DIEA (123.32 mg, 0.95 mmol, 2 equiv) and 5-amino-2-methoxypyridine (59.23 mg, 0.47 mmol, 1.00 equiv). This was followed by the addition of HATU (217.68 mg, 0.57 mmol, 1.20 equiv) in portions at 0° C. The resulting solution was stirred for 2 h at room temperature. The crude product (1 g) was purified by Prep-HPLC with the following conditions: Column, XBridge Prep C18 OBD Column, 19 cm, 150 mm, 5 um; mobile phase, Water (0.1% NH$_3$·H$_2$O) and AcCN/MeOH=1:1 (30% Phase B up to 70% in 11 min); Detector, 254 nm. This resulted in 127 mg (33.97%) of N-(6-methoxypyridin-3-yl)-2-[methyl[2-(2,6-naphthyridin-3-yl)-5H,6H,7H-cyclopenta[d]pyrimidin-4-yl]amino]acetamide; tris(trifluoroacetic acid) as orange solid. LCMS (ES, m/z): [M+H]$^+$: 442. $^1$H-NMR (300 MHz, DMSO-d$_6$, ppm): δ 10.61 (s, 1H), 9.70 (s, 1H), 9.43 (s, 1H), 9.14 (s, 1H), 8.91 (d, J=5.6 Hz, 1H), 8.44 (d, J=2.7 Hz, 1H), 8.22 (d, J=5.7 Hz, 1H), 7.96 (dd, J=8.9, 2.8 Hz, 1H), 6.79 (d, J=8.9 Hz, 1H), 4.75 (s, 2H), 3.78 (s, 3H), 3.63 (s, 3H), 3.36-3.30 (m, 2H), 3.11 (t, J=7.8 Hz, 2H), 2.19-2.02 (m, 2H).

Example 1.265

Synthesis of 2-{[2-(4-ethoxypyridin-2-yl)-5H,6H,7H-cyclopenta[d]pyrimidin-4-yl](methyl)amino}-N-(2-methoxypyrimidin-5-yl)acetamide (Compound 259)

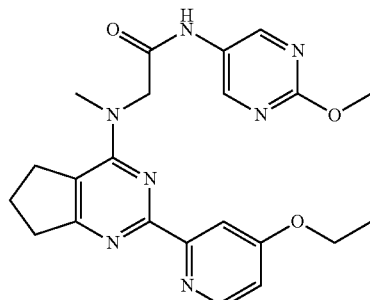

Compound 259 was synthesized similar to Compound 135 by replacing of 4-methoxy-2-(tributylstannyl)pyridine with 4-ethoxy-2-(tributylstannyl)pyridine and replacing oxolan-3-amine with 2-methoxypyrimidin-5-amine. LCMS (ES) [M+1]$^+$ m/z: 436. $^1$H NMR (300 MHz, DMSO-d6) δ 10.49 (s, 1H), 8.76 (s, 2H), 8.42 (d, J=5.5 Hz, 1H), 7.72 (d, J=2.5 Hz, 1H), 6.98 (dd, J=5.7, 2.5 Hz, 1H), 4.39 (s, 2H), 4.05 (q, J=6.9 Hz, 2H), 3.87 (s, 3H), 3.38 (s, 3H), 3.21 (t, J=7.4 Hz, 2H), 2.83 (t, J=7.8 Hz, 2H), 2.07-1.96 (m, 2H), 1.29 (t, J=7.0 Hz, 3H).

Example 1.266

Synthesis of 2-({2-[4-(2-hydroxy-2-methylpropoxy)pyridin-2-yl]-5H,6H,7H-cyclopenta[d]pyrimidin-4-yl}(methyl)amino)-N-(2-methoxypyrimidin-5-yl)acetamide (Compound 260)

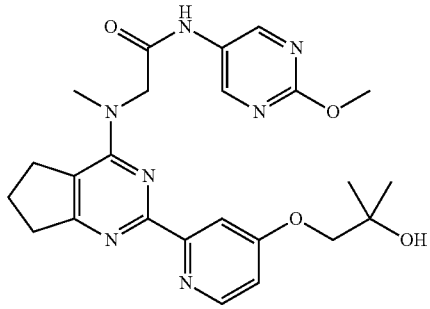 [SMILES: COc1ncc(NC(=O)CN(C)c2nc(-c3cc(OCC(C)(C)O)ccn3)nc3c2CCC3)cn1]

Compound 260 was synthesized similar to Compound 210 by replacing 5-amino-2-methoxypyridine with 2-methoxypyrimidin-5-amine. LCMS (ES) [M+1]$^+$ m/z: 480. $^1$H NMR (300 MHz, DMSO-d6) δ 10.47 (s, 1H), 8.74 (s, 2H), 8.43 (d, J=5.6 Hz, 1H), 7.77 (d, J=2.5 Hz, 1H), 7.03 (dd, J=5.7, 2.6 Hz, 1H), 4.66 (s, 1H), 4.42 (s, 2H), 3.87 (s, 3H), 3.80 (s, 2H), 3.38 (s, 3H), 3.22 (t, J=7.3 Hz, 2H), 2.84 (t, J=7.8 Hz, 2H), 2.08-1.99 (m, 2H), 1.16 (s, 6H).

Example 1.267

Synthesis of N-tert-butyl-2-{[2-(6-methoxyisoquinolin-3-yl)-5H,6H,7H-cyclopenta[d]pyrimidin-4-yl](methyl)amino}acetamide (Compound 261)

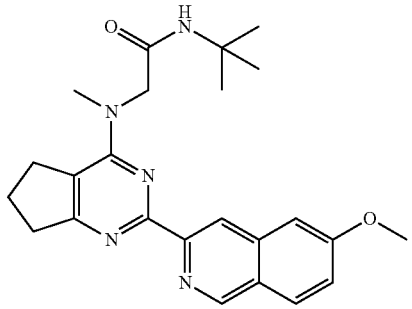 [SMILES: COc1ccc2cnc(-c3nc4c(c(N(C)CC(=O)NC(C)(C)C)n3)CCC4)cc2c1]

Compound 261 was synthesized similar to Compound 24 by replacing 4-methyl-2-(tributylstannyl)pyridine with 6-methoxy-3-(trimethylstannyl)isoquinoline. LCMS (ES) [M+1]$^+$ m/z 420. $^1$H NMR (300 MHz, DMSO-d$_6$) δ 9.23 (s, 1H), 8.80 (s, 1H), 8.16 (HCOOH), 8.08 (d, J=9.0 Hz, 1H), 7.81 (s, 1H), 7.50 (s, 1H), 7.33 (dd, J=8.9, 2.5 Hz, 1H), 4.19 (s, 2H), 3.94 (s, 3H), 3.33 (s, 3H), 3.17 (t, J=7.5 Hz, 2H), 2.85 (t, J=7.9 Hz, 2H), 2.04-1.99 (m, 2H), 1.23 (s, 9H).

Example 1.268

Synthesis of N-tert-butyl-2-{[2-(7-methoxyisoquinolin-3-yl)-5H,6H,7H-cyclopenta[d]pyrimidin-4-yl](methyl)amino}acetamide (Compound 262)

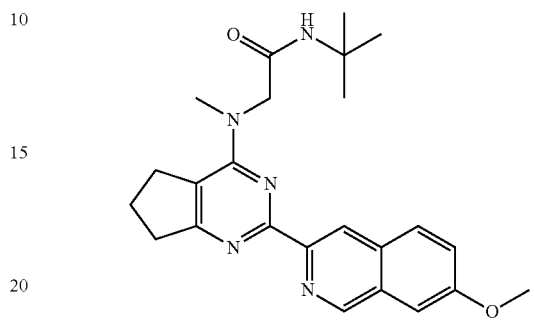

Compound 262 was synthesized similar to Compound 24 by replacing 4-methyl-2-(tributylstannyl)pyridine with 7-methoxy-3-(trimethylstannyl)isoquinoline. LCMS (ES) [M+1]$^+$ m/z 420. $^1$H NMR (300 MHz, DMSO-d$_6$) δ 9.28 (s, 1H), 8.79 (s, 1H), 8.17 (HCOOH), 8.03 (d, J=9.0 Hz, 1H), 7.79 (s, 1H), 7.59 (d, J=2.5 Hz, 1H), 7.48 (dd, J=9.0, 2.5 Hz, 1H), 4.19 (s, 2H), 3.95 (s, 3H), 3.32 (s, 3H), 3.17 (t, J=7.3 Hz, 2H), 2.84 (t, J=7.8 Hz, 2H), 2.06-1.99 (m, 2H), 1.23 (s, 9H).

Example 1.269

Synthesis of 2-({2-[4-(2-hydroxyethoxy)pyridin-2-yl]-5H,6H,7H-cyclopenta[d]pyrimidin-4-yl}(methyl)amino)-1-(piperidin-1-yl)ethan-1-one (Compound 263)

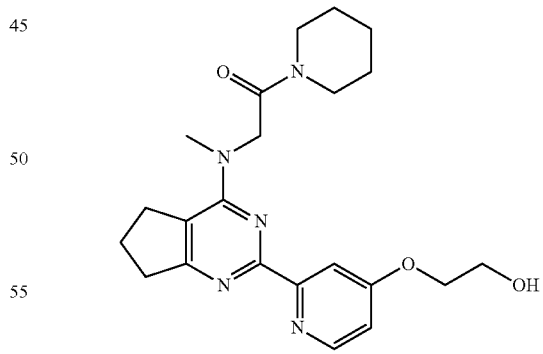

Compound 263 was synthesized similar to Compound 144 by replacing cyclohexylamine with piperidine. LCMS (ES) [M+1]$^+$ m/z 412. $^1$H NMR (300 MHz, DMSO-d$_6$) δ 8.45 (d, J=5.7 Hz, 1H), 7.75 (d, J=2.7 Hz, 1H), 7.03 (dd, J=5.7, 2.7 Hz, 1H), 4.92 (t, J=5.4 Hz, 1H), 4.51 (s, 2H), 4.13 (t, J=4.8 Hz, 2H), 3.75 (q, J=5.1 Hz, 2H), 3.47-3.37 (m, 4H), 3.25 (s, 3H), 3.13 (t, J=7.5 Hz, 2H), 2.81 (t, J=7.8 Hz, 2H), 2.04-1.93 (m, 2H), 1.61 (s, 4H), 1.44 (s, 2H).

Example 1.270

Synthesis of N-(6-fluoropyridin-3-yl)-2-[methyl({2-[1-(oxan-2-yl)-1H-pyrazolo[3,4-c]pyridin-5-yl]-5H,6H,7H-cyclopenta[d]pyrimidin-4-yl})amino]acetamide (Compound 264)

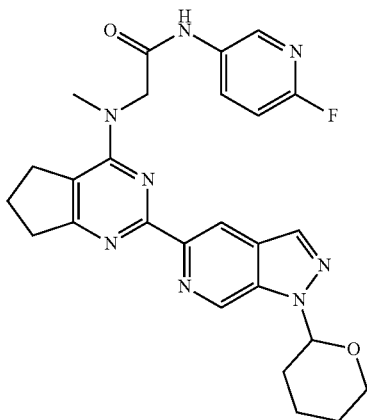 [SMILES: CN(CC(=O)Nc1ccc(F)nc1)c1nc(-c2cc3cnn(C4CCCCO4)c3cn2)nc2c1CCC2]

Compound 264 was synthesized similar to Compound 135 by replacing 4-methoxy-2-(tributylstannyl)pyridine with 1-(oxan-2-yl)-5-(tributylstannyl)-1H-pyrazolo[3,4-c]pyridine and replacing oxolan-3-amine with 6-fluoro-3-pyridinylamine. LCMS (ES) [M+1]$^+$ m/z: 503.2. $^1$H NMR (400 MHz, DMSO-d6) δ 9.39 (s, 1H), 9.10-8.94 (m, 1H), 8.52 (d, J=2.3 Hz, 1H), 8.37 (s, 1H), 8.22 (ddd, J=8.8, 7.3, 2.8 Hz, 1H), 7.17 (dd, J=8.8, 3.2 Hz, 1H), 6.18 (dd, J=9.2, 2.5 Hz, 1H), 4.73 (s, 2H), 3.92-3.76 (m, 2H), 3.58 (s, 3H), 3.25 (m, 2H), 3.08 (t, J=7.9 Hz, 2H), 2.45-2.30 (m, 1H), 2.16-2.01 (m, 4H), 1.82-1.70 (m, 1H), 1.66-1.57 (m, 2H).

Example 1.271

Synthesis of N-(5-methoxypyridin-2-yl)-2-[methyl(2-{1H-pyrazolo[3,4-c]pyridin-5-yl}-5H,6H,7H-cyclopenta[d]pyrimidin-4-yl)amino]acetamide (Compound 265)

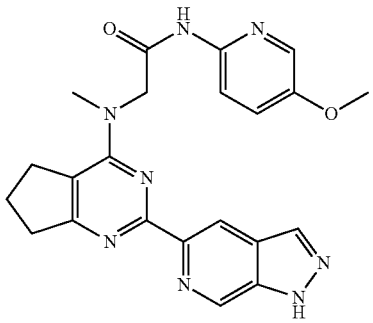 [SMILES: COc1ccc(NC(=O)CN(C)c2nc(-c3cc4cn[nH]c4cn3)nc3c2CCC3)nc1]

Compound 265 was synthesized similar to Compound 266 by replacing 6-fluoropyridine-3-amine with 5-methoxy-pyridin-2-amine. LCMS (ES+): [M+H]$^+$=431.1. $^1$H NMR (400 MHz, DMSO-d6) δ 13.88 (s, 1H), 10.77 (s, 1H), 9.11 (s, 1H), 8.78 (d, J=1.3 Hz, 1H), 8.16-8.09 (m, 2H), 7.96 (d, J=9.0 Hz, 1H), 7.39 (dd, J=9.1, 3.1 Hz, 1H), 4.58 (s, 2H), 3.78 (s, 3H), 3.30-3.18 (m, 9H), 2.92 (t, J=7.8 Hz, 2H), 2.05 (p, J=7.9 Hz, 2H).

Example 1.272

Synthesis of N-(5-methoxypyridin-2-yl)-2-[methyl(2-{1H-pyrazolo[3,4-c]pyridin-5-yl}-5H,6H,7H-cyclopenta[d]pyrimidin-4-yl)amino]acetamide (Compound 266)

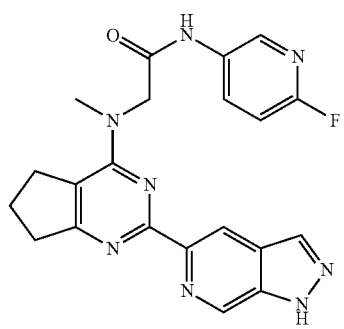 [SMILES: CN(CC(=O)Nc1ccc(F)nc1)c1nc(-c2cc3cn[nH]c3cn2)nc2c1CCC2]

Scheme 112

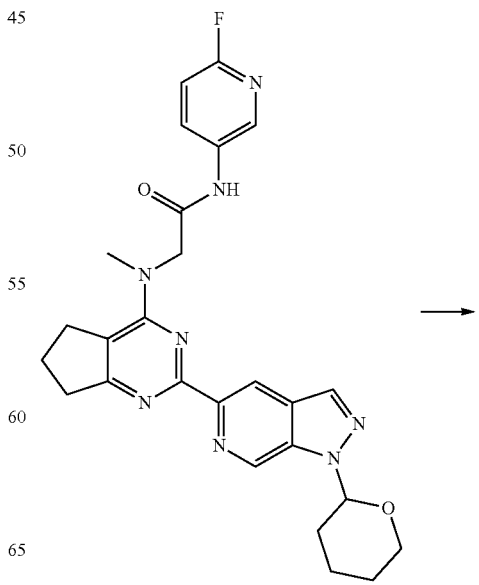

-continued

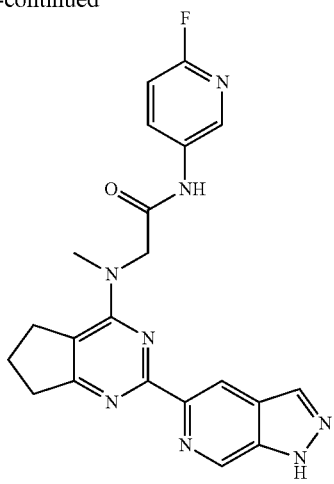

N-(6-Fluoropyridin-3-yl)-2-[methyl({2-[1-(oxan-2-yl)-1H-pyrazolo[3,4-c]pyridin-5-yl]-5H,6H,7H-cyclopenta[d]pyrimidin-4-yl})amino]acetamide (53 mg; 0.11 mmol; 1 eq.) was dissolved in methanol (1 ml) and cooled in an ice water bath. Hydrogen chloride solution (1 mL; 6 mol/L isopropanol) was added slowly and the reaction was stirred at 25° C. After 3 h, more HCl (0.2 ml) was added and the reaction stirred for an additional 1.5 h. The reaction solvent was evaporated and the residue was purified by reverse phase chromatography (Waters XSelect CSH C18 column, 0-60% acetonitrile/0.1% aqueous formic acid gradient) to give N-(6-fluoropyridin-3-yl)-2-[methyl(2-{1H-pyrazolo[3,4-c]pyridin-5-yl}-5H,6H,7H-cyclopenta[d]pyrimidin-4-yl)amino]acetamide (22 mg, 49%) as a white solid. LCMS (ES+): [M+H]$^+$=419.0. $^1$H NMR (400 MHz, dmso) δ 13.83 (s, 1H), 10.73 (s, 1H), 9.08 (s, 1H), 8.78-8.73 (m, 1H), 8.48 (d, J=2.8 Hz, 1H), 8.21 (ddd, J=8.8, 7.3, 2.8 Hz, 1H), 8.16 (s, 1H), 7.16 (dd, J=8.9, 3.2 Hz, 1H), 4.52 (s, 2H), 3.45 (s, 3H), 3.27-3.19 (m, 2H), 2.95-2.86 (m, 2H), 2.11-1.98 (m, 2H).

Example 1.273

Synthesis of 2-[methyl(2-{1H-pyrazolo[3,4-c]pyridin-5-yl}-5H,6H,7H-cyclopenta[d]pyrimidin-4-yl)amino]-N-(6-methylpyridin-3-yl)acetamide (Compound 267)

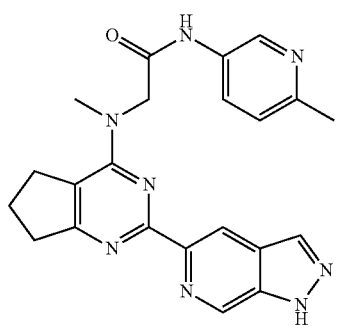 [SMILES: Cc1ccc(NC(=O)CN(C)c2nc(-c3cc4cn[nH]c4cn3)nc3c2CCC3)cn1]

Compound 267 was synthesized similar to Compound 266 by replacing 6-fluoropyridine-3-amine with 6-methylpyridin-3-amine. LCMS (ES+): [M+H]$^+$=415.1. $^1$H NMR (400 MHz, dmso) δ 11.81 (s, 1H), 9.22 (s, 1H), 9.09 (s, 1H), 9.02 (s, 1H), 8.50-8.31 (m, 2H), 7.69-7.63 (m, 1H), 4.83 (s, 2H), 3.61 (s, 3H), 3.09 (t, J=7.9 Hz, 2H), 2.55 (s, 3H), 2.17-2.09 (m, 2H).

Example 1.274

Synthesis of N-(6-methoxypyridin-3-yl)-2-{methyl[2-(2,7-naphthyridin-3-yl)-5H,6H,7H-cyclopenta[d]pyrimidin-4-yl]amino}acetamide (Compound 268)

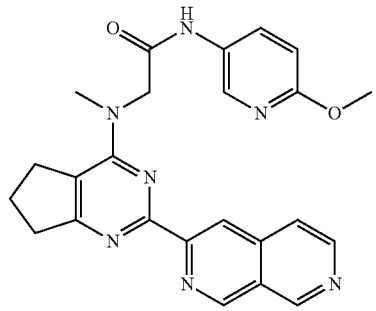 [SMILES: COc1ccc(NC(=O)CN(C)c2nc(-c3cc4ccncc4cn3)nc3c2CCC3)cn1]

Scheme 113

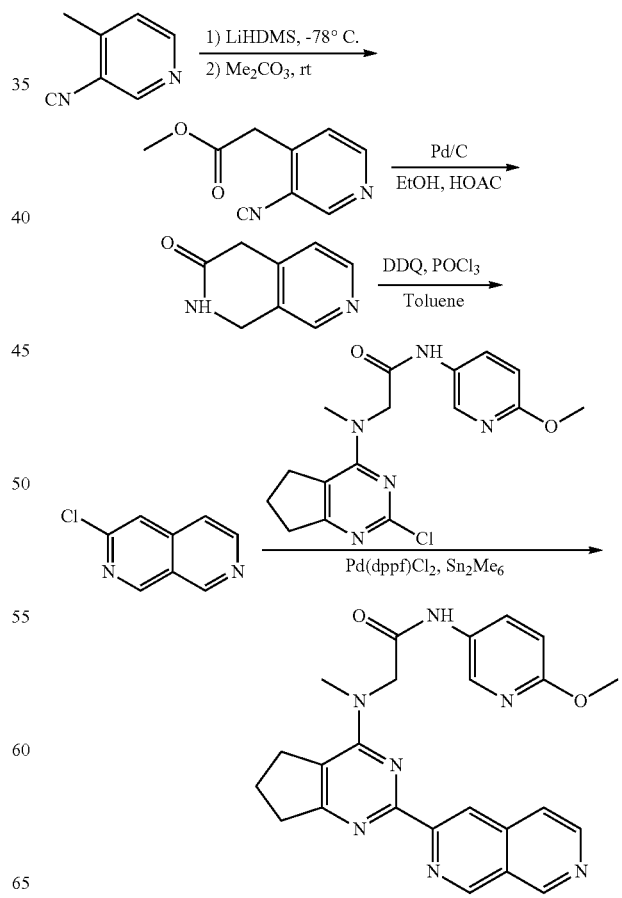

Step 1


To a solution of 4-methylpyridine-3-carbonitrile (10 g, 84.646 mmol, 1.00 equiv) in THF (100 mL) was added dropwise LiHDMS (1.0 M in THF, 170 mL, 169.292 mmol, 2 equiv)) at −78° C. under N₂ atmosphere. The reaction mixture was stirred at −78° C. for 1 h. A solution of dimethyl carbonate (9.50 g, 105.464 mmol, 1.25 equiv) in 50 mL THE was added dropwise and the mixture was stirred for another 1 h at −78° C. The resulting mixture was stirred for 2 h at −78° C. to 0° C. under nitrogen atmosphere. The reaction was quenched with NH₄Cl (200 mL) and the resulting mixture was extracted with EtOAc (2×200 mL). The combined organic layers were washed with water (1×100 mL), dried over anhydrous Na₂SO₄ and filtered. The filtrate was concentrated under reduced pressure and the residue was purified by silica gel column chromatography, eluted with PE/EtOAc (10:1) to yield methyl 2-(3-cyanopyridin-4-yl)acetate (10.1 g, 67.73%) as a yellow oil. LCMS (ES) [M+1]⁺ m/z: 177;

Step 2


To a solution of methyl 2-(3-cyanopyridin-4-yl)acetate (10.00 g, 56.762 mmol, 1.00 equiv) in EtOH (200.00 mL) and AcOH (20.00 mL) was added Pd/C (1.21 g, 11.352 mmol, 0.20 equiv) under nitrogen atmosphere in a 500 mL 3-necked round-bottom flask. The mixture was charged with H₂ (1 atm) at 40° C. for overnight. The resulting mixture was filtered; the filter cake was washed with MeOH (3×100 mL). The filtrate was concentrated under reduced pressure. The residue was purified by silica gel column chromatography, eluted with CH₂Cl₂/MeOH (10:1) to afford 2,4-dihydro-1H-2,7-naphthyridin-3-one (4 g, 47.56%) as a yellow oil. LCMS (ES) [M+1]⁺ m/z: 149;

Step 3

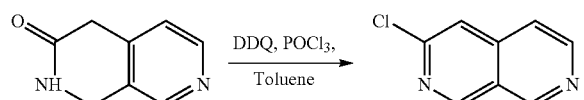

A solution of 2,4-dihydro-1H-2,7-naphthyridin-3-one (1.00 g, 6.749 mmol, 1.00 equiv) and DDQ (1.69 g, 7.424 mmol, 1.10 equiv) in Toluene (30.00 mL) was stirred for 1 h at room temperature under air atmosphere. To the above mixture was added POCl₃ (10.00 mL, 65.236 mmol, 15.90 equiv). The resulting mixture was stirred for additional 16 h at 90° C. The resulting mixture was concentrated under reduced pressure. The reaction was quenched with water at room temperature. The mixture was adjusted to pH 8 with saturated NaHCO₃ (aq.). The resulting mixture was extracted with EtOAc (2×200 mL). The combined organic layers were washed with brine (1×100 mL), dried over anhydrous Na₂SO₄ and filtered. the filtrate was concentrated under reduced pressure and the residue was purified by silica gel column chromatography, eluted with PE/EtOAc (1:1) to afford 3-chloro-2,7-naphthyridine (50 mg, 4.50%) as a yellow solid. LCMS (ES) [M+1]⁺ m/z: 165.

Step 4

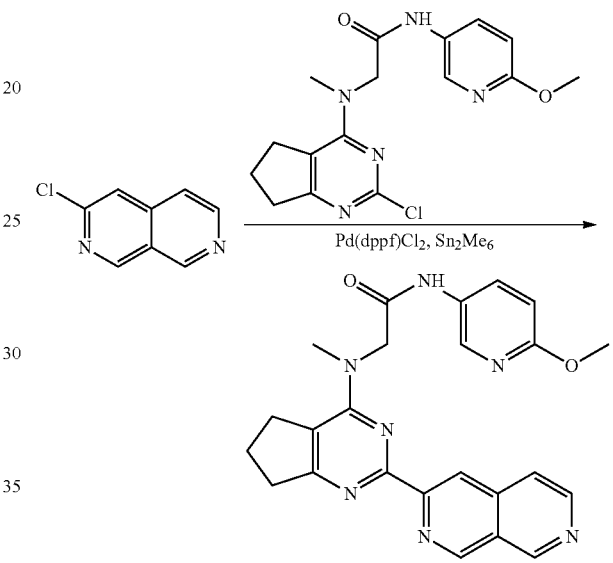

To a solution of 3-chloro-2,7-naphthyridine (220.00 mg, 1.337 mmol, 1.00 equiv) and hexamethyldistannane (481.72 mg, 1.471 mmol, 1.10 equiv) in toluene (5.00 mL, 46.995 mmol) were added Pd(dppf)Cl2 CH2Cl2 (108.89 mg, 0.134 mmol, 0.10 equiv). After stirring for 2 h at 100° C. under a nitrogen atmosphere, the mixture was allowed to cool down to room temperature. The mixture was then added 2-([2-chloro-5H,6H,7H-cyclopenta[d]pyrimidin-4-yl](methyl)amino)-N-(6-methoxypyridin-3-yl)acetamide (325.42 mg, 0.936 mmol, 0.70 equiv) and Pd(PPh₃)₄ (108.89 mg, 0.134 mmol, 0.10 equiv). The resulting mixture was stirred for additional 16 h at 100° C. After cooling the resulting mixture was concentrated under reduced pressure and the residue was purified by silica gel column chromatography, eluted with PE/THF (1:10) to provide N-(6-methoxypyridin-3-yl)-2-[methyl[2-(2,7-naphthyridin-3-yl)-5H,6H,7H-cyclopenta[d]pyrimidin-4-yl]amino]acetamide (30 mg, 7.3%) as a white solid. LCMS (ES) [M+1]+ m/z: 442; 1H NMR (300 MHz, DMSO-d6) δ 10.35 (s, 1H), 9.58 (d, J=5.2 Hz, 2H), 8.87-8.62 (m, 2H), 8.39 (d, J=2.7 Hz, 1H), 7.93 (dd, J=8.9, 2.7 Hz, 1H), 7.74 (d, J=5.8 Hz, 1H), 6.77 (d, J=8.9 Hz, 1H), 4.47 (s, 2H), 3.79 (s, 3H), 3.42 (s, 3H), 3.31-3.11 (m, 2H), 2.89 (t, J=7.8 Hz, 2H), 2.07-2.02 (m, 2H).

Example 1.275

Synthesis of 2-({2-[4-(2-hydroxyethoxy)pyridin-2-yl]-5H,6H,7H-cyclopenta[d]pyrimidin-4-yl}(methyl)amino)-N-(4-methoxyphenyl)acetamide (Compound 269)

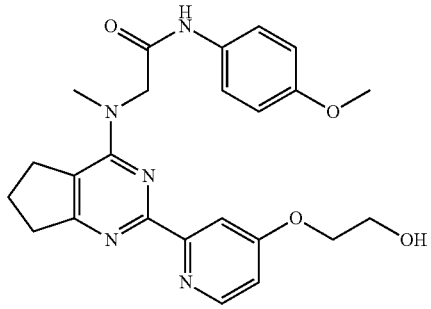 [SMILES: COc1ccc(NC(=O)CN(C)c2nc(-c3cc(OCCO)ccn3)nc3c2CCC3)cc1]

Compound 269 was synthesized similar to Compound 144 by replacing cyclohexylamine with 4-methoxyaniline. LCMS (ES) [M+1]⁺ m/z 450. ¹H NMR (300 MHz, DMSO-d₆) δ 10.07 (s, 1H), 8.44 (d, J=5.6 Hz, 1H), 7.80 (d, J=2.6 Hz, 1H), 7.55-7.43 (m, 2H), 7.00 (dd, J=5.6, 2.6 Hz, 1H), 6.92-6.79 (m, 2H), 4.90 (t, J=5.4 Hz, 1H), 4.39 (s, 2H), 4.03 (t, J=4.7 Hz, 2H), 3.71 (s, 3H), 3.77-3.62 (m, 2H), 3.35 (s, 3H), 3.20 (t, J=7.3 Hz, 2H), 2.83 (t, J=7.8 Hz, 2H), 2.01 (p, J=7.8 Hz, 2H).

Example 1.276

Synthesis of 2-({2-[5-(hydroxymethyl)isoquinolin-3-yl]-5H,6H,7H-cyclopenta[d]pyrimidin-4-yl}(methyl)amino)-N-(6-methylpyridin-3-yl)acetamide (Compound 270)

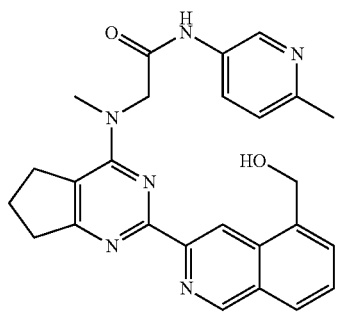 [SMILES: Cc1ccc(NC(=O)CN(C)c2nc(-c3cc4c(CO)cccc4cn3)nc3c2CCC3)cn1]

Scheme 114

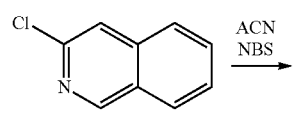

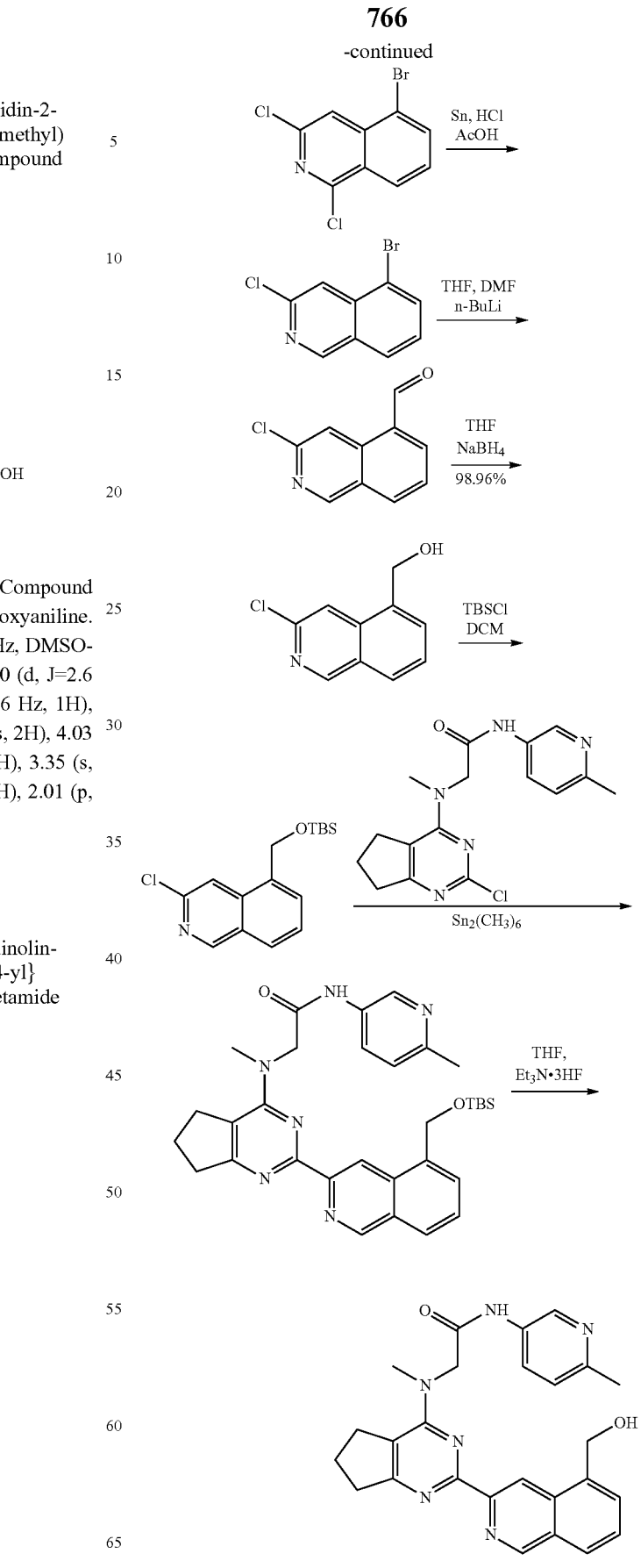

Step 1

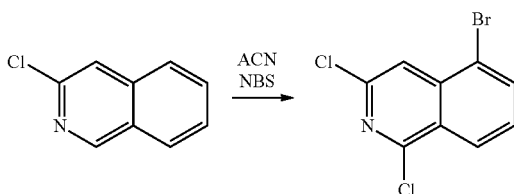

Into a 1000-mL round-bottom flask was placed 1,3-dichloroisoquinoline (30.00 g, 151.477 mmol, 1.00 equiv), NBS (28.31 g, 159.051 mmol, 1.05 equiv), AcCN (600.00 mL) and $H_2SO_4$ (30.00 mL). The resulting solution was stirred for 90 h at room temperature. The solids were collected by filtration. This resulted in 18 g (42.91%) of 5-bromo-1,3-dichloroisoquinoline as a yellow solid. LCMS (ES) $[M+1]^+$ m/z 276.

Step 2

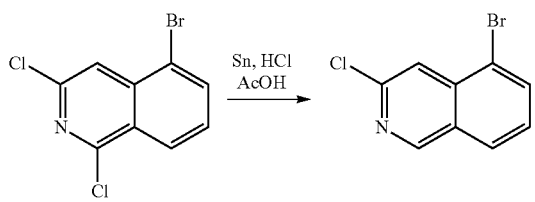 [SMILES: Clc1cc2c(Br)cccc2c(Cl)n1 ; Clc1cc2c(Br)cccc2cn1]

Into a 500-mL round-bottom flask was placed 5-bromo-1,3-dichloroisoquinoline (15.00 g, 54.163 mmol, 1.00 equiv), AcOH (150.00 mL), HCl (30.00 mL) and Sn (19.34 g, 162.490 mmol, 3 equiv). The resulting solution was stirred for 0.5 hr at 60° C. The resulting solution was extracted with 3×200 mL of ethyl acetate, organic layers were combined, washed with 3×200 ml of brine and filtered. The filtrate was concentrated and the residue was applied onto a silica gel column with ethyl acetate/petroleum ether (1:5). This resulted in 5.5 g (41.87%) of 5-bromo-3-chloroisoquinoline as a light yellow solid. LCMS (ES) $[M+1]^+$ m/z 242.

Step 3

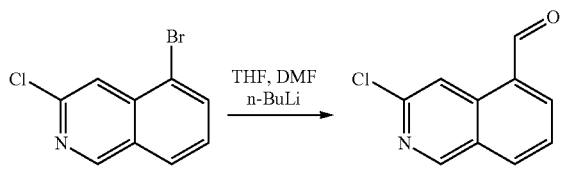 [SMILES: Clc1cc2c(Br)cccc2cn1 ; O=Cc1cccc2cnc(Cl)cc12]

Into a 100-mL 3-necked round-bottom flask purged and maintained with an inert atmosphere of nitrogen, was placed 5-bromo-3-chloroisoquinoline (3.00 g, 12.371 mmol, 1.00 equiv), THE (30.00 mL). This was followed by the addition of n-BuLi in hexanes (5.9 mL, 14.862 mmol, 1.20 equiv) dropwise with stirring at −78° C. The resulting solution was stirred for 0.5 hr at −78° C. To this was added DMF (2.71 g, 37.113 mmol, 3.00 equiv) dropwise with stirring at −78° C. The resulting solution was warmed up to room temperature and stirred for an additional 2 hr. The reaction was then quenched by the addition of 100 mL of $NH_4Cl$. The resulting solution was extracted with 2×50 mL of ethyl acetate. Organic layers were combined, washed with brine and dried over anhydrous sodium sulfate. The mixture was filtered, and the filtrate was concentrated. The residue was applied onto a silica gel column with ethyl acetate/petroleum ether (1:1). This resulted in 730 mg (30.7%) of 3-chloroisoquinoline-5-carbaldehyde as a light yellow solid. LCMS (ES) $[M+1]^+$ m/z 192.

Step 4

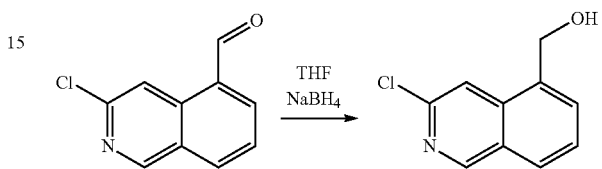

Into a 40-mL round-bottom flask was placed 3-chloroisoquinoline-5-carbaldehyde (730.00 mg, 3.810 mmol, 1.00 equiv), THE (10.00 mL) and $NaBH_4$ (432.41 mg, 11.429 mmol, 3 equiv). The resulting solution was stirred for 2 hr at room temperature. The reaction was then quenched by the addition of 10 mL of water and extracted with 3×20 mL of ethyl acetate. The combined organic layers were washed with 3×20 mL of brine, dried over anhydrous sodium sulfate and concentrated. The residue was applied onto a silica gel column with ethyl acetate/petroleum ether (1:1). This resulted in 730 mg (98.9%) of (3-chloroisoquinolin-5-yl)methanol as a light yellow solid. LCMS (ES) $[M+1]^+$ m/z 194.

Step 5

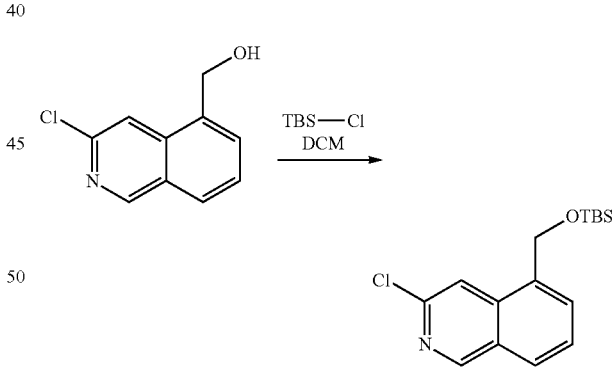

Into a 40-mL round-bottom flask were placed (3-chloroisoquinolin-5-yl)methanol (730.00 mg, 3.770 mmol, 1.00 equiv), DCM (10 mL), TBSCl (852.35 mg, 5.655 mmol, 1.50 equiv), imidazole (513.31 mg, 7.540 mmol, 2 equiv). The resulting solution was stirred for 12 hr at room temperature. The resulting mixture was concentrated. The residue was applied onto a silica gel column with ethyl acetate/petroleum ether (1:10). This resulted in 800 mg (68.9%) of 5-[[(tert-butyldimethylsilyl)oxy]methyl]-3-chloroisoquinoline as yellow oil. LCMS (ES) $[M+1]^+$ m/z 308.

Step 6

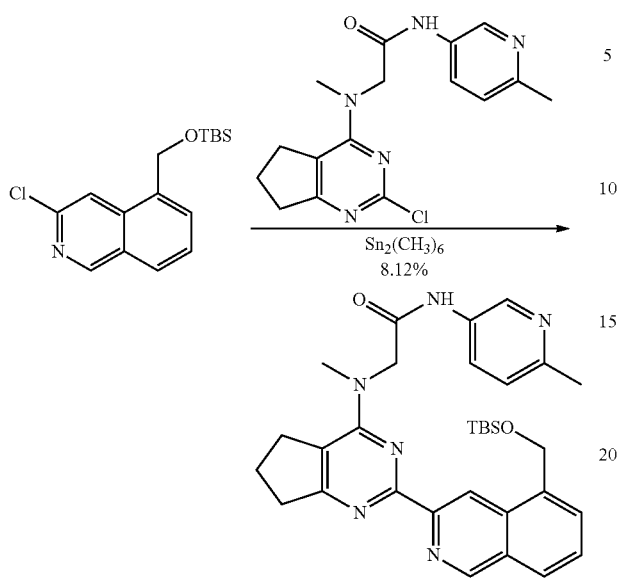

Into a 40-mL round-bottom flask were placed 2-([2-chloro-5H,6H,7H-cyclopenta[d]pyrimidin-4-yl](methyl)amino)-N-(6-methylpyridin-3-yl)acetamide (215.53 mg, 0.650 mmol, 1.00 equiv), hexamethyldistannane (212.82 mg, 0.650 mmol, 1 equiv), Dioxane (6 mL) and Pd(dppf)Cl$_2$·CH$_2$Cl$_2$ (52.92 mg, 0.065 mmol, 0.10 equiv). The resulting solution was stirred for 3 h at 100° C. and was cooled and added 5-[[(tert-butyldimethylsilyl)oxy]methyl]-3-chloroisoquinoline (200.00 mg, 0.650 mmol, 1.00 equiv) and Pd(dppf)Cl$_2$·CH$_2$Cl$_2$ (52.92 mg, 0.065 mmol, 0.10 equiv), The resulting solution was then stirred for overnight at 100° C. The resulting mixture was concentrated, the residue was applied onto a silica gel column with dichloromethane/methanol (1:0-10:1). This resulted in 120 mg (8.12%) of 2-((2-(5-(((tert-butyldimethylsilyl)oxy)methyl)isoquinolin-3-yl)-6,7-dihydro-5H-cyclopenta[d]pyrimidin-4-yl)(methyl)amino)-N-(6-methylpyridin-3-yl)acetamide as a brown solid. LCMS (ES) [M+1]$^+$ m/z 569.

Step 7

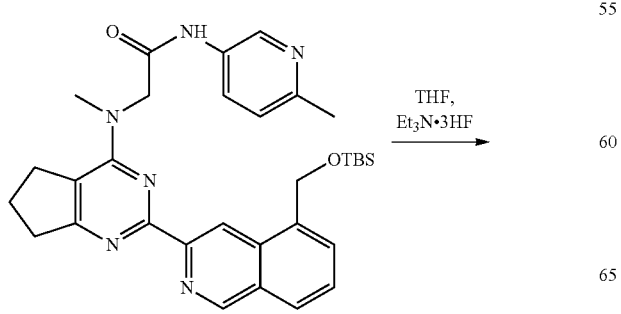

-continued


Into a 40 mL round-bottom flask were placed 2-[[2-(5-[[(tert-butyldimethylsilyl)oxy]methyl]isoquinolin-3-yl)-5H,6H,7H-cyclopenta[d]pyrimidin-4-yl](methyl)amino]-N-(6-methylpyridin-3-yl)acetamide (120.00 mg, 0.211 mmol, 1.00 equiv), THF (3.00 mL) and Et$_3$N·3HF (170.05 mg, 1.055 mmol, 5.00 equiv). The resulting solution was stirred for 12 h at room temperature. The pH value of the solution was adjusted to 7~8 with NH$_3$H$_2$O. The resulting mixture was concentrated and the crude product was purified by Prep-HPLC with the following conditions: Column, SunFire Prep C18 OBD Column, 19*150 mm 5 um 10 nm; mobile phase, Water (0.1% FA) and ACN (48.0% ACN up to 53.0% in 7 min, hold 95.0% in 1 min, down to 48.0% in 1 min, hold 48.0% in 1 min); Detector, UV 220 nm. This resulted in 41.6 mg (43.38%) of 2-({2-[5-(hydroxymethyl)isoquinolin-3-yl]-5H,6H,7H-cyclopenta[d]pyrimidin-4-yl}(methyl)amino)-N-(6-methylpyridin-3-yl)acetamide as a white solid. LCMS (ES) [M+1]$^+$ m/z 455. $^1$H NMR (300 MHz, DMSO-d6) δ 10.40 (s, 1H), 9.37 (s, 1H), 8.88 (s, 1H), 8.61 (d, J=2.6 Hz, 1H), 8.07 (d, J=8.1 Hz, 1H), 7.90 (dd, J=8.4, 2.6 Hz, 1H), 7.82 (d, J=7.1 Hz, 1H), 7.74-7.63 (m, 1H), 7.16 (d, J=8.5 Hz, 1H), 5.40 (br, 1H), 4.98 (d, J=4.2 Hz, 2H), 4.51 (s, 2H), 3.39 (s, 3H), 3.23 (t, J=7.1 Hz, 2H), 2.90 (t, J=7.9 Hz, 2H), 2.38 (s, 3H), 2.09-1.97 (m, 2H).

Example 1.277

Synthesis of N-(3-fluorophenyl)-2-{methyl[2-(1-methyl-1H-imidazol-4-yl)-5H,6H,7H-cyclopenta[d]pyrimidin-4-yl]amino}acetamide (Compound 271)

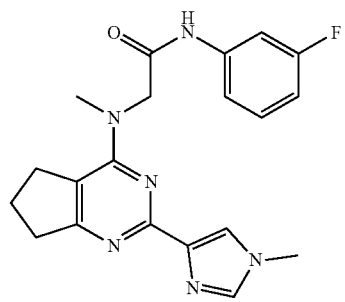 [SMILES: CN(CC(=O)Nc1cccc(F)c1)c1nc(-c2cn(C)cn2)nc2c1CCC2]

Compound 271 was synthesized similar to compound 142 by replacing cyclohexylamine with 3-fluoroaniline. LCMS (ES) [M+1]$^+$ m/z: 381; $^1$H-NMR (300 MHz, DMSO-d$_6$, ppm): δ 10.43 (s, 1H), 7.69-7.55 (m, 3H), 7.41-7.26 (m, 2H), 6.93-6.80 (m, 1H), 4.36 (s, 2H), 3.61 (s, 3H), 3.32 (s, 3H), 3.13 (t, J=7.2 Hz, 2H), 2.75 (t, J=7.8 Hz, 2H), 2.01-1.91 (m, 2H).

Example 1.278

Synthesis of N-(3-methoxyphenyl)-2-{methyl[2-(1-methyl-1H-imidazol-4-yl)-5H,6H,7H-cyclopenta[d]pyrimidin-4-yl]amino}acetamide (Compound 272)

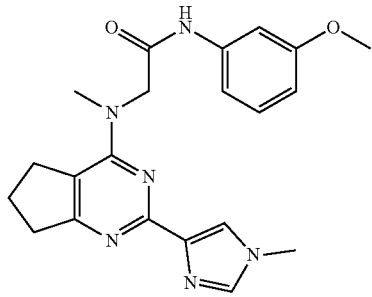 [SMILES: COc1cccc(NC(=O)CN(C)c2nc(-c3cn(C)cn3)nc3c2CCC3)c1]

Compound 272 was synthesized similar to compound 142 by replacing cyclohexylamine with 3-methoxyaniline. LCMS (ES) [M+1]$^+$ m/z: 393; $^1$H-NMR (300 MHz, DMSO-d$_6$, ppm): δ 10.19 (s, 1H), 7.67 (d, J=1.5 Hz, 1H), 7.58 (d, J=1.2 Hz, 1H), 7.33 (t, J=2.1 Hz, 1H), 7.25-7.11 (m, 2H), 6.63-6.59 (m, 1H), 4.35 (s, 2H), 3.69 (s, 3H), 3.61 (s, 3H), 3.31 (s, 3H), 3.13 (t, J=7.2 Hz, 2H), 2.74 (t, J=7.8 Hz, 2H), 2.01-1.90 (m, 2H).

Example 1.279

Synthesis of (2R)-2-{[2-(isoquinolin-3-yl)-5H,6H,7H-cyclopenta[d]pyrimidin-4-yl](methyl)amino}-N-(pyridazin-4-yl)propanamide (Compound 273)

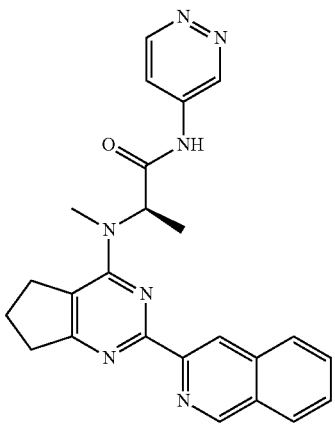 [SMILES: C[C@H](C(=O)Nc1ccnnc1)N(C)c1nc(-c2cc3ccccc3cn2)nc2c1CCC2]

Compound 273 was synthesized similar to compound 108 by replacing cyclohexylamine with 4-pyridazinylamine and by replacing 2-(tributylstannyl)pyridine with 3-(tributylstannyl)isoquinoline. LCMS (ES+): [M+H]$^+$=426. $^1$H NMR (400 MHz, DMSO-d6) δ 11.87 (s, 1H), 9.62-9.55 (m, 2H), 9.15 (s, 1H), 9.09 (d, J=6.2 Hz, 1H), 8.39-8.26 (m, 2H), 8.22 (dd, J=6.2, 2.7 Hz, 1H), 7.96 (dddd, J=34.5, 8.1, 7.0, 1.2 Hz, 2H), 5.66 (d, J=7.7 Hz, 1H), 3.54 (s, 3H), 3.47-3.29 (m, 2H), 3.17-3.06 (m, 2H), 2.26-2.08 (m, 2H), 1.70 (d, J=7.1 Hz, 3H).

Example 1.280

Synthesis of (2R)-2-{[2-(isoquinolin-3-yl)-5H,6H,7H-cyclopenta[d]pyrimidin-4-yl](methyl)amino}-N-[6-(trifluoromethyl)pyridin-3-yl]propanamide (Compound 274)

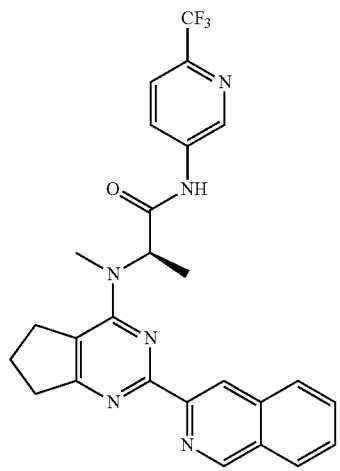 [SMILES: C[C@H](C(=O)Nc1ccc(C(F)(F)F)nc1)N(C)c1nc(-c2cc3ccccc3cn2)nc2c1CCC2]

Compound 274 was synthesized similar to compound 108 by replacing cyclohexylamine with 6-trifluoropyridin-3-amine. LCMS (ES+): [M+H]$^+$=426. $^1$H NMR (400 MHz, DMSO-d6) δ 11.87 (s, 1H), 9.62-9.55 (m, 2H), 9.15 (s, 1H), 9.09 (d, J=6.2 Hz, 1H), 8.39-8.26 (m, 2H), 8.22 (dd, J=6.2, 2.7 Hz, 1H), 7.96 (dddd, J=34.5, 8.1, 7.0, 1.2 Hz, 2H), 5.66 (d, J=7.7 Hz, 1H), 3.54 (s, 3H), 3.47-3.29 (m, 2H), 3.17-3.06 (m, 2H), 2.26-2.08 (m, 2H), 1.70 (d, J=7.1 Hz, 3H).

Example 1.281

Synthesis of N-(1-hydroxy-2-methylpropan-2-yl)-2-({2-[1-(3-hydroxypropyl)-1H-imidazol-4-yl]-5H,6H,7H-cyclopenta[d]pyrimidin-4-yl}(methyl)amino)acetamide (Compound 275)

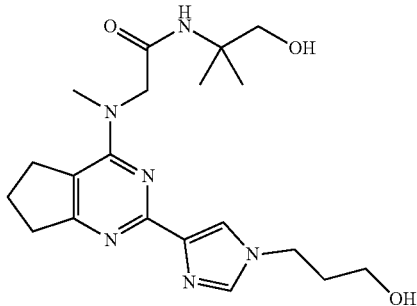 [SMILES: CN(CC(=O)NC(C)(C)CO)c1nc(-c2cn(CCCO)cn2)nc2c1CCC2]

Scheme 115

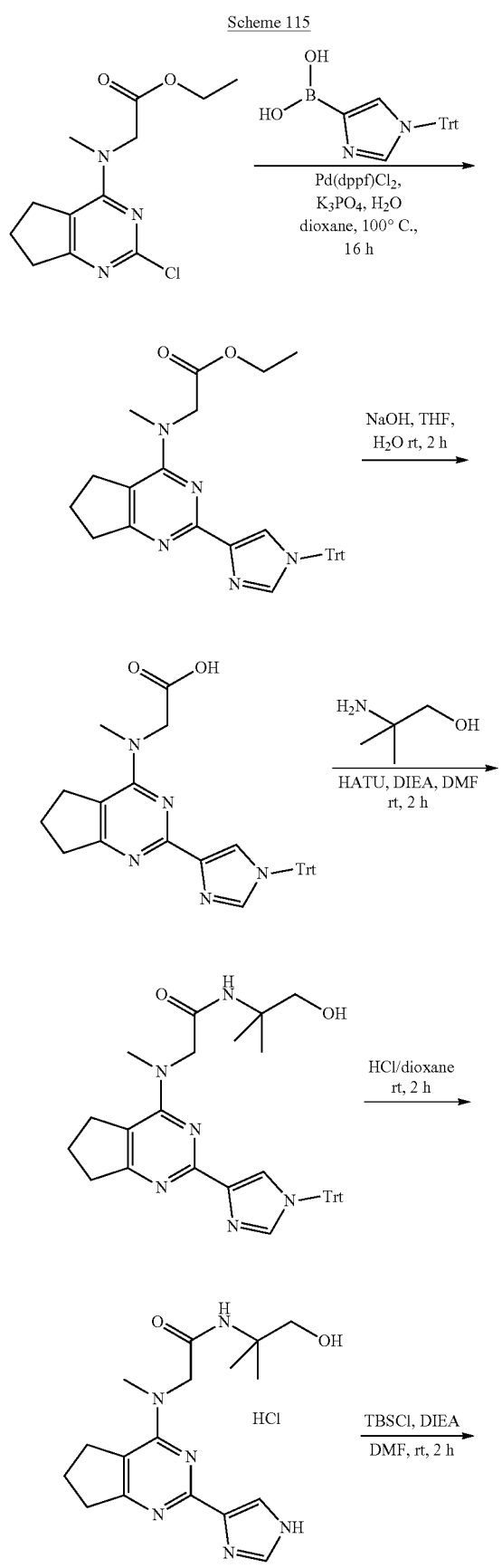

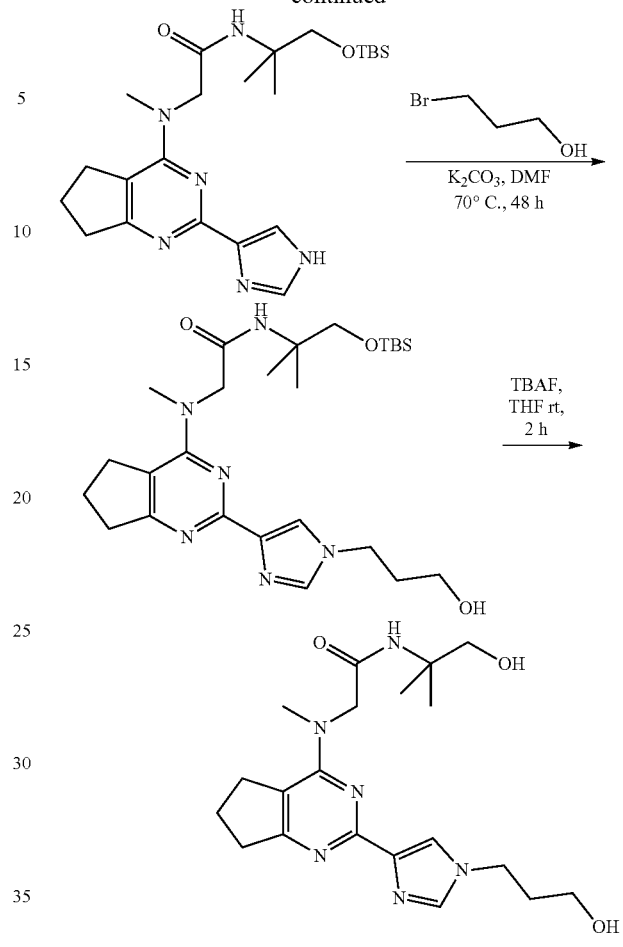

Step 1

Into a 100-mL round-bottom flask were placed ethyl N-(2-chloro-6,7-dihydro-5H-cyclopenta[d]pyrimidin-4-yl)-N-methylglycinate (2.00 g, 7.415 mmol, 1.00 equiv), dioxane (20.00 mL, 236.082 mmol, 31.84 equiv), water (2 mL), 1-(triphenylmethyl)imidazol-4-ylboronic acid (3.94 g, 11.122 mmol, 1.50 equiv), K₃PO₄ (3.15 g, 14.830 mmol, 2.00 equiv) and Pd(dppf)Cl₂ (0.54 g, 0.741 mmol, 0.10 equiv). The resulting solution was stirred for 16 hr at 100° C. The resulting mixture was concentrated. The residue was applied onto a silica gel column with ethyl acetate/petroleum ether (1:3). This resulted in 0.88 g (21.83%) of ethyl N-methyl-N-(2-(1-trityl-1H-imidazol-4-yl)-6,7-dihydro-5H-cyclopenta[d]pyrimidin-4-yl)glycinate as a yellow solid. LCMS (ES) [M+1]⁺ m/z: 544.

Step 2

Into a 100-mL round-bottom flask were placed ethyl N-methyl-N-(2-(1-trityl-1H-imidazol-4-yl)-6,7-dihydro-5H-cyclopenta[d]pyrimidin-4-yl)glycinate (800.00 mg, 1.471 mmol, 1.00 equiv), THF (5.00 mL, 61.715 mmol, 41.94 equiv), H₂O (5.00 mL, 277.542 mmol, 188.61 equiv) and NaOH (117.71 mg, 2.943 mmol, 2.00 equiv). The resulting solution was stirred for 2 hr at 25° C. The resulting solution was diluted with 20 mL of water. The pH value of the solution was adjusted to 6 with HCl (1 mol/L). The solids were collected by filtration. This resulted in 640 mg (84.35%) of N-methyl-N-(2-(1-trityl-1H-imidazol-4-yl)-6, 7-dihydro-5H-cyclopenta[d]pyrimidin-4-yl)glycine as an off-white solid. LCMS (ES) [M+1]⁺ m/z: 516.

Step 3

Into a 25-mL round-bottom flask were placed N-methyl-N-(2-(1-trityl-1H-imidazol-4-yl)-6,7-dihydro-5H-cyclopenta[d]pyrimidin-4-yl)glycine (640.00 mg, 1.241 mmol, 1.00 equiv), DMF (10 mL), 2-amino-2-methyl-1-propanol (110.64 mg, 1.241 mmol, 1.00 equiv), HATU (707.93 mg, 1.862 mmol, 1.50 equiv) and DIEA (481.26 mg, 3.724 mmol, 3.00 equiv). The resulting solution was stirred for 2 hr at 25° C. The crude reaction mixture was filtered and subjected to reverse phase preparative HPLC (Prep-C18, 20-45 uM, 120 g, Tianjin Bonna-Agela Technologies; gradient elution of 40% MeCN in water to 50% MeCN in water over a 10 min period, water contains 0.1% $NH_3H_2O$). This resulted in (250 mg, 34.33%) N-(1-hydroxy-2-methylpropan-2-yl)-2-(methyl(2-(1-trityl-1H-imidazol-4-yl)-6,7-dihydro-5H-cyclopenta[d]pyrimidin-4-yl)amino)acetamide as a light yellow solid. LCMS (ES) $[M+1]^+$ m/z: 587.

Step 4

Into a 25-mL round-bottom flask were placed N-(1-hydroxy-2-methylpropan-2-yl)-2-(methyl(2-(1-trityl-1H-imidazol-4-yl)-6,7-dihydro-5H-cyclopenta[d]pyrimidin-4-yl)amino)acetamide (250.00 mg, 0.426 mmol, 1.00 equiv), HCl (gas) in 1,4-dioxane (10.00 mL). The resulting solution was stirred for 2 hr at 25° C. The solids were collected by filtration. This resulted in 150 mg (92.43%) of 2-((2-(1H-imidazol-4-yl)-6,7-dihydro-5H-cyclopenta[d]pyrimidin-4-yl)(methyl)amino)-N-(1-hydroxy-2-methylpropan-2-yl)acetamide hydrochloride as a yellow solid. LCMS (ES) $[M+1]^+$ m/z: 381.

Step 5

Into a 100-mL round-bottom flask were placed 2-((2-(1H-imidazol-4-yl)-6,7-dihydro-5H-cyclopenta[d]pyrimidin-4-yl)(methyl)amino)-N-(1-hydroxy-2-methylpropan-2-yl)acetamide hydrochloride (150.00 mg, 0.394 mmol, 1.00 equiv), dimethylformamide (10 mL), DIEA (152.70 mg, 1.181 mmol, 3.00 equiv) and t-butyldimethylchlorosilane (71.23 mg, 0.473 mmol, 1.20 equiv). The resulting solution was stirred for 16 hr at 25° C. The crude reaction mixture was filtered and subjected to reverse phase preparative HPLC (Prep-C18, 20-45 uM, 120 g, Tianjin Bonna-Agela Technologies; gradient elution of 50% MeCN in water to 60% MeCN in water over a 10 min period, water contains 0.1% $NH_3H_2O$) to provide -((2-(1H-imidazol-4-yl)-6,7-dihydro-5H-cyclopenta[d]pyrimidin-4-yl)(methyl)amino)-N-(1-((tert-butyldimethylsilyl)oxy)-2-methylpropan-2-yl)acetamide as a light yellow solid (120 mg, 66.43%). LCMS (ES) $[M+1]^+$ m/z: 459.

Step 6

Into a 100 mL round-bottom flask were placed 2-((2-(1H-imidazol-4-yl)-6,7-dihydro-5H-cyclopenta[d]pyrimidin-4-yl)(methyl)amino)-N-(1-((tert-butyldimethylsilyl)oxy)-2-methylpropan-2-yl)acetamide (120.00 mg, 0.262 mmol, 1.00 equiv), dimethylformamide (10 mL), 3-bromopropanol (72.73 mg, 0.523 mmol, 2.00 equiv), $K_2CO_3$ (108.47 mg, 0.785 mmol, 3.00 equiv). The resulting solution was stirred for 48 hr at 70° C. The residue was applied onto a silica gel column with dichloromethane/methanol (10:1). The collected fractions were combined and concentrated. This resulted in 80 mg (59.17%) of N-(1-((tert-butyldimethylsilyl)oxy)-2-methylpropan-2-yl)-2-((2-(1-(3-hydroxypropyl)-1H-imidazol-4-yl)-6,7-dihydro-5H-cyclopenta[d]pyrimidin-4-yl)(methyl)amino)acetamide as a yellow solid. LCMS (ES) $[M+1]^+$ m/z: 517.

Step 7

Into a 100-mL round-bottom flask were placed N-(1-((tert-butyldimethylsilyl)oxy)-2-methylpropan-2-yl)-2-((2-(1-(3-hydroxypropyl)-1H-imidazol-4-yl)-6,7-dihydro-5H-cyclopenta[d]pyrimidin-4-yl)(methyl)amino)acetamide (80.00 mg, 0.155 mmol, 1.00 equiv), tetrahydrofuran (5 mL), TBAF (4.05 mg, 0.015 mmol, 0.10 equiv). The resulting solution was stirred for 2 hr at 25° C. The crude reaction mixture was filtered and subjected to reverse phase preparative HPLC (Prep-C18, 20-45 uM, 120 g, Tianjin Bonna-Agela Technologies; gradient elution of 25% MeCN in water to 35% MeCN in water over a 10 min period, water contains 0.1% $NH_3H_2O$). This resulted in (18.6 mg, 29.85%) N-(1-hydroxy-2-methylpropan-2-yl)-2-((2-(1-(3-hydroxypropyl)-1H-imidazol-4-yl)-6,7-dihydro-5H-cyclopenta[d]pyrimidin-4-yl)(methyl)amino)acetamide as an off-white solid LCMS (ES) $[M+1]^+$ m/z: 403. $^1$H NMR (300 MHz, DMSO-d6) δ 7.77 (d, J=1.4 Hz, 1H), 7.63 (d, J=1.4 Hz, 1H), 7.47 (s, 1H), 4.95 (t, J=5.9 Hz, 1H), 4.65 (t, J=5.1 Hz, 1H), 4.10 (s, 2H), 4.05 (t, J=7.0 Hz, 2H), 3.49-3.35 (m, 4H), 3.21 (s, 3H), 3.08 (t, J=7.2 Hz, 2H), 2.73 (t, J=7.8 Hz, 2H), 1.92 (dt, J=13.2, 7.3 Hz, 4H), 1.18 (s, 6H).

Example 1.282

Synthesis of 2-[(2-{4-[(1-hydroxy-2-methylpropan-2-yl)oxy]pyridin-2-yl}-5H,6H,7H-cyclopenta[d]pyrimidin-4-yl)(methyl)amino]-N-(2-methoxypyrimidin-5-yl)acetamide (Compound 276)

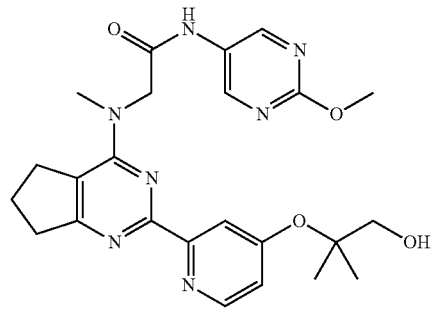 [SMILES: COc1ncc(NC(=O)CN(C)c2nc(-c3cc(OC(C)(C)CO)ccn3)nc3c2CCC3)cn1]

Compound 276 was synthesized similar to compound 144 by replacing cyclohexylamine with 2-methoxypyrimidin-5-amine and replacing 4-[2-(oxan-2-yloxy)ethoxy]-2-(trimethylstannyl)pyridine with 4-[[2-methyl-1-(oxan-2-yloxy)propan-2-yl]oxy]-2-(trimethylstannyl)pyridine. LCMS (ES) $[M+1]^+$ m/z: 480; $^1$H-NMR (300 MHz, DMSO-$d_6$, ppm): δ 10.49 (s, 1H), 8.74 (s, 2H), 8.43 (d, J=5.4 Hz, 1H), 7.77 (d, J=2.4 Hz, 1H), 7.03 (dd, J=5.7, 2.7 Hz, 1H), 4.67 (s, 1H), 4.42 (s, 2H), 3.87 (s, 3H), 3.80 (s, 2H), 3.24 (s, 3H), 3.22 (t, J=7.2 Hz, 2H), 2.84 (t, J=7.8 Hz, 2H), 2.07-1.99 (m, 2H), 1.16 (s, 6H).

Example 1.283

Synthesis of (2R)—N-(3-fluorophenyl)-2-{methyl[2-(1-methyl-1H-imidazol-4-yl)-5H,6H,7H-cyclopenta[d]pyrimidin-4-yl]amino}propanamide (Compound 277)

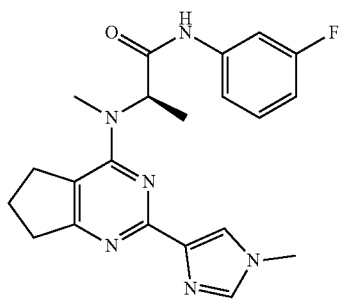 [SMILES: C[C@H](C(=O)Nc1cccc(F)c1)N(C)c1nc(-c2cn(C)cn2)nc2c1CCC2]

Compound 277 was synthesized similar to compound 108 by replacing 1-cyclohexylamine with 3-fluoroaniline and by replacing 2-(tributylstannyl)pyridine with 1-methyl-4-(tributylstannyl)imidazole. LCMS (ES) [M+1]$^+$ m/z: 395; $^1$H-NMR (300 MHz, DMSO-d$_6$, ppm): δ 10.60 (s, 1H), 8.14 (s, HCOOH), 7.78 (d, J=1.2 Hz, 1H), 7.69 (d, J=1.5 Hz, 1H), 7.66 (dt, J=12.0, 2.4 Hz, 1H), 7.45-7.40 (m, 1H), 7.32-7.24 (m, 1H), 6.83 (td, J=8.4, 2.7 Hz, 1H), 5.26 (q, J=7.2 Hz, 1H), 3.68 (s, 3H), 3.22-3.14 (m, 1H), 3.13 (s, 3H), 3.08-2.97 (m, 1H), 2.86-2.66 (m, 2H), 2.06-1.86 (m, 2H), 1.43 (d, J=7.2 Hz, 3H).

Example 1.284

Synthesis of (2R)—N-(3-methoxyphenyl)-2-{methyl[2-(1-methyl-1H-imidazol-4-yl)-5H,6H,7H-cyclopenta[d]pyrimidin-4-yl]amino}propanamide (Compound 278)

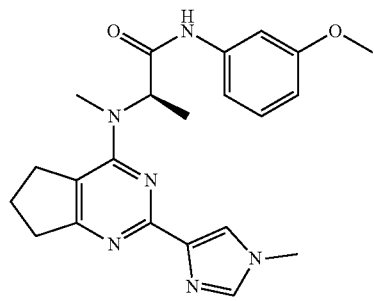 [SMILES: COc1cccc(NC(=O)[C@@H](C)N(C)c2nc(-c3cn(C)cn3)nc3c2CCC3)c1]

Compound 278 was synthesized similar to compound 108 by replacing 1-cyclohexylamine with 3-methoxyaniline and by replacing 2-(tributylstannyl)pyridine with 1-methyl-4-(tributylstannyl)imidazole. LCMS (ES) [M+1]$^+$ m/z: 407; $^1$H-NMR (300 MHz, DMSO-d$_6$, ppm): δ 10.58 (s, 1H), 8.17 (s, HCOOH), 7.81 (d, J=1.5 Hz, 1H), 7.72 (d, J=1.2 Hz, 1H), 7.31 (t, J=2.1 Hz, 1H), 7.29-7.23 (m, 1H), 7.14 (t, J=8.1 Hz, 1H), 6.60-6.55 (m, 1H), 5.29 (q, J=7.2 Hz, 1H), 3.69 (s, 3H), 3.63 (s, 3H), 3.21-3.10 (m, 1H), 3.13 (s, 3H), 3.06-2.96 (m, 1H), 2.86-2.66 (m, 2H), 2.03-1.86 (m, 2H), 1.42 (d, J=7.2 Hz, 3H).

Example 1.285

Synthesis of 2-({2-[4-(2-hydroxyethoxy)pyridin-2-yl]-5H,6H,7H-cyclopenta[d]pyrimidin-4-yl}(methyl)amino)-N-(3-methoxyphenyl)acetamide (Compound 279)

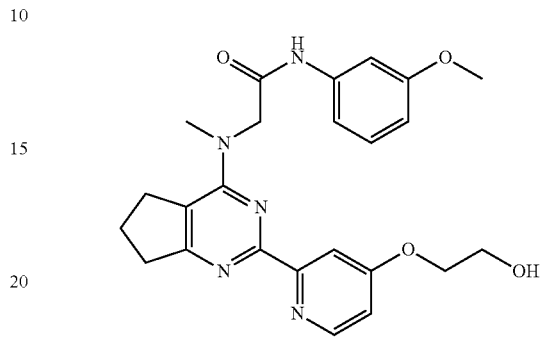

Scheme 116

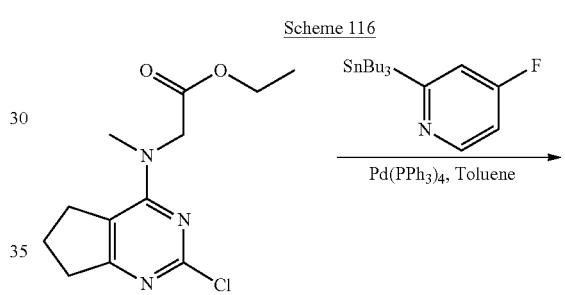

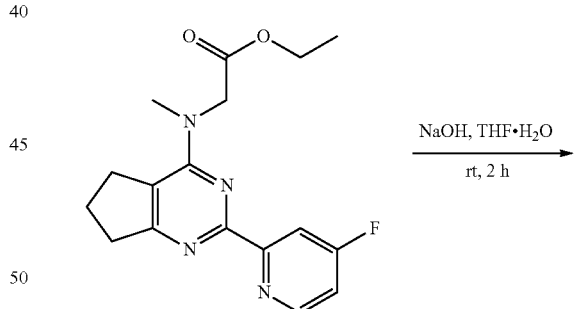

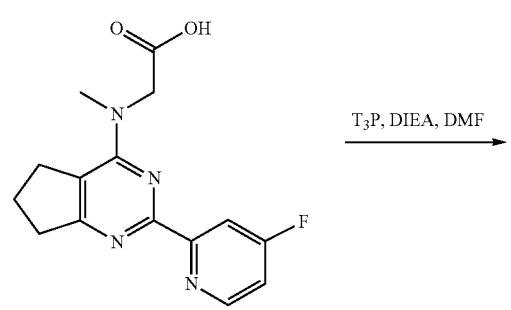

-continued

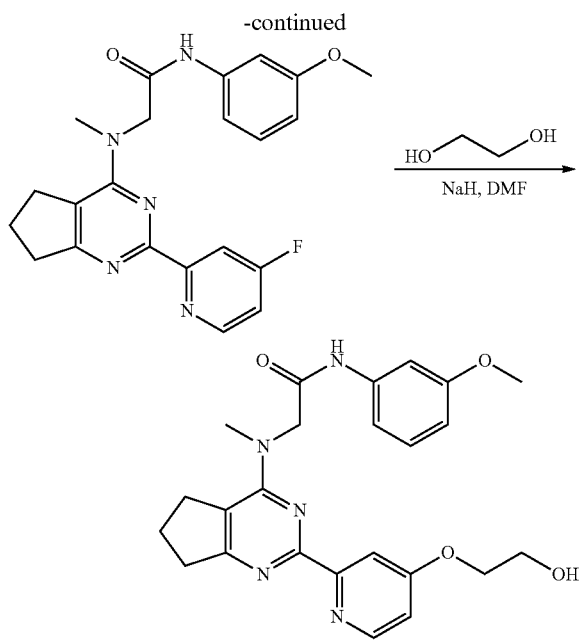

Step 1

Into a 250 mL three necked round bottom flask purged and maintained with an inert atmosphere of nitrogen, was placed ethyl N-(2-chloro-6,7-dihydro-5H-cyclopenta[d]pyrimidin-4-yl)-N-methylglycinate (2.0 g, 7.4 mmol, 1.00 equiv), toluene (40.00 mL), 4-fluoro-2-(tributylstannyl)pyridine (4.3 g, 11.1 mmol, 1.5 equiv), Pd(PPh$_3$)$_4$ (780 mg, 0.74 mmol, 0.10 equiv). The mixture was stirred for 36 h at 110° C. in oil bath. The reaction mixture was cooled to room temperature, concentrated to remove the solvent; the residue was purified by silica gel column with dichloromethane/methanol (25:1). This resulted in 1.4 g (57% yield) of ethyl N-(2-(4-fluoropyridin-2-yl)-6,7-dihydro-5H-cyclopenta[d]pyrimidin-4-yl)-N-methylglycinate as yellow solid. LCMS (ES) [M+1]+ m/z: 331.

Step 2

Into a 250 mL round-bottom flask, was placed ethyl N-(2-(4-fluoropyridin-2-yl)-6,7-dihydro-5H-cyclopenta[d]pyrimidin-4-yl)-N-methylglycinate (1.4 g, 4.2 mmol, 1 equiv), tetrahydrofuran (30 mL), water (15 mL), lithiumol (0.21 g, 8.4 mmol, 2.00 equiv). The resulting solution was stirred for 2 hr at 25° C. The resulting mixture was concentrated. The resulting solution was diluted with 50 mL of water. The pH value of the solution was adjusted to 4 with HCl (1 mol/L). The solids were collected by filtration. This resulted in 0.68 g (53%) of N-(2-(4-fluoropyridin-2-yl)-6,7-dihydro-5H-cyclopenta[d]pyrimidin-4-yl)-N-methylglycine as an off-white solid. LCMS (ES) [M+1]+ m/z 303.

Step 3

Into a 8 mL vial were placed m-anisidine (102 mg, 0.83 mmol, 1.00 equiv), DMF (5 mL), 3-[2-(4-fluoropyridin-2-yl)-5H,6H,7H-cyclopenta[d]pyrimidin-4-yl]butanoic acid (250 mg, 0.83 mmol, 1.00 equiv) and DIEA (322 mg, 2.49 mmol, 3.00 equiv). This was followed by the addition of T3P (317 mg, 1.00 mmol, 1.20 equiv) at 0° C. The resulting solution was stirred for 2 hr at 25° C. The reaction was then quenched by the addition of 50 mL of water. The resulting solution was extracted with 3×100 mL of ethyl acetate and the organic layers combined. The resulting mixture was washed with 3×100 ml of brine and concentrated under vacuum. The residue was applied onto a silica gel column with dichloromethane/methanol (20:1). This resulted in 180 mg (53.25%) of 2-[[2-(4-fluoropyridin-2-yl)-5H,6H,7H-cyclopenta[d]pyrimidin-4-yl](methyl)amino]-N-(3-methoxyphenyl)acetamide as light brown oil. LCMS (ES) [M+1]+ m/z 408.

Step 2

Into a 50 mL 3-necked round-bottom flask were placed ethylene glycol (114 mg, 1.84 mmol, 5.00 equiv), THF (5 mL). This was followed by the addition of NaH (18 mg, 0.74 mmol, 2.00 equiv) at 0° C. The resulting solution was stirred for 30 min at 0° C. To this was added 2-[[2-(4-fluoropyridin-2-yl)-5H,6H,7H-cyclopenta[d]pyrimidin-4-yl](methyl)amino]-N-(3-methoxyphenyl)acetamide (150 mg, 0.37 mmol, 1.00 equiv) at 0° C. The resulting solution was stirred for 1 hr at 25° C. The reaction was then quenched by the addition of 30 mL of water. The resulting solution was extracted with 2×50 mL of ethyl acetate, the organic layers were combined and concentrated under vacuum. The residue was dissolved in 5 mL of MeOH. The crude product was purified by Prep-HPLC with the following conditions (Prep-HPLC-001): Column, Sunfire Prep C18 OBD Column, 50*250 mm, 5 µm 10 nm; mobile phase, Water (0.1% FA) and ACN (5% PhaseB up to 35% in 15 min). This resulted in 61.0 mg (36.86%) of 2-([2-[4-(2-hydroxyethoxy)pyridin-2-yl]-5H,6H,7H-cyclopenta[d]pyrimidin-4-yl](methyl)amino)-N-(3-methoxyphenyl)acetamide as a white solid. LCMS (ES) [M+1]+ m/z 450. $^1$H NMR (300 MHz, DMSO-d$_6$) δ10.22 (s, 1H), 8.46 (d, J=5.7 Hz, 1H), 8.14 (s, 0.4HCOOH), 7.80 (d, J=2.5 Hz, 1H), 7.30 (t, J=2.2 Hz, 1H), 7.19 (t, J=8.0 Hz, 1H), 7.15-7.08 (m, 1H), 7.04 (dd, J=5.7, 2.6 Hz, 1H), 6.67-6.57 (m, 1H), 4.90 (t, J=5.4 Hz, 1H), 4.44 (s, 2H), 4.03 (t, J=4.7 Hz, 2H), 3.69 (s, 3H), 3.69-3.64 (m, 2H), 3.37 (s, 3H), 3.21 (t, J=7.3 Hz, 2H), 2.85 (t, J=7.8 Hz, 2H), 2.05-1.93 (m, 2H).

Example 1.286

Synthesis of N-(3-fluorophenyl)-2-({2-[4-(2-hydroxy-2-methylpropoxy)pyridin-2-yl]-5H,6H,7H-cyclopenta[d]pyrimidin-4-yl}(methyl)amino)acetamide (Compound 280)

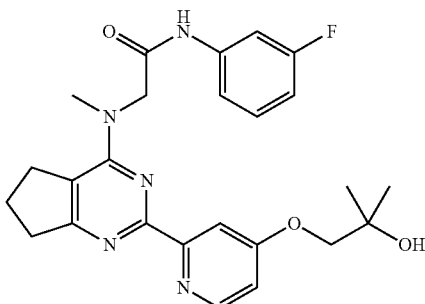

Scheme 117

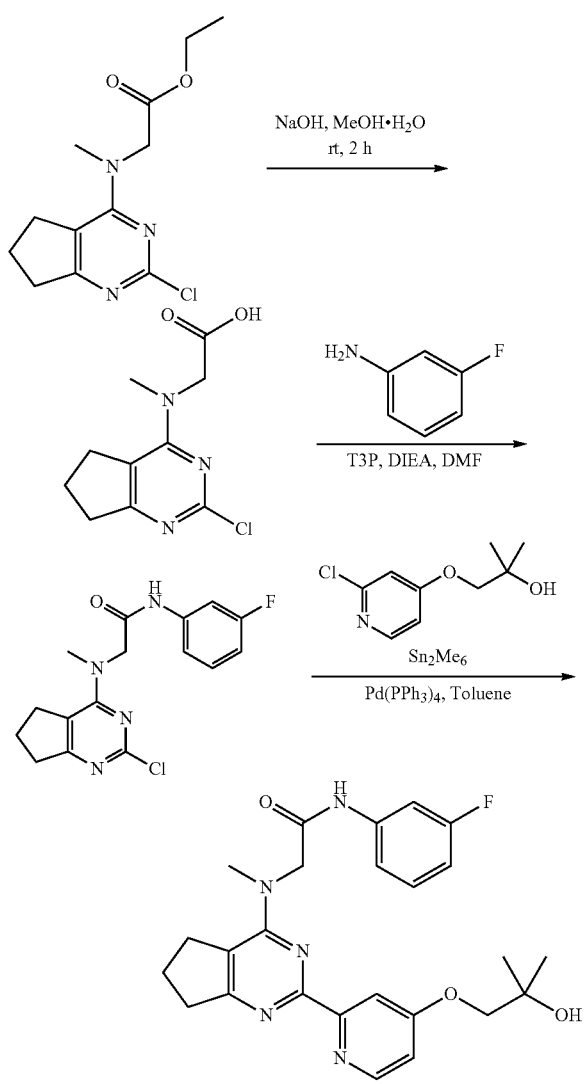

Step 1
Into a 100-mL round-bottom flask were placed a mixture of ethyl N-(2-chloro-6,7-dihydro-5H-cyclopenta[d]pyrimidin-4-yl)-N-methylglycinate (3.00 g, 11.1 mmol, 1.00 equiv), MeOH (30.0 mL), H2O (6.00 mL), NaOH (889 mg, 0.022 mmol, 2.00 equiv). The resulting solution was stirred for 2 hours at room temperature. The resulting mixture was concentrated. The resulting solution was diluted with 50 mL of H$_2$O. The pH value of the solution was adjusted to 4 with HCl (2 mol/L). The solids were collected by filtration and concentrated. This resulted in 1.3 g (48.36%) of N-(2-chloro-6,7-dihydro-5H-cyclopenta[d]pyrimidin-4-yl)-N-methylglycine as a white solid. LCMS (ES) [M+1]+ m/z 270.

Step 2
Into a 50-mL round-bottom flask were was placed N-(2-chloro-5H,6H,7H-cyclopenta[d]pyrimidin-4-yl)-N-methylglycine (3.7 g, 15.29 mmol, 1.00 equiv), DMF (30.00 mL), HATU (6.97 g, 18.34 mmol, 1.20 equiv), DIEA (5.92 g, 45.86 mmol, 3.00 equiv), 3-fluoroaniline (2.04 g, 18.34 mmol, 1.20 equiv). The resulting solution was stirred for 2 hr at 25° C. The resulting solution was extracted with 3×100 mL of ethyl acetate and the organic layers combined. The resulting mixture was washed with 3×100 of brine and concentrated under vacuum. The residue was applied onto a silica gel column with DCM/MeOH (10:1). This resulted in 3.20 g (62.50%) of 2-([2-chloro-5H,6H,7H-cyclopenta[d]pyrimidin-4-yl](methyl)amino)-N-(3-fluorophenyl)acetamide as yellow solid. LCMS (ES) [M+1]+ m/z 335.

Step 3
Into a 40-mL vial purged and maintained with an inert atmosphere of nitrogen were placed 1-[(2-chloropyridin-4-yl)oxy]-2-methylpropan-2-ol (1.00 g, 4.96 mmol, 1.00 equiv), Sn$_2$Me$_6$ (1.71 g, 5.21 mmol, 1.05 equiv), toluene (30 mL), Pd(PPh$_3$)$_4$ (0.57 g, 0.50 mmol, 0.10 equiv). The resulting solution was stirred for 2 hr at 100° C. To this was added 2-([2-chloro-5H,6H,7H-cyclopenta[d]pyrimidin-4-yl](methyl)amino)-N-(3-fluorophenyl)acetamide (1.16 g, 3.471 mmol, 0.7 equiv), Pd(PPh$_3$)$_4$ (0.57 g, 0.496 mmol, 0.10 equiv). The resulting solution was stirred for overnight at 100° C. The resulting mixture was concentrated under vacuum. The residue was applied onto a silica gel column with dichloromethane/methanol (20:1). The crude product was purified by Prep-HPLC with the following conditions: Column, Sunfire Prep C18 OBD Column, 50*250 mm, 5 μm 10 nm; mobile phase A, Water (0.1% FA) and mobile phase B, AcCN (5% mobile Phase B up to 40% in 15 min); This resulted in 48.2 mg (2.09%) of N-(3-fluorophenyl)-2-({2-[4-(2-hydroxy-2-methylpropoxy)pyridin-2-yl]-5H,6H,7H-cyclopenta[d]pyrimidin-4-yl}(methyl)amino)acetamide as a white solid. LCMS (ES) [M+1]+ m/z 466. $^1$H NMR (300 MHz, DMSO-d$_6$) δ 10.43 (s, 1H), 8.44 (d, J=5.6 Hz, 1H), 7.78 (d, J=2.5 Hz, 1H), 7.60-7.49 (m, 1H), 7.37-7.24 (m, 2H), 7.02 (dd, J=5.6, 2.6 Hz, 1H), 6.92-6.80 (m, 1H), 4.65 (s, 1H), 4.44 (s, 2H), 3.80 (s, 2H), 3.36 (s, 3H), 3.21 (t, J=7.3 Hz, 2H), 2.84 (t, J=7.8 Hz, 2H), 2.07-1.99 (m, 2H), 1.17 (s, 6H).

Example 1.287

Synthesis of 2-{[2-(4-methoxypyridin-2-yl)-5H,6H,7H-cyclopenta[d]pyrimidin-4-yl](methyl)amino}-N-(1-methyl-6-oxo-1,6-dihydropyridin-3-yl)acetamide (Compound 281)

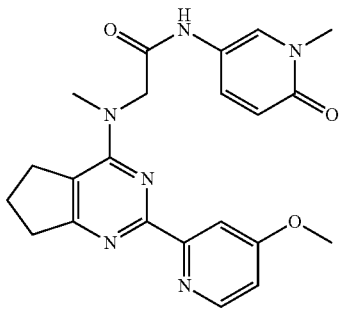 [SMILES: COc1ccnc(-c2nc3c(c(N(C)CC(=O)Nc4ccc(=O)n(C)c4)n2)CCC3)c1]

Compound 281 was synthesized similar to compound 135 replacing oxolan-3-amine with 5-amino-1-methylpyridin-2-one. LCMS (ES) [M+1]+ m/z: 421; $^1$H-NMR (300 MHz, DMSO-d$_6$, ppm): δ 10.01 (s, 1H), 8.46 (d, J=5.6 Hz, 1H), 8.07 (d, J=2.8 Hz, 1H), 7.78 (d, J=2.6 Hz, 1H), 7.40 (dd, J=9.7, 2.9 Hz, 1H), 7.02 (dd, J=5.6, 2.6 Hz, 1H), 6.38 (d, J=9.6 Hz, 1H), 4.35 (s, 2H), 3.83 (s, 3H), 3.37 (s, 3H), 3.35 (s, 3H), 3.20 (t, J=7.3 Hz, 2H), 2.84 (t, J=7.8 Hz, 2H), 2.04-1.99 (m, 2H).

Example 1.288

Synthesis of 2-[(2-{2H,3H-[1,4]dioxino[2,3-c]pyridin-7-yl}-5H,6H,7H-cyclopenta[d]pyrimidin-4-yl)(methyl)amino]-N-(3-fluorophenyl)acetamide (Compound 282)

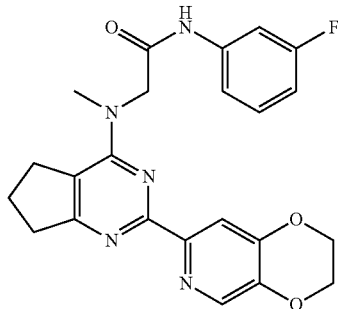 [SMILES: CN(CC(=O)Nc1cccc(F)c1)c1nc(-c2cc3c(cn2)OCCO3)nc2c1CCC2]

Compound 282 was synthesized similar to compound 280 by replacing 1-[(2-chloropyridin-4-yl)oxy]-2-methylpropan-2-ol with 7-bromo-2H,3H-[1,4]dioxino[2,3-c]pyridine. LCMS (ES) [M+1]$^+$ m/z: 436; $^1$H-NMR (300 MHz, DMSO-d$_6$, ppm): δ 10.42 (s, 1H), 8.16 (0.3 HCOOH), 8.14 (s, 1H), 7.77 (s, 1H), 7.55 (dd, J=12.0, 2.1 Hz, 1H), 7.38-7.25 (m, 2H), 6.92-6.80 (m, 1H), 4.45 (s, 2H), 4.41 (s, 4H), 3.35 (s, 3H), 3.18 (t, J=7.3 Hz, 2H), 2.80 (t, J=7.8 Hz, 2H), 2.04-1.94 (m, 2H).

Example 1.289

Synthesis of 2-{[2-(isoquinolin-3-yl)-5H,6H,7H-cyclopenta[d]pyrimidin-4-yl](methyl)amino}-N-[5-(trifluoromethoxy)pyridin-3-yl]acetamide (Compound 283)

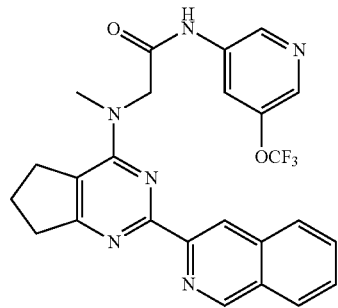 [SMILES: CN(CC(=O)Nc1cncc(OC(F)(F)F)c1)c1nc(-c2cc3ccccc3cn2)nc2c1CCC2]

Compound 283 was synthesized similar to compound 135 by replacing of 4-methoxy-2-(tributylstannyl)pyridine with 3-(trimethylstannyl)isoquinoline and replacing oxolan-3-amine with 3-amino-5-trifluoromethoxypyridine. LCMS (ES) [M+1]$^+$ m/z: 495. $^1$H NMR (300 MHz, Chloroform-d) δ 10.96 (s, 1H), 9.33 (s, 1H), 8.80 (d, J=2.1 Hz, 1H), 8.71 (s, 1H), 8.33 (d, J=2.5 Hz, 1H), 8.23 (s, 1H), 8.14 (d, J=7.7 Hz, 1H), 7.78-7.69 (m, 3H), 4.51 (s, 2H), 3.44 (s, 3H), 3.24 (m, 2H), 2.88 (m, 2H), 2.05 (m, 2H).

Example 1.290

Synthesis of 2 2-({2-[4-(2-hydroxyethoxy)pyridin-2-yl]-5H,6H,7H-cyclopenta[d]pyrimidin-4-yl}(methyl)amino)-N-(5-methylpyrazin-2-yl)acetamide (Compound 284)

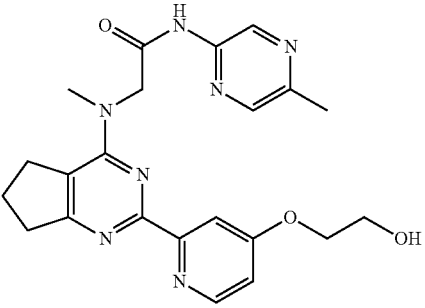 [SMILES: Cc1cnc(NC(=O)CN(C)c2nc(-c3cc(OCCO)ccn3)nc3c2CCC3)cn1]

Compound 284 was synthesized similar to compound 44 by replacing of tert-butylamine with 5-methylpyrazin-2-amine. LCMS (ES) [M+1]$^+$ m/z: 436.2. $^1$H NMR (300 MHz, Chloroform-d) δ 9.59 (br, 1H), 9.40 (s, 1H), 8.62-8.61 (m, 1H), 8.08 (s, 1H), 7.92 (s, 1H), 6.89-6.88 (s, 1H), 4.43-4.42 (m, 2H), 4.21-4.20 (m, 2H), 4.01-4.00 (m, 2H), 3.28 (s, 3H), 3.03-3.01 (m, 2H), 2.76-2.75 (m, 2H), 2.49 (s, 3H), 2.13-4.11 (m, 2H).

Example 1.291

Synthesis of 2-({2-[4-(2-hydroxyethoxy)pyridin-2-yl]-5H,6H,7H-cyclopenta[d]pyrimidin-4-yl}(methyl)amino)-N-(6-methoxypyridazin-3-yl)acetamide (Compound 285)

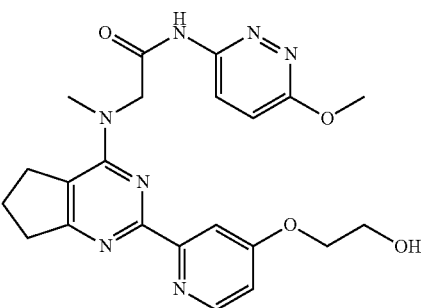

Compound 285 was synthesized similar to compound 44 by replacing of tert-butylamine with 6-methoxypyridazin-3-amine. LCMS (ES) [M+1]$^+$ m/z: 452. $^1$H NMR (300 MHz, DMSO-d$_6$, ppm) δ 11.15 (s, 1H), 8.41 (d, J=5.7 Hz, 1H), 8.21 (d, J=9.6 Hz, 1H), 8.15 (HCOOH), 7.74 (d, J=2.7 Hz, 1H), 7.22 (d, J=9.6 Hz, 1H), 6.98 (dd, J=5.7, 2.7 Hz, 1H), 4.85 (br, 1H), 4.55 (s, 2H), 4.00-3.97 (m, 5H), 3.66 (t, J=4.8 Hz, 2H), 3.36 (s, 3H), 3.21 (t, J=7.2 Hz, 2H), 2.83 (t, J=7.8 Hz, 2H), 2.07-1.96 (m, 2H).

Example 1.292

Synthesis of 2-({2-[4-(2-hydroxyethoxy)pyridin-2-yl]-5H,6H,7H-cyclopenta[d]pyrimidin-4-yl}(methyl)amino)-N-(6-methylpyridazin-3-yl)acetamide (Compound 286)

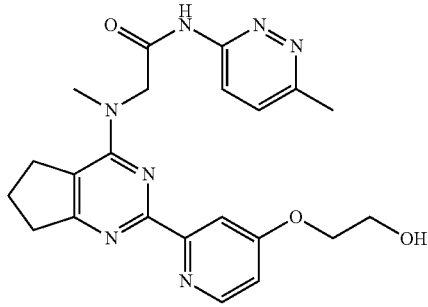 [SMILES: Cc1ccc(NC(=O)CN(C)c2nc(-c3cc(OCCO)ccn3)nc3c2CCC3)nn1]

Compound 286 was synthesized similar to compound 44 by replacing tert-butylamine with 6-methypyridazin-3-amine. LCMS (ES) [M+1]+ m/z: 436. $^1$H NMR (300 MHz, DMSO-d$_6$, ppm δ 11.23 (s, 1H), 8.40 (d, J=5.6 Hz, 1H), 8.15 (d, 9.4 Hz), 8.14 (HCOOH), 7.71 (d, J=2.6 Hz, 1H), 7.52 (d, J=9.2 Hz, 1H), 6.96 (dd, J=5.6, 2.5 Hz, 1H), 4.86 (s, 1H), 4.55 (s, 2H), 3.97 (t, J=4.8 Hz, 2H), 3.63 (s, 2H), 3.35 (s, 2H), 3.21 (t, J=7.5 Hz, 2H), 2.83 (t, J=7.9 Hz, 2H), 2.55 (s, 3H), 2.06-1.95 (m, 2H).

Example 1.293

Synthesis of 2-{[2-(4-methoxypyridin-2-yl)-5H,6H,7H-cyclopenta[d]pyrimidin-4-yl](methyl)amino}-N-(1-methyl-2-oxo-1,2-dihydropyridin-4-yl)acetamide (Compound 287)

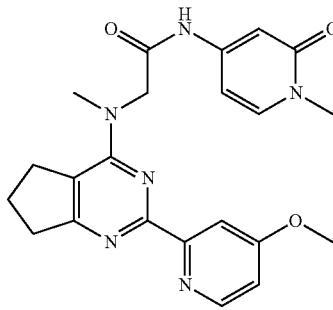

Compound 287 was synthesized similar to compound 135 by replacing oxolan-3-amine with 4-amino-1-methylpyridin-2-one hydrochloride. LCMS (ES) [M+1]+ m/z: 421; $^1$H-NMR (300 MHz, DMSO-d$_6$, ppm): δ 10.36 (s, 1H), 8.44 (d, J=5.6 Hz, 1H), 7.74 (d, J=2.5 Hz, 1H), 7.58 (d, J=7.4 Hz, 1H), 7.00 (dd, J=5.6, 2.6 Hz, 1H), 6.71 (d, J=2.2 Hz, 1H), 6.39 (dd, J=7.4, 2.3 Hz, 1H), 4.42 (s, 2H), 3.80 (s, 3H), 3.36 (s, 3H), 3.33 (s, 3H), 3.20 (t, J=7.3 Hz, 2H), 2.84 (t, J=7.7 Hz, 2H), 2.04-1.99 (m, 2H).

Example 1.294

Synthesis of 2-[methyl(2-{1H-pyrazolo[3,4-c]pyridin-5-yl}-5H,6H,7H-cyclopenta[d]pyrimidin-4-yl)amino]-N-[6-(trifluoromethyl)pyridin-3-yl]acetamide (Compound 288)

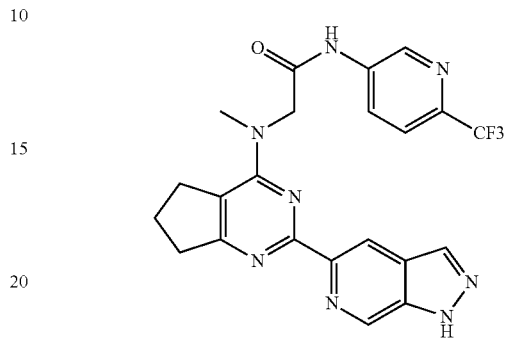

Compound 288 was synthesized similar to compound 135 by replacing 4-methoxy-2-(tributylstannyl)pyridine with 1-(oxan-2-yl)-5-(tributylstannyl)-1H-pyrazolo[3,4-c]pyridine and by replacing oxolan-3-amine with 6-trifluoropyridin-3-amine. LCMS (ES+): [M+H]+=469.1. $^1$H NMR (400 MHz, DMSO-d6) δ 11.71 (s, 1H), 9.20 (s, 1H), 9.11 (s, 1H), 9.05 (s, 1H), 8.40 (d, J=8.7 Hz, 1H), 8.29 (s, 1H), 7.86 (d, J=8.6 Hz, 1H), 4.83 (s, 2H), 3.61 (s, 2H), 3.35-3.32 (m, 2H), 3.11-3.04 (m, 2H), 2.18-2.05 (m, 2H).

Example 1.295

Synthesis of N-(4-fluorophenyl)-2-[methyl(2-{1H-pyrazolo[3,4-c]pyridin-5-yl}-5H,6H,7H-cyclopenta[d]pyrimidin-4-yl)amino]acetamide (Compound 289)

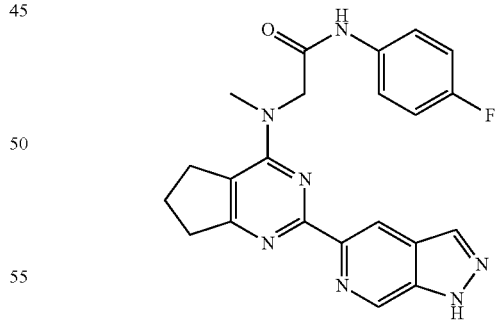

Compound 289 was synthesized similar to compound 135 by replacing 4-methoxy-2-(tributylstannyl)pyridine with 1-(oxan-2-yl)-5-(tributylstannyl)-1H-pyrazolo[3,4-c]pyridine and by replacing oxolan-3-amine with 4-fluoroaniline. LCMS (ES+): [M+H]+=418.1. $^1$H NMR (400 MHz, DMSO-d6) δ 10.65 (s, 1H), 9.15 (s, 1H), 8.88 (s, 1H), 8.20 (s, 1H), 7.73-7.67 (m, 2H), 7.18-7.12 (m, 2H), 4.60 (s, 2H), 3.51 (s, 3H), 3.26-3.24 (m, 2H), 3.01-2.96 (m, 2H), 2.12-2.03 (m, 2H).

Example 1.296

Synthesis of 2-({2-[4-(2-hydroxyethoxy)pyridin-2-yl]-5H,6H,7H-cyclopenta[d]pyrimidin-4-yl}(methyl)amino)-N-(5-methoxypyrazin-2-yl)acetamide (Compound 290)

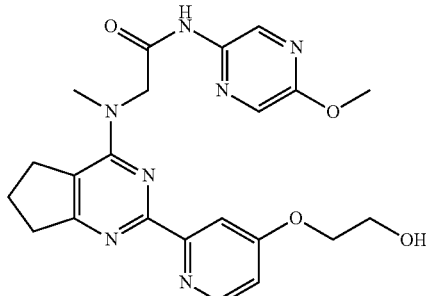

Compound 290 was synthesized similar to compound 44 by replacing tert-butylamine with 5-methoxypyrazin-2-amine. LCMS (ES) [M+1]+ m/z: 452. ¹H NMR (300 MHz, DMSO-d₆, ppm) δ 10.79 (s, 1H), 8.81 (s, 1H), 8.41 (d, J=5.5 Hz, 1H), 8.11 (d, J=1.5 Hz, 1H), 7.73 (d, J=2.6 Hz, 1H), 6.97 (dd, J=5.6, 2.6 Hz, 1H), 4.85 (br, 1H), 4.58 (s, 2H), 4.00 (t, J=4.7 Hz, 2H), 3.85 (s, 3H), 3.71-3.63 (m, 2H), 3.41 (s, 3H), 3.33-3.15 (m, 2H), 2.83 (t, J=7.9 Hz, 2H), 2.08-1.88 (m, 2H).

Example 1.297

Synthesis of 2-({2-[4-(2-hydroxyethoxy)pyridin-2-yl]-5H,6H,7H-cyclopenta[d]pyrimidin-4-yl}(methyl)amino)-N-(2-methylpyrimidin-5-yl)acetamide (Compound 291)

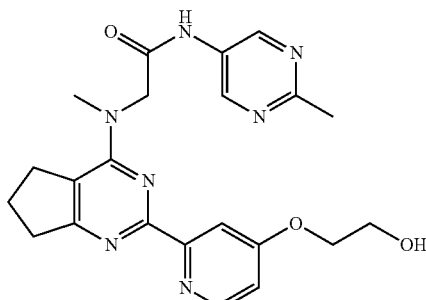

Compound 291 was synthesized similar to compound 44 by replacing tert-butylamine with 2-methylpyrimidin-5-amine. LCMS (ES) [M+1]+ m/z: 436. ¹H NMR (300 MHz, DMSO-d₆, ppm) δ10.73 (s, 1H), 8.89 (s, 2H), 8.42 (d, J=5.6 Hz, 1H), 8.36 (s, 1H), 7.76 (d, J=2.5 Hz, 1H), 7.01 (dd, J=5.7, 2.6 Hz, 1H), 4.45 (s, 2H), 4.04 (t, J=4.8 Hz, 2H), 3.70 (q, J=5.0 Hz, 2H), 3.36 (s, 3H), 3.22 (t, J=7.3 Hz, 2H), 2.84 (t, J=7.8 Hz, 2H), 2.55 (s, 3H), 2.15-1.96 (m, 2H).

Example 1.298

Synthesis of 2-({2-[4-(2-hydroxyethoxy)pyridin-2-yl]-5H,6H,7H-cyclopenta[d]pyrimidin-4-yl}(methyl)amino)-N-(3-methylphenyl)acetamide (Compound 292)

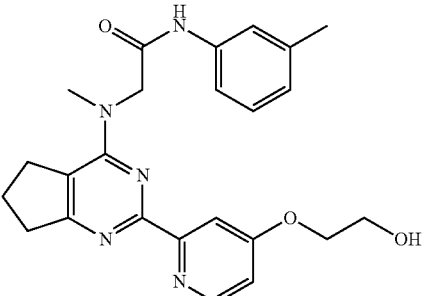

Compound 292 was synthesized similar to compound 44 by replacing tert-butylamine with m-toluidine. LCMS (ES) [M+1]+ m/z: 434. ¹H NMR (300 MHz, DMSO-d₆, ppm) δ 10.12 (s, 1H), 8.44 (d, J=5.6 Hz, 1H), 7.79 (d, J=2.5 Hz, 1H), 7.46-7.33 (m, 2H), 7.19-7.13 (m, 1H), 7.00 (dd, J=5.6, 2.5 Hz, 1H), 6.85 (d, J=7.5 Hz, 1H), 4.88 (t, J=5.4 Hz, 1H), 4.42 (s, 2H), 4.02 (t, J=4.7 Hz, 2H), 3.66 (q, J=5.0 Hz, 2H), 3.36 (s, 3H), 3.20 (t, J=7.3 Hz, 2H), 2.83 (t, J=7.9 Hz, 2H), 2.25 (s, 3H), 2.07-1.96 (m, 2H).

Example 1.299

Synthesis of 2-({2-[4-(2-aminoethoxy)pyridin-2-yl]-5H,6H,7H-cyclopenta[d]pyrimidin-4-yl}(methyl)amino)-N-(3-fluorophenyl)acetamide (Compound 293)

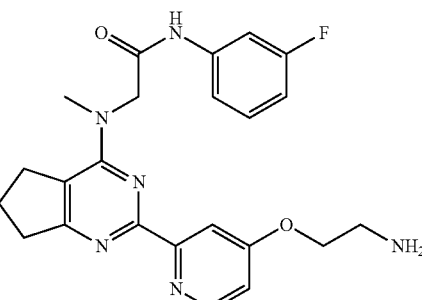

Scheme 118

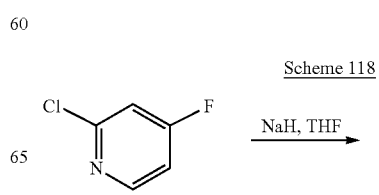

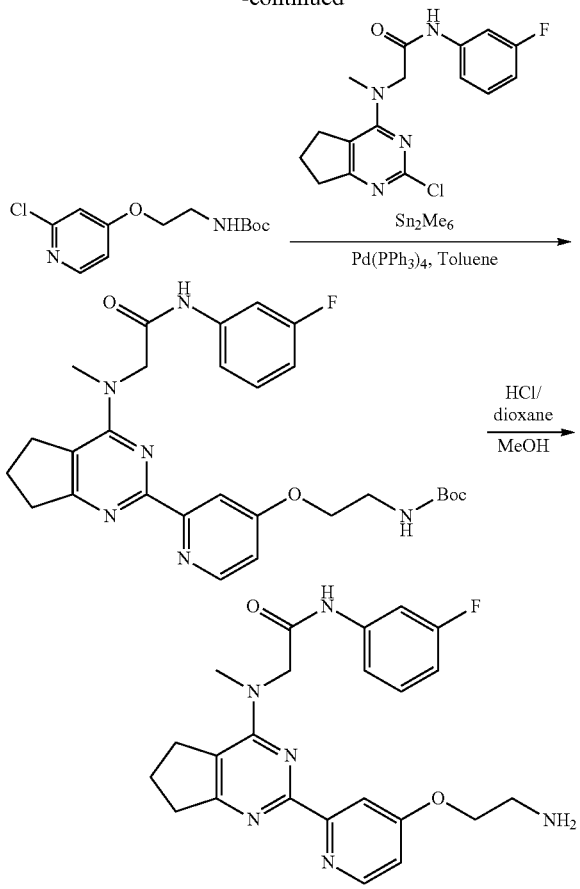

Step 1

Into a 50-mL 3-necked round-bottom flask were placed tert-butyl N-(2-hydroxyethyl)carbamate (1.47 g, 9.12 mmol, 1.20 equiv) and THF (10 mL). This was followed by the addition of NaH (0.22 g, 9.17 mmol, 1.20 equiv) at 0° C. The resulting solution was stirred for 30 min at 0° C. and was added 2-chloro-4-fluoropyridine (1.00 g, 7.60 mmol, 1.00 equiv). After stirred for 2 hr at 25° C., the reaction was quenched by the addition of 50 mL of water. The resulting mixture was extracted with 3×100 mL of ethyl acetate, the organic layers were combined, washed with 3×100 ml of brine, dried over anhydrous sodium sulfate. The solids were filtered out and the filtrate was concentrated under vacuum. This resulted in 1.5 g (49.34%) of tert-butyl N-[2-[(2-chloropyridin-4-yl)oxy]ethyl]carbamate as yellow oil. LCMS (ES) [M+1]+ m/z 273.

Step 2. Into a 40-mL vial purged and maintained with an inert atmosphere of nitrogen were placed tert-butyl N-[2-[(2-chloropyridin-4-yl)oxy]ethyl]carbamate (1.00 g, 3.67 mmol, 1.00 equiv), Toluene (30 mL), Sn₂Me₆ (1.26 g, 3.85 mmol, 1.05 equiv) and Pd(PPh₃)₄ (0.42 mg, 0.36 mmol, 0.1 equiv). The resulting solution was stirred for 4 h at 100° C. To this was added C2-([2-chloro-5H,6H,7H-cyclopenta[d]pyrimidin-4-yl](methyl)amino)-N-(3-fluorophenyl)acetamide (0.86 g, 2.57 mmol, 0.7 equiv), Pd(PPh₃)₄ (0.42 g, 0.36 mmol, 0.1 equiv). After stirred for overnight at 100° C., the mixture was concentrated under vacuum. The residue was applied onto a silica gel column with dichloromethane/methanol (20:1). This resulted in 300 mg (15.25%) of tert-butyl N-[2-([2-[4-([[(3-fluorophenyl)carbamoyl]methyl](methyl)amino)-5H,6H,7H-cyclopenta[d]pyrimidin-2-yl]pyridin-4-yl]oxy)ethyl]carbamate as brown oil. LCMS (ES) [M+1]+ m/z 537.

Step 3

Into a 50-mL round-bottom flask were placed tert-butyl N-[2-([2-[4-([[(3-fluorophenyl)carbamoyl]methyl](methyl)amino)-5H,6H,7H-cyclopenta[d]pyrimidin-2-yl]pyridin-4-yl]oxy)ethyl]carbamate (300 mg, 1.00 equiv), DCM (2 mL) and HCl (gas) in 1,4-dioxane (2 mL). The resulting solution was stirred for 2 hr at 25° C. The resulting mixture was concentrated under vacuum. The residue was dissolved in 5 mL of MeOH. The crude product was purified by Prep-HPLC with the following conditions: Column, Sunfire Prep C18 OBD Column, 50*250 mm, 5 μm 10 nm; mobile phase A, Water (0.1% FA) and mobile phase B, AcCN (5% mobile Phase B up to 35% in 15 min); Detector, UV 254 nm. This resulted in 60.5 mg of 2-({2-[4-(2-aminoethoxy)pyridin-2-yl]-5H,6H,7H-cyclopenta[d]pyrimidin-4-yl}(methyl)amino)-N-(3-fluorophenyl)acetamide as a white solid. LCMS (ES) [M+1]+ m/z 437. ¹H NMR (300 MHz, DMSO-d₆): δ 10.56 (s, 1H), 8.69 (d, J=6.0 Hz, 1H), 8.07 (br, 3H), 7.96 (d, J=2.6 Hz, 1H), 7.65-7.54 (m, 1H), 7.44-7.27 (m, 3H), 6.97-6.84 (m, 1H), 4.65 (s, 2H), 4.37 (s, 2H), 3.48 (s, 3H), 3.26 (s, 4H), 3.00 (t, J=7.9 Hz, 2H), 2.08-3.02 (m, 2H).

Example 1.300

Synthesis of 2-[(2-{4-[2-(dimethylamino)ethoxy]pyridin-2-yl}-5H,6H,7H-cyclopenta[d]pyrimidin-4-yl)(methyl)amino]-N-(3-fluorophenyl)acetamide (Compound 294)

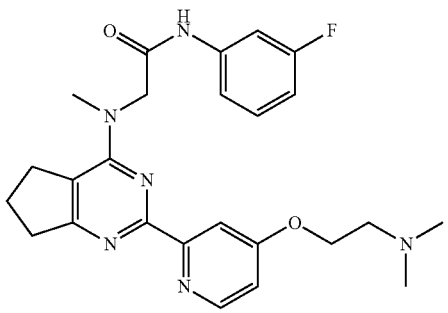 [SMILES: CN(C)CCOc1ccnc(-c2nc3c(c(N(C)CC(=O)Nc4cccc(F)c4)n2)CCC3)c1]

Compound 294 was synthesized similar to compound 348 replacing tert-butylamine with 3-fluoroaniline. LCMS (ES) [M+1]+ m/z: 465. ¹H NMR (300 MHz, DMSO-d₆) δ 10.44 (s, 1H), 8.43 (d, J=5.6 Hz, 1H), 8.18 (s, 1H), 7.75 (d, J=2.5 Hz, 1H), 7.60-7.50 (m, 1H), 7.38-7.25 (m, 2H), 7.00 (dd, J=5.6, 2.6 Hz, 1H), 6.93-6.80 (m, 1H), 4.43 (s, 2H), 4.07 (t, J=5.5 Hz, 2H), 3.37 (s, 3H), 3.21 (t, J=7.3 Hz, 2H), 2.83 (t, J=7.8 Hz, 2H), 2.59 (t, J=5.5 Hz, 2H), 2.21 (s, 6H), 2.06-1.96 (m, 2H).

Example 1.301

Synthesis of 2-({2-[4-(2-hydroxyethoxy)pyridin-2-yl]-5H,6H,7H-cyclopenta[d]pyrimidin-4-yl}(methyl)amino)-N-(5-methoxypyrimidin-2-yl)acetamide (Compound 295)

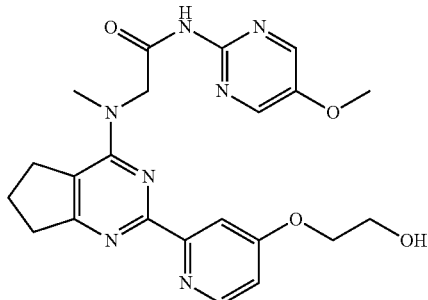

Compound 295 was synthesized similar to compound 44 replacing tert-butylamine with 5-methoxypyrimidin-2-amine. LCMS (ES) [M+1]+ m/z: 452. ¹H NMR (300 MHz, DMSO-d$_6$) δ 10.67 (s, 1H), 8.47-8.39 (m, 3H), 7.77 (d, J=2.6 Hz, 1H), 6.98 (dd, J=5.6, 2.6 Hz, 1H), 4.88 (s, 1H), 4.62 (s, 2H), 4.02 (t, J=4.7 Hz, 2H), 3.88 (s, 3H), 3.67 (t, J=4.7 Hz, 2H), 3.33 (s, 3H), 3.19 (t, J=7.4 Hz, 2H), 2.83 (t, J=7.8 Hz, 2H), 2.15-1.96 (m, 2H).

Example 1.302

Synthesis of 2-({2-[4-(2-hydroxyethoxy)pyridin-2-yl]-5H,6H,7H-cyclopenta[d]pyrimidin-4-yl}(methyl)amino)-N-(1-methyl-1H-pyrazol-4-yl)acetamide (Compound 296)

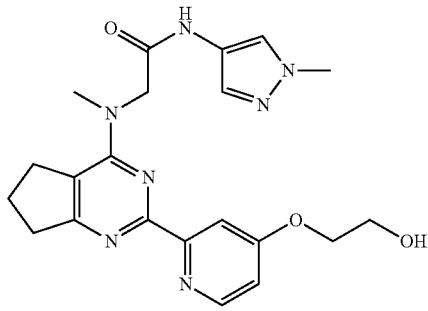 [SMILES: CN(CC(=O)Nc1cnn(C)c1)c1nc(-c2cc(OCCO)ccn2)nc2c1CCC2]

Compound 296 was synthesized similar to compound 44 replacing tert-butylamine with 1-methylpyrazol-4-amine. LCMS (ES) [M+1]+ m/z: 424. ¹H NMR (300 MHz, DMSO-d6) δ 10.23 (s, 1H), 8.46 (d, J=5.7 Hz, 1H), 7.84 (s, 1H), 7.77 (d, J=2.5 Hz, 1H), 7.40 (s, 1H), 7.02 (dd, J=5.7, 2.3 Hz, 1H), 4.92 (t, J=5.4 Hz, 1H), 4.35 (s, 2H), 4.06 (t, J=4.8 Hz, 2H), 3.76 (s, 3H), 3.72 (d, J=5.0 Hz, 2H), 3.32 (s, 3H), 3.19 (t, J=7.3 Hz, 2H), 2.83 (t, J=7.8 Hz, 2H), 2.06-1.95 (m, 2H).

Example 1.303

Synthesis of 2-({2-[6-(hydroxymethyl)isoquinolin-3-yl]-5H,6H,7H-cyclopenta[d]pyrimidin-4-yl}(methyl)amino)-N-(6-methylpyridin-3-yl)acetamide (Compound 297)

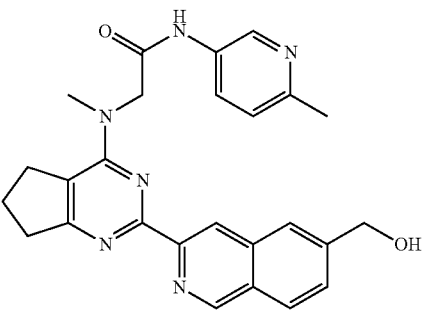 [SMILES: Cc1ccc(NC(=O)CN(C)c2nc(-c3cc4cc(CO)ccc4cn3)nc3c2CCC3)cn1]

Compound 297 was synthesized similar to compound 270 replacing 5-[[(tert-butyldimethylsilyl)oxy]methyl]-3-(trimethylstannyl)isoquinoline with 6-(((tert-butyldimethylsilyl)oxy)methyl)-3-(trimethylstannyl)isoquinoline. LCMS (ES) [M+1]+ m/z: 455. ¹H NMR (300 MHz, DMSO-d6) δ 10.51 (s, 1H), 9.33 (s, 1H), 8.69 (d, J=2.3 Hz, 2H), 8.13 (d, J=8.6 Hz, 1H), 7.96 (dd, J=8.4, 2.6 Hz, 1H), 7.70-7.64 (m, 2H), 7.18 (d, J=8.4 Hz, 1H), 5.49 (t, J=5.5 Hz, 1H), 4.68 (d, J=5.3 Hz, 2H), 4.49 (s, 2H), 3.45 (s, 3H), 3.29-3.22 (m, 2H), 2.96-2.85 (m, 2H), 2.39 (s, 3H), 2.11-2.00 (m, 2H).

Example 1.304

Synthesis of 2-{[2-(5-fluoropyridin-2-yl)-5H,6H,7H-cyclopenta[d]pyrimidin-4-yl](methyl)amino}-N-(6-methylpyridin-3-yl)acetamide (Compound 298)

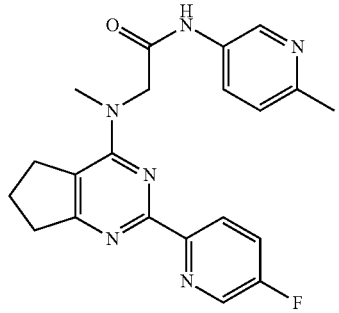 [SMILES: Cc1ccc(NC(=O)CN(C)c2nc(-c3ccc(F)cn3)nc3c2CCC3)cn1]

Compound 298 was synthesized similar to Compound 24 by replacing 2-tributylstannylpyridine with 5-fluoro-2-(tributylstannyl)pyridine and by replacing tert-bytylamine with 6-methylpyridin-3-amine. LCMS (ES+): [M+H]+ =393.1. ¹H NMR (400 MHz, DMSO-d6) δ 10.77 (s, 1H), 8.75 (d, J=2.8 Hz, 1H), 8.69 (d, J=2.6 Hz, 1H), 8.51 (dd, J=8.9, 4.6 Hz, 1H), 7.98-7.87 (m, 2H), 7.25 (d, J=8.4 Hz, 1H), 4.64 (s, 2H), 3.49 (s, 3H), 3.27-3.24 (m, 2H), 3.00-2.95 (m, 2H), 2.42 (s, 3H), 2.12-2.03 (m, 2H).

Example 1.305

Synthesis of N-tert-butyl-2-{[2-(5-fluoropyridin-2-yl)-5H,6H,7H-cyclopenta[d]pyrimidin-4-yl](methyl)amino}acetamide (Compound 299)

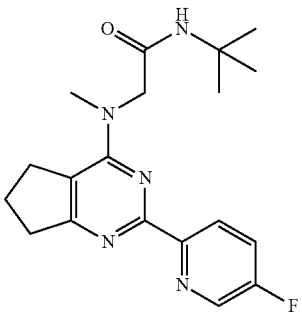 [SMILES: CN(CC(=O)NC(C)(C)C)c1nc(-c2ccc(F)cn2)nc2c1CCC2]

Compound 299 was synthesized similar to Compound 24 by replacing 2-tributylstannylpyridine with 5-fluoro-2-(tributylstannyl)pyridine. LCMS (ES+): [M+H]$^+$=358.1. $^1$H NMR (400 MHz, dmso) δ 8.79 (d, J=2.8 Hz, 1H), 8.55 (dd, J=8.8, 4.6 Hz, 1H), 8.02 (td, J=8.7, 2.9 Hz, 1H), 7.88 (s, 1H), 4.30 (s, 2H), 3.40 (s, 3H), 3.22-3.18 (m, 2H), 3.01-2.93 (m, 2H), 2.12-2.01 (m, 2H), 1.24 (s, 9H).

Example 1.306

Synthesis of N-tert-butyl-2-{[2-(5-chloropyridin-2-yl)-5H,6H,7H-cyclopenta[d]pyrimidin-4-yl](methyl)amino}acetamide (Compound 300)

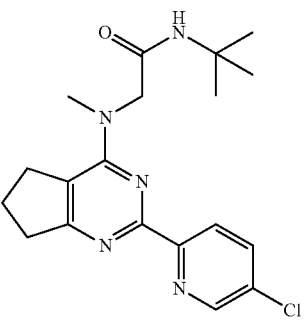 [SMILES: CN(CC(=O)NC(C)(C)C)c1nc(-c2ccc(Cl)cn2)nc2c1CCC2]

Compound 300 was synthesized similar to Compound 24 by replacing 2-tributylstannylpyridine with 5-chloro-2-(tributylstannyl)pyridine. LCMS (ES+): [M+H]$^+$=374. $^1$H NMR (400 MHz, DMSO-d6) δ 8.71 (dd, J=2.5, 0.7 Hz, 1H), 8.38 (dd, J=8.5, 0.7 Hz, 1H), 8.03 (dd, J=8.5, 2.5 Hz, 1H), 7.68 (s, 1H), 4.15 (s, 2H), 3.27 (s, 3H), 3.17-3.10 (m, 2H), 2.86-2.79 (m, 2H), 2.04-1.94 (m, 2H), 1.23 (s, 9H).

Example 1.307

Synthesis of N-tert-butyl-2-[methyl(2-{[1,3]thiazolo[4,5-c]pyridin-6-yl}-5H,6H,7H-cyclopenta[d]pyrimidin-4-yl)amino]acetamide (Compound 301)

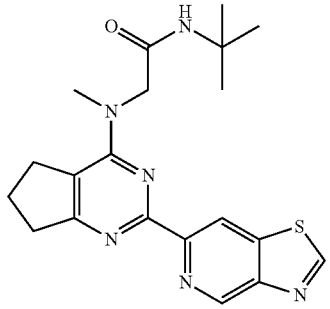 [SMILES: CN(CC(=O)NC(C)(C)C)c1nc(-c2cc3scnc3cn2)nc2c1CCC2]

Compound 301 was synthesized similar to compound 245 replacing 2-chloro-4-(oxetan-3-yloxy)pyridine with 6-bromo-[1,3]thiazolo[4,5-c]pyridine. LCMS (ES) [M+1]$^+$ m/z: 397. $^1$H NMR (300 MHz, DMSO-d6) δ 9.58 (s, 1H), 9.42 (d, J=0.9 Hz, 1H), 9.25 (d, J=0.9 Hz, 1H), 8.14 (0.5 HCOOH), 7.79 (s, 1H), 4.18 (s, 2H), 3.34 (s, 3H), 3.18 (t, J=7.3 Hz, 2H), 2.86 (t, J=7.8 Hz, 2H), 2.05-1.99 (m, 2H), 1.22 (s, 9H).

Example 1.308

Synthesis of 2-({2-[4-(2-hydroxy-2-methylpropoxy)pyridin-2-yl]-5H,6H,7H-cyclopenta[d]pyrimidin-4-yl}(methyl)amino)-N-(6-methylpyridin-3-yl)acetamide (Compound 302)

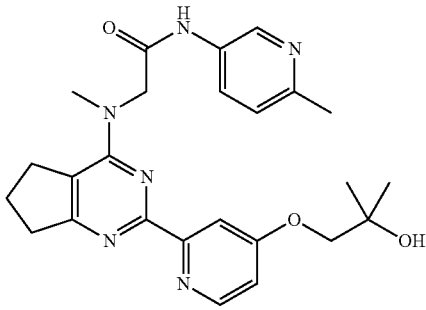 [SMILES: Cc1ccc(NC(=O)CN(C)c2nc(-c3cc(OCC(C)(C)O)ccn3)nc3c2CCC3)cn1]

Compound 302 was synthesized similar to compound 210 replacing 5-amino-2-methoxypyridine with 6-methylpyridin-3-amine. LCMS (ES) [M+1]$^+$ m/z: 463. $^1$H NMR (300 MHz, DMSO-d$_6$) δ 10.36 (s, 1H), 8.60 (d, J=2.6 Hz, 1H), 8.45 (d, J=5.7 Hz, 1H), 8.14 (s, HCOOH), 7.88 (dd, J=8.4, 2.6 Hz, 1H), 7.79 (d, J=2.5 Hz, 1H), 7.17 (d, J=8.4 Hz, 1H), 7.05 (dd, J=5.8, 2.6 Hz, 1H), 4.73 (s, 1H), 4.43 (s, 2H), 3.81 (s, 2H), 3.38 (s, 3H), 3.22 (t, J=7.2 Hz, 2H), 2.85 (t, J=7.8 Hz, 2H), 2.39 (s, 3H), 2.04-1.96 (m, 2H), 1.17 (s, 6H).

Example 1.309

Synthesis of N-tert-butyl-2-{[2-(5-fluoro-4-methylpyridin-2-yl)-5H,6H,7H-cyclopenta[d]pyrimidin-4-yl](methyl)amino}acetamide (Compound 303)

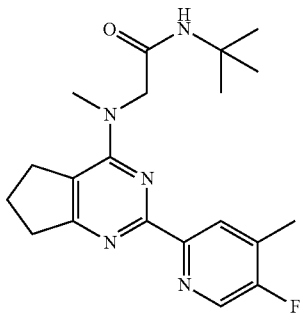 [SMILES: Cc1cc(-c2nc3c(c(N(C)CC(=O)NC(C)(C)C)n2)CCC3)ncc1F]

Compound 303 was synthesized similar to compound 24 by replacing 2-tributylstannylpyridine with 5-fluoro-4-methyl-2-(tributylstannyl)pyridine. LCMS (ES+): [M+H]$^+$ =372.2. $^1$H NMR (400 MHz, DMSO-d6) δ 8.50 (d, J=1.1 Hz, 1H), 8.30 (dd, J=6.5, 0.9 Hz, 1H), 7.69 (s, 1H), 4.14 (s, 2H), 3.27 (s, 3H), 3.17-3.11 (m, 2H), 2.83-2.76 (m, 2H), 2.37 (dd, J=1.7, 0.7 Hz, 3H), 2.02-1.93 (m, 2H), 1.22 (s, 9H).

Example 1.310

Synthesis of N-(6-methoxypyridin-3-yl)-2-[methyl(2-{[1,3]thiazolo[4,5-c]pyridin-6-yl}-5H,6H,7H-cyclopenta[d]pyrimidin-4-yl)amino]acetamide (Compound 304)

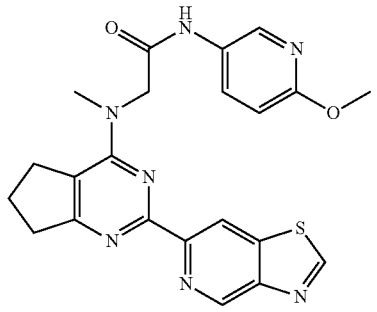 [SMILES: COc1ccc(NC(=O)CN(C)c2nc(-c3cc4scnc4cn3)nc3c2CCC3)cn1]

Compound 304 was synthesized similar to compound 258 replacing 3-chloro-2,6-naphthyridine with 6-bromo-[1,3]thiazolo[4,5-c]pyridine. LCMS (ES) [M+1]$^+$ m/z: 448. $^1$H NMR (300 MHz, DMSO-d6) δ 10.34 (s, 1H), 9.55 (s, 1H), 9.38 (d, J=0.9 Hz, 1H), 9.11 (d, J=0.9 Hz, 1H), 8.39 (d, J=2.6 Hz, 1H), 7.92 (dd, J=8.9, 2.7 Hz, 1H), 6.78 (d, J=8.9 Hz, 1H), 4.44 (s, 2H), 3.79 (s, 3H), 3.42 (s, 3H), 3.23 (t, J=7.2 Hz, 2H), 2.87 (t, J=7.8 Hz, 2H), 2.12-1.95 (m, 2H).

Example 1.311

Synthesis (2R)—N-tert-butyl-2-[methyl({2-[4-(oxetan-3-yloxy)pyridin-2-yl]-5H,6H,7H-cyclopenta[d]pyrimidin-4-yl})amino]propanamide (Compound 305)

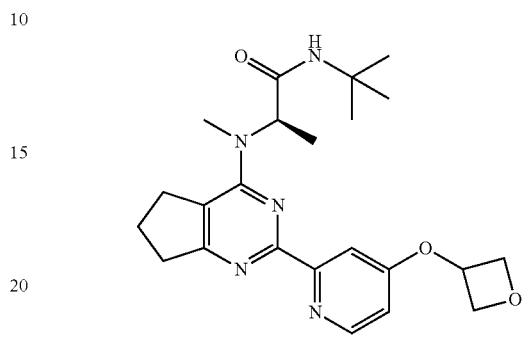

Compound 305 was synthesized similar to compound 101 by replacing 4-methoxy-2-(tributylstannyl)pyridine with 4-(oxetan-3-yloxy)-2-(trimethylstannyl)pyridine. LCMS (ES) [M+1]$^+$ m/z: 414. $^1$H NMR (300 MHz, DMSO-d6) δ 8.49 (d, J=5.6 Hz, 1H), 8.15 (s, HCOOH), 7.90 (d, J=2.5 Hz, 1H), 7.81 (s, 1H), 7.06 (dd, J=5.7, 2.6 Hz, 1H), 5.09 (q, J=7.0 Hz, 1H), 4.16 (t, J=4.9 Hz, 2H), 3.77 (t, J=4.9 Hz, 1H), 3.21-3.01 (m, 2H), 3.11 (s, 3H), 2.95-2.72 (m, 2H), 2.13-1.84 (m, 2H), 1.32 (d, J=7.0 Hz, 3H), 1.20 (s, 9H).

Example 1.312

Synthesis 2-{[2-(5-fluoro-4-methoxypyridin-2-yl)-5H,6H,7H-cyclopenta[d]pyrimidin-4-yl](methyl)amino}-N-(6-methylpyridin-3-yl)acetamide (Compound 306)

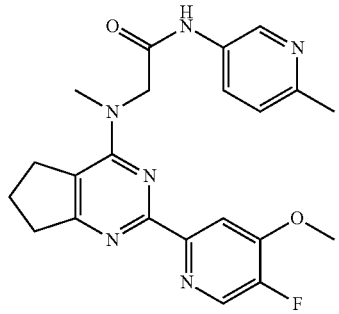 [SMILES: COc1cc(-c2nc3c(c(N(C)CC(=O)Nc4ccc(C)nc4)n2)CCC3)ncc1F]

Compound 306 was synthesized similar to compound 24 by replacing 2-tributylstannylpyridine with 5-fluoro-4-methoxy-2-(tributylstannyl)pyridine and by replacing tert-butylamine with 6-methylpyridin-3-amine. LCMS (ES+): [M+H]$^+$=423.1. $^1$H NMR (400 MHz, DMSO-d6) δ 11.74 (s, 1H), 8.97-8.91 (m, 1H), 8.71 (d, J=2.7 Hz, 1H), 8.28 (d, J=8.1 Hz, 1H), 8.03 (s, 1H), 7.62 (d, J=8.6 Hz, 1H), 4.82 (s, 2H), 3.90 (s, 3H), 3.60 (s, 3H), 3.50-3.46 (m, 2H), 3.09-3.05 (m, 2H), 2.57 (s, 3H), 2.17-2.08 (m, 2H).

Example 1.313

Synthesis N-(3-fluorophenyl)-2-[(2-{4-[(1-hydroxy-cyclopropyl)methoxy]pyridin-2-yl}-5H,6H,7H-cyclopenta[d]pyrimidin-4-yl)(methyl)amino]acetamide (Compound 307)

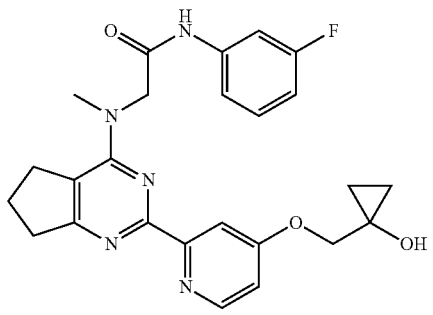 [SMILES: CN(CC(=O)Nc1cccc(F)c1)c1nc(-c2cc(OCC3(O)CC3)ccn2)nc2c1CCC2]

Compound 307 was synthesized similar to compound 252 by replacing 1-(2-hydroxyethyl)pyrrolidine with {1-[(tert-butyldimethylsilyl)oxy]cyclopropyl}methanol. LCMS (ES) [M+1]$^+$ m/z: 464.2. $^1$H NMR (300 MHz, DMSO-d$_6$) δ 10.41 (s, 1H), 8.43 (d, J=5.6 Hz, 1H), 7.84 (d, J=2.5 Hz, 1H), 7.55 (ddd, J=11.4, 3.4, 1.9 Hz, 1H), 7.45-7.21 (m, 2H), 7.10 (dd, J=5.6, 2.5 Hz, 1H), 6.86 (ddt, J=8.8, 5.5, 2.9 Hz, 1H), 4.98 (s, 1H), 4.45 (s, 2H), 3.65 (s, 2H), 3.34 (s, 3H), 3.20 (t, J=7.3 Hz, 2H), 2.83 (t, J=7.8 Hz, 2H), 2.05-1.96 (m, 2H), 0.93 (t, J=6.6 Hz, 2H), 0.86 (d, J=5.0 Hz, 2H).

Example 1.314

Synthesis of N-(6-cyclopropylpyridin-3-yl)-2-({2-[4-(2-hydroxyethoxy)pyridin-2-yl]-5H,6H,7H-cyclopenta[d]pyrimidin-4-yl}(methyl)amino)acetamide (Compound 308)

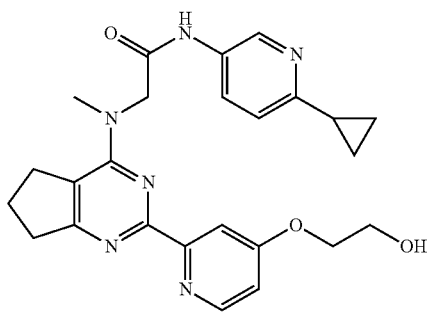 [SMILES: CN(CC(=O)Nc1ccc(C2CC2)nc1)c1nc(-c2cc(OCCO)ccn2)nc2c1CCC2]

Compound 308 was synthesized similar to compound 44 by replacing tert-butylamine with 6-cyclopropyl-3-aminopyridine. LCMS (ES) [M+1]$^+$ m/z: 461. $^1$H NMR (300 MHz, DMSO-d$_6$, ppm) δ 10.34 (s, 1H), 8.55 (d, J=2.5 Hz, 1H), 8.44 (d, J=5.6 Hz, 1H), 8.14 (HCOOH), 7.88 (dd, J=8.5, 2.6 Hz, 1H), 7.78 (d, J=2.5 Hz, 1H), 7.20 (d, J=8.5 Hz, 1H), 7.02 (dd, J=5.6, 2.6 Hz, 1H), 4.95 (s, 1H), 4.42 (s, 2H), 4.03 (t, J=4.8 Hz, 2H), 3.68 (t, J=4.8 Hz, 2H), 3.37 (s, 3H), 3.21 (t, J=7.3 Hz, 2H), 2.84 (t, J=7.9 Hz, 2H), 2.06-1.97 (m, 3H), 0.95-0.77 (m, 4H).

Example 1.315

Synthesis of (2R)-2-({2-[4-(2-hydroxyethoxy)pyridin-2-yl]-5H,6H,7H-cyclopenta[d]pyrimidin-4-yl}(methyl)amino)-N-(6-methoxypyridin-3-yl)propanamide (Compound 309)

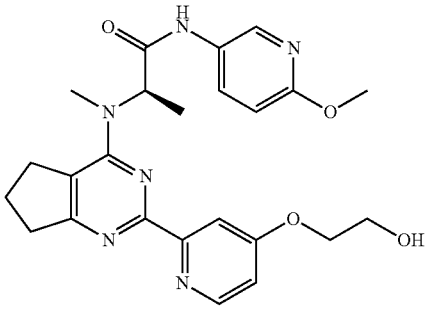 [SMILES: COc1ccc(NC(=O)[C@@H](C)N(C)c2nc(-c3cc(OCCO)ccn3)nc3c2CCC3)cn1]

Compound 309 was synthesized similar to compound 251 replacing 3-fluoroaniline with 5-amino-2-methoxypyridine. LCMS (ES) [M+1]$^+$ m/z: 465. $^1$H NMR (300 MHz, DMSO-d$_6$, ppm) δ 10.43 (s, 1H), 8.48 (d, J=5.6 Hz, 1H), 8.33 (d, J=2.6 Hz, 1H), 7.93-7.83 (m, 2H), 7.07 (dd, J=5.6, 2.6 Hz, 1H), 6.76 (d, J=8.9 Hz, 1H), 5.26 (q, J=6.9 Hz, 1H), 4.94 (t, J=5.4 Hz, 1H), 4.13 (t, J=4.8 Hz, 2H), 3.79 (s, 3H), 3.74 (q, J=4.9 Hz, 2H), 3.20 (s, 3H), 3.24-3.06 (m, 2H), 2.98-2.78 (m, 2H), 2.12-1.92 (m, 2H), 1.46 (d, J=7.0 Hz, 3H).

Example 1.316

Synthesis of (2R)-2-({2-[4-(2-hydroxyethoxy)pyridin-2-yl]-5H,6H,7H-cyclopenta[d]pyrimidin-4-yl}(methyl)amino)-N-(1-methyl-1H-pyrazol-4-yl)propanamide (Compound 310)

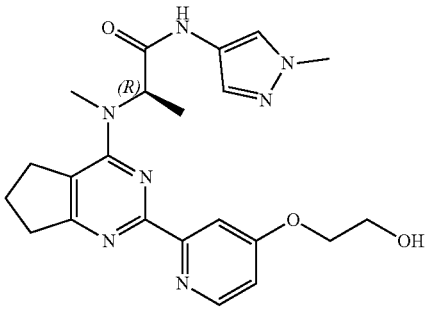

Compound 310 was synthesized similar to compound 251 replacing 3-fluoroaniline with 1-methylpyrazol-4-amine. LCMS (ES) [M+1]$^+$ m/z: 438. $^1$H NMR (300 MHz, DMSO-d$_6$, ppm) δ 10.41 (s, 1H), 8.54 (d, J=5.7 Hz, 1H), 7.88 (d, J=2.6 Hz, 1H), 7.84 (s, 1H), 7.38 (s, 1H), 7.12 (dd, J=5.9, 2.7 Hz, 1H), 5.26 (q, J=7.1 Hz, 1H), 4.96 (t, J=5.2 Hz, 1H), 4.17 (s, 2H), 3.87-3.68 (m, 5H), 3.23-3.09 (m, 5H), 3.03-2.77 (m, 2H), 2.23-1.91 (m, 2H), 1.44 (d, J=7.0 Hz, 3H).

Example 1.317

Synthesis of (2R)—N-tert-butyl-2-({2-[4-(2-hydroxyethoxy)pyridin-2-yl]-5H,6H,7H-cyclopenta[d]pyrimidin-4-yl}(methyl)amino)propanamide (Compound 311)

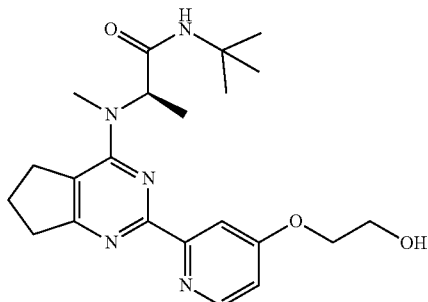

Compound 311 was synthesized similar to compound 251 replacing 3-fluoroaniline with 2-methylpropan-2-amine. LCMS (ES) [M+1]⁺ m/z: 414. ¹H NMR (300 MHz, DMSO-d₆, ppm) δ 8.49 (d, J=5.6 Hz, 1H), 8.15 (s, HCOOH), 7.90 (d, J=2.5 Hz, 1H), 7.81 (s, 1H), 7.06 (dd, J=5.7, 2.6 Hz, 1H), 5.09 (q, J=7.0 Hz, 1H), 4.16 (t, J=4.9 Hz, 2H), 3.77 (t, J=4.9 Hz, 1H), 3.21-3.01 (m, 2H), 3.11 (s, 3H), 2.95-2.72 (m, 2H), 2.13-1.84 (m, 2H), 1.32 (d, J=7.0 Hz, 3H), 1.20 (s, 9H).

Example 1.318

Synthesis of (2R)—N-(6-methoxypyridin-3-yl)-2-[methyl({2-[4-(oxetan-3-yloxy)pyridin-2-yl]-5H,6H,7H-cyclopenta[d]pyrimidin-4-yl})amino]propanamide (Compound 312)

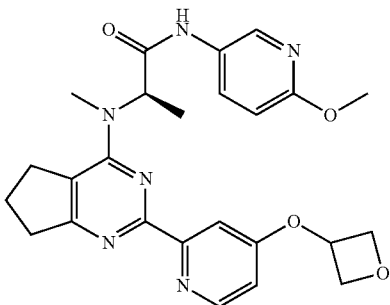

Compound 312 was synthesized similar to compound 245 replacing N-tert-butyl-2-([2-chloro-5H,6H,7H-cyclopenta[d]pyrimidin-4-yl](methyl)amino)acetamide with (2R)-2-([2-chloro-5H,6H,7H-cyclopenta[d]pyrimidin-4-yl](methyl)amino)-N-(6-methoxypyridin-3-yl)propanamide. LCMS (ES) [M+1]⁺ m/z: 477. ¹H NMR (300 MHz, DMSO-d₆, ppm) δ 10.35 (s, 1H), 8.50 (d, J=5.6 Hz, 1H), 8.33 (d, J=2.6 Hz, 1H), 8.15 (s, HCOOH), 7.89 (dd, J=8.9, 2.7 Hz, 1H), 7.73 (d, J=2.6 Hz, 1H), 6.91 (dd, J=5.6, 2.6 Hz, 1H), 6.75 (d, J=8.9 Hz, 1H), 5.50-5.42 (m, 1H), 5.20 (q, J=7.0 Hz, 1H), 4.97 (td, J=6.7, 4.1 Hz, 2H), 4.64-4.53 (m, 2H), 3.79 (s, 3H), 3.33-3.05 (m, 5H), 2.96-2.73 (m, 2H), 2.18-1.86 (m, 2H), 1.47 (d, J=7.0 Hz, 3H).

Example 1.319

Synthesis of N-(4-fluorophenyl)-2-[methyl(2-{1-methyl-1H-pyrazolo[3,4-c]pyridin-5-yl}-5H,6H,7H-cyclopenta[d]pyrimidin-4-yl)amino]acetamide (Compound 313)

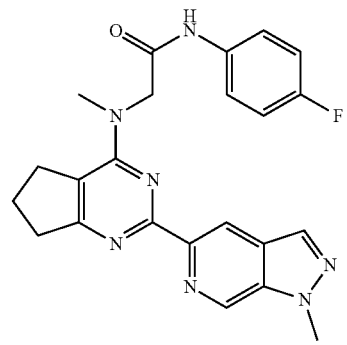 [SMILES: CN(CC(=O)Nc1ccc(F)cc1)c1nc(-c2cc3cnn(C)c3cn2)nc2c1CCC2]

Compound 313 was synthesized similar to compound 24 by replacing 2-tributylstannylpyridine with 1-methyl-5-(tributylstannyl)-1H-pyrazolo[3,4-c]pyridine and by replacing tert-butylamine with 4-fluoroaniline. LCMS (ES+): [M+H]⁺=432.1. ¹H NMR (400 MHz, DMSO-d6) δ 10.70 (s, 1H), 9.37 (s, 1H), 8.95 (s, 1H), 8.26 (s, 1H), 7.71 (dd, J=8.9, 5.0 Hz, 2H), 7.16 (dd, J=8.9 Hz, 2H), 4.69 (s, 2H), 4.27 (s, 3H), 3.58 (s, 3H), 3.39-3.38 (m, 2H), 3.11-3.04 (m, 2H), 2.17-2.06 (m, 2H).

Example 1.320

Synthesis of N-(4-fluorophenyl)-2-[methyl(2-{2-methyl-2H-pyrazolo[3,4-c]pyridin-5-yl}-5H,6H,7H-cyclopenta[d]pyrimidin-4-yl)amino]acetamide (Compound 314)

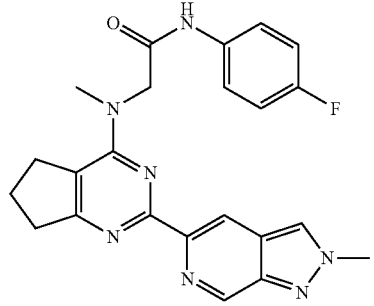 [SMILES: CN(CC(=O)Nc1ccc(F)cc1)c1nc(-c2cc3cn(C)nc3cn2)nc2c1CCC2]

Compound 314 was synthesized similar to compound 24 by replacing 2-tributylstannylpyridine with 2-methyl-5-(tributylstannyl)-1H-pyrazolo[3,4-c]pyridine and by replacing tert-butylamine with 4-fluoroaniline. LCMS (ES+): [M+H]⁺=432.1. ¹H NMR (400 MHz, DMSO-d6) δ 10.77-10.64 (m, 1H), 9.30 (s, 1H), 8.93 (d, J=1.3 Hz, 1H), 8.69 (s, 1H), 7.74-7.65 (m, 2H), 7.15 (dd, J=8.9 Hz, 2H), 4.65 (s, 2H), 4.33 (s, 3H), 3.53 (s, 3H), 3.04-2.99 (m, 2H), 2.13-2.05 (m, 2H).

801

Example 1.321

Synthesis of 2-({2-[4-({[1-(3-fluorophenyl)-1H-1,2,4-triazol-5-yl]methyl}(methyl)amino)-5H,6H,7H-cyclopenta[d]pyrimidin-2-yl]pyridin-4-yl}oxy)ethan-1-ol (Compound 315)

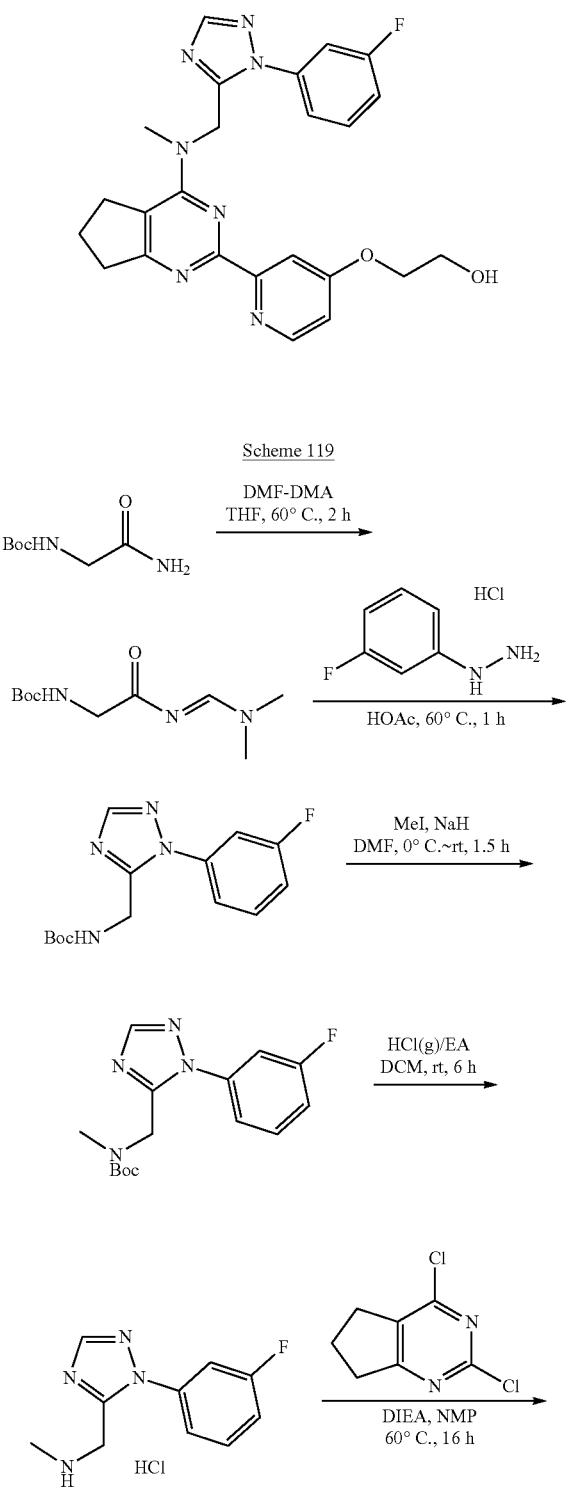

Scheme 119

802

-continued

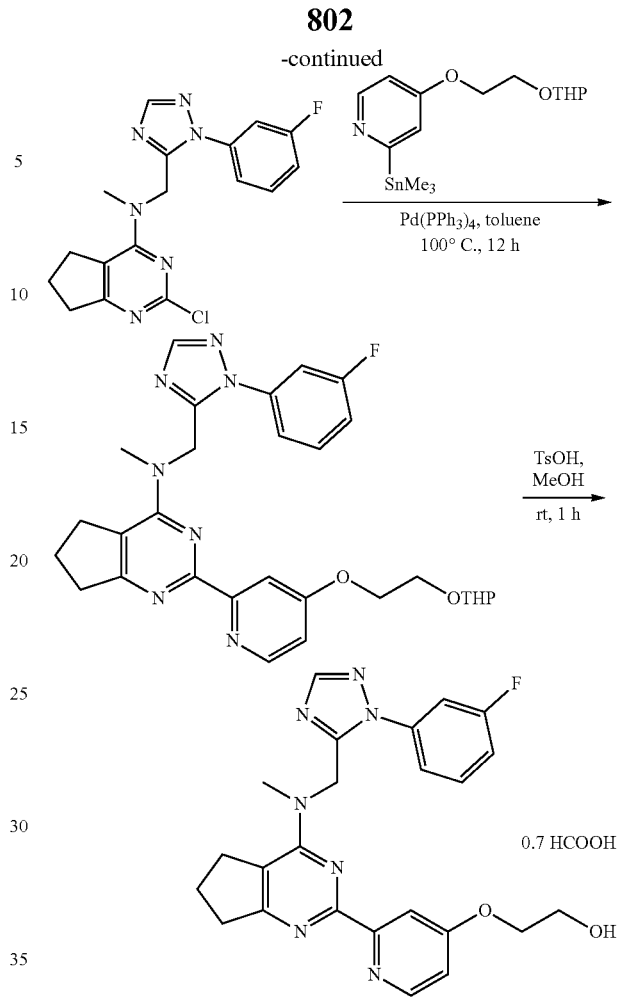

Step 1

Into a 50 mL round-bottom flask were added tert-butyl N-(carbamoylmethyl)carbamate (2.0 g, 11.48 mmol, 1.00 equiv), THF (20 mL) and DMF-DMA (2.74 g, 22.99 mmol, 2.00 equiv) at room temperature. The resulting mixture was stirred for 2 h at 60° C. The resulting mixture was cooled to room temperature and concentrated under reduced pressure. This resulted in 2.5 g of tert-butyl (2-(((dimethylamino)methylene)amino)-2-oxoethyl)carbamate as a yellow oil. The crude product was used to the next step directly without further purification. LCMS (ES) [M+1]+ m/z: 230.

Step 2

Into a 100 mL round-bottom flask were added tert-butyl (2-(((dimethylamino)methylene)amino)-2-oxoethyl)carbamate (2.5 g, 10.90 mmol, 1.00 equiv), HOAc (30 mL) and (3-fluorophenyl)hydrazine hydrochloride (1.77 g, 10.90 mmol, 1.00 equiv) at room temperature. The resulting mixture was stirred for 1 h at 60° C. The resulting mixture was cooled to room temperature and concentrated under reduced pressure. The residue was purified by silica gel column chromatography, eluted with PE/EA (5:1) to afford tert-butyl ((1-(3-fluorophenyl)-1H-1,2,4-triazol-5-yl)methyl)carbamate (1.5 g, 45% in total from step one) as a brown solid. LCMS (ES) [M+1]+ m/z: 293.

Step 3

Into a 100 mL 3-necked round-bottom flask were added tert-butyl ((1-(3-fluorophenyl)-1H-1,2,4-triazol-5-yl)methyl)carbamate (1.5 g, 5.13 mmol, 1.00 equiv) and DMF (30 mL). To the above mixture was added NaH (60% in mineral oil) (190 mg, 7.92 mmol, 1.50 equiv) in portions at 0° C. The resulting mixture was stirred for additional 30 min at the same temperature. To the above mixture was added CH₃I (1.75 g, 12.31 mmol, 2.4 equiv) dropwise at 0° C. The resulting mixture was stirred for additional 1 h at room temperature. The reaction was quenched by the addition of water (30 mL), extracted with EtOAc (50 mL*2). The combined organic phases were washed with brine (30 mL*3), dried over anhydrous sodium sulfate. After filtration, the filtrate was concentrated under reduced pressure. The residue was purified by silica gel column chromatography, eluted with PE/EA (3:1) to afford tert-butyl ((1-(3-fluorophenyl)-1H-1,2,4-triazol-5-yl)methyl)(methyl)carbamate (1.5 g, 95%) as a yellow oil. LCMS (ES) [M+1]⁺ m/z: 307.

Step 4

Into a 100 mL round-bottom flask were added tert-butyl ((1-(3-fluorophenyl)-1H-1,2,4-triazol-5-yl)methyl)(methyl)carbamate (1.5 g, 4.90 mmol, 1.00 equiv), DCM (30 mL) and HCl (g) (2 M in Et₂O) (30 mL) at room temperature. The resulting mixture was stirred for 6 h at room temperature. The resulting mixture was concentrated under vacuum. This resulted in 1.5 g crude of 1-(1-(3-fluorophenyl)-1H-1,2,4-triazol-5-yl)-N-methylmethanamine hydrochloride as a yellow solid used in the next step directly without further purification. LCMS (ES) [M−HCl+1]⁺ m/z: 207.

Step 5

Into a 100 mL round-bottom flask were added 2,4-dichloro-5H,6H,7H-cyclopenta[d]pyrimidine (777 mg, 4.11 mmol, 1.00 equiv), NMP (30 mL), 1-(1-(3-fluorophenyl)-1H-1,2,4-triazol-5-yl)-N-methylmethanamine hydrochloride (1.56 g, 6.17 mmol, 1.5 equiv) and DIEA (1.6 g, 12.38 mmol, 3.00 equiv) at room temperature. The resulting mixture was stirred for 16 h at 60° C. The reaction was cooled to room temperature and quenched by the addition of water (30 mL), extracted with EtOAc (50 mL*2). The combined organic phases were washed with brine (30 mL), concentrated under reduced pressure. The residue was purified by silica gel column chromatography, eluted with PE/EA (1:1) to afford 2-chloro-N-((1-(3-fluorophenyl)-1H-1,2,4-triazol-5-yl)methyl)-N-methyl-6,7-dihydro-5H-cyclopenta[d]pyrimidin-4-amine (1.0 g, 68%) as a yellow oil. LCMS (ES) [M+1]⁺ m/z: 359.

Step 6

Into a 40 mL vial were added 2-chloro-N-((1-(3-fluorophenyl)-1H-1,2,4-triazol-5-yl)methyl)-N-methyl-6,7-dihydro-5H-cyclopenta[d]pyrimidin-4-amine (650 mg, 1.81 mmol, 0.70 equiv), toluene (30 mL), 4-[2-(oxan-2-yloxy)ethoxy]-2-(trimethylstannyl)pyridine (1 g, 2.59 mmol, 1.00 equiv) and Pd(PPh₃)₄ (300 mg, 0.26 mmol, 0.10 equiv) at room temperature. The resulting mixture was stirred for 12 h at 100° C. under nitrogen atmosphere. The reaction mixture was cooled to room temperature, concentrated under reduced pressure to remove the solvent, the residue was purified by silica gel column chromatography, eluted with CH₂Cl₂/MeOH (10:1) to afford N-((1-(3-fluorophenyl)-1H-1,2,4-triazol-5-yl)methyl)-N-methyl-2-(4-(2-((tetrahydro-2H-pyran-2-yl)oxy)ethoxy)pyridin-2-yl)-6,7-dihydro-5H-cyclopenta[d]pyrimidin-4-amine (300 mg, 21%) as a yellow oil. LCMS (ES) [M+1]⁺ m/z: 546.

Step 7

Into a 20 mL vial were added N-((1-(3-fluorophenyl)-1H-1,2,4-triazol-5-yl)methyl)-N-methyl-2-(4-(2-((tetrahydro-2H-pyran-2-yl)oxy)ethoxy)pyridin-2-yl)-6,7-dihydro-5H-cyclopenta[d]pyrimidin-4-amine (300 mg, 0.55 mmol, 1.00 equiv), MeOH (5 mL) and TsOH (95 mg, 0.55 mmol, 1.00 equiv) at room temperature. The resulting solution was stirred for 1 h at room temperature. The reaction solution was purified by Prep-HPLC with the following conditions: Sunfire Prep C18 OBD Column, 50*250 mm, 5 μm, 10 nm, mobile phase, water (0.1% FA) and CH₃CN (5% Phase B up to 23% in 12 min), Detector, UV 254 nm. The fraction of the target was freezing dried, this resulted in 158.4 mg (57%) of 2-((2-(4-(((1-(3-fluorophenyl)-1H-1,2,4-triazol-5-yl)methyl)(methyl)amino)-6,7-dihydro-5H-cyclopenta[d]pyrimidin-2-yl)pyridin-4-yl)oxy)ethan-1-ol formate as a brown semi-solid. LCMS [M+H]⁺: 462. ¹H NMR (300 MHz, DMSO-d₆) δ 8.41 (d, J=5.6 Hz, 1H), 8.07 (s, 1H), 7.66 (dt, J=9.0, 1.8 Hz, 1H), 7.66-7.47 (m, 3H), 7.39-7.26 (m, 1H), 7.01 (dd, J=5.6, 2.6 Hz, 1H), 5.15 (s, 2H), 4.11 (t, J=4.8 Hz, 2H), 3.77 (t, J=4.8 Hz, 2H), 3.29 (s, 3H), 3.06 (t, J=7.3 Hz, 2H), 2.79 (t, J=7.8 Hz, 2H), 2.00-1.90 (p, J=7.6 Hz, 2H).

Example 1.322

Synthesis of (2R)-2-({2-[4-(2-hydroxyethoxy)pyridin-2-yl]-5H,6H,7H-cyclopenta[d]pyrimidin-4-yl}(methyl)amino)-N-(6-methylpyridin-3-yl)propanamide (Compound 316)

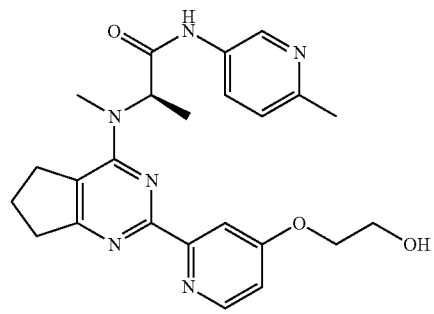 [SMILES: Cc1ccc(NC(=O)[C@@H](C)N(C)c2nc(-c3cc(OCCO)ccn3)nc3c2CCC3)cn1]

Compound 316 was synthesized similar to compound 251 by replacing 3-fluoroaniline with 6-methylpyridin-3-am. LCMS (ES) [M+1]⁺ m/z: 449. ¹H NMR (300 MHz, DMSO-d₆, ppm) δ 10.58 (s, 1H), 8.61 (d, J=2.6 Hz, 1H), 8.47 (d, J=5.6 Hz, 1H), 8.16 (s, HCOOH), 7.91 (dd, J=8.4, 2.6 Hz, 1H), 7.86 (d, J=2.5 Hz, 1H), 7.15 (d, J=8.4 Hz, 1H), 7.06 (dd, J=5.6, 2.6 Hz, 1H), 5.26 (q, J=6.9 Hz, 1H), 4.12 (t, J=4.8 Hz, 2H), 3.75 (t, J=4.7 Hz, 2H), 3.19 (s, 3H), 3.26-3.00 (m, 2H), 2.96-2.70 (m, 2H), 2.37 (s, 3H), 2.17-1.84 (m, 2H), 1.46 (d, J=7.0 Hz, 3H).

Example 1.323

Synthesis of N-tert-butyl-2-[methyl(2-{4-[(3S)-oxolan-3-yloxy]pyridin-2-yl}-5H,6H,7H-cyclopenta[d]pyrimidin-4-yl)amino]acetamide (Compound 317)

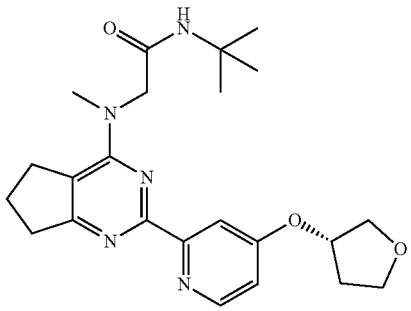 [SMILES: CN(CC(=O)NC(C)(C)C)c1nc(-c2cc(O[C@H]3CCOC3)ccn2)nc2c1CCC2]

Compound 317 was synthesized similar to compound 174 by replacing 2-methyl-2-((tetrahydro-2H-pyran-2-yl)oxy)propan-1-ol with (3S)-oxolan-3-ol. LCMS (ES) [M+1]+ m/z: 426. $^1$H NMR (300 MHz, DMSO-$d_6$, ppm) δ 8.48 (d, J=5.6 Hz, 1H), 7.84 (d, J=2.6 Hz, 1H), 7.69 (s, 1H), 7.04 (dd, J=5.7, 2.6 Hz, 1H), 5.22 (t, J=3.2 Hz, 1H), 4.11 (s, 2H), 3.95 (dd, J=10.3, 4.5 Hz, 1H), 3.93-3.73 (m, 3H), 3.27 (s, 3H), 3.15 (t, J=7.3 Hz, 2H), 2.81 (t, J=7.8 Hz, 2H), 2.39-2.21 (m, 1H), 2.04-1.97 (m, 3H), 1.25 (s, 9H).

Example 1.324

Synthesis of N-tert-butyl-2-[methyl(2-{4-[(3R)-oxolan-3-yloxy]pyridin-2-yl}-5H,6H,7H-cyclopenta[d]pyrimidin-4-yl)amino]acetamide (Compound 318)

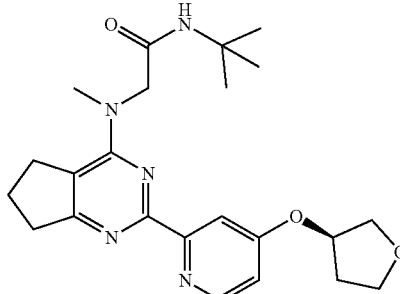

Compound 318 was synthesized similar to compound 174 by replacing 2-methyl-2-((tetrahydro-2H-pyran-2-yl)oxy)propan-1-ol with (3R)-oxolan-3-ol. LCMS (ES) [M+1]+ m/z: 426. $^1$H NMR (300 MHz, DMSO-$d_6$, ppm) δ 8.48 (d, J=5.6 Hz, 1H), 7.84 (d, J=2.6 Hz, 1H), 7.69 (s, 1H), 7.04 (dd, J=5.7, 2.6 Hz, 1H), 5.22 (t, J=3.2 Hz, 1H), 4.11 (s, 2H), 3.95 (dd, J=10.3, 4.5 Hz, 1H), 3.93-3.73 (m, 3H), 3.27 (s, 3H), 3.15 (t, J=7.3 Hz, 2H), 2.81 (t, J=7.8 Hz, 2H), 2.39-2.21 (m, 1H), 2.04-1.97 (m, 3H), 1.25 (s, 9H).

Example 1.325

Synthesis of 2-({2-[4-({[4-(3-fluorophenyl)-4H-1,2,4-triazol-3-yl]methyl}(methyl)amino)-5H,6H,7H-cyclopenta[d]pyrimidin-2-yl]pyridin-4-yl}oxy)ethan-1-ol (Compound 319)

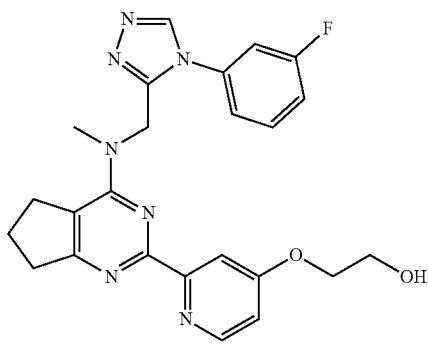 [SMILES: CN(Cc1nncn1-c1cccc(F)c1)c1nc(-c2cc(OCCO)ccn2)nc2c1CCC2]

Scheme 120

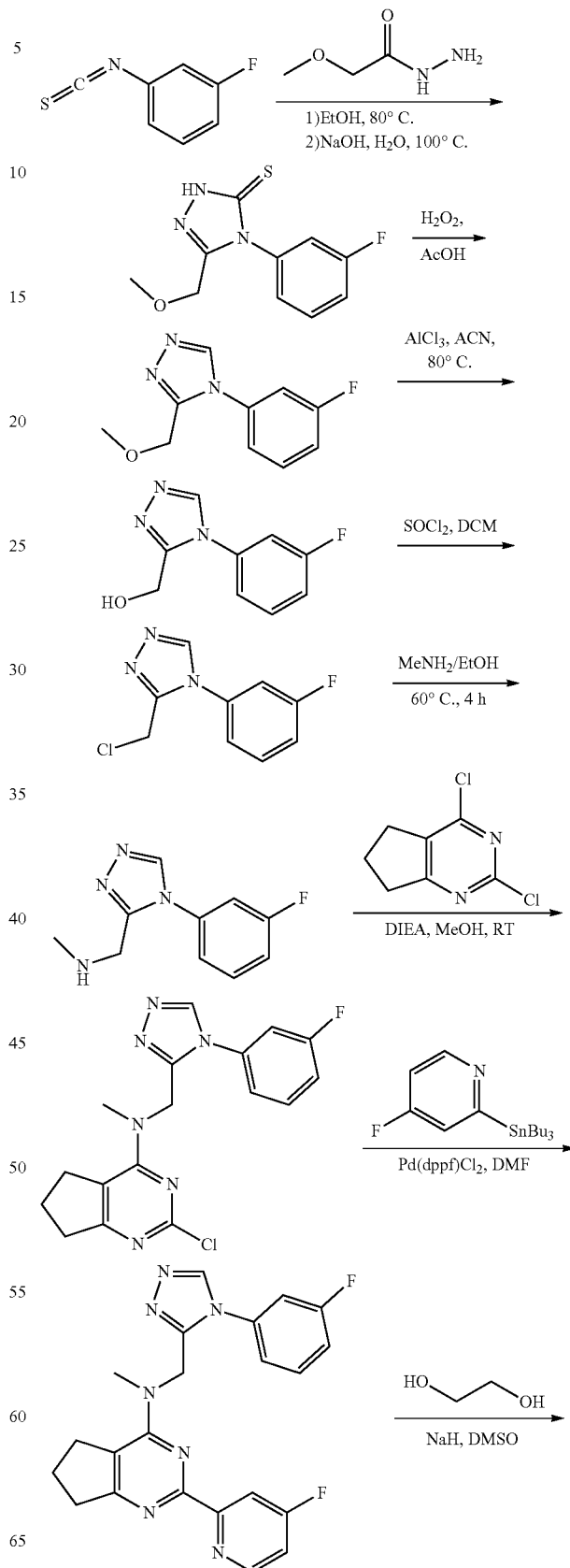

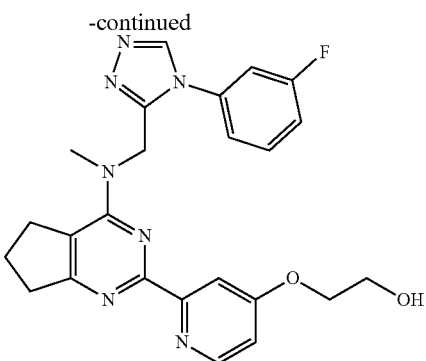

Step 1

Into a 250-mL round-bottom flask, was placed 1-fluoro-3-isothiocyanatobenzene (5 g, 32.643 mmol, 1.00 equiv), 2-methoxyacetohydrazide (3.98 g, 38.229 mmol, 1.17 equiv) and EtOH (60.00 mL). The resulting solution was stirred for 1 hr at 80 degrees C. The precipitate was collected and recrystallized from H$_2$O. The solid and NaOH (130.57 mL, 261.144 mmol, 8.00 equiv) was placed into a 250 mL round-bottom flask. The resulting solution was allowed to react, with stirring, for an additional 1 hr at 100 degrees C. The resulting solution was transferred to a beaker, neutralized to 6 with HCl (2 mol/L), applied to suction filtration, washed with water. This resulted in 6 g (76.9%) of 4-(3-fluorophenyl)-5-(methoxymethyl)-2H-1,2,4-triazole-3-thione as a white solid. LCMS (ES) [M+1]$^+$ m/z: 240.

Step 2

A solution of starting 4-(3-fluorophenyl)-5-(methoxymethyl)-2H-1,2,4-triazole-3-thione (5.5 g, 22.987 mmol, 1.00 equiv) in CH$_2$Cl$_2$ (40 mL) was cooled to 0° C., and a 30% aqueous solution of H$_2$O$_2$ (1.18 mL, 50.649 mmol, 2.20 equiv) in AcOH (27 mL) was added in portions under cooling and stirring. Then the ice bath was removed, and the stirring was continued at ambient temperature for 3 h. The reaction mixture was alkalized under cooling with NaOH to pH 10. The organic layer was separated, and the aqueous one was washed with CH$_2$Cl$_2$ (2×100 mL). The combined extracts were dried with Na$_2$SO$_4$ and evaporated. The residue was purified by column chromatography (DCM/MeOH, 100:0~70:30). This resulted in 3.2 g (67.18%) of 4-(3-fluorophenyl)-3-(methoxymethyl)-1,2,4-triazole as a off-white solid. LCMS (ES) [M+1]$^+$ m/z: 208.

Step 3

Into a 250-mL round-bottom flask, was placed 4-(3-fluorophenyl)-3-(methoxymethyl)-1,2,4-triazole (3.00 g, 14.478 mmol, 1.00 equiv), AlCl$_3$ (19.31 g, 144.782 mmol, 10 equiv), AcCN (100.00 mL). The resulting solution was stirred for 16 hr at 80° C. The reaction mixture was cooled, and the crude product was purified by Flash-Prep-HPLC with the following conditions (IntelFlash-1): Column, C18 silica gel; mobile phase, H$_2$O(FA)/ACN=10:1 increasing to H$_2$O(FA)/ACN=5:1 within 15 min. This resulted in 1.2 g (42.90%) of [4-(3-fluorophenyl)-1,2,4-triazol-3-yl]methanol as a yellow solid. LCMS (ES) [M+1]$^+$ m/z: 194.

Step 4

Into a 100-mL round-bottom flask were placed [4-(3-fluorophenyl)-1,2,4-triazol-3-yl]methanol (1.20 g, 6.212 mmol, 1.00 equiv), SOCl$_2$ (1.11 g, 9.330 mmol, 1.50 equiv), DCM (30.00 mL). The resulting solution was stirred for 6 hr at room temperature. The resulting mixture was concentrated under vacuum. The resulting solution was extracted with 3×30 mL of dichloromethane and the organic layers combined and dried over anhydrous sodium sulfate and concentrated. This resulted in 1.28 g (97.37%) of 3-(chloromethyl)-4-(3-fluorophenyl)-1,2,4-triazole as colorless oil. LCMS (ES) [M+1]$^+$ m/z: 212.

Step 5

Into a 100-mL round-bottom flask were placed 3-(chloromethyl)-4-(3-fluorophenyl)-1,2,4-triazole (1.20 g, 5.671 mmol, 1.00 equiv), Methylamine in ethanol (30 wt. % 0.86 g, 8.372 mmol, 1.48 equiv), EtOH (30.00 mL). The resulting solution was stirred for 4 hr at 60° C. The resulting solution was extracted with 3×30 mL of dichloromethane and the organic layers combined and dried over anhydrous sodium sulfate and concentrated. This resulted in 1.0 g (85.51%) of [[4-(3-fluorophenyl)-1,2,4-triazol-3-yl]methyl](methyl) amine as a white solid. LCMS (ES) [M+1]$^+$ m/z: 207.

Step 6

Into a 100 mL round-bottom flask were placed [[4-(3-fluorophenyl)-1,2,4-triazol-3-yl]methyl](methyl)amine (1.00 g, 4.849 mmol, 1.00 equiv), 2,4-dichloro-5H,6H,7H-cyclopenta[d]pyrimidine (1.10 g, 5.819 mmol, 1.20 equiv), DIEA (1.25 g, 9.698 mmol, 2 equiv), MeOH (20.00 mL). The resulting solution was stirred for 8 hr at room temperature. The resulting solution was extracted with 3×30 mL of dichloromethane and the organic layers combined, dried over anhydrous sodium sulfate and concentrated under vacuum. The residue was applied onto a silica gel column with ethyl acetate/petroleum ether (3:1). This resulted in 1 g (57.47%) of 2-chloro-N-[[4-(3-fluorophenyl)-1,2,4-triazol-3-yl]methyl]-N-methyl-5H,6H,7H-cyclopenta[d]pyrimidin-4-amine as a white solid. LCMS (ES) [M+1]$^+$ m/z: 359.

Step 6

Into a 100-mL round-bottom flask purged and maintained with an inert atmosphere of nitrogen, was placed 2-chloro-N-[[4-(3-fluorophenyl)-1,2,4-triazol-3-yl]methyl]-N-methyl-5H,6H,7H-cyclopenta[d]pyrimidin-4-amine (700.00 mg, 1.951 mmol, 1.00 equiv), 4-fluoro-2-(tributylstannyl)pyridine (903.99 mg, 2.341 mmol, 1.20 equiv), Pd(dppf)Cl$_2$ (285.49 mg, 0.390 mmol, 0.2 equiv), DMF (30.00 mL). The resulting solution was stirred for 16 hr at 120° C. The reaction mixture was cooled. The residue was applied onto a silica gel column with dichloromethane/methanol (10:1). This resulted in 230 mg (28.11%) of N-[[4-(3-fluorophenyl)-1,2,4-triazol-3-yl]methyl]-2-(4-fluoropyridin-2-yl)-N-methyl-5H,6H,7H-cyclopenta[d]pyrimidin-4-amine as brown oil. LCMS (ES) [M+1]$^+$ m/z: 420.

Step 7

Into a 100-mL round-bottom flask, was placed N-[[4-(3-fluorophenyl)-1,2,4-triazol-3-yl]methyl]-2-(4-fluoropyridin-2-yl)-N-methyl-5H,6H,7H-cyclopenta[d]pyrimidin-4-amine (200.00 mg, 0.477 mmol, 1.00 equiv), NaH (57.21 mg, 2.384 mmol, 5 equiv), DMSO (10.00 mL). The resulting solution was stirred for 30 min at 0° C. and ethylene glycol (147.98 mg, 2.384 mmol, 5.00 equiv) was added, the solution was stirred for 2 hr at room temperature. The resulting solution was extracted with 3×30 mL of dichloromethane and the organic layers combined, dried over anhydrous sodium sulfate and concentrated. The residue was purified by prep-HPLC with the following conditions: Column: Sunfire Prep C18 OBD Column, 50*250 mm, 5 μm 10 nm; Mobile Phase A: Water (0.1% FA), Mobile Phase B: AcCN; Flow rate: 90 mL/min; Gradient: 5% B to 35% B in 15 min, 35% B; Wave Length: 220 nm. This resulted in 63.9 mg (29.04%) of 2-([2-[4-([[4-(3-fluorophenyl)-1,2,4-triazol-3-yl]methyl](methyl)amino)-5H,6H,7H-cyclopenta[d]pyrimidin-2-yl]pyridin-4-yl]oxy)ethanol 2-([2-[4-([[4-(3-fluorophenyl)-1,2,4-triazol-3-yl]methyl](methyl)amino)-5H,6H,7H-cyclopenta[d]pyrimidin-2-yl]pyridin-4-yl]oxy)ethanol formate a brown solid. LCMS (ES) [M+1]$^+$ m/z: 462. $^1$H NMR (300 MHz, DMSO-d$_6$) δ 8.72 (s, 1H), 8.43 (d, J=5.6 Hz, 1H), 7.67 (d, J=2.6 Hz, 1H), 7.63-7.53 (m, 1H), 7.48-7.33 (m, 2H), 7.25-7.19 (m, 1H), 7.02 (dd, J=5.7, 2.6 Hz, 1H), 5.13 (s, 2H), 4.16 (t, J=4.9 Hz, 2H), 3.78 (t, J=4.8 Hz, 2H), 3.14 (s, 3H), 2.99 (t, J=7.3 Hz, 2H), 2.77 (t, J=7.8 Hz, 2H), 1.98-1.88 (m, 2H).
Example 1.326
Synthesis of (3S)-1-(3-fluorophenyl)-3-({2-[4-(2-hydroxyethoxy)pyridin-2-yl]-5H,6H,7H-cyclopenta[d]pyrimidin-4-yl}(methyl)amino)piperidin-2-one (Compound 320)
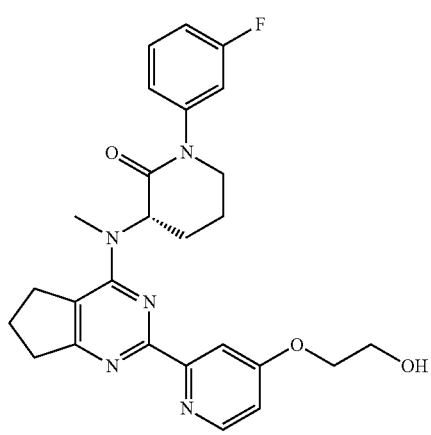
Assumed
Scheme 121
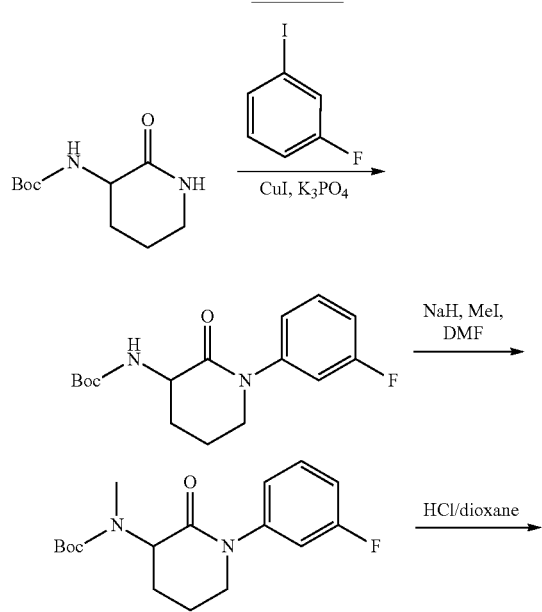
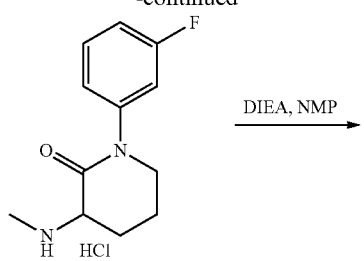
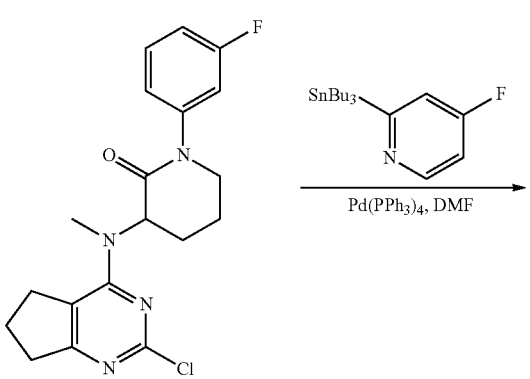
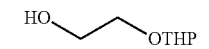
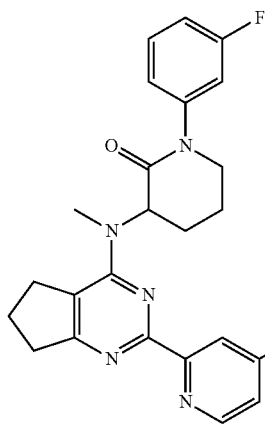

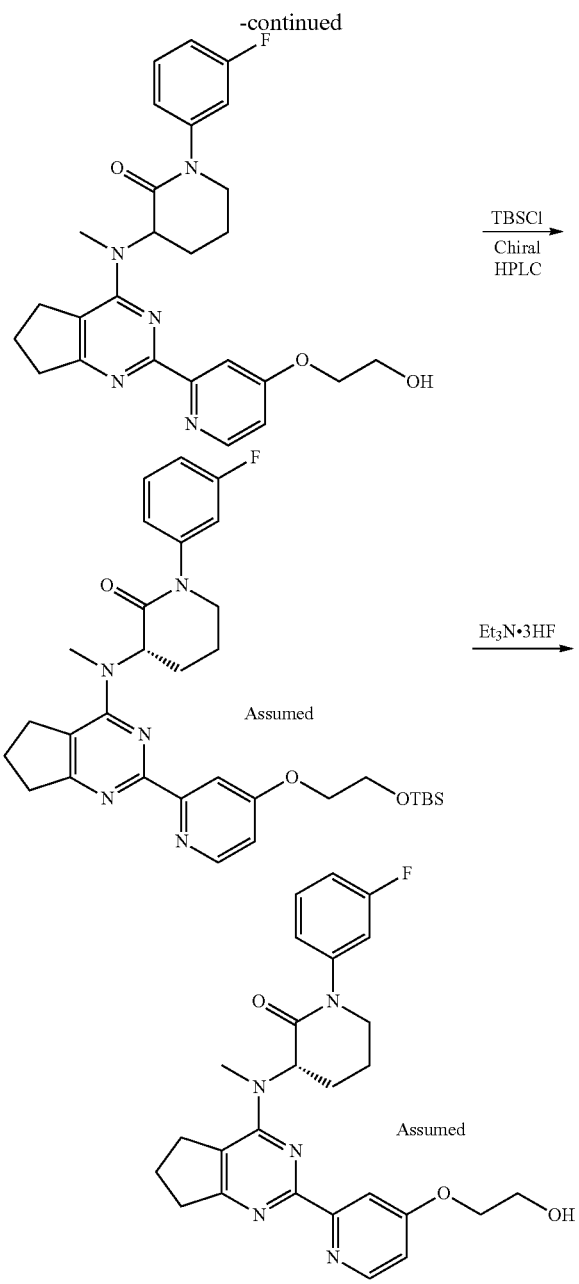

Step 1

Into a 250-mL round-bottom flask purged and maintained with an inert atmosphere of nitrogen, was placed tert-butyl N-(2-oxopiperidin-3-yl)carbamate (10.00 g, 46.67 mmol, 1.00 equiv), methyl[(methylamino)methyl]amine (0.69 g, 9.31 mmol, 0.20 equiv), 1-fluoro-3-iodobenzene (12.43 g, 56.01 mmol, 1.20 equiv), dioxane (100.00 mL), K$_3$PO$_4$ (19.81 g, 93.34 mmol, 2.00 equiv), CuI (0.89 g, 4.67 mmol, 0.10 equiv). The resulting solution was stirred for overnight at 110° C. The reaction mixture was cooled to room temperature. The solids were filtered out. The resulting mixture was concentrated. The residue was applied onto a silica gel column with THF/PE (15%). This resulted in 8 g (55.59%) of tert-butyl N-[1-(3-fluorophenyl)-2-oxopiperidin-3-yl]carbamate as yellow solid. LCMS (ES) [M+1]$^+$ m/z: 309.

Step 2

Into a 250-mL 3-necked round-bottom flask, was placed tert-butyl N-[1-(3-fluorophenyl)-2-oxopiperidin-3-yl]carbamate (8.00 g, 25.94 mmol, 1.00 equiv), DMF (100.00 mL). This was followed by the addition of NaH (0.93 g, 38.75 mmol, 1.49 equiv), in portions at 0° C. To this was added MeI (4.42 g, 31.13 mmol, 1.20 equiv) dropwise with stirring at 0° C. The resulting solution was stirred for 3 h at room temperature. The reaction was then quenched by the addition of 50 mL of water/ice. The resulting solution was extracted with 3×100 mL of ethyl acetate and the organic layers combined and dried over anhydrous sodium sulfate and concentrated. The residue was applied onto a silica gel column with THF/PE (20%). This resulted in 6.5 g (77.71%) of tert-butyl N-[1-(3-fluorophenyl)-2-oxopiperidin-3-yl]-N-methylcarbamate as colorless oil. LCMS (ES) [M+1]$^+$ m/z: 323.

Step 3

Into a 250-mL round-bottom flask, was placed tert-butyl N-[1-(3-fluorophenyl)-2-oxopiperidin-3-yl]-N-methylcarbamate (6.50 g, 20.16 mmol, 1.00 equiv), DCM (20.00 mL). This was followed by the addition of HCl (gas) in 1,4-dioxane (10.08 mL, 40.32 mmol, 2.00 equiv) dropwise with stirring at 0° C. The resulting solution was stirred for 3 h at room temperature. The solids were collected by filtration. This resulted in 5 g (95.85%) of 1-(3-fluorophenyl)-3-(methylamino)piperidin-2-one hydrochloride as a white solid. LCMS (ES) [M−HCl+1]+ m/z: 223.

Step 4

Into a 100-mL round-bottom flask, was placed 2,4-dichloro-5H,6H,7H-cyclopenta[d]pyrimidine (2.00 g, 10.58 mmol, 1.00 equiv), 1-(3-fluorophenyl)-3-(methylamino)piperidin-2-one hydrochloride (2.74 g, 10.58 mmol, 1.00 equiv), NMP (20.00 mL), DIEA (4.10 g, 31.74 mmol, 3.00 equiv). The resulting solution was stirred for 5 h at 60° C. The reaction mixture was cooled to room temperature. The crude product (5 g) was purified by Prep-HPLC with the following conditions: Column, XBridge Prep C18 OBD Column, 19 cm, 150 mm, 5 um; mobile phase, Water (0.1% NH$_3$·H$_2$O) and CAN (30% Phase B up to 80% in 11 min); Detector, 254. This resulted in 2 g (50.43%) of 3-([2-chloro-5H,6H,7H-cyclopenta[d]pyrimidin-4-yl](methyl)amino)-1-(3-fluorophenyl)piperidin-2-one as yellow solid. LCMS (ES) [M+1]$^+$ m/z: 375.

Step 5

Into a 40-mL vial purged and maintained with an inert atmosphere of nitrogen, was placed 3-([2-chloro-5H,6H,7H-cyclopenta[d]pyrimidin-4-yl](methyl)amino)-1-(3-fluorophenyl)piperidin-2-one (2.00 g, 5.34 mmol, 1.00 equiv), DMF (20.00 mL), 4-fluoro-2-(tributylstannyl)pyridine (2.68 g, 6.94 mmol, 1.30 equiv), Pd(PPh$_3$)$_4$ (0.62 g, 0.54 mmol, 0.10 equiv). The resulting solution was stirred for overnight at 120° C. The reaction mixture was cooled to room temperature. The resulting mixture was concentrated. The residue was applied onto a silica gel column with THF/PE (60%). This resulted in 1 g (43.04%) of 1-(3-fluorophenyl)-3-[[2-(4-fluoropyridin-2-yl)-5H,6H,7H-cyclopenta[d]pyrimidin-4-yl](methyl)amino]piperidin-2-one as yellow oil. LCMS (ES) [M+1]$^+$ m/z: 436.

Step 6

Into a 100-mL 3-necked round-bottom flask, was placed 2-(oxan-2-yloxy)ethanol (0.30 g, 2.05 mmol, 1.00 equiv), DMF (10.00 mL). This was followed by the addition of NaH (0.10 g, 4.17 mmol, 2.03 equiv), in portions at 0° C. To this was added 1-(3-fluorophenyl)-3-[[2-(4-fluoropyridin-2-yl)-5H,6H,7H-cyclopenta[d]pyrimidin-4-yl](methyl)amino]piperidin-2-one (0.98 g, 2.26 mmol, 1.10 equiv) dropwise with stirring at 0° C. The resulting solution was stirred for 3 h at room temperature. The reaction was then quenched by the addition of 10 mL of water/ice. The resulting solution was extracted with 3×20 mL of ethyl acetate and the organic layers combined and dried over anhydrous sodium sulfate and concentrated. The residue was applied onto a silica gel column with THF/PE (50%). This resulted in 0.7 g (60.73%) of 1-(3-fluorophenyl)-3-[methyl(2-[4-[2-(oxan-2-yloxy)ethoxy]pyridin-2-yl]-5H,6H,7H- cyclopenta[d]pyrimidin-4-yl)amino]piperidin-2-one as a yellow oil. LCMS (ES) [M+1]$^+$ m/z: 562.

Step 7

Into a 40-mL vial, was placed 1-(3-fluorophenyl)-3-[methyl(2-[4-[2-(oxan-2-yloxy)ethoxy]pyridin-2-yl]-5H,6H,7H-cyclopenta[d]pyrimidin-4-yl)amino]piperidin-2-one (700.00 mg, 1.25 mmol, 1.00 equiv), MeOH (10.00 mL), PTSA (42.92 mg, 0.25 mmol, 0.20 equiv). The resulting solution was stirred for 3 h at room temperature. The crude product (0.8 g) was purified by Prep-HPLC with the following conditions: Column, XBridge Prep C18 OBD Column, 19 cm, 150 mm, 5 um; mobile phase, Water (0.1% NH$_3$·H$_2$O) and CAN (30% Phase B up to 70% in 11 min); Detector, 254. This resulted in 400 mg (67.21%) of 1-(3-fluorophenyl)-3-([2-[4-(2-hydroxyethoxy)pyridin-2-yl]-5H,6H,7H-cyclopenta[d]pyrimidin-4-yl](methyl)amino)piperidin-2-one as white solid. LCMS (ES) [M+1]$^+$ m/z: 478.

Step 8

Into a 100-mL round-bottom flask, was placed 1-(3-fluorophenyl)-3-([2-[4-(2-hydroxyethoxy)pyridin-2-yl]-5H,6H,7H-cyclopenta[d]pyrimidin-4-yl](methyl)amino)piperidin-2-one (400.00 mg, 0.84 mmol, 1.00 equiv), DCM (6.00 mL), imidazole (85.54 mg, 1.26 mmol, 1.50 equiv). This was followed by the addition of t-butyldimethylchlorosilane (151.50 mg, 1.01 mmol, 1.20 equiv), in portions at 0° C. The resulting solution was stirred for 5 h at room temperature. The resulting mixture was concentrated. The crude product (500 mg) was purified by Prep-CHIRAL-HPLC with the following conditions: Column, YMC Cellulose-SC, 250*21.5 mm, 5 μm; mobile phase, Acetonitrile and Ethanol (0.2% DEA) (70% in 10 min); Detector, 254. This resulted in 220 mg (44.38%) of (3S)-3-[[2-(4-[2-[(tert- butyldimethylsilyl)oxy]ethoxy]pyridin-2-yl)-5H,6H,7H-cyclopenta[d]pyrimidin-4-yl](methyl)amino]-1-(3-fluorophenyl)piperidin-2-one as white solid. LCMS (ES) [M+1]$^+$ m/z: 592.

Step 9

Into a 40-mL vial, was placed (3S)-3-[[2-(4-[2-[(tert-butyldimethylsilyl)oxy]ethoxy]pyridin-2-yl)-5H,6H,7H-cyclopenta[d]pyrimidin-4-yl](methyl)amino]-1-(3-fluorophenyl)piperidin-2-one (220.00 mg, 0.37 mmol, 1.00 equiv), THF (6.00 mL), Et$_3$N·3HF (299.64 mg, 1.86 mmol, 5.00 equiv). The resulting solution was stirred for overnight at room temperature. The crude product (0.3 g) was purified by Prep-HPLC with the following conditions: Column, XBridge Prep C18 OBD Column, 19 cm, 150 mm, 5 um; mobile phase, Water (0.1% FA) and CAN (5% Phase B up to 40% in 11 min); Detector, 254. This resulted in 130 mg (73.23%) of (3S)-1-(3-fluorophenyl)-3-([2-[4-(2-hydroxyethoxy)pyridin-2-yl]-5H,6H,7H-cyclopenta[d]pyrimidin-4-yl](methyl)amino)piperidin-2-one as white solid. Chiral analytical HPLC condition: Column, (R,R)-WHELK-O1 50*4.6 mm, 3.5 um; mobile phase, n-hexane and Ethanol (0.2% DEA) (50% in 6 min); Detector, 254, Retention time: 3.233 min. LCMS (ES, m/z): [M+H]$^+$: 478. $^1$H-NMR (300 MHz, DMSO-d$_6$, ppm): δ 8.45 (d, J=5.6 Hz, 1H), 7.76 (d, J=2.6 Hz, 1H), 7.34-7.23 (m, 1H), 7.12-6.93 (m, 4H), 4.92 (d, J=6.3 Hz, 1H), 4.61 (s, 1H), 4.14 (t, J=4.9 Hz, 3H), 3.75 (d, J=5.1 Hz, 2H), 3.56 (d, J=11.6 Hz, 1H), 3.30 (s, 3H), 3.21 (q, J=6.8 Hz, 2H), 2.83 (t, J=7.9 Hz, 2H), 2.55 (s, 1H), 2.10-1.98 (m, 5H).

Example 1.327

Synthesis of (3R)-1-(3-fluorophenyl)-3-({2-[4-(2-hydroxyethoxy)pyridin-2-yl]-5H,6H,7H-cyclopenta[d]pyrimidin-4-yl}(methyl)amino)piperidin-2-one (Compound 321)

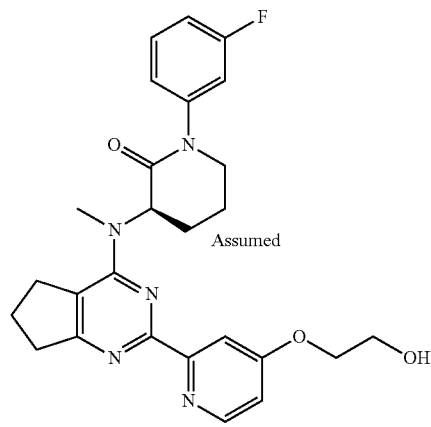 [SMILES: CN(c1nc(-c2cc(OCCO)ccn2)nc2c1CCC2)[C@@H]1CCCN(c2cccc(F)c2)C1=O]

Scheme 122

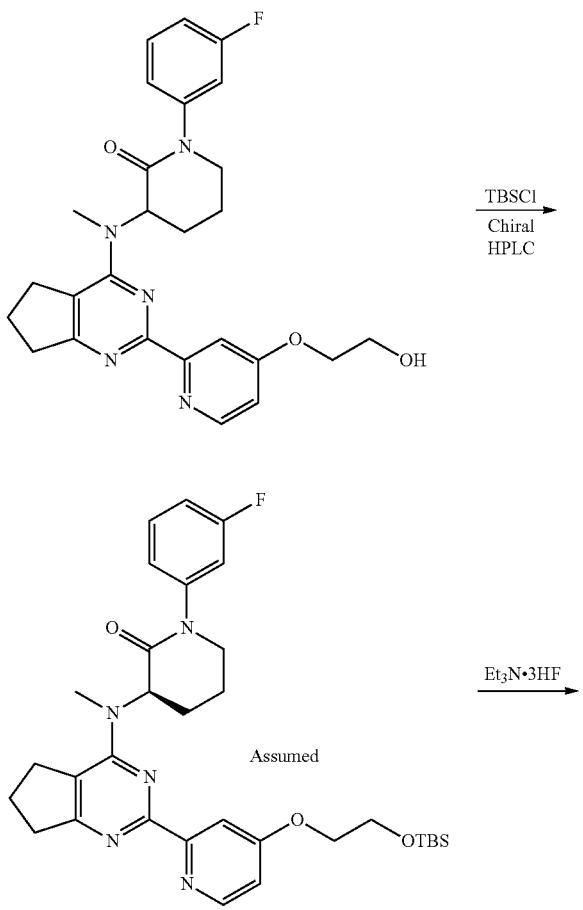

-continued

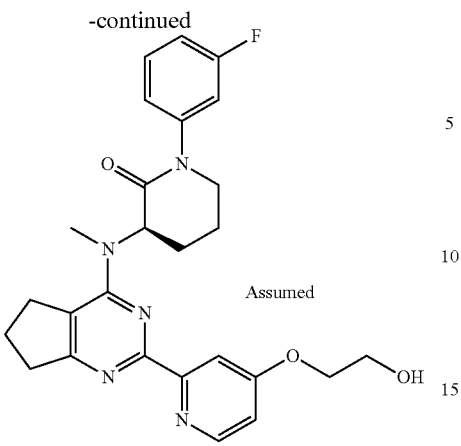

Assumed

Step 1

Into a 100-mL round-bottom flask, was placed 1-(3-fluorophenyl)-3-([2-[4-(2-hydroxyethoxy)pyridin-2-yl]-5H,6H,7H-cyclopenta[d]pyrimidin-4-yl](methyl)amino)piperidin-2-one (400.00 mg, 0.84 mmol, 1.00 equiv), DCM (6.00 mL), imidazole (85.54 mg, 1.26 mmol, 1.50 equiv). This was followed by the addition of t-butyldimethylchlorosilane (151.50 mg, 1.01 mmol, 1.20 equiv), in portions at 0° C. The resulting solution was stirred for 5 h at room temperature. The resulting mixture was concentrated. The crude product (500 mg) was purified by Prep-CHIRAL-HPLC with the following conditions: Column, YMC Cellulose-SC, 250*21.5 mm, 5 µm; mobile phase, Acetonitrile and Ethanol (0.2% DEA) (70% in 10 min); Detector, 254. This resulted in 220 mg (44.38%) of (3R)-3-[[2-(4-[2-[(tert-butyldimethylsilyl)oxy]ethoxy]pyridin-2-yl)-5H,6H,7H-cyclopenta[d]pyrimidin-4-yl](methyl)amino]-1-(3-fluorophenyl)piperidin-2-one as a white solid. LCMS (ES) [M+1]+ m/z: 592.

Step 2

Into a 40-mL vial, was placed (3S)-3-[[2-(4-[2-[(tert-butyldimethylsilyl)oxy]ethoxy]pyridin-2-yl)-5H,6H,7H-cyclopenta[d]pyrimidin-4-yl](methyl)amino]-1-(3-fluorophenyl)piperidin-2-one (220.00 mg, 0.37 mmol, 1.00 equiv), THF (6.00 mL), Et$_3$N·3HF (299.64 mg, 1.86 mmol, 5.00 equiv). The resulting solution was stirred for overnight at room temperature. The crude product (0.3 g) was purified by Prep-HPLC with the following conditions: Column, XBridge Prep C18 OBD Column, 19 cm, 150 mm, 5 um; mobile phase, Water (0.1% FA) and CAN (5% Phase B up to 40% in 11 min); Detector, 254. This resulted in 109 mg (61.40%) of (3R)-1-(3-fluorophenyl)-3-([2-[4-(2-hydroxyethoxy)pyridin-2-yl]-5H,6H,7H-cyclopenta[d]pyrimidin-4-yl](methyl)amino)piperidin-2-one as white solid. Chiral analytical HPLC condition: Column, (R,R)-WHELK-O1 50*4.6 mm, 3.5 um; mobile phase, n-hexane and Ethanol (0.2% DEA) (50% in 6 min); Detector, 254, Retention time: 2.274 min. LCMS (ES, m/z): [M+H]+: 478. $^1$H-NMR (300 MHz, DMSO-d$_6$, ppm): δ 8.45 (d, J=5.7 Hz, 1H), 7.76 (d, J=2.6 Hz, 1H), 7.30 (q, J=8.1, 7.3 Hz, 1H), 7.10-6.94 (m, 4H), 4.94 (s, 1H), 4.63 (s, 1H), 4.15 (t, J=4.9 Hz, 3H), 3.75 (d, J=4.7 Hz, 2H), 3.56 (d, J=11.4 Hz, 1H), 3.31 (s, 3H), 3.19 (dt, J=11.9, 7.8 Hz, 2H), 2.83 (t, J=7.9 Hz, 2H), 2.55 (s, 1H), 2.10-1.98 (m, 5H).

Example 1.328

Synthesis of N-tert-butyl-N-methyl-2-[methyl({2-[4-(oxetan-3-yloxy)pyridin-2-yl]-5H,6H,7H-cyclopenta[d]pyrimidin-4-yl})amino]acetamide (Compound 322)

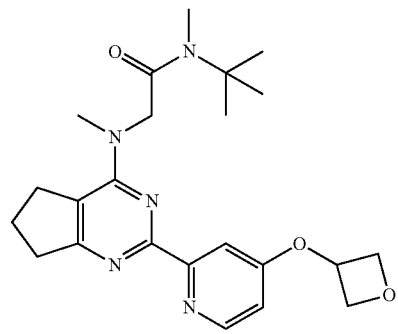 [SMILES: CN(CC(=O)N(C)C(C)(C)C)c1nc(-c2cc(OC3COC3)ccn2)nc2c1CCC2]

Compound 322 was synthesized similar to compound 253 by replacing 5-amino-2-methoxypyridine with tert-butyl (methyl)amine. LCMS (ES) [M+1]+ m/z: 426. $^1$H NMR (300 MHz, DMSO-d$_6$, ppm) δ 8.41 (d, J=5.7 Hz, 1H), 7.59 (d, J=2.6 Hz, 1H), 6.79 (dd, J=5.8, 2.6 Hz, 1H), 5.41-5.31 (m, 1H), 4.97 (t, J=6.7 Hz, 2H), 4.55 (dd, J=7.7, 4.5 Hz, 2H), 3.20 (s, 3H), 3.07 (t, J=7.5 Hz, 2H), 2.90 (s, 3H), 2.77 (t, J=7.8 Hz, 2H), 1.99-1.88 (m, 2H), 1.25 (s, 9H).

Example 1.329

Synthesis of 2-[methyl({2-[4-(oxetan-3-yloxy)pyridin-2-yl]-5H,6H,7H-cyclopenta[d]pyrimidin-4-yl})amino]-1-(piperidin-1-yl)ethan-1-one (Compound 323)

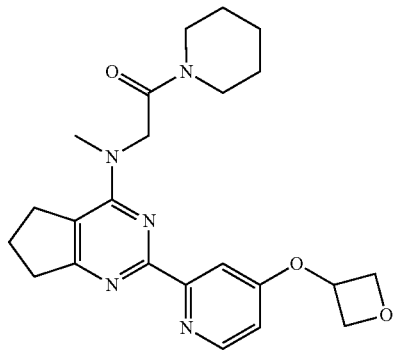 [SMILES: CN(CC(=O)N1CCCCC1)c1nc(-c2cc(OC3COC3)ccn2)nc2c1CCC2]

Compound 323 was synthesized similar to compound 253 by replacing 5-amino-2-methoxypyridine with piperidine. LCMS (ES) [M+1]+ m/z: 424. $^1$H NMR (300 MHz, DMSO-d$_6$, ppm) δ 8.48 (d, J=5.6 Hz, 1H), 7.65 (d, J=2.6 Hz, 1H), 6.86 (dd, J=5.6, 2.6 Hz, 1H), 5.49-5.43 (m, 1H), 4.97 (t, J=6.7 Hz, 2H), 4.58 (dd, J=7.5, 4.9 Hz, 2H), 4.51 (s, 2H), 3.50-3.38 (m, 4H), 3.25 (s, 3H), 3.14 (t, J=7.4 Hz, 2H), 2.81 (t, J=7.9 Hz, 2H), 2.04-1.96 (m, 2H), 1.69-1.57 (m, 4H), 1.51-1.40 (m, 2H).

Example 1.330

Synthesis of 2-[methyl({2-[4-(oxetan-3-yloxy)pyridin-2-yl]-5H,6H,7H-cyclopenta[d]pyrimidin-4-yl})amino]-N-(6-methylpyridin-3-yl)acetamide (Compound 324)

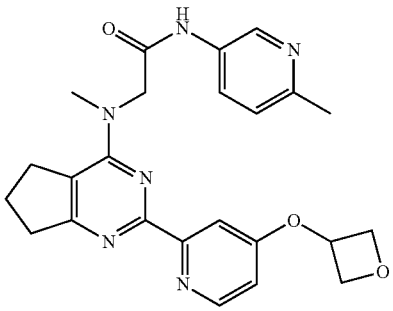 [SMILES: Cc1ccc(NC(=O)CN(C)c2nc(-c3cc(OC4COC4)ccn3)nc3c2CCC3)cn1]

Compound 324 was synthesized similar to compound 253 by replacing 5-amino-2-methoxypyridine with 6-methylpyridin-3-amine. LCMS (ES) [M+1]+ m/z: 447. ¹H NMR (300 MHz, DMSO-d$_6$, ppm) δ 10.35 (s, 1H), 8.62 (d, J=2.5 Hz, 1H), 8.45 (d, J=5.6 Hz, 1H), 7.92 (dd, J=8.4, 2.6 Hz, 1H), 7.63 (d, J=2.5 Hz, 1H), 7.18 (d, J=8.4 Hz, 1H), 6.84 (dd, J=5.6, 2.6 Hz, 1H), 5.36-5.33 (m, 1H), 4.95-4.85 (m, 2H), 4.52 (dd, J=7.6, 4.8 Hz, 2H), 4.42 (s, 2H), 3.37 (s, 3H), 3.21 (t, J=7.4 Hz, 2H), 2.83 (t, J=7.8 Hz, 2H), 2.40 (s, 3H), 2.04-1.99 (m, 2H).

Example 1.331

Synthesis of N-(4-chlorophenyl)-2-[methyl({2-[4-(oxetan-3-yloxy)pyridin-2-yl]-5H,6H,7H-cyclopenta[d]pyrimidin-4-yl})amino]acetamide (Compound 325)

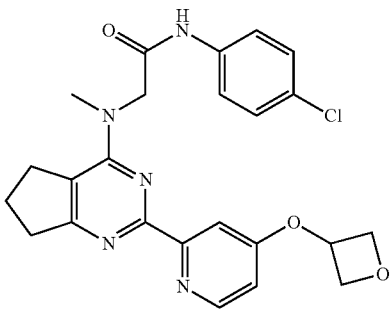 [SMILES: CN(CC(=O)Nc1ccc(Cl)cc1)c1nc(-c2cc(OC3COC3)ccn2)nc2c1CCC2]

Compound 325 was synthesized similar to compound 253 by replacing 5-amino-2-methoxypyridine with 4-chloroaniline. LCMS (ES) [M+1]+ m/z: 466. ¹H NMR (300 MHz, DMSO-d$_6$, ppm) δ 10.36 (s, 1H), 8.46 (d, J=5.6 Hz, 1H), 7.65 (d, J=8.8 Hz, 2H), 7.62 (d, J=2.6 Hz, 1H), 7.35 (d, J=8.8 Hz, 2H), 6.85 (dd, J=5.6, 2.6 Hz, 1H), 5.41-5.28 (m, 1H), 4.90 (t, J=6.7 Hz, 2H), 4.51 (dd, J=7.5, 4.7 Hz, 2H), 4.42 (s, 2H), 3.21 (t, J=7.3 Hz, 2H), 2.83 (t, J=7.8 Hz, 2H), 2.08-1.93 (m, 2H).

Example 1.332

Synthesis of 2-[methyl({2-[4-(oxetan-3-yloxy)pyridin-2-yl]-5H,6H,7H-cyclopenta[d]pyrimidin-4-yl})amino]-N-(4-methylphenyl)acetamide (Compound 326)

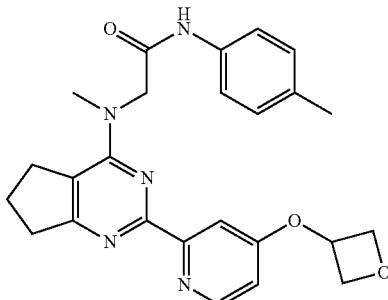

Compound 326 was synthesized similar to compound 253 by replacing 5-amino-2-methoxypyridine with 4-methylaniline. LCMS (ES) [M+1]+ m/z: 446. ¹H NMR (300 MHz, DMSO-d$_6$, ppm) δ 10.11 (s, 1H), 8.46 (d, J=5.7 Hz, 1H), 7.64 (t, J=1.9 Hz, 1H), 7.49 (d, J=8.0 Hz, 2H), 7.10 (d, J=8.0 Hz, 2H), 6.91-6.82 (m, 1H), 5.38-5.29 (m, 1H), 4.90 (t, J=6.7 Hz, 2H), 4.51 (dd, J=7.4, 4.7 Hz, 2H), 4.41 (s, 2H), 3.36 (s, 3H), 3.21 (t, J=7.4 Hz, 2H), 2.83 (t, J=7.9 Hz, 2H), 2.24 (s, 3H), 2.11-1.93 (m, 2H).

Example 1.333

Synthesis of N-(4-methoxyphenyl)-2-[methyl({2-[4-(oxetan-3-yloxy)pyridin-2-yl]-5H,6H,7H-cyclopenta[d]pyrimidin-4-yl})amino]acetamide (Compound 327)

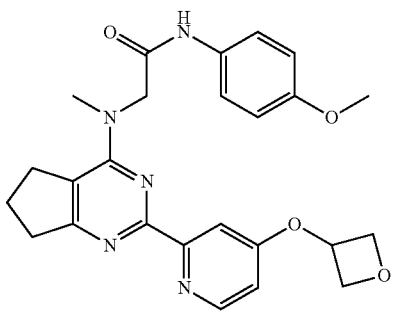

Compound 327 was synthesized similar to compound 253 by replacing 5-amino-2-methoxypyridine with p-anisidine. LCMS (ES) [M+1]+ m/z: 462. ¹H NMR (300 MHz, DMSO-d$_6$, ppm) δ 10.05 (s, 1H), 8.46 (d, J=5.6 Hz, 1H), 7.64 (d, J=2.5 Hz, 1H), 7.57-7.46 (m, 2H), 6.93-6.82 (m, 3H), 5.38-5.31 (m, 1H), 4.96-4.85 (m, 2H), 4.52 (dd, J=7.5, 4.7 Hz, 2H), 4.38 (s, 2H), 3.71 (s, 3H), 3.31 (s, 3H), 3.20 (t, J=7.3 Hz, 2H), 2.83 (t, J=7.8 Hz, 2H), 2.11-1.93 (m, 2H).

Example 1.334

Synthesis of N-tert-butyl-2-[methyl(2-{[1,3]thiazolo[5,4-c]pyridin-6-yl}-5H,6H,7H-cyclopenta[d]pyrimidin-4-yl)amino]acetamide (Compound 328)

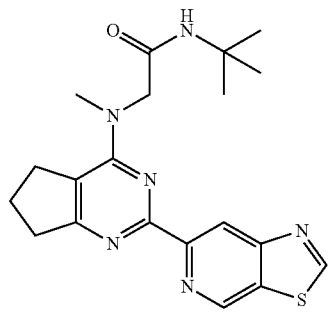 [SMILES: CN(CC(=O)NC(C)(C)C)c1nc(-c2cc3ncsc3cn2)nc2c1CCC2]

Compound 328 was synthesized similar to compound 245 by replacing 2-chloro-4-(oxetan-3-yloxy)pyridine with 6-chloro-[1,3]thiazolo[5,4-c]pyridine. LCMS (ES) [M+1]$^+$ m/z: 397. $^1$H NMR (300 MHz, DMSO-d6) δ 9.71 (s, 1H), 9.51 (d, J=0.9 Hz, 1H), 9.01 (d, J=0.9 Hz, 1H), 8.12 (HCOOH), 7.84 (s, 1H), 4.18 (s, 2H), 3.34 (s, 3H), 3.18 (t, J=7.3 Hz, 2H), 2.87 (d, J=7.8 Hz, 2H), 2.05-1.97 (m, 2H), 1.24 (s, 9H).

Example 1.335

Synthesis of N-(6-methoxypyridin-3-yl)-2-[methyl(2-{[1,3]thiazolo[5,4-c]pyridin-6-yl}-5H,6H,7H-cyclopenta[d]pyrimidin-4-yl)amino]acetamide (Compound 329)

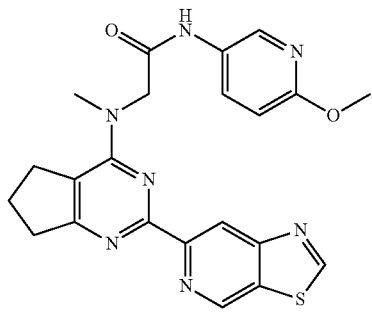 [SMILES: COc1ccc(NC(=O)CN(C)c2nc(-c3cc4ncsc4cn3)nc3c2CCC3)cn1]

Compound 329 was synthesized similar to compound 258 by replacing 3-chloro-2,6-naphthyridine with 6-chloro-[1,3]thiazolo[5,4-c]pyridine. LCMS (ES) [M+1]$^+$ m/z: 448. $^1$H NMR (300 MHz, DMSO-d6) δ 9.71 (s, 1H), 9.49 (d, J=0.9 Hz, 1H), 8.93 (d, J=0.9 Hz, 1H), 8.37 (d, J=2.7 Hz, 1H), 7.91 (dd, J=8.9, 2.7 Hz, 1H), 6.76 (d, J=8.9 Hz, 1H), 4.47 (s, 2H), 3.79 (s, 3H), 3.40 (s, 3H), 3.22 (t, J=7.8 Hz, 2H), 2.87 (t, J=7.8 Hz, 2H), 2.07-2.01 (m, 2H).

Example 1.336

Synthesis of 2-[(2-{4-[(1-hydroxycyclopropyl)methoxy]pyridin-2-yl}-5H,6H,7H-cyclopenta[d]pyrimidin-4-yl)(methyl)amino]-N-(6-methylpyridin-3-yl)acetamide (Compound 330)

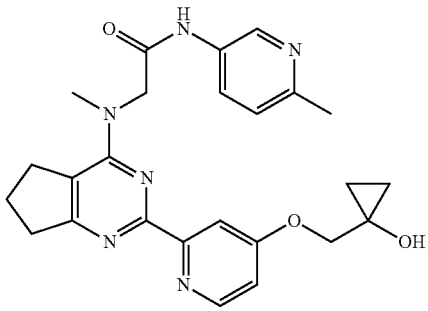 [SMILES: Cc1ccc(NC(=O)CN(C)c2nc(-c3cc(OCC4(O)CC4)ccn3)nc3c2CCC3)cn1]

Compound 330 was synthesized similar to Compound 252 by replacing 1-(2-hydroxyethyl)pyrrolidine with {1-[(tert-butyldimethylsilyl)oxy]cyclopropyl}methanol and replacing 3-fluoroaniline with 6-methyl-3-aminopyridine. LCMS (ES) [M+1]$^+$ m/z: 461.2. $^1$H NMR (300 MHz, DMSO-d$_6$) δ 10.34 (s, 1H), 8.59 (d, J=2.6 Hz, 1H), 8.43 (d, J=5.6 Hz, 1H), 8.17 (s, 1H), 7.99-7.75 (m, 2H), 7.38-6.94 (m, 2H), 4.43 (s, 2H), 3.67 (s, 2H), 3.35 (s, 3H), 3.20 (t, J=7.1 Hz, 2H), 2.83 (t, J=7.8 Hz, 2H), 2.40 (s, 3H), 2.05-1.95 (m, 2H), 0.93 (d, J=5.1 Hz, 2H), 0.87 (d, J=5.2 Hz, 2H).

Example 1.337

Synthesis of 2-({2-[4-(2-hydroxyethoxy)pyridin-2-yl]-5,5-dimethyl-5H,6H,7H-cyclopenta[d]pyrimidin-4-yl}(methyl)amino)-N-(6-methylpyridin-3-yl)acetamide (Compound 331)

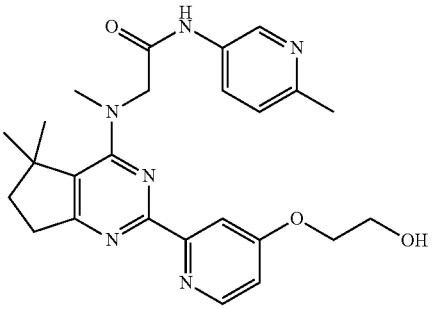 [SMILES: Cc1ccc(NC(=O)CN(C)c2nc(-c3cc(OCCO)ccn3)nc3c2C(C)(C)CC3)cn1]

Scheme 123

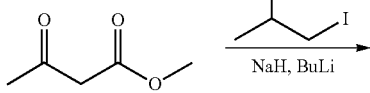

821

-continued

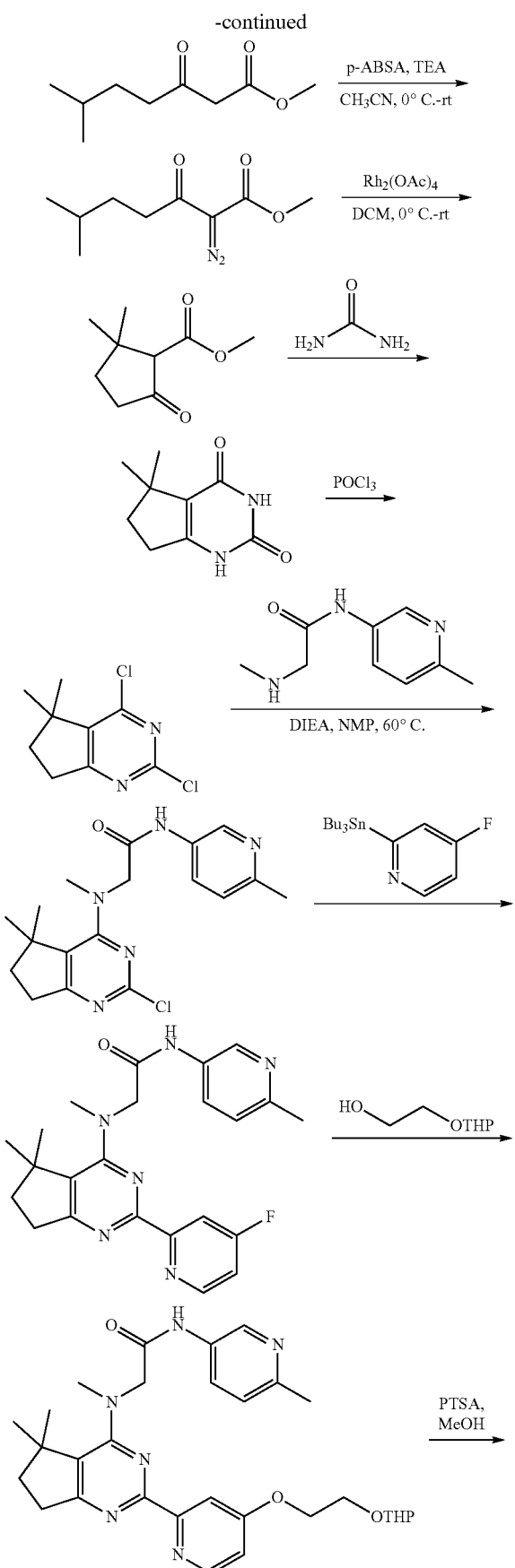

822

-continued

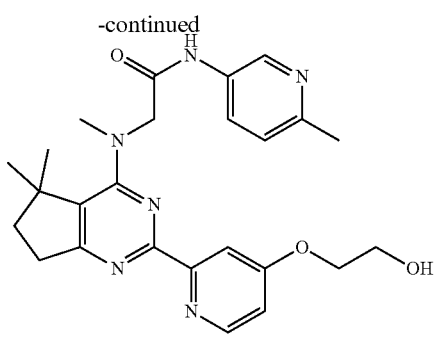

Step 1

Into a 500-mL 3-necked round-bottom flask purged and maintained with an inert atmosphere of nitrogen, was placed NaH (6.82 g, 284.19 mmol, 1.10 equiv), THF (300.00 mL). To this was added methyl acetoacetate (30.00 g, 258.36 mmol, 1.00 equiv) dropwise at 0° C. The resulting solution was stirred for 15 min at 0° C. To this was added n-BuLi (108.51 mL, 271.27 mmol, 1.05 equiv) dropwise with stirring at 0° C. in 15 min. To the mixture was added 1-iodo-2-methylpropane (71.32 g, 387.54 mmol, 1.50 equiv) dropwise with stirring at 0° C. in 30 min. The resulting solution was stirred for 30 min at room temperature. The pH value of the solution was adjusted to 6 with HCl (1 mol/L). The resulting solution was extracted with 3×500 mL of ether and the organic layers combined. The resulting solution was extracted with 3×500 mL of NaCl and the organic layers combined and dried over anhydrous sodium sulfate and concentrated. The residue was applied onto a silica gel column with PE/THF (4%). This resulted in 18 g (40.45%) of methyl 6-methyl-3-oxoheptanoate as a yellow liquid.

Step 2

Into a 500-mL 3-necked round-bottom flask purged and maintained with an inert atmosphere of nitrogen, was placed methyl 6-methyl-3-oxoheptanoate (18.00 g, 104.52 mmol, 1.00 equiv), CH₃CN (400.00 mL), 4-acetamidobenzene-sulfonyl azide (25.11 g, 104.52 mmol, 1.00 equiv). This was followed by the addition of Et₃N (31.73 g, 313.55 mmol, 3.00 equiv) dropwise with stirring at 0° C. The resulting solution was stirred for overnight at room temperature. The resulting mixture was concentrated. The resulting solution was diluted with 300 mL of ether/n-hexane=1:1. The solids were filtered out. The resulting mixture was concentrated. The residue was applied onto a silica gel column with THF/PE (10%). This resulted in 17.8 g (85.92%) of methyl 2-diazo-6-methyl-3-oxoheptanoate as a yellow oil.

Step 3

Into a 500-mL 3-necked round-bottom flask purged and maintained with an inert atmosphere of nitrogen, was placed Rh₂(OAc)₄ (0.39 g, 0.87 mmol, 0.01 equiv), DCM (250.00 mL). This was followed by the addition of a solution of methyl 2-diazo-6-methyl-3-oxoheptanoate (17.30 g, 87.27 mmol, 1.00 equiv) in DCM (50 mL) dropwise with stirring at 0° C. The resulting solution was stirred for 4 h at room temperature. The resulting solution was extracted with 3×200 mL of dichloromethane and the organic layers combined and dried over anhydrous sodium sulfate and concentrated. The residue was applied onto a silica gel column with THF/PE (5.6%). This resulted in 12.57 g (84.62%) of methyl 2,2-dimethyl-5-oxocyclopentane-1-carboxylate as a dark green liquid. LCMS (ES) [M+1]⁺ m/z: 171.

Step 4

Into a 500-mL round-bottom flask, was placed methyl 2,2-dimethyl-5-oxocyclopentane-1-carboxylate (12.00 g, 70.50 mmol, 1.00 equiv), urea (12.70 g, 211.47 mmol, 3.00 equiv), EtOH (225.00 mL), HCl (gas) in 1,4-dioxane (45.00 mL). The resulting solution was stirred for 3 h at 100° C. The reaction mixture was cooled to room temperature. The resulting mixture was concentrated. The resulting solution was diluted with 200 mL of 5% NaOH. The resulting solution was stirred for 1 h at 80° C. The reaction mixture was cooled to 0° C. The pH value of the solution was adjusted to 3 with HCl (1 mol/L). The solids were collected by filtration. This resulted in 6.5 g (51.16%) of 5,5-dimethyl-1H,3H,6H,7H-cyclopenta[d]pyrimidine-2,4-dione as a grey solid. LCMS (ES) [M−1]+ m/z: 179.

Step 5

Into a 250-mL round-bottom flask, was placed 5,5-dimethyl-1H,3H,6H,7H-cyclopenta[d]pyrimidine-2,4-dione (6.50 g, 36.07 mmol, 1.00 equiv), Et$_3$N (3.65 g, 36.07 mmol, 1.00 equiv). This was followed by the addition of POCl$_3$ (80.00 mL) dropwise with stirring at room temperature. The resulting solution was stirred for 2 h at 80° C. The reaction mixture was cooled to room temperature. The resulting mixture was concentrated. The resulting solution was diluted with 200 mL of water/ice. The pH value of the solution was adjusted to 7-8 with Na$_2$CO$_3$. The resulting solution was extracted with 3×200 mL of dichloromethane and the organic layers combined and dried over anhydrous sodium sulfate and concentrated. The residue was applied onto a silica gel column with THF/PE (10%). This resulted in 7.15 g (91.31%) of 2,4-dichloro-5,5-dimethyl-6H,7H-cyclopenta[d]pyrimidine as light yellow liquid. LCMS (ES) [M+1]+ m/z: 217.

Step 6

Into a 40-mL vial, was placed 2,4-dichloro-5,5-dimethyl-6H,7H-cyclopenta[d]pyrimidine (1.00 g, 4.61 mmol, 1.00 equiv), 2-(methylamino)-N-(6-methylpyridin-3-yl)acetamide (1.07 g, 5.97 mmol, 1.30 equiv), NMP (20.00 mL), DIEA (2.98 g, 23.03 mmol, 5.00 equiv). The resulting solution was stirred for 6 h at 60° C. The reaction mixture was cooled to room temperature. The crude product (3 g) was purified by Prep-HPLC with the following conditions: Column, XBridge Prep C18 OBD Column, 19 cm, 150 mm, 5 um; mobile phase, Water (0.1% FA) and CAN (20% Phase B up to 60% in 11 min); Detector, 254. This resulted in 500 mg (30.16%) of 2-([2-chloro-5,5-dimethyl-6H,7H-cyclopenta[d]pyrimidin-4-yl](methyl)amino)-N-(6-methylpyridin-3-yl)acetamide as off-white solid. LCMS (ES) [M+1]+ m/z: 360.

Step 7

Into a 40-mL vial, was placed 2-([2-chloro-5,5-dimethyl-6H,7H-cyclopenta[d]pyrimidin-4-yl](methyl)amino)-N-(6-methylpyridin-3-yl)acetamide (500.00 mg, 1.39 mmol, 1.00 equiv), toluene (10.00 mL), 4-fluoro-2-(tributylstannyl)pyridine (804.78 mg, 2.08 mmol, 1.50 equiv), Pd(PPh$_3$)$_4$ (160.56 mg, 0.14 mmol, 0.10 equiv). The resulting solution was stirred for overnight at 120° C. The reaction mixture was cooled to room temperature. The resulting mixture was concentrated. The residue was applied onto a silica gel column with THF/PE (45%). This resulted in 300 mg (51.35%) of 2-[[2-(4-fluoropyridin-2-yl)-5,5-dimethyl-6H,7H-cyclopenta[d]pyrimidin-4-yl](methyl)amino]-N-(6-methylpyridin-3-yl)acetamide as white solid. LCMS (ES) [M+1]+ m/z: 421.

Step 8

Into a 40-mL vial, was placed 2-(oxan-2-yloxy)ethanol (208.59 mg, 1.43 mmol, 2.00 equiv), DMF (10.00 mL). This was followed by the addition of NaH (42.80 mg, 1.78 mmol, 2.50 equiv), in portions at 0° C. The resulting solution was stirred for 0.5 h at room temperature. To this was added 2-[[2-(4-fluoropyridin-2-yl)-5,5-dimethyl-6H,7H-cyclopenta[d]pyrimidin-4-yl](methyl)amino]-N-(6-methylpyridin-3-yl)acetamide (300.00 mg, 0.71 mmol, 1.00 equiv), in portions at 0° C. The resulting solution was stirred for 2 h at room temperature. The reaction was then quenched by the addition of 20 mL of water/ice. The resulting solution was extracted with 3×40 mL of ethyl acetate and the organic layers combined and dried over anhydrous sodium sulfate and concentrated. The crude product (0.5 g) was purified by Prep-HPLC with the following conditions: Column, XBridge Prep C18 OBD Column, 19 cm, 150 mm, 5 um; mobile phase, Water (0.1% NH$_3$·H$_2$O) and CAN (20% Phase B up to 60% in 11 min); Detector, 254. This resulted in 230 mg (58.97%) of 2-[(5,5-dimethyl-2-[4-[2-(oxan-2-yloxy)ethoxy]pyridin-2-yl]-6H,7H-cyclopenta[d]pyrimidin-4-yl)(methyl)amino]-N-(6-methylpyridin-3-yl)acetamide as off-white solid. LCMS (ES) [M+1]+ m/z: 547.

Step 9

Into a 20-mL vial, was placed 2-[(5,5-dimethyl-2-[4-[2-(oxan-2-yloxy)ethoxy]pyridin-2-yl]-6H,7H-cyclopenta[d]pyrimidin-4-yl)(methyl)amino]-N-(6-methylpyridin-3-yl)acetamide (230.00 mg, 0.42 mmol, 1.00 equiv), MeOH (5.00 mL), PTSA (36.23 mg, 0.21 mmol, 0.50 equiv). The resulting solution was stirred for 1 h at room temperature. The crude product (0.2 g) was purified by Prep-HPLC with the following conditions: Column, XBridge Prep C18 OBD Column, 19 cm, 150 mm, 5 um; mobile phase A, Water (0.1% NH$_3$·H$_2$O) and mobile phase B, AcCN (20% Phase B up to 60% in 11 min); Detector, 254 nm. This resulted in 166.5 mg (85.56%) of 2-([2-[4-(2-hydroxyethoxy)pyridin-2-yl]-5,5-dimethyl-6H,7H-cyclopenta[d]pyrimidin-4-yl](methyl)amino)-N-(6-methylpyridin-3-yl)acetamide as white solid. LCMS (ES, m/z): [M+H]+: 463. $^1$H-NMR (300 MHz, DMSO-d$_6$, ppm): δ 10.51 (s, 1H), 8.59 (d, J=2.6 Hz, 1H), 8.42 (d, J=5.7 Hz, 1H), 7.89 (dd, J=8.4, 2.5 Hz, 1H), 7.77 (d, J=2.5 Hz, 1H), 7.16 (d, J=8.4 Hz, 1H), 7.01 (dd, J=5.6, 2.5 Hz, 1H), 5.00 (t, J=5.1 Hz, 1H), 4.30 (s, 2H), 4.01 (t, J=4.8 Hz, 2H), 3.67 (q, J=4.9 Hz, 2H), 3.32 (s, 3H), 2.88 (t, J=7.3 Hz, 2H), 2.39 (s, 3H), 1.89 (t, J=7.3 Hz, 2H), 1.46 (s, 6H).

Example 1.338 and 1.339

Synthesis of Racemic N-tert-butyl-2-{methyl[2-(4-{[(2S,3S)-2-methyloxetan-3-yl]oxy}pyridin-2-yl)-5H,6H,7H-cyclopenta[d]pyrimidin-4-yl]amino}acetamide (Compound 332) and Racemic N-tert-butyl-2-{methyl[2-(4-{[(2R,3S)-2-methyloxetan-3-yl]oxy}pyridin-2-yl)-5H,6H,7H-cyclopenta[d]pyrimidin-4-yl]amino}acetamide (Compound 333)

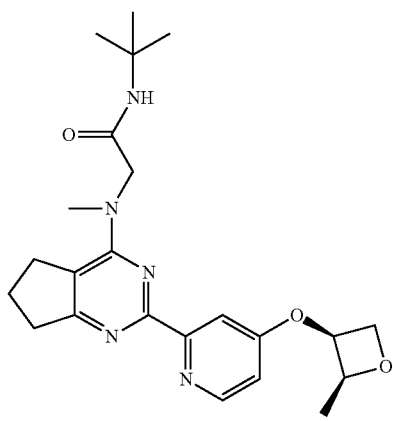

cis

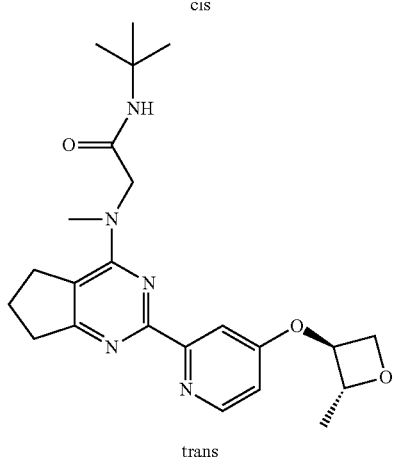

trans

Scheme 124

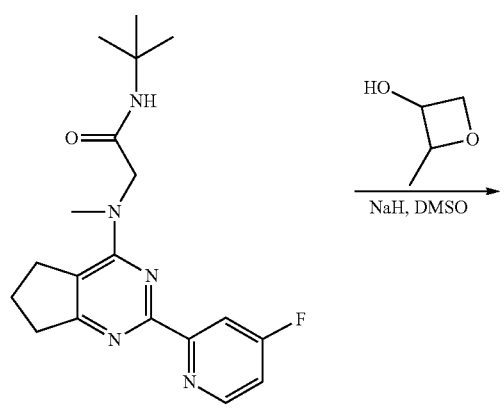

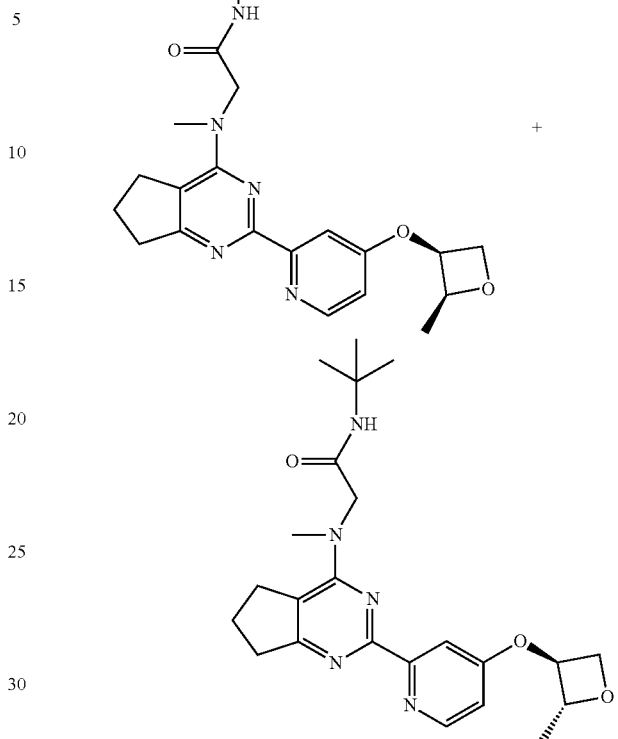

Into a 50-mL 3-necked round-bottom flask, was placed 2-methyloxetan-3-ol (222 mg, 2.52 mmol, 3.00 equiv), DMSO (5 mL). This was followed by the addition of NaH (101 mg, 2.52 mmol, 3.00 equiv, 60%) at 0° C. The resulting solution was stirred for 30 min at 25° C. To this was added a solution of N-tert-butyl-2-[[2-(4-fluoropyridin-2-yl)-5H,6H,7H-cyclopenta[d]pyrimidin-4-yl](methyl)amino]acetamide (300 mg, 0.84 mmol, 1.00 equiv) in DMSO (2 mL) dropwise with stirring at 0° C. The resulting solution was stirred for 1 hr at 25° C. The reaction was then quenched by the addition of 1 mL of water. The crude product was purified by Prep-HPLC with the following conditions (2 #SHIMADZU (HPLC-01)): Column, Atlantis Prep T3 OBD Column, 19*150 mm 5 um; mobile phase, Water (0.05% TFA) and ACN (16% Phase B up to 30% in 15 min); Detector, UV. 254 nm. This resulted in 108.8 mg (33.78%) of racemic N-tert-butyl-2-[methyl[2-(4-[[(2R,3 S)-2-methyloxetan-3-yl]oxy]pyridin-2-yl)-5H,6H,7H-cyclopenta[d]pyrimidin-4-yl]amino]acetamide (Compound 332); tris(trifluoroacetic acid salt) as an off-white solid and 53.7 mg (23.72%) of racemic N-tert-butyl-2-[methyl[2-(4-[[(2S,3S)-2-methyloxetan-3-yl]oxy]pyridin-2-yl)-5H,6H,7H-cyclopenta[d]pyrimidin-4-yl]amino]acetamide (Compound 333); trifluoroacetic acid as an off-white solid.

Compound 332: LCMS (ES) [M+1]$^+$ m/z 426. $^1$H NMR (300 MHz, DMSO-d$_6$) δ 8.48 (d, J=5.6 Hz, 1H), 7.79 (d, J=2.5 Hz, 1H), 7.69 (s, 1H), 6.91 (dd, J=5.6, 2.6 Hz, 1H), 5.44 (q, J=5.7 Hz, 1H), 5.21 (p, J=6.3 Hz, 1H), 4.93-4.83 (m, 1H), 4.49 (dd, J=7.4, 4.8 Hz, 1H), 4.23-4.04 (m, 2H), 3.27 (s, 3H), 3.15 (t, J=7.4 Hz, 2H), 2.81 (t, J=7.8 Hz, 2H), 1.98 (q, J=7.8 Hz, 2H), 1.30 (d, J=6.5 Hz, 3H), 1.26 (s, 9H).

Compound 333: LCMS (ES) [M+1]$^+$ m/z 426. $^1$H NMR (300 MHz, DMSO-d$_6$) δ 8.69 (d, J=5.8 Hz, 1H), 8.04-7.98

(m, 2H), 7.22 (dd, J=5.9, 2.7 Hz, 1H), 5.26 (t, J=5.3 Hz, 1H), 4.89 (t, J=6.5 Hz, 2H), 4.40 (t, J=6.4 Hz, 1H), 4.35 (s, 2H), 3.47 (s, 3H), 3.25 (s, 2H), 3.04 (t, J=7.9 Hz, 2H), 2.10 (t, J=7.6 Hz, 2H), 1.50 (d, J=6.3 Hz, 3H), 1.27 (s, 9H).

Example 1.340

Synthesis of 2-({2-[4-(2-hydroxyethoxy)pyridin-2-yl]-5H,6H,7H-cyclopenta[d]pyrimidin-4-yl}(methyl)amino)-N-(4-methoxyphenyl)-N-methylacetamide (Compound 334)

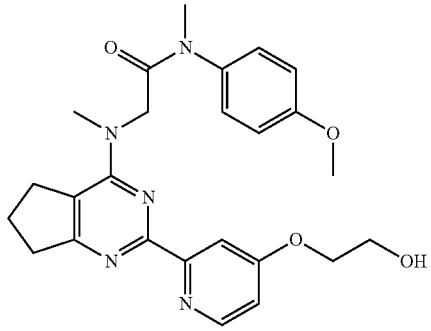 [SMILES: COc1ccc(N(C)C(=O)CN(C)c2nc(-c3cc(OCCO)ccn3)nc3c2CCC3)cc1]

Compound 334 was synthesized similar to compound 44 by replacing tert-butylamine with 4-methoxy-N-methylaniline. LCMS (ES) [M+1]⁺ m/z: 464. ¹H NMR (300 MHz, DMSO-d6) δ 8.52 (d, J=5.7 Hz, 1H), 7.78 (s, 1H), 7.48 (d, J=8.4 Hz, 2H), 7.05-7.03 (m, 3H), 4.95 (t J=5.5 Hz, 1H), 4.19-4.15 (m, 4H), 3.79 (s, 5H), 3.29 (s, 3H), 3.27-3.22 (m, 5H), 3.14 (s, 2H), 2.92-2.71 (m, 2H), 2.13-1.85 (m, 2H).

Example 1.341

Synthesis of 2-({2-[4-(2-hydroxyethoxy)pyridin-2-yl]-5H,6H,7H-cyclopenta[d]pyrimidin-4-yl}(methyl)amino)-1-(5-methoxy-2,3-dihydro-1H-indol-1-yl)ethan-1-one (Compound 335)

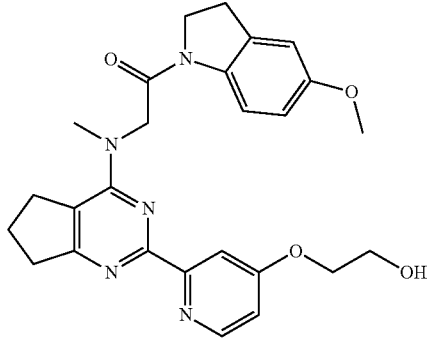 [SMILES: COc1ccc2c(c1)CCN2C(=O)CN(C)c1nc(-c2cc(OCCO)ccn2)nc2c1CCC2]

Compound 335 was synthesized similar to compound 44 by replacing tert-butylamine with 5-methoxy-2,3-dihydro-1H-indole. LCMS (ES) [M+1]⁺ m/z: 476. ¹H NMR (300 MHz, DMSO-d6) δ 8.42 (d, J=5.6 Hz, 1H), 7.90 (d, J=8.7 Hz, 1H), 7.70 (d, J=2.5 Hz, 1H), 6.98 (dd, J=5.8, 2.6 Hz, 1H), 6.87 (d, J=2.6 Hz, 1H), 6.68 (d, J=8.7 Hz, 1H), 4.88 (t, J=5.3 Hz, 1H), 4.57 (s, 2H), 4.25 (t, J=8.3 Hz, 2H), 3.97 (d, J=4.9 Hz, 2H), 3.71 (s, 3H), 3.63 (q, J=4.6 Hz, 2H), 3.33 (s, 3H), 3.18 (t, J=7.7 Hz, 4H), 2.82 (t, J=7.9 Hz, 2H), 2.02-1.96 (m, 2H).

Example 1.342

Synthesis of N-tert-butyl-2-[methyl(2-{2-methyl-2H-pyrazolo[3,4-c]pyridin-5-yl}-5H,6H,7H-cyclopenta[d]pyrimidin-4-yl)amino]acetamide (Compound 336)

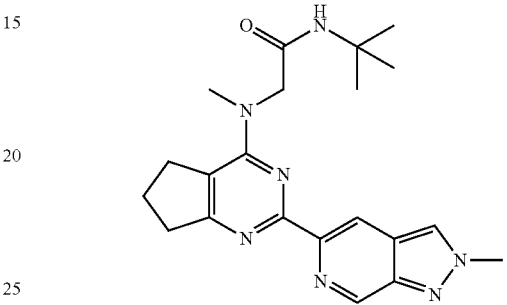

Compound 336 was synthesized similar to compound 24 by replacing 2-tributylstannylpyridine with 2-methyl-5-(tributylstannyl)-2H-pyrazolo[3,4-c]pyridine. LCMS (ES+): [M+H]⁺=394.1. ¹H NMR (400 MHz, DMSO-d6) δ 9.37 (s, 1H), 9.03 (s, 1H), 8.84 (s, 1H), 8.06 (s, 1H), 4.45-4.32 (m, 6H), 3.51 (s, 2H), 3.09-3.03 (m, 2H), 2.15-2.07 (m, 2H), 1.25 (s, 9H).

Example 1.343

Synthesis of 2-({2-[4-(2-hydroxy-2-methylpropoxy)pyridin-2-yl]-5H,6H,7H-cyclopenta[d]pyrimidin-4-yl}(methyl)amino)-N-[1-(trifluoromethyl)cyclopropyl]acetamide (Compound 337)

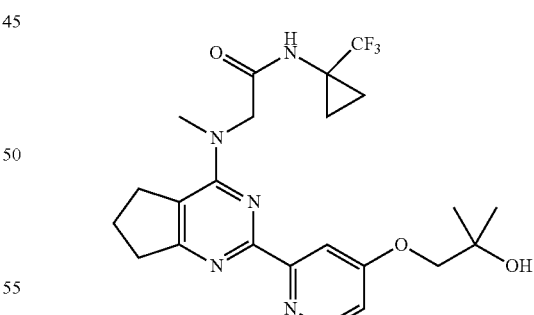

Compound 337 was synthesized similar to compound 280 by replacing 3-fluoroaniline with 1-(trifluoromethyl)cyclopropan-1-amine hydrochloride. LCMS (ES) [M+1]⁺ m/z: 480. ¹H NMR (300 MHz, DMSO-d6) δ 9.07 (s, 1H), 8.46 (d, J=5.6 Hz, 1H), 8.18 (s, HCOOH), 7.76 (d, J=2.5 Hz, 1H), 7.05 (dd, J=5.7, 2.6 Hz, 1H), 4.69 (s, 1H), 4.18 (s, 2H), 3.87 (s, 2H), 3.28 (s, 3H), 3.15 (t, J=7.3 Hz, 2H), 2.83 (t, J=7.8 Hz, 2H), 2.08-1.92 (m, 2H), 1.24 (s, 6H), 1.22-1.07 (m, 2H), 1.04-0.94 (m, 2H).

Example 1.344

Synthesis of 2-[methyl({2-[4-(oxetan-3-yloxy)pyridin-2-yl]-5H,6H,7H-cyclopenta[d]pyrimidin-4-yl})amino]-N-[1-(trifluoromethyl)cyclopropyl]acetamide (Compound 338)

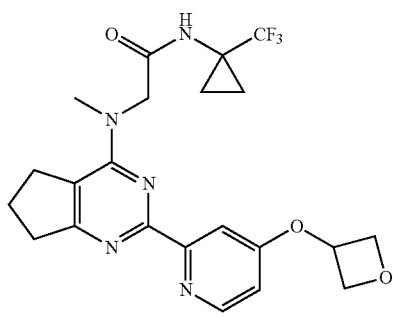 [SMILES: CN(CC(=O)NC1(C(F)(F)F)CC1)c1nc(-c2cc(OC3COC3)ccn2)nc2c1CCC2]

Compound 338 was synthesized similar to compound 253 by replacing 5-amino-2-methoxypyridine with 1-(trifluoromethyl)cyclopropan-1-amine hydrochloride. LCMS (ES) [M+1]$^+$ m/z: 464. $^1$H NMR (300 MHz, DMSO-d6) δ 8.98 (s, 1H), 8.48 (d, J=5.5 Hz, 1H), 7.63 (d, J=2.6 Hz, 1H), 6.89 (dd, J=5.6, 2.6 Hz, 1H), 5.54-5.41 (m, 1H), 5.15-4.91 (m, 2H), 4.64-4.54 (m, 2H), 4.18 (s, 2H), 3.33 (s, 3H), 3.16 (t, J=7.3 Hz, 2H), 2.82 (t, J=7.8 Hz, 2H), 2.07-1.94 (m, 2H), 1.25-1.14 (m, 2H), 1.03-0.96 (s, 2H).

Example 1.345

Synthesis of N-(4-chlorophenyl)-2-({2-[4-(2-hydroxyethoxy)pyridin-2-yl]-5H,6H,7H-cyclopenta[d]pyrimidin-4-yl}(methyl)amino)acetamide (Compound 339)

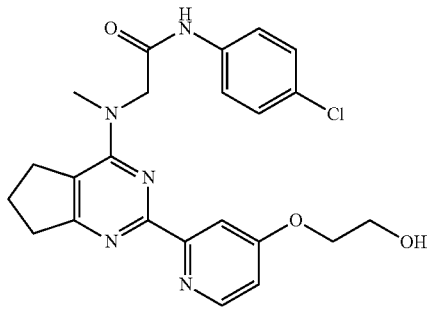 [SMILES: CN(CC(=O)Nc1ccc(Cl)cc1)c1nc(-c2cc(OCCO)ccn2)nc2c1CCC2]

Compound 339 was synthesized similar to compound 44 by replacing tert-butylamine with 4-chloroaniline. LCMS (ES) [M+1]$^+$ m/z: 454. $^1$H NMR (300 MHz, DMSO-d6) δ 10.37 (s, 1H), 8.45 (d, J=5.7 Hz, 1H), 8.14 (s, 0.5HCOOH), 7.78 (d, J=2.4 Hz, 1H), 7.64 (d, J=8.9 Hz, 2H), 7.36 (d, J=8.9 Hz, 2H), 7.02 (s, 1H), 4.93 (t, J=5.3 Hz, 1H), 4.43 (s, 2H), 4.05 (t, J=4.7 Hz, 2H), 3.69 (d, J=5.0 Hz, 2H), 3.37 (s, 3H), 3.24 (t, J=7.1 Hz, 2H), 2.87 (t, J=7.9 Hz, 2H), 2.04-1.93 (m, 2H).

Example 1.346

Synthesis of N-(4-chlorophenyl)-2-({2-[4-(2-hydroxyethoxy)pyridin-2-yl]-5H,6H,7H-cyclopenta[d]pyrimidin-4-yl}(methyl)amino)acetamide (Compound 340)

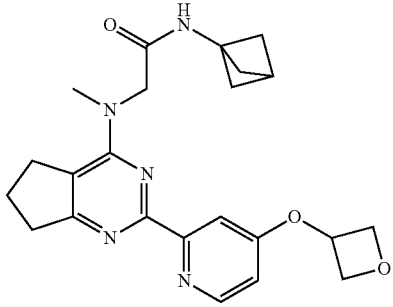 [SMILES: CN(CC(=O)NC12CC(C1)C2)c1nc(-c2cc(OC3COC3)ccn2)nc2c1CCC2]

Compound 340 was synthesized similar to compound 253 by replacing 5-amino-2-methoxypyridine with bicyclo[1.1.1]pentan-1-amine hydrochloride. LCMS (ES) [M+1]$^+$ m/z: 422. $^1$H NMR (300 MHz, DMSO-d$_6$, ppm) δ 8.70 (s, 1H), 8.50 (dd, J=5.6, 1.4 Hz, 1H), 7.68 (d, J=2.4 Hz, 1H), 6.90 (dt, J=5.6, 2.8 Hz, 1H), 5.58-5.43 (m, 1H), 5.05-4.94 (m, 2H), 4.59 (dd, J=7.7, 4.8 Hz, 2H), 4.13 (s, 2H), 3.30 (s, 3H), 3.16 (t, J=7.3 Hz, 2H), 2.83 (t, J=7.8 Hz, 2H), 2.38 (s, 1H), 2.08-1.97 (m, 2H), 1.98 (s, 6H).

Example 1.347

Synthesis of N-tert-butyl-2-[(2-{furo[3,2-c]pyridin-6-yl}-5H,6H,7H-cyclopenta[d]pyrimidin-4-yl)(methyl)amino]acetamide (Compound 341)

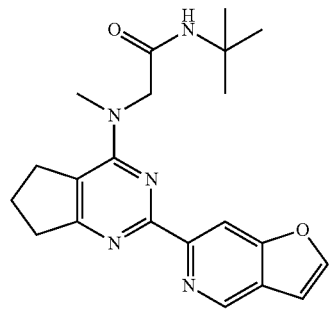 [SMILES: CN(CC(=O)NC(C)(C)C)c1nc(-c2cc3occc3cn2)nc2c1CCC2]

Compound 341 was synthesized similar to compound 245 replacing 2-chloro-4-(oxetan-3-yloxy)pyridine with 6-chlorofuro[3,2-c]pyridine. LCMS (ES) [M+1]$^+$ m/z: 380. $^1$H NMR (300 MHz, DMSO-d6) δ 9.03 (s, 1H), 8.60 (s, 1H), 8.20 (d, J=2.2 Hz, 2H), 8.15 (s, 0.5HCOOH), 7.79 (s, 1H), 7.20-7.13 (m, 1H), 4.15 (s, 2H), 3.32 (s, 3H), 3.17 (t, J=7.4 Hz, 2H), 2.84 (t, J=7.8 Hz, 2H), 2.05-1.96 (m, 2H), 1.25 (s, 9H).

Example 1.348

Synthesis of 2-[methyl(2-{4-[(3R)-oxolan-3-yloxy]pyridin-2-yl}-5H,6H,7H-cyclopenta[d]pyrimidin-4-yl)amino]-1-(piperidin-1-yl)ethan-1-one (Compound 342)

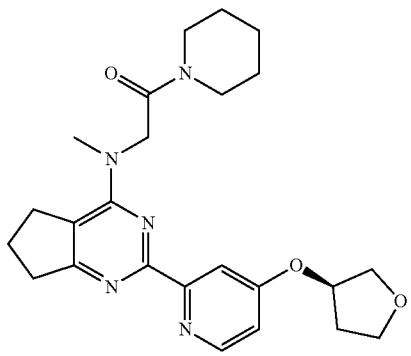 [SMILES: CN(CC(=O)N1CCCCC1)c1nc(-c2cc(O[C@@H]3CCOC3)ccn2)nc2c1CCC2]

Compound 342 was synthesized similar to compound 318 by replacing tert-butylamine with piperidine. LCMS (ES) [M+1]$^+$ m/z: 438. $^1$H NMR (300 MHz, DMSO-d6) δ 8.47 (d, J=5.6 Hz, 1H), 8.15 (s, 0.5HCOOH), 7.71 (d, J=2.5 Hz, 1H), 7.04 (dd, J=5.7, 2.6 Hz, 1H), 5.25-5.16 (m, 1H), 4.49 (s, 2H), 3.94 (dd, J=10.3, 4.5 Hz, 1H), 3.90-3.73 (m, 3H), 3.52-3.40 (m, 4H), 3.25 (s, 3H), 3.14 (t, J=7.3 Hz, 2H), 2.81 (t, J=7.9 Hz, 2H), 2.38-2.20 (m, 1H), 2.04-1.94 (m, 3H), 1.71-1.61 (m, 4H), 1.52-1.43 (m, 2H).

Example 1.349

Synthesis of 2-[methyl(2-{4-[(3S)-oxolan-3-yloxy]pyridin-2-yl}-5H,6H,7H-cyclopenta[d]pyrimidin-4-yl)amino]-1-(piperidin-1-yl)ethan-1-one (Compound 343)

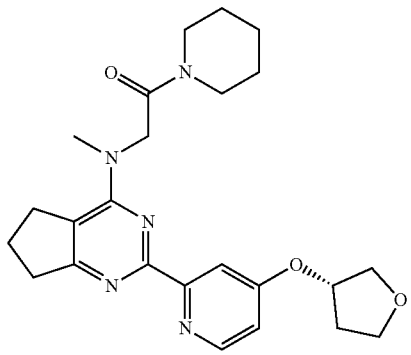 [SMILES: CN(CC(=O)N1CCCCC1)c1nc(-c2cc(O[C@H]3CCOC3)ccn2)nc2c1CCC2]

Compound 343 was synthesized similar to compound 317 by replacing tert-butylamine with piperidine. LCMS (ES) [M+1]$^+$ m/z: 438. $^1$H NMR (300 MHz, DMSO-d6) δ 8.47 (d, J=5.6 Hz, 1H), 8.15 (s, 0.5HCOOH), 7.71 (d, J=2.5 Hz, 1H), 7.04 (dd, J=5.7, 2.6 Hz, 1H), 5.25-5.16 (m, 1H), 4.49 (s, 2H), 3.94 (dd, J=10.3, 4.5 Hz, 1H), 3.90-3.73 (m, 3H), 3.51-3.41 (m, 4H), 3.25 (s, 3H), 3.14 (t, J=7.3 Hz, 2H), 2.81 (t, J=7.9 Hz, 2H), 2.38-2.20 (m, 1H), 2.04-1.94 (m, 3H), 1.71-1.61 (m, 4H), 1.52-1.43 (m, 2H).

Example 1.350

Synthesis of 2-[(2-{4-[2-(dimethylamino)ethoxy]pyridin-2-yl}-5H,6H,7H-cyclopenta[d]pyrimidin-4-yl)(methyl)amino]-N-(6-methoxypyridin-3-yl)acetamide (Compound 344)

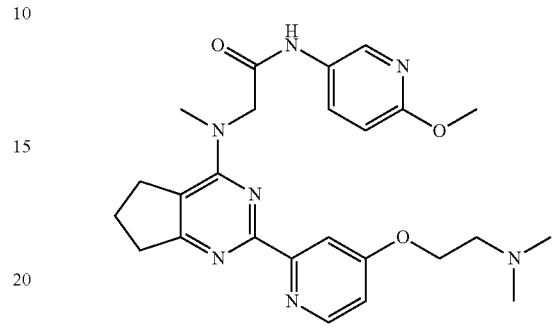

Compound 344 was synthesized similar to compound 187 by replacing ethane-1,2-diol with dimethylaminoethanol. LCMS (ES) [M+1]$^+$ m/z: 478. $^1$H NMR (300 MHz, DMSO-d6) δ 10.27 (s, 1H), 8.44 (d, J=5.6 Hz, 1H), 8.34 (d, J=2.6 Hz, 1H), 8.17 (s, 0.7HCOOH), 7.89 (dd, J=8.9, 2.7 Hz, 1H), 7.76 (d, J=2.6 Hz, 1H), 7.01 (dd, J=5.6, 2.6 Hz, 1H), 6.78 (d, J=8.9 Hz, 1H), 4.39 (s, 2H), 4.07 (t, J=5.6 Hz, 2H), 3.81 (s, 3H), 3.38 (s, 3H), 3.22 (t, J=7.3 Hz, 2H), 2.83 (t, J=7.8 Hz, 2H), 2.58 (t, J=5.6 Hz, 2H), 2.20 (s, 6H), 2.06-1.99 (m, 2H).

Example 1.351

Synthesis of N-(3-fluorophenyl)-2-[methyl(2-{4-[(1s,3s)-3-hydroxycyclobutoxy]pyridin-2-yl}-5H,6H,7H-cyclopenta[d]pyrimidin-4-yl)amino]acetamide (Compound 345)

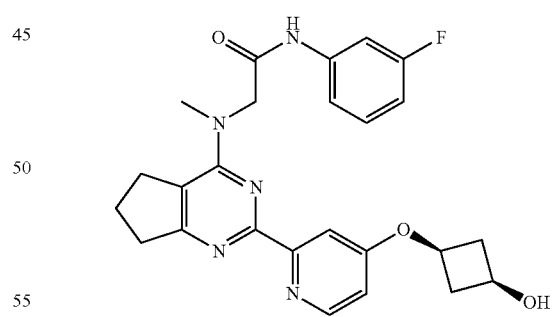

Compound 345 was synthesized similar to compound 280 replacing 1-[(2-chloropyridin-4-yl)oxy]-2-methylpropan-2-ol with 4-((1s,3s)-3-(benzyloxy)cyclobutoxy)-2-chloropyridine. LCMS (ES) [M+1]$^+$ m/z: 464. $^1$H NMR (300 MHz, DMSO-d6) δ 8.55 (d, J=6.0 Hz, 1H), 7.89 (d, J=2.5 Hz, 1H), 7.55 (d, J=11.5 Hz, 1H), 7.43-7.28 (m, 2H), 7.17 (dd, J=6.1, 2.7 Hz, 1H), 6.92-6.81 (m, 1H), 4.60 (s, 2H), 4.53-4.37 (m, 1H), 4.03-3.87 (m, 1H), 3.59 (s, 3H), 3.39 (t, J=7.4 Hz, 2H), 3.08 (t, J=7.9 Hz, 2H), 3.00-2.85 (m, 2H), 2.30-2.16 (m, 2H), 2.13-1.98 (m, 2H).

Example 1.352

Synthesis of N-(6-methoxypyridin-3-yl)-2-[methyl(2-{4-[(3R)-oxolan-3-yloxy]pyridin-2-yl}-5H,6H,7H-cyclopenta[d]pyrimidin-4-yl)amino]acetamide (Compound 346)

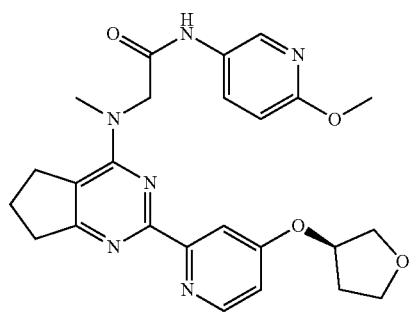 [SMILES: COc1ccc(NC(=O)CN(C)c2nc(-c3cc(O[C@@H]4CCOC4)ccn3)nc3c2CCC3)cn1]

Compound 346 was synthesized similar to compound 187 by replacing ethane-1,2-diol with (3R)-oxolan-3-ol. LCMS (ES) [M+1]$^+$ m/z: 477. $^1$H NMR (300 MHz, DMSO-d6) δ 10.26 (s, 1H), 8.45 (d, J=5.6 Hz, 1H), 8.35 (d, J=2.6 Hz, 1H), 7.89 (dd, J=8.9, 2.7 Hz, 1H), 7.73 (d, J=2.5 Hz, 1H), 7.00 (dd, J=5.7, 2.6 Hz, 1H), 6.78 (d, J=8.9 Hz, 1H), 5.13-5.06 (m, 1H), 4.39 (s, 2H), 3.80 (s, 3H), 3.90-3.65 (m, 4H), 3.37 (s, 3H), 3.21 (t, J=7.3 Hz, 2H), 2.83 (t, J=7.8 Hz, 2H), 2.29-2.11 (m, 1H), 2.09-1.85 (m, 3H).

Example 1.353

Synthesis of N-(6-methoxypyridin-3-yl)-2-[methyl(2-{4-[(3S)-oxolan-3-yloxy]pyridin-2-yl}-5H,6H,7H-cyclopenta[d]pyrimidin-4-yl)amino]acetamide (Compound 347)

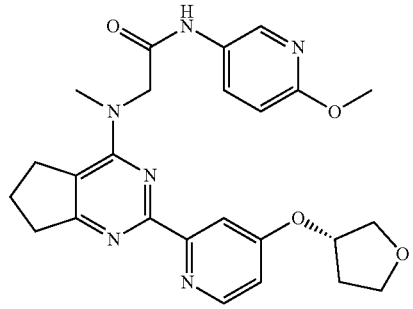 [SMILES: COc1ccc(NC(=O)CN(C)c2nc(-c3cc(O[C@H]4CCOC4)ccn3)nc3c2CCC3)cn1]

Compound 347 was synthesized similar to compound 187 by replacing ethane-1,2-diol with (3S)-oxolan-3-ol. LCMS (ES) [M+1]$^+$ m/z: 477. $^1$H NMR (300 MHz, DMSO-d6) δ 10.26 (s, 1H), 8.45 (d, J=5.6 Hz, 1H), 8.35 (d, J=2.6 Hz, 1H), 7.89 (dd, J=8.9, 2.7 Hz, 1H), 7.73 (d, J=2.5 Hz, 1H), 7.00 (dd, J=5.7, 2.6 Hz, 1H), 6.78 (d, J=8.9 Hz, 1H), 5.13-5.06 (m, 1H), 4.39 (s, 2H), 3.80 (s, 3H), 3.90-3.65 (m, 4H), 3.37 (s, 3H), 3.21 (t, J=7.3 Hz, 2H), 2.83 (t, J=7.8 Hz, 2H), 2.29-2.11 (m, 1H), 2.09-1.85 (m, 3H).

Example 1.354

Synthesis of N-{bicyclo[1.1.1]pentan-1-yl}-2-({2-[4-(2-hydroxyethoxy)pyridin-2-yl]-5H,6H,7H-cyclopenta[d]pyrimidin-4-yl}(methyl)amino)acetamide (Compound 349)

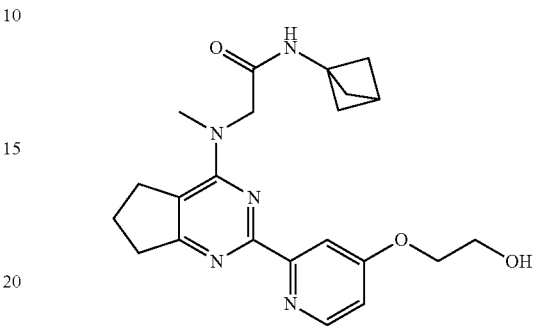

Compound 349 was synthesized similar to compound 187 replacing 6-methoxypyridin-3-amine with bicyclo[1.1.1]pentan-1-amine hydrochloride. LCMS (ES) [M+1]$^+$ m/z: 410. $^1$H NMR (300 MHz, DMSO-d6) δ 8.73 (s, 1H), 8.47 (d, J=5.6 Hz, 1H), 8.15 (s, 0.5HCOOH), 7.81 (d, J=2.6 Hz, 1H), 7.04 (dd, J=5.7, 2.6 Hz, 1H), 4.93 (s, 1H), 4.20-4.09 (m, 4H), 3.77 (s, 2H), 3.27 (s, 3H), 3.16 (t, J=7.3 Hz, 2H), 2.82 (t, J=7.8 Hz, 2H), 2.37 (s, 1H), 2.05-1.93 (m, 2H), 1.92 (s, 6H).

Example 1.355

Synthesis of 2-({2-[4-(2-hydroxyethoxy)pyridin-2-yl]-5H,6H,7H-cyclopenta[d]pyrimidin-4-yl}(methyl)amino)-N-(3-methyl-1,2-thiazol-5-yl)acetamide (Compound 350)

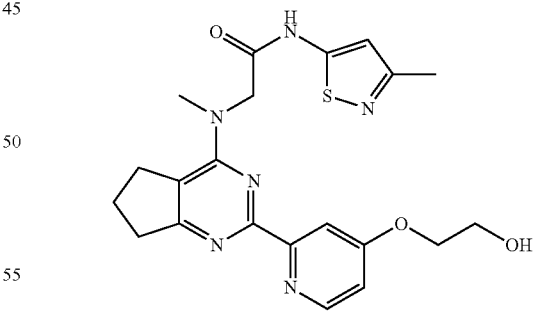

Compound 350 was synthesized similar to compound 187 by replacing 6-methoxypyridin-3-amine with 3-methylisothiazol-5-amine hydrochloride. LCMS (ES) [M+1]$^+$ m/z: 441. $^1$H NMR (300 MHz, DMSO-d6) δ 12.11 (s, 1H), 8.45 (d, J=5.7 Hz, 1H), 8.14 (s, HCOOH), 7.68 (d, J=2.7 Hz, 1H), 7.01 (dd, J=5.7, 2.4 Hz, 1H), 6.75 (s, 1H), 4.92 (br, 1H), 4.53 (s, 2H), 4.03 (t, J=4.8 Hz, 2H), 3.73-3.70 (m, 2H), 3.39 (s, 3H), 3.22 (t, J=7.5 Hz, 2H), 2.84 (t, J=7.8 Hz, 2H), 2.30 (s, 3H), 2.04-1.99 (m, 2H).

835
Example 1.356
Synthesis of 2-({2-[4-({[1-(3-fluorophenyl)-1H-1,2,4-triazol-3-yl]methyl}(methyl)amino)-5H,6H,7H-cyclopenta[d]pyrimidin-2-yl]pyridin-4-yl}oxy)ethan-1-ol (Compound 351)
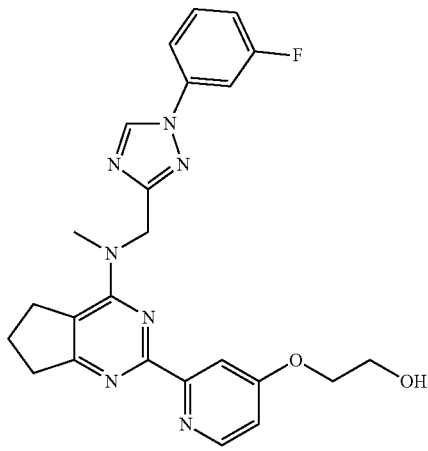 [SMILES: CN(Cc1ncn(-c2cccc(F)c2)n1)c1nc(-c2cc(OCCO)ccn2)nc2c1CCC2]
Scheme 125
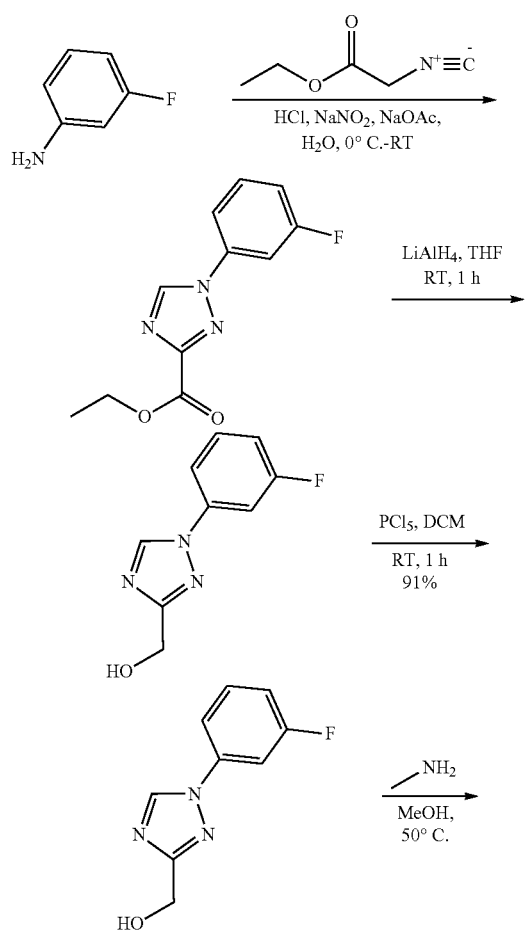
836
-continued
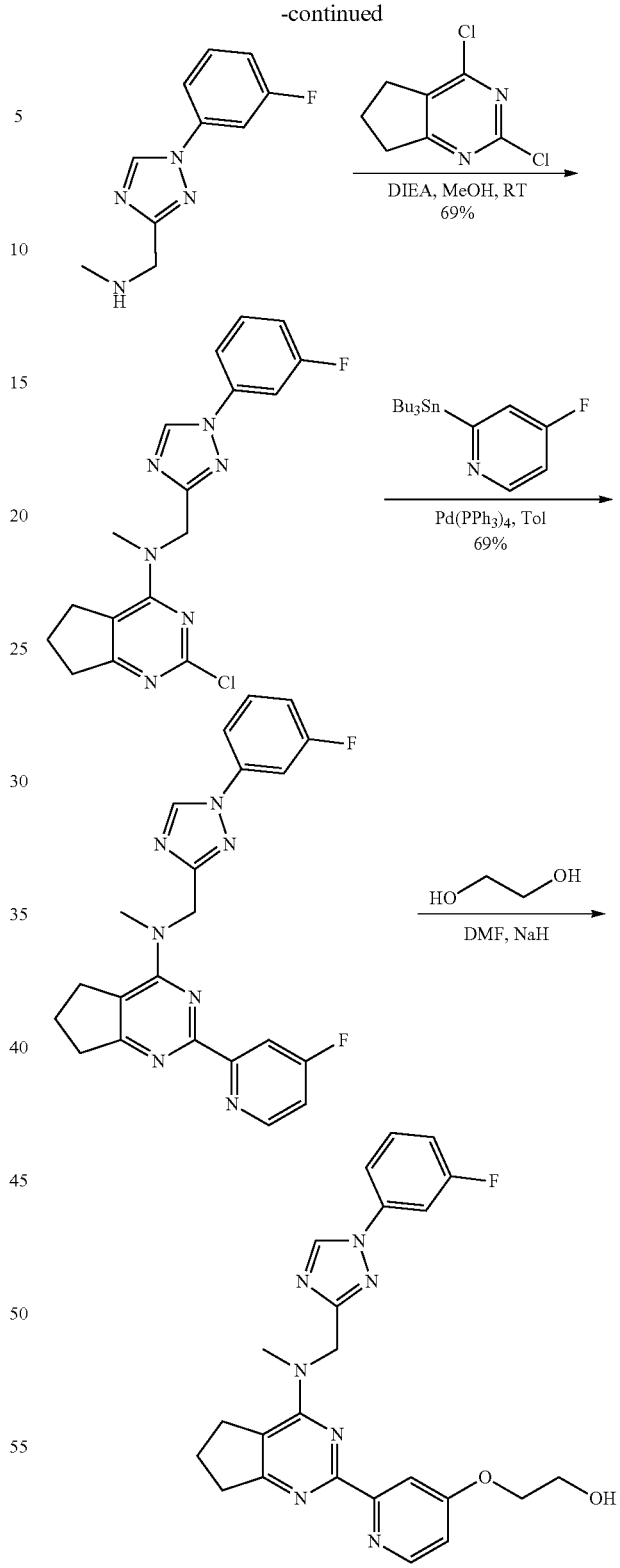
Step 1
A solution of 3-fluoroaniline (10.00 g, 89.994 mmol, 1.00 equiv) in a mixture of water (50.00 mL) and concentrated hydrochloric acid (30.00 mL) was cooled to 0 degrees C. A solution of sodium nitrite (7.45 g, 107.992 mmol, 1.20 equiv) in water (10.00 mL) was added maintaining the temperature between 0 degrees C. and 5 degrees C. Stirring was continued for 5 min at 0° C. This solution was added drop wise to a mixture of acetic acid sodium salt (55.37 g, 674.952 mmol, 7.50 equiv) and ethyl 2-isocyanoacetate (11.20 g, 99.013 mmol, 1.10 equiv) in a mixture of water (100.00 mL) and methanol (10.00 mL). The reaction mixture was stirred at 0° C. for 30 min and was allowed to warm to room temperature. Stirring was continued for overnight. The resulting solution was extracted with 2×300 mL of ethyl acetate. The resulting mixture was washed with 2×300 of brine. The mixture was dried over anhydrous sodium sulfate and concentrated under vacuum. The residue was applied onto a silica gel column with ethyl acetate/petroleum ether (EA). This resulted in 5.5 g (25.98%) of ethyl 1-(3-fluorophenyl)-1H-1,2,4-triazole-3-carboxylate as a light yellow solid. LCMS (ES) $[M+1]^+$ m/z: 236.

Into a 250-mL 3-necked round-bottom flask, was placed ethyl 1-(3-fluorophenyl)-1H-1,2,4-triazole-3-carboxylate (5.50 g, 23.383 mmol, 1.00 equiv), THF (60.00 mL). This was followed by the addition of LiAlH$_4$ (1.33 g, 35.042 mmol, 1.50 equiv) at 0° C. The resulting solution was stirred for 1 h at 0° C. The reaction was then quenched by the addition of 1.5 mL of water, 1.5 mL of 15% NaOH, 4.5 mL of water. The mixture was dried over anhydrous magnesium sulfate. The solids were filtered out. The resulting mixture was concentrated under vacuum. The residue was applied onto a silica gel column with ethyl acetate/petroleum ether (EA). This resulted in 2.2 g (48.70%) of (1-(3-fluorophenyl)-1H-1,2,4-

Step 3

Into a 100-mL 3-necked round-bottom flask, was placed (1-(3-fluorophenyl)-1H-1,2,4-triazol-3-yl)methanol (2.00 g, 10.353 mmol, 1.00 equiv), DCM (30.00 mL), PCl$_5$ (4.31 g, 20.697 mmol, 2.00 equiv). The resulting solution was stirred for 1 h at room temperature. The reaction was then quenched by the addition of 30 mL of NH$_4$Cl (aq). The resulting solution was extracted with 2×40 mL of dichloromethane. The resulting mixture was washed with 2×40 ml of brine. The mixture was dried over anhydrous sodium sulfate and concentrated under vacuum. The residue was applied onto a silica gel column with ethyl acetate/petroleum ether (1:1). This resulted in 2 g (91.29%) of 3-(chloromethyl)-1-(3-fluorophenyl)-1H-1,2,4-triazole as a light yellow solid. LCMS (ES) $[M+1]^+$ m/z: 212.

Step 4

Into a 40-mL round-bottom flask, was placed 3-(chloromethyl)-1-(3-fluorophenyl)-1H-1,2,4-triazole (2.00 g, 9.451 mmol, 1.00 equiv), MeOH (20.00 mL), Methylamine (2M in methanol, 20.00 mL). The resulting solution was stirred for 4 h at 50° C. in an oil bath. The resulting mixture was concentrated under vacuum. The residue was applied onto a silica gel column with dichloromethane/methanol (10:1). This resulted in 1.5 g (76.96%) of 1-(1-(3-fluorophenyl)-1H-1,2,4-triazol-3-yl)-N-methylmethanamine as a off-white solid. LCMS (ES) $[M+1]^+$ m/z: 207.

Step 5

Into a 100-mL 3-necked round-bottom flask, was placed 2,4-dichloro-5H,6H,7H-cyclopenta[d]pyrimidine (1.38 g, 7.300 mmol, 1.00 equiv), MeOH (30.00 mL), DIEA (2.35 g, 18.184 mmol, 2.50 equiv). This was followed by the addition of 1-(1-(3-fluorophenyl)-1H-1,2,4-triazol-3-yl)-N-methylmethanamine (1.50 g, 7.274 mmol, 1.00 equiv) at 0° C. The resulting solution was stirred for 16 h at room temperature. The resulting mixture was concentrated under vacuum. The residue was applied onto a silica gel column with dichloromethane/methanol (10:1). This resulted in 1.8 g (68.97%) of 2-chloro-N-((1-(3-fluorophenyl)-1H-1,2,4-triazol-3-yl)methyl)-N-methyl-6,7-dihydro-5H-cyclopenta[d]pyrimidin-4-amine as light yellow oil. LCMS (ES) $[M+1]+^+$ m/z: 359.

Step 6

Into a 40-mL sealed tube purged and maintained with an inert atmosphere of nitrogen, was placed 2-chloro-N-((1-(3-fluorophenyl)-1H-1,2,4-triazol-3-yl)methyl)-N-methyl-6,7-dihydro-5H-cyclopenta[d] pyrimidin-4-amine (200.00 mg, 0.557 mmol, 1.00 equiv), Toluene (6.00 mL), 4-fluoro-2-(tributylstannyl)pyridine (322.85 mg, 0.836 mmol, 1.50 equiv), Pd(PPh$_3$)$_4$ (64.41 mg, 0.056 mmol, 0.10 equiv). The resulting solution was stirred for 16 h at 100° C. in an oil bath. The resulting mixture was concentrated under vacuum. The residue was applied onto a silica gel column with dichloromethane/methanol (10:1). This reaction was repeated 10 times and obtained 650 mg (69.44%) of N-((1-(3-fluorophenyl)-1H-1,2,4-triazol-3-yl)methyl)-2-(4-fluoropyridin-2-yl)-N-methyl-6,7-dihydro-5H-cyclopenta[d]pyrimidin-4-amine as a light yellow oil. LCMS (ES) $[M+1]^+$ m/z: 420.

Step 7

Into a 50-mL 3-necked round-bottom flask, was placed ethylene glycol (887.87 mg, 14.305 mmol, 20.00 equiv), DMF (3 mL). This was followed by the addition of NaH (85.82 mg, 3.576 mmol, 5.00 equiv) at 0 degrees C. To this was added N-((1-(3-fluorophenyl)-1H-1,2,4-triazol-3-yl)methyl)-2-(4-fluoropyridin-2-yl)-N-methyl-6,7-dihydro-5H-cyclopenta[d]pyrimidin-4-amine (300.00 mg, 0.715 mmol, 1.00 equiv) at degrees C. The resulting solution was stirred for 2 h at room temperature. The resulting solution was extracted with 2×20 mL of dichloromethane/methanol (10:1). The resulting mixture was washed with 2×20 ml of brine. The mixture was dried over anhydrous sodium sulfate and concentrated under vacuum. The crude product was purified by Prep-HPLC with the following conditions: SunFire Prep C18 OBD Column, 50*250 mm 5 um 10 nm; mobile phase, phase A: H$_2$O (0.05% NH$_3$·H$_2$O); phase B: CH$_3$CN (10% CH$_3$CN up to 50% CH$_3$CN in 15 min). This resulted in 216.1 mg (65.47%) of 2-({2-[4-({[1-(3-fluorophenyl)-1H-1,2,4-triazol-3-yl]methyl}(methyl)amino)-5H,6H,7H-cyclopenta[d]pyrimidin-2-yl]pyridin-4-yl}oxy)ethan-1-ol as a white solid. LCMS (ES) $[M+1]^+$ m/z: 462. $^1$H NMR (300 MHz, DMSO-d$_6$, ppm): δ 9.27 (s, 1H), 8.45 (d, J=5.6 Hz, 1H), 7.86 (d, J=2.6 Hz, 1H), 7.80-7.66 (m, 2H), 7.63-7.55 (m, 1H), 7.32-7.19 (m, 1H), 7.02 (dd, J=5.7, 2.6 Hz, 1H), 5.00 (s, 2H), 4.93 (t, J=5.5 Hz, 1H), 4.13 (t, J=4.9 Hz, 2H), 3.77-3.72 (m, J=5.0 Hz, 2H), 3.38 (s, 3H), 3.25 (t, J=7.3 Hz, 2H), 2.83 (t, J=7.9 Hz, 2H), 2.06-1.95 (m, 2H).

Example 1.357

Synthesis of N-tert-butyl-2-[methyl({2-[4-(1-methyl-1H-pyrazol-4-yl)pyridin-2-yl]-5H,6H,7H-cyclopenta[d]pyrimidin-4-yl})amino]acetamide (Compound 352)

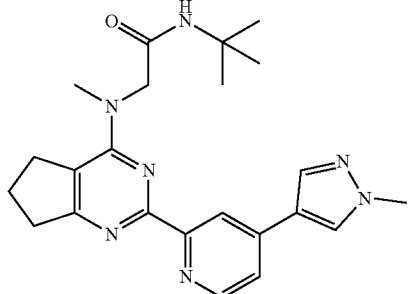

Compound 352 was synthesized similar to compound 245 by replacing 2-chloro-4-(oxetan-3-yloxy)pyridine with 2-chloro-4-(1-methyl-1H-pyrazol-4-yl)pyridine. LCMS (ES) [M+1]⁺ m/z: 420. ¹H NMR (300 MHz, DMSO-d6) δ 8.57 (dd, J=5.1, 0.8 Hz, 1H), 8.47 (s, 1H), 8.41 (dd, J=1.8, 0.8 Hz, 1H), 8.14 (d, J=0.8 Hz, 1H), 7.65 (s, 1H), 7.60 (dd, J=5.1, 1.8 Hz, 1H), 4.19 (s, 2H), 3.91 (s, 3H), 3.30 (s, 3H), 3.17 (t, J=7.4 Hz, 2H), 2.84 (t, J=7.8 Hz, 2H), 2.05-1.95 (m, 2H), 1.18 (s, 9H).

Example 1.358

Synthesis of N-(1-cyclopropyl-1H-pyrazol-4-yl)-2-({2-[4-(2-hydroxyethoxy)pyridin-2-yl]-5H,6H,7H-cyclopenta[d]pyrimidin-4-yl}(methyl)amino)acetamide (Compound 353)

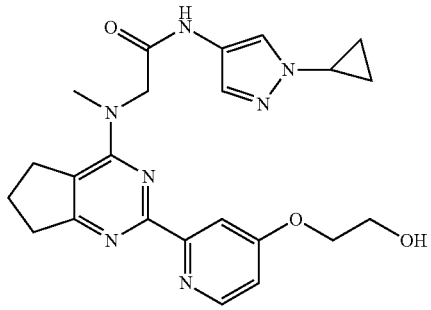 [SMILES: CN(CC(=O)Nc1cnn(C2CC2)c1)c1nc(-c2cc(OCCO)ccn2)nc2c1CCC2]

Compound 353 was synthesized similar to compound 187 by replacing 6-methoxypyridin-3-amine with 1-cyclopropylpyrazol-4-amine. LCMS (ES) [M+1]⁺ m/z: 450. ¹H NMR (300 MHz, DMSO-d6) δ 10.28 (s, 1H), 8.46 (d, J=5.6 Hz, 1H), 7.87 (s, 1H), 7.77 (d, J=2.6 Hz, 1H), 7.40 (s, 1H), 7.02 (dd, J=5.6, 2.6 Hz, 1H), 4.94 (s, 1H), 4.35 (s, 2H), 4.07-4.04 (m, 2H), 3.71-3.66 (m, 2H), 3.65-3.62 (m, 1H), 3.30 (s, 3H), 3.22-3.16 (m, 2H), 2.85-2.80 (m, 2H), 2.02-1.98 (m, 2H), 0.98-0.95 (m, 4H).

Example 1.359

Synthesis of 2-({2-[4-(2-hydroxyethoxy)pyridin-2-yl]-5H,6H,7H-cyclopenta[d]pyrimidin-4-yl}(methyl)amino)-1-(pyrrolidin-1-yl)ethan-1-one (Compound 354)

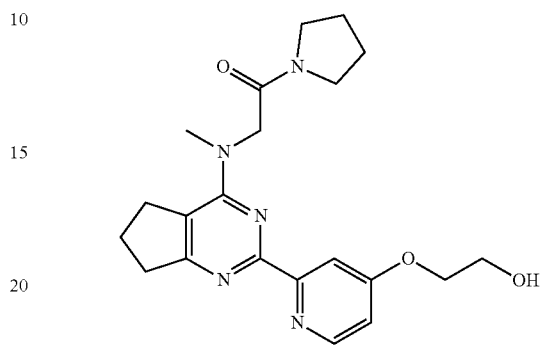

Compound 354 was synthesized similar to compound 187 by replacing 6-methoxypyridin-3-amine with pyrrolidine. LCMS (ES) [M+1]⁺ m/z: 398. ¹H NMR (300 MHz, DMSO-d6) δ 8.46 (d, J=5.6 Hz, 1H), 8.15 (s, 1H), 7.72 (d, J=2.5 Hz, 1H), 7.03 (dd, J=5.8, 2.5 Hz, 1H), 4.93 (br, 1H), 4.39 (s, 2H), 4.13 (t, J=4.8 Hz, 2H), 3.75 (t, J=4.9 Hz, 2H), 3.54 (t, J=6.8 Hz, 2H), 3.34-3.29 (m, 5H), 3.21-3.14 (t, J=7.4 Hz, 2H), 2.92-2.81 (m, 2H), 1.96-1.85 (m, 4H), 1.79-1.68 (m, 2H).

Example 1.360

Synthesis of 1-(4,4-difluoropiperidin-1-yl)-2-({2-[4-(2-hydroxyethoxy)pyridin-2-yl]-5H,6H,7H-cyclopenta[d]pyrimidin-4-yl}(methyl)amino)ethan-1-one (Compound 355)

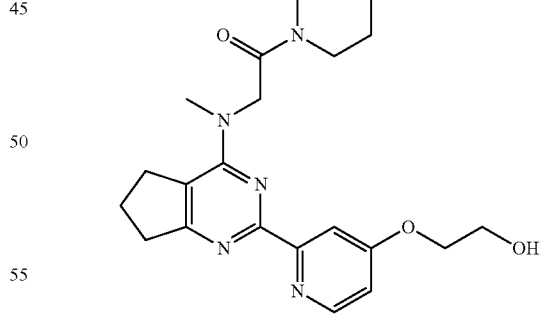

Compound 355 was synthesized similar to compound 187 by replacing 6-methoxypyridin-3-amine with 4,4-difluoropiperidine. LCMS (ES) [M+1]⁺ m/z: 448. ¹H NMR (300 MHz, DMSO-d6) δ 8.42 (d, J=5.6 Hz, 1H), 8.16 (s, 0.6HCOOH), 7.77 (d, J=2.6 Hz, 1H), 7.03 (dd, J=5.7, 2.6 Hz, 1H), 4.57 (s, 2H), 4.12 (t, J=5.0 Hz, 2H), 3.75 (t, J=4.9 Hz, 2H), 3.69-3.52 (m, 4H), 3.28 (s, 3H), 3.16 (t, J=7.3 Hz, 2H), 2.82 (t, J=7.9 Hz, 2H), 2.23-2.14 (m, 2H), 1.99-2.83 (m, 4H).

Example 1.361

Synthesis of 2-({2-[4-(2-acetamidoethoxy)pyridin-2-yl]-5H,6H,7H-cyclopenta[d]pyrimidin-4-yl}(methyl)amino)-N-(3-fluorophenyl)acetamide (Compound 356)

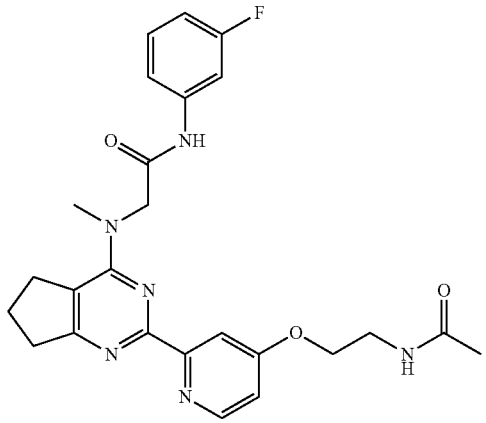 [SMILES: CC(=O)NCCOc1ccnc(-c2nc3c(c(N(C)CC(=O)Nc4cccc(F)c4)n2)CCC3)c1]

Compound 356 was synthesized similar to compound 187 by replacing 6-methoxypyridin-3-amine with 3-fluoroaniline and replacing ethane-1,2-diol with N-(2-hydroxyethyl)acetamide. LCMS (ES) [M+1]$^+$ m/z: 479. $^1$H NMR (300 MHz, DMSO-d6) δ 10.45 (s, 1H), 8.45 (d, J=5.6 Hz, 1H), 8.07 (t, J=5.3 Hz, 1H), 7.78 (d, J=2.5 Hz, 1H), 7.64-7.53 (m, 1H), 7.40-7.27 (m, 2H), 7.02 (dd, J=5.7, 2.6 Hz, 1H), 6.86 (ddt, J=8.9, 7.2, 2.6 Hz, 1H), 4.45 (s, 2H), 4.05 (t, J=5.5 Hz, 2H), 3.39 (d, J=5.5 Hz, 2H), 3.36 (s, 3H), 3.21 (t, J=7.3 Hz, 2H), 2.84 (t, J=7.8 Hz, 2H), 2.05-1.96 (m, 2H), 1.83 (s, 3H).

Example 1.362

Synthesis of 1-(azepan-1-yl)-2-({2-[4-(2-hydroxyethoxy)pyridin-2-yl]-5H,6H,7H-cyclopenta[d]pyrimidin-4-yl}(methyl)amino)ethan-1-one (Compound 357)

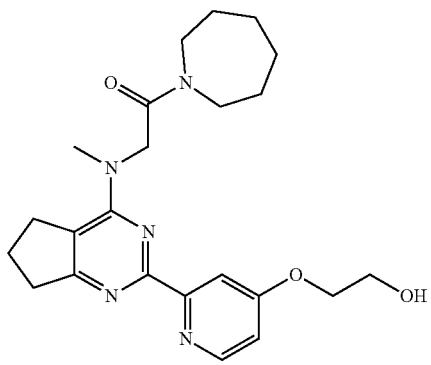 [SMILES: CN(CC(=O)N1CCCCCC1)c1nc(-c2cc(OCCO)ccn2)nc2c1CCC2]

Compound 357 was synthesized similar to compound 187 by replacing 6-methoxypyridin-3-amine with azepane. LCMS (ES) [M+1]$^+$ m/z: 426. $^1$H NMR (300 MHz, DMSO-d6) δ 8.44 (d, J=5.6 Hz, 1H), 8.14 (s, 1H), 7.72 (d, J=2.6 Hz, 1H), 7.02 (dd, J=5.6, 2.6 Hz, 1H), 4.92 (s, 1H), 4.54 (s, 2H), 4.12 (t, J=4.9 Hz, 2H), 3.80-3.72 (m, 2H), 3.50 (t, J=6.0 Hz, 2H), 3.41 (t, J=5.9 Hz, 2H), 3.26 (s, 3H), 3.15 (t, J=7.3 Hz, 2H), 2.81 (t, J=7.9 Hz, 2H), 2.03-1.98 (m, 2H), 1.84-1.72 (m, 2H), 1.61-1.40 (m, 6H).

Example 1.363

Synthesis of 1-(azepan-1-yl)-2-[methyl({2-[4-(oxetan-3-yloxy)pyridin-2-yl]-5H,6H,7H-cyclopenta[d]pyrimidin-4-yl})amino]ethan-1-one (Compound 358)

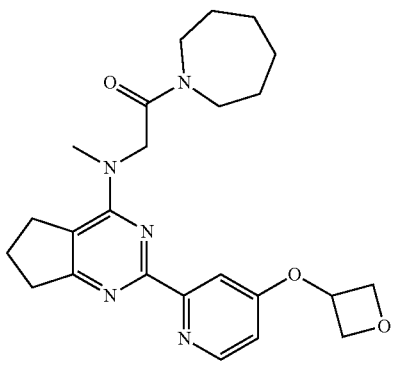 [SMILES: CN(CC(=O)N1CCCCCC1)c1nc(-c2cc(OC3COC3)ccn2)nc2c1CCC2]

Compound 358 was synthesized similar to compound 187 replacing 6-methoxypyridin-3-amine with azepane and replacing ethan-1,2-diol with oxetan-3-ol. LCMS (ES) [M+1]$^+$ m/z: 438. $^1$H NMR (300 MHz, DMSO-d6) δ 8.47 (d, J=5.6 Hz, 1H), 7.61 (d, J=2.6 Hz, 1H), 6.87 (dd, J=5.6, 2.6 Hz, 1H), 5.50-5.43 (m, 1H), 5.02-4.91 (m, 2H), 4.63-4.52 (m, 4H), 3.50 (t, J=6.0 Hz, 2H), 3.42 (t, J=5.9 Hz, 2H), 3.26 (s, 3H), 3.15 (t, J=7.3 Hz, 2H), 2.81 (t, J=7.8 Hz, 2H), 2.04-1.94 (m, 2H), 1.88-1.79 (m, 2H), 1.62-1.43 (m, 6H).

Example 1.364

Synthesis of 1-(4-fluoropiperidin-1-yl)-2-({2-[4-(2-hydroxyethoxy)pyridin-2-yl]-5H,6H,7H-cyclopenta[d]pyrimidin-4-yl}(methyl)amino)ethan-1-one (Compound 359)

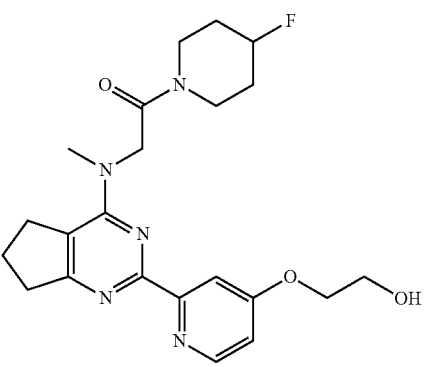 [SMILES: CN(CC(=O)N1CCC(F)CC1)c1nc(-c2cc(OCCO)ccn2)nc2c1CCC2]

Compound 359 was synthesized similar to compound 187 by replacing 6-methoxypyridin-3-amine with 4-fluoropiperidine. LCMS (ES) [M+1]$^+$ m/z: 430. $^1$H NMR (300 MHz, DMSO-d6) δ 8.45 (d, J=5.4 Hz, 1H), 7.75 (s, 1H), 7.02 (dd, J=5.4, 2.5 Hz, 1H), 5.00-4.84 (m, 2H), 4.63-4.45 (m, 2H), 4.13-4.10 (m, 2H), 3.76-3.74 (d, J=6 Hz, 2H), 3.70-3.40 (m, 4H), 3.27 (s, 3H), 3.17-3.12 (m, 2H), 2.83-2.78 (m, 2H), 2.20-1.50 (m, 6H).

Example 1.365

Synthesis of N-tert-butyl-2-[ethyl({2-[4-(2-hydroxy-ethoxy)pyridin-2-yl]-5H,6H,7H-cyclopenta[d]pyrimidin-4-yl})amino]acetamide (Compound 360)

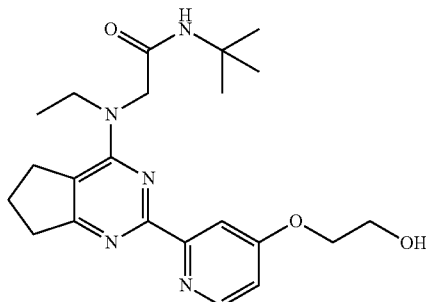

Compound 360 was synthesized similar to compound 126. LCMS (ES) [M+1]+ m/z: 414. $^1$H NMR (300 MHz, DMSO-d6) δ 8.47 (d, J=5.6 Hz, 1H), 7.86 (d, J=2.5 Hz, 1H), 7.70 (s, 1H), 7.04 (dd, J=5.7, 2.5 Hz, 1H), 4.92 (s, 1H), 4.19-4.06 (m, 4H), 3.76 (t, J=4.9 Hz, 2H), 3.65 (q, J=7.0 Hz, 2H), 3.07 (t, J=7.2 Hz, 2H), 2.82 (t, J=7.8 Hz, 2H), 2.05-1.95 (m, 2H), 1.23-1.16 (m, 12H).

Example 1.366

Synthesis of N-tert-butyl-2-({2-[4-(2-hydroxy-ethoxy)pyridin-2-yl]-5,5-dimethyl-5H,6H,7H-cyclopenta[d]pyrimidin-4-yl}(methyl)amino)acetamide (Compound 361)

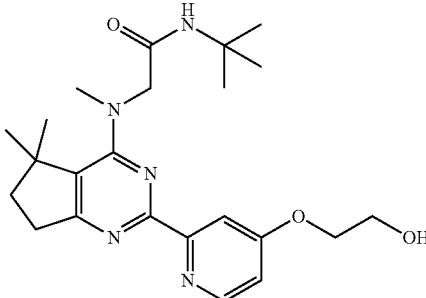

Compound 361 was synthesized similar to compound 331 by replacing 2-(methylamino)-N-(6-methylpyridin-3-yl)acetamide with N-tert-butyl-2-(methylamino)acetamide hydrochloride. LCMS (ES) [M+1]+ m/z: 428. $^1$H NMR (300 MHz, DMSO-d6) δ 8.48 (d, J=5.6 Hz, 1H), 7.86 (d, J=2.6 Hz, 1H), 7.67 (s, 1H), 7.05 (dd, J=5.7, 2.6 Hz, 1H), 4.91 (s, 1H), 4.15 (t, J=5.0 Hz, 2H), 4.03 (s, 2H), 3.77 (s, 2H), 3.18 (s, 3H), 2.86 (t, J=7.2 Hz, 2H), 1.87 (t, J=7.3 Hz, 2H), 1.43 (s, 6H), 1.21 (s, 9H).

Example 1.367

Synthesis of 2-({2-[4-(2-hydroxyethoxy)pyridin-2-yl]-5,5-dimethyl-5H,6H,7H-cyclopenta[d]pyrimidin-4-yl}(methyl)amino)-1-(piperidin-1-yl)ethan-1-one (Compound 362)

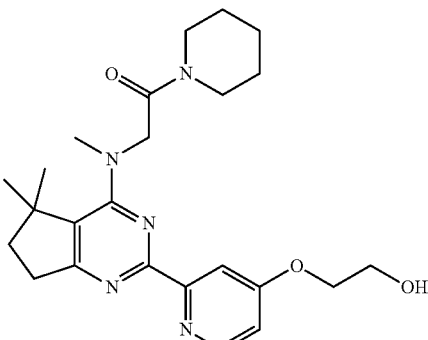

Compound 362 was synthesized similar to compound 331 by replacing 2-(methylamino)-N-(6-methylpyridin-3-yl)acetamide with 2-(methylamino)-1-(piperidin-1-yl)ethanone hydrochloride. LCMS (ES) [M+1]+ m/z: 440. $^1$H NMR (300 MHz, DMSO-d6) δ 8.46 (d, J=5.6 Hz, 1H), 7.72 (d, J=2.6 Hz, 1H), 7.04 (dd, J=5.6, 2.5 Hz, 1H), 4.91 (t, J=5.4 Hz, 1H), 4.38 (s, 2H), 4.13 (t, J=4.9 Hz, 2H), 3.76 (q, J=5.1 Hz, 2H), 3.44 (d, J=17.6 Hz, 4H), 3.21 (s, 3H), 2.85 (t, J=7.3 Hz, 2H), 1.87 (t, J=7.2 Hz, 2H), 1.61 (s, 4H), 1.44 (s, 8H).

Example 1.368

Synthesis of 2-({2-[4-(2-hydroxyethoxy)pyridin-2-yl]-5,5-dimethyl-5H,6H,7H-cyclopenta[d]pyrimidin-4-yl}(methyl)amino)-N-(6-methoxypyridin-3-yl)acetamide (Compound 363)

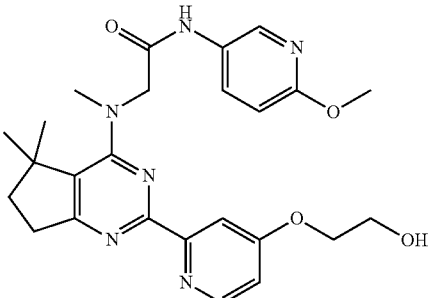

Compound 363 was synthesized similar to compound 331 by replacing 2-(methylamino)-N-(6-methylpyridin-3-yl)acetamide with N-(6-methoxypyridin-3-yl)-2-(methylamino)acetamide hydrochloride. LCMS (ES) [M+1]+ m/z: 479. $^1$H NMR (300 MHz, DMSO-d6) δ 10.44 (s, 1H), 8.42 (d, J=5.6 Hz, 1H), 8.33 (d, J=2.6 Hz, 1H), 7.87 (dd, J=9.0, 2.6 Hz, 1H), 7.79 (d, J=2.5 Hz, 1H), 7.02 (dd, J=5.7, 2.5 Hz, 1H), 6.77 (d, J=8.8 Hz, 1H), 4.91 (s, 1H), 4.29 (s, 2H), 4.02 (t, J=4.8 Hz, 2H), 3.80 (d, J=1.5 Hz, 3H), 3.68 (t, J=4.7 Hz, 2H), 3.30 (s, 3H), 2.88 (t, J=7.2 Hz, 2H), 1.89 (t, J=7.2 Hz, 2H), 1.46 (s, 6H).

Example 1.369

Synthesis of 1-{3-azabicyclo[3.1.1]heptan-3-yl}-2-({2-[4-(2-hydroxyethoxy)pyridin-2-yl]-5H,6H,7H-cyclopenta[d]pyrimidin-4-yl}(methyl)amino)ethan-1-one (Compound 364)

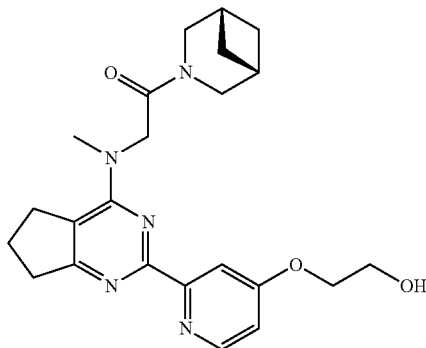 [SMILES: CN(CC(=O)N1C[C@H]2C[C@@H](C1)C2)c1nc(-c2cc(OCCO)ccn2)nc2c1CCC2]

Compound 364 was synthesized similar to compound 187 by replacing 6-methoxypyridin-3-amine with 3-azabicyclo[3.1.1]heptane hydrochloride. LCMS (ES) [M+1]⁺ m/z: 424. ¹H NMR (300 MHz, DMSO-d6) δ 8.45 (d, J=5.7 Hz, 1H), 8.17 (s, HCOOH), 7.74 (d, J=2.7 Hz, 1H), 7.04 (dd, J=6.0, 3.0 Hz, 1H), 4.50 (s, 2H), 4.14 (t, J=5.1 Hz, 2H), 3.84 (d, J=2.4 Hz, 2H), 3.76 (t, J=5.1 Hz, 2H), 3.53 (d, J=2.4 Hz, 2H), 3.31 (s, 3H), 3.17 (t, J=7.2 Hz, 2H), 2.83 (t, J=8.1 Hz, 2H), 2.48-2.43 (m, 2H), 2.19-2.10 (m, 2H), 2.03-1.93 (m, 2H), 1.32 (dt, J=6.8, 4.1 Hz, 2H).

Example 1.370

Synthesis of N-tert-butyl-2-[(2-{furo[2,3-c]pyridin-5-yl}-5H,6H,7H-cyclopenta[d]pyrimidin-4-yl)(methyl)amino]acetamide (Compound 365)

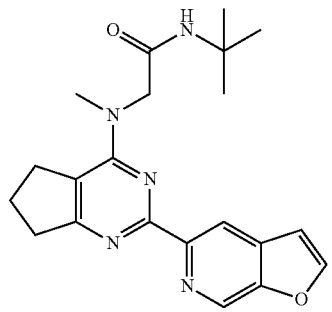 [SMILES: CN(CC(=O)NC(C)(C)C)c1nc(-c2cc3ccoc3cn2)nc2c1CCC2]

Compound 365 was synthesized similar to compound 245 by replacing 2-chloro-4-(oxetan-3-yloxy)pyridine with 5-chlorofuro[2,3-c]pyridine. LCMS (ES) [M+1]⁺ m/z: 380. ¹H NMR (300 MHz, DMSO-d6) δ 9.00 (s, 1H), 8.73 (s, 1H), 8.32-8.24 (m, 1H), 8.14 (s, 0.5 HCOOH), 7.74 (s, 1H), 7.10 (d, J=2.4 Hz, 1H), 4.16 (s, 2H), 3.30 (s, 3H), 3.15 (t, J=7.3 Hz, 2H), 2.83 (t, J=7.8 Hz, 2H), 2.05-1.95 (m, 2H), 1.24 (s, 9H).

Example 1.371

Synthesis of N-tert-butyl-2-[(2-{4-[(2R)-2-hydroxypropoxy]pyridin-2-yl}-5H,6H,7H-cyclopenta[d]pyrimidin-4-yl)(methyl)amino]acetamide (Compound 366)

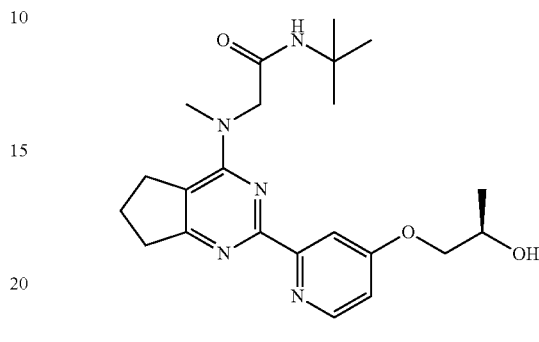

Compound 366 was synthesized similar to compound 174 by replacing 2-methyl-2-((tetrahydro-2H-pyran-2-yl)oxy)propan-1-ol with (2R)-2-(oxan-2-yloxy)propan-1-ol. Analytical chiral HPLC conditions: Column, Lux-cellulose-2, 100*4.6 mm, 3 um; mobile phase A, Ethanol; mobile phase B, CH₃CN; Flow rate: 1 mL/min; Gradient: 20% B in 6 min; 254 nm. Retention time: 2.123 min. LCMS (ES) [M+1]⁺ m/z: 414. ¹H NMR (300 MHz, DMSO-d6) δ 8.47 (dd, J=5.7, 1.3 Hz, 1H), 7.99-7.78 (m, 1H), 7.69 (s, 1H), 7.05-7.02 (m, 1H), 4.94 (d, J=3.9 Hz, 1H), 4.13 (s, 2H), 4.04-3.93 (m, 3H), 3.26 (s, 3H), 3.13 (t, J=7.3 Hz, 2H), 2.81 (t, J=7.8 Hz, 2H), 2.03-1.93 (m, 2H), 1.25 (s, 9H), 1.23 (d, J=7.5 Hz, 3H).

Example 1.372

Synthesis of 2-({2-[4-(2-hydroxyethoxy)pyridin-2-yl]-5H,6H,7H-cyclopenta[d]pyrimidin-4-yl}(methyl)amino)-N-(2-methylbutan-2-yl)acetamide (Compound 367)

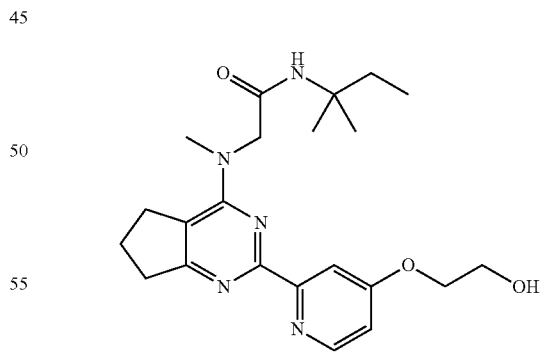

Compound 367 was synthesized similar to compound 44 by replacing tert-butylamine with 2-methylbutan-2-amine. LCMS (ES) [M+1]⁺ m/z: 414. ¹H NMR (300 MHz, DMSO-d6) δ 8.46 (d, J=5.6 Hz, 1H), 7.84 (d, J=2.5 Hz, 1H), 7.49 (s, 1H), 7.04 (dd, J=5.6, 2.6 Hz, 1H), 4.91 (t, J=5.4 Hz, 1H), 4.20-4.10 (m, 4H), 3.76 (q, J=5.1 Hz, 2H), 3.25 (s, 3H), 3.14 (t, J=7.2 Hz, 2H), 2.81 (t, J=7.8 Hz, 2H), 2.15-1.91 (m, 2H), 1.61 (q, J=7.5 Hz, 2H), 1.18 (s, 6H), 0.71 (t, J=7.4 Hz, 3H).

Example 1.373

Synthesis of 1-(2,2-dimethylpyrrolidin-1-yl)-2-({2-[4-(2-hydroxyethoxy)pyridin-2-yl]-5H,6H,7H-cyclopenta[d]pyrimidin-4-yl}(methyl)amino)ethan-1-one (Compound 368)

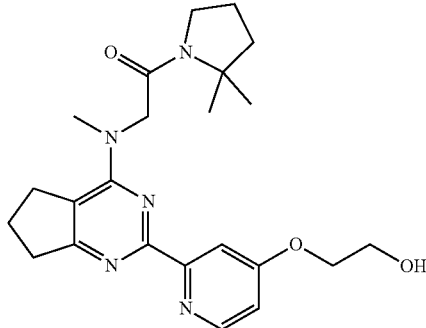

Compound 368 was synthesized similar to compound 44 by replacing tert-butylamine with 2,2-dimethylpyrrolidine. LCMS (ES) [M+1]⁺ m/z: 426. ¹H NMR (300 MHz, DMSO-d6) δ 8.46 (d, J=5.5 Hz, 1H), 7.77 (d, J=2.6 Hz, 1H), 7.07-6.99 (m, 1H), 4.91 (s, 1H), 4.30 (s, 2H), 4.13 (t, J=4.9 Hz, 2H), 3.78-3.74 (m, 2H), 3.60 (t, J=6.8 Hz, 2H), 3.29 (s, 3H), 3.12 (t, J=7.1 Hz, 2H), 2.80 (t, J=7.8 Hz, 2H), 2.04-1.75 (m, 4H), 1.74-1.69 (m, 2H), 1.31 (s, 6H).

Example 1.374

Synthesis of N-tert-butyl-2-({2-[4-(2-acetamidoethoxy)pyridin-2-yl]-5H,6H,7H-cyclopenta[d]pyrimidin-4-yl}(methyl)amino)acetamide (Compound 369)

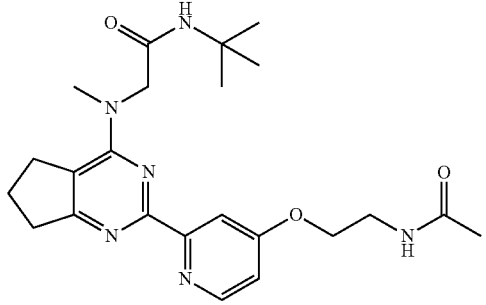 [SMILES: CC(=O)NCCOc1ccnc(-c2nc3c(c(N(C)CC(=O)NC(C)(C)C)n2)CCC3)c1]

Compound 369 was synthesized similar to compound 348 by replacing dimethylaminoethanol with N-(2-hydroxyethyl)acetamide. LCMS (ES) [M+1]⁺ m/z: 441. ¹H NMR (300 MHz, DMSO-d6) δ 8.48 (d, J=5.6 Hz, 1H), 8.16 (s, 1HCOOH), 8.11 (t, J=5.5 Hz, 1H), 7.85 (d, J=2.5 Hz, 1H), 7.68 (s, 1H), 7.05 (dd, J=5.6, 2.6 Hz, 1H), 4.17-4.13 (m, 4H), 3.45 (q, J=5.6 Hz, 2H), 3.26 (s, 3H), 3.13 (t, J=7.3 Hz, 2H), 2.81 (t, J=7.8 Hz, 2H), 2.03-1.96 (p, J=7.6 Hz, 2H), 1.84 (s, 3H), 1.24 (s, 9H).

Example 1.375

Synthesis of N-tert-butyl-2-({2-[4-(2-acetamidoethoxy)pyridin-2-yl]-5H,6H,7H-cyclopenta[d]pyrimidin-4-yl}(methyl)amino)acetamide (Compound 369)

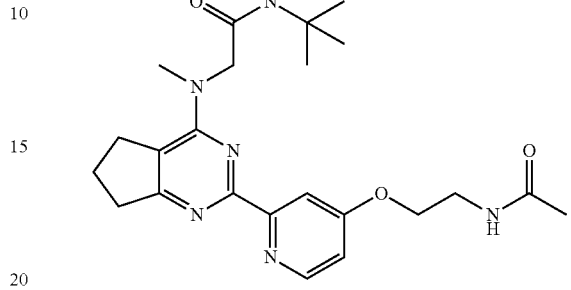

Compound 369 was synthesized similar to compound 348 by replacing dimethylaminoethanol with N-(2-hydroxyethyl)acetamide. LCMS (ES) [M+1]⁺ m/z: 441. ¹H NMR (300 MHz, DMSO-d6) δ 8.48 (d, J=5.6 Hz, 1H), 8.16 (s, 1HCOOH), 8.11 (t, J=5.5 Hz, 1H), 7.85 (d, J=2.5 Hz, 1H), 7.68 (s, 1H), 7.05 (dd, J=5.6, 2.6 Hz, 1H), 4.17-4.13 (m, 4H), 3.45 (q, J=5.6 Hz, 2H), 3.26 (s, 3H), 3.13 (t, J=7.3 Hz, 2H), 2.81 (t, J=7.8 Hz, 2H), 2.03-1.96 (p, J=7.6 Hz, 2H), 1.84 (s, 3H), 1.24 (s, 9H).

Example 1.376

Synthesis of N-tert-butyl-2-[(2-{4-[(2S)-2-hydroxypropoxy]pyridin-2-yl}-5H,6H,7H-cyclopenta[d]pyrimidin-4-yl)(methyl)amino]acetamide (Compound 370)

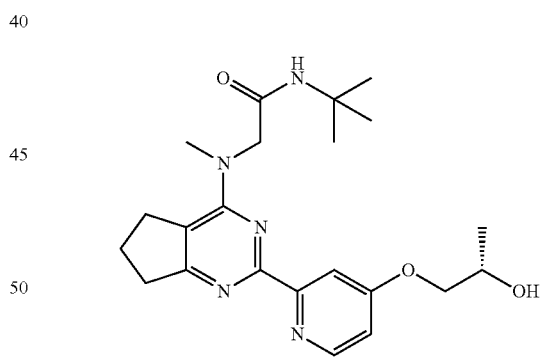

Compound 370 was synthesized similar to compound 174 by replacing 2-methyl-2-((tetrahydro-2H-pyran-2-yl)oxy)propan-1-ol with (2S)-2-(oxan-2-yloxy)propan-1-ol. Analytical chiral HPLC conditions: Column, Lux-cellulose-2, 100*4.6 mm, 3 um; mobile phase A, Ethanol; mobile phase B, CH₃CN; Flow rate: 1 mL/min; Gradient: 20% B in 6 min; 254 nm. Retention time: 3.022 min. LCMS (ES) [M+1]⁺ m/z: 414. ¹H NMR (300 MHz, DMSO-d6) δ 8.47 (d, J=5.7 Hz, 1H), 7.84 (d, J=2.4 Hz, 1H), 7.68 (s, 1H), 7.04 (dd, J=5.7, 2.4 Hz, 1H), 4.93 (d, J=3.9 Hz, 1H), 4.13 (s, 2H), 4.04-3.93 (m, 3H), 3.26 (s, 3H), 3.14 (t, J=7.5 Hz, 2H), 2.81 (t, J=7.8 Hz, 2H), 2.04-1.93 (m, 2H), 1.24 (s, 9H), 8.47 (d, J=5.7 Hz, 3H).

Example 1.377

Synthesis of 2-{[2-(4-methoxypyridin-2-yl)-5H,6H,7H-cyclopenta[d]pyrimidin-4-yl](methyl)amino}-N-[(3S)-oxolan-3-yl]acetamide (Compound 371)

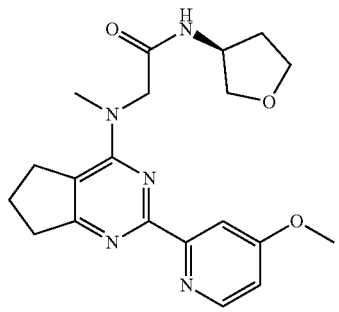 [SMILES: COc1ccnc(-c2nc3c(c(N(C)CC(=O)N[C@H]4CCOC4)n2)CCC3)c1]

Compound 371 was synthesized similar to Compound 135 by replacing oxolan-3-amine with (S)-tetrahydrofuran-3-amine. Analytical chiral HPLC conditions: Column, CHIRALCEL OX-3, 50*4.6 mm, 3 um; mobile phase A, n-Hexane; mobile phase B, Ethanol; Flow rate: 1 mL/min; Gradient: 50% B in 20 min; 270 nm. Retention time: 7.945 min. LCMS (ES) [M+1]$^+$ m/z: 384. $^1$H NMR (300 MHz, DMSO-d6) δ 8.49 (d, J=5.7 Hz, 1H), 8.38 (d, J=6.9 Hz, 1H), 7.81 (d, J=2.7 Hz, 1H), 7.06 (dd, J=5.4, 2.4 Hz, 1H), 4.31-4.25 (m, 1H), 4.20 (d, J=2.4 Hz, 2H), 3.90 (s, 3H), 3.78-3.60 (m, 3H), 3.46 (dd, J=9.0, 4.2 Hz, 1H), 3.28 (s, 3H), 3.18 (t, J=7.2 Hz, 2H), 2.85 (t, J=7.8 Hz, 2H), 2.11-1.92 (m, 3H), 1.77-1.67 (m, 1H).

Example 1.378

Synthesis of 2-{[2-(4-methoxypyridin-2-yl)-5H,6H,7H-cyclopenta[d]pyrimidin-4-yl](methyl)amino}-N-[(3R)-oxolan-3-yl]acetamide (Compound 372)

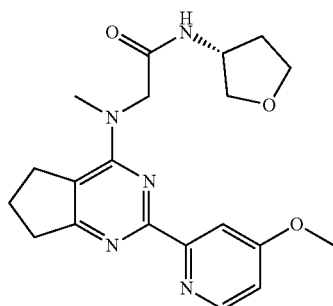

Compound 372 was synthesized similar to Compound 135 by replacing oxolan-3-amine with (R)-tetrahydrofuran-3-amine. Analytical chiral HPLC conditions: Column, CHIRALCEL OX-3, 50*4.6 mm, 3 um; mobile phase A, n-Hexane; mobile phase B, Ethanol; Flow rate: 1 mL/min; Gradient: 50% B in 20 min; 270 nm. Retention time: 10.028 min. LCMS (ES) [M+1]$^+$ m/z: 384. $^1$H NMR (300 MHz, DMSO-d6) δ 8.48 (d, J=5.7 Hz, 1H), 8.38 (d, J=6.9 Hz, 1H), 7.80 (d, J=2.7 Hz, 1H), 7.04 (dd, J=5.4, 2.7 Hz, 1H), 4.31-4.25 (m, 1H), 4.20 (d, J=2.7 Hz, 2H), 3.90 (s, 3H), 3.78-3.60 (m, 3H), 3.46 (dd, J=9.0, 4.2 Hz, 1H), 3.28 (s, 3H), 3.15 (t, J=7.2 Hz, 2H), 2.82 (t, J=7.8 Hz, 2H), 2.10-1.94 (m, 3H), 1.77-1.67 (m, 1H).

Example 1.379

Synthesis of 2-{[2-(4-methoxypyridin-2-yl)-5H,6H,7H-cyclopenta[d]pyrimidin-4-yl](methyl)amino}-N-(oxetan-3-yl)acetamide (Compound 373)

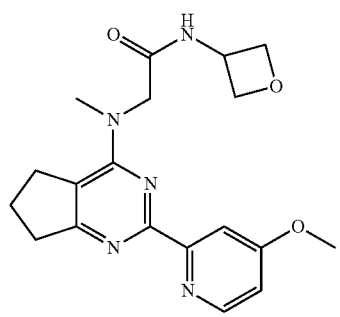 [SMILES: COc1ccnc(-c2nc3c(c(N(C)CC(=O)NC4COC4)n2)CCC3)c1]

Compound 373 was synthesized similar to Compound 135 by replacing oxolan-3-amine with oxetan-3-amine. LCMS (ES) [M+1]$^+$ m/z: 370. $^1$H NMR (300 MHz, DMSO-d6) δ 8.96 (d, J=6.9 Hz, 1H), 8.48 (d, J=5.4 Hz, 1H), 7.79 (d, J=2.7 Hz, 1H), 7.03 (dd, J=5.7, 2.7 Hz, 1H), 4.87-4.78 (m, 1H), 4.67 (t, J=6.9 Hz, 2H), 4.43 (t, J=6.3 Hz, 2H), 4.20 (s, 2H), 3.89 (s, 3H), 3.29 (s, 3H), 3.16 (t, J=7.2 Hz, 2H), 2.82 (t, J=7.8 Hz, 2H), 2.08-1.94 (m, 2H).

Example 1.380

Synthesis of 2-({2-[4-(2-hydroxyethoxy)pyridin-2-yl]-5H,6H,7H-cyclopenta[d]pyrimidin-4-yl}(methyl)amino)-N-(oxetan-3-yl)acetamide (Compound 374)

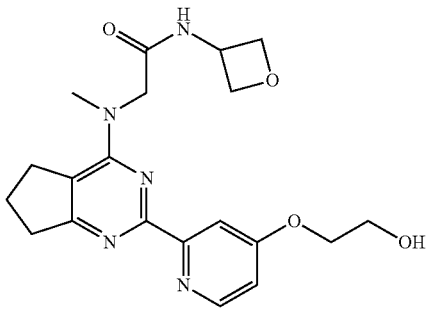 [SMILES: CN(CC(=O)NC1COC1)c1nc(-c2cc(OCCO)ccn2)nc2c1CCC2]

Compound 374 was synthesized similar to Compound 44 by replacing tert-butylamine with oxetan-3-amine. LCMS (ES) [M+1]$^+$ m/z: 400. $^1$H NMR (300 MHz, DMSO-d6) δ 8.94 (d, J=6.8 Hz, 1H), 8.48 (d, J=5.7 Hz, 1H), 7.79 (d, J=2.5 Hz, 1H), 7.04 (dd, J=5.7, 2.6 Hz, 1H), 4.93 (t, J=5.5 Hz, 1H), 4.90-4.74 (m, 1H), 4.73-4.63 (m, 2H), 4.44 (t, J=6.3 Hz, 2H), 4.20 (s, 2H), 4.14 (t, J=4.9 Hz, 2H), 3.80-3.72 (m, 2H), 3.29 (s, 3H), 3.16 (t, J=7.3 Hz, 2H), 2.82 (t, J=7.8 Hz, 2H), 2.02-1.97 (m, 2H).

Example 1.381

Synthesis of 2-({2-[4-(2-hydroxyethoxy)pyridin-2-yl]-5H,6H,7H-cyclopenta[d]pyrimidin-4-yl}(methyl)amino)-1-{5-methoxy-1H,2H,3H-pyrrolo[2,3-c]pyridin-1-yl}ethan-1-one (Compound 375)

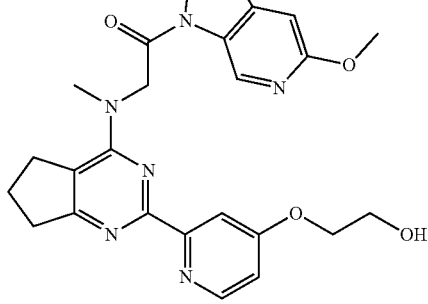

Compound 375 was synthesized similar to Compound 44 by replacing tert-butylamine with 5-methoxy-2,3-dihydro-1H-pyrrolo[2,3-c]pyridine. LCMS (ES) [M+1]$^+$ m/z: 477. $^1$H NMR (300 MHz, DMSO-d6) δ 8.63 (s, 1H), 8.43-8.41 (m, 1H), 8.13 (s, 1HCOOH), 7.69 (s, 1H), 7.02-6.95 (m, 1H), 6.77 (m, 1H), 4.89-4.87 (m, 1H), 4.59 (s, 2H), 4.32-4.26 (m, 2H), 4.01-3.99 (m, 2H), 3.78 (s, 3H), 3.65-3.63 (m, 2H), 3.38 (s, 3H), 3.26-3.20 (m, 4H), 2.86-2.73 (m, 2H), 2.07-1.95 (m, 2H).

Example 1.382

Synthesis of 2-({2-[4-(2-hydroxyethoxy)pyridin-2-yl]-5H,6H,7H-cyclopenta[d]pyrimidin-4-yl}(methyl)amino)-N-(1-methylcyclobutyl)acetamide (Compound 376)

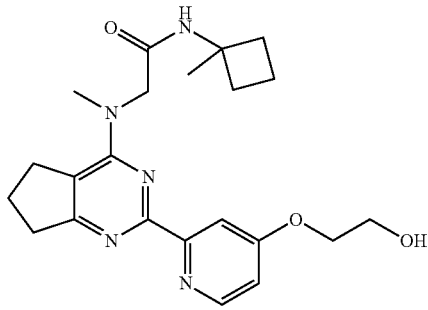 [SMILES: CN(CC(=O)NC1(C)CCC1)c1nc(-c2cc(OCCO)ccn2)nc2c1CCC2]

Compound 376 was synthesized similar to Compound 44 by replacing tert-butylamine with 1-methylcyclobutan-1-amine. LCMS (ES) [M+1]$^+$ m/z: 412. $^1$H NMR (300 MHz, DMSO-d6) δ 8.46 (d, J=5.6 Hz, 1H), 8.15 (s, 1H), 7.85 (d, J=2.6 Hz, 1H), 7.04 (dd, J=5.7, 2.6 Hz, 1H), 4.92 (t, J=5.4 Hz, 1H), 4.19-4.10 (m, 4H), 3.76 (q, J=5.1 Hz, 2H), 3.27 (s, 3H), 3.15 (t, J=7.2 Hz, 2H), 2.82 (t, J=7.8 Hz, 2H), 2.28-2.18 (m, 2H), 2.04-1.95 (m, 2H), 1.89-1.78 (m, 2H), 1.78-1.65 (m, 2H), 1.33 (s, 3H).

Example 1.383

Synthesis of 2-[(2-{4-[(2R)-2-hydroxypropoxy]pyridin-2-yl}-5H,6H,7H-cyclopenta[d]pyrimidin-4-yl)(methyl)amino]-N-(1-methylcyclobutyl)acetamide (Compound 377)

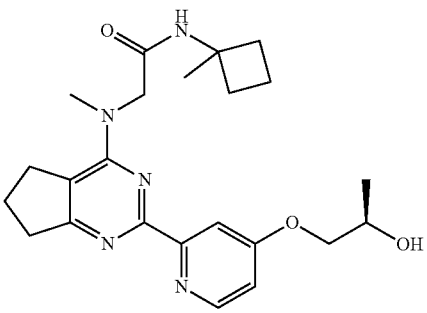 [SMILES: C[C@@H](O)COc1ccnc(-c2nc3c(c(N(C)CC(=O)NC4(C)CCC4)n2)CCC3)c1]

Compound 377 was synthesized similar to Compound 174 by replacing 2-methyl-2-((tetrahydro-2H-pyran-2-yl)oxy)propan-1-ol with (2R)-2-(oxan-2-yloxy)propan-1-ol and by replacing tert-butylamine with 1-methylcyclobutan-1-amine. Analytical chiral HPLC conditions: Column, Lux-cellulose-2, 100*4.6 mm, 3 um; mobile phase A, Ethanol; mobile phase B, CH$_3$CN; Flow rate: 1 mL/min; Gradient: 10% B in 8 min; 254 nm. Retention time: 2.712 min. LCMS (ES) [M+1]$^+$ m/z: 426. $^1$H NMR (300 MHz, DMSO-d6) δ 8.46 (d, J=5.6 Hz, 1H), 8.14 (s, 1H), 7.84 (d, J=2.6 Hz, 1H), 7.04 (dd, J=5.6, 2.6 Hz, 1H), 4.93 (d, J=4.1 Hz, 1H), 4.13 (s, 2H), 4.03-3.92 (m, 3H), 3.27 (s, 3H), 3.15 (t, J=7.3 Hz, 2H), 2.82 (t, J=7.9 Hz, 2H), 2.27-2.21 (m, 2H), 2.05-1.94 (m, 2H), 1.91-1.76 (m, 2H), 1.76-1.65 (m, 2H), 1.34 (s, 3H), 1.18 (d, J=5.8 Hz, 3H).

Example 1.384

Synthesis of 2-[(2-{4-[(2S)-2-hydroxypropoxy]pyridin-2-yl}-5H,6H,7H-cyclopenta[d]pyrimidin-4-yl)(methyl)amino]-N-(1-methylcyclobutyl)acetamide (Compound 378)

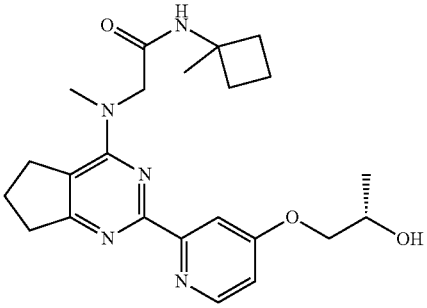 [SMILES: C[C@H](O)COc1ccnc(-c2nc3c(c(N(C)CC(=O)NC4(C)CCC4)n2)CCC3)c1]

Compound 378 was synthesized similar to Compound 174 by replacing 2-methyl-2-((tetrahydro-2H-pyran-2-yl)oxy)propan-1-ol with (2S)-2-(oxan-2-yloxy)propan-1-ol and by replacing tert-butylamine with 1-methylcyclobutan-1-amine. Analytical chiral HPLC conditions: Column, Lux-cellulose-2, 100*4.6 mm, 3 um; mobile phase A, Ethanol; mobile phase B, CH$_3$CN; Flow rate: 1 mL/min; Gradient:

10% B in 8 min; 254 nm. Retention time: 4.827 min. LCMS (ES) [M+1]+ m/z: 426. 1H NMR (300 MHz, DMSO-d6) δ 8.46 (d, J=5.6 Hz, 1H), 8.14 (s, 1H), 7.84 (d, J=2.6 Hz, 1H), 7.04 (dd, J=5.6, 2.6 Hz, 1H), 4.93 (d, J=4.1 Hz, 1H), 4.13 (s, 2H), 4.03-3.92 (m, 3H), 3.27 (s, 3H), 3.15 (t, J=7.3 Hz, 2H), 2.82 (t, J=7.9 Hz, 2H), 2.27-2.18 (m, 2H), 2.05-1.94 (m, 2H), 1.91-1.76 (m, 2H), 1.76-1.65 (m, 2H), 1.34 (s, 3H), 1.18 (d, J=5.8 Hz, 3H).
Example 1.385
Synthesis of N-[(4-benzyl-1,3-oxazol-2-yl)methyl]-2-(4-methoxypyridin-2-yl)-N-methyl-5H,6H,7H-cyclopenta[d]pyrimidin-4-aminemide (Compound 379)
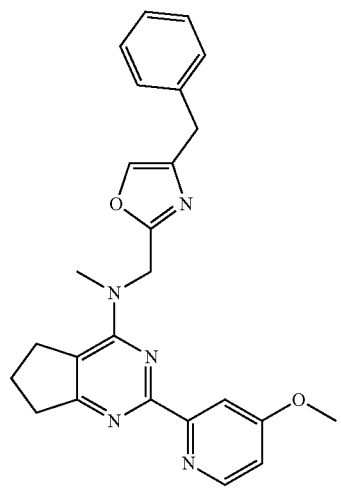 [SMILES: COc1ccnc(-c2nc3c(c(N(C)Cc4nc(Cc5ccccc5)co4)n2)CCC3)c1]
Scheme 126
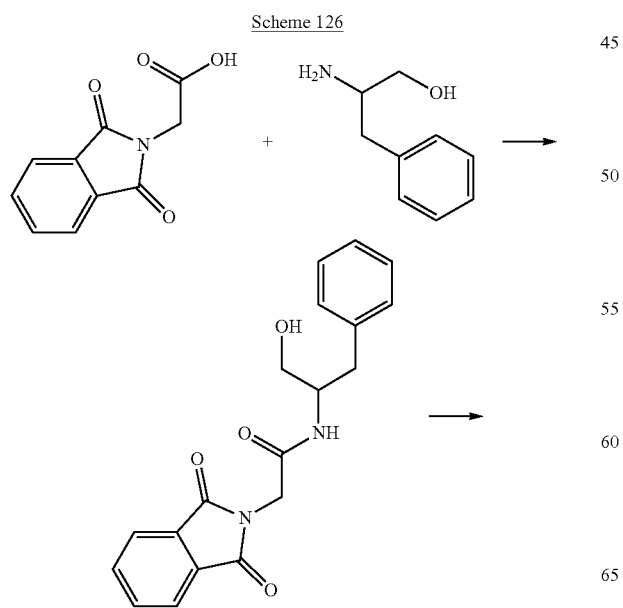
-continued
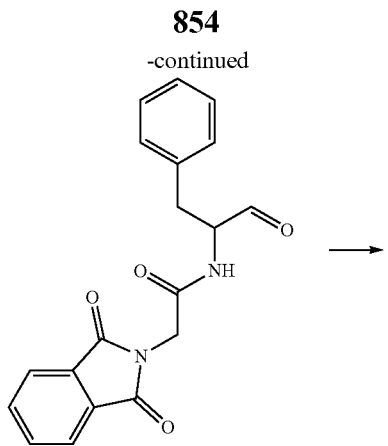
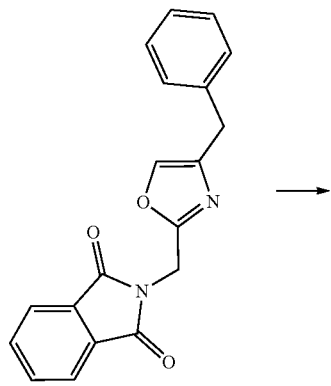
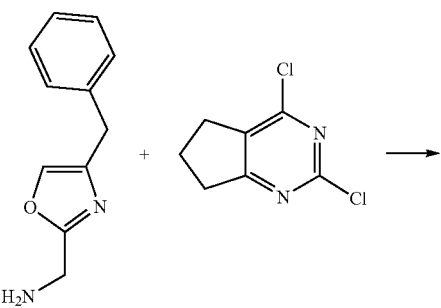
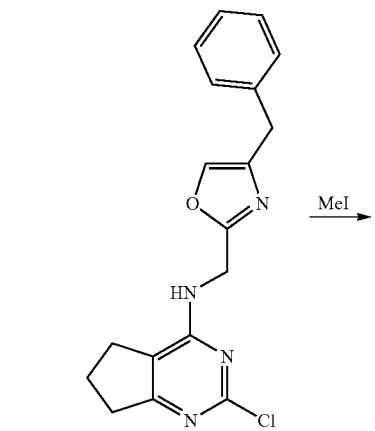

855
-continued

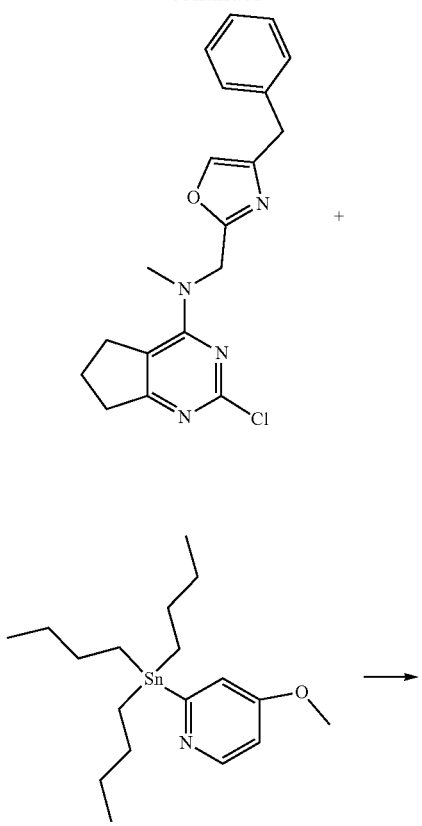

Step 1

856
-continued

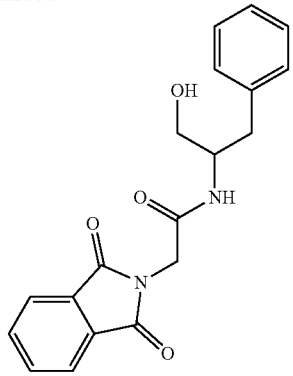

(1,3-Dioxo-1,3-dihydro-2H-isoindol-2-yl)acetic acid (2 g; 9.75 mmol; 1 eq.) was dissolved in N,N-dimethylformamide (40 ml) and cooled in an ice bath. 2-Amino-3-phenyl-1-propanol (1.55 g; 10.24 mmol; 1.05 eq.), 1-[bis(dimethylamino)methylene]-1H-1,2,3-triazolo[4,5-b]pyridinium 3-oxid hexafluorophosphate (HATU) (5.56 g; 14.62 mmol; 1.5 eq.) and Hunig's base (5.1 mL; 29.24 mmol; 3 eq.) were then added. The reaction was stirred to 25° C. over 3.5 h. Ethyl acetate (100 ml), water and sodium bicarbonate solution (50 ml) were added, the phases were separated and the aqueous phase was extracted once (50 ml). The combined organics phases were washed with water, saturated sodium chloride solution and dried over sodium sulfate. After evaporation the residue was purified by silica gel chromatography (ethyl acetate/hexanes gradient) to give 2-(1,3-dioxo-2,3-dihydro-1H-isoindol-2-yl)-N-(1-hydroxy-3-phenylpropan-2-yl)acetamide (1.97 g, 60%) as a white solid. LCMS (ES+): [M+H]$^+$=339.1.

Step 2

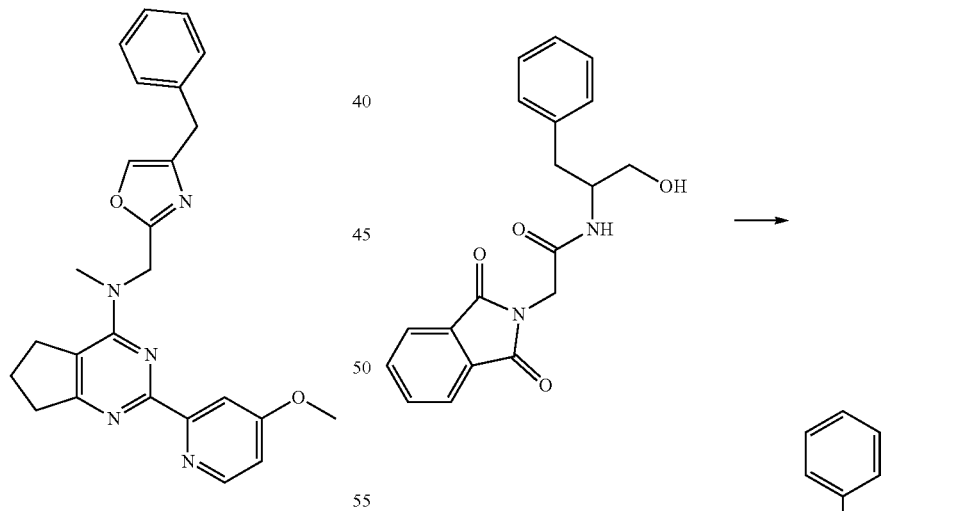

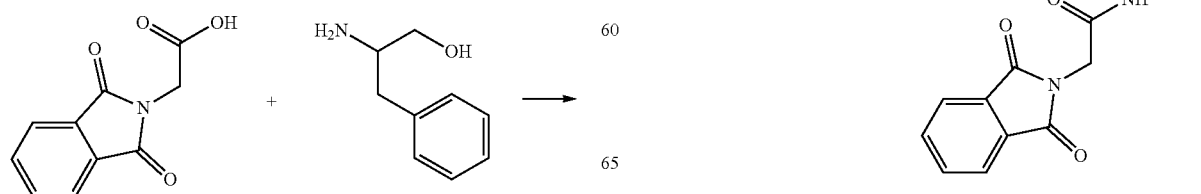

2-(1,3-Dioxo-2,3-dihydro-1H-isoindol-2-yl)-N-(1-hydroxy-3-phenylpropan-2-yl)acetamide (1.97 g; 5.82 mmol; 1 eq.) was dissolved in dichloromethane (150 ml) and cooled in an ice bath. 1,1-Bis(acetyloxy)-3-oxo-3H-1 5,2-benziodaoxol-1-yl acetate (Dess-Martin periodinane) (2.83 g; 6.46 mmol; 1.11 eq.) was added and the reaction was stirred to 25° C. over 2 h. Sodium bicarbonate solution and sodium thiosulfate solution were added and the mixture was stirred for 10 m. The phases were separated, the aqueous phase was extracted with dichloromethane (2×50 ml), the combined organic phases were washed with saturated sodium chloride solution and dried over sodium sulfate. Evaporation of solvent gave 2-(1,3-dioxo-2,3-dihydro-1H-isoindol-2-yl)-N-(1-oxo-3-phenylpropan-2-yl)acetamide as a solid which was used as is. LCMS (ES+): [M+H]$^+$=337.1.

Step 3

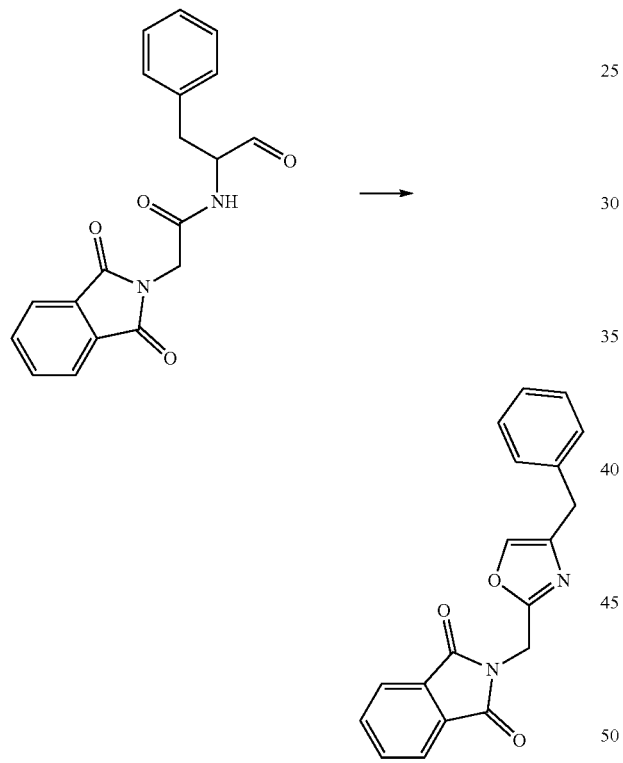

1,1,1,2,2,2-Hexachloroethane (5.16 g; 21.8 mmol; 2.7 eq.) and triphenylphosphine (5.76 g; 22 mmol; 2.7 eq.) were dissolved in tetrahydrofuran (30 ml) and stirred for 10 m. 2-(1,3-Dioxo-2,3-dihydro-1H-isoindol-2-yl)-N-(1-oxo-3-phenylpropan-2-yl)acetamide (3.62 g; 8.07 mmol; 1 eq.) suspended in THF (8 ml) was added and the mixture was stirred for 10 m. Pyridine (4.18 mL; 51.7 mmol; 6.4 eq.) in THF (1 ml) was then added dropwise over 15 m. The reaction was stirred in heat block at 80° C. for 18 h. After evaporation, the residue was purified by silica gel chromatography (ethyl acetate/hexanes gradient) to give 2-[(4-benzyl-1,3-oxazol-2-yl)methyl]-2,3-dihydro-1H-isoindole-1,3-dione (1.19 g, 46%) as yellow crystals. LCMS (ES+): [M+H]$^+$=319.0.

Step 4

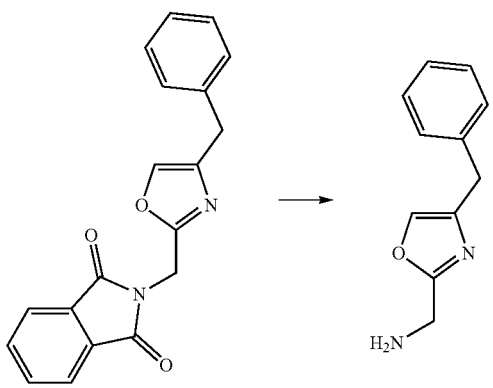 [SMILES: O=C1c2ccccc2C(=O)N1Cc1nc(Cc2ccccc2)co1 ; NCc1nc(Cc2ccccc2)co1]

2-[(4-Benzyl-1,3-oxazol-2-yl)methyl]-2,3-dihydro-1H-isoindole-1,3-dione (1.19 g; 3.74 mmol; 1 eq.) was suspended in ethanol (37 ml). Hydrazine (1.7 mL; 18.7 mmol; 5.00 eq.) was added and the reaction was heated in a sand bath at 90° C. for 2 h. The reaction was cooled, diluted with ethanol (20 ml), filtered and rinsed with more ethanol (20 ml). After evaporation the residue was purified by reverse phase chromatography (acetonitrile/water gradient) to give (4-benzyl-1,3-oxazol-2-yl)methanamine (0.31 g, 44%) as an oil. LCMS (ES+): [M+H]$^+$=189.1.

Step 5

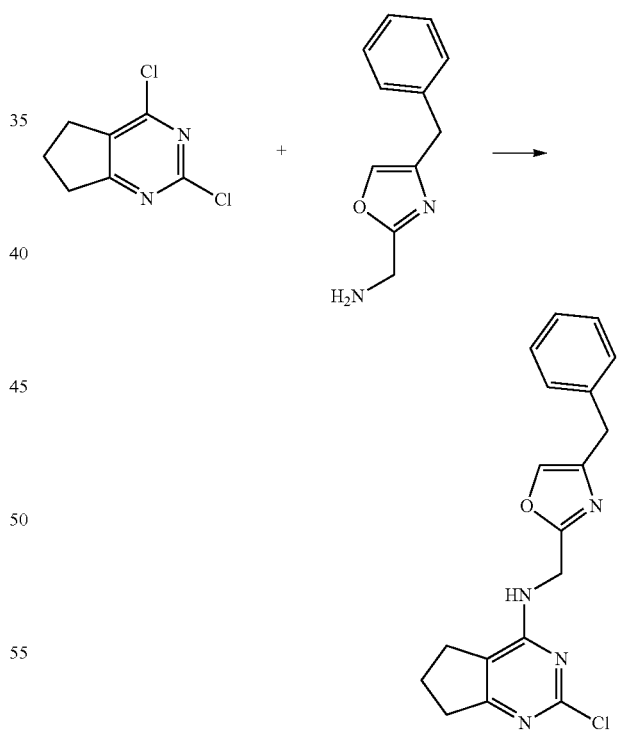

2,4-Dichloro-6,7-dihydro-5H-cyclopenta[d]pyrimidine (140 mg; 0.74 mmol; 1 eq.) was added to an acetonitrile solution (5 ml) of (4-benzyl-1,3-oxazol-2-yl)methanamine (153 mg; 0.81 mmol; 1.1 eq.) Hunig's base (0.39 mL; 2.22 mmol; 3 eq.) was added and the reaction was stirred in 60° C. heat block for 66 h. The solvent was evaporated and the residue was purified by silica gel chromatography (ethyl acetate/dichloromethane gradient) to give N-[(4-benzyl-1,3- oxazol-2-yl)methyl]-2-chloro-5H,6H,7H-cyclopenta[d]pyrimidin-4-amine (107 mg, 42%) as a solid. LCMS (ES+): [M+H]⁺=341.0.

Step 6

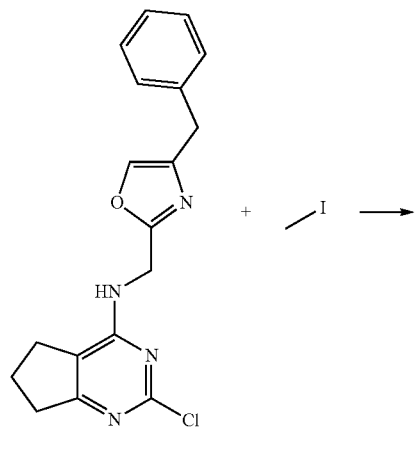

N-[(4-Benzyl-1,3-oxazol-2-yl)methyl]-2-chloro-5H,6H,7H-cyclopenta[d]pyrimidin-4-amine (107 mg; 0.31 mmol; 1 eq.) was dissolved in N,N-dimethylformamide (3 ml) and cooled in an ice bath. Iodomethane (195 µL; 3.14 mmol; 10 eq.) was added followed by sodium hydride (38 mg; 0.94 mmol; 3 eq.) and stirred to 25° C. over 2.5 h. Water (1 ml), ethyl acetate (50 ml) and sodium bicarbonate solution (10 ml) were added, the phases were separated and the aqueous phase was extracted with ethyl acetate (1×10 ml). The combined organic phases were washed with water, saturated sodium chloride solution and dried over sodium sulfate. After evaporation of solvent, the residue was purified by silica gel chromatography (ethyl acetate/hexanes gradient) to give N-[(4-benzyl-1,3-oxazol-2-yl)methyl]-2-chloro-N-methyl-5H,6H,7H-cyclopenta[d]pyrimidin-4-amine (92 mg, 83%) as a film. LCMS (ES+): [M+H]⁺=355.0.

Step 7

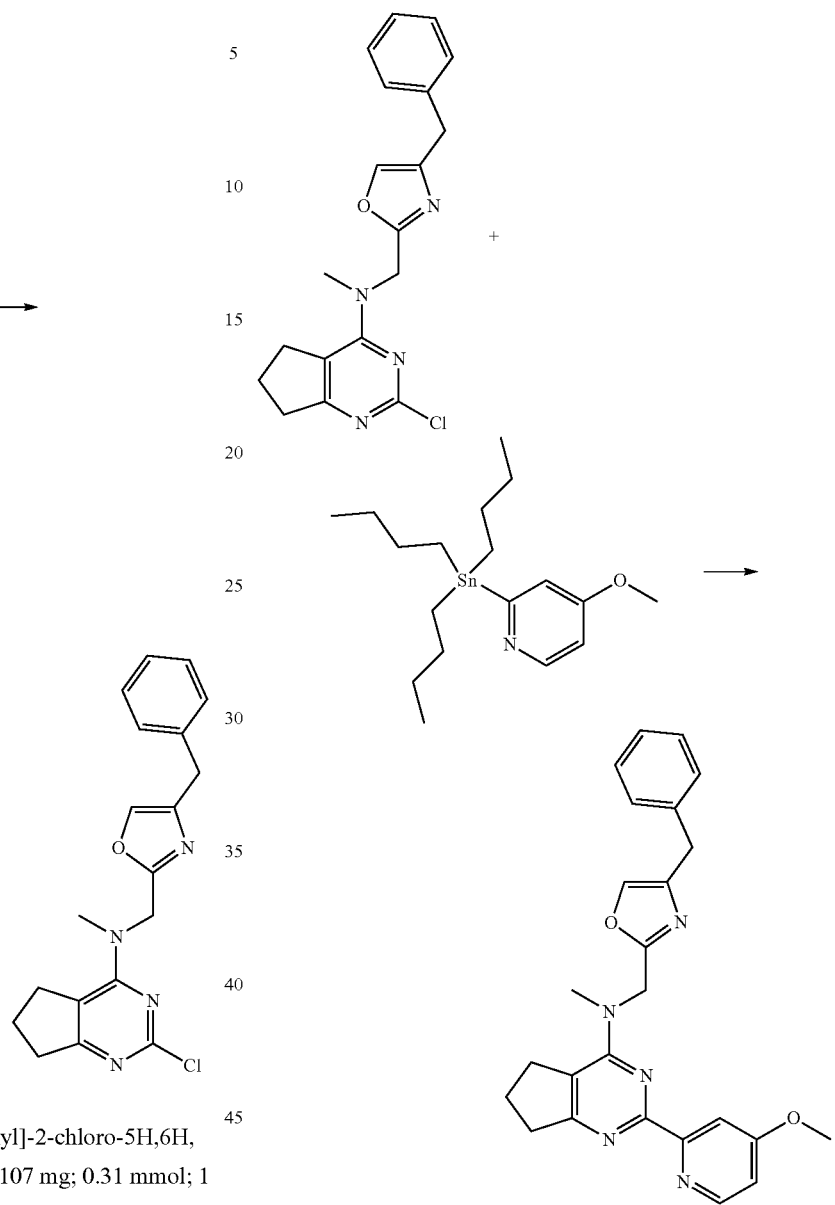

N-[(4-Benzyl-1,3-oxazol-2-yl)methyl]-2-chloro-N-methyl-5H,6H,7H-cyclopenta[d]pyrimidin-4-amine (63 mg; 0.17 mmol; 1 eq.) was dissolved in toluene (2 ml). 4-Methoxy-2-(tributylstannyl)pyridine (156 mg; 0.35 mmol; 2 eq.) in 1 ml toluene was added and the solution was purged with Ar gas. [1,1'-Bis(diphenylphosphino)ferrocene]dichloropalladium(II), complex with dichloromethane (14 mg; 17.5 umol; 0.1 eq) was added and the reaction vessel was sealed and stirred in a heat block at 110° C. for 17 h. The solvent was evaporated and the residue was purified by reverse phase chromatography (Waters XSelect CSH C18 column, 0-90% acetonitrile/0.1% aqueous formic acid gradient) to give N-[(4-benzyl-1,3-oxazol-2-yl)methyl]-2-(4-methoxypyridin-2-yl)-N-methyl-5H,6H,7H-cyclopenta[d] pyrimidin-4-amine (22 mg, 40%) as a pink solid. LCMS (ES+): [M+H]⁺=428.2. ¹H NMR (400 MHz, dmso) δ 8.45 (d, J=5.5 Hz, 1H), 7.78 (s, 2H), 7.73 (s, 1H), 7.32-7.12 (m, 5H), 7.01 (d, J=5.5 Hz, 1H), 4.94 (s, 2H), 3.86 (s, 3H), 3.77 (s, 2H), 3.20-3.15 (m, 2H), 2.86-2.75 (m, 2H), 2.04-1.89 (m, 2H).

Example 1.386

Synthesis of 2-(4-methoxypyridin-2-yl)-N-methyl-N-[(4-phenyl-1,3-oxazol-2-yl)methyl]-5H,6H,7H-cyclopenta[d]pyrimidin-4-amine (Compound 380)

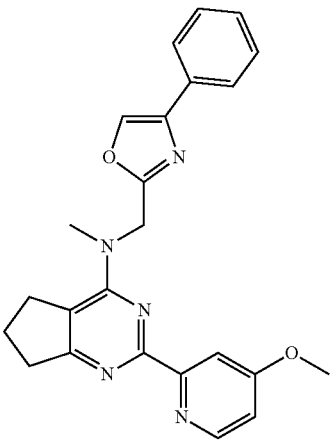 [SMILES: COc1ccnc(-c2nc3c(c(N(C)Cc4nc(-c5ccccc5)co4)n2)CCC3)c1]

Compound 380 was synthesized similar to Compound 379 by replacing 2-amino-3-phenyl-1-propanol with 2-amino-2-phenylethanol gave 2-(4-methoxypyridin-2-yl)-N-methyl-N-[(4-phenyl-1,3-oxazol-2-yl)methyl]-5H,6H, 7H-cyclopenta[d]pyrimidin-4-amine as a tan solid. LCMS (ES+): [M+H]⁺=414.2. ¹H NMR (400 MHz, dmso) δ 8.53 (s, 1H), 8.45 (d, J=5.6 Hz, 1H), 7.82 (d, J=2.6 Hz, 1H), 7.77-7.71 (m, 2H), 7.44-7.37 (m, 2H), 7.33-7.27 (m, 1H), 7.00 (dd, J=5.6, 2.6 Hz, 1H), 5.04 (s, 2H), 3.84 (s, 3H), 3.42 (s, 3H), 3.26-3.22 (m, 2H), 2.87-2.80 (m, 2H), 2.06-1.96 (m, 2H).

Example 1.387

Synthesis of N-tert-butyl-2-[(2-{4-[(1-hydroxycyclopentyl)methoxy]pyridin-2-yl}-5H,6H,7H-cyclopenta[d]pyrimidin-4-yl)(methyl)amino]acetamide (Compound 381)

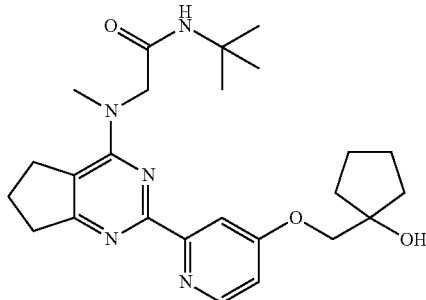

Compound 381 was synthesized similar to 174 by replacing 2-methyl-2-((tetrahydro-2H-pyran-2-yl)oxy)propan-1-ol with [1-(oxan-2-yloxy)cyclopentyl]methanol. LCMS (ES) [M+1]⁺ m/z: 454. ¹H NMR (300 MHz, DMSO-d6) δ 8.47 (d, J=5.6 Hz, 1H), 7.83 (d, J=2.5 Hz, 1H), 7.67 (s, 1H), 7.05 (dd, J=5.7, 2.6 Hz, 1H), 4.61 (s, 1H), 4.14 (s, 2H), 4.01 (s, 2H), 3.26 (s, 3H), 3.14 (t, J=7.3 Hz, 2H), 2.82 (t, J=7.8 Hz, 2H), 2.04-1.96 (m, 2H), 1.86-1.51 (m, 8H), 1.25 (s, 9H).

Example 1.388

Synthesis of 2-({2-[4-(2-hydroxy-2-methylpropoxy)pyridin-2-yl]-5H,6H,7H-cyclopenta[d]pyrimidin-4-yl}(methyl)amino)-1-(piperidin-1-yl)ethan-1-oneide (Compound 382)

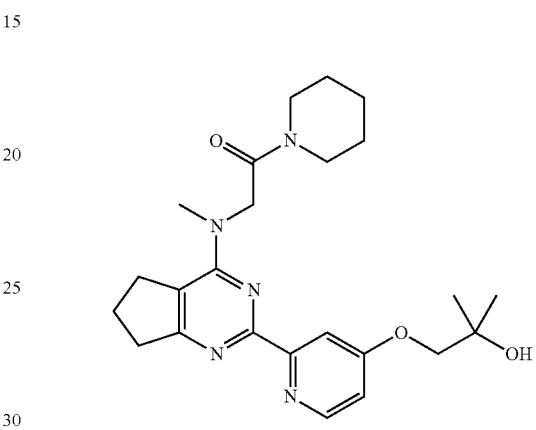

Compound 382 was synthesized similar to 174 by replacing tert-butylamine with piperidine. LCMS (ES) [M+1]⁺ m/z: 440. ¹H NMR (300 MHz, DMSO-d6) δ 8.45 (d, J=5.6 Hz, 1H), 7.73 (d, J=2.5 Hz, 1H), 7.03 (dd, J=5.7, 2.6 Hz, 1H), 4.72 (s, 1H), 4.51 (s, 2H), 3.85 (s, 2H), 3.45 (dt, J=11.2, 5.1 Hz, 4H), 3.26 (s, 3H), 3.14 (t, J=7.3 Hz, 2H), 2.81 (t, J=7.8 Hz, 2H), 2.06-1.92 (m, 2H), 1.61 (s, 4H), 1.47-1.39 (m, 2H), 1.23 (s, 6H).

Example 1.389

Synthesis of N-{bicyclo[1.1.1]pentan-1-yl}-2-({2-[4-(2-hydroxy-2-methylpropoxy)pyridin-2-yl]-5H, 6H,7H-cyclopenta[d]pyrimidin-4-yl}(methyl)amino) acetamide (Compound 383)

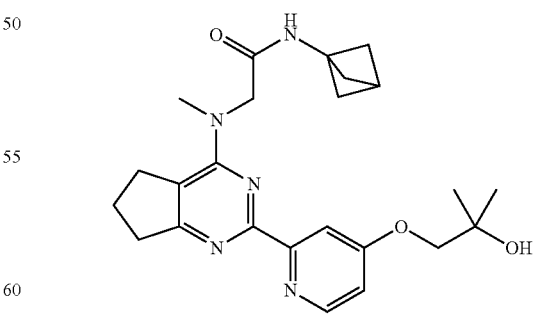

Compound 383 was synthesized similar to 174 by replacing tert-butylamine with bicyclo[1.1.1]pentan-1-amine. LCMS (ES) [M+1]⁺ m/z: 438. ¹H NMR (300 MHz, DMSO-d6) δ 8.74 (s, 1H), 8.47 (d, J=5.6 Hz, 1H), 7.79 (d, J=2.6 Hz, 1H), 7.05 (dd, J=5.7, 2.6 Hz, 1H), 4.70 (s, 1H), 4.12 (s, 2H), 3.87 (s, 2H), 3.27 (s, 3H), 3.15 (t, J=7.2 Hz, 2H), 2.82 (t, J=7.7 Hz, 2H), 2.37 (s, 1H), 2.03-1.91 (m, 7H), 1.24 (s, 6H).

Example 1.390

Synthesis of N-tert-butyl-2-{[2-(4-{[(2R)-1-hydroxypropan-2-yl]oxy}pyridin-2-yl)-5H,6H,7H-cyclopenta[d]pyrimidin-4-yl](methyl)amino}acetamide (Compound 384)

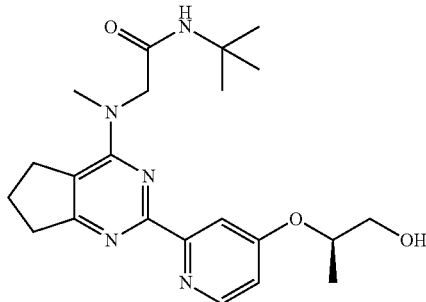

Compound 384 was synthesized similar to 174 by replacing 2-methyl-2-((tetrahydro-2H-pyran-2-yl)oxy)propan-1-ol with (2R)-1-((tetrahydro-2H-pyran-2-yl)oxy)propan-2-ol. Analytical chiral HPLC conditions: Column, CHIRALCEL OX-3, 50*4.6 mm, 3 um; mobile phase A, n-Hexane; mobile phase B, Ethanol; Flow rate: 1 mL/min; Gradient: 50% B in 10 min; 270 nm. Retention time: 4.949 min. LCMS (ES) [M+1]$^+$ m/z: 414. $^1$H NMR (300 MHz, DMSO-d6) δ 8.45 (d, J=5.4 Hz, 1H), 7.83 (d, J=2.4 Hz, 1H), 7.68 (s, 1H), 7.05 (dd, J=5.7, 2.4 Hz, 1H), 4.93 (t, J=5.6 Hz, 1H), 4.70-4.60 (m, 1H), 4.18-4.06 (m, 2H), 3.63-3.48 (m, 2H), 3.26 (s, 3H), 3.14 (t, J=7.2 Hz, 2H), 2.81 (t, J=7.8 Hz, 2H), 2.04-1.93 (m, 2H), 1.27 (s, 3H), 1.25 (s, 9H).

Example 1.391

Synthesis of N-tert-butyl-2-{[2-(4-{[(2S)-1-hydroxypropan-2-yl]oxy}pyridin-2-yl)-5H,6H,7H-cyclopenta[d]pyrimidin-4-yl](methyl)amino}acetamide (Compound 385)

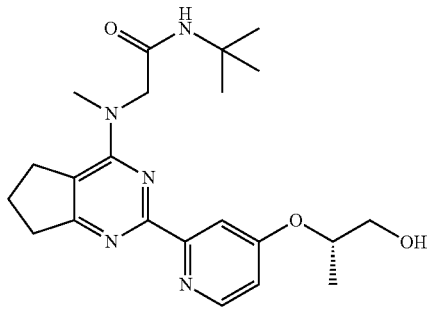 [SMILES: C[C@@H](CO)Oc1ccnc(-c2nc3c(c(N(C)CC(=O)NC(C)(C)C)n2)CCC3)c1]

Compound 385 was synthesized similar to 174 by replacing 2-methyl-2-((tetrahydro-2H-pyran-2-yl)oxy)propan-1-ol with (2S)-1-((tetrahydro-2H-pyran-2-yl)oxy)propan-2-ol. LCMS (ES) [M+1]$^+$ m/z: 414. $^1$H NMR (300 MHz, DMSO-d6) δ 8.45 (d, J=5.7 Hz, 1H), 7.83 (d, J=2.6 Hz, 1H), 7.69 (s, 1H), 7.06 (dd, J=5.7, 2.6 Hz, 1H), 4.93 (t, J=5.6 Hz, 1H), 4.69-4.60 (m, 1H), 4.22-4.02 (m, 2H), 3.56 (tq, J=11.5, 6.2, 5.8 Hz, 2H), 3.26 (s, 3H), 3.14 (t, J=7.3 Hz, 2H), 2.81 (t, J=7.8 Hz, 2H), 2.04-1.96 (m, 2H), 1.24 (d, J=6.1 Hz, 3H), 1.21 (s, 9H).

Example 1.392

Synthesis of N-tert-butyl-2-[(2-{4-[(2S)-2-hydroxy-3-methylbutoxy]pyridin-2-yl}-5H,6H,7H-cyclopenta[d]pyrimidin-4-yl)(methyl)amino]acetamide (Compound 386)

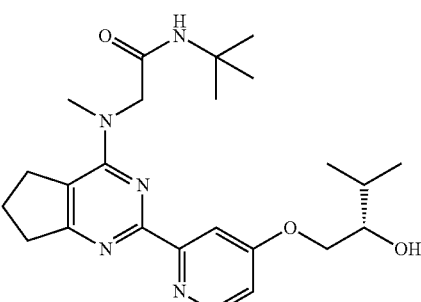

Compound 386 was synthesized similar to 174 by replacing 2-methyl-2-((tetrahydro-2H-pyran-2-yl)oxy)propan-1-ol with (2S)-3-methyl-2-(oxan-2-yloxy)butan-1-ol. Analytical chiral HPLC conditions: Column, Lux-cellulose-2, 100*4.6 mm, 3 um; mobile phase A, AcCN; mobile phase B, Methanol; Flow rate: 1 mL/min; Gradient: 50% B in 15 min; 254 nm. Retention time: 9.997 min. LCMS (ES) [M+1]$^+$ m/z: 442. $^1$H NMR (300 MHz, DMSO-d6) δ 8.47 (d, J=5.6 Hz, 1H), 7.83 (d, J=2.5 Hz, 1H), 7.66 (s, 1H), 7.06 (dd, J=5.7, 2.6 Hz, 1H), 4.86 (d, J=5.3 Hz, 1H), 4.13 (s, 2H), 4.09 (dd, J=10.1, 4.5 Hz, 1H), 4.00 (dd, J=10.1, 6.2 Hz, 1H), 3.60 (q, J=5.1 Hz, 1H), 3.26 (s, 3H), 3.14 (t, J=7.3 Hz, 2H), 2.81 (t, J=7.8 Hz, 2H), 2.04-1.96 (p, J=7.7 Hz, 2H), 1.92-1.76 (m, 1H), 1.24 (s, 9H), 0.93 (dd, J=6.8, 5.3 Hz, 6H).

Example 1.393

Synthesis of N-tert-butyl-2-[(2-{4-[(2R)-2-hydroxy-3-methylbutoxy]pyridin-2-yl}-5H,6H,7H-cyclopenta[d]pyrimidin-4-yl)(methyl)amino]acetamide (Compound 387)

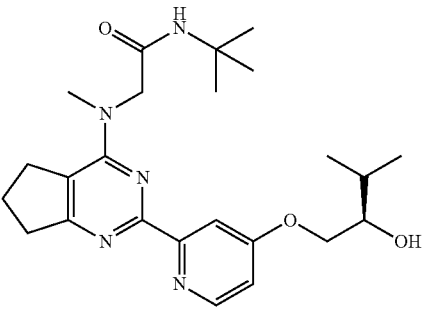 [SMILES: CC(C)[C@@H](O)COc1ccnc(-c2nc3c(c(N(C)CC(=O)NC(C)(C)C)n2)CCC3)c1]

Compound 387 was synthesized similar to 174 by replacing 2-methyl-2-((tetrahydro-2H-pyran-2-yl)oxy)propan-1-ol with (2R)-3-methyl-2-(oxan-2-yloxy)butan-1-ol. Analytical chiral HPLC conditions: Column, Lux-cellulose-2, 100*4.6 mm, 3 um; mobile phase A, AcCN; mobile phase B, Methanol; Flow rate: 1 mL/min; Gradient: 50% B in 15 min; 254 nm. Retention time: 2.582 min. LCMS (ES) [M+1]+ m/z: 442. ¹H NMR (300 MHz, DMSO-d6) δ 8.48 (d, J=5.6 Hz, 1H), 7.84 (d, J=2.5 Hz, 1H), 7.67 (s, 1H), 7.08 (dd, J=5.7, 2.6 Hz, 1H), 4.87 (d, J=5.3 Hz, 1H), 4.14 (s, 2H), 4.09 (J=10.1, 4.5 Hz, 1H), 4.01 (dd, J=10.1, 6.2 Hz, 1H), 3.60 (t, J=5.3 Hz, 1H), 3.27 (s, 3H), 3.14 (t, J=7.3 Hz, 2H), 2.82 (t, J=7.8 Hz, 2H), 2.02-1.97 (m, 2H), 1.83 (dt, J=13.4, 6.7 Hz, 1H), 1.24 (s, 9H), 0.93 (dd, J=6.8, 5.2 Hz, 6H).

Example 1.394

Synthesis of N-tert-butyl-2-[(2-{4-[(1-hydroxycyclobutyl)methoxy]pyridin-2-yl}-5H,6H,7H-cyclopenta[d]pyrimidin-4-yl)(methyl)amino]acetamide (Compound 388)

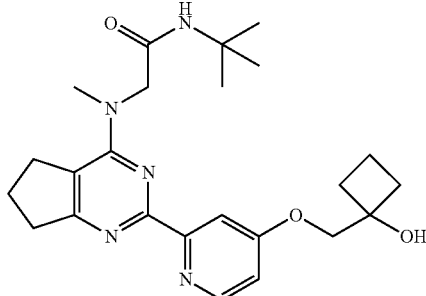

Compound 388 was synthesized similar to 174 by replacing 2-methyl-2-((tetrahydro-2H-pyran-2-yl)oxy)propan-1-ol with [1-(oxan-2-yloxy)cyclobutyl]methanol. LCMS (ES) [M+1]+ m/z: 440. ¹H NMR (300 MHz, DMSO-d6) δ 8.47 (d, J=5.6 Hz, 1H), 7.85 (d, J=2.5 Hz, 1H), 7.67 (s, 1H), 7.07 (dd, J=5.7, 2.6 Hz, 1H), 5.29 (s, 1H), 4.13 (s, 2H), 4.06 (s, 2H), 3.26 (s, 3H), 3.14 (t, J=7.3 Hz, 2H), 2.81 (t, J=7.8 Hz, 2H), 2.17 (d, J=10.2 Hz, 2H), 2.00 (h, J=8.7, 7.8 Hz, 4H), 1.62 (dq, J=19.4, 9.7 Hz, 2H), 1.24 (s, 9H).

Example 1.395

Synthesis of 2-({2-[4-(2-hydroxy-2-methylpropoxy)pyridin-2-yl]-5H,6H,7H-cyclopenta[d]pyrimidin-4-yl}(methyl)amino)-N-(propan-2-yl)acetamide (Compound 389)

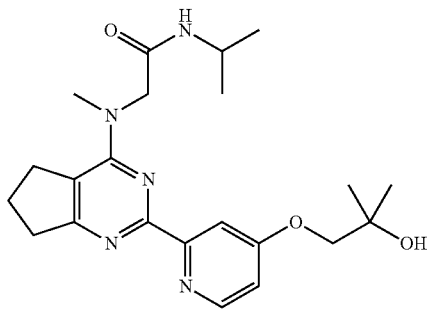 [SMILES: CC(C)NC(=O)CN(C)c1nc(-c2cc(OCC(C)(C)O)ccn2)nc2c1CCC2]

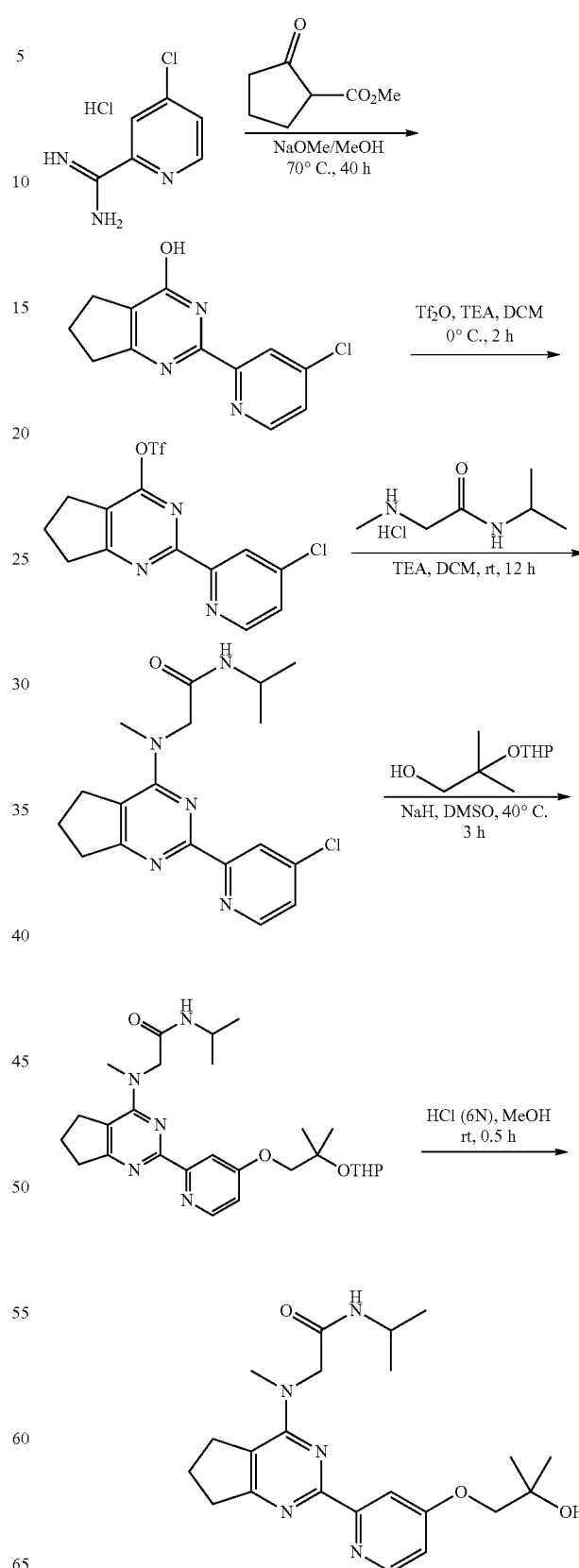

Scheme 127

Step 1

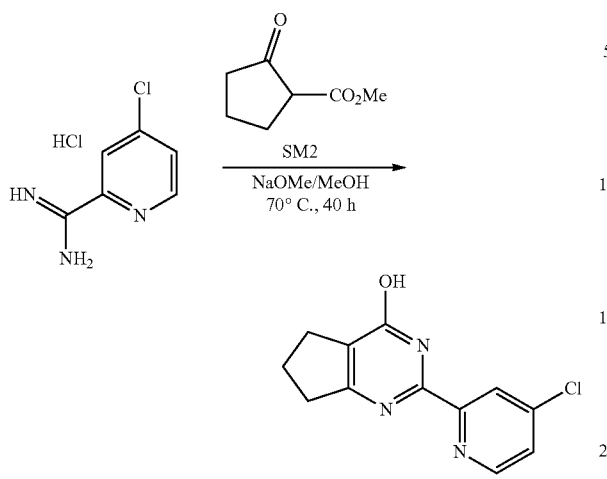

Into a 1 L round-bottom flask were added 4-chloropicolinimidamide hydrochloride (60.0 g, 312 mmol, 1.00 equiv) in MeOH (600 mL), methyl 2-oxocyclopentane-1-carboxylate (66.6 g, 468 mmol, 1.5 equiv), and NaOMe (42.18 g, 781 mmol, 2.5 equiv) in MeOH at room temperature. The mixture was stirred for 40 hours at 70° C. under a nitrogen atmosphere. The precipitated solids were collected by filtration and washed with MeOH (1×1 500 mL). This resulted in 2-(4-chloropyridin-2-yl)-6,7-dihydro-5H-cyclopenta[d]pyrimidin-4-ol (62 g, 80.12%) as a brown solid. LCMS (ES) [M+1]⁺ m/z 248.

Step 2

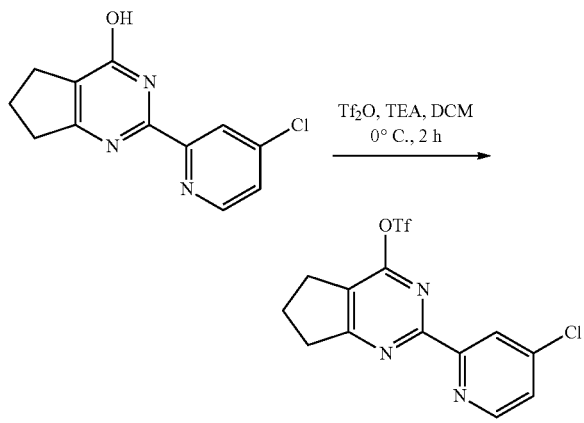

Into a 1 L 3-necked round-bottom flask were added 2-(4-chloropyridin-2-yl)-6,7-dihydro-5H-cyclopenta[d]pyrimidin-4-ol (60 g, 242 mmol, 1.00 equiv) in DCM and TEA (123 g, 1211 mmol, 5.0 equiv). A stirred mixture of Tf₂O (137 g, 484 mmol, 2.0 equiv) in DCM was added dropwise at 0° C. The resulting mixture was stirred for an additional 2 hours at 0° C. The reaction was quenched by the addition of NH₄Cl (aq. 500 mL) at room temperature. The resulting mixture was extracted with DCM (3×600 mL), and the organic layer was separated and dried over anhydrous Na₂SO₄. The resulting mixture was filtered and the filtrate was concentrated under reduced pressure. The residue was purified by silica gel column chromatography, eluted with PE/EA (3:1) to afford 2-(4-chloropyridin-2-yl)-6,7-dihydro-5H-cyclopenta[d]pyrimidin-4-yl trifluoromethanesulfonate (63 g, 68.48%) as an off-white solid. LCMS (ES) [M+1]⁺ m/z 380.

Step 3

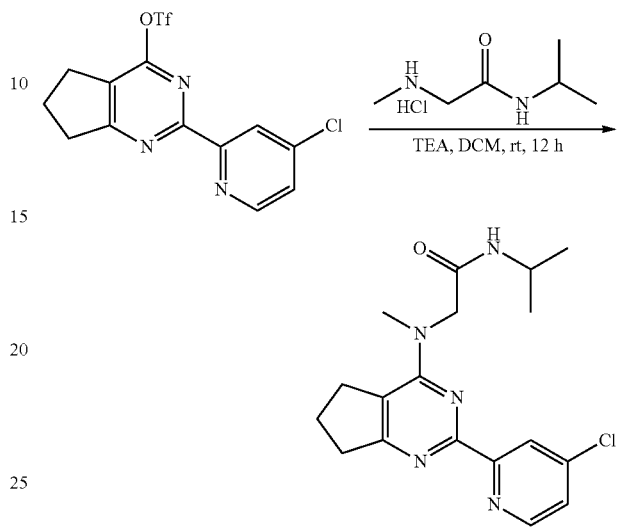

Into a 500 mL three-necked round bottom flask were added 2-(4-chloropyridin-2-yl)-6,7-dihydro-5H-cyclopenta[d]pyrimidin-4-yl trifluoromethanesulfonate (15.0 g, 39.6 mmol, 1.00 equiv), TEA (16.0 g, 158.4 mmol, 4.00 equiv), and dichloromethane (300 mL). This was followed by the addition of N-isopropyl-2-(methylamino)acetamide hydrochloride (8.5 g, 51.5 mmol, 1.30 equiv) at room temperature. The mixture was stirred for 12 h. The reaction was quenched with H₂O (200 mL), and extracted with dichloromethane (2×100 mL). The organic layers were combined, and dried over anhydrous sodium sulfate. After filtration, the filtrate was concentrated under reduced pressure. The residue was triturated in ethyl acetate/hexane (1:3). The solid was collected by filtration and dried under an infrared lamp for 3 h. This resulted in 13.0 g (91%) 2-((2-(4-chloropyridin-2-yl)-6,7-dihydro-5H-cyclopenta[d]pyrimidin-4-yl)(methyl)amino)-N-isopropylacetamide as an off-white solid. LCMS (ES, m/z): [M+H]⁺: 360.

Step 4

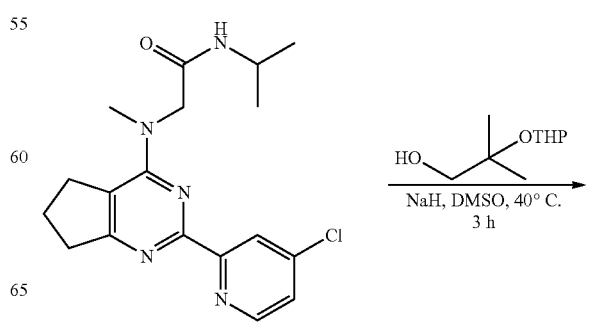

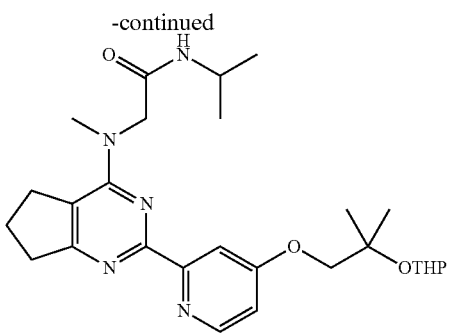

Into a 500 mL three-necked round bottom flask were placed 2-methyl-2-((tetrahydro-2H-pyran-2-yl)oxy)propan-1-ol (12.6 g, 72.4 mmol, 2.00 equiv) and DMSO (150 mL). NaH (60% in mineral oil) (2.9 g, 72.4 mmol, 2.00 equiv) was added at ° C. and stirred for 1 h. After that, 2-((2-(4-chloropyridin-2-yl)-6,7-dihydro-5H-cyclopenta[d]pyrimidin-4-yl)(methyl)amino)-N-isopropylacetamide (13.0 g, 36.2 mmol, 1.00 equiv) was added in three portions and the mixture was stirred for an additional 3 h at 40° C. The reaction mixture was cooled to room temperature, quenched with H$_2$O (200 mL), and extracted with ethyl acetate (3×100 mL). The organic layers were combined, washed with brine (2×100 mL), and dried over anhydrous sodium sulfate. After filtration, the filtrate was concentrated under reduced pressure. The residue was purified by Prep-HPLC with the following conditions: C18-500 g, CH$_3$CN/H$_2$O (NH$_4$HCO$_3$ 0.1%), from 15% to 70% in 30 min, Flow rate, 150 mL/min, Detector, UV 254 nm. This resulted in 15.0 g (83%) N-isopropyl-2-(methyl(2-(4-(2-methyl-2-((tetrahydro-2H-pyran-2-yl)oxy)propoxy)pyridin-2-yl)-6,7-dihydro-5H-cyclopenta[d]pyrimidin-4-yl)amino)acetamide as a brown solid. LCMS (ES, m/z): [M+H]$^+$: 498.

Step 5

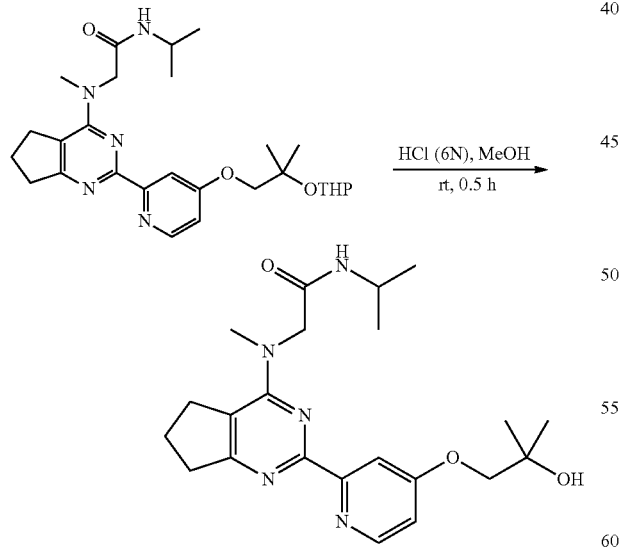

Into a 250 mL three-necked round bottom flask were added N-isopropyl-2-(methyl(2-(4-(2-methyl-2-((tetrahydro-2H-pyran-2-yl)oxy)propoxy)pyridin-2-yl)-6,7-dihydro-5H-cyclopenta[d]pyrimidin-4-yl)amino)acetamide (15.0 g, 30.2 mmol, 1.00 equiv), methanol (100 mL), and HCl (c) (5 mL). The mixture was stirred for 0.5 h and diluted with H$_2$O (200 mL). Its pH was adjusted to 9 with K$_2$CO$_3$ solid, and then extracted with dichloromethane (2×300 mL). The combined organic phases were dried over anhydrous sodium sulfate. After filtration, the filtrate was concentrated under reduced pressure, the residue was triturated in CH$_3$CN (120 mL), and the solid was collected by filtration to give 7.38 g 2-((2-(4-(2-hydroxy-2-methylpropoxy)pyridin-2-yl)-6,7-dihydro-5H-cyclopenta[d]pyrimidin-4-yl)(methyl)amino)-N-isopropylacetamide as a white solid. LCMS (ES, m/z): [M+H]$^+$: 414. $^1$H-NMR (300 MHz, DMSO-d$_6$, ppm): δ 8.48 (d, J=5.7 Hz, 1H), 8.04 (d, J=7.8 Hz, 1H), 7.82 (d, J=2.4 Hz, 1H), 7.05 (dd, J=5.7, 2.7 Hz, 1H), 4.70 (s, 1H), 4.15 (s, 2H), 3.93-3.82 (m, 3H), 3.27 (s, 3H), 3.15 (t, J=7.2 Hz, 2H), 2.82 (t, J=7.8 Hz, 2H), 2.04-1.94 (m, 2H), 1.24 (s, 6H), 1.05 (d, J=6.6 Hz, 6H).

Example 1.396

Synthesis of N-ethyl-2-({2-[4-(2-hydroxy-2-methylpropoxy)pyridin-2-yl]-5H,6H,7H-cyclopenta[d]pyrimidin-4-yl}(methyl)amino)acetamide (Compound 390)

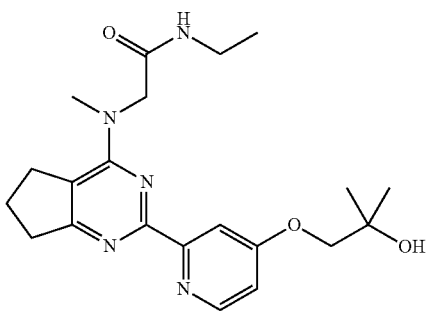 [SMILES: CCNC(=O)CN(C)c1nc(-c2cc(OCC(C)(C)O)ccn2)nc2c1CCC2]

Compound 390 was synthesized similar to 389 by replacing propane-2-amine with ethylamine. LCMS (ES) [M+1]$^+$ m/z: 400. $^1$H NMR (300 MHz, DMSO-d6) δ 8.47 (d, J=5.6 Hz, 1H), 8.18 (t, J=5.1 Hz, 1H), 7.81 (d, J=2.5 Hz, 1H), 7.04 (dd, J=5.7, 2.5 Hz, 1H), 4.70 (s, 1H), 4.15 (s, 2H), 3.86 (s, 2H), 3.27 (s, 3H), 3.18-3.07 (m, 4H), 2.82 (t, J=7.8 Hz, 2H), 2.04-1.94 (m, 2H), 1.23 (s, 6H), 1.04 (t, J=6.6 Hz, 3H).

Example 1.397

Synthesis of 1-(4,4-difluoropiperidin-1-yl)-2-({2-[4-(2-hydroxy-2-methylpropoxy)pyridin-2-yl]-5H,6H,7H-cyclopenta[d]pyrimidin-4-yl}(methyl)amino)ethan-1-one (Compound 391)

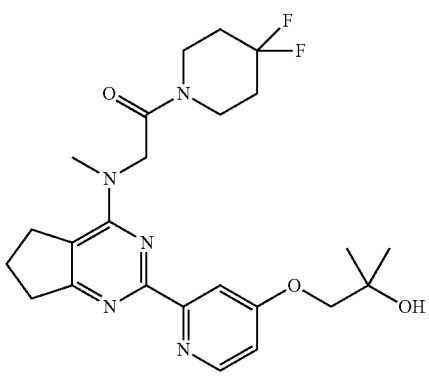 [SMILES: CN(CC(=O)N1CCC(F)(F)CC1)c1nc(-c2cc(OCC(C)(C)O)ccn2)nc2c1CCC2]

Compound 391 was synthesized similar to 389 by replacing propane-2-amine with ethylamine. LCMS (ES) [M+1]⁺ m/z: 476. ¹H NMR (300 MHz, DMSO-d6) δ 8.42 (d, J=5.6 Hz, 1H), 8.15 (s, HCOOH), 7.76 (d, J=2.5 Hz, 1H), 7.03 (dd, J=5.6, 2.5 Hz, 1H), 4.71 (s, 1H), 4.58 (s, 2H), 3.85 (s, 2H), 3.61-3.54 (m, 4H), 3.29 (s, 3H), 3.17 (t, J=7.2 Hz, 2H), 2.82 (t, J=7.8 Hz, 2H), 2.31-2.09 (m, 2H), 1.99-1.79 (m, 4H), 1.22 (s, 6H).

Example 1.398

Synthesis of 2-({2-[4-(2-hydroxyethoxy)pyridin-2-yl]-5H,6H,7H-cyclopenta[d]pyrimidin-4-yl}(methyl)amino)-N-(3-methylpentan-3-yl)acetamide (Compound 392)

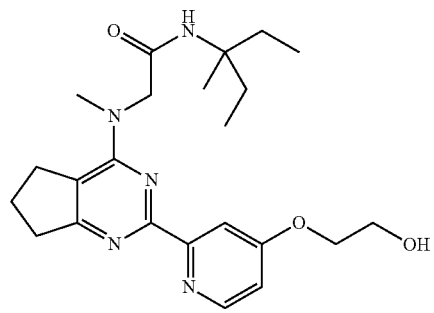 [SMILES: CCC(C)(CC)NC(=O)CN(C)c1nc(-c2cc(OCCO)ccn2)nc2c1CCC2]

Compound 392 was synthesized similar to Compound 44 by replacing Intermediate II with 2-({2-chloro-5H,6H,7H-cyclopenta[d]pyrimidin-4-yl}(methyl)amino)-N-(3-methylpentan-3-yl)acetamide. LCMS (ES) [M+1]⁺ m/z: 428. ¹H NMR (300 MHz, DMSO-d6) δ 8.46 (d, J=5.6 Hz, 1H), 8.16 (s, HCOOH), 7.83 (d, J=2.5 Hz, 1H), 7.33 (s, 1H), 7.03 (dd, J=5.6, 2.6 Hz, 1H), 4.20 (s, 2H), 4.14 (t, J=4.9 Hz, 2H), 3.76 (t, J=4.9 Hz, 2H), 3.25 (s, 3H), 3.14 (t, J=7.3 Hz, 2H), 2.81 (t, J=7.9 Hz, 2H), 2.03-1.96 (m, 2H), 1.71 (dq, J=14.7, 7.4 Hz, 2H), 1.56-1.38 (m, 2H), 1.09 (s, 3H), 0.70 (t, J=7.4 Hz, 6H).

Example 1.399 and Example 1.400

Synthesis of N-tert-butyl-2-[(2-{4-[(2R)-2-hydroxybutoxy]pyridin-2-yl}-5H,6H,7H-cyclopenta[d]pyrimidin-4-yl)(methyl)amino]acetamide (Compound 393) and N-tert-butyl-2-[(2-{4-[(2R)-2-hydroxybutoxy]pyridin-2-yl}-5H,6H,7H-cyclopenta[d]pyrimidin-4-yl)(methyl)amino]acetamide (Compound 394)

Compound 393

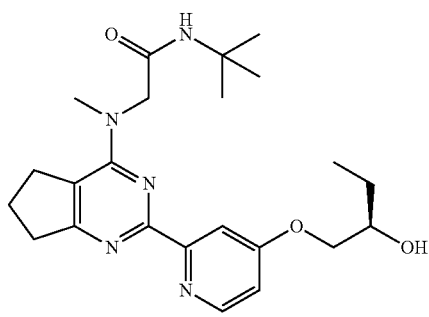

Compound 394

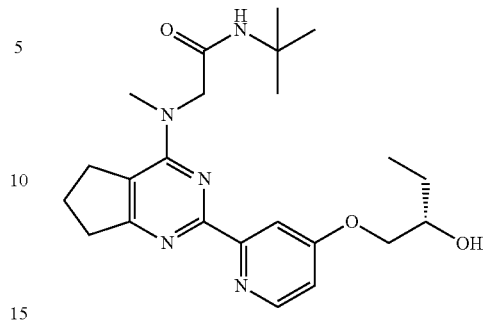

Scheme 128

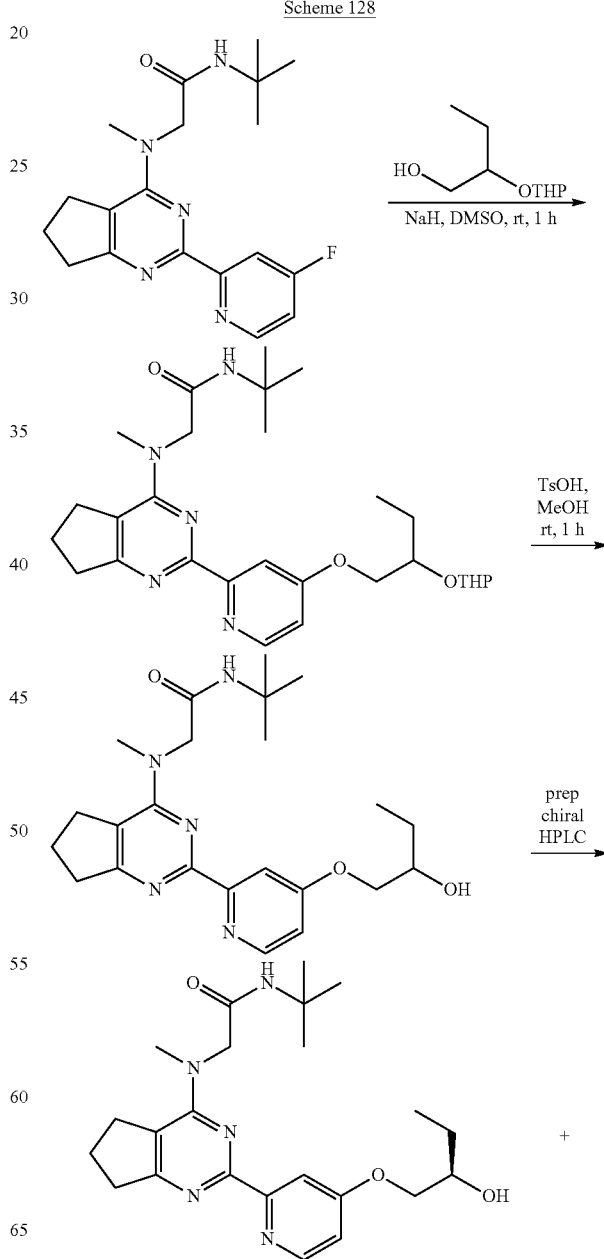

Step 1

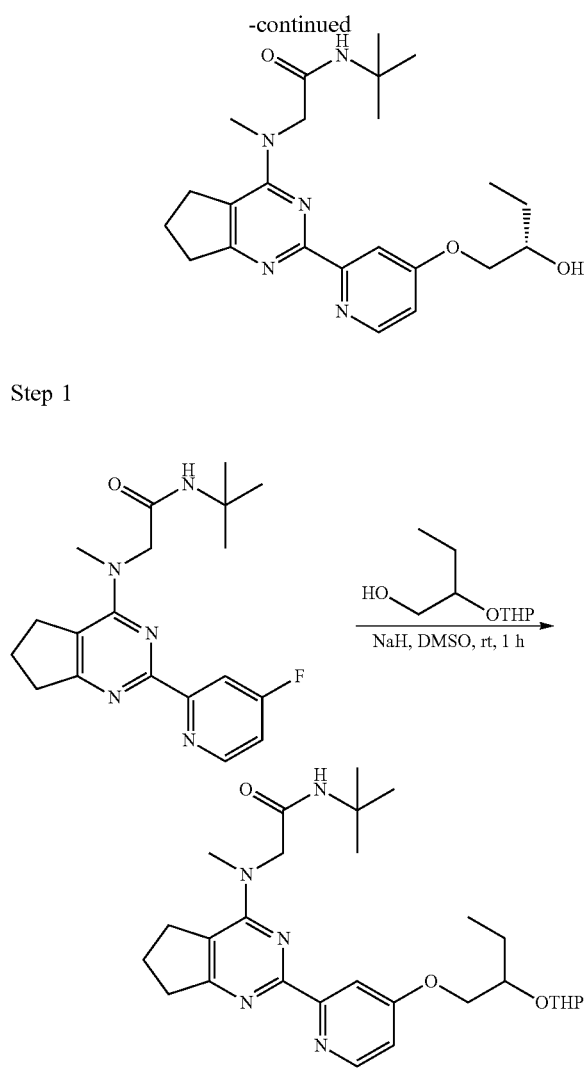

Into a 20-mL vail were placed 2-((tetrahydro-2H-pyran-2-yl)oxy)butan-1-ol (390 mg, 2.24 mmol, 2.00 equiv) and DMSO (4.00 mL). NaH (60% in mineral oil) (90 mg, 2.24 mmol, 2.00 equiv) was added and the mixture was stirred at room temperature for 0.5 h, and added N-(tert-butyl)-2-((2-(4-fluoropyridin-2-yl)-6,7-dihydro-5H-cyclopenta[d]pyrimidin-4-yl)(methyl)amino)acetamide (400 mg, 1.12 mmol, 1.00 equiv). The resulting solution was stirred for 1 h at room temperature, and then quenched with cooled water, extracted with 3*30 mL of ethyl acetate. The combined organic phases were washed with brine (20 mL*2), dried over anhydrous sodium sulfate, filtered and the filtrate was concentrated under reduced pressure. This resulted in 841 mg crude of N-(tert-butyl)-2-(methyl(2-(4-(2-((tetrahydro-2H-pyran-2-yl)oxy)butoxy)pyridin-2-yl)-6,7-dihydro-5H-cyclopenta[d]pyrimidin-4-yl)amino)acetamide as yellow oil and used to the next step without further purification. LCMS (ES)[M+1]⁺ m/z: 512.

Step 2

Into a 50-mL round-bottom flask, was placed N-(tert-butyl)-2-(methyl(2-(4-(2-((tetrahydro-2H-pyran-2-yl)oxy) butoxy)pyridin-2-yl)-6,7-dihydro-5H-cyclopenta[d]pyrimidin-4-yl)amino)acetamide (841 mg, 1.65 mmol, 1.00 equiv), MeOH (5.0 mL), TsOH (284 mg, 1.65 mmol, 1.00 equiv). The mixture was stirred for 1 h at room temperature. The reaction mixture was purified by Prep-HPLC with the following conditions: Welch Xtimate C18, 21.2*250 mm, 5 um, Mobile phase, Water (10 mmol/L NH₄HCO₃) and CH₃CN (25% Phase B up to 65% in 15 min), Detector, UV 254 nm. 520 mg of N-(tert-butyl)-2-((2-(4-(2-hydroxybutoxy)pyridin-2-yl)-6,7-dihydro-5H-cyclopenta[d]pyrimidin-4-yl)(methyl)amino)acetamide was obtained as white solid. LCMS (ES)[M+1]⁺ m/z: 428.

Step 3

-continued

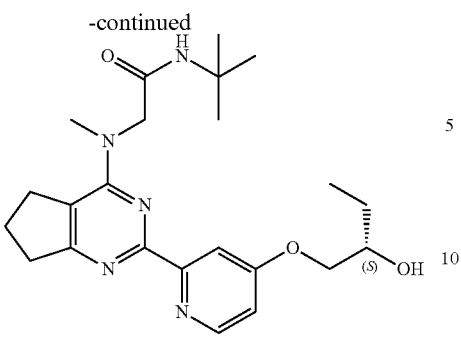

Chiral HPLC separation: 300 mg of N-(tert-butyl)-2-((2-(4-(2-hydroxybutoxy)pyridin-2-yl)-6,7-dihydro-5H-cyclopenta[d]pyrimidin-4-yl)(methyl)amino)acetamide was separated by Prep-chiral HPLC with the following conditions: Column, Lux 5 um Cellulose-4, 2.12*25 cm, 5 μm, Mobile Phase, MeOH and EtOH (50% Phase B in 23 min), Detector, UV 254 nm. The fraction at 7 min was freezing dried, this resulted in 110 mg of (R)—N-(tert-butyl)-2-((2-(4-(2-hydroxybutoxy)pyridin-2-yl)-6,7-dihydro-5H-cyclopenta[d]pyrimidin-4-yl)(methyl)amino)acetamide (Compound 393) and The fraction at 16 min, 120 mg (S)—N-(tert-butyl)-2-((2-(4-(2-hydroxybutoxy)pyridin-2-yl)-6,7-dihydro-5H-cyclopenta[d]pyrimidin-4-yl)(methyl)amino)acetamide (Compound 394) as a white solid.

Compound 393: Analytical chiral HPLC conditions: Column, Lux-cellulose-4, 100*4.6 mm, 3 um; mobile phase A, Ethanol; mobile phase B, Methanol; Flow rate: 1 mL/min; Gradient: 50% B in 6 min; 254 nm. Retention time: 2.239 min. LCMS (ES)[M+1]$^+$ m/z: 428. $^1$H NMR (300 MHz, DMSO-d$_6$) δ 8.48 (d, J=5.7 Hz, 1H), 7.84 (d, J=2.4 Hz, 1H), 7.67 (s, 1H), 7.07 (dd, J=5.7, 2.4 Hz, 1H), 4.90 (d, J=5.1 Hz, 1H), 4.13 (s, 2H), 4.00 (d, J=5.4 Hz, 2H), 3.77-3.71 (m, 1H), 3.26 (s, 3H), 3.14 (t, J=7.2 Hz, 2H), 2.84 (t, J=7.8 Hz, 2H), 2.04-1.94 (m, 2H), 1.66-1.40 (m, 2H), 1.25 (s, 9H), 0.96 (t, J=7.5 Hz, 3H).

Compound 394: Analytical chiral HPLC conditions: Column, Lux-cellulose-4, 100*4.6 mm, 3 um; mobile phase A, Ethanol; mobile phase B, Methanol; Flow rate: 1 mL/min; Gradient: 50% B in 6 min; 254 nm. Retention time: 4.139 min. LCMS (ES)[M+1]$^+$ m/z: 428. $^1$H NMR (300 MHz, DMSO-d$_6$) δ 8.48 (d, J=5.7 Hz, 1H), 7.84 (d, J=2.4 Hz, 1H), 7.67 (s, 1H), 7.07 (dd, J=5.7, 2.4 Hz, 1H), 4.90 (d, J=5.1 Hz, 1H), 4.13 (s, 2H), 4.00 (d, J=5.4 Hz, 2H), 3.77-3.71 (m, 1H), 3.26 (s, 3H), 3.14 (t, J=7.2 Hz, 2H), 2.84 (t, J=7.8 Hz, 2H), 2.04-1.94 (m, 2H), 1.66-1.40 (m, 2H), 1.25 (s, 9H), 0.96 (t, J=7.5 Hz, 3H).

Example 1.401

Synthesis of N-tert-butyl-2-({2-[4-(2-ethyl-2-hydroxybutoxy)pyridin-2-yl]-5H,6H,7H-cyclopenta[d]pyrimidin-4-yl}(methyl)amino)acetamide (Compound 395)

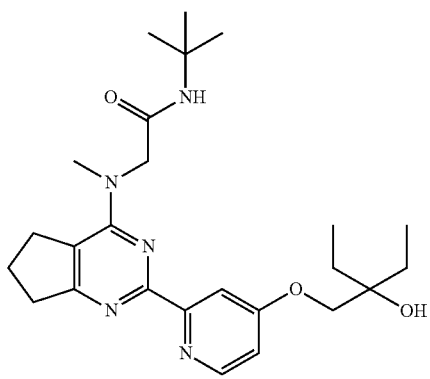 [SMILES: CCC(O)(CC)COc1ccnc(-c2nc3c(c(N(C)CC(=O)NC(C)(C)C)n2)CCC3)c1]

Compound 395 was synthesized similar to Compound 174 by replacing 2-methyl-2-((tetrahydro-2H-pyran-2-yl)oxy)propan-1-ol with 2-ethyl-2-(oxan-2-yloxy)butan-1-ol. LCMS (ES) [M+1]$^+$ m/z: 456. $^1$H NMR (300 MHz, DMSO-d6) δ 8.47 (d, J=5.6 Hz, 1H), 7.81 (d, J=2.5 Hz, 1H), 7.67 (s, 1H), 7.06 (dd, J=5.7, 2.6 Hz, 1H), 4.41 (s, 1H), 4.13 (s, 2H), 3.87 (s, 2H), 3.26 (s, 3H), 3.14 (t, J=7.3 Hz, 2H), 2.81 (t, J=7.9 Hz, 2H), 2.07-1.88 (m, 2H), 1.61-1.50 (m, 4H), 1.25 (s, 9H), 0.85 (t, J=7.4 Hz, 6H).

Example 1.402

Synthesis of N-tert-butyl-2-[(2-{4-[(1-hydroxycyclohexyl)methoxy]pyridin-2-yl}-5H,6H,7H-cyclopenta[d]pyrimidin-4-yl)(methyl)amino]acetamide (Compound 396)

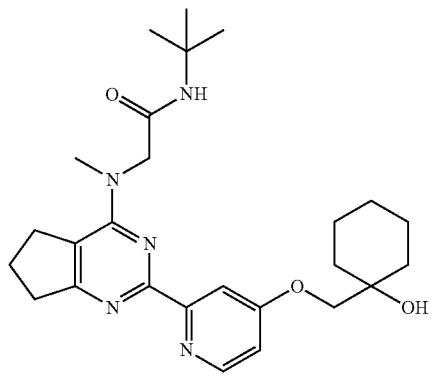 [SMILES: CN(CC(=O)NC(C)(C)C)c1nc(-c2cc(OCC3(O)CCCCC3)ccn2)nc2c1CCC2]

Compound 396 was synthesized similar to Compound 174 by replacing 2-methyl-2-((tetrahydro-2H-pyran-2-yl)oxy)propan-1-ol with 1-(hydroxymethyl)cyclohexan-1-ol. LCMS (ES) [M+1]$^+$ m/z: 468. $^1$H NMR (300 MHz, DMSO-d6) δ 8.47 (d, J=5.6 Hz, 1H), 7.82 (d, J=2.5 Hz, 1H), 7.68 (s, 1H), 7.06 (dd, J=5.8, 2.5 Hz, 1H), 4.43 (s, 1H), 4.14 (s, 2H), 3.87 (s, 2H), 3.27 (s, 3H), 3.15 (t, J=7.2 Hz, 2H), 2.82 (t, J=7.8 Hz, 2H), 2.05-1.97 (m, 2H), 1.86-1.33 (m, 9H), 1.25 (s, 9H), 1.25-1.15 (m, 1H).

Example 1.403

Synthesis of 2-({2-[4-(2-hydroxy-2-methylpropoxy)pyridin-2-yl]-5H,6H,7H-cyclopenta[d]pyrimidin-4-yl}(methyl)amino)-N-[(1R,2S)-2-hydroxycyclopentyl]acetamide (Compound 397)

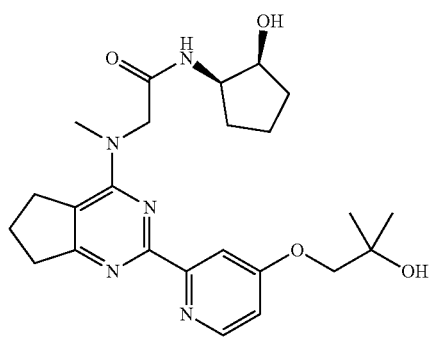 [SMILES: CN(CC(=O)N[C@@H]1CCC[C@@H]1O)c1nc(-c2cc(OCC(C)(C)O)ccn2)nc2c1CCC2]

Compound 397 was synthesized similar to 210 by replacing 5-amino-2-methoxypyridine with (1S,2R)-2-aminocyclopentan-1-ol. Analytical chiral HPLC conditions: Column, (S,S)-WHELK-O1, 100*4.6 mm, 3 um; mobile phase A, n-Hexane; mobile phase B, ethanol; Flow rate: 1 mL/min; Gradient: 50% B in 10 min; 254 nm. Retention time: 3.293 min. LCMS (ES) [M+1]+ m/z: 456. $^1$H NMR (300 MHz, DMSO-d6) δ 8.46 (d, J=5.6 Hz, 1H), 7.79 (d, J=2.5 Hz, 1H), 7.69 (d, J=7.8 Hz, 1H), 7.04 (dd, J=5.6, 2.6 Hz, 1H), 4.72 (s, 2H), 4.31 (d, J=16.6 Hz, 1H), 4.20 (d, J=16.7 Hz, 1H), 3.94-3.87 (m, 4H), 3.26 (s, 3H), 3.14 (t, J=7.6 Hz, 2H), 2.82 (t, J=7.9 Hz, 2H), 2.01-1.96 (m, 2H), 1.81-1.63 (m, 3H), 1.58-1.39 (m, 3H), 1.23 (s, 6H).

Example 1.404

Synthesis of N-cyclopropyl-2-({2-[4-(2-hydroxy-2-methylpropoxy)pyridin-2-yl]-5H,6H,7H-cyclopenta[d]pyrimidin-4-yl}(methyl)amino)acetamide (Compound 398)

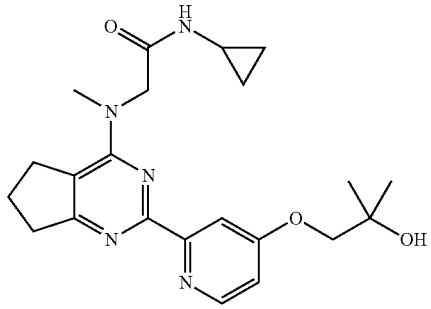 [SMILES: CN(CC(=O)NC1CC1)c1nc(-c2cc(OCC(C)(C)O)ccn2)nc2c1CCC2]

Compound 398 was synthesized similar to 389 by replacing propane-2-amine with cyclopropylamine. LCMS (ES) [M+1]+ m/z: 412. $^1$H NMR (300 MHz, DMSO-d6) δ 8.47 (d, J=5.6 Hz, 1H), 8.25 (d, J=4.1 Hz, 1H), 7.79 (d, J=2.5 Hz, 1H), 7.04 (dd, J=5.7, 2.5 Hz, 1H), 4.70 (s, 1H), 4.14 (s, 2H), 3.87 (s, 2H), 3.27 (s, 3H), 3.15 (t, J=7.3 Hz, 2H), 2.82 (t, J=7.8 Hz, 2H), 2.63 (dq, J=7.4, 3.8 Hz, 1H), 2.04-1.95 (m, 2H), 1.24 (s, 6H), 0.69-0.46 (m, 2H), 0.45-0.39 (m, 2H).

Example 1.405

Synthesis of 2-({2-[4-(2-hydroxy-2-methylpropoxy)pyridin-2-yl]-5H,6H,7H-cyclopenta[d]pyrimidin-4-yl}(methyl)amino)-1-(morpholin-4-yl)ethan-1-oneide (Compound 399)

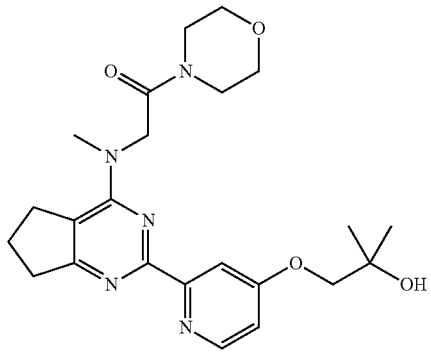 [SMILES: CN(CC(=O)N1CCOCC1)c1nc(-c2cc(OCC(C)(C)O)ccn2)nc2c1CCC2]

Compound 399 was synthesized similar to 389 by replacing propane-2-amine with morpholine. LCMS (ES) [M+1]+ m/z: 442. $^1$H NMR (300 MHz, DMSO-d6) δ 8.46 (d, J=5.6 Hz, 1H), 7.75 (d, J=2.5 Hz, 1H), 7.04 (dd, J=5.6, 2.6 Hz, 1H), 4.70 (s, 1H), 4.52 (s, 2H), 3.86 (d, J=4.8 Hz, 2H), 3.72-3.41 (m, 8H), 3.28 (s, 3H), 3.16 (t, J=7.3 Hz, 2H), 2.81 (t, J=7.9 Hz, 2H), 2.11-1.91 (m, 2H), 1.24 (s, 6H).

Example 1.406

Synthesis of N-tert-butyl-2-[(2-{4-[2-(diethylamino)ethoxy]pyridin-2-yl}-5H,6H,7H-cyclopenta[d]pyrimidin-4-yl)(methyl)amino]acetamide (Compound 400)

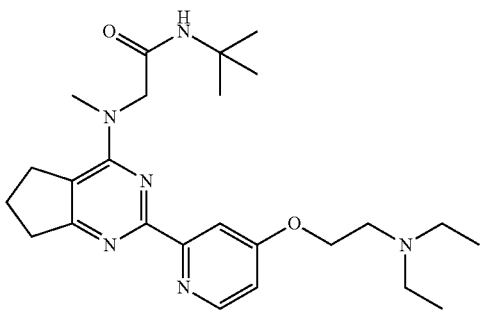 [SMILES: CCN(CC)CCOc1ccnc(-c2nc3c(c(N(C)CC(=O)NC(C)(C)C)n2)CCC3)c1]

Compound 400 was synthesized similar to Compound 348 by replacing Dimethylaminoethanol with Diethylaminoethanol. LCMS (ES) [M+1]+ m/z: 455. $^1$H NMR (300 MHz, DMSO-d6) δ 8.47 (d, J=5.6 Hz, 1H), 7.83 (d, J=2.5 Hz, 1H), 7.67 (s, 1H), 7.05 (dd, J=5.6, 2.6 Hz, 1H), 4.16 (t, J=6.1 Hz, 2H), 4.13 (s, 2H), 3.26 (s, 3H), 3.15 (t, J=7.3 Hz, 2H), 2.87-2.76 (m, 4H), 2.63-2.52 (m, 4H), 2.02-1.99 (m, 2H), 1.25 (s, 9H), 0.98 (t, J=7.1 Hz, 6H).

Example 1.407

Synthesis of N-tert-butyl-2-[methyl(2-{4-[2-(pyrrolidin-1-yl)ethoxy]pyridin-2-yl}-5H,6H,7H-cyclopenta[d]pyrimidin-4-yl)amino]acetamide (Compound 401)

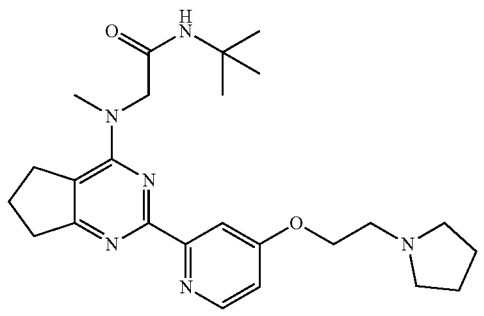 [SMILES: CN(CC(=O)NC(C)(C)C)c1nc(-c2cc(OCCN3CCCC3)ccn2)nc2c1CCC2]

Compound 401 was synthesized similar to Compound 348 by replacing Dimethylaminoethanol with hydroxyethylpyrrolidine. LCMS (ES) [M+1]+ m/z: 454. $^1$H NMR (300 MHz, DMSO-d6) δ 8.47 (d, J=5.6 Hz, 1H), 7.84 (d, J=2.5 Hz, 1H), 7.69 (s, 1H), 7.05 (dd, J=5.6, 2.6 Hz, 1H), 4.21 (t, J=5.8 Hz, 2H), 4.13 (s, 2H), 3.27 (s, 3H), 3.14 (t, J=7.3

2H), 2.85-2.78 (m, 4H), 2.62-2.43 (m, 4H), 2.04-1.94 (m, 2H), 1.77-1.61 (m, 4H), 1.25 (s, 9H).

Example 1.408

Synthesis of N-tert-butyl-2-{[2-(4-{[(2S)-1-(dimethylamino)propan-2-yl]oxy}pyridin-2-yl)-5H,6H,7H-cyclopenta[d]pyrimidin-4-yl](methyl)amino}acetamide (Compound 402)

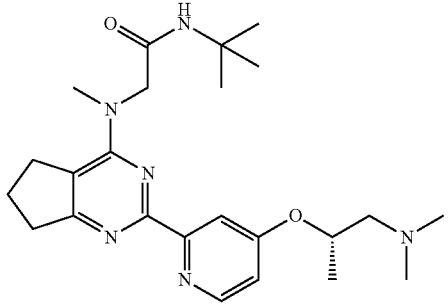 [SMILES: C[C@@H](CN(C)C)Oc1ccnc(-c2nc3c(c(N(C)CC(=O)NC(C)(C)C)n2)CCC3)c1]

Compound 402 was synthesized similar to Compound 348 by replacing Dimethylaminoethanol with (S)-1-(dimethylamino)propan-2-ol. LCMS (ES) [M+1]$^+$ m/z: 441. $^1$H NMR (300 MHz, DMSO-d6) δ 8.45 (d, J=5.6 Hz, 1H), 7.82 (d, J=2.6 Hz, 1H), 7.68 (s, 1H), 7.07 (dd, J=5.7, 2.6 Hz, 1H), 4.83-4.77 (m, 1H), 4.11 (s, 2H), 3.26 (s, 3H), 3.14 (t, J=7.3 Hz, 2H), 2.81 (t, J=7.8 Hz, 2H), 2.59-2.52 (m, 1H), 2.39 (dd, J=12.8, 5.5 Hz, 1H), 2.21 (s, 6H), 2.04-1.97 (m, 2H), 1.28 (d, J=6.1 Hz, 3H), 1.25 (s, 9H).

Example 1.409

Synthesis of 2-{[2-(4-{[(tert-butylcarbamoyl)methyl](methyl)amino}-5H,6H,7H-cyclopenta[d]pyrimidin-2-yl)pyridin-4-yl]oxy}-N,N-dimethylacetamide (Compound 403)

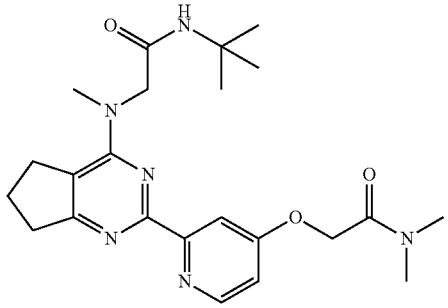 [SMILES: CN(C)C(=O)COc1ccnc(-c2nc3c(c(N(C)CC(=O)NC(C)(C)C)n2)CCC3)c1]

Compound 403 was synthesized similar to Compound 348 by replacing Dimethylaminoethanol with 2-hydroxy-N,N-dimethylacetamide. LCMS (ES) [M+1]$^+$ m/z: 441. $^1$H NMR (300 MHz, DMSO-d6) δ 8.45 (d, J=5.6 Hz, 1H), 7.83 (d, J=2.6 Hz, 1H), 7.66 (s, 1H), 6.98 (dd, J=5.7, 2.6 Hz, 1H), 5.00 (s, 2H), 4.13 (s, 2H), 3.25 (s, 3H), 3.12 (t, J=7.3 Hz, 2H), 3.01 (s, 3H), 2.85 (s, 3H), 2.81 (t, J=7.8 Hz, 2H), 2.01-1.96 (m, 2H), 1.24 (s, 9H).

Example 1.410

Synthesis of N-tert-butyl-2-[(2-{4-[2-(dimethylamino)-2-methylpropoxy]pyridin-2-yl}-5H,6H,7H-cyclopenta[d]pyrimidin-4-yl)(methyl)amino]acetamide (Compound 404)

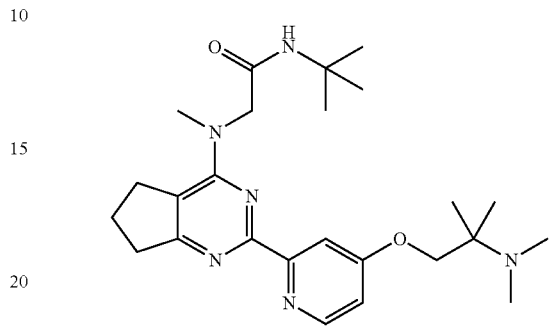

Compound 404 was synthesized similar to Compound 348 by replacing Dimethylaminoethanol with 2-(dimethylamino)-2-methylpropan-1-ol. LCMS (ES) [M+1]$^+$ m/z: 455. $^1$H NMR (300 MHz, DMSO-d6) δ 8.49 (d, J=5.6 Hz, 1H), 8.20 (s, 2H), 7.83 (d, J=2.5 Hz, 1H), 7.67 (s, 1H), 7.09 (dd, J=5.6, 2.5 Hz, 1H), 4.14 (s, 2H), 4.05 (s, 2H), 3.26 (s, 3H), 3.15 (t, J=7.2 Hz, 2H), 2.81 (t, J=7.8 Hz, 2H), 2.36 (s, 6H), 2.04-1.97 (m, 2H), 1.25 (s, 9H), 1.19 (s, 6H).

Example 1.411

Synthesis of N-tert-butyl-2-[(2-{4-[(4-hydroxyoxan-4-yl)methoxy]pyridin-2-yl}-5H,6H,7H-cyclopenta[d]pyrimidin-4-yl)(methyl)amino]acetamide (Compound 405)

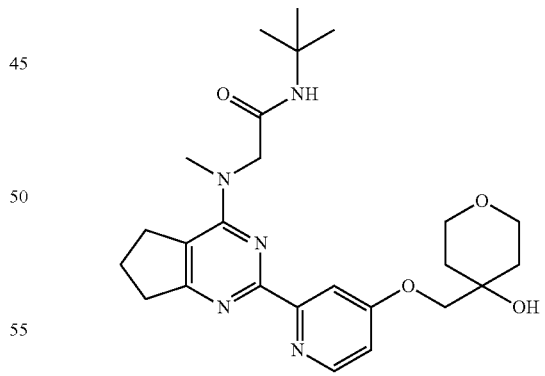

Compound 405 was synthesized similar to Compound 174 by replacing 2-methyl-2-((tetrahydro-2H-pyran-2-yl)oxy)propan-1-ol with 4-(hydroxymethyl)tetrahydro-2H-pyran-4-ol. LCMS (ES) [M+1]$^+$ m/z: 470. $^1$H NMR (300 MHz, DMSO-d6) δ 8.48 (d, J=5.6 Hz, 1H), 7.84 (d, J=2.6 Hz, 1H), 7.67 (s, 1H), 7.06 (dd, J=5.6, 2.6 Hz, 1H), 4.77 (s, 1H), 4.14 (s, 2H), 3.92 (s, 2H), 3.76-3.63 (m, 4H), 3.26 (s, 3H), 3.15 (t, J=7.3 Hz, 2H), 2.82 (t, J=7.8 Hz, 2H), 2.02-1.93 (m, 2H), 1.86-1.70 (m, 2H), 1.57-1.43 (m, 2H), 1.25 (s, 9H).

Example 1.412

Synthesis of N-tert-butyl-2-{[2-(4-{[(2R)-1-(dimethylamino)propan-2-yl]oxy}pyridin-2-yl)-5H,6H,7H-cyclopenta[d]pyrimidin-4-yl](methyl)amino}acetamide (Compound 406)

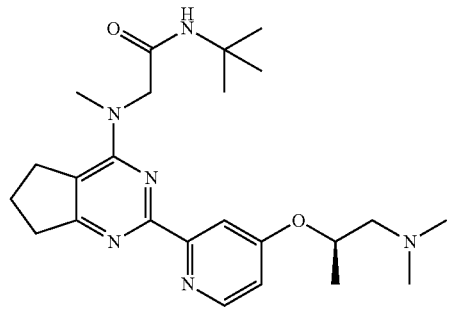 [SMILES: C[C@H](CN(C)C)Oc1ccnc(-c2nc3c(c(N(C)CC(=O)NC(C)(C)C)n2)CCC3)c1]

Compound 406 was synthesized similar to Compound 348 by replacing Dimethylaminoethanol with (R)-1-(dimethylamino)propan-2-ol. LCMS (ES) [M+1]⁺ m/z: 441. ¹H NMR (300 MHz, DMSO-d6) δ 8.47 (d, J=5.7 Hz, 1H), 7.82 (d, J=2.4 Hz, 1H), 7.67 (s, 1H), 7.09 (dd, J=5.7, 2.7 Hz, 1H), 4.84-4.78 (m, 1H), 4.12 (s, 2H), 3.27 (s, 3H), 3.15 (t, J=7.2 Hz, 2H), 2.84 (t, J=7.8 Hz, 2H), 2.61-2.55 (m, 1H), 2.46-2.40 (m, 1H), 2.23 (s, 6H), 2.04-1.94 (m, 2H), 1.30 (d, J=6.0 Hz, 3H), 1.26 (s, 9H).

Example 1.413

Synthesis of N-tert-butyl-2-{[2-(4-{[1-(dimethylamino)-2-methylpropan-2-yl]oxy}pyridin-2-yl)-5H,6H,7H-cyclopenta[d]pyrimidin-4-yl](methyl)amino}acetamide (Compound 407)

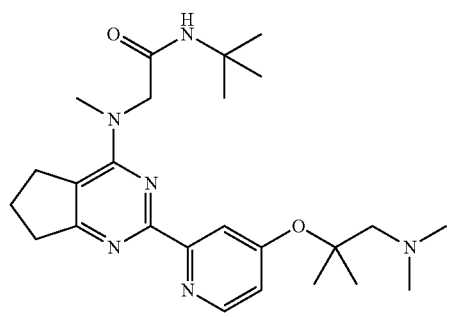 [SMILES: CN(C)CC(C)(C)Oc1ccnc(-c2nc3c(c(N(C)CC(=O)NC(C)(C)C)n2)CCC3)c1]

Compound 407 was synthesized similar to Compound 348 by replacing Dimethylaminoethanol with 1-(dimethylamino)-2-methylpropan-2-ol. LCMS (ES) [M+1]⁺ m/z: 455. ¹H NMR (300 MHz, DMSO-d6) δ 8.44 (d, J=5.5 Hz, 1H), 7.82 (d, J=2.6 Hz, 1H), 7.63 (s, 1H), 7.09 (dt, J=5.0, 2.1 Hz, 1H), 4.15 (s, 2H), 3.24 (s, 3H), 3.13 (t, J=7.4 Hz, 2H), 2.81 (t, J=7.8 Hz, 2H), 2.58 (s, 2H), 2.28 (s, 6H), 2.02-1.96 (m, 2H), 1.44 (s, 6H), 1.26 (d, J=1.6 Hz, 9H).

Example 1.414

Synthesis of (2R)—N-tert-butyl-2-[(2-{4-[2-(dimethylamino)ethoxy]pyridin-2-yl}-5H,6H,7H-cyclopenta[d]pyrimidin-4-yl)(methyl)amino]propanamide (Compound 408)

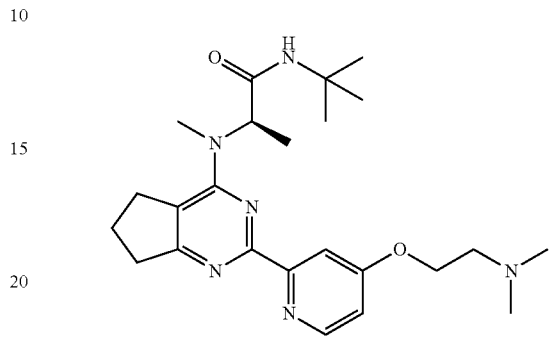

Scheme 129

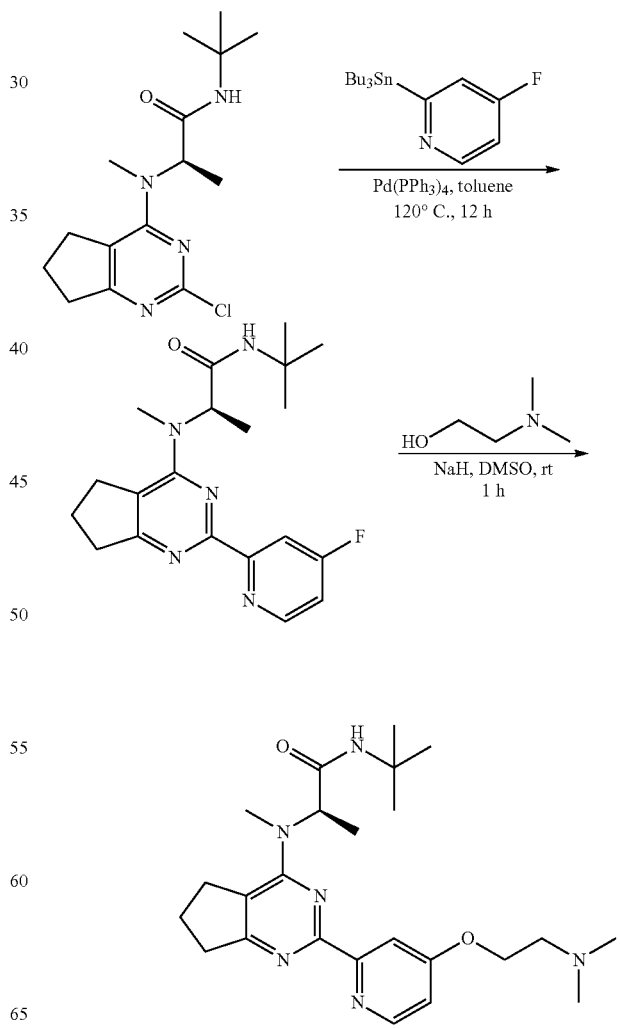

Step 1

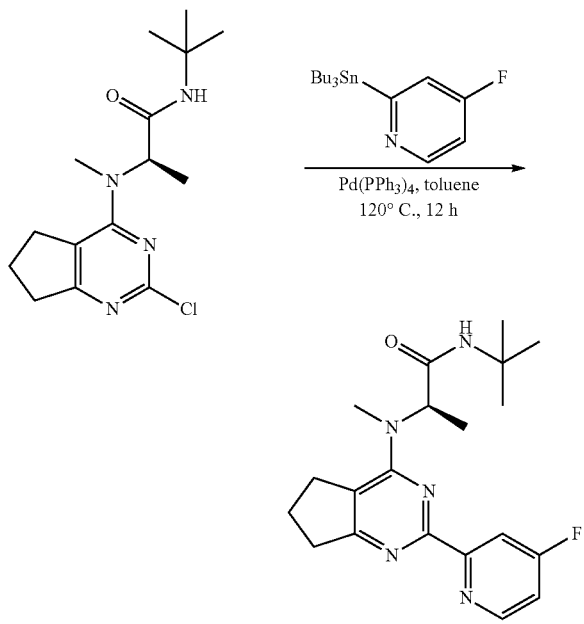

Into a 40 mL vial were added (2R)—N-tert-butyl-2-({2-chloro-5H,6H,7H-cyclopenta[d]pyrimidin-4-yl}(methyl)amino)propanamide (330 mg, 1.06 mmol, 1.00 equiv) and toluene (20 mL), 4-fluoro-2-(tributylstannyl)pyridine (615 mg, 1.59 mmol, 1.50 equiv), Pd(PPh₃)₄ (123 mg, 0.10 mmol, 0.10 equiv). The resulting mixture was stirred for 12 h at 120° C. under nitrogen atmosphere. The resulting mixture was concentrated under vacuum. The residue was purified by silica gel column chromatography, eluted with CH₂Cl₂/MeOH (10:1) to afford (2R)—N-tert-butyl-2-{[2-(4-fluoro-pyridin-2-yl)-5H,6H,7H-cyclopenta[d]pyrimidin-4-yl](methyl)amino}propanamide (240 mg, 61%) as a brown solid. LCMS (ES) [M+1]⁺ m/z: 372.

Step 2

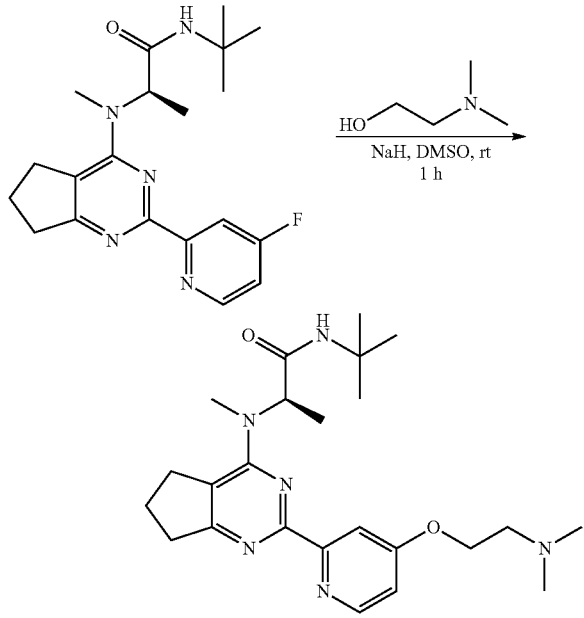

Into a 20 mL vial were added dimethylaminoethanol (115 mg, 1.29 mmol, 2.00 equiv) and DMSO (3 mL), To the above mixture was added NaH (60% in mineral oil) (52 mg, 1.29 mmol, 2.00 equiv) in portions. The resulting mixture was stirred for 0.5 h at room temperature. To the above mixture was added (2R)—N-tert-butyl-2-{[2-(4-fluoropyridin-2-yl)-5H,6H,7H-cyclopenta[d]pyrimidin-4-yl](methyl)amino}propanamide (240 mg, 0.64 mmol, 1.00 equiv) in portions. The resulting mixture was stirred for additional 1 h at room temperature. The reaction was quenched with water (1 mL) and purified by Prep-HPLC with the following conditions: Sunfire Prep C18 OBD Column, 50*250 mm, 5 μm, 10 nm, mobile phase, water (0.1% NH₄OH) and CH₃CN (5% CH₃CN up to 25% in 15 min), Detector, 254 nm UV) to afford (2R)—N-tert-butyl-2-[(2-{4-[2-(dimethylamino)ethoxy]pyridin-2-yl}-5H,6H,7H-cyclopenta[d]pyrimidin-4-yl)(methyl)amino]propanamide (112.8 mg, 40%) as a white solid. LCMS (ES) [M+1]⁺ m/z: 441. ¹H NMR (300 MHz, DMSO-d6) δ 8.49 (d, J=5.6 Hz, 1H), 7.89 (d, J=2.5 Hz, 1H), 7.80 (s, 1H), 7.06 (dd, J=5.7, 2.6 Hz, 1H), 5.06 (q, J=7.0 Hz, 1H), 4.21 (t, J=5.7 Hz, 2H), 3.22 (dt, J=15.6, 7.8 Hz, 1H), 3.12 (s, 3H), 3.13-2.99 (m, 1H), 2.97-2.72 (m, 2H), 2.66 (t, J=5.7 Hz, 2H), 2.23 (s, 6H), 2.06-1.97 (m, 2H), 1.32 (d, J=7.0 Hz, 3H), 1.20 (s, 9H).

Example 1.415

Synthesis of N-tert-butyl-2-({2-[4-(2-hydroxy-2-methylpropoxy)pyridin-2-yl]-5H,6H,7H-cyclopenta[d]pyrimidin-4-yl}amino)acetamide (Compound 409)

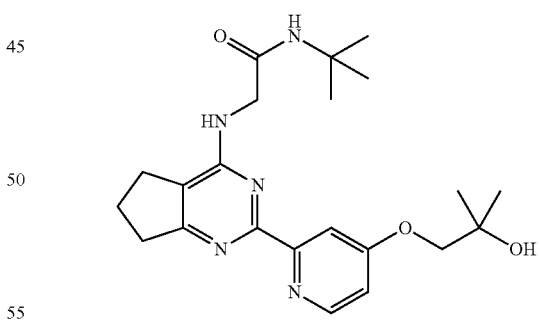

Compound 409 was synthesized similar to Compound 174 by replacing N-(tert-butyl)-2-(methylamino)acetamide with tert-butyl 2-aminoacetate. LCMS (ES) [M+1]⁺ m/z: 414. ¹H NMR (300 MHz, DMSO-d6) δ 8.46 (d, J=5.6 Hz, 1H), 7.84 (d, J=2.5 Hz, 1H), 7.69 (s, 1H), 7.14 (t, J=5.9 Hz, 1H), 7.04 (dd, J=5.6, 2.6 Hz, 1H), 4.70 (s, 1H), 3.94 (d, J=5.8 Hz, 2H), 3.86 (s, 2H), 2.84 (t, J=7.7 Hz, 2H), 2.74 (t, J=7.4 Hz, 2H), 2.09-2.05 (m, 2H), 1.25 (s, 9H), 1.24 (s, 6H).

Example 1.416

Synthesis of N-(1-cyclopropyl-1H-pyrazol-4-yl)-2-[(2-{4-[2-(dimethylamino)ethoxy]pyridin-2-yl}-5H,6H,7H-cyclopenta[d]pyrimidin-4-yl)(methyl)amino]acetamide (Compound 410)

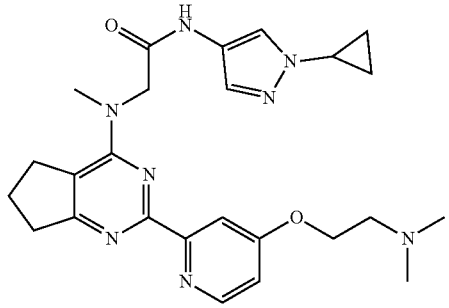 [SMILES: CN(C)CCOc1ccnc(-c2nc3c(c(N(C)CC(=O)Nc4cnn(C5CC5)c4)n2)CCC3)c1]

Compound 410 was synthesized similar to Compound 348 by replacing tert-butylamine with 1-cyclopropyl-1H-pyrazol-4-amine. LCMS (ES) [M+1]$^+$ m/z: 477. $^1$H NMR (300 MHz, DMSO-d6) δ 10.24 (s, 1H), 8.46 (d, J=5.6 Hz, 1H), 7.88 (s, 1H), 7.76 (d, J=2.6 Hz, 1H), 7.39 (s, 1H), 7.02 (dd, J=5.7, 2.5 Hz, 1H), 4.34 (s, 2H), 4.11 (t, J=5.5 Hz, 2H), 3.64 (tt, J=7.2, 4.0 Hz, 1H), 3.32 (s, 3H), 3.19 (t, J=7.3 Hz, 2H), 2.83 (t, J=7.8 Hz, 2H), 2.60 (t, J=5.5 Hz, 2H), 2.21 (s, 6H), 2.05-1.95 (m, 2H), 1.02-0.83 (m, 4H).

Example 1.417

Synthesis of N-tert-butyl-2-{methyl[2-(4-{[(2R)-1-methylpyrrolidin-2-yl]methoxy}pyridin-2-yl)-5H,6H,7H-cyclopenta[d]pyrimidin-4-yl]amino}acetamide (Compound 411)

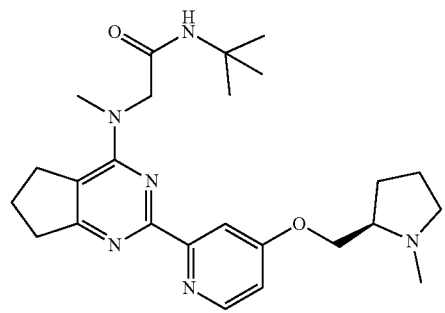 [SMILES: CN(CC(=O)NC(C)(C)C)c1nc(-c2cc(OC[C@H]3CCCN3C)ccn2)nc2c1CCC2]

Compound 411 was synthesized similar to Compound 348 by replacing dimethylaminoethanol with (R)-(1-methylpyrrolidin-2-yl)methanol. LCMS (ES) [M+1]$^+$ m/z: 453. $^1$H NMR (300 MHz, DMSO-d6) δ 8.47 (d, J=5.6 Hz, 1H), 7.82 (d, J=2.4 Hz, 1H), 7.65 (s, 1H), 7.05 (dd, J=5.6, 2.4 Hz, 1H), 4.15-4.11 (m, 3H), 4.01-3.96 (m, 1H), 3.26 (s, 3H), 3.16 (t, J=7.2 Hz, 2H), 2.99-2.96 (m, 1H), 2.83 (t, J=7.6 Hz, 2H), 2.67-2.65 (m, 1H), 2.40 (s, 3H), 2.26-2.24 (m, 1H), 2.02-1.95 (m, 3H), 1.75-1.63 (m, 3H), 1.24 (s, 9H).

Example 1.418

Synthesis of N-tert-butyl-2-{methyl[2-(4-{[(2S)-1-methylpyrrolidin-2-yl]methoxy}pyridin-2-yl)-5H,6H,7H-cyclopenta[d]pyrimidin-4-yl]amino}acetamide (Compound 412)

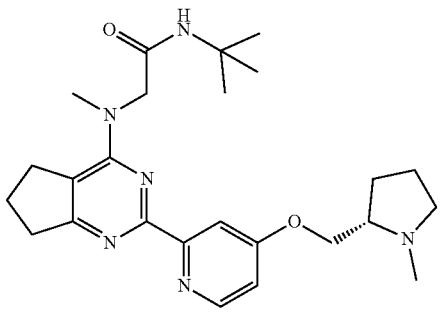 [SMILES: CN(CC(=O)NC(C)(C)C)c1nc(-c2cc(OC[C@@H]3CCCN3C)ccn2)nc2c1CCC2]

Compound 412 was synthesized similar to Compound 348 by replacing dimethylaminoethanol with (S)-(1-methylpyrrolidin-2-yl)methanol. LCMS (ES) [M+1]$^+$ m/z: 453. $^1$H NMR (300 MHz, DMSO-d6) δ 8.47 (d, J=5.4 Hz, 1H), 7.82 (d, J=2.4 Hz, 1H), 7.67 (s, 1H), 7.05 (dd, J=5.7, 2.4 Hz, 1H), 4.16-4.11 (m, 3H), 4.01-3.97 (m, 1H), 3.26 (s, 3H), 3.16 (t, J=7.2 Hz, 2H), 2.99-2.96 (m, 1H), 2.83 (t, J=7.5 Hz, 2H), 2.67-2.65 (m, 1H), 2.40 (s, 3H), 2.26-2.24 (m, 1H), 2.02-1.95 (m, 3H), 1.75-1.63 (m, 3H), 1.24 (s, 9H).

Example 1.419

Synthesis of N-tert-butyl-2-[(2-{4-[2-(dimethylamino)ethoxy]pyridin-2-yl}-5,5-dimethyl-5H,6H,7H-cyclopenta[d]pyrimidin-4-yl)(methyl)amino]acetamide (Compound 413)

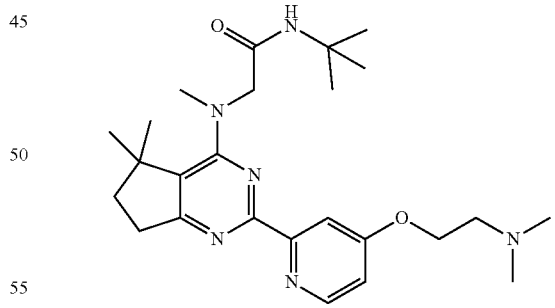

Compound 413 was synthesized similar to Compound 331 by replacing 2-(methylamino)-N-(6-methylpyridin-3-yl)acetamide with N-tert-butyl-2-(methylamino)acetamide hydrochloride and by replacing ethane-1,2-diol with dimethylaminoethanol. LCMS (ES) [M+1]$^+$ m/z: 455. $^1$H NMR (300 MHz, DMSO-d6) δ 8.48 (d, J=5.6 Hz, 1H), 7.85 (d, J=2.6 Hz, 1H), 7.66 (s, 1H), 7.07 (dd, J=5.6, 2.6 Hz, 1H), 4.20 (t, J=5.7 Hz, 2H), 4.03 (s, 2H), 3.19 (s, 3H), 2.86 (t, J=7.3 Hz, 2H), 2.66 (t, J=5.7 Hz, 2H), 2.23 (s, 6H), 1.87 (t, J=7.3 Hz, 2H), 1.43 (s, 6H), 1.22 (s, 9H).

Example 1.420

Synthesis of N-tert-butyl-2-{[2-(4-{[(4R)-2,2-dimethyl-1,3-dioxolan-4-yl]methoxy}pyridin-2-yl)-5H,6H,7H-cyclopenta[d]pyrimidin-4-yl](methyl)amino}acetamide (Compound 414)

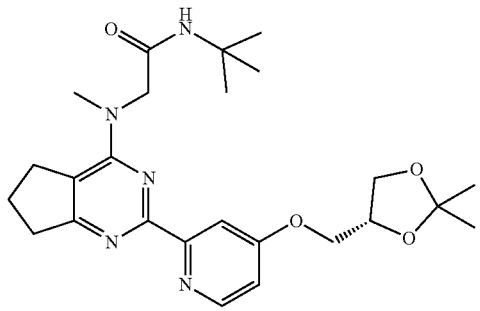 [SMILES: CN(CC(=O)NC(C)(C)C)c1nc(-c2cc(OC[C@@H]3COC(C)(C)O3)ccn2)nc2c1CCC2]

Compound 414 was synthesized similar to Compound 34 by replacing 4-methoxy-2-(trimethylstannyl)pyridine with 4-{[(4S)-2,2-dimethyl-1,3-dioxolan-4-yl]methoxy}-2-(tributylstannyl)pyridine. LCMS (ES) [M+1]⁺ m/z: 470.2. ¹H NMR (400 MHz, DMSO-d6) δ 8.50-8.47 (m, 1H), 7.87-7.85 (m, 1H), 7.69 (s, 1H), 7.08 (dd, J=5.6, 2.6 Hz, 1H), 4.48-4.40 (m, 1H), 4.23-4.17 (m, 1H), 4.15-4.06 (m, 4H), 3.79 (dd, J=8.4, 6.4 Hz, 1H), 3.27 (s, 3H), 3.14 (t, J=7.3 Hz, 2H), 2.81 (t, J=7.8 Hz, 2H), 2.03-1.95 (m, 2H), 1.37-1.35 (m, 3H), 1.32-1.30 (m, 3H), 1.24 (s, 9H).

Example 1.421

Synthesis of N-tert-butyl-2-[(2-{4-[(2R)-2,3-dihydroxypropoxy]pyridin-2-yl}-5H,6H,7H-cyclopenta[d]pyrimidin-4-yl)(methyl)amino]acetamidede (Compound 415)

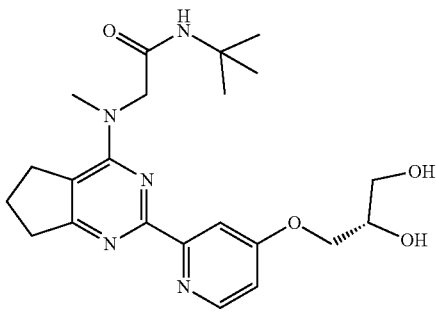 [SMILES: CN(CC(=O)NC(C)(C)C)c1nc(-c2cc(OC[C@@H](O)CO)ccn2)nc2c1CCC2]

Scheme 130

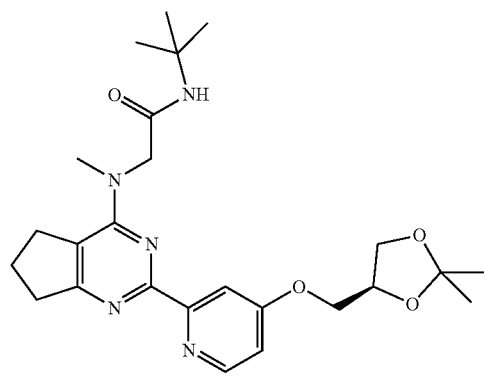

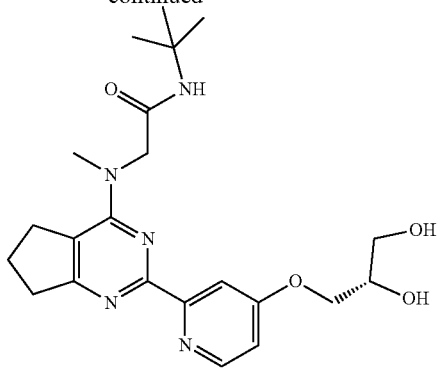

To a solution of N-Tert-butyl-2-{[2-(4-{[(4S)-2,2-dimethyl-1,3-dioxolan-4-yl]methoxy}pyridin-2-yl)-5H,6H,7H-cyclopenta[d]pyrimidin-4-yl](methyl)amino}acetamide (44 mg; 0.09 mmol; 1 eq.) in methanol (1 ml) was added HCl (1 ml of 5-6 M HCl in isopropanol). After stirred at 25° C. for 1 h, the mixture was concentrated and the residue was purified by reverse phase chromatography (Waters XSelect CSH C18 column, 0-70% acetonitrile/0.1% aqueous formic acid gradient) to give N-tert-butyl-2-[(2-{4-[(2R)-2,3-dihydroxypropoxy]pyridin-2-yl}-5H,6H,7H-cyclopenta[d]pyrimidin-4-yl)(methyl)amino]acetamide (32 mg, 80%) as a solid. LCMS (ES+): [M+H]⁺=470.2. ¹H NMR (400 MHz, DMSO-d6) δ 8.47 (d, J=5.6 Hz, 1H), 7.86-7.82 (m, 1H), 7.69 (s, 1H), 7.04 (dd, J=5.7, 2.6 Hz, 1H), 5.01 (d, J=5.1 Hz, 1H), 4.73 (s, 1H), 4.17-4.11 (m, 3H), 4.01 (dd, J=10.0, 6.0 Hz, 1H), 3.86-3.79 (m, 1H), 3.49-3.44 (m, 2H), 3.26 (s, 3H), 3.16-3.10 (m, 2H), 2.84-2.78 (m, 2H), 2.02-1.94 (m, 2H), 1.24 (s, 9H).

Example 1.422

Synthesis of N-tert-butyl-2-[methyl(2-{4-[(1-methylazetidin-3-yl)oxy]pyridin-2-yl}-5H,6H,7H-cyclopenta[d]pyrimidin-4-yl)amino]acetamide (Compound 416)

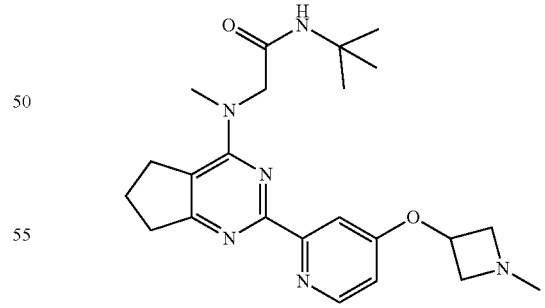

Compound 416 was synthesized similar to Compound 348 by replacing dimethylaminoethanol with 1-methylazetidin-3-ol. LCMS (ES) [M+1]⁺ m/z: 425. ¹H NMR (300 MHz, DMSO-d6) δ 8.46 (d, J=5.6 Hz, 1H), 7.78 (d, J=2.5 Hz, 1H), 7.71 (s, 1H), 6.91 (dd, J=5.6, 2.6 Hz, 1H), 4.95 (q, J=5.6 Hz, 1H), 4.12 (s, 2H), 3.83-3.72 (m, 2H), 3.26 (s, 3H), 3.14 (t, J=7.3 Hz, 2H), 3.00 (dd, J=8.0, 5.5 Hz, 2H), 2.80 (t, J=7.8 Hz, 2H), 2.30 (s, 3H), 2.03-1.96 (m, 2H), 1.26 (s, 9H).

Example 1.423

Synthesis of 2-[(2-{4-[2-(dimethylamino)ethoxy]pyridin-2-yl}-5H,6H,7H-cyclopenta[d]pyrimidin-4-yl)(methyl)amino]-1-(pyrrolidin-1-yl)ethan-1-one (Compound 417)

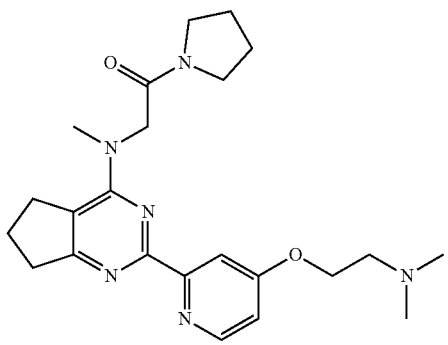 [SMILES: CN(C)CCOc1ccnc(-c2nc3c(c(N(C)CC(=O)N4CCCC4)n2)CCC3)c1]

Compound 417 was synthesized similar to Compound 348 by replacing tert-butylamine with pyrrolidine. LCMS (ES) [M+1]$^+$ m/z: 425. $^1$H NMR (300 MHz, DMSO-d6) δ 8.46 (d, J=5.6 Hz, 1H), 8.17 (s, HCOOH), 7.69 (d, J=2.6 Hz, 1H), 7.04 (dd, J=5.6, 2.6 Hz, 1H), 4.39 (s, 2H), 4.19 (t, J=5.7 Hz, 2H), 3.54 (t, J=6.8 Hz, 2H), 3.32 (t, J=6.8 Hz, 2H), 3.29 (s, 3H), 3.15 (t, J=7.3 Hz, 2H), 2.81 (t, J=7.8 Hz, 2H), 2.68 (t, J=5.6 Hz, 2H), 2.25 (s, 6H), 2.06-1.88 (m, 4H), 1.89-1.82 (m, 2H).

Example 1.424

Synthesis of 2-[(2-{4-[2-(dimethylamino)ethoxy]pyridin-2-yl}-5H,6H,7H-cyclopenta[d]pyrimidin-4-yl)(methyl)amino]-N-[1-(trifluoromethyl)cyclopropyl]acetamide (Compound 418)

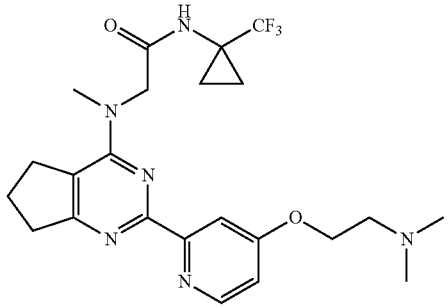 [SMILES: CN(C)CCOc1ccnc(-c2nc3c(c(N(C)CC(=O)NC4(C(F)(F)F)CC4)n2)CCC3)c1]

Compound 418 was synthesized similar to Compound 348 by replacing tert-butylamine with 1-(trifluoromethyl)cyclopropan-1-amine. LCMS (ES) [M+1]$^+$ m/z: 479. $^1$H NMR (300 MHz, DMSO-d6) δ 9.04 (s, 1H), 8.46 (d, J=5.6 Hz, 1H), 7.74 (d, J=2.5 Hz, 1H), 7.05 (dd, J=5.6, 2.6 Hz, 1H), 4.25-4.13 (m, 4H), 3.28 (s, 3H), 3.15 (t, J=7.3 Hz, 2H), 2.82 (t, J=7.9 Hz, 2H), 2.66 (t, J=5.7 Hz, 2H), 2.23 (s, 6H), 2.04-1.97 (m, 2H), 1.24-1.13 (m, 2H), 1.00-0.91 (m, 2H).

Example 1.425

Synthesis of N-tert-butyl-2-[methyl(2-{4-[2-(methylamino)ethoxy]pyridin-2-yl}-5H,6H,7H-cyclopenta[d]pyrimidin-4-yl)amino]acetamide (Compound 419)

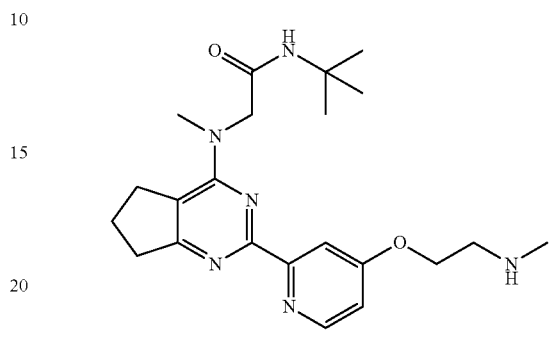

Compound 419 was synthesized similar to Compound 348 by replacing dimethylaminoethanol with tert-butyl N-(2-hydroxyethyl)-N-methylcarbamate. LCMS (ES) [M+1]$^+$ m/z: 413. $^1$H NMR (300 MHz, DMSO-d6) δ 9.36 (br, 2H), 8.76 (d, J=6.0 Hz, 1H), 8.17 (s, 1H), 8.11 (br, 1H), 7.50 (dd, J=6.1, 2.6 Hz, 1H), 4.62 (t, J=5.0 Hz, 2H), 4.42 (s, 2H), 3.45-3.36 (m, 5H), 3.23 (t, J=7.9 Hz, 2H), 3.01 (t, J=7.9 Hz, 2H), 2.68-2.61 (m, 3H), 2.14-2.03 (m, 2H), 1.25 (s, 9H).

Example 1.426

Synthesis of 2-({2-[4-(2-hydroxy-2-methylpropoxy)pyridin-2-yl]-5H,6H,7H-cyclopenta[d]pyrimidin-4-yl}(methyl)amino)-1-(pyrrolidin-1-yl)ethan-1-one (Compound 420)

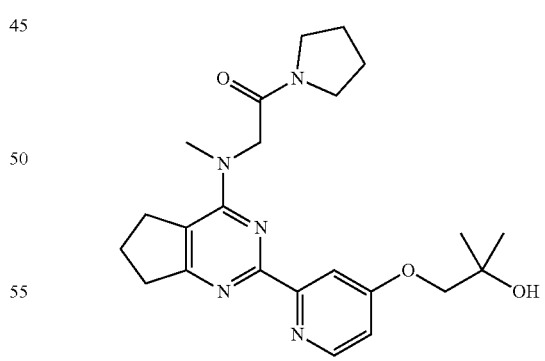

Compound 420 was synthesized similar to Compound 389 by replacing propane-2-amine with pyrrolidine. LCMS (ES) [M+1]$^+$ m/z: 426. $^1$H NMR (300 MHz, DMSO-d6) δ 8.45 (d, J=5.6 Hz, 1H), 7.71 (s, 1H), 7.06-6.99 (m, 1H), 4.70 (s, 1H), 4.40 (s, 2H), 3.85 (s, 2H), 3.56 (t, J=6.8 Hz, 2H), 3.33-3.31 (m, 2H), 3.30 (s, 3H), 3.15 (t, J=7.3 Hz, 2H), 2.81 (t, J=7.9 Hz, 2H), 1.97 (dp, J=14.0, 7.4 Hz, 4H), 1.79 (p, J=6.8 Hz, 2H), 1.22 (s, 6H).

Example 1.427

Synthesis of N-cyclopentyl-2-({2-[4-(2-hydroxy-2-methylpropoxy)pyridin-2-yl]-5H,6H,7H-cyclopenta[d]pyrimidin-4-yl}(methyl)amino)acetamide (Compound 421)

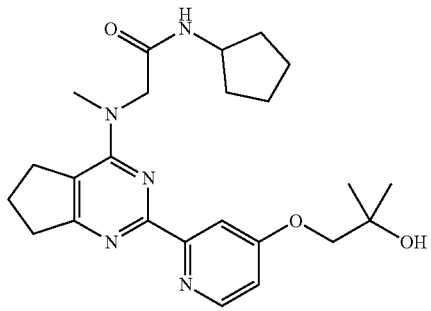 [SMILES: CN(CC(=O)NC1CCCC1)c1nc(-c2cc(OCC(C)(C)O)ccn2)nc2c1CCC2]

Compound 421 was synthesized similar to Compound 389 by replacing propane-2-amine with 1-cyclopentylamine. LCMS (ES) [M+1]⁺ m/z: 440. ¹H NMR (300 MHz, DMSO-d6) δ 8.47 (d, J=5.6 Hz, 1H), 8.28 (s, 1H), 8.09 (d, J=7.5 Hz, 1H), 7.80 (d, J=2.5 Hz, 1H), 7.05 (dd, J=5.7, 2.6 Hz, 1H), 4.17 (s, 2H), 4.06-3.95 (m, 1H), 3.87 (s, 2H), 3.27 (s, 3H), 3.15 (t, J=7.3 Hz, 2H), 2.82 (t, J=7.8 Hz, 2H), 2.02-1.95 (m, 2H), 1.77 (dq, J=13.1, 6.8, 6.2 Hz, 2H), 1.57 (tq, J=5.7, 2.8 Hz, 2H), 1.51-1.31 (m, 4H), 1.24 (s, 6H).

Example 1.428

Synthesis of 2-({2-[4-(2-hydroxy-2-methylpropoxy)pyridin-2-yl]-5H,6H,7H-cyclopenta[d]pyrimidin-4-yl}(methyl)amino)-N-[(3R)-oxolan-3-yl]acetamide (Compound 422)

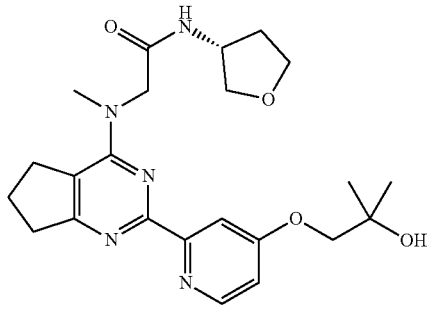 [SMILES: CN(CC(=O)N[C@@H]1CCOC1)c1nc(-c2cc(OCC(C)(C)O)ccn2)nc2c1CCC2]

Compound 422 was synthesized similar to Compound 389 by replacing propane-2-amine with (R)-tetrahydrofuran-3-amine. LCMS (ES) [M+1]⁺ m/z: 442. ¹H NMR (300 MHz, DMSO-d6) δ 8.49 (d, J=5.7 Hz, 1H), 8.40 (d, J=6.9 Hz, 1H), 7.81 (d, J=2.4 Hz, 1H), 7.09 (dd, J=5.7, 2.7 Hz, 1H), 4.70 (s, 1H), 4.32-4.24 (m, 1H), 4.21 (d, J=1.8 Hz, 2H), 3.88 (s, 2H), 3.78-3.70 (m, 2H), 3.67-3.60 (m, 1H), 3.46 (dd, J=8.7, 3.9 Hz, 1H), 3.28 (s, 3H), 3.18 (t, J=7.2 Hz, 2H), 2.86 (t, J=7.8 Hz, 2H), 2.11-1.95 (m, 3H), 1.78-1.68 (m, 1H), 1.24 (s, 6H).

Example 1.429

Synthesis of 2-[(2-{4-[2-(dimethylamino)-2-methylpropoxy]pyridin-2-yl}-5H,6H,7H-cyclopenta[d]pyrimidin-4-yl)(methyl)amino]-N-[1-(trifluoromethyl)cyclopropyl]acetamide (Compound 423)

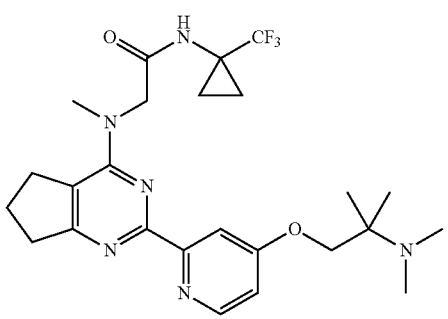 [SMILES: CN(CC(=O)NC1(C(F)(F)F)CC1)c1nc(-c2cc(OCC(C)(C)N(C)C)ccn2)nc2c1CCC2]

Compound 423 was synthesized similar to Compound 348 by replacing tert-butylamine with 1-(trifluoromethyl)cyclopropan-1-amine and by replacing dimethylaminoethanol with 2-(dimethylamino)-2-methylpropan-1-ol. LCMS (ES) [M+1]⁺ m/z: 507. ¹H NMR (300 MHz, DMSO-d6) δ 9.04 (s, 1H), 8.46 (d, J=5.6 Hz, 1H), 7.75 (d, J=2.5 Hz, 1H), 7.07 (dd, J=5.7, 2.5 Hz, 1H), 4.17 (s, 2H), 3.98 (s, 2H), 3.29 (s, 3H), 3.15 (t, J=7.4 Hz, 2H), 2.82 (t, J=7.8 Hz, 2H), 2.25 (s, 6H), 2.06-1.93 (m, 2H), 1.28-1.11 (m, 2H), 1.12 (s, 6H), 1.01-0.92 (m, 2H).

Example 1.430

Synthesis of 2-[(2-{4-[2-(dimethylamino)ethoxy]pyridin-2-yl}-5H,6H,7H-cyclopenta[d]pyrimidin-4-yl)(methyl)amino]-N-[(3R)-oxolan-3-yl]acetamide (Compound 424)

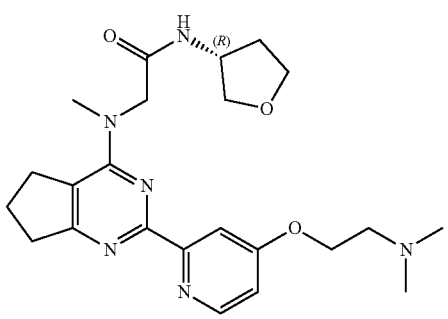

Scheme 131

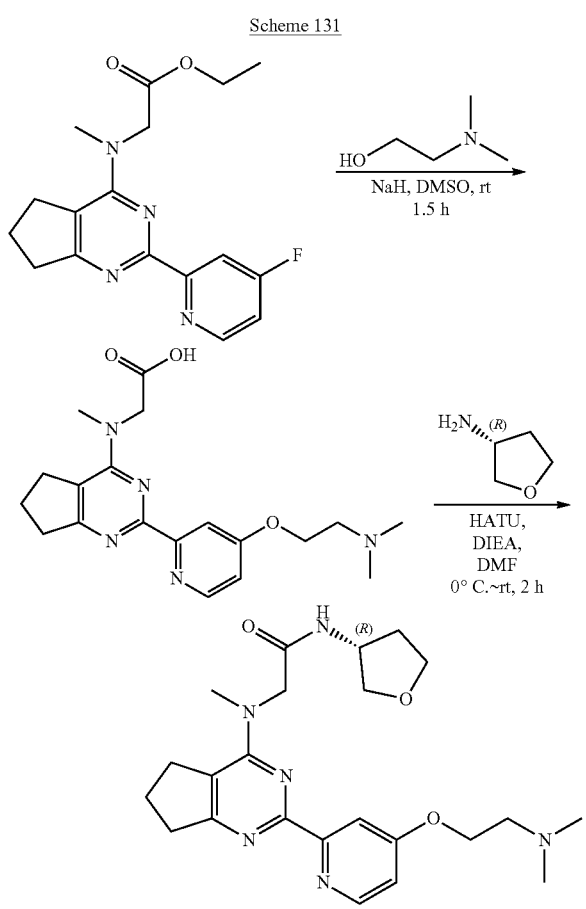

Step 1

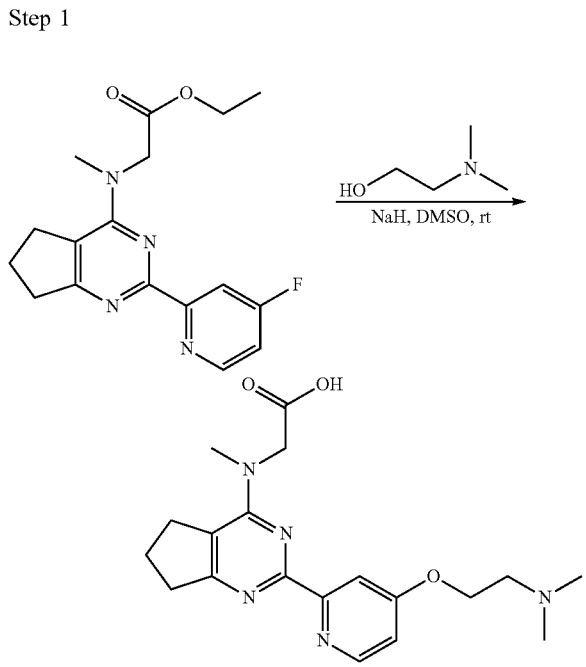

Into a 20 mL vial were added dimethylaminoethanol (354 mg, 3.97 mmol, 2.00 equiv), DMSO (5 mL). To the above mixture, NaH (60% in mineral oil) (159 mg, 3.97 mmol, 2.00 equiv). The resulting mixture was stirred for 30 min at room temperature, followed by the addition of ethyl 2-{[2-(4-fluoropyridin-2-yl)-5,6,7,8-tetrahydroquinazolin-4-yl](methyl)amino}acetate (683 mg, 1.98 mmol, 1.00 equiv). The resulting mixture was stirred for additional 1 h at room temperature. The reaction was quenched with water (2 mL) at room temperature. The mixture was acidified to pH 7 with HCOOH. The residue was purified by reverse phase flash chromatography with the following conditions: C18-120 g column, H$_2$O (0.05% FA)/MeCN, 10% to 100% gradient in 10 min, detector, UV 254 nm. This resulted in N-(2-(4-(2-(dimethylamino)ethoxy)pyridin-2-yl)-6,7-dihydro-5H-cyclopenta[d]pyrimidin-4-yl)-N-methylglycine formate (410 mg, 53%) as a white solid. LCMS (ES, m/z): [M−HCOOH+H]$^+$: 372.

Step 2

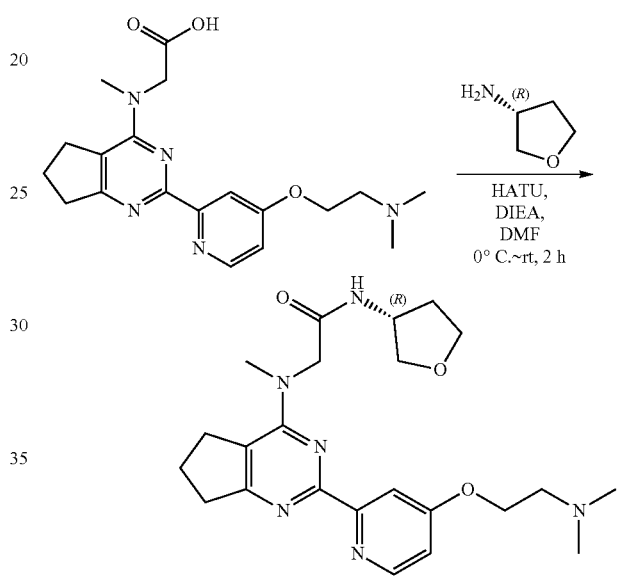

Into a 20 mL vial were added N-(2-(4-(2-(dimethylamino)ethoxy)pyridin-2-yl)-6,7-dihydro-5H-cyclopenta[d]pyrimidin-4-yl)-N-methylglycine formate (410 mg, 1.10 mmol, 1.00 equiv), DMF (5 mL), (3R)-oxolan-3-amine (125 mg, 1.43 mmol, 1.30 equiv), DIEA (428 mg, 3.31 mmol, 3.00 equiv). HATU (546 mg, 1.44 mmol, 1.30 equiv) was added at 0° C. The resulting mixture was stirred for 2 h at room temperature. The crude product was purified by Chiral-Prep-HPLC with the following conditions: XBridge Shield RP18 OBD Column, 19*150 mm, 5 μm, mobile phase, water (0.05% NH$_3$·H$_2$O) and CH$_3$CN (16% up to 33% in 8 min). This resulted in (R)-2-((2-(4-(2-(dimethylamino)ethoxy)pyridin-2-yl)-6,7-dihydro-5H-cyclopenta[d]pyrimidin-4-yl)(methyl)amino)-N-(tetrahydrofuran-3-yl)acetamide (102.6 mg, 21%) as an off-white solid. LCMS (ES, m/z): [M+H]$^+$: 441. $^1$H NMR (300 MHz, DMSO-d$_6$) δ 8.47 (d, J=5.6 Hz, 1H), 8.36 (d, J=6.9 Hz, 1H), 7.78 (d, J=2.5 Hz, 1H), 7.05 (dd, J=5.7, 2.6 Hz, 1H), 4.32-4.14 (m, 5H), 3.80-3.59 (m, 3H), 3.45 (dd, J=8.9, 4.1 Hz, 1H), 3.28 (s, 3H), 3.16 (t, J=7.3 Hz, 2H), 2.82 (t, J=7.8 Hz, 2H), 2.66 (t, J=5.7 Hz, 2H), 2.23 (s, 6H), 2.15-1.91 (m, 3H), 1.81-1.65 (m, 1H).

Example 1.431

Synthesis of N-tert-butyl-2-[(2-{4-[(1-hydroxy-2-methylpropan-2-yl)oxy]pyridin-2-yl}-5H,6H,7H-cyclopenta[d]pyrimidin-4-yl)(methyl)amino]acetamide (Compound 425)

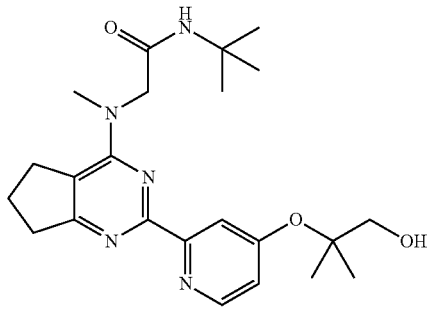 [SMILES: CN(CC(=O)NC(C)(C)C)c1nc(-c2cc(OC(C)(C)CO)ccn2)nc2c1CCC2]

Compound 425 was synthesized similar to Compound 44 by replacing 4-[2-(oxan-2-yloxy)ethoxy]-2-(trimethylstannyl)pyridine with 4-{[2-methyl-1-(oxan-2-yloxy)propan-2-yl]oxy}-2-(tributylstannyl)pyridine. LCMS (ES+): [M+H]$^+$=428.1. $^1$H NMR (400 MHz, DMSO-d$_6$) δ 8.49-8.42 (m, 1H), 7.87-7.80 (m, 1H), 7.69-7.62 (m, 1H), 7.14-7.03 (m, 1H), 5.04 (t, J=5.9 Hz, 1H), 4.16-4.11 (m, 2H), 3.86 (s, 1H), 3.50 (d, J=5.8 Hz, 1H), 3.27-3.23 (m, 3H), 3.18-3.09 (m, 2H), 2.85-2.77 (m, 2H), 2.04-1.93 (m, 2H), 1.39 (s, 3H), 1.24 (s, 9H), 1.23 (s, 3H).

Example 1.432

Synthesis of N-tert-butyl-2-[methyl({2-[4-(3,3,3-trifluoro-2-hydroxypropoxy)pyridin-2-yl]-5H,6H,7H-cyclopenta[d]pyrimidin-4-yl})amino]acetamide (Compound 426)

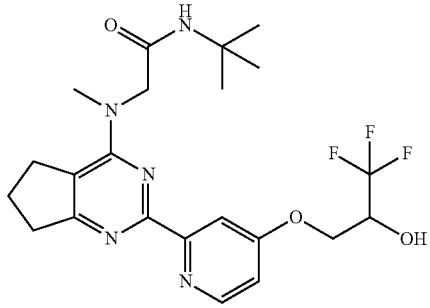 [SMILES: CN(CC(=O)NC(C)(C)C)c1nc(-c2cc(OCC(O)C(F)(F)F)ccn2)nc2c1CCC2]

Compound 426 was synthesized similar to Compound 174 by 2-methyl-2-((tetrahydro-2H-pyran-2-yl)oxy)propan-1-ol with 3,3,3-trifluoro-2-(oxan-2-yloxy)propan-1-ol. LCMS (ES+): [M+H]$^+$=453.1. $^1$H NMR (400 MHz, DMSO-d$_6$) δ 8.51 (d, J=5.6 Hz, 1H), 7.85 (d, J=2.5 Hz, 1H), 7.65 (s, 1H), 7.12 (dd, J=5.7, 2.6 Hz, 1H), 6.72 (d, J=6.6 Hz, 1H), 4.48-4.39 (m, 1H), 4.36 (dd, J=10.7, 4.1 Hz, 1H), 4.25 (dd, J=10.7, 6.1 Hz, 1H), 4.14 (s, 2H), 3.25 (s, 3H), 3.16-3.09 (m, 2H), 2.86-2.78 (m, 2H), 2.04-1.93 (m, 2H), 1.23 (s, 9H).

Example 1.433

Synthesis of N-tert-butyl-2-({2-[4-(2-hydroxyethoxy)-6-methylpyridin-2-yl]-5H,6H,7H-cyclopenta[d]pyrimidin-4-yl}(methyl)amino)acetamide (Compound 427)

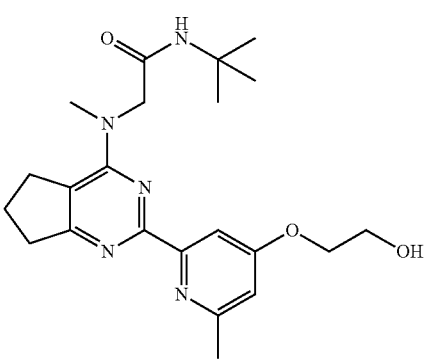 [SMILES: Cc1cc(OCCO)cc(-c2nc3c(c(N(C)CC(=O)NC(C)(C)C)n2)CCC3)n1]

Scheme 132

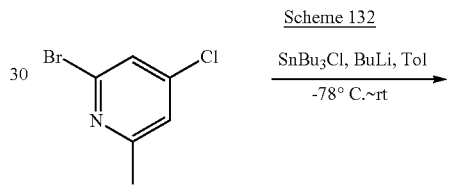

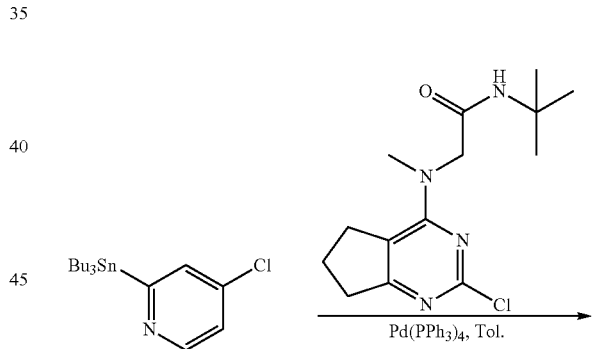

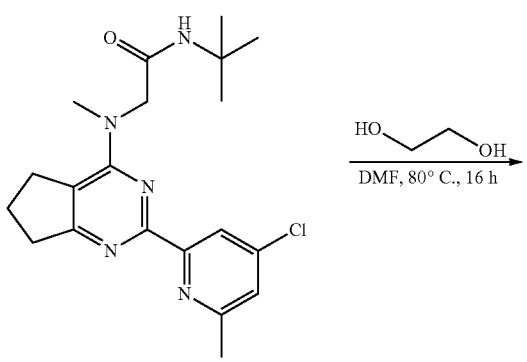

-continued

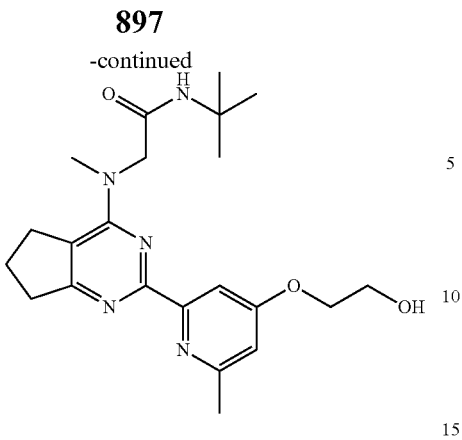

Step 1

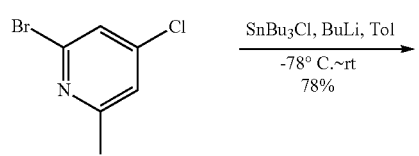

Into a 100-mL 3-necked round-bottom flask purged and maintained with an inert atmosphere of nitrogen, was placed a mixture of 2-bromo-4-chloro-6-methylpyridine (1.00 g, 4.88 mmol, 1.00 equiv), Tol (30 mL), n-BuLi (2.4 mL, 1.2 equiv) at −78 degrees C., after over 30 mins, was added SnBu₃Cl (1.75 g, 5.37 mmol, 1.1 equiv) was dropwised at −78 degrees C. The resulting solution was stirred for 16 hours at −78 degrees C. to rt. The resulting mixture was washed with 1×30 ml of NH₄Cl and 1×30 ml of aq NaHCO₃, and 1×30 ml of aq. NaCl. The mixture was dried over anhydrous sodium sulfate and concentrated. This resulted in 1.6 g (78.82%) of 4-chloro-2-methyl-6-(tributylstannyl) pyridine as yellow oil. LCMS (ES) [M+1]⁺ m/z 418.

Step 2

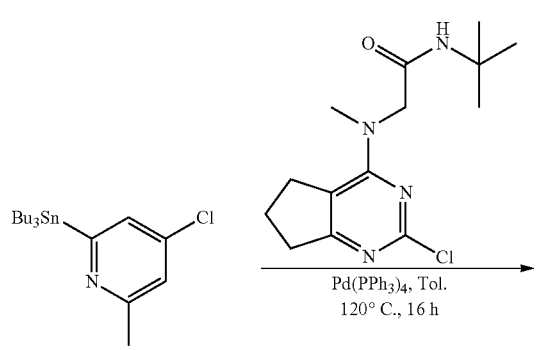

-continued

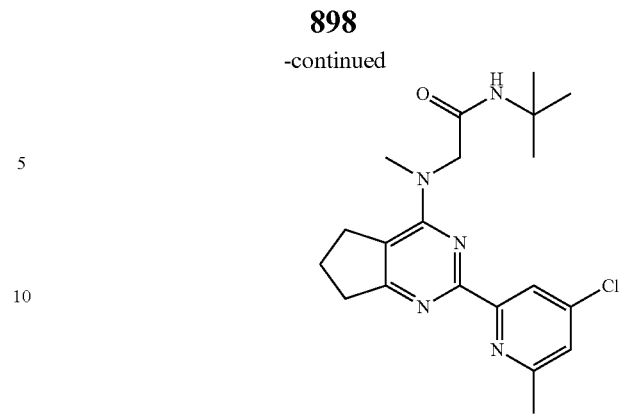

Into a 40-mL vial purged and maintained with an inert atmosphere of nitrogen, was placed a mixture of 2-bromo-4-chloro-6-methylpyridine (1.0 g, 23.98 mmol, 1.00 equiv), Toluene (20.0 mL), N-(tert-butyl)-2-((2-chloro-6,7-dihydro-5H-cyclopenta[d]pyrimidin-4-yl)(methyl)amino)acetamide (710 mg, 23.98 mmol, 1.0 equiv), Pd(PPh₃)₄ (277 mg, 2.40 mmol, 0.10 equiv). The resulting solution was stirred for 16 hours at 120 degrees C. The resulting mixture was concentrated. The residue was applied onto a silica gel column with MeOH/DCM (13/87). This resulted in 800 mg (86.96%) of 4-chloro-2-methyl-6-(tributylstannyl)pyridine as a yellow solid. LCMS (ES) [M+1]⁺ m/z 388.

Step 3

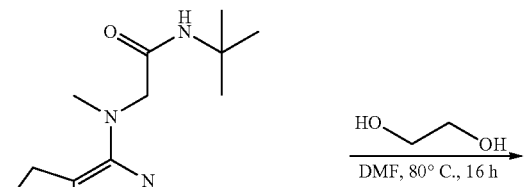

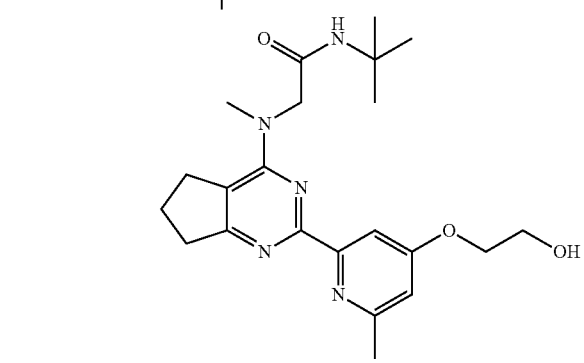

Into a 8-mL vial, was placed a mixture of NaH (60%) (165 mg, 2.06 mmol, 4.00 equiv), DMF (4.0 mL), ethane-1,2-diol (320 mg, 2.58 mmol, 5.0 equiv), N-(tert-butyl)-2-((2-(4-chloro-6-methylpyridin-2-yl)-6,7-dihydro-5H-cyclopenta[d]pyrimidin-4-yl)(methyl)amino)acetamide (200 mg, 0.516 mmol, 1.00 equiv). The resulting solution was stirred for 16 hours at 80 degrees C. The reaction was then quenched by the addition of 0.5 mL of water. The crude product was purified by Prep-HPLC with the following conditions: SunFire Prep C18 OBD Column, 30*50 mm, 5 μm 10 nm; Mobile Phase A: Water (0.1% FA), Mobile Phase B: AcCN; Flow rate: 90 mL/min; Gradient: 5% B to 35% B in 12 min, 35% B; Wave Length: 220 nm; RT1 (min): 12; Number Of Runs: 0. This resulted in 70 mg (32.86%) of N-(tert-butyl)-2-((2-(4-(2-hydroxyethoxy)-6-methylpyridin-2-yl)-6,7-dihydro-5H-cyclopenta[d]pyrimidin-4-yl)(methyl)amino)acetamide formate as a white solid. LCMS (ES) [M−46+1]+ m/z 414. ¹H NMR (400 MHz, DMSO-d6, ppm): δ 8.21 (s, 1H), 7.67 (d, J=2.4 Hz, 1H), 7.65 (s, 1H), 6.90 (d, J=2.3 Hz, 1H), 4.15-4.08 (m, 4H), 3.74 (t, J=4.9 Hz, 2H), 3.25 (s, 3H), 3.13 (t, J=7.3 Hz, 2H), 2.81 (t, J=7.9 Hz, 2H), 2.48 (s, 3H), 2.04-1.92 (m, 1H), 1.23 (s, 9H).

Example 1.434

Synthesis of 2-[(2-{4-[2-(dimethylamino)ethoxy]pyridin-2-yl}-5H,6H,7H-cyclopenta[d]pyrimidin-4-yl)(methyl)amino]-N-(propan-2-yl)acetamide (Compound 428)

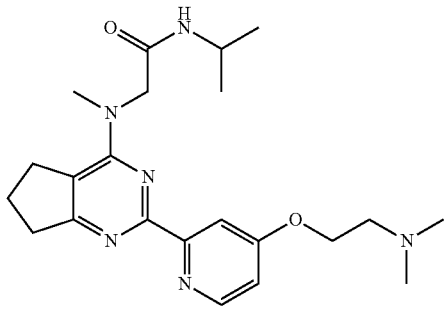 [SMILES: CC(C)NC(=O)CN(C)c1nc(-c2cc(OCCN(C)C)ccn2)nc2c1CCC2]

Compound 428 was synthesized similar to Compound 389 by replacing 2-methyl-2-(oxan-2-yloxy)propan-1-ol with dimethylaminoethanol. LCMS (ES) [M+1]+ m/z: 413. ¹H NMR (300 MHz, DMSO-d6) δ 8.47 (dd, J=5.6, 1.2 Hz, 1H), 8.00 (d, J=7.8 Hz, 1H), 7.80 (d, J=2.5 Hz, 1H), 7.10-7.00 (m, 1H), 4.20 (t, J=5.6 Hz, 2H), 4.15 (s, 2H), 3.94-3.80 (m, 1H), 3.27 (s, 3H), 3.15 (t, J=7.3 Hz, 2H), 2.82 (t, J=7.8 Hz, 2H), 2.66 (t, J=5.6 Hz, 2H), 2.23 (s, 6H), 2.04-1.97 (m, 2H), 1.05 (dd, J=6.6, 1.2 Hz, 6H).

Example 1.435

Synthesis of 2-[methyl(2-{4-[2-(pyrrolidin-1-yl)ethoxy]pyridin-2-yl}-5H,6H,7H-cyclopenta[d]pyrimidin-4-yl)amino]-N-(propan-2-yl)acetamide (Compound 429)

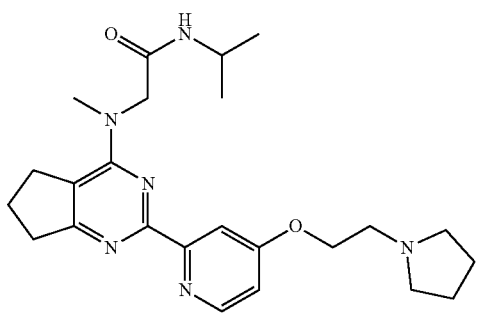 [SMILES: CC(C)NC(=O)CN(C)c1nc(-c2cc(OCCN3CCCC3)ccn2)nc2c1CCC2]

Compound 429 was synthesized similar to Compound 389 by replacing 2-methyl-2-(oxan-2-yloxy)propan-1-ol with hydroxyethylpyrrolidine. LCMS (ES) [M+1]+ m/z: 439. ¹H NMR (300 MHz, DMSO-d6) δ 8.47 (d, J=5.6 Hz, 1H), 7.99 (d, J=7.8 Hz, 1H), 7.80 (d, J=2.5 Hz, 1H), 7.05 (dd, J=5.6, 2.6 Hz, 1H), 4.22 (t, J=5.7 Hz, 2H), 4.15 (s, 2H), 3.87 (dq, J=13.5, 6.7 Hz, 1H), 3.27 (s, 3H), 3.15 (t, J=7.3 Hz, 2H), 2.87-2.76 (m, 4H), 2.59-2.53 (m, 4H), 2.04-1.97 (m, 2H), 1.75-1.61 (m, 4H), 1.04 (d, J=6.6 Hz, 6H).

Example 1.436

Synthesis of 2-[methyl(2-{4-[2-(morpholin-4-yl)ethoxy]pyridin-2-yl}-5H,6H,7H-cyclopenta[d]pyrimidin-4-yl)amino]-N-(propan-2-yl)acetamide (Compound 430)

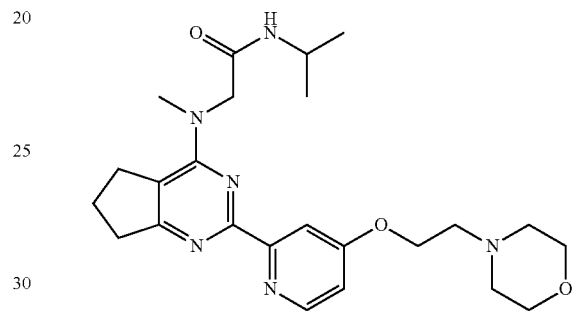

Compound 430 was synthesized similar to Compound 389 by replacing 2-methyl-2-(oxan-2-yloxy)propan-1-ol with 4-morpholineethanol. LCMS (ES) [M+1]+ m/z: 455. ¹H NMR (300 MHz, DMSO-d6) δ 8.47 (d, J=5.6 Hz, 1H), 7.99 (d, J=7.8 Hz, 1H), 7.81 (d, J=2.5 Hz, 1H), 7.05 (dd, J=5.6, 2.6 Hz, 1H), 4.24 (t, J=5.6 Hz, 2H), 4.15 (s, 2H), 3.96-3.78 (m, 1H), 3.64-3.53 (m, 4H), 3.27 (s, 3H), 3.15 (t, J=7.3 Hz, 2H), 2.82 (t, J=7.8 Hz, 2H), 2.73 (t, J=5.6 Hz, 2H), 2.50-2.47 (m, 4H), 2.04-1.97 (m, 2H), 1.04 (d, J=6.6 Hz, 6H).

Example 1.437

Synthesis of 2-[(2-{4-[(1-hydroxycyclopropyl)methoxy]pyridin-2-yl}-5H,6H,7H-cyclopenta[d]pyrimidin-4-yl)(methyl)amino]-N-(propan-2-yl)acetamide (Compound 431)

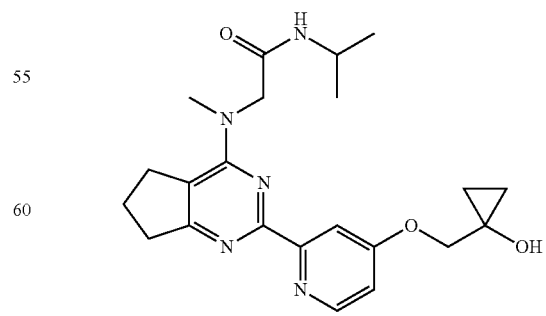

Compound 431 was synthesized similar to Compound 389 by replacing 2-methyl-2-(oxan-2-yloxy)propan-1-ol with (1-((tetrahydro-2H-pyran-2-yl)oxy)cyclopropyl)methanol. LCMS (ES) [M+1]+ m/z: 412. ¹H NMR (300 MHz, DMSO-d6) δ 8.47 (d, J=5.6 Hz, 1H), 8.00 (d, J=8.0 Hz, 1H), 7.83 (d, J=2.4 Hz, 1H), 7.05 (dd, J=5.6, 2.8 Hz, 1H), 5.63 (s, 1H), 4.16 (s, 2H), 4.12 (s, 2H), 3.91-3.83 (m, 1H), 3.30 (s, 3H), 3.17 (t, J=7.2 Hz, 2H), 2.84 (t, J=7.6 Hz, 2H), 2.03-1.96 (m, 2H), 1.05 (d, J=6.4 Hz, 6H), 0.74-0.65 (m, 4H).

Example 1.438

Synthesis of 2-[methyl(2-{4-[2-(4-methylpiperazin-1-yl)ethoxy]pyridin-2-yl}-5H,6H,7H-cyclopenta[d]pyrimidin-4-yl)amino]-N-(propan-2-yl)acetamide (Compound 432)

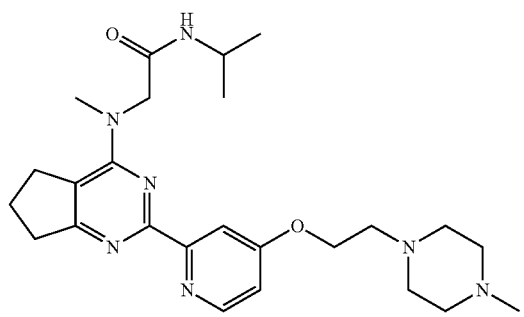 [SMILES: CC(C)NC(=O)CN(C)c1nc(-c2cc(OCCN3CCN(C)CC3)ccn2)nc2c1CCC2]

Compound 432 was synthesized similar to Compound 389 by replacing 2-methyl-2-(oxan-2-yloxy)propan-1-ol with 2-(4-methylpiperazin-1-yl)ethanol. LCMS (ES) [M+1]+ m/z: 468. ¹H NMR (300 MHz, DMSO-d6) δ 8.47 (d, J=5.6 Hz, 1H), 7.99 (d, J=7.7 Hz, 1H), 7.80 (d, J=2.5 Hz, 1H), 7.05 (dd, J=5.7, 2.5 Hz, 1H), 4.22 (t, J=5.7 Hz, 2H), 4.15 (s, 2H), 3.95-3.81 (m, 1H), 3.27 (s, 3H), 3.15 (t, J=7.3 Hz, 2H), 2.82 (t, J=7.8 Hz, 2H), 2.72 (t, J=5.7 Hz, 2H), 2.59-2.50 (m, 4H), 2.40-2.28 (m, 4H), 2.15 (s, 3H), 2.04-1.94 (p, J=7.6 Hz, 2H), 1.05 (d, J=6.6 Hz, 6H).

Example 1.439 and Example 1.440

Synthesis of (2R)-2-[(2-{4-[2-(dimethylamino)ethoxy]pyridin-2-yl}-5H,6H,7H-cyclopenta[d]pyrimidin-4-yl)(methyl)amino]-N-(propan-2-yl)propanamide (Compound 433) and (2S)-2-[(2-{4-[2-(dimethylamino)ethoxy]pyridin-2-yl}-5H,6H,7H-cyclopenta[d]pyrimidin-4-yl)(methyl)amino]-N-(propan-2-yl)propanamide (Compound 434)

Compound 433

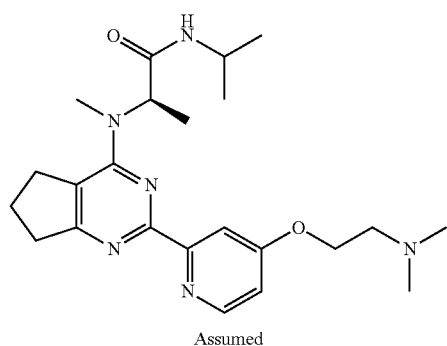

Assumed

Compound 434

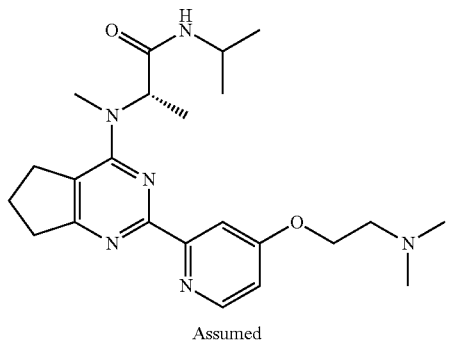

Assumed

Scheme 133

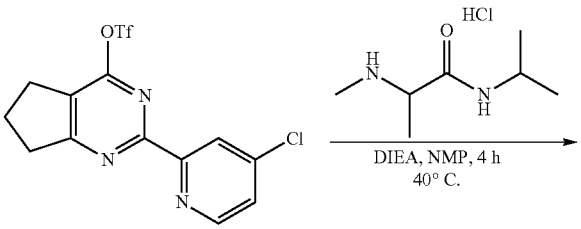

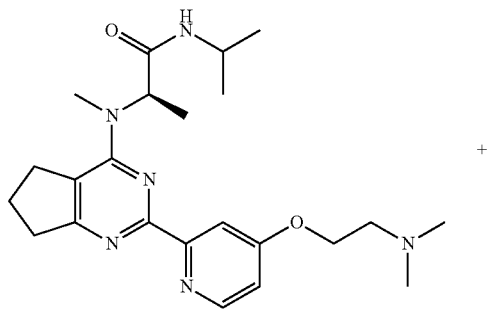

Compound 433
Assumed

903

-continued

904

Step 2

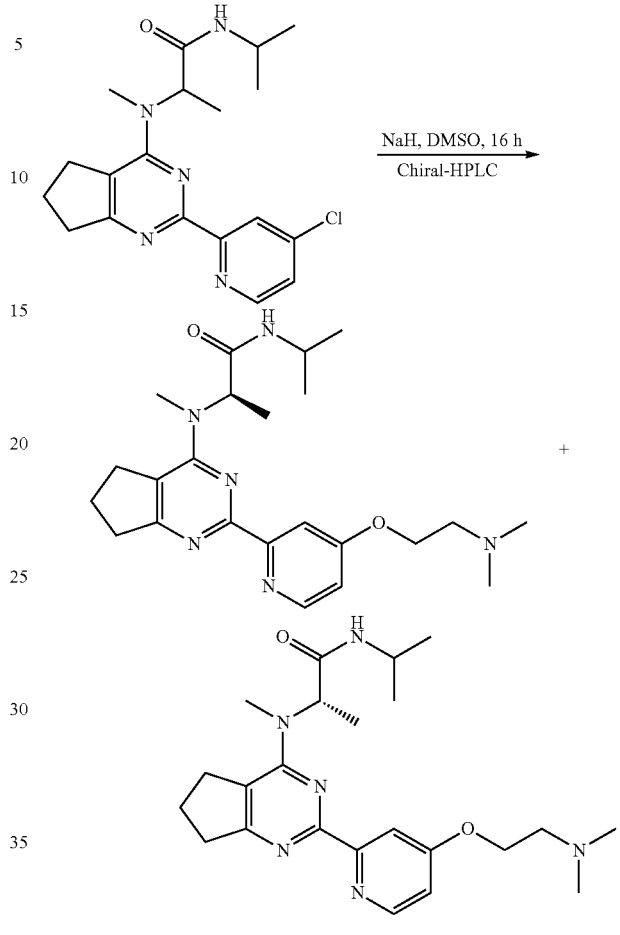

Compound 434
Assumed

Step 1

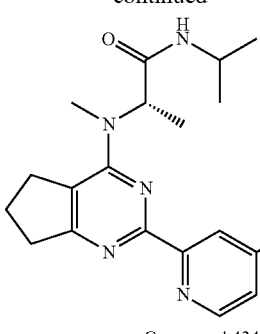

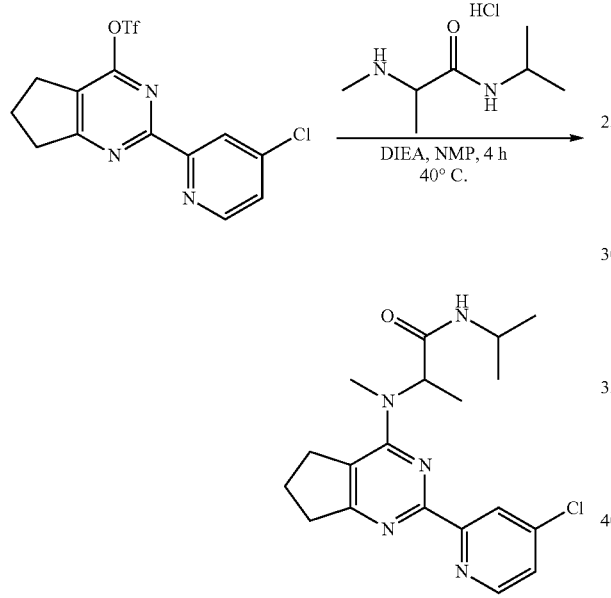

Into a 100 mL round-bottom flask were added 2-(4-chloropyridin-2-yl)-5H,6H,7H-cyclopenta[d]pyrimidin-4-yl trifluoromethanesulfonate (2.5 g, 6.58 mmol, 1.00 equiv), N-isopropyl-2-(methylamino)propanamide (1.42 g, 9.88 mmol, 1.5 equiv), NMP (20 mL), and DIEA (2.55 g, 19.75 mmol, 3 equiv) at room temperature. The resulting mixture was stirred for 4 h at 40° C. The reaction was quenched with water at room temperature and the resulting mixture was extracted with EtOAc (3×200 mL). The combined organic layers were washed with brine (3×200 mL), and dried over anhydrous Na$_2$SO$_4$. After filtration, the filtrate was concentrated under reduced pressure. The crude product was recrystallized from EtOAc (100 mL) to afford 2-{[2-(4-chloropyridin-2-yl)-5H,6H,7H-cyclopenta[d]pyrimidin-4-yl](methyl)amino}-N-isopropylpropanamide (1 g, 40.63%) as a light yellow solid. LCMS (ES) [M+1]$^+$ m/z 374.

Into a 40 mL vial were added dimethylaminoethanol (238 mg, 2.67 mmol, 2 equiv) and DMSO (5 mL) at 0° C. To the above mixture was added NaH (107 mg, 2.67 mmol, 2 equiv) in portions at 0° C. The resulting mixture was stirred for an additional 30 min at room temperature. To the mixture was then added 2-{[2-(4-chloropyridin-2-yl)-5H,6H,7H-cyclopenta[d]pyrimidin-4-yl](methyl)amino}-N-isopropylpropanamide (500 mg, 1.34 mmol, 1.00 equiv) in DMSO dropwise at 0° C. The resulting solution was stirred for 1 hr at room temperature. The crude product was purified by Chiral-Prep-HPLC with the following conditions (Prep-HPLC-003): Column, SunFire Prep C18 OBD Column, 19*150 mm, 5 μm 10 nm; mobile phase, Water (0.05% TFA) and ACN (35% ACN up to 88% in 8 min). The crude product was purified again by Chiral-Prep-HPLC with the following conditions (XA-Prep Chiral HPLC-01): Column, CHIRAL ART Cellulose-SB, 3*25 cm, 5 um; mobile phase, Hex (0.5% 2M NH3-MeOH)— and EtOH (0.5% 2M NH3-MeOH)— (hold 30% EtOH (0.5% 2M NH3-MeOH)— in 12 min This resulted in (2R)-2-[(2-{4-[2-(dimethylamino)ethoxy]pyridin-2-yl}-5H,6H,7H-cyclopenta[d]pyrimidin-4-yl)(methyl)amino]-N-isopropylpropanamide (111.6 mg, 39.13%) and (2S)-2-[(2-{4-[2-(dimethylamino)ethoxy]pyridin-2-yl}-5H,6H,7H-cyclopenta[d]pyrimidin-4-yl)(methyl)amino]-N-isopropylpropanamide (114.9 mg, 36.36%) as a white solid.

Compound 433: Analytical chiral HPLC conditions: Column, YMC-cellulose-SB, 100*4.6 mm, 3 um; mobile phase A, n-Hexane; mobile phase B, ethanol; Flow rate: 1 mL/min; Gradient: 10% B in 10 min; 254 nm. Retention time: 3.067 min. LCMS (ES) [M+1]⁺ m/z 427. ¹H NMR (400 MHz, DMSO-d₆) δ 8.49 (d, J=5.6 Hz, 1H), 8.21 (d, J=8.0 Hz, 1H), 7.87 (d, J=2.5 Hz, 1H), 7.10-7.04 (m, 1H), 5.07 (q, J=7.0 Hz, 1H), 4.24 (t, J=5.6 Hz, 2H), 3.95-3.82 (m, 1H), 3.28-3.15 (m, 1H), 3.11-3.03 (m, 4H), 2.95-2.75 (m, 2H), 2.72 (t, J=5.7 Hz, 2H), 2.27 (s, 6H), 2.11-1.88 (m, 2H), 1.34 (d, J=7.0 Hz, 3H), 1.08 (d, J=6.6 Hz, 3H), 0.91 (d, J=6.6 Hz, 3H).

Compound 434: Analytical chiral HPLC conditions: Column, YMC-cellulose-SB, 100*4.6 mm, 3 um; mobile phase A, n-Hexane; mobile phase B, ethanol; Flow rate: 1 mL/min; Gradient: 10% B in 10 min; 254 nm. Retention time: 4.820 min. LCMS (ES) [M+1]⁺ m/z 427. ¹H NMR (400 MHz, DMSO-d₆) δ 8.49 (d, J=5.6 Hz, 1H), 8.21 (d, J=8.0 Hz, 1H), 8.17 (s, HCOOH), 7.87 (d, J=2.5 Hz, 1H), 7.10-7.04 (m, 1H), 5.07 (q, J=7.0 Hz, 1H), 4.24 (t, J=5.6 Hz, 2H), 3.95-3.82 (m, 1H), 3.28-3.15 (m, 1H), 3.11 (s, 4H), 2.95-2.75 (m, 2H), 2.72 (t, J=5.7 Hz, 2H), 2.27 (s, 6H), 2.11-1.88 (m, 2H), 1.34 (d, J=7.0 Hz, 3H), 1.08 (d, J=6.6 Hz, 3H), 0.91 (d, J=6.6 Hz, 3H).

Example 1.440

Synthesis of (2R)-2-[(2-{4-[2-(dimethylamino) ethoxy]pyridin-2-yl}-5H,6H,7H-cyclopenta[d]pyrimidin-4-yl)(methyl)amino]-N-(propan-2-yl)propanamide (Compound 433)

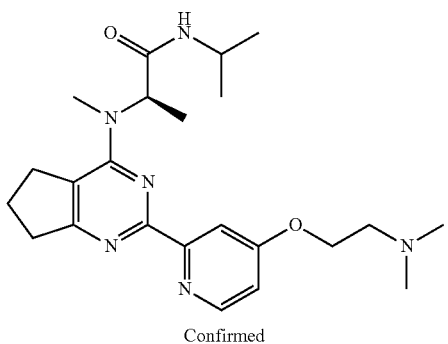 [SMILES: CC(C)NC(=O)[C@@H](C)N(C)c1nc(-c2cc(OCCN(C)C)ccn2)nc2c1CCC2]

Confirmed

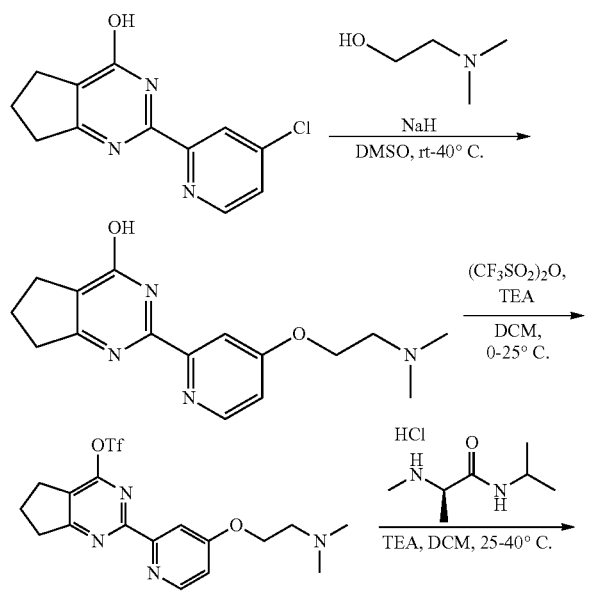

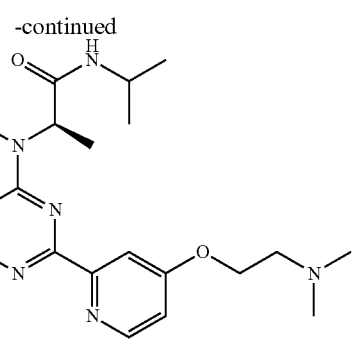

Step 1

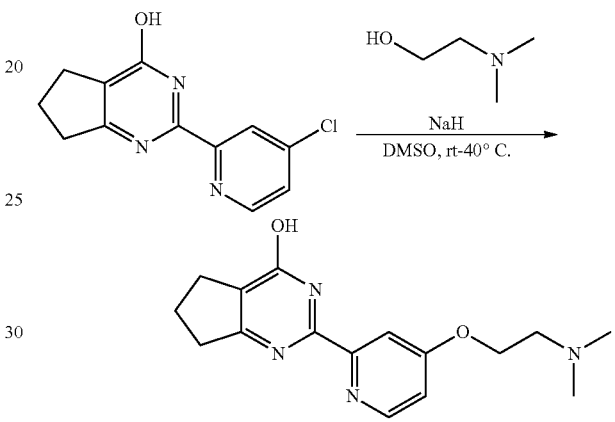

To a stirred mixture of dimethylaminoethanol (2.10 g, 24.22 mmol, 3.00 equiv) in DMSO (30 mL) was added NaH (0.97 g, 24.22 mmol, 3.00 equiv) in portions at room temperature under N₂ atmosphere. The reaction was stirred at room temperature for 30 min before 2-(4-chloropyridin-2-yl)-5H,6H,7H-cyclopenta[d]pyrimidin-4-ol (2.0 g, 8.07 mmol, 1.00 equiv) was added. The resulting mixture was stirred at 40° C. for 1 h and quenched with H₂O (5 mL) at 15° C. The reaction mixture was purified by prep-HPLC (Column, C18; mobile phase, Mobile phase: MeCN=5/1B: Water Flow rate: 50 mL/min Column: DAICEL CHIRALPAK IC, 250*20 mm, 220 nm Gradient: 50% B in 20 min; 220 nm) to give 2-{4-[2-(dimethylamino)ethoxy]pyridin-2-yl}-5H,6H,7H-cyclopenta[d]pyrimidin-4-ol (2.1 g, 86.58%) as an-off white solid. LCMS (ES) [M+1]⁺ m/z: 301.

Step 2

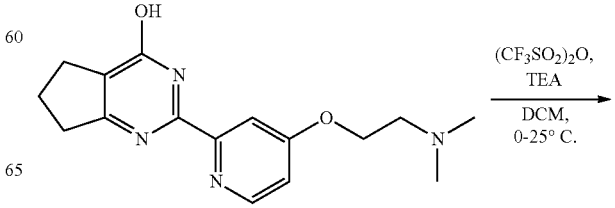

-continued

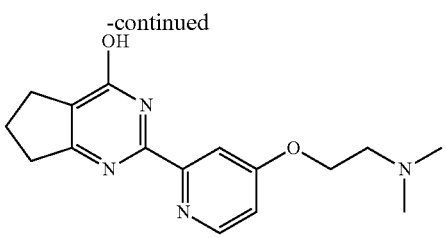

To a stirred solution of 2-{4-[2-(dimethylamino)ethoxy]pyridin-2-yl}-5H,6H,7H-cyclopenta[d]pyrimidin-4-ol (2.00 g, 6.66 mmol, 1.00 equiv) and TEA (2.70 g, 26.63 mmol, 4.00 equiv) in DCM (30 mL) was added $(CF_3SO_2)_2O$ (3.76 g, 13.31 mmol, 2.00 equiv) dropwise at 0° C. under $N_2$ atmosphere. After the reaction was stirred at 0-25° C. for 5 h, the reaction was quenched by the addition of water (20 mL) at 0° C. The resulting solution was extracted with DCM (50 mL×3), the combined organic layers were washed with brine, dried over anhydrous sodium sulfate, and concentrated under vacuum. This resulted in 2-{4-[2-(dimethylamino)ethoxy]pyridin-2-yl}-5H,6H,7H-cyclopenta[d]pyrimidin-4-yl trifluoromethanesulfonate (2.6 g, 90.30%) as a brown oil, which was used in the next step directly.

Step 3

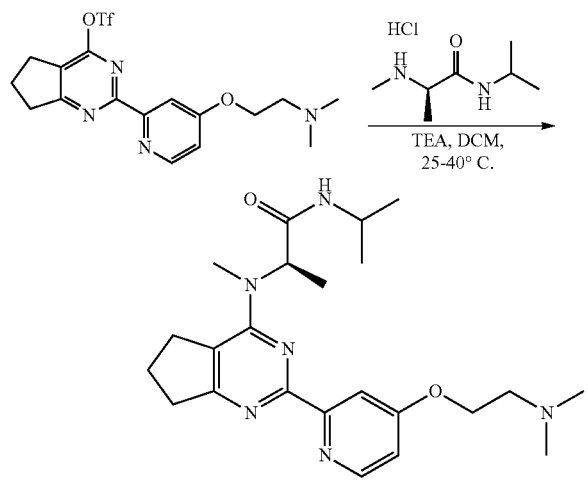

To a stirred solution 2-{4-[2-(dimethylamino)ethoxy]pyridin-2-yl}-5H,6H,7H-cyclopenta[d]pyrimidin-4-yl trifluoromethanesulfonate (2.50 g, 5.78 mmol, 1.00 equiv) and TEA (2.93 g, 28.90 mmol, 5.00 equiv) in DCM (50 mL) was added (2R)—N-isopropyl-2-(methylamino)propanamide hydrochloride (1.57 g, 8.67 mmol, 1.50 equiv) in one portion at 25° C., the resulting reaction was stirred at 25-40° C. for 16 h. The reaction was quenched with water (30 mL) at 0° C., extracted with DCM (50 mL×5). The combined organic layers were washed with brine (50 mL), dried over anhydrous $Na_2SO_4$. After filtration, the filtrate was concentrated under reduced pressure. The crude product (2.1 g) was purified by Prep-HPLC with the following conditions (Column, C18; mobile phase, Mobile phase: MeCN=5/1B: Water Flow rate: 40 mL/min Column: DAICEL CHIRALPAK IC, 250*20 mm, 220 nm Gradient: 50% B in 25 min; 220 nm)) to afford 750 mg (99.75% purity) of the desired product as a white solid. The 750 mg (99.75% purity) of the desired product was trituration with heptane/EtOAc (50:1, 50 mL) for 1 h and filtered. The filtrate was concentrated to give (2R)-2-[(2-{4-[2-(dimethylamino)ethoxy]pyridin-2-yl}-5H,6H,7H-cyclopenta[d]pyrimidin-4-yl)(methyl)amino]-N-isopropylpropanamide (375 mg, 15.21% yield, 99.903% purity) as a white solid. Analytical chiral HPLC conditions: Column, YMC-cellulose-SB, 100*4.6 mm, 3 um; mobile phase A, n-Hexane; mobile phase B, ethanol; Flow rate: 1 mL/min; Gradient: 10% B in 10 min; 254 nm. Retention time: 3.341 min LCMS (ES) $[M+1]^+$ m/z: 427. $^1H$ NMR (400 MHz, DMSO-$d_6$) δ 8.49 (d, J=5.6 Hz, 1H), 8.21 (d, J=8.0 Hz, 1H), 7.86 (d, J=2.5 Hz, 1H), 7.07 (dd, J=5.6, 2.6 Hz, 1H), 5.07 (d, J=7.1 Hz, 1H), 4.22 (t, J=5.7 Hz, 2H), 3.89 (dt, J=7.7, 6.4 Hz, 1H), 3.26-3.17 (m, 1H), 3.11 (s, 3H), 3.10-3.04 (m, 1H), 2.94-2.75 (m, 2H), 2.67 (t, J=5.7 Hz, 2H), 2.23 (s, 6H), 2.10-1.87 (m, 2H), 1.34 (d, J=7.0 Hz, 3H), 1.08 (d, J=6.6 Hz, 3H), 0.91 (d, J=6.5 Hz, 3H).

Example 1.441

Synthesis of 2-[(2-{4-[2-(dimethylamino)ethoxy]pyridin-2-yl}-5,5-dimethyl-5H,6H,7H-cyclopenta[d]pyrimidin-4-yl)(methyl)amino]-N-(propan-2-yl)acetamide (Compound 435)

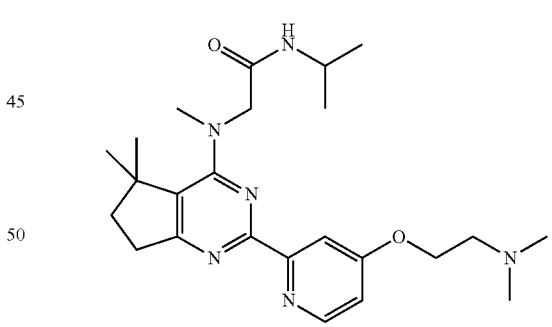

Compound 435 was synthesized similar to Compound 331 by replacing 2-(methylamino)-N-(6-methylpyridin-3-yl)acetamide with N-isopropyl-2-(methylamino)acetamide hydrochloride and by replacing ethane-1,2-diol with dimethylaminoethanol. LCMS (ES) $[M+1]^+$ m/z: 441. $^1H$ NMR (400 MHz, DMSO-$d_6$) δ 8.49 (d, J=5.6 Hz, 1H), 8.12 (d, J=7.8 Hz, 1H), 7.81 (d, J=2.5 Hz, 1H), 7.07 (dd, J=5.6, 2.6 Hz, 1H), 4.20 (t, J=5.7 Hz, 2H), 4.05 (s, 2H), 3.85 (dq, J=13.5, 6.7 Hz, 1H), 3.20 (s, 3H), 2.87 (t, J=7.3 Hz, 2H), 2.66 (t, J=5.7 Hz, 2H), 2.23 (s, 6H), 1.87 (t, J=7.3 Hz, 2H), 1.43 (s, 6H), 1.03 (d, J=6.6 Hz, 6H).

Example 1.442

Synthesis of 2-[methyl(2-{4-[2-(3-oxomorpholin-4-yl)ethoxy]pyridin-2-yl}-5H,6H,7H-cyclopenta[d]pyrimidin-4-yl)amino]-N-(propan-2-yl)acetamide (Compound 436)

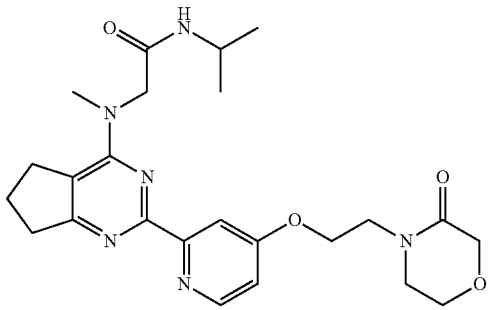 [SMILES: CC(C)NC(=O)CN(C)c1nc(-c2cc(OCCN3CCOCC3=O)ccn2)nc2c1CCC2]

Compound 436 was synthesized similar to Compound 389 by replacing 2-methyl-2-(oxan-2-yloxy)propan-1-ol with 4-(2-(benzyloxy)ethyl)morpholin-3-one. LCMS (ES) [M+1]⁺ m/z: 469. ¹H NMR (400 MHz, DMSO-d₆) δ 8.50 (d, J=5.6 Hz, 1H), 8.00 (d, J=8.0 Hz, 1H), 7.81 (d, J=2.8 Hz, 1H), 7.08 (dd, J=4.8, 2.8 Hz, 1H), 4.32 (t, J=5.6 Hz, 2H), 4.15 (s, 2H), 4.05 (s, 2H), 3.92-3.85 (m, 1H), 3.84 (t, J=4.8 Hz, 2H), 3.76 (t, J=5.6 Hz, 2H), 3.53 (t, J=5.2 Hz, 2H), 3.27 (s, 3H), 3.17 (t, J=7.2 Hz, 2H), 2.84 (t, J=7.6 Hz, 2H), 2.03-1.96 (m, 2H), 1.05 (d, J=6.8 Hz, 6H).

Example 1.443

Synthesis of N-tert-butyl-2-{methyl[2-(4-{[(3R)-1-methylpyrrolidin-3-yl]oxy}pyridin-2-yl)-5H,6H,7H-cyclopenta[d]pyrimidin-4-yl]amino}acetamide (Compound 437)

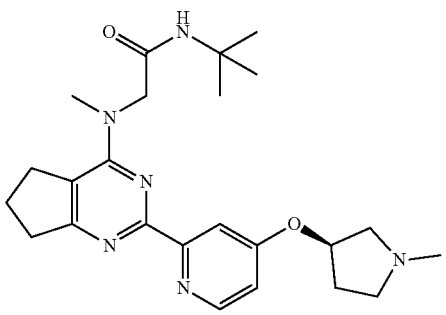 [SMILES: CN1CC[C@@H](Oc2ccnc(-c3nc4c(c(N(C)CC(=O)NC(C)(C)C)n3)CCC4)c2)C1]

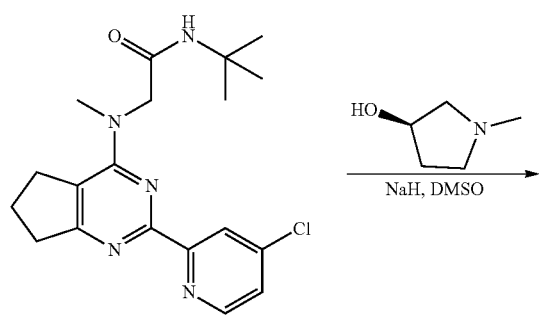

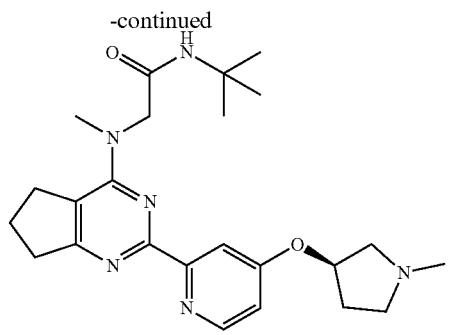

Into a 40 mL vial were added (3R)-1-methylpyrrolidin-3-ol (108 mg, 1.07 mmol, 2 equiv) and DMSO (5 mL) at 0° C. To the above mixture was added NaH (43 mg, 1.07 mmol, 2 equiv) in portions at 0° C. The resulting mixture was stirred for additional 30 min at room temperature and was added N-tert-butyl-2-{[2-(4-chloropyridin-2-yl)-5H,6H,7H-cyclopenta[d]pyrimidin-4-yl](methyl)amino}acetamide (200 mg, 0.54 mmol, 1.00 equiv) in DMSO dropwise at 0° C. The resulting solution was stirred for 1 hr at room temperature and the crude product was purified by Chiral-Prep-HPLC with the following conditions (Prep-HPLC-003): Column, SunFire Prep C18 OBD Column, 19*150 mm, 5 μm 10 nm; mobile phase, Water (0.1% FA) and ACN (15% ACN up to 55% in 8 min); This resulted in N-tert-butyl-2-{methyl[2-(4-{[(3R)-1-methylpyrrolidin-3-yl]oxy}pyridin-2-yl)-5H,6H,7H-cyclopenta[d]pyrimidin-4-yl]amino}acetamide; (formate) (93.6 mg, 32.98%) as a light brown semi-solid. LCMS (ES) [M+1]⁺ m/z: 439. ¹H NMR (400 MHz, DMSO-d₆) δ 8.46 (d, J=5.6 Hz, 1H), 7.81 (d, J=2.5 Hz, 1H), 7.69 (s, 1H), 6.99 (dd, J=5.6, 2.6 Hz, 1H), 5.10-5.02 (m, 1H), 4.12 (s, 2H), 3.27 (s, 3H), 3.15 (t, J=7.3 Hz, 2H), 2.93-2.85 (m, 1H), 2.81 (t, J=7.8 Hz, 2H), 2.75-2.65 (m, 2H), 2.49-2.33 (m, 2H), 2.31 (s, 3H), 2.05-1.93 (m, 2H), 1.88-1.77 (m, 1H), 1.25 (s, 9H).

Example 1.444

Synthesis of N-tert-butyl-2-{methyl[2-(4-{[(3S)-1-methylpyrrolidin-3-yl]oxy}pyridin-2-yl)-5H,6H,7H-cyclopenta[d]pyrimidin-4-yl]amino}acetamide (Compound 438)

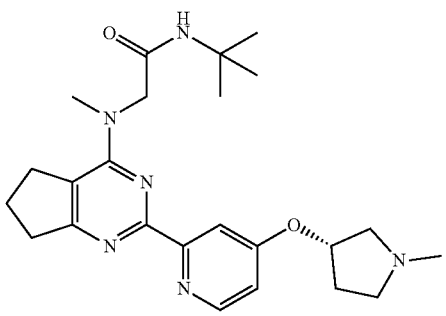 [SMILES: CN1CC[C@H](Oc2ccnc(-c3nc4c(c(N(C)CC(=O)NC(C)(C)C)n3)CCC4)c2)C1]

Compound 438 was synthesized similar to Compound 348 by replacing dimethylaminoethanol with (3S)-1-methylpyrrolidin-3-ol. LCMS (ES) [M+1]⁺ m/z: 439. ¹H NMR (400 MHz, DMSO-d₆) δ 8.46 (d, J=5.6 Hz, 1H), 7.81 (d, J=2.5 Hz, 1H), 7.69 (s, 1H), 6.99 (dd, J=5.6, 2.6 Hz, 1H), 5.10-5.02 (m, 1H), 4.12 (s, 2H), 3.27 (s, 3H), 3.15 (t, J=7.3

Hz, 2H), 2.93-2.85 (m, 1H), 2.81 (t, J=7.8 Hz, 2H), 2.75-2.65 (m, 2H), 2.49-2.33 (m, 2H), 2.31 (s, 3H), 2.05-1.93 (m, 2H), 1.88-1.77 (m, 1H), 1.25 (s, 9H).

Example 1.445

Synthesis of 2-({2-[4-(2-hydroxy-2-methylpropoxy)pyridin-2-yl]-5,5-dimethyl-5H,6H,7H-cyclopenta[d]pyrimidin-4-yl}(methyl)amino)-N-(propan-2-yl)acetamide (Compound 439)

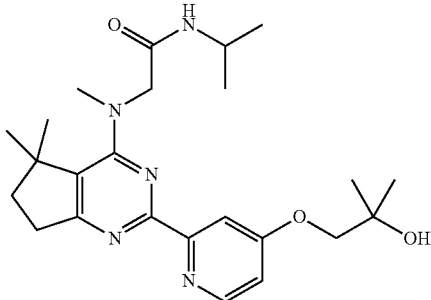

Compound 439 was synthesized similar to Compound 331 by replacing by replacing 2-(methylamino)-N-(6-methylpyridin-3-yl)acetamide with N-isopropyl-2-(methylamino)acetamide hydrochloride and by replacing ethane-1,2-diol with 2-methyl-2-(oxan-2-yloxy)propan-1-ol. LCMS (ES) [M+1]$^+$ m/z: 442. $^1$H NMR (400 MHz, DMSO-d$_6$) δ 8.49 (d, J=5.6 Hz, 1H), 8.18 (d, J=7.8 Hz, 1H), 7.83 (d, J=2.5 Hz, 1H), 7.07 (dd, J=5.7, 2.6 Hz, 1H), 4.70 (s, 1H), 4.06 (s, 2H), 3.87 (s, 2H), 3.92-3.79 (m, 1H), 3.20 (s, 3H), 2.87 (t, J=7.2 Hz, 2H), 1.88 (t, J=7.3 Hz, 2H), 1.43 (s, 6H), 1.24 (s, 6H), 1.02 (d, J=6.6 Hz, 6H).

Example 1.446

Synthesis of N-tert-butyl-2-({2-[4-(2-hydroxy-2-methylpropoxy)-6-methylpyridin-2-yl]-5H,6H,7H-cyclopenta[d]pyrimidin-4-yl}(methyl)amino)acetamide (Compound 440)

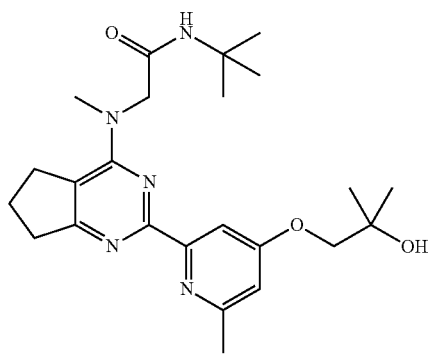 [SMILES: Cc1cc(OCC(C)(C)O)cc(-c2nc3c(c(N(C)CC(=O)NC(C)(C)C)n2)CCC3)n1]

Compound 440 was synthesized similar to Compound 427 by replacing by replacing ethane-1,2-diol with 2-methyl-2-((tetrahydro-2H-pyran-2-yl)oxy)propan-1-ol. LCMS (ES) [M+1]$^+$ m/z: 442. $^1$H NMR (300 MHz, DMSO-d6, ppm): 7.72-7.59 (m, 2H), 6.98-6.88 (m, 1H), 4.67 (br, 1H), 4.13 (s, 2H), 3.83 (s, 2H), 3.26 (s, 3H), 3.19-3.02 (m, 2H), 2.91-2.74 (m, 2H), 2.50 (s, 3H), 2.13-1.86 (m, 2H), 1.45-1.11 (m, 15H).

Example 1.447

Synthesis of N-ethyl-2-[(2-{4-[(1-hydroxycyclopropyl)methoxy]pyridin-2-yl}-5H,6H,7H-cyclopenta[d]pyrimidin-4-yl)(methyl)amino]acetamide (Compound 441)

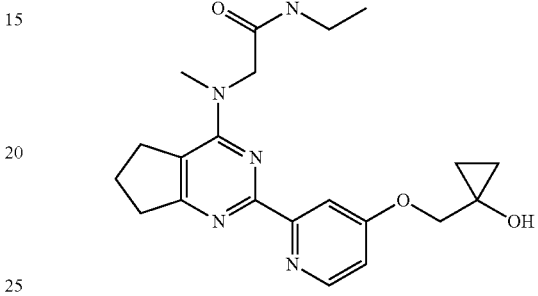

Compound 441 was synthesized similar to Compound 389 by replacing 2-methyl-2-(oxan-2-yloxy)propan-1-ol with (1-((tetrahydro-2H-pyran-2-yl)oxy)cyclopropyl)methanol and by replacing propane-2-amine with ethylamine. LCMS (ES) [M+1]$^+$ m/z: 398. $^1$H NMR (400 MHz, DMSO-d$_6$) δ 8.46 (d, J=5.6 Hz, 1H), 8.15 (t, J=5.8 Hz, 1H), 7.81 (d, J=2.6 Hz, 1H), 7.04 (dd, J=5.6, 2.6 Hz, 1H), 5.64 (s, 1H), 4.17 (s, 2H), 4.12 (s, 2H), 3.31 (s, 3H), 3.20-3.09 (m, 4H), 2.82 (t, J=7.9 Hz, 2H), 2.03-1.95 (m, 2H), 1.00 (t, J=7.2 Hz, 3H), 0.71 (d, J=3.5 Hz, 2H), 0.70-0.63 (m, 2H).

Example 1.448

Synthesis of N-ethyl-2-({2-[4-(2-ethyl-2-hydroxybutoxy)pyridin-2-yl]-5H,6H,7H-cyclopenta[d]pyrimidin-4-yl}(methyl)amino)acetamide (Compound 442)


Compound 442 was synthesized similar to Compound 389 by replacing 2-methyl-2-(oxan-2-yloxy)propan-1-ol with 2-ethyl-2-((tetrahydro-2H-pyran-2-yl)oxy)butan-1-ol and by replacing propane-2-amine with ethylamine. LCMS (ES) [M+1]$^+$ m/z: 428. $^1$H NMR (300 MHz, DMSO-d6) δ 8.47 (d, J=5.6 Hz, 1H), 8.18 (t, J=5.7 Hz, 1H), 7.80 (d, J=2.5 Hz, 1H), 7.05 (dd, J=5.7, 2.6 Hz, 1H), 4.43 (s, 1H), 4.17 (s, 2H), 3.88 (s, 2H), 3.28 (s, 3H), 3.20-3.07 (m, 4H), 2.82 (t, J=7.8 Hz, 2H), 2.04-1.94 (m, 2H), 1.62-1.46 (m, 4H), 1.00 (t, J=7.2 Hz, 3H), 0.85 (t, J=7.5 Hz, 6H).

Example 1.449

Synthesis of 2-({2-[4-(2-ethyl-2-hydroxybutoxy)pyridin-2-yl]-5H,6H,7H-cyclopenta[d]pyrimidin-4-yl}(methyl)amino)-N-methylacetamide (Compound 443)

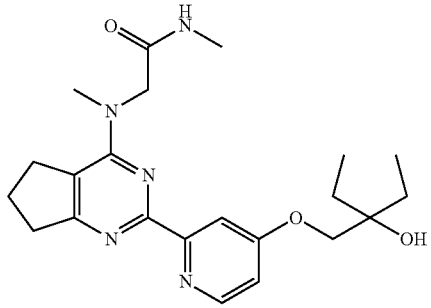 [SMILES: CCC(O)(CC)COc1ccnc(-c2nc3c(c(N(C)CC(=O)NC)n2)CCC3)c1]

Compound 443 was synthesized similar to Compound 389 by replacing 2-methyl-2-(oxan-2-yloxy)propan-1-ol with 2-ethyl-2-((tetrahydro-2H-pyran-2-yl)oxy)butan-1-ol and by replacing propane-2-amine with methylamine. LCMS (ES) [M+1]$^+$ m/z: 414. $^1$H NMR (400 MHz, DMSO-d$_6$) δ 8.47 (d, J=5.6 Hz, 1H), 8.14 (s, 1HCOOH), 8.12 (d, J=4.9 Hz, 1H), 7.78 (d, J=2.5 Hz, 1H), 7.08-7.01 (m, 1H), 4.42 (s, 1H), 4.18 (s, 2H), 3.89 (s, 2H), 3.28 (s, 3H), 3.16 (t, J=7.3 Hz, 2H), 2.82 (t, J=7.8 Hz, 2H), 2.63 (d, J=4.5 Hz, 3H), 2.04-1.94 (m, 2H), 1.62-1.48 (m, 4H), 0.86 (t, J=7.5 Hz, 6H).

Example 1.450

Synthesis of 2-[(2-{4-[(4-hydroxyoxan-4-yl)methoxy]pyridin-2-yl}-5H,6H,7H-cyclopenta[d]pyrimidin-4-yl)(methyl)amino]-N-(propan-2-yl)acetamide (Compound 444)

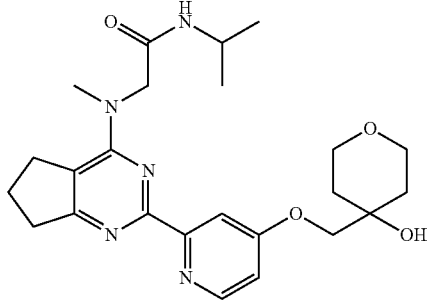 [SMILES: CC(C)NC(=O)CN(C)c1nc(-c2cc(OCC3(O)CCOCC3)ccn2)nc2c1CCC2]

Compound 444 was synthesized similar to Compound 389 by replacing 2-methyl-2-(oxan-2-yloxy)propan-1-ol with (4-(ethoxymethoxy)tetrahydro-2H-pyran-4-yl)methanol. LCMS (ES) [M+1]$^+$ m/z: 456. $^1$H NMR (300 MHz, DMSO-d$_6$) δ 8.48 (d, J=5.6 Hz, 1H), 8.15 (s, 1HCOOH), 8.02 (d, J=7.8 Hz, 1H), 7.83 (d, J=2.5 Hz, 1H), 7.06 (dd, J=5.7, 2.6 Hz, 1H), 4.79 (s, 1H), 4.16 (s, 2H), 3.93 (s, 2H), 3.92-3.79 (m, 1H), 3.67 (dd, J=7.0, 2.4 Hz, 4H), 3.27 (s, 3H), 3.15 (t, J=7.3 Hz, 2H), 2.82 (t, J=7.8 Hz, 2H), 2.04-1.94 (m, 2H), 1.85-1.67 (m, 2H), 1.50 (d, J=13.3 Hz, 2H), 1.04 (d, J=6.6 Hz, 6H)

Example 1.451

Synthesis of N-tert-butyl-2-[(2-{4-[(2R)-2-hydroxy-2-methylbutoxy]pyridin-2-yl}-5H,6H,7H-cyclopenta[d]pyrimidin-4-yl)(methyl)amino]acetamide (Compound 445)

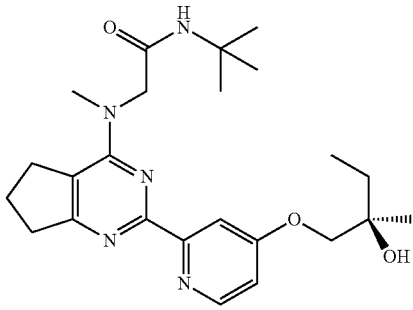 [SMILES: CC[C@@](C)(O)COc1ccnc(-c2nc3c(c(N(C)CC(=O)NC(C)(C)C)n2)CCC3)c1]

Compound 445 was synthesized similar to Compound 174 by replacing 2-methyl-2-(oxan-2-yloxy)propan-1-ol with (2R)-2-methyl-2-((tetrahydro-2H-pyran-2-yl)oxy)butyl (2S)-2-phenylpropanoate. LCMS (ES) [M+1]$^+$ m/z: 442. $^1$H NMR (300 MHz, DMSO-d$_6$) δ 8.48 (d, J=5.4 Hz, 1H), 7.82 (d, J=2.7 Hz, 1H), 7.67 (s, 1H), 7.07 (dd, J=5.4, 2.4 Hz, 1H), 4.55 (s, 1H), 4.14 (s, 2H), 3.90 (q, J=12.0, 9.3 Hz, 2H), 3.27 (s, 3H), 3.14 (d, J=7.3 Hz, 2H), 2.82 (t, J=7.8 Hz, 2H), 2.01-1.96 (m, 2H), 1.57 (q, J=7.5 Hz, 2H), 1.25 (s, 9H), 1.19 (s, 3H), 0.88 (t, J=7.5 Hz, 3H).

Example 1.452

Synthesis of N-tert-butyl-2-[(2-{4-[(2R)-2-hydroxy-2-methylbutoxy]pyridin-2-yl}-5H,6H,7H-cyclopenta[d]pyrimidin-4-yl)(methyl)amino]acetamide (Compound 446)

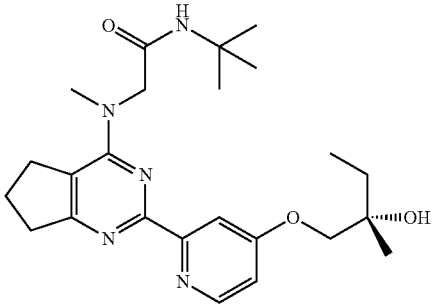 [SMILES: CC[C@](C)(O)COc1ccnc(-c2nc3c(c(N(C)CC(=O)NC(C)(C)C)n2)CCC3)c1]

Compound 446 was synthesized similar to Compound 174 by replacing 2-methyl-2-(oxan-2-yloxy)propan-1-ol with (2R)-2-methyl-2-((tetrahydro-2H-pyran-2-yl)oxy)butyl (2S)-2-phenylpropanoate. LCMS (ES) [M+1]$^+$ m/z: 442. $^1$H NMR (300 MHz, DMSO-d$_6$) δ 8.48 (d, J=5.4 Hz, 1H), 7.82 (d, J=2.7 Hz, 1H), 7.67 (s, 1H), 7.07 (dd, J=5.4, 2.4 Hz, 1H), 4.55 (s, 1H), 4.14 (s, 2H), 3.90 (q, J=12.0, 9.3 Hz, 2H), 3.27 (s, 3H), 3.17 (s, 1H), 3.14 (d, J=7.3 Hz, 2H), 2.82 (t, J=7.8 Hz, 2H), 1.99 (p, J=7.7 Hz, 2H), 1.57 (q, J=7.5 Hz, 2H), 1.25 (s, 9H), 1.19 (s, 3H), 0.88 (t, J=7.5 Hz, 3H).

Example 1.453

Synthesis of N-ethyl-2-[(2-{4-[(4-hydroxyoxan-4-yl)methoxy]pyridin-2-yl}-5H,6H,7H-cyclopenta[d]pyrimidin-4-yl)(methyl)amino]acetamide (Compound 447)

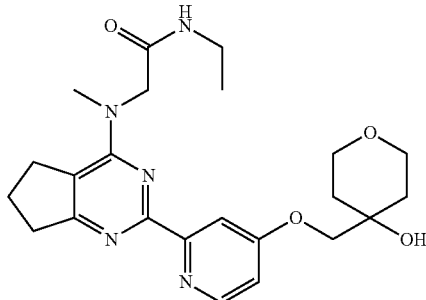

Compound 447 was synthesized similar to Compound 389 by replacing 2-methyl-2-(oxan-2-yloxy)propan-1-ol with (4-(ethoxymethoxy)tetrahydro-2H-pyran-4-yl)methanol and by replacing propane-2-amine with ethylamine. LCMS (ES) [M+1]⁺ m/z: 441. ¹H NMR (300 MHz, DMSO-d₆) δ 8.48 (d, J=5.6 Hz, 1H), 8.18 (t, J=5.6 Hz, 1H), 7.82 (d, J=2.5 Hz, 1H), 7.07 (dd, J=5.7, 2.6 Hz, 1H), 4.80 (s, 1H), 4.18 (s, 2H), 3.94 (s, 2H), 3.76-3.63 (m, 4H), 3.29 (s, 3H), 3.21-3.05 (m, 4H), 2.83 (t, J=7.8 Hz, 2H), 2.05-1.95 (m, 2H), 1.76 (dt, J=13.4, 8.3 Hz, 2H), 1.51 (d, J=13.3 Hz, 2H), 1.01 (t, J=7.2 Hz, 3H).

Example 1.454

Synthesis of 2-[(2-{4-[(2R)-2-hydroxy-3-methoxypropoxy]pyridin-2-yl}-5H,6H,7H-cyclopenta[d]pyrimidin-4-yl)(methyl)amino]-N-(propan-2-yl)acetamide (Compound 448)

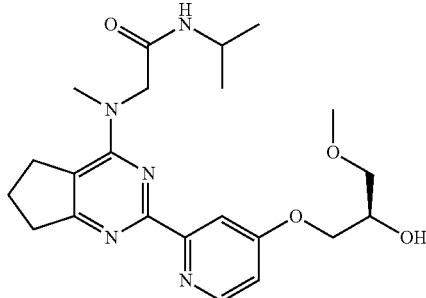

Compound 448 was synthesized similar to Compound 389 by replacing 2-methyl-2-(oxan-2-yloxy)propan-1-ol with (2S)-3-methoxy-2-(oxan-2-yloxy)propan-1-ol. LCMS (ES) [M+1]⁺ m/z: 430. ¹H NMR (300 MHz, DMSO-d₆) δ 8.47 (d, J=5.6 Hz, 1H), 8.01 (d, J=7.8 Hz, 1H), 7.82 (d, J=2.5 Hz, 1H), 7.04 (dd, J=5.6, 2.6 Hz, 1H), 5.19 (d, J=5.0 Hz, 1H), 4.16 (s, 2H), 4.13-3.92 (m, 3H), 3.86 (dt, J=13.5, 6.8 Hz, 1H), 3.48-3.38 (m, 2H), 3.30 (s, 3H), 3.27 (s, 3H), 3.15 (t, J=7.3 Hz, 2H), 2.82 (t, J=7.8 Hz, 2H), 2.04-1.96 (m, 2H), 1.05 (d, J=6.5 Hz, 6H).

Example 1.455

Synthesis of 2-({2-[4-(2-hydroxy-2-methylpropoxy)pyridin-2-yl]-6,6-dimethyl-5H,6H,7H-cyclopenta[d]pyrimidin-4-yl}(methyl)amino)-N-(propan-2-yl)acetamide (Compound 449)

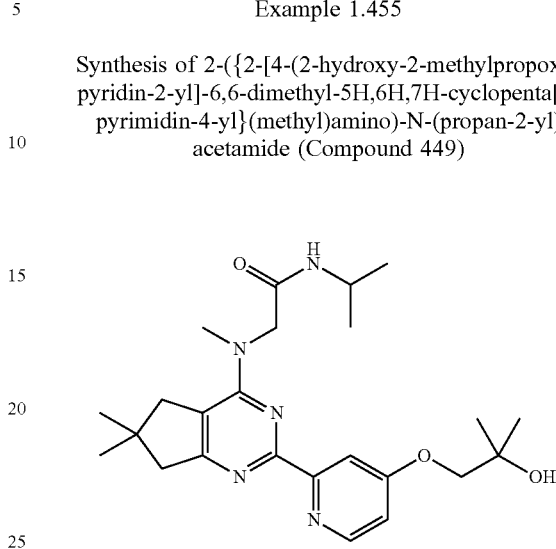

Compound 449 was synthesized similar to Compound 389 by replacing methyl 2-oxocyclopentane-1-carboxylate with 4,4-dimethyl-2-oxocyclopentane-1-carboxylate. LCMS (ES) [M+1]⁺ m/z: 442. ¹H NMR (400 MHz, DMSO-d₆) δ 8.47 (d, J=5.5 Hz, 1H), 8.00 (d, J=7.8 Hz, 1H), 7.81 (d, J=2.6 Hz, 1H), 7.04 (dd, J=5.7, 2.7 Hz, 1H), 4.70 (s, 1H), 4.13 (s, 2H), 3.92-3.82 (m, 3H), 3.24 (s, 3H), 2.95 (s, 2H), 2.66 (s, 2H), 1.24 (s, 6H), 1.15 (s, 6H), 1.05 (d, J=6.6 Hz, 6H).

Example 1.456

Synthesis of 2-({2-[4-(2-hydroxy-2-methylpropoxy)pyridin-2-yl]-7,7-dimethyl-5H,6H,7H-cyclopenta[d]pyrimidin-4-yl}(methyl)amino)-N-(propan-2-yl)acetamide (Compound 450)

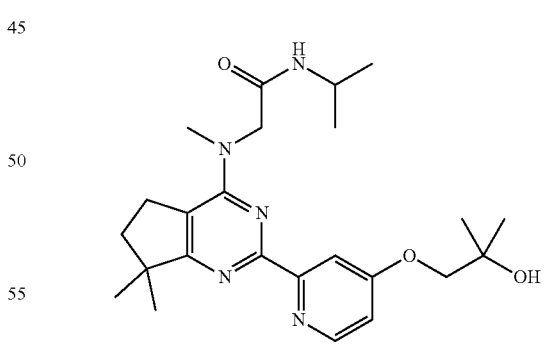

Compound 450 was synthesized similar to Compound 389 by replacing methyl 2-oxocyclopentane-1-carboxylate with 3,3-dimethyl-2-oxocyclopentane-1-carboxylate. LCMS (ES) [M+1]⁺ m/z: 442. ¹H NMR (300 MHz, DMSO-d₆) δ 8.50 (d, J=5.6 Hz, 1H), 8.02 (d, J=7.8 Hz, 1H), 7.81 (d, J=2.5 Hz, 1H), 7.06 (dd, J=5.7, 2.6 Hz, 1H), 4.73 (s, 1H), 4.16 (s, 2H), 3.95-3.80 (m, 3H), 3.28 (s, 3H), 3.10 (t, J=7.0 Hz, 2H), 1.87 (t, J=7.0 Hz, 2H), 1.23 (d, J=5.9 Hz, 12H), 1.05 (d, J=6.6 Hz, 7H).

Example 1.457

Synthesis of N-tert-butyl-2-[(2-{4-[(2S)-2,3-dihydroxypropoxy]pyridin-2-yl}-5H,6H,7H-cyclopenta[d]pyrimidin-4-yl)(methyl)amino]acetamide (Compound 451)

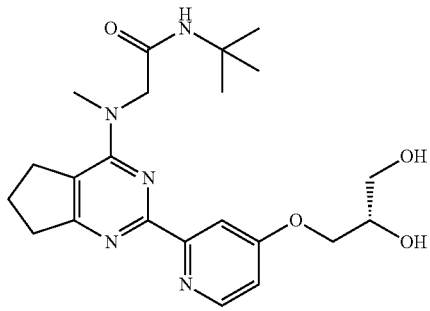 [SMILES: CN(CC(=O)NC(C)(C)C)c1nc(-c2cc(OC[C@@H](O)CO)ccn2)nc2c1CCC2]

Compound 451 was synthesized similar to Compound 415 by replacing N-Tert-butyl-2-{[2-(4-{[(4S)-2,2-dimethyl-1,3-dioxolan-4-yl]methoxy}pyridin-2-yl)-5H,6H,7H-cyclopenta[d]pyrimidin-4-yl](methyl)amino}acetamide with N-Tert-butyl-2-{[2-(4-{[(4R)-2,2-dimethyl-1,3-dioxolan-4-yl]methoxy}pyridin-2-yl)-5H,6H,7H-cyclopenta[d]pyrimidin-4-yl](methyl)amino}acetamide. LCMS (ES) [M+1]$^+$ m/z: 430.2. $^1$H NMR (400 MHz, DMSO-$d_6$) δ 8.47 (d, J=5.6 Hz, 1H), 7.85 (d, J=2.5 Hz, 1H), 7.68 (s, 1H), 7.05 (dd, J=5.7, 2.6 Hz, 1H), 5.00 (d, J=5.1 Hz, 1H), 4.76-4.67 (m, 1H), 4.18-4.10 (m, 3H), 4.02 (dd, J=10.0, 6.0 Hz, 1H), 3.86-3.79 (m, 1H), 3.50-3.44 (m, 2H), 3.26 (s, 3H), 3.16-3.10 (m, 2H), 2.84-2.78 (m, 2H), 2.03-1.94 (m, 2H), 1.24 (s, 9H).

Example 1.458

Synthesis of N-tert-butyl-2-[(2-{4-[(2S)-3-fluoro-2-hydroxypropoxy]pyridin-2-yl}-5H,6H,7H-cyclopenta[d]pyrimidin-4-yl)(methyl)amino]acetamide (Compound 452)

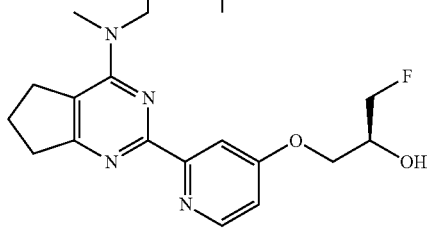

Scheme 134

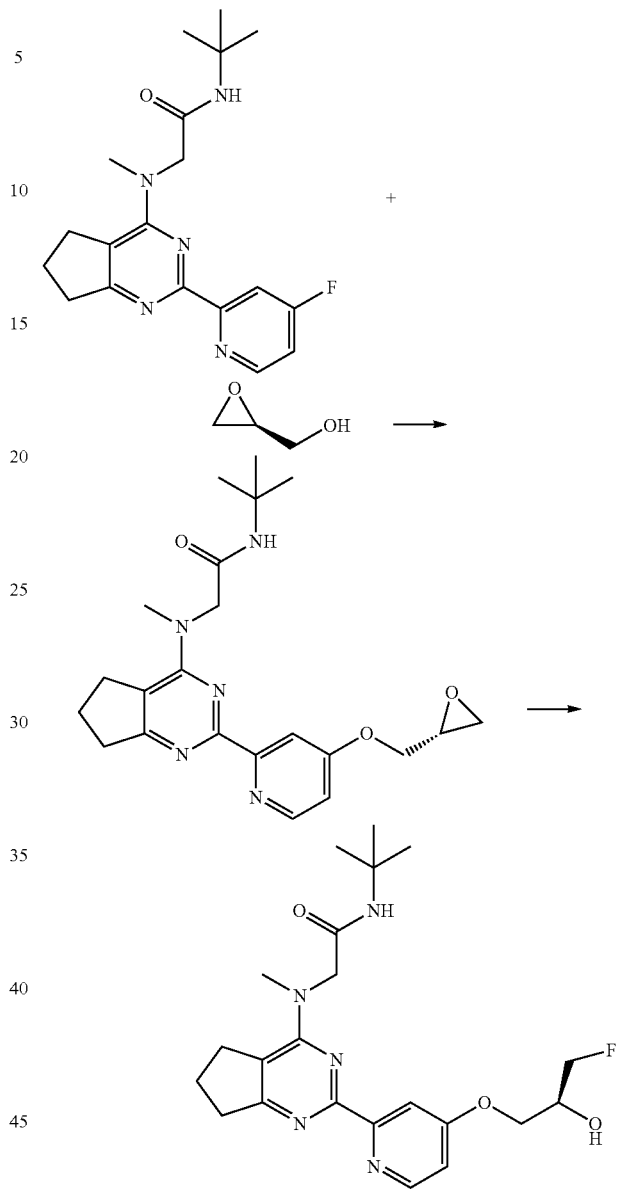

Step 1

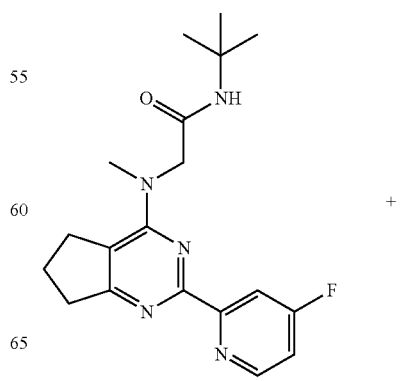

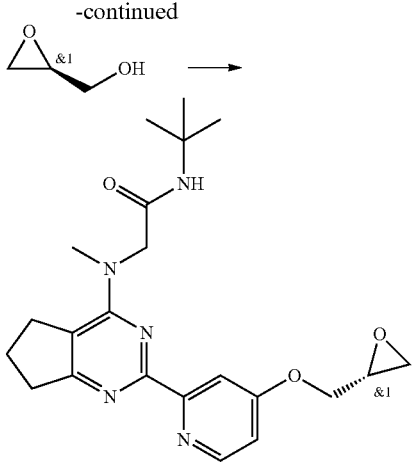

(2S)-2-Oxiranylmethanol (28 mg; 0.38 mmol; 1.1 eq.) was dissolved in N,N-dimethylformamide (1.5 ml). and cooled in an ice bath. Sodium hydride (60%, 30 mg; 0.76 mmol; 2.2 eq.) was added. N-Tert-butyl-2-{[2-(4-fluoropyridin-2-yl)-5H,6H,7H-cyclopenta[d]pyrimidin-4-yl](methyl)amino}acetamide (123 mg; 0.34 mmol; 1 eq.) (gcxy02152) dissolved in DMF (2 ml) was added slowly and the reaction was stirred at 25° C. for 18 h. Water (20 ml) was carefully added and the mixture was extracted with ethyl acetate (3×25 ml). The combined organic phases were washed with saturated sodium chloride solution and dried over sodium sulfate. After evaporation, the residue was purified by reverse phase chromatography (Waters XSelect CSH C18 column, 0-70% acetonitrile/0.1% aqueous formic acid gradient) to give N-tert-butyl-2-[methyl(2-{4-[(2R)-oxiran-2-ylmethoxy]pyridin-2-yl}-5H,6H,7H-cyclopenta[d]pyrimidin-4-yl)amino]acetamide (35 mg, 25%) as an off-white solid. LCMS (ES+): [M+H]$^+$=412.1.

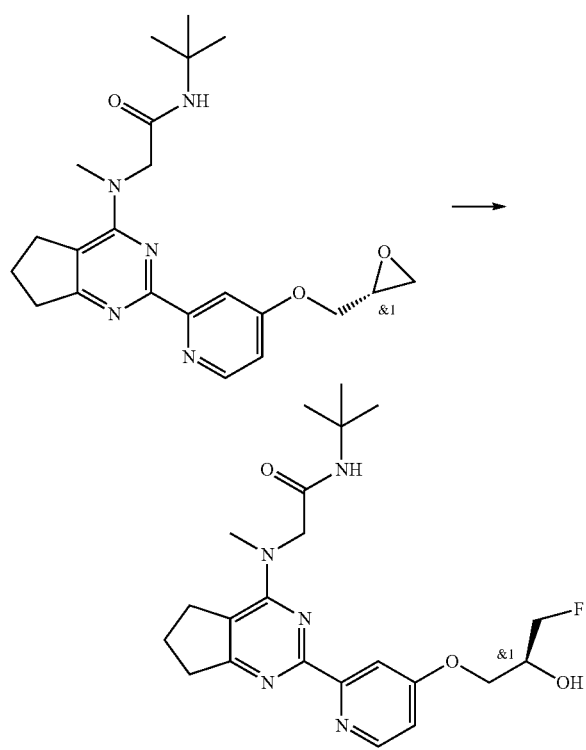

N-Tert-butyl-2-[methyl(2-{4-[(2R)-oxiran-2-ylmethoxy]pyridin-2-yl}-5H,6H,7H-cyclopenta[d]pyrimidin-4-yl)amino]acetamide (40 mg; 0.1 mmol; 1 eq.) was suspended in toluene (5 ml). Tetrabutylammonium fluoride (0.49 mL; 1 mol/L THF; 0.49 mmol; 5 eq.) was added slowly. The reaction was warmed to 80° C. in a sand bath for 3 h. Solvents were evaporated and the residue was purified by reverse phase chromatography (Waters XSelect CSH C18 column, 0-60% acetonitrile/0.1% aqueous formic acid gradient) to give N-tert-butyl-2-[(2-{4-[(2S)-3-fluoro-2-hydroxypropoxy]pyridin-2-yl}-5H,6H,7H-cyclopenta[d]pyrimidin-4-yl)(methyl)amino]acetamide (18 mg, 43%) as a white solid. LCMS (ES+): [M+H]$^+$=432.1. $^1$H NMR (400 MHz, DMSO-d6) δ 8.48 (d, J=5.6 Hz, 1H), 7.85 (d, J=2.5 Hz, 1H), 7.68 (s, 1H), 7.06 (dd, J=5.6, 2.6 Hz, 1H), 5.52 (s, 1H), 4.62-4.53 (m, 1H), 4.50-4.41 (m, 1H), 4.15-4.04 (m, 5H), 3.26 (s, 3H), 3.16-3.11 (m, 3H), 2.84-2.77 (m, 2H), 2.03-1.94 (m, 2H), 1.24 (s, 9H).

Example 1.459

Synthesis of (2R)-2-({2-[4-(2-hydroxy-2-methylpropoxy)pyridin-2-yl]-5H,6H,7H-cyclopenta[d]pyrimidin-4-yl}(methyl)amino)-N-(propan-2-yl)propanamide (Compound 453)

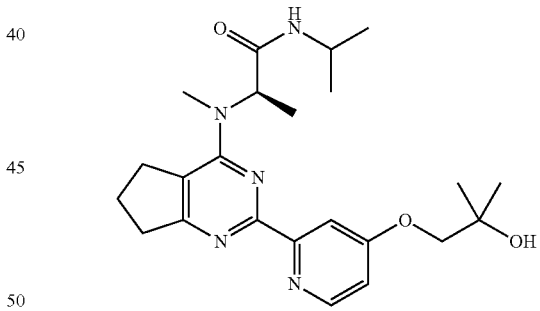

Compound 453 was synthesized similar to Compound 389 by replacing N-isopropyl-2-(methylamino)acetamide hydrochloride with (2R)—N-isopropyl-2-(methylamino)propenamide. LCMS (ES) [M+1]$^+$ m/z: 428. $^1$H NMR (400 MHz, DMSO-d$_6$) δ 8.50 (d, J=5.6 Hz, 1H), 8.27 (d, J=8.0 Hz, 1H), 7.88 (d, J=2.6 Hz, 1H), 7.07 (dd, J=5.7, 2.6 Hz, 1H), 5.11 (q, J=7.0 Hz, 1H), 4.70 (s, 1H), 3.89 (s, 2H), 4-3.85 (m, 1H), 3.28-3.16 (m, 1H), 3.11-3.04 (m, 4H), 2.96-2.77 (m, 2H), 2.10-1.92 (m, 2H), 1.34 (d, J=7.0 Hz, 3H), 1.24 (s, 6H), 1.09 (d, J=6.6 Hz, 3H), 0.90 (d, J=6.5 Hz, 3H).

Example 1.460

Synthesis of N-tert-butyl-2-[(2-{4-[2-(dimethyl-amino)ethoxy]pyridin-2-yl}-6,6-dimethyl-5H,6H,7H-cyclopenta[d]pyrimidin-4-yl)(methyl)amino]acetamide (Compound 454)

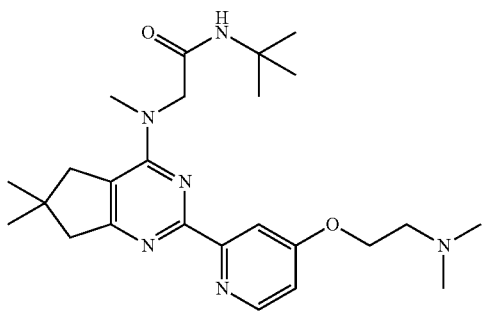

Compound 454 was synthesized similar to Compound 348 by replacing methyl 2-oxocyclopentane-1-carboxylate with 4,4-dimethyl-2-oxocyclopentane-1-carboxylate. LCMS (ES) [M+1]$^+$ m/z: 455. $^1$H NMR (400 MHz, DMSO-d$_6$) δ 8.47 (d, J=5.7 Hz, 1H), 7.83 (d, J=2.6 Hz, 1H), 7.65 (s, 1H), 7.05 (dd, J=5.7, 2.7 Hz, 1H), 4.20 (t, J=5.7 Hz, 2H), 4.10 (s, 2H), 3.24 (s, 3H), 2.95 (s, 2H), 2.70-2.63 (m, 4H), 2.23 (s, 6H), 1.25 (s, 9H), 1.15 (s, 6H).

Example 1.461

Synthesis of 2-[(2-{4-[2-(dimethylamino)ethoxy]pyridin-2-yl}-6,6-dimethyl-5H,6H,7H-cyclopenta[d]pyrimidin-4-yl)(methyl)amino]-N-(propan-2-yl)acetamide (Compound 455)

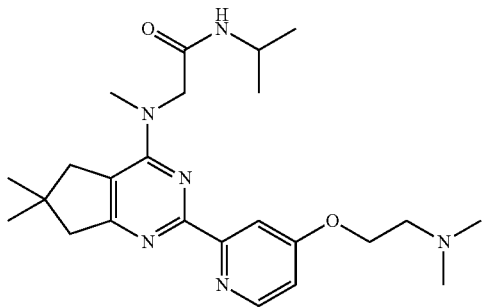

Compound 455 was synthesized similar to Compound 348 by replacing methyl 2-oxocyclopentane-1-carboxylate with 4,4-dimethyl-2-oxocyclopentane-1-carboxylate and by replacing tert-butylamine with propan-2-amine. LCMS (ES) [M+1]$^+$ m/z: 441. $^1$H NMR (400 MHz, DMSO-d$_6$) δ 8.47 (d, J=5.5 Hz, 1H), 8.21 (s, 2HCOOH), 7.97 (d, J=7.9 Hz, 1H), 7.80 (d, J=2.6 Hz, 1H), 7.05 (dd, J=5.7, 2.6 Hz, 1H), 4.20 (t, J=5.7 Hz, 2H), 4.12 (s, 2H), 3.92-3.83 (m, 1H), 3.24 (s, 3H), 2.95 (s, 2H), 2.72-2.64 (m, 4H), 2.24 (s, 6H), 1.15 (s, 6H), 1.05 (d, J=6.6 Hz, 6H).

Example 1.462

Synthesis of 2-[(2-{4-[2-(dimethylamino)ethoxy]pyridin-2-yl}-7,7-dimethyl-5H,6H,7H-cyclopenta[d]pyrimidin-4-yl)(methyl)amino]-N-(propan-2-yl)acetamide (Compound 456)

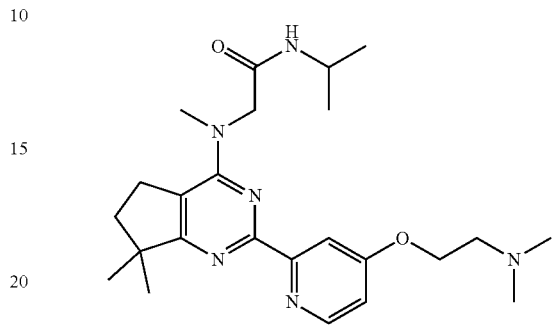

Compound 456 was synthesized similar to Compound 348 by replacing methyl 2-oxocyclopentane-1-carboxylate with 3,3-dimethyl-2-oxocyclopentane-1-carboxylate and by replacing tert-butylamine with propan-2-amine. LCMS (ES) [M+1]$^+$ m/z: 441. $^1$H NMR (300 MHz, DMSO-d6, ppm): δ 8.50 (d, J=5.6 Hz, 1H), 8.00 (d, J=7.8 Hz, 1H), 7.81 (d, J=2.5 Hz, 1H), 7.07 (dd, J=5.7, 2.6 Hz, 1H), 4.19 (t, J=5.7 Hz, 2H), 4.14 (s, 2H), 3.87 (dq, J=13.3, 6.6 Hz, 1H), 3.28 (s, 3H), 3.10 (t, J=7.0 Hz, 2H), 2.66 (t, J=5.7 Hz, 2H), 2.23 (s, 6H), 1.87 (t, J=7.0 Hz, 2H), 1.22 (s, 6H), 1.05 (d, J=6.6 Hz, 6H).

Example 1.463

Synthesis of N-tert-butyl-2-[(2-{4-[2-(dimethylamino)ethoxy]pyridin-2-yl}-7,7-dimethyl-5H,6H,7H-cyclopenta[d]pyrimidin-4-yl)(methyl)amino]acetamide (Compound 457)

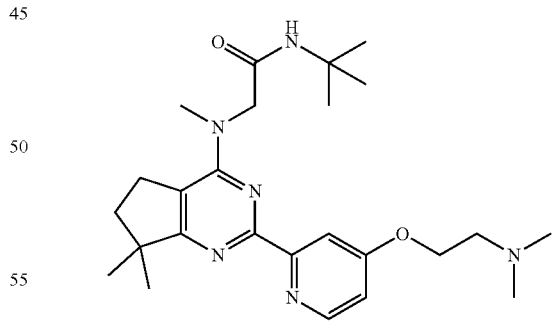

Compound 457 was synthesized similar to Compound 348 by replacing methyl 2-oxocyclopentane-1-carboxylate with 3,3-dimethyl-2-oxocyclopentane-1-carboxylate. LCMS (ES) [M+1]$^+$ m/z: 441. $^1$H NMR (300 MHz, DMSO-d6, ppm): δ 8.51 (d, J=5.6 Hz, 1H), 7.84 (d, J=2.5 Hz, 1H), 7.69 (s, 1H), 7.08 (dd, J=5.7, 2.6 Hz, 1H), 4.22 (t, J=5.7 Hz, 2H), 4.13 (s, 2H), 3.28 (s, 3H), 3.12 (t, J=7.0 Hz, 2H), 2.68 (t, J=5.7 Hz, 2H), 2.23 (s, 6H), 1.89 (t, J=7.0 Hz, 2H), 1.25 (s, 9H), 1.22 (s, 6H).

Example 1.464

Synthesis of N-[(2R)-1-hydroxypropan-2-yl]-2-{[2-(4-methoxypyridin-2-yl)-5H,6H,7H-cyclopenta[d]pyrimidin-4-yl](methyl)amino}acetamidede (Compound 458)

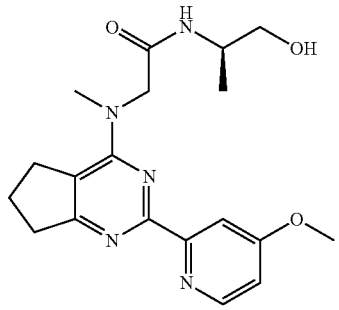 [SMILES: COc1ccnc(-c2nc3c(c(N(C)CC(=O)N[C@H](C)CO)n2)CCC3)c1]

Compound 458 was synthesized similar to Compound 135 by replacing oxolan-3-amine with (R)-2-amino-1-propanol. LCMS (ES) [M+1]$^+$ m/z: 372. $^1$H NMR (300 MHz, DMSO-d6, ppm): δ 8.48 (d, J=5.6 Hz, 1H), 7.88 (d, J=8.2 Hz, 1H), 7.82 (d, J=2.6 Hz, 1H), 7.04 (dd, J=5.7, 2.6 Hz, 1H), 4.65 (t, J=5.6 Hz, 1H), 4.22 (d, J=16.4 Hz, 1H), 4.15 (d, J=16.4 Hz, 1H), 3.90 (s, 3H), 3.80 (p, J=6.8 Hz, 1H), 3.39-3.32 (m, 1H), 3.27 (s, 3H), 3.21 (q, J=5.4, 4.6 Hz, 1H), 3.16 (q, J=7.4, 5.5 Hz, 2H), 2.82 (t, J=7.9 Hz, 2H), 2.02-1.95 (m, 2H), 1.01 (d, J=6.7 Hz, 3H).

Example 1.465

Synthesis of N-[(2S)-1-hydroxypropan-2-yl]-2-{[2-(4-methoxypyridin-2-yl)-5H,6H,7H-cyclopenta[d]pyrimidin-4-yl](methyl)amino}acetamide (Compound 459)

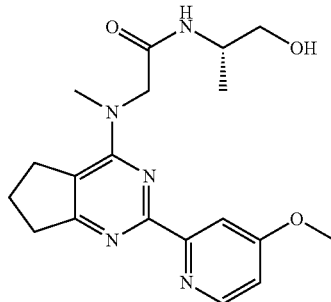

Compound 459 was synthesized similar to Compound 135 by replacing oxolan-3-amine with (S)-2-amino-1-propanol. LCMS (ES) [M+1]$^+$ m/z: 372. $^1$H NMR (300 MHz, DMSO-d6, ppm): δ 8.48 (d, J=5.6 Hz, 1H), 7.88 (d, J=8.1 Hz, 1H), 7.82 (d, J=2.6 Hz, 1H), 7.04 (dd, J=5.7, 2.6 Hz, 1H), 4.65 (t, J=5.6 Hz, 1H), 4.22 (d, J=16.4 Hz, 1H), 4.14 (d, J=16.4 Hz, 1H), 3.89 (s, 3H), 3.78 (q, J=6.7 Hz, 1H), 3.33 (d, J=6.0 Hz, 1H), 3.26 (s, 3H), 3.25-3.11 (m, 3H), 2.82 (t, J=7.8 Hz, 2H), 2.04-1.93 (m, 2H), 1.00 (d, J=6.7 Hz, 3H).

Example 1.466

Synthesis of N-tert-butyl-2-[methyl(2-{4-[2-(morpholin-4-yl)ethoxy]pyridin-2-yl}-5H,6H,7H-cyclopenta[d]pyrimidin-4-yl)amino]acetamide (Compound 460)

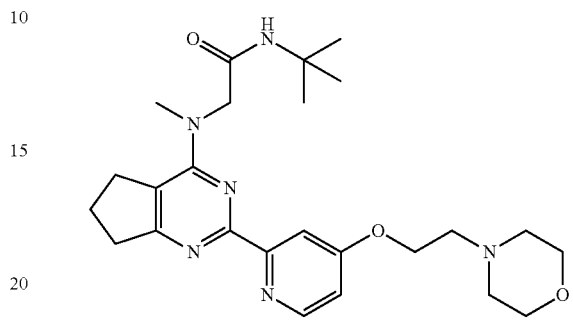

Compound 460 was synthesized similar to Compound 348 by replacing dimethylaminoethanol with 4-morpholineethanol. LCMS (ES) [M+1]$^+$ m/z: 469. $^1$H NMR (300 MHz, DMSO-d6, ppm): δ 8.47 (d, J=5.6 Hz, 1H), 7.84 (d, J=2.5 Hz, 1H), 7.68 (s, 1H), 7.06 (dd, J=5.7, 2.6 Hz, 1H), 4.24 (t, J=5.6 Hz, 2H), 4.13 (s, 2H), 3.59 (d, J=9.3 Hz, 4H), 3.27 (s, 3H), 3.15 (t, J=7.3 Hz, 2H), 2.88-2.67 (m, 4H), 2.48 (d, J=4.5 Hz, 4H), 2.01-1.96 (m, 2H), 1.25 (s, 9H).

Example 1.467

Synthesis of N-tert-butyl-2-{methyl[2-(4-{2-[(1S,4S)-2-oxa-5-azabicyclo[2.2.1]heptan-5-yl]ethoxy}pyridin-2-yl)-5H,6H,7H-cyclopenta[d]pyrimidin-4-yl]amino}acetamide (Compound 461)

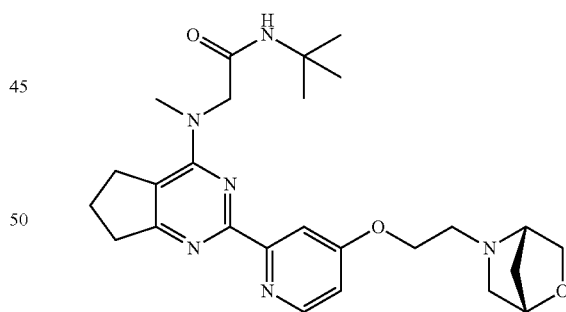

Compound 461 was synthesized similar to Compound 508 by replacing bis(methyl-d3)amine hydrochloride with (1S,4S)-2-oxa-5-azabicyclo[2.2.1]heptane hydrochloride. LCMS (ES) [M+1]$^+$ m/z: 481. $^1$H NMR (400 MHz, DMSO-d6, ppm): δ 8.47 (d, J=5.5 Hz, 1H), 8.16 (s, 2HCOOH), 7.83 (d, J=2.6 Hz, 1H), 7.66 (s, 1H), 7.05 (dd, J=5.7, 2.6 Hz, 1H), 4.34 (s, 1H), 4.17 (t, J=5.7 Hz, 2H), 4.13 (s, 2H), 3.86 (d, J=7.6 Hz, 1H), 3.61-3.50 (m, 2H), 3.26 (s, 3H), 3.15 (t, J=7.3 Hz, 2H), 2.97 (dq, J=11.6, 6.6, 6.2 Hz, 2H), 2.92-2.88 (m, 1H), 2.81 (t, J=7.9 Hz, 2H), 2.53 (d, J=6.8 Hz, 1H), 2.00-1.96 (m, 2H), 1.74 (d, J=9.4 Hz, 1H), 1.60 (d, J=9.6 Hz, 1H), 1.25 (s, 9H).

Example 1.468

Synthesis of N-tert-butyl-2-{methyl[2-(4-{2-[(1R,4R)-2-oxa-5-azabicyclo[2.2.1]heptan-5-yl]ethoxy}pyridin-2-yl)-5H,6H,7H-cyclopenta[d]pyrimidin-4-yl]amino}acetamide (Compound 462)

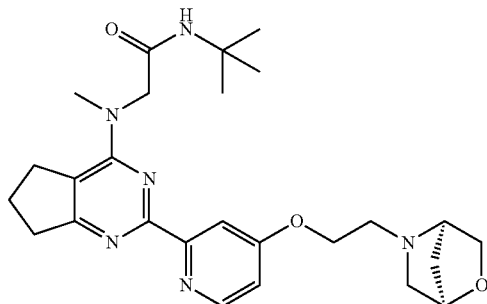

Compound 462 was synthesized similar to Compound 348 by replacing dimethylaminoethanol with 2-[(1R,4R)-2-oxa-5-azabicyclo[2.2.1]heptan-5-yl]ethanol. LCMS (ES) [M+1]+ m/z: 481. ¹H NMR (400 MHz, DMSO-d6, ppm): δ 8.47 (d, J=5.6 Hz, 1H), 8.16 (s, 2HCOOH), 7.83 (d, J=2.5 Hz, 1H), 7.67 (s, 1H), 7.05 (dd, J=5.7, 2.5 Hz, 1H), 4.35 (s, 1H), 4.22-4.10 (m, 4H), 3.86 (d, J=7.6 Hz, 1H), 3.59 (s, 1H), 3.53 (dd, J=7.6, 1.8 Hz, 1H), 3.26 (s, 3H), 3.14 (t, J=7.3 Hz, 2H), 3.07-2.86 (m, 3H), 2.81 (t, J=7.8 Hz, 2H), 2.55-2.50 (m, 1H), 2.02-1.96 (m, 2H), 1.75 (dd, J=9.5, 2.1 Hz, 1H), 1.60 (d, J=9.4 Hz, 1H), 1.24 (s, 9H).

Example 1.469

Synthesis of N-tert-butyl-2-{[2-(4-{2-[(3R)-3-methoxypyrrolidin-1-yl]ethoxy}pyridin-2-yl)-5H,6H,7H-cyclopenta[d]pyrimidin-4-yl](methyl)amino}acetamide (Compound 463)

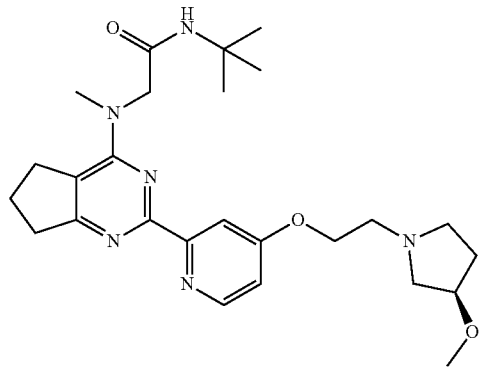 [SMILES: CO[C@@H]1CCN(CCOc2ccnc(-c3nc4c(c(N(C)CC(=O)NC(C)(C)C)n3)CCC4)c2)C1]

Compound 463 was synthesized similar to Compound 508 by replacing bis(methyl-d3)amine hydrochloride with (3R)-3-methoxypyrrolidine hydrochloride. LCMS (ES) [M+1]+ m/z: 483. ¹H NMR (400 MHz, DMSO-d6, ppm): δ 8.48 (d, J=5.6 Hz, 1H), 8.16 (s, 2HCOOH), 7.84 (d, J=2.6 Hz, 1H), 7.67 (s, 1H), 7.06 (dd, J=5.7, 2.6 Hz, 1H), 4.23 (t, J=5.6 Hz, 2H), 4.13 (s, 2H), 3.95-3.85 (m, 1H), 3.27 (s, 3H), 3.18 (s, 3H), 3.14 (7 J=7.3 Hz, 2H), 2.90 (t, J=5.6 Hz, 2H), 2.89-2.73 (m, 3H), 2.77- 2.52 (m, 3H), 2.01-1.93 (m, 3H), 1.73-1.53 (m, 1H), 1.25 (s, 9H).

Example 1.470

Synthesis of N-tert-butyl-2-{[2-(4-{2-[(3S)-3-methoxypyrrolidin-1-yl]ethoxy}pyridin-2-yl)-5H,6H,7H-cyclopenta[d]pyrimidin-4-yl](methyl)amino}acetamide (Compound 464)

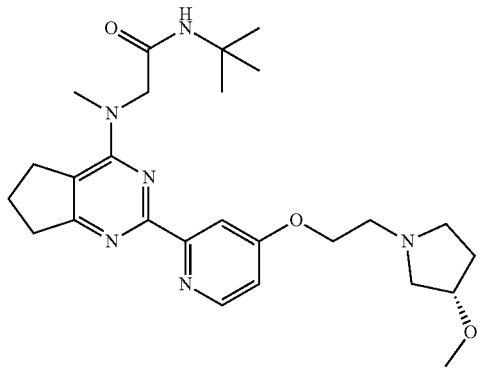 [SMILES: CO[C@H]1CCN(CCOc2ccnc(-c3nc4c(c(N(C)CC(=O)NC(C)(C)C)n3)CCC4)c2)C1]

Compound 464 was synthesized similar to Compound 508 by replacing bis(methyl-d3)amine hydrochloride with (3S)-3-methoxypyrrolidine hydrochloride. LCMS (ES) [M+1]+ m/z: 483. ¹H NMR (400 MHz, DMSO-d6, ppm): δ 8.49 (d, J=5.6 Hz, 1H), 8.15 (s, 1.5HCOOH), 7.84 (d, J=2.5 Hz, 1H), 7.67 (s, 1H), 7.07 (dd, J=5.7, 2.6 Hz, 1H), 4.25 (t, J=5.6 Hz, 2H), 4.14 (s, 2H), 3.94-3.89 (m, 1H), 3.26 (s, 3H), 3.18 (s, 3H), 3.14 (t, J=7.3 Hz, 2H), 2.96 (t, J=5.6 Hz, 2H), 2.89 (dd, J=10.5, 6.1 Hz, 1H), 2.83-2.77 (m, 3H), 2.73 (dd, J=10.5, 3.0 Hz, 1H), 2.69-2.62 (m, 1H), 2.06-1.95 (m, 3H), 1.75-1.68 (m, 1H), 1.24 (s, 9H).

Example 1.471

Synthesis of N-tert-butyl-2-[(2-{4-[2-(1H-imidazol-1-yl)ethoxy]pyridin-2-yl}-5H,6H,7H-cyclopenta[d]pyrimidin-4-yl)(methyl)amino]acetamide (Compound 465)

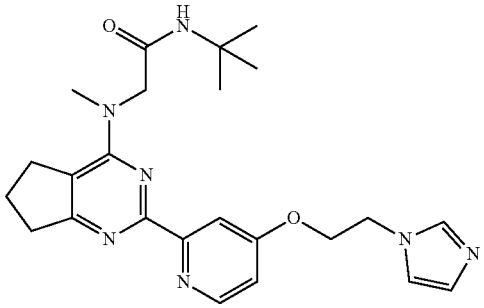 [SMILES: CN(CC(=O)NC(C)(C)C)c1nc(-c2cc(OCCn3ccnc3)ccn2)nc2c1CCC2]

Compound 465 was synthesized similar to Compound 348 by replacing dimethylaminoethanol with 1-(2-hydroxyethyl)imidazole. LCMS (ES) [M+1]+ m/z: 450. ¹H NMR (300 MHz, DMSO-d6, ppm): δ 8.48 (d, J=5.6 Hz, 1H), 7.82 (d, J=2.6 Hz, 1H), 7.75-7.63 (m, 2H), 7.27 (t, J=1.3 Hz, 1H), 7.04 (dd, J=5.6, 2.6 Hz, 1H), 6.91 (d, J=1.1 Hz, 1H), 4.42 (s, 4H), 4.14 (s, 2H), 3.26 (s, 3H), 3.14 (t, J=7.3 Hz, 2H), 2.81 (t, J=7.8 Hz, 2H), 2.01-1.96 (m, 2H), 1.23 (s, 10H).

Example 1.472

Synthesis of N-tert-butyl-2-[methyl(2-{4-[2-(1H-1,2,3,4-tetrazol-1-yl)ethoxy]pyridin-2-yl}-5H,6H,7H-cyclopenta[d]pyrimidin-4-yl)amino]acetamide (Compound 466)

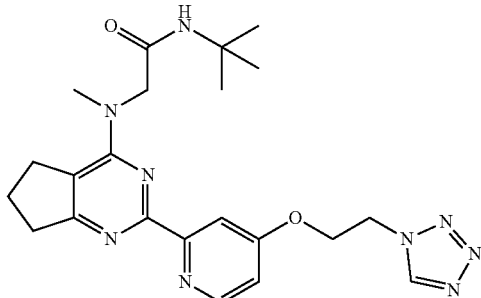

Compound 466 was synthesized similar to Compound 348 by replacing dimethylaminoethanol with 2-(1H-1,2,3,4-tetrazol-1-yl)ethan-1-ol. LCMS (ES) [M+1]$^+$ m/z: 452.2. $^1$H NMR (400 MHz, DMSO-d6, ppm): δ 9.52 (s, 1H), 8.54 (d, J=5.7 Hz, 1H), 7.84 (d, J=2.6 Hz, 1H), 7.71 (s, 1H), 7.15 (dd, J=5.8, 2.6 Hz, 1H), 4.96-4.91 (m, 2H), 4.68-4.63 (m, 2H), 4.17 (s, 2H), 3.29 (s, 3H), 3.17-3.12 (m, 2H), 2.88-2.81 (m, 2H), 2.04-1.96 (m, 2H), 1.19 (s, 9H).

Example 1.473

Synthesis of N-tert-butyl-2-{[2-(4-ethoxypyridin-2-yl)-5H,6H,7H-cyclopenta[d]pyrimidin-4-yl](methyl)amino}acetamide (Compound 467)

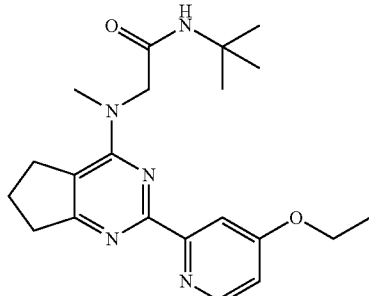

Compound 467 was synthesized similar to Compound 34 by replacing 4-methoxy-2-(trimethylstannyl)pyridine with 4-ethoxy-2-(tributylstannyl)pyridine. LCMS (ES+): [M+H]$^+$=384.2. $^1$H NMR (400 MHz, DMSO-d6) δ 8.48 (d, J=5.7 Hz, 1H), 7.86 (d, J=2.5 Hz, 1H), 7.72 (s, 1H), 7.06 (dd, J=5.7, 2.6 Hz, 1H), 4.19 (q, J=7.0 Hz, 2H), 4.13 (s, 2H), 3.28 (s, 3H), 3.19-3.11 (m, 2H), 2.86-2.79 (m, 2H), 2.04-1.94 (m, 2H), 1.37 (t, J=7.0 Hz, 3H), 1.24 (s, 9H).

Example 1.474

Synthesis of N-tert-butyl-2-[methyl(2-{4-[2-(pyridazin-3-yloxy)ethoxy]pyridin-2-yl}-5H,6H,7H-cyclopenta[d]pyrimidin-4-yl)amino]acetamide (Compound 468)

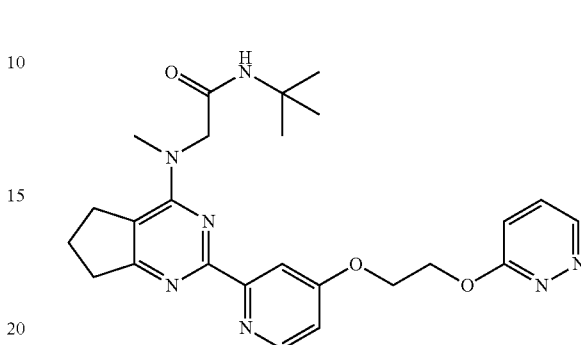

Compound 468 was synthesized similar to Compound 348 by replacing dimethylaminoethanol with 2-(pyridazin-3-yloxy)ethan-1-ol. LCMS (ES) [M+1]$^+$ m/z: 478.2. $^1$H NMR (400 MHz, DMSO-d6, ppm): δ 8.92 (dd, J=4.5, 1.3 Hz, 1H), 8.50 (d, J=5.6 Hz, 1H), 7.91 (d, J=2.6 Hz, 1H), 7.68 (s, 1H), 7.65 (dd, J=8.9, 4.5 Hz, 1H), 7.26 (dd, J=8.9, 1.3 Hz, 1H), 7.12 (dd, J=5.7, 2.6 Hz, 1H), 4.83-4.78 (m, 2H), 4.57-4.53 (m, 2H), 4.10 (s, 2H), 3.27 (s, 3H), 3.17-3.12 (m, 2H), 2.84-2.78 (m, 2H), 2.03-1.94 (m, 2H), 1.18 (s, 9H).

Example 1.475

Synthesis of 2-({2-[4-(2-ethyl-2-hydroxybutoxy)pyridin-2-yl]-5H,6H,7H-cyclopenta[d]pyrimidin-4-yl}(methyl)amino)-N-[(1R,2S)-2-hydroxycyclopentyl]acetamidede (Compound 469)

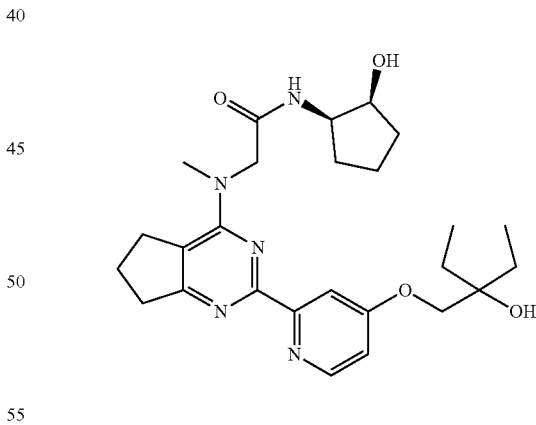

Scheme 135

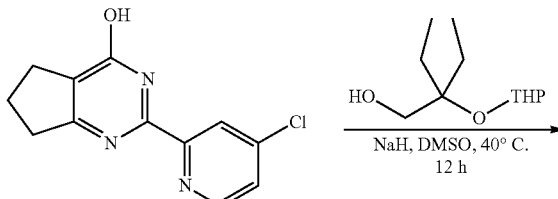

-continued

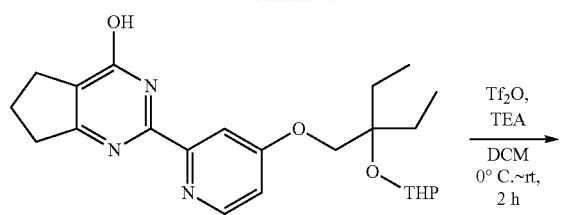

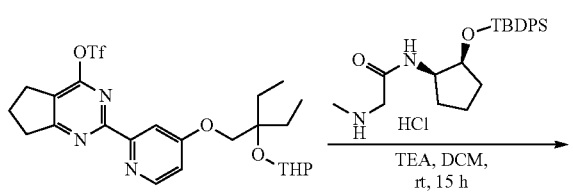

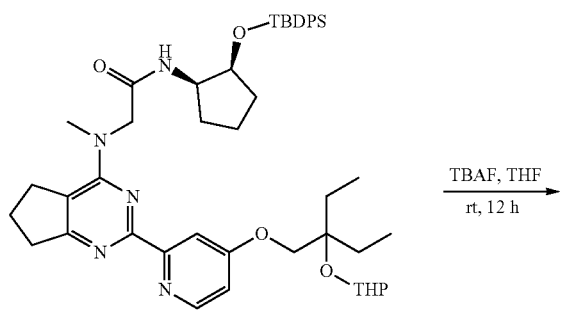

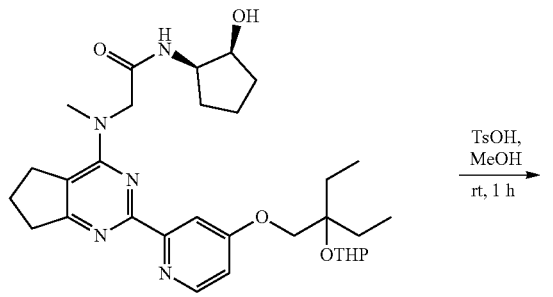

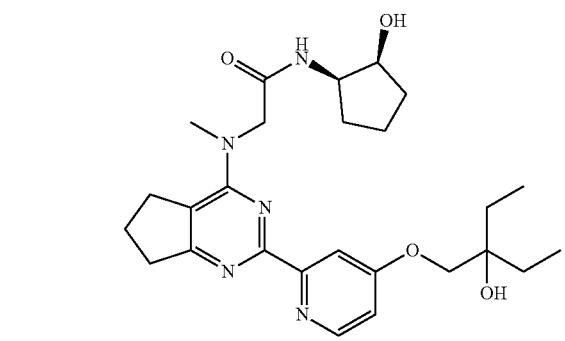

Step 1

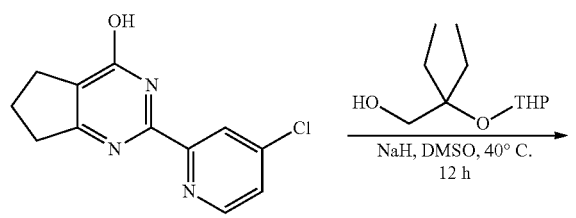

-continued

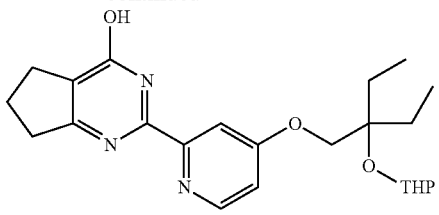

Into a 20-mL vial, was placed NaH (60% in mineral oil) (68 mg, 1.71 mmol, 1.50 equiv), DMSO (4.0 mL), After cooled to 0° C., 2-ethyl-2-((tetrahydro-2H-pyran-2-yl)oxy)butan-1-ol (300 mg, 1.71 mmol, 1.50 equiv) was added and stirred at room temperature and stirred for 0.5 h. This was followed by 2-(4-chloropyridin-2-yl)-6,7-dihydro-5H-cyclopenta[d]pyrimidin-4-ol (282 mg, 1.14 mmol, 1.00 equiv) was added. The resulting solution was stirred for 12 h at 40° C., the reaction mixture was cooled to room temperature and quenched with H₂O (1.0 mL), the resulting solution was purified by Prep-HPLC with the following conditions: Sunfire Prep C18 OBD Column, 50*250 mm, 5 μm, 10 nm, Mobile phase A, water (0.05% NH₃·H₂O) and CH₃CN (25% Phase B up to 60% in 12 min), Detector, 220 nm. 305 mg of 2-(4-(2-ethyl-2-((tetrahydro-2H-pyran-2-yl)oxy)butoxy)pyridin-2-yl)-6,7-dihydro-5H-cyclopenta[d]pyrimidin-4-ol was obtained as a yellow oil. LCMS (ES) [M+1]⁺ m/z: 414.

Step 2

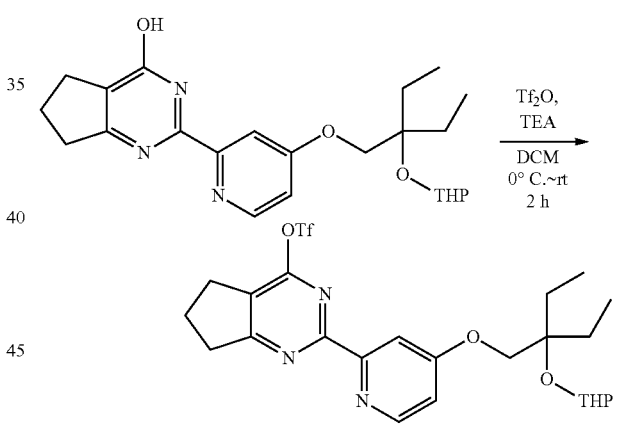

Into a 50-mL three necked round-bottom flask were placed 2-(4-(2-ethyl-2-((tetrahydro-2H-pyran-2-yl)oxy)butoxy)pyridin-2-yl)-6,7-dihydro-5H-cyclopenta[d]pyrimidin-4-ol (305 mg, 0.74 mmol, 1.00 equiv), DCM (10.00 mL) and TEA (0.51 mL, 3.69 mmol, 5.00 equiv). This was followed by the addition of trifluoromethanesulfonic anhydride (0.14 ml, 0.96 mmol, 1.30 equiv) at 0° C. The resulting solution was stirred for 2 h at room temperature. The reaction was quenched with H₂O (10 mL) and extracted with DCM (20 mL*3). Organic layers were combined, dried over anhydrous sodium sulfate and filtered. The filtrate was concentrated under reduced pressure, the residue was used to the next step without further purification. This resulted in 763 mg crude of 2-(4-(2-ethyl-2-((tetrahydro-2H-pyran-2-yl)oxy)butoxy)pyridin-2-yl)-6,7-dihydro-5H-cyclopenta[d]pyrimidin-4-yl trifluoromethanesulfonate purple oil. LCMS: (ES) [M+1]⁺ m/z: 546.

Step 3

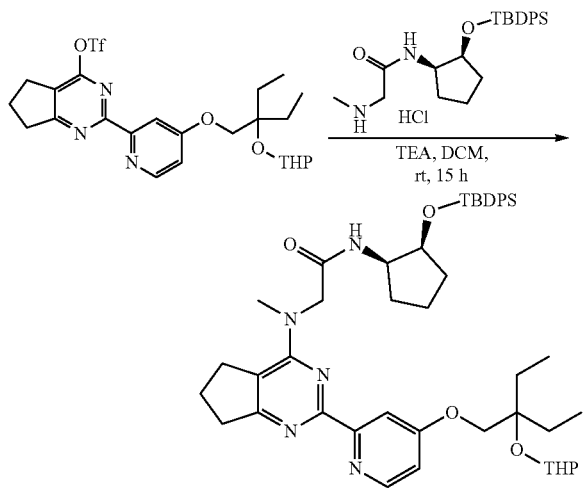

Into a 100-mL round-bottom flask were placed 2-(4-(2-ethyl-2-((tetrahydro-2H-pyran-2-yl)oxy)butoxy)pyridin-2-yl)-6,7-dihydro-5H-cyclopenta[d]pyrimidin-4-yl trifluoromethanesulfonate (763 mg, 1.40 mmol, 1.00 equiv) and DCM (10.0 mL). This was followed by the addition of TEA (0.59 mL, 4.20 mmol, 3.00 equiv) and N-((1R,2S)-2-((tert-butyldiphenylsilyl)oxy)cyclopentyl)-2-(methylamino)acetamide hydrochloride (874 mg, 1.96 mmol, 1.40 equiv). The resulting solution was stirred for 12 h at 40° C. The reaction was quenched with H$_2$O (20 mL), extracted with DCM (20 mL*2). Organic layers were combined, dried over anhydrous sodium sulfate and filtered. The filtrate was concentrated under reduced pressure, the residue was used to the next step without further purification. This resulted in 1.1 g crude of N-((1R,2S)-2-((tert-butyldiphenylsilyl)oxy)cyclopentyl)-2-((2-(4-(2-ethyl-2-((tetrahydro-2H-pyran-2-yl)oxy)butoxy)pyridin-2-yl)-6,7-dihydro-5H-cyclopenta[d]pyrimidin-4-yl)(methyl)amino)acetamide a brown oil. LCMS: (ES) [M+1]$^+$ m/z: 806.

Step 4

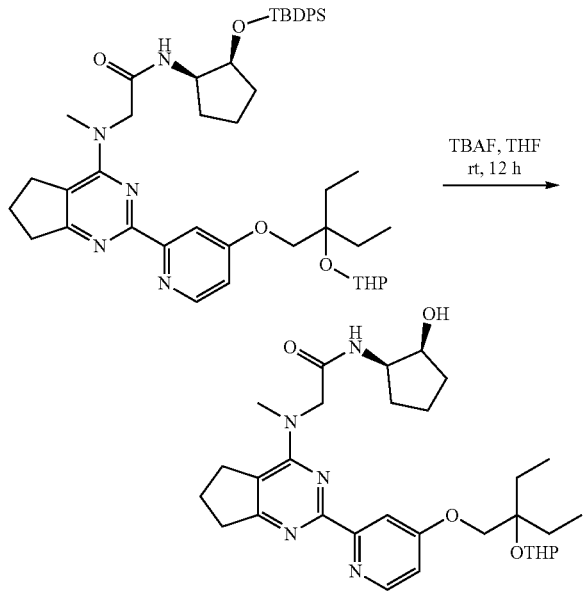

Into a 100-mL round-bottom flask were placed N-((1R,2S)-2-((tert-butyldiphenylsilyl)oxy)cyclopentyl)-2-((2-(4-(2-ethyl-2-((tetrahydro-2H-pyran-2-yl)oxy)butoxy)pyridin-2-yl)-6,7-dihydro-5H-cyclopenta[d]pyrimidin-4-yl)(methyl)amino)acetamide (1.10 g, 1.37 mmol, 1.00 equiv), THF (10.00 mL) and TBAF (0.37 mL, 1.37 mmol, 1.00 equiv). The reaction solution was stirred for 12 h at room temperature. The resulting solution was concentrated under reduced pressure, the residue was purified by Prep-HPLC with the following conditions: Welch-XB C18 50*250, 10 um, Mobile phase A, water (0.05% NH$_3$·H$_2$O) and CH$_3$CN (30% Phase B up to 80% in 15 min), Detector, 220 nm. 268 mg of 2-((2-(4-(2-ethyl-2-((tetrahydro-2H-pyran-2-yl)oxy)butoxy)pyridin-2-yl)-6,7-dihydro-5H-cyclopenta[d]pyrimidin-4-yl)(methyl)amino)-N-((1R,2S)-2-hydroxycyclopentyl)acetamide was obtained as an orange solid. LCMS (ES) [M+1]$^+$ m/z: 568.

Step 5

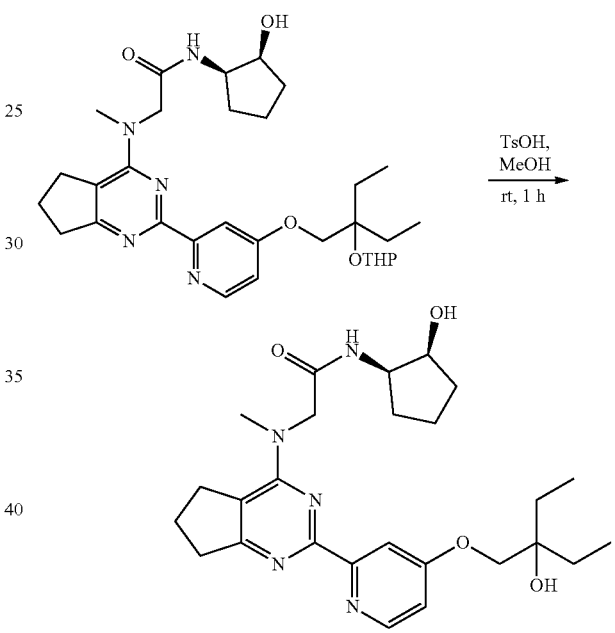

Into a 8-mL vial were placed 2-((2-(4-(2-ethyl-2-((tetrahydro-2H-pyran-2-yl)oxy)butoxy)pyridin-2-yl)-6,7-dihydro-5H-cyclopenta[d]pyrimidin-4-yl)(methyl)amino)-N-((1R,2S)-2-hydroxycyclopentyl)acetamide (268 mg, 0.47 mmol, 1.00 equiv), MeOH (3.0 mL) and TsOH (81 mg, 0.47 mmol, 1.00 equiv). The mixture was stirred for 1 h at room temperature. The reaction mixture was purified by Prep-HPLC with the following conditions: Welch-XB C18 50*250, 10 um, Mobile phase, water (0.5% NH$_3$·H$_2$O) and CH$_3$CN/MeOH 1:1 (25% Phase B up to 75% in 15 min), Detector, 220 nm. 130 mg of 2-((2-(4-(2-ethyl-2-hydroxybutoxy)pyridin-2-yl)-6,7-dihydro-5H-cyclopenta[d]pyrimidin-4-yl)(methyl)amino)-N-((1R,2S)-2-hydroxycyclopentyl)acetamide was obtained as a white solid. LCMS (ES, m/z): [M+H]$^+$: 484. $^1$H-NMR (300 MHz, DMSO-d6, ppm): δ 8.48 (d, J=5.6 Hz, 1H), 7.80 (d, J=2.5 Hz, 1H), 7.68 (d, J=7.8 Hz, 1H), 7.07 (dd, J=5.6, 2.6 Hz, 1H), 4.69 (d, J=3.8 Hz, 1H), 4.44 (s, 1H), 4.31 (d, J=16.6 Hz, 1H), 4.20 (d, J=16.6 Hz, 1H), 3.96-3.81 (m, 4H), 3.26 (s, 3H), 3.19-3.12 (m, 2H), 2.85 (t, J=7.8 Hz, 2H), 2.04-1.94 (m, 2H), 1.80-1.63 (m, 3H), 1.59-1.35 (m, 7H), 0.88 (t, J=7.4 Hz, 6H).

Example 1.476

Synthesis of N-tert-butyl-2-[(2-{4-[2-(dimethyl-amino)ethoxy]pyridin-2-yl}-5H,6H,7H-cyclopenta[d]pyrimidin-4-yl)(2,2,2-trifluoroethyl)amino]acetamide (Compound 470)

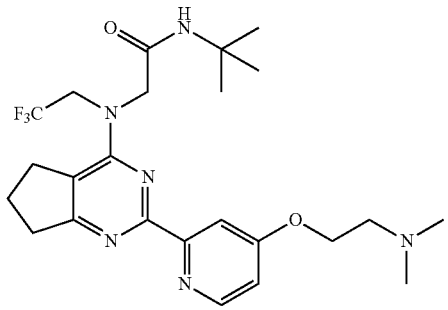 [SMILES: CN(C)CCOc1ccnc(-c2nc3c(c(N(CC(=O)NC(C)(C)C)CC(F)(F)F)n2)CCC3)c1]

Scheme 136

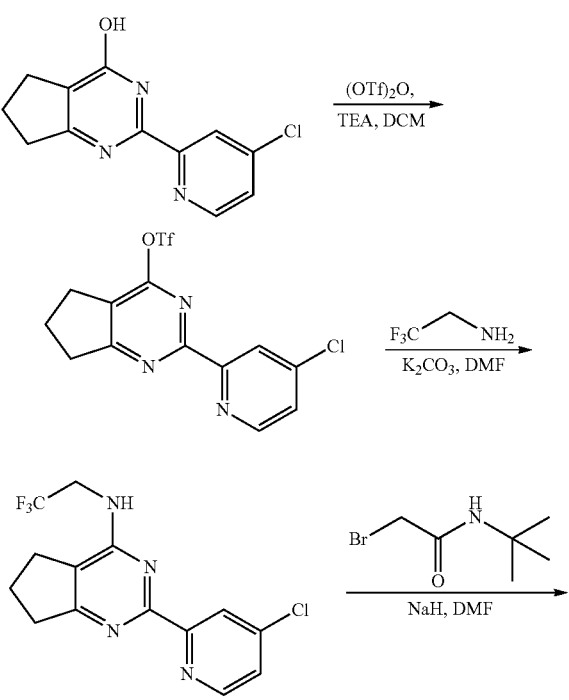

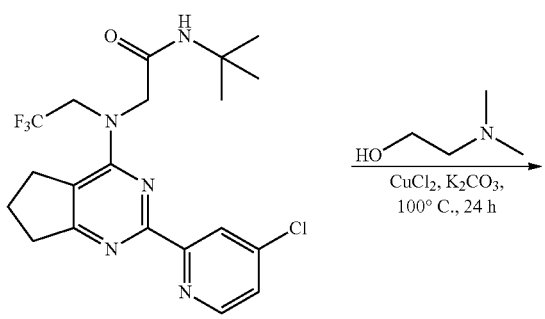

-continued

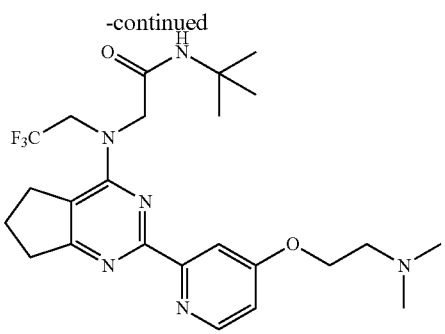

Step 1

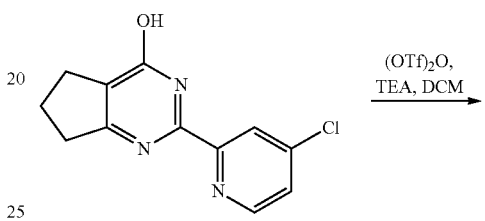

To a stirred mixture of 2-(4-chloropyridin-2-yl)-5H,6H,7H-cyclopenta[d]pyrimidin-4-ol (10 g, 40.375 mmol, 1.00 equiv) and TEA (8.17 g, 80.750 mmol, 2 equiv) in DCM (200 mL) was added (trifluoromethane)sulfonyl trifluoromethanesulfonate (22.78 g, 80.750 mmol, 2 equiv) dropwise at 0° C. The resulting mixture was stirred for 4 h at room temperature under nitrogen atmosphere. The resulting mixture was extracted with $CH_2Cl_2$ (3×300 mL). The combined organic layers were dried over anhydrous $Na_2SO_4$. After filtration, the filtrate was concentrated under reduced pressure. The residue was purified by silica gel column chromatography, eluted with PE/EA (1:2) to afford 2-(4-chloropyridin-2-yl)-5H,6H,7H-cyclopenta[d]pyrimidin-4-yl trifluoromethanesulfonate (10 g, 65.22%) as off-white solid. LCMS (ES) [M+1]+ m/z: 380.

Step 2

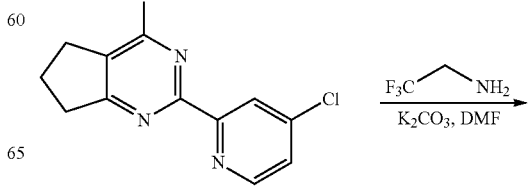

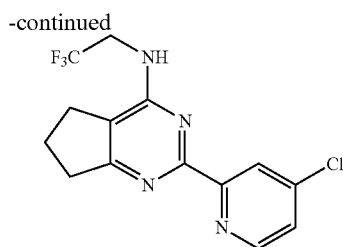

To a stirred mixture of 2-(4-chloropyridin-2-yl)-5H,6H,7H-cyclopenta[d]pyrimidin-4-yl trifluoromethanesulfonate (3 g, 7.900 mmol, 1.00 equiv) and 2,2,2-trifluoroethylamine (7.83 g, 79.000 mmol, 10 equiv) in DMF was added $K_2CO_3$ (3.28 g, 23.700 mmol, 3 equiv) in portions at room temperature. The resulting mixture was extracted with $CH_2Cl_2$ (3×50 mL). The combined organic layers were dried over anhydrous $Na_2SO_4$. After filtration, the filtrate was concentrated under reduced pressure. The residue was purified by reverse flash chromatography with the following conditions: column, silica gel; mobile phase, MeCN in water (0.1% $NH_3$), 10% to 60% gradient in 20 min to afford 2-(4-chloropyridin-2-yl)-N-(2,2,2-trifluoroethyl)-5H,6H,7H-cyclopenta[d]pyrimidin-4-amine (500 mg, 19.25%) as a white solid. LCMS (ES) [M+1]$^+$ m/z: 329.

Step 3

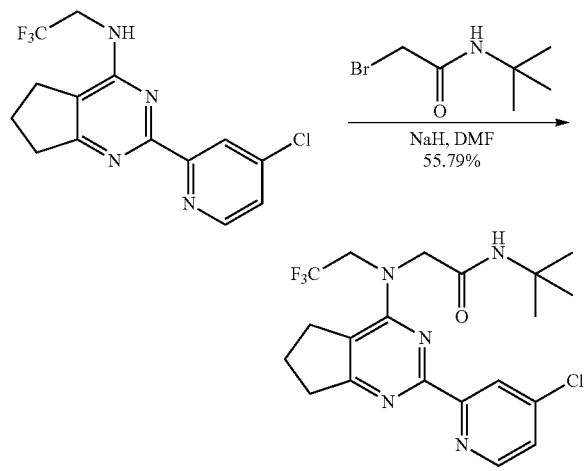

To a stirred solution of 2-(4-chloropyridin-2-yl)-N-(2,2,2-trifluoroethyl)-5H,6H,7H-cyclopenta[d]pyrimidin-4-amine (400 mg, 1.217 mmol, 1.00 equiv) in DMF was added NaH (58.40 mg, 2.434 mmol, 2 equiv) in portions at 0° C. under nitrogen atmosphere. The resulting mixture was stirred for 30 min at 0° C. under nitrogen atmosphere. To the above mixture was added 2-bromo-N-tert-butylacetamide (354.23 mg, 1.826 mmol, 1.5 equiv) in portions at ° C. The resulting mixture was stirred for additional 4 h at room temperature. The resulting mixture was extracted with $CH_2Cl_2$ (3×30 mL). The combined organic layers were dried over anhydrous $Na_2SO_4$ and filtered. The filtrate was concentrated under reduced pressure. The residue was purified by silica gel column chromatography, eluted with $CH_2Cl_2$/MeOH (10:1) to afford N-tert-butyl-2-{[2-(4-chloropyridin-2-yl)-5H,6H,7H-cyclopenta[d]pyrimidin-4-yl](2,2,2-trifluoroethyl)amino}acetamide (300 mg, 55.79%) as an off-white solid. LCMS (ES) [M+1]$^+$ m/z: 442.

Step 4

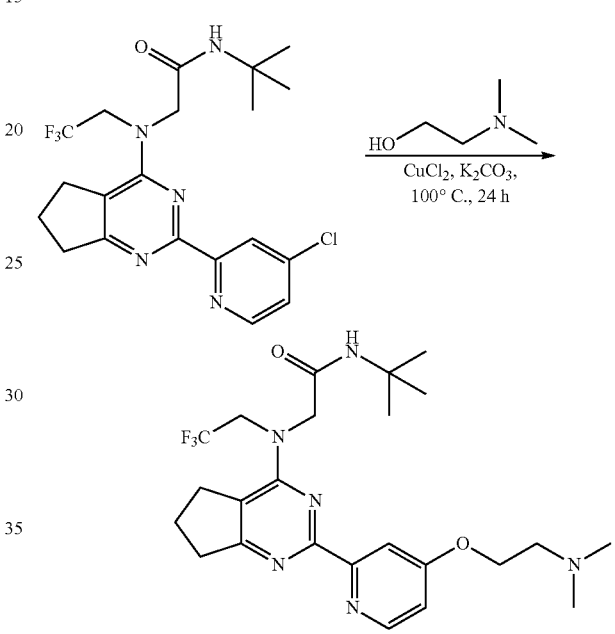

To a stirred solution of N-tert-butyl-2-{[2-(4-chloropyridin-2-yl)-5H,6H,7H-cyclopenta[d]pyrimidin-4-yl](2,2,2-trifluoroethyl)amino}acetamide (130 mg, 0.294 mmol, 1.00 equiv) and dimethylaminoethanol (10 mL) was added $CuCl_2$ (3.96 mg, 0.029 mmol, 0.1 equiv) and $K_2CO_3$ (81.32 mg, 0.588 mmol, 2 equiv) in portions at 100° C. The resulting mixture was extracted with $CH_2Cl_2$ (3×30 mL). The combined organic layers were dried over anhydrous $Na_2SO_4$ and filtered. The filtrate was concentrated under reduced pressure. The crude product was purified by Prep-HPLC with the following conditions (Sunfire Prep C18 XBridge Column, 19*150 mm; mobile phase A, Water (0.0.05% NH3) and mobile phase B, AcCN (25% Phase B up to 72% in 7 min)) to afford N-tert-butyl-2-[(2-{4-[2-(dimethylamino)ethoxy]pyridin-2-yl}-5H,6H,7H-cyclopenta[d]pyrimidin-4-yl)(2,2,2-trifluoroethyl)amino]acetamide (49.3 mg, 33.88%) as a white solid. LCMS (ES) [M+1]$^+$ m/z: 495. $^1$H NMR (400 MHz, DMSO-d$_6$) δ 8.49 (d, J=5.5 Hz, 1H), 7.83 (s, 1H), 7.68 (s, 1H), 7.07 (s, 1H), 4.59 (q, J=9.2 Hz, 2H), 4.27-4.17 (m, 4H), 3.07 (t, J=7.3 Hz, 2H), 2.86 (t, J=8.0 Hz, 2H), 2.67 (t, J=5.7 Hz, 2H), 2.23 (s, 6H), 2.05-1.97 (m, 2H), 1.24 (s, 9H).

Example 1.477

Synthesis of 1-[(3R)-3-hydroxypyrrolidin-1-yl]-2-{[2-(4-methoxypyridin-2-yl)-5H,6H,7H-cyclopenta[d]pyrimidin-4-yl](methyl)amino}ethan-1-one (Compound 471)

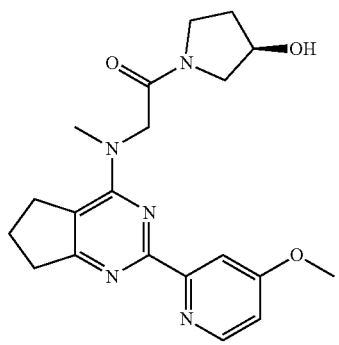 [SMILES: COc1ccnc(-c2nc3c(c(N(C)CC(=O)N4CC[C@@H](O)C4)n2)CCC3)c1]

Compound 471 was synthesized similar to Compound 135 by replacing oxolan-3-amine with (3R)-pyrrolidin-3-ol. LCMS (ES) [M+1]⁺ m/z: 384. ¹H NMR (300 MHz, DMSO-d6, ppm): δ 8.47 (d, J=5.6 Hz, 1H), 7.74 (dd, J=4.2, 2.6 Hz, 1H), 7.02 (dd, J=5.6, 2.6 Hz, 1H), 5.07 (d, J=3.4 Hz, 1H), 4.94 (d, J=3.4 Hz, 1H), 4.60-4.19 (m, 3H), 3.88 (s, 3H), 3.77-3.54 (m, 2H), 3.50-3.36 (m, 1H), 3.31-3.23 (m, 4H), 3.14 (t, J=7.4 Hz, 2H), 2.81 (t, J=7.9 Hz, 2H), 2.05-1.78 (m, 4H).

Example 1.478

Synthesis of 1-[(3S)-3-hydroxypyrrolidin-1-yl]-2-{[2-(4-methoxypyridin-2-yl)-5H,6H,7H-cyclopenta[d]pyrimidin-4-yl](methyl)amino}ethan-1-one (Compound 472)

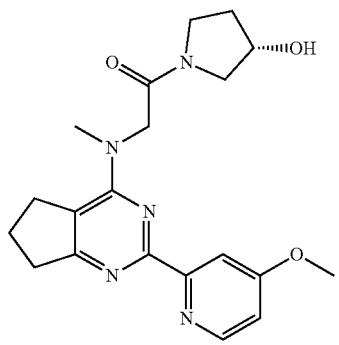 [SMILES: COc1ccnc(-c2nc3c(c(N(C)CC(=O)N4CC[C@H](O)C4)n2)CCC3)c1]

Compound 472 was synthesized similar to Compound 135 by replacing oxolan-3-amine with (3S)-pyrrolidin-3-ol. LCMS (ES) [M+1]⁺ m/z: 384. ¹H NMR (300 MHz, DMSO-d6, ppm): δ 8.47 (d, J=5.6 Hz, 1H), 7.74 (dd, J=4.2, 2.6 Hz, 1H), 7.02 (dd, J=5.6, 2.6 Hz, 1H), 5.07 (d, J=3.5 Hz, 0.5H), 4.94 (d, J=3.5 Hz, 0.5H) 4.60-4.21 (m, 3H), 3.88 (s, 3H), 3.75-3.51 (m, 2H), 3.49-3.35 (m, 1H), 3.32-3.21 (m, 4H), 3.14 (t, J=7.3 Hz, 2H), 2.81 (t, J=7.9 Hz, 2H), 2.12-1.67 (m, 4H).

Example 1.479

Synthesis of N-tert-butyl-2-{[2-(4-{2-[(3R)-3-fluoropyrrolidin-1-yl]ethoxy}pyridin-2-yl)-5H,6H,7H-cyclopenta[d]pyrimidin-4-yl](methyl)amino}acetamide (Compound 473)

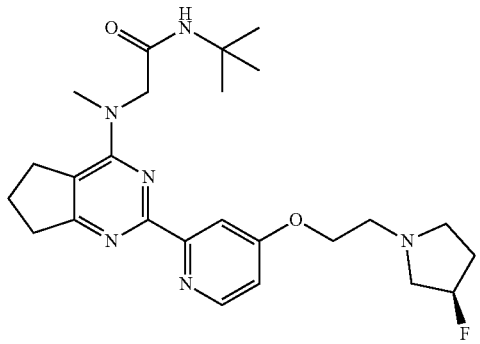 [SMILES: CN(CC(=O)NC(C)(C)C)c1nc(-c2cc(OCCN3CC[C@@H](F)C3)ccn2)nc2c1CCC2]

Compound 473 was synthesized similar to Compound 508 by replacing bis(methyl-d3)amine hydrochloride with (3R)-3-fluoropyrrolidine hydrochloride. LCMS (ES) [M+1]⁺ m/z: 471. ¹H NMR (400 MHz, DMSO-d₆) δ 8.48 (d, J=5.5 Hz, 1H), 7.84 (d, J=2.5 Hz, 1H), 7.67 (s, 1H), 7.06 (dd, J=5.7, 2.6 Hz, 1H), 5.20 (dt, J=55.6, 5.8 Hz, 1H), 4.23 (t, J=5.6 Hz, 2H), 4.13 (s, 2H), 3.27 (s, 3H), 3.15 (t, J=7.3 Hz, 2H), 2.99-2.77 (m, 6H), 2.79-2.63 (m, 1H), 2.43 (q, J=8.0 Hz, 1H), 2.23-2.05 (m, 1H), 2.04-1.78 (m, 3H), 1.25 (s, 9H).

Example 1.480

Synthesis of N-tert-butyl-2-{[2-(4-{2-[(3S)-3-fluoropyrrolidin-1-yl]ethoxy}pyridin-2-yl)-5H,6H,7H-cyclopenta[d]pyrimidin-4-yl](methyl)amino}acetamide (Compound 474)

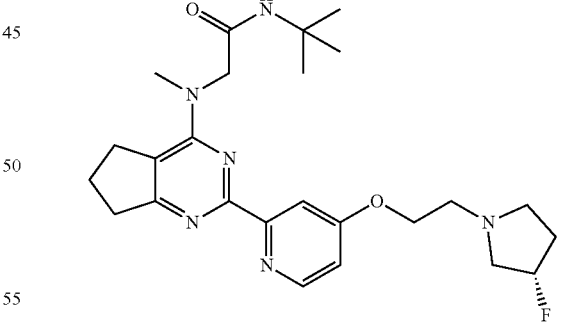

Compound 474 was synthesized similar to Compound 508 by replacing bis(methyl-d3)amine hydrochloride with (3S)-3-fluoropyrrolidine hydrochloride. LCMS (ES) [M+1]⁺ m/z: 471. ¹H NMR (400 MHz, DMSO-d₆) δ 8.48 (d, J=5.4 Hz, 1H), 8.16 (s, 1.3 HCOOH) 7.84 (d, J=2.7 Hz, 1H), 7.67 (s, 1H), 7.06 (dd, J=5.9, 2.7 Hz, 1H), 5.20 (dt, J=55.8, 5.8 Hz, 1H), 4.23 (t, J=5.7 Hz, 2H), 4.13 (s, 2H), 3.27 (s, 3H), 3.15 (t, J=7.4 Hz, 2H), 3.00-2.77 (m, 6H), 2.79-2.63 (m, 1H), 2.43 (q, J=7.9 Hz, 1H), 2.23-2.04 (m, 1H), 2.04-1.79 (m, 3H), 1.25 (s, 9H).

Example 1.481

Synthesis of N-tert-butyl-2-[(2-{4-[3-(dimethylamino)propyl]pyridin-2-yl}-5H,6H,7H-cyclopenta[d]pyrimidin-4-yl)(methyl)amino]acetamide (Compound 475)

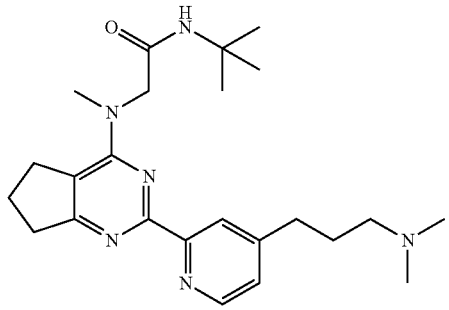 [SMILES: CN(C)CCCc1ccnc(-c2nc3c(c(N(C)CC(=O)NC(C)(C)C)n2)CCC3)c1]

Scheme 137

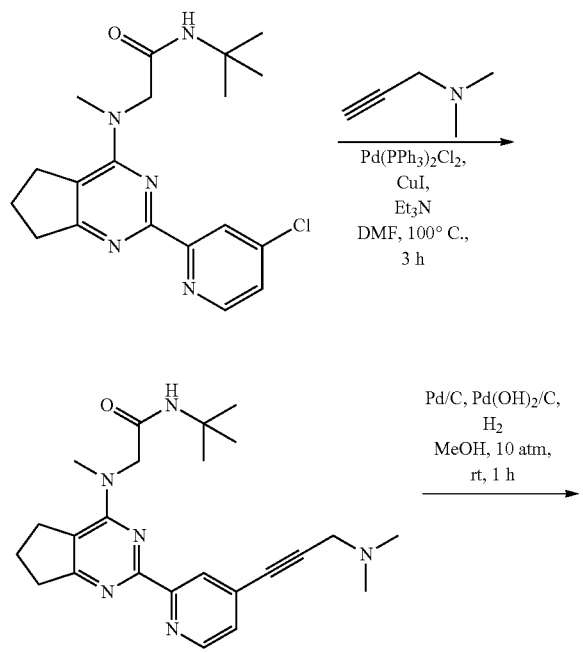

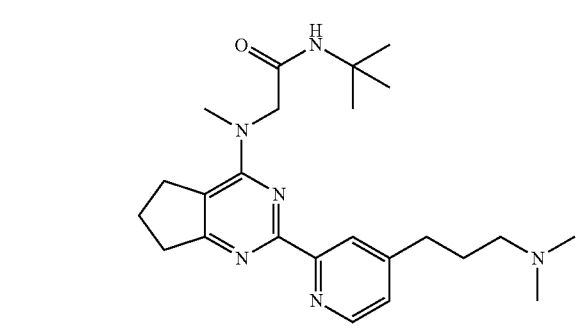

Step 1

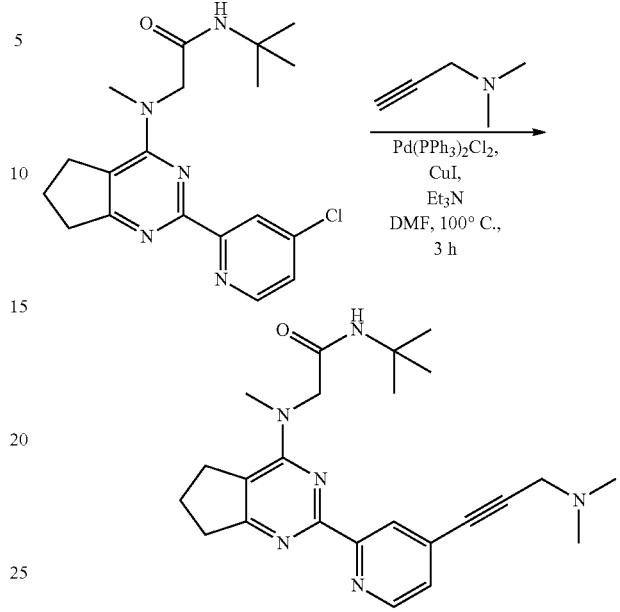

Into a 40 mL vial were added N-tert-butyl-2-{[2-(4-chloropyridin-2-yl)-5H,6H,7H-cyclopenta[d]pyrimidin-4-yl](methyl)amino}acetamide (415 mg, 1.11 mmol, 1.00 equiv), dimethyl(prop-2-yn-1-yl)amine (185 mg, 2.23 mmol, 2.00 equiv), DMF (10 mL), CuI (21 mg, 0.11 mmol, 0.10 equiv), Et$_3$N (337 mg, 3.33 mmol, 3.00 equiv) and Pd(PPh$_3$)Cl$_2$ (79 mg, 0.11 mmol, 0.10 equiv) at room temperature. The resulting mixture was stirred for 3 h at 100° C. under nitrogen atmosphere. The reaction was cooled to room temperature, the residue was purified by reverse flash chromatography with the following conditions: C18-120 g column, mobile phase, Phase B, MeCN, Phase A, water, 10% to 50% gradient in 10 min, detector, UV 254 nm. This resulted in N-(tert-butyl)-2-((2-(4-(3-(dimethylamino)prop-1-yn-1-yl)pyridin-2-yl)-6,7-dihydro-5H-cyclopenta[d]pyrimidin-4-yl)(methyl)amino)acetamide (140 mg, 30%) as a white solid. LCMS (ES, m/z): [M+H]$^+$: 421.

Step 2

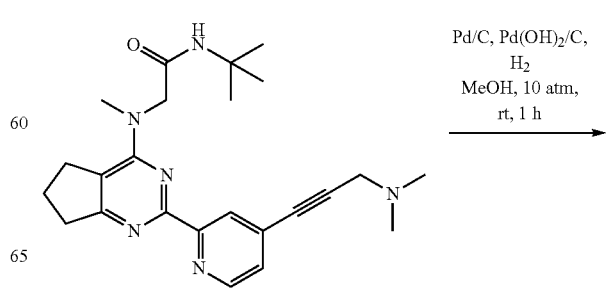

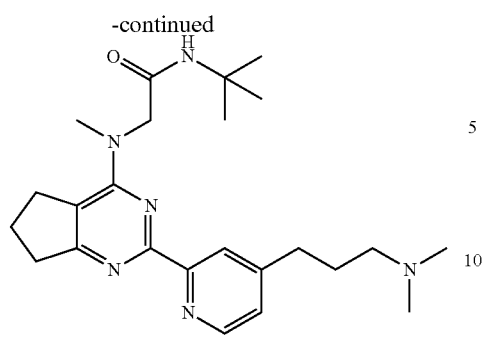

J=8.2, 5.6, 4.1 Hz, 4H), 2.82 (t, J=7.8 Hz, 2H), 2.23 (t, J=6.8 Hz, 2H), 2.07 (s, 6H), 2.02-1.94 (m, 2H).

Example 1.483

Synthesis of 2-{[2-(4-methoxypyridin-2-yl)-5H,6H,7H-cyclopenta[d]pyrimidin-4-yl](methyl)amino}-1-(morpholin-4-yl)ethan-1-one (Compound 477)

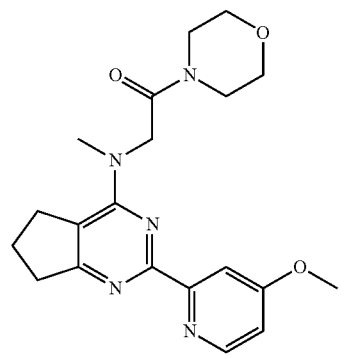

To a solution of N-tert-butyl-2-[(2-{4-[3-(dimethylamino)prop-1-yn-1-yl]pyridin-2-yl}-5H,6H,7H-cyclopenta[d]pyrimidin-4-yl)(methyl)amino]acetamide (140 mg, 0.33 mmol, 1.00 equiv) in 20 mL MeOH was added Pd/C (10%, 50 mg), Pd(OH)$_2$/C (50 mg) under hydrogen atmosphere in a 50 mL pressure tank reactor. The mixture was hydrogenated at room temperature for 1 h under hydrogen atmosphere, filtered through a celite pad and the filtrate was concentrated under reduced pressure. The crude product was purified by Prep-HPLC with the following conditions: Sunfire Prep C18 OBD Column, 50*250 mm, 5 μm 10 nm, mobile phase, water (0.1% FA) and CH$_3$CN (hold 5% Phase B in 3 min, up to 23% in 12 min), Detector, UV 254 nm. This resulted in N-(tert-butyl)-2-((2-(4-(3-(dimethylamino)propyl)pyridin-2-yl)-6,7-dihydro-5H-cyclopenta[d]pyrimidin-4-yl)(methyl)amino)acetamide (74.8 mg, 43%) as a brown solid. LCMS (ES, m/z): [M+H]$^+$: 425. $^1$H-NMR (300 MHz, DMSO-d$_6$) δ 8.55 (d, J=4.9 Hz, 1H), 8.23 (s, 2HCOOH), 8.15 (d, J=1.5 Hz, 1H), 7.69 (s, 1H), 7.31 (dd, J=4.9, 1.7 Hz, 1H), 4.16 (s, 2H), 3.27 (s, 3H), 3.15 (t, J=7.2 Hz, 2H), 2.82 (t, J=7.8 Hz, 2H), 2.76-2.65 (m, 2H), 2.48-2.37 (m, 2H), 2.28 (s, 6H), 2.07-1.91 (m, 2H), 1.82 (p, J=7.6 Hz, 2H), 1.24 (s, 9H).

Compound 477 was synthesized similar to Compound 135 by replacing oxolan-3-amine with morpholine. LCMS (ES) [M+1]$^+$ m/z: 384. $^1$H NMR (300 MHz, DMSO-d6, ppm): δ 8.49 (d, J=5.6 Hz, 1H), 7.78 (d, J=2.6 Hz, 1H), 7.06 (dd, J=5.7, 2.6 Hz, 1H), 4.55 (s, 2H), 3.90 (s, 3H), 3.67-3.65 (m, 2H), 3.58-3.53 (m, 4H), 3.45-3.43 (m, 2H), 3.28 (s, 3H), 3.15 (t, J=7.4 Hz, 2H), 2.83 (t, J=7.8 Hz, 2H), 2.00 (p, J=7.8 Hz, 2H).

Example 1.482

Synthesis of N-[2-(dimethylamino)ethyl]-2-{[2-(4-methoxypyridin-2-yl)-5H,6H,7H-cyclopenta[d]pyrimidin-4-yl](methyl)amino}acetamide (Compound 476)

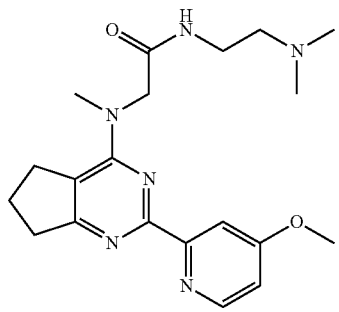 [SMILES: COc1ccnc(-c2nc3c(c(N(C)CC(=O)NCCN(C)C)n2)CCC3)c1]

Compound 476 was synthesized similar to Compound 135 by replacing oxolan-3-amine with (2-aminoethyl)dimethylamine. LCMS (ES) [M+1]$^+$ m/z: 385. $^1$H NMR (300 MHz, DMSO-d6, ppm): δ 8.48 (d, J=5.6 Hz, 1H), 8.06 (t, J=5.8 Hz, 1H), 7.81 (d, J=2.6 Hz, 1H), 7.04 (dd, J=5.6, 2.6 Hz, 1H), 4.18 (s, 2H), 3.90 (s, 3H), 3.27 (s, 3H), 3.17 (dq, Example 1.484

Synthesis of 2-[(2-{4-[2-(dimethylamino)ethoxy]pyridin-2-yl}-5H,6H,7H-cyclopenta[d]pyrimidin-4-yl)(methyl)amino]-N-(2,2,2-trifluoroethyl)acetamide (Compound 478)

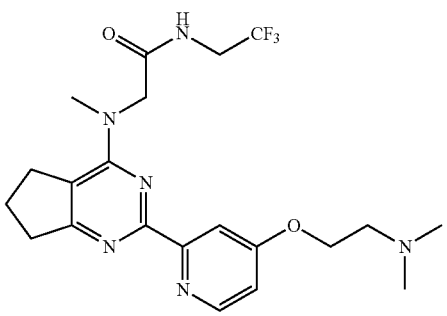 [SMILES: CN(C)CCOc1ccnc(-c2nc3c(c(N(C)CC(=O)NCC(F)(F)F)n2)CCC3)c1]

Compound 478 was synthesized similar to Compound 348 by replacing tert-butylamine with trifluoroethaylamine. LCMS (ES+): [M+H]$^+$=453.1. $^1$H NMR (400 MHz, dmso) δ 8.93 (t, J=6.4 Hz, 1H), 8.46 (d, J=5.6 Hz, 1H), 7.77 (d, J=2.5 Hz, 1H), 7.04 (dd, J=5.7, 2.6 Hz, 1H), 4.28 (s, 2H), 4.22 (t, J=5.6 Hz, 2H), 3.92 (qd, J=9.8, 6.3 Hz, 2H), 3.29 (s, 3H), 3.19-3.12 (m, 2H), 2.86-2.79 (m, 2H), 2.75 (t, J=5.6 Hz, 2H), 2.29 (s, 6H), 2.04-1.94 (m, 2H).

Example 1.485

Synthesis of 2-({2-[4-(2-hydroxy-2-methylpropoxy)pyridin-2-yl]-5H,6H,7H-cyclopenta[d]pyrimidin-4-yl}(methyl)amino)-N-(2,2,2-trifluoroethyl)acetamide (Compound 479)

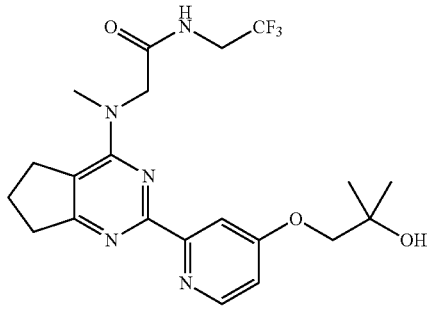 [SMILES: CN(CC(=O)NCC(F)(F)F)c1nc(-c2cc(OCC(C)(C)O)ccn2)nc2c1CCC2]

Compound 479 was synthesized similar to Compound 389 by replacing tertbutylamine with trifluoroethylamine. LCMS (ES+): [M+H]⁺=454.1. ¹H NMR (400 MHz, dmso) δ 8.97 (t, J=6.4 Hz, 1H), 8.45 (d, J=5.7 Hz, 1H), 7.77 (d, J=2.5 Hz, 1H), 7.04 (dd, J=5.6, 2.6 Hz, 1H), 4.77-4.62 (m, 1H), 4.28 (s, 2H), 3.92 (qd, J=9.7, 6.3 Hz, 2H), 3.86 (s, 2H), 3.29 (s, 3H), 3.17-3.10 (m, 2H), 2.86-2.77 (m, 2H), 2.03-1.94 (m, 2H), 1.22 (s, 6H).

Example 1.486

Synthesis of N-tert-butyl-2-[methyl(2-{4-[3-(methylamino)propyl]pyridin-2-yl}-5H,6H,7H-cyclopenta[d]pyrimidin-4-yl)amino]acetamide (Compound 480)

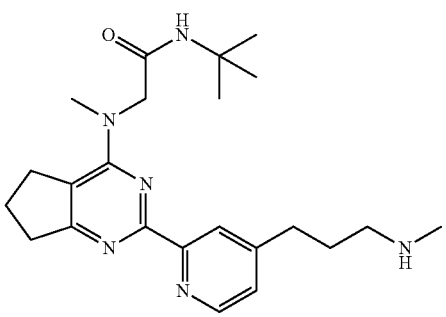 [SMILES: CNCCCc1ccnc(-c2nc3c(c(N(C)CC(=O)NC(C)(C)C)n2)CCC3)c1]

Scheme 138

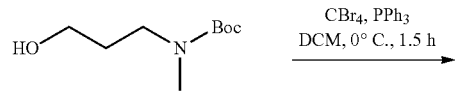

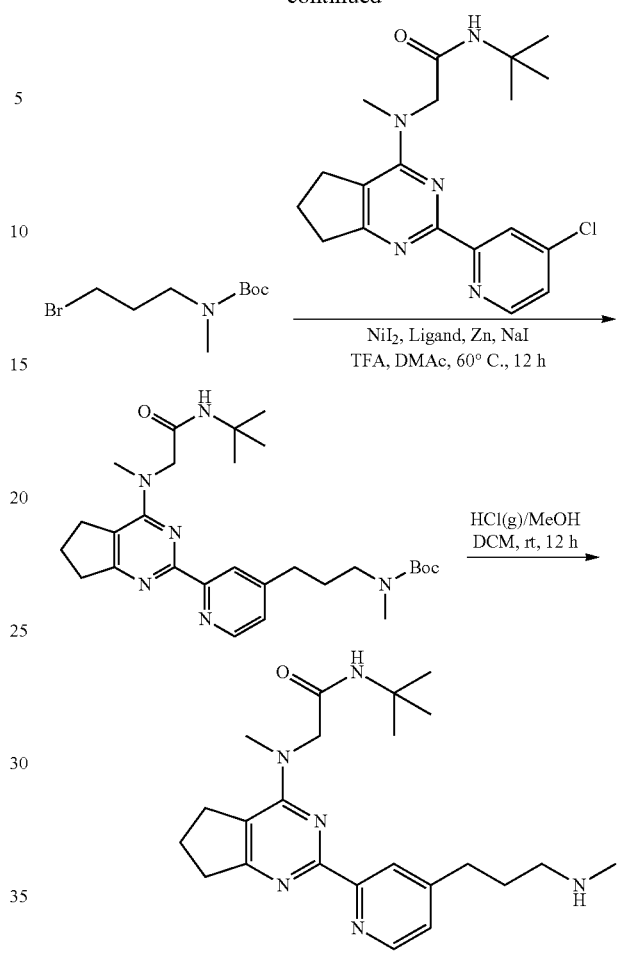

Step 1

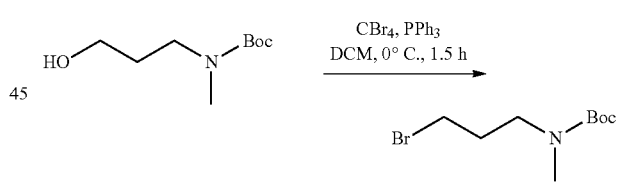

Into a 100 mL round-bottom flask were placed tert-butyl (3-hydroxypropyl)(methyl)carbamate (2.00 g, 10.60 mmol, 1.00 equiv), DCM (20.00 mL) and PPh₃ (3.67 g, 13.80 mmol, 1.30 equiv). This was followed by addition of CBr₄ (5.20 g, 13.80 mmol, 1.30 equiv) at 0° C. The resulting solution was stirred for 1.5 h at 0° C. The reaction mixture was quenched with H₂O (50.00 mL), extracted with DCM (100 mL*2). The combined organic phase was washed with Na₂CO₃ (aq), brine and dried over anhydrous sodium sulfate. After filtration, the filtrate was concentrated under reduced pressure. The residue was purified by silica gel column with petroleum ether/ethyl acetate (93%/7%). This resulted in 2.6 g of tert-butyl (3-bromopropyl)(methyl)carbamate as light yellow oil.

Step 2

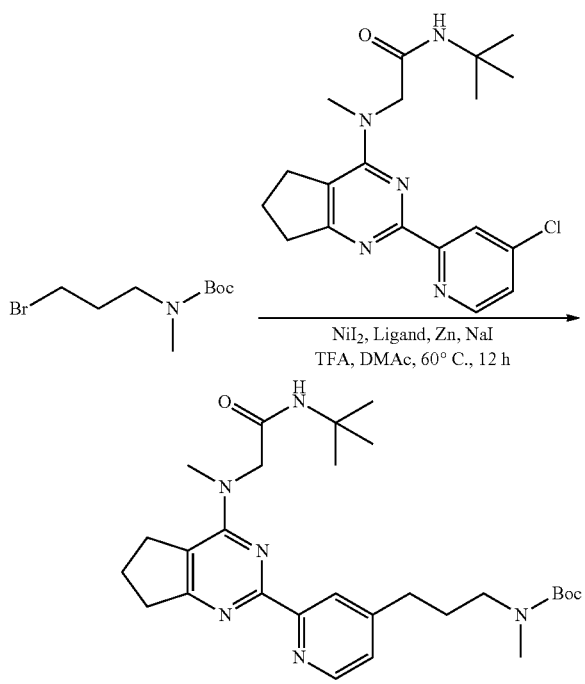

Into a 40-mL vial purged and maintained with an inert atmosphere of hydrogen were placed DMAC (10 mL), picolinimidamide hydrochloride (14 mg, 0.09 mmol, 0.05 equiv), NiI$_2$ (28 mg, 0.09 mmol, 0.05 equiv), sodium iodide (71 mg, 0.47 mmol, 0.25 equiv), tert-butyl (3-bromopropyl)(methyl)carbamate (577 mg, 2.30 mmol, 1.20 equiv), N-(tert-butyl)-2-((2-(4-chloropyridin-2-yl)-6,7-dihydro-5H-cyclopenta[d]pyrimidin-4-yl)(methyl)amino)acetamide (700 mg, 1.88 mmol, 1.00 equiv), zinc metal powder (246 mg, 3.76 mmol, 2.00 equiv), and trifluoroacetic acid (22 mg, 0.19 mmol, 0.10 equiv). The reaction mixture was heated to 60° C. and stirred for 12 h. The reaction mixture was purified by Prep-HPLC with the following conditions: Welch-XB C18 50*250, 10 um, Mobile phase A, water (0.1% TFA) and CH$_3$CN (13% Phase B up to 47% in 12 min), Detector, 220 nm. This resulted in 252 mg of tert-butyl (3-(2-(4-((2-(tert-butylamino)-2-oxoethyl)(methyl)amino)-6,7-dihydro-5H-cyclopenta[d]pyrimidin-2-yl)pyridin-4-yl)propyl)(methyl)carbamate as a light yellow oil. LCMS: (ES) [M+1]$^+$ m/z: 511.

Step 3

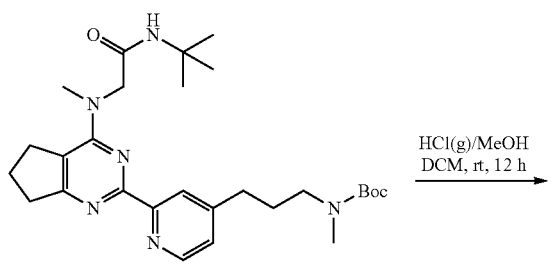

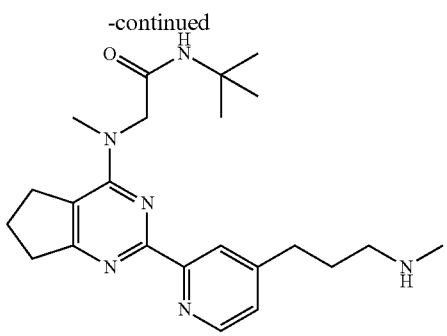

Into a 20-mL vial were placed tert-butyl (3-(2-(4-((2-(tert-butylamino)-2-oxoethyl)(methyl)amino)-6,7-dihydro-5H-cyclopenta[d]pyrimidin-2-yl)pyridin-4-yl)propyl)(methyl)carbamate (252 mg, 0.79 mmol, 1.00 equiv), HCl (g)/MeOH (4 M) (0.78 mL), DCM (3 mL). The mixture was stirred for 12 h at room temperature. The reaction mixture was purified by Prep-HPLC with the following conditions: Sunfire Prep C18 OBD Column, 50*250 mm, 5 μm, 10 nm, Mobile phase, water (0.1% FA) and CH$_3$CN (5% Phase B up to 25% in 12 min), Detector, 220 nm. 169 mg of N-(tert-butyl)-2-(methyl(2-(4-(3-(methylamino)propyl)pyridin-2-yl)-6,7-dihydro-5H-cyclopenta[d]pyrimidin-4-yl)amino)acetamide was obtained as off white solid. LCMS (ES, m/z): [M+H]$^+$: 411. $^1$H NMR (300 MHz, DMSO-d6, ppm): δ 8.58 (d, J=4.9 Hz, 1H), 8.30 (s, 1.4 HCOOH), 8.17 (s, 1H), 7.76 (s, 1H), 7.33 (dd, J=4.9, 1.7 Hz, 1H), 4.17 (s, 2H), 3.26 (s, 3H), 3.17 (t, J=7.3 Hz, 2H), 2.84-2.73 (m, 6H), 2.49 (s, 3H), 2.04-1.88 (m, 4H), 1.24 (s, 9H).

Example 1.487

Synthesis of N-tert-butyl-2-({2-[4-(3-hydroxy-3-methylbutyl)pyridin-2-yl]-5H,6H,7H-cyclopenta[d]pyrimidin-4-yl}(methyl)amino)acetamide (Compound 481)

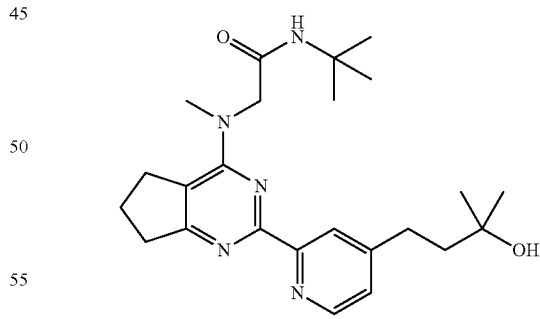

Compound 481 was synthesized similar to Compound 475 by replacing dimethyl(prop-2-yn-1-yl)amine with 2-methyl-3-butyn-2-ol. LCMS (ES) [M+1]$^+$ m/z: 426. $^1$H NMR (300 MHz, DMSO-d6, ppm): δ 8.53 (d, J=4.9 Hz, 1H), 8.16 (s, 0.7HCOOH), 8.14 (d, J=1.7 Hz, 1H), 7.69 (s, 1H), 7.28 (dd, J=5.0, 1.7 Hz, 1H), 4.16 (s, 2H), 3.27 (s, 3H), 3.15 (t, J=7.3 Hz, 2H), 2.82 (t, J=7.8 Hz, 2H), 2.76-2.67 (m, 2H), 2.07-1.91 (m, 2H), 1.75-1.64 (m, 2H), 1.24 (s, 9H), 1.17 (s, 6H).

Example 1.488

Synthesis of N-tert-butyl-2-{[2-(4-hydroxypyridin-2-yl)-5H,6H,7H-cyclopenta[d]pyrimidin-4-yl](methyl)amino}acetamide (Compound 482)

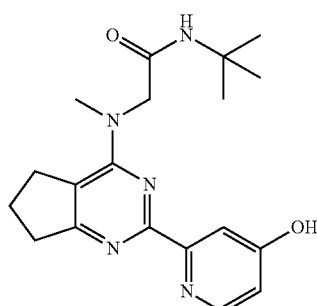

Scheme 139

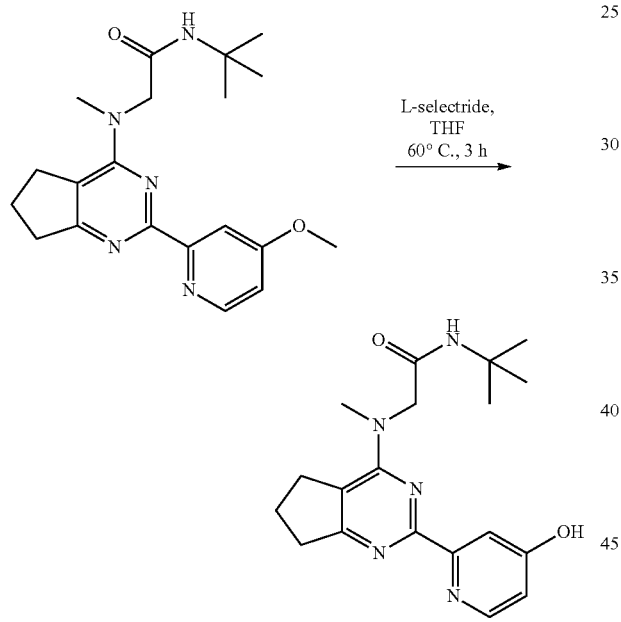

Into a 20 mL vial were added N-tert-butyl-2-{[2-(4-methoxypyridin-2-yl)-5H,6H,7H-cyclopenta[d]pyrimidin-4-yl](methyl)amino}acetamide (200 mg, 0.54 mmol, 1.00 equiv) and THF (5 mL). To the above mixture was added L-selectride (1.62 mL, 1.62 mmol, 3.00 equiv) dropwise under nitrogen atmosphere. The resulting mixture was stirred for additional 3 h at 60° C. The mixture was cooled down to room temperature. The reaction was quenched with water (5 mL), concentrated under vacuum to remove the solvent, the residue was purified by Prep-HPLC with the following conditions: Sunfire Prep C18 OBD Column, 50*250 mm, 5 μm, 10 nm, mobile phase, water (0.05% NH₃H₂O) and CH₃CN (10% up to 70% in 15 min) to afford N-tert-butyl-2-{[2-(4-hydroxypyridin-2-yl)-5H,6H,7H-cyclopenta[d]pyrimidin-4-yl](methyl)amino}acetamide (49.5 mg, 26%) as an off-white solid. LCMS (ES, m/z): [M+H]⁺: 356. ¹H-NMR (300 MHz, DMSO-d₆, ppm): δ 7.71 (s, 1H), 7.64 (d, J=7.4 Hz, 1H), 7.10 (s, 1H), 6.14 (d, J=7.4 Hz, 1H), 4.13 (s, 2H), 3.30 (s, 3H), 3.16 (t, J=7.3 Hz, 2H), 2.84 (t, J=7.8 Hz, 2H), 2.02-1.97 (m, 2H), 1.24 (s, 9H).

Example 1.489

Synthesis of 2-({2-[4-(2-aminoethoxy)pyridin-2-yl]-5H,6H,7H-cyclopenta[d]pyrimidin-4-yl}(methyl)amino)-N-tert-butylacetamide (Compound 483)

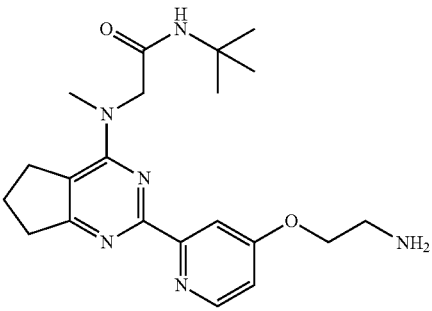 [SMILES: CN(CC(=O)NC(C)(C)C)c1nc(-c2cc(OCCN)ccn2)nc2c1CCC2]

Compound 483 was synthesized similar to Compound 348 by replacing dimethylaminoethanol with ethanolamine. LCMS (ES) [M+1]⁺ m/z: 399. ¹H NMR (300 MHz, DMSO-d6, ppm): δ 8.75 (d, J=6.0 Hz, 1H), 8.20 (br, 3H), 8.04 (d, J=2.6 Hz, 1H), 7.88 (s, 1H), 7.47 (dd, J=6.1, 2.6 Hz, 1H), 4.49 (t, J=5.1 Hz, 2H), 4.38 (s, 2H), 3.42 (s, 3H), 3.33 (q, J=5.5 Hz, 2H), 3.20 (s, 2H), 3.02 (t, J=7.9 Hz, 2H), 2.18-2.00 (m, 2H), 1.26 (s, 9H).

Example 1.490

Synthesis of N-tert-butyl-2-[(2-{4-[2-(dimethylamino)ethoxy]pyridin-2-yl}-5H,6H,7H-cyclopenta[d]pyrimidin-4-yl)amino]acetamide (Compound 484)

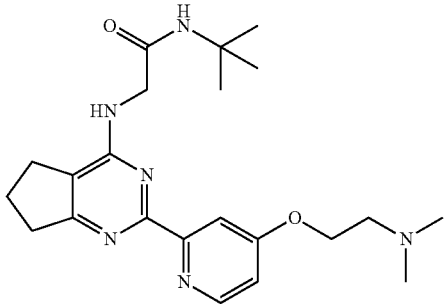 [SMILES: CN(C)CCOc1ccnc(-c2nc3c(c(NCC(=O)NC(C)(C)C)n2)CCC3)c1]

Compound 484 was synthesized similar to Compound 348 by replacing N-(tert-butyl)-2-(methylamino)acetamide hydrochloride with 2-amino-N-tert-butylacetamide hydrochloride. LCMS (ES) [M+1]⁺ m/z: 413. ¹H NMR (300 MHz, DMSO-d6, ppm): δ 8.46 (d, J=5.6 Hz, 1H), 7.86 (d, J=2.6 Hz, 1H), 7.69 (s, 1H), 7.14 (t, J=5.8 Hz, 1H), 7.04 (dd, J=5.7, 2.6 Hz, 1H), 4.19 (t, J=5.6 Hz, 2H), 3.93 (d, J=5.7 Hz, 2H), 2.83 (t, J=7.7 Hz, 2H), 2.78-2.70 (m, 2H), 2.66 (t, J=5.6 Hz, 2H), 2.23 (s, 6H), 2.14-1.98 (m, 2H), 1.25 (s, 9H).

Example 1.491

Synthesis of N-tert-butyl-2-[(2-{4-[2-(methylamino)ethoxy]pyridin-2-yl}-5H,6H,7H-cyclopenta[d]pyrimidin-4-yl)amino]acetamide (Compound 485)

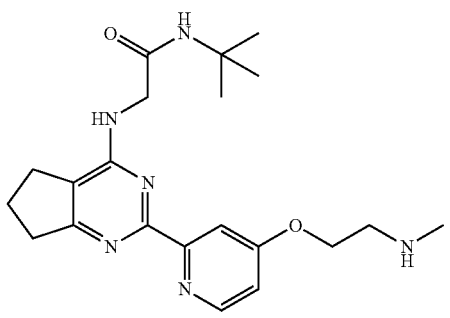 [SMILES: CNCCOc1ccnc(-c2nc3c(c(NCC(=O)NC(C)(C)C)n2)CCC3)c1]

Compound 485 was synthesized similar to Compound 348 by replacing N-(tert-butyl)-2-(methylamino)acetamide hydrochloride with 2-amino-N-tert-butylacetamide hydrochloride and by replacing dimethylaminoethanol with methylethanolamine. LCMS (ES) [M+1]$^+$ m/z: 399. $^1$H NMR (300 MHz, DMSO-d6, ppm): δ 9.23 (br, 2H), 8.69 (d, J=5.9 Hz, 1H), 8.41 (br, 1H), 8.08 (d, J=2.6 Hz, 1H), 7.95 (s, 1H), 7.38 (dd, J=6.2, 2.5 Hz, 1H), 4.56 (t, J=5.0 Hz, 2H), 4.16 (d, J=5.8 Hz, 2H), 2.99 (t, J=7.5 Hz, 2H), 2.81 (t, J=7.4 Hz, 2H), 2.65 (s, 3H), 2.19-2.09 (m, 2H), 1.25 (s, 9H).

Example 1.492

Synthesis of 2-{[2-(4-{[(2R)-1-(dimethylamino)propan-2-yl]oxy}pyridin-2-yl)-5H,6H,7H-cyclopenta[d]pyrimidin-4-yl](methyl)amino}-N-[1-(trifluoromethyl)cyclopropyl]acetamide (Compound 486)

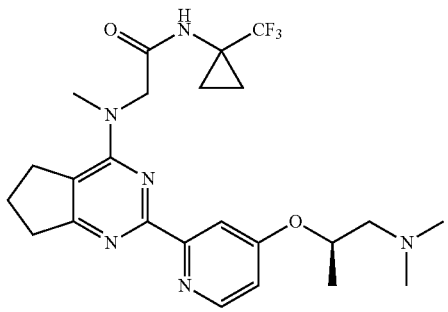 [SMILES: C[C@H](CN(C)C)Oc1ccnc(-c2nc3c(c(N(C)CC(=O)NC4(C(F)(F)F)CC4)n2)CCC3)c1]

Compound 486 was synthesized similar to Compound 348 by replacing dimethylaminoethanol with (2R)-1-(dimethylamino)propan-2-ol and by replacing tert-butylamine with 1-(trifluoromethyl)cyclopropan-1-amine. LCMS (ES) [M+1]$^+$ m/z: 493. $^1$H NMR (300 MHz, DMSO-d6, ppm): δ 9.02 (s, 1H), 8.45 (dd, J=5.7, 1.7 Hz, 1H), 8.17 (s, 1.7HCOOH), 7.73 (t, J=2.2 Hz, 1H), 7.13-7.03 (m, 1H), 4.86-4.80 (m, J=7.9 Hz, 1H), 4.16 (s, 2H), 3.28 (s, 3H), 3.15 (t, J=7.3 Hz, 2H), 2.82 (t, J=7.8 Hz, 2H), 2.70-2.59 (m, 1H), 2.52-2.49 (m, 1H), 2.27 (s, 6H), 2.04-1.94 (m, 2H), 1.29 (dd, J=6.1, 1.6 Hz, 3H), 1.22-1.15 (m, 2H), 1.03-0.95 (m, 2H).

Example 1.493

Synthesis of 2-{methyl[2-(4-{[(3R)-1-methylpyrrolidin-3-yl]oxy}pyridin-2-yl)-5H,6H,7H-cyclopenta[d]pyrimidin-4-yl]amino}-N-[1-(trifluoromethyl)cyclopropyl]acetamide (Compound 487)

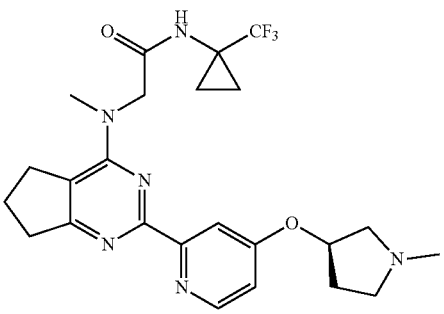 [SMILES: CN1CC[C@@H](Oc2ccnc(-c3nc4c(c(N(C)CC(=O)NC5(C(F)(F)F)CC5)n3)CCC4)c2)C1]

Compound 487 was synthesized similar to Compound 348 by replacing dimethylaminoethanol with (3R)-1-methylpyrrolidin-3-ol and by replacing tert-butylamine with 1-(trifluoromethyl)cyclopropan-1-amine. LCMS (ES) [M+1]$^+$ m/z: 491. $^1$H NMR (300 MHz, DMSO-d6, ppm): δ 9.02 (s, 1H), 8.45 (d, J=5.6 Hz, 1H), 8.17 (s, 1HCOOH), 7.68 (d, J=2.5 Hz, 1H), 6.99 (dd, J=5.6, 2.5 Hz, 1H), 5.09-5.00 (m, 1H), 4.18 (s, 2H), 3.28 (s, 3H), 3.15 (t, J=7.3 Hz, 2H), 2.82 (t, J=8.0 Hz, 3H), 2.76-2.63 (m, 2H), 2.42-2.31 (m, 2H), 2.29 (s, 3H), 2.06-1.93 (m, 2H), 1.86-1.75 (m, 1H), 1.24-1.13 (m, 2H), 1.03-0.94 (m, 2H).

Example 1.494

Synthesis of N-tert-butyl-2-{[2-(4-{[(3R,5R)-1,5-dimethylpyrrolidin-3-yl]oxy}pyridin-2-yl)-5H,6H,7H-cyclopenta[d]pyrimidin-4-yl](methyl)amino}acetamide (Compound 488)

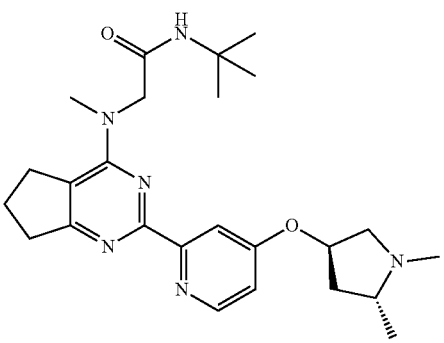 [SMILES: C[C@@H]1C[C@@H](Oc2ccnc(-c3nc4c(c(N(C)CC(=O)NC(C)(C)C)n3)CCC4)c2)CN1C]

Compound 488 was synthesized similar to Compound 348 by replacing dimethylaminoethanol with (3R,5R)-1,5-dimethylpyrrolidin-3-ol. LCMS (ES) [M+1]$^+$ m/z: 453. $^1$H NMR (300 MHz, DMSO-d6, ppm): δ 8.45 (d, J=5.6 Hz, 1H), 7.81 (d, J=2.5 Hz, 1H), 7.70 (s, 1H), 6.99 (dd, J=5.7, 2.5 Hz, 1H), 5.02-4.96 (m, 1H), 4.11 (s, 2H), 3.62 (dd, J=10.2, 6.6 Hz, 1H), 3.27 (s, 3H), 3.15 (t, J=7.3 Hz, 2H), 2.81 (t, J=7.9 Hz, 2H), 2.41 (dt, J=11.4, 6.0 Hz, 1H), 2.28-2.24 (m, 1H), 2.24 (s, 3H), 2.05-1.91 (m, 3H), 1.91-1.78 (m, 1H), 1.26 (s, 9H), 1.06 (d, J=5.9 Hz, 3H).

Example 1.495

Synthesis of N-tert-butyl-2-{methyl[2-(4-{[(3R)-1-methylpiperidin-3-yl]oxy}pyridin-2-yl)-5H,6H,7H-cyclopenta[d]pyrimidin-4-yl]amino}acetamide (Compound 489)

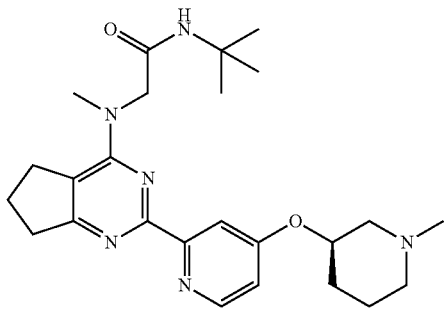 [SMILES: CN1CCC[C@@H](Oc2ccnc(-c3nc4c(c(N(C)CC(=O)NC(C)(C)C)n3)CCC4)c2)C1]

Compound 489 was synthesized similar to Compound 348 by replacing dimethylaminoethanol with (3R)-1-methylpiperidin-3-ol. LCMS (ES) [M+1]+ m/z: 453. ¹H NMR (300 MHz, DMSO-d6, ppm): δ 8.47 (d, J=5.7 Hz, 1H), 8.18 (s, 1.7 HCOOH), 7.84 (d, J=2.5 Hz, 1H), 7.71 (s, 1H), 7.09 (dd, J=5.7, 2.6 Hz, 1H), 4.66 (dt, J=8.0, 4.1 Hz, 1H), 4.11 (s, 2H), 3.27 (s, 3H), 3.14 (t, J=7.3 Hz, 2H), 2.93 (dd, J=10.6, 3.4 Hz, 1H), 2.81 (t, J=7.8 Hz, 2H), 2.66-2.51 (m, 1H), 2.28 (s, 3H), 2.36-2.16 (m, 2H), 2.05-1.92 (m, 3H), 1.84-1.71 (m, 1H), 1.69-1.55 (m, 1H), 1.52-1.38 (m, 1H), 1.25 (s, 9H).

Example 1.496

Synthesis of N-tert-butyl-2-{methyl[2-(4-{[(3S)-1-methylpiperidin-3-yl]oxy}pyridin-2-yl)-5H,6H,7H-cyclopenta[d]pyrimidin-4-yl]amino}acetamide (Compound 490)

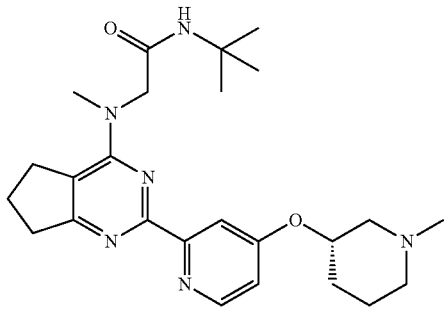 [SMILES: CN1CCC[C@H](Oc2ccnc(-c3nc4c(c(N(C)CC(=O)NC(C)(C)C)n3)CCC4)c2)C1]

Compound 490 was synthesized similar to Compound 348 by replacing dimethylaminoethanol with (3S)-1-methylpiperidin-3-ol. LCMS (ES) [M+1]+ m/z: 453. ¹H NMR (300 MHz, DMSO-d6, ppm): δ 8.47 (d, J=5.7 Hz, 1H), 8.18 (s, 1.7 HCOOH), 7.84 (d, J=2.5 Hz, 1H), 7.71 (s, 1H), 7.09 (dd, J=5.7, 2.6 Hz, 1H), 4.66 (dt, J=8.0, 4.1 Hz, 1H), 4.11 (s, 2H), 3.27 (s, 3H), 3.14 (t, J=7.3 Hz, 2H), 2.93 (dd, J=10.6, 3.4 Hz, 1H), 2.81 (t, J=7.8 Hz, 2H), 2.66-2.51 (m, 1H), 2.28 (s, 3H), 2.36-2.16 (m, 2H), 2.05-1.92 (m, 3H), 1.84-1.71 (m, 1H), 1.69-1.55 (m, 1H), 1.52-1.38 (m, 1H), 1.25 (s, 9H).

Example 1.497

Synthesis of N-tert-butyl-2-{[2-(4-{[(3R)-1-(2,2-difluoroethyl)pyrrolidin-3-yl]oxy}pyridin-2-yl)-5H,6H,7H-cyclopenta[d]pyrimidin-4-yl](methyl)amino}acetamide (Compound 491)

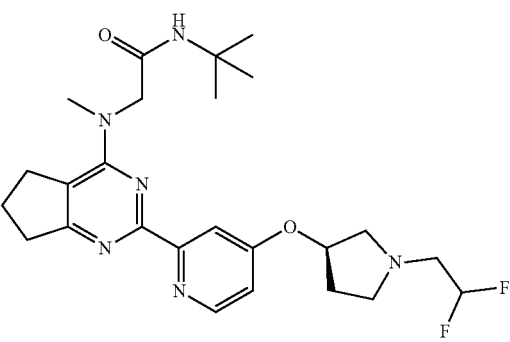 [SMILES: CN(CC(=O)NC(C)(C)C)c1nc(-c2cc(O[C@@H]3CCN(CC(F)F)C3)ccn2)nc2c1CCC2]

Compound 491 was synthesized similar to Compound 348 by replacing dimethylaminoethanol with (3R)-1-(2,2-difluoroethyl)pyrrolidin-3-ol. LCMS (ES) [M+1]+ m/z: 489. ¹H NMR (300 MHz, DMSO-d6, ppm): δ 8.46 (d, J=5.6 Hz, 1H), 7.81 (d, J=2.5 Hz, 1H), 7.69 (s, 1H), 7.00 (dd, J=5.7, 2.6 Hz, 1H), 6.12 (tt, J=55.8, 4.2 Hz, 1H), 5.06 (dt, J=7.1, 3.3 Hz, 1H), 4.12 (s, 2H), 3.27 (s, 3H), 3.14 (t, J=7.3 Hz, 2H), 3.02 (dd, J=10.7, 6.0 Hz, 1H), 2.95-2.74 (m, 6H), 2.65-2.55 (m, 1H), 2.34 (dt, J=13.6, 6.9 Hz, 1H), 2.02-1.95 (m, 2H), 1.88-1.70 (m, 1H), 1.25 (s, 9H).

Example 1.498

Synthesis of N-tert-butyl-2-({2-[4-(2-hydroxy-2-methylpropoxy)pyridin-2-yl]-5-oxo-5H,6H,7H-cyclopenta[d]pyrimidin-4-yl}(methyl)amino)acetamide (Compound 492)

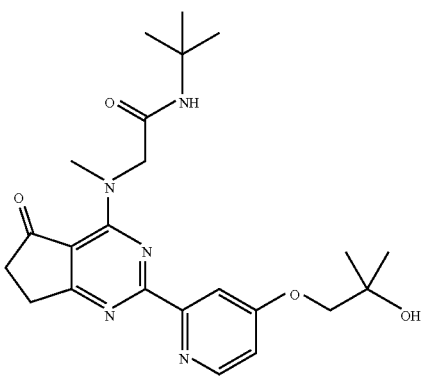 [SMILES: CN(CC(=O)NC(C)(C)C)c1nc(-c2cc(OCC(C)(C)O)ccn2)nc2c1C(=O)CC2]

953

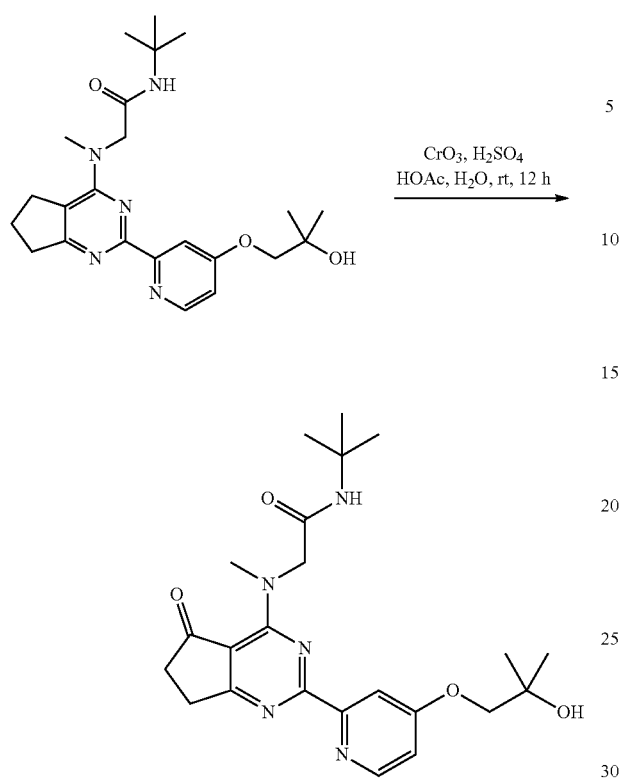

To a stirred solution of N-tert-butyl-2-({2-[4-(2-hydroxy-2-methylpropoxy)pyridin-2-yl]-5H,6H,7H-cyclopenta[d]pyrimidin-4-yl}(methyl)amino)acetamide (400 mg, 0.94 mmol, 1.00 equiv) in HOAc (1.5 mL) and $H_2SO_4$ (0.3 mL) were added $CrO_3$ (196 mg, 1.96 mmol, 2.0 equiv) in HOAc (2.0 mL) and $H_2O$ (0.4 mL) dropwise below 10° C. under air atmosphere. The resulting mixture was stirred for 16 h at room temperature. The mixture was basified to pH-13 with (3 N) NaOH in $H_2O$, extracted with $CH_2Cl_2$/MeOH=10:1 (3*30 mL). The combined organic layers were washed with brine (1*30 mL), dried over anhydrous $Na_2SO_4$. After filtration, the filtrate was concentrated under reduced pressure. The residue was purified by Prep-HPLC with the following conditions: C18 OBD Column, 50*250 mm, 5 μm, 10 nm, mobile phase, $CH_3CN/H_2O$ (FA: 0.1%), from 5% to 35% in 12 min, Flow rate, 80 mL/min, Detector, UV 254 nm. This result in N-tert-butyl-2-({2-[4-(2-hydroxy-2-methylpropoxy)pyridin-2-yl]-5-oxo-6H,7H-cyclopenta[d]pyrimidin-4-yl}(methyl)amino)acetamide (65 mg, 16%) as a white solid. LCMS (ES, m/z): $[M+H]^+$: 442. $^1$H-NMR (300 MHz, DMSO-$d_6$, ppm): δ 8.55 (d, J=5.6 Hz, 1H), 7.92 (d, J=2.5 Hz, 1H), 7.74 (s, 1H), 7.15 (dd, J=5.6, 2.6 Hz, 1H), 4.72 (s, 1H), 4.42 (s, 2H), 3.89 (s, 2H), 3.34 (s, 3H), 3.12-2.97 (m, 2H), 2.69-2.58 (m, 2H), 1.25 (s, 6H), 1.23 (s, 9H).

Example 1.499

Synthesis of N-tert-butyl-2-[(2-{4-[2-(dimethylamino)ethoxy]pyridin-2-yl}-5-hydroxy-5H,6H,7H-cyclopenta[d]pyrimidin-4-yl)(methyl)amino]acetamide (Compound 493)

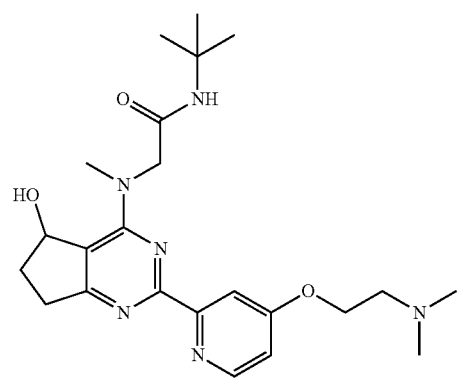 [SMILES: CN(C)CCOc1ccnc(-c2nc3c(c(N(C)CC(=O)NC(C)(C)C)n2)C(O)CC3)c1]

Scheme 140

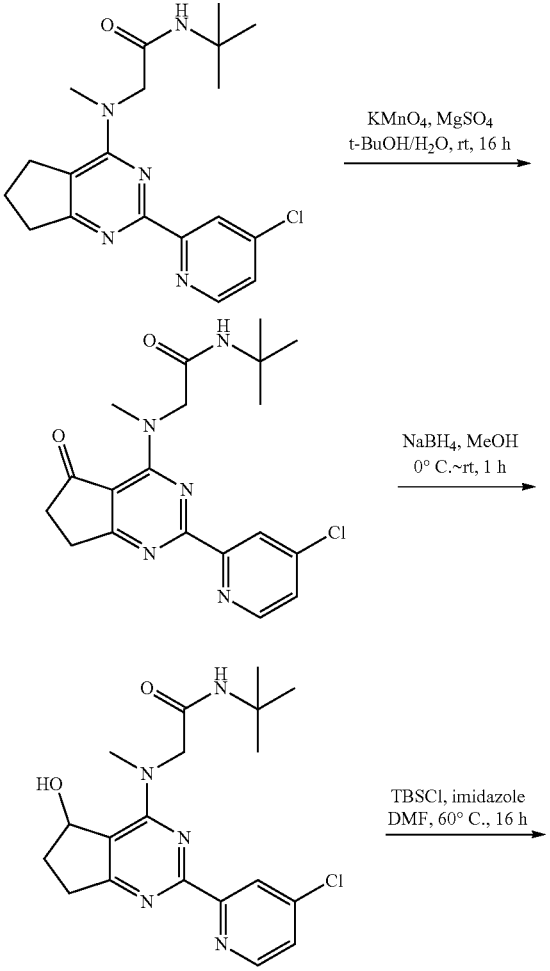

Step 1

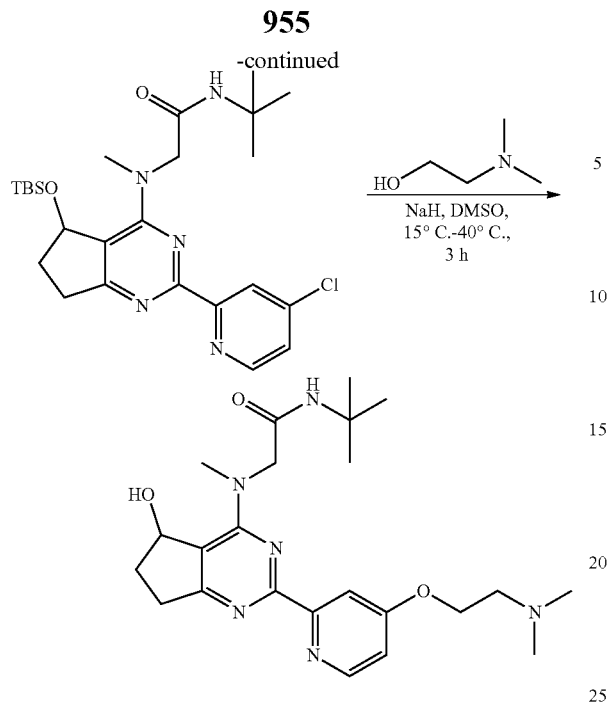

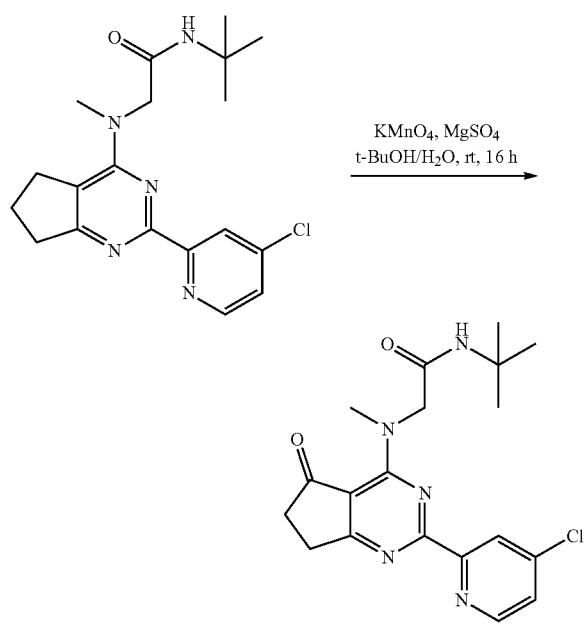

To a stirred mixture of N-tert-butyl-2-{[2-(4-chloropyridin-2-yl)-5H,6H,7H-cyclopenta[d]pyrimidin-4-yl](methyl)amino}acetamide (1.0 g, 2.67 mmol, 1.00 equiv) in t-BuOH (10.0 mL) and H₂O (2.0 mL) was added MgSO₄ (0.97 g, 8.02 mmol, 3.00 equiv) and KMnO₄ (850 mg, 5.35 mmol, 2.00 equiv) in portions at 0° C. The resulting solution was stirred for 16 h at room temperature, filtered and concentrated, the residue was purified by Prep-HPLC with the following conditions: Sunfire Prep C18 OBD Column, 50*250 mm, 5 μm, 10 nm, mobile phase, water (0.1% FA) and CH₃CN (15% up to 50% in 12 min), Detector, UV 220 nm to afford N-tert-butyl-2-{[2-(4-chloropyridin-2-yl)-5-oxo-6H,7H-cyclopenta[d]pyrimidin-4-yl](methyl)amino}acetamide (350 mg, 33.7%) as a yellow solid. LCMS (ES) [M+1]⁺ m/z: 388.

Step 2

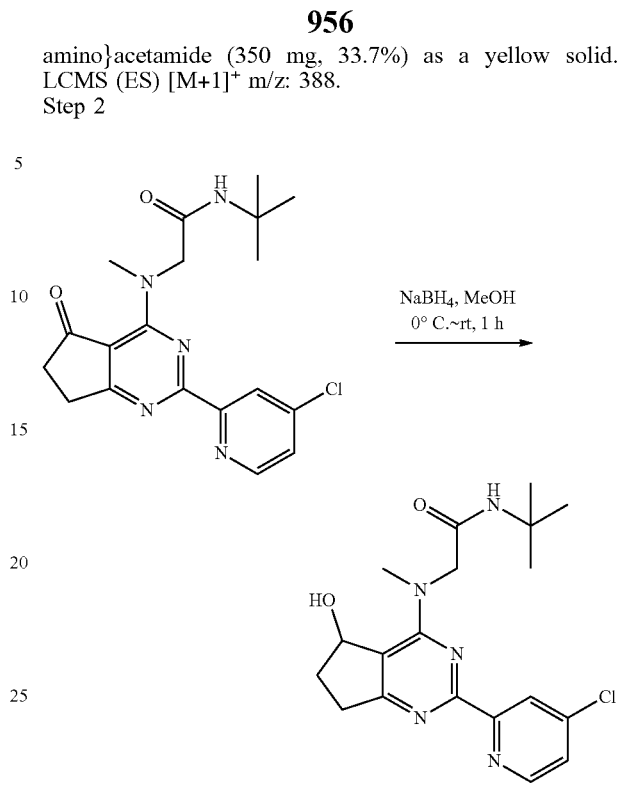

To a stirred solution of N-tert-butyl-2-{[2-(4-chloropyridin-2-yl)-5-oxo-6H,7H-cyclopenta[d]pyrimidin-4-yl](methyl)amino}acetamide (300 mg, 0.77 mmol, 1.00 equiv) in MeOH (10 mL) was added NaBH₄ (58 mg, 1.54 mmol, 2.00 equiv) in portions at 0° C. under N₂ atmosphere. The resulting solution was stirred for 1 h at the same temperature. The reaction was then quenched by the addition of water/ice (10 mL), extracted with EtOAc (30 mL*5). The combined organic layers were washed with brine (10 mL), dried over anhydrous Na₂SO₄. After filtration, the filtrate was concentrated under reduced pressure. This resulted in N-tert-butyl-2-{[2-(4-chloropyridin-2-yl)-5-hydroxy-5H,6H,7H-cyclopenta[d]pyrimidin-4-yl](methyl)amino}acetamide (286 mg, 95%) as a yellow solid used to the next step directly without further purification. LCMS (ES) [M+1]⁺ m/z: 390.

Step 3

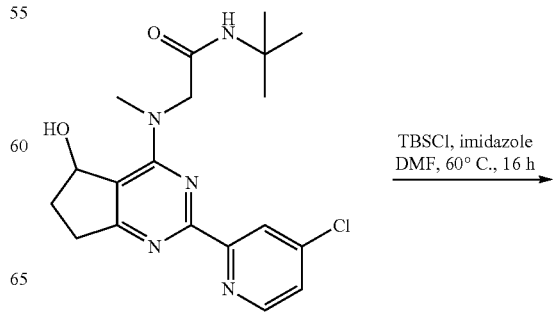

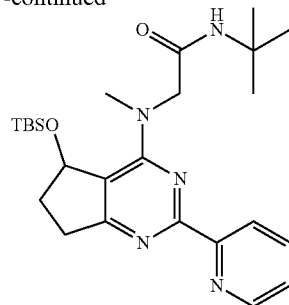

To a stirred solution of N-tert-butyl-2-{[2-(4-chloropyridin-2-yl)-5-hydroxy-5H,6H,7H-cyclopenta[d]pyrimidin-4-yl](methyl)amino}acetamide (300 mg, 0.76 mmol, 1.00 equiv) in DMF (8 mL) was added imidazole (157 mg, 2.31 mmol, 3.00 equiv) and TBSCl (232 mg, 1.53 mmol, 2.00 equiv) in portions at room temperature. The reaction was stirred at 60° C. for 16 h. The reaction was quenched with water (10 mL) at room temperature, extracted with EtOAc (3*30 mL). The combined organic layers were washed with brine (20 mL*1), dried over anhydrous Na₂SO₄. After filtration, the filtrate was concentrated under reduced pressure. The residue was purified by silica gel column chromatography, eluted with THF/PE (1:100 to 1:1) to afford N-tert-butyl-2-({5-[(tert-butyldimethylsilyl)oxy]-2-(4-chloropyridin-2-yl)-5H,6H,7H-cyclopenta[d]pyrimidin-4-yl}(methyl)amino)acetamide (370 mg, 95%) as an off-white solid. LCMS (ES) [M+1]⁺ m/z: 504.

Step 4

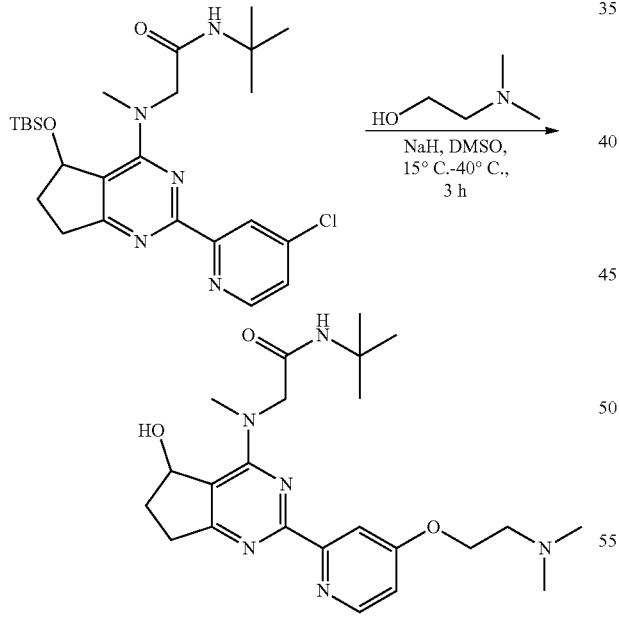

To a solution of dimethylaminoethanol (124 mg, 1.39 mmol, 2.00 equiv) in DMSO (5.0 mL) was added sodium hydride (60% in mineral oil, 55 mg, 1.39 mmol, 2.00 equiv) at 15° C. After the reaction was stirred at 15~25° C. for 1 h, N-tert-butyl-2-({5-[(tert-butyldimethylsilyl)oxy]-2-(4-chloropyridin-2-yl)-5H,6H,7H-cyclopenta[d]pyrimidin-4-yl}(methyl)amino)acetamide (350 mg, 0.69 mmol, 1.00 equiv) was added in one portion. Then the resulting mixture was stirred for another 2 h at 40° C. The reaction was cooled to room temperature and purified by Prep_HPLC with conditions: Kinetex EVO C18 Column, 21.2*150, 5 um, mobile phase A, water (0.1% FA) and mobile phase B, CH₃CN (10% Phase B up to 50% in 15 min), Detector, UV 254 nm, to give N-tert-butyl-2-[(2-{4-[2-(dimethylamino)ethoxy]pyridin-2-yl}-5-hydroxy-5H,6H,7H-cyclopenta[d]pyrimidin-4-yl)(methyl)amino]acetamide (72 mg, 23.43%) as an off white solid. LCMS (ES) [M+1]⁺ m/z: 443. ¹H NMR (400 MHz, DMSO-d₆) δ 8.48 (d, J=5.6 Hz, 1H), 7.84 (d, J=2.5 Hz, 1H), 7.68 (s, 1H), 7.07 (dd, J=5.7, 2.5 Hz, 1H), 5.32 (d, J=7.1 Hz, 1H), 5.27-5.20 (m, 1H), 4.34-4.09 (m, 4H), 3.36 (s, 3H), 3.04 (dt, J=16.9, 8.4 Hz, 1H), 2.66 (t, J=5.6 Hz, 3H), 2.23 (s, 6H), 2.25-2.15 (m, 1H), 1.93 (dd, J=13.6, 8.2 Hz, 1H), 1.25 (s, 9H).

Example 1.500

Synthesis of N-tert-butyl-2-[(2-{4-[2-(dimethylamino)ethoxy]pyridin-2-yl}-7-hydroxy-5H,6H,7H-cyclopenta[d]pyrimidin-4-yl)(methyl)amino]acetamide (Compound 494)

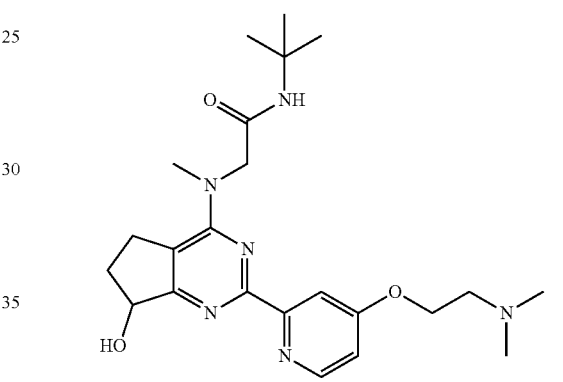

Scheme 141

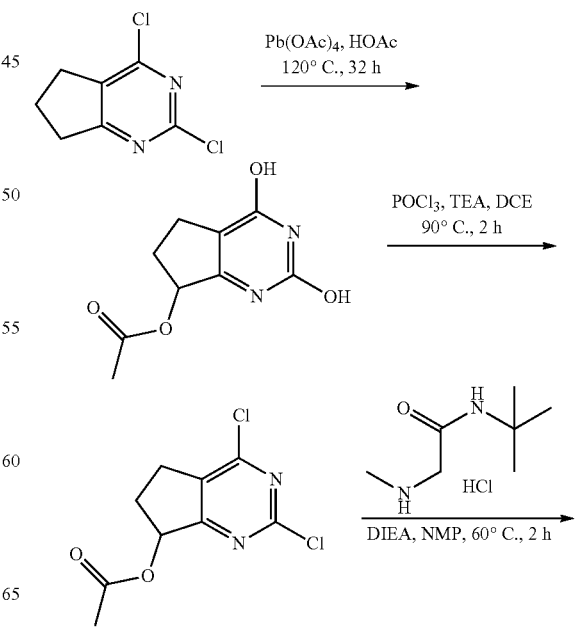

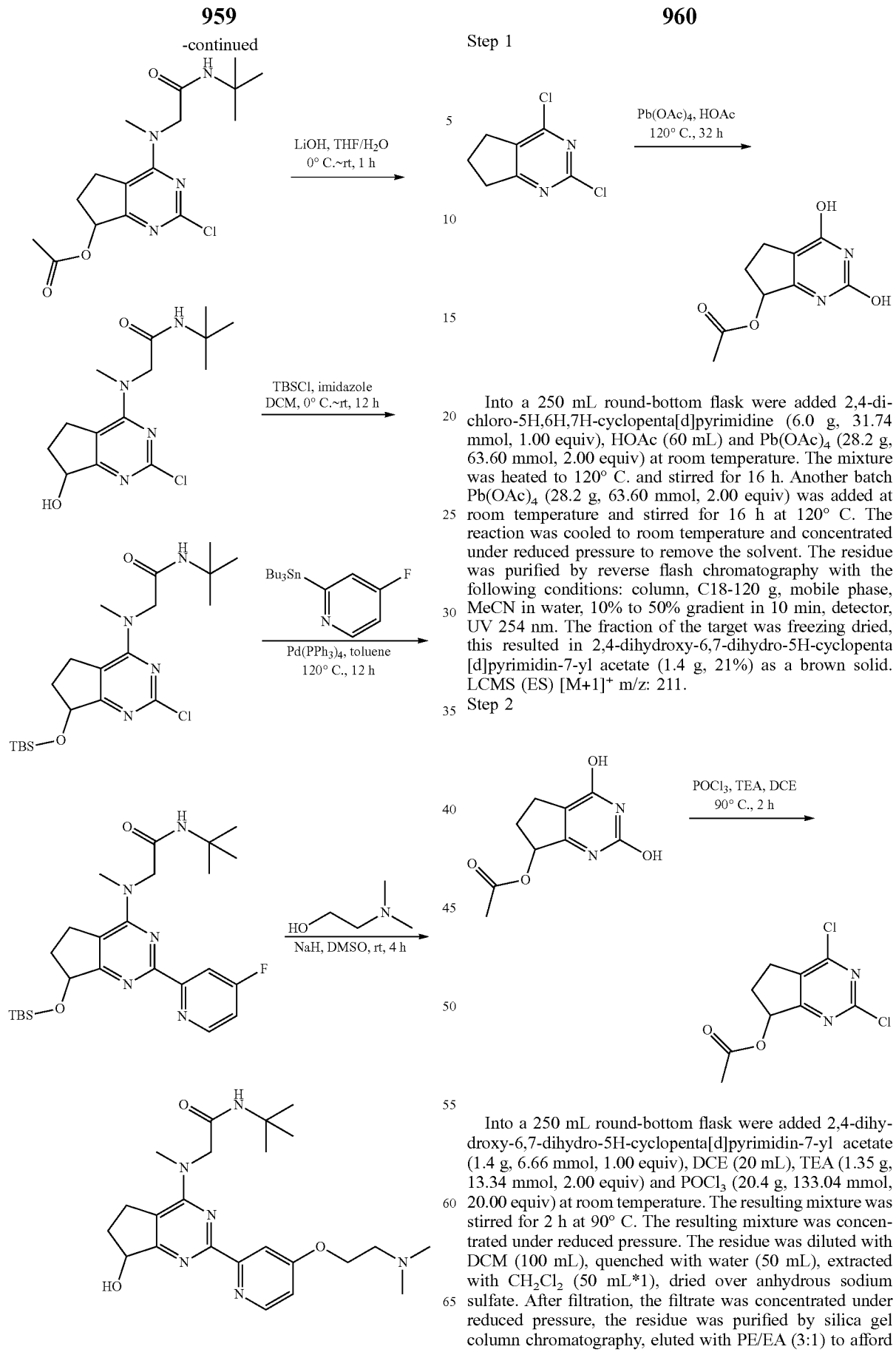

Step 1

Into a 250 mL round-bottom flask were added 2,4-dichloro-5H,6H,7H-cyclopenta[d]pyrimidine (6.0 g, 31.74 mmol, 1.00 equiv), HOAc (60 mL) and Pb(OAc)$_4$ (28.2 g, 63.60 mmol, 2.00 equiv) at room temperature. The mixture was heated to 120° C. and stirred for 16 h. Another batch Pb(OAc)$_4$ (28.2 g, 63.60 mmol, 2.00 equiv) was added at room temperature and stirred for 16 h at 120° C. The reaction was cooled to room temperature and concentrated under reduced pressure to remove the solvent. The residue was purified by reverse flash chromatography with the following conditions: column, C18-120 g, mobile phase, MeCN in water, 10% to 50% gradient in 10 min, detector, UV 254 nm. The fraction of the target was freezing dried, this resulted in 2,4-dihydroxy-6,7-dihydro-5H-cyclopenta[d]pyrimidin-7-yl acetate (1.4 g, 21%) as a brown solid. LCMS (ES) [M+1]$^+$ m/z: 211.

Step 2

Into a 250 mL round-bottom flask were added 2,4-dihydroxy-6,7-dihydro-5H-cyclopenta[d]pyrimidin-7-yl acetate (1.4 g, 6.66 mmol, 1.00 equiv), DCE (20 mL), TEA (1.35 g, 13.34 mmol, 2.00 equiv) and POCl$_3$ (20.4 g, 133.04 mmol, 20.00 equiv) at room temperature. The resulting mixture was stirred for 2 h at 90° C. The resulting mixture was concentrated under reduced pressure. The residue was diluted with DCM (100 mL), quenched with water (50 mL), extracted with CH$_2$Cl$_2$ (50 mL*1), dried over anhydrous sodium sulfate. After filtration, the filtrate was concentrated under reduced pressure, the residue was purified by silica gel column chromatography, eluted with PE/EA (3:1) to afford

961

2,4-dichloro-6,7-dihydro-5H-cyclopenta[d]pyrimidin-7-yl acetate (1.3 g, 79%) as a yellow oil. LCMS (ES) [M+1]+ m/z: 247.
Step 3

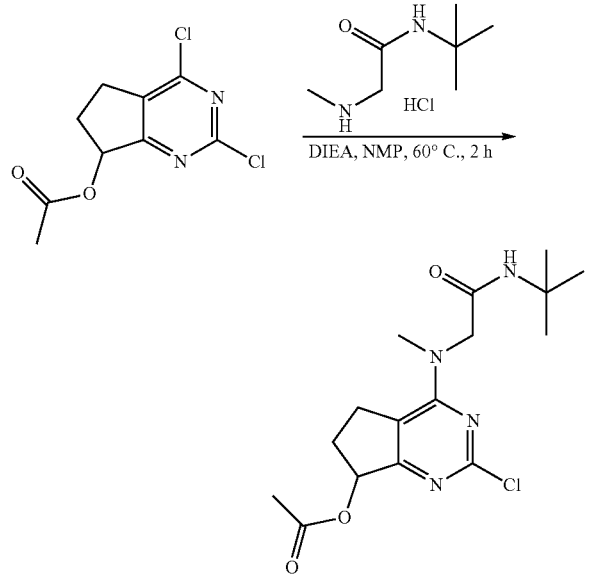

Into a 40 mL vial were added 2,4-dichloro-6,7-dihydro-5H-cyclopenta[d]pyrimidin-7-yl acetate (1.3 g, 5.26 mmol, 1.00 equiv), NMP (15 mL), DIEA (2.04 g, 15.78 mmol, 3.00 equiv) and N-tert-butyl-2-(methylamino)acetamide hydrochloride (1.43 g, 7.92 mmol, 1.50 equiv) at room temperature. The resulting mixture was stirred for 2 h at 60° C. The reaction was cooled to room temperature, quenched with water (20 mL), the aqueous layer was extracted with EtOAc (30 mL*3). The combined organic phase was washed with brine (20 mL*3), dried over anhydrous sodium sulfate. After filtration, the filtrate was concentrated under reduced pressure. The residue was purified by silica gel column chromatography, eluted with PE/EA (1:1) to afford 4-((2-(tert-butylamino)-2-oxoethyl)(methyl)amino)-2-chloro-6,7-dihydro-5H-cyclopenta[d]pyrimidin-7-yl acetate (1.5 g, 80%) as a yellow solid. LCMS (ES) [M+1]+ m/z: 355.
Step 4

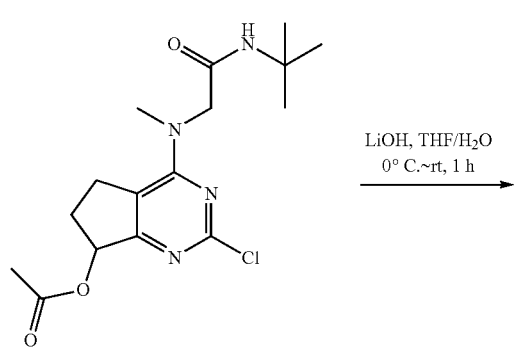

962

-continued

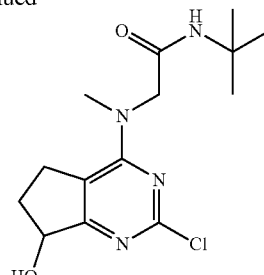

Into a 50 mL round-bottom flask were added 4-((2-(tert-butylamino)-2-oxoethyl)(methyl)amino)-2-chloro-6,7-dihydro-5H-cyclopenta[d]pyrimidin-7-yl acetate (1.5 g, 4.23 mmol, 1.00 equiv), THF (18 mL), LiOH (0.20 g, 8.45 mmol, 2.00 equiv) and H2O (9 mL) at room temperature. The resulting mixture was stirred for 1 h at room temperature. The reaction was diluted with water (30 mL), extracted with EtOAc (30 mL*2). The combined organic phase was dried over anhydrous sodium, filtered and the filtrate was concentrated under reduced pressure. The crude product was used to the next step directly without further purification. LCMS (ES) [M+1]+ m/z: 313.
Step 5

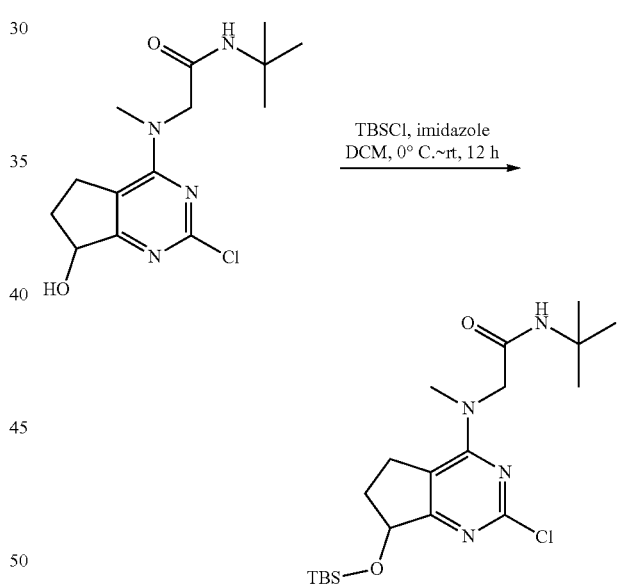

Into a 50 mL round-bottom flask were added N-(tert-butyl)-2-((2-chloro-7-hydroxy-6,7-dihydro-5H-cyclopenta[d]pyrimidin-4-yl)(methyl)amino)acetamide (1.2 g, 3.84 mmol, 1.00 equiv), DCM (15 mL), imidazole (0.52 g, 7.67 mmol, 2.00 equiv) and TBSCl (0.69 g, 4.60 mmol, 1.20 equiv) at room temperature. The resulting mixture was stirred for 12 h at room temperature. The reaction was quenched with water (30 mL), the aqueous layer was extracted with EtOAc (50 mL*2). The residue was purified by silica gel column chromatography, eluted with PE/EA (10:1) to afford N-(tert-butyl)-2-((7-((tert-butyldimethylsilyl)oxy)-2-chloro-6,7-dihydro-5H-cyclopenta[d]pyrimidin-4-yl)(methyl)amino)acetamide (1.3 g, 79%) as a white solid. LCMS (ES) [M+1]+ m/z: 427.

Step 6

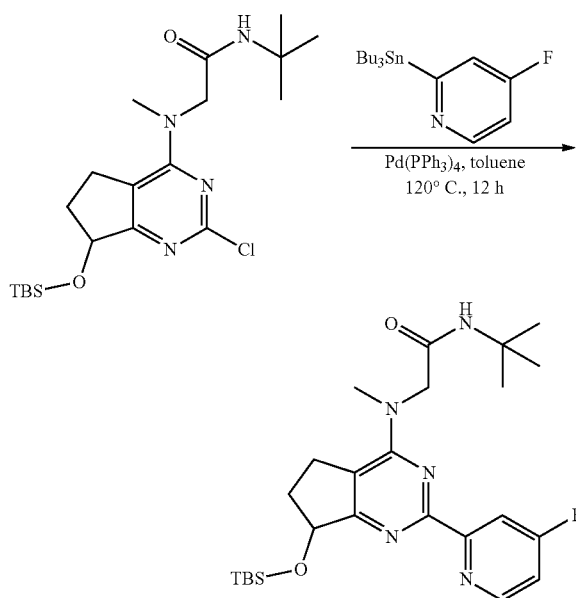

Into a 40 mL vial were added N-(tert-butyl)-2-((7-((tert-butyldimethylsilyl)oxy)-2-chloro-6,7-dihydro-5H-cyclopenta[d]pyrimidin-4-yl)(methyl)amino)acetamide (1.3 g, 3.05 mmol, 1.00 equiv), toluene (20 mL), 4-fluoro-2-(tributylstannyl)pyridine (1.88 g, 4.87 mmol, 1.60 equiv) and Pd(PPh$_3$)$_4$ (350 mg, 0.30 mmol, 0.10 equiv) at room temperature. The resulting mixture was stirred for 12 h at 120° C. under nitrogen atmosphere. The reaction was cooled to room temperature, concentrated under reduced pressure. The residue was purified by silica gel column chromatography, eluted with ethyl acetate to afford N-(tert-butyl)-2-((7-((tert-butyldimethylsilyl)oxy)-2-(4-fluoropyridin-2-yl)-6,7-dihydro-5H-cyclopenta[d]pyrimidin-4-yl)(methyl)amino)acetamide (900 mg, 61%) as a yellow solid. LCMS (ES) [M+1]$^+$ m/z: 488.

Step 7

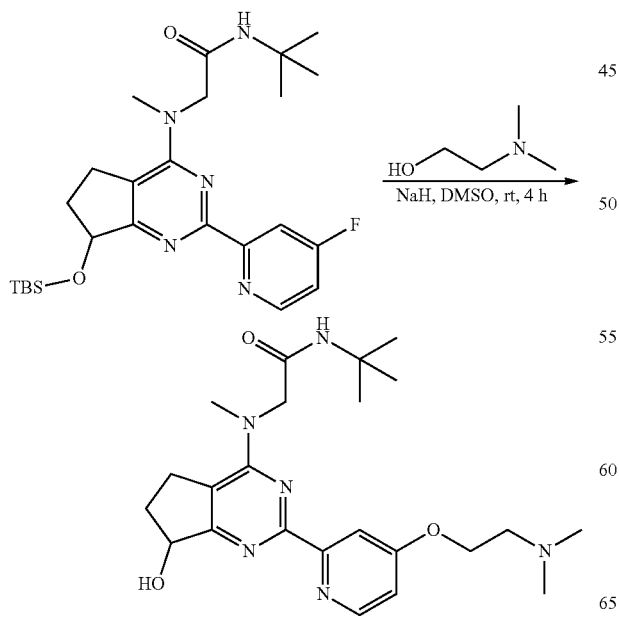

Into a 20 mL vial were added dimethylaminoethanol (158 mg, 1.77 mmol, 2.00 equiv), DMSO (7 mL), NaH (60% in mineral oil) (71 mg, 1.78 mmol, 2.00 equiv). The resulting mixture was stirred for 30 min at room temperature. To the above mixture was added N-tert-butyl-2-({7-[(tert-butyldimethylsilyl)oxy]-2-(4-fluoropyridin-2-yl)-5H,6H,7H-cyclopenta[d]pyrimidin-4-yl}(methyl)amino)acetamide (432 mg, 0.89 mmol, 1.00 equiv) at room temperature. The resulting mixture was stirred for additional 4 h at room temperature. The reaction was quenched with water (0.5 mL) and purified by Prep-HPLC with the following conditions: XBridge Shield RP18 OBD Column, 19*150 mm, 5 μm, mobile phase, water (0.05% NH$_3$·H$_2$O) and CH$_3$CN (16% up to 33% in 8 min). This resulted in N-(tert-butyl)-2-((2-(4-(2-(dimethylamino)ethoxy)pyridin-2-yl)-7-hydroxy-6,7-dihydro-5H-cyclopenta[d]pyrimidin-4-yl)(methyl)amino)acetamide (57 mg, 14.54%) as an off-white solid. LCMS (ES, m/z): [M+H]$^+$: 443. $^1$H-NMR (300 MHz, DMSO-d$_6$) δ 8.48 (d, J=5.6 Hz, 1H), 7.87 (d, J=2.6 Hz, 1H), 7.70 (s, 1H), 7.07 (dd, J=5.7, 2.6 Hz, 1H), 5.44 (s, 1H), 4.82 (t, J=6.5 Hz, 1H), 4.20 (t, J=5.7 Hz, 2H), 4.14 (s, 2H), 3.29 (s, 3H), 3.18 (ddd, J=13.8, 8.4, 4.4 Hz, 1H), 2.99 (dt, J=15.1, 7.1 Hz, 1H), 2.67 (t, J=5.6 Hz, 2H), 2.28 (dt, J=7.5, 4.9 Hz, 1H), 2.23 (s, 6H), 1.77 (dt, J=13.6, 6.8 Hz, 1H), 1.25 (s, 9H).

Example 1.501

Synthesis of N-tert-butyl-2-[(2-{4-[2-(dimethylamino)ethoxy]pyridin-2-yl}-5H,6H,7H-cyclopenta[b]pyridin-4-yl)(methyl)amino]acetamide (Compound 495)

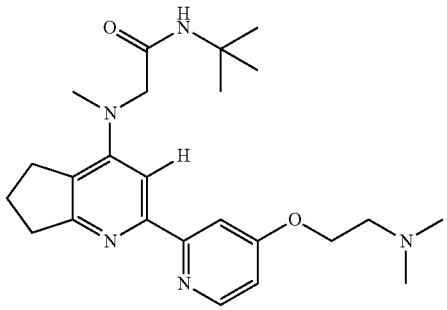 [SMILES: CN(C)CCOc1ccnc(-c2cc(N(C)CC(=O)NC(C)(C)C)c3c(n2)CCC3)c1]

Scheme 142

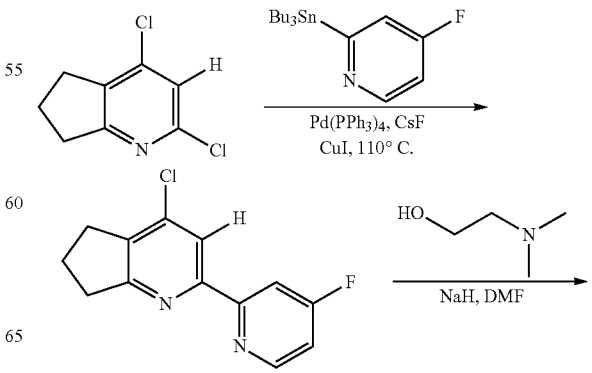

-continued

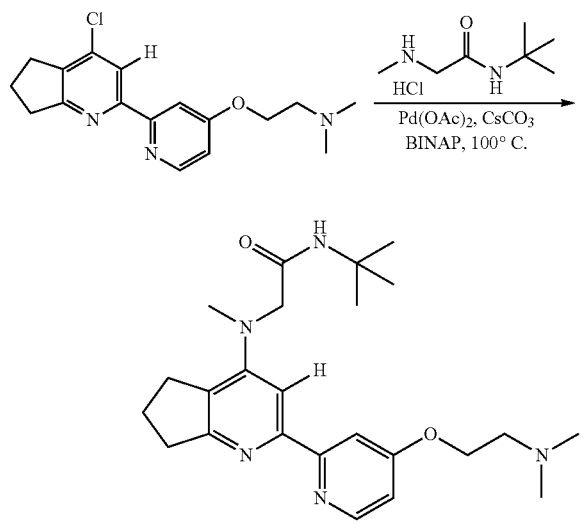

Step 1

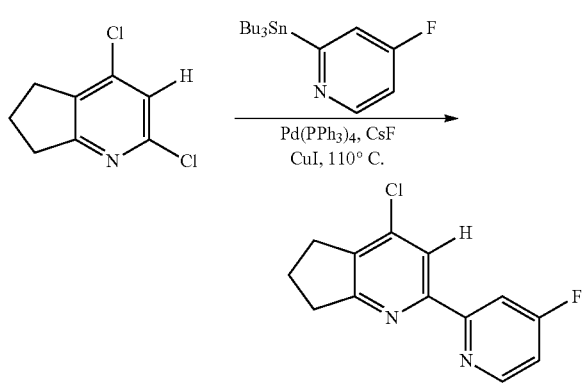

Into a 50 mL round-bottom flask were added 2,4-dichloro-5H,6H,7H-cyclopenta[b]pyridine (500.00 mg, 2.66 mmol, 1.00 equiv), 4-fluoro-2-(tributylstannyl)pyridine (1129.37 mg, 2.93 mmol, 1.10 equiv), DMF (25.00 mL), CsF (807.78 mg, 5.32 mmol, 2.00 equiv), CuI (50.64 mg, 0.27 mmol, 0.10 equiv) and Pd(PPh$_3$)$_4$ (307.25 mg, 0.27 mmol, 0.10 equiv). The resulting mixture was stirred for overnight at 110° C. under nitrogen atmosphere. The mixture was allowed to cool down to room temperature. The reaction was quenched with Water/Ice. The resulting mixture was extracted with EA (3×30 mL). The combined organic layers were washed with brine (3×100 mL), dried over anhydrous Na$_2$SO$_4$. After filtration, the filtrate was concentrated under reduced pressure. The residue was purified by silica gel column chromatography, eluted with THF/PE (5%) to afford 2-{4-chloro-5H,6H,7H-cyclopenta[b]pyridin-2-yl}-4-fluoropyridine (185.00 mg, 27.98%) as white solid. LCMS (ES) [M+1]$^+$ m/z: 249.

Step 2

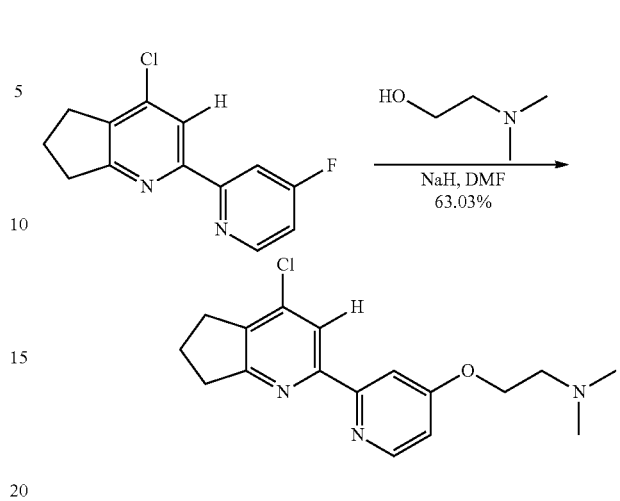

Into a 40 mL vial were added dimethylaminoethanol (1290.35 mg, 14.48 mmol, 20.00 equiv) and DMF (20.00 mL). To the above solution was added NaH (60%) (86.85 mg, 2.172 mmol, 3.00 equiv) in portions at 0° C. The resulting mixture was stirred for additional 30 min at room temperature. To the above mixture was added 2-{4-chloro-5H,6H,7H-cyclopenta[b]pyridin-2-yl}-4-fluoropyridine (180.00 mg, 0.72 mmol, 1.00 equiv) in portions at room temperature. The resulting mixture was stirred for additional 1 h at 50° C. The mixture was allowed to cool down to room temperature and quenched with sat. NH$_4$Cl (aq.). The aqueous layer was extracted with DCM:MeOH (10:1) (3×30 mL). The combined organic layers were dried over anhydrous Na$_2$SO$_4$. After filtration, the filtrate was concentrated under reduced pressure. The residue was purified by silica gel column chromatography, eluted with DCM/MeOH (10%) to afford {2-[(2-{4-chloro-5H,6H,7H-cyclopenta[b]pyridin-2-yl}pyridin-4-yl)oxy]ethyl}dimethylamine (145.00 mg, 63.03%) as a yellow solid. LCMS (ES) [M+1]$^+$ m/z: 318.

Step 3

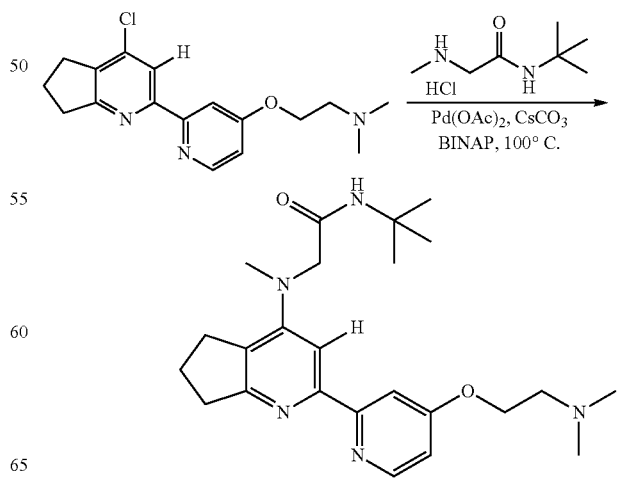

Into a 40 mL vial were added {2-[(2-{4-chloro-5H,6H,7H-cyclopenta[b]pyridin-2-yl}pyridin-4-yl)oxy]ethyl}dimethylamine (140.00 mg, 0.44 mmol, 1.00 equiv), N-tert-butyl-2-(methylamino)acetamide hydrochloride (79.59 mg, 0.44 mmol, 1.00 equiv), BINAP (54.86 mg, 0.09 mmol, 0.20 equiv), Cs$_2$CO$_3$ (287.05 mg, 0.88 mmol, 2.00 equiv), 1,4-dioxane (14.00 mL) and Pd(OAc)$_2$ (9.89 mg, 0.04 mmol, 0.10 equiv). The resulting mixture was stirred for 1 h at 100° C. under nitrogen atmosphere. The mixture was allowed to cool down to room temperature and quenched with Water/Ice. The aqueous layer was extracted with DCM:MeOH (10:1) (3×30 mL). The combined organic layers were dried over anhydrous Na$_2$SO$_4$. After filtration, the filtrate was concentrated under reduced pressure. The crude product was purified by Prep-HPLC with the following conditions: Column, Sunfire Prep C18 OBD Column, 50*250 mm 5 um 10 nm; mobile phase, Water (0.1% FA) and ACN (5% Phase B up to 20% in 13 min); Detector, 254. This resulted in N-tert-butyl-2-[(2-{4-[2-(dimethylamino)ethoxy]pyridin-2-yl}-5H,6H,7H-cyclopenta[b]pyridin-4-yl)(methyl)amino]acetamide; bis(formic acid) (132.50 mg, 58.11%) as yellow gum. LCMS (ES, m/z): [M+H]$^+$: 426. $^1$H-NMR (300 MHz, DMSO-d$_6$, ppm): δ 8.43 (d, J=5.6 Hz, 1H), 8.18 (s, 2HCOOH), 7.86 (d, J=2.5 Hz, 1H), 7.57 (s, 1H), 7.54 (s, 1H), 6.97 (dd, J=5.9, 2.6 Hz, 1H), 4.24 (t, J=5.5 Hz, 2H), 3.94 (s, 2H), 3.06 (s, 3H), 3.01 (t, J=7.3 Hz, 2H), 2.85 (t, J=7.6 Hz, 2H), 2.79 (t, J=5.8 Hz, 2H), 2.32 (s, 6H), 2.02-1.97 (m, 2H), 1.27 (s, 9H).

Example 1.502

Synthesis of N-tert-butyl-2-{[2-(4-{[(3R)-1-ethylpyrrolidin-3-yl]oxy}pyridin-2-yl)-5H,6H,7H-cyclopenta[d]pyrimidin-4-yl](methyl)amino}acetamide (Compound 496)

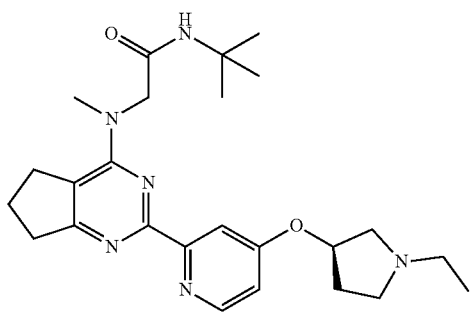 [SMILES: CCN1CC[C@@H](Oc2ccnc(-c3nc4c(c(N(C)CC(=O)NC(C)(C)C)n3)CCC4)c2)C1]

Compound 496 was synthesized similar to Compound 348 by replacing dimethylaminoethanol with (3R)-1-ethylpyrrolidin-3-ol. LCMS (ES) [M+1]$^+$ m/z: 453. $^1$H NMR (300 MHz, DMSO-d6, ppm): δ 8.48 (d, J=5.7 Hz, 1H), 8.28 (br, HCOOH), 7.82 (d, J=2.4 Hz, 1H), 7.72 (s, 1H), 7.02 (dd, J=5.7, 2.7 Hz, 1H), 5.14-5.08 (m, 1H), 4.12 (s, 2H), 3.27 (s, 3H), 3.14 (t, J=2.4 Hz, 2H), 3.06 (dd, J=11.1, 5.7 Hz, 1H), 2.92-2.78 (m, 4H), 2.67-2.60 (m, 3H), 2.42-2.30 (m, 1H), 2.04-1.82 (m, 3H), 1.25 (s, 9H), 1.08 (t, J=7.2 Hz, 3H).

Example 1.503

Synthesis of N-tert-butyl-2-{[2-(4-{[(3R)-1-(2-fluoroethyl)pyrrolidin-3-yl]oxy}pyridin-2-yl)-5H,6H,7H-cyclopenta[d]pyrimidin-4-yl](methyl)amino}acetamide (Compound 497)

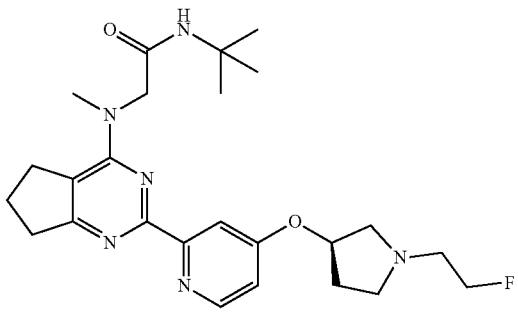 [SMILES: CN(CC(=O)NC(C)(C)C)c1nc(-c2cc(O[C@@H]3CCN(CCF)C3)ccn2)nc2c1CCC2]

Compound 497 was synthesized similar to Compound 348 by replacing dimethylaminoethanol with (3R)-1-(2-fluoroethyl)pyrrolidin-3-ol. LCMS (ES) [M+1]$^+$ m/z: 471. $^1$H NMR (300 MHz, DMSO-d6, ppm): δ 8.47 (d, J=5.6 Hz, 1H), 8.17 (1.60 HCOOH), 7.83 (d, J=2.5 Hz, 1H), 7.72 (s, 1H), 7.01 (dd, J=5.7, 2.6 Hz, 1H), 5.11-5.01 (m, 1H), 4.61 (t, J=4.9 Hz, 1H), 4.46 (t, J=4.9 Hz, 1H), 4.12 (s, 2H), 3.27 (s, 3H), 3.15 (t, J=7.3 Hz, 2H), 2.97 (dd, J=10.7, 6.0 Hz, 1H), 2.88-2.73 (m, 5H), 2.71 (t, J=4.9 Hz, 1H), 2.60-2.46 (m, 1H), 2.43-2.25 (m, 1H), 2.01-1.96 (m, 2H), 1.89-1.74 (m, 1H), 1.25 (s, 9H).

Example 1.504

Synthesis of N-tert-butyl-2-[methyl({2-[4-(methylsulfanyl)pyridin-2-yl]-5H,6H,7H-cyclopenta[d]pyrimidin-4-yl})amino]acetamide (Compound 498)

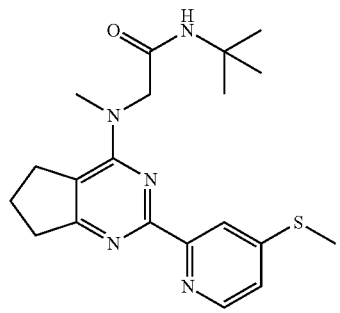 [SMILES: CSc1ccnc(-c2nc3c(c(N(C)CC(=O)NC(C)(C)C)n2)CCC3)c1]

Compound 498 was synthesized similar to Compound 348 by replacing dimethylaminoethanol with MeSNa. LCMS (ES) [M+1]$^+$ m/z: 386. $^1$H NMR (300 MHz, DMSO-d6, ppm): δ 8.48 (d, J=5.2 Hz, 1H), 8.15 (d, J=1.8 Hz, 1H), 7.68 (s, 1H), 7.30 (dd, J=5.3, 2.0 Hz, 1H), 4.14 (s, 2H), 3.27 (s, 3H), 3.15 (t, J=7.3 Hz, 2H), 2.82 (t, J=7.8 Hz, 2H), 2.58 (s, 3H), 2.08-1.86 (m, 2H), 1.25 (s, 9H).

969

Example 1.505

Synthesis of N-tert-butyl-2-{[2-(4-{[2-(dimethylamino)ethyl]sulfanyl}pyridin-2-yl)-5H,6H,7H-cyclopenta[d]pyrimidin-4-yl](methyl)amino}acetamide (Compound 499)

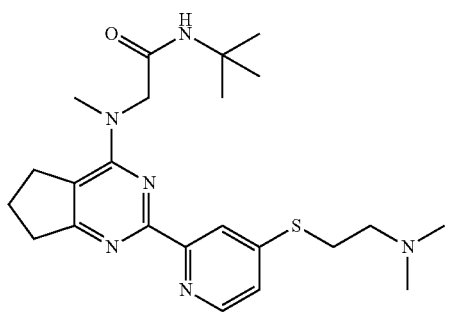 [SMILES: CN(C)CCSc1ccnc(-c2nc3c(c(N(C)CC(=O)NC(C)(C)C)n2)CCC3)c1]

Compound 499 was synthesized similar to Compound 348 by replacing dimethylaminoethanol with 2-(Dimethylamino)ethanethiol. LCMS (ES) [M+1]$^+$ m/z: 443. $^1$H NMR (300 MHz, DMSO-d6, ppm): δ 8.47 (d, J=5.2 Hz, 1H), 8.16 (s, 0.5HCOOH), 8.15 (d, J=2.5 Hz 1H), 7.67 (s, 1H), 7.33 (dd, J=5.3, 2.0 Hz, 1H), 4.14 (s, 2H), 3.26 (s, 3H), 3.25-3.20 (m, 2H), 3.13 (t, J=7.3 Hz, 2H), 2.81 (t, J=7.8 Hz, 2H), 2.58 (t, J=7.0 Hz, 2H), 2.23 (s, 6H), 2.01-1.96 (m, 2H), 1.25 (s, 9H).

Example 1.506

Synthesis of N-cyclopropyl-2-[(2-{4-[2-(dimethylamino)ethoxy]pyridin-2-yl}-5H,6H,7H-cyclopenta[d]pyrimidin-4-yl)(methyl)amino]acetamide (Compound 500)

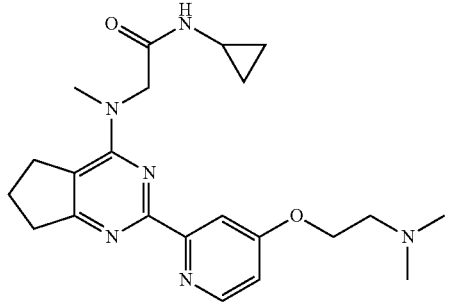 [SMILES: CN(C)CCOc1ccnc(-c2nc3c(c(N(C)CC(=O)NC4CC4)n2)CCC3)c1]

Compound 500 was synthesized similar to Compound 348 by replacing tert-butylamine with 1-cyclopropylamine. LCMS (ES) [M+1]$^+$ m/z: 411. $^1$H NMR (300 MHz, DMSO-d6, ppm): δ 8.48 (d, J=5.6 Hz, 1H), 8.24 (d, J=4.1 Hz, 1H), 7.80 (d, J=2.5 Hz, 1H), 7.05 (dd, J=5.7, 2.6 Hz, 1H), 4.26 (t, J=5.5 Hz, 2H), 4.13 (s, 2H), 3.27 (s, 3H), 3.14 (t, J=7.3 Hz, 2H), 2.89-2.76 (m, 4H), 2.63 (tq, J=8.3, 4.8 Hz, 1H), 2.36 (s, 6H), 2.04-1.94 (m, 2H), 0.67-0.50 (m, 2H), 0.47-0.36 (m, 2H).

970

Example 1.507

Synthesis of N-tert-butyl-2-({2-[4-(2-hydroxy-2-methylpropoxy)pyridin-2-yl]-7-oxo-5H,6H,7H-cyclopenta[d]pyrimidin-4-yl}(methyl)amino)acetamide (Compound 501)

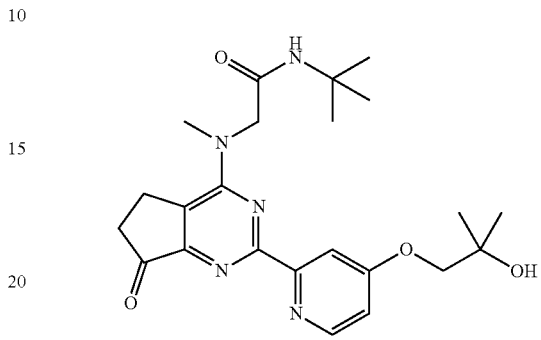

Scheme 143

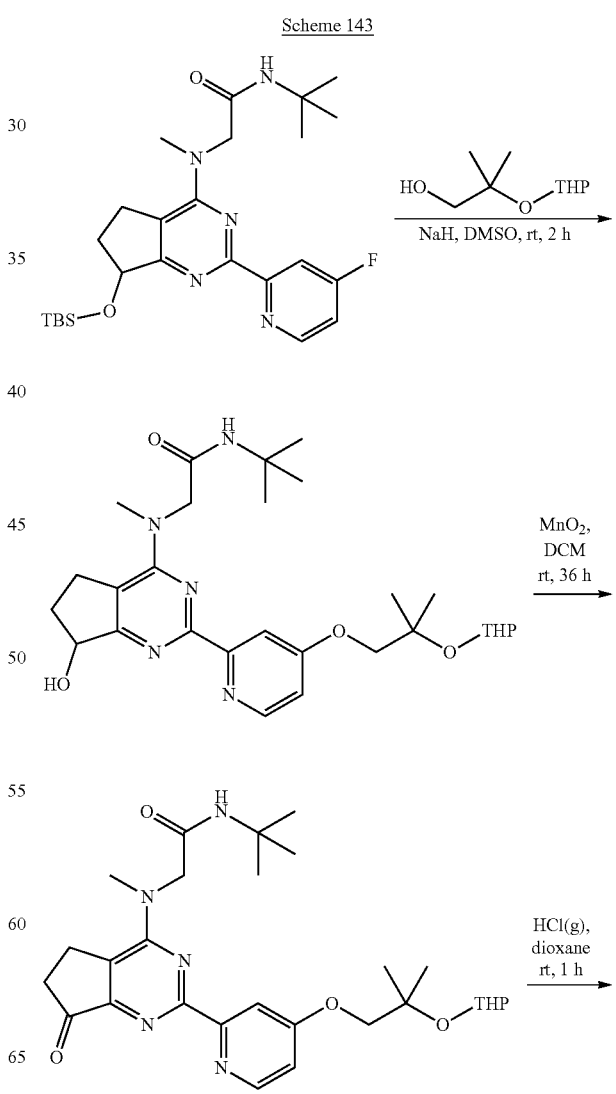

971
-continued

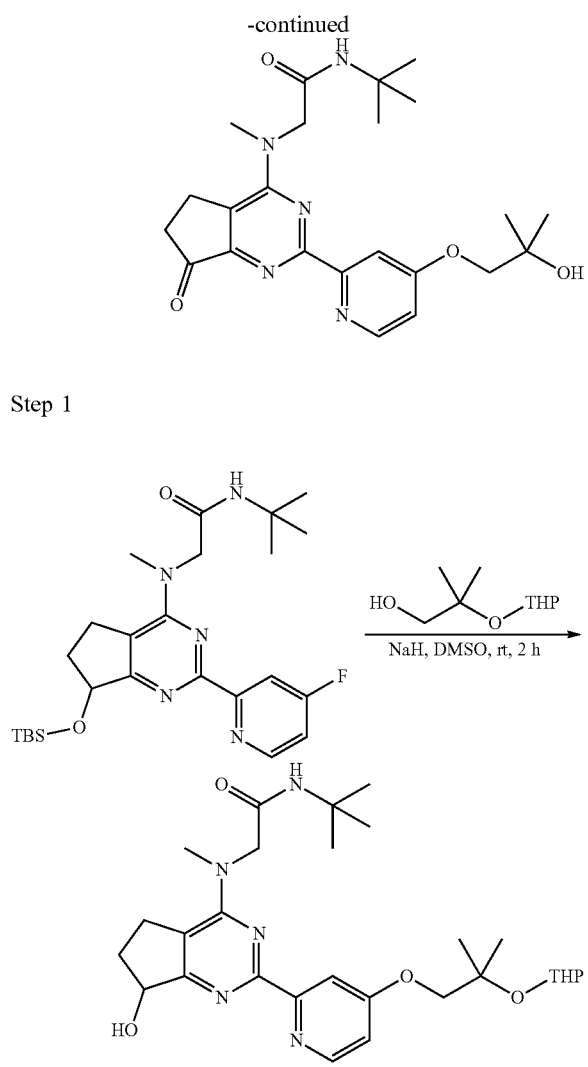

Step 1

Into a 40 mL vial were added 2-methyl-2-(oxan-2-yloxy) propan-1-ol (643 mg, 3.69 mmol, 2.00 equiv), DMSO (16 mL) and NaH (60% in mineral oil) (148 mg, 3.70 mmol, 2.00 equiv) at room temperature. The resulting mixture was stirred for 30 min at room temperature. To the above mixture was added N-(tert-butyl)-2-((7-((tert-butyldimethylsilyl) oxy)-2-(4-fluoropyridin-2-yl)-6,7-dihydro-5H-cyclopenta [d]pyrimidin-4-yl)(methyl)amino)acetamide (900 mg, 1.84 mmol, 1.00 equiv) at room temperature. The resulting mixture was stirred for additional 2 h at room temperature. The reaction was quenched with water (2 mL) and purified by reverse flash chromatography with the following conditions: C18-120 g, column, mobile phase, MeCN in water, 10% to 80% gradient in 10 min, detector, UV 254 nm, Flow rate, 70 mL/min. This resulted in N-(tert-butyl)-2-((7-hydroxy-2-(4-(2-methyl-2-((tetrahydro-2H-pyran-2-yl)oxy)propoxy)pyridin-2-yl)-6,7-dihydro-5H-cyclopenta[d]pyrimidin-4-yl) (methyl)amino)acetamide (500 mg, 51%) as a yellow solid. LCMS (ES) [M+1]+ m/z: 528.

972
Step 2

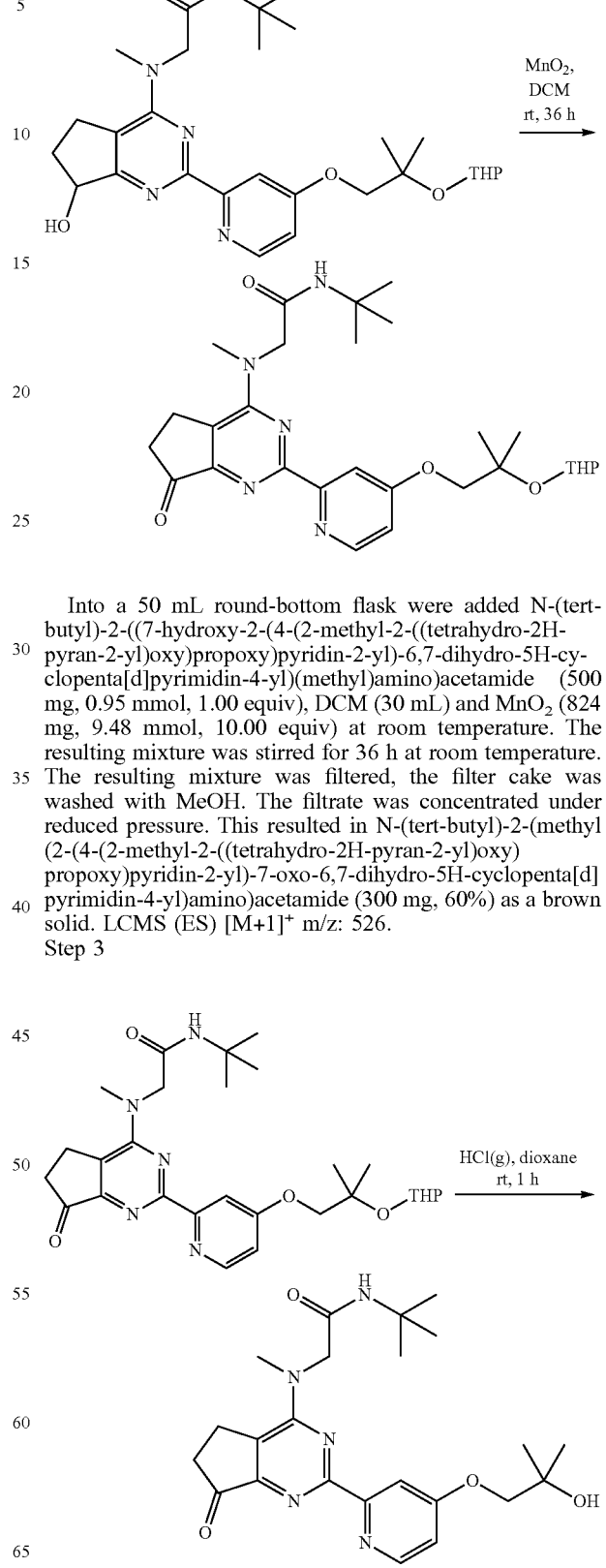

Into a 50 mL round-bottom flask were added N-(tert-butyl)-2-((7-hydroxy-2-(4-(2-methyl-2-((tetrahydro-2H-pyran-2-yl)oxy)propoxy)pyridin-2-yl)-6,7-dihydro-5H-cyclopenta[d]pyrimidin-4-yl)(methyl)amino)acetamide (500 mg, 0.95 mmol, 1.00 equiv), DCM (30 mL) and MnO₂ (824 mg, 9.48 mmol, 10.00 equiv) at room temperature. The resulting mixture was stirred for 36 h at room temperature. The resulting mixture was filtered, the filter cake was washed with MeOH. The filtrate was concentrated under reduced pressure. This resulted in N-(tert-butyl)-2-(methyl (2-(4-(2-methyl-2-((tetrahydro-2H-pyran-2-yl)oxy) propoxy)pyridin-2-yl)-7-oxo-6,7-dihydro-5H-cyclopenta[d] pyrimidin-4-yl)amino)acetamide (300 mg, 60%) as a brown solid. LCMS (ES) [M+1]+ m/z: 526.
Step 3

Into a 50 mL round-bottom flask were added N-(tert-butyl)-2-(methyl(2-(4-(2-methyl-2-((tetrahydro-2H-pyran-2-yl)oxy)propoxy)pyridin-2-yl)-7-oxo-6,7-dihydro-5H-cyclopenta[d]pyrimidin-4-yl)amino)acetamide (300 mg, 0.57 mmol, 1.00 equiv), dioxane (10 mL) and HCl (gas) (2 M) in 1,4-dioxane (0.1 mL) at room temperature. The resulting mixture was stirred for 1 h at room temperature and concentrated to remove the solvent. The residue was dissolved in CH$_3$CN (5 mL) and purified by Prep-HPLC with the following conditions: SunFire Prep C18 OBD Column, 19*150 mm, 5 um, mobile phase, water (0.1% TFA) and CH$_3$CN (36% up to 68% in 7 min). This resulted in N-(tert-butyl)-2-((2-(4-(2-hydroxy-2-methylpropoxy)pyridin-2-yl)-7-oxo-6,7-dihydro-5H-cyclopenta[d]pyrimidin-4-yl)(methyl)amino)acetamide as a yellow solid. LCMS (ES) [M−TFA+1]$^+$ m/z: 442. $^1$H NMR (300 MHz, DMSO-d$_6$) δ 8.76 (d, J=6.9 Hz, 1H), 8.21 (d, J=2.7 Hz, 1H), 7.90 (s, 1H), 7.73 (dd, J=7.0, 2.8 Hz, 1H), 4.37 (s, 2H), 4.22 (s, 2H), 3.60-3.33 (m, 5H), 2.77-2.68 (m, 2H), 1.27 (s, 6H), 1.24 (s, 9H).

Example 1.508

Synthesis of N-tert-butyl-2-{[2-(4-{[(3R,5S)-1,5-dimethylpyrrolidin-3-yl]oxy}pyridin-2-yl)-5H,6H,7H-cyclopenta[d]pyrimidin-4-yl](methyl)amino}acetamide (Compound 502)

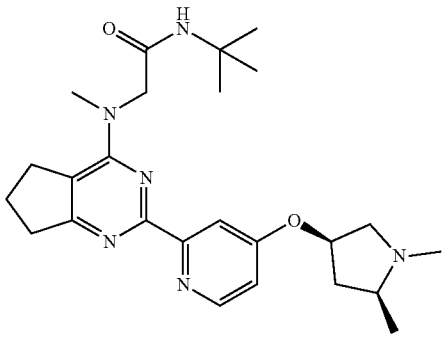 [SMILES: C[C@H]1C[C@@H](Oc2ccnc(-c3nc4c(c(N(C)CC(=O)NC(C)(C)C)n3)CCC4)c2)CN1C]

Compound 502 was synthesized similar to Compound 348 by replacing dimethylaminoethanol with (3R,5S)-1,5-dimethylpyrrolidin-3-ol. LCMS (ES) [M+1]$^+$ m/z: 453. $^1$H NMR (300 MHz, DMSO-d6, ppm): δ 8.45 (d, J=5.6 Hz, 1H), 8.17 (s, 1HCOOH), 7.80 (d, J=2.5 Hz, 1H), 7.71 (s, 1H), 6.96 (dd, J=5.6, 2.6 Hz, 1H), 4.99-4.89 (m, 1H), 4.12 (d, J=2.4 Hz, 2H), 3.27 (s, 3H), 3.20-3.08 (m, 3H), 2.81 (t, J=7.9 Hz, 2H), 2.60 (dt, J=15.0, 7.8 Hz, 1H), 2.53-2.50 (m, 1H), 2.22 (s, 3H), 2.27-2.13 (m, 1H), 2.06-1.94 (m, 2H), 1.54-1.39 (m, 1H), 1.25 (s, 9H), 1.09 (d, J=6.0 Hz, 3H).

Example 1.509

Synthesis of (2R)—N-tert-butyl-2-{methyl[2-(4-{[(3R)-1-methylpyrrolidin-3-yl]oxy}pyridin-2-yl)-5H,6H,7H-cyclopenta[d]pyrimidin-4-yl]amino}propanamide (Compound 503)

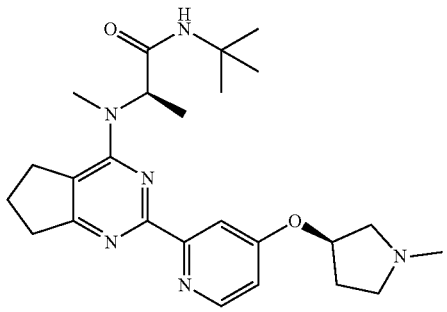 [SMILES: C[C@H](C(=O)NC(C)(C)C)N(C)c1nc(-c2cc(O[C@@H]3CCN(C)C3)ccn2)nc2c1CCC2]

Compound 503 was synthesized similar to Compound 101 by replacing 4-methoxy-2-(tributylstannyl)pyridine with (R)-4-((1-methylpyrrolidin-3-yl)oxy)-2-(trimethylstannyl)pyridine. LCMS (ES) [M+1]$^+$ m/z: 453. $^1$H NMR (300 MHz, DMSO-d6, ppm): δ 8.48 (d, J=5.7 Hz, 1H), 8.19 (s, 2H), 7.85 (d, J=2.5 Hz, 1H), 7.79 (s, 1H), 7.01 (dd, J=5.6, 2.6 Hz, 1H), 5.10 (t, J=4.6 Hz, 1H), 5.04 (q, J=7.2 Hz, 1H), 3.29-2.99 (m, 2H), 3.13 (s, 3H), 2.95 (dd, J=10.9, 5.8 Hz, 1H), 2.87-2.71 (m, 4H), 2.58-2.50 (m, 1H), 2.44-2.37 (m, 1H), 2.36 (s, 3H), 2.14-1.76 (m, 3H), 1.33 (d, J=7.0 Hz, 3H), 1.21 (s, 9H).

Example 1.510

Synthesis of (2R)-2-{methyl[2-(4-{[(3R)-1-methylpyrrolidin-3-yl]oxy}pyridin-2-yl)-5H,6H,7H-cyclopenta[d]pyrimidin-4-yl]amino}-N-(propan-2-yl)propanamide (Compound 504)

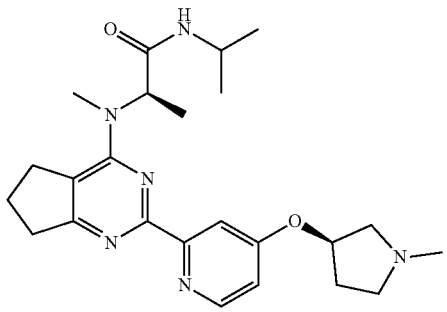 [SMILES: CC(C)NC(=O)[C@@H](C)N(C)c1nc(-c2cc(O[C@@H]3CCN(C)C3)ccn2)nc2c1CCC2]

Compound 504 was synthesized similar to Compound 101 by replacing 4-methoxy-2-(tributylstannyl)pyridine with (R)-4-((1-methylpyrrolidin-3-yl)oxy)-2-(trimethylstannyl)pyridine and by replacing tert-butylamine with isopropylamine. LCMS (ES) [M+1]$^+$ m/z: 439. $^1$H NMR (300 MHz, DMSO-d6, ppm): δ 8.49 (d, J=5.6 Hz, 1H), 8.18 (s, HCOOH), 8.17 (d, J=9.1 Hz, 1H), 7.81 (d, J=2.5 Hz, 1H), 7.01 (dd, J=5.6, 2.6 Hz, 1H), 5.17-5.08 (m, 1H), 5.06 (q, J=6.9 Hz, 1H), 3.98-3.80 (m, 1H), 3.31-3.02 (m, 2H), 3.11 (s, 3H), 2.99-2.71 (m, 5H), 2.56-2.51 (m, 1H), 2.46-2.36 (m, 1H), 2.36 (s, 3H), 2.10-1.78 (m, 3H), 1.34 (d, J=7.0 Hz, 3H), 1.08 (d, J=6.6 Hz, 3H), 0.92 (d, J=6.6 Hz, 3H).

Example 1.511

Synthesis of 2-[methyl(2-{4-[2-(thiomorpholin-4-yl)ethoxy]pyridin-2-yl}-5H,6H,7H-cyclopenta[d]pyrimidin-4-yl)amino]-N-(propan-2-yl)acetamide (Compound 505)

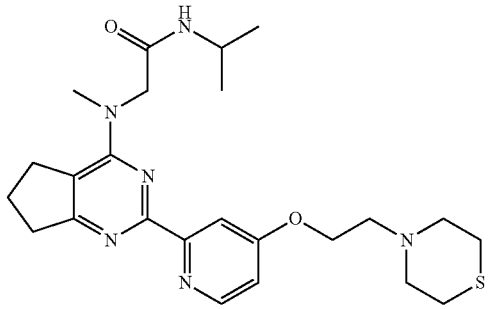 [SMILES: CC(C)NC(=O)CN(C)c1nc(-c2cc(OCCN3CCSCC3)ccn2)nc2c1CCC2]

Compound 505 was synthesized similar to Compound 389 by replacing dimethylaminoethanol with 2-thiomorpholinoacetate and by replacing tert-butylamine with isopropyl amine. LCMS (ES) [M+1]⁺ m/z: 471. ¹H NMR (300 MHz, DMSO-d6, ppm): δ 8.47 (d, J=5.6 Hz, 1H), 7.99 (d, J=7.8 Hz, 1H), 7.80 (d, J=2.6 Hz, 1H), 7.05 (dd, J=5.6, 2.6 Hz, 1H), 4.22 (t, J=5.7 Hz, 2H), 4.15 (s, 2H), 3.87 (dq, J=13.4, 6.7 Hz, 1H), 3.27 (s, 3H), 3.15 (t, J=7.3 Hz, 2H), 2.82 (t, J=7.8 Hz, 2H), 2.78 (dd, J=6.1, 4.0 Hz, 6H), 2.64-2.57 (m, 4H), 2.05-1.93 (m, 2H), 1.04 (d, J=6.6 Hz, 6H).

Example 1.512

Synthesis of N-tert-butyl-2-[methyl(2-{4-[2-(methylsulfanyl)ethoxy]pyridin-2-yl}-5H,6H,7H-cyclopenta[d]pyrimidin-4-yl)amino]acetamide (Compound 506)

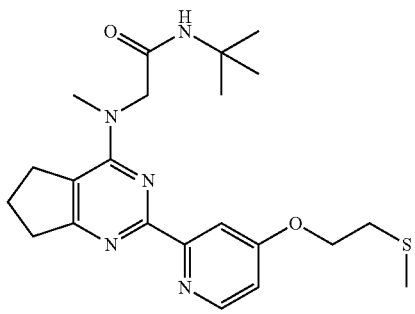 [SMILES: CSCCOc1ccnc(-c2nc3c(c(N(C)CC(=O)NC(C)(C)C)n2)CCC3)c1]

Scheme 144

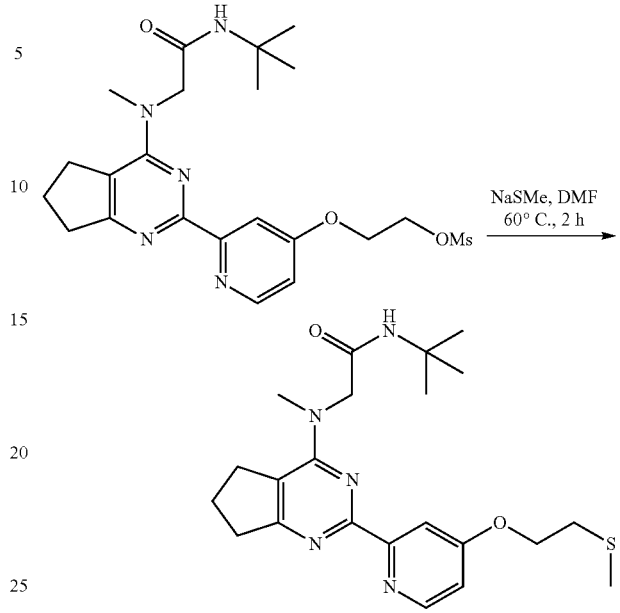

Into a 50 mL round-bottom flask were added 2-{[2-(4-{[(tert-butylcarbamoyl)methyl](methyl)amino}-5H,6H,7H-cyclopenta[d]pyrimidin-2-yl)pyridin-4-yl]oxy}ethyl methanesulfonate (500 mg, 1.05 mmol, 1.00 equiv), DMF (5.0 mL) and (methylsulfanyl)sodium (220 mg, 3.14 mmol, 3.00 equiv) at room temperature. The resulting mixture was stirred for 2 h at 60° C. The reaction was cooled to room temperature and quenched with water (1.0 mL), purified by reverse flash chromatography with the following conditions: C18 silica gel, mobile phase, water (0.05% NH₃·H₂O), 10% to 80% gradient in 10 min, detector, UV 254 nm. This resulted in N-tert-butyl-2-[methyl(2-{4-[2-(methylsulfanyl)ethoxy]pyridin-2-yl}-5H,6H,7H-cyclopenta[d]pyrimidin-4-yl)amino]acetamide (400 mg, 89%) as a yellow semi-solid. LCMS (ES) [M+1]⁺ m/z: 430. ¹H NMR (400 MHz, DMSO-d6, ppm): δ 8.48 (d, J=5.6 Hz, 1H), 7.84 (d, J=2.4 Hz, 1H), 7.67 (s, 1H), 7.05 (dd, J=5.6, 2.8 Hz, 1H), 4.30 (t, J=6.4 Hz, 2H), 4.12 (s, 2H), 3.32 (s, 3H), 3.14 (t, J=6.8 Hz, 2H), 2.88 (t, J=6.8 Hz, 2H), 2.50 (t, J=1.6 Hz, 2H), 2.17 (s, 3H), 2.0 (m, 2H), 1.24 (s, 9H).

Example 1.513

Synthesis of N-tert-butyl-2-({2-[4-(2-methanesulfonylethoxy)pyridin-2-yl]-5H,6H,7H-cyclopenta[d]pyrimidin-4-yl}(methyl)amino)acetamide (Compound 507)

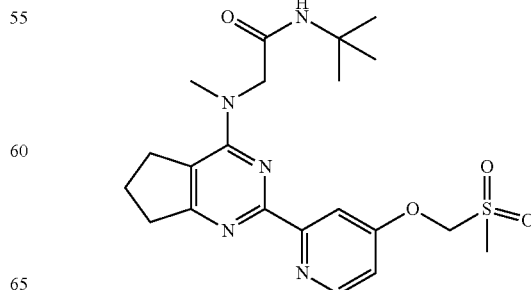

Scheme 145

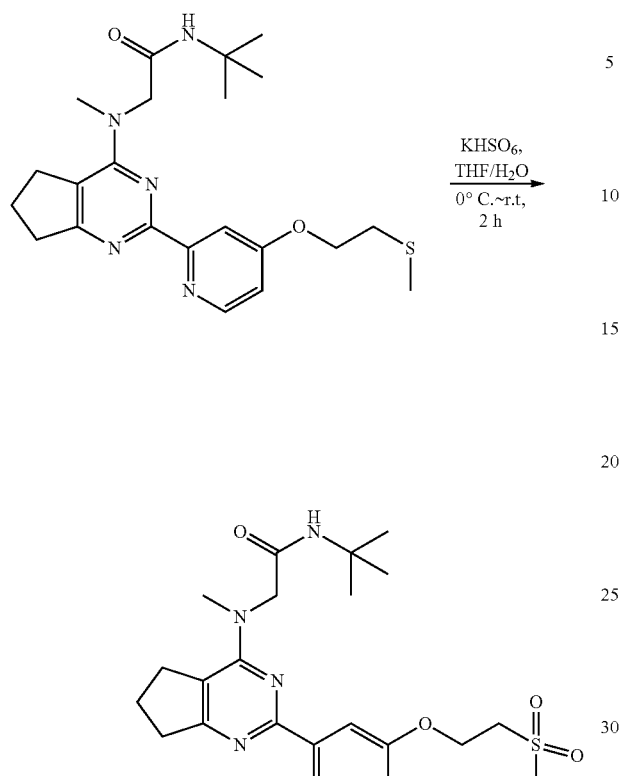

Into a 40 mL vial were added N-tert-butyl-2-[methyl(2-{4-[2-(methylsulfanyl)ethoxy]pyridin-2-yl}-5H,6H,7H-cyclopenta[d]pyrimidin-4-yl)amino]acetamide (200 mg, 0.47 mmol, 1.00 equiv), THF (4.0 mL), H₂O (0.5 mL) and potassium peroxymonosulfate (1.14 g, 1.86 mmol, 4.00 equiv) at 0° C. The resulting mixture was stirred for 2 h at room temperature. The residue was dissolved in MeOH (10 mL). The resulting mixture was filtered, the filter cake was washed with MeOH (2*5 mL). The filtrate was concentrated under reduced pressure. The residue was dissolved in MeOH (5 mL) and purified by Prep-HPLC with the following conditions: Sunfire Prep C18 OBD Column, 50*250 mm, 5 μm, 10 nm, mobile phase, water (0.1% FA) and CH₃CN (5% up to 35% in 12 min) to afford N-tert-butyl-2-({2-[4-(2-methanesulfonylethoxy)pyridin-2-yl]-5H,6H,7H-cyclopenta[d]pyrimidin-4-yl}(methyl)amino)acetamide formate (124.8 mg, 53%) as a white solid. LCMS (ES) [M+1]⁺ m/z 462. ¹H NMR (400 MHz, DMSO-d₆) δ 8.52 (d, J=5.6 Hz, 1H), 8.15 (s, 1H), 7.85 (d, J=2.5 Hz, 1H), 7.64 (s, 1H), 7.12 (dd, J=5.6, 2.6 Hz, 1H), 4.53 (t, J=5.7 Hz, 2H), 4.15 (s, 2H), 3.68 (t, J=5.7 Hz, 2H), 3.25 (s, 3H), 3.14 (t, J=7.28 Hz, 2H), 3.11 (s, 3H), 2.82 (t, J=7.8 Hz, 2H), 2.00-1.96 (m, 2H), 1.24 (s, 9H).

Example 1.513

Synthesis of N-tert-butyl-2-({2-[4-(2-hydroxy-2-methylpropoxy)pyridin-2-yl]-5H,6H,7H-cyclopenta[d]pyrimidin-4-yl}((2H3)methyl)amino)acetamide (Compound 509)

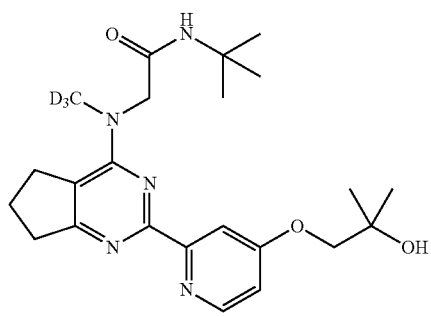 [SMILES: [2H]C([2H])([2H])N(CC(=O)NC(C)(C)C)c1nc(-c2cc(OCC(C)(C)O)ccn2)nc2c1CCC2]

Scheme 146

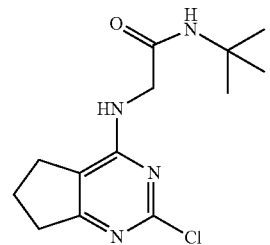

(Boc)₂O, TEA, DMAP

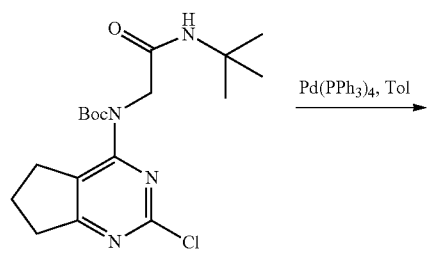

Pd(PPh₃)₄, Tol

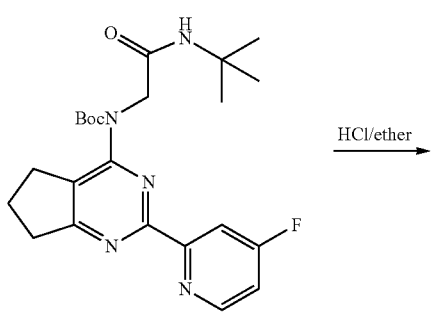

HCl/ether

979

-continued

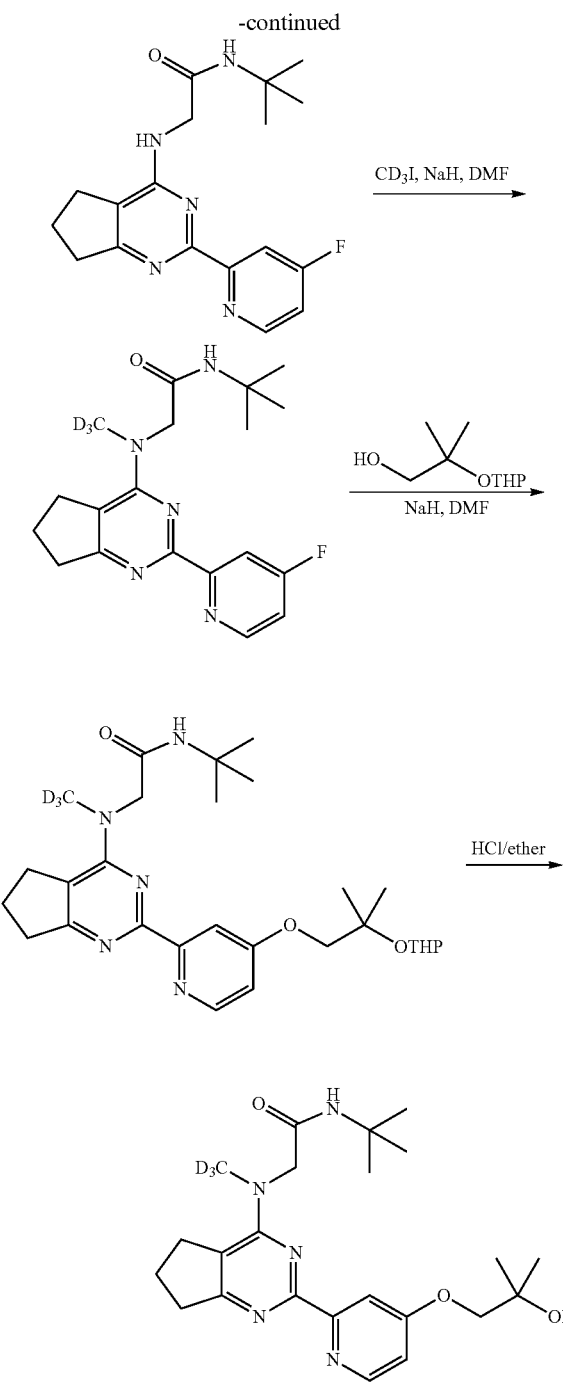

Step 1

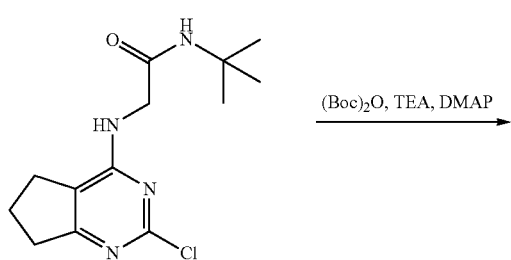

980

-continued

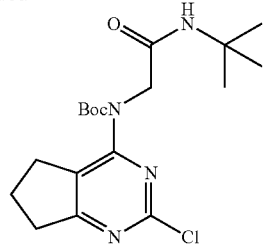

A mixture of N-tert-butyl-2-({2-chloro-5H,6H,7H-cyclopenta[d]pyrimidin-4-yl}amino)acetamide (2 g, 7.073 mmol, 1.00 equiv), (Boc)₂O (3.09 g, 14.146 mmol, 2 equiv), TEA (1.43 g, 14.146 mmol, 2 equiv) and DMAP (0.17 g, 1.415 mmol, 0.2 equiv) in DCM (30 mL) was stirred for 24 h at room temperature. The resulting mixture was extracted with CH₂Cl₂ (3×100 mL). The combined organic layers were dried over anhydrous Na₂SO₄. After filtration, the filtrate was concentrated under reduced pressure. The residue was purified by silica gel column chromatography, eluted with PE/THF (2:1) to afford tert-butyl (2-(tert-butylamino)-2-oxoethyl)(2-chloro-6,7-dihydro-5H-cyclopenta[d]pyrimidin-4-yl)carbamate (1.6 g, 59.08%) as a white solid. LCMS (ES) [M+1]⁺ m/z: 383.

Step 2

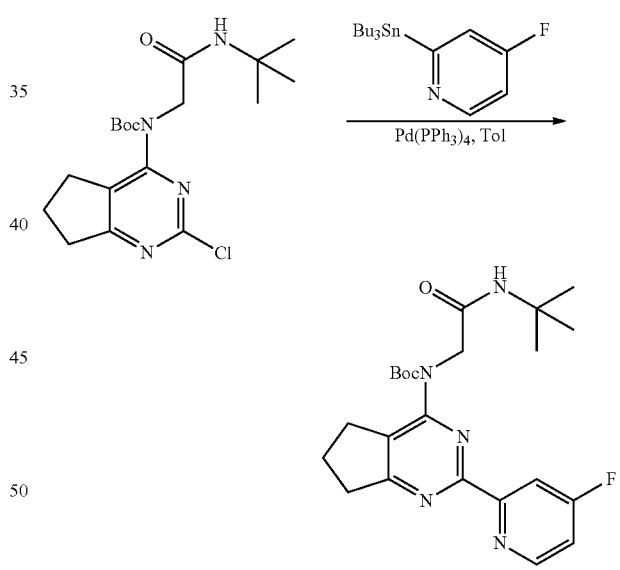

A mixture of tert-butyl (2-(tert-butylamino)-2-oxoethyl)(2-chloro-6,7-dihydro-5H-cyclopenta[d]pyrimidin-4-yl)carbamate (1 g, 2.612 mmol, 1.00 equiv), 4-fluoro-2-(tributylstannyl)pyridine (1.51 g, 3.918 mmol, 1.5 equiv) and Pd(PPh₃)₄ (0.60 g, 0.522 mmol, 0.2 equiv) in Toluene (20 mL) was stirred for 16 h at 100 degrees C. under nitrogen atmosphere. The resulting mixture was concentrated under vacuum. The residue was purified by silica gel column chromatography, eluted with PE/THF (1:1) to afford tert-butyl N-[(tert-butylcarbamoyl)methyl]-N-[2-(4-fluoropyridin-2-yl)-5H,6H,7H-cyclopenta[d]pyrimidin-4-yl]carbamate 1.0 g (86.33%) as an off-white solid. LCMS (ES) [M+1]⁺ m/z: 444.

Step 3

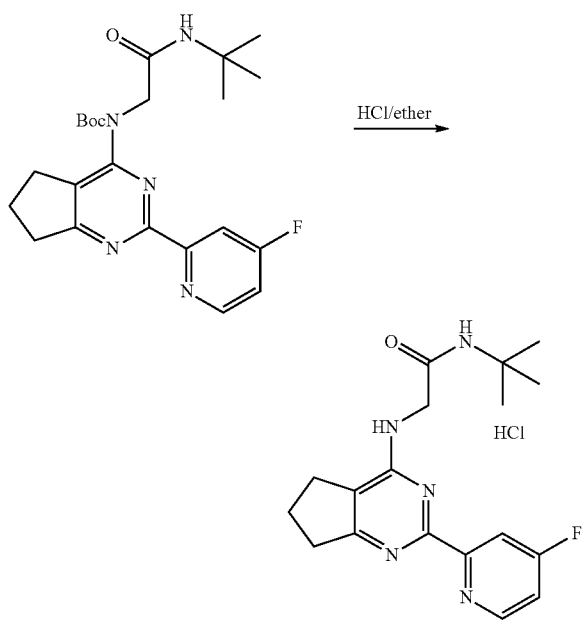

To a stirred solution of tert-butyl N-[(tert-butylcarbamoyl)methyl]-N-[2-(4-fluoropyridin-2-yl)-5H,6H,7H-cyclopenta[d]pyrimidin-4-yl]carbamate (500 mg, 1.127 mmol, 1.00 equiv) in EA (20 mL, 204.301 mmol, 181.22 equiv) was added HCl in ether (2M) (1.69 mL, 3.381 mmol, 3 equiv) in portions at room temperature. The resulting mixture was concentrated under reduced pressure to afford N-tert-butyl-2-{[2-(4-fluoropyridin-2-yl)-5H,6H,7H-cyclopenta[d]pyrimidin-4-yl]amino}acetamide hydrochloride (360 mg, 92.99%) as a white solid. LCMS (ES) [M−HCl+1]+ m/z: 344.

Step 4

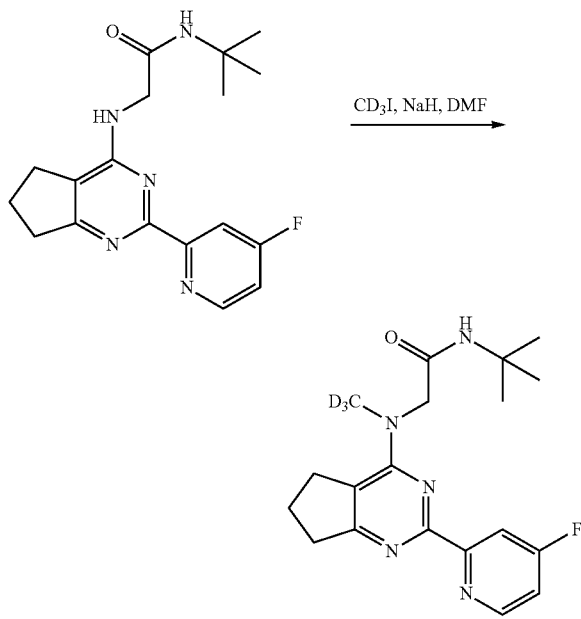

To a stirred solution of N-tert-butyl-2-{[2-(4-fluoropyridin-2-yl)-5H,6H,7H-cyclopenta[d]pyrimidin-4-yl]amino}acetamide (360 mg, 1.048 mmol, 1.00 equiv) in DMF was added NaH (50.31 mg, 2.096 mmol, 2 equiv) in portions at 0 degrees C. under nitrogen atmosphere. The resulting mixture was stirred for 20 min at 0 degrees C. under nitrogen atmosphere. To the above mixture was added $CD_3I$ (227.94 mg, 1.572 mmol, 1.50 equiv) dropwise at 0 degrees C. The resulting mixture was stirred for additional 6 h at room temperature. The resulting mixture was extracted with $CH_2Cl_2$ (3×50 mL). The combined organic layers were dried over anhydrous $Na_2SO_4$. After filtration, the filtrate was concentrated under reduced pressure. The residue was purified by silica gel column chromatography, eluted with PE/EA (1:4) to afford N-(tert-butyl)-2-((2-(4-fluoropyridin-2-yl)-6,7-dihydro-5H-cyclopenta[d]pyrimidin-4-yl)(methyl-d3)amino)acetamide (300 mg, 79.39%) as a white solid. LCMS (ES) [M+1]+ m/z: 361.

Step 5

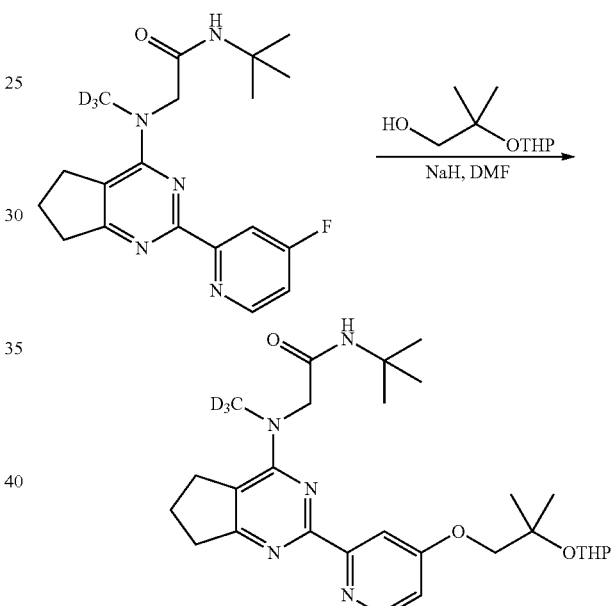

To a stirred solution of 2-methyl-2-(oxan-2-yloxy)propan-1-ol (435.05 mg, 2.496 mmol, 3 equiv) in DMF (30 mL) was added NaH (39.95 mg, 1.664 mmol, 2 equiv) in portions at 0 degrees C. under nitrogen atmosphere. The resulting mixture was stirred for 20 min at 0 degrees C. under nitrogen atmosphere. To the above mixture was added N-(tert-butyl)-2-((2-(4-fluoropyridin-2-yl)-6,7-dihydro-5H-cyclopenta[d]pyrimidin-4-yl)(methyl-d3)amino)acetamide (300 mg, 0.832 mmol, 1.00 equiv) in portions at 0 degrees C. The resulting mixture was stirred for additional 4 h at room temperature. The resulting mixture was extracted with $CH_2Cl_2$ (3×30 mL). The combined organic layers were dried over anhydrous $Na_2SO_4$. After filtration, the filtrate was concentrated under reduced pressure. The residue was purified by silica gel column chromatography, eluted with PE/EA (1:4) to afford N-(tert-butyl)-2-((methyl-d3)(2-(4-(2-methyl-2-((tetrahydro-2H-pyran-2-yl)oxy)propoxy)pyridin-2-yl)-6,7-dihydro-5H-cyclopenta[d]pyrimidin-4-yl)amino)acetamide (300 mg, 70.03%) as a white solid. LCMS (ES) [M+1]+ m/z: 515.

Step 6

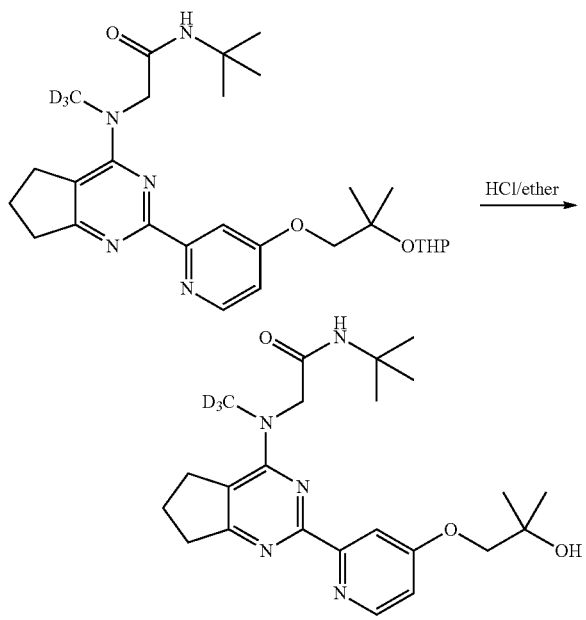

A mixture of N-(tert-butyl)-2-((methyl-d3)(2-(4-(2-methyl-2-((tetrahydro-2H-pyran-2-yl)oxy)propoxy)pyridin-2-yl)-6,7-dihydro-5H-cyclopenta[d]pyrimidin-4-yl)amino)acetamide (300 mg, 0.583 mmol, 1.00 equiv) in EtOAc (5 mL) and HCl (g) in ether (2M) (0.58 mL, 1.166 mmol, 2 equiv) was stirred for 3 h at room temperature. The crude product was purified by Prep-HPLC with the following conditions (Prep-HPLC-001): Column, Sunfire Prep C18 OBD Column, 50*250 mm, 5 μm 10 nm; mobile phase, Water (0.1% FA) and ACN (5% PhaseB up to 25% in 15 min) to afford N-(tert-butyl)-2-((2-(4-(2-hydroxy-2-methylpropoxy)pyridin-2-yl)-6,7-dihydro-5H-cyclopenta[d]pyrimidin-4-yl)(methyl-d3)amino)acetamide (175.9 mg, 70.09%) as a yellow green solid. LCMS (ES) [M+1]+ m/z: 431. $^1$H NMR (300 MHz, DMSO-d$_6$) δ 8.47 (d, J=5.6 Hz, 1H), 7.83 (d, J=2.5 Hz, 1H), 7.68 (s, 1H), 7.05 (dd, J=5.9, 2.6 Hz, 1H), 4.13 (s, 2H), 3.86 (s, 2H), 3.14 (t, J=7.2 Hz, 2H), 2.81 (t, J=7.7 Hz, 2H), 2.04-1.93 (m, 2H), 1.25 (s, 9H), 1.24 (s, 6H).

Example 1.513

Synthesis of N-tert-butyl-2-{[2-(4-{2-[di(2H3)methylamino]ethoxy}pyridin-2-yl)-5H,6H,7H-cyclopenta[d]pyrimidin-4-yl](methyl)amino}acetamide (Compound 508)

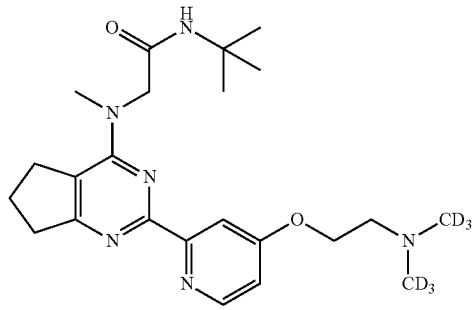 [SMILES: [2H]C([2H])([2H])N(CCOc1ccnc(-c2nc3c(c(N(C)CC(=O)NC(C)(C)C)n2)CCC3)c1)C([2H])([2H])[2H]]

Scheme 147

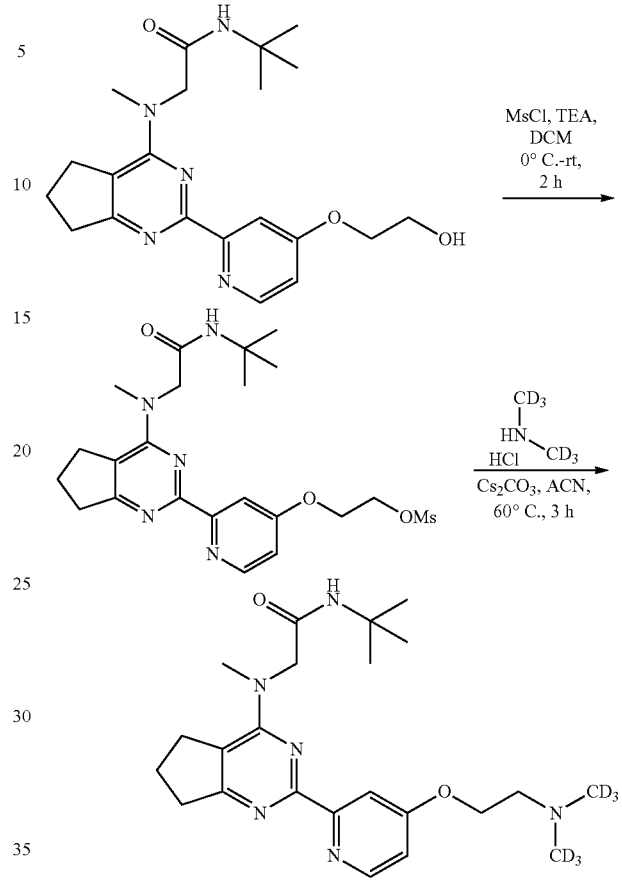

Step 1

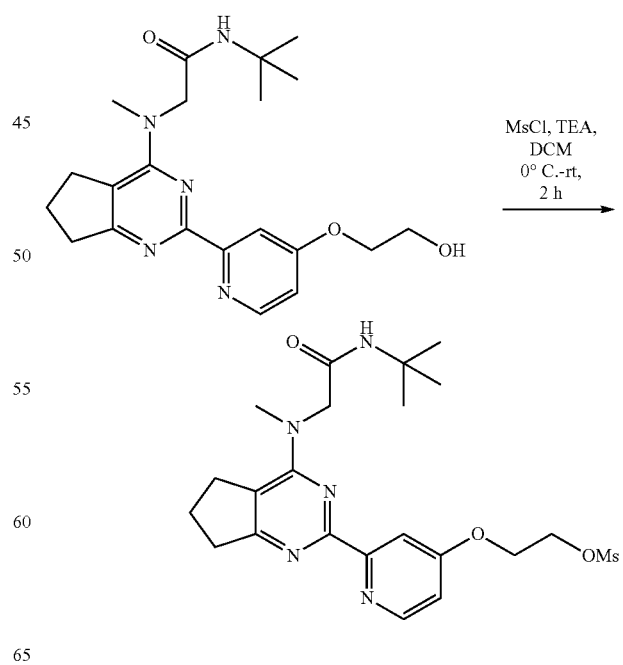

To a stirred solution of N-tert-butyl-2-({2-[4-(2-hydroxyethoxy)pyridin-2-yl]-5H,6H,7H-cyclopenta[d]pyrimidin-4- yl}(methyl)amino)acetamide (1.4 g, 3.50 mmol, 1.00 equiv) in DCM (20 mL) at 0° C. were added TEA (709 mg, 7.00 mmol, 2.0 equiv) and methanesulfonyl chloride (482 mg, 4.20 mmol, 1.2 equiv) dropwise. The resulting mixture was stirred for 2 h at room temperature and was diluted with 30 mL H$_2$O. The mixture was extracted with CH$_2$Cl$_2$ (3×20 mL). The combined organic layers were washed with brine (50 mL), dried over anhydrous Na$_2$SO$_4$. After filtration, the filtrate was concentrated under reduced pressure. The residue was purified by silica gel column chromatography, eluted with CH$_2$Cl$_2$/MeOH (10:1) to afford 2-{[2-(4-{[(tert-butylcarbamoyl)methyl](methyl)amino}-5H,6H,7H-cyclopenta[d]pyrimidin-2-yl)pyridin-4-yl]oxy}ethyl methanesulfonate (1.3 g, 77.6%) as a white solid. LCMS (ES) [M+1]$^+$ m/z: 478.

Step 2

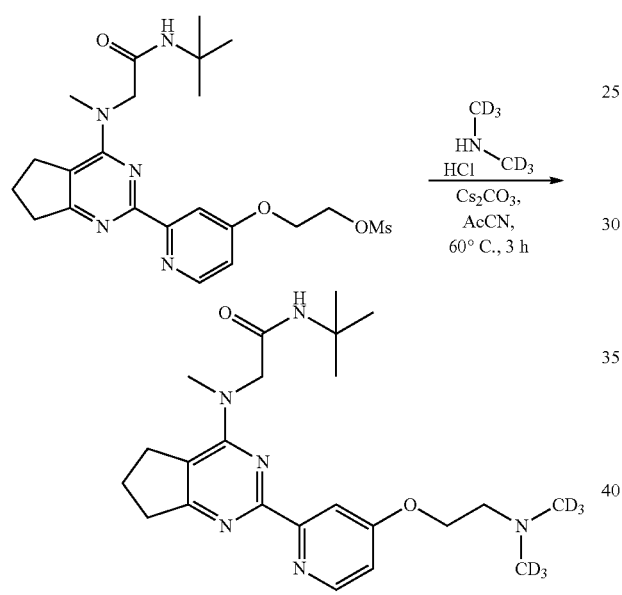

To a stirred mixture of 2-{[2-(4-{[(tert-butylcarbamoyl)methyl](methyl)amino}-5H,6H,7H-cyclopenta[d]pyrimidin-2-yl)pyridin-4-yl]oxy}ethyl methanesulfonate (300 mg, 0.62 mmol, 1.00 equiv) and bis(methyl-d3)amine hydrochloride (64 mg, 1.25 mmol, 2.00 equiv) in CH$_3$CN (5 mL) was added Cs$_2$CO$_3$ (818 mg, 2.51 mmol, 4.00 equiv). The resulting mixture was stirred for 3 h at 60° C. The mixture was cooled down to room temperature and filtered. The filtrate was purified by Prep-HPLC with the following conditions: XBridge Prep C18 OBD Column, 19*150 mm, 5 um, mobile phase, water (10 mmol/L NH$_4$HCO$_3$) and CH$_3$CN (30% Phase B up to 40% in 7 min), Detector, UV 254 nm. The desired fraction was freeze-dried to afford N-tert-butyl-2-{[2-(4-{2-[di(2H3)methylamino]ethoxy}pyridin-2-yl)-5H,6H,7H-cyclopenta[d]pyrimidin-4-yl](methyl)amino}acetamide (114.7 mg, 42.2%) as a white solid. LCMS (ES) [M+1]$^+$ m/z: 433. $^1$H NMR (300 MHz, DMSO-d$_6$) δ 8.47 (d, J=5.6 Hz, 1H), 7.84 (d, J=2.6 Hz, 1H), 7.68 (s, 1H), 7.05 (dd, J=5.7, 2.6 Hz, 1H), 4.19 (t, J=5.7 Hz, 2H), 4.13 (s, 2H), 3.27 (s, 3H), 3.15 (t, J=7.3 Hz, 2H), 2.81 (t, J=7.8 Hz, 2H), 2.66 (t, J=5.7 Hz, 2H), 2.01-1.96 (m, 2H), 1.25 (s, 9H).

2. BIOLOGICAL EXAMPLES

Example 2.1

Biological In-Vitro Ferroportin Internalization Assay

The protocol for this assay is generally as described in WO2018/128828, incorporated herein by reference in its entirety. Functional internalization of ferroportin protein was measured using a stably-transfected CHO cell line expressing the human ferroportin tagged to a luciferase reporter. Cells were plated for 24 h in the presence of ferric ammonium citrate (FAC). Ferroportin protein expression was induced with doxycycline for 24 h. The next day, the compounds were added. Test compounds were dissolved in DMSO. Cells were incubated with the test compounds for 6 h, and subsequently luciferase activity was measured using the Nano-Glo Luciferase Assay System and Glomax (Promega, Madison, Wis.).

The average pEC$_{50}$ was determined for the test compounds. The data is provided in Table 2 below.

TABLE 2

| Cmpd No. from Table 1 | pEC$_{50}$ |
| --- | --- |
| 1 | 6.9 |
| 2 | 6.6 |
| 3 | 6.8 |
| 4 | 6.4 |
| 5 | 6.2 |
| 6 | 6.5 |
| 7 | 6.6 |
| 8 | 5 |
| 9 | 6.2 |
| 10 | 6.6 |
| 11 | 6.3 |
| 12 | 5.8 |
| 13 | 6.4 |
| 14 | 6.8 |
| 15 | 6.9 |
| 16 | 6.6 |
| 17 | 6.6 |
| 18 | 7.1 |
| 19 | 5.4 |
| 20 | 6.7 |
| 21 | 6.9 |
| 22 | 7 |
| 23 | 6.9 |
| 24 | 7.6 |
| 25 | 7.1 |
| 26 | 6.6 |
| 27 | 6.8 |
| 28 | 5.9 |
| 29 | 5.9 |
| 30 | 5.7 |
| 31 | 6.2 |
| 32 | 7.2 |
| 33 | 5.7 |
| 34 | 7.9 |
| 35 | 7 |
| 36 | 7.3 |
| 37 | 6.6 |
| 38 | 6.6 |
| 39 | 6.3 |
| 40 | 7.1 |
| 41 | 7.3 |
| 42 | 7.3 |
| 43 | 7 |
| 44 | 7.9 |
| 45 | 7.2 |
| 46 | 5.1 |
| 47 | 5.7 |
| 48 | 6.8 |
| 49 | 7.1 |

TABLE 2-continued

| Cmpd No. from Table 1 | pEC$_{50}$ |
|---|---|
| 50 | 5.6 |
| 51 | 7.5 |
| 52 | 6.8 |
| 53 | 6.6 |
| 54 | 6.9 |
| 55 | 6.3 |
| 56 | 6.7 |
| 57 | 7.5 |
| 58 | 6.7 |
| 59 | 6.8 |
| 60 | 7.6 |
| 61 | 7.1 |
| 62 | 7.6 |
| 63 | 7.2 |
| 64 | 7.8 |
| 65 | 7.6 |
| 66 | 7.7 |
| 67 | 6.6 |
| 68 | 7.2 |
| 69 | 7 |
| 70 | 7.4 |
| 71 | 5.9 |
| 72 | 5.5 |
| 73 | 6.8 |
| 74 | 7.5 |
| 75 | 7.5 |
| 76 | 6 |
| 77 | 7 |
| 78 | 7.4 |
| 79 | 6.5 |
| 80 | 6.8 |
| 81 | 6.8 |
| 82 | 6.8 |
| 83 | 6.9 |
| 84 | 6.6 |
| 85 | 5.5 |
| 86 | 6.8 |
| 87 | 6.6 |
| 88 | 7.1 |
| 89 | 7.3 |
| 90 | 7.4 |
| 91 | 7.3 |
| 92 | 6.5 |
| 93 | 6.1 |
| 94 | 6.3 |
| 95 | 7.3 |
| 96 | 6.6 |
| 97 | 7.1 |
| 98 | 7 |
| 99 | 7.3 |
| 100 | 7.5 |
| 101 | 8.2 |
| 102 | 7.1 |
| 103 | 6.4 |
| 104 | 7.2 |
| 105 | 7.7 |
| 106 | 5.4 |
| 107 | 5.7 |
| 108 | 7.6 |
| 109 | 7 |
| 110 | 7.9 |
| 111 | 7.2 |
| 112 | 8 |
| 113 | 7.7 |
| 114 | 7.6 |
| 115 | 7.1 |
| 116 | 7.4 |
| 117 | 6.9 |
| 118 | 7.8 |
| 119 | 7.7 |
| 120 | 7.2 |
| 121 | 7.9 |
| 122 | 7.8 |
| 123 | 7.2 |
| 124 | 7 |
| 125 | 7.5 |
| 126 | 7.9 |
| 127 | 7.1 |

TABLE 2-continued

| Cmpd No. from Table 1 | pEC$_{50}$ |
|---|---|
| 128 | 7.4 |
| 129 | 7.2 |
| 130 | 6.9 |
| 131 | 7.1 |
| 132 | 7.3 |
| 133 | 7 |
| 134 | 6.9 |
| 135 | 7.4 |
| 136 | 7.7 |
| 137 | 7.8 |
| 138 | 7.8 |
| 139 | 7.5 |
| 140 | 7 |
| 141 | 7.1 |
| 142 | 7.4 |
| 143 | 7.2 |
| 144 | 7.5 |
| 145 | 6.9 |
| 146 | 6.8 |
| 147 | 6.7 |
| 148 | 7.6 |
| 149 | 7.2 |
| 150 | 7.3 |
| 151 | 8.1 |
| 152 | 7.9 |
| 153 | 7.6 |
| 154 | 7.4 |
| 155 | 7.5 |
| 156 | 7.9 |
| 157 | 7.3 |
| 158 | 6.2 |
| 159 | 8.0 |
| 160 | 5.2 |
| 161 | 7.4 |
| 162 | 5.7 |
| 163 | 5.4 |
| 164 | 5.0 |
| 165 | 7.4 |
| 166 | 6.7 |
| 167 | 7.9 |
| 168 | 7.3 |
| 169 | 7.3 |
| 170 | 7.8 |
| 171 | 7.2 |
| 172 | 7.5 |
| 173 | 6.8 |
| 174 | 8.2 |
| 175 | <5.0 |
| 176 | 7.8 |
| 177 | 6.9 |
| 178 | 7.2 |
| 179 | 7.7 |
| 180 | 5.2 |
| 181 | 6.5 |
| 182 | 7.6 |
| 183 | 8 |
| 184 | 7.7 |
| 185 | 7.2 |
| 186 | 7 |
| 187 | 7.9 |
| 188 | 6.7 |
| 189 | 7.7 |
| 190 | 7.8 |
| 191 | 7 |
| 192 | 6.5 |
| 193 | 6.8 |
| 194 | 5.4 |
| 195 | 6.9 |
| 196 | 5.6 |
| 197 | 7.4 |
| 198 | 8.1 |
| 199 | 7.9 |
| 200 | 7.6 |
| 201 | 7.4 |
| 202 | 7.5 |
| 203 | 6.3 |
| 204 | 6.9 |
| 205 | 7.5 |

TABLE 2-continued

| Cmpd No. from Table 1 | pEC$_{50}$ |
|---|---|
| 206 | 6.9 |
| 207 | 7.2 |
| 208 | 5.7 |
| 209 | 8 |
| 210 | 7.9 |
| 211 | 7.9 |
| 212 | 7.1 |
| 213 | 6.4 |
| 214 | 7.8 |
| 215 | 7.5 |
| 216 | 6.6 |
| 217 | 6.9 |
| 218 | 7 |
| 219 | 7.1 |
| 220 | 7 |
| 221 | 7 |
| 222 | 7.2 |
| 223 | 7.8 |
| 224 | 7.9 |
| 225 | 6.8 |
| 226 | 7.1 |
| 227 | 7.2 |
| 228 | 7.1 |
| 229 | 7.9 |
| 230 | 6.6 |
| 231 | 6.2 |
| 232 | 7 |
| 233 | 7.4 |
| 234 | 6.4 |
| 235 | 7.5 |
| 236 | 7.4 |
| 237 | 7.1 |
| 238 | 7.5 |
| 239 | 7.8 |
| 240 | 7.1 |
| 241 | 8 |
| 242 | 7.7 |
| 243 | 7.4 |
| 244 | 6.4 |
| 245 | 7.7 |
| 246 | 7.3 |
| 247 | 7.2 |
| 248 | 7.1 |
| 249 | 7.2 |
| 250 | 7.4 |
| 251 | 8.3 |
| 252 | 7.9 |
| 253 | 7.6 |
| 254 | 7 |
| 255 | 6.9 |
| 256 | 6.6 |
| 257 | 7 |
| 258 | 6.3 |
| 259 | 7.1 |
| 260 | 7.6 |
| 261 | 7.6 |
| 262 | 7.1 |
| 263 | 8 |
| 264 | 6.5 |
| 265 | 7.5 |
| 266 | 7.3 |
| 267 | 7.1 |
| 268 | 6 |
| 269 | 8.4 |
| 270 | 7.5 |
| 271 | 7.4 |
| 272 | 7.8 |
| 273 | 7.8 |
| 274 | 6.8 |
| 275 | 7 |
| 276 | 7.7 |
| 277 | 8.2 |
| 278 | 7.8 |
| 279 | 8.2 |
| 280 | 8.3 |
| 281 | 7.3 |
| 282 | 7.5 |
| 283 | 6.6 |

TABLE 2-continued

| Cmpd No. from Table 1 | pEC$_{50}$ |
|---|---|
| 284 | 7.7 |
| 285 | 7.8 |
| 286 | 7.5 |
| 287 | 7.2 |
| 288 | 7.1 |
| 289 | 7.5 |
| 290 | 7.6 |
| 291 | 7.3 |
| 292 | 8.1 |
| 293 | 7.9 |
| 294 | 7.9 |
| 295 | 7 |
| 296 | 7.6 |
| 297 | 7.5 |
| 298 | 6.1 |
| 299 | 6.1 |
| 300 | 6.2 |
| 301 | 6.9 |
| 302 | 7.9 |
| 303 | 6.4 |
| 304 | 6.8 |
| 305 | 7.8 |
| 306 | 6.6 |
| 307 | 7.4 |
| 308 | 8.1 |
| 309 | 8.1 |
| 310 | 7.4 |
| 311 | 8.4 |
| 312 | 7.7 |
| 313 | 7.3 |
| 314 | 7.6 |
| 315 | 6.8 |
| 316 | 7.8 |
| 317 | 7.9 |
| 318 | 7.9 |
| 319 | 6.4 |
| 320 | 7.1 |
| 321 | 7.1 |
| 322 | 7.7 |
| 323 | 7.5 |
| 324 | 7.4 |
| 325 | 7.9 |
| 326 | 7.9 |
| 327 | 7.9 |
| 328 | 6.8 |
| 329 | 6.8 |
| 330 | 7.8 |
| 331 | 8.3 |
| 332 | 7.8 |
| 333 | 7.8 |
| 334 | 7.2 |
| 335 | 8.4 |
| 336 | 7.8 |
| 337 | 7.4 |
| 338 | 7.1 |
| 339 | 8.2 |
| 340 | 7.7 |
| 341 | 7.6 |
| 342 | 7.6 |
| 343 | 7.7 |
| 344 | 7.6 |
| 345 | 6.7 |
| 346 | 7.6 |
| 347 | 7.6 |
| 348 | 8.0 |
| 349 | 7.8 |
| 350 | 7.7 |
| 351 | 7.6 |
| 352 | 7.6 |
| 353 | 7.8 |
| 354 | 7.7 |
| 355 | 7.7 |
| 356 | 8.3 |
| 357 | 7.7 |
| 358 | 7.7 |
| 359 | 7.5 |
| 360 | 7.8 |
| 361 | 8.1 |

TABLE 2-continued

| Cmpd No. from Table 1 | pEC$_{50}$ |
|---|---|
| 362 | 8 |
| 363 | 8.3 |
| 364 | 8.1 |
| 365 | 7.4 |
| 366 | 7.7 |
| 367 | 8 |
| 368 | 7.8 |
| 369 | 7.7 |
| 370 | 8.2 |
| 371 | 7.5 |
| 372 | 7.5 |
| 373 | 7.3 |
| 374 | 7.2 |
| 375 | 8 |
| 376 | 8 |
| 377 | 7.8 |
| 378 | 8 |
| 379 | 7.2 |
| 380 | 6.6 |
| 381 | 8.3 |
| 382 | 7.8 |
| 383 | 7.8 |
| 384 | 8.1 |
| 385 | 8.2 |
| 386 | 8.4 |
| 387 | 8.2 |
| 388 | 8.2 |
| 389 | 7.9 |
| 390 | 7.8 |
| 391 | 7.7 |
| 392 | 8.3 |
| 393 | 8.1 |
| 394 | 8.3 |
| 395 | 8.4 |
| 396 | 8.5 |
| 397 | 7.6 |
| 398 | 8.1 |
| 399 | 7.5 |
| 400 | 8.2 |
| 401 | 8.3 |
| 402 | 7.8 |
| 403 | 7.6 |
| 404 | 8 |
| 405 | 8.3 |
| 406 | 7.7 |
| 407 | 6.6 |
| 408 | 8.5 |
| 409 | 7.6 |
| 410 | 7.3 |
| 411 | 8.2 |
| 412 | 8.1 |
| 413 | 8 |
| 414 | 8.3 |
| 415 | 7.7 |
| 416 | 8 |
| 417 | 7.1 |
| 418 | 7.5 |
| 419 | 7.6 |
| 420 | 8 |
| 421 | 8.2 |
| 422 | 7.4 |
| 423 | 7.7 |
| 424 | 7 |
| 425 | 8.3 |
| 426 | 8.4 |
| 427 | 7.6 |
| 428 | 7.5 |
| 429 | 8 |
| 430 | 8 |
| 431 | 7.4 |
| 432 | 7.5 |
| 433 | 8.0 |
| 434 | 7.4 |
| 435 | 7.8 |
| 436 | 7.3 |
| 437 | 8.0 |
| 438 | 7.7 |
| 439 | 7.8 |
| 440 | 8 |
| 441 | 7.5 |
| 442 | 8 |
| 443 | 7.8 |
| 444 | 7.9 |
| 445 | 8.3 |
| 446 | 8.2 |
| 447 | 7.6 |
| 448 | 7.4 |
| 449 | 7.2 |
| 450 | 6.4 |
| 451 | 7.8 |
| 452 | 8.4 |
| 453 | 8.1 |
| 454 | 7.9 |
| 455 | 7.7 |
| 456 | 6.2 |
| 457 | 6.3 |
| 458 | 7.3 |
| 459 | 7.3 |
| 460 | 8.2 |
| 461 | 8.3 |
| 462 | 8.4 |
| 463 | 8.1 |
| 464 | 8.0 |
| 465 | 8.3 |
| 466 | 7.9 |
| 467 | 8.3 |
| 468 | 8.5 |
| 469 | 8.3 |
| 470 | 7.2 |
| 471 | 7.4 |
| 472 | 7.4 |
| 473 | 8.3 |
| 474 | 8.3 |
| 475 | 7.6 |
| 476 | 6.7 |
| 477 | 6.9 |
| 478 | 7.6 |
| 479 | 7.9 |
| 480 | 7.3 |
| 481 | 7.7 |
| 482 | 6.1 |
| 483 | 7.2 |
| 484 | 7 |
| 485 | 7.1 |
| 486 | 7.4 |
| 487 | 7.5 |
| 488 | 7.8 |
| 489 | 8.2 |
| 490 | 7.9 |
| 491 | 8.2 |
| 492 | 6.6 |
| 493 | 6.9 |
| 494 | 6.3 |
| 495 | 7.4 |
| 496 | 8.0 |
| 497 | 8.2 |
| 498 | 7.5 |
| 499 | 8.2 |
| 500 | 7.3 |
| 501 | 6.4 |
| 502 | 8.2 |
| 503 | 8.5 |
| 504 | 7.9 |
| 505 | 8.8 |
| 506 | 8.0 |
| 507 | 7.9 |
| 508 | 7.6 |
| 509 | 8.2 |

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:
1. A compound of Formula (I'):

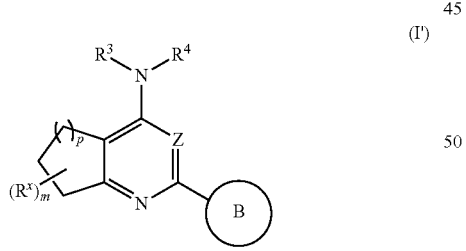

or a pharmaceutically acceptable salt thereof; wherein,
Z is N;
Ring B is

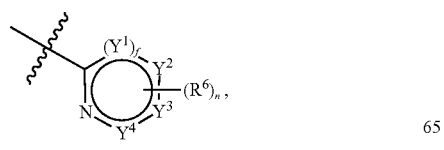

wherein indicates the point of attachment to the remainder of the molecule;

$R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_{10}$ alkoxy, hydroxy-$C_1$-$C_{10}$-alkyl, cyano, —$NR^G R^H$, halo-$C_1$-$C_3$ alkoxy, —O—($C_1$-$C_6$ alkyl)-$R^{bb}$, —O—$R^{bb}$, —($C_1$-$C_6$ alkyl)-$NR^{G1}R^{H1}$, —S—$C_1$-$C_3$ alkyl, —S—$C_1$-$C_3$ alkyl-$NR^{G1}R^{H1}$, halo-$C_1$-$C_3$ alkyl, —O—$R^{cc}$—O—$R^{dd}$, 5- to 7-membered monocyclic heteroaryl, and $C_3$-$C_6$ cycloalkyl; wherein, the alkyl moiety in hydroxy-$C_1$-$C_{10}$ alkoxy or —O—($C_1$-$C_6$ alkyl)-$R^{bb}$ is optionally substituted with cyano, hydroxy, hydroxy-$C_1$-$C_3$-alkyl, halogen, or $C_1$-$C_3$ alkoxy;

$R^{bb}$ is 4- to 7-membered monocyclic or bridged heterocyclyl, $C_3$-$C_7$ cycloalkyl, 5- or 6-membered monocyclic heteroaryl, —$SO_2$—$C_1$-$C_3$ alkyl, —S—$C_1$-$C_3$ alkyl, —C(O)$NR^{G1}R^{H1}$, or —$NR^G R^H$;

$R^{cc}$ is $C_1$-$C_3$ alkyl; and
$R^{dd}$ is $C_1$-$C_3$ alkyl or a 6-membered heteroaryl;
wherein, said cycloalkyl, heterocyclyl, or heteroaryl of $R^6$, $R^{bb}$, or $R^{dd}$ is optionally substituted with one or two substituents, each independently selected from the group consisting of hydroxy, halogen, halo-$C_1$-$C_3$ alkyl, oxo, $C_1$-$C_3$ alkoxy, and $C_1$-$C_3$ alkyl;

$R^{G1}$ and $R^{H1}$ are each independently hydrogen or $C_1$-$C_3$ alkyl;

and,
$R^G$ and $R^H$ are each independently hydrogen, —C(O)$R^{Ga}$, or optionally deuterated $C_1$-$C_3$ alkyl; wherein,
$R^{Ga}$ is $C_1$-$C_3$ alkyl or hydrogen;

or,
two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- to 6-membered monocyclic heteroaryl fused with Ring B; wherein,
said heterocyclyl, phenyl, cycloalkyl, or heteroaryl fused with ring B is optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl;

n is 0, 1, 2, or 3;
$Y^1$, $Y^2$, $Y^3$, and $Y^4$ are each independently selected from the group consisting of CH, N, NH, O, S, SH, S—$R^6$, N—$R^6$, and C—$R^6$, provided that 1 or 2 of $Y^1$, $Y^2$, $Y^3$, and $Y^4$ can be N, N—$R^6$, NH, O, SH or S—$R^6$;

f is 0 or 1;
p is 1 or 2;
$R^X$, in each instance, is halogen, $C_1$-$C_6$ alkyl, $C_1$-$C_3$ alkoxy, hydroxy, oxo, or cyano;
m is 0, 1, or 2;
$R^3$ is selected from the group consisting of hydrogen, optionally deuterated $C_1$-$C_3$ alkyl, hydroxy-$C_1$-$C_3$ alkyl, halo-$C_1$-$C_3$ alkyl, cyclopropyl, and phenyl;

$R^4$ is

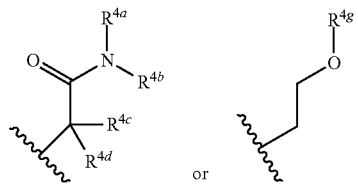

or wherein, $R^{4a}$ and $R^{4b}$ are each independently selected from the group consisting of hydrogen, $C_1$-$C_{10}$ alkyl, hydroxy-$C_1$-$C_6$ alkyl, halo-$C_1$-$C_3$ alkyl, $C_1$-$C_3$ alkoxy-$C_1$-$C_6$ alkyl, —$C_1$-$C_6$ alkyl-$NR^{J1}R^{J2}$, $C_3$-$C_7$ cycloalkyl, 4- to 10-membered monocyclic, fused bicyclic, bridged bicyclic, or spiro heterocyclyl, $C_6$-$C_{10}$ monocyclic or fused bicyclic aryl, 5- to 10-membered monocyclic or fused bicyclic heteroaryl, ($C_6$-$C_{10}$ monocyclic or fused bicyclic aryl)-$C_1$-$C_3$ alkyl, and (5- to 10-membered monocyclic or fused bicyclic heteroaryl)-$C_1$-$C_3$ alkyl;

$R^{J1}$ and $R^{J2}$ are independently hydrogen or $C_1$-$C_3$ alkyl;

wherein the cycloalkyl, heterocyclyl, aryl, heteroaryl, aryl-alkyl, or heteroaryl-alkyl of $R^{4a}$ or $R^{4g}$ is optionally substituted with one, two, or three substituents, each independently selected from the group consisting of halogen, $C_1$-$C_6$ alkyl, halo-$C_1$-$C_3$ alkyl, hydroxy, $C_1$-$C_3$ alkoxy, halo-$C_1$-$C_3$ alkoxy, oxo, $C_3$-$C_7$ cycloalkyl, and 5- to 10-membered monocyclic, fused bicyclic, or spiro heterocyclyl;

$R^{4b}$ is hydrogen or $C_1$-$C_6$ alkyl; or $R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy; or $R^{4b}$ and $R^{4c}$ taken together with the atom to which each is attached form a 5- to 7-membered monocyclic heterocyclyl optionally substituted with one, two, or three substituents, each independently selected from the group consisting of hydroxy, halogen, and $C_1$-$C_3$ alkyl; or $R^{4c}$ and $R^{4d}$ are each independently selected from the group consisting of hydrogen, $C_1$-$C_3$ alkoxy, hydroxy, $C_1$-$C_3$ alkyl-thio-$C_1$-$C_3$ alkyl, hydroxy-$C_1$-$C_6$ alkyl, $C_1$-$C_6$ alkoxy-$C_1$-$C_3$ alkyl, $C_3$-$C_7$ cycloalkyl, and $C_1$-$C_3$ alkyl; or $R^{4c}$ and $R^{4d}$ taken together with the atom to which each is attached form a $C_3$-$C_7$ cycloalkyl.

2. The compound of claim 1, or a pharmaceutically acceptable salt thereof wherein p is 1.

3. The compound of claim 1, or a pharmaceutically acceptable salt thereof, wherein $Y^1$, $Y^2$, $Y^3$, and $Y^4$ are each CH or C—$R^6$.

4. The compound of claim 3, a pharmaceutically acceptable salt thereof, wherein $Y^1$ is CH, $Y^2$ is C—$R^6$, $Y^3$ is CH, and $Y^4$ is CH.

5. The compound of claim 1, or a pharmaceutically acceptable salt thereof, wherein $Y^3$ is N and $Y^1$, $Y^2$, and $Y^4$ are each CH or C—$R^6$.

6. The compound of claim 1, or a pharmaceutically acceptable salt thereof, wherein $Y^2$ is N and $Y^1$, $Y^3$, $Y^4$ are each CH or C—$R^6$.

7. The compound of claim 1, or a pharmaceutically acceptable salt thereof, wherein $R^6$, in each instance, is selected from the group consisting of halogen, hydroxy, $C_1$-$C_3$ alkoxy, $C_1$-$C_3$ alkyl, $C_1$-$C_3$ alkoxy-$C_1$-$C_3$ alkyl, hydroxy-$C_1$-$C_{10}$ alkoxy, hydroxy-$C_1$-$C_{10}$-alkyl, —O—($C_1$-$C_6$ alkyl)-$R^{bb}$, halo-$C_1$-$C_3$ alkoxy, —O—$R^{cc}$—O—$R^{dd}$, halo-$C_1$-$C_3$ alkyl, —($C_1$-$C_6$ alkyl)- $NR^{GI}R^{HI}$, —S—$CH_3$, —S($CH_2$)$_2$N($CH_3$)$_2$, and —$NR^GR^H$; wherein, $R^{bb}$ is —$NR^GR^H$, —C(O)N($CH_3$)$_2$, —S(O)$_2$$CH_3$, or —$SCH_3$;

$R^G$ and $R^H$ are each independently hydrogen, optionally deuterated $C_1$-$C_3$ alkyl, or —C(O)$R^{Ga}$, wherein $R^{Ga}$ is $C_1$-$C_3$ alkyl;

$R^{GI}$ and $R^{HI}$ are each independently hydrogen or $C_1$-$C_3$ alkyl;

$R^{cc}$ and $R^{dd}$ are each independently $C_1$-$C_3$ alkyl; and, wherein the alkyl moiety in hydroxy-$C_1$-$C_{10}$ alkoxy is optionally substituted with hydroxy, halogen, or $C_1$-$C_3$ alkoxy.

8. The compound of claim 7, or a pharmaceutically acceptable salt thereof, wherein $R^6$, in each instance, is selected from the group consisting of methoxy, ethoxy, methyl, fluoro, chloro, ethyl, —N($CH_3$)$_2$, hydroxy, —$OCH_2CH_2OH$, —$CH_2OH$, —$CH_2OCH_3$, —$OCH_2CH_2NH_2$, $OCH_2CH_2N(CH_3)_2$, —$OCH_2C(CH_3)_2OH$, —$OCH_2CF_3$, —$OCHF_2$, —$OCF_3$, —$OCH_2CH_2OCH_3$, —$OCH_2CH_2F$, —$OC(CH_3)_2CH_2OH$, —$OCH_2CH(CH_3)OH$, —$OCH_2CH_2NHC(O)CH_3$, —$OC(CH_3)_2CH_2N(CH_3)_2$, —$OCH(CH_3)CH_2OH$, —$OCH_2CH(CH(CH_3)_2)OH$, —$OCH_2CH(CH_2CH_3)OH$, —$OCH_2C(CH_2CH_3)_2OH$, —$OCH_2CH_2N(CH_2CH_3)_2$, —$OCH(CH_3)CH_2N(CH_3)_2$, —$OCH_2C(O)N(CH_3)_2$, —$OCH_2C(CH_3)_2N(CH_3)_2$, —$OCH_2CH(CH_2OH)OH$, —$OCH_2CH_2NH(CH_3)$, —$OCH_2CH(CF_3)OH$, —$OCH_2C(CH_3)(CH_2CH_3)OH$, —$OCH_2CH(CH_2OCH_3)OH$, —$OCH_2CH(CH_2F)OH$, —($CH_2$)$_3$N($CH_3$)$_2$, —($CH_2$)$_2$N($CH_3$)H, —O($CH_2$)$_2$S(O)$_2$$CH_3$, —O($CH_2$)$_2$$SCH_3$, —($CH_2$)$_2$C($CH_3$)$_2$OH, —$OCH_2CH_2N(CD_3)_2$, and —$CH_2CH_2OH$.

9. The compound of claim 1, or a pharmaceutically acceptable salt thereof, wherein $R^6$, in each instance, is selected from the group consisting of —O—($C_1$-$C_6$ alkyl)-$R^{bb}$, —O—$R^{cc}$—O—$R^{dd}$, 5- to 7-membered monocyclic heteroaryl, and $C_3$-$C_6$ cycloalkyl; wherein, $R^{cc}$ is $C_1$-$C_3$ alkyl and $R^{dd}$ is 6-membered heteroaryl;

$R^{bb}$ is 4- to 7-membered monocyclic or bridged heterocyclyl, 5- or 6-membered monocyclic heteroaryl, or $C_3$-$C_7$ cycloalkyl; and wherein said cycloalkyl, heteroaryl, or heterocyclyl of $R^6$, $R^{bb}$, or $R^{dd}$ is optionally substituted with one or two substituents, each independently selected from the group consisting of hydroxy, halogen, $C_1$-$C_3$ alkoxy, oxo, halo-$C_1$-$C_3$ alkyl, and $C_1$-$C_3$ alkyl.

10. The compound of claim 9, or a pharmaceutically acceptable salt thereof, wherein $R^6$, in each instance, is selected from the group consisting of cyclopropyl, —O—$R^{bb}$, —O—($CH_2$)—$R^{bb}$, —O—($CH_2$)$_2$—$R^{bb}$, —O—($CH_2$)$_2$—O-pyridazinyl, and optionally $C_1$-$C_3$ alkyl-substituted imidazolyl; wherein, $R^{bb}$ is selected from the group consisting of cyclopropyl, cyclobutyl, cyclopentyl, cyclohexyl, tetrahydrofuranyl, tetrahydropyranol, oxetanyl, dioxolanyl, azetidinyl, morpholinyl, piperazinyl, 2-oxa-5-azabicyclo[2.2.1]heptane, imidazolyl, tetrazolyl, pyridazinyl, piperidinyl, thiomorpholinyl, and pyrrolidinyl, each optionally substituted with hydroxy, oxo, fluoro, —$CF_3$, —$CH_2CF_3$, —$CH_2CHF_2$, —$CH_2CH_2F$, methoxy, ethyl, or methyl.

11. The compound of claim 10, a pharmaceutically acceptable salt thereof wherein $R^6$, in each instance, is selected from the group consisting of

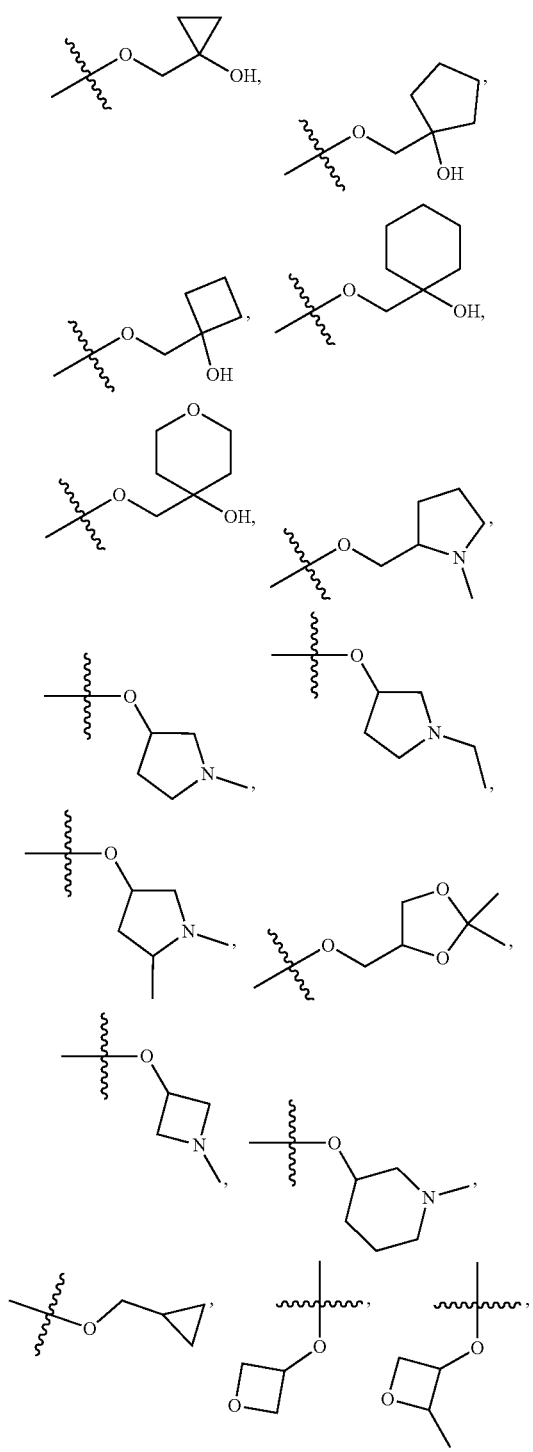

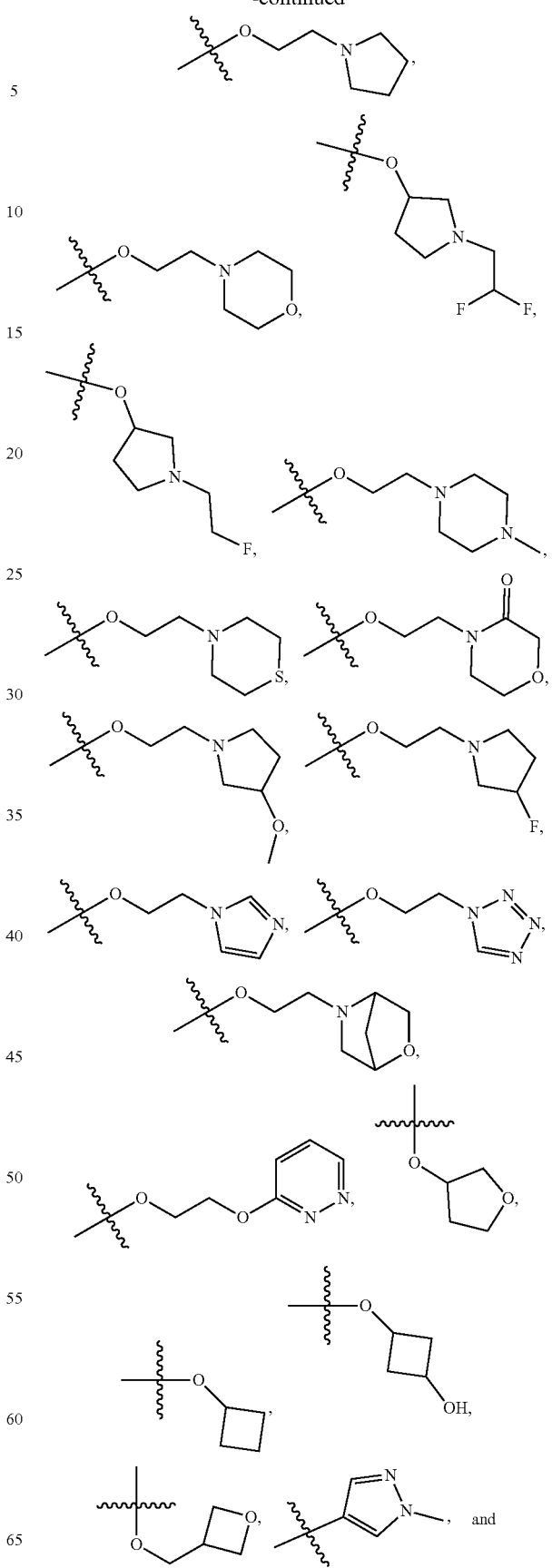

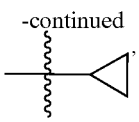

where ⧘ indicates the point of attachment to Ring B.

12. The compound of claim 1, or a pharmaceutically acceptable salt thereof, wherein two $R^6$ groups, taken together with the atom to which each is attached, form a 5- or 6-membered monocyclic heterocyclyl fused with Ring B, a $C_4$-$C_7$ cycloalkyl fused with Ring B, a phenyl fused with Ring B, or a 5- or 6-membered monocyclic heteroaryl fused with Ring B, each optionally substituted with one or two substituents, each independently selected from the group consisting of $C_1$-$C_3$ alkoxy, hydroxy, hydroxy-$C_1$-$C_3$-alkyl, $C_1$-$C_3$ alkyl, $C_3$-$C_7$ cycloalkyl, and 5- or 6-membered monocyclic heterocyclyl.

13. The compound of claim 12, or a pharmaceutically acceptable salt thereof, wherein two $R^6$ groups, taken together with the atom to which each is attached, form a pyrazolyl, dioxanyl, pyridinyl, pyrimidinyl, thiazolyl, furanyl, dioxolanyl, or phenyl ring fused with Ring B, wherein said ring is optionally substituted with one substituent selected from the group consisting of hydroxy, methoxy, tetrahydropyranyl, —$CH_2OH$, and methyl.

14. The compound of claim 1, or a pharmaceutically acceptable salt thereof, wherein f is 1.

15. The compound of claim 1, or a pharmaceutically acceptable salt thereof, wherein f is 0 and Ring B is

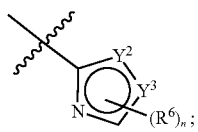

wherein,
n is 0 or 1; and
$Y^2$ and $Y^3$ are each independently selected from the group consisting of CH, N, NH, $NR^6$, S, O, and $CR^6$, provided that only one of $Y^2$ and $Y^3$ can be N, NH, $NR^6$, S, or O.

16. The compound of claim 1, or a pharmaceutically acceptable salt thereof, wherein n is 1.

17. The compound of claim 1, or a pharmaceutically acceptable salt thereof, wherein $R^3$ is selected from the group consisting of hydrogen, methyl, —$CD_3$, ethyl, phenyl, —$CH_2CF_3$, and —$CH_2CH_2OH$.

18. The compound of claim 1, or a pharmaceutically acceptable salt thereof, wherein $R^3$ is methyl.

19. The compound of claim 1, or a pharmaceutically acceptable salt thereof, wherein $R^4$ is a (5- to 10-membered monocyclic or fused bicyclic heteroaryl)-methyl, wherein said heteroaryl is optionally substituted with one or two substituents, each independently selected from the group consisting of phenyl, $C_3$-$C_7$ cycloalkyl, —($C_1$-$C_3$ alkyl)-phenyl, and 5- to 7-membered monocyclic heterocyclyl, and wherein said phenyl either alone or in —($C_1$-$C_3$ alkyl)-phenyl, cycloalkyl, or heterocyclyl is optionally substituted with one or two substituents, each individually selected from the group consisting of $C_1$-$C_3$ alkyl, halogen, and hydroxy.

20. The compound of claim 1, or a pharmaceutically acceptable salt thereof, wherein $R^4$ is

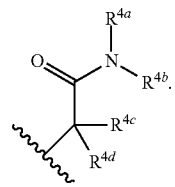

21. The compound of claim 20, or a pharmaceutically acceptable salt thereof, wherein $R^{4c}$ is selected from the group consisting of hydrogen, methyl, isopropyl, —$CH_2OH$, —$CH_2OC(CH_3)_3$, and —$CH_2CH_2SCH_3$; and $R^{4d}$ is selected from the group consisting of hydrogen and methyl; or, $R^{4c}$ and $R^{4d}$ taken together with the atom to which each is attached form a cyclopropyl ring.

22. The compound of claim 21, or a pharmaceutically acceptable salt thereof, wherein $R^{4c}$ and $R^{4d}$ are each hydrogen.

23. The compound of claim 20, or a pharmaceutically acceptable salt thereof, wherein $R^{4b}$ is hydrogen.

24. The compound of claim 20, or a pharmaceutically acceptable salt thereof, wherein $R^{4a}$ is $C_1$-$C_6$ alkyl.

25. The compound of claim 24, or a pharmaceutically acceptable salt thereof, wherein $R^{4a}$ is methyl, ethyl, isopropyl, tert-butyl, or 3-methylpentan-3-yl.

26. The compound of claim 20, or a pharmaceutically acceptable salt thereof, wherein $R^{4a}$ is phenyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic or fused bicyclic heterocyclyl.

27. The compound of claim 20, or a pharmaceutically acceptable salt thereof, wherein $R^{4a}$ is:
5- to 10-membered monocyclic or fused bicyclic heteroaryl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic, fused bicyclic, or spiro heterocyclyl;
$C_3$-$C_7$ cycloalkyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic or fused bicyclic heterocyclyl
or,
4- to 10-membered monocyclic or fused bicyclic heterocyclyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, oxo, $C_3$-$C_7$ cycloalkyl, and 5- to 10-membered monocyclic or fused bicyclic heterocyclyl.

28. The compound of claim 20, a pharmaceutically acceptable salt thereof, wherein $R^{4a}$ is ($C_6$-$C_{10}$ monocyclic or fused bicyclic aryl)-$C_1$-$C_3$ alkyl or (5- to 10-membered monocyclic or fused bicyclic heteroaryl)-$C_1$-$C_3$ alkyl, optionally substituted with one or two substituents, each independently selected from the group consisting of halogen, $C_1$-$C_6$ alkyl, halo-$C_1$-$C_3$ alkyl, hydroxy, $C_1$-$C_3$ alkoxy, $C_3$-$C_7$ cycloalkyl, and 5- to 10-membered monocyclic, fused bicyclic heterocyclyl.

29. The compound of claim 20, or a pharmaceutically acceptable salt thereof, wherein $R^{4a}$ is selected from the group consisting of hydroxy-$C_1$-$C_6$ alkyl, halo-$C_1$-$C_3$ alkyl, $C_1$-$C_3$ alkoxy-$C_1$-$C_6$ alkyl, and —$C_1$-$C_6$ alkyl-$NR^{J1}R^{J2}$, wherein $R^1$ and $R^2$ are each independently hydrogen or $C_1$-$C_3$ alkyl.

30. The compound of claim 29, or a pharmaceutically acceptable salt thereof, wherein $R^{4a}$ is selected from the group consisting of —$C(CH_3)_2CH_2OH$, —$CH_2CH_2OH$, —$C(CH_3)_2CH_2OCH_3$, —$CH(CH_3)CH_2OH$, —$CH_2CH_2N(CH_3)_2$, and —$CH_2CF_3$.

31. The compound of claim 20, or a pharmaceutically acceptable salt thereof, wherein $R^{4a}$ and $R^{4b}$ taken together with the atom to which each is attached form a 5- to 10-membered monocyclic, fused bicyclic, or bridged bicyclic heterocyclyl, optionally substituted with one or two substituents, each independently selected from the group consisting of halogen, $C_1$-$C_6$ alkyl, halo-$C_1$-$C_3$ alkyl, hydroxy, and $C_1$-$C_3$ alkoxy.

32. The compound of claim 20, or a pharmaceutically acceptable salt thereof, wherein $R^{4b}$ and $R^{4c}$ taken together with the atom to which each is attached form a 5- to 7-membered monocyclic heterocyclyl, optionally substituted with one or two substituents, each independently selected from $C_1$-$C_3$ alkyl.

33. The compound of claim 1, or a pharmaceutically acceptable salt thereof, wherein $R^4$ is

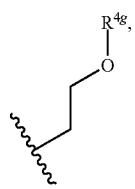

wherein $R^{49}$ is selected from the group consisting of $C_6$-$C_{10}$ monocyclic or fused bicyclic aryl and $C_1$-$C_3$ alkyl.

34. The compound of claim 1, or a pharmaceutically acceptable salt thereof, selected from the group consisting of:

| Compound No. | Structure |
|---|---|
| 5 | 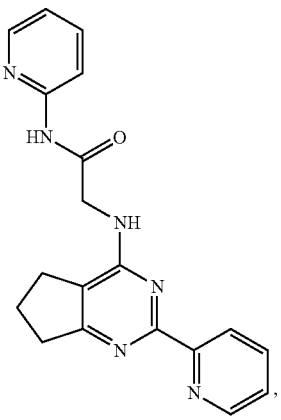 [SMILES: O=C(CNc1nc(-c2ccccn2)nc2c1CCC2)Nc1ccccn1] |
| 6 | 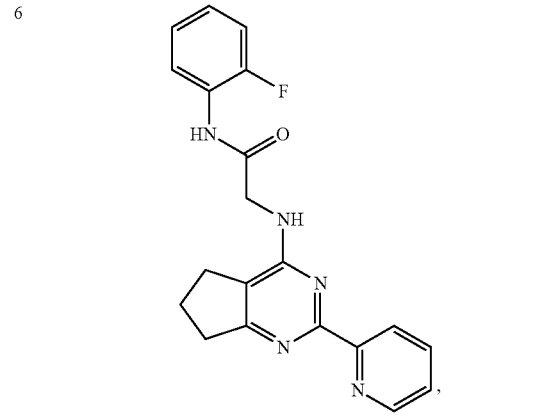 |
| 7 | 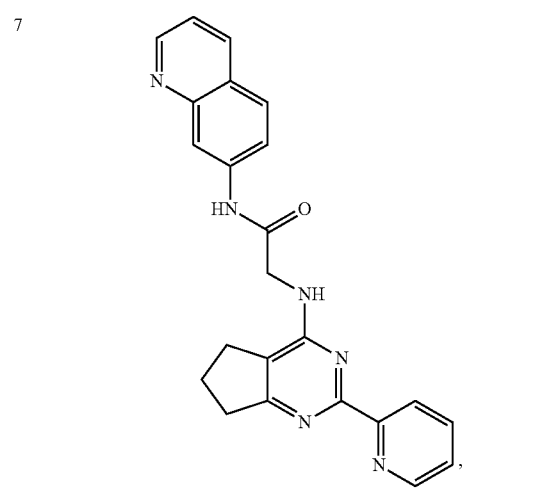 |
| 8 | 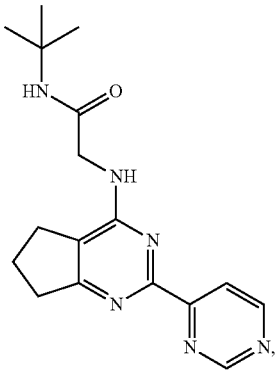 [SMILES: CC(C)(C)NC(=O)CNc1nc(-c2ccncn2)nc2c1CCC2] |

| Compound No. | Structure |
|---|---|
| 10 | 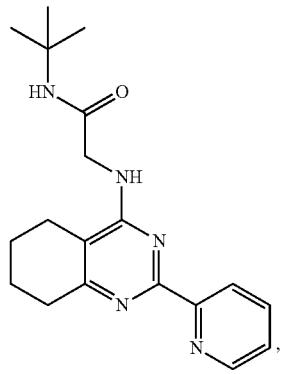 [SMILES: CC(C)(C)NC(=O)CNc1nc(-c2ccccn2)nc2c1CCCC2] |
| 12 | 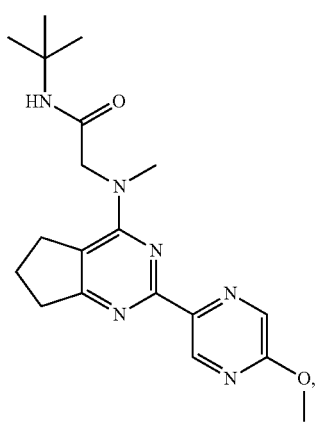 [SMILES: COc1cnc(-c2nc3c(c(N(C)CC(=O)NC(C)(C)C)n2)CCC3)cn1] |
| 15 | 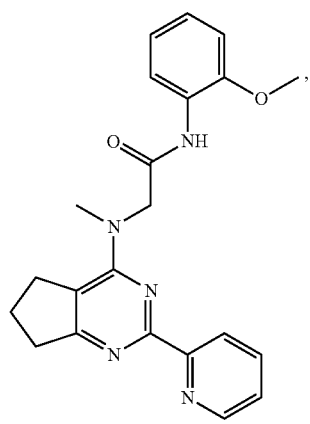 [SMILES: COc1ccccc1NC(=O)CN(C)c1nc(-c2ccccn2)nc2c1CCC2] |
| Compound No. | Structure |
|---|---|
| 17 | 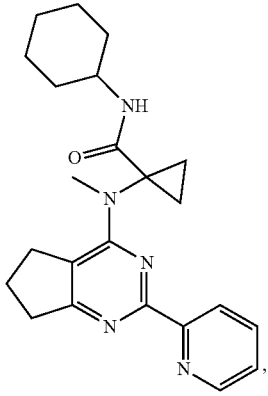 [SMILES: CN(c1nc(-c2ccccn2)nc2c1CCC2)C1(C(=O)NC2CCCCC2)CC1] |
| 19 | 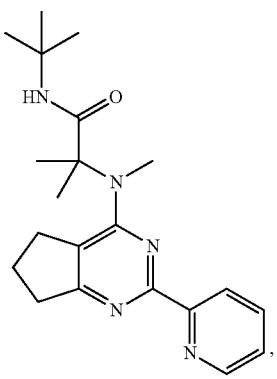 [SMILES: CN(c1nc(-c2ccccn2)nc2c1CCC2)C(C)(C)C(=O)NC(C)(C)C] |
| 20 | 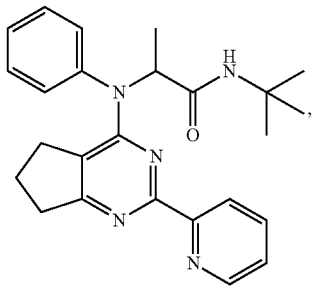 [SMILES: CC(C(=O)NC(C)(C)C)N(c1ccccc1)c1nc(-c2ccccn2)nc2c1CCC2] |
| 21 | 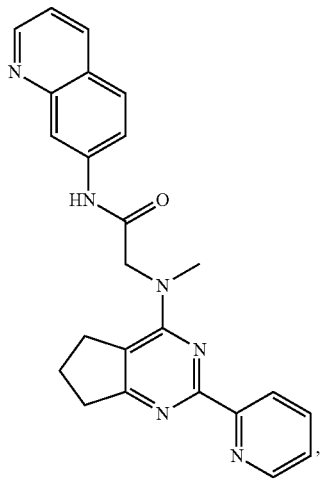 [SMILES: CN(CC(=O)Nc1ccc2cccnc2c1)c1nc(-c2ccccn2)nc2c1CCC2] |

| Compound No. | Structure |
|---|---|
| 22 | 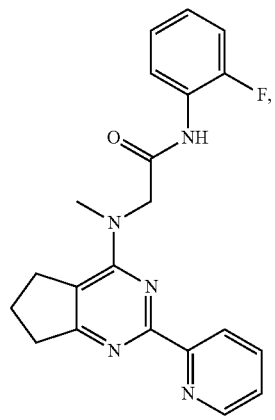 [SMILES: CN(CC(=O)Nc1ccccc1F)c1nc(-c2ccccn2)nc2c1CCC2] |
| 23 | 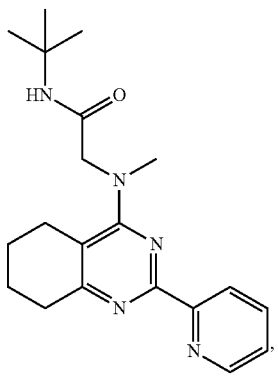 [SMILES: CN(CC(=O)NC(C)(C)C)c1nc(-c2ccccn2)nc2c1CCCC2] |
| 24 | 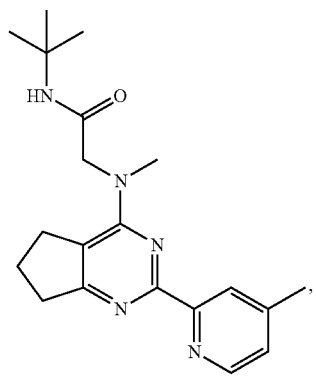 [SMILES: Cc1ccnc(-c2nc3c(c(N(C)CC(=O)NC(C)(C)C)n2)CCC3)c1] |
| Compound No. | Structure |
|---|---|
| 25 | 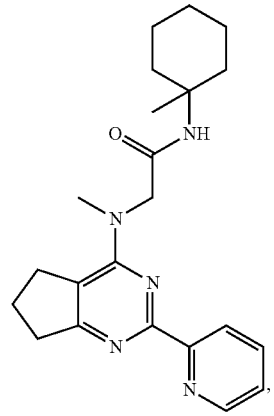 [SMILES: CN(CC(=O)NC1(C)CCCCC1)c1nc(-c2ccccn2)nc2c1CCC2] |
| 26 | 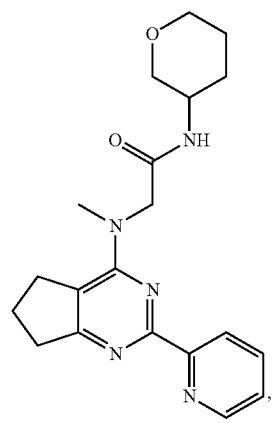 [SMILES: CN(CC(=O)NC1CCCOC1)c1nc(-c2ccccn2)nc2c1CCC2] |
| 27 | 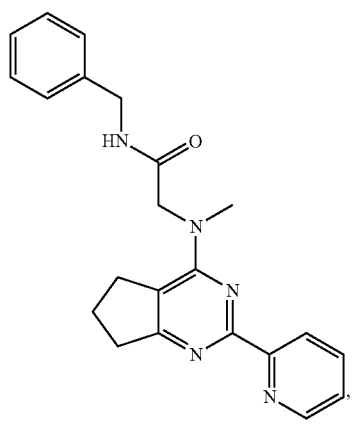 [SMILES: CN(CC(=O)NCc1ccccc1)c1nc(-c2ccccn2)nc2c1CCC2] |

1007
-continued
| Compound No. | Structure |
|---|---|
| 28 | 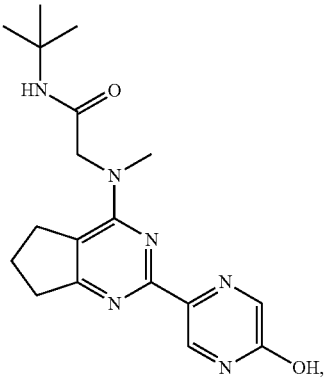 [SMILES: CN(CC(=O)NC(C)(C)C)c1nc(-c2cnc(O)cn2)nc2c1CCC2] |
| 31 | 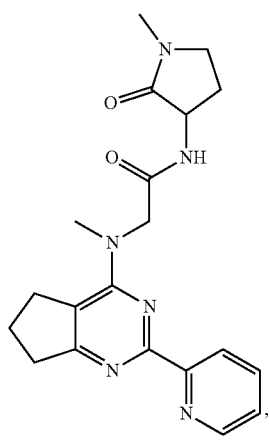 [SMILES: CN1CCC(NC(=O)CN(C)c2nc(-c3ccccn3)nc3c2CCC3)C1=O] |
| 32 | 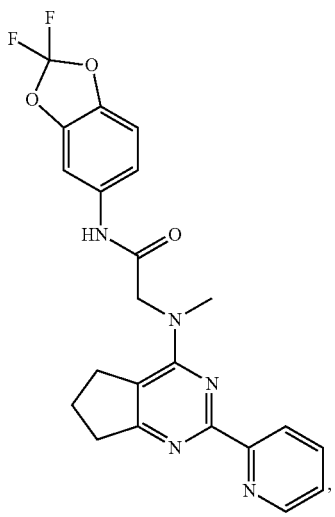 [SMILES: CN(CC(=O)Nc1ccc2c(c1)OC(F)(F)O2)c1nc(-c2ccccn2)nc2c1CCC2] |
1008
-continued
| Compound No. | Structure |
|---|---|
| 33 | 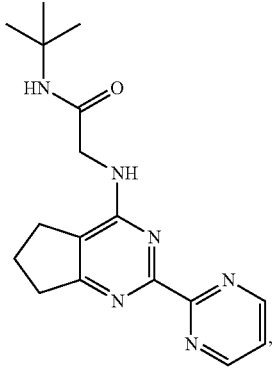 [SMILES: CC(C)(C)NC(=O)CNc1nc(-c2ncccn2)nc2c1CCC2] |
| 34 | 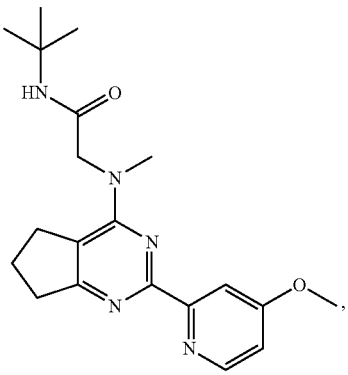 [SMILES: COc1ccnc(-c2nc3c(c(N(C)CC(=O)NC(C)(C)C)n2)CCC3)c1] |
| 35 | 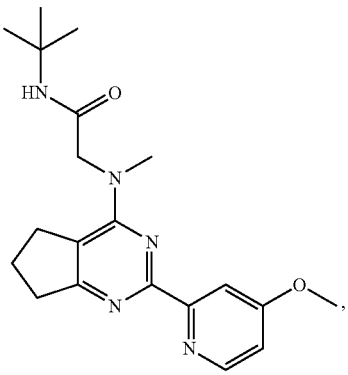 [SMILES: COc1ccnc(-c2nc3c(c(N(C)CC(=O)NC(C)(C)C)n2)CCC3)c1] |
| 36 | 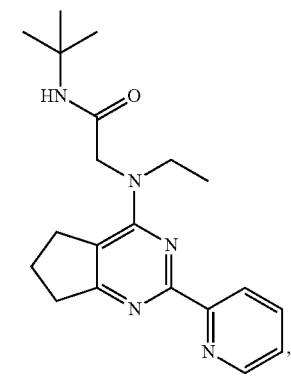 [SMILES: CCN(CC(=O)NC(C)(C)C)c1nc(-c2ccccn2)nc2c1CCC2] |

| Compound No. | Structure |
|---|---|
| 37 | 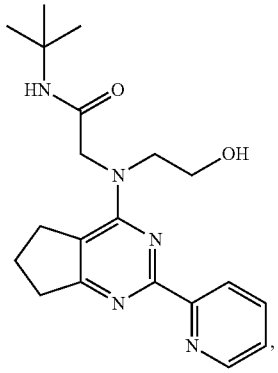 [SMILES: CC(C)(C)NC(=O)CN(CCO)c1nc(-c2ccccn2)nc2c1CCC2] |
| 38 | 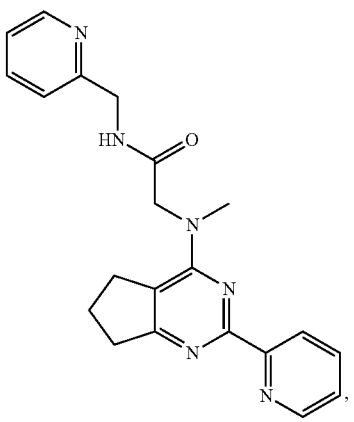 [SMILES: CN(CC(=O)NCc1ccccn1)c1nc(-c2ccccn2)nc2c1CCC2] |
| 39 | 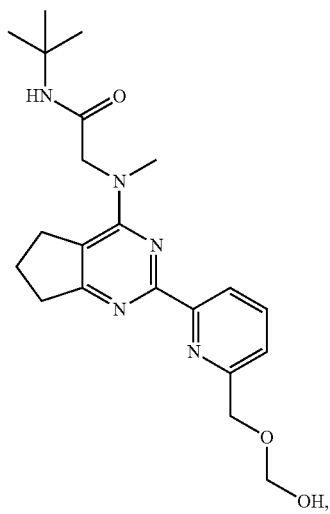 [SMILES: CN(CC(=O)NC(C)(C)C)c1nc(-c2cccc(COCO)n2)nc2c1CCC2] |
| Compound No. | Structure |
|---|---|
| 40 | 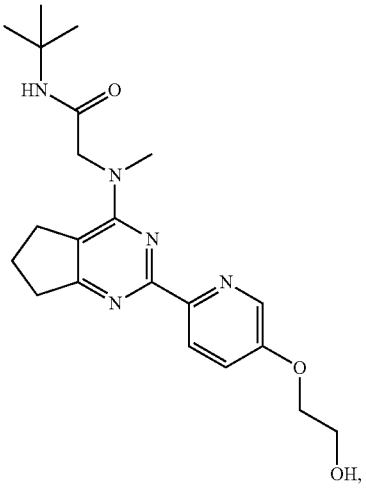 [SMILES: CN(CC(=O)NC(C)(C)C)c1nc(-c2ccc(OCCO)cn2)nc2c1CCC2] |
| 41 | 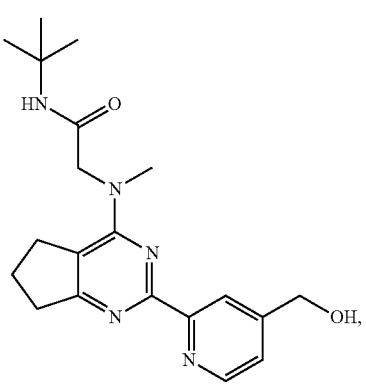 [SMILES: CN(CC(=O)NC(C)(C)C)c1nc(-c2cc(CO)ccn2)nc2c1CCC2] |
| 42 | 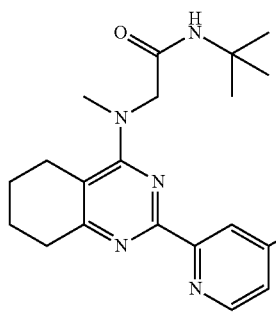 |
| 43 | 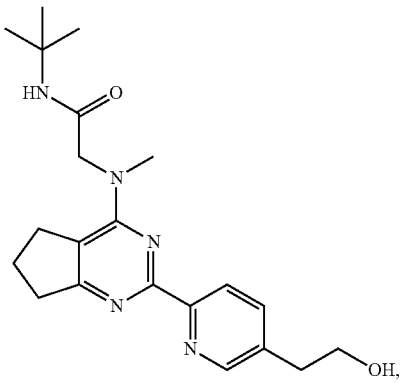 |

| Compound No. | Structure |
|---|---|
| 44 | 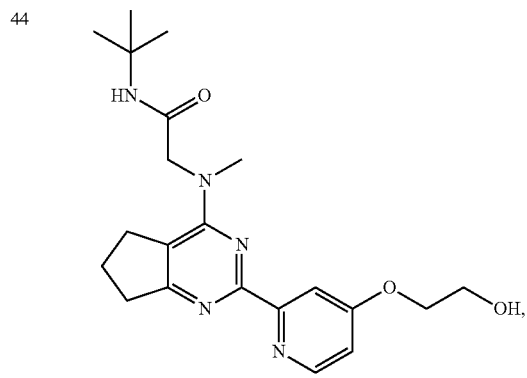 |
| 51 | 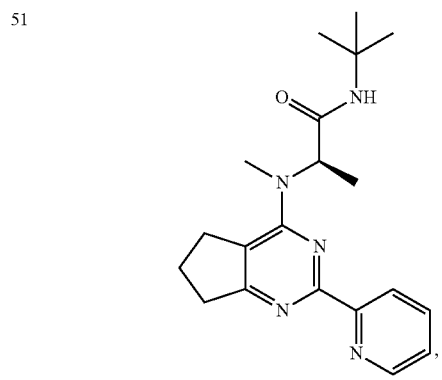 |
| 52 | 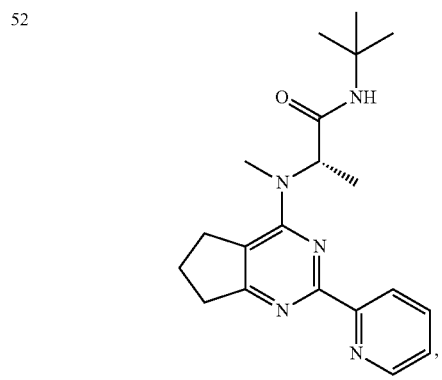 |
| 55 | 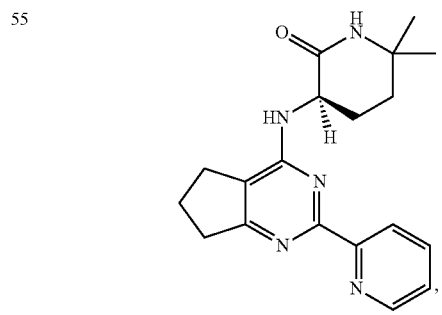 |
| Compound No. | Structure |
|---|---|
| 56 | 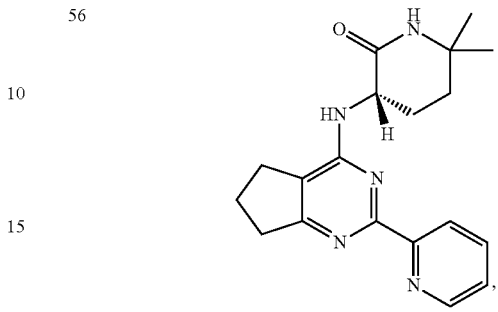 |
| 57 | 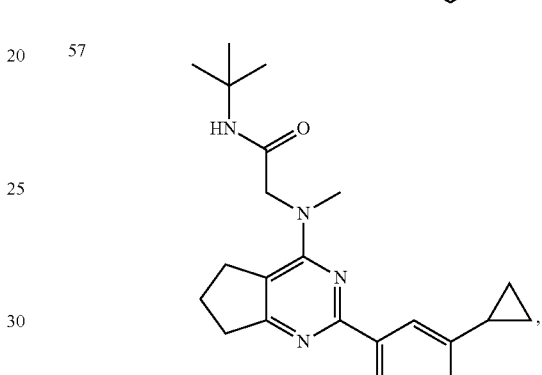 |
| 58 | 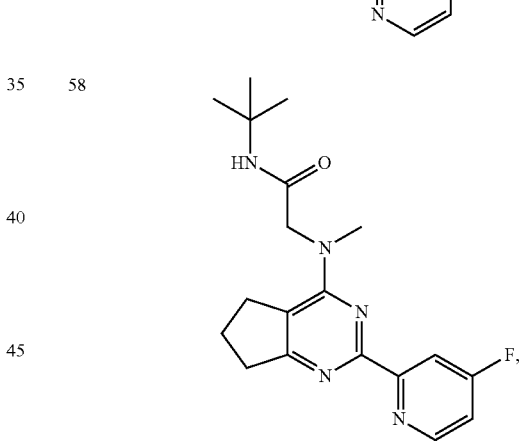 |
| 59 | 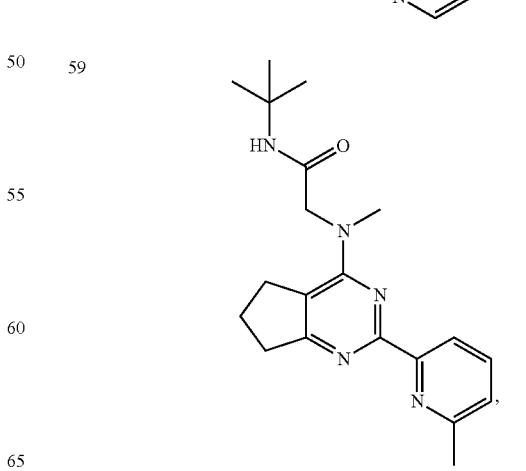 |

| Compound No. | Structure |
|---|---|
| 60 | 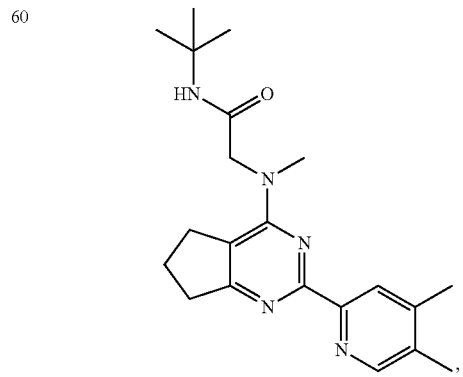 |
| 61 | 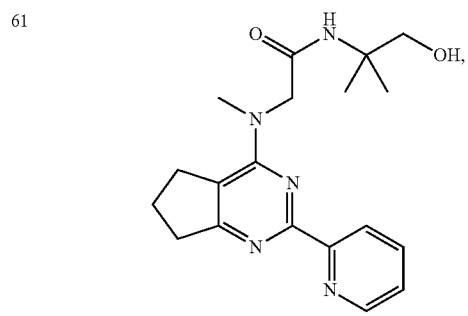 |
| 62 | 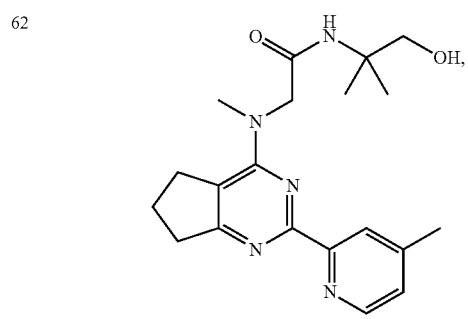 |
| 63 | 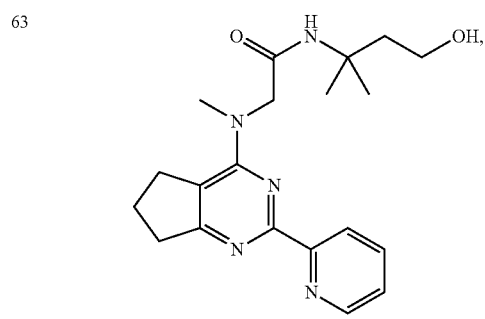 |
| Compound No. | Structure |
|---|---|
| 64 | 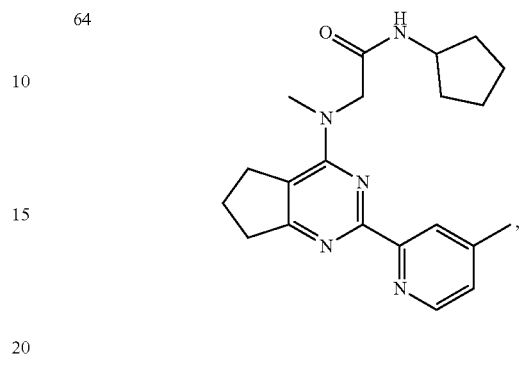 |
| 65 | 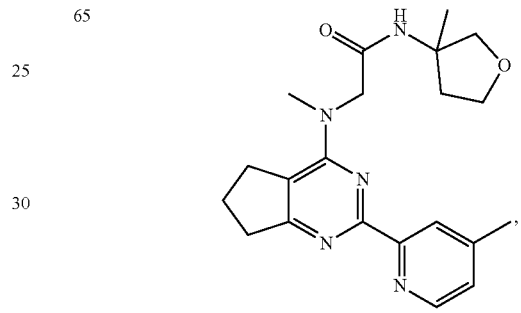 |
| 66 | 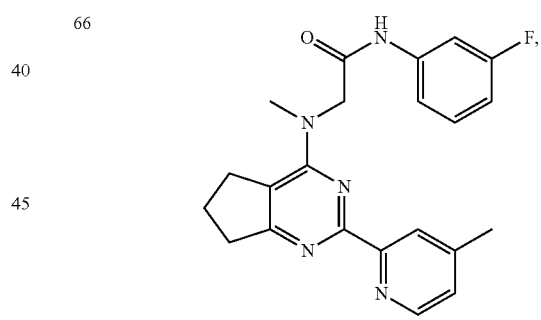 |
| 69 | 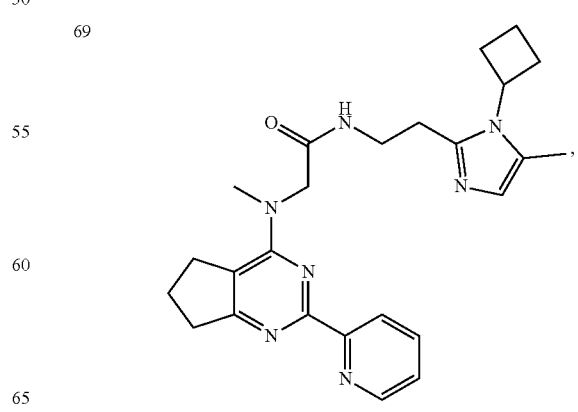 |

| Compound No. | Structure |
|---|---|
| 70 | 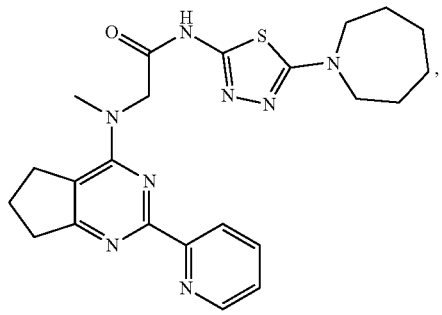 [SMILES: CN(CC(=O)Nc1nnc(N2CCCCCC2)s1)c1nc(-c2ccccn2)nc2c1CCC2] |
| 73 | 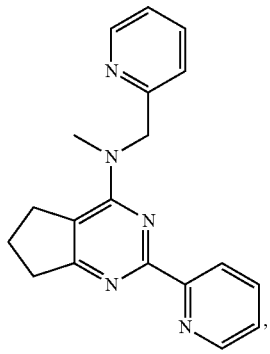 [SMILES: CN(Cc1ccccn1)c1nc(-c2ccccn2)nc2c1CCC2] |
| 74 | 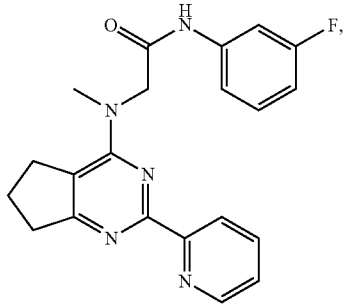 [SMILES: CN(CC(=O)Nc1cccc(F)c1)c1nc(-c2ccccn2)nc2c1CCC2] |
| 75 | 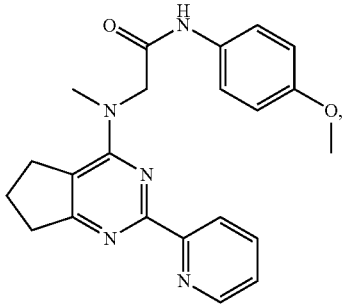 [SMILES: COc1ccc(NC(=O)CN(C)c2nc(-c3ccccn3)nc3c2CCC3)cc1] |
| Compound No. | Structure |
|---|---|
| 76 | 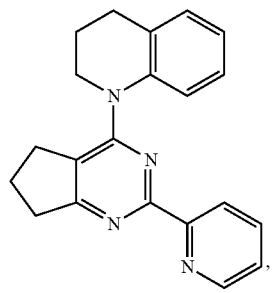 [SMILES: c1ccc(-c2nc3c(c(N4CCCc5ccccc54)n2)CCC3)nc1] |
| 77 | 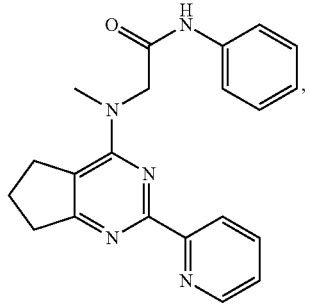 [SMILES: CN(CC(=O)Nc1ccccc1)c1nc(-c2ccccn2)nc2c1CCC2] |
| 78 | 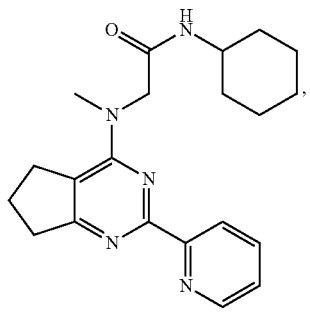 [SMILES: CN(CC(=O)NC1CCOCC1)c1nc(-c2ccccn2)nc2c1CCC2] |
| 79 | 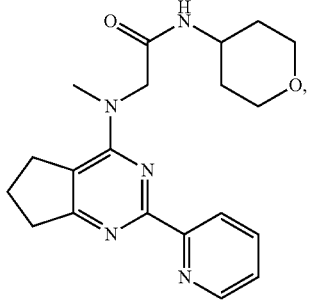 |

| Compound No. | Structure |
|---|---|
| 80 | 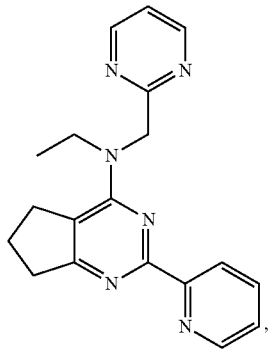 [SMILES: CCN(Cc1ncccn1)c1nc(-c2ccccn2)nc2c1CCC2] |
| 81 | 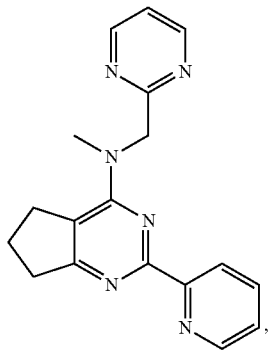 [SMILES: CN(Cc1ncccn1)c1nc(-c2ccccn2)nc2c1CCC2] |
| 82 | 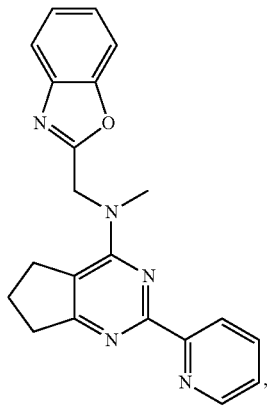 [SMILES: CN(Cc1nc2ccccc2o1)c1nc(-c2ccccn2)nc2c1CCC2] |
| 84 | 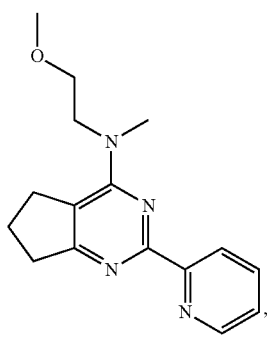 [SMILES: COCCN(C)c1nc(-c2ccccn2)nc2c1CCC2] |
| Compound No. | Structure |
|---|---|
| 86 | 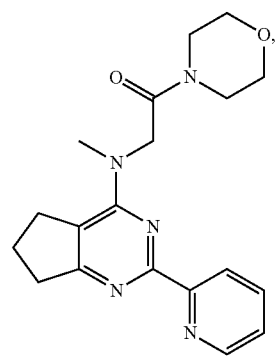 [SMILES: CN(CC(=O)N1CCOCC1)c1nc(-c2ccccn2)nc2c1CCC2] |
| 87 | 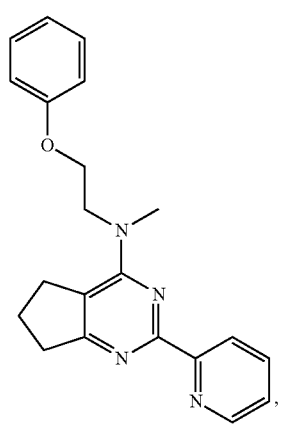 [SMILES: CN(CCOc1ccccc1)c1nc(-c2ccccn2)nc2c1CCC2] |
| 88 | 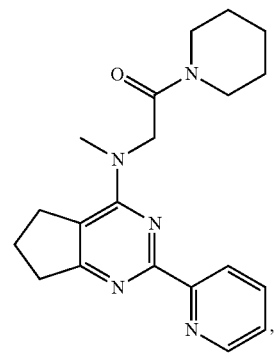 [SMILES: CN(CC(=O)N1CCCCC1)c1nc(-c2ccccn2)nc2c1CCC2] |
| 89 | 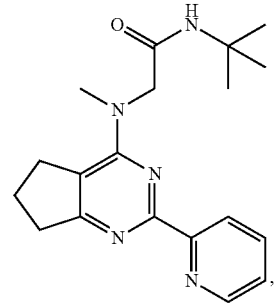 [SMILES: CN(CC(=O)NC(C)(C)C)c1nc(-c2ccccn2)nc2c1CCC2] |

| Compound No. | Structure |
|---|---|
| 90 | 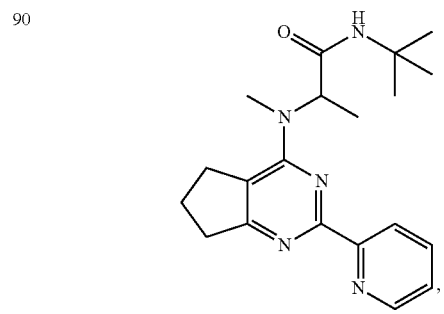 |
| 91 | 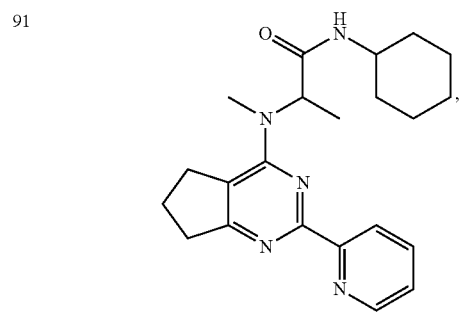 |
| 95 | 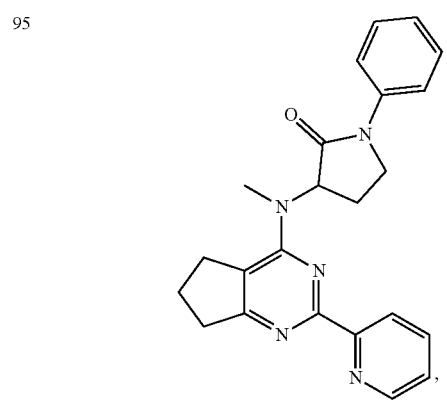 |
| 98 | 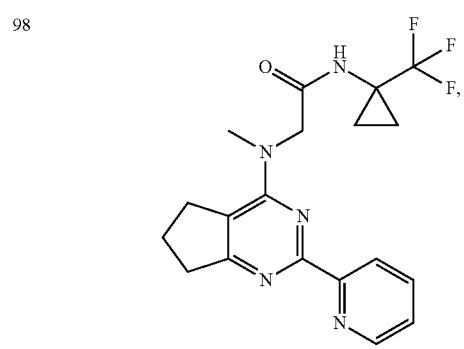 |
| Compound No. | Structure |
|---|---|
| 99 | 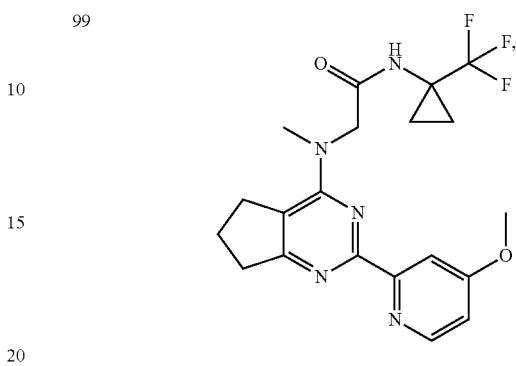 |
| 100 | 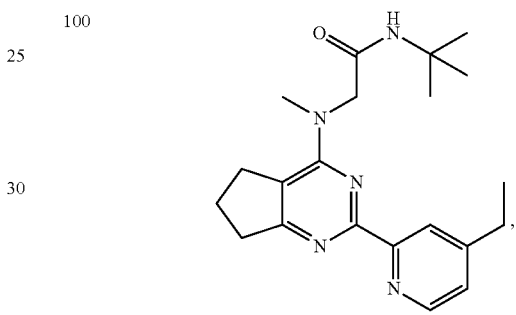 |
| 101 | 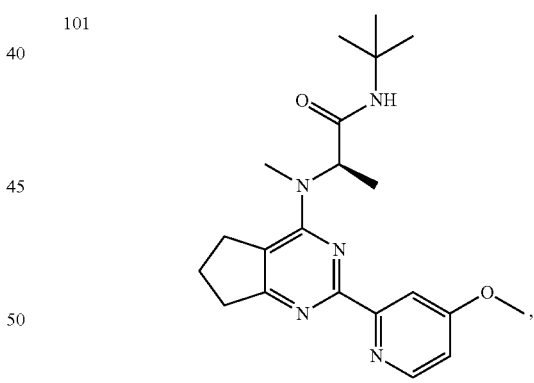 |
| 102 | 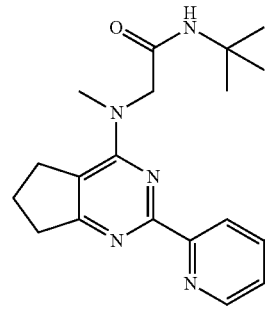 |

| Compound No. | Structure |
|---|---|
| 103 | 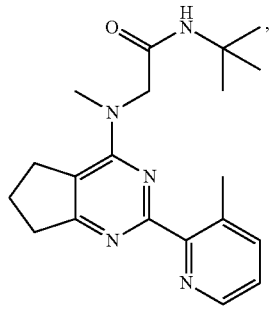 [SMILES: Cc1cccnc1-c1nc2c(c(N(C)CC(=O)NC(C)(C)C)n1)CCC2] |
| 104 | 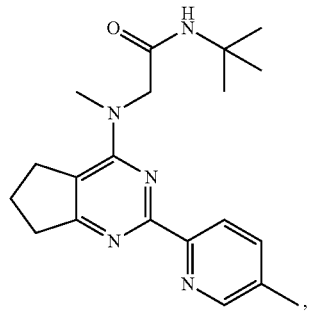 [SMILES: Cc1ccc(-c2nc3c(c(N(C)CC(=O)NC(C)(C)C)n2)CCC3)nc1] |
| 105 | 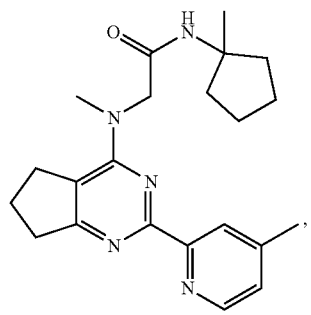 [SMILES: Cc1ccnc(-c2nc3c(c(N(C)CC(=O)NC4(C)CCCC4)n2)CCC3)c1] |
| 106 | 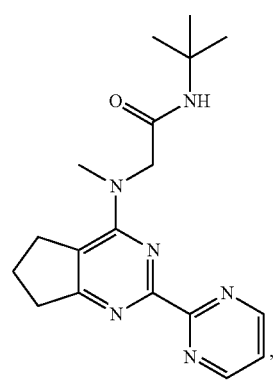 [SMILES: CN(CC(=O)NC(C)(C)C)c1nc(-c2ncccn2)nc2c1CCC2] |
| Compound No. | Structure |
|---|---|
| 107 | 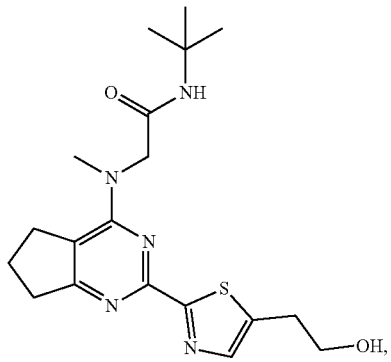 [SMILES: CN(CC(=O)NC(C)(C)C)c1nc(-c2ncc(CCO)s2)nc2c1CCC2] |
| 108 | 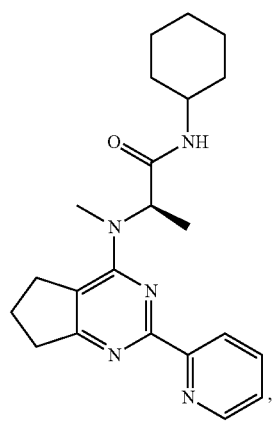 [SMILES: C[C@H](C(=O)NC1CCCCC1)N(C)c1nc(-c2ccccn2)nc2c1CCC2] |
| 109 | 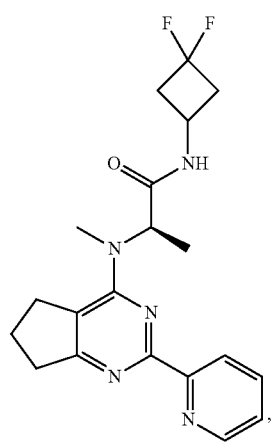 [SMILES: C[C@H](C(=O)NC1CC(F)(F)C1)N(C)c1nc(-c2ccccn2)nc2c1CCC2] |

| Compound No. | Structure |
|---|---|
| 110 | 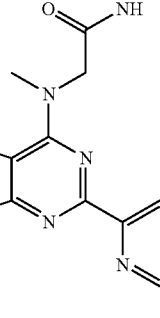 |
| 111 | 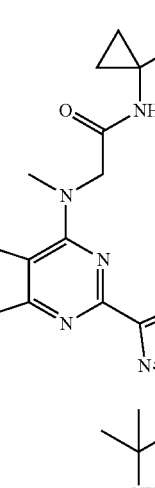 |
| 112 | 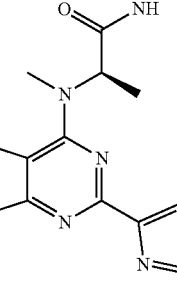 |
| 113 | 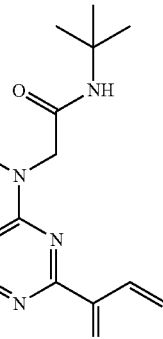 |
| Compound No. | Structure |
|---|---|
| 114 | 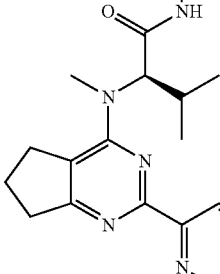 |
| 115 | 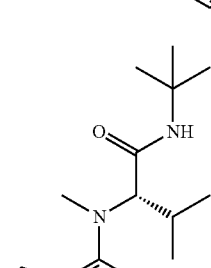 |
| 116 | 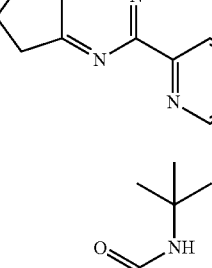 |
| 117 | 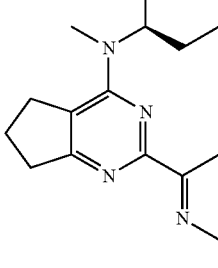 |

| Compound No. | Structure |
|---|---|
| 118 | 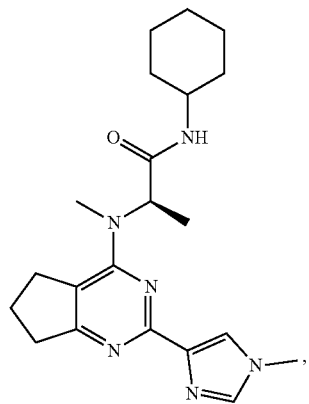 [SMILES: C[C@H](C(=O)NC1CCCCC1)N(C)c1nc(-c2cn(C)cn2)nc2c1CCC2] |
| 119 | 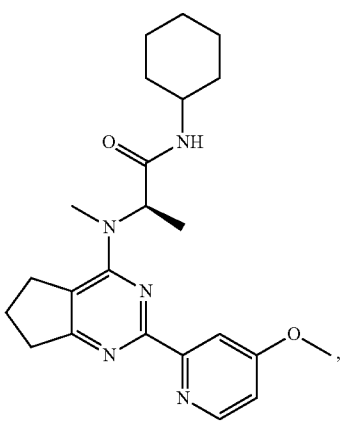 [SMILES: COc1ccnc(-c2nc3c(c(N(C)[C@H](C)C(=O)NC4CCCCC4)n2)CCC3)c1] |
| 120 | 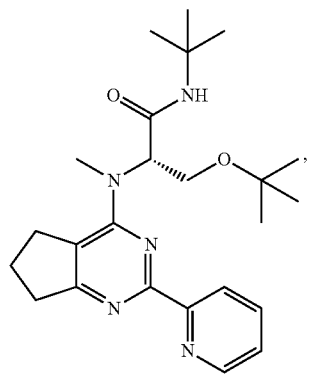 [SMILES: CN(c1nc(-c2ccccn2)nc2c1CCC2)[C@@H](COC(C)(C)C)C(=O)NC(C)(C)C] |
| Compound No. | Structure |
|---|---|
| 121 | 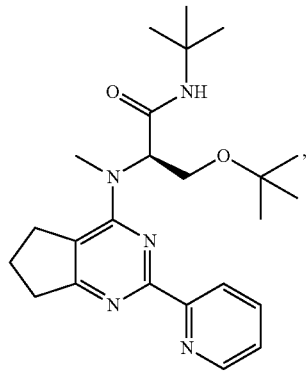 [SMILES: CN(c1nc(-c2ccccn2)nc2c1CCC2)[C@H](COC(C)(C)C)C(=O)NC(C)(C)C] |
| 122 | 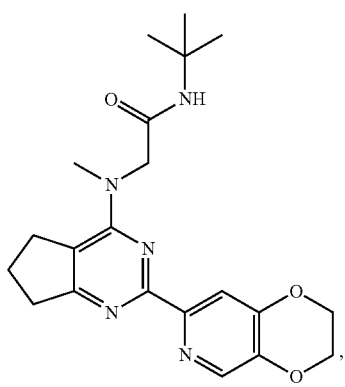 [SMILES: CN(CC(=O)NC(C)(C)C)c1nc(-c2cc3c(cn2)OCCO3)nc2c1CCC2] |
| 123 | 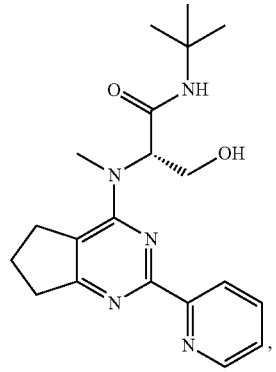 [SMILES: CN(c1nc(-c2ccccn2)nc2c1CCC2)[C@@H](CO)C(=O)NC(C)(C)C] |
| 124 | 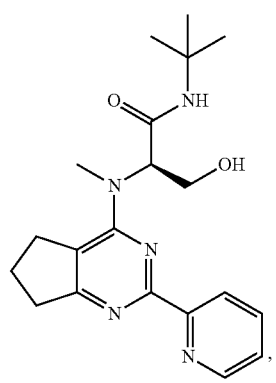 [SMILES: CN(c1nc(-c2ccccn2)nc2c1CCC2)[C@H](CO)C(=O)NC(C)(C)C] |

US 11,746,100 B2
| 1027 -continued | | 1028 -continued | |
|---|---|---|---|
| Compound No. | Structure | Compound No. | Structure |
| 125 | 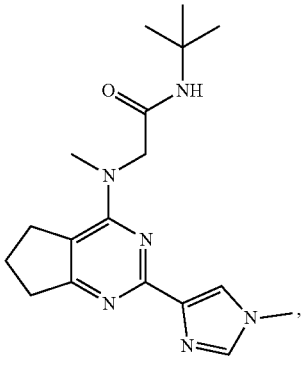 [SMILES: CN(CC(=O)NC(C)(C)C)c1nc(-c2cn(C)cn2)nc2c1CCC2] | 129 | 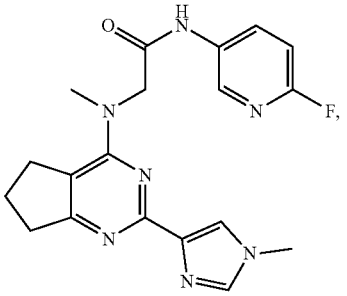 |
| 126 | 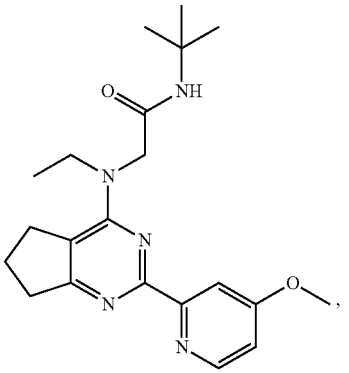 [SMILES: CCN(CC(=O)NC(C)(C)C)c1nc(-c2cc(OC)ccn2)nc2c1CCC2] | 130 | 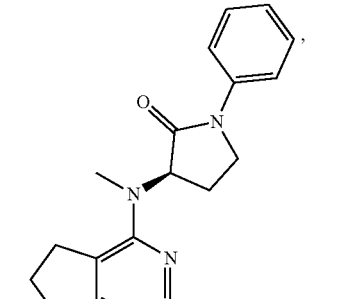 |
| 127 | 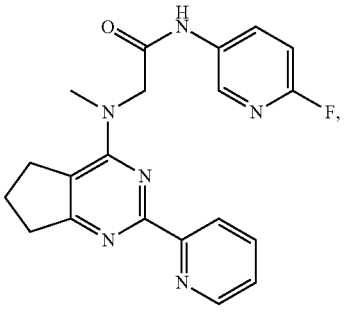 [SMILES: CN(CC(=O)Nc1ccc(F)nc1)c1nc(-c2ccccn2)nc2c1CCC2] | 131 | 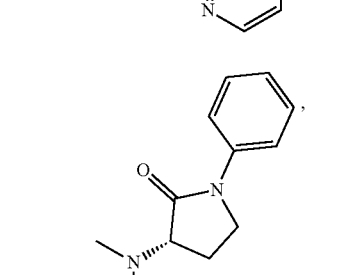 |
| 128 | 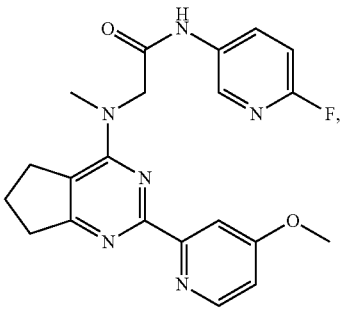 [SMILES: COc1ccnc(-c2nc3c(c(N(C)CC(=O)Nc4ccc(F)nc4)n2)CCC3)c1] | 132 | 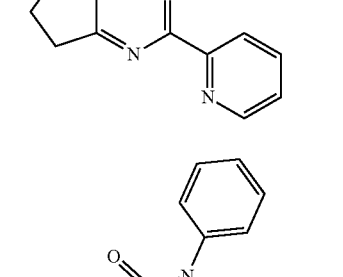 |

1029
-continued
| Compound No. | Structure |
|---|---|
| 133 | 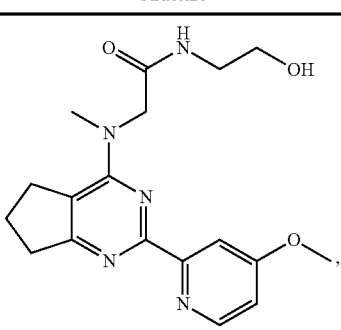 |
| 134 | 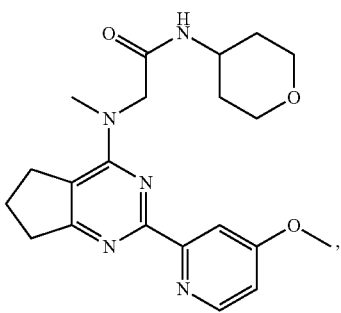 [SMILES: COc1ccnc(-c2nc3c(c(N(C)CC(=O)NC4CCOCC4)n2)CCC3)c1] |
| 135 | 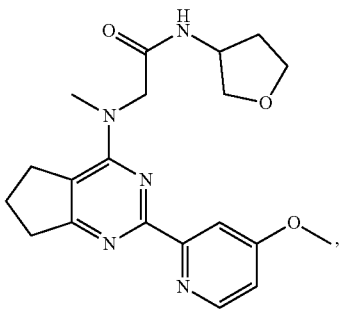 [SMILES: COc1ccnc(-c2nc3c(c(N(C)CC(=O)NC4CCOC4)n2)CCC3)c1] |
| 136 | 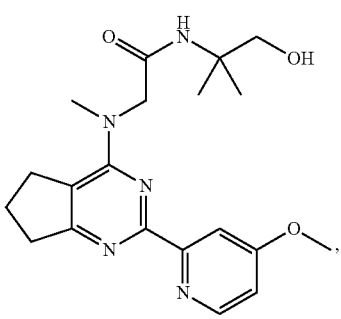 [SMILES: COc1ccnc(-c2nc3c(c(N(C)CC(=O)NC(C)(C)CO)n2)CCC3)c1] |
| 137 | 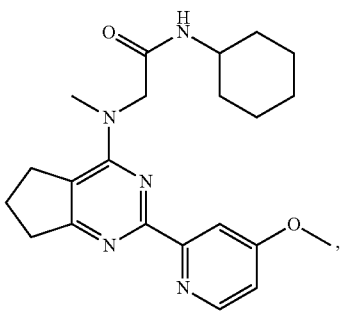 [SMILES: COc1ccnc(-c2nc3c(c(N(C)CC(=O)NC4CCCCC4)n2)CCC3)c1] |
1030
-continued
| Compound No. | Structure |
|---|---|
| 138 | 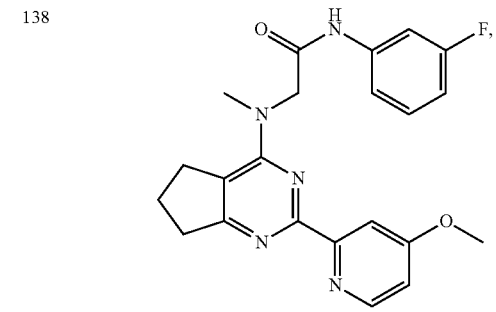 |
| 139 | 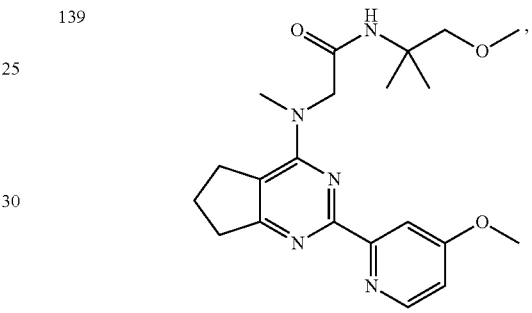 |
| 140 | 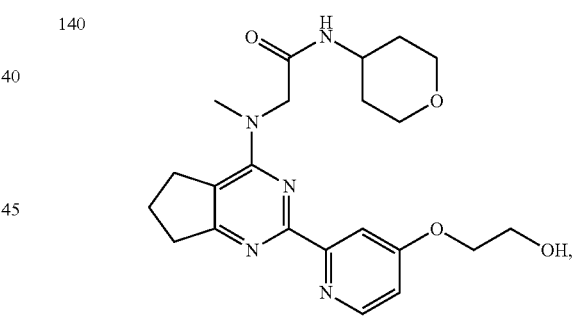 |
| 141 | 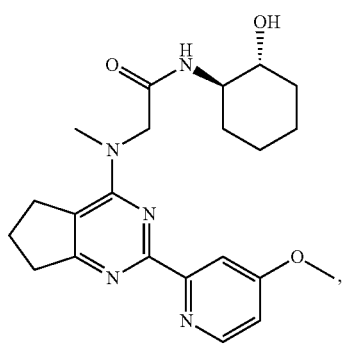 [SMILES: COc1ccnc(-c2nc3c(c(N(C)CC(=O)N[C@@H]4CCCC[C@H]4O)n2)CCC3)c1] |

| Compound No. | Structure |
|---|---|
| 142 | 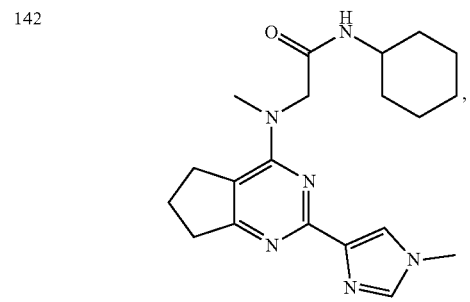 |
| 143 | 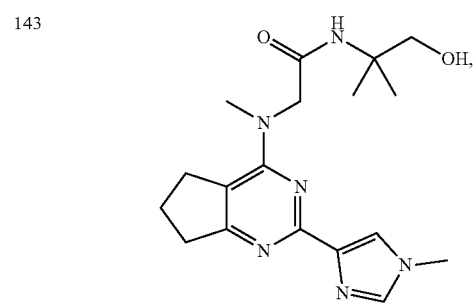 |
| 144 | 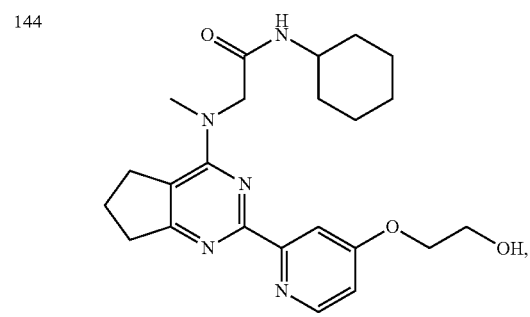 |
| 145 | 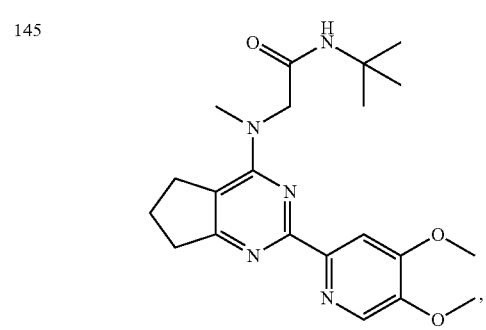 |
| 146 | 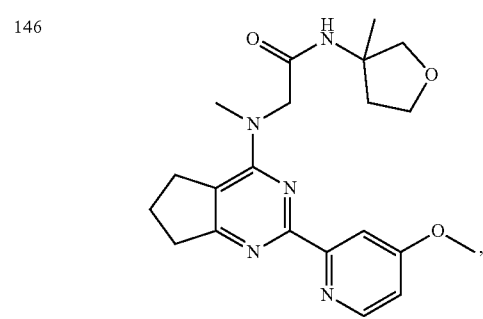 |
| Compound No. | Structure |
|---|---|
| 147 | 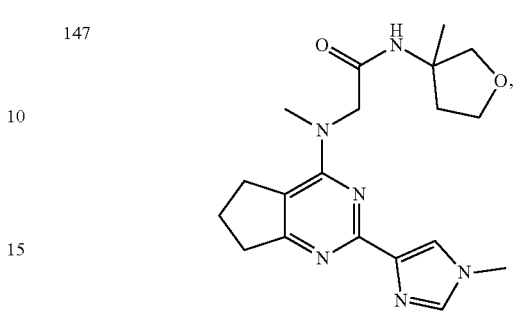 |
| 148 | 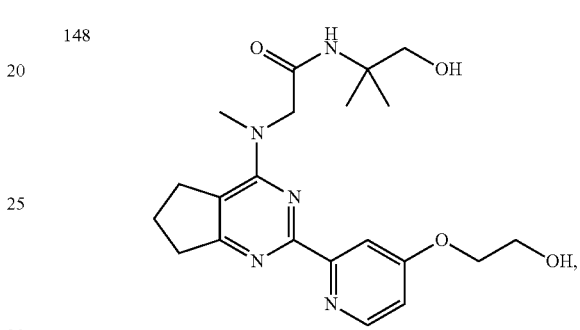 |
| 149 | 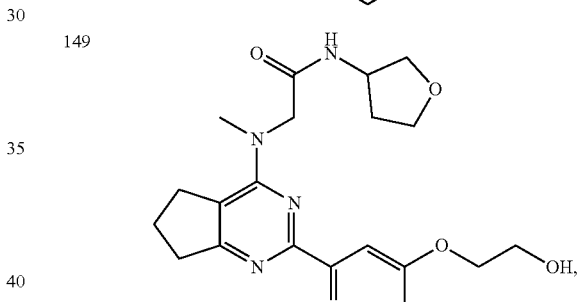 |
| 150 | 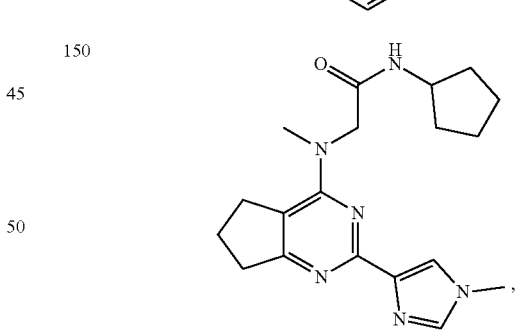 |
| 151 | 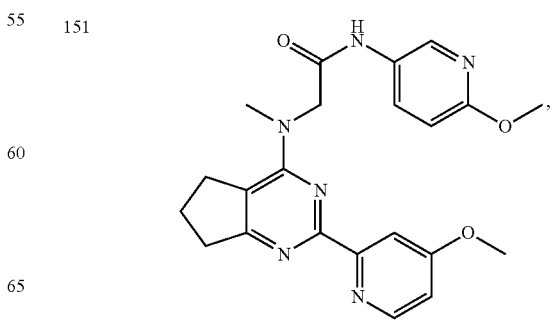 |

| Compound No. | Structure |
|---|---|
| 152 | 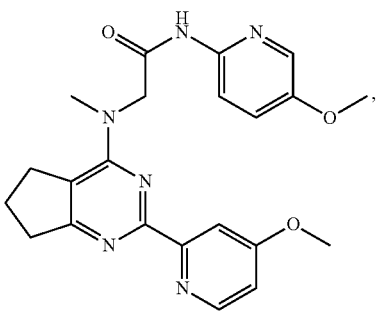 [SMILES: COc1ccc(NC(=O)CN(C)c2nc(-c3cc(OC)ccn3)nc3c2CCC3)nc1] |
| 153 | 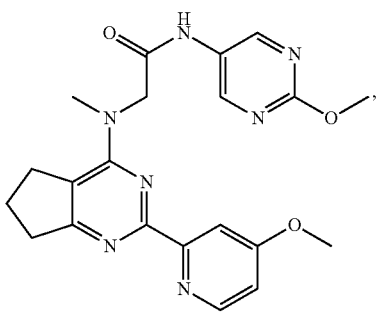 [SMILES: COc1ccnc(-c2nc3c(c(N(C)CC(=O)Nc4cnc(OC)nc4)n2)CCC3)c1] |
| 154 | 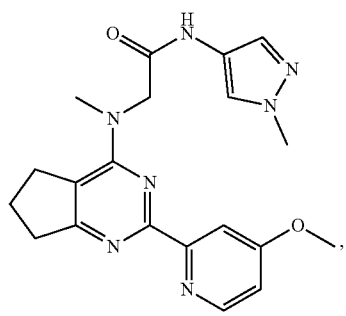 [SMILES: COc1ccnc(-c2nc3c(c(N(C)CC(=O)Nc4cnn(C)c4)n2)CCC3)c1] |
| 155 | 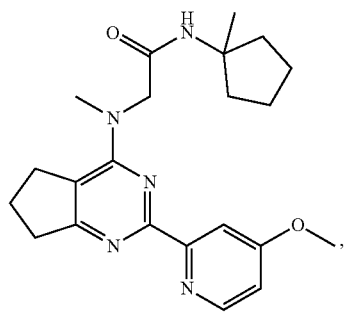 [SMILES: COc1ccnc(-c2nc3c(c(N(C)CC(=O)NC4(C)CCCC4)n2)CCC3)c1] |
| Compound No. | Structure |
|---|---|
| 156 | 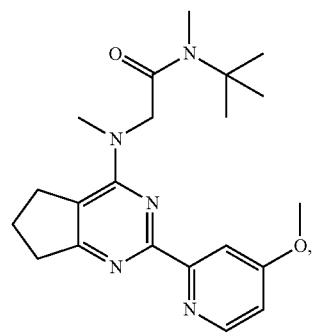 [SMILES: COc1ccnc(-c2nc3c(c(N(C)CC(=O)N(C)C(C)(C)C)n2)CCC3)c1] |
| 157 | 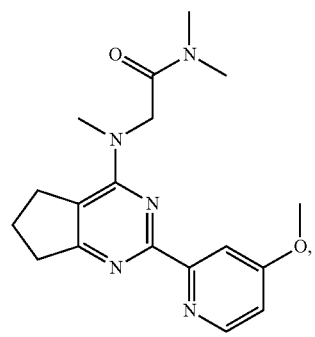 [SMILES: COc1ccnc(-c2nc3c(c(N(C)CC(=O)N(C)C)n2)CCC3)c1] |
| 158 | 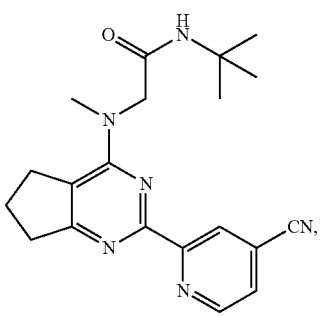 [SMILES: CN(CC(=O)NC(C)(C)C)c1nc(-c2cc(C#N)ccn2)nc2c1CCC2] |
| 159 | 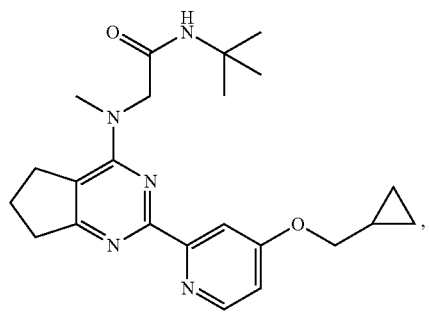 [SMILES: CN(CC(=O)NC(C)(C)C)c1nc(-c2cc(OCC3CC3)ccn2)nc2c1CCC2] |

| Compound No. | Structure |
|---|---|
| 160 | 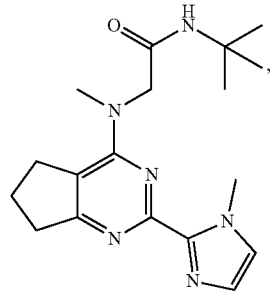 [SMILES: CN(CC(=O)NC(C)(C)C)c1nc(-c2nccn2C)nc2c1CCC2] |
| 161 | 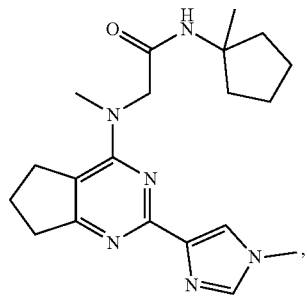 [SMILES: CN(CC(=O)NC1(C)CCCC1)c1nc(-c2cn(C)cn2)nc2c1CCC2] |
| 162 | 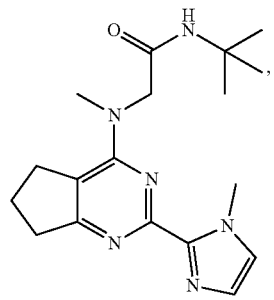 [SMILES: CN(CC(=O)NC(C)(C)C)c1nc(-c2nccn2C)nc2c1CCC2] |
| 163 | 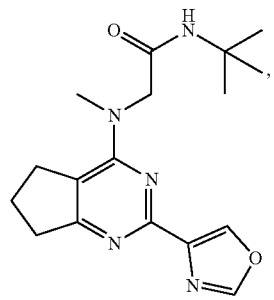 [SMILES: CN(CC(=O)NC(C)(C)C)c1nc(-c2cocn2)nc2c1CCC2] |
| 164 | 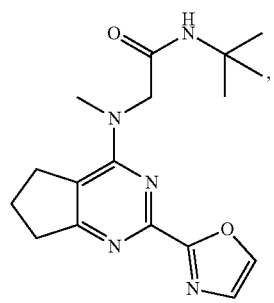 [SMILES: CN(CC(=O)NC(C)(C)C)c1nc(-c2ncco2)nc2c1CCC2] |
| Compound No. | Structure |
|---|---|
| 165 | 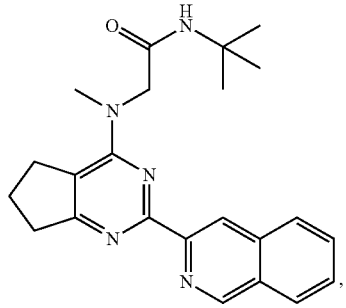 [SMILES: CN(CC(=O)NC(C)(C)C)c1nc(-c2cc3ccccc3cn2)nc2c1CCC2] |
| 166 | 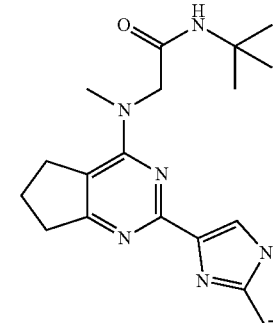 |
| 167 | 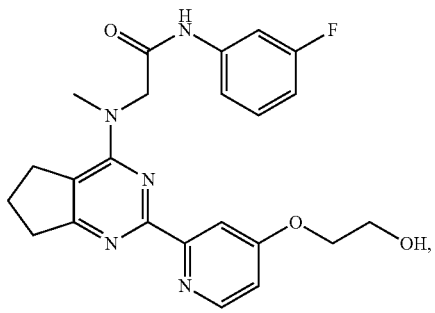 [SMILES: CN(CC(=O)Nc1cccc(F)c1)c1nc(-c2cc(OCCO)ccn2)nc2c1CCC2] |
| 168 | 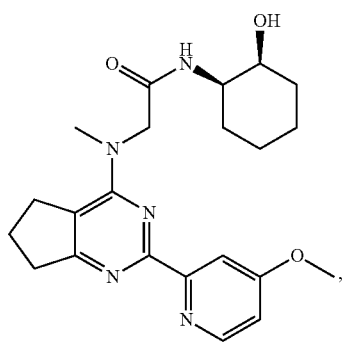 [SMILES: COc1ccnc(-c2nc3c(c(N(C)CC(=O)N[C@@H]4CCCC[C@@H]4O)n2)CCC3)c1] |

| Compound No. | Structure |
|---|---|
| 169 | 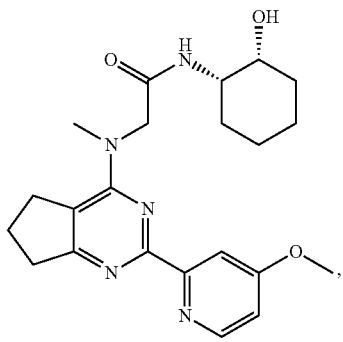 [SMILES: COc1ccnc(-c2nc3c(c(N(C)CC(=O)N[C@H]4CCCC[C@H]4O)n2)CCC3)c1] |
| 170 | 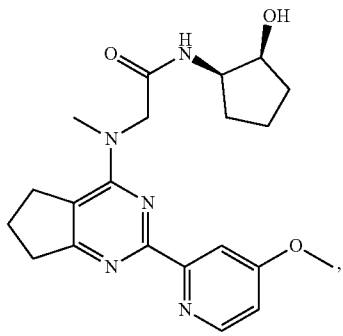 [SMILES: COc1ccnc(-c2nc3c(c(N(C)CC(=O)N[C@@H]4CCC[C@@H]4O)n2)CCC3)c1] |
| 171 | 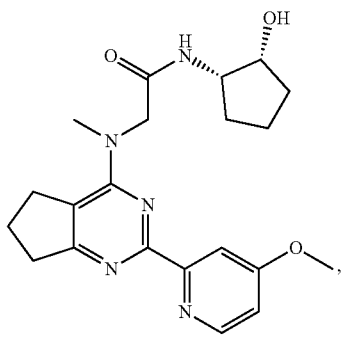 [SMILES: COc1ccnc(-c2nc3c(c(N(C)CC(=O)N[C@H]4CCC[C@H]4O)n2)CCC3)c1] |
| 172 | 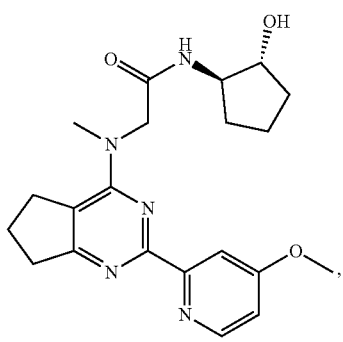 [SMILES: COc1ccnc(-c2nc3c(c(N(C)CC(=O)N[C@@H]4CCC[C@H]4O)n2)CCC3)c1] |
| Compound No. | Structure |
|---|---|
| 173 | 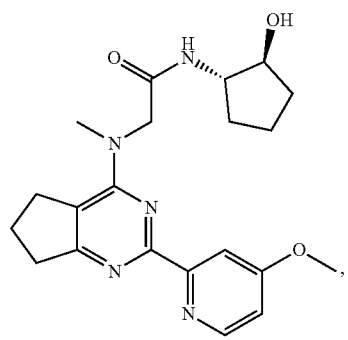 [SMILES: COc1ccnc(-c2nc3c(c(N(C)CC(=O)N[C@H]4CCC[C@@H]4O)n2)CCC3)c1] |
| 174 | 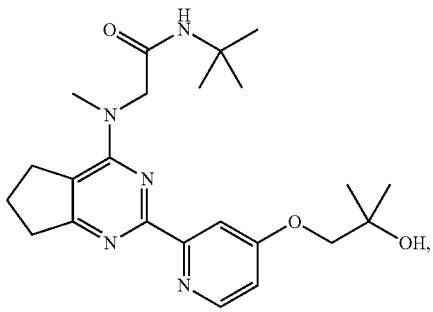 [SMILES: CN(CC(=O)NC(C)(C)C)c1nc(-c2cc(OCC(C)(C)O)ccn2)nc2c1CCC2] |
| 175 | 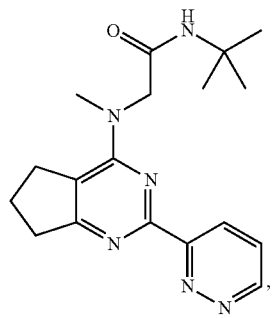 [SMILES: CN(CC(=O)NC(C)(C)C)c1nc(-c2cccnn2)nc2c1CCC2] |
| 176 | 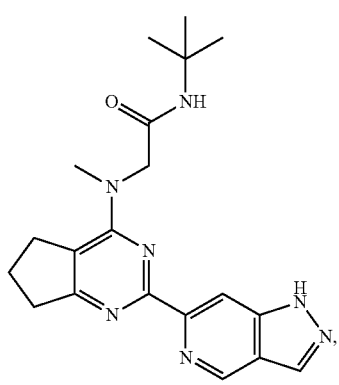 [SMILES: CN(CC(=O)NC(C)(C)C)c1nc(-c2cc3[nH]ncc3cn2)nc2c1CCC2] |

1039-continued
| Compound No. | Structure |
|---|---|
| 177 | 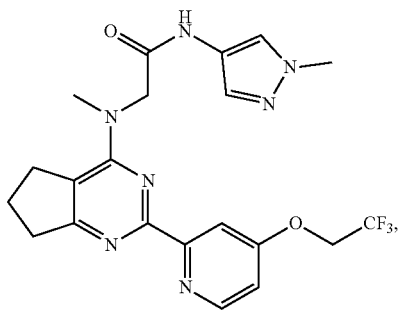 [SMILES: CN(CC(=O)Nc1cnn(C)c1)c1nc(-c2cc(OCC(F)(F)F)ccn2)nc2c1CCC2] |
| 178 | 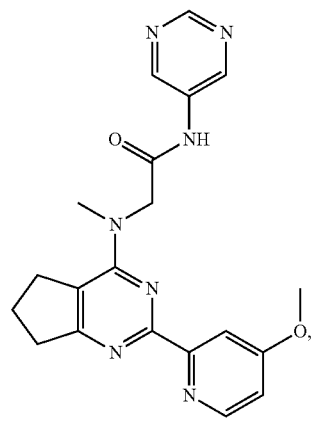 [SMILES: COc1ccnc(-c2nc3c(c(N(C)CC(=O)Nc4cncnc4)n2)CCC3)c1] |
| 179 | 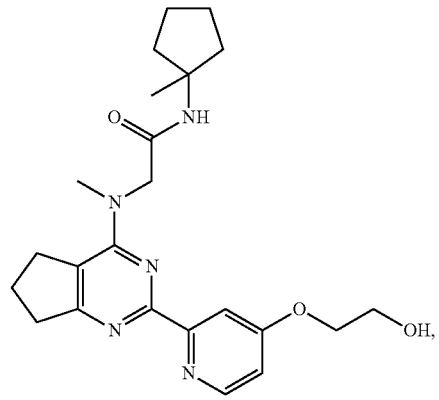 [SMILES: CN(CC(=O)NC1(C)CCCC1)c1nc(-c2cc(OCCO)ccn2)nc2c1CCC2] |
| 180 | 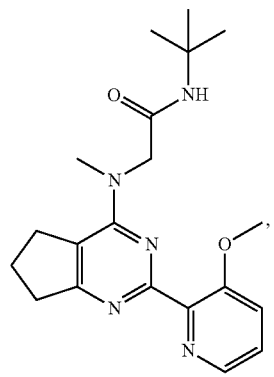 [SMILES: COc1cccnc1-c1nc2c(c(N(C)CC(=O)NC(C)(C)C)n1)CCC2] |
1040-continued
| Compound No. | Structure |
|---|---|
| 181 | 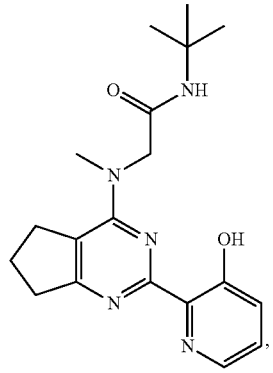 [SMILES: CN(CC(=O)NC(C)(C)C)c1nc(-c2ncccc2O)nc2c1CCC2] |
| 182 | 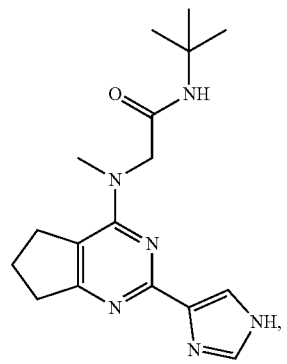 [SMILES: CN(CC(=O)NC(C)(C)C)c1nc(-c2c[nH]cn2)nc2c1CCC2] |
| 183 | 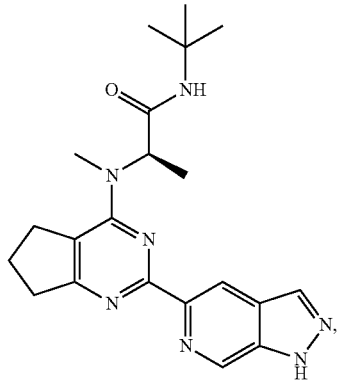 [SMILES: C[C@H](C(=O)NC(C)(C)C)N(C)c1nc(-c2cc3cn[nH]c3cn2)nc2c1CCC2] |
| 184 | 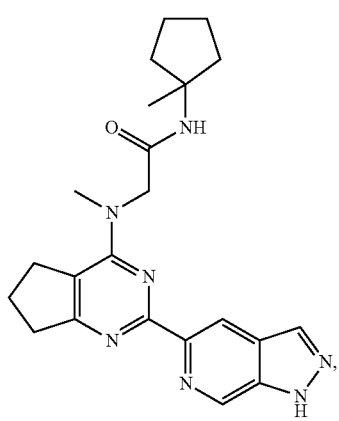 [SMILES: CN(CC(=O)NC1(C)CCCC1)c1nc(-c2cc3cn[nH]c3cn2)nc2c1CCC2] |

TABLE -continued
| Compound No. | Structure |
|---|---|
| 185 | 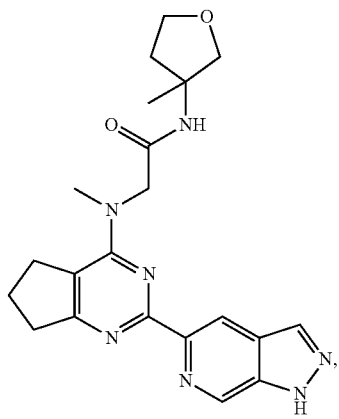 [SMILES: CN(CC(=O)NC1(C)CCOC1)c1nc(-c2cc3cn[nH]c3cn2)nc2c1CCC2] |
| 186 | 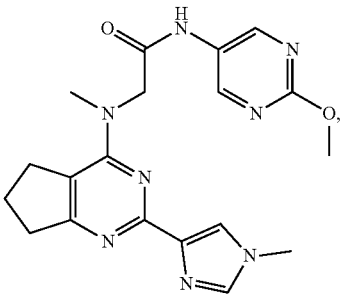 [SMILES: COc1ncc(NC(=O)CN(C)c2nc(-c3cn(C)cn3)nc3c2CCC3)cn1] |
| 187 | 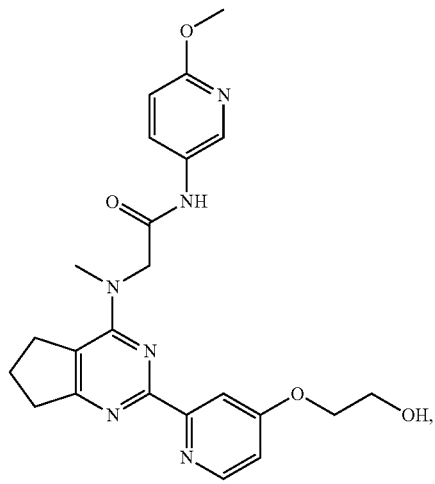 [SMILES: COc1ccc(NC(=O)CN(C)c2nc(-c3cc(OCCO)ccn3)nc3c2CCC3)cn1] |
| 189 | 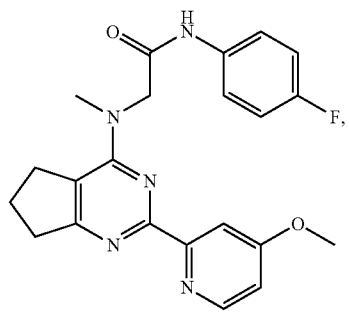 [SMILES: COc1ccnc(-c2nc3c(c(N(C)CC(=O)Nc4ccc(F)cc4)n2)CCC3)c1] |
| 190 | 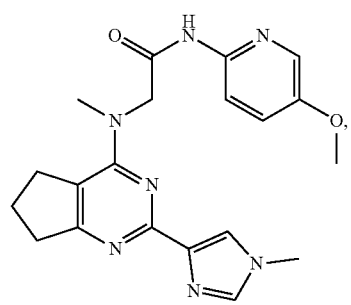 [SMILES: COc1ccc(NC(=O)CN(C)c2nc(-c3cn(C)cn3)nc3c2CCC3)nc1] |
| 191 | 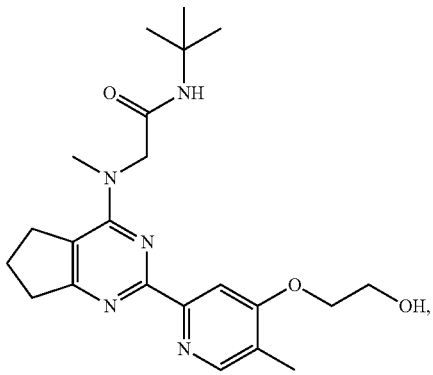 [SMILES: Cc1cnc(-c2nc3c(c(N(C)CC(=O)NC(C)(C)C)n2)CCC3)cc1OCCO] |
| 192 | 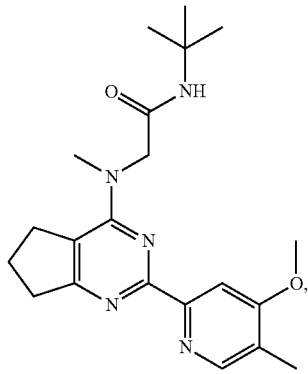 [SMILES: COc1cc(-c2nc3c(c(N(C)CC(=O)NC(C)(C)C)n2)CCC3)ncc1C] |
| 193 | 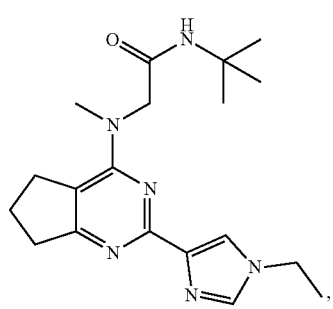 [SMILES: CCn1cnc(-c2nc3c(c(N(C)CC(=O)NC(C)(C)C)n2)CCC3)c1] |

-continued

| Compound No. | Structure |
|---|---|
| 194 | 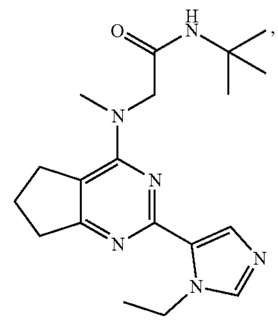 [SMILES: CCn1cncc1-c1nc2c(c(N(C)CC(=O)NC(C)(C)C)n1)CCC2] |
| 195 | 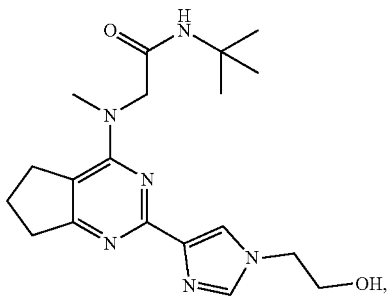 [SMILES: CN(CC(=O)NC(C)(C)C)c1nc(-c2cn(CCO)cn2)nc2c1CCC2] |
| 196 | 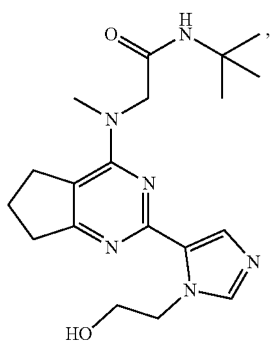 [SMILES: CN(CC(=O)NC(C)(C)C)c1nc(-c2cncn2CCO)nc2c1CCC2] |
| 197 | 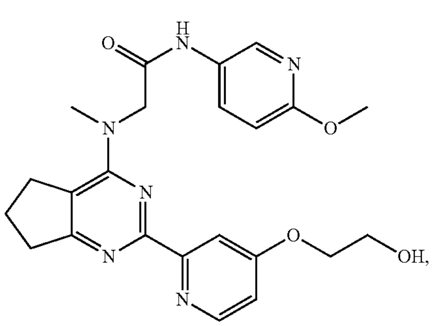 |

-continued

| Compound No. | Structure |
|---|---|
| 198 | 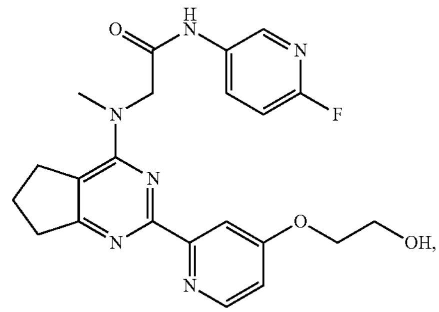 [SMILES: CN(CC(=O)Nc1ccc(F)nc1)c1nc(-c2cc(OCCO)ccn2)nc2c1CCC2] |
| 199 | 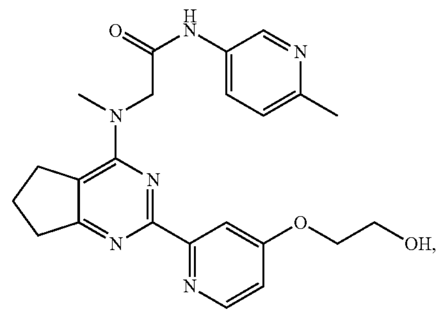 |
| 200 | 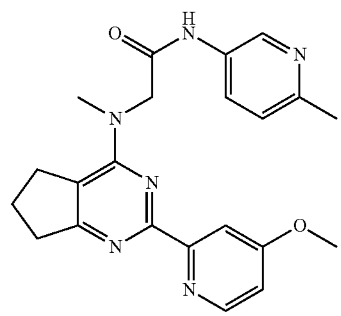 |
| 201 | 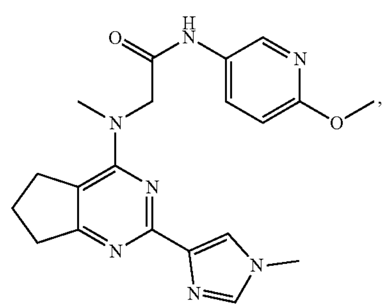 [SMILES: COc1ccc(NC(=O)CN(C)c2nc(-c3cn(C)cn3)nc3c2CCC3)cn1] |
| 202 | 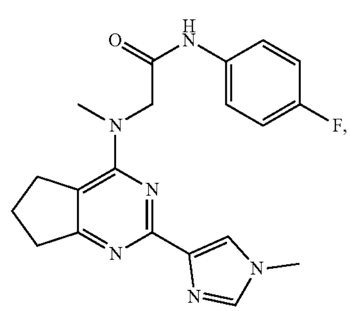 [SMILES: CN(CC(=O)Nc1ccc(F)cc1)c1nc(-c2cn(C)cn2)nc2c1CCC2] |

| Compound No. | Structure |
|---|---|
| 204 | 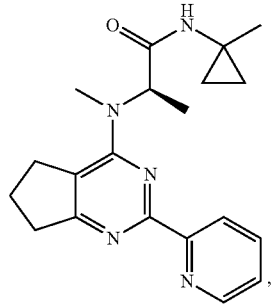 [SMILES: C[C@H](C(=O)NC1(C)CC1)N(C)c1nc(-c2ccccn2)nc2c1CCC2] |
| 205 | 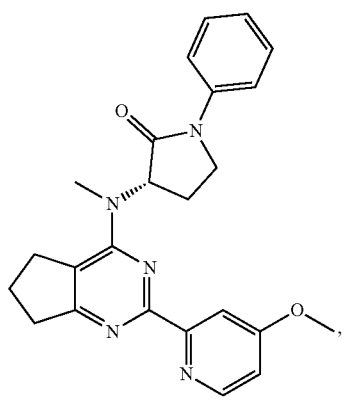 [SMILES: COc1ccnc(-c2nc3c(c(N(C)[C@H]4CCN(c5ccccc5)C4=O)n2)CCC3)c1] |
| 206 | 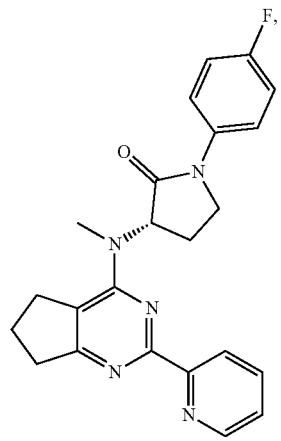 [SMILES: CN(c1nc(-c2ccccn2)nc2c1CCC2)[C@H]1CCN(c2ccc(F)cc2)C1=O] |
| 207 | 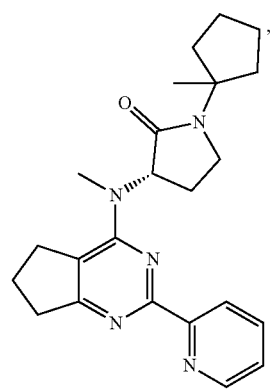 [SMILES: CN(c1nc(-c2ccccn2)nc2c1CCC2)[C@H]1CCN(C2(C)CCCC2)C1=O] |
| Compound No. | Structure |
|---|---|
| 208 | 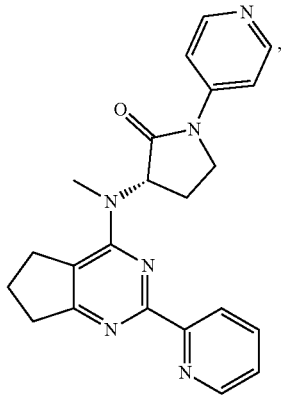 [SMILES: CN(c1nc(-c2ccccn2)nc2c1CCC2)[C@H]1CCN(c2ccncc2)C1=O] |
| 209 | 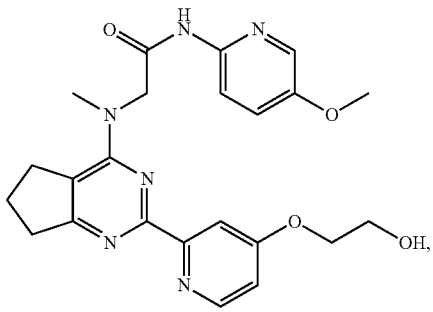 |
| 210 | 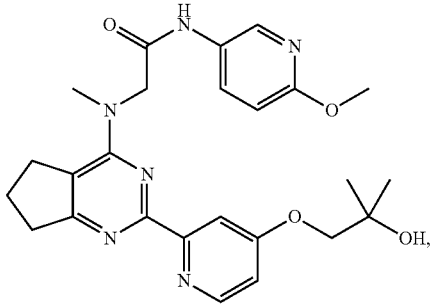 |
| 211 | 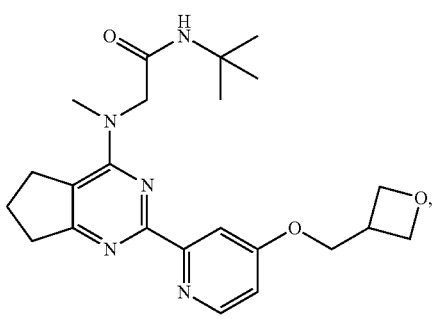 [SMILES: CN(CC(=O)NC(C)(C)C)c1nc(-c2cc(OCC3COC3)ccn2)nc2c1CCC2] |

| Compound No. | Structure |
|---|---|
| 212 | 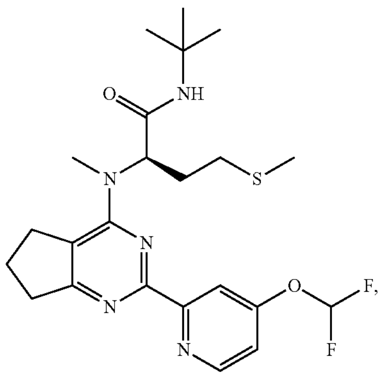 [SMILES: CSCC[C@H](C(=O)NC(C)(C)C)N(C)c1nc(-c2cc(OC(F)F)ccn2)nc2c1CCC2] |
| 213 | 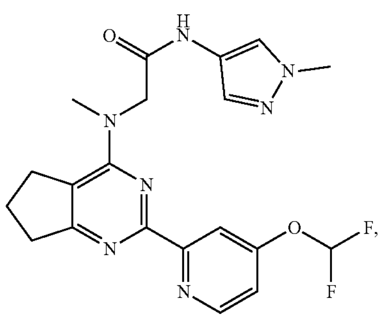 [SMILES: CN(CC(=O)Nc1cnn(C)c1)c1nc(-c2cc(OC(F)F)ccn2)nc2c1CCC2] |
| 214 | 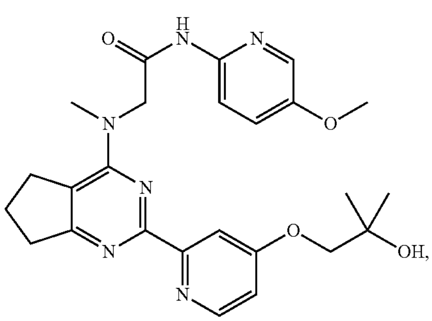 [SMILES: COc1ccc(NC(=O)CN(C)c2nc(-c3cc(OCC(C)(C)O)ccn3)nc3c2CCC3)nc1] |
| 215 | 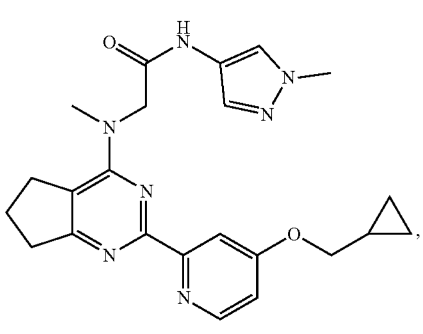 [SMILES: CN(CC(=O)Nc1cnn(C)c1)c1nc(-c2cc(OCC3CC3)ccn2)nc2c1CCC2] |

| Compound No. | Structure |
|---|---|
| 216 | 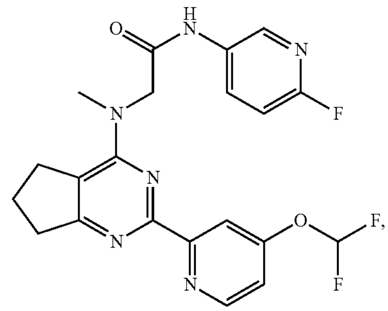 [SMILES: CN(CC(=O)Nc1ccc(F)nc1)c1nc(-c2cc(OC(F)F)ccn2)nc2c1CCC2] |
| 217 | 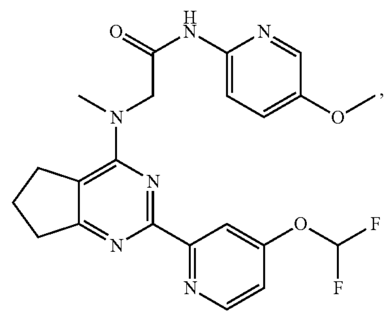 [SMILES: COc1ccc(NC(=O)CN(C)c2nc(-c3cc(OC(F)F)ccn3)nc3c2CCC3)nc1] |
| 218 | 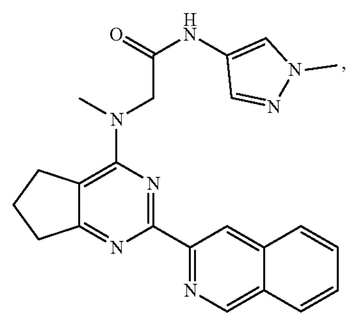 [SMILES: CN(CC(=O)Nc1cnn(C)c1)c1nc(-c2cc3ccccc3cn2)nc2c1CCC2] |
| 219 | 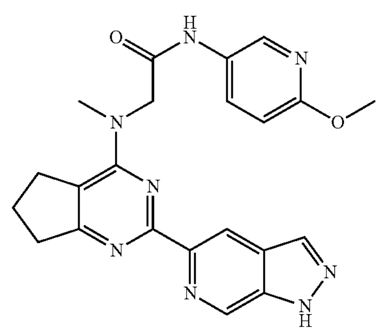 |
| 220 | 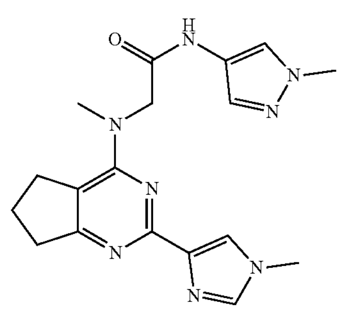 |

| Compound No. | Structure |
|---|---|
| 221 | 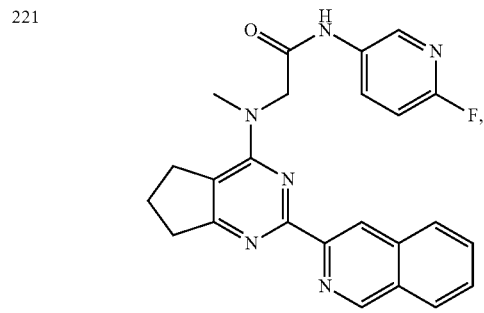 |
| 222 | 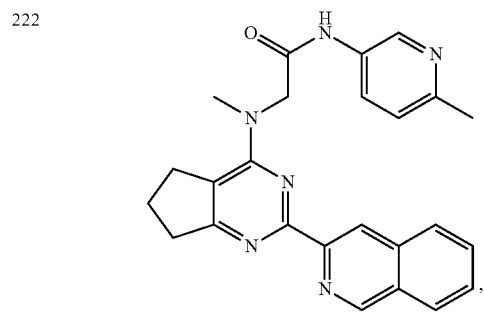 |
| 223 | 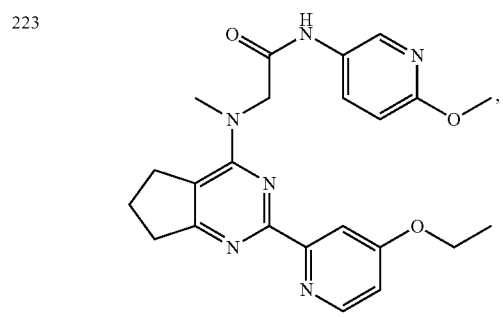 |
| 224 | 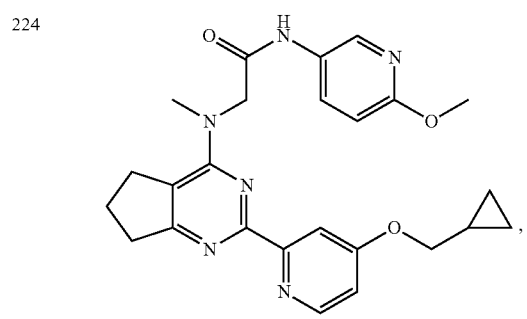 |
| Compound No. | Structure |
|---|---|
| 225 | 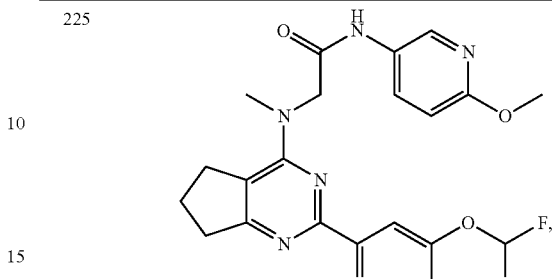 |
| 226 | 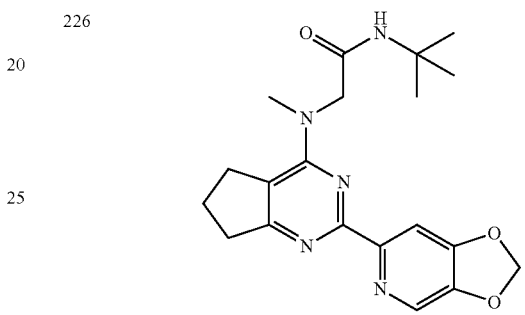 |
| 227 | 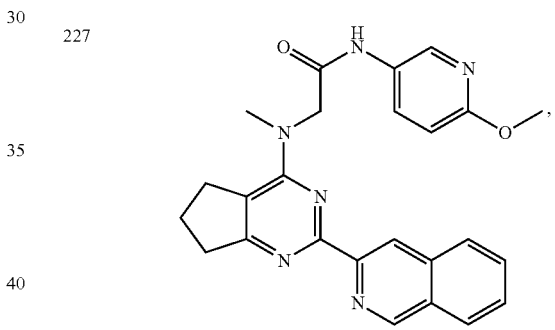 |
| 228 | 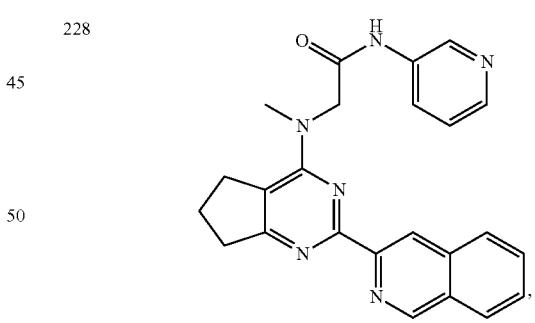 |
| 229 | 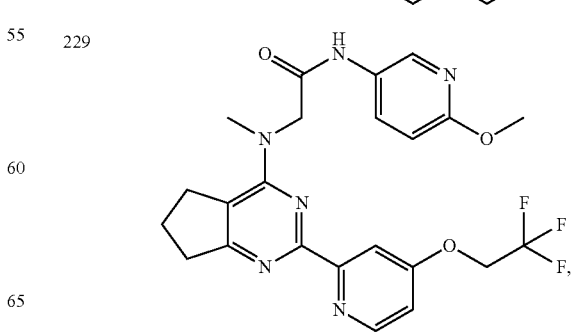 |

-continued

| Compound No. | Structure |
|---|---|
| 230 | (structure) |
| 231 | (structure) |
| 232 | (structure) |
| 233 | (structure) |

-continued

| Compound No. | Structure |
|---|---|
| 234 | (structure) |
| 235 | (structure) |
| 236 | (structure) |
| 237 | (structure) |
| 238 | (structure) |

-continued
| Compound No. | Structure |
|---|---|
| 239 | 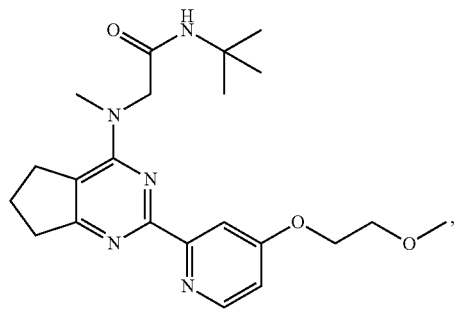 [SMILES: COCCOc1ccnc(-c2nc3c(c(N(C)CC(=O)NC(C)(C)C)n2)CCC3)c1] |
| 240 | 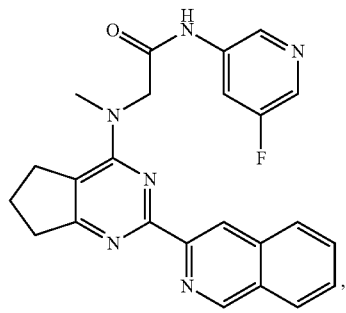 [SMILES: CN(CC(=O)Nc1cncc(F)c1)c1nc(-c2cc3ccccc3cn2)nc2c1CCC2] |
| 241 | 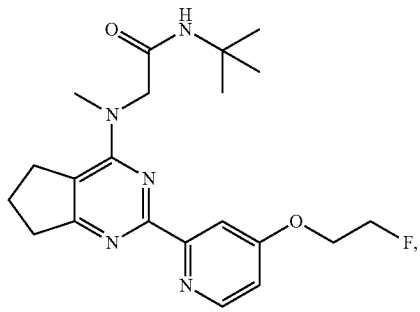 [SMILES: CN(CC(=O)NC(C)(C)C)c1nc(-c2cc(OCCF)ccn2)nc2c1CCC2] |
| 242 | 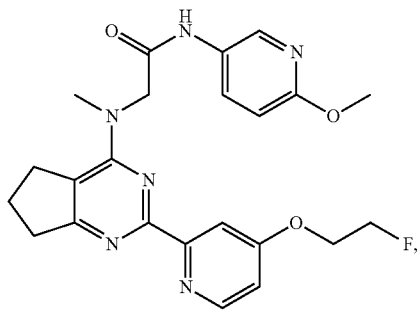 [SMILES: COc1ccc(NC(=O)CN(C)c2nc(-c3cc(OCCF)ccn3)nc3c2CCC3)cn1] |
-continued
| Compound No. | Structure |
|---|---|
| 243 | 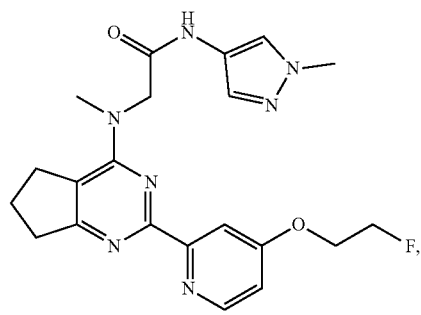 [SMILES: CN(CC(=O)Nc1cnn(C)c1)c1nc(-c2cc(OCCF)ccn2)nc2c1CCC2] |
| 244 | 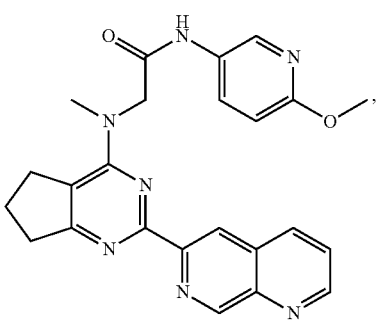 [SMILES: COc1ccc(NC(=O)CN(C)c2nc(-c3cc4cccnc4cn3)nc3c2CCC3)cn1] |
| 245 | 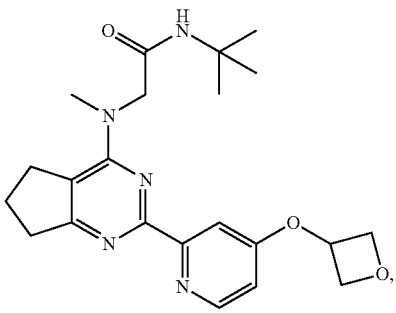 [SMILES: CN(CC(=O)NC(C)(C)C)c1nc(-c2cc(OC3COC3)ccn2)nc2c1CCC2] |
| 246 | 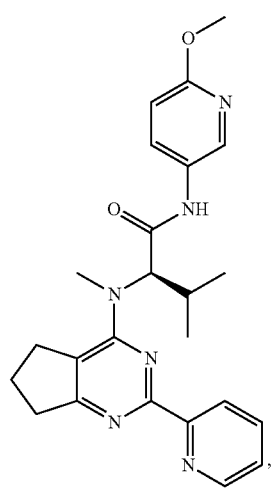 [SMILES: COc1ccc(NC(=O)[C@@H](C(C)C)N(C)c2nc(-c3ccccn3)nc3c2CCC3)cn1] |

1055
-continued
| Compound No. | Structure |
|---|---|
| 247 | 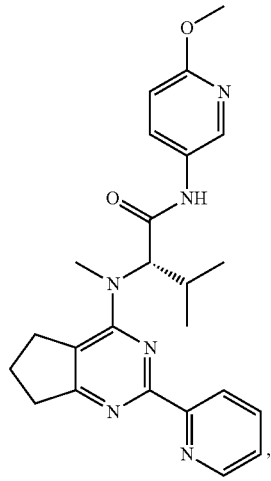 [SMILES: COc1ccc(NC(=O)[C@H](C(C)C)N(C)c2nc(-c3ccccn3)nc3c2CCC3)cn1] |
| 248 | 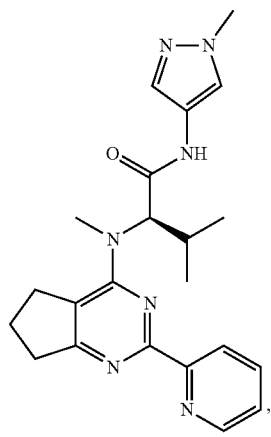 [SMILES: CC(C)[C@H](C(=O)Nc1cnn(C)c1)N(C)c1nc(-c2ccccn2)nc2c1CCC2] |
| 249 | 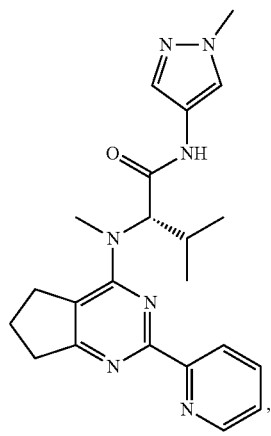 [SMILES: CC(C)[C@@H](C(=O)Nc1cnn(C)c1)N(C)c1nc(-c2ccccn2)nc2c1CCC2] |
1056
-continued
| Compound No. | Structure |
|---|---|
| 250 | 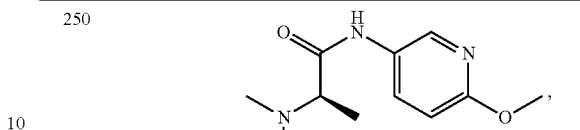 |
| 251 | 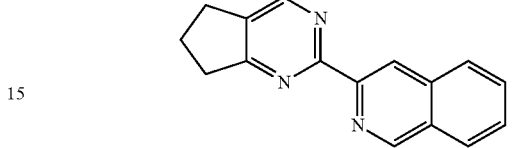 |
| 252 | 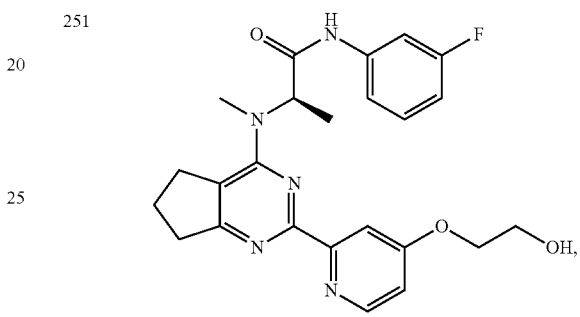 |
| 253 | 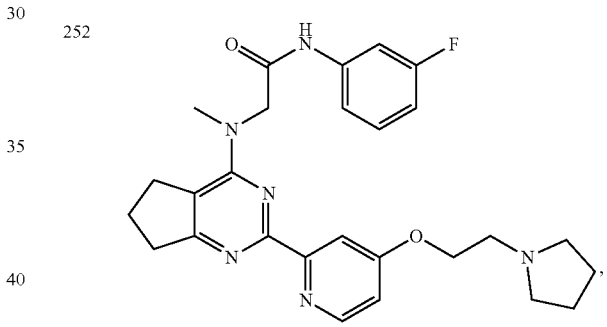 |
| 254 | 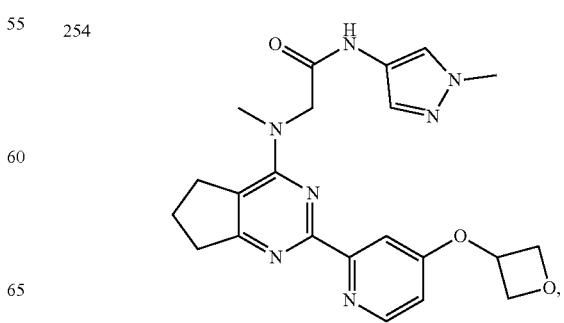 |

| Compound No. | Structure |
|---|---|
| 255 | 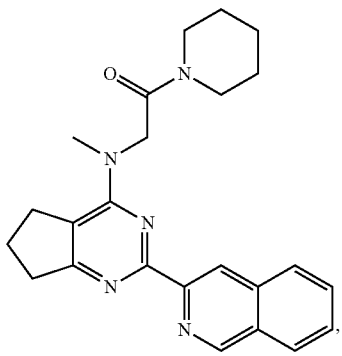 [SMILES: CN(CC(=O)N1CCCCC1)c1nc(-c2cc3ccccc3cn2)nc2c1CCC2] |
| 256 | 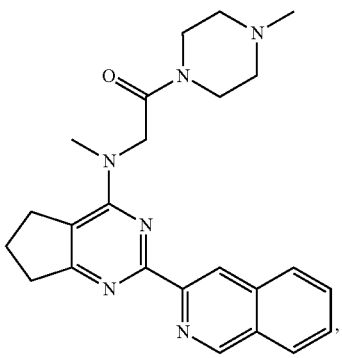 [SMILES: CN1CCN(C(=O)CN(C)c2nc(-c3cc4ccccc4cn3)nc3c2CCC3)CC1] |
| 257 | 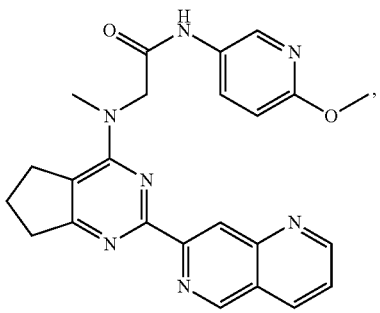 |
| 258 | 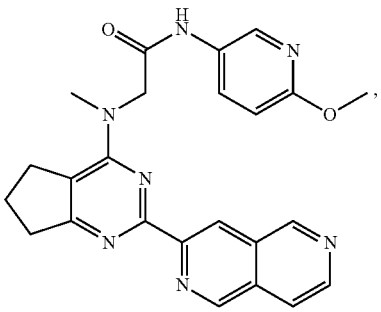 [SMILES: COc1ccc(NC(=O)CN(C)c2nc(-c3cc4cnccc4cn3)nc3c2CCC3)cn1] |
| Compound No. | Structure |
|---|---|
| 259 | 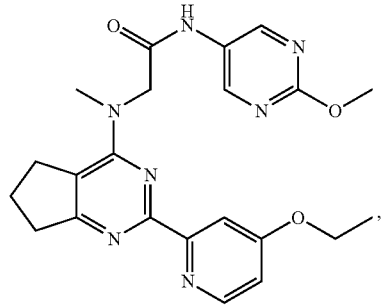 [SMILES: CCOc1ccnc(-c2nc3c(c(N(C)CC(=O)Nc4cnc(OC)nc4)n2)CCC3)c1] |
| 260 | 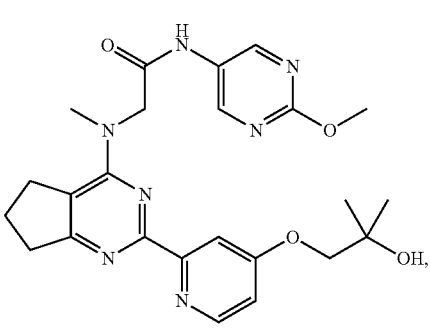 [SMILES: COc1ncc(NC(=O)CN(C)c2nc(-c3cc(OCC(C)(C)O)ccn3)nc3c2CCC3)cn1] |
| 261 | 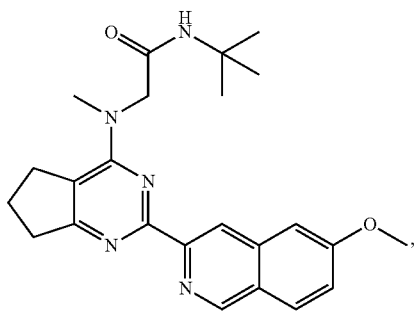 [SMILES: COc1ccc2cnc(-c3nc4c(c(N(C)CC(=O)NC(C)(C)C)n3)CCC4)cc2c1] |
| 262 | 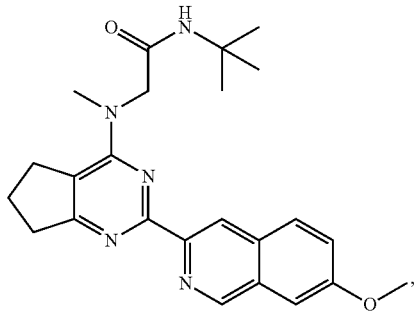 [SMILES: COc1ccc2cc(-c3nc4c(c(N(C)CC(=O)NC(C)(C)C)n3)CCC4)ncc2c1] |

US 11,746,100 B2
1059 -continued
| Compound No. | Structure |
|---|---|
| 263 | 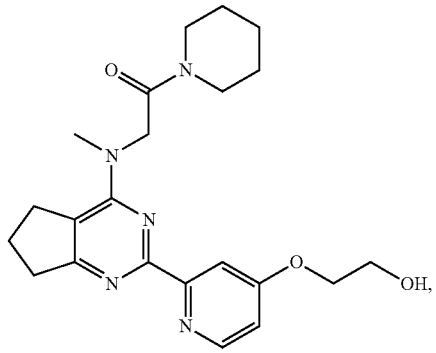 [SMILES: CN(CC(=O)N1CCCCC1)c1nc(-c2cc(OCCO)ccn2)nc2c1CCC2] |
| 264 | 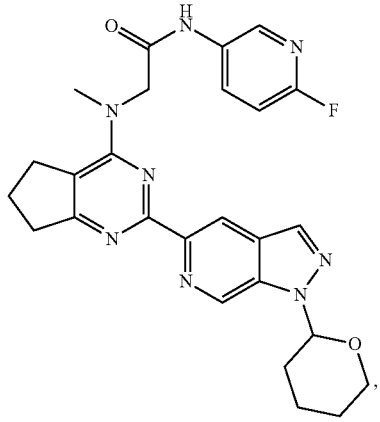 [SMILES: CN(CC(=O)Nc1ccc(F)nc1)c1nc(-c2cc3cnn(C4CCCCO4)c3cn2)nc2c1CCC2] |
| 265 | 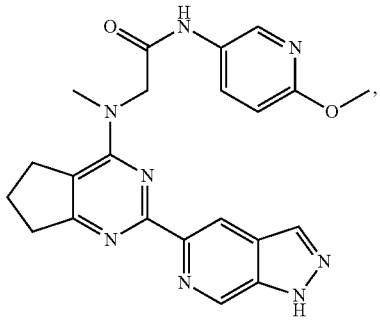 [SMILES: COc1ccc(NC(=O)CN(C)c2nc(-c3cc4cn[nH]c4cn3)nc3c2CCC3)cn1] |
| 266 | 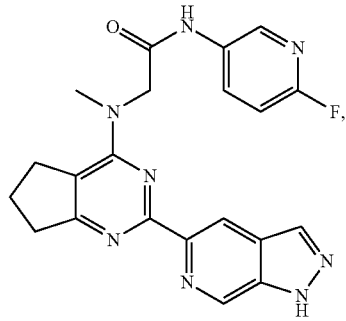 [SMILES: CN(CC(=O)Nc1ccc(F)nc1)c1nc(-c2cc3cn[nH]c3cn2)nc2c1CCC2] |
1060 -continued
| Compound No. | Structure |
|---|---|
| 267 | 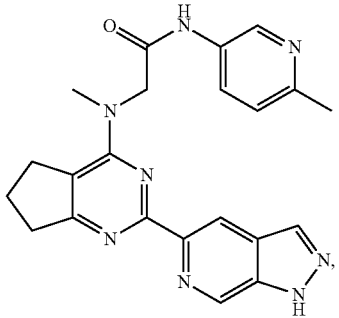 [SMILES: Cc1ccc(NC(=O)CN(C)c2nc(-c3cc4cn[nH]c4cn3)nc3c2CCC3)cn1] |
| 268 | 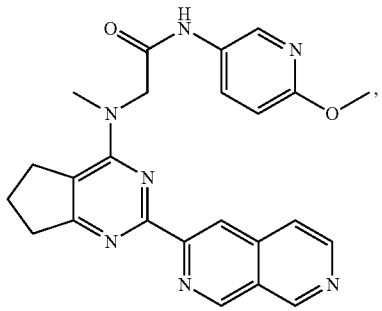 [SMILES: COc1ccc(NC(=O)CN(C)c2nc(-c3cc4ccncc4cn3)nc3c2CCC3)cn1] |
| 269 | 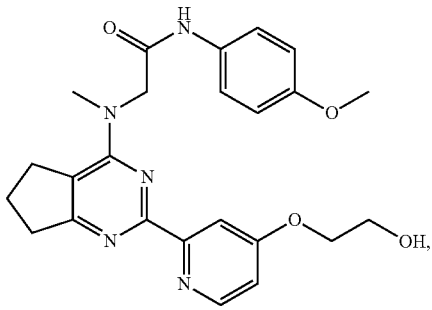 [SMILES: COc1ccc(NC(=O)CN(C)c2nc(-c3cc(OCCO)ccn3)nc3c2CCC3)cc1] |
| 270 | 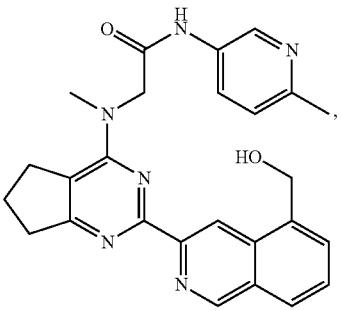 [SMILES: Cc1ccc(NC(=O)CN(C)c2nc(-c3cc4c(CO)cccc4cn3)nc3c2CCC3)cn1] |
| 271 | 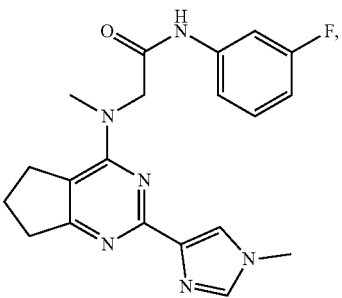 [SMILES: CN(CC(=O)Nc1cccc(F)c1)c1nc(-c2cn(C)cn2)nc2c1CCC2] |

| Compound No. | Structure |
|---|---|
| 272 | 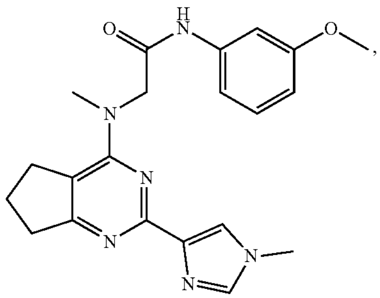 [SMILES: COc1cccc(NC(=O)CN(C)c2nc(-c3cn(C)cn3)nc3c2CCC3)c1] |
| 273 | 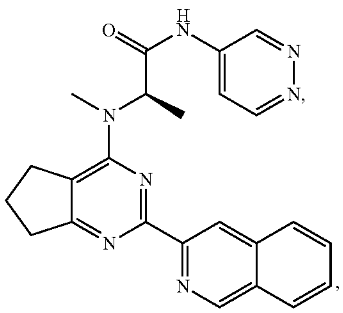 [SMILES: C[C@H](C(=O)Nc1ccnnc1)N(C)c1nc(-c2cc3ccccc3cn2)nc2c1CCC2] |
| 274 | 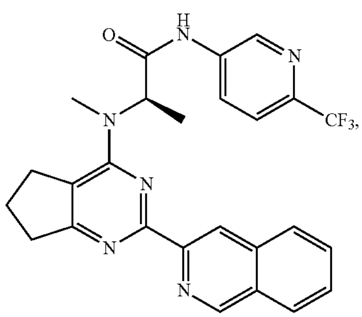 [SMILES: C[C@H](C(=O)Nc1ccc(C(F)(F)F)nc1)N(C)c1nc(-c2cc3ccccc3cn2)nc2c1CCC2] |
| 275 | 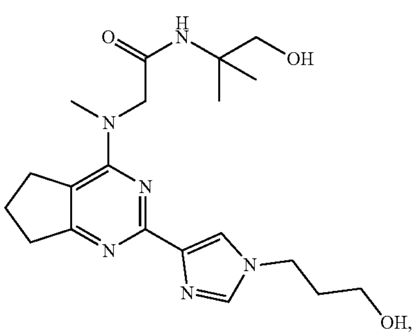 [SMILES: CN(CC(=O)NC(C)(C)CO)c1nc(-c2cn(CCCO)cn2)nc2c1CCC2] |
| 276 | 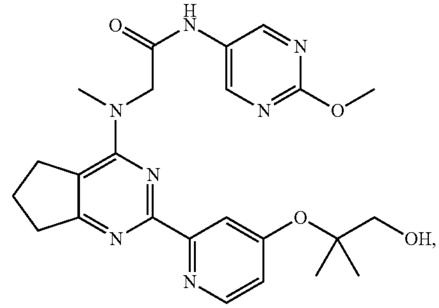 [SMILES: COc1ncc(NC(=O)CN(C)c2nc(-c3cc(OC(C)(C)CO)ccn3)nc3c2CCC3)cn1] |
| 277 | 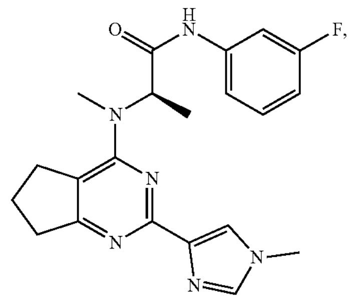 [SMILES: C[C@H](C(=O)Nc1cccc(F)c1)N(C)c1nc(-c2cn(C)cn2)nc2c1CCC2] |
| 278 | 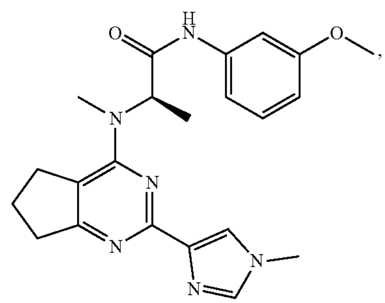 [SMILES: COc1cccc(NC(=O)[C@@H](C)N(C)c2nc(-c3cn(C)cn3)nc3c2CCC3)c1] |
| 279 | 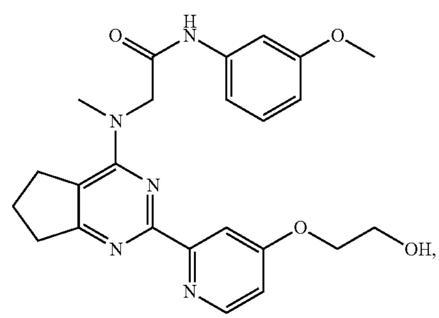 [SMILES: COc1cccc(NC(=O)CN(C)c2nc(-c3cc(OCCO)ccn3)nc3c2CCC3)c1] |
| 280 | 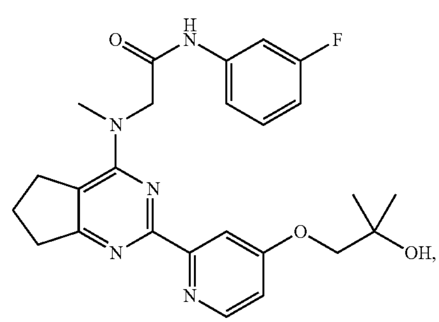 [SMILES: CN(CC(=O)Nc1cccc(F)c1)c1nc(-c2cc(OCC(C)(C)O)ccn2)nc2c1CCC2] |

| Compound No. | Structure |
|---|---|
| 281 | 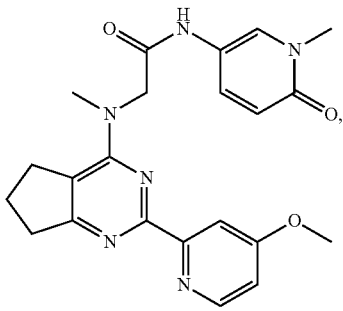 [SMILES: COc1ccnc(-c2nc3c(c(N(C)CC(=O)Nc4ccc(=O)n(C)c4)n2)CCC3)c1] |
| 282 | 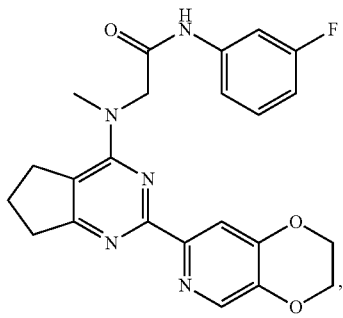 [SMILES: CN(CC(=O)Nc1cccc(F)c1)c1nc(-c2cc3c(cn2)OCCO3)nc2c1CCC2] |
| 283 | 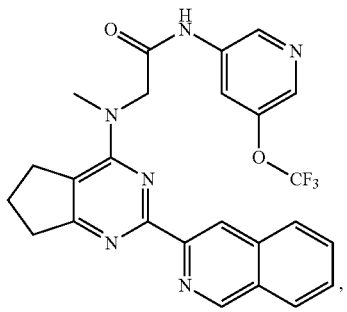 [SMILES: CN(CC(=O)Nc1cncc(OC(F)(F)F)c1)c1nc(-c2cc3ccccc3cn2)nc2c1CCC2] |
| 284 | 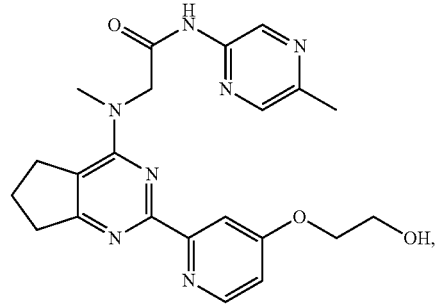 [SMILES: Cc1cnc(NC(=O)CN(C)c2nc(-c3cc(OCCO)ccn3)nc3c2CCC3)cn1] |
| Compound No. | Structure |
|---|---|
| 285 | 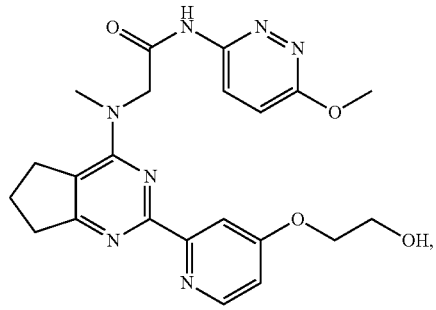 |
| 286 | 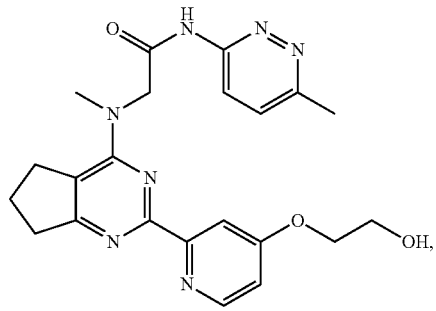 [SMILES: Cc1ccc(NC(=O)CN(C)c2nc(-c3cc(OCCO)ccn3)nc3c2CCC3)nn1] |
| 287 | 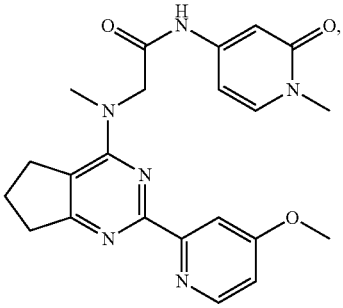 [SMILES: COc1ccnc(-c2nc3c(c(N(C)CC(=O)Nc4ccn(C)c(=O)c4)n2)CCC3)c1] |
| 288 | 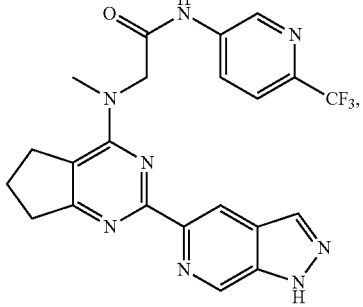 |

| Compound No. | Structure |
|---|---|
| 289 | 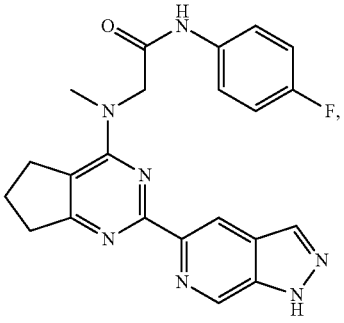 [SMILES: CN(CC(=O)Nc1ccc(F)cc1)c1nc(-c2cc3cn[nH]c3cn2)nc2c1CCC2] |
| 290 | 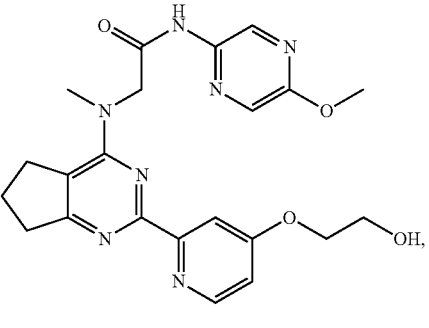 |
| 291 | 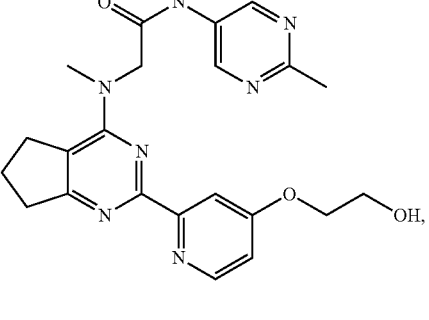 |
| 292 | 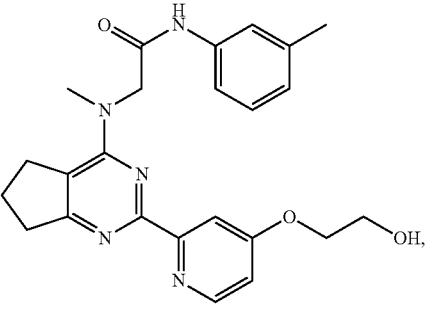 [SMILES: Cc1cccc(NC(=O)CN(C)c2nc(-c3cc(OCCO)ccn3)nc3c2CCC3)c1] |
| Compound No. | Structure |
|---|---|
| 293 | 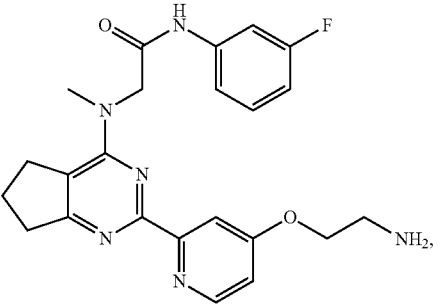 [SMILES: CN(CC(=O)Nc1cccc(F)c1)c1nc(-c2cc(OCCN)ccn2)nc2c1CCC2] |
| 294 | 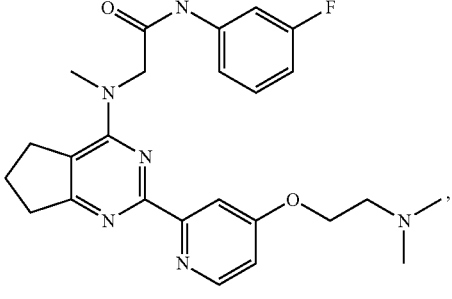 |
| 295 | 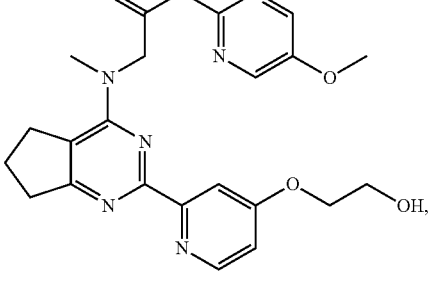 |
| 296 | 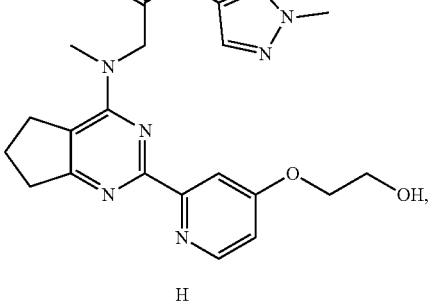 |
| 297 | 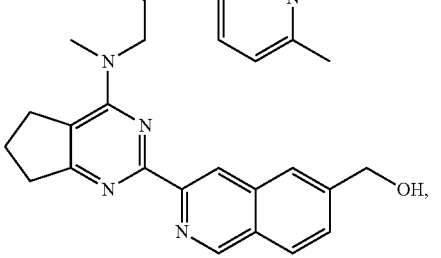 |

| Compound No. | Structure |
|---|---|
| 298 | 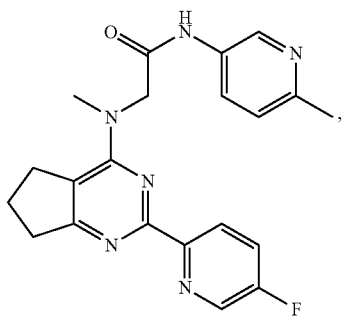 [SMILES: Cc1ccc(NC(=O)CN(C)c2nc(-c3ccc(F)cn3)nc3c2CCC3)cn1] |
| 299 | 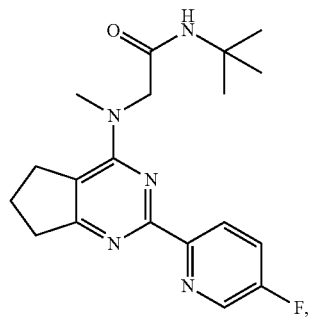 [SMILES: CN(CC(=O)NC(C)(C)C)c1nc(-c2ccc(F)cn2)nc2c1CCC2] |
| 300 | 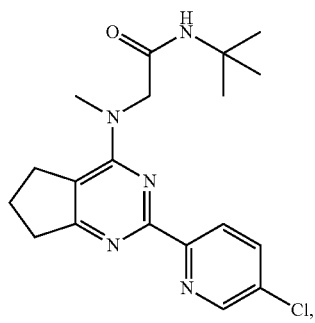 [SMILES: CN(CC(=O)NC(C)(C)C)c1nc(-c2ccc(Cl)cn2)nc2c1CCC2] |
| 301 | 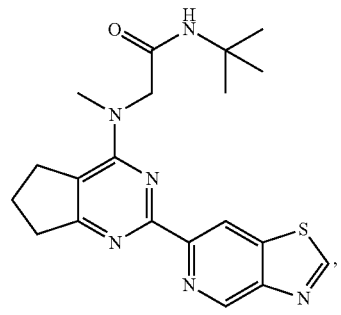 [SMILES: CN(CC(=O)NC(C)(C)C)c1nc(-c2cc3scnc3cn2)nc2c1CCC2] |
| Compound No. | Structure |
|---|---|
| 302 | 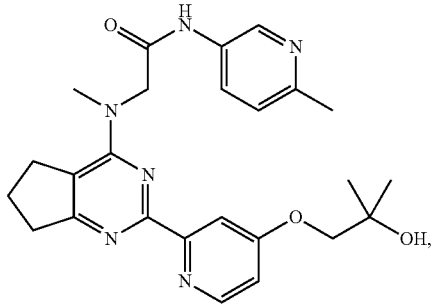 [SMILES: Cc1ccc(NC(=O)CN(C)c2nc(-c3cc(OCC(C)(C)O)ccn3)nc3c2CCC3)cn1] |
| 303 | 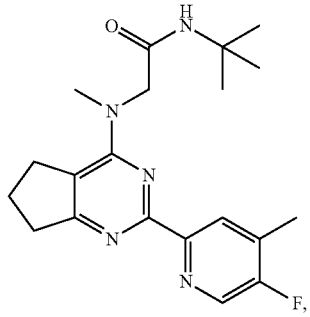 [SMILES: Cc1cc(-c2nc3c(c(N(C)CC(=O)NC(C)(C)C)n2)CCC3)ncc1F] |
| 304 | 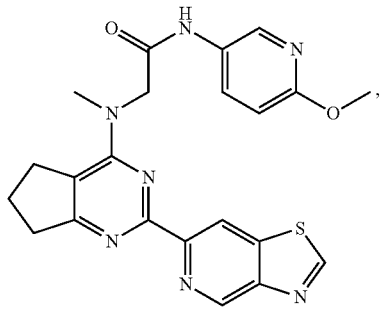 [SMILES: COc1ccc(NC(=O)CN(C)c2nc(-c3cc4scnc4cn3)nc3c2CCC3)cn1] |
| 305 | 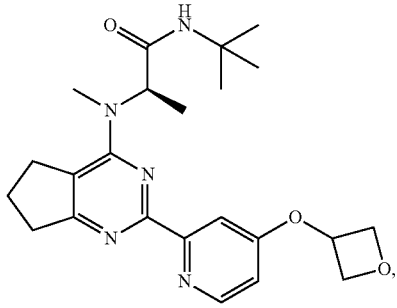 [SMILES: C[C@H](C(=O)NC(C)(C)C)N(C)c1nc(-c2cc(OC3COC3)ccn2)nc2c1CCC2] |

US 11,746,100 B2
| Compound No. | Structure |
|---|---|
| 306 | 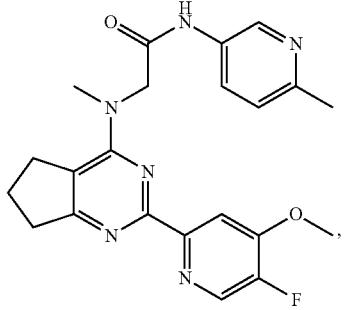 [SMILES: COc1cc(-c2nc3c(c(N(C)CC(=O)Nc4ccc(C)nc4)n2)CCC3)ncc1F] |
| 307 | 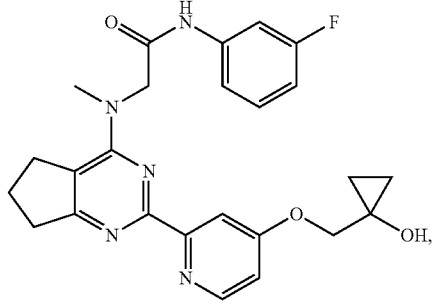 [SMILES: CN(CC(=O)Nc1cccc(F)c1)c1nc(-c2cc(OCC3(O)CC3)ccn2)nc2c1CCC2] |
| 308 | 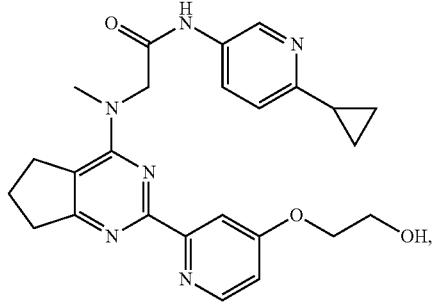 [SMILES: CN(CC(=O)Nc1ccc(C2CC2)nc1)c1nc(-c2cc(OCCO)ccn2)nc2c1CCC2] |
| 309 | 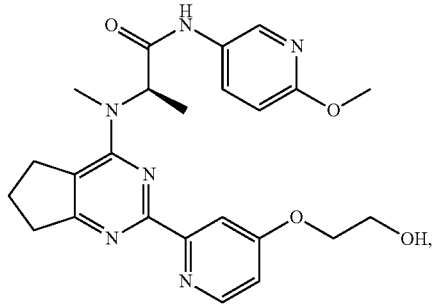 [SMILES: COc1ccc(NC(=O)[C@@H](C)N(C)c2nc(-c3cc(OCCO)ccn3)nc3c2CCC3)cn1] |
| Compound No. | Structure |
|---|---|
| 310 | 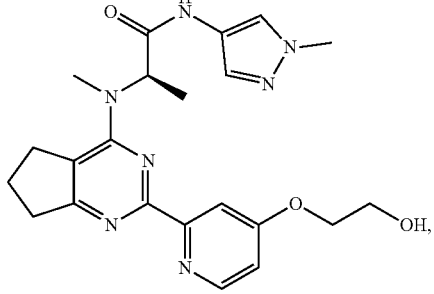 |
| 311 | 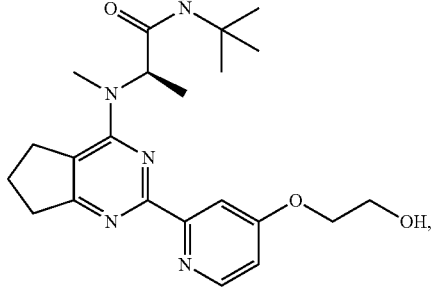 |
| 312 | 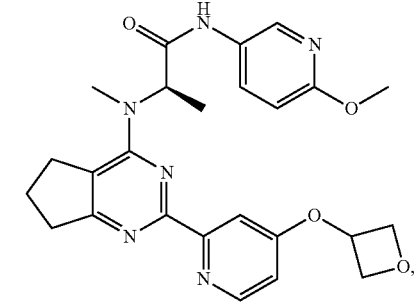 [SMILES: COc1ccc(NC(=O)[C@@H](C)N(C)c2nc(-c3cc(OC4COC4)ccn3)nc3c2CCC3)cn1] |
| 313 | 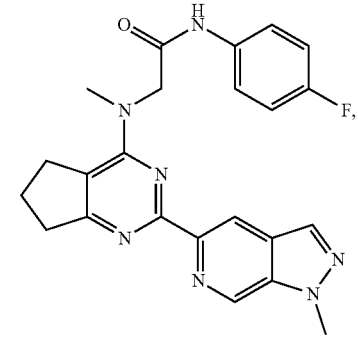 [SMILES: CN(CC(=O)Nc1ccc(F)cc1)c1nc(-c2cc3cnn(C)c3cn2)nc2c1CCC2] |

| Compound No. | Structure |
|---|---|
| 314 | 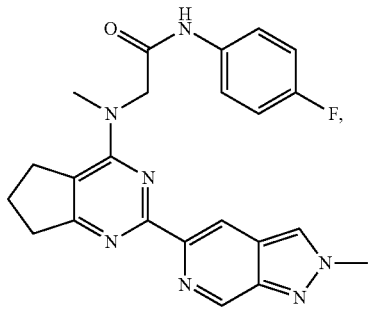 [SMILES: CN(CC(=O)Nc1ccc(F)cc1)c1nc(-c2cc3cn(C)nc3cn2)nc2c1CCC2] |
| 315 | 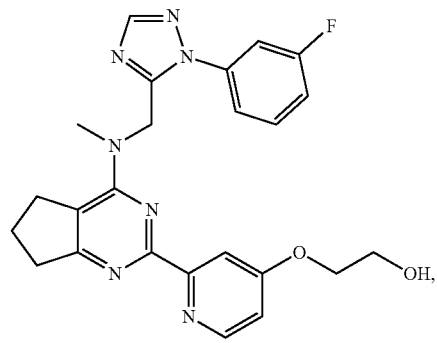 [SMILES: CN(Cc1ncnn1-c1cccc(F)c1)c1nc(-c2cc(OCCO)ccn2)nc2c1CCC2] |
| 316 | 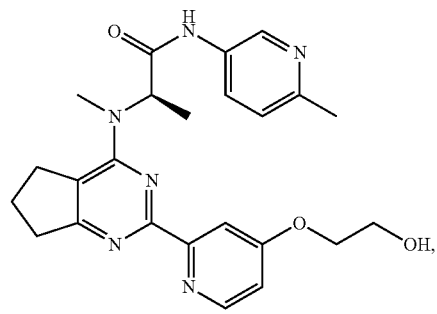 |
| 317 | 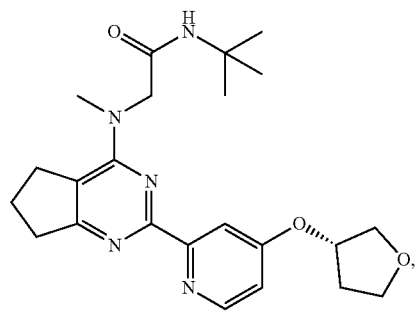 [SMILES: CN(CC(=O)NC(C)(C)C)c1nc(-c2cc(O[C@H]3CCOC3)ccn2)nc2c1CCC2] |
| Compound No. | Structure |
|---|---|
| 318 | 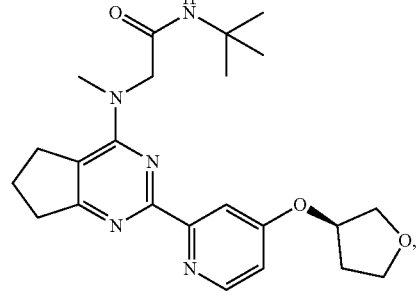 |
| 319 | 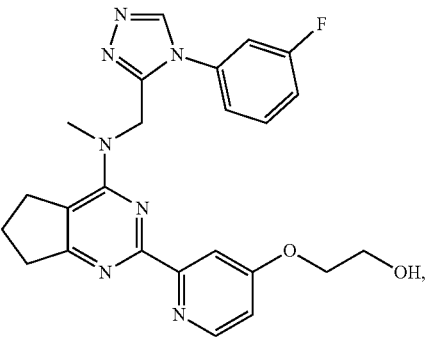 [SMILES: CN(Cc1nncn1-c1cccc(F)c1)c1nc(-c2cc(OCCO)ccn2)nc2c1CCC2] |
| 320 | 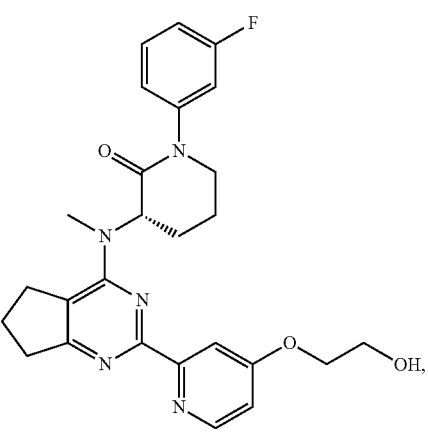 [SMILES: CN(c1nc(-c2cc(OCCO)ccn2)nc2c1CCC2)[C@H]1CCCN(c2cccc(F)c2)C1=O] |
| 321 | 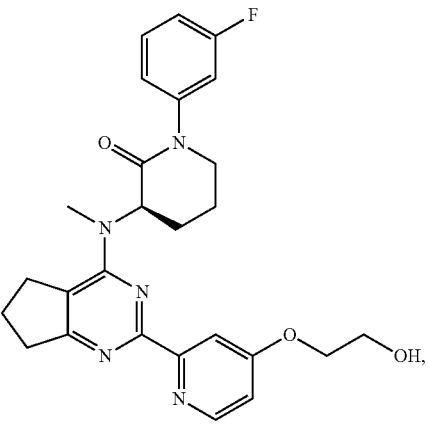 [SMILES: CN(c1nc(-c2cc(OCCO)ccn2)nc2c1CCC2)[C@@H]1CCCN(c2cccc(F)c2)C1=O] |

-continued
| Compound No. | Structure |
|---|---|
| 322 | 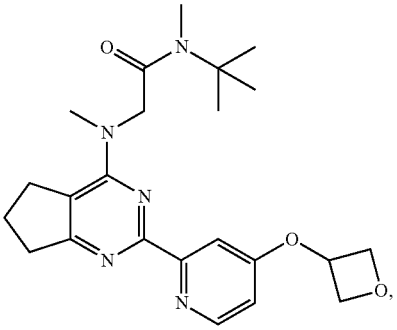 [SMILES: CN(CC(=O)N(C)C(C)(C)C)c1nc(-c2cc(OC3COC3)ccn2)nc2c1CCC2] |
| 323 | 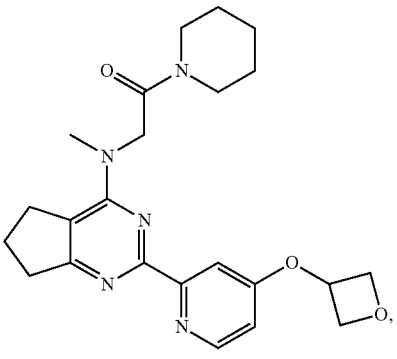 [SMILES: CN(CC(=O)N1CCCCC1)c1nc(-c2cc(OC3COC3)ccn2)nc2c1CCC2] |
| 324 | 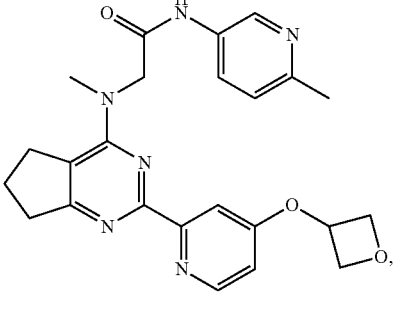 |
| 325 | 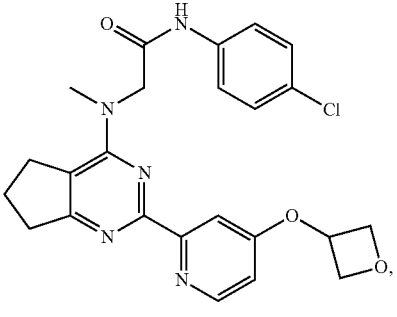 [SMILES: CN(CC(=O)Nc1ccc(Cl)cc1)c1nc(-c2cc(OC3COC3)ccn2)nc2c1CCC2] |
-continued
| Compound No. | Structure |
|---|---|
| 326 | 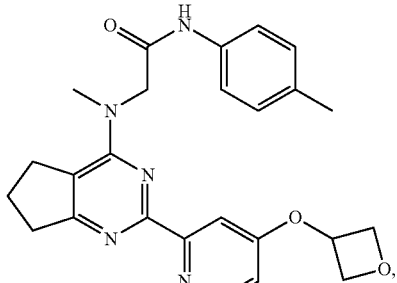 |
| 327 | 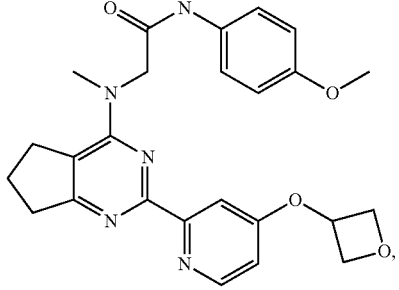 |
| 328 | 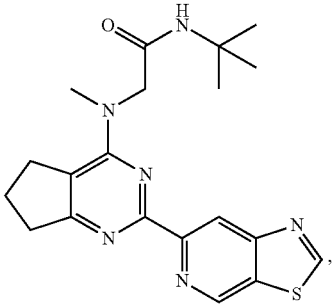 [SMILES: CN(CC(=O)NC(C)(C)C)c1nc(-c2cc3ncsc3cn2)nc2c1CCC2] |
| 329 | 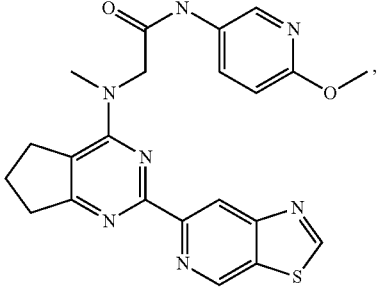 |
| 330 | 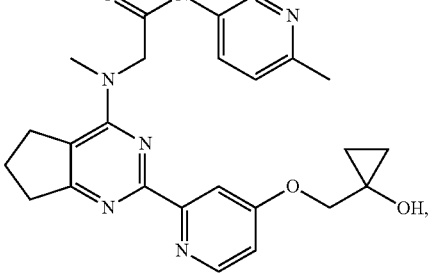 |

| Compound No. | Structure |
|---|---|
| 331 | 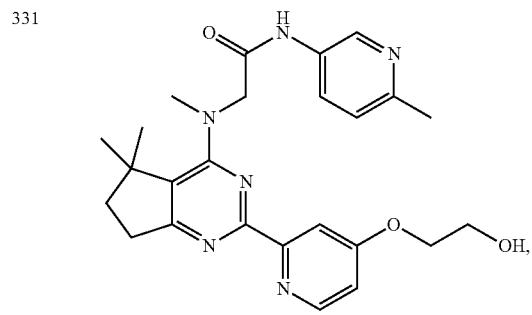 |
| 332 | 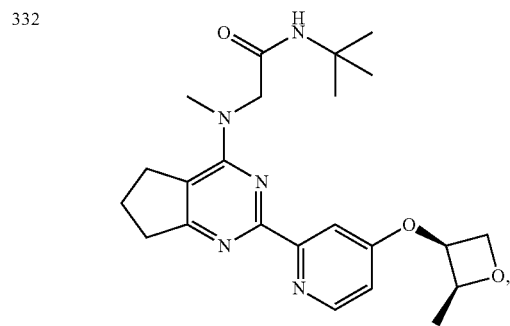 |
| 333 | 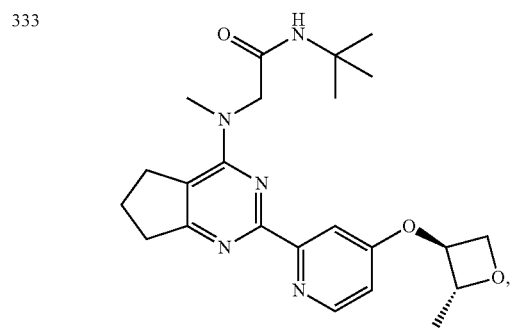 |
| 334 | 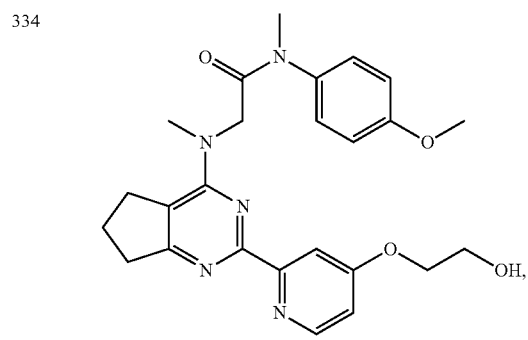 |
| Compound No. | Structure |
|---|---|
| 335 | 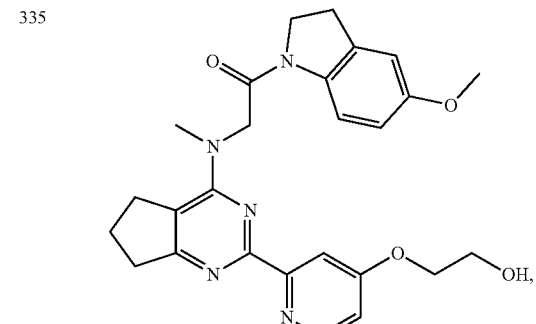 |
| 336 | 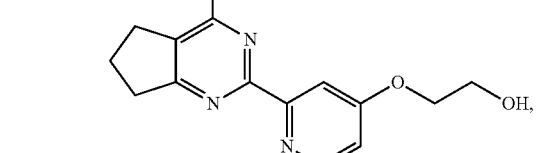 |
| 337 | 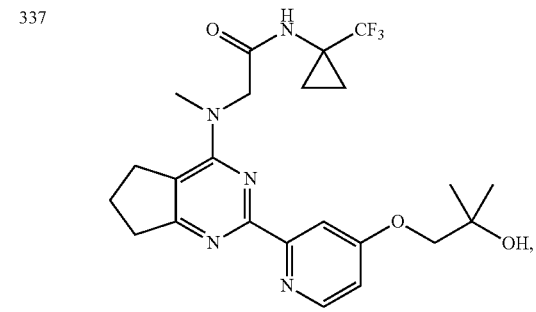 |
| 338 | 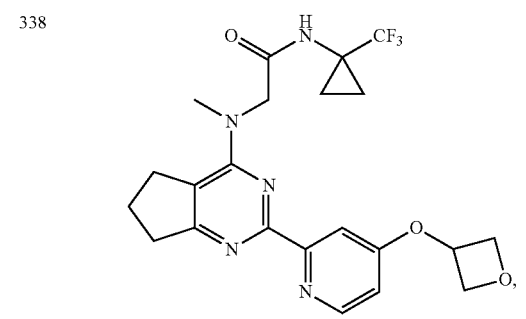 |

1077
-continued
| Compound No. | Structure |
|---|---|
| 339 | 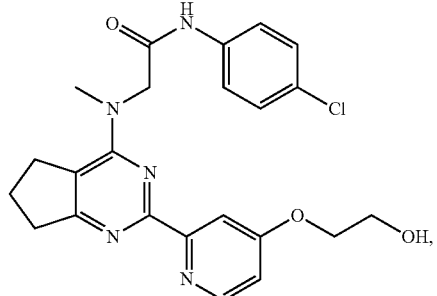 |
| 340 | 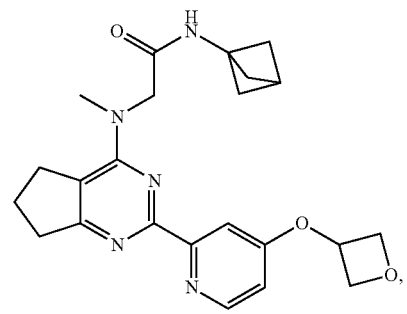 [SMILES: CN(CC(=O)NC12CC(C1)C2)c1nc(-c2cc(OC3COC3)ccn2)nc2c1CCC2] |
| 341 | 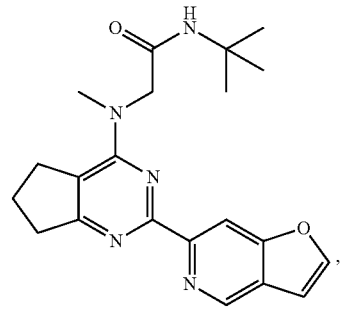 [SMILES: CN(CC(=O)NC(C)(C)C)c1nc(-c2cc3occc3cn2)nc2c1CCC2] |
| 342 | 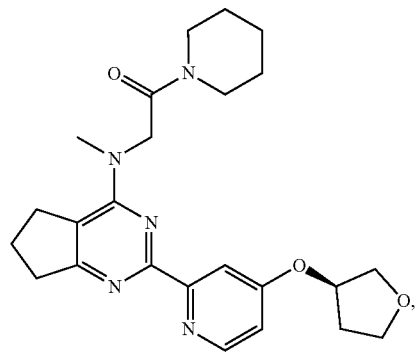 [SMILES: CN(CC(=O)N1CCCCC1)c1nc(-c2cc(O[C@@H]3CCOC3)ccn2)nc2c1CCC2] |
1078
-continued
| Compound No. | Structure |
|---|---|
| 343 | 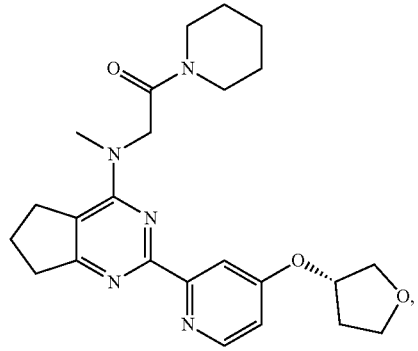 [SMILES: CN(CC(=O)N1CCCCC1)c1nc(-c2cc(O[C@H]3CCOC3)ccn2)nc2c1CCC2] |
| 344 | 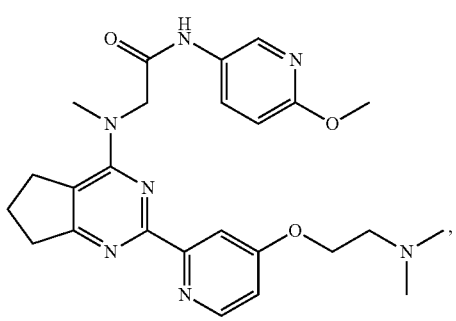 [SMILES: COc1ccc(NC(=O)CN(C)c2nc(-c3cc(OCCN(C)C)ccn3)nc3c2CCC3)cn1] |
| 345 | 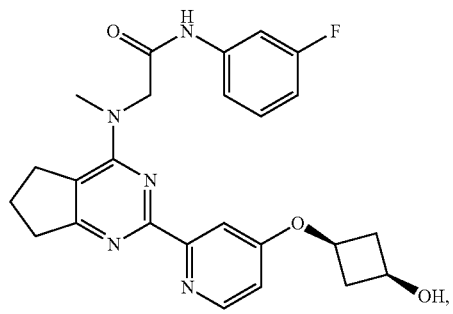 [SMILES: CN(CC(=O)Nc1cccc(F)c1)c1nc(-c2cc(O[C@H]3C[C@@H](O)C3)ccn2)nc2c1CCC2] |
| 346 | 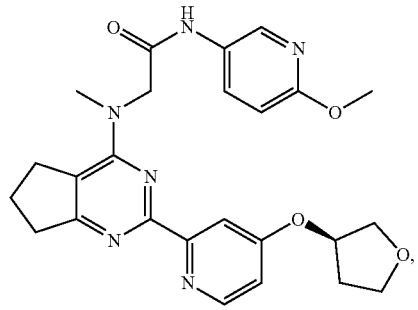 [SMILES: COc1ccc(NC(=O)CN(C)c2nc(-c3cc(O[C@@H]4CCOC4)ccn3)nc3c2CCC3)cn1] |

| Compound No. | Structure |
|---|---|
| 347 | 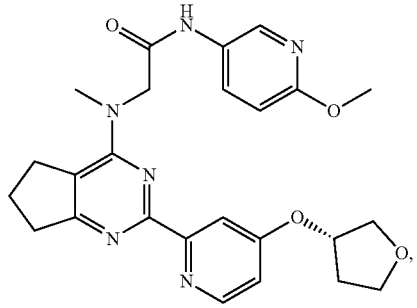 [SMILES: COc1ccc(NC(=O)CN(C)c2nc(-c3cc(O[C@H]4CCOC4)ccn3)nc3c2CCC3)cn1] |
| 348 | 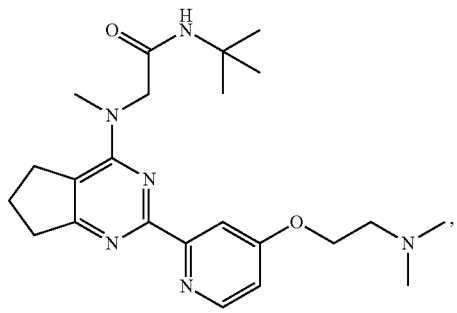 [SMILES: CN(C)CCOc1ccnc(-c2nc3c(c(N(C)CC(=O)NC(C)(C)C)n2)CCC3)c1] |
| 349 | 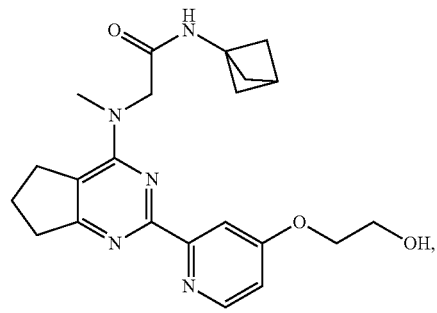 [SMILES: CN(CC(=O)NC12CC(C1)C2)c1nc(-c2cc(OCCO)ccn2)nc2c1CCC2] |
| 350 | 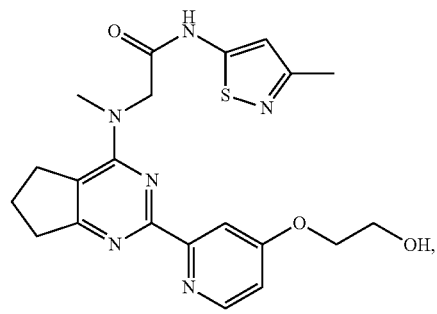 [SMILES: Cc1cc(NC(=O)CN(C)c2nc(-c3cc(OCCO)ccn3)nc3c2CCC3)sn1] |
| Compound No. | Structure |
|---|---|
| 351 | 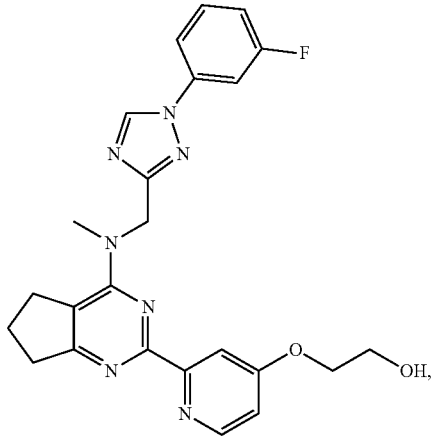 [SMILES: CN(Cc1ncn(-c2cccc(F)c2)n1)c1nc(-c2cc(OCCO)ccn2)nc2c1CCC2] |
| 352 | 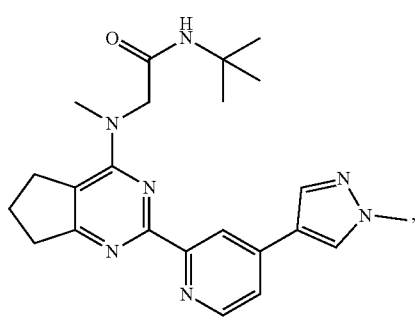 [SMILES: CN(CC(=O)NC(C)(C)C)c1nc(-c2cc(-c3cnn(C)c3)ccn2)nc2c1CCC2] |
| 353 | 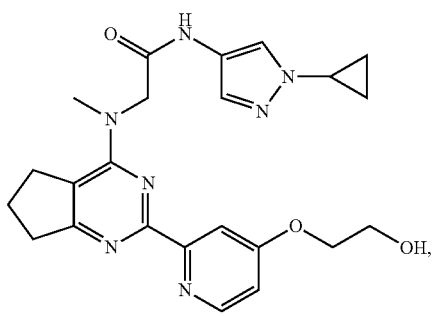 [SMILES: CN(CC(=O)Nc1cnn(C2CC2)c1)c1nc(-c2cc(OCCO)ccn2)nc2c1CCC2] |
| 354 | 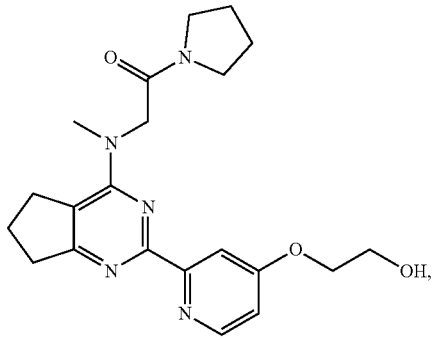 [SMILES: CN(CC(=O)N1CCCC1)c1nc(-c2cc(OCCO)ccn2)nc2c1CCC2] |

| Compound No. | Structure |
|---|---|
| 355 | 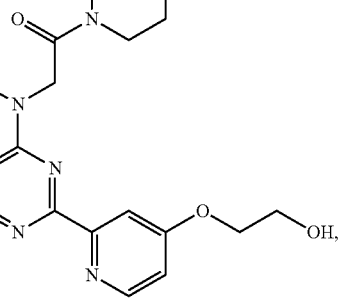 |
| 356 | |
| 357 | |
| 358 | |
| Compound No. | Structure |
|---|---|
| 359 | 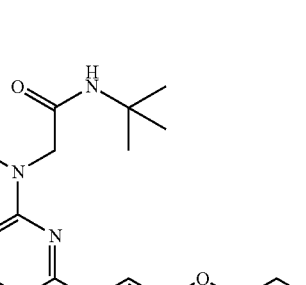 |
| 360 | |
| 361 | |
| 362 | |

| Compound No. | Structure |
|---|---|
| 363 | 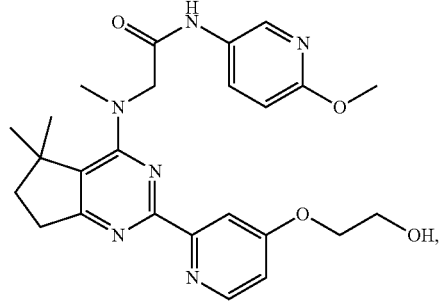 [SMILES: COc1ccc(NC(=O)CN(C)c2nc(-c3cc(OCCO)ccn3)nc3c2C(C)(C)CC3)cn1] |
| 364 | 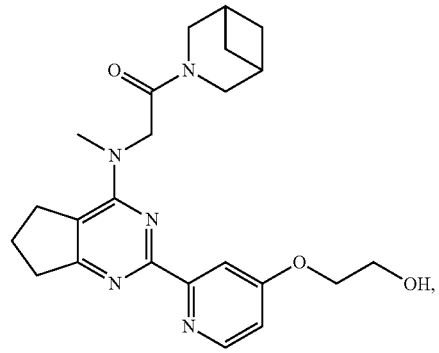 [SMILES: CN(CC(=O)N1CC2CC(C2)C1)c1nc(-c2cc(OCCO)ccn2)nc2c1CCC2] |
| 365 | 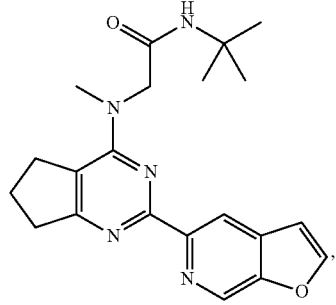 [SMILES: CN(CC(=O)NC(C)(C)C)c1nc(-c2cc3ccoc3cn2)nc2c1CCC2] |
| 366 | 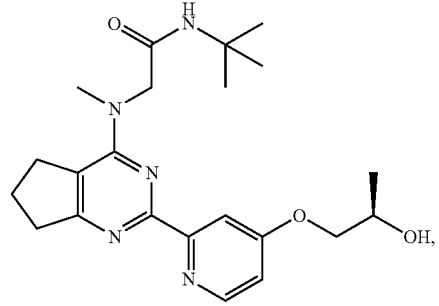 [SMILES: C[C@@H](O)COc1ccnc(-c2nc3c(c(N(C)CC(=O)NC(C)(C)C)n2)CCC3)c1] |
| Compound No. | Structure |
|---|---|
| 367 | 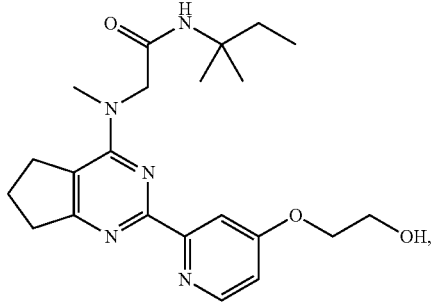 [SMILES: CCC(C)(C)NC(=O)CN(C)c1nc(-c2cc(OCCO)ccn2)nc2c1CCC2] |
| 368 | 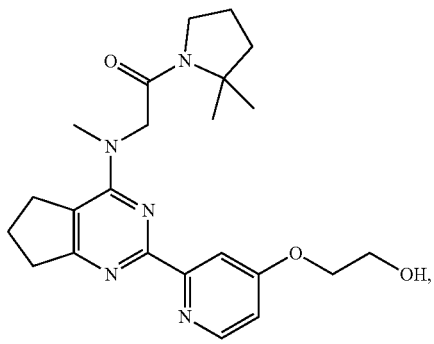 [SMILES: CN(CC(=O)N1CCCC1(C)C)c1nc(-c2cc(OCCO)ccn2)nc2c1CCC2] |
| 369 | 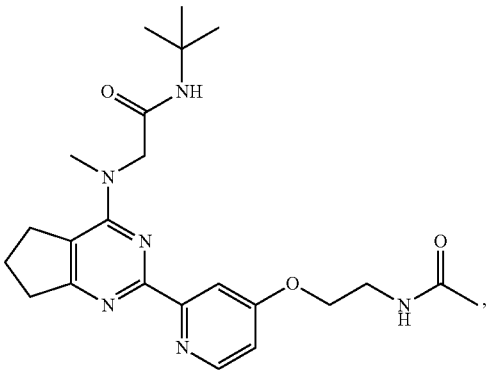 [SMILES: CC(=O)NCCOc1ccnc(-c2nc3c(c(N(C)CC(=O)NC(C)(C)C)n2)CCC3)c1] |
| 370 | 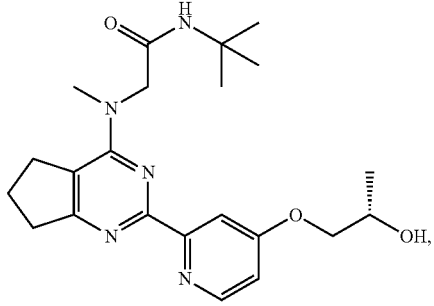 [SMILES: C[C@H](O)COc1ccnc(-c2nc3c(c(N(C)CC(=O)NC(C)(C)C)n2)CCC3)c1] |

| Compound No. | Structure |
|---|---|
| 371 | 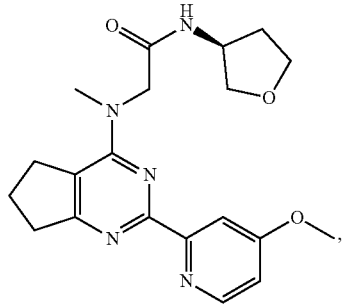 [SMILES: COc1ccnc(-c2nc3c(c(N(C)CC(=O)N[C@H]4CCOC4)n2)CCC3)c1] |
| 372 | 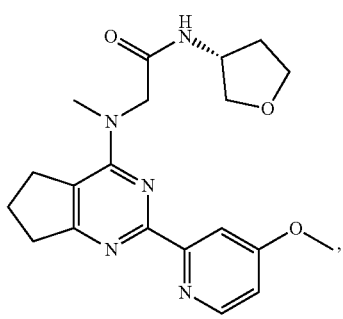 [SMILES: COc1ccnc(-c2nc3c(c(N(C)CC(=O)N[C@@H]4CCOC4)n2)CCC3)c1] |
| 373 | 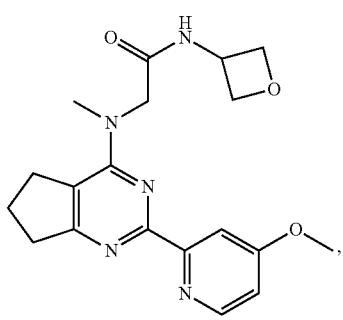 [SMILES: COc1ccnc(-c2nc3c(c(N(C)CC(=O)NC4COC4)n2)CCC3)c1] |
| 374 | 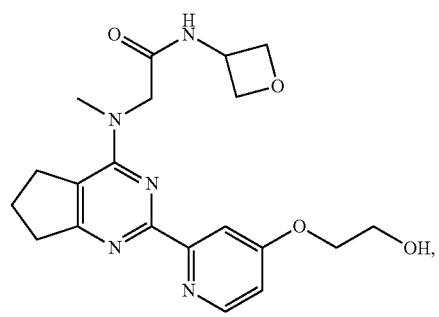 [SMILES: CN(CC(=O)NC1COC1)c1nc(-c2cc(OCCO)ccn2)nc2c1CCC2] |
| Compound No. | Structure |
|---|---|
| 375 | 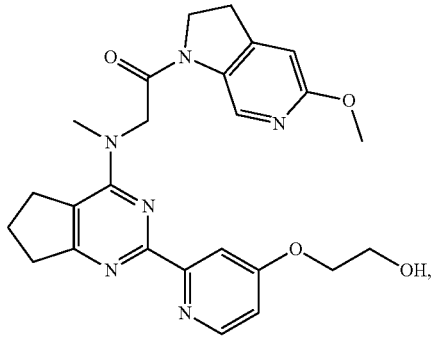 [SMILES: COc1cc2c(cn1)N(C(=O)CN(C)c1nc(-c3cc(OCCO)ccn3)nc3c1CCC3)CC2] |
| 376 | 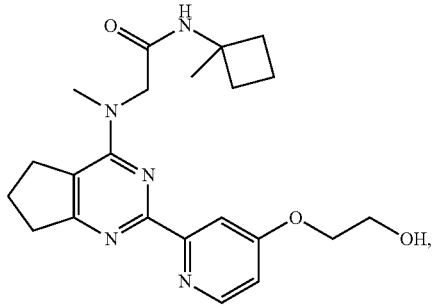 [SMILES: CN(CC(=O)NC1(C)CCC1)c1nc(-c2cc(OCCO)ccn2)nc2c1CCC2] |
| 377 | 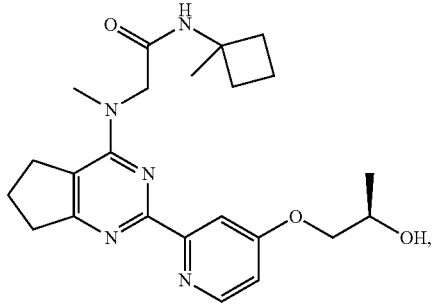 [SMILES: C[C@@H](O)COc1ccnc(-c2nc3c(c(N(C)CC(=O)NC4(C)CCC4)n2)CCC3)c1] |
| 378 | 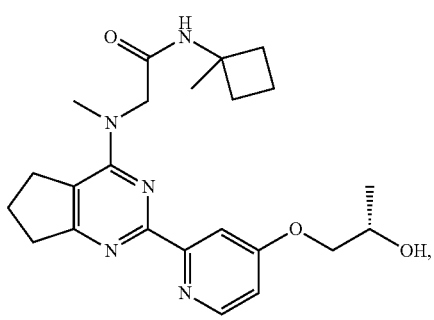 [SMILES: C[C@H](O)COc1ccnc(-c2nc3c(c(N(C)CC(=O)NC4(C)CCC4)n2)CCC3)c1] |

| Compound No. | Structure |
|---|---|
| 379 | 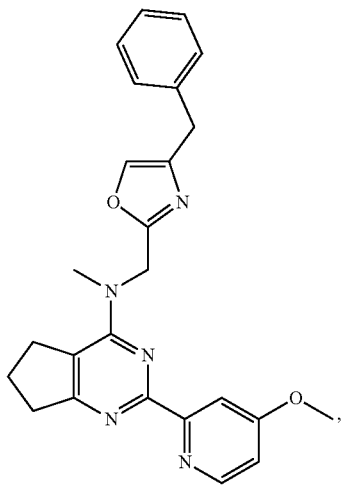 [SMILES: COc1ccnc(-c2nc3c(c(N(C)Cc4nc(Cc5ccccc5)co4)n2)CCC3)c1] |
| 380 | 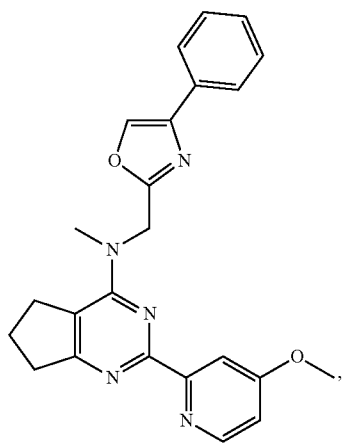 [SMILES: COc1ccnc(-c2nc3c(c(N(C)Cc4nc(-c5ccccc5)co4)n2)CCC3)c1] |
| 381 | 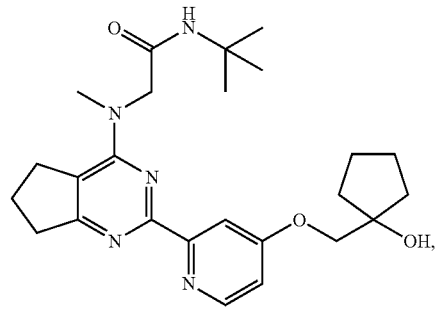 [SMILES: CN(CC(=O)NC(C)(C)C)c1nc(-c2cc(OCC3(O)CCCC3)ccn2)nc2c1CCC2] |
| Compound No. | Structure |
|---|---|
| 382 | 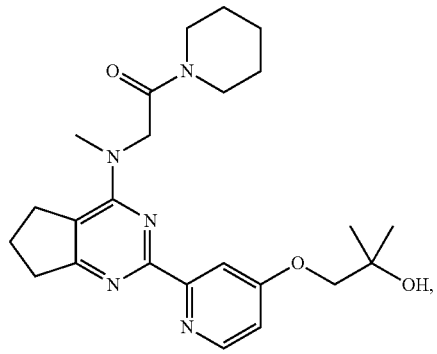 [SMILES: CN(CC(=O)N1CCCCC1)c1nc(-c2cc(OCC(C)(C)O)ccn2)nc2c1CCC2] |
| 383 | 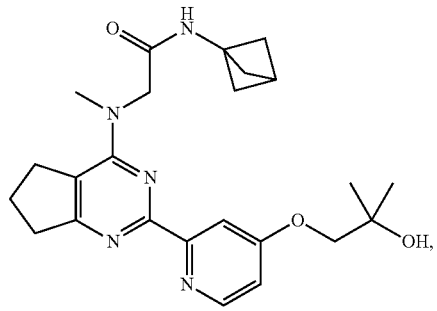 [SMILES: CN(CC(=O)NC12CC(C1)C2)c1nc(-c2cc(OCC(C)(C)O)ccn2)nc2c1CCC2] |
| 384 | 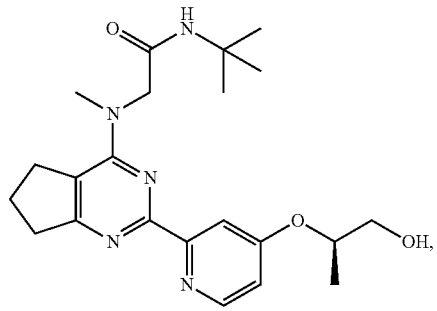 [SMILES: C[C@H](CO)Oc1ccnc(-c2nc3c(c(N(C)CC(=O)NC(C)(C)C)n2)CCC3)c1] |
| 385 | 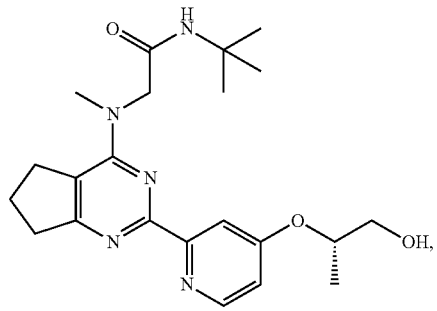 [SMILES: C[C@@H](CO)Oc1ccnc(-c2nc3c(c(N(C)CC(=O)NC(C)(C)C)n2)CCC3)c1] |

| Compound No. | Structure |
|---|---|
| 386 | 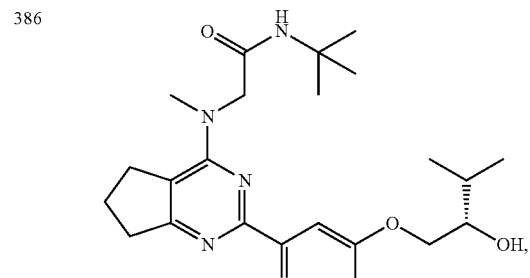 |
| 387 | 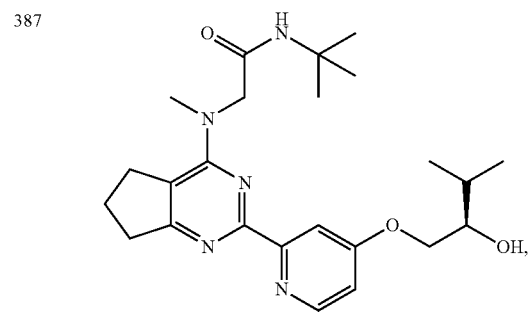 |
| 388 | 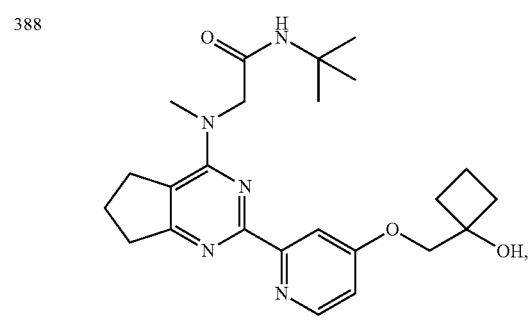 |
| 389 | 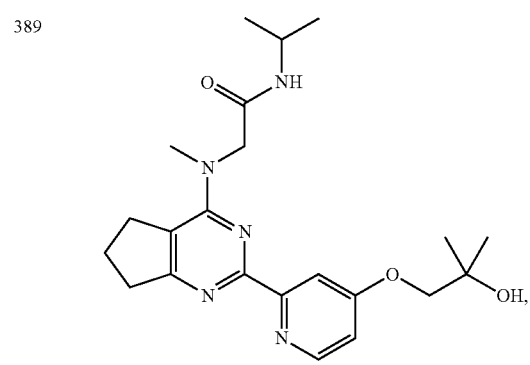 |
| 390 | 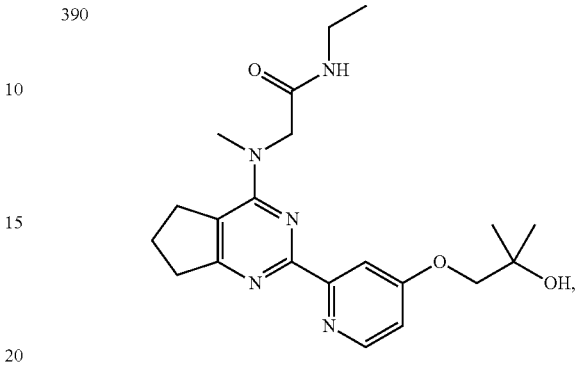 |
| 391 | 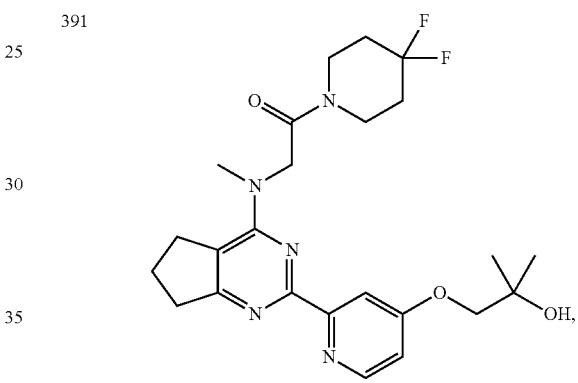 |
| 392 | 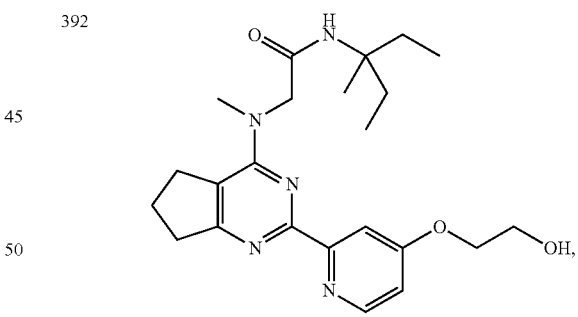 |
| 393 | 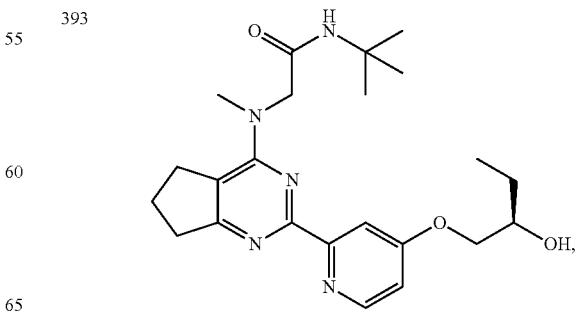 |

| Compound No. | Structure |
|---|---|
| 394 | 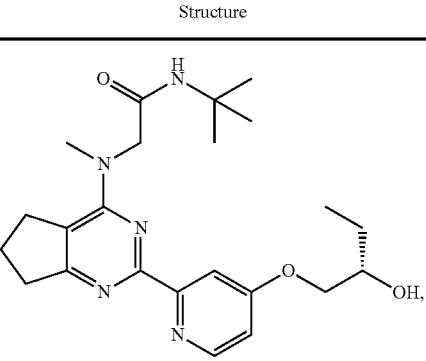 |
| 395 | 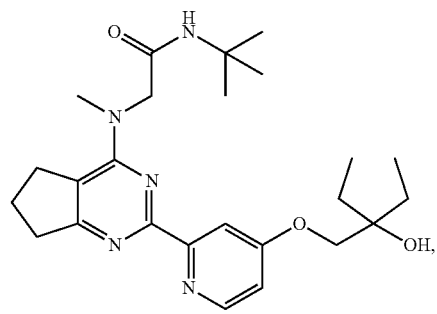 [SMILES: CCC(O)(CC)COc1ccnc(-c2nc3c(c(N(C)CC(=O)NC(C)(C)C)n2)CCC3)c1] |
| 396 | 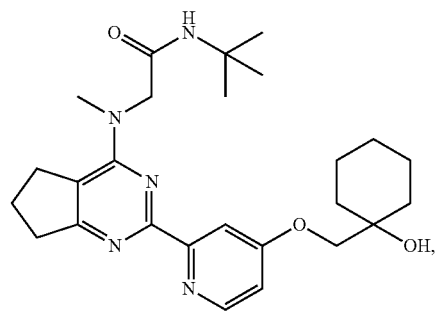 |
| 397 | 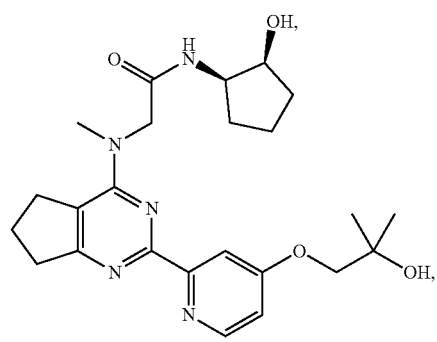 [SMILES: CN(CC(=O)N[C@@H]1CCC[C@@H]1O)c1nc(-c2cc(OCC(C)(C)O)ccn2)nc2c1CCC2] |
| Compound No. | Structure |
|---|---|
| 398 | 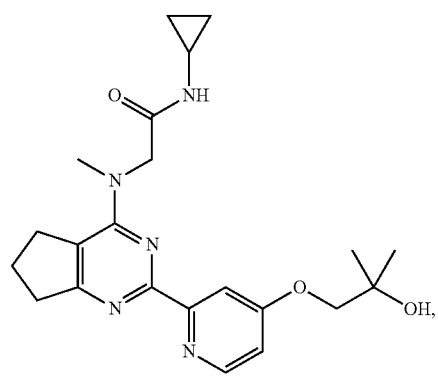 [SMILES: CN(CC(=O)NC1CC1)c1nc(-c2cc(OCC(C)(C)O)ccn2)nc2c1CCC2] |
| 399 | 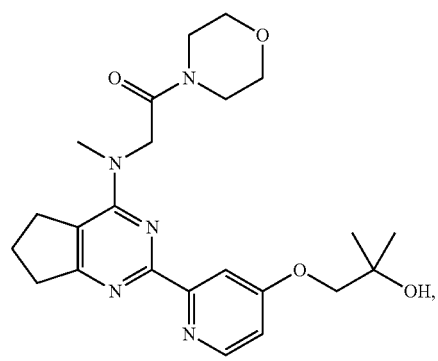 [SMILES: CN(CC(=O)N1CCOCC1)c1nc(-c2cc(OCC(C)(C)O)ccn2)nc2c1CCC2] |
| 400 | 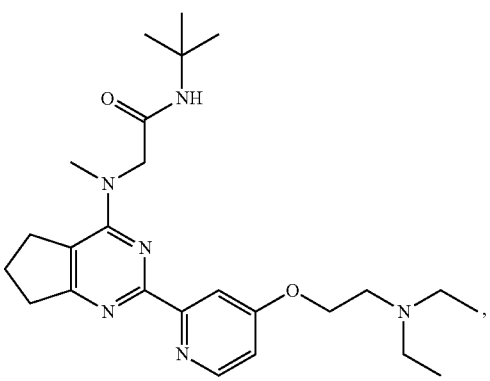 [SMILES: CCN(CC)CCOc1ccnc(-c2nc3c(c(N(C)CC(=O)NC(C)(C)C)n2)CCC3)c1] |
| 401 | 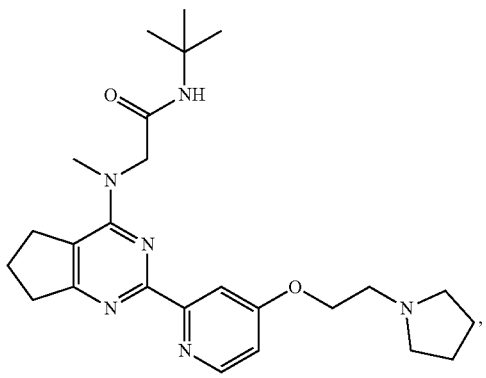 [SMILES: CN(CC(=O)NC(C)(C)C)c1nc(-c2cc(OCCN3CCCC3)ccn2)nc2c1CCC2] |

-continued
| Compound No. | Structure |
|---|---|
| 402 | 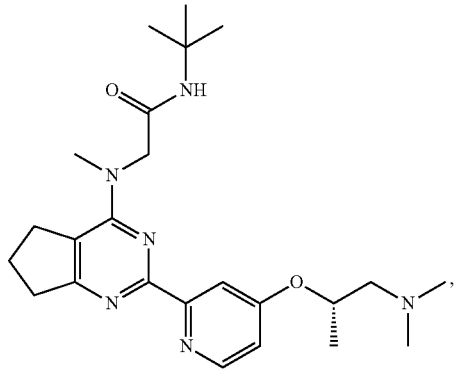 [SMILES: C[C@@H](CN(C)C)Oc1ccnc(-c2nc3c(c(N(C)CC(=O)NC(C)(C)C)n2)CCC3)c1] |
| 403 | 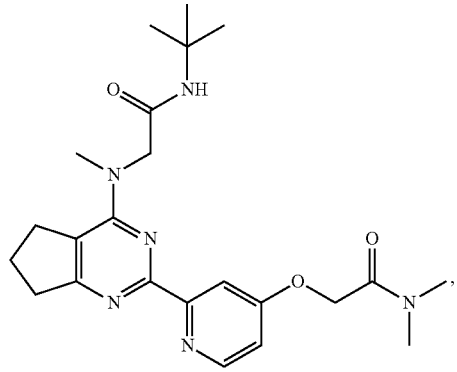 [SMILES: CN(C)C(=O)COc1ccnc(-c2nc3c(c(N(C)CC(=O)NC(C)(C)C)n2)CCC3)c1] |
| 404 | 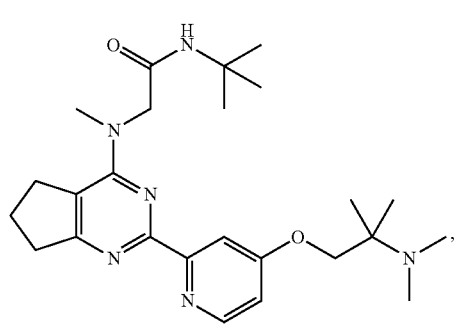 [SMILES: CN(CC(=O)NC(C)(C)C)c1nc(-c2cc(OCC(C)(C)N(C)C)ccn2)nc2c1CCC2] |
| 405 | 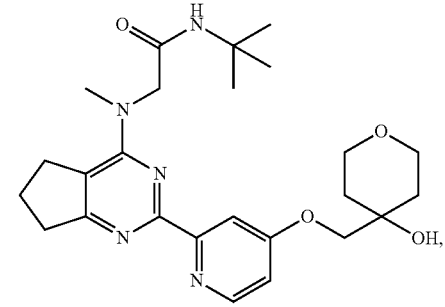 [SMILES: CN(CC(=O)NC(C)(C)C)c1nc(-c2cc(OCC3(O)CCOCC3)ccn2)nc2c1CCC2] |
-continued
| Compound No. | Structure |
|---|---|
| 406 | 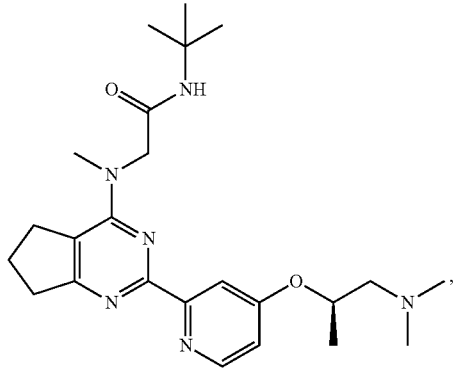 [SMILES: C[C@H](CN(C)C)Oc1ccnc(-c2nc3c(c(N(C)CC(=O)NC(C)(C)C)n2)CCC3)c1] |
| 407 | 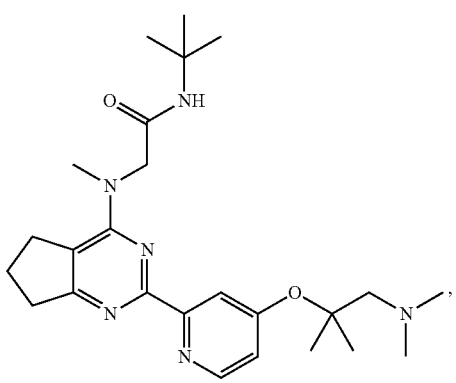 [SMILES: CN(C)CC(C)(C)Oc1ccnc(-c2nc3c(c(N(C)CC(=O)NC(C)(C)C)n2)CCC3)c1] |
| 408 | 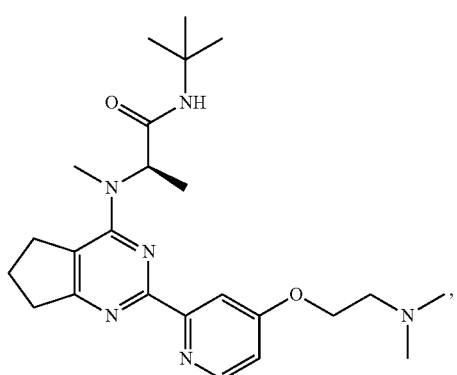 |
| 409 | 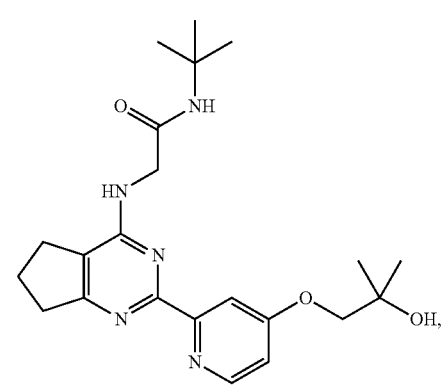 [SMILES: CC(C)(O)COc1ccnc(-c2nc3c(c(NCC(=O)NC(C)(C)C)n2)CCC3)c1] |

TABLE -continued
| Compound No. | Structure |
|---|---|
| 410 | 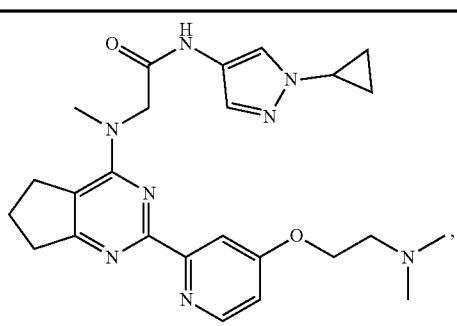 |
| 411 | 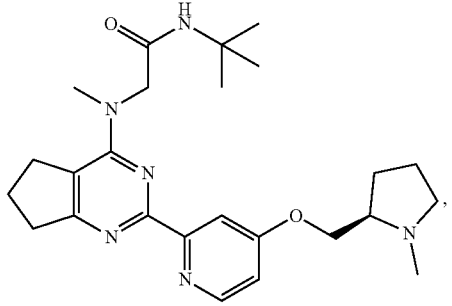 [SMILES: CN(CC(=O)NC(C)(C)C)c1nc(-c2cc(OC[C@H]3CCCN3C)ccn2)nc2c1CCC2] |
| 412 | 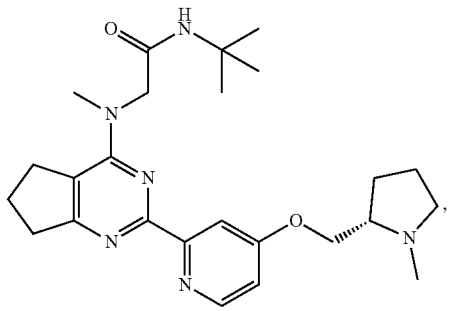 [SMILES: CN(CC(=O)NC(C)(C)C)c1nc(-c2cc(OC[C@@H]3CCCN3C)ccn2)nc2c1CCC2] |
| 413 | 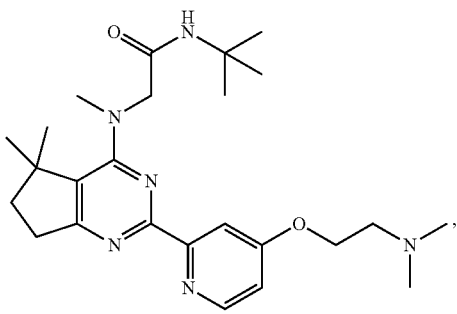 |
| 414 | 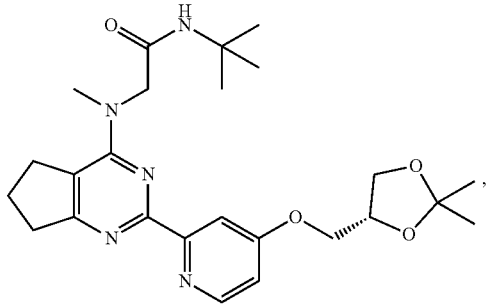 [SMILES: CN(CC(=O)NC(C)(C)C)c1nc(-c2cc(OC[C@@H]3COC(C)(C)O3)ccn2)nc2c1CCC2] |
| 415 | 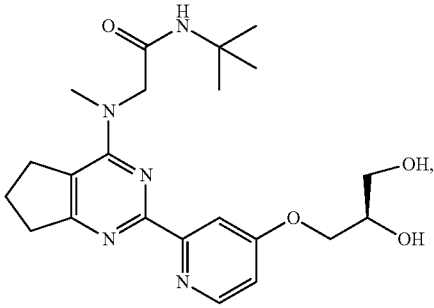 [SMILES: CN(CC(=O)NC(C)(C)C)c1nc(-c2cc(OC[C@H](O)CO)ccn2)nc2c1CCC2] |
| 416 | 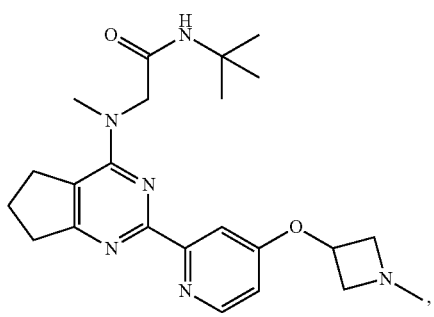 [SMILES: CN1CC(Oc2ccnc(-c3nc4c(c(N(C)CC(=O)NC(C)(C)C)n3)CCC4)c2)C1] |
| 417 | 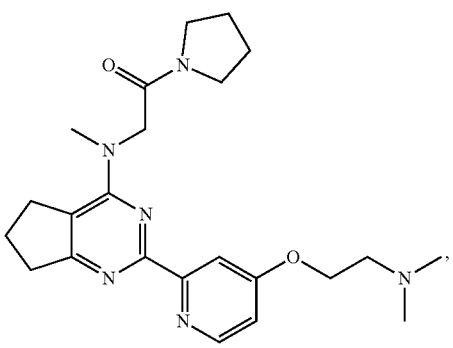 [SMILES: CN(C)CCOc1ccnc(-c2nc3c(c(N(C)CC(=O)N4CCCC4)n2)CCC3)c1] |
| 418 | 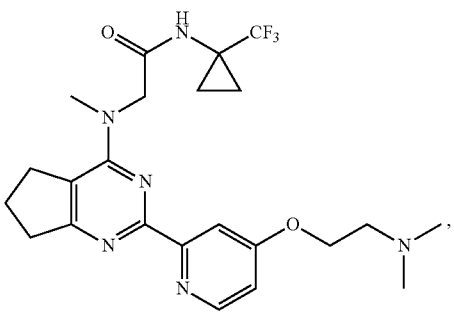 [SMILES: CN(C)CCOc1ccnc(-c2nc3c(c(N(C)CC(=O)NC4(C(F)(F)F)CC4)n2)CCC3)c1] |

| Compound No. | Structure |
|---|---|
| 419 | 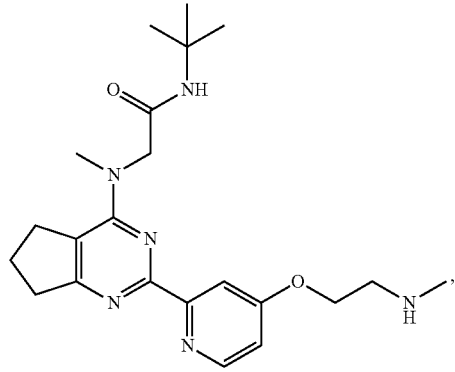 [SMILES: CNCCOc1ccnc(-c2nc3c(c(N(C)CC(=O)NC(C)(C)C)n2)CCC3)c1] |
| 420 | 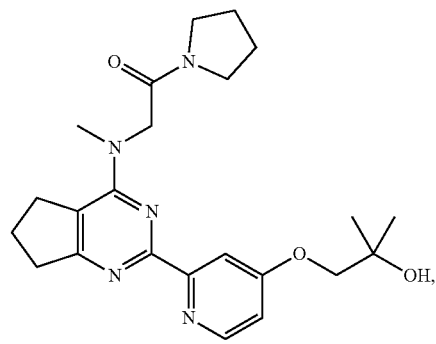 [SMILES: CN(CC(=O)N1CCCC1)c1nc(-c2cc(OCC(C)(C)O)ccn2)nc2c1CCC2] |
| 421 | 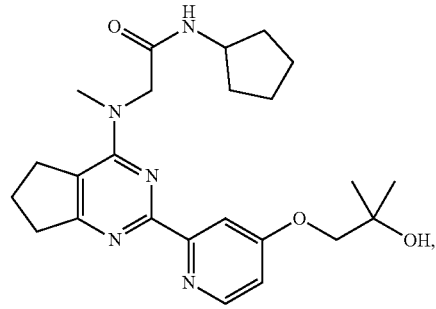 |
| 422 | 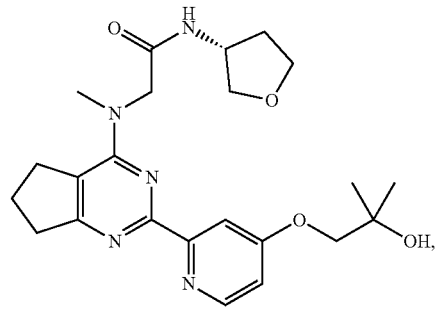 [SMILES: CN(CC(=O)N[C@@H]1CCOC1)c1nc(-c2cc(OCC(C)(C)O)ccn2)nc2c1CCC2] |
| 423 | 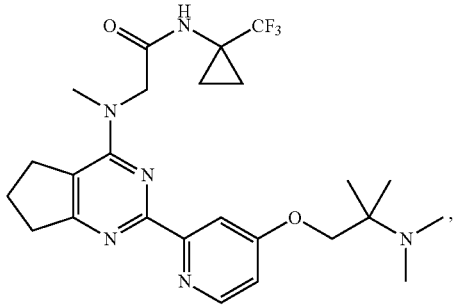 [SMILES: CN(CC(=O)NC1(C(F)(F)F)CC1)c1nc(-c2cc(OCC(C)(C)N(C)C)ccn2)nc2c1CCC2] |
| 424 | 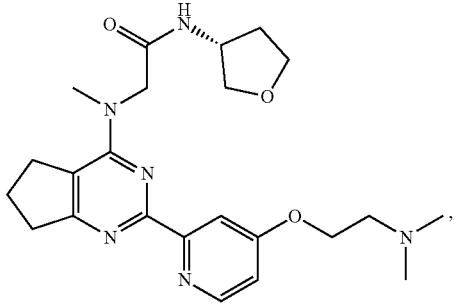 [SMILES: CN(C)CCOc1ccnc(-c2nc3c(c(N(C)CC(=O)N[C@@H]4CCOC4)n2)CCC3)c1] |
| 425 | 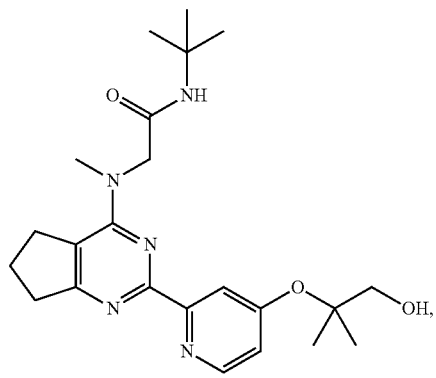 [SMILES: CN(CC(=O)NC(C)(C)C)c1nc(-c2cc(OC(C)(C)CO)ccn2)nc2c1CCC2] |
| 426 | 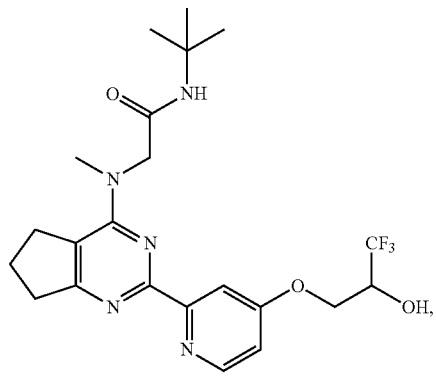 [SMILES: CN(CC(=O)NC(C)(C)C)c1nc(-c2cc(OCC(O)C(F)(F)F)ccn2)nc2c1CCC2] |

| Compound No. | Structure |
|---|---|
| 427 | 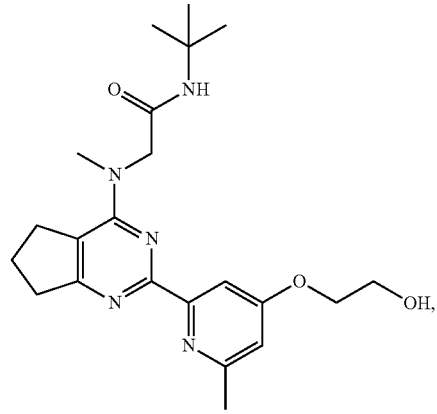 [SMILES: Cc1cc(OCCO)cc(-c2nc3c(c(N(C)CC(=O)NC(C)(C)C)n2)CCC3)n1] |
| 428 | 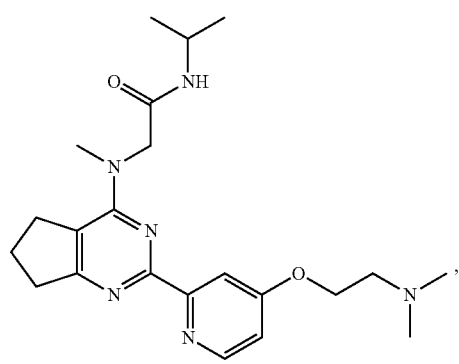 [SMILES: CC(C)NC(=O)CN(C)c1nc(-c2cc(OCCN(C)C)ccn2)nc2c1CCC2] |
| 429 | 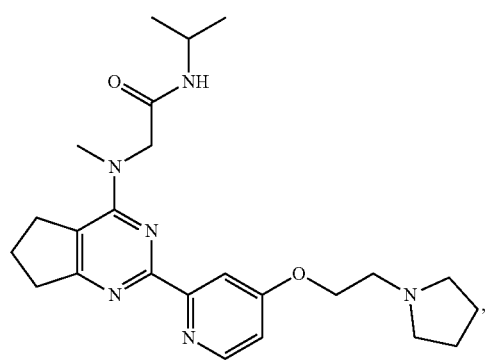 [SMILES: CC(C)NC(=O)CN(C)c1nc(-c2cc(OCCN3CCCC3)ccn2)nc2c1CCC2] |
| 430 | 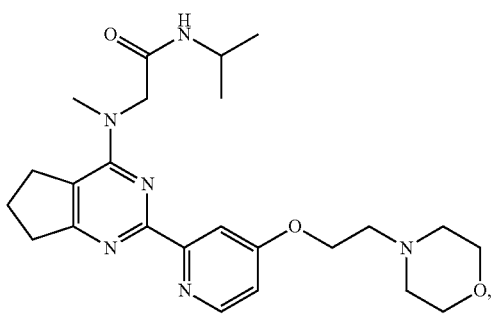 [SMILES: CC(C)NC(=O)CN(C)c1nc(-c2cc(OCCN3CCOCC3)ccn2)nc2c1CCC2] |
| Compound No. | Structure |
|---|---|
| 431 | 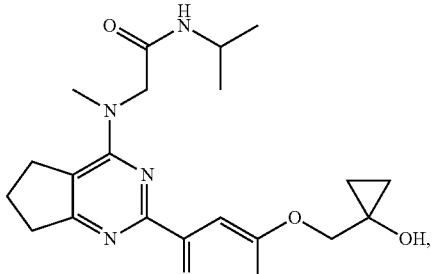 |
| 432 | 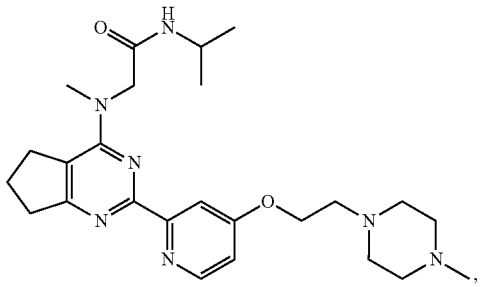 [SMILES: CC(C)NC(=O)CN(C)c1nc(-c2cc(OCCN3CCN(C)CC3)ccn2)nc2c1CCC2] |
| 433 | 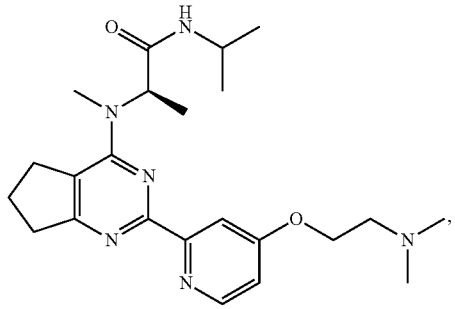 [SMILES: CC(C)NC(=O)[C@@H](C)N(C)c1nc(-c2cc(OCCN(C)C)ccn2)nc2c1CCC2] |
| 434 | 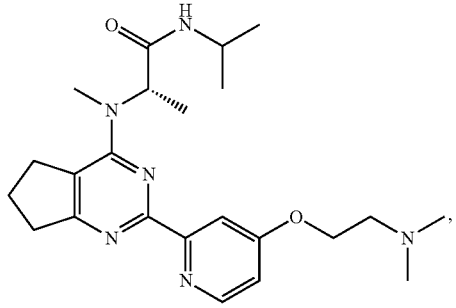 [SMILES: CC(C)NC(=O)[C@H](C)N(C)c1nc(-c2cc(OCCN(C)C)ccn2)nc2c1CCC2] |
| 435 | 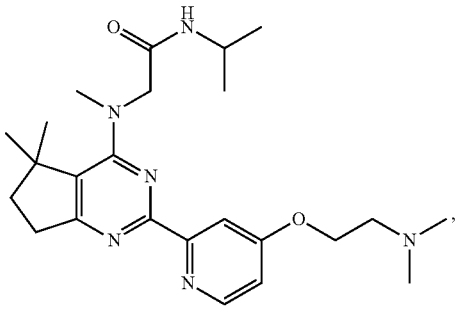 |

| Compound No. | Structure |
|---|---|
| 436 | (structure) |
| 437 | (structure) |
| 438 | (structure) |
| 439 | (structure) |
| 440 | (structure) |
| 441 | (structure) |
| 442 | (structure) |
| 443 | (structure) |

1103
-continued
| Compound No. | Structure |
|---|---|
| 444 | 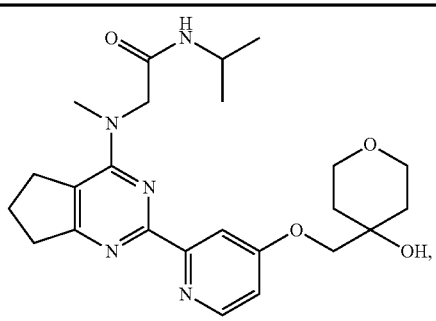 |
| 445 | 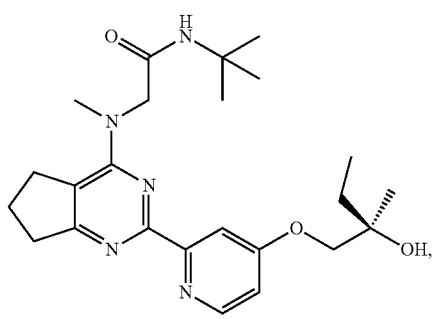 [SMILES: CC[C@@](C)(O)COc1ccnc(-c2nc3c(c(N(C)CC(=O)NC(C)(C)C)n2)CCC3)c1] |
| 446 | 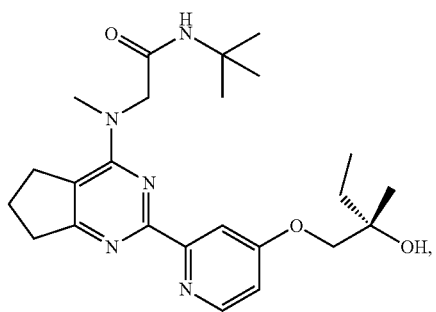 [SMILES: CC[C@](C)(O)COc1ccnc(-c2nc3c(c(N(C)CC(=O)NC(C)(C)C)n2)CCC3)c1] |
| 447 | 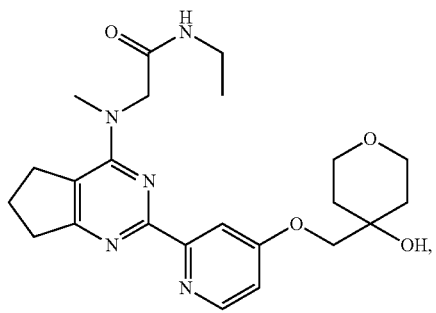 [SMILES: CCNC(=O)CN(C)c1nc(-c2cc(OCC3(O)CCOCC3)ccn2)nc2c1CCC2] |
| 448 | 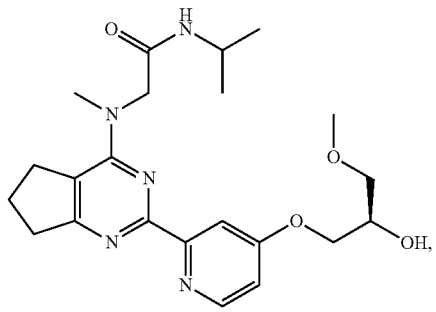 [SMILES: COC[C@@H](O)COc1ccnc(-c2nc3c(c(N(C)CC(=O)NC(C)C)n2)CCC3)c1] |
1104
-continued
| Compound No. | Structure |
|---|---|
| 449 | 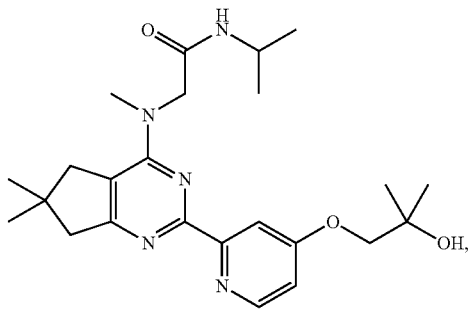 [SMILES: CC(C)NC(=O)CN(C)c1nc(-c2cc(OCC(C)(C)O)ccn2)nc2c1CC(C)(C)C2] |
| 450 | 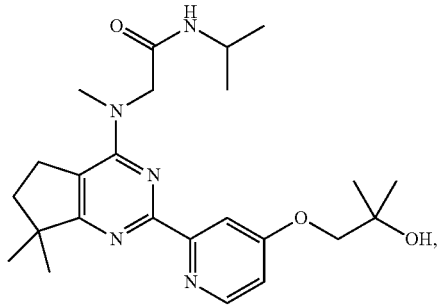 [SMILES: CC(C)NC(=O)CN(C)c1nc(-c2cc(OCC(C)(C)O)ccn2)nc2c1CCC2(C)C] |
| 451 | 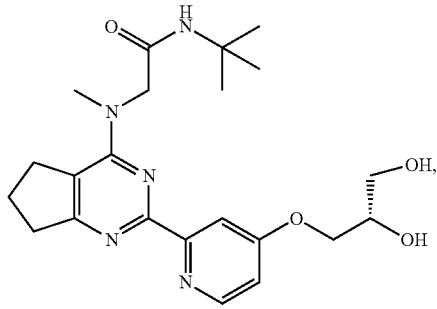 [SMILES: CN(CC(=O)NC(C)(C)C)c1nc(-c2cc(OC[C@@H](O)CO)ccn2)nc2c1CCC2] |
| 452 | 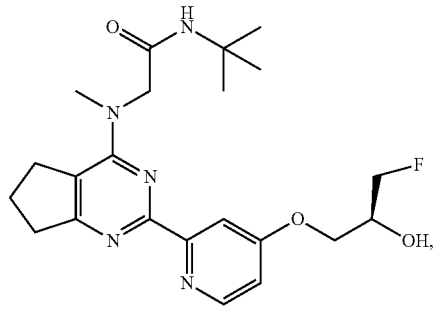 [SMILES: CN(CC(=O)NC(C)(C)C)c1nc(-c2cc(OC[C@H](O)CF)ccn2)nc2c1CCC2] |

| Compound No. | Structure |
|---|---|
| 453 | 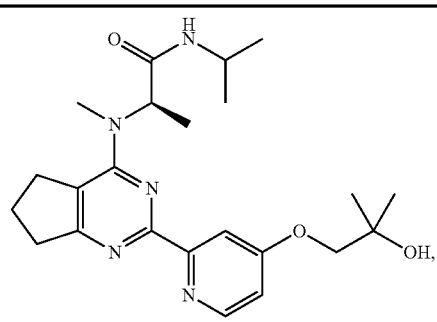 |
| 454 | 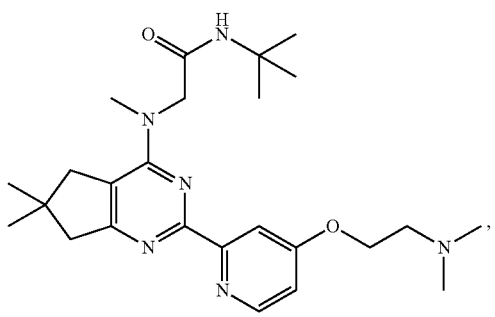 |
| 455 | 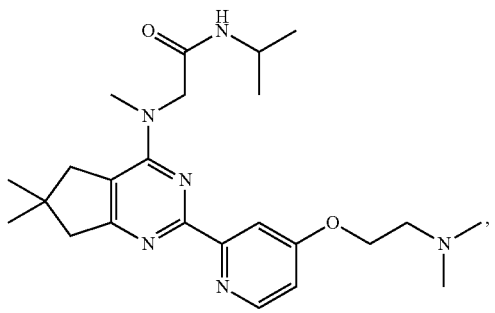 |
| 456 | 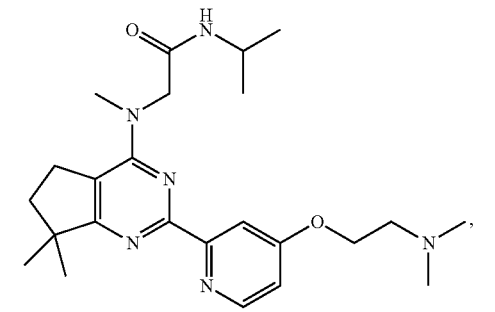 |
| 457 | 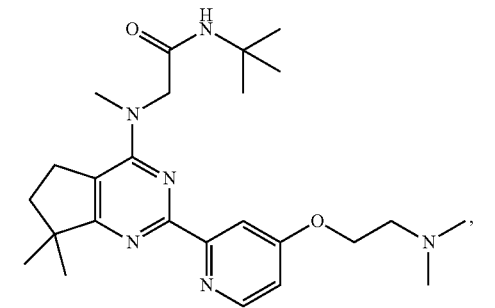 |
| Compound No. | Structure |
|---|---|
| 458 | 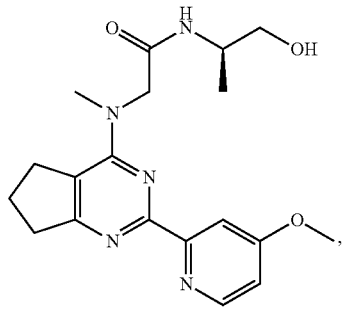 [SMILES: COc1ccnc(-c2nc3c(c(N(C)CC(=O)N[C@H](C)CO)n2)CCC3)c1] |
| 459 | 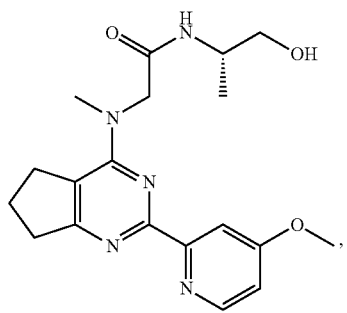 [SMILES: COc1ccnc(-c2nc3c(c(N(C)CC(=O)N[C@@H](C)CO)n2)CCC3)c1] |
| 460 | 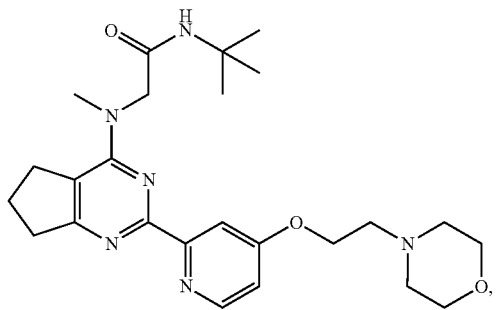 [SMILES: CN(CC(=O)NC(C)(C)C)c1nc(-c2cc(OCCN3CCOCC3)ccn2)nc2c1CCC2] |
| 461 | 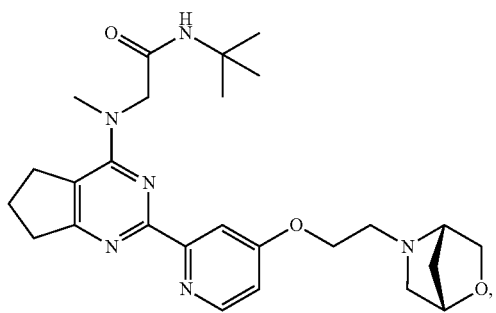 [SMILES: CN(CC(=O)NC(C)(C)C)c1nc(-c2cc(OCCN3C[C@@H]4C[C@H]3CO4)ccn2)nc2c1CCC2] |

| Compound No. | Structure |
|---|---|
| 462 | 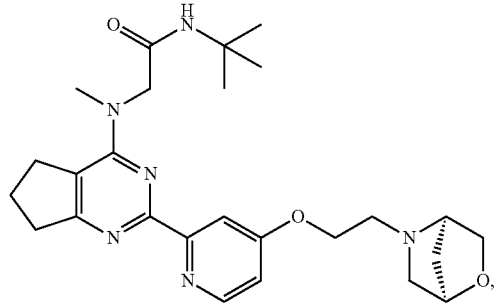 [SMILES: CN(CC(=O)NC(C)(C)C)c1nc(-c2cc(OCCN3C[C@H]4C[C@@H]3CO4)ccn2)nc2c1CCC2] |
| 463 | 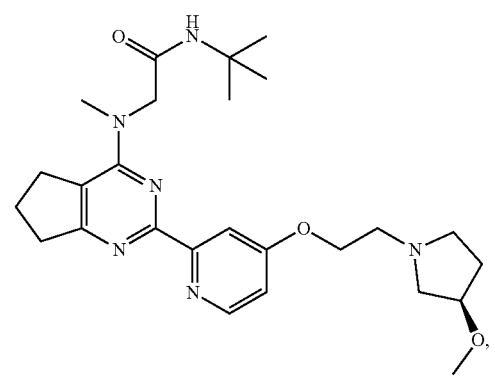 [SMILES: CO[C@@H]1CCN(CCOc2ccnc(-c3nc4c(c(N(C)CC(=O)NC(C)(C)C)n3)CCC4)c2)C1] |
| 464 | 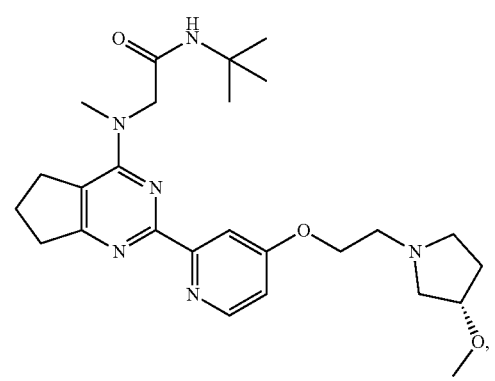 [SMILES: CO[C@H]1CCN(CCOc2ccnc(-c3nc4c(c(N(C)CC(=O)NC(C)(C)C)n3)CCC4)c2)C1] |
| 465 | 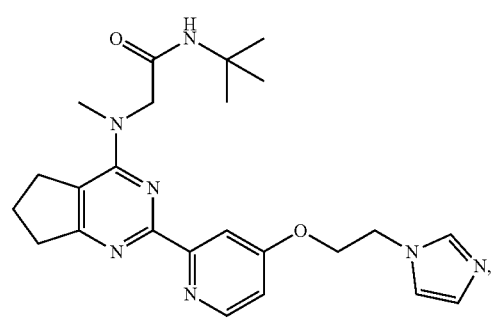 [SMILES: CN(CC(=O)NC(C)(C)C)c1nc(-c2cc(OCCn3ccnc3)ccn2)nc2c1CCC2] |
| Compound No. | Structure |
|---|---|
| 466 | 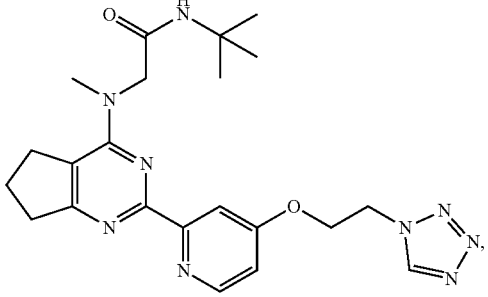 |
| 467 | 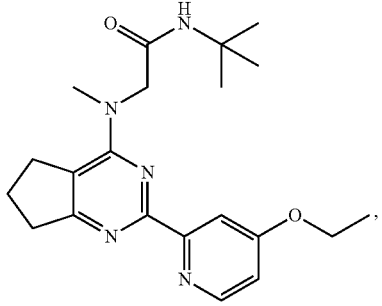 [SMILES: CCOc1ccnc(-c2nc3c(c(N(C)CC(=O)NC(C)(C)C)n2)CCC3)c1] |
| 468 | 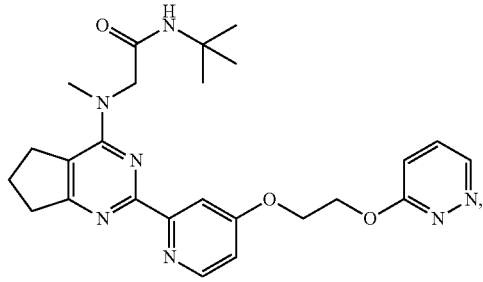 [SMILES: CN(CC(=O)NC(C)(C)C)c1nc(-c2cc(OCCOc3cccnn3)ccn2)nc2c1CCC2] |
| 469 | 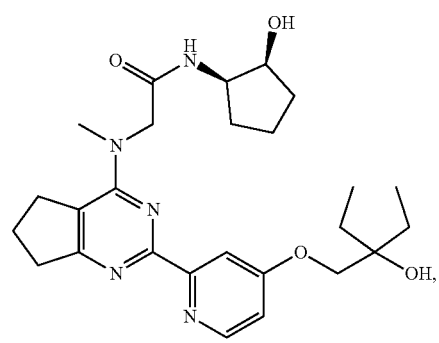 [SMILES: CCC(O)(CC)COc1ccnc(-c2nc3c(c(N(C)CC(=O)N[C@@H]4CCC[C@@H]4O)n2)CCC3)c1] |
| 470 | 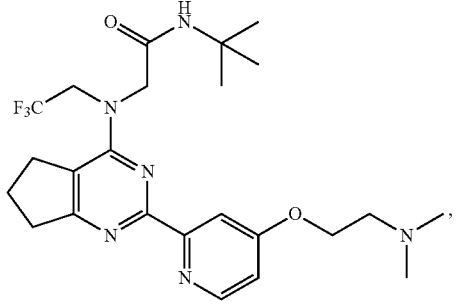 [SMILES: CN(C)CCOc1ccnc(-c2nc3c(c(N(CC(=O)NC(C)(C)C)CC(F)(F)F)n2)CCC3)c1] |

| Compound No. | Structure |
|---|---|
| 471 | 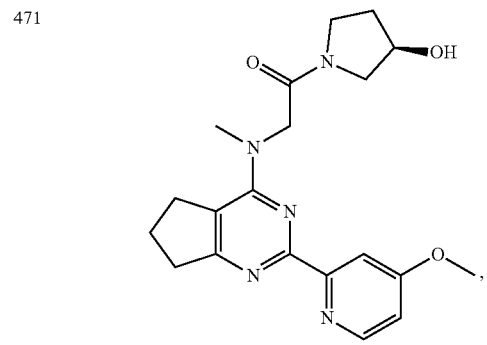 |
| 472 | |
| 473 | 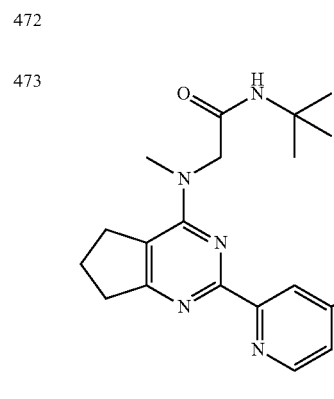 |
| 474 | 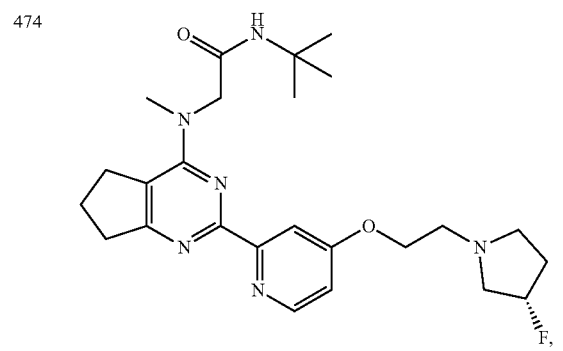 |
| 475 | 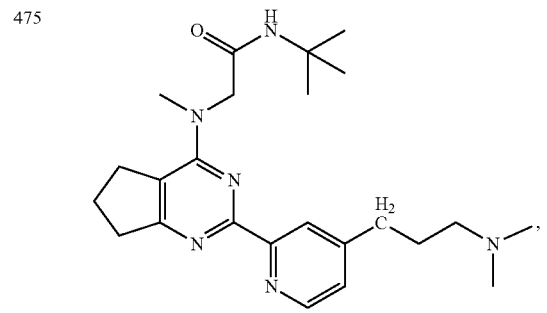 |
| Compound No. | Structure |
|---|---|
| 476 | 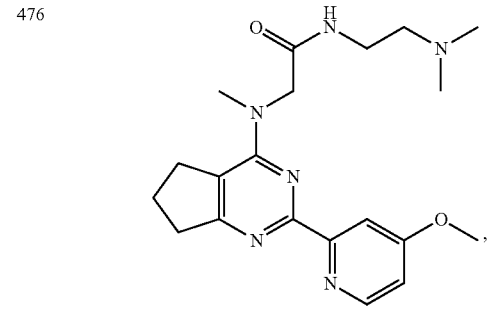 |
| 477 | 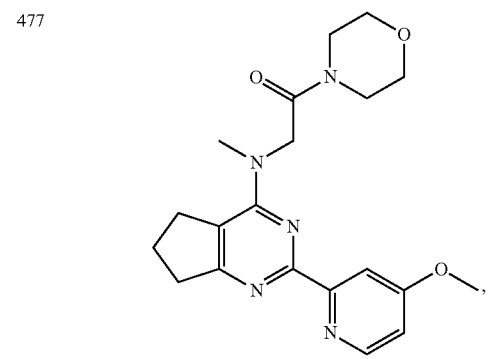 |
| 478 | 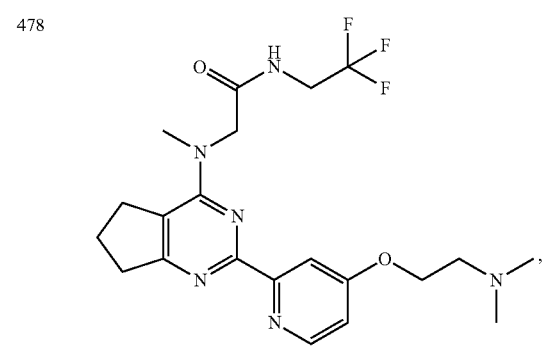 |
| 479 | 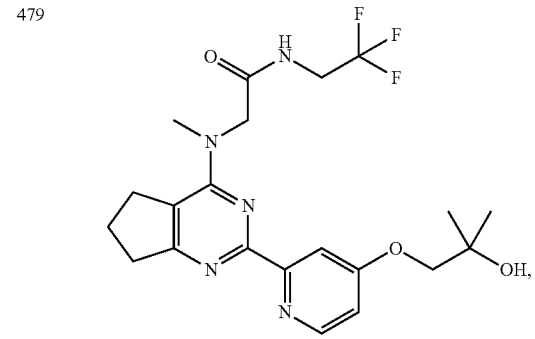 |

1111
-continued
| Compound No. | Structure |
|---|---|
| 480 | 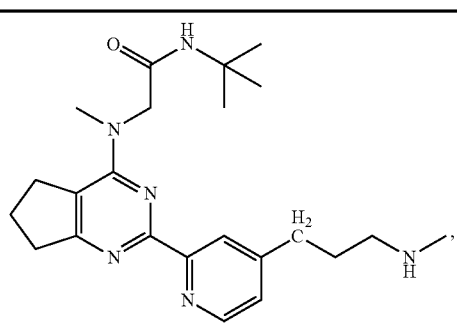 |
| 481 | 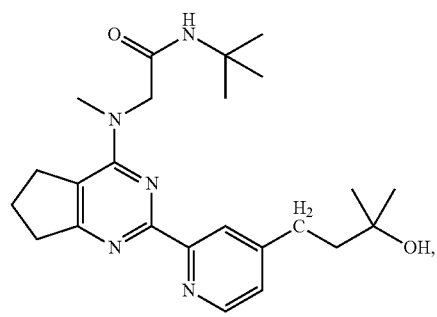 [SMILES: CN(CC(=O)NC(C)(C)C)c1nc(-c2cc(CCC(C)(C)O)ccn2)nc2c1CCC2] |
| 482 | 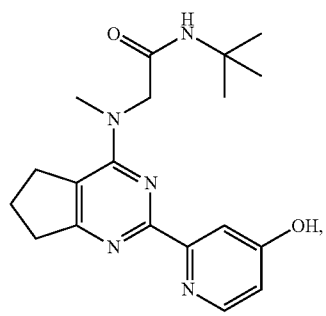 [SMILES: CN(CC(=O)NC(C)(C)C)c1nc(-c2cc(O)ccn2)nc2c1CCC2] |
| 483 | 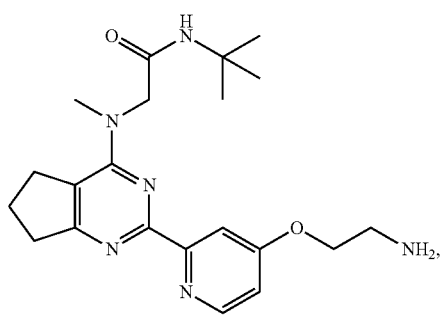 [SMILES: CN(CC(=O)NC(C)(C)C)c1nc(-c2cc(OCCN)ccn2)nc2c1CCC2] |
| 484 | 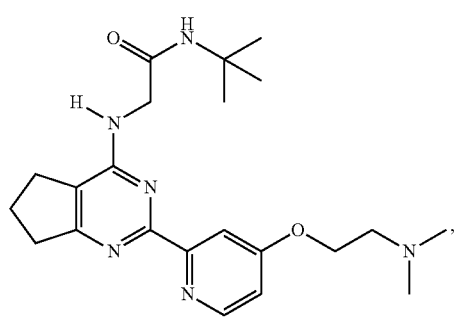 [SMILES: CN(C)CCOc1ccnc(-c2nc3c(c(NCC(=O)NC(C)(C)C)n2)CCC3)c1] |
1112
-continued
| Compound No. | Structure |
|---|---|
| 485 | 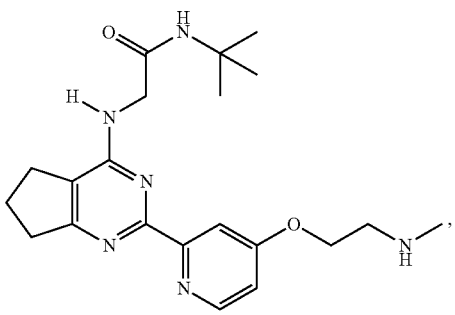 [SMILES: CNCCOc1ccnc(-c2nc3c(c(NCC(=O)NC(C)(C)C)n2)CCC3)c1] |
| 486 | 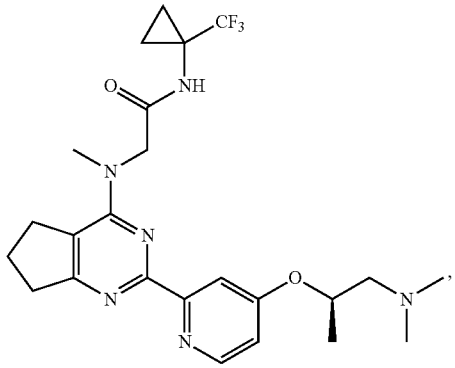 [SMILES: C[C@H](CN(C)C)Oc1ccnc(-c2nc3c(c(N(C)CC(=O)NC4(C(F)(F)F)CC4)n2)CCC3)c1] |
| 487 | 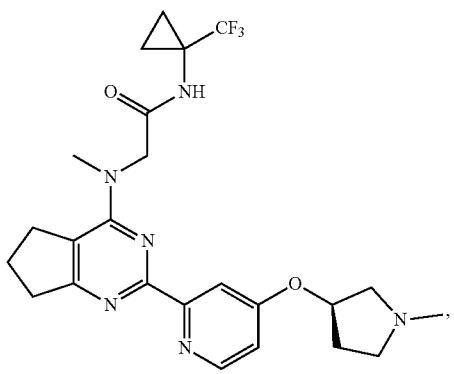 [SMILES: CN1CC[C@@H](Oc2ccnc(-c3nc4c(c(N(C)CC(=O)NC5(C(F)(F)F)CC5)n3)CCC4)c2)C1] |
| 488 | 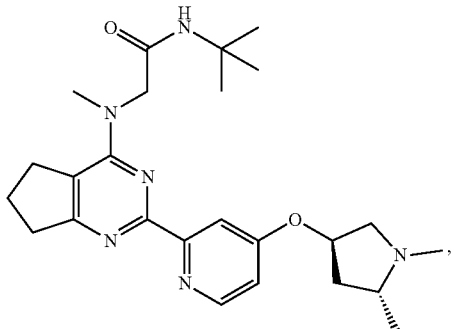 |

-continued
| Compound No. | Structure |
|---|---|
| 489 | 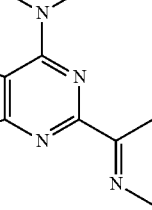 |
| 490 | 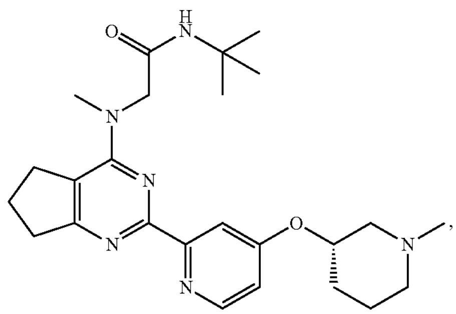 [SMILES: CN1CCC[C@H](Oc2ccnc(-c3nc4c(c(N(C)CC(=O)NC(C)(C)C)n3)CCC4)c2)C1] |
| 491 | 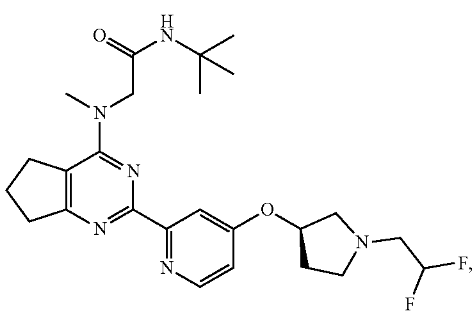 [SMILES: CN(CC(=O)NC(C)(C)C)c1nc(-c2cc(O[C@@H]3CCN(CC(F)F)C3)ccn2)nc2c1CCC2] |
| 492 | 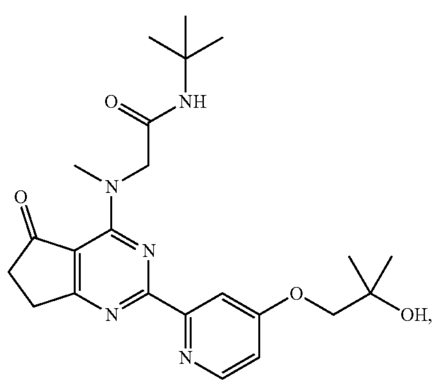 [SMILES: CN(CC(=O)NC(C)(C)C)c1nc(-c2cc(OCC(C)(C)O)ccn2)nc2c1C(=O)CC2] |
-continued
| Compound No. | Structure |
|---|---|
| 493 | 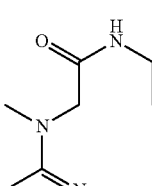 |
| 494 | 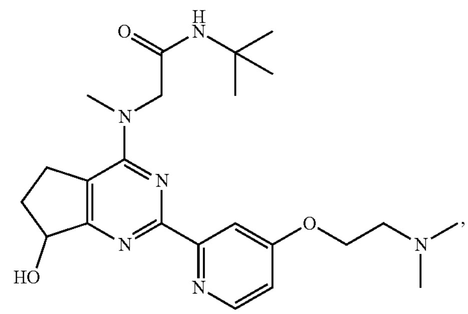 [SMILES: CN(C)CCOc1ccnc(-c2nc3c(c(N(C)CC(=O)NC(C)(C)C)n2)CCC3O)c1] |
| 496 | 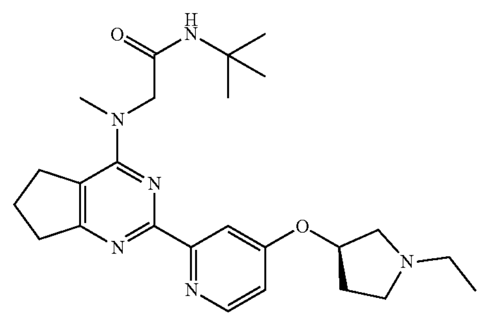 |
| 497 | 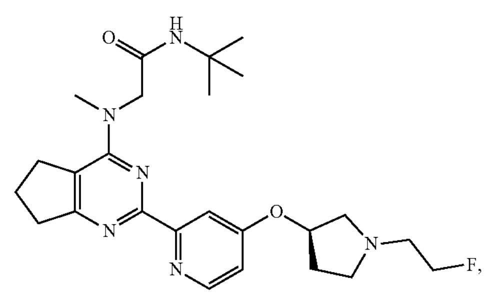 [SMILES: CN(CC(=O)NC(C)(C)C)c1nc(-c2cc(O[C@@H]3CCN(CCF)C3)ccn2)nc2c1CCC2] |
| 498 | 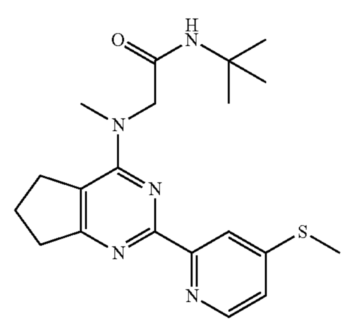 |

| Compound No. | Structure |
|---|---|
| 499 | 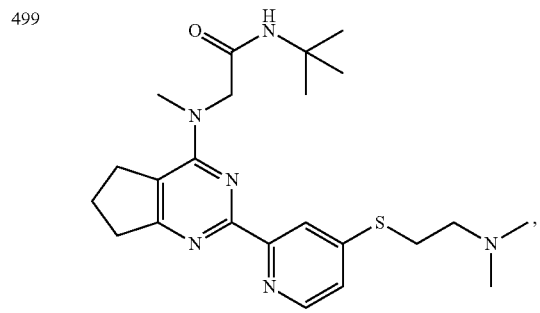 |
| 500 | 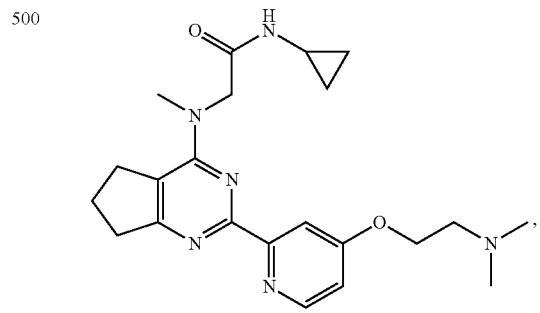 |
| 501 | 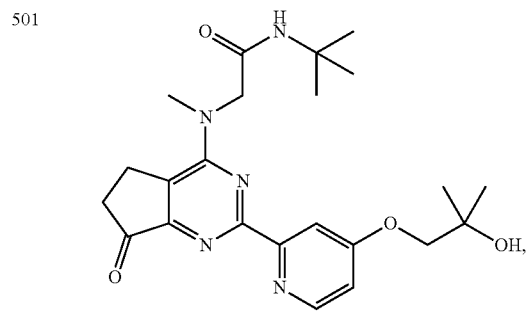 |
| 502 | 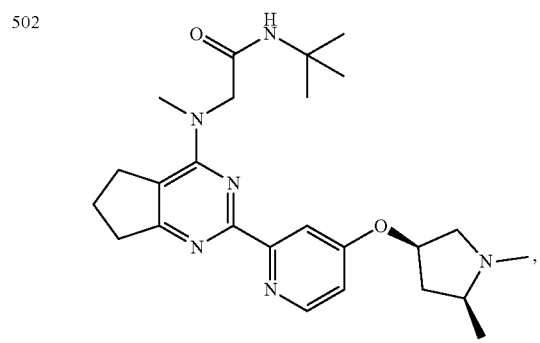 |
| Compound No. | Structure |
|---|---|
| 503 | 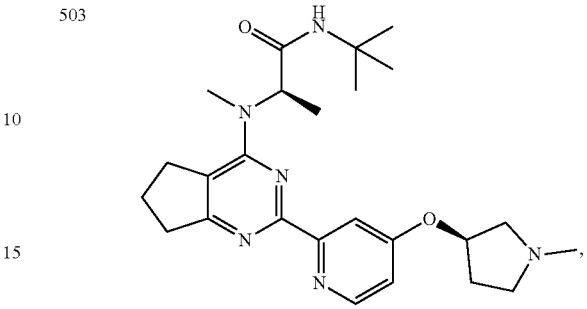 |
| 504 | 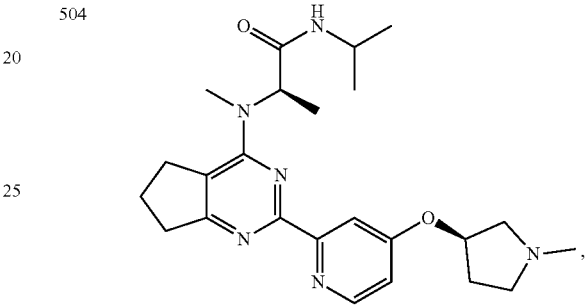 |
| 505 | 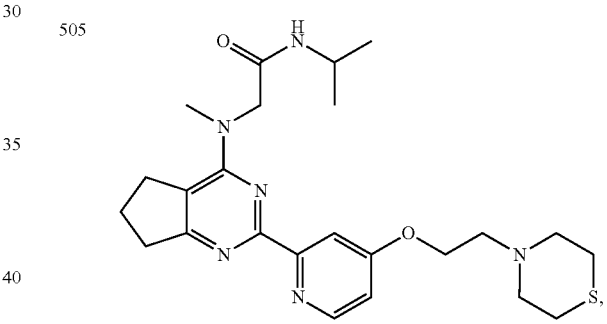 |
| 506 | 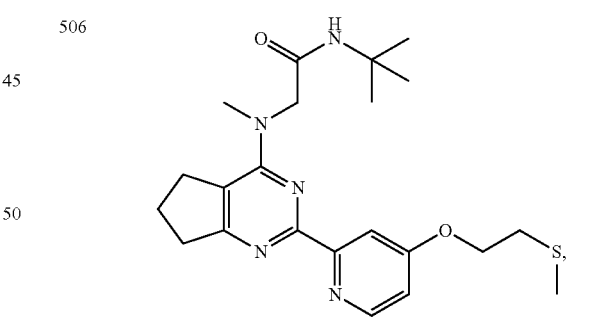 |
| 507 | 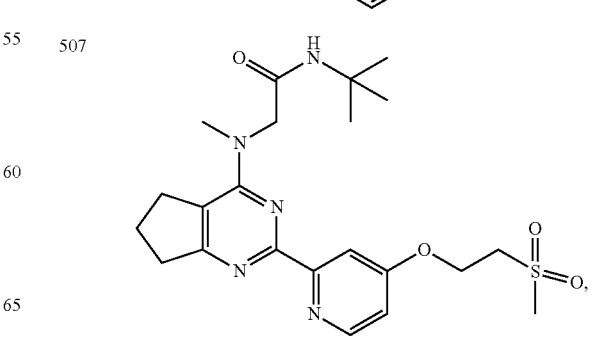 |

-continued

| Compound No. | Structure |
|---|---|
| 508 | 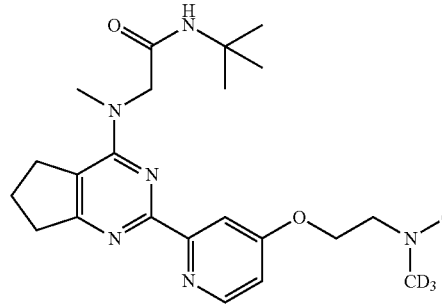 and |
| 509 | 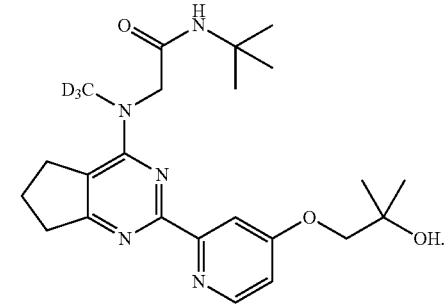 [SMILES: [2H]C([2H])([2H])N(CC(=O)NC(C)(C)C)c1nc(-c2cc(OCC(C)(C)O)ccn2)nc2c1CCC2] |

35. A pharmaceutical composition comprising a compound according to claim 1 or a pharmaceutically acceptable salt thereof, and a pharmaceutically acceptable excipient.

36. A method of inhibiting iron transport mediated by ferroportin in a subject, comprising administering to the subject an effective amount of a compound of claim 1, or a pharmaceutically acceptable salt thereof.

37. A compound of formula:

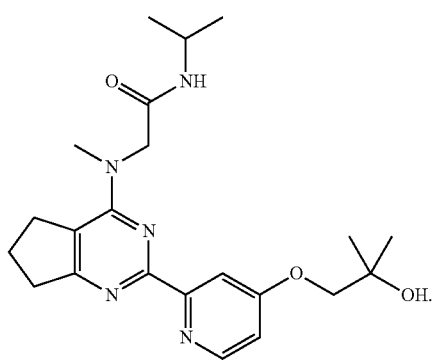 [SMILES: CC(C)NC(=O)CN(C)c1nc(-c2cc(OCC(C)(C)O)ccn2)nc2c1CCC2]

38. A compound of formula:

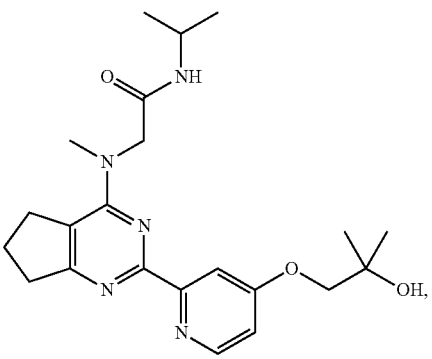 [SMILES: CC(C)NC(=O)CN(C)c1nc(-c2cc(OCC(C)(C)O)ccn2)nc2c1CCC2]

or a pharmaceutically acceptable salt thereof.

39. A compound of formula:

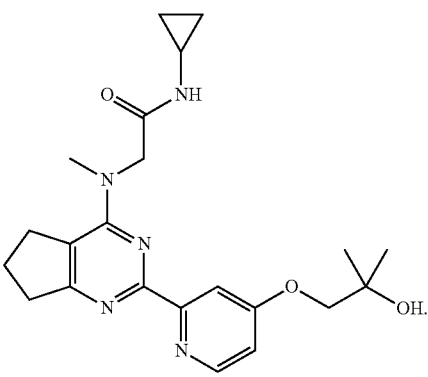 [SMILES: CN(CC(=O)NC1CC1)c1nc(-c2cc(OCC(C)(C)O)ccn2)nc2c1CCC2]

40. A compound of formula:

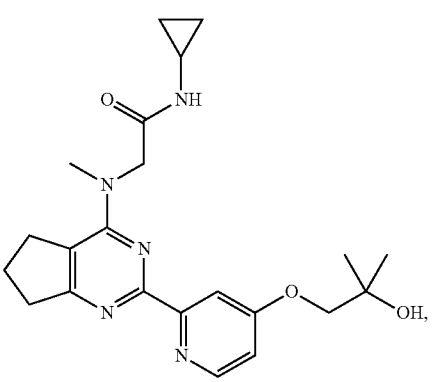 [SMILES: CN(CC(=O)NC1CC1)c1nc(-c2cc(OCC(C)(C)O)ccn2)nc2c1CCC2]

or a pharmaceutically acceptable salt thereof.

41. A pharmaceutical composition comprising a compound according to claim 37, and a pharmaceutically acceptable excipient.

42. A pharmaceutical composition comprising a compound according to claim 38, or a pharmaceutically acceptable salt thereof, and a pharmaceutically acceptable excipient.

43. A pharmaceutical composition comprising a compound according to claim 39, and a pharmaceutically acceptable excipient.

44. A pharmaceutical composition comprising a compound according to claim 40, or a pharmaceutically acceptable salt thereof, and a pharmaceutically acceptable excipient.

45. A method of inhibiting iron transport mediated by ferroportin in a subject, comprising administering to the subject an effective amount of a compound of claim 37.

46. A method of inhibiting iron transport mediated by ferroportin in a subject, comprising administering to the subject an effective amount of a compound of claim 38, or a pharmaceutically acceptable salt thereof.

47. A method of inhibiting iron transport mediated by ferroportin in a subject, comprising administering to the subject an effective amount of a compound of claim 39.

48. A method of inhibiting iron transport mediated by ferroportin in a subject, comprising administering to the subject an effective amount of a compound of claim 40, or a pharmaceutically acceptable salt thereof.

* * * * *